US008895585B2

(12) United States Patent
Fujiwara et al.

(10) Patent No.: US 8,895,585 B2
(45) Date of Patent: Nov. 25, 2014

(54) NICOTINAMIDE DERIVATIVE OR SALT THEREOF

(71) Applicants: Hideyasu Fujiwara, Ashigarakami-gun (JP); Kimihiko Sato, Ashigarakami-gun (JP); Shinsuke Mizumoto, Ashigarakami-gun (JP); Yuichiro Sato, Toyama (JP); Hideki Kurihara, Ashigarakami-gun (JP); Yohei Kubo, Ashigarakami-gun (JP); Hiyoku Nakata, Ashigarakami-gun (JP); Yasutaka Baba, Ashigarakami-gun (JP); Takashi Tamura, Ashigarakami-gun (JP); Hidenobu Kuniyoshi, Ashigarakami-gun (JP); Shinji Hagiwara, Ashigarakami-gun (JP); Mari Yamamoto, Toyama (JP)

(72) Inventors: Hideyasu Fujiwara, Ashigarakami-gun (JP); Kimihiko Sato, Ashigarakami-gun (JP); Shinsuke Mizumoto, Ashigarakami-gun (JP); Yuichiro Sato, Toyama (JP); Hideki Kurihara, Ashigarakami-gun (JP); Yohei Kubo, Ashigarakami-gun (JP); Hiyoku Nakata, Ashigarakami-gun (JP); Yasutaka Baba, Ashigarakami-gun (JP); Takashi Tamura, Ashigarakami-gun (JP); Hidenobu Kuniyoshi, Ashigarakami-gun (JP); Shinji Hagiwara, Ashigarakami-gun (JP); Mari Yamamoto, Toyama (JP)

(73) Assignee: FUJIFILM Corporation, Tokyo (JP)

( * ) Notice: Subject to any disclaimer, the term of this patent is extended or adjusted under 35 U.S.C. 154(b) by 11 days.

(21) Appl. No.: 13/730,000

(22) Filed: Dec. 28, 2012

(65) Prior Publication Data
US 2013/0116430 A1 May 9, 2013

Related U.S. Application Data

(63) Continuation of application No. PCT/JP2011/065530, filed on Jun. 30, 2011.

(30) Foreign Application Priority Data

Jun. 30, 2010 (JP) ................................. 2010-150495

(51) Int. Cl.
C07D 213/82 (2006.01)

(52) U.S. Cl.
USPC ........... 514/332; 514/333; 514/336; 514/337; 514/338; 514/339; 514/353; 546/255; 546/256; 546/264; 546/268.1; 546/306

(58) Field of Classification Search
USPC ......... 514/332, 333, 336, 337, 338, 339, 353; 546/255, 256, 264, 268.1, 306
See application file for complete search history.

(56) References Cited

U.S. PATENT DOCUMENTS

| 6,797,706 B1 | 9/2004 | Hisamichi et al. |
| 2007/0197782 A1 | 8/2007 | Clough et al. |
| 2008/0139561 A1 | 6/2008 | Davies et al. |
| 2012/0142671 A1* | 6/2012 | Jia et al. ................... 514/212.08 |

FOREIGN PATENT DOCUMENTS

| CN | 101155800 A | 4/2008 |
| CN | 101675034 A | 3/2010 |
| EP | 1 184 376 A1 | 3/2002 |
| JP | 2008013499 A | 1/2008 |
| JP | 2008528664 A | 7/2008 |
| WO | 0075113 A1 | 12/2000 |
| WO | 2006/082392 A1 | 8/2006 |
| WO | 2006082392 A1 | 8/2006 |
| WO | 2007120980 A2 | 10/2007 |
| WO | 2007/124221 A1 | 11/2007 |
| WO | 2008/140066 A2 | 11/2008 |
| WO | 2009026107 A1 | 2/2009 |
| WO | 2009/036996 A2 | 3/2009 |
| WO | 2009131687 A2 | 10/2009 |
| WO | 2009136995 A2 | 11/2009 |
| WO | 2009145856 A1 | 12/2009 |
| WO | 2010144647 A1 | 12/2010 |

OTHER PUBLICATIONS

Takanobu Taniguchi, et al. "Molecular Cloning of a Porcine Gene syk That Encodes a 72-kDa Protein-Tyrosine Kinase Showing High Susceptibility to Proteolysis," The Journal of Biological Chemistry, vol. 266, pp. 15790-15796, Aug. 25, 1991.

Peter Valent et al, "Signal Transduction-Associated and Cell Activation-Linked Antigens Expressed in Human Mast Cells," International Journal of Hematology, vol. 75, No. 4, pp. 357-362, 2002.

(Continued)

Primary Examiner — Kahsay Habte
(74) Attorney, Agent, or Firm — Sughrue Mion, PLLC

(57) ABSTRACT

An object of the present invention is to provide to a compound and a pharmaceutical composition, which have excellent Syk-inhibitory activity. The present invention provides a nicotinamide derivative represented by the following formula (I) (wherein $R^1$ represents a halogen atom; $R^2$ represents a $C_{1-12}$ alkyl group, a $C_{2-12}$ alkenyl group, a $C_{2-12}$ alkynyl group, a $C_{3-8}$ cycloalkyl group, an aryl group, an ar-$C_{1-6}$ alkyl group or a heterocyclic group, each optionally having at least one substituent; $R^3$ represents an aryl group or a heterocyclic group each optionally having at least one substituent; and $R^4$ and $R^5$ each independently represent a hydrogen atom; and $R^2$ and $R^4$ may form a cyclic amino group optionally having at least one substituent together with the nitrogen atom to which they bind) or a salt thereof, and a pharmaceutical composition for use in the treatment of a Syk-related disease which comprises the nicotinamide derivative or a salt thereof.

29 Claims, 2 Drawing Sheets

(56) References Cited

OTHER PUBLICATIONS

Tsung H. Lin et al, "Integrin-Mediated Tyrosine Phosphorylation and Cytokine Message Induction in Monocytic Cells," The Journal of Biological Chemistry, vol. 270, No. 27, pp. 16189-16197, Jul. 7, 1995.
Elena Bulanova et al, "The IL-15Rα Chain Signals Through Association with Syk in Human B Cells," The Journal of Immunology, vol. 167, No. 11, pp. 6292-6302, 2001.
Brian R. Wong et al., "Targeting Syk as a Treatment for Allergic and Autoimmune Disorders," Expert Opinion on Investigational Drugs., vol. 13, No. 7, pp. 743-762, 2004.
Marina Ulanova et al., "Spleen Tyrosine Kinase (Sky) as a Novel Target for Allergic Asthma and Rhinitis," Expert Opinion on Therapeutic Targets, vol. 9, No. 5, pp. 901-921, 2005.
Malini Bajpai, "Fostamatinib, a Syk Inhibitor Prodrug for the Treatment of Inflammatory Diseases," IDrugs, vol. 12, No. 3, pp. 174-185, 2009.
International Search Report and written opinion issued on Sep. 20, 2011 in International Application No. PCT/JP2011/065530.
International Preliminary Report on Patentability issued on Feb. 21, 2013 in PCT/JP2011/065530.
Office Action dated Aug. 22, 2013 in Chinese Patent Application 201180031719.6.
Extended European Search Report dated Nov. 13, 2013 in European Application No. 11801034.7.
Huan-Zhang Xie, "Pharmacophere modeling study based on known Spleen tyrosine kinase inhibitors together with virtual screening for identifying novel inhibitors", Bioorganic & Medicinal Chemistry Letters, Pergamon, GB, vol. 19, No. 7 (Apr. 1, 2009), pp. 1944-1949.
Office Action dated May 5, 2014 in corresponding Chinese Patent Application No. 201180031719.6.
U.S. Appl. No. 14/317,001, filed Jun. 27, 2014.
International Preliminary Report on Patentability (Chapter I) mailed Jul. 10, 2014 for PCT/JP2011/080597.
English translation of International Preliminary Report on Patentability (Chapter I) mailed Jul. 10, 2014 for PCT/JP2011/080597.
Office Action dated Aug. 12, 2014 in Japanese Application No. 2012-522731.
Substantive Examination Report dated Aug. 29, 2014 in counterpart Philippine Patent Application No. 1/2012/502572.
Office Action from the Taiwan Intellectual Property Office issued Sep. 25, 2014 in a counterpart Taiwanese Patent Application No. 100123081.

* cited by examiner

Example 8-1

Example 6-49

Example 4-17

Compound concentration (uM)

NICOTINAMIDE DERIVATIVE OR SALT THEREOF

TECHNICAL FIELD

The present invention relates to a nicotinamide derivative having Syk-inhibitory activity or a salt thereof.

BACKGROUND ART

Spleen Tyrosine Kinase (Syk), which is a non-receptor type intracellular tyrosine kinase, plays essential roles for activation of B cells and in an intracellular signaling system mediated by an Fc receptor. For example, Syk is associated with a FcεRI signal that is an immunoglobulin E receptor in mast cells, basophils and other cells, and thus it regulates generation of inflammatory mediators such as histamine or leukotrien, as well as cytokine, from these cells. At the same time, Syk plays a role in transmitting activation signals caused by stimulation of Fcγ receptor into monocytes, dendritic cells and other cells (Non Patent Documents 1 and 2). Moreover, it has been reported that Syk is also associated with cytokine signaling caused by integrin, IL-13, IL-15 and the like (Non Patent Documents 3 and 4).

In the case of a B-cell, a signal is transmitted into the cell mediated by a BCR (B-cell antigen receptor) expressed on the cell membrane, so that activation and differentiation of the cell is induced, resulting in generation of an antibody. It has been reported that Syk is essential for such an activation and differentiation process (Non Patent Document 5).

It is anticipated that it is possible to suppress various cell responses by inhibiting Syk (Non Patent Documents 5 and 6).

In the case of a type I allergy, which is an immediate-type allergy reaction, for example, immunoglobulin E (IgE) binds to FcεRI, which is a high-affinity IgE receptor, and an allergen then binds thereto to promote activation of the FcεRI and the release of inflammatory mediator. As a result, allergic symptoms are expressed. It is anticipated that inhibition of Syk activity will lead to the suppression of the activation of the FcεRI, and that it will be useful for the treatment of representative type I allergy-related diseases such as bronchial asthma, allergic rhinitis, hives, and atopic dermatitis.

Moreover, it is considered that inhibition of Syk activity leads to the suppression of the activation and/or maturation of immune B cells and the generation of antibodies, and that such inhibition of Syk activity can also regulate immune reactions other than type I allergy. Accordingly, it is also anticipated that inhibition of Syk activity will be effective for autoimmune diseases (rheumatoid arthritis, systemic lupus erythematosus, etc.), autoimmune hemolytic anemia, nephrotic syndrome, contact dermatitis, and the like. Furthermore, since inhibition of Syk activity also leads to the suppression of the activation of macrophages, it is anticipated that inhibition of Syk will be also effective for idiopathic thrombocytopenic purpura.

Further, inhibition of Syk activity suppresses not only immune and/or inflammatory diseases, but also activation and proliferation of lymphocytes, including B-cells as typical examples. Thus, it is anticipated that inhibition of Syk will be also effective for the treatment of various types of proliferative diseases such as lymphoma and lymphocytic leukemia. Still further, since inhibition of Syk activity regulates proliferation and differentiation of bone marrow cells, it is anticipated that it will be also effective for acute myelocytic leukemia.

On the other hand, Syk has been known to be involved in signaling mediated by integrin which is a cell adhesion molecule. Since Syk is expressed in blood platelets and is involved in the activation thereof, an inhibitor of such Syk is anticipated to be effective as a therapeutic agent for diseases associated with the activation of blood platelets.

A large number of compounds having Syk-inhibitory activity have been reported (Patent Documents 1 to 4). In clinical tests in which rheumatoid arthritis and idiopathic thrombocytopenic purpura have been targeted, useful compounds (Non Patent Document 7) and compounds having Syk and/or JAK inhibitory activity (Patent Documents 5 to 8) have been reported.

PRIOR ART DOCUMENTS

Patent Documents

[Patent Document 1] International Publication WO00/75113
[Patent Document 2] JP Patent Publication (Kokai) No. 2008-013499 A
[Patent Document 3] International Publication WO07/120,980
[Patent Document 4] International Publication WO07/124,221
[Patent Document 5] International Publication WO09/026,107
[Patent Document 6] International Publication WO09/131,687
[Patent Document 7] International Publication WO09/136,995
[Patent Document 8] International Publication WO09/145,856

Non Patent Documents

[Non Patent Document 1] The Journal of Biological Chemistry, Vol. 266, pp. 15790-15796, 1991
[Non Patent Document 2] International Journal of Hematology, Vol. 75, No. 4, pp. 357-362, 2002
[Non Patent Document 3] The Journal of Biological Chemistry, Vol. 270, pp. 16189-16197, 1995
[Non Patent Document 4] The Journal of Immunology, Vol. 167, No. 11, pp. 6292-6302, 2001
[Non Patent Document 5] Expert Opinion on Investigational Drugs, Vol. 13, No. 7, pp. 743-762, 2004
[Non Patent Document 6] Expert Opinion on Therapeutic Targets, Vol. 9, No. 5, pp. 901-921, 2005
[Non Patent Document 7] IDrugs, Vol. 12, No. 3, pp. 174-185, 2009

SUMMARY OF INVENTION

Object to be Solved by the Invention

To date, various Syk inhibitors have been reported, but they have not been placed on the market yet. It has been desired to develop a compound and a pharmaceutical composition, which have excellent Syk-inhibitory activity.

Means for Solving the Object

As a result of intensive studies directed towards achieving the aforementioned object, the present inventors have found that a nicotinamide derivative having a specific structure or a salt thereof has excellent Syk-inhibitory activity, thereby completing the present invention.

Specifically, the nicotinamide derivative of the present invention or a pharmaceutically acceptable salt thereof is characterized in that it is represented by the following formula (I):

[Formula 1]

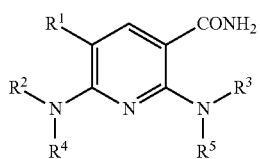

(I)

wherein $R^1$ represents a halogen atom;

$R^2$ represents a $C_{1-12}$ alkyl group optionally having at least one substituent, a $C_{2-12}$ alkenyl group optionally having at least one substituent, a $C_{2-12}$ alkynyl group optionally having at least one substituent, a $C_{3-8}$ cycloalkyl group optionally having at least one substituent, an aryl group optionally having at least one substituent, an ar-$C_{1-6}$ alkyl group optionally having at least one substituent or a heterocyclic group optionally having at least one substituent;

$R^3$ represents an aryl group optionally having at least one substituent or a heterocyclic group optionally having at least one substituent; and $R^4$ and $R^5$ each independently represent a hydrogen atom, a $C_{1-12}$ alkyl group optionally having at least one substituent, a $C_{2-12}$ alkenyl group optionally having at least one substituent, or a $C_{2-12}$ alkynyl group optionally having at least one substituent.

In addition, the present invention provides a pharmaceutical composition comprising the above-described nicotinamide derivative or a salt thereof, particularly, a pharmaceutical composition for use in the treatment of a Syk-related disease, which comprises the above-described nicotinamide derivative or a salt thereof, and a pharmaceutical composition for use in the treatment of a disease selected from the group consisting of rheumatism and idiopathic thrombocytopenic purpura, which comprises the above-described nicotinamide derivative or a salt thereof.

From a further viewpoint, the present invention provides: use of the above-described nicotinamide derivative or a salt thereof for production of the above-described pharmaceutical composition; a method for treating a Syk-related disease, which comprises a step of administering a therapeutically effective amount of the above-described nicotinamide derivative or a salt thereof to mammals including a human; and a method for treating a disease selected from the group consisting of rheumatism and idiopathic thrombocytopenic purpura, which comprises a step of administering a therapeutically effective amount of the above-described nicotinamide derivative or a salt thereof to mammals including a human.

Effects of the Invention

The nicotinamide derivative of the present invention or a salt thereof has excellent Syk-inhibitory activity, and it is useful as a pharmaceutical composition for use in the treatment of a Syk-related disease.

DESCRIPTION OF EMBODIMENTS

Figure 1:
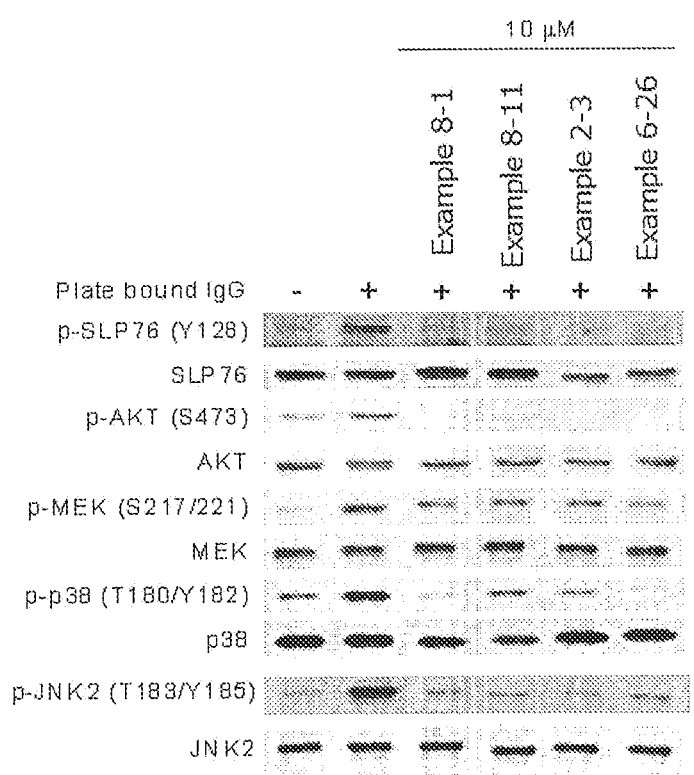
FIG. 1 shows the results of an intracellular phosphorylation signaling assay.

Hereinafter, the compound of the present invention will be described in detail.

The following definitions are applied in the present specification, unless otherwise specified.

The term "halogen atom" is used herein to mean a fluorine atom, a chlorine atom, a bromine atom or an iodine atom.

The term "$C_{1-12}$ alkyl group" is used herein to mean a linear or branched $C_{1-12}$ alkyl group, such as methyl, ethyl, propyl, isopropyl, butyl, sec-butyl, isobutyl, tert-butyl, pentyl, isopentyl, hexyl, heptyl and octyl groups.

The term "$C_{1-6}$ alkyl group" is used herein to mean a linear or branched $C_{1-6}$ alkyl group, such as methyl, ethyl, propyl, isopropyl, butyl, sec-butyl, isobutyl, tert-butyl, pentyl, isopentyl and hexyl groups.

The term "$C_{2-12}$ alkenyl group" is used herein to mean a linear or branched $C_{2-12}$ alkenyl group, such as vinyl, allyl, propenyl, isopropenyl, butenyl, isobutenyl, 1,3-butadienyl, pentenyl, hexenyl, heptenyl and octenyl groups.

The term "$C_{2-6}$ alkenyl group" is used herein to mean a linear or branched $C_{2-6}$ alkenyl group, such as vinyl, allyl, propenyl, isopropenyl, butenyl, isobutenyl, 1,3-butadienyl, pentenyl and hexenyl groups.

The term "$C_{2-12}$ alkynyl group" is used herein to mean a linear or branched $C_{2-12}$ alkynyl group, such as ethynyl, propynyl, butynyl, pentynyl, hexynyl, heptynyl and octynyl groups.

The term "$C_{2-6}$ alkynyl group" is used herein to mean a linear or branched $C_{2-6}$ alkynyl group, such as ethynyl, propynyl, butynyl, pentynyl and hexynyl groups.

The term "$C_{3-8}$ cycloalkyl group" is used herein to mean a $C_{3-8}$ cycloalkyl group, such as cyclopropyl, cyclobutyl, cyclopentyl and cyclohexyl groups.

The term "$C_{5-7}$ cycloalkyl group" is used herein to mean a cyclopentyl, cyclohexyl or cycloheptyl group.

The term "aryl group" is used herein to mean a phenyl, naphthyl, indanyl or indenyl group.

The term "ar-$C_{1-6}$ alkyl group" is used herein to mean an ar-$C_{1-6}$ alkyl group, such as benzyl, 2-phenylpropan-2-yl, diphenylmethyl, trityl, phenethyl and naphthylmethyl groups.

The term "$C_{1-6}$ alkylene group" is used herein to mean a linear or branched $C_{1-6}$ alkylene group, such as methylene, ethylene, propylene, butylene and hexylene groups.

The term "$C_{2-6}$ alkenylene group" is used herein to mean a linear or branched $C_{2-6}$ alkenylene group, such as vinylene, propenylene, butenylene and pentenylene groups.

The term "$C_{2-6}$ alkynylene group" is used herein to mean a linear or branched $C_{2-6}$ alkynylene group, such as ethynylene, propynylene, butynylene and pentynylene groups.

The term "$C_{1-6}$ alkoxy group" is used herein to mean a linear or branched $C_{1-6}$ alkyloxy group, such as methoxy, ethoxy, propoxy, isopropoxy, butoxy, isobutoxy, sec-butoxy, tert-butoxy, pentyloxy and hexyloxy groups.

The term "ar-$C_{1-6}$ alkoxy group" is used herein to mean an ar-$C_{1-6}$ alkyloxy group, such as benzyloxy, phenethyloxy and naphthylmethyloxy groups.

The term "aryloxy group" is used herein to mean a phenoxy or naphthyloxy group.

The term "$C_{1-6}$ alkoxy $C_{1-6}$ alkyl group" is used herein to mean a $C_{1-6}$ alkyloxy $C_{1-6}$ alkyl group, such as methoxymethyl and 1-ethoxyethyl groups.

The term "ar-$C_{1-6}$ alkoxy $C_{1-6}$ alkyl group" is used herein to mean an ar-$C_{1-6}$ alkyloxy $C_{1-6}$ alkyl group, such as benzyloxymethyl and phenethyloxymethyl groups.

The term "$C_{2-12}$ alkanoyl group" is used herein to mean a linear or branched $C_{2-12}$ alkanoyl group, such as acetyl, propionyl, valeryl, isovaleryl and pivaloyl groups.

The term "aroyl group" is used herein to mean a benzoyl or naphthoyl group.

The term "heterocyclic carbonyl group" is used herein to mean a nicotinoyl, thenoyl, pyrrolidinocarbonyl or furoyl group.

The term "(α-substituted) amino acetyl group" is used herein to mean an (α-substituted) amino acetyl group having an optionally protected N-terminus, which is derived from amino acids (wherein the amino acids include glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline and hydroxyproline).

The term "acyl group" is used herein to mean a formyl group, a succinyl group, a glutaryl group, a maleoyl group, a phthaloyl group, a $C_{2-12}$ alkanoyl group, an aroyl group, a heterocyclic carbonyl group or an (α-substituted) amino acetyl group.

The term "acyl $C_{1-6}$ alkyl group" is used herein to mean an acyl $C_{1-6}$ alkyl group, such as acetylmethyl, benzoylmethyl and 1-benzoylethyl groups.

The term "$C_{2-6}$ alkanoyloxy group" is used herein to mean a linear or branched $C_{2-6}$ alkanoyloxy group, such as acetyloxy and propionyloxy groups.

The term "aroyloxy group" is used herein to mean a benzoyloxy or naphthoyloxy group.

The term "acyloxy group" is used herein to mean a $C_{2-6}$ alkanoyloxy group or aroyloxy group.

The term "acyloxy $C_{1-6}$ alkyl group" is used herein to mean an acyloxy $C_{1-6}$ alkyl group, such as acetoxymethyl, propionyloxymethyl, pivaloyloxymethyl, benzoyloxymethyl and 1-(benzoyloxy)ethyl groups.

The term "$C_{1-6}$ alkoxycarbonyl group" (wherein $C_{1-6}$ means the number of carbon atoms contained in the alkoxy group) is used herein to mean a linear or branched $C_{1-6}$ alkyloxycarbonyl group, such as methoxycarbonyl, ethoxycarbonyl, isopropoxycarbonyl, tert-butoxycarbonyl and 1,1-dimethylpropoxycarbonyl groups.

The term "ar-$C_{1-6}$ alkoxycarbonyl group" (wherein $C_{1-6}$ means the number of carbon atoms contained in the alkoxy group) is used herein to mean an ar-$C_{1-6}$ alkyloxycarbonyl group, such as benzyloxycarbonyl and phenethyloxycarbonyl groups.

The term "aryloxycarbonyl group" is used herein to mean a phenyloxycarbonyl or naphthyloxycarbonyl group.

The term "$C_{1-6}$ alkylsulfonyl group" is used herein to mean a $C_{1-6}$ alkylsulfonyl group, such as methylsulfonyl, ethylsulfonyl and propylsulfonyl groups.

The term "arylsulfonyl group" is used herein to mean a benzenesulfonyl, p-toluenesulfonyl or naphthalenesulfonyl group.

The term "silyl group" is used herein to mean a trimethylsilyl, triethylsilyl or tributylsilyl group.

The term "monocyclic nitrogen-containing heterocyclic group" is used herein to mean a monocyclic nitrogen-containing heterocyclic group containing only a nitrogen atom as a heteroatom that forms the ring, such as azetidinyl, pyrrolidinyl, pyrrolinyl, pyrrolyl, piperidyl, tetrahydropyridyl, pyridyl, homopiperidinyl, octahydroazocinyl, imidazolidinyl, imidazolinyl, imidazolyl, pyrazolidinyl, pyrazolinyl, pyrazolyl, piperazinyl, pyrazinyl, pyridazinyl, pyrimidinyl, homopiperazinyl, triazolyl and tetrazolyl groups.

The term "monocyclic oxygen-containing heterocyclic group" is used herein to mean a tetrahydrofuranyl, furanyl, tetrahydropyranyl or pyranyl group.

The term "monocyclic sulfur-containing heterocyclic group" is used herein to mean a thienyl group.

The term "monocyclic nitrogen/oxygen-containing heterocyclic group" is used herein to mean a monocyclic nitrogen/oxygen-containing heterocyclic group containing only a nitrogen atom and an oxygen atom as heteroatoms forming the ring, such as oxazolyl, isoxazolyl, oxadiazolyl and morpholinyl groups.

The term "monocyclic nitrogen/sulfur-containing heterocyclic group" is used herein to mean a monocyclic nitrogen/sulfur-containing heterocyclic group containing only a nitrogen atom and a sulfur atom as heteroatoms forming the ring, such as thiazolyl, isothiazolyl, thiadiazolyl, thiomorpholinyl, 1-oxide-thiomorpholinyl and 1,1-dioxide-thiomorpholinyl groups.

The term "monocyclic heterocyclic group" is used herein to mean a monocyclic nitrogen-containing heterocyclic group, a monocyclic oxygen-containing heterocyclic group, a monocyclic sulfur-containing heterocyclic group, a monocyclic nitrogen/oxygen-containing heterocyclic group or a monocyclic nitrogen/sulfur-containing heterocyclic group.

The term "bicyclic nitrogen-containing heterocyclic group" is used herein to mean a bicyclic nitrogen-containing heterocyclic group containing only a nitrogen atom as a heteroatom forming the ring, such as indolinyl, indolyl, isoindolinyl, isoindolyl, benzimidazolyl, indazolyl, benzotriazolyl, quinolyl, tetrahydroquinolinyl, quinolyl, tetrahydroisoquinolinyl, isoquinolinyl, quinolizinyl, cinnolinyl, phthalazinyl, quinazolinyl, dihydroquinoxalinyl, quinoxalinyl, naphthyridinyl, pyrrolopyridyl, imidazopyridyl, indolidinyl, dihydrocyclopentapyridyl, triazolopyridyl, pyrazolopyridyl, pyridopyrazyl, purinyl, pteridinyl and quinuclidinyl groups.

The term "bicyclic oxygen-containing heterocyclic group" is used herein to mean a bicyclic oxygen-containing heterocyclic group containing only an oxygen atom as a heteroatom forming the ring, such as 2,3-dihydrobenzofuranyl, benzofuranyl, isobenzofuranyl, chromanyl, chromenyl, isochromanyl, 1,3-benzodioxolyl, 1,3-benzodioxanyl and 1,4-benzodioxanyl groups.

The term "bicyclic sulfur-containing heterocyclic group" is used herein to mean a bicyclic sulfur-containing heterocyclic group containing only a sulfur atom as a heteroatom forming the ring, such as 2,3-dihydrobenzothienyl and benzothienyl groups.

The term "bicyclic nitrogen/oxygen-containing heterocyclic group" is used herein to mean a bicyclic nitrogen/oxygen-containing heterocyclic group containing only a nitrogen atom and an oxygen atom as heteroatoms forming the ring, such as benzoxazolyl, benzoisoxazolyl, benzoxadiazolyl, benzomorpholinyl, dihydropyranopyridyl, dihydrodioxinopyridyl, 1,3-dioxolopyridyl and dihydropyridooxazinyl groups.

The term "bicyclic nitrogen/sulfur-containing heterocyclic group" is used herein to mean a bicyclic nitrogen/sulfur-containing heterocyclic group containing a nitrogen atom and a sulfur atom as heteroatoms forming the ring, such as benzothiazolyl, benzoisothiazolyl, benzothiadiazolyl and thiazolopyridyl groups.

The term "bicyclic heterocyclic group" is used herein to mean a bicyclic nitrogen-containing heterocyclic group, a bicyclic oxygen-containing heterocyclic group, a bicyclic sulfur-containing heterocyclic group, a bicyclic nitrogen/oxygen-containing heterocyclic group, or a bicyclic nitrogen/sulfur-containing heterocyclic group.

The term "heterocyclic group" is used herein to mean a monocyclic heterocyclic group or a bicyclic heterocyclic group.

The term "cyclic amino group" is used herein to mean a 4-, 5-, 6- or 7-membered ring, condensed ring, or bridged ring cyclic amino group, which contains one or more nitrogen atoms as heteroatoms forming the ring and which may further optionally contain one or more oxygen atoms or sulfur atoms, such as azetidinyl, pyrrolidinyl, piperidinyl, homopiperidinyl, imidazolidinyl, piperazinyl, homopiperazinyl, morpholinyl, thiomorpholinyl, tetrahydroquinolinyl, tetrahydroisoquinolinyl, benzomorpholinyl, dihydropyridooxazinyl and quinuclidinyl groups.

The amino-protecting group includes all groups that can be used as ordinary protecting groups for amino groups. Examples of such an amino-protecting group include groups described in W. Greene et al., Protective Groups in Organic Synthesis, 4th edition, pp. 696 to 926, 2007, John Wiley & Sons, INC. Specific examples include an ar-$C_{1-6}$ alkyl group, a $C_{1-6}$ alkoxy $C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group, and a silyl group.

The hydroxyl-protecting group includes all groups that can be used as ordinary protecting groups for hydroxyl groups. Examples of such a hydroxyl-protecting group include groups described in W. Greene et al., Protective Groups in Organic Synthesis, 4th edition, pp. 16 to 299, 2007, John Wiley & Sons, INC. Specific examples include a $C_{1-6}$ alkyl group, a $C_{2-6}$ alkenyl group, an ar-$C_{1-6}$ alkyl group, a $C_{1-6}$ alkoxy $C_{1-6}$ alkyl group, an ar-$C_{1-6}$ alkoxy $C_{1-6}$ alkyl group, acyl group, a $C_{1-6}$ alkoxycarbonyl group, an ar-$C_{1-6}$ alkoxycarbonyl group, a $C_{1-6}$ alkylsulfonyl group, an arylsulfonyl group, a silyl group, a tetrahydrofuranyl group, and a tetrahydropyranyl group.

The carboxyl-protecting group includes all groups that can be used as ordinary protecting groups for carboxyl groups. Examples of such a carboxyl-protecting group include groups described in W. Greene et al., Protective Groups in Organic Synthesis, 4th edition, pp. 533 to 643, 2007, John Wiley & Sons, INC. Specific examples include a $C_{1-6}$ alkyl group, a $C_{2-6}$ alkenyl group, an aryl group, an ar-$C_{1-6}$ alkyl group, a $C_{1-6}$ alkoxy $C_{1-6}$ alkyl group, an ar-$C_{1-6}$ alkoxy $C_{1-6}$ alkyl group, an acyl $C_{1-6}$ alkyl group, an acyloxy $C_{1-6}$ alkyl group, and a silyl group.

Examples of a leaving group include a halogen atom, a $C_{1-6}$ alkylsulfonyloxy group, and an arylsulfonyloxy group.

Aliphatic hydrocarbons include pentane, hexane, and cyclohexane.

Halogenated hydrocarbons include methylene chloride, chloroform, and dichloroethane.

Alcohols include methanol, ethanol, propanol, 2-propanol, butanol, and 2-methyl-2-propanol.

Glycols include ethylene glycol, propylene glycol, and diethylene glycol.

Ethers include diethyl ether, diisopropyl ether, dioxane, tetrahydrofuran, anisole, ethylene glycol dimethyl ether, diethylene glycol dimethyl ether, and diethylene glycol diethyl ether.

Ketones include acetone, 2-butanone, and 4-methyl-2-pentanone.

Esters include methyl acetate, ethyl acetate, propyl acetate, and butyl acetate.

Amides include N,N-dimethylformamide, N,N-dimethylacetamide, and 1-methyl-2-pyrrolidone.

Nitriles include acetonitrile and propionitrile.

Sulfoxides include dimethyl sulfoxide.

Aromatic hydrocarbons include benzene, toluene, and xylene.

Salts of the compound represented by the formula [1] include generally known salts, namely, the salts of basic groups such as amino groups, and the salts of acidic groups such as hydroxyl or carboxyl groups.

Examples of the salts of basic groups include: salts with mineral acids such as hydrochloric acid, hydrobromic acid, nitric acid, and sulfuric acid; salts with organic carboxylic acids such as formic acid, acetic acid, citric acid, oxalic acid, fumaric acid, maleic acid, succinic acid, malic acid, tartaric acid, aspartic acid, trichloroacetic acid, and trifluoroacetic acid; and salts with sulfonic acids such as methanesulfonic acid, benzenesulfonic acid, p-toluenesulfonic acid, mesitylenesulfonic acid, and naphthalenesulfonic acid.

Examples of the salts of acidic groups include: salts with alkaline metals such as sodium and potassium; salts with alkaline earth metals such as calcium and magnesium; ammonium salts; and salts with nitrogen-containing organic bases such as trimethylamine, triethylamine, tributylamine, pyridine, N,N-dimethyl aniline, N-methyl piperidine, N-methyl morpholine, diethylamine, dicyclohexylamine, procaine, dibenzylamine, N-benzyl-β-phenethylamine, 1-ephenamine, and N,N'-dibenzylethylenediamine.

Among the above-described salts, pharmaceutically acceptable salts are preferable.

The nicotinamide derivative of the present invention is characterized in that it is represented by the following formula (I):

[Formula 2]

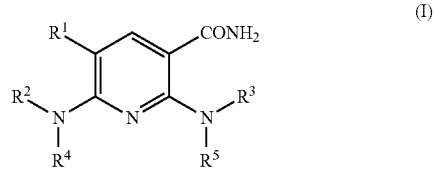

$R^1$ is a halogen atom. $R^1$ is preferably a fluorine atom, a chlorine atom, or a bromine atom, more preferably a fluorine atom or a chlorine atom, and most preferably a fluorine atom.

$R^2$ is a $C_{1-12}$ alkyl, $C_{2-12}$ alkenyl, $C_{2-12}$ alkynyl, $C_{3-8}$ cycloalkyl, aryl, ar-$C_{1-6}$ alkyl or heterocyclic group, each optionally having at least one substituent.

$R^2$ is preferably a $C_{1-12}$ alkyl, $C_{2-12}$ alkenyl, $C_{2-12}$ alkynyl, $C_{3-8}$ cycloalkyl, aryl, ar-$C_{1-6}$ alkyl or heterocyclic group, each optionally having at least one substituent selected from the following substituent group $\alpha_{1-1}$.

The substituent group $\alpha_{1-1}$ consists of a halogen atom; a cyano group; a nitro group; an oxo group; an optionally protected carboxyl group; an optionally protected hydroxyl group; an optionally protected amino group; a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent; and a group represented by the formula -$Q^1$-$Q^2$-$NR^6R^7$ (wherein $R^6$ and $R^7$ each independently represent a hydrogen atom; an amino-protecting group; a $C_{1-6}$ alkyl, $C_{2-6}$ alkenyl, $C_{2-6}$ alkynyl, $C_{3-8}$ cycloalkyl, $C_{1-6}$ alkoxy, aryl or heterocyclic group, each optionally having at least one substituent; or $R^6$ and $R^7$ may form a cyclic amino group optionally having at least one substituent, together with the nitrogen atom to which they bind; $Q^1$ represents —NH—; a $C_{1-6}$ alkylene, $C_{2-6}$ alkenylene or $C_{2-6}$ alkynylene group, each optionally having at least one substituent; or a bond; $Q^2$ represents a group represented by —C(=$X^7$)— (wherein $X^7$ represents an oxygen atom, a sulfur atom, or a group represented by =$NR^{29}$ (wherein $R^{29}$ represents a hydrogen atom, or a $C_{1-12}$ alkyl, $C_{2-12}$ alkenyl, $C_{2-12}$ alkynyl, $C_{3-8}$ cycloalkyl or $C_{1-6}$ alkoxy group, each optionally having at least one substituent)), a $C_{1-6}$ alkylene group, or a bond).

With regard to $R^6$ and $R^7$, the substituent optionally possessed by the $C_{1-6}$ alkyl, $C_{2-6}$ alkenyl, $C_{2-6}$ alkynyl, $C_{3-8}$ cycloalkyl, $C_{1-6}$ alkoxy, aryl or heterocyclic group is not particularly limited. A preferred example is a halogen atom, and among others, a fluorine atom is preferable.

When $R^6$ and $R^7$ may form a cyclic amino group together with the nitrogen atom to which they bind, the substituent optionally possessed by the cyclic amino group is not particularly limited. A preferred example is a halogen atom, and among others, a fluorine atom is preferable.

With regard to $Q^1$, the substituent that binds to the $C_{1-6}$ alkylene, $C_{2-6}$ alkenylene or $C_{2-6}$ alkynylene group is not particularly limited. A preferred example is a halogen atom, and among others, a fluorine atom is preferable.

With regard to $R^{29}$, the substituent optionally possessed by the $C_{1-12}$ alkyl, $C_{2-12}$ alkenyl, $C_{2-12}$ alkynyl, $C_{3-8}$ cycloalkyl or $C_{1-6}$ alkoxy group is not particularly limited. A preferred example is a halogen atom, and among others, a fluorine atom is preferable.

Moreover, $R^2$ is more preferably a $C_{1-12}$ alkyl, $C_{2-12}$ alkenyl, $C_{2-12}$ alkynyl, $C_{3-8}$ cycloalkyl, aryl, ar-$C_{1-6}$ alkyl or heterocyclic group, each optionally having at least one substituent selected from a substituent group $\alpha_{1-2}$.

The substituent group $\alpha_{1-2}$ consists of a halogen atom; a cyano group; a nitro group; an oxo group; an optionally protected carboxyl group; an optionally protected hydroxyl group; an optionally protected amino group; a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent selected from a substituent group $\beta_{1-1}$; and the formula -$Q^1$-$Q^2$-$NR^6R^7$ (wherein $Q^1$, $Q^2$, $R^6$ and $R^7$ have the same definitions as those described above)

The substituent group $\beta_{1-1}$ consists of a halogen atom; a cyano group; a nitro group; an oxo group; an optionally protected carboxyl group; an optionally protected hydroxyl group; an optionally protected amino group; and a $C_{1-6}$ alkyl, $C_{3-8}$ cycloalkyl, $C_{1-6}$ alkoxy, aryl or heterocyclic group, each optionally having at least one halogen atom.

Furthermore, $R^2$ is further preferably a $C_{1-12}$ alkyl, $C_{2-12}$ alkenyl, $C_{2-12}$ alkynyl, $C_{3-8}$ cycloalkyl, aryl, ar-$C_{1-6}$ alkyl or heterocyclic group, each optionally having at least one substituent selected from a substituent group $\alpha_{1-3}$.

The substituent group $\alpha_{1-3}$ consists of a cyano group; an oxo group; an optionally protected hydroxyl group; an optionally protected amino group; an aryl, $C_{1-6}$ alkoxy or heterocyclic group, each optionally having at least one substituent selected from a substituent group $\beta_{1-2}$; and the formula -$Q^1$-$Q^2$-$NR^6R^7$ (wherein $Q^1$, $Q^2$, $R^6$ and $R^7$ have the same definitions as those described above), wherein the substituent group $\beta_{1-2}$ consists of a halogen atom and an optionally protected amino group.

Still further, $R^2$ is further preferably a $C_{1-12}$ alkyl or $C_{3-8}$ cycloalkyl group, each optionally having, as a substituent, an optionally protected amino group or a heterocyclic group having at least one substituent, and is still further preferably a $C_{1-12}$ alkyl or $C_{3-8}$ cycloalkyl group having an amino group as a substituent.

A preferred example of $R^2$ is a substituent represented by any one of the following formulae (II) to (V) and (VII). $R^2$ is preferably a substituent represented by the formula (II), (III) or (VII), and is more preferably a substituent represented by the formula (II) or (III):

[Formula 3]

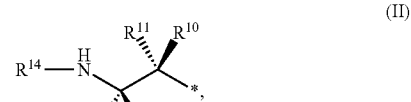
(II)

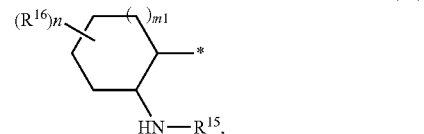
(III)

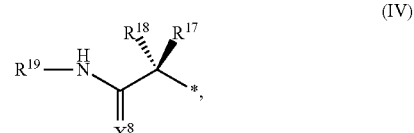
(IV)

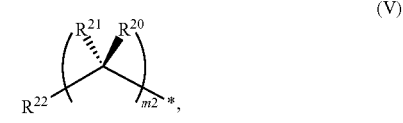
(V)

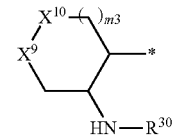
(VII)

wherein $R^{10}$, $R^{11}$, $R^{12}$, $R^{13}$, $R^{16}$, $R^{17}$, $R^{18}$, $R^{20}$ and $R^{21}$ each independently represent a hydrogen atom, or a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent, $R^{14}$, $R^{15}$, $R^{19}$ and $R^{30}$ each independently represent a hydrogen atom, or a $C_{1-12}$ alkyl or acyl group, each optionally having at least one substituent, $X^8$ represents an oxygen atom, a sulfur atom or =$NR^{23}$ (wherein $R^{23}$ represents a hydrogen atom, or a $C_{1-12}$ alkyl, $C_{2-12}$ alkenyl, $C_{2-12}$ alkynyl, $C_{3-8}$ cycloalkyl or $C_{1-6}$ alkoxy group, each optionally having at least one substituent), $R^{22}$ represents a heterocyclic group optionally having at least one substituent, $X^9$ and $X^{10}$ each independently represent an oxygen atom, —$NR^{31}$— (wherein $R^{31}$ represents a hydrogen atom, or a $C_{1-12}$ alkyl, $C_{2-12}$ alkenyl, $C_{2-12}$ alkynyl, $C_{3-8}$ cycloalkyl, $C_{1-6}$ alkoxy, acyl, $C_{1-6}$ alkoxycarbonyl, aryloxycarbonyl or heterocyclic oxycarbonyl group, each optionally having at least one substituent), or a methylene group (wherein either one of $X^9$ and $X^{10}$ represents a methylene group, and when m3 is 0, $X^{10}$ represents a methylene group), m1 and m3 each independently represents an integer from 0 to 2, m2 represents an integer of 1 or 2, wherein $R^{20}$ and $R^{21}$ may be different from each other when m2 is 2, n represents an integer from 0 to 4, $R^{16}$s may be different from one another when n is 2 to 4, and wherein $R^{10}$ and $R^{11}$, $R^{12}$ and $R^{13}$, $R^{17}$ and $R^{18}$, and $R^{20}$ and $R^{21}$ may each together form a $C_{3-8}$ cycloalkyl or heterocyclic group, each optionally having at least one substituent.

It is preferable that $R^{10}$, $R^{11}$, $R^{12}$, $R^{13}$, $R^{16}$, $R^{17}$, $R^{18}$, $R^{20}$ and $R^{21}$ each independently represent a hydrogen atom, or a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent selected from the following substituent group $\gamma_{1-1}$.

The substituent group $\gamma_{1-1}$ consists of a halogen atom; a cyano group; a nitro group; an oxo group; an optionally protected carboxyl group; an optionally protected hydroxyl group; an optionally protected amino group; a $C_{1-6}$ alkyl, $C_{3-8}$ cycloalkyl or heterocyclic group optionally having at least one substituent; and the formula -$Q^5$-$Q^6$-$NR^{27}R^{28}$ (wherein $R^{27}$ and $R^{28}$ each independently represent a hydrogen atom; an amino-protecting group; or a $C_{1-6}$ alkyl, $C_{2-6}$ alkenyl, $C_{2-6}$ alkynyl, $C_{3-8}$ cycloalkyl, $C_{1-6}$ alkoxy, aryl or heterocyclic group, each optionally having at least one substituent; $Q^5$ represents —NH—; a $C_{1-6}$ alkylene, $C_{2-6}$ alkenylene or $C_{2-6}$ alkynylene group, each optionally having at least one substituent; or a bond; and $Q^6$ represents —C(=O)—, a $C_{1-6}$ alkylene group or a bond).

With regard to $R^{27}$ and $R^{28}$, the substituent optionally possessed by the $C_{1-6}$ alkyl, $C_{2-6}$ alkenyl, $C_{2-6}$ alkynyl, $C_{3-8}$ cycloalkyl, $C_{1-6}$ alkoxy, aryl or heterocyclic group is not particularly limited. A preferred example is a halogen atom, and among others, a fluorine atom is preferable.

With regard to $Q^5$, the substituent optionally possessed by the $C_{1-6}$ alkylene, $C_{2-6}$ alkenylene or $C_{2-6}$ alkynylene group is not particularly limited. A preferred example is a halogen atom, and among others, a fluorine atom is preferable.

With regard to the substituent represented by the above-described formula (II), it is preferable that $R^{10}$, $R^{12}$ and $R^{13}$ each independently represent a hydrogen atom, or a $C_{1-6}$ alkyl, $C_{1-6}$ alkoxy, aryl or heterocyclic group, each optionally having at least one substituent selected from the above-described substituent $\gamma_{1-1}$.

$R^{10}$ and $R^{11}$, and $R^{12}$ and $R^{13}$ may each together form a $C_{3-8}$ cycloalkyl or heterocyclic group optionally having a substituent. Preferably, they may form a $C_{5-7}$ cycloalkyl, monocyclic oxygen-containing heterocyclic group, or bicyclic oxygen-containing heterocyclic group optionally having a substituent.

It is preferable that $R^{10}$ and $R^{11}$ each independently represent a hydrogen atom, or a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent selected from the above-described substituent $\gamma_{1-1}$. It is more preferable that $R^{10}$ and $R^{11}$ each independently represent a hydrogen atom, or a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent selected from the following substituent group $\gamma_{1-2}$. It is further preferable that $R^{10}$ and $R^{11}$ each independently represent a hydrogen atom, or a $C_{1-6}$ alkyl, $C_{3-8}$ cycloalkyl, aryl or heterocyclic group, each optionally having at least one substituent selected from the following substituent group $\gamma_{1-2}$ Preferred examples of the heterocyclic group used herein include imidazolyl, pyridyl, thienyl, triazolyl, furanyl and pyrazolyl groups. Of these, an imidazolyl, pyridyl or thienyl group is preferable. Moreover, as an aryl group, a phenyl group is preferable.

The substituent group $\gamma_{1-2}$ consists of a halogen atom, and a $C_{1-6}$ alkyl, $C_{3-8}$ cycloalkyl, aryl or heterocyclic group, optionally having at least one substituent.

Preferred examples of the heterocyclic group used herein include imidazolyl, pyridyl, thienyl, triazolyl, furanyl and pyrazolyl groups. Moreover, as an aryl group, a phenyl group is preferable. The substituent optionally possessed by the $C_{1-6}$ alkyl, $C_{3-8}$ cycloalkyl, aryl or heterocyclic group is not particularly limited. A preferred example is a halogen atom, and among others, a fluorine atom is preferable.

With regard to $R^{10}$ and $R^{11}$, either one of $R^{10}$ and $R^{11}$, and preferably $R^{11}$ is a hydrogen atom, and the other one, and preferably $R^{10}$ is preferably a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, optionally having at least one substituent selected from the above-described substituent group $\gamma_{1-1}$, and is more preferably a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, optionally having at least one substituent selected from the above-described substituent group 71-2. Preferred examples of the heterocyclic group used herein include imidazolyl, pyridyl, thienyl, triazolyl, furanyl and pyrazolyl groups.

$R^{12}$ and $R^{13}$ each independently represent, preferably a hydrogen atom, or a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent selected from the above-described substituent group $\gamma_{1-1}$, more preferably a hydrogen atom, or a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent selected from the above-described substituent group $\gamma_{1-2}$, and further preferably a hydrogen atom, or a $C_{1-6}$ alkyl or $C_{3-8}$ cycloalkyl group, each optionally having at least one substituent selected from the above-described substituent group $\gamma_{1-2}$.

$R^{14}$ represents a hydrogen atom, or a $C_{1-12}$ alkyl or acyl group, each optionally having at least one substituent, preferably a hydrogen atom, or a $C_{1-6}$ alkyl or acyl group, and more preferably a hydrogen atom.

The substituent represented by the above-described formula (II) is preferably a substituent represented by the following formula (II-1), more preferably a substituent represented by the following formula (II-2), and further preferably a substituent represented by the following formula (II-3):

[Formula 4]

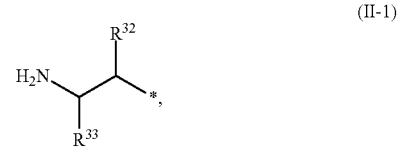

(II-1)

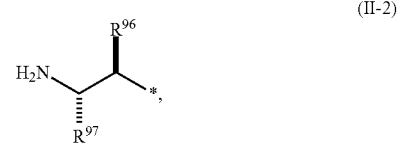

(II-2)

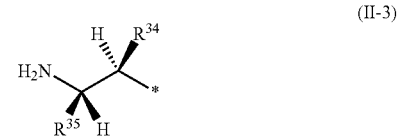

(II-3)

wherein $R^{32}$, $R^{33}$, $R^{96}$, $R^{97}$, $R^{34}$ and $R^{35}$ each independently represent a hydrogen atom, or a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent selected from the above-described substituent group $\gamma_{1-2}$.

$R^{32}$, $R^{96}$ and $R^{34}$ each independently represent, preferably a hydrogen atom, or a $C_{1-6}$ alkyl, $C_{3-8}$ cycloalkyl, aryl or heterocyclic group, each optionally having at least one substituent selected from the substituent group $\gamma_{1-2}$, and more preferably an alkyl group; an alkyl group substituted with a cycloalkyl group; a cycloalkyl group; or a cycloalkyl group substituted with an alkyl group, each containing 3 to 5 carbon atoms in total, or an alkoxyalkyl group containing 2 to 4 carbon atoms in total. By applying the present substituent, toxicity can be reduced.

Preferred examples of the alkyl group, the alkyl group substituted with a cycloalkyl group, the cycloalkyl group, or the cycloalkyl group substituted with an alkyl group, each containing 3 to 5 carbon atoms in total, include linear or branched pentyl, n-butyl, i-butyl, t-butyl, n-propyl, i-propyl, cyclopropyl, cyclopropylmethyl and cyclopropylethyl groups. Of these, n-butyl, i-butyl, n-propyl and cyclopropyl groups are preferable.

Preferred examples of the alkoxyalkyl group containing 2 to 4 carbon atoms in total include methoxymethyl, methoxyethyl, ethoxymethyl and ethoxyethyl groups.

$R^{32}$, $R^{96}$ and $R^{34}$ are preferably a methyl group or ethyl group substituted with a heterocyclic group, and more preferably a methyl group substituted with a heterocyclic group. Preferred examples of the heterocyclic group used herein include imidazolyl, pyridyl, thienyl, triazolyl, furanyl and pyrazolyl groups. By applying the present substituent, toxicity can be further reduced.

$R^{33}$, $R^{97}$ and $R^{35}$ each independently represent, preferably a hydrogen atom, or a $C_{1-6}$ alkyl or $C_{3-8}$ cycloalkyl group, more preferably a hydrogen atom, or a $C_{1-6}$ alkyl group, and further preferably a $C_{1-3}$ alkyl group. Preferred examples include a methyl group and an ethyl group.

The total number of carbon atoms contained in $R^{32}$ and $R^{33}$, the total number of carbon atoms contained in $R^{96}$ and $R^{97}$, and the total number of carbon atoms contained in $R^{34}$ and $R^{35}$ are each preferably from 4 to 6. By applying the present substituent, toxicity can be further reduced.

The substituent represented by the above-described formula (III) is preferably a substituent represented by any one of the following formulae (III-1) to (III-3):

[Formula 5]

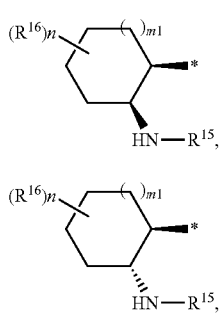

(III-1)

(III-2)

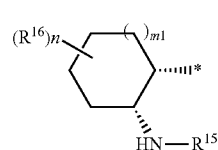

(III-3)

wherein $R^{15}$, $R^{16}$, m1 and n have the same definitions as those described above.

Preferred formulae are (III-1) and (III-2), and a more preferred formula is (III-1).

In the above-described formula (III) and the above-described formulae (III-1) to (III-3), $R^{16}$ represents, preferably a hydrogen atom, or a $C_{1-6}$ alkyl, $C_{1-6}$ alkoxy, aryl or heterocyclic group, each optionally having at least one substituent selected from the above-described substituent group $\gamma_{1-1}$, more preferably a hydrogen atom, or a $C_{1-6}$ alkyl, $C_{1-6}$ alkoxy or aryl group, each optionally having at least one substituent selected from the above-described substituent group $\gamma_{1-1}$, and further preferably a hydrogen atom, or a $C_{1-6}$ alkyl, $C_{1-6}$ alkoxy or aryl group.

m1 is an integer from 0 to 2, and is preferably 1.

n is an integer from 0 to 4, and $R^{16}$s may be different from one another when n is 2 to 4. n is preferably an integer from 0 to 2, and more preferably 0.

$R^{15}$ represents a hydrogen atom, or a $C_{1-12}$ alkyl or acyl group, each optionally having at least one substituent, preferably a hydrogen atom, or a $C_{1-6}$ alkyl or acyl group, and more preferably a hydrogen atom.

When $R^2$ is a substituent represented by the above-described formula (III), it is preferably the following formula (III-4), more preferably the following formula (III-5), and further preferably the following formula (III-6).

[Formula 6]

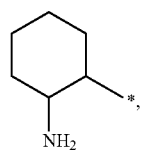

(III-4)

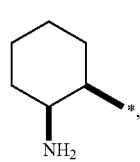

(III-5)

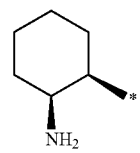

(III-6)

With regard to the substituent represented by the above-described formula (IV), $R^{17}$ and $R^{18}$ each independently represent, preferably a hydrogen atom, or a $C_{1-6}$ alkyl, $C_{1-6}$ alkoxy, aryl or heterocyclic group, each optionally having at least one substituent selected from the above-described substituent group $\gamma_{1-1}$, more preferably a hydrogen atom, or a $C_{1-6}$ alkyl, $C_{1-6}$ alkoxy or aryl group, each optionally having at least one substituent selected from the above-described substituent group γ$_{1-1}$, and further preferably a hydrogen atom, or a C$_{1-6}$ alkyl, C$_{1-6}$ alkoxy or aryl group.

R$^{17}$ and R$^{18}$ may together form a C$_{3-8}$ cycloalkyl or heterocyclic group optionally having a substituent. Among others, a C$_{5-7}$ cycloalkyl or oxygen-containing heterocyclic group optionally having a substituent is preferable.

R$^{17}$ is preferably a hydrogen atom. In addition, R$^{18}$ is preferably a C$_{1-6}$ alkyl, C$_{1-6}$ alkoxy, aryl or heterocyclic group, each optionally having at least one substituent selected from the above-described substituent group γ$_{1-1}$, more preferably a C$_{1-6}$ alkyl, C$_{1-6}$ alkoxy or aryl group, each optionally having at least one substituent selected from the above-described substituent group γ$_{1-1}$, and further preferably a C$_{1-6}$ alkyl, C$_{1-6}$ alkoxy or aryl group.

R$^{19}$ is a hydrogen atom, or a C$_{1-12}$ alkyl or acyl group each optionally having at least one substituent, preferably a hydrogen atom, a C$_{1-12}$ alkyl or acyl group, and more preferably a hydrogen atom.

With regard to the substituent represented by the above-described formula (V), R$^{20}$ and R$^{21}$ each independently represent, preferably a hydrogen atom, or a C$_{1-6}$ alkyl, C$_{1-6}$ alkoxy, aryl or heterocyclic group, each optionally having at least one substituent selected from the above-described substituent group γ$_{1-1}$, more preferably a hydrogen atom, or a C$_{1-6}$ alkyl, C$_{1-6}$ alkoxy or aryl group, each optionally having at least one substituent selected from the above-described substituent group γ$_{1-1}$, and further preferably a hydrogen atom, or a C$_{1-6}$ alkyl group, C$_{1-6}$ alkoxy group or aryl group.

R$^{20}$ and R$^{21}$ may together form a C$_{3-8}$ cycloalkyl or heterocyclic group optionally having a substituent. Among others, a C$_{5-7}$ cycloalkyl or oxygen-containing heterocyclic group optionally having a substituent is preferable.

R$^{22}$ is a heterocyclic group optionally having a substituent.

m2 is an integer of 1 or 2. R$^{20}$ and R$^{21}$ may be different from each other when m2 is 2. m2 is preferably 1.

R$^4$ and R$^5$ each independently represent a hydrogen atom, or a C$_{1-12}$ alkyl, C$_{2-12}$ alkenyl or C$_{2-12}$ alkynyl group, each optionally having at least one substituent. R$^4$ and R$^5$ represent, preferably a hydrogen atom, or a C$_{1-6}$ alkyl, C$_{2-6}$ alkenyl or C$_{2-6}$ alkynyl group, more preferably a hydrogen atom, or a C$_{1-6}$ alkyl group, and further preferably a hydrogen atom.

With regard to the substituent represented by the above-described formula (VII), m3 is an integer from 0 to 2, and is preferably 1.

R$^{30}$ represents a hydrogen atom, or a C$_{1-12}$ alkyl or acyl group each optionally having at least one substituent, preferably a hydrogen atom, a C$_{1-6}$ alkyl or acyl group, and more preferably a hydrogen atom.

X$^9$ and X$^{10}$ each independently represent an oxygen atom, —NR$^{31}$— (wherein R$^{31}$ represents a hydrogen atom, or a C$_{1-12}$ alkyl, C$_{2-12}$ alkenyl, C$_{2-12}$ alkynyl, C$_{3-8}$ cycloalkyl, C$_{1-6}$ alkoxy, acyl or C$_{1-6}$ alkoxycarbonyl group, each optionally having at least one substituent), or a methylene group (wherein either one of X$^9$ and X$^{10}$ represents a methylene group, and when m3 is 0, X$^{10}$ represents a methylene group).

R$^{31}$ represents a hydrogen atom, or a C$_{1-12}$ alkyl, C$_{2-12}$ alkenyl, C$_{2-12}$ alkynyl, C$_{3-8}$ cycloalkyl, C$_{1-6}$ alkoxy, acyl, C$_{1-6}$ alkoxycarbonyl, aryloxycarbonyl or heterocyclic oxycarbonyl group, each optionally having at least one substituent, preferably a hydrogen atom, or a C$_{1-12}$ alkyl, C$_{3-8}$ cycloalkyl, C$_{1-6}$ alkoxy, acyl, C$_{1-6}$ alkoxycarbonyl, aryloxycarbonyl or heterocyclic oxycarbonyl group, each optionally having at least one substituent, more preferably a hydrogen atom, or a C$_{1-6}$ alkyl, C$_{3-6}$ cycloalkyl, C$_{1-6}$ alkoxy, acyl, C$_{1-6}$ alkoxycarbonyl, aryloxycarbonyl or heterocyclic oxycarbonyl group, each optionally having at least one substituent, and further preferably a hydrogen atom, or a C$_{1-6}$ alkyl, C$_{3-6}$ cycloalkyl, C$_{1-6}$ alkoxy, acyl, C$_{1-6}$ alkoxycarbonyl, aryloxycarbonyl or heterocyclic oxycarbonyl group.

The nicotinamide derivative of the present invention is preferably represented by the following formula (I-1).

[Formula 7]

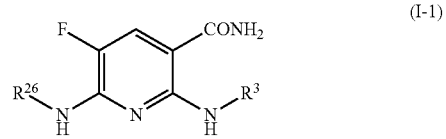

(I-1)

wherein R$^3$ represents the same substituent as that described above, and its preferred range is also the same as that described above. R$^{26}$ represents a substituent represented by any one of the above-described formulae (II) to (V) and (VII), and its preferred range is also the same as that described above.

In the above-described formula (I) and (I-1), R$^3$ represents an aryl or heterocyclic group each optionally having at least one substituent.

R$^3$ preferably represents an aryl or heterocyclic group each optionally having at least one substituent selected from the substituent group α$_{2-1}$.

The substituent group α$_{2-1}$ consists of a halogen atom; a cyano group; a nitro group; an oxo group; an optionally protected carboxyl group; an optionally protected hydroxyl group; an optionally protected amino group; a C$_{1-6}$ alkyl, C$_{2-6}$ alkenyl, C$_{2-6}$ alkynyl, C$_{3-8}$ cycloalkyl, aryl, C$_{1-6}$ alkoxy, aryloxy, acyl, C$_{1-6}$ alkylsulfonyl, arylsulfonyl or heterocyclic group, each optionally having at least one substituent; and the formula -Q$^3$-Q$^4$-NR$^{24}$R$^{25}$ (wherein R$^{24}$ and R$^{25}$ each independently represent a hydrogen atom; an amino-protecting group; a C$_{1-6}$ alkyl, C$_{2-6}$ alkenyl, C$_{2-6}$ alkynyl, C$_{3-8}$ cycloalkyl, C$_{1-6}$ alkoxy, ar-C$_{1-6}$ alkyl, aryl or heterocyclic group, each optionally having at least one substituent; or R$^{24}$ and R$^{25}$ may form a cyclic amino group optionally having at least one substituent together with the nitrogen atom to which they bind; Q$^3$ represents —NH—; a C$_{1-6}$ alkylene, C$_{2-6}$ alkenylene or C$_{2-6}$ alkynylene group, each optionally having at least one substituent; or a bond; and Q$^4$ represents —C(=O)—, a C$_{1-6}$ alkylene group, or a bond).

With regard to R$^{24}$ and R$^{25}$, the substituent optionally possessed by the C$_{1-6}$ alkyl, C$_{2-6}$ alkenyl, C$_{2-6}$ alkynyl, C$_{3-8}$ cycloalkyl, C$_{1-6}$ alkoxy, ar-C$_{1-6}$ alkyl, aryl or heterocyclic group is not particularly limited. A preferred example is a halogen atom, and among others, a fluorine atom is preferable.

The substituent optionally possessed by the cyclic amino group that is formed by R$^{24}$ and R$^{25}$, together with the nitrogen atom to which they bind, is not particularly limited. A preferred example is a halogen atom, and among others, a fluorine atom is preferable.

With regard to Q$^3$, the substituent optionally possessed by the C$_{1-6}$ alkylene, C$_{2-6}$ alkenylene or C$_{2-6}$ alkynylene group is not particularly limited. A preferred example is a halogen atom, and among others, a fluorine atom is preferable.

Moreover, R$^3$ is more preferably an aryl or heterocyclic group, each optionally having at least one substituent selected from a substituent group α$_{2-2}$.

The substituent group α$_{2-2}$ consists of a halogen atom; a cyano group; a nitro group; an oxo group; an optionally protected carboxyl group; an optionally protected hydroxyl group; an optionally protected amino group; a C$_{1-6}$ alkyl, C$_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent selected from a substituent group $\beta_{2-1}$; and the formula -$Q^3$-$Q^4$-$NR^{24}R^{25}$ (wherein $Q^3$, $Q^4$, $R^{24}$ and $R^{25}$ have the same definitions as those described above).

The substituent group $\beta_{2-1}$ consists of a halogen atom; a cyano group; a nitro group; an oxo group; an optionally protected carboxyl group; an optionally protected hydroxyl group; an optionally protected amino group, and a $C_{1-6}$ alkyl, $C_{3-8}$ cycloalkyl, $C_{1-6}$ alkoxy, ar-$C_{1-6}$ alkyl, aryl or heterocyclic group, each optionally having at least one halogen atom.

Furthermore, $R^3$ is further preferably an aryl or heterocyclic group, each optionally having at least one substituent selected from a substituent group $\alpha_{2-3}$.

The substituent group $\alpha_{2-3}$ consists of a halogen atom; a cyano group; a nitro group; an oxo group; an optionally protected carboxyl group; an optionally protected amino group; a $C_{1-6}$ alkyl, $C_{3-8}$ cycloalkyl, aryl, $C_{1-6}$ alkoxy, aryloxy, acyl, $C_{1-6}$ alkylsulfonyl or heterocyclic group, each optionally having at least one substituent selected from a substituent group $\beta_{2-2}$; and the formula -$Q^3$-$Q^4$-$NR^{24}R^{25}$ (wherein $Q^3$, $Q^4$, $R^{24}$ and $R^{25}$ have the same definitions as those described above).

The substituent group $\beta_{2-2}$ consists of a halogen atom; an optionally protected hydroxyl group; and a $C_{1-6}$ alkyl, $C_{3-8}$ cycloalkyl, $C_{1-6}$ alkoxy, aryl or heterocyclic group, each optionally having at least one halogen atom.

$R^3$ represents an aryl or heterocyclic group optionally having at least one substituent. Preferred examples of the aryl or heterocyclic group include monocyclic and bicyclic groups.

Preferred examples of the aryl group include phenyl, naphthyl and indanyl groups. Among such aryl groups, a phenyl group is preferable.

Preferred examples of a monocyclic heterocyclic group include pyridyl, pyrimidinyl, pyridazinyl, thiazolyl and thienyl groups. As such monocyclic heterocyclic groups, pyridyl and pyridazinyl groups are preferable, and a pyridyl group is more preferable.

Preferred examples of a bicyclic heterocyclic group include quinolyl, isoquinolyl, quinoxalinyl, quinazolinyl, indazolyl, indolyl, indazolyl, imidazopyridyl, benzothiazolyl, benzoxazolyl, benzothiadiazolyl, benzimidazolyl, pyrrolopyridyl, pyrazolopyridyl, pyridopyrazyl, thiazolopyridyl, naphthyridinyl, 1,3-benzodioxolyl, 1,4-benzodioxanyl, isoindolinyl, tetrahydroisoquinolinyl, and dihydropyrido oxazinyl groups. As such bicyclic heterocyclic groups, quinolyl, isoquinolyl, quinoxalinyl, indolyl, pyrrolopyridyl, indazolyl and imidazopyridyl groups are preferable, quinoxalinyl and indazolyl group are more preferable, and an indazolyl group is further preferable.

$R^3$ represents an aryl or heterocyclic group optionally having at least one substituent. As such an aryl or heterocyclic group, phenyl, pyridyl, pyridazinyl, quinoxalinyl and indazolyl groups are preferable, pyridyl. As such an aryl or heterocyclic group, pyridyl, quinoxalinyl and indazolyl groups are more preferable, and pyridyl and indazolyl group are further preferable. By applying the present substituent, toxicity can be further reduced.

The monocyclic heterocyclic group is preferably a 5-membered ring or 6-membered ring group.

A preferred 6-membered ring is a pyridyl or pyrimidinyl group. Preferred examples of the pyridyl and pyrimidinyl group include a pyridin-5-yl group optionally having a substituent(s) at positions 2 and/or 3, a pyridin-4-yl group optionally having a substituent(s) at positions 2 and/or 6, a pyrimidin-4-yl group optionally having a substituent(s) at positions 2 and/or 6, and a pyrimidin-5-yl group optionally having a substituent at position 2.

$R^3$ is preferably a phenyl, pyridyl, pyridazinyl, quinoxalinyl or indazolyl group, each optionally having at least one substituent, is more preferably a phenyl, pyridyl, pyridazinyl, quinoxalinyl or indazolyl group, each optionally having at least one substituent selected from the substituent group $\alpha_{2-1}$, is further preferably a phenyl, pyridyl, pyridazinyl, quinoxalinyl or indazolyl group, each optionally having at least one substituent selected from the substituent group $\alpha_{2-2}$, and is still further preferably a phenyl, pyridyl, pyridazinyl, quinoxalinyl or indazolyl group, each optionally having at least one substituent selected from the substituent group $\alpha_{2-3}$.

When $R^3$ is a pyridyl group optionally having at least one substituent, the substituent optionally possessed by the pyridyl group is preferably selected from the substituent group $\alpha_{2-1}$, is more preferably selected from a substituent group $\alpha_{2-4}$, is further preferably selected from a substituent group $\alpha_{2-5}$, and is still further preferably selected from a substituent group $\alpha_{2-6}$.

The substituent group $\alpha_{2-4}$ consists of a halogen atom; a cyano group; a nitro group; an oxo group; an optionally protected carboxyl group; an optionally protected hydroxyl group; an optionally protected amino group; a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent selected from a substituent group $\beta_{2-3}$; and the formula -$Q^3$-$Q^4$-$NR^{24}R^{25}$ (wherein $Q^3$, $Q^4$, $R^{24}$ and $R^{25}$ have the same definitions as those described above).

The substituent group $\beta_{2-3}$ consists of a halogen atom; a cyano group; a nitro group; an oxo group; an optionally protected carboxyl group; an optionally protected hydroxyl group; an optionally protected amino group; and a $C_{1-6}$ alkyl, $C_{3-8}$ cycloalkyl, -$Q^5$m4-$R^{36}$ (wherein $Q^5$ represents a $C_{1-6}$ alkyleneoxy group (wherein the $R^{36}$ side is an alkylene group), $R^{36}$ represents a hydrogen atom, or a $C_{1-6}$ alkyl, $C_{3-8}$ cycloalkyl, aryl or heterocyclic group, and m4 represents an integer from 1 to 3, and $Q^5$s may be different from one another when m4 is 2 or 3), aryl or heterocyclic group, each optionally having at least one halogen atom.

The substituent group $\alpha_{2-5}$ consists of a halogen atom; a cyano group; a nitro group; an oxo group; an optionally protected carboxyl group; an optionally protected amino group; a $C_{1-6}$ alkyl, $C_{3-8}$ cycloalkyl, aryl, $C_{1-6}$ alkoxy, aryloxy, acyl, $C_{1-6}$ alkylsulfonyl or heterocyclic group, each optionally having at least one substituent selected from a substituent group $\beta_{2-4}$; and the formula -$Q^3$-$Q^4$-$NR^{24}R^{25}$ (wherein $Q^3$, $Q^4$, $R^{24}$ and $R^{25}$ have the same definitions as those described above).

The substituent group $\beta_{2-4}$ consists of a halogen atom; an optionally protected hydroxyl group; and a $C_{1-6}$ alkyl, $C_{3-8}$ cycloalkyl, -$Q^5$m4-$R^{36}$ (wherein $Q^5$, $R^{36}$, m4 have the same definitions as those described above), aryl or heterocyclic group, each optionally having at least one halogen atom.

The substituent group $\alpha_{2-6}$ consists of a halogen atom; and a $C_{1-6}$ alkyl, $C_{3-8}$ cycloalkyl, aryl, $C_{1-6}$ alkoxy or heterocyclic group, each optionally having at least one substituent selected from a substituent group $\beta_{2-5}$.

The substituent group $\beta_{2-5}$ consists of a halogen atom; and a $C_{1-6}$ alkyl, $C_{3-8}$ cycloalkyl, -$Q^5$m4-$R^{36}$ (wherein $Q^5$, $R^{36}$, m4 have the same definitions as those described above), aryl or heterocyclic group, each optionally having at least one halogen atom.

When $R^3$ is a pyridyl group optionally having at least one substituent, the pyridyl group is preferably represented by the following formula (VIII-1) or (VIII-2), and is more preferably represented by the following formula (VIII-1):

[Formula 8]

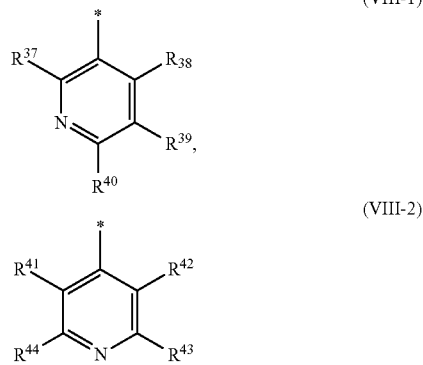

wherein $R^{37}$, $R^{38}$, $R^{39}$, $R^{40}$, $R^{41}$, $R^{42}$, $R^{43}$ and $R^{44}$ each independently represent a hydrogen atom, or a substituent selected from the above-described substituent group $\alpha_{2-6}$.

$R^{37}$ and $R^{38}$ each independently represent, preferably a hydrogen atom or a halogen atom, more preferably a hydrogen atom or a fluorine atom, and further preferably a hydrogen atom.

$R^{39}$ is more preferably a hydrogen atom; a halogen atom; or a $C_{1-6}$ alkyl, aryl, $C_{1-6}$ alkoxy or heterocyclic group, optionally having at least one substituent each independently selected from among a halogen atom, $C_{1-6}$ alkyl and $C_{3-8}$ cycloalkyl groups, and $-Q^5 m4-R^{36}$ (wherein $Q^5$, $R^{36}$, m4 have the same definitions as those described above), and is further preferably a halogen atom; or a $C_{1-6}$ alkyl, aryl, $C_{1-6}$ alkoxy or 5-membered ring heterocyclic group, optionally having at least one substituent each independently selected from among a halogen atom, $C_{1-6}$ alkyl, $C_{3-8}$ cycloalkyl and $-Q^5 m4-R^{36}$ (wherein $Q^5$, $R^{36}$, m4 have the same definitions as those described above).

Herein, preferred examples of the 5-membered ring heterocyclic group include pyrrolyl, pyrrolidinyl, pyrazolyl, oxazolyl, oxadiazolyl, imidazolyl, triazolyl and furanyl groups. Among these groups, triazolyl and furanyl groups are more preferable. This 5-membered ring heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, and is further preferably unsubstituted or substituted with a fluorine atom or a methyl group.

The aryl group is preferably a phenyl group.

The $C_{1-6}$ alkyl group is preferably a $C_{1-3}$ alkyl group, and more preferably a $C_{1-2}$ alkyl group.

The $C_{1-6}$ alkoxy group is preferably a $C_{1-3}$ alkoxy group, and more preferably a $C_{1-2}$ alkoxy group.

The halogen atom is preferably a fluorine atom or a chlorine atom, and more preferably a fluorine atom.

The $C_{3-8}$ cycloalkyl group is preferably a cyclopropyl group.

The $Q^5$ is preferably a $C_{1-3}$ alkyleneoxy group, and more preferably a $C_{1-2}$ alkyleneoxy group.

The $R^{36}$ is preferably a hydrogen atom, $C_{1-3}$ alkyl or cyclopropyl group, and more preferably a hydrogen atom, or a $C_{1-2}$ alkyl group.

The m4 is preferably an integer of 1 or 2.

$R^{40}$ is more preferably a hydrogen atom; a halogen atom; or a $C_{1-6}$ alkyl, aryl, $C_{1-6}$ alkoxy or heterocyclic group, optionally having at least one substituent each independently selected from among a halogen atom, $C_{1-6}$ alkyl, $C_{3-8}$ cycloalkyl and $-Q^5 m4-R^{36}$ (wherein $Q^5$, $R^{32}$, m3, $Q^6$ have the same definitions as those described above), and is further preferably a halogen atom; or a $C_{1-6}$ alkyl, aryl, $C_{1-6}$ alkoxy, or 5-membered ring or 6-membered ring heterocyclic group, optionally having at least one substituent each independently selected from among a halogen atom, $C_{1-6}$ alkyl, $C_{3-8}$ cycloalkyl and $-Q^5 m4-R^{36}$ (wherein $Q^5$, $R^{36}$, m4, $Q^6$ have the same definitions as those described above).

Herein, preferred examples of the 5-membered ring heterocyclic group include pyrrolyl, pyrrolidinyl, pyrazolyl, oxazolyl, oxadiazolyl, imidazolyl, triazolyl and furanyl groups. Among these groups, triazolyl and furanyl groups are more preferable. This 5-membered ring heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, and is further preferably unsubstituted or substituted with a fluorine atom or a methyl group.

A preferred example of the 6-membered ring heterocyclic group is a morpholinyl group. This 6-membered ring heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, is further preferably unsubstituted or substituted with a fluorine atom or a methyl group, and is still further preferably unsubstituted.

The aryl group is preferably a phenyl group.

The $C_{1-6}$ alkyl group is preferably a $C_{1-3}$ alkyl group, and more preferably a $C_{1-2}$, alkyl group.

The $C_{1-6}$ alkoxy group is preferably a $C_{1-3}$ alkoxy group, and more preferably a $C_{1-2}$ alkoxy group.

The halogen atom is preferably a fluorine atom or a chlorine atom, and more preferably a fluorine atom.

The $C_{3-8}$ cycloalkyl is preferably a cyclopropyl group.

The $Q^5$ is preferably a $C_{1-3}$ alkyleneoxy group, and more preferably a $C_{1-2}$ alkyleneoxy group.

The $R^{36}$ is preferably a hydrogen atom, a $C_{1-3}$ alkyl or cyclopropyl group, and more preferably a hydrogen atom or a $C_{1-2}$ alkyl group.

The m4 is preferably an integer of 1 or 2.

When $R^{39}$ is a 5-membered ring heterocyclic group optionally having at least one substituent selected from among a halogen atom, $C_{1-6}$ alkyl, $C_{3-8}$ cycloalkyl and $-Q^5 m4-R^{36}$ (wherein $Q^5$, $R^{36}$, m4 have the same definitions as those described above), $R^{40}$ is preferably a halogen atom, or a $C_{1-6}$ alkyl or $C_{1-6}$ alkoxy group.

Herein, preferred examples of the 5-membered ring heterocyclic group include pyrrolyl, pyrrolidinyl, pyrazolyl, oxazolyl, oxadiazolyl, imidazolyl, triazolyl and furanyl groups. Among these groups, triazolyl and furanyl groups are more preferable. This 5-membered ring heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, and is further preferably unsubstituted or substituted with a fluorine atom or a methyl group.

The $C_{1-6}$ alkyl group is preferably a $C_{1-3}$ alkyl group, and more preferably a $C_{1-2}$ alkyl group.

The $C_{1-6}$ alkoxy group is preferably a $C_{1-3}$ alkoxy group, and more preferably a $C_{1-2}$ alkoxy group.

The halogen atom is preferably a fluorine atom or a chlorine atom, and more preferably a fluorine atom.

The $C_{3-8}$ cycloalkyl group is preferably a cyclopropyl group.

The $Q^5$ is preferably a $C_{1-3}$ alkyleneoxy group, and more preferably a $C_{1-2}$ alkyleneoxy group.

The $R^{36}$ is preferably a hydrogen atom, a $C_{1-3}$ alkyl or cyclopropyl group, and more preferably a hydrogen atom or a $C_{1-2}$ alkyl group.

The m4 is preferably an integer of 1 or 2.

When $R^{39}$ is a halogen atom; or a $C_{1-6}$ alkyl or $C_{1-6}$ alkoxy group optionally having at least one halogen atom, $R^{40}$ is preferably a 5-membered ring or 6-membered ring heterocyclic group optionally having at least one substituent each independently selected from among a halogen atom, $C_{1-6}$ alkyl, $C_{3-8}$ cycloalkyl and -$Q^5$m4-$R^{36}$ (wherein $Q^5$, $R^{36}$, m4 have the same definitions as those described above).

Herein, preferred examples of the 5-membered ring heterocyclic group include pyrrolyl, pyrrolidinyl, pyrazolyl, oxazolyl, oxadiazolyl, imidazolyl, triazolyl and furanyl groups. Among these groups, triazolyl and furanyl groups are more preferable. This 5-membered ring heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, and is further preferably unsubstituted or substituted with a fluorine atom or a methyl group.

A preferred example of the 6-membered ring heterocyclic group is a morpholinyl group. This 6-membered ring heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, is further preferably unsubstituted or substituted with a fluorine atom or a methyl group, and is still further preferably unsubstituted.

The aryl group is preferably a phenyl group.

The $C_{1-6}$ alkyl group is preferably a $C_{1-3}$ alkyl group, and more preferably a $C_{1-2}$ alkyl group.

The $C_{1-6}$ alkoxy group is preferably a $C_{1-3}$ alkoxy group, and more preferably a $C_{1-2}$ alkoxy group.

The halogen atom is preferably a fluorine atom or a chlorine atom, and more preferably a fluorine atom.

The $C_{3-8}$ cycloalkyl group is preferably a cyclopropyl group.

The $Q^5$ is preferably a $C_{1-3}$ alkyleneoxy group, and more preferably a $C_{1-2}$ alkyleneoxy group.

The $R^{36}$ is preferably a hydrogen atom, $C_{1-3}$ alkyl or cyclopropyl group, and more preferably a hydrogen atom or a $C_{1-2}$ alkyl group.

The m4 is preferably an integer of 1 or 2.

Further, a compound in which $R^{39}$ represents a fluorine atom or a methyl or ethyl group and $R^{40}$ represents a morpholinyl group, is preferable.

$R^{41}$ and $R^{42}$ each independently represent, preferably a hydrogen atom or a halogen atom, more preferably a hydrogen atom or a fluorine atom, and further preferably a hydrogen atom.

$R^{43}$ and $R^{44}$ each represent, more preferably a hydrogen atom; a halogen atom; or a $C_{1-6}$ alkyl, aryl, $C_{1-6}$ alkoxy or heterocyclic group, optionally having at least one substituent each independently selected from among a halogen atom, $C_{1-6}$ alkyl, $C_{3-8}$ cycloalkyl and -$Q^5$m4-$R^{36}$ (wherein $Q^5$, $R^{36}$, m4 have the same definitions as those described above), further preferably a hydrogen atom; a halogen atom; or a $C_{1-6}$ alkyl or $C_{1-6}$ alkoxy group optionally having at least one substituent each independently selected from among a halogen atom, $C_{1-6}$ alkyl, $C_{3-8}$ cycloalkyl and -$Q^5$m4-$R^{36}$ (wherein $Q^5$, $R^{36}$, m4 have the same definitions as those described above), and still further preferably a hydrogen atom; a halogen atom; or a $C_{1-6}$ alkyl or $C_{1-6}$ alkoxy group.

Herein, preferred examples of the heterocyclic group include pyrrolyl, pyrrolidinyl, pyrazolyl, oxazolyl, oxadiazolyl, imidazolyl, triazolyl and furanyl groups. Among these groups, triazolyl and furanyl groups are more preferable. This heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, and is further preferably unsubstituted or substituted with a fluorine atom or a methyl group.

The aryl group is preferably a phenyl group.

The $C_{1-6}$ alkyl group is preferably a $C_{1-3}$ alkyl group, and more preferably a $C_{1-2}$ alkyl group.

The $C_{1-6}$ alkoxy group is preferably a $C_{1-3}$ alkoxy group, and more preferably a $C_{1-2}$ alkoxy group.

The halogen atom is preferably a fluorine atom or a chlorine atom, and more preferably a fluorine atom.

The $C_{3-8}$ cycloalkyl is preferably a cyclopropyl group.

The $Q^5$ is preferably a $C_{1-3}$ alkyleneoxy group, and more preferably a $C_{1-2}$ alkyleneoxy group.

The $R^{36}$ is preferably a hydrogen atom, $C_{1-3}$ alkyl or cyclopropyl groups, and more preferably a hydrogen atom or a $C_{1-2}$ alkyl group.

The m4 is preferably an integer of 1 or 2.

Among pyridyl groups represented by the above-described formula (VIII-1), a pyridyl group represented by the following formula (VIII-3) is more preferable. Among pyridyl groups represented by the above-described formula (VIII-2), a pyridyl group represented by the following formula (VIII-4) is more preferable. Among others, the pyridyl group represented by the following formula (VIII-3) is further preferable.

[Formula 9]

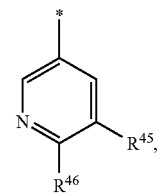

(VIII-3)

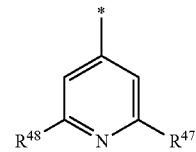

(VIII-4)

wherein $R^{45}$, $R^{46}$, $R^{47}$ and $R^{48}$ independently represent a hydrogen atom, or a substituent selected from the above-described substituent group $\alpha_{2-6}$.

$R^{45}$ is more preferably a hydrogen atom; a halogen atom; or a $C_{1-6}$ alkyl, aryl, $C_{1-6}$ alkoxy or heterocyclic group optionally having at least one substituent each independently selected from among a halogen atom, $C_{1-6}$ alkyl, $C_{3-8}$ cycloalkyl and -$Q^5$m4-$R^{36}$ (wherein $Q^5$, $R^{36}$, m4 have the same definitions as those described above), and is further preferably a halogen atom; or a $C_{1-6}$ alkyl, aryl, $C_{1-6}$ alkoxy or 5-membered ring heterocyclic group optionally having at least one substituent each independently selected from among a halogen atom, $C_{1-6}$ alkyl, $C_{3-8}$ cycloalkyl and -$Q^5$m4-$R^{36}$ (wherein $Q^5$, $R^{36}$, m4 have the same definitions as those described above).

Herein, preferred examples of the 5-membered ring heterocyclic group include pyrrolyl, pyrrolidinyl, pyrazolyl, oxazolyl, oxadiazolyl, imidazolyl, triazolyl and furanyl groups. Among these groups, triazolyl and furanyl groups are more preferable. This 5-membered ring heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, and is further preferably unsubstituted or substituted with a fluorine atom or a methyl group.

The $C_{1-6}$ alkyl group is preferably a $C_{1-3}$ alkyl group, and more preferably a $C_{1-2}$ alkyl group.

The $C_{1-6}$ alkoxy group is preferably a $C_{1-3}$ alkoxy group, and more preferably a $C_{1-2}$ alkoxy group.

The halogen atom is preferably a fluorine atom or a chlorine atom, and more preferably a fluorine atom.

The $C_{3-8}$ cycloalkyl is preferably a cyclopropyl group.

The $Q^5$ is preferably a $C_{1-3}$ alkyleneoxy group, and more preferably a $C_{1-2}$ alkyleneoxy group.

The $R^{36}$ is preferably a hydrogen atom, $C_{1-3}$ alkyl or cyclopropyl groups, and more preferably a hydrogen atom, or a $C_{1-2}$ alkyl group.

The m4 is preferably an integer of 1 or 2.

$R^{46}$ is more preferably a hydrogen atom; a halogen atom; or a $C_{1-6}$ alkyl, aryl, $C_{1-6}$ alkoxy or heterocyclic group optionally having at least one substituent each independently selected from among a halogen atom, $C_{1-6}$ alkyl, $C_{3-8}$ cycloalkyl and -$Q^5$m4-$R^{36}$ (wherein $Q^5$, $R^{32}$, m3, $Q^6$ have the same definitions as those described above), and is further preferably a halogen atom; or a $C_{1-6}$ alkyl, aryl, $C_{1-6}$ alkoxy, or 5-membered ring or 6-membered ring heterocyclic group optionally having at least one substituent each independently selected from among a halogen atom, $C_{1-6}$ alkyl, $C_{3-8}$ cycloalkyl and -$Q^5$m4-$R^{36}$ (wherein $Q^5$, $R^{36}$, m4, $Q^6$ have the same definitions as those described above).

Herein, preferred examples of the 5-membered ring heterocyclic group include pyrrolyl, pyrrolidinyl, pyrazolyl, oxazolyl, oxadiazolyl, imidazolyl, triazolyl and furanyl groups. Among these groups, triazolyl and furanyl groups are preferable. This 5-membered ring heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, and is further preferably unsubstituted or substituted with a fluorine atom or a methyl group.

A preferred example of the 6-membered ring heterocyclic group is a morpholinyl group. This 6-membered ring heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, is further preferably unsubstituted or substituted with a fluorine atom or a methyl group, and is still further preferably unsubstituted.

The aryl group is preferably a phenyl group.

The $C_{1-6}$ alkyl group is preferably a $C_{1-3}$ alkyl group, and more preferably a $C_{1-2}$ alkyl group.

The $C_{1-6}$ alkoxy group is preferably a $C_{1-3}$ alkoxy group, and more preferably a $C_{1-2}$ alkoxy group.

The halogen atom is preferably a fluorine atom or a chlorine atom, and more preferably a fluorine atom.

The $C_{3-8}$ cycloalkyl is preferably a cyclopropyl group.

The $Q^5$ is preferably a $C_{1-3}$ alkyleneoxy group, and more preferably a $C_{1-2}$ alkyleneoxy group.

The $R^{36}$ is preferably a hydrogen atom, $C_{1-3}$ alkyl or cyclopropyl groups, and more preferably a hydrogen atom or a $C_{1-2}$ alkyl group.

The m4 is preferably an integer of 1 or 2.

When $R^{45}$ is a 5-membered ring heterocyclic group optionally having at least one substituent selected from among a halogen atom, $C_{1-6}$ alkyl, $C_{3-8}$ cycloalkyl and -$Q^5$m4-$R^{36}$ (wherein $Q^5$, $R^{36}$, m4 have the same definitions as those described above), $R^{46}$ is preferably a halogen atom, a $C_{1-6}$ alkyl or $C_{1-6}$ alkoxy group.

Herein, preferred examples of the 5-membered ring heterocyclic group include pyrrolyl, pyrrolidinyl, pyrazolyl, oxazolyl, oxadiazolyl, imidazolyl, triazolyl and furanyl groups. Among these groups, triazolyl and furanyl groups are more preferable. This 5-membered ring heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, and is further preferably unsubstituted or substituted with a fluorine atom or a methyl group.

The $C_{1-6}$ alkyl group is preferably a $C_{1-3}$ alkyl group, and more preferably a $C_{1-2}$ alkyl group.

The $C_{1-6}$ alkoxy group is preferably a $C_{1-3}$ alkoxy group, and more preferably a $C_{1-2}$ alkoxy group.

The halogen atom is preferably a fluorine atom or a chlorine atom, and more preferably a fluorine atom.

The $C_{3-8}$ cycloalkyl is preferably a cyclopropyl group.

The $Q^5$ is preferably a $C_{1-3}$ alkyleneoxy group, and more preferably a $C_{1-2}$ alkyleneoxy group.

The $R^{36}$ is preferably a hydrogen atom, $C_{1-3}$ alkyl or cyclopropyl groups, and more preferably a hydrogen atom, or a $C_{1-2}$ alkyl group.

The m4 is preferably an integer of 1 or 2.

When $R^{45}$ is a halogen atom; or a $C_{1-6}$ alkyl or $C_{1-6}$ alkoxy group optionally having at least one halogen atom, $R^{46}$ is preferably a 5-membered ring or 6-membered ring heterocyclic group optionally having at least one substituent each independently selected from among a halogen atom, $C_{1-6}$ alkyl, $C_{3-8}$ cycloalkyl and -$Q^5$m4-$R^{36}$ (wherein $Q^5$, $R^{36}$, m4 have the same definitions as those described above).

Herein, preferred examples of the 5-membered ring heterocyclic group include pyrrolyl, pyrrolidinyl, pyrazolyl, oxazolyl, oxadiazolyl, imidazolyl, triazolyl and furanyl groups. Among these groups, triazolyl and furanyl group are more preferable. This 5-membered ring heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, and is further preferably unsubstituted or substituted with a fluorine atom or a methyl group.

A preferred example of the 6-membered ring heterocyclic group is a morpholinyl group. This 6-membered ring heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, is further preferably unsubstituted or substituted with a fluorine atom or a methyl group, and is still further preferably unsubstituted.

The aryl group is preferably a phenyl group.

The $C_{1-6}$ alkyl group is preferably a $C_{1-3}$ alkyl group, and more preferably a $C_{1-2}$ alkyl group.

The $C_{1-6}$ alkoxy group is preferably a $C_{1-3}$ alkoxy group, and more preferably a $C_{1-2}$ alkoxy group.

The halogen atom is preferably a fluorine atom or a chlorine atom, and more preferably a fluorine atom.

The $C_{3-8}$ cycloalkyl is preferably a cyclopropyl group.

The $Q^5$ is preferably a $C_{1-3}$ alkyleneoxy group, and more preferably a $C_{1-2}$ alkyleneoxy group.

The $R^{36}$ is preferably a hydrogen atom, $C_{1-3}$ alkyl or cyclopropyl groups, and more preferably a hydrogen atom or a $C_{1-2}$ alkyl group.

The m4 is preferably an integer of 1 or 2.

Further, a compound in which $R^{45}$ represents a fluorine atom or a methyl or ethyl group and $R^{46}$ represents a morpholinyl group, is preferable.

$R^{47}$ and $R^{48}$ each represent, more preferably a hydrogen atom; a halogen atom; or a $C_{1-6}$ alkyl, aryl, $C_{1-6}$ alkoxy or heterocyclic group optionally having at least one substituent each independently selected from among a halogen atom, $C_{1-6}$ alkyl, $C_{3-8}$ cycloalkyl and -$Q^5$m4-$R^{36}$ (wherein $Q^5$, $R^{36}$, m4 have the same definitions as those described above), further preferably a hydrogen atom; a halogen atom; or a $C_{1-6}$ alkyl or $C_{1-6}$ alkoxy group optionally having at least one substituent each independently selected from among a halogen atom, $C_{1-6}$ alkyl, $C_{3-8}$ cycloalkyl and -$Q^5$m4-$R^{36}$ (wherein $Q^5$, $R^{36}$, m4 have the same definitions as those described above), and still further preferably a hydrogen atom, a halogen atom, or a $C_{1-6}$ alkyl or $C_{1-6}$ alkoxy group.

Herein, preferred examples of the heterocyclic group include pyrrolyl, pyrrolidinyl, pyrazolyl, oxazolyl, oxadiazolyl, imidazolyl, triazolyl and furanyl groups. Among these groups, triazolyl and furanyl groups are more preferable. This heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, and is further preferably unsubstituted or substituted with a fluorine atom or a methyl group.

The aryl group is preferably a phenyl group.

The $C_{1-6}$ alkyl group is preferably a $C_{1-3}$ alkyl group, and more preferably a $C_{1-2}$ alkyl group.

The $C_{1-6}$ alkoxy group is preferably a $C_{1-3}$ alkoxy group, and more preferably a $C_{1-2}$ alkoxy group.

The halogen atom is preferably a fluorine atom or a chlorine atom, and more preferably a fluorine atom.

The $C_{3-8}$ cycloalkyl is preferably a cyclopropyl group.

The $Q^5$ is preferably a $C_{1-3}$ alkyleneoxy group, and more preferably a $C_{1-2}$ alkyleneoxy group.

The $R^{36}$ is preferably a hydrogen atom, $C_{1-3}$ alkyl or cyclopropyl groups, and more preferably a hydrogen atom, or a $C_{1-2}$ alkyl group.

The m4 is preferably an integer of 1 or 2.

When $R^3$ is an indazolyl group optionally having at least one substituent, it is preferably an indazolyl group represented by any one of the following formulae (IX-1) to (IX-6), is more preferably an indazolyl group represented by the formula (IX-1) or (IX-2), and is further preferably an indazolyl group represented by the formula (IX-1):

[Formula 10]

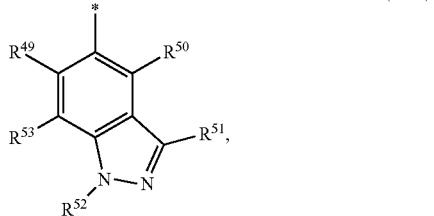
(IX-1)

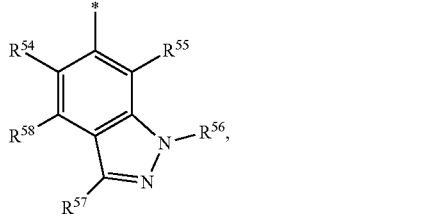
(IX-2)

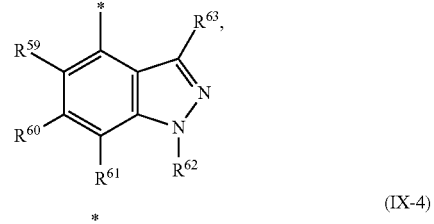
(IX-3)

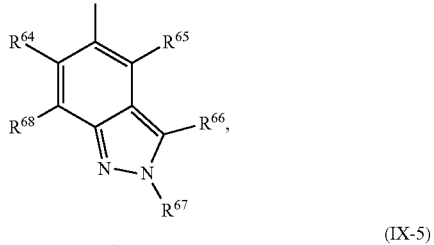
(IX-4)

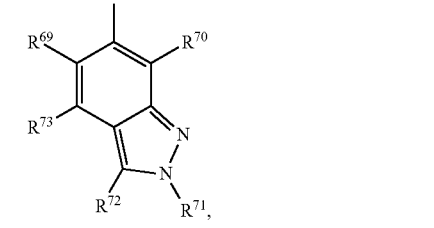
(IX-5)

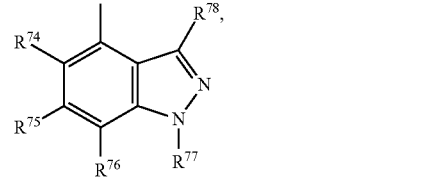
(IX-6)

wherein $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{75}$, $R^{76}$, $R^{77}$ and $R^{78}$ each independently represent a hydrogen atom, or a substituent selected from the above-described substituent group α$_{2-6}$.

$R^{49}$, $R^{50}$, $R^{54}$, $R^{55}$, $R^{59}$, $R^{60}$, $R^{64}$, $R^{65}$, $R^{69}$, $R^{70}$, $R^{74}$ and $R^{75}$ each independently represent, preferably a hydrogen atom or a halogen atom, more preferably a hydrogen atom or a fluorine atom, and further preferably a hydrogen atom.

$R^{53}$, $R^{58}$, $R^{61}$, $R^{68}$, $R^{73}$ and $R^{76}$ each independently represent, preferably a halogen atom, or a C$_{1-6}$ alkyl, aryl or C$_{1-6}$ alkoxy group, more preferably a hydrogen atom or a halogen atom, further preferably a hydrogen atom or a fluorine atom, and still further preferably a hydrogen atom.

$R^{51}$, $R^{57}$, $R^{63}$, $R^{66}$, $R^{72}$ and $R^{78}$ each independently represent, preferably a hydrogen atom; a halogen atom; or a C$_{1-6}$ alkyl, C$_{3-8}$ cycloalkyl, C$_{1-6}$ alkoxy or aryl group optionally having at least one substituent each independently selected from among C$_{1-6}$ alkyl, C$_{3-8}$ cycloalkyl, and -Q$^5$m4-R$^{36}$ (wherein Q$^5$, R$^{32}$, m4 have the same definitions as those described above), optionally having at least one halogen atom.

Herein, the C$_{1-6}$ alkyl group is preferably a C$_{1-3}$ alkyl group, and more preferably a C$_{1-2}$ alkyl group.

The C$_{1-6}$ alkoxy group is preferably a C$_{1-3}$ alkoxy group, and more preferably a C$_{1-2}$ alkoxy group.

The halogen atom is preferably a fluorine atom or a chlorine atom, and more preferably a fluorine atom.

The C$_{3-8}$ cycloalkyl is preferably a cyclopropyl group.

The Q$^5$ is preferably a C$_{1-3}$ alkyleneoxy group, and more preferably a C$_{1-2}$ alkyleneoxy group.

The R$^{36}$ is preferably a hydrogen atom, C$_{1-3}$ alkyl or cyclopropyl groups, and more preferably a hydrogen atom or a C$_{1-2}$ alkyl group.

The m4 is preferably an integer of 1 or 2.

$R^{52}$, $R^{56}$, $R^{62}$, $R^{67}$, $R^{71}$ and $R^{77}$ each independently represent, preferably a hydrogen atom; a halogen atom; or a C$_{1-6}$ alkyl, C$_{3-8}$ cycloalkyl, C$_{1-6}$ alkoxy or aryl group optionally having at least one substituent each independently selected from among C$_{1-6}$ alkyl, C$_{3-8}$ cycloalkyl, and -Q$^5$m4-R$^{36}$ (wherein Q$^5$, R$^{36}$, m4 have the same definitions as those described above), optionally having at least one halogen atom.

Herein, the C$_{1-6}$ alkyl group is preferably a C$_{1-3}$ alkyl group, and more preferably a C$_{1-2}$ alkyl group.

The C$_{1-6}$ alkoxy group is preferably a C$_{1-3}$ alkoxy group, and more preferably a C$_{1-2}$ alkoxy group.

The halogen atom is preferably a fluorine atom or a chlorine atom, and more preferably a fluorine atom.

The C$_{3-8}$ cycloalkyl is preferably a cyclopropyl group.

The aryl is preferably a phenyl group.

The Q$^5$ is preferably a C$_{1-3}$ alkyleneoxy group, and more preferably a C$_{1-2}$ alkyleneoxy group.

The R$^{36}$ is preferably a hydrogen atom, C$_{1-3}$ alkyl or cyclopropyl groups, and more preferably a hydrogen atom or a C$_{1-2}$ alkyl group.

The m4 is preferably an integer of 1 or 2.

With regard to the combinations such as $R^{51}$ and $R^{52}$, $R^{56}$ and $R^{57}$, $R^{62}$ and $R^{63}$, $R^{66}$ and $R^{67}$, $R^{71}$ and $R^{72}$, and $R^{77}$ and $R^{78}$, at least either one preferably represents a halogen atom; or a C$_{1-6}$ alkyl, C$_{3-8}$ cycloalkyl or C$_{1-6}$ alkoxy group optionally having at least one substituent each independently selected from among C$_{1-6}$ alkyl, C$_{3-8}$ cycloalkyl, and -Q$^5$m4-R$^{36}$ (wherein Q$^5$, R$^{36}$, m4 have the same definitions as those described above) optionally having at least one halogen atom.

Herein, the C$_{1-6}$ alkyl group is preferably a C$_{1-3}$ alkyl group, and more preferably a C$_{1-2}$ alkyl group.

The C$_{1-6}$ alkoxy group is preferably a C$_{1-3}$ alkoxy group, and more preferably a C$_{1-2}$ alkoxy group.

The halogen atom is preferably a fluorine atom or a chlorine atom, and more preferably a fluorine atom.

The C$_{3-8}$ cycloalkyl is preferably a cyclopropyl group.

The Q$^5$ is preferably a C$_{1-3}$ alkyleneoxy group, and more preferably a C$_{1-2}$ alkyleneoxy group.

The R$^{36}$ is preferably a hydrogen atom, C$_{1-3}$ alkyl or cyclopropyl groups, and more preferably a hydrogen atom, or a C$_{1-2}$ alkyl group.

The m4 is preferably an integer of 1 or 2.

Among the indazolyl groups represented by the above-described formula (IX-1), an indazolyl group represented by the following formula (IX-7) is more preferable. Among the indazolyl groups represented by the above-described formula (IX-2), an indazolyl group represented by the following formula (IX-8) is more preferable. Among others, the indazolyl group represented by the formula (IX-7) is further preferable:

[Formula 11]

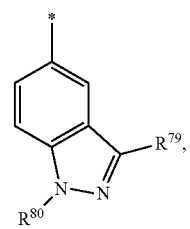

(IX-7)

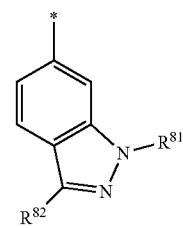

(IX-8)

wherein $R^{79}$, $R^{80}$, $R^{81}$ and $R^{82}$ each independently represent a hydrogen atom, or a substituent selected from the above-described substituent group α$_{2-6}$, wherein $R^{79}$ is the same substituent as $R^{51}$, and the preferred range of $R^{79}$ is also the same as that of $R^{51}$, $R^{80}$ is the same substituent as $R^{52}$, and the preferred range of $R^{80}$ is also the same as that of $R^{52}$, $R^{81}$ is the same substituent as $R^{56}$, and the preferred range of $R^{81}$ is also the same as that of $R^{56}$, and $R^{82}$ is the same substituent as $R^{57}$, and the preferred range of $R^{82}$ is also the same as that of $R^{57}$.

When $R^3$ is a phenyl group optionally having at least one substituent, the substituent optionally possessed by the phenyl group is more preferably a halogen atom; or C$_{1-6}$ alkyl, aryl, C$_{1-6}$ alkoxy or heterocyclic group optionally having at least one substituent each independently selected from among a halogen atom, C$_{1-6}$ alkyl, C$_{3-8}$ cycloalkyl and -Q$^5$m4-R$^{36}$ (wherein Q$^5$, R$^{32}$, m3, Q$^6$ have the same definitions as those described above), and is further preferably a halogen atom; or a C$_{1-6}$ alkyl, aryl, C$_{1-6}$ alkoxy, or 5-membered ring or 6-membered ring heterocyclic group, optionally having at least one substituent each independently selected from among a halogen atom, C$_{1-6}$ alkyl, C$_{3-8}$ cycloalkyl and -Q$^5$m4-R$^{36}$ (wherein Q$^5$, R$^{36}$, m4, Q$^6$ have the same definitions as those described above).

Herein, preferred examples of the 5-membered ring heterocyclic group include pyrrolyl, pyrrolidinyl, pyrazolyl, oxazolyl, oxadiazolyl, imidazolyl, triazolyl and furanyl groups. Among these groups, triazolyl and furanyl groups are more preferable. This 5-membered ring heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, and is further preferably unsubstituted or substituted with a fluorine atom or a methyl group.

A preferred example of the 6-membered ring heterocyclic group is a morpholinyl group. This 6-membered ring heterocyclic group is preferably unsubstituted or substituted with a substituent selected from the group consisting of a fluorine atom, a chlorine atom, a methyl group, an ethyl group and a propyl group, is more preferably unsubstituted or substituted with a substituent selected from among a fluorine atom, a methyl group and an ethyl group, is further preferably unsubstituted or substituted with a fluorine atom or a methyl group, and is still further preferably unsubstituted.

The aryl group is preferably a phenyl group.

The $C_{1-6}$ alkyl group is preferably a $C_{1-3}$ alkyl group, and more preferably a $C_{1-2}$ alkyl group.

The $C_{1-6}$ alkoxy group is preferably a $C_{1-3}$ alkoxy group, and more preferably a $C_{1-2}$ alkoxy group.

The halogen atom is preferably a fluorine atom or a chlorine atom, and more preferably a fluorine atom.

The $C_{3-8}$ cycloalkyl is preferably a cyclopropyl group.

The $Q^5$ is preferably a $C_{1-3}$ alkyleneoxy group, and more preferably a $C_{1-2}$ alkyleneoxy group.

The $R^{36}$ is preferably a hydrogen atom, $C_{1-3}$ alkyl or cyclopropyl groups, and more preferably a hydrogen atom, or a $C_{1-2}$ alkyl group.

The m4 is preferably an integer of 1 or 2.

When $R^3$ is a quinoxalinyl group optionally having at least one substituent, the substituent optionally possessed by the quinoxalinyl group is preferably a halogen atom; or a $C_{1-6}$ alkyl, $C_{3-8}$ cycloalkyl, $C_{1-6}$ alkoxy or aryl group optionally having at least one substituent each independently selected from among $C_{1-6}$ alkyl, $C_{3-8}$ cycloalkyl, and $-Q^5 m4-R^{36}$ (wherein $Q^5$, $R^{32}$, m4 have the same definitions as those described above), optionally having at least one halogen atom.

Herein, the $C_{1-6}$ alkyl group is preferably a $C_{1-3}$ alkyl group, and more preferably a $C_{1-2}$ alkyl group.

The $C_{1-6}$ alkoxy group is preferably a $C_{1-3}$ alkoxy group, and more preferably a $C_{1-2}$ alkoxy group.

The halogen atom is preferably a fluorine atom or a chlorine atom, and more preferably a fluorine atom.

The $C_{3-8}$ cycloalkyl is preferably a cyclopropyl group.

The aryl group is preferably a phenyl group.

The $Q^5$ is preferably a $C_{1-3}$ alkyleneoxy group, and more preferably a $C_{1-2}$ alkyleneoxy group.

The $R^{36}$ is preferably a hydrogen atom, $C_{1-3}$ alkyl or cyclopropyl groups, and more preferably a hydrogen atom or a $C_{1-2}$ alkyl group.

The m4 is preferably an integer of 1 or 2.

The nicotinamide derivative of the present invention or a pharmaceutically acceptable salt thereof is preferably represented by the following formula (I-2), is more preferably represented by the following formula (I-3), is further preferably represented by the following formula (I-4), and is still further preferably represented by the following formula (I-5):

[Formula 12]

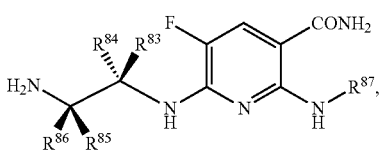
(I-2)

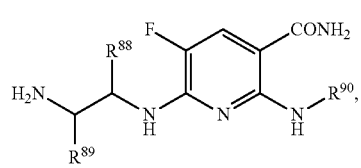
(I-3)

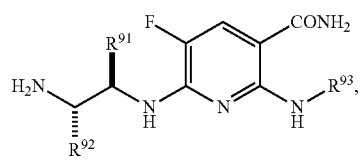
(I-4)

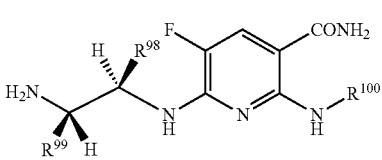
(I-5)

wherein
$R^{83}$ is the same substituent as $R^{10}$, and the preferred range of $R^{83}$ is also the same as that of $R^{10}$,
$R^{84}$ is the same substituent as $R^{11}$, and the preferred range of $R^{84}$ is also the same as that of $R^{11}$,
$R^{85}$ is the same substituent as $R^{12}$, and the preferred range of $R^{85}$ is also the same as that of $R^{12}$,
$R^{86}$ is the same substituent as $R^{13}$, and the preferred range of $R^{86}$ is also the same as that of $R^{13}$,
$R^{88}$ is the same substituent as $R^{32}$, and the preferred range of $R^{88}$ is also the same as that of $R^{32}$,
$R^{89}$ is the same substituent as $R^{33}$, and the preferred range of $R^{89}$ is also the same as that of $R^{33}$,
$R^{91}$ is the same substituent as $R^{96}$, and the preferred range of $R^{91}$ is also the same as that of $R^{96}$,
$R^{92}$ is the same substituent as $R^{97}$, and the preferred range of $R^{92}$ is also the same as that of $R^{97}$,
$R^{98}$ is the same substituent as $R^{34}$, and the preferred range of $R^{98}$ is also the same as that of $R^{34}$,
$R^{99}$ is the same substituent as $R^{35}$, and the preferred range of $R^{99}$ is also the same as that of $R^{35}$,
$R^{87}$ is the same substituent as $R^3$, and the preferred range of $R^{87}$ is also the same as that of $R^3$,
$R^{90}$ is the same substituent as $R^3$, and the preferred range of $R^{90}$ is also the same as that of $R^3$,
$R^{93}$ is the same substituent as $R^3$, and the preferred range of $R^{93}$ is also the same as that of $R^3$, and
$R^{100}$ is the same substituent as $R^3$, and the preferred range of $R^{100}$ is also the same as that of $R^3$.

In the above formulae, each of $R^{87}$, $R^{90}$, $R^{93}$ and $R^{100}$ preferably represents an indazolyl group or pyridyl group optionally having at least one substituent. When each of $R^{87}$, $R^{90}$, $R^{93}$ and $R^{100}$ is a pyridyl group optionally having at least one substituent, it is preferably the pyridyl group represented by the above-described formula (VIII-1) or (VIII-2), and more preferably the pyridyl group represented by the following formula (VIII-1). The preferred ranges of the pyridyl groups represented by the above-described formulae (VIII-1) and (VIII-2) are the same as those described above. When each of $R^{87}$, $R^{90}$, $R^{93}$ and $R^{100}$ is an indazolyl group optionally having at least one substituent, it is preferably the indazolyl group represented by any one of the above-described formulae (IX-1) to (IX-6), more preferably the indazolyl group represented by the formula (IX-1) or (IX-2), and further preferably the indazolyl group represented by the formula (IX-1). The preferred ranges of the indazolyl groups represented by the above-described formulae (IX-1) to (IX-6) are the same as those described above.

The nicotinamide derivative of the present invention or a pharmaceutically acceptable salt thereof is preferably represented by the following formula (I-6), is more preferably represented by the following formula (I-7), and is further preferably represented by the following formula (I-8):

[Formula 13]

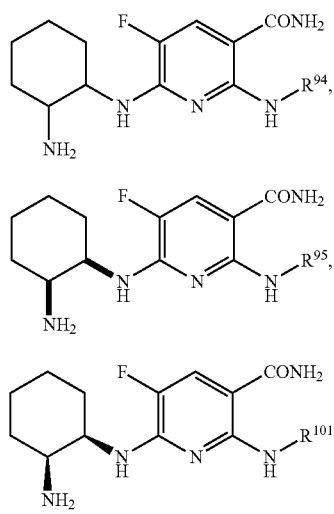

wherein $R^{94}$ is the same substituent as $R^3$, and the preferred range of $R^{94}$ is also the same as that of $R^3$, $R^{95}$ is the same substituent as $R^3$, and the preferred range of $R^{95}$ is also the same as that of $R^3$, and $R^{101}$ is the same substituent as $R^3$, and the preferred range of $R^{101}$ is also the same as that of $R^3$.

In the above formulae, each of $R^{94}$, $R^{95}$ and $R^{101}$ is more preferably a pyridyl group optionally having at least one substituent, further preferably the pyridyl group represented by the above-described formula (VIII-1) or (VIII-2), and still further preferably the pyridyl group represented by the following formula (VIII-1). The preferred ranges of the pyridyl groups represented by the above-described formulae (VIII-1) and (VIII-2) are the same as those described above.

The nicotinamide derivative of the present invention or a pharmaceutically acceptable salt thereof is preferably represented by the following formula (I-9), is more preferably represented by the following formula (I-10), and is further preferably represented by the following formula (I-11):

[Formula 14]

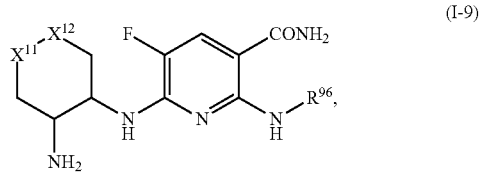

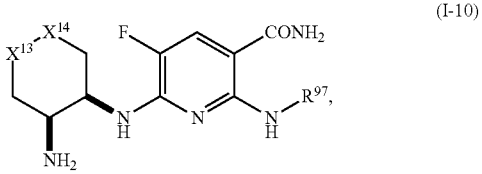

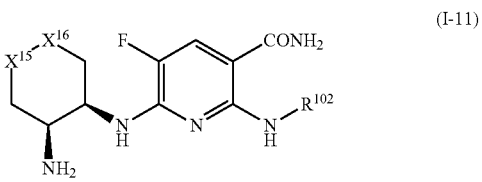

wherein $R^{96}$ is the same substituent as $R^3$, and the preferred range of $R^{96}$ is also the same as that of $R^3$, $R^{97}$ is the same substituent as $R^3$, and the preferred range of $R^{97}$ is also the same as that of $R^3$, $R^{102}$ is the same substituent as $R^3$, and the preferred range of $R^{102}$ is also the same as that of $R^3$, $X^{11}$ is the same substituent as $X^9$, and the preferred range of $X^{11}$ is also the same as that of $X^9$, $X^{12}$ is the same substituent as $X^{10}$, and the preferred range of $X^{12}$ is also the same as that of $X^{10}$, $X^{13}$ is the same substituent as $X^9$, and the preferred range of $X^{13}$ is also the same as that of $X^9$, $X^{14}$ is the same substituent as $X^{10}$, and the preferred range of $X^{14}$ is also the same as that of $X^{10}$, $X^{15}$ is the same substituent as $X^9$, and the preferred range of $X^{15}$ is also the same as that of $X^9$, and $X^{16}$ is the same substituent as $X^{19}$, and the preferred range of $X^{16}$ is also the same as that of $X^{10}$.

It is to be noted that, in the above formulae, $R^{96}$, $R^{97}$ and $R^{102}$ each represent, more preferably a pyridyl group optionally having at least one substituent, further preferably the pyridyl group represented by the above-described formula (VIII-1) or (VIII-2), and still further preferably the pyridyl group represented by the following formula (VIII-1). Preferred ranges of the pyridyl groups represented by the formula (VIII-1) and (VIII-2) are the same as those described above.

Preferred examples of the compound represented by the formula [1] of the present invention include the following compounds:

6-(cis-2-aminocyclohexylamino)-5-fluoro-2-(5-phenylpyridin-3-ylamino)nicotinamide;
6-(cis-2-aminocyclohexylamino)-5-fluoro-2-(3-methylphenylamino)nicotinamide;
6-(cis-2-aminocyclohexylamino)-5-fluoro-2-(4-(morpholin-4-yl)phenylamino)nicotinamide;
6-(cis-2-aminocyclohexylamino)-5-fluoro-2-(3,4,5-trimethoxyphenylamino)nicotinamide;
6-(cis-2-aminocyclohexylamino)-5-fluoro-2-(2-methoxypyridin-4-ylamino)nicotinamide;
6-(cis-2; aminocyclohexylamino)-2-(2,6-dimethoxypyridin-4-ylamino)-5-fluoronicotinamide;

6-(cis-2-aminocyclohexylamino)-5-fluoro-2-(2-(morpholin-4-yl)pyridin-4-ylamino)nicotinamide;
6-(cis-2-aminocyclohexylamino)-5-fluoro-2-(6-(morpholin-4-yl)pyridin-3-ylamino)nicotinamide;
6-(cis-2-aminocyclohexylamino)-5-fluoro-2-(pyrimidin-5-ylamino)nicotinamide;
6-(cis-2-aminocyclohexylamino)-5-fluoro-2-(1,5-naphthyridin-3-ylamino)nicotinamide;
6-(cis-2-aminocyclohexylamino)-5-fluoro-2-(1,6-naphthyridin-3-ylamino)nicotinamide;
6-(cis-2-aminocyclohexylamino)-5-fluoro-2-(1,6-naphthyridin-8-ylamino)nicotinamide;
6-(cis-2-aminocyclohexylamino)-5-fluoro-2-(8-nitroquinolin-3-ylamino)nicotinamide;
6-(cis-2-aminocyclohexylamino)-5-fluoro-2-(1-methyl-1H-pyrrolo[2,3-c]pyridin-4-ylamino)nicotinamide;
6-(cis-2-aminocyclohexylamino)-5-fluoro-2-(1-(2-(pyrrolidin-1-yl)ethyl)-1H-pyrrolo[2,3-c]pyridin-4-ylamino)nicotinamide;
2-(8-acetylaminoquinolin-3-ylamino)-6-(cis-2-aminocyclohexylamino)-5-fluoronicotinamide;
6-(cis-2-aminocyclohexylamino)-5-fluoro-2-(5-(anilinocarbonyl)pyridin-3-ylamino)nicotinamide;
6-(cis-2-aminocyclohexylamino)-5-fluoro-2-(1-methyl-1H-pyrrolo[2,3-b]pyridin-5-ylamino)nicotinamide;
6-(cis-2-aminocyclohexylamino)-5-fluoro-2-(1-methyl-1H-pyrrolo[2,3-b]pyridin-4-ylamino)nicotinamide;
methyl 5-(3-aminocarbonyl-6-(cis-2-aminocyclohexylamino)-5-fluoropyridin-2-ylamino)nicotinate;
6-(cis-2-aminocyclohexylamino)-5-fluoro-2-(6-methylpyridin-3-ylamino)nicotinamide;
6-(cis-2-aminocyclohexylamino)-5-fluoro-2-(2-methylpyridin-4-ylamino)nicotinamide;
6-(cis-2-aminocyclohexylamino)-5-fluoro-2-(1-(2-(pyrrolidin-1-yl)ethyl)-1H-pyrrolo[2,3-b]pyridin-5-ylamino)nicotinamide;
6-(cis-2-aminocyclohexylamino)-5-fluoro-2-(1-(2-(pyrrolidin-1-yl)ethyl)-1H-pyrrolo[2,3-b]pyridin-4-ylamino)nicotinamide;
6-(cis-2-aminocyclohexylamino)-5-fluoro-2-(1-(2-(morpholin-4-yl)ethyl)-1H-pyrrolo[2,3-b]pyridin-4-ylamino)nicotinamide;
6-(cis-2-aminocyclohexylamino)-5-fluoro-2-[1,3]thiazolo[4,5-b]pyridin-6-ylamino)nicotinamide;
6-(cis-2-aminocyclohexylamino)-2-(1-(2-(diethylamino)ethyl)-1H-pyrrolo[2,3-b]pyridin-4-ylamino)-5-fluoronicotinamide;
6-(cis-2-aminocyclohexylamino)-5-fluoro-2-(1-(2-methoxyethyl)-1H-pyrrolo[2,3-b]pyridin-4-ylamino)nicotinamide;
6-(cis-2-aminocyclohexylamino)-5-fluoro-2-(1-isobutyl-1H-pyrrolo[2,3-b]pyridin-4-ylamino)nicotinamide;
6-(cis-2-aminocyclohexylamino)-2-(1-cyclopropyl-1H-pyrrolo[2,3-b]pyridin-4-ylamino)-5-fluoronicotinamide;
6-(cis-2-aminocyclohexylamino)-2-(1-(cyclopropylmethyl)-1H-pyrrolo[2,3-b]pyridin-4-ylamino)-5-fluoronicotinamide;
6-(cis-2-aminocyclohexylamino)-5-fluoro-2-(5-(2H-1,2,3-triazol-2-yl)pyridin-3-ylamino)-nicotinamide;
6-(cis-2-aminocyclohexylamino)-5-fluoro-2-(5-(1H-pyrrol-2-yl)pyridin-3-ylamino)nicotinamide;
6-(cis-2-aminocyclohexylamino)-5-fluoro-2-(5-(2-thienyl)pyridin-3-ylamino)nicotinamide;
6-(cis-2-aminocyclohexylamino)-2-(5-cyclopropylpyridin-3-ylamino)-5-fluoronicotinamide;
6-(cis-2-aminocyclohexylamino)-5-fluoro-2-(5-(2-furyl)pyridin-3-ylamino)nicotinamide;
6-(cis-2-aminocyclohexylamino)-2-(8-aminoquinolin-3-ylamino)-5-fluoronicotinamide;
6-(cis-2-aminocyclohexylamino)-5-fluoro-2-(1H-pyrrolo[2,3-b]pyridin-4-ylamino)nicotinamide;
6-(cis-2-aminocyclohexylamino)-5-fluoro-2-(1H-pyrrolo[2,3-b]pyridin-5-ylamino)nicotinamide;
6-(cis-2-aminocyclohexylamino)-5-fluoro-2-(1H-pyrrolo[2,3-c]pyridin-4-ylamino)nicotinamide;
2-(8-(aminocarbonyl)aminoquinolin-3-ylamino)-6-(cis-2-aminocyclohexylamino)-5-fluoronicotinamide;
6-(2-aminoethylamino)-5-fluoro-2-(pyridin-4-ylamino)nicotinamide;
6-(2-aminoethylamino)-5-fluoro-2-(quinolin-6-ylamino)nicotinamide;
6-(cis-2-aminocyclohexylamino)-2-(2,1,3-benzothiadiazol-5-ylamino)-5-fluoronicotinamide;
6-(cis-2-aminocyclohexylamino)-2-(1,3-benzothiazol-6-ylamino)-5-fluoronicotinamide;
6-(cis-2-aminocyclohexylamino)-5-fluoro-2-(1-methyl-1H-indazol-6-ylamino)nicotinamide;
6-(cis-2-aminocyclohexylamino)-5-fluoro-2-(2-methyl-1,3-benzoxazol-6-ylamino)nicotinamide;
6-(2-aminoethylamino)-2-(1,3-benzothiazol-6-ylamino)-5-fluoronicotinamide;
6-(cis-2-aminocyclohexylamino)-5-fluoro-2-(2-methyl-1,3-benzoxazol-5-ylamino)nicotinamide;
6-(cis-2-aminocyclohexylamino)-5-fluoro-2-(5-methylpyridin-3-ylamino)nicotinamide;
6-(cis-2-aminocyclohexylamino)-2-(1,3-dimethyl-1H-pyrazolo[3,4-b]pyridin-5-ylamino)-5-fluoronicotinamide;
6-(cis-2-aminocyclohexylamino)-2-(2,3-dihydro-1,4-benzodioxin-6-ylamino)-5-fluoronicotinamide;
6-(cis-2-aminocyclohexylamino)-5-fluoro-2-(3-(2H-1,2,3-triazol-2-yl)phenylamino)nicotinamide;
6-(cis-2-aminocyclohexylamino)-5-fluoro-2-(6-methoxyquinolin-3-ylamino)nicotinamide;
6-(cis-2-aminocyclohexylamino)-5-fluoro-2-(quinolin-5-ylamino)nicotinamide;
6-(cis-2-aminocyclohexylamino)-5-fluoro-2-(quinoxalin-6-ylamino)nicotinamide;
6-(cis-2-aminocyclohexylamino)-2-(1,3-benzothiazol-5-ylamino)-5-fluoronicotinamide;
6-(2-aminoethylamino)-5-fluoro-2-(isoquinolin-4-ylamino)nicotinamide;
6-(2-aminoethylamino)-5-fluoro-2-(quinolin-5-ylamino)nicotinamide;
6-(cis-2-aminocyclohexylamino)-5-fluoro-2-(1-methyl-1H-indazol-5-ylamino)nicotinamide;
6-(cis-2-aminocyclohexylamino)-5-fluoro-2-(1-methyl-1H-benzoimidazol-6-ylamino) nicotinamide;
6-(cis-2-aminocyclohexylamino)-5-fluoro-2-(quinazolin-6-ylamino)nicotinamide;
6-(cis-2-aminocyclohexylamino)-5-fluoro-2-(quinazolin-7-ylamino)nicotinamide;
cis-6-(2-aminocyclohexylamino)-5-fluoro-2-(1-methyl-1H-benzoimidazol-5-ylamino)nicotinamide;
6-(cis-2-aminocyclohexylamino)-5-fluoro-2-(2-methylquinolin-6-ylamino)nicotinamide;
6-(cis-2-aminocyclohexylamino)-5-fluoro-2-(quinolin-7-ylamino)nicotinamide;
6-(cis-2-aminocyclohexylamino)-5-fluoro-2-(1-methyl-1H-indazol-4-ylamino)nicotinamide;
6-(cis-2-aminocyclohexylamino)-5-fluoro-2-(2-methylquinoxalin-6-ylamino)nicotinamide;
6-(cis-2-aminocyclohexylamino)-5-fluoro-2-(1-(2-(pyrrolidin-1-yl)ethyl)-1H-indazol-5-ylamino)nicotinamide;

6-(cis-2-aminocyclohexylamino)-5-fluoro-2-(2-(2-(pyrrolidin-1-yl)ethyl)-2H-indazol-5-ylamino)nicotinamide;
6-(cis-2-aminocyclohexylamino)-5-fluoro-2-(1H-indazol-5-ylamino)nicotinamide;
6-(2-aminoethylamino)-2-(3,5-dimethoxyphenylamino)-5-fluoronicotinamide;
6-(cis-2-aminocyclohexylamino)-5-fluoro-2-(quinolin-3-ylamino)nicotinamide;
6-(cis-2-aminocyclohexylamino)-5-fluoro-2-(quinolin-6-ylamino)nicotinamide;
6-(cis-2-aminocyclohexylamino)-2-(3-chlorophenylamino)-5-fluoronicotinamide;
6-(2-aminoethylamino)-5-fluoro-2-(quinolin-3-ylamino)nicotinamide;
6-(cis-2-aminocyclohexylamino)-5-fluoro-2-(isoquinolin-4-ylamino)nicotinamide;
6-(cis-2-aminocyclohexylamino)-5-fluoro-2-(1,8-naphthyridin-3-ylamino)nicotinamide;
5-fluoro-6-(2-(1H-imidazol-5-yl)ethylamino)-2-(quinolin-3-ylamino)nicotinamide;
6-((1R)-2-amino-2-oxo-1-phenylethylamino)-5-fluoro-2-(quinolin-6-ylamino)nicotinamide;
6-((2R)-1-amino-4-methyl-1-oxopentan-2-ylamino)-5-fluoro-2-(quinolin-6-ylamino)nicotinamide;
6-((2R)-1-amino-1-oxobutan-2-ylamino)-5-fluoro-2-(quinolin-6-ylamino)nicotinamide;
6-((2S)-2-aminobutylamino)-5-fluoro-2-(quinolin-6-ylamino)nicotinamide;
6-((2S)-2-amino-3-methylbutylamino)-5-fluoro-2-(quinolin-6-ylamino)nicotinamide
6-((2S)-2-amino-2-phenylethylamino)-5-fluoro-2-(quinolin-6-ylamino)nicotinamide;
6-((2R)-2-amino-3-methoxypropylamino)-5-fluoro-2-(quinolin-6-ylamino)nicotinamide;
6-((2S)-2-aminopropylamino)-5-fluoro-2-(quinolin-6-ylamino)nicotinamide;
6-((2S)-2-amino-4-methylpentylamino)-5-fluoro-2-(quinolin-6-ylamino)nicotinamide;
6-(3-aminopropylamino)-2-(3,5-dimethoxyphenylamino)-5-fluoronicotinamide;
6-(cis-2-aminocyclohexylamino)-2-(3,5-dimethoxyphenylamino)-5-fluoronicotinamide;
6-((1R,2S)-2-aminocyclohexylamino)-2-(3,5-dimethoxyphenylamino)-5-fluoronicotinamide;
6-(cis-2-aminocyclohexylamino)-5-chloro-2-(quinolin-3-ylamino)nicotinamide;
6-(cis-2-aminocyclohexylamino)-5-bromo-2-(quinolin-3-ylamino)nicotinamide;
6-(cis-2-aminocyclohexylamino)-5-chloro-2-(3-methoxyphenylamino)nicotinamide;
6-(cis-2-aminocyclohexylamino)-5-chloro-2-(5-methylpyridin-3-ylamino)nicotinamide; and
6-(cis-2-aminocyclohexylamino)-5-bromo-2-(5-methylpyridin-3-ylamino)nicotinamide.

The compound represented by the formula [1] of the present invention is preferably a compound having a Syk-inhibitory activity IC50, which is 50 nM or less and also having IC50 in a TNFα generation assay, which is 130 nM or less. More specific examples of such a compound include compounds wherein, in Table 21 that shows the results of a test performed according to a test method described in a "Syk enzyme assay" in Test Example 1 below, the Syk-inhibitory activity $IC_{50}$ is 50 nM or less (that is, evaluation standards are A and B), and in Table 22 that shows the results of a test performed according to a test method described in a "TNFα generation assay" in Test Example 2 below, the $IC_{50}$ is 130 nM or less (that is, evaluation standards are A and B).

Preferred examples of the compound represented by the formula [1] of the present invention include the following compounds.
Example 4-17: 6-(cis-2-aminocyclohexylamino)-5-fluoro-2-(6-methylpyridin-3-ylamino)nicotinamide;
Example 4-228: 6-((cis-2-aminocyclohexyl)amino)-2-((5-cyano-6-morpholinopyridin-3-yl)amino)-5-fluoronicotinamide;
Example 6-49: 6-(cis-2-aminocyclohexylamino)-5-fluoro-2-(5-methylpyridin-3-ylamino)nicotinamide;
Example 6-117:
(R)-6-((1-amino-4-methylpentan-2-yl)amino)-5-fluoro-2-((quinolin-6-yl)amino)nicotinamide;
Example 6-157: (R)-6-(1-amino-4-methylpentan-2-yl)amino)-5-fluoro-2-((2-(2-methoxyethoxy)pyridin-4-yl)amino)nicotinamide;
Example 6-165:
64-(1R,2S)-2-aminocyclohexylamino)-5-fluoro-2-((6-morpholinopyridin-3-yl)amino)nicotinamide;
Example 6-168:
2-((5-(1H-pyrazol-1-yl)pyridin-3-yl)amino)-6-((1R,2S)-2-aminocyclohexylamino)-5-fluoronicotinamide;
Example 6-177:
(R)-6-((1-amino-4-methylpentan-2-yl)amino)-2-((5,6-dimethylpyridin-3-yl)amino)-5-fluoronicotinamide;
Example 6-211:
6-(((2S,3R)-2-aminopentane3-yl)amino)-2-((1-ethyl-1H-indazol-5-yl)amino)-5-fluoronicotinamide;
Example 6-249:
6-(((2S,3R)-2-aminohexane-3-yl)amino)-5-fluoro-2-((2-methoxypyridin-4-yl)amino)nicotinamide;
Example 6-257:
6-(((2S,3R)-2-aminopentane3-yl)amino)-5-fluoro-2-((5-(2-fluorophenyl)pyridin-3-yl)amino)nicotinamide;
Example 6-263:
6-(((2S,3R)-2-aminopentane3-yl)amino)-5-fluoro-2-((1-methoxyisoquinolin-6-yl)amino)nicotinamide;
Example 6-268:
6-(((2S,3R)-2-aminopentane3-yl)amino)-5-fluoro-2-((1-methyl-1H-indazol-4-yl)amino)nicotinamide;
Example 6-296:
6-(((2S,3R)-2-aminohexane3-yl)amino)-2-((5,6-dimethylpyridin-3-yl)amino)-5-fluoronicotinamide;
Example 6-301:
6-(((2S,3R)-2-aminohexane3-yl)amino)-5-fluoro-2-((5-fluoropyridin-3-yl)amino)nicotinamide;
Example 6-311
6-(((2S,3R)-2-aminohexane3-yl)amino)-5-fluoro-2-((2-propoxypyridin-4-yl)amino)nicotinamide;
Example 6-322:
(R)-6-((1-amino-4-methylpentan-2-yl)amino)-2-((1-ethyl-1H-indazol-5-yl)amino)-5-fluoronicotinamide;
Example 6-342:
6-(((2R,3S)-3-amino-1-cyclopropylbutan-2-yl)amino)-2-((1-ethyl-1H-indazol-5-yl)amino)-5-fluoronicotinamide;
Example 6-368:
6-(((1R,2S)-2-amino-1-cyclopropylpropyl)amino)-5-fluoro-2-(quinolin-6-ylamino)nicotinamide;
Example 6-375:
6-(((1R,2S)-2-aminocyclohexyl)amino)-5-fluoro-2-((6-methyl-5-(2H-1,2,3-triazol-2-yl)pyridin-3-yl)amino)nicotinamide;
Example 6-377:
6-(((1R,2S)-2-aminocyclohexyl)amino)-5-fluoro-2-((6-methoxy-5-(2H-1,2,3-triazol-2-yl)pyridin-3-yl)amino)nicotinamide;

Example 6-383:
6-(((2S,3R)-2-amino-5-methylhexane3-yl)amino)-5-fluoro-2-((1-methyl-1H-indazol-5-yl)amino)nicotinamide;
Example 6-384:
6-(((2S,3R)-2-amino-5-methylhexane3-yl)amino)-2-((1-ethyl-1H-indazol-5-yl)amino)-5-fluoronicotinamide;
Example 6-395:
6-(((1R,2S)-2-aminocyclohexyl)amino)-5-fluoro-2-((5-fluoro-6-morpholinopyridin-3-yl)amino)nicotinamide;
Example 6-433:
6-(((1R,2S)-2-aminocyclohexyl)amino)-2-(2-ethoxy-3-fluoropyridin-4-yl)amino)-5-fluoronicotinamide;
Example 6-435:
6-(((2R,3S)-3-amino-1-cyclopropylbutan-2-yl)amino)-2-((5,6-dimethylpyridin-3-yl)amino)-5-fluoronicotinamide;
Example 6-468:
6-(((2S,3S)-3-amino-1-methoxybutan-2-yl)amino)-5-fluoro-2-(quinolin-6-ylamino)nicotinamide; and
Example 8-1: 6-(2-aminoethylamino)-2-(3,5-dimethoxyphenylamino)-5-fluoronicotinamide.

The pharmaceutical composition of the present invention is characterized in that it comprises the above-described nicotinamide derivative of the present invention or a salt thereof. The pharmaceutical composition of the present invention can be preferably used as a pharmaceutical composition for the treatment of a Syk-related disease.

An example of the Syk-related disease is a disease selected from the group consisting of rheumatism and idiopathic thrombocytopenic purpura. The pharmaceutical composition of the present invention can be preferably used as a pharmaceutical composition for the treatment of these diseases.

When isomers (for example, optical isomers, geometric isomers, tautomers, etc.) are present in the compound represented by the formula [1] or a salt thereof, the present invention includes these isomers. In addition, the present invention also includes solvates, hydrates, and various forms of crystals.

Next, a method for producing the compound of the present invention will be described.

The compound of the present invention can be produced by combining well-known methods. For example, the present compound can be produced according to production methods as described below.

[Production Method 1]

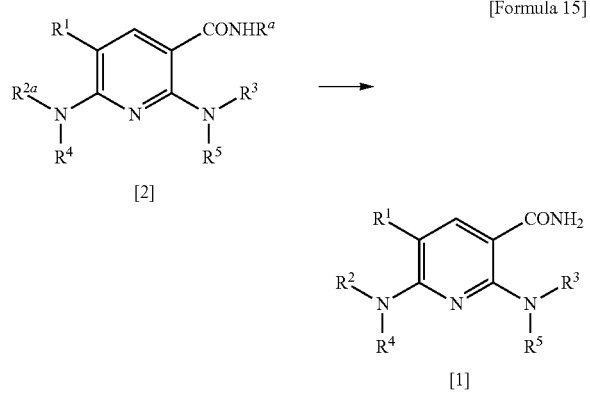

[Formula 15]

wherein $R^{2a}$ represents a $C_{1-12}$ alkyl, $C_{2-12}$ alkenyl, $C_{2-12}$ alkynyl, $C_{3-8}$ cycloalkyl, aryl, ar-$C_{1-6}$ alkyl or heterocyclic group, having at least one amino group protected by an amino-protecting group; $R^a$ represents an amino-protecting group; and $R^1$, $R^2$, $R^3$, $R^4$ and $R^5$ have the same meanings as those described above.

The compound of the formula [1] can be produced by deprotecting the compound of the formula [2] in the presence of an acid. This reaction can be carried out, for example, by the method described in W. Greene et al., Protective Groups in Organic Synthesis, 4th edition, pp. 696 to 926, 2007, John Wiley & Sons, INC.

Examples of the acid used in this reaction include: inorganic acids such as hydrochloric acid, sulfuric acid, phosphoric acid, hydrogen chloride, and hydrogen bromide; organic carboxylic acids such as acetic acid, trichloroacetic acid, and trifluoroacetic acid; and organic sulfonic acids such as methanesulfonic acid and p-toluenesulfonic acid.

The acid may be used in a molar concentration 1 time or more, and preferably 1 to 5 times, as compared with that of the compound of the formula [2]. In addition, the acid may be used as a solvent.

This reaction may be carried out in the coexistence of a solvent, as necessary. The solvent used is not particularly limited, as long as it does not affect the reaction. Examples of such a solvent include aliphatic hydrocarbons, halogenated hydrocarbons, alcohols, glycols, ethers, ketones, esters, amides, nitriles, sulfoxides, aromatic hydrocarbons, and water. These solvents may be used in combination.

It is preferable to use an acid or an aqueous solution of an acid as a solvent.

This reaction may be carried out at a temperature from 0° C. to the boiling point of a solvent, and preferably from 10° C. to 40° C., for 1 minute to 24 hours.

[Production Method 2]

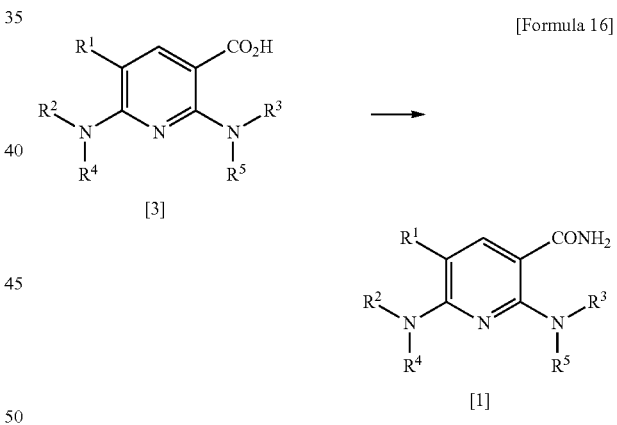

[Formula 16]

wherein $R^1$, $R^2$, $R^3$, $R^4$ and $R^5$ have the same meanings as those described above.

The compound of the formula [1] can be produced by allowing the compound of the formula [3] to react with ammonia or ammonium salts in the presence of a condensation agent and in the presence of a base.

The solvent used in this reaction is not particularly limited, as long as it does not affect the reaction. Examples of such a solvent include aliphatic hydrocarbons, halogenated hydrocarbons, alcohols, glycols, ethers, ketones, esters, amides, nitriles, sulfoxides, aromatic hydrocarbons, and water. These solvents may be used in combination.

Preferred solvents are amides.

Examples of the condensation agent used in this reaction include: carbodiimides such as N,N'-dicyclohexylcarbodiimide and N-ethyl-N'-(3-dimethylaminopropyl)carbodiimide;

carbonyls such as carbonyldiimidazole; acid azides such as diphenylphosphoryl azide; acid cyanides such as diethylphosphoryl cyanide; 2-ethoxy-1-ethoxycarbonyl-1,2-dihydroquinoline; O-benzotriazol-1-yl-1,1,3,3-tetramethyluronium hexafluorophosphate; and O-(7-azabenzotriazol-1-yl)-1,1,3,3-tetramethyluronium hexafluorophosphate.

Examples of the base used in this reaction include: metal alkoxides such as sodium methoxide, sodium ethoxide, potassium tert-butoxide, and sodium tert-butoxide; inorganic bases such as sodium hydroxide, potassium hydroxide, sodium hydrogencarbonate, sodium carbonate, potassium carbonate, sodium hydride, and potassium hydride; and organic bases such as triethylamine, diisopropylethylamine, and pyridine.

Examples of the ammonium salts include ammonium chloride, ammonium bromide, and ammonium acetate.

Ammonia or ammonium salts may be used in a molar concentration 1 to 100 times, and preferably 1 to 10 times, as compared with than that of the compound of the formula [3].

The condensation agent and the base may each be used in a molar concentration 1 time or more, and preferably 1 to 5 times, as compared with that of the compound of the formula [3].

This reaction may be carried out in the presence of a reaction promoter.

Examples of such a reaction promoter include 1-hydroxybenzotriazole and N-hydroxysuccinimide.

The reaction promoter may be used in a molar concentration 1 time or more, and preferably 1 to 5 times, as compared with than that of the compound of the formula [3].

This reaction may be carried out at a temperature from −20° C. to 150° C., and preferably from 0° C. to 100° C., for 1 minute to 24 hours.

[Production Method 3]

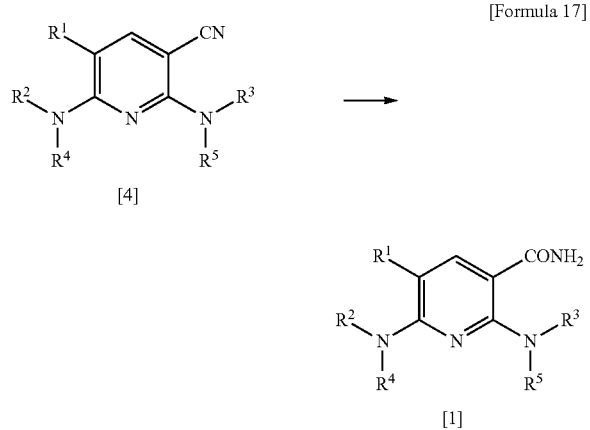

wherein $R^1$, $R^2$, $R^3$, $R^4$ and $R^5$ have the same meanings as those described above.

The compound of the formula [1] can be produced by hydrolyzing the compound of the formula [4] in the presence of a base and in the presence of a hydrogen peroxide solution.

The solvent used in this reaction is not particularly limited, as long as it does not affect the reaction. Examples of such a solvent include aliphatic hydrocarbons, halogenated hydrocarbons, alcohols, glycols, ethers, ketones, esters, amides, sulfoxides, aromatic hydrocarbons, and water. These solvents may be used in combination.

Preferred solvents are alcohols and water.

Examples of the base used in this reaction include: metal alkoxides such as sodium methoxide, sodium ethoxide, potassium tert-butoxide, and sodium tert-butoxide; inorganic bases such as sodium hydroxide, potassium hydroxide, sodium hydrogencarbonate, sodium carbonate, potassium carbonate, sodium hydride, and potassium hydride; and organic bases such as triethylamine, diisopropylethylamine, and pyridine.

The base may be used in a molar concentration 1 time or more, and preferably 1 to 5 times, as compared with than that of the compound of the formula [4].

The hydrogen peroxide may be used in a molar concentration 1 time or more, and preferably 1 to 10 times, as compared with that of the compound of the formula [4].

This reaction may be carried out at a temperature from 0° C. to the boiling point of a solvent, and preferably from 10° C. to 40° C., for 1 minute to 24 hours.

[Production Method 4]

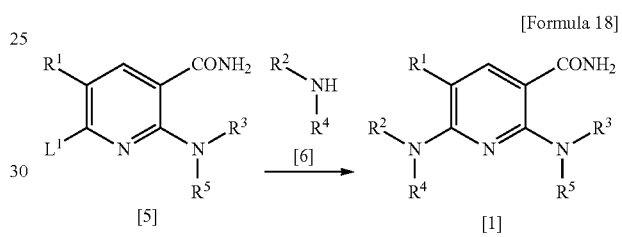

wherein $L^1$ represents a benzotriazol-1-yloxy group or a succinimido-1-yloxy group; and $R^1$, $R^2$, $R^3$, $R^4$ and $R^5$ have the same meanings as those described above.

The compound of the formula [1] can be produced by allowing the compound of the formula [5] to react with the compound of the formula [6] in the presence of a base.

For example, tryptophan is known as a compound of the formula [6].

The solvent used in this reaction is not particularly limited, as long as it does not affect the reaction. N-methylmorpholine is preferable.

Examples of the base used in this reaction include: inorganic bases such as sodium hydrogencarbonate, sodium carbonate, potassium carbonate, cesium carbonate, and tripotassium phosphate; and organic bases such as pyridine, 4-(dimethylamino)pyridine, triethylamine, and diisopropylethylamine.

The base may be used in a molar concentration 1 to 50 times, and preferably 1 to 5 times, as compared with that of the compound of the formula [5].

The compound of the formula [6] may be used in a molar concentration 1 to 50 times, and preferably 1 to 2 times, as compared with that of the compound of the formula [5].

This reaction may be carried out at a temperature from 0° C. to the boiling point of a solvent, and preferably from 0° C. to 150° C., for 1 minute to 24 hours.

Next, a method for producing the compounds represented by the formulae [2], [3], [4] and [5], which are used as raw materials in the production of the compound of the present invention, will be described.

[Production Method A1]

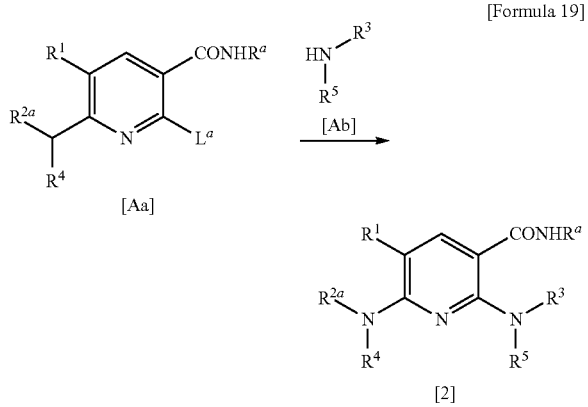

wherein $L^a$ represents a leaving group; and $R^1$, $R^{2a}$, $R^3$, $R^4$, $R^5$ and $R^a$ have the same meanings as those described above.

The compound of the formula [2] can be produced by allowing the compound of the formula [Aa] to react with the compound of the formula [Ab] in the presence or absence of a base, in the presence of a palladium catalyst, and in the presence or absence of a ligand.

The compound of the formula [Aa] can be produced, for example, by a Production Method A2 as described later.

For example, 6-aminoquinoline is known as a compound of the formula [Ab].

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These solvents may be used in combination.

Preferred solvents are ethers.

Examples of the base used in this reaction as desired include: inorganic bases such as sodium hydrogencarbonate, sodium carbonate, potassium carbonate, cesium carbonate, and tripotassium phosphate; and organic bases such as pyridine, 4-(dimethylamino)pyridine, triethylamine, and diisopropylethylamine.

The base may be used in a molar concentration 1 to 50 times, and preferably 1 to 5 times, as compared with that of the compound of the formula [Aa].

Examples of the palladium catalyst used in this reaction include: metallic palladium such as palladium carbon and palladium black; inorganic palladium salts such as palladium chloride; organic palladium salts such as palladium acetate; organic palladium complexes such as tetrakis(triphenylphosphine)palladium (0), bis(triphenylphosphine)palladium (II) chloride, 1,1'-bis(diphenylphosphino)ferrocene-palladium (II) chloride, and tris(dibenzylideneacetone)dipalladium (0); and polymer-bound organic palladium complexes such as polymer-supported bis(acetate)triphenylphosphine palladium (II) and polymer-supported di(acetate)dicyclohexylphenylphosphine palladium (II). These compounds may be used in combination.

The palladium catalyst may be used in a molar concentration 0.00001 to 1 time, and preferably 0.001 to 0.1 time, as compared with that of the compound of the formula [Aa].

Examples of the ligand used in this reaction as desired include: trialkylphosphines such as trimethylphosphine and tri-tert-butylphosphine; tricycloalkylphosphines such as tricyclohexylphosphine; triarylphosphines such as triphenylphosphine and tritolylphosphine; trialkylphosphites such as trimethylphosphite, triethylphosphite, and tributylphosphite; tricycloalkylphosphites such as tricyclohexylphosphite; triarylphosphites such as triphenylphosphite; imidazolium salts such as 1,3-bis(2,4,6-trimethylphenyl)imidazolium chloride; diketones such as acetylacetone and octafluoroacetylacetone; amines such as trimethylamine, triethylamine, tripropylamine, and triisopropylamine; and 4,5-bis(diphenylphosphino)-9,9-dimethyl-xanthene, 1,1'-bis(diphenylphosphino)ferrocene, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, 2-(di-tert-butylphosphino)-2',4',6'-triisopropylbiphenyl, and 2-(di-tert-butylphosphino)biphenyl. These compounds may be used in combination.

The ligand may be used in a molar concentration 0.00001 to 1 time, and preferably 0.001 to 0.5 time, as compared with that of the compound of the formula [Aa].

The compound of the formula [Ab] may be used in a molar concentration 1 to 50 times, and preferably 1 to 2 times, as compared with that of the compound of the formula [Aa].

This reaction may be preferably carried out in an inert gas (e.g. nitrogen, argon) atmosphere at a temperature from 40° C. to 170° C. for 1 minute to 96 hours.

[Production Method A2]

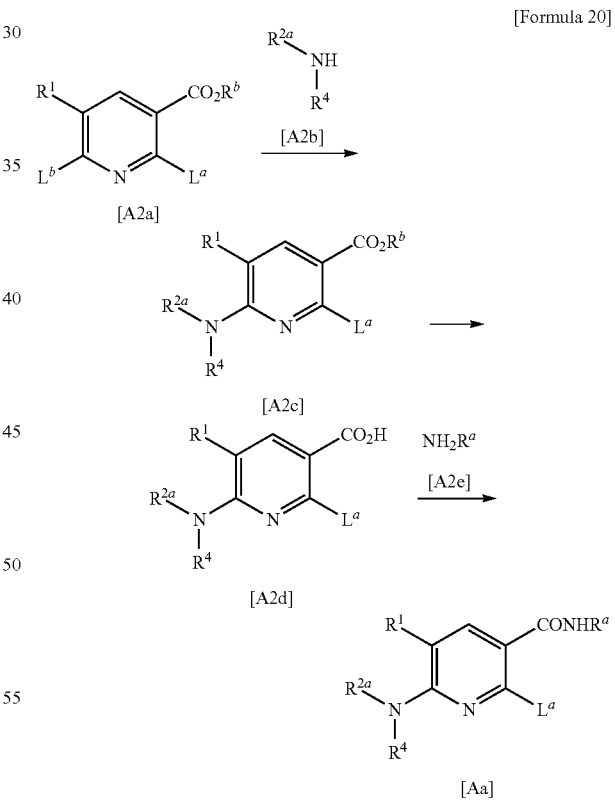

wherein $R^b$ represents a carboxyl-protecting group; $L^b$ represents a leaving group; and $R^1$, $R^{2a}$, $R^4$, $R^a$ and $L^a$ have the same meanings as those described above.

(A2-1)

The compound of the formula [A2c] can be produced by allowing the compound of the formula [A2a] to react with the compound of the formula [A2b] in the presence of a base.

For example, methyl 2,6-dichloro-5-fluoronicotinate is known as a compound of the formula [A2a].

For example, tert-butyl (2-aminoethyl)carbamate and tert-butyl(2-aminocyclohexyl)carbamate are known as compounds of the formula [A2b].

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These solvents may be used in combination.

Preferred solvents are amides and ethers.

Examples of the base used in this reaction include: inorganic bases such as sodium hydrogencarbonate, sodium carbonate, potassium carbonate, cesium carbonate, and tripotassium phosphate; and organic bases such as pyridine, 4-(dimethylamino)pyridine, triethylamine, and diisopropylethylamine.

The base may be used in a molar concentration 1 to 50 times, and preferably 1 to 5 times, as compared with that of the compound of the formula [A2a].

The compound of the formula [A2b] may be used in a molar concentration 1 to 50 times, and preferably 1 to 2 times, as compared with that of the compound of the formula [A2a].

This reaction may be carried out at a temperature from 0° C. to the boiling point of a solvent, and preferably from 10° C. to 40° C., for 1 minute to 24 hours.

The compound of the formula [A2c] can also be produced by allowing the compound of the formula [A2a] to react with ethylenediamine, cyclohexanediamine or the like in the presence of a base in accordance with the above-described production method, and then protecting an amino group.

Protection of an amino group can be carried out, for example, by the method described in W. Greene et al., Protective Groups in Organic Synthesis, 4th edition, pp. 696 to 926, 2007, John Wiley & Sons, INC.

(A2-2)

The compound of the formula [A2d] can be produced by hydrolyzing the compound of the formula [A2c] in the presence of an acid or a base.

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These solvents may be used in combination.

Preferred solvents are alcohols and water.

Examples of the acid used in this reaction include mineral acids such as hydrochloric acid, hydrobromic acid, and sulfuric acid.

The acid may be used in a molar concentration 1 to 1000 times, and preferably 1 to 100 times, as compared with that of the compound of the formula [A2c].

Examples of the base used in this reaction include inorganic bases such as sodium hydroxide, potassium hydroxide, sodium hydrogencarbonate, sodium carbonate, potassium carbonate, sodium hydride, and potassium hydride.

The base may be used in a molar concentration 1 to 1000 times, and preferably 1 to 10 times, as compared with that of the compound of the formula [A2c].

This reaction may be carried out at a temperature from 0° C. to the boiling point of a solvent, and preferably from 0° C. to 100° C., for 1 minute to 24 hours.

(A2-3)

The compound of the formula [Aa] can be produced by allowing the compound of the formula [A2d] to react with the compound of the formula [A2d] in accordance with the Production Method 2.

For example, 2-phenyl-2-propanamine is known as a compound of the formula [A2e].

[Production Method B1]

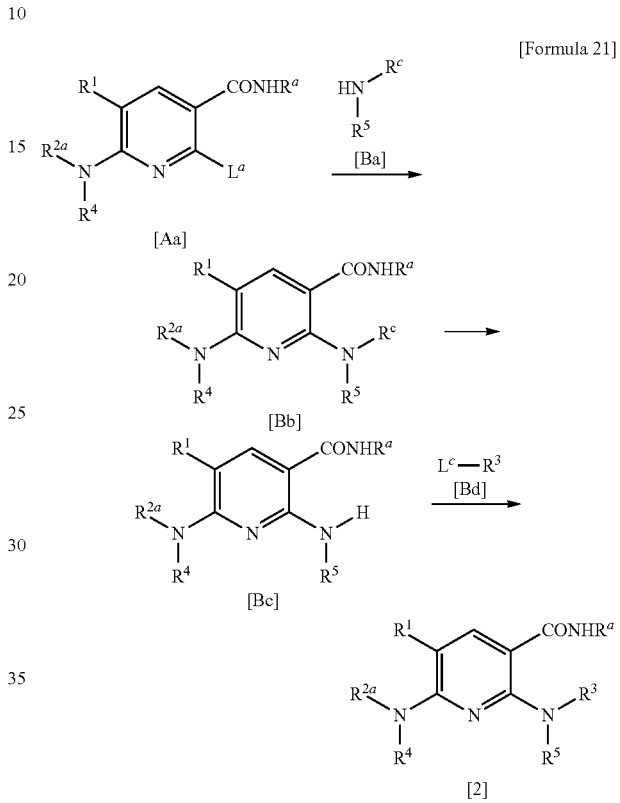

[Formula 21]

wherein $R^c$ represents an amino-protecting group; $L^c$ represents a leaving group; and $R^1$, $R^{2a}$, $R^3$, $R^4$, $R^5$, $R^a$ and $L^a$ have the same meanings as those described above.

(B1-1)

The compound of the formula [Bb] can be produced by allowing the compound of the formula [Aa] to react with the compound of the formula [Ba] in accordance with the Production Method A1.

For example, benzylamine is known as a compound of the formula [Ba].

(B1-2)

The compound of the formula [Bc] can be produced by deprotecting the compound of the formula [Bb]. This reaction can be carried out, for example, by the method described in W. Greene et al., Protective Groups in Organic Synthesis, 4th edition, pp. 696 to 926, 2007, John Wiley & Sons, INC.

When $R^c$ is, for example, a benzyl group, a 4-methoxybenzyl group or a 2,4-dimethoxybenzyl group, the compound of the formula [Bc] can be produced by reducing the compound of the formula [Bb] in the presence of a metal catalyst.

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These solvents may be used in combination.

Preferred solvents are alcohols and ethers.

Examples of the metal catalyst used in this reaction include: metallic palladium such as palladium carbon and palladium black; palladium salts such as palladium oxide and palladium hydroxide; nickel metals such as Raney nickel; and platinum salts such as platinum oxide.

The metal catalyst may be used in an amount 0.001 to 5 times (W/W), and preferably 0.01 to 1 time (W/W), as compared with the amount of the compound of the formula [Bb].

Examples of the reducing agent include: hydrogen; formic acid; formates such as sodium formate, ammonium formate, and triethyl ammonium formate; and cyclohexene and cyclohexadiene.

The reducing agent may be used in a molar concentration 2 to 100 times, and preferably 2 to 10 times, as compared with that of the compound of the formula [Bb].

This reaction may be carried out at a temperature from 0° C. to the boiling point of a solvent, and preferably from 10° C. to 40° C., for 1 minute to 24 hours.

(B1-3)

The compound of the formula [2] can be produced by allowing the compound of the formula [Bc] to react with the compound of the formula [Bd] in accordance with the Production Method A1.

For example, 2-methyl-5-chloropyridine is known as a compound of the formula [Bd].

[Production Method B2]

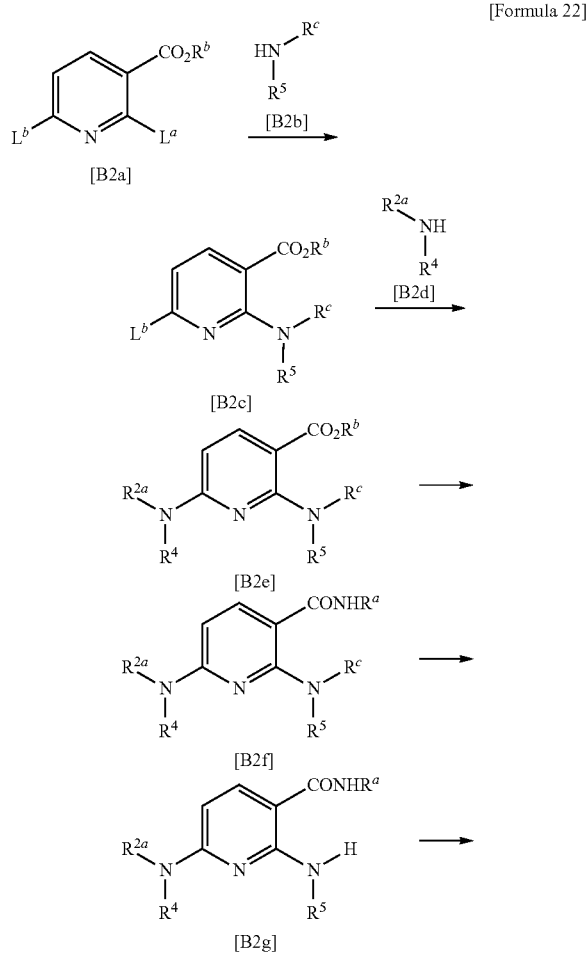

[Formula 22]

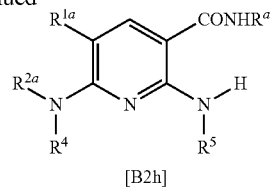

[B2h]

wherein $R^{1a}$ represents a chlorine atom or a bromine atom; and $R^{2a}, R^4, R^5, R^a, R^b, R^c, L^a$ and $L^b$ have the same meanings as those described above.

(B2-1)

The compound of the formula [B2c] can be produced by allowing the compound of the formula [B2a] to react with the compound of the formula [B2b] in accordance with the Production Method A2-1.

For example, ethyl 2,6-dichloronicotinate is known as a compound of the formula [B2a].

For example, benzylamine is known as a compound of the formula [B2b].

(B2-2)

The compound of the formula [B2e] can be produced by allowing the compound of the formula [B2c] to react with the compound of the formula [B2d] in the presence of a base.

For example, tert-butyl (2-aminoethyl)carbamate and tert-butyl (2-aminocyclohexyl)carbamate are known as compounds of the formula [B2d].

The solvent used in this reaction is not particularly limited, as long as it does not affect the reaction. N-methylmorpholine is preferable.

Examples of the base used in this reaction include: inorganic bases such as sodium hydrogencarbonate, sodium carbonate, potassium carbonate, cesium carbonate, and tripotassium phosphate; and organic bases such as pyridine, 4-(dimethylamino)pyridine, triethylamine, and diisopropylethylamine.

The base may be used in a molar concentration 1 to 50 times, and preferably 1 to 5 times, as compared with that of the compound of the formula [B2c].

The compound of the formula [B2d] may be used in a molar concentration 1 to 50 times, and preferably 1 to 2 times, as compared with that of the compound of the formula [B2c].

This reaction may be preferably carried out at a temperature from 100° C. to 200° C. for 1 minute to 48 hours.

The compound of the formula [B2e] can also be produced by allowing the compound of the formula [B2c] to react with ethylenediamine, cyclohexanediamine or the like in the presence of a base in accordance with the above-described production method, and then protecting an amino group.

Protection of an amino group can be carried out, for example, by the method described in W. Greene et al., Protective Groups in Organic Synthesis, 4th edition, pp. 696 to 926, 2007, John Wiley & Sons, INC.

(B2-3)

The compound of the formula [B2f] can be produced from the compound of the formula [B2e] in accordance with the Production Methods A2-2 and A2-3.

(B2-4)

The compound of the formula [B2g] can be produced by deprotecting the compound of the formula [B2f] in accordance with the Production Method B1-2.

(B2-5)

The compound of the formula [B2h] can be produced by halogenating the compound of the formula [B2g] in the presence of a halogenating agent.

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These solvents may be used in combination.

Preferred solvents are amides.

Examples of the halogenating agent used in this reaction include: halogens such as chlorine and bromine; imides such as N-chlorosuccinimide, N-bromosuccinimide, N-chlorophthalimide, and N-bromophthalimide; hydantoins such as 1,3-dibromo-5,5-dimethylhydantoin, and 1,3-dichloro-5,5-dimethylhydantoin; and sulfuryl chloride.

Preferred halogenating agents include imides.

The halogenating agent may be used in a molar concentration 1 time or more, and preferably 1 to 3 times, as compared with that of the compound of the formula [B2g].

This reaction is preferably carried out in the presence of a radical generator.

The radical generator is not particularly limited, as long as it is a commonly used radical generator. Examples of such a radical generator include: dialkyl peroxides such as di-tert-butyl peroxide, di-tert-amyl peroxide, and di(2-methyl-2-pentyl)peroxide; diacyl peroxides such as dibenzoyl peroxide, dicumyl peroxide and diphthaloyl peroxide; alkyl hydroperoxides such as tert-butyl hydroperoxide and cumyl hydroperoxide; percarboxylic acids such as perbenzoic acid, monoperoxyphthalic acid, performic acid, and peracetic acid; peroxo compounds of inorganic acids, such as persulfuric acid; and organic azo compounds such as 2,2'-azobisisobutyronitrile, 2,2'-azobis(2,4-dimethylvaleronitrile), 2,2'-azobis(2-methylbutyronitrile), 2,2'-azobisisovaleronitrile, 1,1'-azobis(cyclohexanecarbonitrile), 2,2'-azobis(4-methoxy-2,4-dimethylvaleronitrile), 2,2'-azobis(2-amidinopropane) dihydrochloride, and dimethyl 2,2'-azobisisobutyrate.

Preferred radical generators include organic azo compounds. Among such organic azo compounds, 2,2'-azobisisobutyronitrile, 2,2'-azobis(2,4-dimethylvaleronitrile) and 2,2'-azobis(4-methoxy-2,4-dimethylvaleronitrile) are more preferable.

The amount of the radical generator used is not particularly limited. The radical generator is used in a molar concentration 0.01 time or more, and preferably 0.05 to 1 time, as compared with that of the compound of the formula [B2g].

This reaction may be carried out at a temperature from 0° C. to 200° C., and preferably from 20° C. to 100° C., for 1 minute to 24 hours.

[Production Method C1]

[Formula 23]

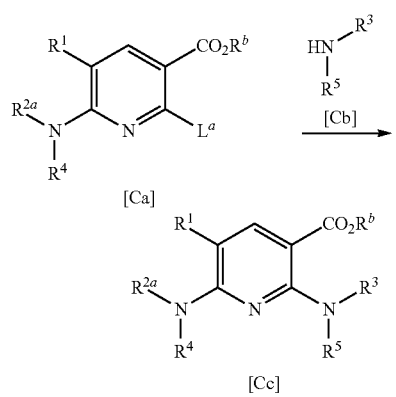

wherein $R^1$, $R^{2a}$, $R^3$, $R^4$, $R^5$, $R^b$ and $L^a$ have the same meanings as those described above.

(C1-1)

The compound of the formula [Cc] can be produced by allowing the compound of the formula [Ca] to react with the compound of the formula [Cb] in accordance with the Production Method A2-1.

The compound of the formula [Ca] can be produced by a Production Method C4 as described later.

For example, 6-aminoquinoline is known as a compound of the formula [Cb].

(C1-2)

The compound of the formula [3] can be produced by hydrolyzing the compound of the formula [Cc] in the presence of an acid or a base in accordance with the Production Method A2-2.

[Production Method C2]

[Formula 24]

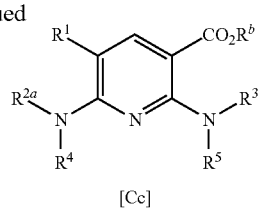

[Cc]

wherein $R^d$ represents a $C_{1-6}$ alkyl group; $L^d$ represents a chlorine atom or a bromine atom; M represents a potassium atom or a sodium atom; and $R^1$, $R^{2a}$, $R^3$, $R^4$, $R^5$ and $R^b$ have the same meanings as those described above.

(C2-1)

The compound of the formula [C2c] can be produced by allowing the compound of the formula [C2a] to react with the compound of the formula [C2b].

For example, methyl 3-amino-3-ethoxyacrylate is known as a compound of the formula [C2a].

For example, 6-aminoquinoline is known as a compound of the formula [C2b].

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These solvents may be used in combination.

Preferred solvents are amides.

The compound of the formula [C2b] may be used in a molar concentration 1 time or more, and preferably 1 to 2 times, as compared with that of the compound of the formula [C2a].

This reaction may be carried out at a temperature from 0° C. to the boiling point of a solvent, and preferably from 10° C. to 40° C., for 1 minute to 24 hours.

(C2-2)

The compound of the formula [C2e] can be produced by allowing the compound of the formula [C2c] to react with the compound of the formula [C2d].

For example, a potassium salt of methyl 2-fluoro-3-hydroxyacrylate is known as a compound of the formula [C2d].

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These solvents may be used in combination.

Preferred solvents are alcohols.

The compound of the formula [C2d] may be used in a molar concentration 1 time or more, and preferably 1 to 2 times, as compared with that of the compound of the formula [C2c].

This reaction may be carried out at a temperature from 0° C. to the boiling point of a solvent, and preferably from 40° C. to 100° C., for 1 minute to 24 hours.

(C2-3)

The compound of the formula [C2f] can be produced by halogenating the compound of the formula [C2e] in the presence of a phosphine and in the presence of a halogenating agent.

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These solvents may be used in combination.

Preferred solvents are ethers.

Examples of the phosphine used in this reaction include: trialkylphosphines such as trimethylphosphine and tri-tert-butylphosphine; tricycloalkylphosphines such as tricyclohexylphosphine; and triarylphosphines such as triphenylphosphine and tritolylphosphine.

Preferred phosphines include triarylphosphines. Among others, triphenylphosphine is more preferable.

The phosphine is used in a molar concentration 1 time or more, and preferably 1 to 3 times, as compared with that of the compound of the formula [C2e].

Examples of the halogenating agent used in this reaction include: halogens such as chlorine and bromine; imides such as N-chlorosuccinimide, N-bromosuccinimide, N-chlorophthalimide, and N-bromophthalimide; hydantoins such as 1,3-dibromo-5,5-dimethylhydantoin, and 1,3-dichloro-5,5-dimethylhydantoin; and sulfuryl chloride.

Preferred halogenating agents include imides. Among such imides, N-chloro succinimide or N-bromosuccinimide is more preferable.

The halogenating agent may be used in a molar concentration 1 time or more, and preferably 1 to 5 times, as compared with that of the compound of the formula [C2e].

This reaction may be carried out at a temperature from 0° C. to the boiling point of a solvent, and preferably from 60° C. to 100° C., for 1 minute to 24 hours.

(C2-4)

The compound of the formula [Cc] can be produced by allowing the compound of the formula [C2f] to react with the compound of the formula [C2g] in accordance with the Production Method A2-1.

[Production Method C3]

[Formula 25]

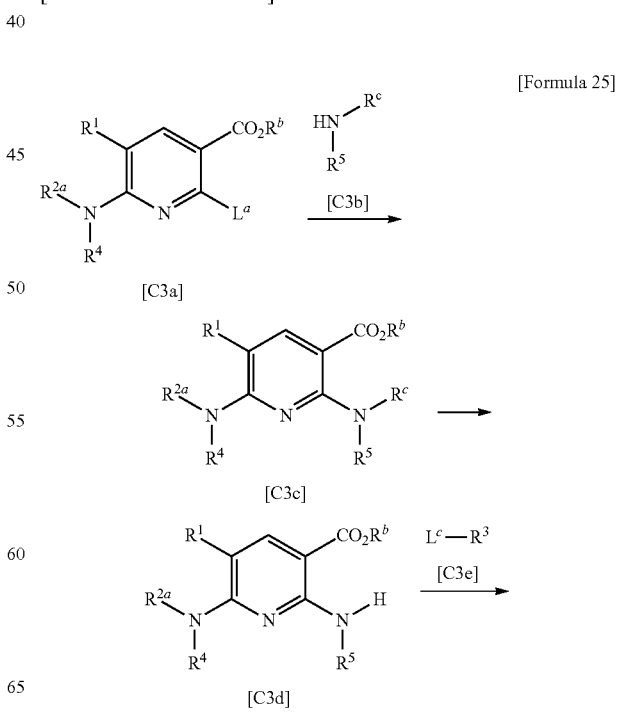

-continued

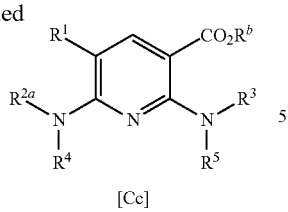

[Cc]

wherein $R^1$, $R^{2a}$, $R^3$, $R^4$, $R^5$, $R^5$, $R^c$, $L^a$ and $L^c$ have the same meanings as those described above.

(C3-1)

The compound of the formula [C3c] can be produced by allowing the compound of the formula [C3a] to react with the compound of the formula [C3b] in accordance with the Production Method A2-1.

The compound of the formula [C3a] can be produced by a Production Method C4 as described later.

For example, benzylamine is known as a compound of the formula [C3b].

(C3-2)

The compound of the formula [C3d] can be produced by deprotecting the compound of the formula [C3c] in accordance with the Production Method B1-2.

(C3-3)

The compound of the formula [Cc] can be produced by allowing the compound of the formula [C3d] to react with the compound of the formula [C3e] in accordance with the Production Method A1.

For example, 2-methyl-5-chloropyridine is known as a compound of the formula [C3e].

[Production Method C4]

[Formula 26]

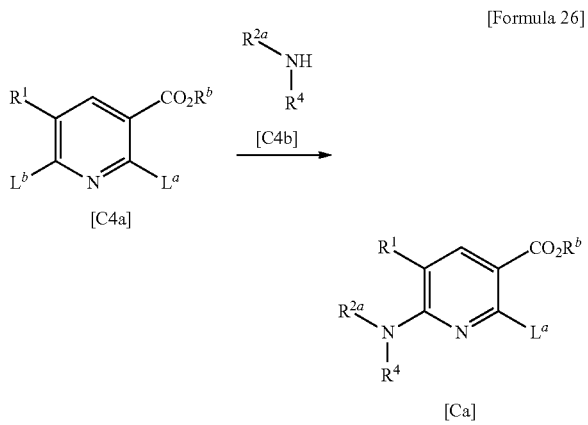

wherein $R^1$, $R^{2a}$, $R^4$, $R^b$, $L^a$ and $L^b$ have the same meanings as those described above.

The compound of the formula [Ca] can be produced by allowing the compound of the formula [C4a] to react with the compound of the formula [C4b] in accordance with the Production Method A2-1.

For example, methyl 2,6-dichloro-5-fluoronicotinate is known as a compound of the formula [C4a].

For example, tert-butyl (2-aminoethyl)carbamate and tert-butyl(2-aminocyclohexyl)carbamate are known as compounds of the formula [C4b].

[Production Method D1]

[Formula 27]

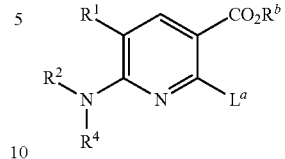
[Da]

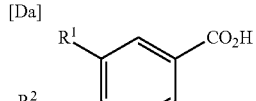
[Db]

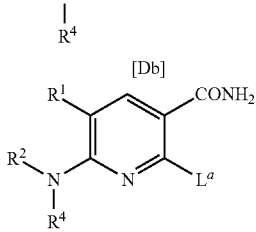
[Dc]

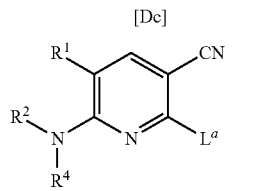
[Dd]

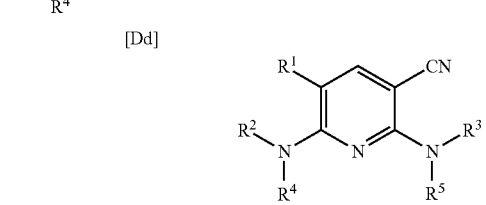
[4]

wherein $R^1$, $R^2$, $R^3$, $R^4$, $R^5$, $R^b$ and $L^a$ have the same meanings as those described above.

(D1-1)

The compound of the formula [Db] can be produced by hydrolyzing the compound of the formula [Da] in the presence of an acid or a base in accordance with the Production Method A2-2.

The compound of the formula [Da] can be produced, for example, in accordance with the Production Method C4.

(D1-2)

The compound of the formula [Dc] can be produced from the compound of the formula [Db] in accordance with the Production Method 2.

(D1-3)

The compound of the formula [Dd] can be produced by allowing the compound of the formula [Dc] to react with a dehydrating agent in the presence of a base.

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These solvents may be used in combination.

Preferred solvents are halogenated hydrocarbons.

Examples of the base used in this reaction include: metal alkoxides such as sodium methoxide, sodium ethoxide, potassium tert-butoxide, and sodium tert-butoxide; inorganic bases such as sodium hydroxide, potassium hydroxide, sodium hydrogencarbonate, sodium carbonate, potassium carbonate, sodium hydride, and potassium hydride; and organic bases such as triethylamine, diisopropylethylamine, and pyridine.

Examples of the dehydrating agent used in this reaction include: acid anhydrides such as acetylformyloxide, acetic anhydride, trichloroacetic anhydride, and trifluoroacetic anhydride; mixed acid anhydrides of organic carboxylic acids such as acetic acid with carbonic acid monoalkyl esters such as ethyl chlorocarbonate and isobutyl chlorocarbonate; mixed acid anhydrides of organic carboxylic acids such as acetic acid with organic acids such as pivalic acid; acid chlorides such as acetyl chloride, trichloroacetyl chloride, and trifluoroacetyl chloride; and acid bromides such as acetyl bromide.

The base and the dehydrating agent may each be used in a molar concentration 1 time or more, and preferably 1 to 5 times, as compared with that of the compound of the formula [Dc].

This reaction may be carried out at a temperature from −20° C. to 100° C., and preferably from 0° C. to 50° C., for 1 minute to 24 hours.

(D1-4)
The compound of the formula [4] can be produced by allowing the compound of the formula [Dd] to react with the compound of the formula [De] in accordance with the Production Method A2-1.

[Production Method D2]

(D2-1)
The compound of the formula [D2c] can be produced by allowing the compound of the formula [D2a] to react with the compound of the formula [D2b] in accordance with the Production Method C2-1.

For example, methyl 2-cyano-acetimidate is known as a compound of the formula [D2a].

For example, 6-aminoquinoline is known as a compound of the formula [D2b].

[D2-2]
The compound of the formula [D2e] can be produced by allowing the compound of the formula [D2c] to react with the compound of the formula [D2d] in accordance with the Production Method C2-2.

For example, a potassium salt of methyl 2-fluoro-3-hydroxyacrylate is known as a compound of the formula [D2d].

(D2-3)
The compound of the formula [D2f] can be produced by halogenating the compound of the formula [D2e] in accordance with the Production Method C2-3.

(D2-4)
The compound of the formula [4] can be produced by allowing the compound of the formula [D2f] to react with the compound of the formula [D2g] in accordance with the Production Method A2-1.

For example, ethylenediamine and cyclohexanediamine are known as compounds of the formula [D2g].

[Production Method D3]

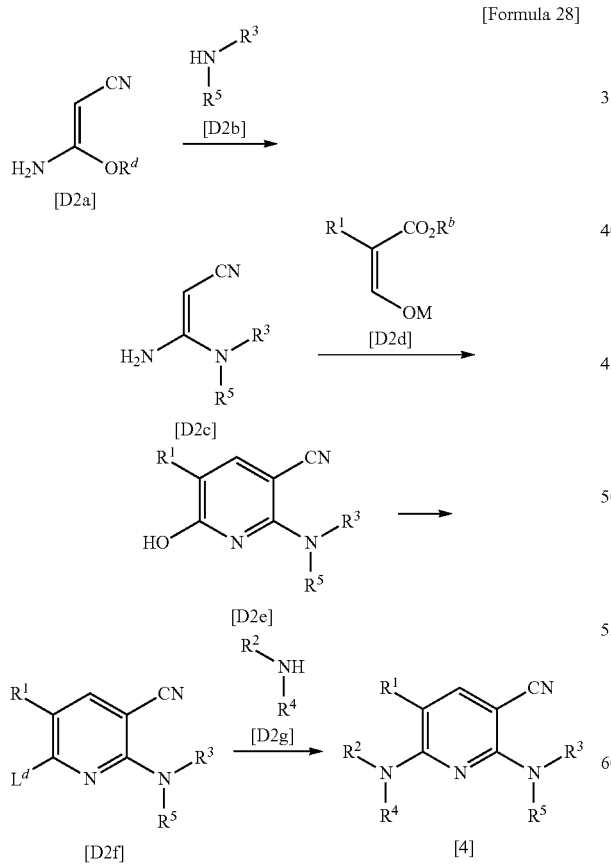

[Formula 28]

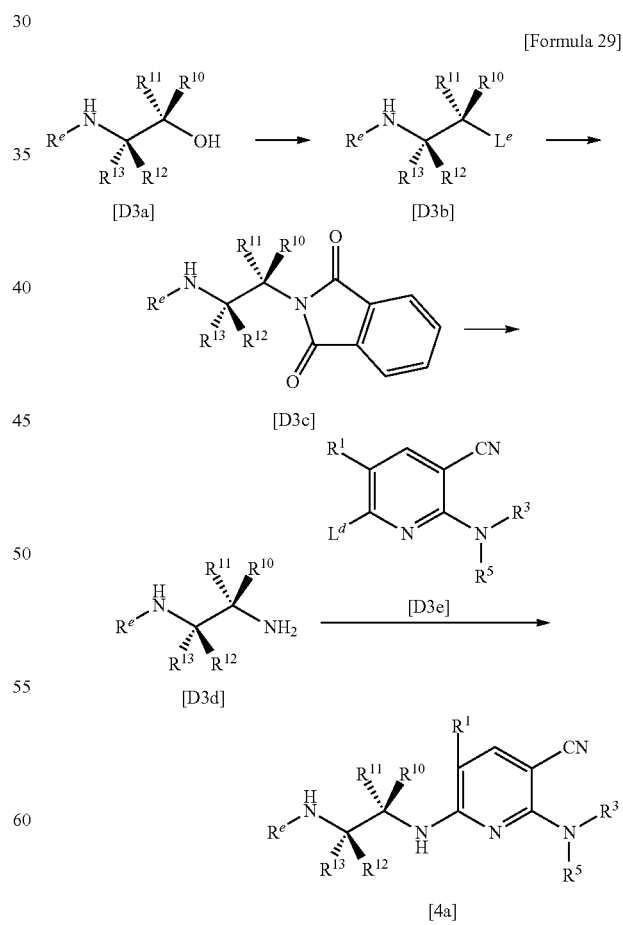

[Formula 29]

wherein $R^1$, $R^2$, $R^3$, $R^4$, $R^5$, $R^b$, $R^d$, M and $L^d$ have the same meanings as those described above.

wherein $R^e$ represents an amino-protecting group; $L^e$ represents a $C_{1-6}$ alkylsulfonyloxy group or an arylsulfonyloxy group; and $R^1$, $R^3$, $R^5$, $R^{10}$, $R^{11}$, $R^{12}$, $R^{13}$ and $L^d$ have the same meanings as those described above.

(D3-1)

The compound of the formula [D3b] can be produced by allowing the compound of the formula [D3a] to react with sulfonyl chloride.

For example, tert-butyl (1-hydroxypropan-2-yl)carbamate is known as a compound of the formula [D3a].

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These solvents may be used in combination.

Preferred solvents are ethers.

Examples of the sulfonyl chloride used in this reaction include methylsulfonyl chloride, ethylsulfonyl chloride, propylsulfonyl chloride, benzenesulfonyl chloride, p-toluenesulfonyl chloride, and naphthalenesulfonyl chloride.

Preferred sulfonyl chlorides include methylsulfonyl chloride and p-toluenesulfonyl chloride. Further, methylsulfonyl chloride is more preferable.

The sulfonyl chloride is used in a molar concentration of 1 time or more, and preferably 1 to 3 times, as compared with that of the compound of the formula [D3a].

Examples of the base used in this reaction as desired include: inorganic bases such as sodium hydrogencarbonate, sodium carbonate, potassium carbonate, cesium carbonate, and tripotassium phosphate; and organic bases such as pyridine, 4-(dimethylamino)pyridine, triethylamine, and diisopropylethylamine.

The base is used in a molar concentration of 1 time or more, and preferably 1 to 3 times, as compared with that of the compound of the formula [D3a].

This reaction may be carried out at a temperature from −78° C. to the boiling point of a solvent, and preferably from 0° C. to 80° C., for 1 minute to 24 hours.

(D3-2)

The compound of the formula [D3c] can be produced by allowing the compound of the formula [D3b] to react with a phthalimide compound.

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These solvents may be used in combination.

Preferred solvents are amides.

Examples of the phthalimide compound used in this reaction include phthalimide sodium and phthalimide potassium.

The phthalimide compound can also be produced in a reaction system, using a phthalimide as a raw material.

A preferred phthalimide compound is phthalimide potassium.

The phthalimide compound is used in a molar concentration 1 time or more, and preferably 1 to 3 times, as compared with that of the compound of the formula [D3b].

This reaction may be carried out at a temperature from 0° C. to the boiling point of a solvent, and preferably from 0° C. to 100° C., for 1 minute to 24 hours.

(D3-3)

The compound of the formula [D3d] can be produced by deprotecting the compound of the formula [D3c]. This reaction can be carried out, for example, by the method described in W. Greene et al., Protective Groups in Organic Synthesis, 4th edition, pp. 696 to 926, 2007, John Wiley & Sons, INC.

In this reaction, deprotection is preferably carried out using hydrazine.

(D3-4)

The compound of the formula [4a] can be produced by allowing the compound of the formula [D3d] to react with the compound of the formula [D3e] in accordance with the Production Method A2-1.

[Production Method D4]

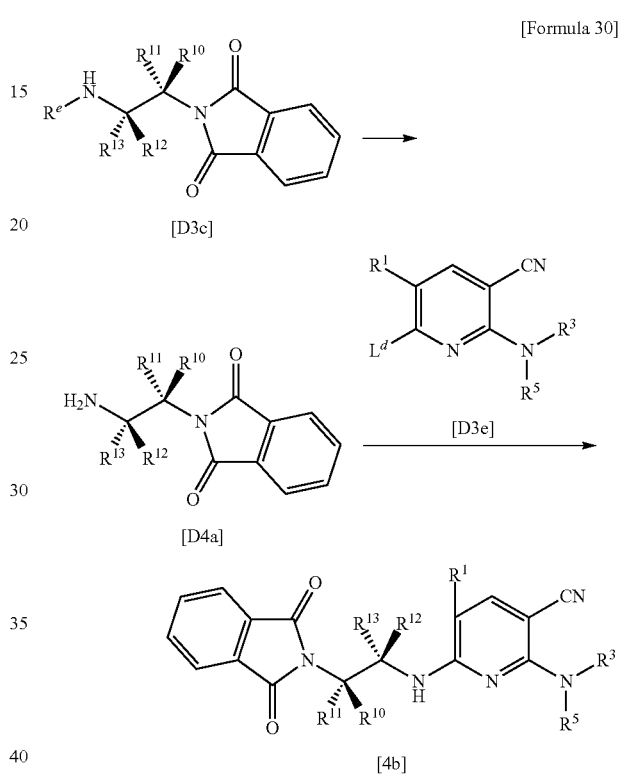

[Formula 30]

wherein $R^1$, $R^3$, $R^5$, $R^{10}$, $R^{11}$, $R^{12}$, $R^{13}$, $R^e$ and $L^d$ have the same meanings as those described above.

(D4-1)

The compound of the formula [D4a] can be produced by deprotecting the compound of the formula [D3c] in accordance with the Production Method B1-2.

(D4-2)

The compound of the formula [4b] can be produced by allowing the compound of the formula [D4a] to react with the compound of the formula [D3e] in accordance with the Production Method A2-1.

[Production Method D5]

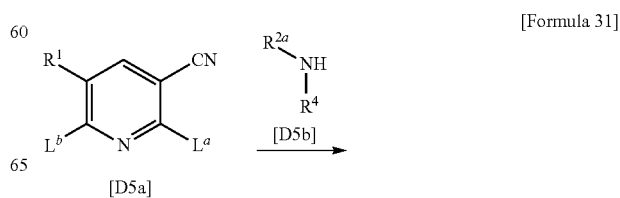

[Formula 31]

-continued

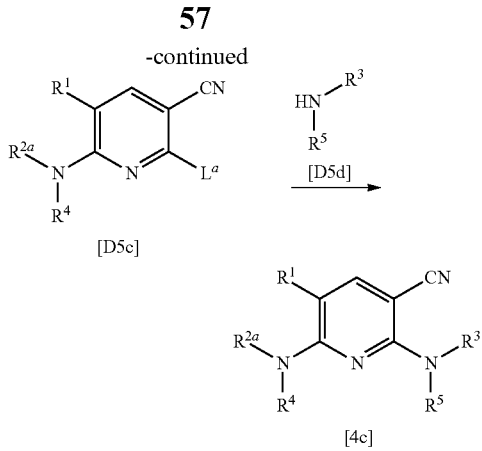

wherein $R^1$, $R^{2a}$, $R^3$, $R^4$, $R^5$, $L^a$ and $L^b$ have the same meanings as those described above.

(D5-1)

The compound of the formula [D5c] can be produced by allowing the compound of the formula [D5a] to react with the compound of the formula [D5b] in accordance with the Production Method A2-1.

For example, 2,6-dichloro-3-cyano-5-fluoropyridine is known as a compound of the formula [D5a].

For example, tert-butyl((1R,2S)-1-cyclopropyl-1-hydroxypropan-2-yl)carbamate is known as a compound of the formula [D5b].

(D5-2)

The compound of the formula [4c] can be produced by allowing the compound of the formula [D5c] to react with the compound of the formula [D5d] in accordance with the Production Method A2-1.

[Production Method E]

[Formula 32]

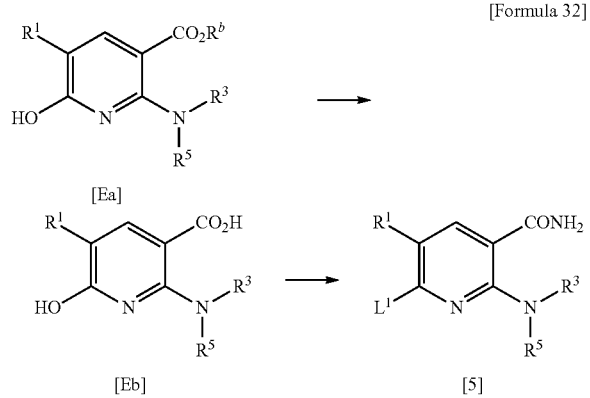

wherein $R^1$, $R^3$, $R^5$, $R^b$ and $L^1$ have the same meanings as those described above.

(E-1)

The compound of the formula [Ea] can be produced, for example, in accordance with the Production Method C2-2.

(E-2)

The compound of the formula [Eb] can be produced by hydrolyzing the compound of the formula [Ea] in the presence of an acid or a base in accordance with the Production Method A2-2.

(E-3)

The compound of the formula [5] can be produced by allowing the compound of the formula [Eb] to react with ammonia or ammonium salts in the presence of a reaction promoter and in the presence of a condensation agent.

The solvent used in this reaction is not particularly limited, as long as it does not affect the reaction. Examples of the solvent include aliphatic hydrocarbons, halogenated hydrocarbons, alcohols, glycols, ethers, ketones, esters, amides, nitriles, sulfoxides, aromatic hydrocarbons, and water. These solvents may be used in combination.

Preferred solvents are amides.

Examples of the condensation agent used in this reaction include: carbodiimides such as N,N'-dicyclohexylcarbodiimide and N-ethyl-N'-(3-dimethylaminopropyl)carbodiimide; carbonyls such as carbonyldiimidazole; acid azides such as diphenylphosphoryl azide; acid cyanides such as diethylphosphoryl cyanide; 2-ethoxy-1-ethoxycarbonyl-1,2-dihydroquinoline; O-benzotriazol-1-yl-1,1,3,3-tetramethyluronium hexafluorophosphate; and O-(7-azabenzotriazol-1-yl)-1,1,3,3-tetramethyluronium hexafluorophosphate.

Examples of the base used in this reaction include: metal alkoxides such as sodium methoxide, sodium ethoxide, potassium tert-butoxide, and sodium tert-butoxide; inorganic bases such as sodium hydroxide, potassium hydroxide, sodium hydrogencarbonate, sodium carbonate, potassium carbonate, sodium hydride, and potassium hydride; and organic bases such as triethylamine, diisopropylethylamine, and pyridine.

Examples of the ammonium salts include ammonium chloride, ammonium bromide, and ammonium acetate.

The ammonia or the ammonia or ammonium salts may be used in a molar concentration 1 to 100 times, and preferably 1 to 10 times, as compared with that of the compound of the formula [Eb].

Examples of the reaction promoter used in this reaction include 1-hydroxybenzotriazole and N-hydroxysuccinimide.

The condensation agent, the base and the reaction promoter may each be used in a molar concentration 1 time or more, and preferably 1 to 5 times, as compared with that of the compound of the formula [Eb].

This reaction may be carried out at a temperature from −20° C. to 150° C., and preferably from 0° C. to 100° C., for 1 minute to 24 hours.

The compounds obtained by the above-described production methods can be converted to other compounds by subjecting them to well-known reactions such as condensation, addition, oxidation, reduction, dislocation, substitution, halogenation, dehydration or hydrolysis, or by combining these reactions, as appropriate.

When amino, hydroxyl and/or carboxyl groups are present in the compounds obtained by the above-described production methods and the intermediates thereof, reactions can be carried out by replacing their protecting groups with other groups, as appropriate. In addition, when two or more protecting groups are present, such protecting groups can be selectively deprotected by subjecting them to well-known reactions.

Among compounds used in the above-described production methods, those that can be in the form of salts can be used as salts. Examples of such salts are the same as the examples of the salt of the compound represented by the formula [1].

When isomers (for example, optical isomers, geometric isomers, tautomers, etc.) are present in the compounds used in the above-described production methods, these isomers can also be used. In addition, when solvates, hydrates, and various forms of crystals are present, these solvates, hydrates, and various forms of crystals can also be used.

When the compound represented by the formula [1] of the present invention is used as a medicament, pharmaceutical additives commonly used in formulation of such a medicament, such as an excipient, a carrier and a diluent, may be mixed into the compound of the present invention, as appropriate. The thus formulated medicament can be orally or parenterally administered in the form of a tablet, a capsule, a powdered medicine, a syrup, a granule, a pill, a suspending agent, an emulsion, a liquid agent, a powdery agent, a suppository, an eye drop, a nasal drop, an ear drop, a patch, an ointment or an injection, according to ordinary methods. An administration method, a dosage, and a number of doses can be selected, as appropriate, depending on the age, body weight and symptoms of a patient. In general, the present medicament may be administered orally or parenterally (e.g. via injection, drip infusion, or administration into a rectal site) at a dosage from 0.01 to 1000 mg/kg to an adult per day, once or dividedly several times.

Next, the usefulness of representative compounds of the present invention will be described in the following Test Examples.

TEST EXAMPLE 1

Syk Enzyme Assay

A glutathione S-transferase (GST)-fused full-length human Syk protein (Carna Biosciences), which had been generated using a Baculovirus expression system, was used in the Syk enzyme assay.

15 µl of a reaction solution (1.2 ng Syk, 20 mM HEPES, 10 mM $MgCl_2$, 50 mM NaCl, 2 mM DTT, 0.05% BSA, pH 7.0) containing a Syk protein and a predetermined concentration of a test compound was shaken for 2 minutes, and it was then left at rest at room temperature for 13 minutes. Thereafter, 5 µl of Biotin-EDPDYEWPSA-NH2 (final concentration: 0.4 µM) serving as a substrate peptide and 5 µl of ATP (final concentration: 27 µM) were added to the reaction solution, and the obtained mixture was then shaken for 2 minutes. The reaction solution was further left at rest at room temperature for 40 minutes, so as to carry out an enzyme reaction.

Thereafter, 50 µl of a reaction termination solution [5 µg/ml Streptavidin, 0.18 µg/ml PT66-K, 30 mM HEPES (pH 7.0), 150 mM KF, 75 mM EDTA, 0.15% BSA, 0.075% Tween20], which contained Streptavidin-Xlent (Cisbio) and Mab PT66-K (Cisbio), was added to the reaction solution to terminate the enzyme reaction. At the same time, the reaction solution was left at rest at room temperature for 1 hour, so as to carry out an antigen-antibody reaction. Thereafter, using EnVision (PerkinElmer), the time-resolved fluorescence was measured at 615 nm and 665 nm, so that the phosphorylation of the substrate peptide was measured.

As a result, the Syk-inhibitory activity ($IC_{50}$) of each compound in the following compound group was found to be 1 µM or less. The compounds in the compound group exhibited excellent Syk-inhibitory activity.

Compound Group: Example 1, Examples 2-1 to 2-7, Example 2-9, Example 2-10, Examples 2-13 to 2-21, Example 3, Examples 4-1 to 4-42, Examples 4-44 to 4-64, Example 5, Example 6-2, Examples 6-6 to 6-11, Example 6-18, Example 6-20, Example 6-21, Example 6-23, Example 6-24, Example 6-26, Example 6-27, Examples 6-29 to 6-65, Example 6-67, Example 6-68, Examples 6-70 to 6-88, Example 7, Example 8-1, Example 8-2, Examples 8-4 to 8-11, Example 9, Example 10-1, Example 10-2, Example 11, Examples 12-1 to 12-6, Example 12-8, Example 12-9, Examples 12-12 to 12-21, Example 12-25, Example 12-27, Example 12-28, Examples 12-31 to 12-34, Example 13, Examples 14-1 to 14-10, Example 15, Example 16-8, Example 16-9, Example 16-17, Example 16-18, Example 17, Example 19, Example 21, Example 22-3, Examples 22-5 to 22-7, Example 23, Example 24, Example 26, Examples 27-1 to 27-6, Example 28, Example 29-1, Examples 29-3 to 29-8, Example 29-12, Example 29-13, Example 30, Example 31-3, Example 31-4, Example 32, Example 33-1, Examples 33-4 to 33-6, Example 34, and Examples 35-1 to 35-9.

TEST EXAMPLE 2

TNFα Generation Assay

THP-1 cells ($2\times10^5$ cells/ml), which were human monocytoid cells, were cultured in the presence of 10 ng/ml IFN-γ (Roche) for 2 days, so that the cells were induced to differentiate into macrophage-like cells. The differentiation-induced THP-1 cells were recovered, and the cells ($1\times10^6$ cell/ml) were then allowed to react with a predetermined concentration of test compound at room temperature for 30 minutes. On the other hand, 100 µl of human IgG (10 µg/ml, SIGMA-ALDRICH) diluted with PBS was added to a 96-well plate, and it was then incubated at room temperature overnight. Thereafter, the resultant was washed with PBS twice to produce a human IgG-coated plate. Subsequently, a cell solution that contained a compound was inoculated on the human IgG-coated plate ($5\times10^4$ cells/well), and it was then cultured for 7 hours. Thereafter, the cultured solution was recovered, and the amount of TNFα secreted into the culture solution was then measured by the ELISA method (Roche/R & D Systems) or the AlphaLISA method (PerkinElmer).

As a result, the TNFα generation inhibitory activity ($IC_{50}$) of each compound in the following compound group was found to be 200 nM or less. The compounds in the compound group exhibited excellent TNFα generation inhibitory activity.

Compound Group: Example 1, Example 2-1, Example 2-3, Example 2-5, Example 2-7, Examples 2-13 to 2-15, Example 2-20, Example 3, Examples 4-2 to 4-8, Examples 4-11 to 4-13, Examples 4-16 to 4-18, Example 4-22, Example 4-23, Example 4-25, Example 4-26, Example 4-28, Examples 4-35 to 4-37, Example 4-40, Example 4-42, Examples 4-53 to 4-55, Examples 4-58 to 4-62, Example 4-64, Example 5, Example 6-26, Example 6-34, Example 6-35, Example 6-40, Example 6-43, Example 6-44, Example 6-46, Examples 6-49 to 6-58, Examples 6-60 to 6-63, Example 6-65, Example 6-70, Example 6-72, Example 6-75, Example 6-76, Example 6-82, Example 6-83, Example 6-87, Example 7, Example 8-4, Example 8-6, Example 8-8, Example 8-11, Example 9, Example 10-1, Example 10-2, Example 11, Example 12-8, Example 12-9, Example 12-31, Example 13, Example 14-1, Example 14-2, Example 14-5, Example 14-6, Example 14-9, Example 14-10, Example 21, Example 22-3, Example 22-5, Example 34, Examples 35-1 to 35-4, and Example 35-7.

The compound of the present invention exhibited excellent Syk-inhibitory activity and TNFα generation inhibitory activity.

EXAMPLES

The present invention is hereafter described with reference to the Reference Examples and the Examples, although the scope of the present invention is not limited thereto.

LC/MS analysis was conducted under the following conditions.

LC/MS analyzer: Waters SQD
Column: Waters BEHC18 1.73 3 μm, 2.1×30 mm
Solvent: Liquid A: 0.1% formic acid-water
Liquid B: 0.1% formic acid-acetonitrile
Gradient cycle: 0.00 min (Liquid A/Liquid B=95/5), 2.00 min (Liquid A/Liquid B=5/95), 3.00 min (Liquid A/Liquid B=5/95), 3.01 min (Liquid A/Liquid B=100/0), 3.80 min (Liquid A/Liquid B=100/0)
Flow rate: 0.5 mL/min (The column temperature was room temperature, and no temperature control was carried out.)
Ionization method: Electron Spray Ionization method (ESI positive and negative ion peaks were detected.)
UV detection: UV 220 nm
MS analysis was conducted under the following conditions.
MS analyzer: Hitachi M-8000
Solvent: Methanol
Ionization method: Electron Spray Ionization method (ESI positive and negative ion peaks were detected.)
NMR spectra are proton NMR spectra. NMR spectra were measured using a JEOL JNM-AL 400 (400 MHz spectrometer) or a BRUKER AVANCE 300 (300 MHz spectrometer), and the δ value was expressed in ppm.
The carrier used for silica gel column chromatography is PSQ100B (spherical shape) (Fuji Silysia Chemical Ltd.), and the PLC glass plate is a PLC glass plate silica gel 60 $F_{254}$ (Merck), unless otherwise specified.
The compound of the formula [1a] is a mixture of a compound of the formula [1b] and a compound of the formula [1c].

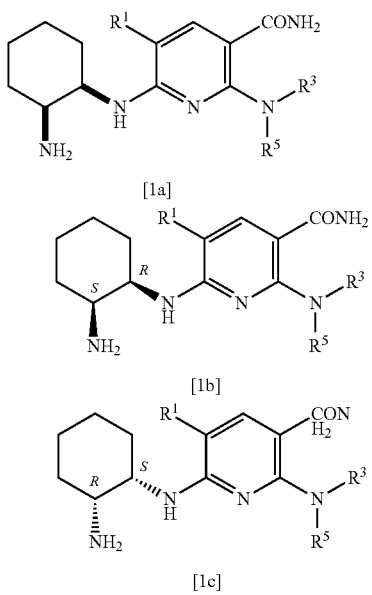

[Formula 33]

Abbreviations used in the Reference Examples and the Examples stand for the terms given below.
Ac: acetyl
Bn: benzyl
Boc: tert-butoxycarbonyl
Bu: butyl
Cbz: benzyloxycarbonyl
dba: 1,3-dibenzylideneacetone
DMF: N,N-dimethylformamide
DMSO-$d_6$: hexadeuterodimethyl sulfoxide
DPPA: diphenylphosphoryl azide
Et: ethyl
HOBt.$H_2$O: 1-hydroxybenzotriazole•monohydrate
Me: methyl
Ms: methanesulfonyl
Ph: phenyl
RT, rt: retention time
SEM: (2-trimethylsilylethoxy)methyl
TBDMS: tert-butyldimethylsilyl
Tf: trifluoromethanesulfonyl
TFA: trifluoroacetic acid
TIPS: triisopropylsilyl
TMS: trimethylsilyl
Ts: p-toluenesulfonyl
WSC.HCl: 1-ethyl-3-(3-dimethylaminopropyl)carbodiimide-hydrochloride
Xantphos: 4,5-bis(diphenylphosphino)-9,9-dimethylxanthene Reference Example 1

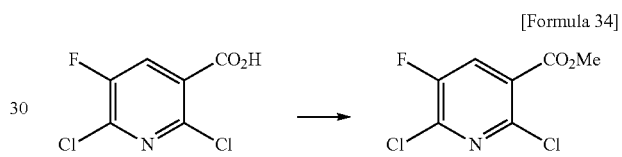

[Formula 34]

Concentrated sulfuric acid (5 ml) was added to a methanol (50 ml) solution containing 2,6-dichloro-5-fluoronicotinic acid (25.0 g), followed by stirring at 50° C. to 60° C. for 6 hours and 30 minutes. The resulting solution was left at rest at room temperature for 15 hours. Concentrated sulfuric acid (5 ml) was added, followed by stirring at 50° C. to 60° C. for 3 hours. The reaction mixture was cooled to room temperature, neutralized with a 2N sodium hydroxide aqueous solution under ice cooling, and basified with sodium hydrogen carbonate, following which ethyl acetate was added. The organic layer was collected, washed with water and then with saturated saline, and dried over anhydrous magnesium sulfate. The solvent was distilled away under reduced pressure, and colorless oily matter of methyl 2,6-dichloro-5-fluoronicotinate (22.2 g) was thus obtained.

$^1$H-NMR (CDCl$_3$, 400 MHz) δ:8.02 (d, 1H, J=7.3 Hz), 3.98 (s, 3H)

Reference Example 2

[Formula 35]

-continued

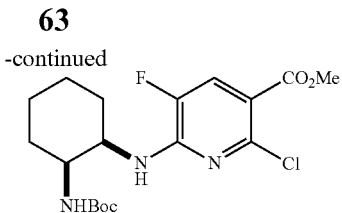

1st Step

Potassium carbonate (14.8 g), cis-cyclohexane-1,2-diamine (12.2 g), and DMF (20 ml) were added to a DMF (180 ml) solution containing methyl 2,6-dichloro-5-fluoronicotinate (20.0 g), followed by stirring at room temperature for 30 minutes. Water, a saturated aqueous ammonium chloride solution, and ethyl acetate were added to the reaction mixture. The organic layer was collected, washed with saturated saline, and dried over anhydrous magnesium sulfate. The solvent was distilled away under reduced pressure, and yellow oily matter (28.3 g) was thus obtained.

2nd Step

Di-tert-butyl dicarbonate (19.5 g) and N,N-dimethylaminopyridine (1.10 g) were added to a tetrahydrofuran (200 ml) solution containing the yellow oily matter (28.3 g) obtained in the 1st step, followed by stirring at room temperature for 30 minutes. The solvent was distilled away under reduced pressure, and a saturated aqueous ammonium chloride solution and ethyl acetate were added. The organic layer was collected, washed with saturated saline, and dried over anhydrous magnesium sulfate. The solvent was distilled away under reduced pressure. Hexane/ethyl acetate (4/1) was added to the obtained residue, solid matter was collected by filtration, and a white solid of methyl 6-(cis-2-(tert-butoxycarbonylamino)cyclohexylamino)-2-chloro-5-fluoronicotinate (15.7 g) was thus obtained.

$^1$H-NMR (CDCl$_3$, 400 MHz) δ:7.72 (d, 1H, J=10.9 Hz), 5.84 (brs, 1H), 4.89 (brs, 1H), 4.27-4.18 (m, 1H), 4.06-3.99 (m, 1H), 3.87 (s, 3H), 2.03-1.31 (m, 17H)

Reference Example 3

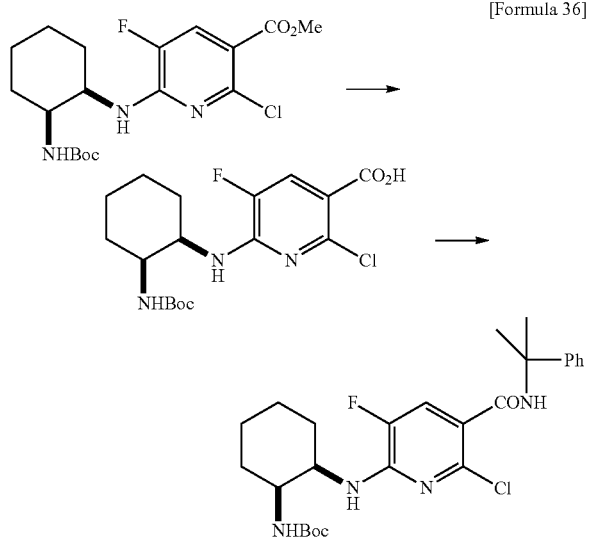

1st Step

A 1N sodium hydroxide aqueous solution (25 ml) was added a solution of tetrahydrofuran (50 ml) and methanol (50 ml) containing methyl-6-(cis-2-(tert-butoxycarbonylamino) cyclohexylamino)-2-chloro-5-fluoronicotinate (5.00 g), followed by stirring at 70° C. for 1 hour. The reaction mixture was cooled to room temperature, the solvent was distilled away under reduced pressure, and a saturated aqueous ammonium chloride solution and ethyl acetate were added. The organic layer was collected, washed with saturated saline, and dried over anhydrous magnesium sulfate, the solvent was distilled away under reduced pressure, and 6-(cis-2-(tert-butoxycarbonylamino)cyclohexylamino)-2-chloro-5-fluoronicotinic acid was thus obtained.

MS (ESI, m/z): 388 (M+H), 410 (M+Na), 386 (M−H)

2nd Step

Cumylamine (1.97 ml), WSC.HCl (2.62 g), and HOBt.H$_2$O (2.10 g) were added to a DMF (60 ml) solution containing 6-(cis-2-(tert-butoxycarbonylamino)cyclohexylamino)-2-chloro-5-fluoronicotinic acid obtained in the 1st step, followed by stirring at room temperature for 4 hours. A saturated aqueous ammonium chloride solution and ethyl acetate were added to the reaction mixture. The organic layer was collected, washed with a saturated aqueous sodium hydrogen carbonate solution and then with saturated saline, and dried over anhydrous magnesium sulfate, and the solvent was distilled away under reduced pressure. Diisopropylether and hexane were added to the obtained residue, solid matter was collected by filtration, and a white solid of tert-butyl cis-2-(6-chloro-3-fluoro-5-(2-phenylpropan-2-ylaminocarbonyl)pyridin-2-ylamino)cyclohexylcarbamate (4.41 g) was thus obtained.

$^1$H-NMR (DMSO-d$_6$, 400 MHz) δ:8.46 (s, 1H), 7.53 (d, 1H, J=10.4 Hz), 7.45-7.39 (m, 2H), 7.33-7.26 (m, 2H), 7.21-7.15 (m, 1H), 6.71-6.54 (m, 2H), 4.09-3.98 (m, 1H), 3.87-3.77 (m, 1H), 1.84-1.17 (m, 23H)

MS (ESI, m/z): 406 (M−Boc+H)

Reference Example 4

The following compound was obtained with reference to US2009/270405 A1.

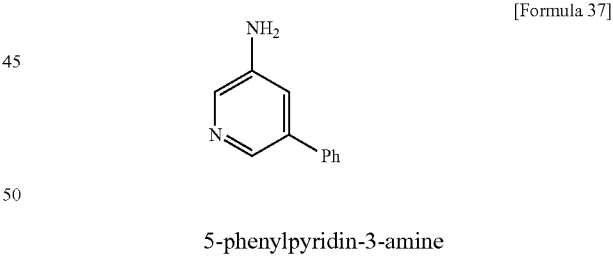

5-phenylpyridin-3-amine

Reference Example 5

The following compound was obtained with reference to US2003/220345 A1 or Helv. Chim. Acta, 1964, 47, 36.

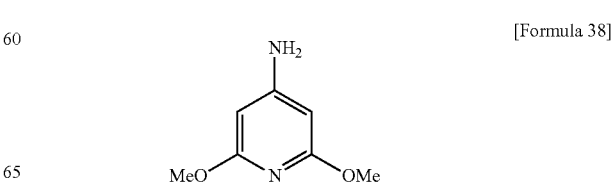

2,6-dimethoxypyridin-4-amine

Reference Example 6

The following compound was obtained with reference to WO2006/118256 A1.

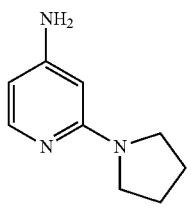
[Formula 39]

2-(pyrrolidin-1-yl)pyridin-4-amine

Reference Example 7

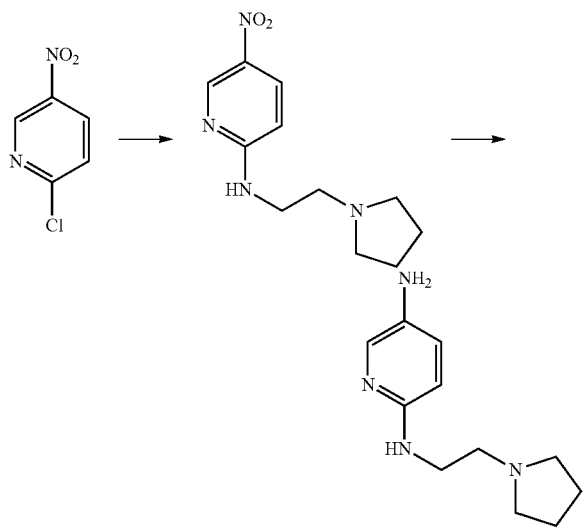
[Formula 40]

1st Step 1-(2-aminoethyl)pyrrolidine (237 μl) was added to a methanol (1 ml) suspension containing 2-chloro-5-nitropyridine (100 mg), followed by stirring at room temperature for 3 hours and 30 minutes. 1-(2-aminoethyl)pyrrolidine (158 μl) was added, followed by stirring for 2 hours. Water and ethyl acetate were added to the reaction mixture. The organic layer was collected, washed with 10% saline and then with saturated saline, and dried over anhydrous magnesium sulfate, and the solvent was distilled away under reduced pressure. Diisopropylether was added to the obtained residue, solid matter was collected by filtration and washed with diisopropylether and hexane, and a yellow solid of 5-nitro-N-(2-(pyrrolidin-1-yl)ethyl)pyridin-2-amine (27 mg) was thus obtained.

MS (ESI, m/z): 237 (M+H), 235 (M−H)

2nd Step

5% Pd/C (8 mg) was added to a methanol (2 ml) solution containing 5-nitro-N-(2-(pyrrolidin-1-yl)ethyl)pyridin-2-amine (27 mg), followed by stirring at room temperature for 2 hours in a hydrogen atmosphere. Insoluble matter was removed by filtration, and filter cake was washed with ethyl acetate. The filtrate was mixed with the washing solution, the solvent was distilled away under reduced pressure, and red oily matter of $N^2$-(2-(pyrrolidin-1-yl)ethyl)pyridin-2,5-diamine (24 mg) was thus obtained.

$^1$H-NMR (CDCl$_3$, 400 MHz) δ:7.72-7.66 (m, 1H), 6.99-6.92 (m, 1H), 6.38-6.32 (m, 1H), 4.66 (brs, 1H), 3.36-3.28 (m, 2H), 2.73-2.68 (m, 2H), 2.59-2.50 (m, 4H), 2.03 (brs, 2H), 1.83-1.73 (m, 4H) MS (ESI, m/z): 207 (M+H)

Reference Example 8

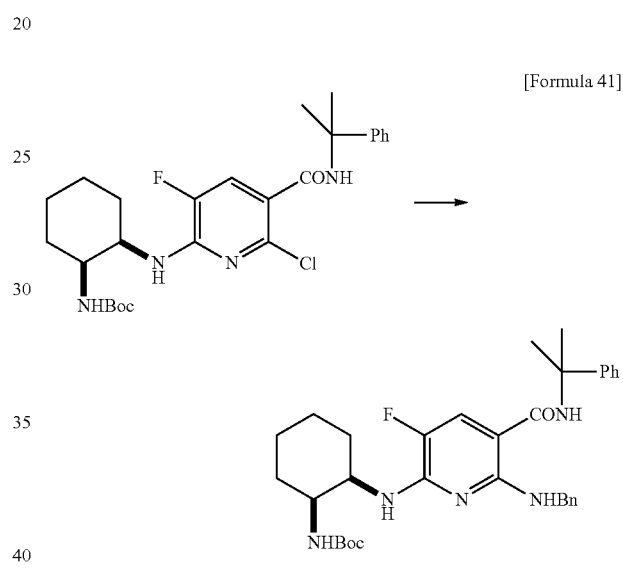
[Formula 41]

The following compound was obtained as described in the 1st step of Example 1.

tert-Butyl cis-2-(6-benzylamino-3-fluoro-5-(2-phenylpropan-2-ylaminocarbonyl)pyridin-2-ylamino)cyclohexylcarbamate MS (ESI, m/z): 576 (M+H), 574 (M−H)

Reference Example 9

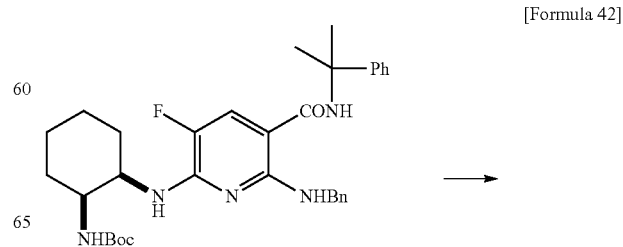
[Formula 42]

-continued

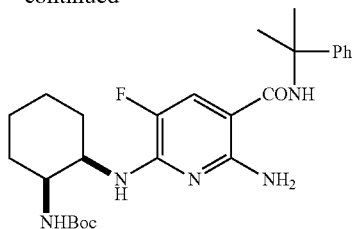

Palladium hydroxide (0.29 g) was added to a solution of tetrahydrofuran (7.2 ml) and methanol (14.3 ml) containing tert-butyl cis-2-(6-benzylamino-3-fluoro-5-(2-phenylpropan-2-ylaminocarbonyl)pyridin-2-ylamino)cyclohexylcarbamate (1.43 g), followed by stirring at room temperature for 1 hour in a hydrogen atmosphere. Insoluble matter was removed by filtration, and filter cake was washed with ethyl acetate. The filtrate was mixed with the washing solution, and the solvent was distilled away under reduced pressure. Diisopropylether and hexane were added to the obtained residue, solid matter was collected by filtration, and a white solid of tert-butyl cis-2-(6-amino-3-fluoro-5-(2-phenylpropan-2-ylaminocarbonyl)pyridin-2-ylamino)cyclohexylcarbamate (870 mg) was thus obtained.

$^1$H-NMR (DMSO-$d_6$, 400 MHz) δ:7.90 (d, 1H, J=12.7 Hz), 7.74 (s, 1H), 7.35-7.30 (m, 2H), 7.29-7.22 (m, 2H), 7.17-7.11 (m, 1H), 6.81 (s, 2H), 6.69 (d, 1H, J=7.7 Hz), 6.11 (d, 1H, J=7.8 Hz), 4.13-4.03 (m, 1H), 3.80-3.72 (m, 1H), 1.84-1.20 (m, 23H)

MS (ESI, m/z): 486 (M+H), 484 (M−H)

Reference Example 10

The following compound was obtained with reference to EP1375486.

[Formula 43]

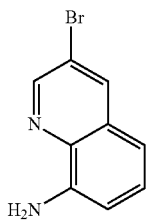

3-bromoquinolin-8-amine

Reference Example 11

The following compound was obtained with reference to WO2007/5668.

[Formula 44]

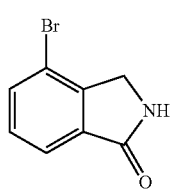

4-bromoisoindolin-1-one

Reference Example 12

[Formula 45]

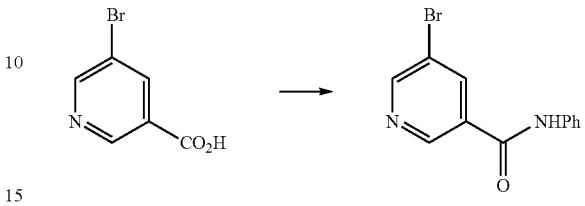

Aniline (99 μl), WSC.HCl (209 mg), and HOBt.H$_2$O (167 mg) were added to a DMF (5 ml) solution containing 5-bromonicotinic acid (200 mg), followed by stirring at room temperature for 3 hours. A saturated aqueous ammonium chloride solution and ethyl acetate were added to the reaction mixture. The organic layer was collected, washed with saturated saline, and dried over anhydrous magnesium sulfate, and the solvent was distilled away under reduced pressure. Diisopropylether and hexane were added to the obtained residue, solid matter was collected by filtration, and a white solid of 5-bromo-N-phenylnicotinamide (268 mg) was thus obtained.

$^1$H-NMR (DMSO-$d_6$, 400 MHz) δ:10.50 (s, 1H), 9.07 (d, 1H, J=2.2 Hz), 8.92 (d, 1H, J=2.0 Hz), 8.55 (dd, 1H, J=2.0, 2.0 Hz), 7.76 (d, 2H, J=7.6 Hz), 7.42-7.35 (m, 2H), 7.14 (t, 1H, J=7.2 Hz)

MS (ESI, m/z): 277, 279 (M+H), 275, 277 (M−H)

Reference Example 13

[Formula 46]

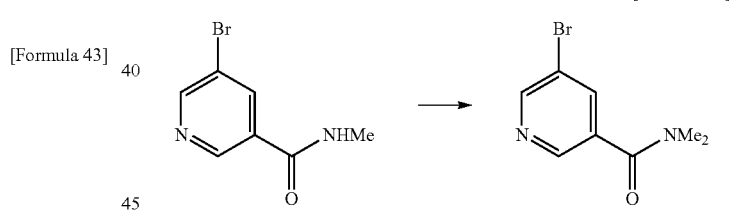

Sodium hydride (60% in oil) (28 mg) was added to a DMF (2.4 ml) solution containing 5-bromo-N-methylnicotinamide (100 mg), followed by stirring at 45° C. for 1 hour. Methyl iodide (43 μl) was added under ice cooling, followed by stirring at room temperature for 1 hour. A saturated aqueous ammonium chloride solution and ethyl acetate were added to the reaction mixture. The organic layer was collected, washed with saturated saline, and dried over anhydrous magnesium sulfate. The solvent was distilled away under reduced pressure. Hexane was added to the obtained residue, solid matter was collected by filtration, and a white solid of 5-bromo-N,N-dimethylnicotinamide (42 mg) was thus obtained.

$^1$H-NMR (DMSO-$d_6$, 400 MHz) δ:8.78 (d, 1H, J=2.2 Hz), 8.61 (d, 1H, J=1.8 Hz), 8.14 (dd, 1H, J=1.9, 2.2 Hz), 3.00 (s, 3H), 2.92 (s, 3H)

MS (ESI, m/z): 229, 231 (M+H)

Reference Example 14

The following compound was obtained with reference to J. Chem. Soc., 1948, 17, 1389.

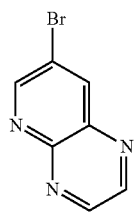

7-bromopyrido[2,3-b]pyrazine

Reference Example 15

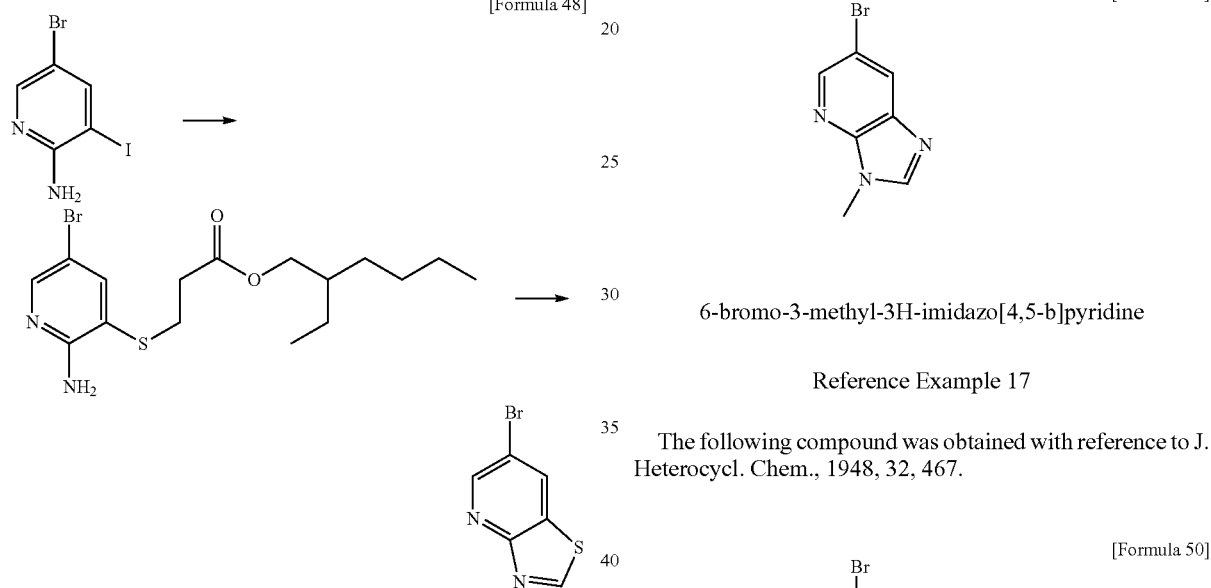

1st Step

Diisopropylethylamine (286 μA), (2-ethylhexyl) 3-mercaptopropionate (167 Pd$_2$(dba)$_3$ (31 mg), and Xantphos (39 mg) were added to a 1,4-dioxane (3.4 ml) solution containing 2-amino-5-bromo-3-iodopyridine (200 mg), followed by stirring at 95° C. for 30 minutes in a nitrogen atmosphere. Water and ethyl acetate were added to the reaction mixture, and insoluble matter was removed by filtration. The organic layer was collected, washed with saturated saline, and dried over anhydrous magnesium sulfate, and the solvent was distilled away under reduced pressure. The obtained residue was purified by silica gel chromatography (hexane:ethyl acetate=100:0 to 65:35), and yellow oily matter (167 mg) was thus obtained.

2nd Step

A 20% sodium ethoxide/ethanol solution (0.5 ml) was added to a tetrahydrofuran (1 ml) solution containing the yellow oily matter (167 mg) obtained in the 1st step, followed by stirring at room temperature for 15 minutes. Formic acid (1 ml) and ethyl orthoformate (2 ml) were added to the reaction mixture, followed by stirring for 30 minutes and then at 100° C. for 1 hour. The reaction mixture was cooled to room temperature, and a saturated aqueous sodium hydrogen carbonate solution and ethyl acetate were added. The organic layer was collected, washed with saturated saline, and dried over anhydrous magnesium sulfate, and the solvent was distilled away under reduced pressure. The obtained residue was purified by silica gel chromatography (hexane:ethyl acetate=10:0 to 2:1), and a yellow solid of 6-bromo[1,3]thiazolo[4,5-b]pyridine (56 mg) was thus obtained.

$^1$H-NMR (CDCl$_3$, 400 MHz) δ:9.28 (s, 1H), 8.84 (d, 1H, J=2.2 Hz), 8.48 (d, 1H, J=2.2 Hz)

MS (ESI, m/z): 215, 217 (M+H),

Reference Example 16

The following compound was obtained with reference to J. Heterocycl. Chem., 1948, 32, 467.

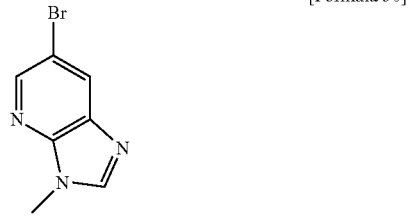

6-bromo-3-methyl-3H-imidazo[4,5-b]pyridine

Reference Example 17

The following compound was obtained with reference to J. Heterocycl. Chem., 1948, 32, 467.

6-bromo-3-methyl-3H-imidazo[4,5-b]pyridine

Reference Example 18

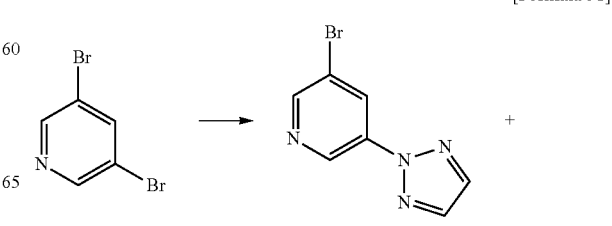

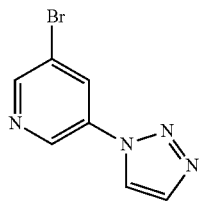

3,5-dibromopyridine (400 mg) and cesium carbonate (550 mg) were added to an N-methylpyrrolidone (4 ml) solution containing 1H-1,2,3-triazole (117 mg), followed by stirring at 100° C. for 21 hours. The reaction mixture was cooled to room temperature, and water and ethyl acetate were added. The organic layer was collected, washed with water and then with saturated saline, and dried over anhydrous magnesium sulfate, and the solvent was distilled away under reduced pressure. The obtained residue was purified by silica gel chromatography (hexane:ethyl acetate=10:0 to 2:3), and a white solid of 3-bromo-5-(2H-1,2,3-triazol-2-yl)pyridine (55 mg) and a white solid of 3-bromo-5-(1H-1,2,3-triazol-1-yl)pyridine (48 mg) were thus obtained.

3-bromo-5-(2H-1,2,3-triazol-2-yl)pyridine $^1$H-NMR (DMSO-$d_6$, 400 MHz) δ:9.24 (d, 1H, J=2.2 Hz), 8.81-8.78 (m, 1H), 8.60 (dd, 1H, J=2.1 Hz, 2.2 Hz), 8.27 (s, 2H)
MS (ESI, m/z): 225, 227 (M+H)

3-bromo-5-(1H-1,2,3-triazol-1-yl)pyridine $^1$H-NMR (DMSO-$d_6$, 400 MHz) δ:9.21-9.19 (m, 1H), 8.97 (d, 1H, J=1.2 Hz), 8.86-8.84 (m, 1H), 8.69 (dd, 1H, J=2.1 Hz, 2.2 Hz), 8.06 (d, 1H, J=1.2 Hz)
MS (ESI, m/z): 225, 227 (M+H)

Reference Example 19

The following compound was obtained with reference to US2008/15191.

[Formula 52]

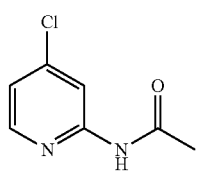

N-(4-chloropyridin-2-yl)acetamide

Reference Example 20

[Formula 53]

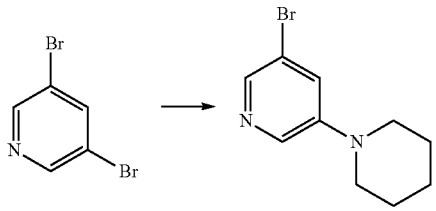

Cesium carbonate (275 mg) and piperidine (83 μl) were added to an N-methylpyrrolidone (2 ml) solution containing 3,5-dibromopyridine (200 mg), followed by stirring at 80° C. for 2 hours. Piperidine (83 μl) was added, followed by stirring at 80° C. for 2 hours. The reaction mixture was cooled to room temperature, and a saturated aqueous ammonium chloride solution and chloroform were added. The organic layer was collected, washed with saturated saline, and dried over anhydrous magnesium sulfate, and the solvent was distilled away under reduced pressure. The obtained residue was purified by silica gel chromatography (hexane:ethyl acetate=20:0 to 17:3), and yellow oily matter of 3-bromo-5-(piperidin-1-yl)pyridine (18 mg) was thus obtained.

$^1$H-NMR (CDCl$_3$, 400 MHz) δ:8.20 (d, 1H, J=2.6 Hz), 8.06 (d, 1H, J=1.8 Hz), 7.28 (dd, 1H, J=2.0 Hz, 2.5 Hz), 3.23-3.18 (m, 4H), 1.74-1.57 (m, 6H)

Reference Example 21

The following compound was obtained with reference to US2009/69305 A1 and US2009/181941 A1.

[Formula 54]

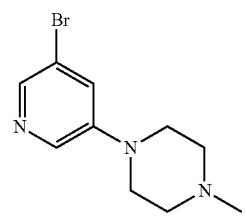

1-(5-bromopyridin-3-yl)-4-methylpiperazine

Reference Example 22

[Formula 55]

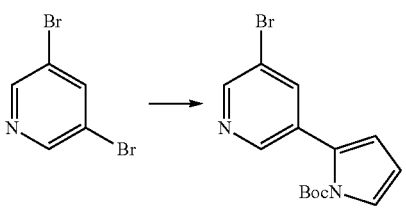

Cesium carbonate (165 mg), 1-(tert-butoxycarbonyl)-1H-pyrrol-2-ylboronic acid (136 mg) and Pd(PPh$_3$)$_4$ (24 mg) were added to a 1,4-dioxane (4 ml) solution containing 3,5-dibromopyridine (100 mg), followed by reflux for 4 hours in a nitrogen atmosphere. The reaction mixture was cooled to room temperature, and water and ethyl acetate were added. The organic layer was collected, washed with saturated saline, and dried over anhydrous sodium sulfate, and the solvent was distilled away under reduced pressure. The obtained residue was purified by silica gel chromatography (silica gel: silica gel 60 (spherical shape) (Kanto Chemical Co., Inc.); hexane:ethyl acetate=4:1), and a white solid of tert-butyl2-(5-bromopyridin-3-yl)-1H-pyrrol-1-carboxylate (73 mg) was thus obtained.

$^1$H-NMR (DMSO-$d_6$, 400 MHz) δ:8.64 (d, 1H, J=2.4 Hz), 8.57 (d, 1H, J=1.9 Hz), 8.14-8.12 (m, 1H), 7.47-7.44 (m, 1H), 6.48-6.45 (m, 1H), 6.36-6.33 (m, 1H), 1.35 (s, 9H)
MS (ESI, m/z): 323 (M+H), 325 (M+H)

Reference Example 23

The following compound was obtained as described in Reference Example 22.

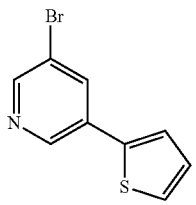

[Formula 56]

3-bromo-5-(2-thienyl)pyridine $^1$H-NMR (DMSO-d$_6$, 400 MHz) δ:8.88 (d, 1H, J=2.0 Hz), 8.62 (d, 1H, 2.2 Hz), 8.36 (dd, 1H, J=2.0, 2.2 Hz), 7.76 (dd, 1H, J=1.2, 3.8 Hz), 7.72 (dd, 1H, J=1.2, 5.1 Hz), 7.21 (dd, 1H, J=3.8, 5.1 Hz)
MS (ESI, m/z): 240 (M+H), 242 (M+H)

Reference Example 24

The following compound was obtained as described in Reference Example 22.

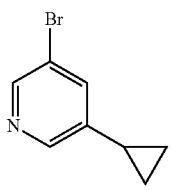

[Formula 57]

3-bromo-5-cyclopropylpyridine $^1$H-NMR (DMSO-d$_6$, 400 MHz) δ:8.45 (d, 1H, J=2.2 Hz), 8.39 (d, 1H, J=2.0 Hz), 7.70 (dd, 1H, J=2.0, 2.2 Hz), 2.01-1.93 (m, 1H), 1.05-0.99 (m, 2H), 0.84-0.78 (m, 2H)

Reference Example 25

The following compound was obtained as described in Reference Example 22.

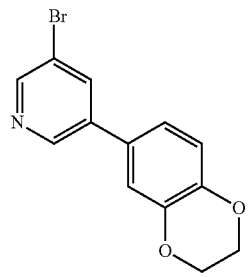

[Formula 58]

3-bromo-5-(2,3-dihydro-1,4-benzodioxin-6-yl)pyridine $^1$H-NMR (DMSO-d$_6$, 400 MHz) δ:8.83 (d, 1H, J=2.0 Hz), 8.63 (d, 1H, J=2.2 Hz), 8.28 (dd, 1H, J=2.0, 2.1 Hz), 7.32 (d, 1H, J=2.2 Hz), 7.26 (dd, 1H, J=2.2, 8.5 Hz), 6.97 (d, 1H, J=8.5 Hz), 4.19 (s, 4H)
MS (ESI, m/z): 292 (M+H), 294 (M+H)

Reference Example 26

The following compound was obtained as described in Reference Example 22.

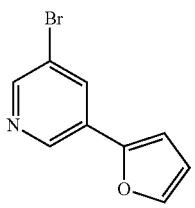

[Formula 59]

3-bromo-5-(2-furyl)pyridine $^1$H-NMR (DMSO-d$_6$, 400 MHz) δ:8.93 (d, 1H, J=2.0 Hz), 8.61 (d, 1H, J=2.2 Hz), 8.34 (dd, 1H, J=2.0, 2.1 Hz), 7.88 (dd, 1H, J=0.7, 1.8 Hz), 7.26 (dd, 1H, J=0.7, 3.4 Hz), 6.68 (dd, 1H, J=1.8, 3.4 Hz)
MS (ESI, m/z): 224 (M+H), 226 (M+H)

Reference Example 27

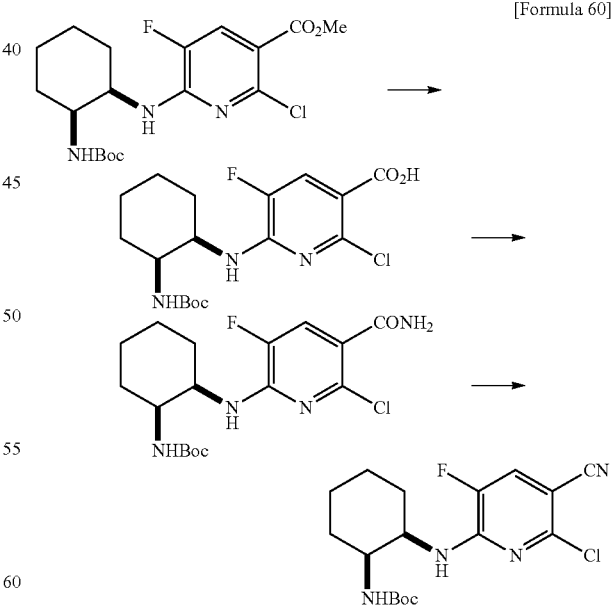

[Formula 60]

1st Step

A 1N sodium hydroxide aqueous solution (15 ml) was added to a solution of tetrahydrofuran (30 ml) and methanol (30 ml) containing methyl 6-(cis-2-(tert-butoxycarbonylamino)cyclohexylamino)-2-chloro-5-fluoronicotinate (3.00 g), followed by stirring at 65° C. for 2 hours. The reaction mixture was cooled to room temperature, the solvent was distilled away under reduced pressure, and a saturated aqueous ammonium chloride solution, tetrahydrofuran, and ethyl acetate were added. The organic layer was collected, washed with saturated saline, and dried over anhydrous magnesium sulfate, and the solvent was distilled away under reduced pressure. Colorless oily matter of 6-(cis-2-(tert-butoxycarbonylamino)cyclohexylamino)-2-chloro-5-fluoronicotinic acid (3.00 g) was thus obtained.

$^1$H-NMR (DMSO-$d_6$, 400 MHz) δ:7.80-7.63 (m, 1H), 6.68 (d, 1H, J=7.7 Hz), 6.44 (brs, 1H), 4.09-3.97 (m, 1H), 3.87-3.75 (m, 1H), 1.87-1.08 (m, 17H)

MS (ESI, m/z): 410, 412 (M+Na), 386, 388 (M−H)

2nd Step

Ammonium chloride (1.10 g), WSC.HCl (2.97 g), HOBt.H$_2$O (2.37 g), and diisopropylethylamine (7.06 ml) were added to a DMF solution (40 ml) containing 6-(cis-2-(tert-butoxycarbonylamino)cyclohexylamino)-2-chloro-5-fluoronicotinic acid (2.00 g), followed by stirring at room temperature for 7 hours. A saturated aqueous ammonium chloride solution, water, and ethyl acetate were added to the reaction mixture. The organic layer was collected, washed with saturated saline, and dried over anhydrous magnesium sulfate, and the solvent was distilled away under reduced pressure. Diisopropylether was added to the obtained residue, solid matter was collected by filtration, and a white solid of tert-butyl cis-2-(5-aminocarbonyl-6-chloro-3-fluoropyridin-2-ylamino)cyclohexylcarbamate (1.75 g) was thus obtained.

$^1$H-NMR (DMSO-$d_6$, 400 MHz) δ:7.72-7.61 (m, 1H), 7.56 (d, 1H, J=10.8 Hz), 7.52-7.46 (m, 1H), 6.71-6.59 (m, 2H), 4.08-3.98 (m, 1H), 3.85-3.77 (m, 1H), 1.82-1.14 (m, 17H)

MS (ESI, m/z): 409 (M+Na)

3rd Step

Trichloroacetyl chloride (0.55 ml) was added dropwise to a dichloromethane (17 ml) suspension containing tert-butyl cis-2-(5-aminocarbonyl-6-chloro-3-fluoropyridin-2-ylamino)cyclohexylcarbamate (1.74 g) and triethylamine (1.38 ml) under ice cooling, followed by stirring at room temperature for 1 hour. The solvent was distilled away under reduced pressure, and a saturated aqueous ammonium chloride solution and ethyl acetate were added. The organic layer was collected, washed with saturated saline, and dried over anhydrous magnesium sulfate, and then the solvent was distilled away under reduced pressure. The obtained residue was purified by silica gel column chromatography (hexane:ethyl acetate=10:0 to 3:1), diisopropylether was added, solid matter was collected by filtration, and a white solid of tert-butyl cis-2-(6-chloro-5-cyano-3-fluoropyridin-2-ylamino)cyclohexylcarbamate (1.26 g) was thus obtained.

$^1$H-NMR (DMSO-$d_6$, 400 MHz) δ:7.96 (d, 1H, J=10.5 Hz), 7.50 (d, 1H, J=5.8 Hz), 6.68 (d, 1H, J=8.0 Hz), 4.10-4.00 (m, 1H), 3.89-3.81 (m, 1H), 1.80-1.08 (m, 17H)

MS (ESI, m/z): 367 (M−H)

Reference Example 28

[Formula 61]

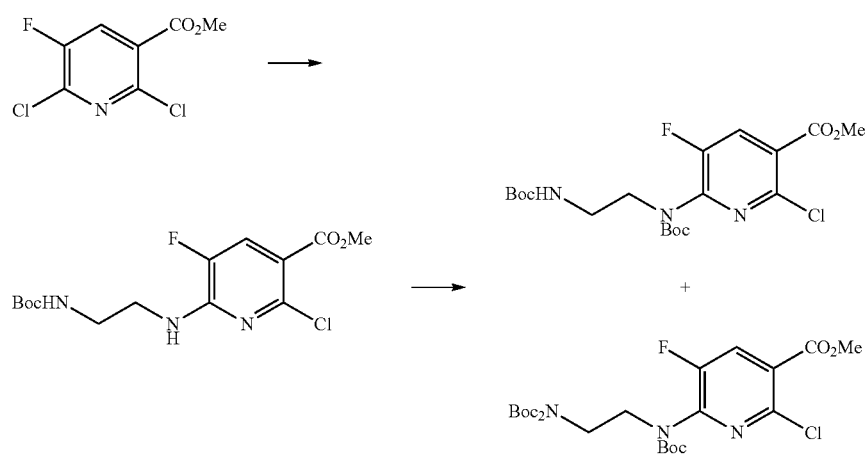

The following compounds were obtained as described in Reference Example 2.

Methyl 6-(2-(tert-butoxycarbonylamino)ethylamino)-2-chloro-5-fluoronicotinate $^1$H-NMR (DMSO-$d_6$, 400 MHz) δ:7.98-7.88 (m, 2H), 7.10-7.00 (m, 1H), 3.91 (s, 3H), 3.56-3.48 (m, 2H), 3.32-3.24 (m, 2H), 1.50 (s, 9H)

Methyl 6-((tert-butoxycarbonyl)(2-(tert-butoxycarbonylamino)ethyl)amino)-2-chloro-5-fluoronicotinate $^1$H-NMR (CDCl$_3$, 400 MHz) δ:7.96 (d, 1H, J=9.3 Hz), 5.39-5.29 (br, 1H), 3.97-3.90 (m, 5H), 3.41-3.31 (m, 2H), 1.46 (s, 9H), 1.40 (s, 9H)

Methyl 6-((2-bis(tert-butoxycarbonyl)aminoethyl)(tert-butoxycarbonyl)amino)-2-chloro-5-fluoronicotinate $^1$H-NMR (CDCl$_3$, 400 MHz) δ:7.93 (d, 1H, J=9.3 Hz), 4.06 (t, 2H, J=6.0 Hz), 3.95 (s, 3H), 3.88 (t, 2H, J=6.0 Hz), 1.47-1.44 (m, 27H)

Reference Example 29

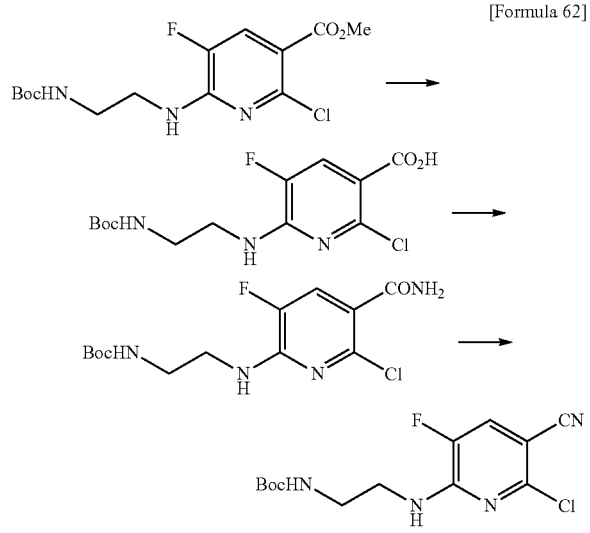

[Formula 62]

The following compound was obtained as described in Reference Example 27.

tert-Butyl 2-(6-chloro-5-cyano-3-fluoropyridin-2-ylamino)ethylcarbamate $^1$H-NMR (DMSO-$d_6$, 400 MHz) δ:8.16 (brs, 1H), 7.96 (d, 1H, J=10.6 Hz), 6.91 (t, 1H, J=5.6 Hz), 3.39 (t, 2H, J=6.2 Hz), 3.13 (dt, 2H, J=5.6, 6.2 Hz), 1.36 (s, 9H)

MS (ESI, m/z): 313 (M−H)

Reference Example 30

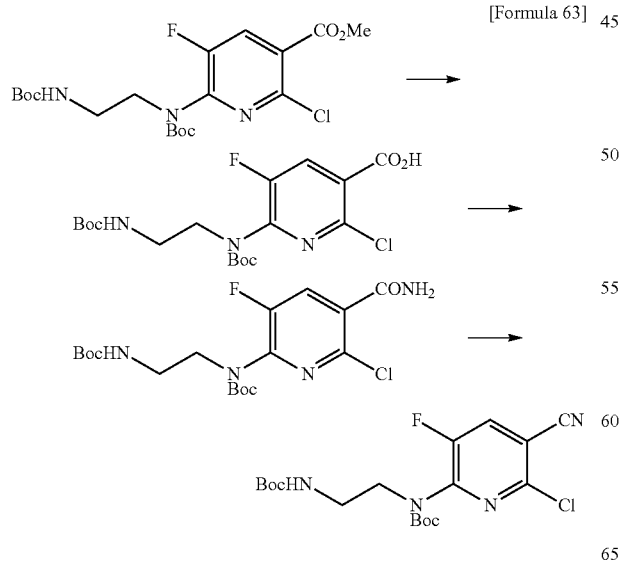

[Formula 63]

The following compounds were obtained as described in Reference Example 27.

6-((tert-butoxycarbonyl)(2-(tert-butoxycarbonylamino)ethyl)amino)-2-chloro-5-fluoronicotinic acid $^1$H-NMR (DMSO-$d_6$, 400 MHz) δ:7.73 (d, 1H, J=8.5 Hz), 6.80-6.73 (m, 1H), 3.65 (t, 2H, J=6.6 Hz), 3.13-3.03 (m, 2H), 1.37 (s, 9H), 1.32 (s, 9H)

tert-Butyl 2-((5-aminocarbonyl-6-chloro-3-fluoropyridin-2-yl)(tert-butoxycarbonyl)amino)ethylcarbamate $^1$H-NMR (CDCl$_3$, 400 MHz) δ:8.02 (d, 1H, J=9.3 Hz), 6.96 (brs, 1H), 6.69 (brs, 1H), 5.33 (brs, 1H), 3.92 (t, 2H, J=5.7 Hz), 3.40-3.32 (m, 2H), 1.45 (s, 9H), 1.40 (s, 9H)

tert-Butyl 2-((tert-butoxycarbonyl)(5-cyano-6-chloro-3-fluoropyridin-2-yl)amino)ethylcarbamate $^1$H-NMR (DMSO-$d_6$, 400 MHz) δ:8.65 (d, 1H, J=9.2 Hz), 6.82-6.72 (br, 1H), 3.81 (t, 2H, J=5.9 Hz), 3.19-3.10 (m, 2H), 1.41 (s, 9H), 1.30 (s, 9H)

Reference Example 31

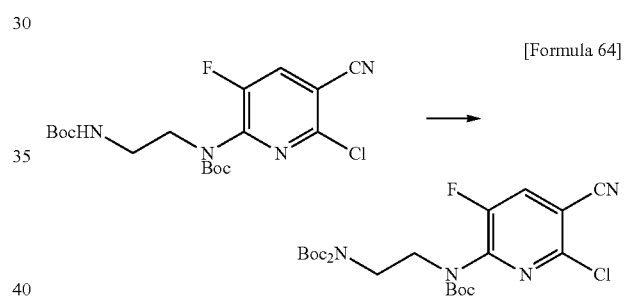

[Formula 64]

The following compound was obtained as described in the 2nd step of Reference Example 2.

Di-tert-butyl 2-((tert-butoxycarbonyl)(5-cyano-6-chloro-3-fluoropyridin-2-yl)amino)ethylimidedicarbamate $^1$H-NMR (CDCl$_3$, 400 MHz) δ:7.64 (d, 1H, J=8.8 Hz), 4.06-4.03 (m, 2H), 3.87-3.83 (m, 2H), 1.45-1.42 (m, 27H)

Reference Example 32

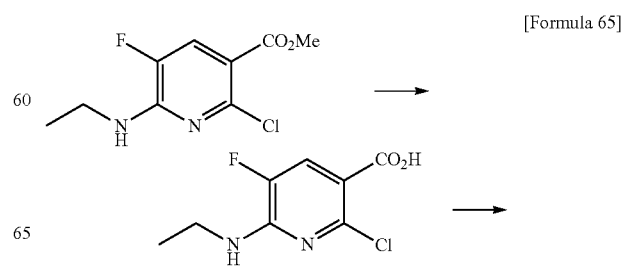

[Formula 65]

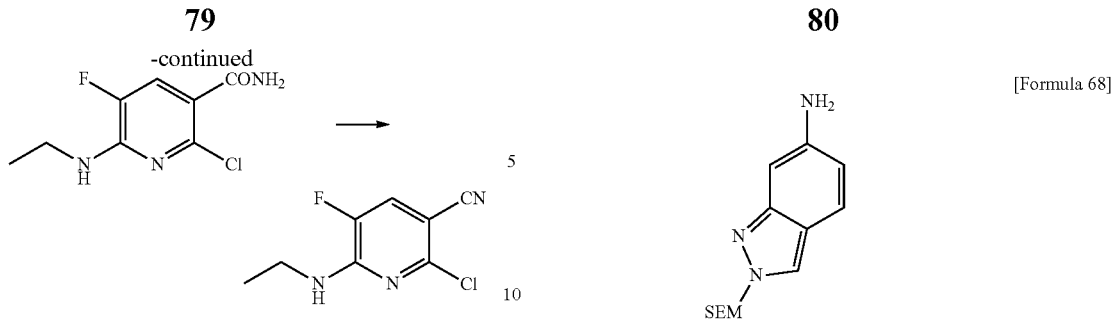

The following compound was obtained as described in Reference Example 27.

2-chloro-6-ethylamino-5-fluoronicotinonitrile $^1$H-NMR (CDCl$_3$, 300 MHz) δ:7.66 (d, 1H, J=8.4 Hz), 3.87 (q, 1H, J=7.2 Hz), 1.47 (s, 9H), 1.26 (t, 3H, J=7.2 Hz)

Reference Example 33

The following compound was obtained with reference to J. Org. Chem., 2006, 71, 5392.

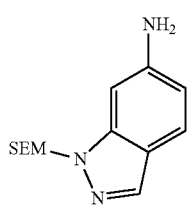

[Formula 66]

1-(2-(trimethylsilyl)ethoxymethyl)-1H-indazol-6-amine

Reference Example 34

The following compound was obtained with reference to WO2009/136995 A2.

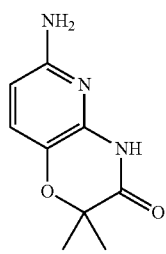

[Formula 67]

6-amino-2,2-dimethyl-2H-pyrido[3,2-b][1,4]oxazin-3(4H)-one

Reference Example 35

The following compound was obtained with reference to J. Org. Chem., 2006, 71, 5392.

[Formula 68]

2-(2-(trimethylsilyl)ethoxymethyl)-2H-indazol-6-amine

Reference Example 36

[Formula 69]

Ammonium chloride (893 mg), water (3 ml), and iron powder (939 mg) were added to an ethanol solution containing 2-methyl-5-nitro-1,3-benzoxazole (500 mg), followed by stirring at 85° C. for 2 hours and 30 minutes. Insoluble matter was removed by filtration and filter cake was washed with water and ethyl acetate. The filtrate was mixed with the washing solution, and ethyl acetate was added. The organic layer was collected, washed with saturated saline, and dried over anhydrous sodium sulfate, and then the solvent was distilled away under reduced pressure. The obtained residue was purified by silica gel column chromatography, and light brown oily matter of 2-methyl-1,3-benzoxazol-5-amine (402 mg) was thus obtained.

$^1$H-NMR (CDCl$_3$, 300 MHz) δ:7.23 (d, 1H, J=9.0 Hz), 6.93 (d, 1H, J=2.4 Hz), 6.64 (dd, 1H, J=2.4, 9.0 Hz), 2.57 (s, 3H)

Reference Example 37

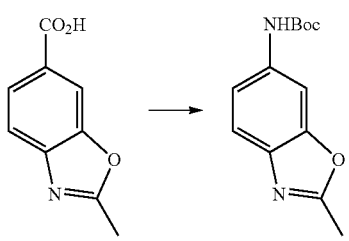

[Formula 70]

Triethylamine (765 μl), tert-butylalcohol (10 ml), and DPPA (1.18 ml) were added to a 1,4-dioxane (20 ml) solution containing 2-methyl-1,3-benzoxazol-6-carboxylic acid (885 mg), followed by stirring at 100° C. for 1 hour and 30 minutes.

The solvent was distilled away under reduced pressure, and a saturated aqueous sodium hydrogen carbonate solution and ethyl acetate were added. The organic layer was collected, washed with saturated saline, and dried over anhydrous sodium sulfate, and then the solvent was distilled away under reduced pressure. The obtained residue was purified by silica gel column chromatography, and a white solid of tert-butyl (2-methyl-1,3-benzoxazol-6-yl)carbamate (1.00 g) was thus obtained.

$^1$H-NMR (CDCl$_3$, 300 MHz) δ: 7.85 (brs, 1H), 7.50 (d, 1H, J=8.7 Hz), 7.00 (d, 1H, J=8.7 Hz), 6.60 (brs, 1H), 2.60 (s, 3H)

Reference Example 38

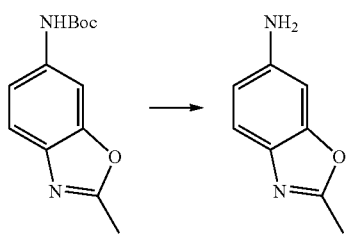

[Formula 71]

TFA (0.5 ml) was added to a chloroform solution (1 ml) containing tert-butyl(2-methyl-1,3-benzoxazol-6-yl) carbamate (50 mg) at 0° C., followed by stirring at room temperature for 3 hours. The solvent was distilled away under reduced pressure. Chloroform was added to the obtained residue, and the solvent was distilled away under reduced pressure. A saturated aqueous sodium hydrogen carbonate solution and chloroform were added to the obtained residue. The organic layer was collected and dried over anhydrous sodium sulfate, the solvent was distilled away under reduced pressure, and a light brown solid of 2-methyl-1,3-benzoxazol-6-amine (24 mg) was thus obtained.

$^1$H-NMR (CDCl$_3$, 300 MHz) δ:7.40 (d, 1H, J=8.7 Hz), 6.79 (d, 1H, J=1.8 Hz), 6.65 (dd, 1H, J=1.8, 8.7 Hz), 3.75 (brs, 2H), 2.58 (s, 3H)

Reference Example 39

The following compound was obtained with reference to J. Heterocyclic. Chem., 1979, 16, 1599.

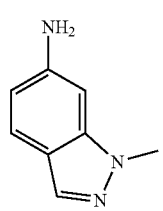

[Formula 72]

1-methyl-1H-indazol-6-amine

Reference Example 40

The following compound was obtained with reference to J. Heterocyclic. Chem., 1979, 16, 1599.

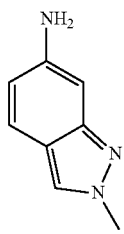

[Formula 73]

1-methyl-2H-indazol-6-amine

Reference Example 41

The following compound was obtained with reference to J. Med. Chem., 2006, 49, 4551.

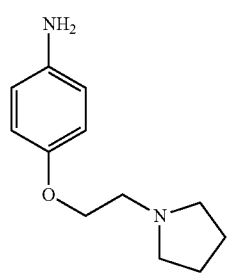

[Formula 74]

4-(2-(pyrrolidin-1-yl)ethoxy)aniline

Reference Example 42

The following compound was obtained with reference to J. Med. Chem., 2006, 49, 4551.

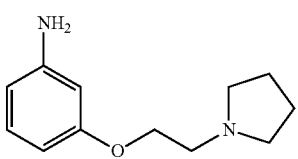

[Formula 75]

3-(2-(pyrrolidin-1-yl)ethoxy)aniline

Reference Example 43

The following compound was obtained with reference to WO2009/090548.

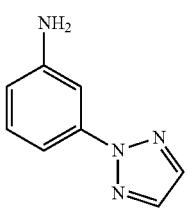

3-(2H-1,2,3-triazol-2-yl)aniline

Reference Example 44

The following compound was obtained with reference to Tetrahedron, 2006, 62, 12351.

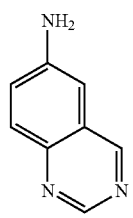

Quinazolin-6-amine

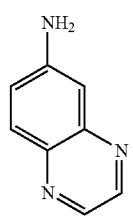

Quinoxalin-6-amine

Reference Example 45

The following compound was obtained with reference to Tetrahedron, 2005, 61, 8218.

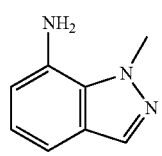

1-methyl-1H-indazol-7-amine

Reference Example 46

The following compound was obtained with reference to J. Med. Chem., 2005, 48, 3417.

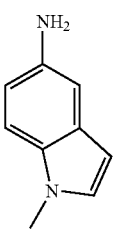

1-methyl-1H-indol-5-amine

Reference Example 47

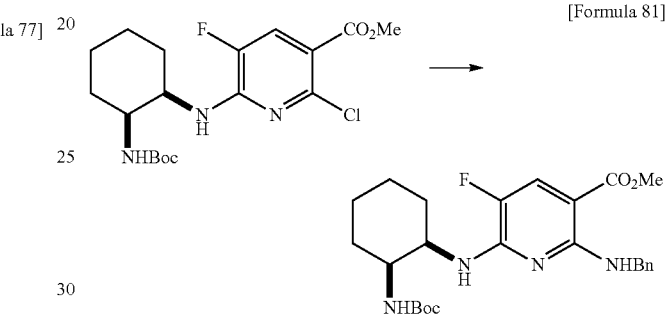

The following compound was obtained as described in the 1st step of Example 1.

Methyl 2-benzylamino-6-(cis-2-(tert-butoxycarbonylamino)cyclohexylamino)-5-fluoronicotinate Reference Example 48

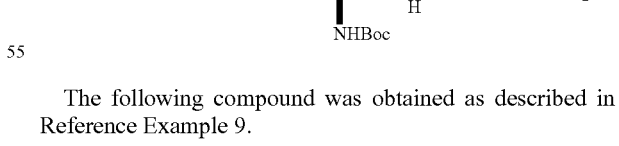

The following compound was obtained as described in Reference Example 9.

Methyl 2-amino-6-(cis-2-(tert-butoxycarbonylamino)cyclohexylamino)-5-fluoronicotinate $^1$H-NMR (DMSO-$d_6$, 400 MHz) δ:7.45 (d, 1H, J=12.0 Hz), 7.10-6.80 (br, 2H), 6.69 (d, 1H, J=7.2 Hz), 6.51 (d, 1H, J=7.2 Hz), 4.18-4.09 (m, 1H), 3.82-3.75 (m, 1H), 3.70 (s, 3H), 1.84-1.69 (m, 2H), 1.63-1.18 (m, 15H)
MS (ESI, m/z): 383 (M+H), 381 (M−H)

Reference Example 49

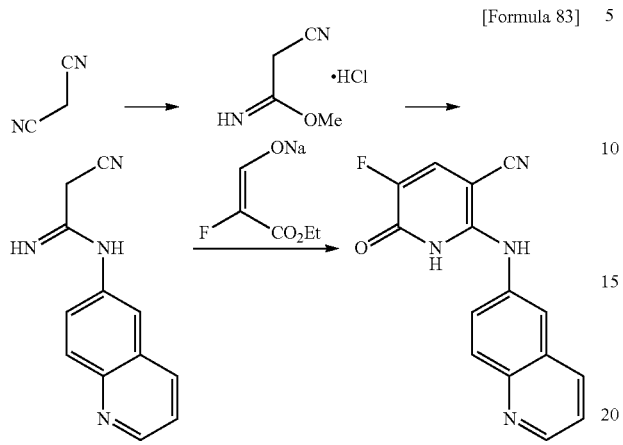

[Formula 83]

1st Step 4N hydrogen chloride/1,4-dioxane (104 ml) was added dropwise to a solution of diisopropylether (200 ml), tetrahydrofuran (50 ml) and methanol (19.1 ml) containing malononitrile (25.0 g) under ice cooling, followed by stirring for 3 hours. Solid matter was collected by filtration and washed with diisopropylether, and white solid (12.8 g) was thus obtained.

2nd Step

Sodium acetate (4.95 g) was added to a DMF (60 ml) solution containing the white solid (4.49 g) obtained in the 1st step and 6-aminoquinoline (4.35 g), followed by stirring at room temperature for 6 hours. A saturated aqueous sodium hydrogen carbonate solution, sodium chloride, and ethyl acetate were added to the reaction mixture. The organic layer was collected and dried over anhydrous magnesium sulfate, and then the solvent was distilled away under reduced pressure. The obtained residue was purified by silica gel column chromatography (chloroform:methanol=100:0 to 20:1), and yellow oily matter of 2-cyano-N-(quinolin-6-yl)acetamidine (4.30 g) was thus obtained.

3rd Step

Ethyl formate (16.1 ml) was added to a hexane (40 ml) suspension containing sodium hydride (60% in oil, 2.4 g) at room temperature, and then fluoroethyl acetate (3.86 ml) was added dropwise under ice cooling, followed by stirring at room temperature for 15 minutes. Ethanol (50 ml) was added to the reaction mixture, and then an ethanol (50 ml) solution containing 2-cyano-N-(quinolin-6-yl)acetamidine (4.20 g) was added dropwise, followed by stirring at 80° C. for 2 hours. The reaction mixture was cooled to room temperature. Then, solid matter was collected by filtration and washed with ethyl acetate, and a yellow solid of 5-fluoro-6-oxo-2-(quinolin-6-ylamino)-1,6-dihydropyridin-3-carbonitrile (3.71 g) was thus obtained.

$^1$H-NMR (DMSO-d$_6$, 400 MHz) δ:8.64 (dd, 1H, J=1.6, 4.3 Hz), 8.51 (s, 1H), 8.19 (s, 1H), 8.16 (d, 1H, J=2.4 Hz), 8.13-8.06 (m, 1H), 7.91 (dd, 1H, J=2.4, 9.2 Hz), 7.80 (d, 1H, J=9.2 Hz), 7.38 (dd, 1H, J=4.2, 8.3 Hz), 7.02 (d, 1H, J=11.0 Hz)

MS (ESI, m/z): 279 (M−H)

Reference Example 50

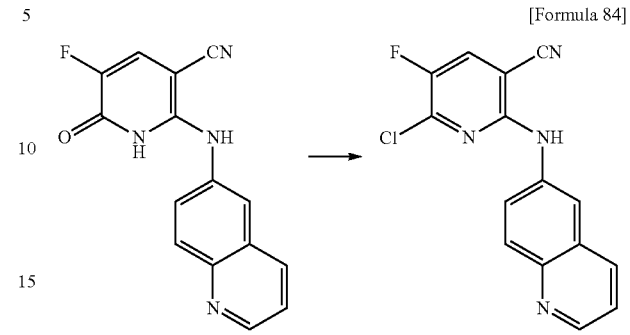

[Formula 84]

A 1,4-dioxane (100 ml) solution containing N-chlorosuccinimide (4.15 g) was added dropwise to a 1,4-dioxane (50 ml) solution containing triphenylphosphine (8.58 g) at 50° C., followed by stirring for 30 minutes. 5-fluoro-6-oxo-2-(quinolin-6-ylamino)-1,6-dihydropyridin-3-carbonitrile (2.61 g) was added to the reaction mixture, followed by stirring at 70° C. for 3 hours. The reaction mixture was cooled to room temperature. Then solid matter was collected by filtration and was washed with tetrahydrofuran, and a gray solid of 6-chloro-5-fluoro-2-(quinolin-6-ylamino)nicotinonitrile (2.34 g) was thus obtained.

$^1$H-NMR (DMSO-d$_6$, 400 MHz) δ:9.85 (s, 1H), 8.80 (dd, 1H, J=1.5, 4.2 Hz), 8.50 (d, 1H, J=8.0 Hz), 8.29-8.23 (m, 1H), 8.02 (d, 1H, J=2.4 Hz), 7.98 (d, 1H, J=9.0 Hz), 7.90 (dd, 1H, J=2.4, 9.0 Hz), 7.49 (dd, 1H, J=4.2, 8.3 Hz)

MS (ESI, m/z): 299 (M+H), 297 (M−H)

Reference Example 51

The following compound was obtained as described in Reference Examples 49 and 50.

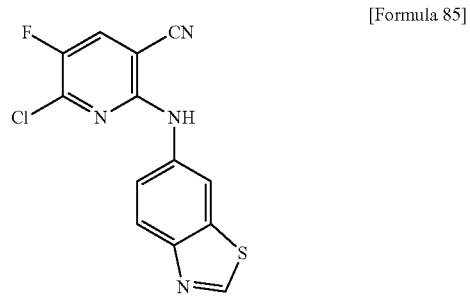 [SMILES: N#Cc1cc(F)c(Cl)nc1Nc1ccc2ncsc2c1]

[Formula 85]

2-(1,3-benzothiazol-6-ylamino)-6-chloro-5-fluoronicotinonitrile $^1$H-NMR (CDCl$_3$, 400 MHz) δ:8.95 (s, 1H), 8.43 (d, 1H, J=2.3 Hz), 8.12 (d, 1H, J=8.8 Hz), 7.64 (d, 1H, J=6.8 Hz), 7.50 (dd, 1H, J=2.3, 8.8 Hz), 7.18 (brs, 1H)

MS (ESI, m/z): 305 (M+H), 303 (M−H)

Reference Example 52

The following compound was obtained as described in Reference Examples 49 and 50.

6-chloro-5-fluoro-2-(quinolin-3-ylamino)nicotinonitrile

[Formula 86]

¹H-NMR (DMSO-d₆, 400 MHz) δ:9.94 (s, 1H), 9.04 (d, 1H, J=2.7 Hz), 8.52 (d, 1H, J=8.1 Hz), 8.37 (d, 1H, J=2.7 Hz), 8.02-7.86 (m, 2H), 7.73-7.54 (m, 2H)
MS (ESI, m/z): 299 (M+H), 297 (M−H)

Reference Example 53

[Formula 87]

1st Step
Isobutyl chloroformate (811 μl) was added dropwise to a mixture of N-benzyloxycarbonyl-D-leucine·dicyclohexylamine salt (2.23 g), 1,2-dimethoxyethane (25 ml), and N-methylmorpholine (687 μl) under ice cooling, followed by stirring at the same temperature for 1 hour. 25% aqueous ammonia solution (3.4 ml) was added to the reaction mixture under ice cooling, followed by stirring at the same temperature for 1 hour. A saturated aqueous sodium hydrogen carbonate solution and ethyl acetate were added to the reaction mixture. The organic layer was collected, washed with saturated saline, and dried over anhydrous magnesium sulfate, and then the solvent was distilled away under reduced pressure. Hexane was added to the obtained residue and solid matter was collected by filtration, and a white solid of N²-benzyloxycarbonyl-D-leucinamide (1.47 g) was thus obtained.

¹H-NMR (DMSO-d₆, 400 MHz) δ:7.45-7.25 (m, 7H), 6.95 (brs, 1H), 5.02 (s, 2H), 4.05-3.90 (m, 1H), 1.70-1.53 (m, 1H), 1.53-1.30 (m, 2H), 0.96-0.76 (m, 6H)

2nd Step
Pd/C (106 mg) was added to an ethanol (20 ml) solution containing N²-benzyloxycarbonyl-D-leucinamide (529 mg), followed by stirring at room temperature for 3 hours in a hydrogen atmosphere. Insoluble matter was removed by filtration, and 1,4-dioxane (2 ml) and 4N hydrogen chloride/1,4-dioxane were added. Solid matter was collected by filtration, and a white solid of D-leucinamide·hydrochloride (308 mg) was thus obtained.

¹H-NMR (DMSO-d₆, 400 MHz) δ:8.24 (brs, 3H), 8.00 (brs, 1H), 7.52 (brs, 1H), 3.75-3.61 (m, 1H), 1.76-1.61 (m, 1H), 1.61-1.50 (m, 2H), 0.97-0.84 (m, 6H)

Reference Example 54

The following compound was obtained as described in Reference Example 53.

[Formula 88]

D-phenylalaninamide-hydrochloride

¹H-NMR (DMSO-d₆, 400 MHz) δ:8.13 (brs, 3H), 7.88 (brs, 1H), 7.56 (brs, 1H), 7.40-7.22 (m, 5H), 4.00-3.88 (m, 1H), 3.09 (dd, 1H, J=6.0, 13.9 Hz), 2.98 (dd, 1H, J=7.8, 13.9 Hz)

Reference Example 55

The following compound was obtained with reference to J. Org. Chem., 2002, 67, 3687.

[Formula 89]

Reference Example 56

[Formula 90]

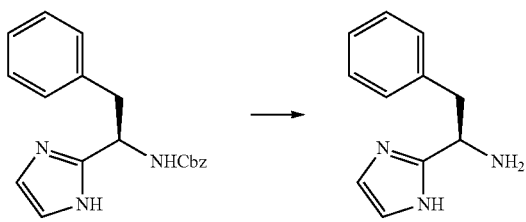
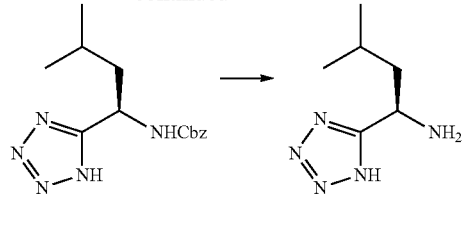

1st Step

Dess-Martin periodinane (849 mg) was added to a dichloromethane (20 ml) solution containing benzyl((2R)-1-hydroxy-3-phenylpropan-2-yl)carbamate (571 mg), followed by stirring at room temperature for 3 hours and 30 minutes. Insoluble matter was removed by filtration, and the solvent was distilled away under reduced pressure. The obtained residue was purified by silica gel chromatography (hexane:ethyl acetate=10:1 to 2:1), and a white solid of benzyl((2R)-1-oxo-3-phenylpropan-2-yl)carbamate (501 mg) was thus obtained.

$^1$H-NMR (DMSO-$d_6$, 400 MHz) δ:9.56 (s, 1H), 7.75 (d, 1H, J=7.8 Hz), 7.50-7.00 (m, 10H), 5.05-4.80 (m, 3H), 3.14 (dd, 1H, J=4.3, 14.2 Hz), 2.70 (dd, 1H, 10.4, 14.2 Hz)

2nd Step

A mixture of benzyl((2R)-1-oxo-3-phenylpropan-2-yl)carbamate (484 mg), glyoxal (359 mg), 2M ammonia/methanol solution (8.55 ml), and methanol (1.71 ml) was stirred at room temperature for 7 hours. Water, sodium chloride, and ethyl acetate were added to the reaction mixture. The organic layer was collected and dried over anhydrous magnesium sulfate, and then the solvent was distilled away under reduced pressure. The obtained residue was purified by silica gel column chromatography (chloroform:methanol=20:0 to 20:1), a liquid mixture of ethyl acetate and isopropanol was added, and solid matter was collected by filtration, and a white solid of benzyl((1R)-1-(1H-imidazol-2-yl)-2-phenylethyl)carbamate (111 mg) was thus obtained.

$^1$H-NMR (DMSO-$d_6$, 400 MHz) δ:11.76 (brs, 1H), 7.69 (d, 1H, J=8.8 Hz), 7.38-7.12 (m, 10H), 6.98 (s, 1H), 6.81 (s, 1H), 5.03-4.80 (m, 3H), 3.23 (dd, 1H, J=5.6, 13.6 Hz), 2.97 (dd, 1H, J=9.3, 13.6 Hz)

3rd Step

The following compound was obtained as described in the 2nd step of Reference Example 53.

(1R)-1-(1H-imidazol-2-yl)-2-phenylethylamine

Reference Example 57

1st Step

The following compound was obtained as described in the 3rd step of Reference Example 27.

Benzyl((1R)-1-cyano-3-methylbutyl)carbamate $^1$H-NMR (CDCl$_3$, 400 MHz) δ:7.42-7.30 (m, 5H), 5.14 (s, 2H), 5.07-4.96 (m, 1H), 4.72-4.57 (m, 1H), 1.90-1.57 (m, 3H), 0.97 (d, 6H, J=6.8 Hz)

MS (ESI, m/z): 269 (M+Na)

2nd Step

Triethylamine•hydrochloride (508 mg) and sodium azide (241 mg) were added to a toluene (12 ml) solution containing benzyl((1R)-1-cyano-3-methylbutyl)carbamate (303 mg), followed by stirring at 100° C. for 5 hours. The reaction mixture was cooled to room temperature, and water and ethyl acetate were added. The organic layer was collected, washed with saturated saline, and dried over anhydrous magnesium sulfate. The solvent was distilled away under reduced pressure, and colorless oily matter of benzyl((1R)-3-methyl-1-(1H-tetrazol-5-yl)butyl)carbamate (310 mg) was thus obtained.

3rd Step

The following compound was obtained as described in the 2nd step of Reference Example 53.

(1R)-3-methyl-1-(1H-tetrazol-5-yl)butyl amine $^1$H-NMR (DMSO-$d_6$, 400 MHz) δ:8.26 (brs, 1H), 4.49-4.38 (m, 1H), 1.90-1.77 (m, 1H), 1.72-1.59 (m, 1H), 1.56-1.41 (m, 1H), 0.88 (d, 3H, J=6.5 Hz), 0.83 (d, 3H, J=6.5 Hz)

Reference Example 58

[Formula 92]

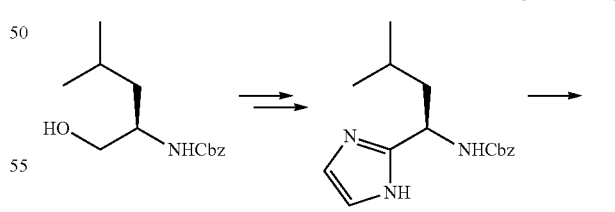

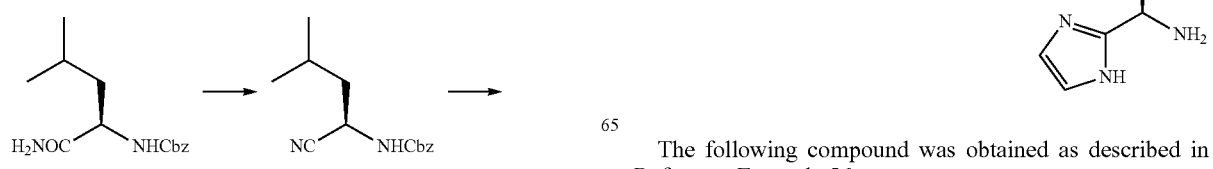

[Formula 91]

The following compound was obtained as described in Reference Example 56.

Benzyl((1R)-1-(1H-imidazol-2-yl)-3-methylbutyl)carbamate

MS (ESI, m/z): 288 (M+H)

Reference Example 59

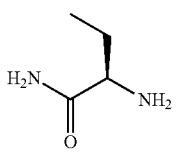

[Formula 93]

The following compound was obtained as described in Reference Example 53.

(2R)-2-aminobutanamide•hydrochloride $^1$H-NMR (DMSO-d$_6$, 400 MHz) δ:8.22 (brs, 3H), 7.95 (brs, 1H), 7.51 (brs, 1H), 3.68-3.62 (m, 1H), 1.82-1.68 (m, 2H), 0.88 (t, 3H, J=7.4 Hz)

Reference Example 60

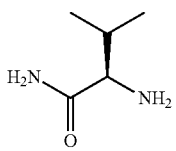

[Formula 94]

The following compound was obtained as described in Reference Example 53.

D-valinamide•hydrochloride $^1$H-NMR (DMSO-d$_6$, 400 MHz) δ:8.09 (brs, 3H), 7.86 (brs, 1H), 7.58 (brs, 1H), 3.53 (d, 1H, J=5.4 Hz), 2.16-2.02 (m, 1H), 0.94 (dd, 6H, J=7.0, 10.1 Hz)

Reference Example 61

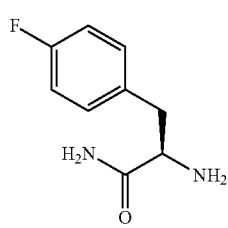

[Formula 95]

The following compound was obtained as described in Reference Example 53.

4-fluoro-D-phenylalaninamide•hydrochloride $^1$H-NMR (DMSO-d$_6$, 400 MHz) δ:8.18 (brs, 3H), 7.95 (brs, 1H), 7.55 (brs, 1H), 7.34-7.26 (m, 2H), 7.20-7.10 (m, 2H), 3.96-3.88 (m, 1H), 3.09 (dd, 1H, J=6.0, 14.0 Hz), 2.98 (dd, 1H, J=7.6, 14.0 Hz)

Reference Example 62

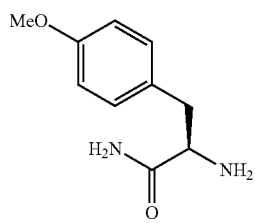

[Formula 96]

The following compound was obtained as described in Reference Example 53.

O-methyl-D-tyrosineamide•hydrochloride $^1$H-NMR (DMSO-d$_6$, 400 MHz) δ:8.16 (brs, 3H), 7.93 (brs, 1H), 7.51 (brs, 1H), 7.18 (d, 2H, J=8.5 Hz), 6.88 (d, 2H, J=8.5 Hz), 3.94-3.83 (m, 1H), 3.72 (s, 3H), 3.02 (dd, 1H, J=6.2, 14.0 Hz), 2.93 (dd, 1H, J=7.3, 14.0 Hz)

Reference Example 63

The following compound was obtained with reference to WO2009/136995.

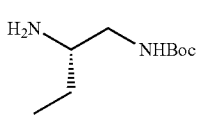

[Formula 97]

(2S)-tert-butyl 2-aminobutylcarbamate

Reference Example 64

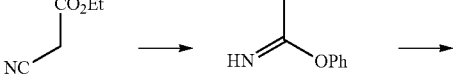

[Formula 98]

1st Step

Hydrogen chloride was introduced into a mixture of ethyl cyanoacetate (56.6 g) and phenol (47.1 g) at −15° C., followed by stirring under ice cooling for 3 hours. The reaction mixture was left at rest at 4° C. for 40 hours. Diethyl ether was added to the reaction mixture. Solid matter was collected by filtration and washed with diethyl ether, and a white solid (60.1 g) was thus obtained.

2nd Step

An ethyl acetate (300 ml) solution containing the white solid (60.1 g) obtained in the 1st step and 3,5-dimethoxyaniline (37.8 g) was refluxed for 2 hours and 30 minutes. The reaction mixture was cooled to room temperature, and ethyl acetate (100 ml) was added, followed by stirring under ice cooling for 1 hour. Solid matter was collected by filtration and washed with ethyl acetate, and a white solid of ethyl 3-(3,5-dimethoxyphenyl)amino-3-iminopropionato•hydrochloride (60.8 g) was thus obtained.

$^1$H-NMR (DMSO-d$_6$, 400 MHz) δ:11.79 (brs, 1H), 9.81 (brs, 1H), 8.97 (brs, 1H), 6.58 (t, 1H, J=2.2 Hz), 6.42 (d, 2H, J=2.2 Hz), 4.20 (q, 2H, J=7.1 Hz), 3.85 (s, 2H), 3.79 (s, 6H), 1.25 (t, 3H, J=7.1 Hz)

3rd Step

[1]

Sodium hydride (60% in oil, 11.3 g) was added to a hexane (250 ml) solution containing fluoroethyl acetate (27.2 ml) and ethyl formate (22.7 ml) under ice cooling, followed by stirring at the same temperature for 1 hour and then at room temperature for 1 hour. Solid matter was collected by filtration and washed with hexane, and solid matter was thus obtained.

[2]

A 1N sodium hydroxide aqueous solution was added to a mixture of ethyl 3-(3,5-dimethoxyphenyl)amino-3-iminopropionato•hydrochloride (28.4 g), water (150 ml), and ethyl acetate (150 ml) so as to alkalify the mixture (pH>10). The organic layer was collected and dried over anhydrous magnesium sulfate, the solvent was distilled away under reduced pressure, and a residue was thus obtained.

[3]

An ethanol (600 ml) solution containing the substances obtained in [1] and [2] was refluxed for 4 hours. The reaction mixture was cooled to room temperature, and the solvent was distilled away under reduced pressure. Ethanol was added to the obtained residue. Solid matter was collected by filtration, dissolved in ethyl acetate, and washed with 1N hydrochloric acid. Then, the solvent was distilled away under reduced pressure, and a gray solid of ethyl 2-(3,5-dimethoxyphenyl)amino-5-fluoro-6-oxo-1,6-dihydropyridin-3-carboxylate (24.6 g) was thus obtained.

$^1$H-NMR (DMSO-d$_6$, 400 MHz) δ:10.11 (s, 1H), 7.84 (d, 1H, J=11.7 Hz), 6.81-6.72 (m, 2H), 6.26-6.22 (m, 1H), 4.28 (q, 2H, J=7.1 Hz), 3.75 (s, 6H), 1.31 (t, 3H, J=7.1 Hz)

Reference Example 65

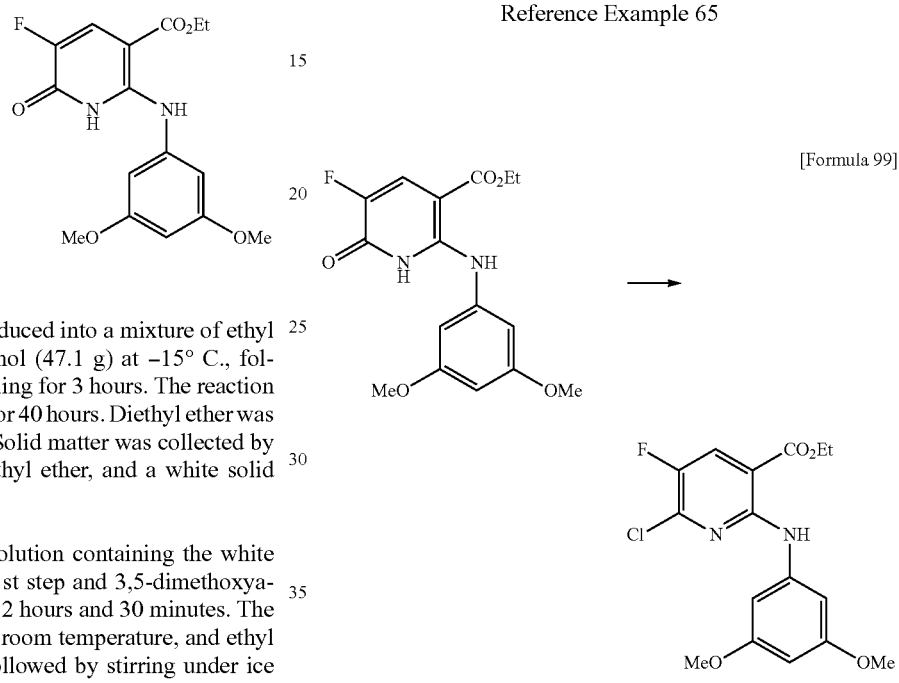

The following compound was obtained as described in Reference Example 50.

Ethyl 6-chloro-2-(3,5-dimethoxyphenylamino)-5-fluoronicotinate $^1$H-NMR (CDCl$_3$, 400 MHz) δ:10.19 (s, 1H), 8.03 (d, 1H, J=8.2 Hz), 6.96 (d, 2H, J=2.2 Hz), 6.22 (t, 1H, J=2.2 Hz), 4.41 (q, 2H, J=7.1 Hz), 3.82 (s, 6H), 1.42 (t, 3H, J=7.1 Hz)

Reference Example 66

The following compound was obtained with reference to WO2009/18344 A1.

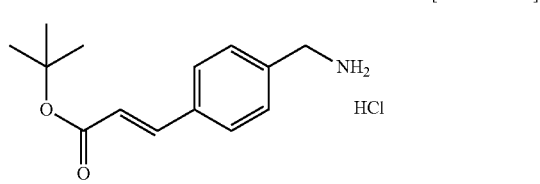

(E)-tert-butyl 3-(4-(aminomethyl)phenyl)acrylate

Reference Example 67

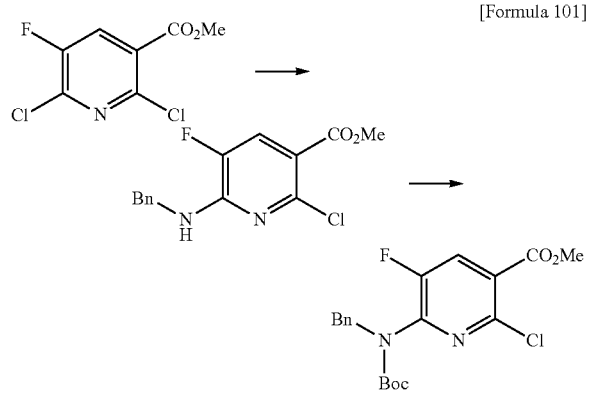

[Formula 101]

The following compound was obtained as described in Reference Example 2.

Methyl 2-chloro-6-(benzyl(tert-butoxycarbonyl)amino)-5-fluoronicotinate

¹H-NMR (CDCl₃, 400 MHz) δ: 7.89 (d, 1H, J=9.1 Hz), 7.32-7.18 (m, 5H), 5.07 (s, 2H), 3.93 (s, 3H), 1.43 (s, 9H)

Reference Example 68

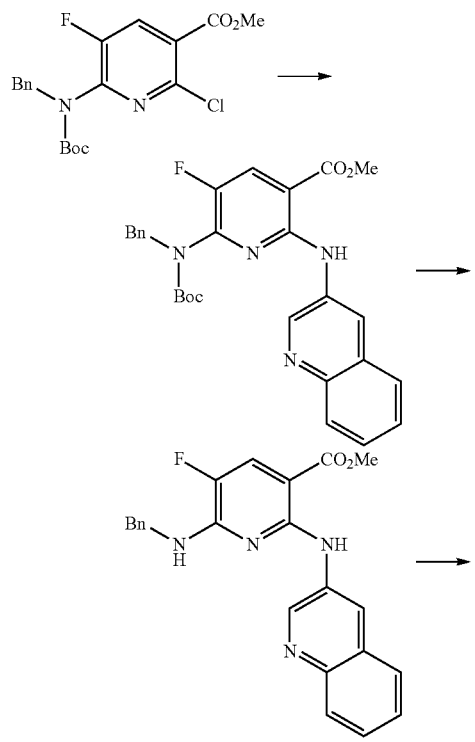

[Formula 102]

The following compound was obtained as described in Example 1 and Reference Example 9.

Methyl 6-amino-5-fluoro-2-(quinolin-3-ylamino)nicotinate

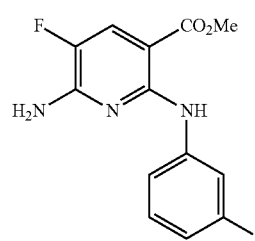

¹H-NMR (DMSO-d₆, 400 MHz) δ:10.56 (s, 1H), 9.14 (d, 1H, J=2.6 Hz), 8.90 (d, 1H, J=2.6 Hz), 7.96-7.90 (m, 2H), 7.74 (d, 1H, J=11.6 Hz), 7.61-7.54 (m, 2H), 7.45 (brs, 2H), 3.83 (s, 3H)
MS (ESI, m/z): 313 (M+H), 311 (M−H)

Reference Example 69

[Formula 103]

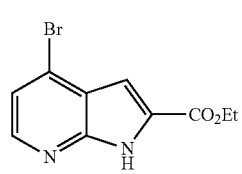

The following compound was obtained as described in Reference Example 67.

Methyl 6-amino-5-fluoro-2-(3-(trifluoromethyl)phenylamino)nicotinate

¹H-NMR (CDCl₃, 400 MHz) δ:10.42 (s, 1H), 8.07 (s, 1H), 7.78 (d, 1H, J=11.1 Hz), 7.76-7.71 (m, 1H), 7.39 (dd, 1H, J=7.9, 7.9 Hz), 7.29-7.23 (m, 1H), 4.99 (brs, 2H), 3.87 (s, 3H)

Reference Example 70

The following compound was obtained with reference to WO2008/49855.

[Formula 104]

Reference Example 71

The following compound was obtained with reference to EP2119706.

[Formula 105]

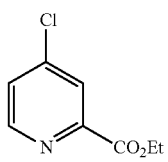

Reference Example 72

[Formula 106]

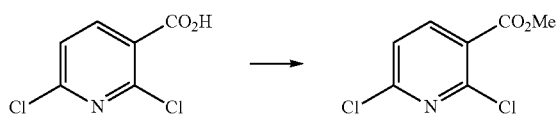

The following compound was obtained as described in Reference Example 1.

Methyl 2,6-dichloronicotinate

¹H-NMR (DMSO-d₆, 400 MHz) δ:8.33 (d, 1H, J=8.0 Hz), 7.73 (d, 1H, J=8.0 Hz), 3.89 (s, 3H)

Reference Example 73

[Formula 107]

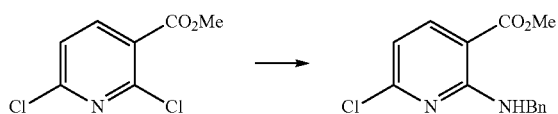

The following compound was obtained as described in the 1st step of Reference Example 2.

Methyl 2-benzylamino-6-chloronicotinate

¹H-NMR (DMSO-d₆, 400 MHz) δ:8.57-8.49 (m, 1H), 8.10 (d, 1H, J=8.0 Hz), 7.37-7.30 (m, 4H), 7.30-7.22 (m, 1H), 6.69 (d, 1H, J=8.0 Hz), 4.64 (d, 2H, J=5.9 Hz), 3.82 (S, 3H)
MS (ESI, m/z): 277 (M+H), 279 (M+H)

Reference Example 74

[Formula 108]

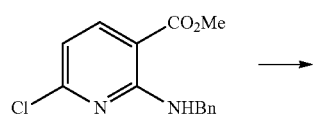

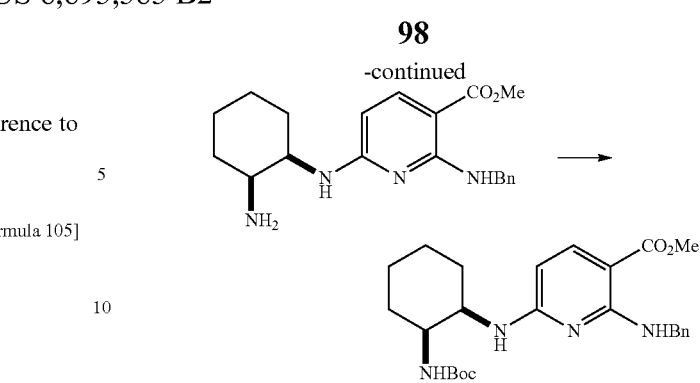

Diisopropylethylamine (7.5 ml) and cis-cyclohexane-1,2-diamine (5.0 g) were added to an N-methylpyrrolidone (50 ml) solution containing methyl 2-benzylamino-6-chloronicotinate (6.0 g), followed by stirring at 120° C. for 11 hours. The reaction mixture was cooled to room temperature, and water and ethyl acetate were added. The organic layer was collected, washed with saturated saline, and dried over anhydrous sodium sulfate, and then the solvent was distilled away under reduced pressure. Di-tert-butyl dicarbonate (4.7 g) was added to a tetrahydrofuran (50 ml) solution containing the obtained residue and the resulting mixture was left at rest at room temperature for 3 days. The solvent was distilled away under reduced pressure. The obtained residue was purified by silica gel column chromatography (silica gel:silica gel 60 (spherical shape) (Kanto Chemical Co., Inc.); hexane:ethyl acetate=3:1), and a light yellow solid of methyl 2-benzylamino-6-(cis-2-(tert-butoxycarbonylamino)cyclohexylamino)nicotinate (7.7 g) was thus obtained.

¹H-NMR (DMSO-d₆, 400 MHz) δ:8.50-8.40 (br, 1H), 7.70-7.57 (m, 1H), 7.37-7.18 (m, 5H), 6.80-6.65 (br, 1H), 6.55-6.42 (br, 1H), 5.87-5.77 (m, 1H), 4.71-4.48 (m, 2H), 4.20-4.09 (m, 1H), 3.73-3.64 (m, 4H), 1.70-1.10 (m, 17H)
MS (ESI, m/z): 455 (M+H), 477 (M+Na)

Reference Example 75

[Formula 109]

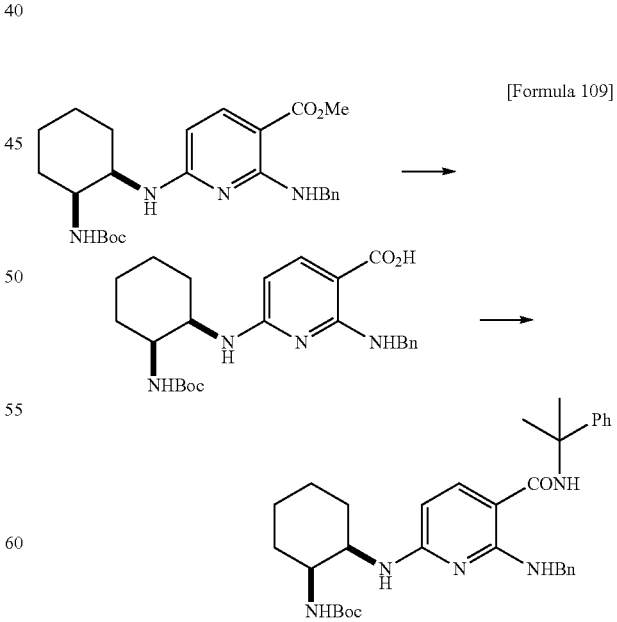

The following compound was obtained as described in Reference Example 3. 2-benzylamino-6-(cis-2-(tert-butoxycarbonylamino)cyclohexylamino)nicotinic acid ¹H-NMR (DMSO-d$_6$, 400 MHz) δ:11.86-11.65 (br, 1H), 8.64-8.53 (br, 1H), 7.63 (d, 1H, J=8.6 Hz), 7.36-7.26 (m, 4H), 7.26-7.18 (m, 1H), 6.70-6.40 (m, 2H), 5.80 (d, 1H, J=8.6 Hz), 4.72-4.50 (m, 2H), 4.15-3.99 (m, 1H), 3.74-3.62 (m, 1H), 1.70-1.13 (m, 17H)

MS (ESI, m/z): 441 (M+H), 463 (M+Na), 439 (M−H)

tert-Butyl cis-2-(6-benzylamino-5-(2-phenylpropan-2-ylaminocarbonyl)pyridin-2-ylamino)cyclohexyl-carbamate $^1$H-NMR (DMSO-d$_6$, 400 MHz) δ:8.96-8.88 (br, 1H), 7.85 (d, 1H, J=8.7 Hz), 7.73-7.66 (br, 1H), 7.34-7.10 (m, 10H), 6.50-6.42 (m, 1H), 6.37-6.26 (m, 1H), 5.78 (d, 1H, J=8.7 Hz), 4.57-4.38 (m, 2H), 4.06-3.95 (m, 1H), 3.70-3.58 (m, 1H), 1.70-1.14 (m, 23H)

MS (ESI, m/z): 558 (M+H)

Reference Example 76

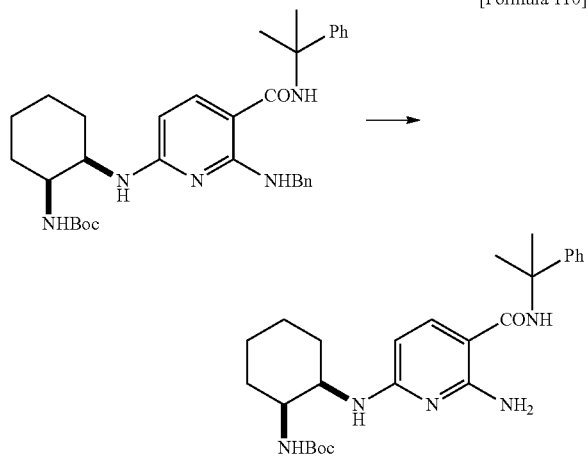

[Formula 110]

The following compound was obtained as described in Reference Example 9. tert-Butyl cis-2-(6-amino-5-(2-phenylpropan-2-ylaminocarbonyl)pyridin-2-ylamino)cyclohexylcarbamate $^1$H-NMR (DMSO-d$_6$, 400 MHz) δ:7.81 (d, 1H, J=8.7 Hz), 7.70-7.63 (br, 1H), 7.35-7.30 (m, 2H), 7.28-7.22 (m, 2H), 7.16-7.10 (m, 1H), 6.82-6.74 (br, 2H), 6.54-6.47 (m, 1H), 6.21-6.13 (m, 1H), 5.80 (d, 1H, J=8.7 Hz), 4.05-3.94 (m, 1H), 3.70-3.62 (m, 1H), 1.80-1.20 (m, 23H)

MS (ESI, m/z): 468 (M+H)

Reference Example 77

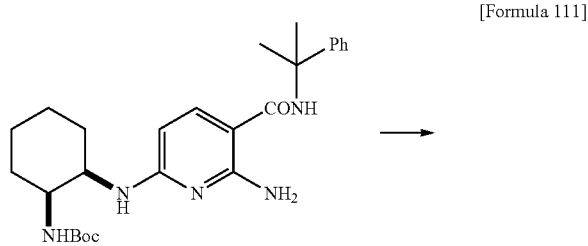

[Formula 111]

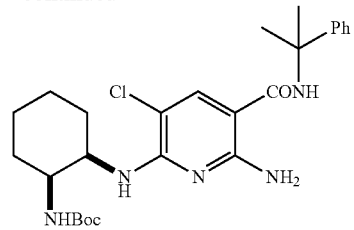

N-chlorosuccinimide (17 mg) was added to a DMF (5 ml) solution containing tert-butyl cis-2-(6-amino-5-(2-phenyl-propan-2-ylaminocarbonyl)pyridin-2-ylamino)cyclohexyl-carbamate (60 mg) at 0° C., followed by stirring for 1 hour. Water and ethyl acetate were added to the reaction mixture. The organic layer was collected, washed with saturated saline, and dried over anhydrous sodium sulfate, and then the solvent was distilled away under reduced pressure. The obtained residue was purified by silica gel chromatography (silica gel: silica gel 60 (spherical shape) (Kanto Chemical Co., Inc.); hexane:ethyl acetate=3:1), and a white solid of tert-butyl cis-2-(6-amino-3-chloro-5-(2-phenylpropan-2-ylaminocarbonyl)pyridin-2-ylamino)cyclohexylcarbamate (50 mg) was thus obtained.

$^1$H-NMR (DMSO-d$_6$, 400 MHz) δ:8.06 (s, 1H), 7.93 (s, 1H), 7.35-7.30 (m, 2H), 7.28-7.22 (m, 2H), 7.17-7.11 (m, 1H), 7.03-6.95 (br, 2H), 6.95-6.89 (m, 1H), 5.85-5.77 (m, 1H), 4.11-4.02 (m, 1H), 3.85-3.77 (m, 1H), 1.80-1.22 (m, 23H)

MS (ESI, m/z): 502 (M+H), 504 (M+H)

Reference Example 78

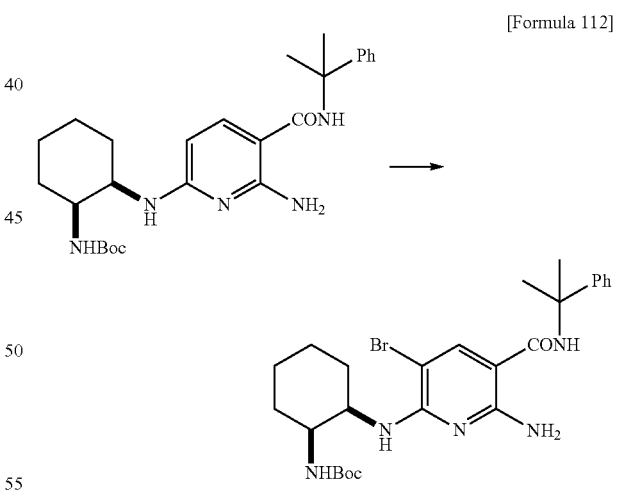

[Formula 112]

N-bromosuccinimide (22 mg) was added to a DMF (5 ml) solution containing tert-butyl cis-2-(6-amino-5-(2-phenyl-propan-2-ylaminocarbonyl)pyridin-2-ylamino)cyclohexyl-carbamate (60 mg) at 0° C., followed by stirring for 1 hour. Water and ethyl acetate were added to the reaction mixture. The organic layer was collected, washed with saturated saline, and dried over anhydrous sodium sulfate, and then the solvent was distilled away under reduced pressure. The obtained residue was purified by silica gel chromatography (silica gel:silica gel 60 (spherical shape) (Kanto Chemical Co., Inc.); hexane:ethyl acetate=4:1 to 3:1), and a white solid of tert-butyl cis-2-(6-amino-3-bromo-5-(2-phenylpropan-2-ylaminocarbonyl)pyridin-2-ylamino)cyclohexylcarbamate (68 mg) was thus obtained.

$^1$H-NMR (DMSO-d$_6$, 400 MHz) δ:8.17 (s, 1H), 7.96 (s, 1H), 7.36-7.30 (m, 2H), 7.30-7.22 (m, 2H), 7.17-7.11 (m, 1H), 7.10-6.94 (m, 3H), 5.70-5.60 (m, 1H), 4.11-4.00 (m, 1H), 3.87-3.78 (m, 1H), 1.80-1.21 (m, 23H)

MS (ESI, m/z): 546 (M+H), 548 (M+H)

Reference Example 79

The following compound was obtained as described in Reference Example 18.

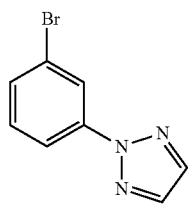

[Formula 113]

2-(3-bromophenyl)-2H-1,2,3-triazole $^1$H-NMR (CDCl$_3$, 400 MHz) δ:8.32-8.28 (m, 1H), 8.08-8.02 (m, 1H), 7.83 (s, 2H), 7.52-7.46 (m, 1H), 7.40-7.32 (m, 1H)

Reference Example 80

The following compound was obtained as described in Reference Example 22.

[Formula 114]

2-(5-bromopyridin-3-yl)thiazole

MS (ESI m/z): 241, 243 (M+H)
$^1$H-NMR (DMSO-d$_6$, 400 MHz) δ:9.13 (d, 1H, J=2.0 Hz), 8.81 (d, 1H, J=2.2 Hz), 8.55-8.53 (m, 1H), 8.04 (d, 1H, J=3.2 Hz), 8.00-7.92 (m, 1H)

Reference Example 81

The following compound was obtained as described in Reference Example 22.

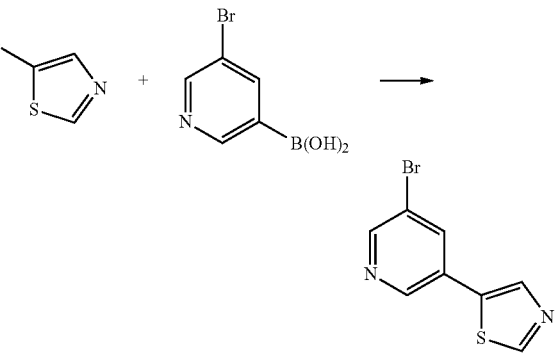

[Formula 115]

5-(5-bromopyridin-3-yl)thiazole

MS (ESI m/z): 241, 243 (M+H)
$^1$H-NMR (DMSO-d$_6$, 400 MHz) δ:9.23-9.21 (m, 1H), 8.93-8.89 (m, 1H), 8.71-8.68 (m, 1H), 8.54 (s, 1H), 8.48-8.45 (m, 1H)

Reference Example 82

The following compound was obtained as described in Reference Example 22.

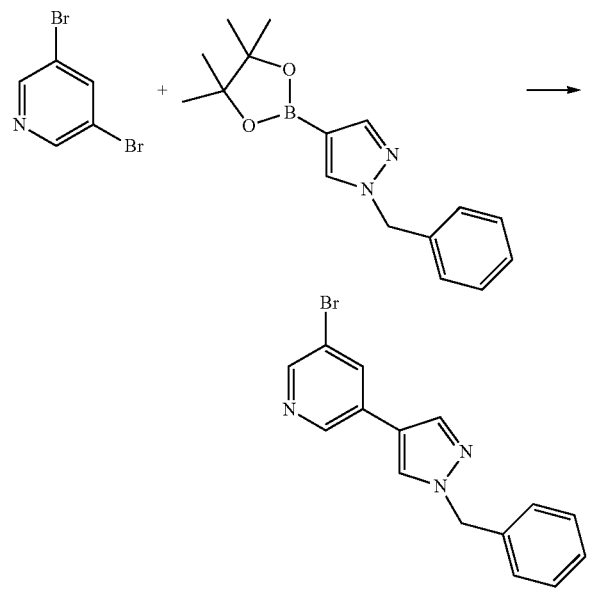

[Formula 116]

3-(1-benzyl-1H-pyrazol-4-yl)-5-bromopyridine

MS (ESI m/z): 312, 314 (M+H)
$^1$H-NMR (DMSO-d$_6$, 400 MHz) δ:8.85 (d, 1H, J=2.0 Hz), 8.51-8.49 (m, 2H), 8.32-8.29 (m, 1H), 8.11 (s, 1H), 7.39-7.25 (m, 5H), 5.36 (s, 2H)

Reference Example 83

The following compound was obtained as described in Reference Example 22.

[Formula 117]

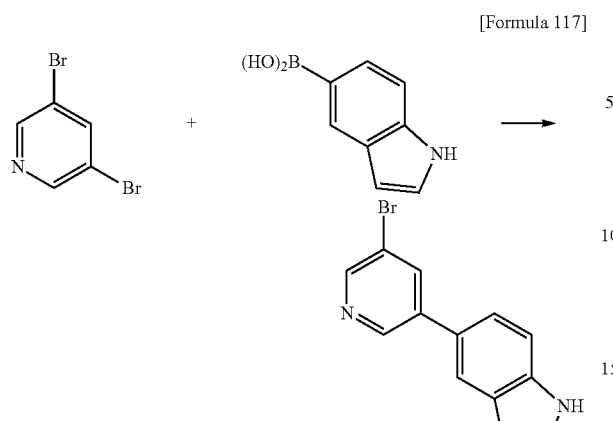

5-(5-bromopyridin-3-yl)-1H-indole

MS (ESI m/z): 273, 275 (M+H)
¹H-NMR (DMSO-d₆, 400 MHz) δ:11.27 (s, 1H), 8.90 (d, 1H, J=1.9 Hz), 8.62 (d, 1H, J=2.2 Hz), 8.34-8.31 (m, 1H), 7.96 (s, 1H), 7.54-7.46 (m, 2H), 7.44-7.41 (m, 1H), 6.53-6.50 (m, 1H)

Reference Example 84

The following compound was obtained as described in Reference Example 22.

[Formula 118]

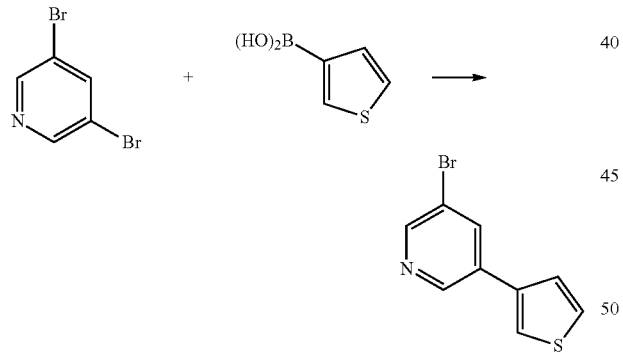

3-bromo-5-(thiophene-3-yl)pyridine

MS (ESI m/z): 240, 242 (M+H)
¹H-NMR (DMSO-d₆, 400 MHz) δ:8.99 (d, 1H, J=1.9 Hz), 8.61 (d, 1H, J=2.2 Hz), 8.45-8.43 (m, 1H), 8.20-8.18 (m, 1H), 7.73-7.71 (m, 2H)

Reference Example 85

The following compound was obtained as described in Reference Example 22.

[Formula 119]

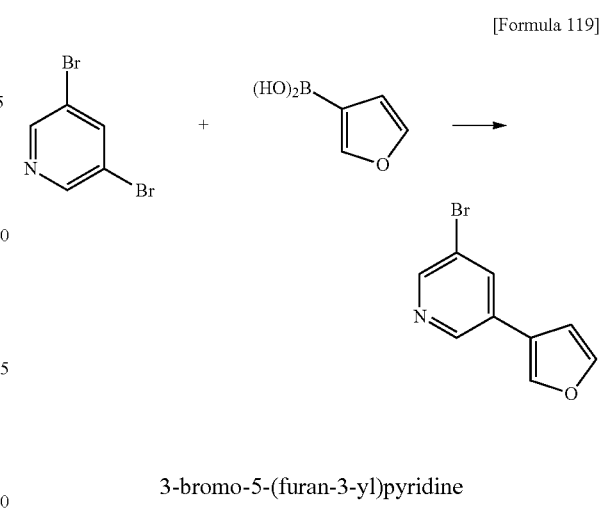

3-bromo-5-(furan-3-yl)pyridine

MS (ESI m/z): 224, 226 (M+H)
¹H-NMR (DMSO-d₆, 400 MHz) δ:8.89 (d, 1H, J=2.0 Hz), 8.58 (d, 1H, J=2.2 Hz), 8.43-8.40 (m, 1H), 8.37-8.34 (m, 1H), 7.15-7.13 (m, 1H)

Reference Example 86

The following compound was obtained as described in Reference Example 22.

[Formula 120]

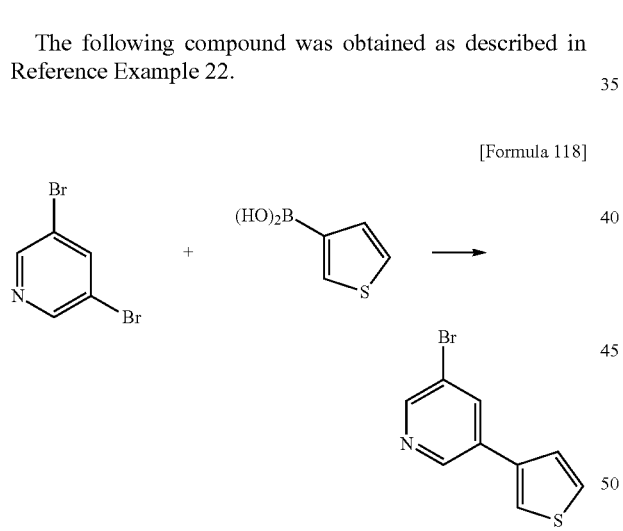

5-bromo-3-(m-toluoyl)pyridine

¹H-NMR (DMSO-d₆, 300 MHz) δ:8.88 (d, 1H, J=2.1 Hz), 8.67 (d, 1H, J=2.1 Hz), 8.35-8.32 (m, 1H), 7.71-7.66 (m, 2H), 7.35-7.30 (m, 2H), 2.37 (s, 3H)

Reference Example 87

The following compound was obtained as described in Reference Example 22.

[Formula 121]

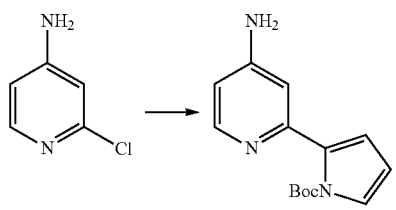

105 tert-Butyl 2-(4-aminopyridin-2-yl)-1H-pyrrol-1-carboxylate

MS (ESI m/z): 260 (M+H)
RT (min): 0.83

Reference Example 88

The following compound was obtained as described in Reference Example 22.

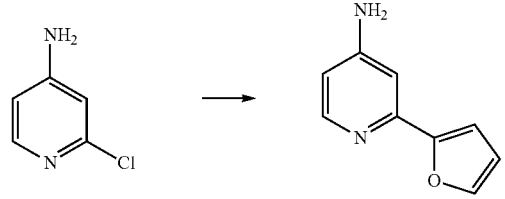
[Formula 122]

2-(furan-2-yl)pyridin-4-amine

MS (ESI m/z): 161 (M+H)
RT (min): 0.46

Reference Example 89

The following compound was obtained as described in Reference Example 22.

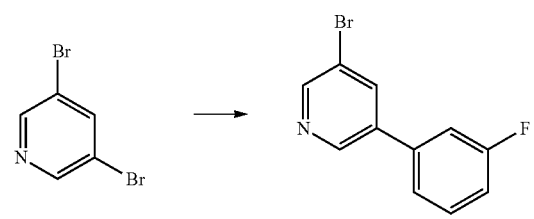
[Formula 123]

3-bromo-5-(3-fluorophenyl)pyridine

MS (ESI m/z): 252, 254 (M+H)
RT (min): 1.56

Reference Example 90

The following compound was obtained as described in Reference Example 22.

106

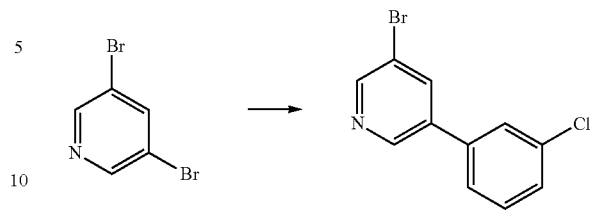
[Formula 124]

3-bromo-5-(3-chlorophenyl)pyridine

MS (ESI m/z): 268, 270, 272 (M+H)
RT (min): 1.70

Reference Example 91

The following compound was obtained as described in Reference Example 22.

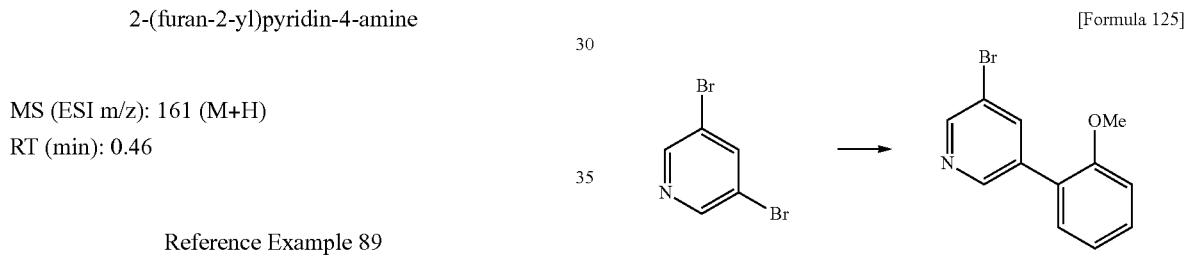
[Formula 125]

3-bromo-5-(2-methoxyphenyl)pyridine

MS (ESI m/z): 264, 266 (M+H)
RT (min): 1.55

Reference Example 92

The following compound was obtained as described in Reference Example 22.

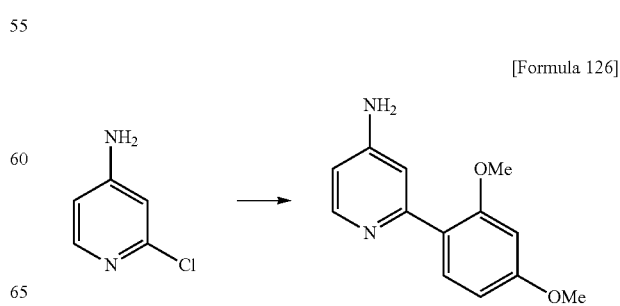
[Formula 126]

2-(2,4-dimethoxyphenyl)pyridin-4-amine

MS (ESI m/z): 231 (M+H)
RT (min): 0.74

Reference Example 93

[Formula 127]

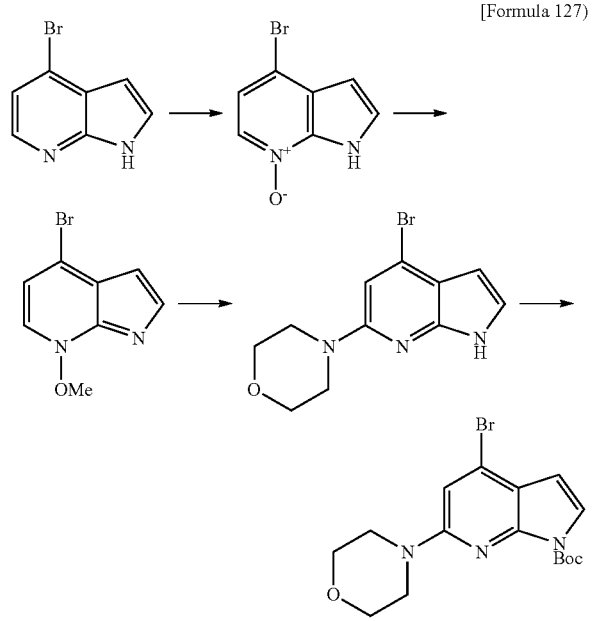

1st Step
m-Chlorobenzoic acid (1.0 g) was added to a chloroform (19 ml) solution containing 4-bromo-7-azaindole (760 mg) under ice cooling, followed by stirring for 30 minutes. Then, chloroform (10 ml) was distilled away under reduced pressure, diisopropylether was added, an insoluble precipitate was collected by filtration, and a white solid of 4-bromo-1H-pyrrolo[2,3-b]pyridine 7-oxide (1.085 g) was thus obtained.
MS (ESI m/z): 213, 215 (M+H)
RT (min): 0.75

2nd Step
Dimethyl sulfate (410 mg) was added to an acetonitrile (7.6 ml) solution containing the white solid of 4-bromo-1H-pyrrolo[2,3-b]pyridine 7-oxide (1.085 g) obtained in the 1st step, followed by stirring at 60° C. for 25.5 hours in a nitrogen atmosphere. Then, the reaction solution was cooled to room temperature and diluted by addition of acetonitrile (7.6 ml).
MS (ESI m/z): 227, 229 (M+H)
RT (min): 0.45

3rd Step
Morpholine (0.22 ml) was added to a portion (1.2 ml) of the acetonitrile solution obtained in the 2nd step in a nitrogen atmosphere, followed by stirring at 60° C. for 30 minutes. The reaction solution was cooled to room temperature, and a saturated aqueous ammonium chloride solution was added. Then, an insoluble precipitate was washed with water, and 4-(4-bromo-1H-pyrrolo[2,3-b]pyridin-6-yl)morpholine (36 mg) was thus obtained.
MS (ESI m/z): 282, 284 (M+H)
RT (min): 1.30

4th Step
Sodium hydride (60% in oil) (6 mg) was added to a DMF (1.3 ml) solution containing 4-(4-bromo-1H-pyrrolo[2,3-b]pyridin-6-yl)morpholine (36 mg) obtained in the 3rd step in a nitrogen atmosphere under ice cooling, followed by stirring for 30 minutes. Then, di-tert-butyl dicarbonate (50 mg) was added, followed by stirring at room temperature for 1 hour. Further, a saturated aqueous ammonium chloride solution was added to the reaction solution, followed by extraction with ethyl acetate. The organic layer was washed with water and saturated saline and dried over anhydrous sodium sulfate. Then, the solvent was distilled away under reduced pressure, the obtained residue was purified by silica gel chromatography (n-hexane:ethyl acetate=1:1 to 0:1), and colorless oily matter of tert-butyl 4-bromo-6-morpholino-1H-pyrrolo[2,3-b]pyridin-1-carboxylate (34 mg) was thus obtained.
MS (ESI m/z): 382, 384 (M+H)
RT (min): 1.98

Reference Example 94

The following compound was obtained as described in Reference Example 93.

[Formula 128]

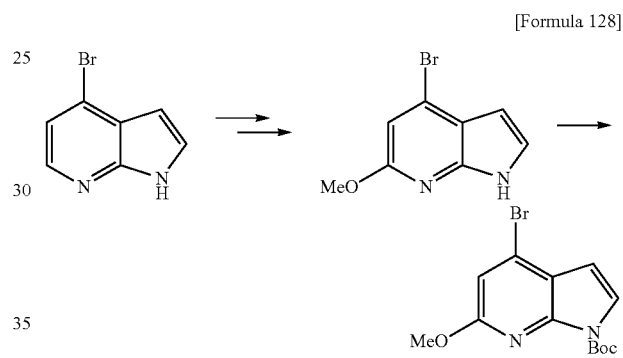

4-bromo-6-methoxy-1H-pyrrolo[2,3-b]pyridine

MS (ESI m/z): 227, 229 (M+H)
RT (min): 1.42 tert-Butyl 4-bromo-6-methoxy-1H-pyrrolo[2,3-b]pyridin-1-carboxylate

MS (ESI m/z): 327, 329 (M+H)
RT (min): 2.12

Reference Example 95

The following compounds were obtained as described in Reference Example 93.

[Formula 129]

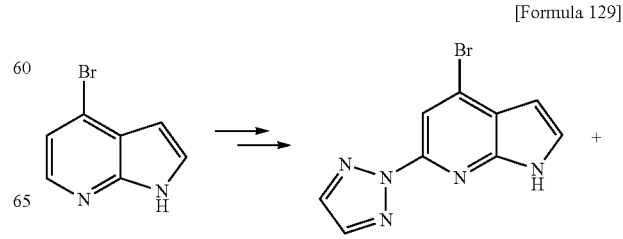

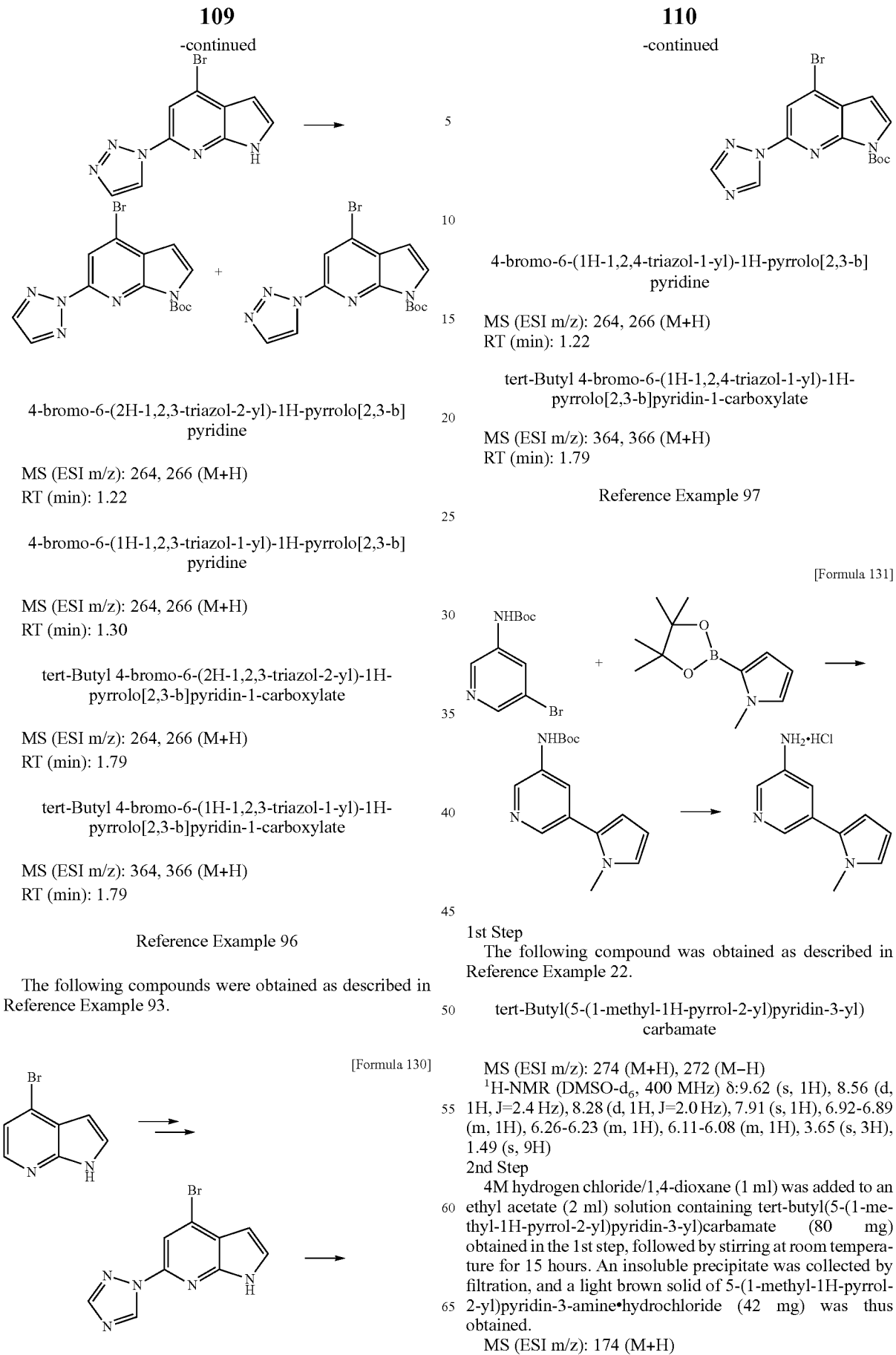

4-bromo-6-(2H-1,2,3-triazol-2-yl)-1H-pyrrolo[2,3-b]pyridine

MS (ESI m/z): 264, 266 (M+H)
RT (min): 1.22

4-bromo-6-(1H-1,2,3-triazol-1-yl)-1H-pyrrolo[2,3-b]pyridine

MS (ESI m/z): 264, 266 (M+H)
RT (min): 1.30 tert-Butyl 4-bromo-6-(2H-1,2,3-triazol-2-yl)-1H-pyrrolo[2,3-b]pyridin-1-carboxylate MS (ESI m/z): 264, 266 (M+H)
RT (min): 1.79 tert-Butyl 4-bromo-6-(1H-1,2,3-triazol-1-yl)-1H-pyrrolo[2,3-b]pyridin-1-carboxylate MS (ESI m/z): 364, 366 (M+H)
RT (min): 1.79

Reference Example 96

The following compounds were obtained as described in Reference Example 93.

[Formula 130]

4-bromo-6-(1H-1,2,4-triazol-1-yl)-1H-pyrrolo[2,3-b]pyridine

MS (ESI m/z): 264, 266 (M+H)
RT (min): 1.22 tert-Butyl 4-bromo-6-(1H-1,2,4-triazol-1-yl)-1H-pyrrolo[2,3-b]pyridin-1-carboxylate MS (ESI m/z): 364, 366 (M+H)
RT (min): 1.79

Reference Example 97

[Formula 131]

1st Step
The following compound was obtained as described in Reference Example 22.

tert-Butyl(5-(1-methyl-1H-pyrrol-2-yl)pyridin-3-yl)carbamate

MS (ESI m/z): 274 (M+H), 272 (M−H)
$^1$H-NMR (DMSO-d$_6$, 400 MHz) δ:9.62 (s, 1H), 8.56 (d, 1H, J=2.4 Hz), 8.28 (d, 1H, J=2.0 Hz), 7.91 (s, 1H), 6.92-6.89 (m, 1H), 6.26-6.23 (m, 1H), 6.11-6.08 (m, 1H), 3.65 (s, 3H), 1.49 (s, 9H)

2nd Step
4M hydrogen chloride/1,4-dioxane (1 ml) was added to an ethyl acetate (2 ml) solution containing tert-butyl(5-(1-methyl-1H-pyrrol-2-yl)pyridin-3-yl)carbamate (80 mg) obtained in the 1st step, followed by stirring at room temperature for 15 hours. An insoluble precipitate was collected by filtration, and a light brown solid of 5-(1-methyl-1H-pyrrol-2-yl)pyridin-3-amine•hydrochloride (42 mg) was thus obtained.
MS (ESI m/z): 174 (M+H)

¹H-NMR (DMSO-d₆, 400 MHz) δ:8.13 (d, 1H, J=1.2 Hz), 7.91 (d, 1H, J=2.0 Hz), 7.71-7.68 (m, 1H), 7.02-7.69 (m, 1H), 6.47-6.43 (m, 1H), 6.16-6.13 (m, 1H), 3.73 (s, 3H)

Reference Example 98

The following compounds were obtained as described in Reference Example 97.

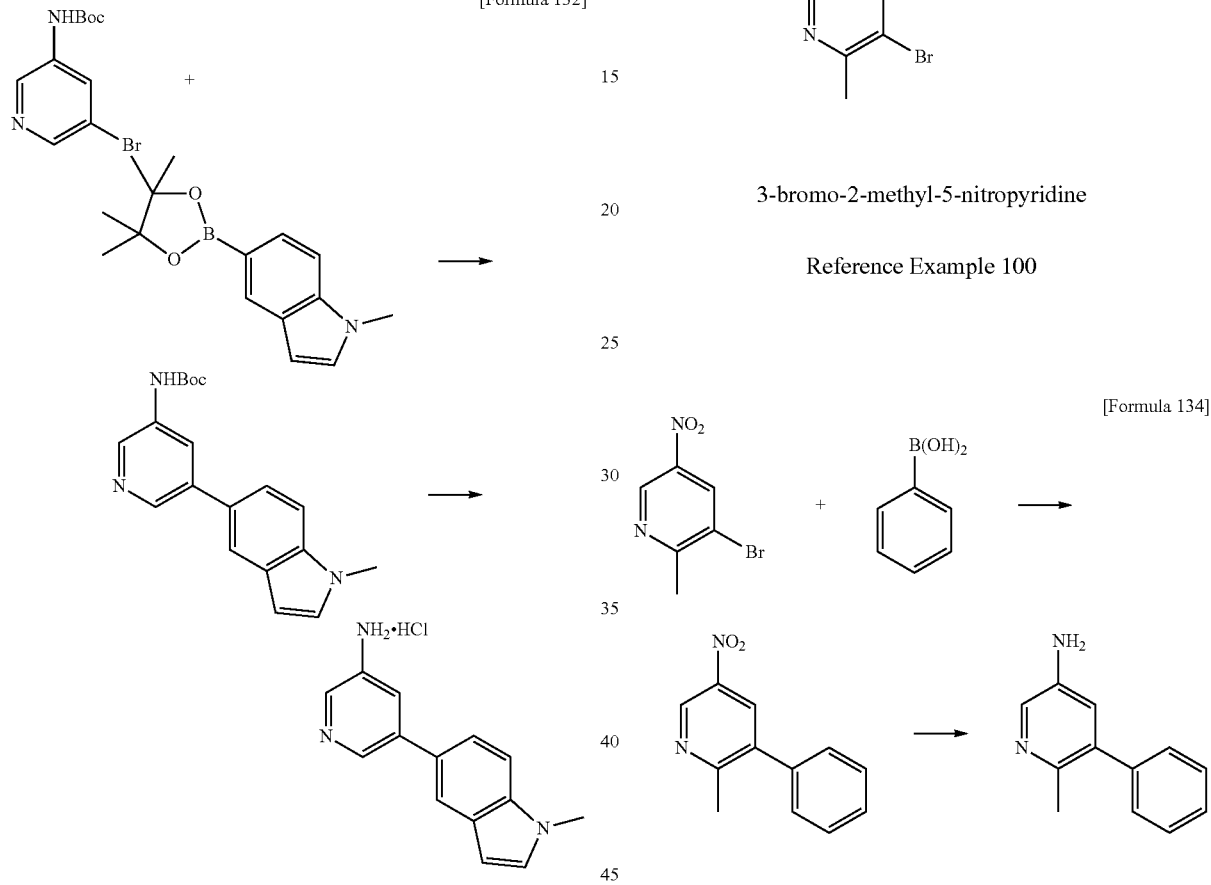

tert-Butyl(5-(1-methyl-1H-indole-5-yl)pyridin-3-yl)carbamate

MS (ESI m/z): 324 (M+H), 322 (M−H)

¹H-NMR (DMSO-d₆, 400 MHz) δ:9.64 (s, 1H), 8.56-8.48 (m, 2H), 8.19 (s, 1H), 7.82 (d, 1H, J=1.2 Hz), 7.56 (d, 1H, J=8.8 Hz), 7.45-7.41 (m, 1H), 7.42-7.38 (m, 1H), 6.53-6.50 (m, 1H), 3.82 (s, 3H), 1.51 (s, 9H)

5-(1-methyl-1H-indole-5-yl)pyridin-3-amine·hydrochloride

MS (ESI m/z): 224 (M+H)

¹H-NMR (CDCl₃, 400 MHz) δ:8.33 (d, 1H, J=2.0 Hz), 8.05 (d, 1H, J=2.7 Hz), 7.82-7.80 (m, 1H), 7.45-7.38 (m, 1H), 7.25-7.21 (m, 1H), 7.10 (d, 1H, J=3.0 Hz), 6.54 (d, 1H, J=3.0 Hz), 3.83 (s, 3H), 3.80-3.70 (m, 2H)

Reference Example 99

The following compound was obtained with reference to US2006/79522 A1.

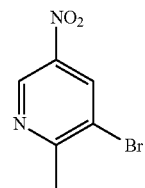

3-bromo-2-methyl-5-nitropyridine

Reference Example 100

[Formula 134]

1st Step

The following compound was obtained as described in Reference Example 22.

2-methyl-5-nitro-3-phenylpyridine

¹H-NMR (DMSO-d₆, 400 MHz) δ:9.28 (d, 1H, J=2.6 Hz), 8.32 (d, 1H, J=2.7 Hz), 7.57-7.47 (m, 5H), 2.58 (s, 3H)

2nd Step

10% Pd/C (30 mg) was added to a methanol/ethyl acetate (1 ml/1 ml) solution containing 2-methyl-5-nitro-3-phenylpyridine (40 mg) obtained in the 1st step, followed by stirring at room temperature for 2.5 hours in a hydrogen atmosphere. Insoluble matter was removed, the solvent was distilled away under reduced pressure, and light yellow oily matter of 2-methyl-5-phenylpyridin-3-amine (32 mg) was thus obtained.

MS (ESI m/z): 185 (M+H)

$^1$H-NMR (DMSO-d$_6$, 400 MHz) δ:7.84 (d, 1H, J=2.7 Hz), 7.47-7.30 (m, 5H), 6.76 (d, 1H, J=2.4 Hz), 5.15 (br, 2H), 2.22 (s, 3H), 1.97 (s, 2H)

Reference Example 101

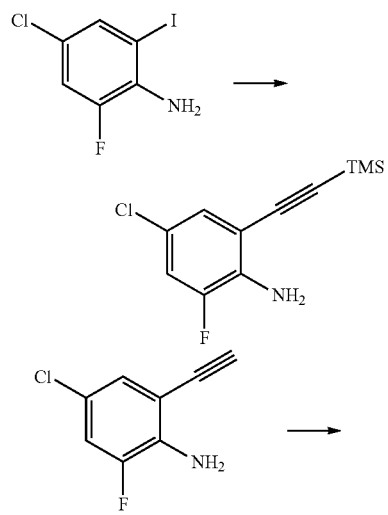

[Formula 135]

1st Step

Triethylamine (4 ml), bis(triphenylphosphine)palladium dichloride (70 mg), copper iodide (38 mg), and trimethylsilylacetylene (1.4 ml) were added to a tetrahydrofuran (4 ml) solution containing 4-chloro-2-fluoro-6-iodoaniline (542 mg) in a nitrogen atmosphere, followed by stirring at room temperature for 30 minutes. Then, ethyl acetate was added to the reaction solution and an insoluble precipitate was removed. The organic layers were combined and the solvent was distilled away under reduced pressure. The residue was purified by silica gel chromatography (n-hexane:ethyl acetate=1:0 to 1:1), and 4-chloro-2-fluoro-6-(((trimethylsilyl)ethynyl)aniline was thus obtained.

MS (ESI m/z): 242, 244 (M+H)
RT (min): 2.11

2nd Step

Potassium carbonate (550 mg) was added to a methanol solution (5 ml) containing the 4-chloro-2-fluoro-6-((trimethylsilyl)ethynyl)aniline obtained in the 1st step, followed by stirring at room temperature for 30 minutes. An insoluble precipitate was removed, and then the solvent was distilled away under reduced pressure. The residue was purified by silica gel chromatography, and colorless oily matter of 4-chloro-2-ethynyl-6-fluoroaniline (214 mg) was thus obtained.

MS (ESI m/z): 170, 172 (M+H)
RT (min): 1.48

3rd Step

Cyclooctadiene chloride dimer (6 mg) was added to a DMF (6 ml) solution containing 4-chloro-2-ethynyl-6-fluoroaniline (214 mg) obtained in the 2nd step, followed by stirring at 85° C. for 16 hours in a nitrogen atmosphere. A saturated aqueous sodium hydrogen carbonate solution was added to the reaction solution, an insoluble precipitate was collected by filtration and washed with water. Then, the obtained solid was dissolved in ethyl acetate, and the organic layer was washed with water and saturated saline and dried over anhydrous sodium sulfate. Thereafter, the solvent was distilled away under reduced pressure, and green oily matter of 5-chloro-7-fluoro-1H-indole (124 mg) was thus obtained.

MS (ESI m/z): 170, 172 (M+H)
RT (min): 1.56

Reference Example 102

The following compound was obtained as described in Reference Example 101.

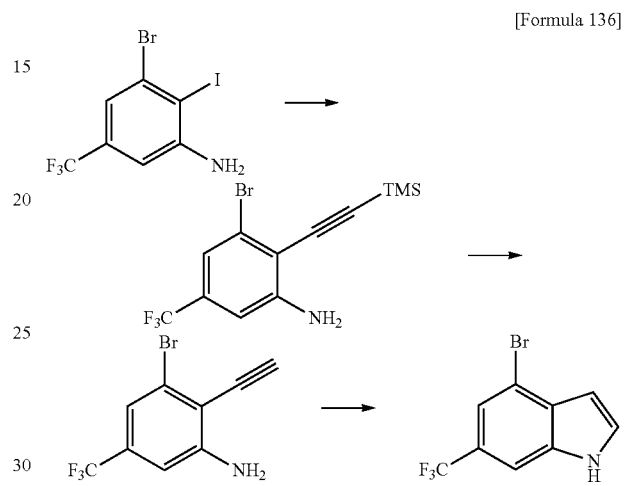

[Formula 136]

3-bromo-2-ethynyl-5-(trifluoromethyl)aniline

MS (ESI m/z): 264, 266 (M+H)
RT (min): 1.65

4-bromo-6-(trifluoromethyl)-1H-indole

MS (ESI m/z): 264, 266 (M+H)
RT (min): 1.75

Reference Example 103

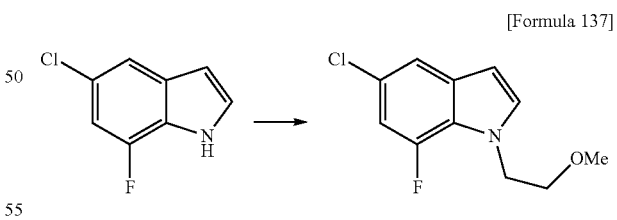

[Formula 137]

5-chloro-7-fluoro-1H-indole (124 mg) and 2-methoxyethyl chloride (17 mg) were added to a DMF (2 ml) suspension containing sodium hydride (61% in oil) (6 mg) in a nitrogen atmosphere under ice cooling, followed by stirring at room temperature for 1 hour. Further, sodium hydride (61% in oil) (6 mg) was added, followed by stirring at 110° C. for 30 minutes. Then, a saturated aqueous ammonium chloride solution and ethyl acetate were added to the reaction solution, the organic layer was collected, washed with saturated saline, and dried over anhydrous sodium sulfate, and then the solvent was distilled away under reduced pressure. The obtained residue was purified by silica gel column chromatography, and 5-chloro-7-fluoro-1-(2-methoxyethyl)-1H-indole (27 mg) was thus obtained.

MS (ESI m/z): 228, 230 (M+H)
RT (min): 1.71

Reference Example 104

The following compound was obtained as described in Reference Example 103.

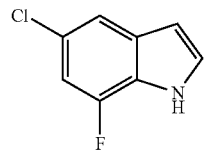  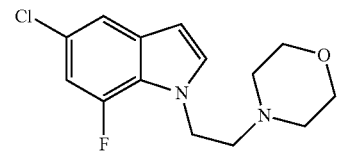

[Formula 138]

4-(2-(5-chloro-7-fluoro-1H-indole-1-yl)ethyl)morpholine

MS (ESI m/z): 283, 285 (M+H)
RT (min): 0.92

Reference Example 105

The following compound was obtained as described in Reference Example 103.

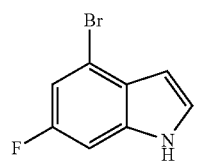  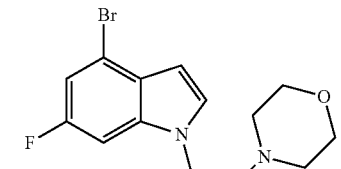

[Formula 139]

4-(2-(5-bromo-6-fluoro-1H-indole-1-yl)ethyl)morpholine

MS (ESI m/z): 327, 329 (M+H)
RT (min): 1.01

Reference Example 106

The following compound was obtained as described in Reference Example 103.

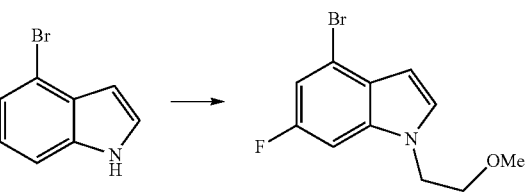

[Formula 140]

4-bromo-6-fluoro-1-(2-methoxyethyl)-1H-indole

MS (ESI m/z): 272, 274 (M+H)
RT (min): 1.70

Reference Example 107

The following compound was obtained as described in Reference Example 103.

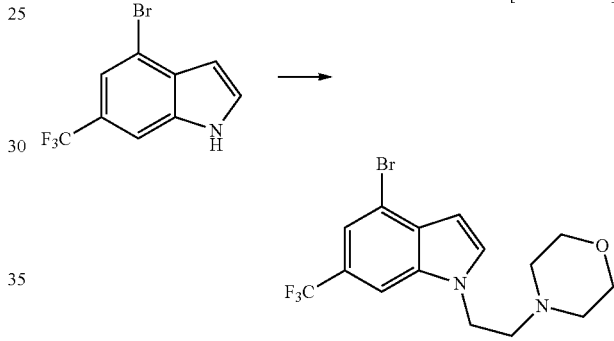

[Formula 141]

4-(2-(4-bromo-6-(trifluoromethyl)-1H-indole-1-yl)ethyl)morpholine

MS (ESI m/z): 377, 379 (M+H)
RT (min): 1.20

Reference Example 108

The following compound was obtained as described in Reference Example 103.

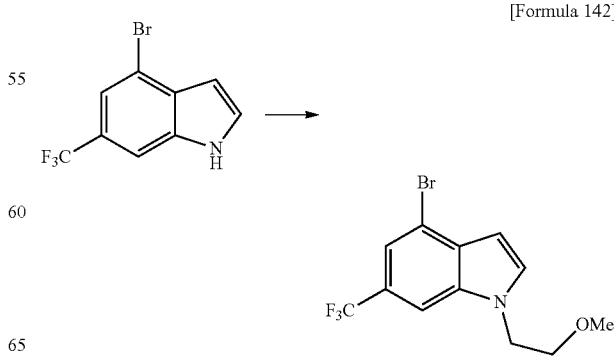

[Formula 142]

4-bromo-(2-methoxyethyl)-6-(trifluoromethyl)-1H-indole

MS (ESI m/z): 322, 324 (M+H)
RT (min): 1.90

Reference Example 110

[Formula 143]

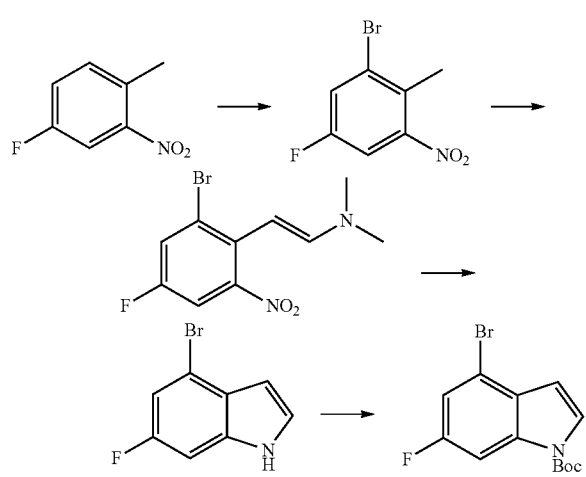

1st Step

Concentrated sulfuric acid (2.5 ml) and N-bromosuccinimide (3.44 g) were added to a TFA solution (8 ml) containing 4-fluoro-2-nitrotoluene (2 g), followed by stirring at room temperature for 15 hours. Then, the reaction solution was poured into ice water, followed by extraction with ethyl acetate. The obtained organic layer was washed with water, a saturated aqueous sodium hydrogen carbonate solution, and saturated saline and dried over anhydrous sodium sulfate. Thereafter, the solvent was distilled away under reduced pressure. The residue was purified by silica gel chromatography, and light yellow oily matter was thus obtained.

2nd Step

N,N-dimethylformamide dimethylacetal (7.7 g) was added to a DMF (20 ml) solution containing the light yellow oily matter obtained in the 1st step in a nitrogen atmosphere, followed by reflux for 30 minutes. The reaction solution was adjusted to room temperature. Water, ethyl acetate, and 1M hydrochloric acid were added, and then the organic layer was separated. The obtained organic layer was washed with 1M hydrochloric acid (×3) and saturated saline and dried over anhydrous sodium sulfate. Thereafter, the solvent was distilled away under reduced pressure, and deep brown oily matter was thus obtained.

3rd Step

An acetic acid (20 ml) solution containing the deep brown oily matter obtained in the 2nd step was added to a mixture of iron powder (3.61 g) and acetic acid (20 ml) at 110° C. for 30 minutes. The resulting mixture was stirred for 1 hour and then diluted with ethyl acetate. Insoluble matter was removed by filtration with Celite, the filtrate was washed with water and 1M hydrochloric acid (×3). The obtained organic layer was poured into a saturated aqueous sodium hydrogen carbonate solution to separate the organic layer, and the organic layer was washed with water and saturated saline and dried over anhydrous sodium sulfate. Thereafter, activated carbon was added and insoluble matter was removed by filtration with Celite. The solvent was distilled away under reduced pressure, and light brown oily matter of 4-bromo-6-fluoro-1H-indole (880 mg) was thus obtained.

MS (ESI m/z): 214, 216 (M+H)
RT (min): 1.56
$^1$H-NMR (DMSO-$d_6$, 300 MHz) δ:11.53 (br, 1H), 7.46 (t, 1H, J=3.0 Hz), 7.24 (dd, 1H, J=5.6, 3.0 Hz), 7.19 (dd, 1H, J=9.2, 2.0 Hz), 6.39 (d, 1H, J=2.0 Hz)

4th Step

The following compound was obtained as described in the 2nd step of Reference Example 2.

tert-Butyl-4-bromo-6-fluoro-1H-indole-carboxylate

Reference Example 111

[Formula 144]

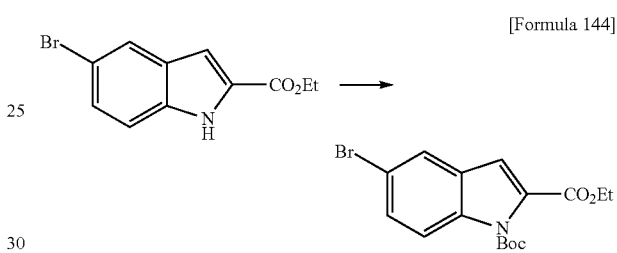

Sodium hydride (61% in oil) (40 mg) was added to a DMF (1 ml) solution containing 2-(ethoxycarbonyl)-5-bromoindole (134 mg) under ice cooling, followed by stirring for 10 minutes. Then, a DMF (1 ml) solution containing di-tert-butyldicarbonate (108 mg) was added, followed by stirring at room temperature for 5 minutes. Water was added to the reaction solution and a solid precipitate was collected by filtration, the obtained solid was purified by silica gel chromatography (n-hexane:ethyl acetate=1:0 to 1:1), and colorless oily matter of tert-butyl 2-ethyl 5-bromo-1H-indole-1,2-dicarboxylate (100 mg) was thus obtained.

$^1$H-NMR (DMSO-$d_6$, 300 MHz) δ:7.96 (t, 1H, J=2.6 Hz), 7.92 (d, 1H, J=9.2 Hz), 7.62 (dd, 1H, J=8.6, 2.0 Hz), 7.24 (s, 1H), 4.33 (q, 2H, J=7.0 Hz), 1.57 (s, 9H), 1.32 (t, 3H, J=7.0 Hz)

Reference Example 112

[Formula 145]

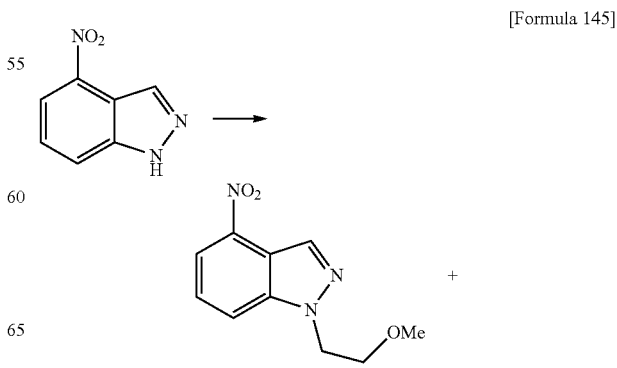

-continued

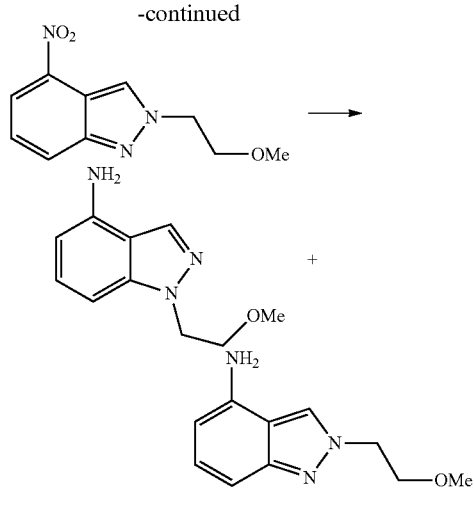

1st Step

Potassium carbonate (200 mg) and 2-chloroethylmethyl-ether (0.1 ml) were added to a DMF (1.5 ml) solution containing 4-nitro-1H-indazole (80 mg), followed by stirring at 60° C. for 4 hours. Subsequently, an insoluble precipitate was collected by filtration and washed with ethyl acetate, and a mixture of 1-(2-methoxyethyl)-4-nitro-1H-indazole and 2-(2-methoxyethyl)-4-nitro-2H-indazole was thus obtained.

1-(2-methoxyethyl)-4-nitro-1H-indazole

MS (ESI m/z): 222 (M+H)
RT (min): 1.19

2-(2-methoxyethyl)-4-nitro-2H-indazole

MS (ESI m/z): 222 (M+H)
RT (min): 1.12

2nd Step

Iron powder (170 mg), ammonium chloride (160 mg), and water (3 ml) were added to an ethanol solution (10 ml) containing the mixture obtained in the 1st step, followed by stirring at 80° C. for 2 hours. Ethyl acetate was added to the reaction solution, insoluble matter was removed, the filtrates were combined, and the solvent was distilled away under reduced pressure. The obtained residue was purified by alumina silica gel column chromatography, and 1-(2-methoxyethyl)-1H-indole-4-amine (49 mg) and 2-(2-methoxyethyl)-2H-indole-4-amine (40 mg) were thus obtained.

1-(2-methoxyethyl)-1H-indazol-4-amine

MS (ESI m/z): 192 (M+H)
RT (min): 0.72

2-(2-methoxyethyl)-2H-indazol-4-amine

MS (ESI m/z): 192 (M+H)
RT (min): 0.53

Reference Example 113

The following compounds were obtained as described in Reference Example 112.

[Formula 146]

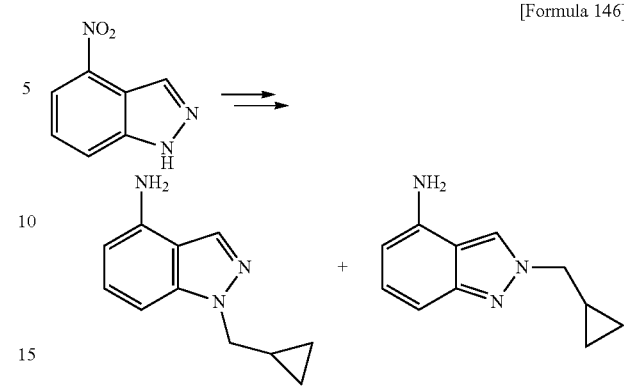

1-(cyclopropylmethyl)-1H-indazol-4-amine

MS (ESI m/z): 188 (M+H)
RT (min): 1.03

2-(cyclopropylmethyl)-2H-indazol-4-amine

MS (ESI m/z): 188 (M+H)
RT (min): 0.69

Reference Example 114

The following compounds were obtained as described in Reference Example 112.

[Formula 147]

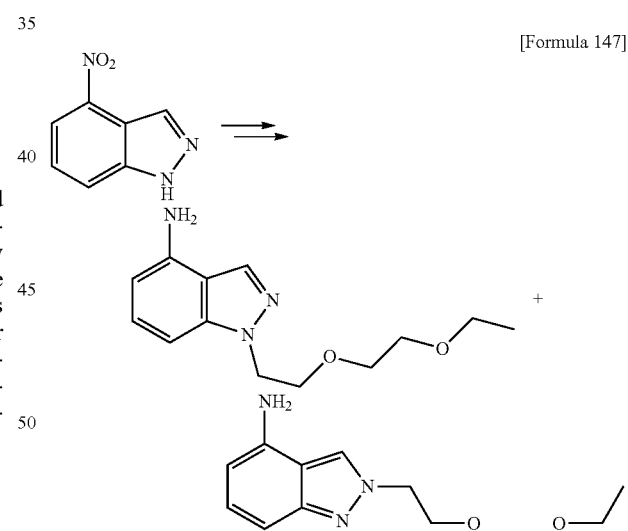

1-(2-(2-ethoxyethoxy)ethyl)-1H-indazol-4-amine

MS (ESI m/z): 250 (M+H)
RT (min): 0.89

2-(2-(2-ethoxyethoxy)ethyl)-2H-indazol-4-amine

MS (ESI m/z): 250 (M+H)
RT (min): 0.71

Reference Example 115

The following compounds were obtained as described in Reference Example 112.

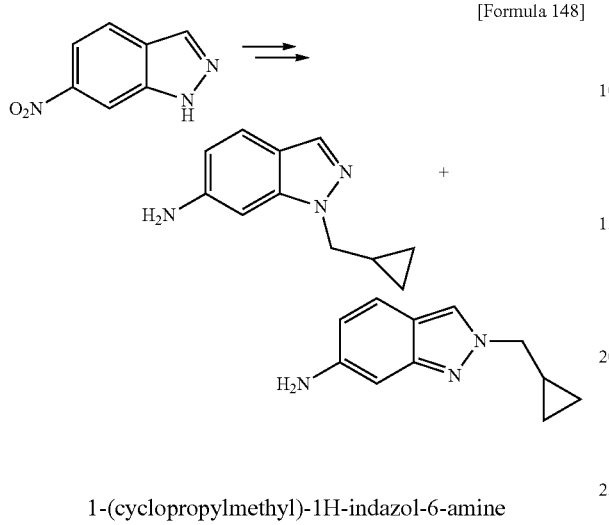

[Formula 148]

1-(cyclopropylmethyl)-1H-indazol-6-amine $^1$H-NMR (DMSO-$d_6$, 300 MHz) δ:8.81 (s, 1H), 8.32 (s, 1H), 8.02 (d, 1H, J=8.6 Hz), 7.95 (dd, 1H, J=8.6, 1.7 Hz), 4.49 (d, 2H, J=7.3 Hz), 1.32 (dd, 1H, J=12.2, 7.3 Hz), 0.47 (m, 4H)

2-(cyclopropylmethyl)-2H-indazol-6-amine $^1$H-NMR (DMSO-$d_6$, 300 MHz) δ:8.69 (s, 1H), 8.64 (s, 1H), 7.99 (d, 1H, J=9.2 Hz), 7.82 (dd, 1H, J=9.2, 2.0 Hz), 4.40 (d, 2H, J=7.3 Hz), 1.49-1.37 (m, 1H), 0.63-0.54 (m, 2H), 0.51-0.46 (m, 2H)

Reference Example 116

The following compounds were obtained as described in Reference Example 112.

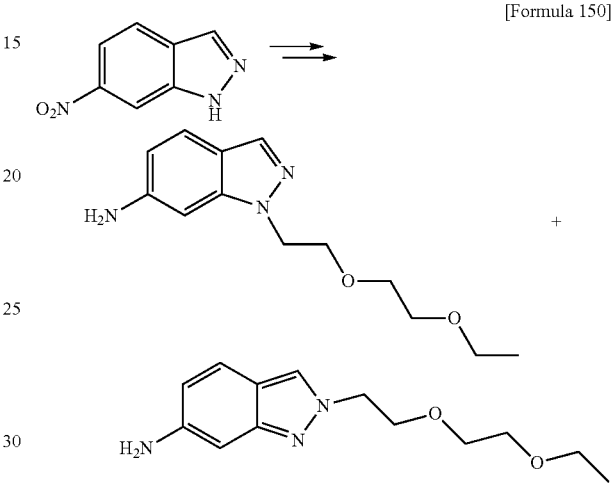

[Formula 149]

6-amino-1-(methoxyethyl)-1H-indazole $^1$H-NMR (DMSO-$d_6$, 300 MHz) δ:8.74 (d, 1H, J=2.0 Hz), 8.33 (s, 1H), 8.01 (d, 1H, J=8.6 Hz), 7.95 (dd, 1H, J=8.6, 2.0 Hz), 4.75 (t, 2H, J=5.0 Hz), 3.77 (t, 2H, J=5.0 Hz), 3.18 (s, 3H)

6-amino-2-(methoxyethyl)-2H-indazole $^1$H-NMR (DMSO-$d_6$, 300 MHz) δ:8.63 (s, 1H), 7.98 (d, 1H, J=9.2 Hz), 7.81 (dd, 1H, J=9.2, 2.0 Hz), 4.70 (t, 2H, J=5.0 Hz), 3.86 (t, 2H, J=5.0 Hz), 3.23 (s, 3H)

Reference Example 117

The following compounds were obtained as described in Reference Example 112.

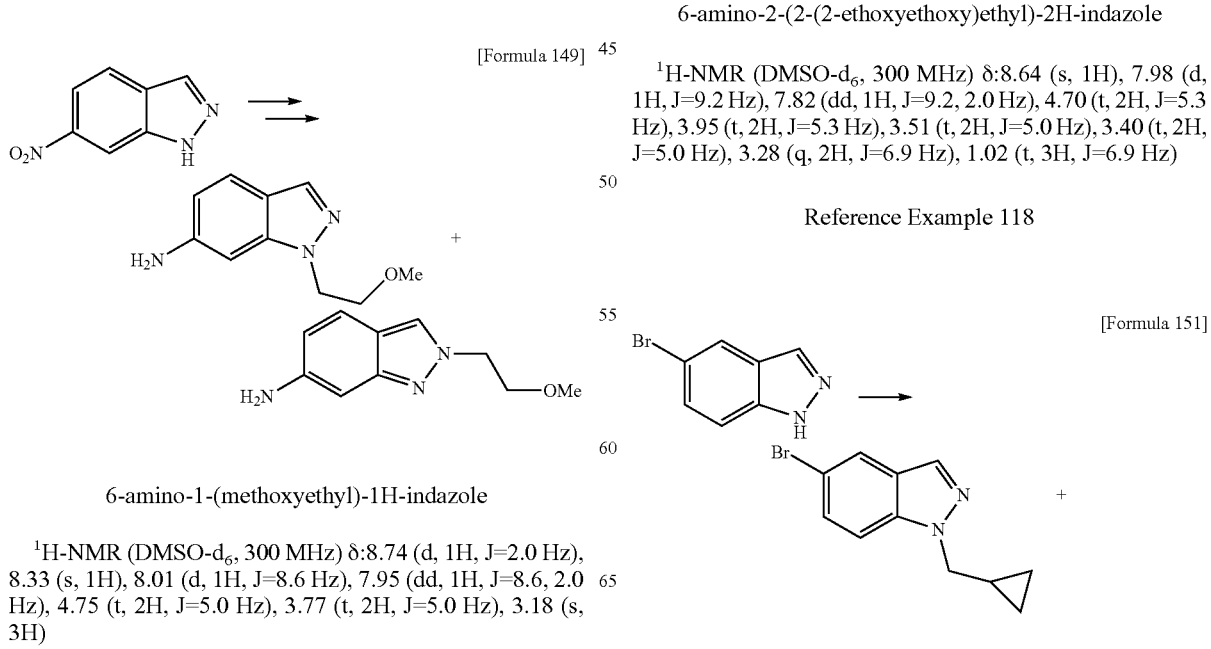

[Formula 150]

6-amino-1-(2-(2-ethoxyethoxy)ethyl)-1H-indazole $^1$H-NMR (DMSO-$d_6$, 300 MHz) δ:8.75 (s, 1H), 8.33 (s, 1H), 8.00 (d, 1H, J=9.2 Hz), 7.94 (dd, 1H, J=9.2, 1.7 Hz), 4.75 (t, 2H, J=5.0 Hz), 3.84 (t, 2H, J=5.0 Hz), 3.45 (t, 2H, J=4.9 Hz), 3.32 (t, 2H, J=4.9 Hz), 3.24 (q, 2H, J=7.0 Hz), 0.94 (t, 3H, J=7.0 Hz)

6-amino-2-(2-(2-ethoxyethoxy)ethyl)-2H-indazole $^1$H-NMR (DMSO-$d_6$, 300 MHz) δ:8.64 (s, 1H), 7.98 (d, 1H, J=9.2 Hz), 7.82 (dd, 1H, J=9.2, 2.0 Hz), 4.70 (t, 2H, J=5.3 Hz), 3.95 (t, 2H, J=5.3 Hz), 3.51 (t, 2H, J=5.0 Hz), 3.40 (t, 2H, J=5.0 Hz), 3.28 (q, 2H, J=6.9 Hz), 1.02 (t, 3H, J=6.9 Hz)

Reference Example 118

[Formula 151]

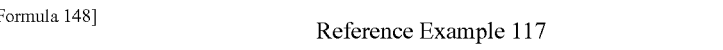

-continued

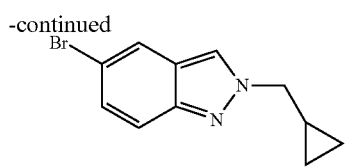

Potassium carbonate (200 mg) and 1-(bromomethyl)cyclopropane (0.1 ml) were added to a DMF (1.5 ml) solution containing 5-bromo-1H-indazole (100 mg), followed by stirring at 60° C. for 4 hours. Ethyl acetate was added to the reaction solution, an insoluble precipitate was removed, and the organic layer was washed with 1M hydrochloric acid (×2) and saturated saline and dried over anhydrous sodium sulfate. Then, the solvent was distilled away under reduced pressure, the obtained solid was purified by silica gel chromatography (n-hexane:ethyl acetate=1:0 to 1:1), and 5-bromo-1-(cyclopropylmethyl)-1H-indazole (63 mg) and 5-bromo-2-(cyclopropylmethyl)-2H-indazole (42 mg) were thus obtained.

5-bromo-1-(cyclopropylmethyl)-1H-indazole

MS (ESI m/z): 251, 253 (M+H)
RT (min): 1.65

5-bromo-2-(cyclopropylmethyl)-2H-indazole

MS (ESI m/z): 251, 253 (M+H)
RT (min): 1.50

Reference Example 119

The following compounds were obtained as described in Reference Example 118

[Formula 152]


+


5-bromo-1-(2-(2-ethoxyethoxy)ethyl)-1H-indazole

MS (ESI m/z): 313, 315 (M+H)
RT (min): 1.49

5-bromo-2-(2-(2-ethoxyethoxy)ethyl)-2H-indazole

MS (ESI m/z): 313, 315 (M+H)
RT (min): 1.39

Reference Example 120

The following compounds were obtained as described in Reference Example 118.

[Formula 153]

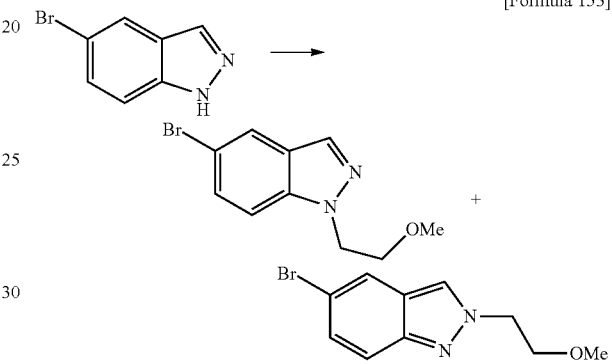

5-bromo-1-(methoxyethyl)-1H-indazole

MS (ESI m/z): 255, 257 (M+H)
RT (min): 1.37

5-bromo-2-(methoxyethyl)-2H-indazole

MS (ESI m/z): 255, 257 (M+H)
RT (min): 1.25

Reference Example 121

The following compound was obtained with reference to Bioorganic and Medicinal Chemistry Letters, 2001, vol. 11, #11, pp. 1401-1406.

[Formula 154]

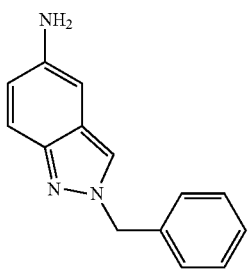

2-benzyl-2H-indazol-5-amine

Reference Example 122

[Formula 155]

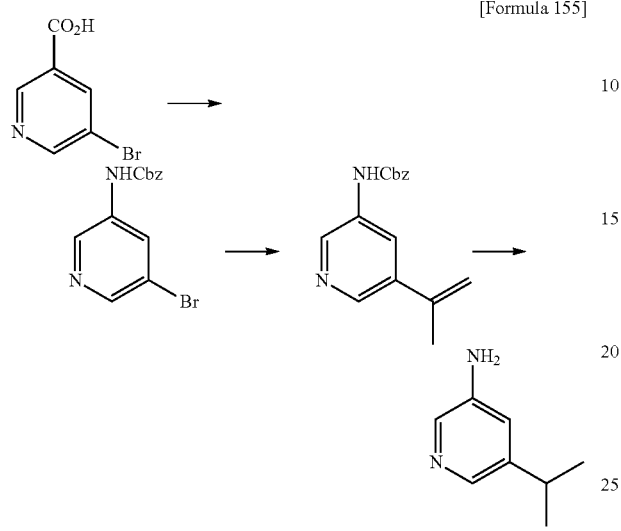

1st Step

Triethylamine (8.3 ml), DPPA (12.8 ml), and tert-butanol (7.6 ml) were added to a toluene (100 ml) solution containing 5-bromo-nicotinic acid (10 g), followed by stirring at 100° C. for 2.5 hours. The reaction solution was poured into water, followed by extraction with ethyl acetate. The resultant was washed with saturated saline and dried over anhydrous sodium sulfate. Then, the solvent was distilled away under reduced pressure, n-hexane:ethyl acetate (=10:1) was added, and an insoluble precipitate was collected by filtration, and a white solid of benzyl(5-bromopyridin-3-yl)carbamate (10.8 g) was thus obtained.

$^1$H-NMR (DMSO-$d_6$, 400 MHz) δ:10.25 (s, 1H), 8.59 (d, 1H, J=2.2 Hz), 8.34 (d, 1H, J=2.2 Hz), 8.20-8.15 (m, 1H), 7.46-7.33 (m, 5H), 5.19 (s, 2H)

2nd step

The following compound was obtained as described in Reference Example 22.

Benzyl(5-(prop-1-ene-2-yl)pyridin-3-yl)carbamate

MS (ESI m/z): 269 (M+H), 267 (M−H)
$^1$H-NMR (DMSO-$d_6$, 400 MHz) δ:10.02 (s, 1H), 8.57-8.54 (m, 1H), 8.39 (d, 1H, J=2.0 Hz), 8.00 (s, 1H), 7.46-7.32 (m, 5H), 5.46 (s, 1H), 5.22-5.20 (m, 1H), 5.18 (s, 2H), 2.10 (s, 3H)

3rd Step

10% Pd/C (106 mg) was added to a methanol/ethyl acetate (2 ml/2 ml) solution containing benzyl(5-(prop-1-ene-2-yl)pyridin-3-yl)carbamate (64 mg) obtained in the 2nd step, followed by stirring at room temperature for 2 hours in a hydrogen atmosphere. Insoluble matter was removed with Celite, the solvent was distilled away under reduced pressure, and colorless oily matter of isopropylpyridin-3-amine (30 mg) was thus obtained.

MS (ESI m/z): 137 (M+H)
$^1$H-NMR (DMSO-$d_6$, 400 MHz) δ:7.74 (d, 1H, J=2.7 Hz), 7.65-7.63 (m, 1H), 6.78-6.75 (m, 1H), 5.17 (br, 2H), 2.80-2.71 (m, 1H), 1.17 (s, 3H), 1.15 (s, 3H)

Reference Example 123

The following compound was obtained with reference to US2003/125267 A1.

[Formula 156]

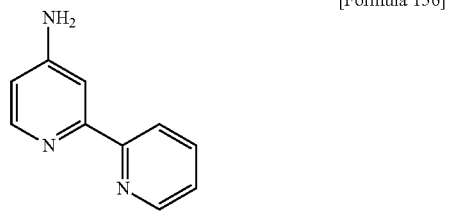

[2,2'-bipyridine]-4-amine

Reference Example 124

[Formula 157]

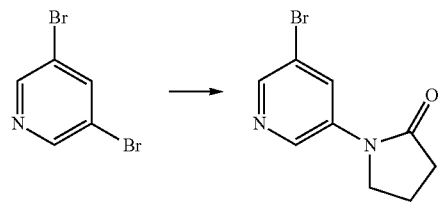

Cesium carbonate (213 mg), pyrrolidin-2-one (45 mg), Xantphos (76 mg), and Pd$_2$(dba)$_3$ (60 mg) were added to a 1,4-dioxane (4 ml) solution containing 3,5-dibromopyridine (100 mg) in a nitrogen atmosphere, followed by reflux for 4 hours. The reaction mixture was adjusted to room temperature and water was added, followed by extraction with ethyl acetate. The resultant was washed with saturated saline and dried over anhydrous sodium sulfate. Then, the solvent was distilled away under reduced pressure, the obtained residue was purified by silica gel chromatography (n-hexane:ethyl acetate=3:1 to 1:1), and a white solid of 1-(5-bromopyridin-3-yl)pyrrolidin-2-one (45 mg) was thus obtained.

MS (ESI m/z): 241, 243 (M+H)
RT (min): 0.91

Reference Example 125

[Formula 158]

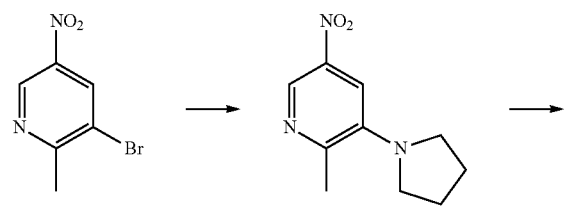

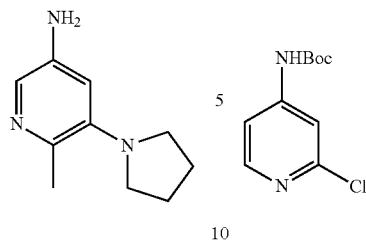

1st Step

The following compound was obtained as described in Reference Example 124.

2-methyl-5-nitro-3-(pyrrolidin-1-yl)pyridine

MS (ESI m/z): 208 (M+H)

$^1$H-NMR (DMSO-d$_6$, 400 MHz) δ:8.79 (d, 1H, J=2.3 Hz), 7.70 (d, 1H, J=2.3 Hz), 3.38-3.32 (m, 4H), 2.67 (s, 3H), 2.05-2.00 (m, 4H)

2nd Step

10% Pd/C (15 mg) was added to a methanol/ethyl acetate (2 ml/2 ml) solution containing 2-methyl-5-nitro-3-(pyrrolidin-1-yl)pyridine (16 mg), followed by stirring at room temperature for 2.5 hours in a hydrogen atmosphere. Insoluble matter was removed with Celite, the solvent was distilled away under reduced pressure, and colorless oily matter of 6-methyl-5-(pyrrolidin-1-yl)pyridin-3-amine (15 mg) was thus obtained.

$^1$H-NMR (CDCl$_3$, 400 MHz) δ:7.58 (d, 1H, J=2.4 Hz), 6.47 (d, 1H, J=2.4 Hz), 3.47 (br, 2H), 3.21-3.15 (m, 4H), 2.45 (s, 3H), 1.96-1.91 (m, 4H)

Reference Example 126

The following compound was obtained as described in Reference Example 124.

[Formula 159]

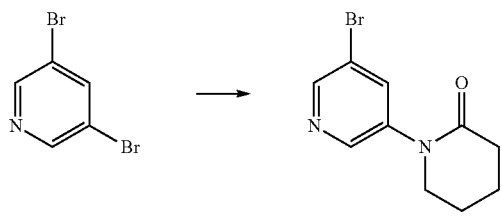

1-(5-bromopyridin-3-yl)piperidine-2-one

MS (ESI m/z): 255, 257 (M+H)
RT (min): 0.88

Reference Example 127

The following compounds were obtained as described in Reference Example 124 and the 2nd step of Reference Example 97.

[Formula 160]

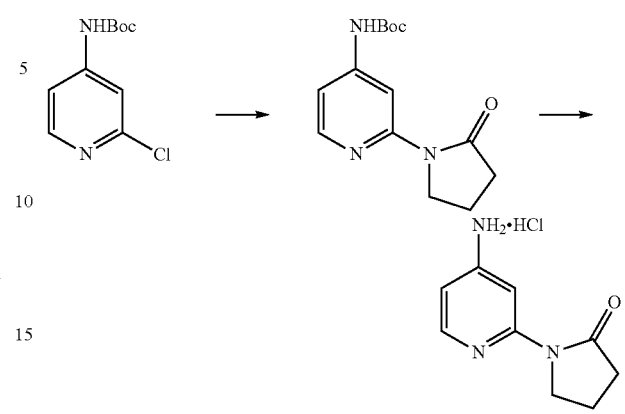

tert-Butyl(2-(2-oxopyrrolidin-1-yl)pyridin-4-yl)carbamate

MS (ESI m/z): 278 (M+H)
RT (min): 0.89

1-(4-aminopyridin-2-yl)pyrrolidin-2-one

MS (ESI m/z): 178 (M+H)
RT (min): 0.21, 0.30

Reference Example 128

[Formula 161]

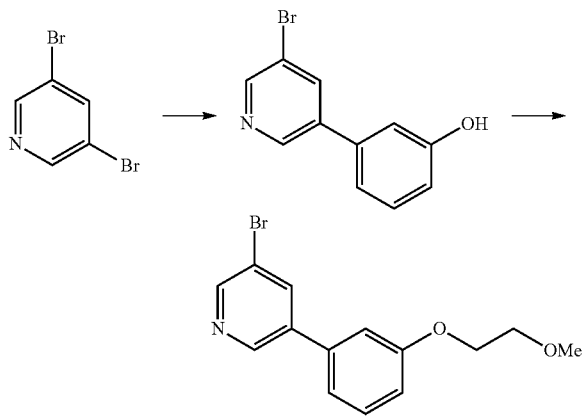

1st Step

The following compound was obtained as described in Reference Example 22.

3-(5-bromopyridin-3-yl)phenol

MS (ESI m/z): 250, 252 (M+H)
RT (min): 1.23

2nd Step

Potassium carbonate (17 mg) and 2-chloroethylmethylether (9 mg) were added to an N,N-dimethylacetamide (2 ml) solution containing 3-(5-bromopyridin-3-yl)phenol (20 mg) obtained in the 1st step, followed by stirring at 80° C. for 6 hours. Water was added, followed by extraction with ethyl acetate. The resultant was washed with saturated saline and dried over anhydrous sodium sulfate. Then, the solvent was distilled away under reduced pressure, the obtained residue was purified by silica gel chromatography (n-hexane:ethyl acetate=7:1 to 3:1), and colorless oily matter of 3-bromo-5-(3-(2-methoxyethoxy)phenyl)pyridine (18 mg) was thus obtained.

MS (ESI m/z): 308, 310 (M+H)
RT (min): 1.62

Reference Example 129

The following compound was obtained as described in Reference Example 128.

[Formula 162]

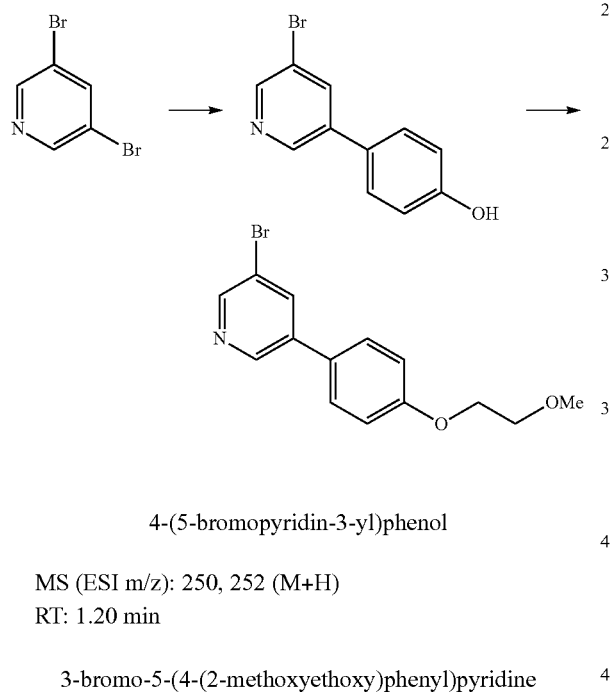

4-(5-bromopyridin-3-yl)phenol

MS (ESI m/z): 250, 252 (M+H)
RT: 1.20 min 3-bromo-5-(4-(2-methoxyethoxy)phenyl)pyridine MS (ESI m/z): 308, 310 (M+H)
RT: 1.50 min Reference Example 130

The following compound was obtained as described in Reference Example 128.

[Formula 163]

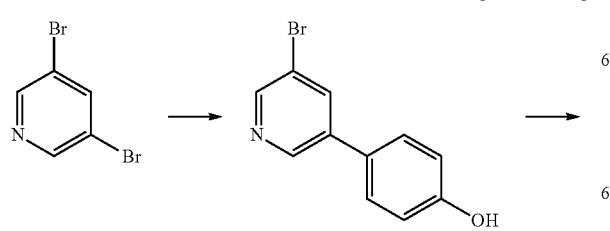

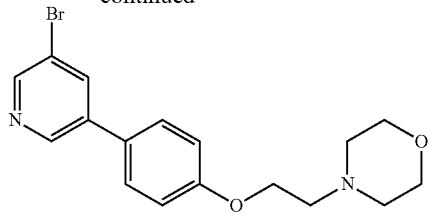

4-(5-bromopyridin-3-yl)phenol

MS (ESI m/z): 250, 252 (M+H)
RT (min): 1.20

4-(2-(4-(5-bromopyridin-3-yl)phenoxy)ethyl)morpholine

MS (ESI m/z): 363, 365 (M+H)
RT (min): 0.90

Reference Example 131

The following compound was obtained as described in the 2nd step of Reference Example 128.

[Formula 164]

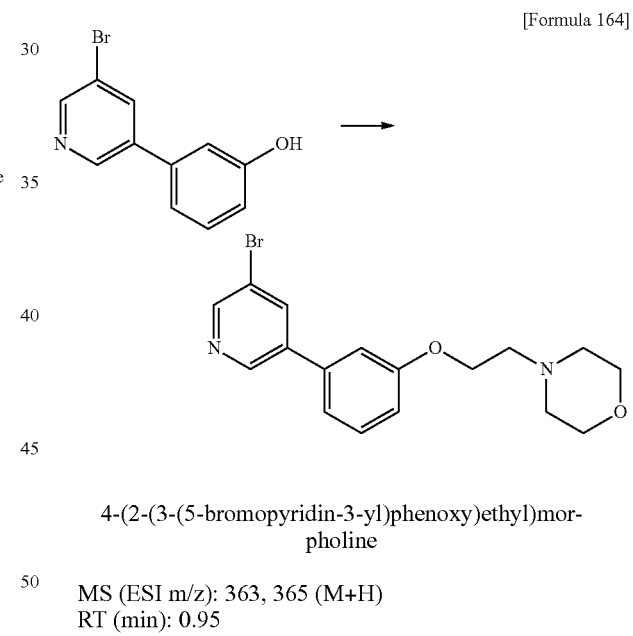

4-(2-(3-(5-bromopyridin-3-yl)phenoxy)ethyl)morpholine

MS (ESI m/z): 363, 365 (M+H)
RT (min): 0.95

Reference Example 132

[Formula 165]

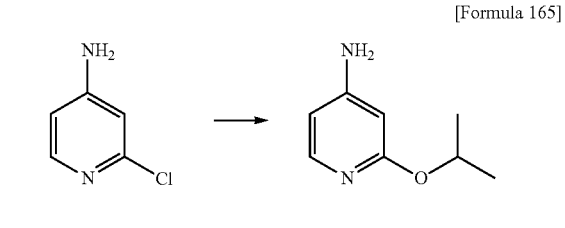

An isopropanol (2 ml) solution containing 2-chloropyridin-4-amine (300 mg), and sodium hydroxide (467 mg) were added to a tube and the tube was sealed, followed by stirring at 170° C. for 3 hours. The reaction solution was cooled to room temperature. Saturated saline was added, followed by extraction with ethyl acetate. Subsequently, the resultant was washed with saturated saline and dried over anhydrous magnesium sulfate, and the solvent was distilled away under reduced pressure. The obtained residue was purified by silica gel chromatography (n-hexane:ethyl acetate=4:1 to 1:1), and light yellow oily matter of 2-isopropoxypyridin-4-amine (168 mg) was thus obtained.

MS (ESI m/z): 153 (M+H)
RT (min): 0.46

Reference Example 133

The following compound was obtained as described in Reference Example 132.

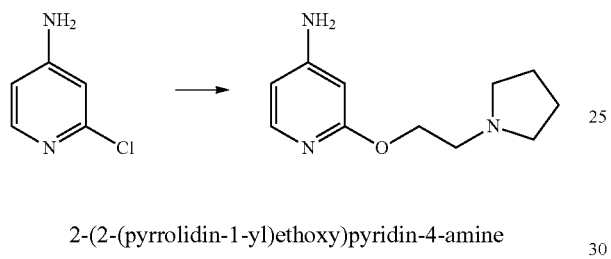

[Formula 166]

2-(2-(pyrrolidin-1-yl)ethoxy)pyridin-4-amine

MS (ESI m/z): 208 (M+H)
RT (min): 0.21

Reference Example 134

The following compound was obtained as described in Reference Example 132.

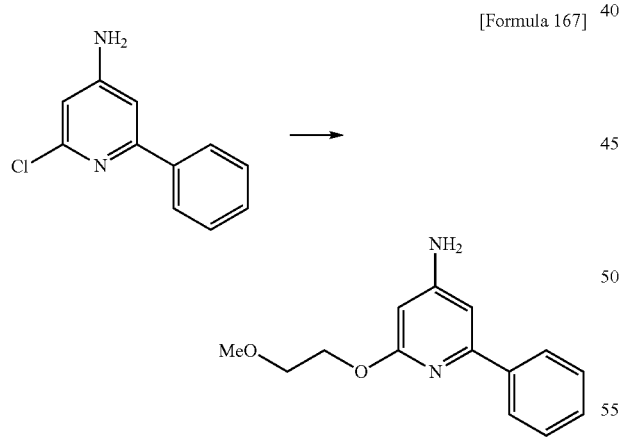

[Formula 167]

2-(2-methoxyethoxy)-6-phenylpyridin-4-amine

MS (ESI m/z): 245 (M+H)
RT (min): 0.69

Reference Example 135

The following compounds were obtained with reference to Tetrahedron, 2004, vol. 60, p. 5487.

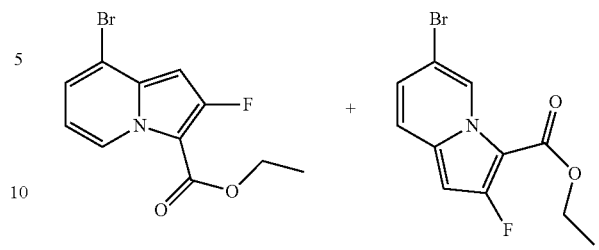

[Formula 168]

Ethyl 8-bromo-2-fluoroindolizine-3-carboxylate

Ethyl 6-bromo-2-fluoroindolizine-3-carboxylate

Reference Example 136

The following compound was obtained with reference to US2009/270405 A1.

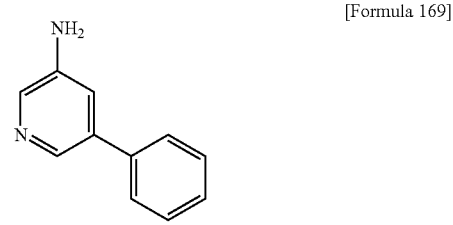 [SMILES: Nc1cncc(-c2ccccc2)c1]

[Formula 169]

5-phenylpyridin-3-amine

Reference Example 137

The following compound was obtained with reference to Journal of the American Chemical Society, 1946, vol. 68, p. 1544.

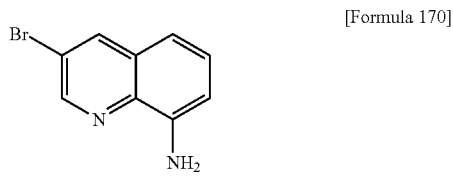 [SMILES: Nc1cccc2cc(Br)cnc12]

[Formula 170]

3-bromoquinolin-8-amine

Reference Example 138

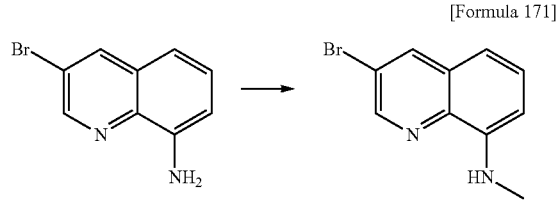

[Formula 171]

A DMF (2 ml) solution containing 3-bromoquinolin-8-amine (223 mg), dimethyl sulfate (189 mg), potassium carbonate (415 mg), and sodium iodide (20 mg) were added to a tube and the tube was sealed, followed by stirring at 95° C. for 17 hours. The reaction solution was cooled to room temperature, ethyl acetate was added, an insoluble precipitate was removed, and the organic layer was washed with 1M hydrochloric acid, water, and saturated saline. Subsequently, the organic layer was dried over anhydrous sodium sulfate, the solvent was distilled away under reduced pressure, the obtained residue was purified by silica gel chromatography (n-hexane:ethyl acetate=0:1 to 1:1), and a yellow solid of 3-bromo-N-methylquinolin-8-amine (52 mg) was thus obtained.

MS (ESI m/z): 237, 239 (M+H)
RT (min): 1.76

Reference Example 139

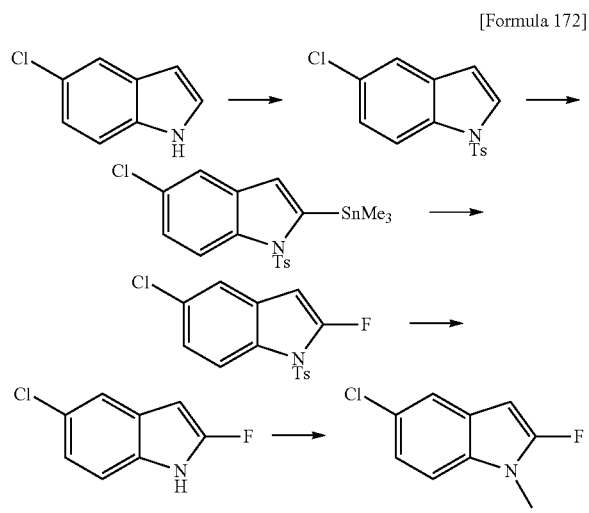

[Formula 172]

1st step
p-Toluenesulfonyl chloride (2 g) and tetrabutyl ammonium hydrogen sulfate (250 mg) were added to a toluene (20 ml) solution containing 5-chloroindole (1.52 g), followed by stirring at room temperature for 11 hours. Water was added to the reaction solution, followed by extraction with ethyl acetate. The resultant was washed with water (×3) and saturated saline and dried over anhydrous sodium sulfate. Subsequently, the solvent was distilled away under reduced pressure, the obtained residue was purified by silica gel chromatography (n-hexane:ethyl acetate=0:1 to 1:1), and a colorless solid of 5-chloro-1-tosyl-1H-indole (3.18 g) was thus obtained.

2nd Step
Lithium diisopropylamide (2M tetrahydrofuran solution) (3.41 ml) was slowly added to a tetrahydrofuran (65 ml) solution containing 5-chloro-1-tosyl-1H-indole (1.98 g) obtained in the 1st step at −78° C. in a nitrogen atmosphere. The reaction solution was adjusted to room temperature. Further, trimethyl tin chloride (1.36 g) was added, followed by stirring for 17 hours. A saturated aqueous potassium fluoride solution was added to the reaction solution and tetrahydrofuran was distilled away under reduced pressure. Ethyl acetate was added, the resultant was washed with saturated saline and dried over anhydrous sodium sulfate, and the solvent was distilled away under reduced pressure. The obtained residue was purified by silica gel chromatography (n-hexane:ethyl acetate=0:1 to 1:1), and colorless viscous oily matter of 5-chloro-1-tosyl-2-(trimethylstannyl)-1H-indole (2.05 g) was thus obtained.

3rd Step
N-fluoro-N'-(chloromethyl)triethylenediamine bis(tetrafluoroborate) (2.33 g) was added to an acetonitrile solution (88 ml) containing 5-chloro-1-tosyl-2-(trimethylstannyl)-1H-indole (2.05 g) obtained in the 2nd step in a nitrogen atmosphere, followed by stirring at room temperature for 16 hours. Chloroform was added to the reaction solution, an insoluble precipitate was removed, and the solvent was distilled away under reduced pressure. The obtained residue was purified by silica gel chromatography (n-hexane:ethyl acetate=0:1 to 1:100), and a light yellow solid of 5-chloro-2-fluoro-1-tosyl-1H-indole (520 mg) was thus obtained.

4th Step
Potassium hydroxide (246 mg) was added to a tetrahydrofuran/ethanol (3 ml/6 ml) solution containing 5-chloro-2-fluoro-1-tosyl-1H-indole (520 mg) obtained in the 3rd step, followed by stirring at 50° C. for 17 hours. Water was added to the reaction solution, followed by extraction with ethyl acetate (×2). The organic layers were combined and washed with saturated saline and dried over anhydrous sodium sulfate. Subsequently, the solvent was distilled away under reduced pressure, the obtained residue was purified by silica gel chromatography (n-hexane:ethyl acetate=0:1 to 1:1), and light yellow oily matter of 5-chloro-2-fluoro-1H-indole (69 mg) was thus obtained.

5th step
Sodium hydride (60% in oil) (16 mg) was added to a DMF (1 ml) solution containing 5-chloro-2-fluoro-1H-indole (45 mg) obtained in the 4th step at room temperature, followed by stirring for 10 minutes. Then, dimethyl sulfate (50 mg) was added, followed by stirring at room temperature for 30 minutes. Water was added to the reaction solution, followed by extraction with ethyl acetate, the resultant was washed with water (×3) and saturated saline and dried over anhydrous sodium sulfate. Subsequently, the solvent was distilled away under reduced pressure, the obtained residue was purified by PLC (n-hexane:ethyl acetate=10:1), and 5-chloro-2-fluoro-1-methyl-1H-indole (18 mg) was thus obtained.

Reference Example 140

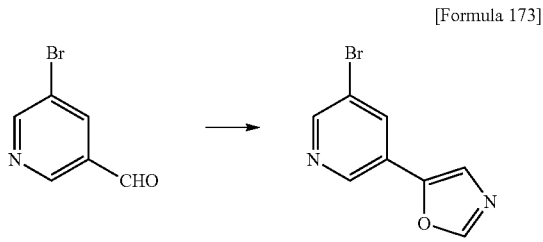 [SMILES: O=Cc1cncc(Br)c1 ; Brc1cncc(-c2cnco2)c1]

[Formula 173]

Toluenesulfonylmethylisocyanide (126 mg) and 1,8-diazabicyclo[5.4.0]undec-7-ene (122 mg) were added to a dichloromethane (4 ml) solution containing 5-bromo-3-pyridinecarboxaldehyde (100 mg) at room temperature, followed by stirring for 5 hours. Water was added to the reaction solution, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane:ethyl acetate=4:1 to 5:2), and a white solid of 5-(5-bromopyridin-3-yl)oxazole (96 mg) was thus obtained.

MS (ESI m/z): 225, 227 (M+H)
RT (min): 1.00

Reference Example 141

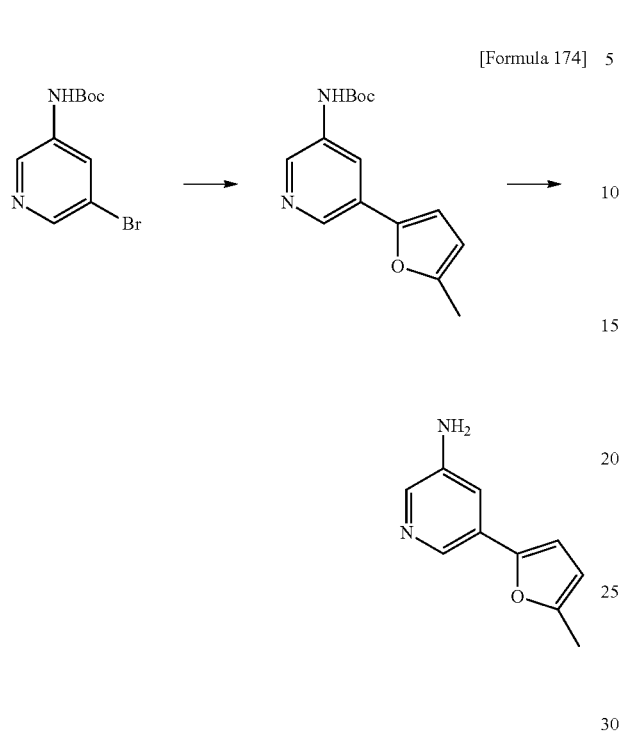

1st Step

The following compound was obtained as described in Reference Example 22.

tert-butyl (5-(5-methylfuran-2-yl)pyridin-3-yl)carbamate

MS (ESI m/z): 275 (M+H)
RT (min): 1.46

2nd Step

TFA (1 ml) was added to a chloroform solution (2 ml) containing tert-butyl(5-(5-methylfuran-2-yl)pyridin-3-yl) carbamate (61 mg) obtained in the 1st step, stirring at room temperature for 2 hours. The solvent was distilled away under reduced pressure, the obtained residue was dissolved in chloroform, and the resultant was washed with water and a saturated aqueous sodium hydrogen carbonate solution. Subsequently, the aqueous layers were combined, followed by extraction with chloroform (×2). The organic layers was combined and dried over anhydrous sodium sulfate. The solvent was distilled away from the obtained organic layers under reduced pressure, and a white solid of 5-(5-methylfuran-2-yl) pyridin-3-amine (46 mg) was thus obtained.

MS (ESI m/z): 175 (M+H)
RT (min): 0.63

Reference Example 142

The following compounds were obtained as described in Reference Example 141.

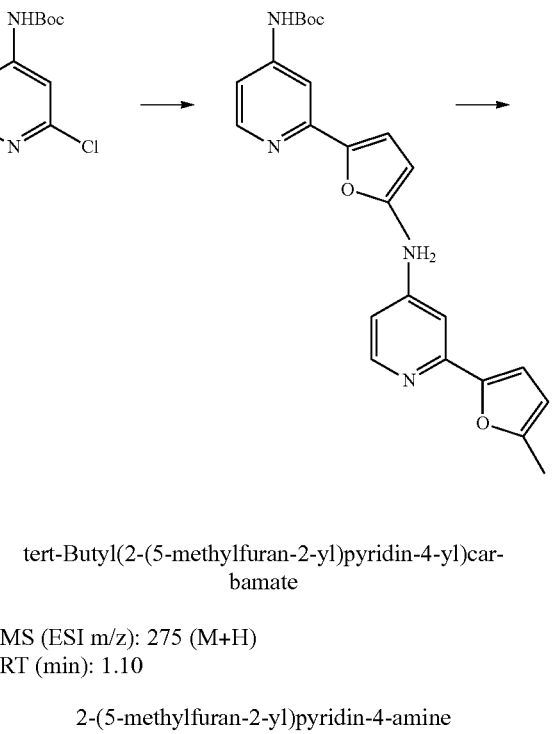

tert-Butyl(2-(5-methylfuran-2-yl)pyridin-4-yl)carbamate

MS (ESI m/z): 275 (M+H)
RT (min): 1.10

2-(5-methylfuran-2-yl)pyridin-4-amine

MS (ESI m/z): 175 (M+H)
RT (min): 0.59

Reference Example 143

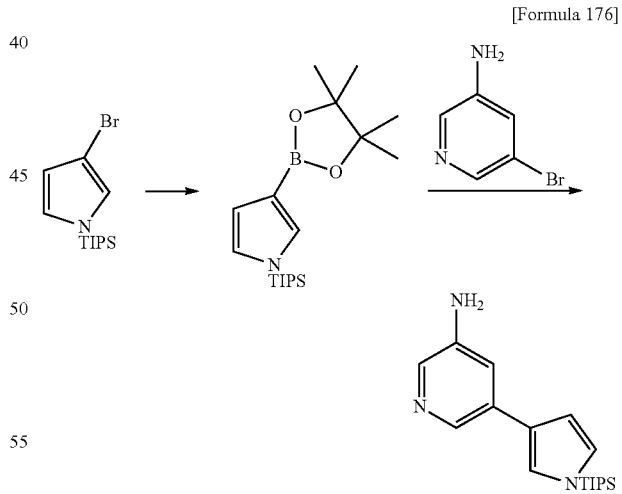

1st Step

Triethylamine (200 mg), bis(pinacolato)diboron (127 mg), 2-dicyclohexylphosphino-2',6'-dimethoxybiphenyl (100 mg), and bis(acetonitrile)palladium dichloride (17 mg) were added to a 1,4-dioxane (4 ml) solution containing 3-bromo-1-(triisopropylsilyl)pyrrole (200 mg) in a nitrogen atmosphere, followed by stirring for 10 hours. Water was added to the reaction solution, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane:ethyl acetate=100:1 to 10:1), and light yellow oily matter of 3-(4,4,5,5-tetramethyl-1,3,2-dioxaborolan-2-yl)-1-(triisopropylsilyl)-1H-pyrrole (58 mg) was thus obtained.

MS (ESI m/z): 350 (M+H)
RT (min): 2.56

2nd Step

The following compound was obtained as described in Reference Example 22.

5-(1-(triisopropylsilyl)-1H-pyrrol-3-yl)pyridin-3-amine

MS (ESI m/z): 316 (M+H)
RT (min): 1.43

Reference Example 144

[Formula 177]

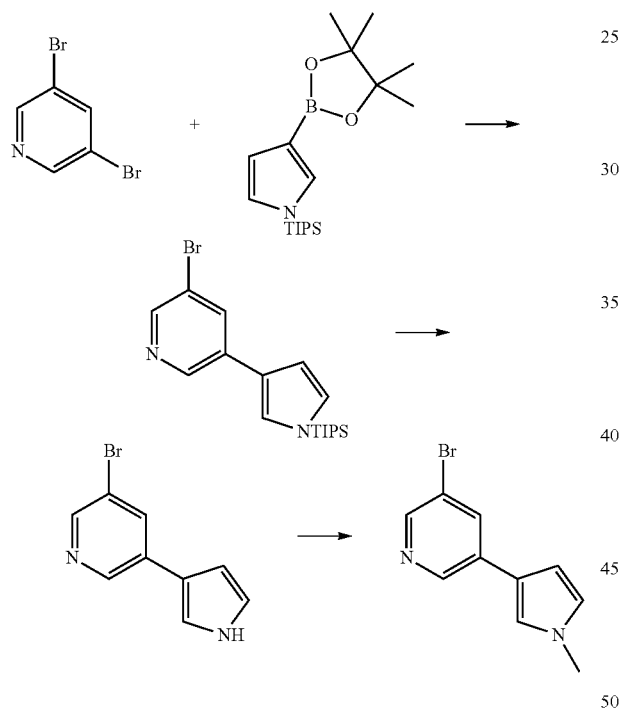

1st Step

The following compound was obtained as described in Reference Example 22.

3-bromo-5-(1-(triisopropylsilyl)-1H-pyrrol-3-yl)pyridine

MS (ESI m/z): 379, 381 (M+H)
RT (min): 2.38

2nd Step

Tetrabutylammonium fluoride (1M tetrahydrofuran solution: 1 ml) was added to a tetrahydrofuran (2 ml) solution containing 3-bromo-5-(1-(triisopropylsilyl)-1H-pyrrol-3-yl)pyridine (71 mg), followed by stirring at room temperature for 2 hours. The reaction solution was poured into water, followed by extraction with ethyl acetate. The resultant was washed with saturated saline and dried over anhydrous sodium sulfate. Then the solvent was distilled away under reduced pressure, the obtained residue was purified by silica gel chromatography (n-hexane:ethyl acetate=5:1 to 2:1), and a white solid of 3-bromo-5-(1H-pyrrol-3-yl)pyridine (28 mg) was thus obtained.

MS (ESI m/z): 223, 225 (M+H)
RT (min): 1.06

3rd Step

Sodium hydride (60% in oil) (6 mg) was added to a DMF (1 ml) solution containing 3-bromo-5-(1H-pyrrol-3-yl)pyridine (28 mg), followed by stirring. Methyl iodide (9 µl) was added, followed by stirring at room temperature for 3 hours. The reaction solution was poured into water, followed by extraction with ethyl acetate. The resultant was washed with saturated saline and dried over anhydrous sodium sulfate. Then, the solvent was distilled away under reduced pressure, the obtained residue was purified by silica gel chromatography (n-hexane:ethyl acetate=30:1 to 3:1), and a white solid of 3-bromo-5-(1-methyl-1H-pyrrol-3-yl)pyridine (18 mg) was thus obtained.

MS (ESI m/z): 237, 239 (M+H)
RT (min): 1.29

Reference Example 145

[Formula 178]

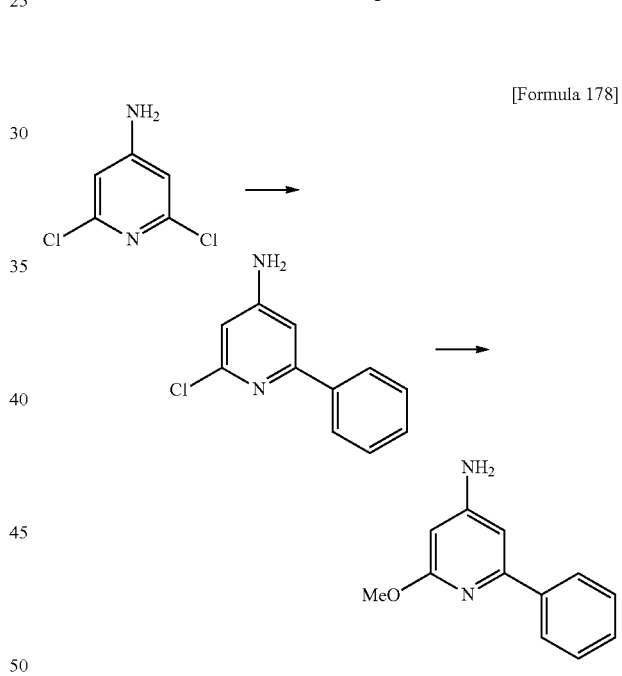

1st Step

Cesium carbonate (300 mg), phenylboronic acid (82 mg), and bis(triphenylphosphine)palladium dichloride (43 mg) were added to a tetrahydrofuran (2 ml) solution containing 4-amino-2,6-dichloropyridine (100 mg) in a nitrogen atmosphere, followed by stirring for 8.5 hours. Water was added to the reaction solution, followed by extraction with ethyl acetate. The resultant was washed with saturated saline and dried over anhydrous magnesium sulfate. Subsequently, the solvent was distilled away under reduced pressure, the obtained residue was purified by silica gel chromatography (n-hexane:ethyl acetate=9:1 to 6:1), and colorless oily matter of 2-chloro-6-phenylpyridin-4-amine (26 mg) was thus obtained.

MS (ESI m/z): 205, 207 (M+H)
RT (min): 1.02

2nd Step

Sodium methoxide (28% methanol solution) (1 ml) was added to a methanol (2 ml) solution containing 2-chloro-6-phenylpyridin-4-amine (26 mg) obtained in the 1st step at room temperature, followed by stirring at 150° C. for 6.5 hours. Water was added to the reaction solution, followed by extraction with ethyl acetate. The resultant was washed with saturated saline and dried over anhydrous magnesium sulfate, and then the solvent was distilled away under reduced pressure. The obtained residue was purified by silica gel chromatography (n-hexane:ethyl acetate=50:1 to 6:1), and 2-methoxy-6-phenylpyridin-4-amine (6 mg) was thus obtained.

MS (ESI m/z): 201 (M+H)
RT (min): 0.64

Reference Example 146

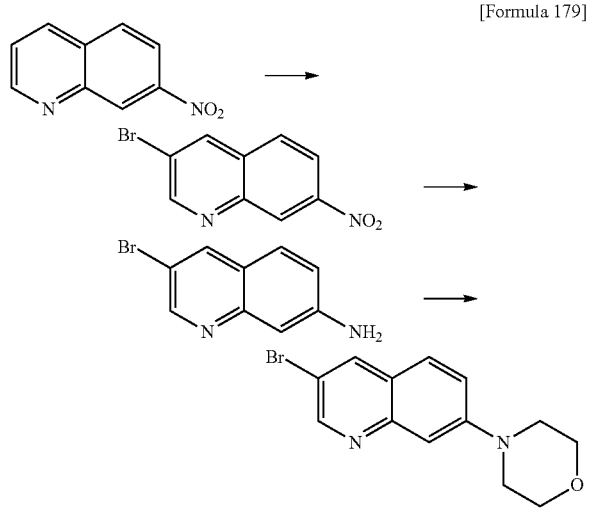

[Formula 179]

1st Step

N-bromosuccinimide (360 mg) was added to an acetic acid (6 ml) solution containing 7-nitroquinoline (700 mg), followed by stirring at 110° C. for 3 hours. N-bromosuccinimide (360 mg) was added again, followed by stirring at 110° C. for 10 minutes. The reaction solution was poured into ice water, an insoluble precipitate was collected by filtration, and light brown 3-bromo-7-nitroquinoline (660 mg) was thus obtained.

MS (ESI m/z): 253, 255 (M+H)
RT (min): 1.44

2nd Step 12M hydrochloric acid (2 ml) and 3-bromo-7-nitroquinoline (660 mg) obtained in the 1st step were added to a suspension of iron powder (3.61 g), ethanol (33 ml) and water (2 ml), followed by reflux for 4 hours. Subsequently, 6M hydrochloric acid (4 ml) was added, followed by reflux for 2.5 hours. Then, the solvent was distilled away under reduced pressure, and an insoluble precipitate was filtered and washed with ethyl acetate. Subsequently, the filtrate was collected, the solvent was again distilled away under reduced pressure, a 28% aqueous ammonia solution was added to the obtained oily matter, and a solid precipitate was filtered and washed with water. Then, the obtained solid was dissolved in ethyl acetate, an insoluble precipitate was removed, and the solvent was distilled away under reduced pressure. Further, diisopropylether was added to the obtained solid, an insoluble precipitate was collected by filtration, and a mixture of a light brown solid of 3-bromo-7-nitroquinoline and 3-bromoquinolin-7-amine (170 mg) was thus obtained.

MS (ESI m/z): 223, 225 (M+H)
RT (min): 0.65

3rd Step

Potassium carbonate (92 mg), sodium iodide (10 mg), and bis(2-chloroethoxy)ethane (64 mg) were added to a tube containing a DMF solution (0.5 ml) containing a portion (50 mg) of the mixture obtained in the 2nd step and the tube was sealed, followed by stirring at 130° C. for 14 hours. Water was added to the reaction solution, followed by extraction with ethyl acetate. The resultant was washed with water (×3) and saturated saline and dried over anhydrous sodium sulfate. Subsequently, the solvent was distilled away under reduced pressure, the obtained residue was purified by silica gel chromatography (n-hexane:ethyl acetate=1:0 to 1:1), and a yellow solid of 4-(3-bromoquinolin-7-yl)morpholine (15 mg) was thus obtained.

MS (ESI m/z): 278, 280 (M+H)
RT (min): 1.45

Reference Example 147

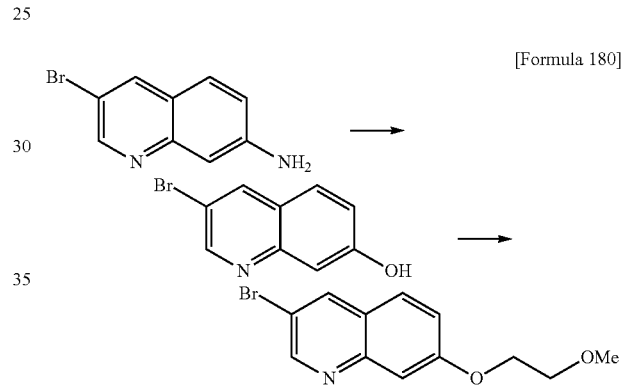

[Formula 180]

1st Step

A 55% sulfuric acid solution (420 ml) containing a portion (33 mg) of the mixture obtained in the 2nd step of Reference Example 146 was irradiated with microwaves (Initiator™, 220° C., 1 hour, 2.45 GHz, 0-240 W). Ice water was added to the reaction solution and neutralized with 28% ammonia water, followed by extraction with ethyl acetate (×2). The resultant was washed with saturated saline and dried over anhydrous sodium sulfate. Subsequently, the solvent was distilled away under reduced pressure, and a light brown solid of 3-bromoquinolin-7-ol (21 mg) was thus obtained.

2nd Step

Sodium hydride (61% in oil) and 2-chloroethylmethylether (6 mg) were added to a DMF solution (0.5 ml) containing 3-bromoquinolin-7-ol (21 mg) obtained in the 1st step in a nitrogen atmosphere, followed by stirring at 120° C. for 30 minutes. Water was added to the reaction solution, an insoluble precipitate was collected by filtration, and light brown 3-bromo-7-(2-methoxyethoxy)quinoline (17 mg) was thus obtained.

MS (ESI m/z): 282, 284 (M+H)
RT (min): 1.33

Reference Example 148-1

The following compound was obtained with reference to Monatshefte fuer Chemie, 1991, vol. 122, #11, pp. 935-942.

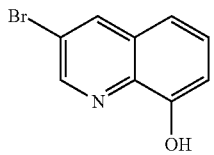

3-bromoquinolin-8-ol

Reference Example 148-2

The following compound was obtained as described in the 2nd step of Reference Example 147.

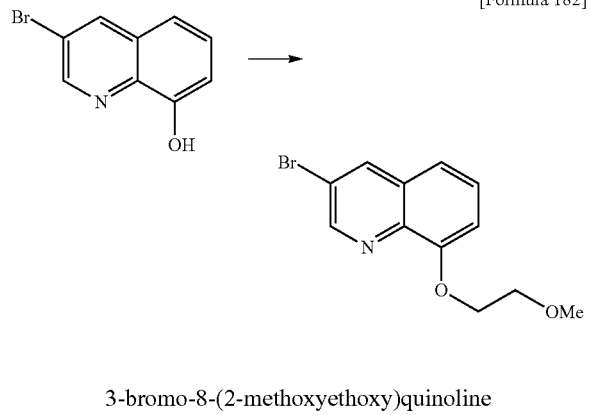

3-bromo-8-(2-methoxyethoxy)quinoline

MS (ESI m/z): 282, 284 (M+H)
RT (min): 1.25

Reference Example 149

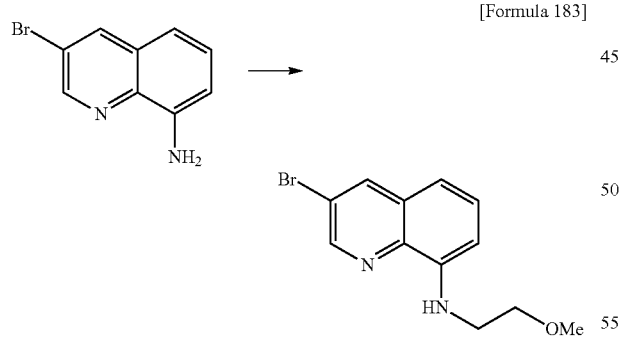

Potassium carbonate (92 mg) and 2-chloroethylmethylether (32 mg) were added to a tube containing a DMF (0.5 ml) solution containing 3-bromoquinolin-8-amine (50 mg) and the tube was sealed, followed by stirring at 110° C.-130° C. for 22 hours. Water was added to the reaction solution, followed by extraction with ethyl acetate. The resultant was washed with water (×3) and saturated saline and dried over anhydrous sodium sulfate. Subsequently, the solvent was distilled away under reduced pressure, the obtained residue was purified by silica gel chromatography (n-hexane:ethyl acetate=1:0 to 1:1), and light yellow oily matter of 3-bromo-N-(2-methoxyethyl)quinolin-8-amine (15 mg) was thus obtained.

MS (ESI m/z): 281, 283 (M+H)
RT (min): 1.86

Reference Example 150

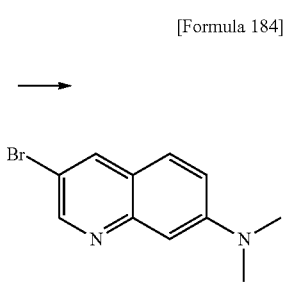

Potassium carbonate (92 mg) and dimethyl sulfate (100 mg) were added to a DMF (0.5 ml) solution containing a portion (50 mg) of the mixture obtained in the 2nd step of Reference Example 146, followed by stirring at 60° C. for 5 hours and at 80° C. for 3 hours. The reaction solution was diluted with ethyl acetate, insoluble matter was removed, the solvent was distilled away under reduced pressure. The obtained residue was purified by silica gel chromatography (n-hexane:ethyl acetate=1:0 to 9:1), and a light yellow solid of 3-bromo-N,N-dimethylquinolin-7-amine (25 mg) was thus obtained.

MS (ESI m/z): 251, 253 (M+H)
RT (min): 1.42

Reference Example 151

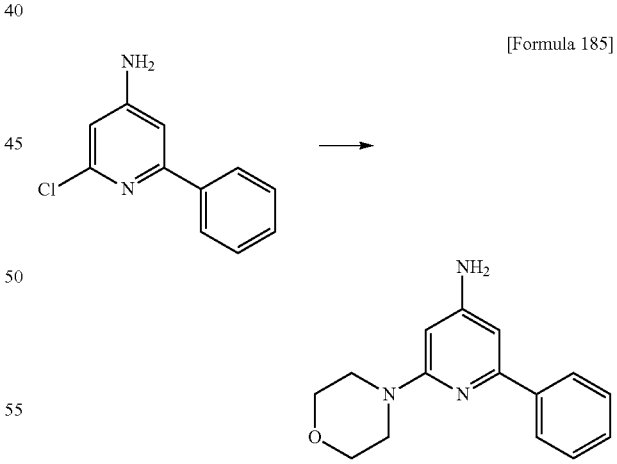

Morpholine (1 ml) was added to 2-chloro-6-phenylpyridin-4-amine (30 mg), followed by stirring at 130° C. for 2 hours and 170° C. for 4 hours. The reaction solution was adjusted to room temperature, and 10% saline was added, followed by extraction with ethyl acetate. The organic layer was washed with saturated saline and dried over anhydrous sodium sulfate. Then, the solvent was distilled away under reduced pressure, the obtained residue was purified by silica gel chromatography (n-hexane:ethyl acetate=2:1 to 1:2), and colorless oily matter of 2-morpholino-6-phenylpyridin-4-amine (24 mg) was thus obtained.

MS (ESI m/z): 256 (M+H)
RT (min): 0.71

Reference Example 152

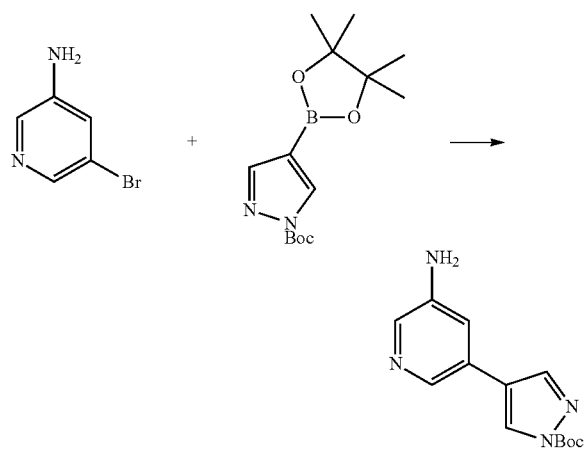

[Formula 186]

Water (0.5 ml), sodium carbonate (92 mg), tert-butyl 4-(4,4,5,5-tetramethyl-1,3,2-dioxaborolan-2-yl)-1H-pyrazol-1-carboxylate (203 mg), and bis(tri-tert-butylphosphine)palladium (30 mg) were added to a tetrahydrofuran (4.5 ml) solution containing 5-bromopyridin-3-amine (100 mg) in a nitrogen atmosphere, followed by stirring for 2.75 hours. Water was added to the reaction solution, followed by extraction with ethyl acetate. The organic layer was washed with saturated saline and dried over anhydrous sodium sulfate. Subsequently, the solvent was distilled away under reduced pressure, the obtained residue was purified by silica gel chromatography (chloroform:methanol=1:0 to 30:1), and a white solid of tert-butyl-4-(5-aminopyridin-3-yl)-1H-pyrazol-1-carboxylate (52 mg) was thus obtained.

MS (ESI m/z): 261 (M+H)
RT (min): 0.75

Reference Example 153

The following compound was obtained as described in Reference Example 152.

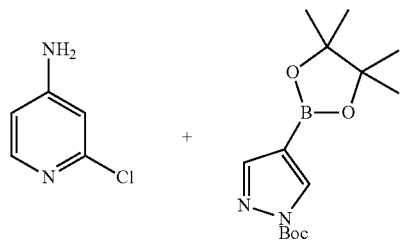

[Formula 187]

MS (ESI m/z): 261 (M+H)
RT (min): 0.74

Reference Example 154

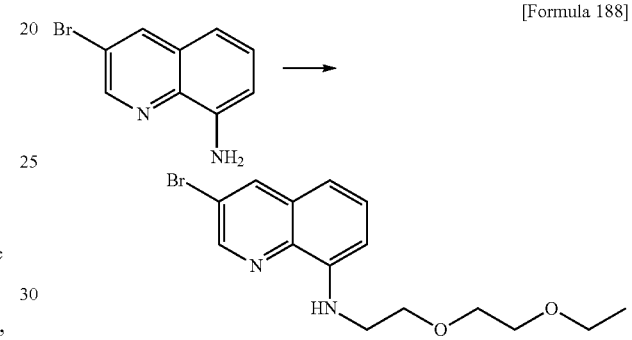

[Formula 188]

Potassium carbonate (69 mg), sodium iodide (20 mg), and 2-(2-ethoxyethoxy)ethyl-4-methylbenzenesulfonate (Tetrahedron Letters, 2009, vol. 50, #37, pp. 5231-5234) were added to a tube containing a DMF (2 ml) solution containing 3-bromoquinolin-8-amine (223 mg) and the tube was sealed, followed by stirring at 130° C. for 7 hours. The reaction solution was adjusted to room temperature, and water was added, followed by extraction with ethyl acetate. The resultant was washed with water (×3) and saturated saline and dried over anhydrous sodium sulfate. Subsequently, the solvent was distilled away under reduced pressure, the obtained residue was purified by silica gel chromatography (n-hexane:ethyl acetate=1:7), and light yellow oily matter of 3-bromo-N-(2-(2-ethoxyethoxy)ethyl)quinolin-8-amine (40 mg) was thus obtained.

MS (ESI m/z): 339, 341 (M+H)
RT (min): 1.82

Reference Example 155

The following compound was obtained as described in Reference Example 154.

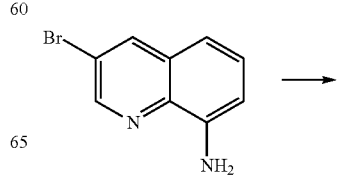

[Formula 189]

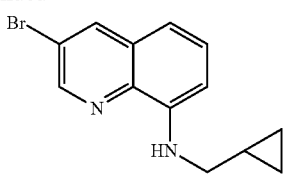

3-bromo-N-(cyclopropylmethyl)quinolin-8-amine

MS (ESI m/z): 277, 279 (M+H)
RT (min): 2.05

Reference Example 156

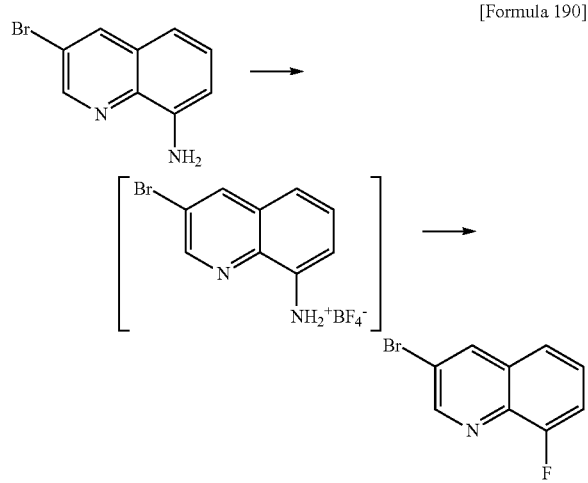

[Formula 190]

A mixture of 3-bromoquinolin-8-amine (38 mg), 48% aqueous fluoroboric acid solution (0.5 ml), and sodium nitrite (16 mg) was stirred at room temperature for 1 hour. Water was poured into the reaction solution and an insoluble precipitate was collected by filtration. Further, the solid collected by filtration was dissolved in 1,2-dichlorobenzene (1 ml) and stirred at 130° C. for 1 hour and at 190° C. for 0.5 hour. 1M hydrochloric acid was added to the reaction solution, followed by extraction with ethyl acetate. The resultant was washed with water (×2) and saturated saline and dried over anhydrous sodium sulfate. Subsequently, the solvent was distilled away under reduced pressure, the obtained residue was purified by silica gel chromatography (n-hexane:ethyl acetate=1:0 to 1:1), and 3-bromo-8-fluoroquinolin-8-amine (32 mg) was thus obtained.

MS (ESI m/z): 226, 228 (M+H)
RT (min): 1.34

Reference Example 157-1

The following compound was obtained with reference to Monatshefte fuer Chemie, 1994, vol. 125, #6/7, pp. 723-730.

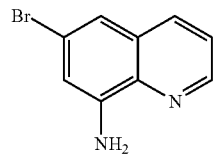

[Formula 191]

6-bromoquinolin-8-amine

Reference Example 157-2

[Formula 192]

Potassium carbonate (69 mg), sodium iodide (5 mg), and dimethyl sulfate (31 mg) were added to a DMF (1 ml) solution containing 6-bromoquinolin-8-amine (37 mg), followed by stirring at 100° C. for 14 hours. The reaction solution was adjusted to room temperature, and water was added, followed by extraction with ethyl acetate. The organic layer was washed with water (×3) and saturated saline and dried over anhydrous sodium sulfate. Subsequently, the solvent was distilled away under reduced pressure, the obtained residue was purified by silica gel chromatography (n-hexane:ethyl acetate=1:0 to 1:1), and 6-bromo-N-methylquinolin-8-amine (17 mg) was thus obtained.

MS (ESI m/z): 237, 239 (M+H)
RT (min): 1.68

Reference Example 158

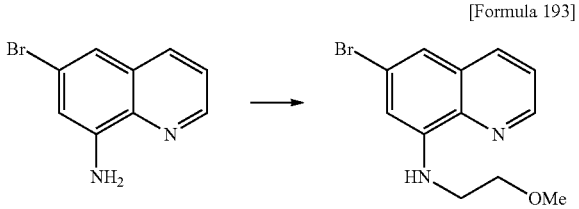 [SMILES: Nc1cc(Br)cc2cccnc12 ; COCCNc1cc(Br)cc2cccnc12]

[Formula 193]

Potassium carbonate (69 mg), sodium iodide (5 mg), and 2-methoxyethyl chloride (24 mg) were added to a DMF (1 ml) solution containing 6-bromoquinolin-8-amine (37 mg), followed by stirring at 140° C. for 12 hours. Further, cesium carbonate (160 mg), sodium iodide (20 mg), N,N-dimethyl-4-aminopyridine (100 mg), and 2-methoxyethyl chloride (120 mg) were added, followed by stirring at 160° C. for 4.5 hours. The reaction solution was adjusted to room temperature, and water was added, followed by extraction with ethyl acetate. The resultant was washed with water (×3) and saturated saline and dried over anhydrous sodium sulfate. Subsequently, the solvent was distilled away under reduced pressure, the obtained residue was purified by silica gel chromatography (n-hexane:ethyl acetate=1:0 to 4:1), and 6-bromo-N-(2-methoxyethyl)quinolin-8-amine (10 mg) was thus obtained.

MS (ESI m/z): 281, 283 (M+H)
RT (min): 1.68

Reference Example 159

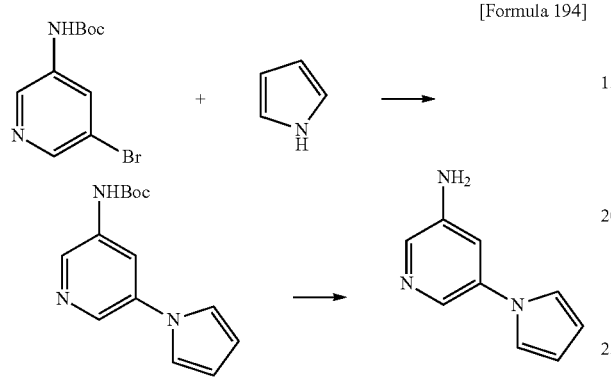

[Formula 194]

1st Step

Cesium carbonate (214 mg), pyrrole (30 mg), Xantphos (63 mg), and Pd$_2$(dba)$_3$ (50 mg) were added to a 1,4-dioxane solution (5 mL) containing tert-butyl(5-bromopyridin-3-yl)carbamate (100 mg) in a nitrogen atmosphere, followed by stirring at 100° C. for 8 hours. The reaction solution was adjusted to room temperature, and water was added, followed by extraction with ethyl acetate. The organic layer was washed with saturated saline and dried over anhydrous sodium sulfate. Then, the solvent was distilled away under reduced pressure, the obtained residue was purified by silica gel chromatography (n-hexane:ethyl acetate=5:1 to 1:1), and a light yellow solid of tert-butyl(5-(1H-pyrrol-1-yl)pyridin-3-yl)carbamate (36 mg) was thus obtained.

MS (ESI m/z): 260 (M+H)
RT (min): 1.38

2nd Step

TFA (1 ml) was added to a chloroform (1 ml) solution containing tert-butyl(5-(1H-pyrrol-1-yl)pyridin-3-yl)carbamate (36 mg) obtained in the 1st step, followed by stirring at room temperature for 1 hour. Then, the solvent was distilled away under reduced pressure and the residue was added to a mixture of chloroform, water, and a 1M sodium hydroxide aqueous solution, followed by extraction with chloroform. The resultant was dried over anhydrous sodium sulfate, the solvent was distilled away under reduced pressure, and a light brown solid of 5-(1H-pyrrol-1-yl)pyridin-3-amine (23 mg) was thus obtained.

MS (ESI m/z): 160 (M+H)
RT (min): 0.52

Reference Example 160

The following compounds were obtained as described in Reference Example 159.

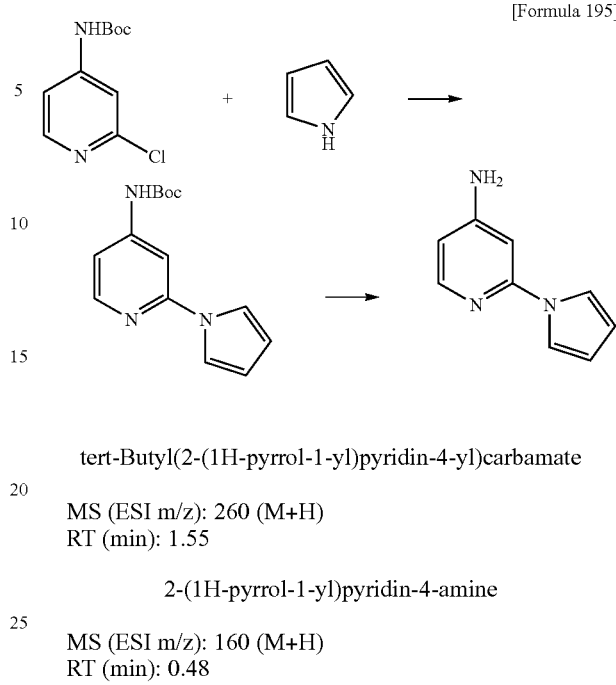

[Formula 195]

tert-Butyl(2-(1H-pyrrol-1-yl)pyridin-4-yl)carbamate

MS (ESI m/z): 260 (M+H)
RT (min): 1.55

2-(1H-pyrrol-1-yl)pyridin-4-amine

MS (ESI m/z): 160 (M+H)
RT (min): 0.48

Reference Example 161

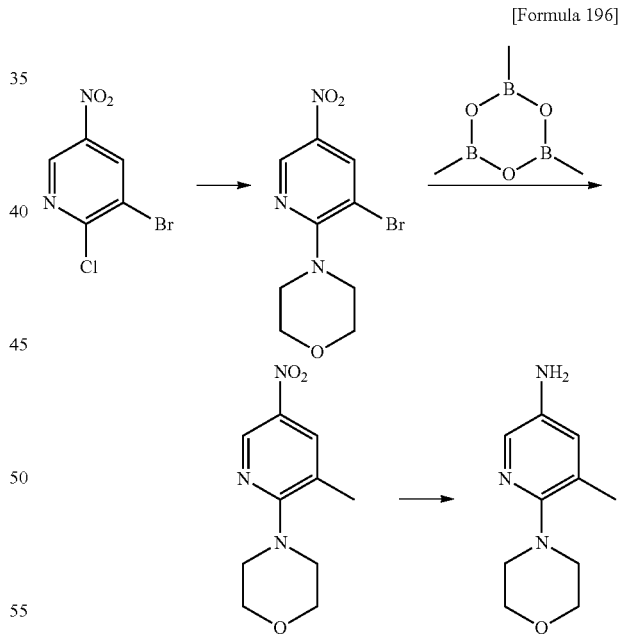

[Formula 196]

1st Step

Triethylamine (191 mg) and morpholine (120 mg) were added to a tetrahydrofuran (4 ml) solution containing 3-bromo-2-chloro-5-nitropyridine (300 mg), followed by stirring for 40 minutes. Water was added to the reaction solution, followed by extraction with ethyl acetate. The resultant was washed with saturated saline and dried over anhydrous sodium sulfate. Subsequently, the solvent was distilled away under reduced pressure, the obtained residue was purified by silica gel chromatography (chloroform:methanol=1:0 to 3:1), and a yellow solid of 4-(3-bromo-5-nitropyridin-2-yl)morpholine (346 mg) was thus obtained.

MS (ESI m/z): 288, 290 (M+H)
RT (min): 1.37

2nd Step

The following compound was obtained as described in Reference Example 22.

4-(3-methyl-5-nitropyridin-2-yl)morpholine

MS (ESI m/z): 224 (M+H)
RT (min): 1.20

3rd Step

A methanol (20 ml) solution containing 4-(3-methyl-5-nitropyridin-2-yl)morpholine (67 mg) was prepared and subjected to a hydrogenation reaction (room temperature; 1 bar; flow rate: 1 ml/min; 10% Pd/C) using H-cube™. Then, the solvent was distilled away under reduced pressure, and a purple solid of 5-methyl-6-morpholinopyridin-3-amine (52.4 mg) was thus obtained.

MS (ESI m/z): 194 (M+H)
RT (min): 0.46

Reference Example 162

The following compounds were obtained as described in Reference Example 161.

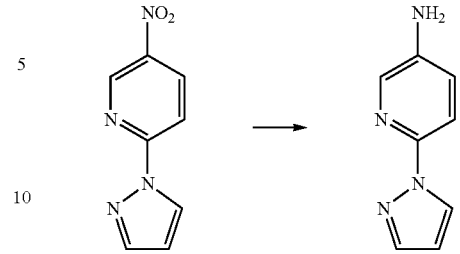

[Formula 198]

6-(1H-pyrazol-1-yl)pyridin-3-amine

MS (ESI m/z): 161 (M+H)
RT (min): 0.67

Reference Example 164

The following compounds were obtained as described in the 2nd and 3rd steps of Reference Example 161.

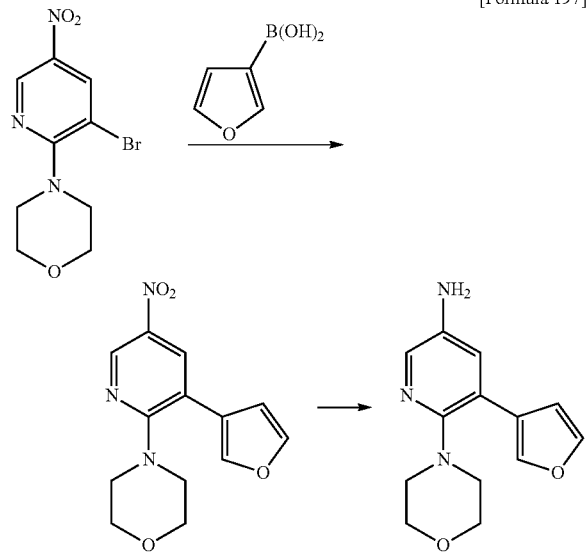

[Formula 197]

4-(3-(furan-3-yl)-5-nitropyridin-2-yl)morpholine

MS (ESI m/z): 276 (M+H)
RT (min): 1.42

5-(furan-3-yl)-6-morpholinopyridin-3-amine

MS (ESI m/z): 246 (M+H)
RT (min): 0.68

Reference Example 163

The following compound was obtained as described in the 3rd step of Reference Example 161.

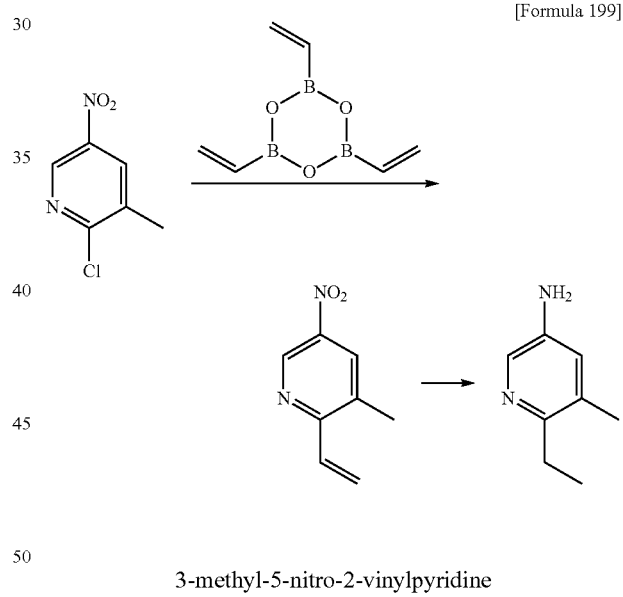

[Formula 199]

3-methyl-5-nitro-2-vinylpyridine

MS (ESI m/z): 165 (M+H)
RT (min): 1.36

6-ethyl-5-methylpyridin-3-amine

MS (ESI m/z): 137 (M+H)
RT (min): 0.47

Reference Example 165

The following compounds were obtained as described in the 2nd and 3rd steps of Reference Example 161.

[Formula 200]

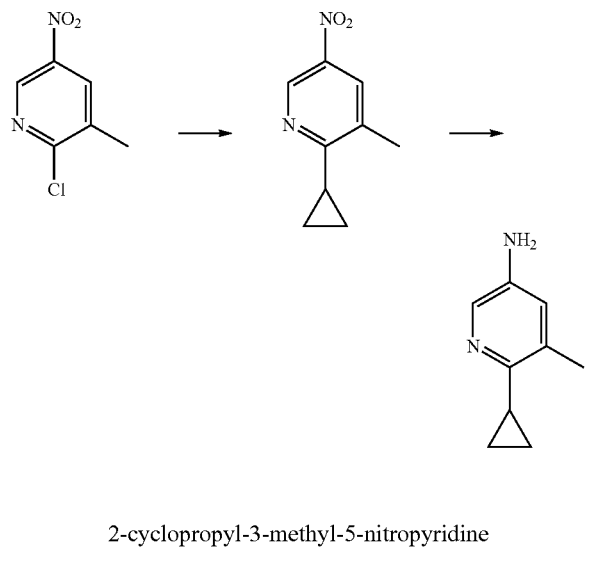

2-cyclopropyl-3-methyl-5-nitropyridine

MS (ESI m/z): 179 (M+H)
RT (min): 1.56

6-cyclopropyl-5-methylpyridin-3-amine

MS (ESI m/z): 149 (M+H)
RT (min): 0.52

Reference Example 166

[Formula 201]

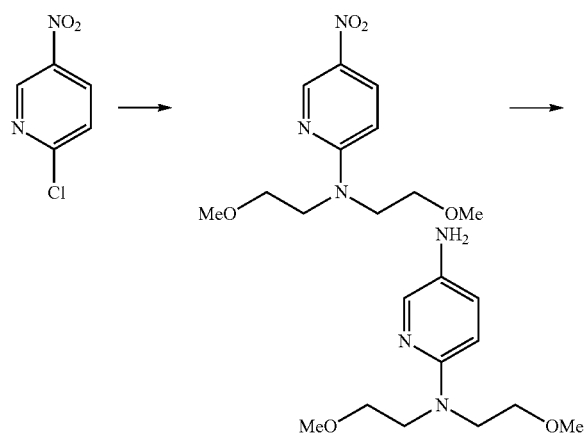

1st Step

Potassium carbonate (262 mg) and bis(2-methoxyethyl) amine (840 mg) were added to a DMF (2 ml) solution containing 2-chloro-5-nitropyridine (100 mg), followed by stirring at room temperature for 5 hours. Water (15 ml) was added to the reaction solution, followed by stirring at room temperature for 1 hour. Insoluble matter was collected by filtration, and a white solid of N,N-bis(2-methoxyethyl)-5-nitropyridin-2-amine (117 mg) was thus obtained.

MS (ESI m/z): 256 (M+H)
RT (min): 1.26

2nd Step

An ethyl acetate/methanol (10 ml/5 ml) solution containing N,N-bis(2-methoxyethyl)-5-nitropyridin-2-amine (20 mg) obtained in the 1st step was prepared and subjected to a hydrogenation reaction (room temperature; 1 bar; flow rate: 1 ml/min; 10% Pd/C) using H-cube™. Then, the solvent was distilled away under reduced pressure, and light peach oily matter of $N^2,N^2$-bis(2-methoxyethyl)pyridin-2,5-diamine (18 mg) was thus obtained.

MS (ESI m/z): 226 (M+H)
RT (min): 0.47

Reference Example 167

[Formula 202]

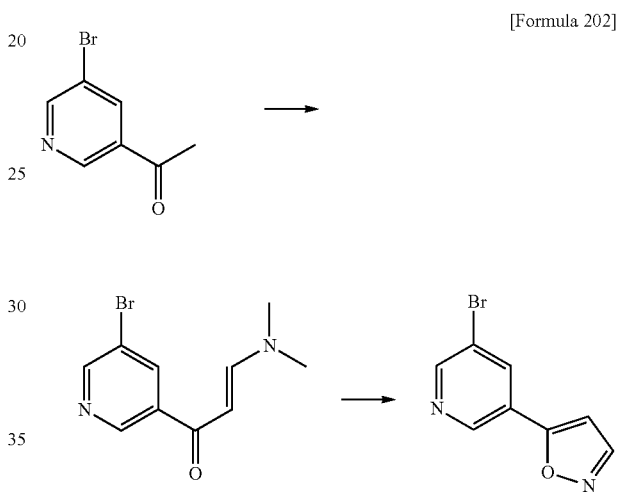

1st Step

An N,N-dimethylformamide dimethylacetal (2 ml) solution containing 1-(5-bromopyridin-3-yl)ethanone (100 mg) (WO2009/87224 A1) was stirred at 100° C. for 5 hours. The solvent was distilled away under reduced pressure, and a yellow solid of 1-(5-bromopyridin-3-yl)-3-(dimethylamino) prop-2-ene-1-one was thus obtained.

MS (ESI m/z): 255, 257 (M+H)
RT (min): 0.89

2nd Step

Hydroxyamine•hydrochloride (42 mg) was added to a methanol (2 ml) solution containing 1-(5-bromopyridin-3-yl)-3-(dimethylamino)prop-2-ene-1-one obtained in the 1st step, followed by reflux for 2 hours. The solvent was distilled away under reduced pressure, and water was added to the obtained residue, followed by extraction with ethyl acetate. Then, the organic layer was washed with saturated saline and dried over anhydrous sodium sulfate, and the solvent was distilled away under reduced pressure. The obtained residue was purified by silica gel chromatography (n-hexane:ethyl acetate=1:0 to 1:3), and a white solid of 5-(5-bromopyridin-3-yl)isoxazole (59.5 mg) was thus obtained.

MS (ESI m/z): 225, 227 (M+H)
RT (min): 1.10

153

Reference Example 168

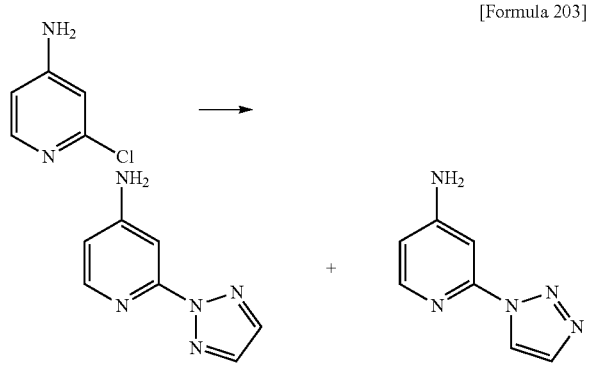
[Formula 203]

Cesium carbonate (1.9 g) and 1H-1,2,3-triazole (540 mg) were added to a tube containing a DMF (2 ml) solution containing 2-chloropyridin-4-amine (500 mg) and the tube was sealed, followed by stirring at 180° C. for 6 hours. Water was added to the reaction solution, followed by extraction with ethyl acetate. The resultant was washed with saturated saline and dried over anhydrous sodium sulfate. Subsequently, the solvent was distilled away under reduced pressure. The obtained residue was purified by silica gel chromatography (n-hexane:ethyl acetate=1:3 to 0:1), and a white solid of 2-(2H-1,2,3-triazol-2-yl)pyridin-4-amine (75.7 mg) and brown oily matter of 2-(1H-1,2,3-triazol-1-yl)pyridin-4-amine (25.1 mg) was thus obtained.

2-(2H-1,2,3-triazol-2-yl)pyridin-4-amine $^1$H-NMR (DMSO-d$_6$, 300 MHz) δ: 8.06 (s, 2H), 7.95 (d, 1H, 5.4 Hz), 7.12 (d, 1H, J=1.8 Hz), 6.54 (dd, 1H, J=1.8, 5.4 Hz), 6.49 (br, 2H)

2-(1H-1,2,3-triazol-1-yl)pyridin-4-amine $^1$H-NMR (DMSO-d$_6$, 300 MHz) δ: 8.70 (s, 1H), 7.97 (d, 1H, J=5.4 Hz), 7.91 (s, 1H), 7.23 (d, 1H, J=2.1 Hz), 6.60 (br, 2H), 6.57 (dd, 1H, J=2.1, 5.4 Hz)

Reference Example 169

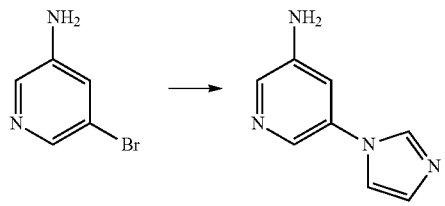
[Formula 204]

Imidazole (42 mg), cesium carbonate (340 mg), trans-N,N'-dimethylcyclohexane-1,2-diamine (74 mg), and copper iodide (50 mg) were added to a tube containing a N,N-dimethylacetamide (2 ml) solution containing 5-bromopyridin-3-amine (90 mg) in a nitrogen atmosphere and the tube was sealed, followed by stirring at 150° C. for 14.5 hours. The reaction solution was adjusted to room temperature, and water was added, followed by extraction with ethyl acetate. The resultant was washed with saturated saline and dried over anhydrous sodium sulfate. Subsequently, the solvent was distilled away under reduced pressure, the obtained residue was purified by silica gel chromatography (chloroform:methanol=1:0 to 10:1), and a brown solid of 5-(1H-imidazol-1-yl)pyridin-3-amine (25.8 mg) was thus obtained.

MS (ESI m/z): 161 (M+H)

RT (min): 0.19

Reference Example 170

The following compound was obtained as described in Reference Example 169.

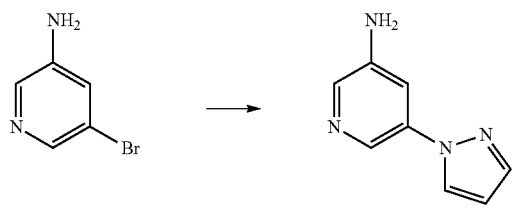
[Formula 205]

5-(1H-pyrazol-1-yl)pyridin-3-amine

MS (ESI m/z): 161 (M+H)

RT (min): 0.38

Reference Example 171

The following compound was obtained with reference to U.S. Pat. No. 6,133,253 A1.

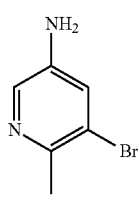
[Formula 206]

5-bromo-6-methylpyridin-3-amine

Reference Example 172

The following compound was obtained as described in Reference Example 169.

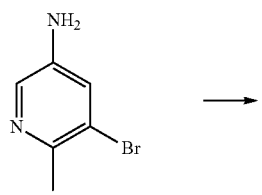
[Formula 207]

-continued

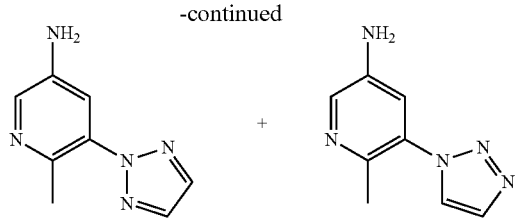

6-methyl-5-(2H-1,2,3-triazol-2-yl)pyridin-3-amine

MS (ESI m/z): 176 (M+H)
RT (min): 0.44
$^1$H-NMR (DMSO-d$_6$, 300 MHz) δ: 8.11 (s, 2H), 7.96 (d, 1H, J=2.7 Hz), 7.25 (d, 1H, J=2.7 Hz), 5.52 (br, 2H), 2.32 (s, 3H)

6-methyl-5-(1H-1,2,3-triazol-1-yl)pyridin-3-amine

MS (ESI m/z): 176 (M+H)
RT (min): 0.20, 0.27

Reference Example 173

The following compound was obtained as described in Reference Example 169.

[Formula 208]

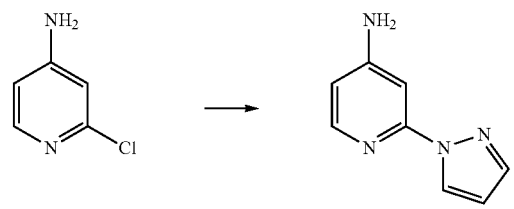

2-(1H-pyrazol-1-yl)pyridin-4-amine

MS (ESI m/z): 161 (M+H)
RT (min): 0.36

Reference Example 174

The following compound was obtained as described in Reference Example 169.

[Formula 209]

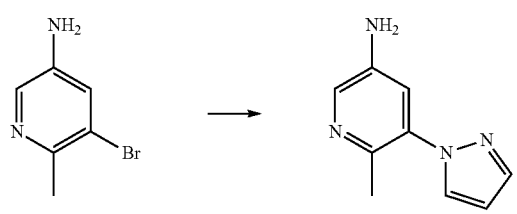

6-methyl-5-(1H-pyrazol-1-yl)pyridin-3-amine

MS (ESI m/z): 175 (M+H)
RT (min): 0.42

Reference Example 175

The following compound was obtained as described in Reference Example 169.

[Formula 210]

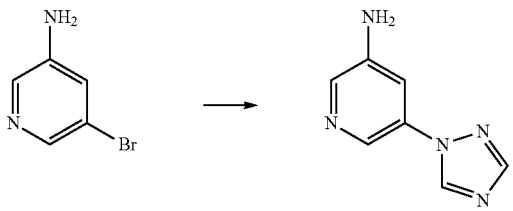

5-(1H-1,2,4-triazol-1-yl)pyridin-3-amine

MS (ESI m/z): 162 (M+H)
RT (min): 0.27

Reference Example 176

The following compound was obtained as described in Reference Example 169.

[Formula 211]

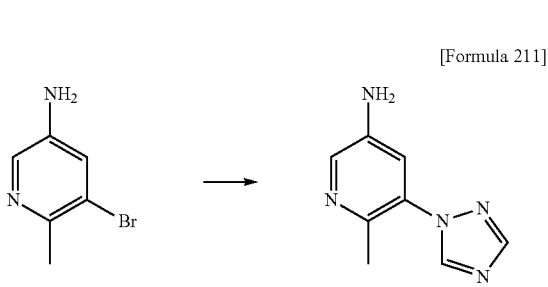

6-methyl-5-(1H-1,2,4-triazol-1-yl)pyridin-3-amine

MS (ESI m/z): 176 (M+H)
RT (min): 0.27

Reference Example 178

[Formula 212]

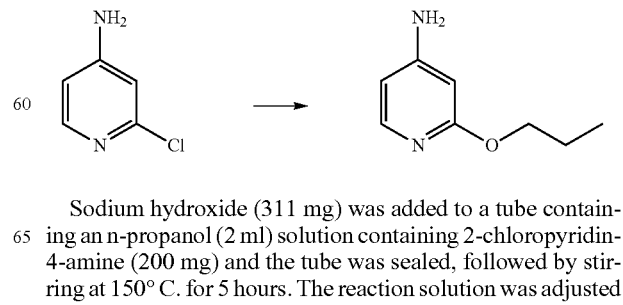

Sodium hydroxide (311 mg) was added to a tube containing an n-propanol (2 ml) solution containing 2-chloropyridin-4-amine (200 mg) and the tube was sealed, followed by stirring at 150° C. for 5 hours. The reaction solution was adjusted to room temperature, and water was added, followed by extraction with toluene. The resultant was washed with saturated saline and dried over anhydrous sodium sulfate. Subsequently, the solvent was distilled away under reduced pressure, the obtained residue was purified by silica gel chromatography (n-hexane:ethyl acetate=7:3 to 2:3), and yellow oily matter of 2-propoxypyridin-4-amine (200 mg) was thus obtained.

MS (ESI m/z): 153 (M+H)
RT (min): 0.48

Reference Example 179

The following compound was obtained as described in Reference Example 178.

[Formula 213]

2-butoxypyridin-4-amine

MS (ESI m/z): 167 (M+H)
RT (min): 0.59

Reference Example 180

The following compound was obtained as described in Reference Example 178.

[Formula 214]

2-isobutoxypyridin-4-amine

MS (ESI m/z): 167 (M+H)
RT (min): 0.58

Reference Example 181

The following compound was obtained as described in Reference Example 178.

[Formula 215]

2-(3-methoxybutyl)pyridin-4-amine

MS (ESI m/z): 197 (M+H)
RT (min): 0.51

Reference Example 182

The following compound was obtained as described in Reference Example 178.

[Formula 216]

2-(benzyloxy)pyridin-4-amine

MS (ESI m/z): 201 (M+H)
RT (min): 0.65

Reference Example 183

[Formula 217]

1st Step
The following compound was obtained as described in Reference Example 22.

159

4-nitro-2-(1-(triisopropylsilyl)-1H-pyrrol-3-yl)pyridine

MS (ESI m/z): 346 (M+H)
RT (min): 2.26

2nd Step

The following compound was obtained as described in the 3rd step of Reference Example 161.

2-(1-(triisopropylsilyl)-1H-pyrrol-3-yl)pyridin-4-amine

MS (ESI m/z): 316 (M+H)
RT (min): 1.42

Reference Example 184

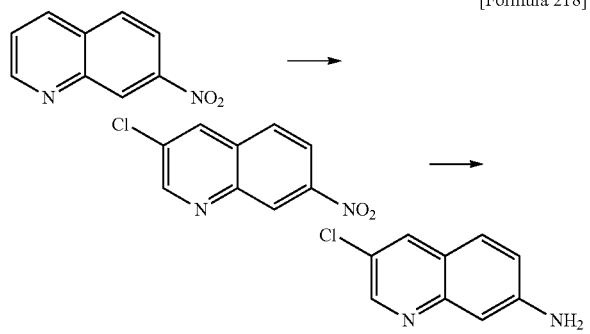

[Formula 218]

1st Step

N-chlorosuccinimide (45 mg) was added to an acetic acid (0.5 ml) solution containing 7-nitroquinoline (39 mg), followed by stirring at 160° C. for 0.5 hours. Water was added to the reaction solution, an insoluble precipitate was purified by silica gel chromatography (n-hexane:ethyl acetate=1:1), and 3-chloro-7-nitroquinoline (12 mg) was thus obtained.

MS (ESI m/z): 209, 211 (M+H)
RT (min): 1.37

2nd Step

Ammonium chloride (19 mg) and iron powder (19 mg) were added to an ethanol solution containing 3-chloro-7-nitroquinoline (12 mg), followed by stirring at 80° C. for 2 hours. The solvent was distilled away under reduced pressure, the obtained residue was purified by silica gel column chromatography (n-hexane:ethyl acetate=1:0 to 0:1), and 3-chloroquinolin-7-amine (7 mg) was thus obtained.

MS (ESI m/z): 179, 181 (M+H)
RT (min): 0.61

Reference Example 185

The following compound was obtained with reference to Journal of Medicinal Chemistry, 1988, vol. 31, #7, pp. 1347-1351.

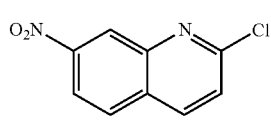

[Formula 219]

160

2-chloro-7-nitroquinoline

Reference Example 186

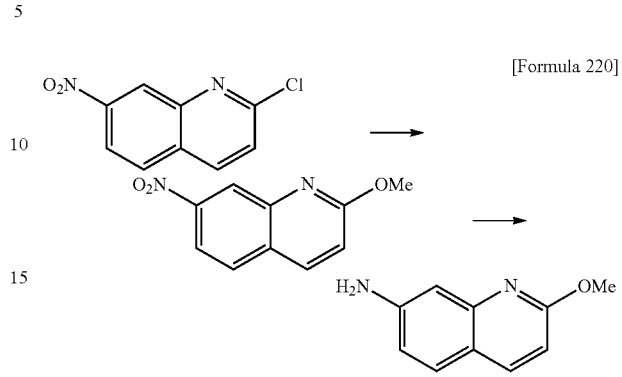

[Formula 220]

1st Step

Sodium methoxide (28% methanol solution) (50 mg) was added to a DMF (1 ml) solution containing 2-chloro-7-nitroquinoline (42 mg), followed by stirring at 0° C. for 5 minutes. A saturated aqueous ammonium chloride solution was added to the reaction solution, an insoluble precipitate was washed with water, and 2-methoxy-7-nitroquinoline (33 mg) was thus obtained.

2nd Step

A methanol (10 ml) solution containing 2-methoxy-7-nitroquinoline (33 mg) obtained in the 1st step was prepared and subjected to a hydrogenation reaction (60° C.; 50 bar; flow rate: 1 ml/min; 10% Pd/C) using H-cube™. Then, the solvent was distilled away under reduced pressure, and a purple solid of 2-methoxyquinolin-7-amine (28 mg) was thus obtained.

MS (ESI m/z): 175 (M+H)
RT (min): 0.55

Reference Example 187

The following compound was obtained as described in Reference Example 186.

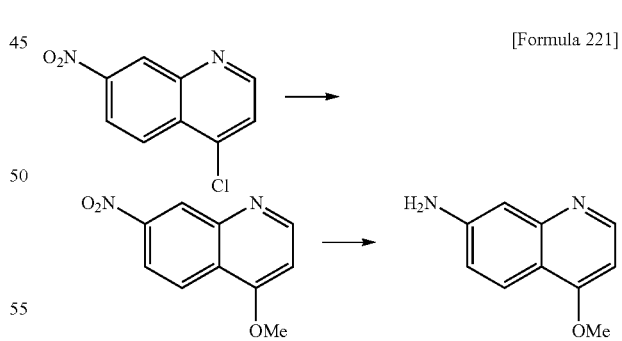

[Formula 221]

4-methoxyquinolin-7-amine

MS (ESI m/z): 175 (M+H)
RT (min): 0.54

Reference Example 188

The following compound was obtained as described in the 1st step of Reference Example 186.

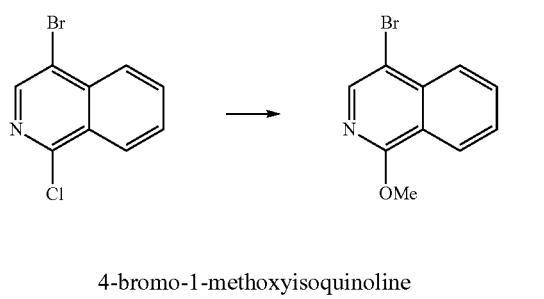

4-bromo-1-methoxyisoquinoline

MS (ESI m/z): 238, 240 (M+H)
RT (min): 1.82

Reference Example 189

The following compound was obtained as described in the 1st step of Reference Example 186.

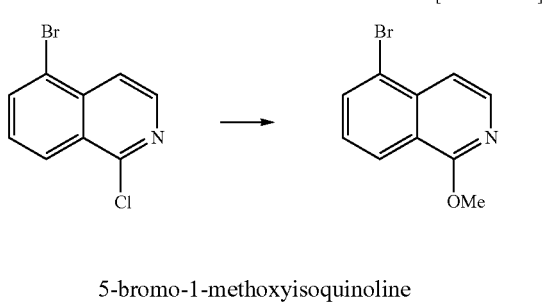

5-bromo-1-methoxyisoquinoline

MS (ESI m/z): 238, 240 (M+H)
RT (min): 1.76

Reference Example 190

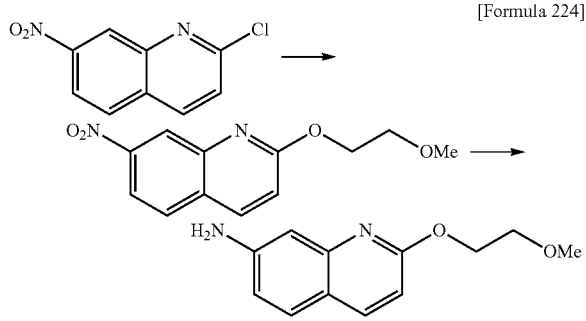

1st Step
Sodium hydride (61% in oil) (4 mg) and methoxyethanol (30 μl) were added to a DMF (1.3 ml) solution containing 2-chloro-7-nitroquinoline (30 mg) under ice cooling, followed by stirring for 0.5 hours. A saturated aqueous ammonium chloride solution was added to the reaction solution and a solid precipitate was collected by filtration.
2nd Step
A methanol (10 ml) solution containing the solid obtained in the 1st step was prepared and subjected to a hydrogenation reaction (60° C.; 50 bar; flow rate: 2 ml/min; 10% Pd/C) using H-cube™. Then, the solvent was distilled away under reduced pressure, and 2-(2-methoxyethoxy)quinolin-7-amine (24 mg) was thus obtained.

MS (ESI m/z): 219 (M+H)
RT (min): 0.64

Reference Example 191

The following compound was obtained as described in Reference Example 190.

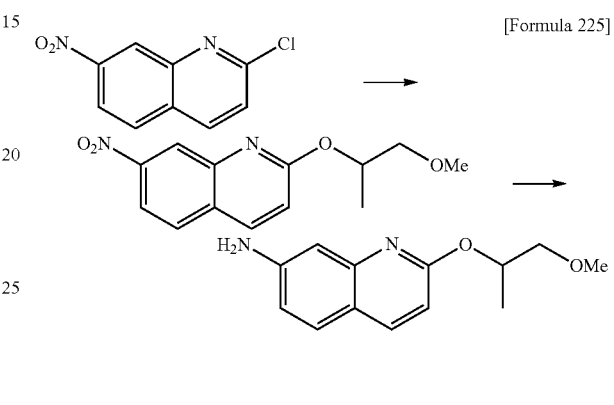

2-((1-methoxypropan-2-yl)oxy)quinolin-7-amine

MS (ESI m/z): 233 (M+H)
RT (min): 0.72

Reference Example 192

The following compound was obtained as described in Reference Example 190.

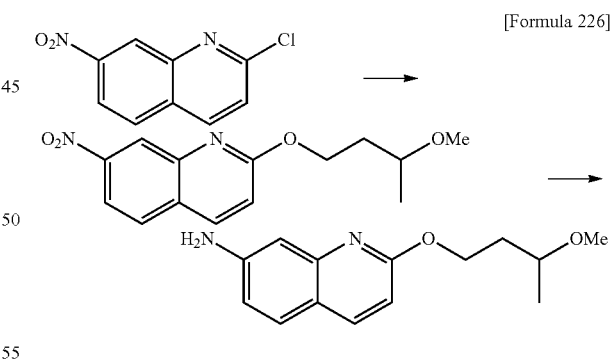

2-(3-methoxybutoxy)-quinolin-7-amine

MS (ESI m/z): 247 (M+H)
RT (min): 0.81

Reference Example 193

The following compound was obtained as described in Reference Example 190.

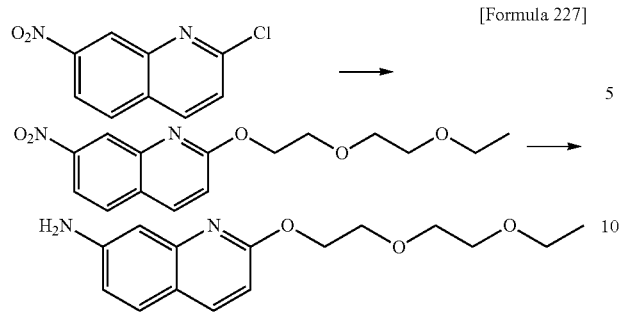

2-(2-(2-ethoxyethoxy)ethoxy)-quinolin-7-amine

MS (ESI m/z): 277 (M+H)
RT (min): 0.79

Reference Example 194

The following compound was obtained as described in Reference Example 190.

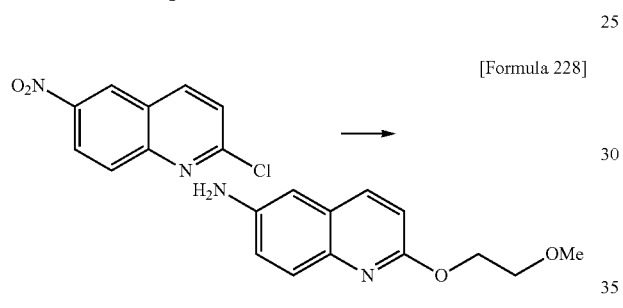

2-(2-methoxyethoxy)quinolin-6-amine

MS (ESI m/z): 219 (M+H)
RT (min): 0.67

Reference Example 195

The following compound was obtained as described in Reference Example 190.

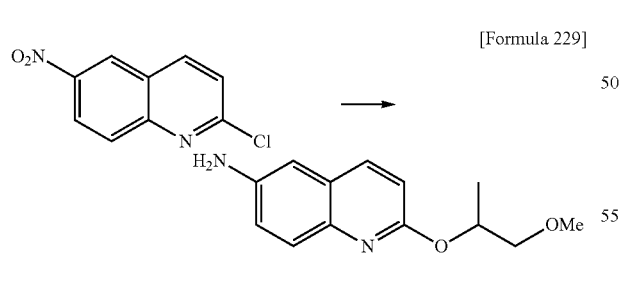

2-((1-methoxypropan-2-yl)oxy)quinolin-6-amine

MS (ESI m/z): 233 (M+H)
RT (min): 0.82

Reference Example 196

The following compound was obtained as described in Reference Example 190.

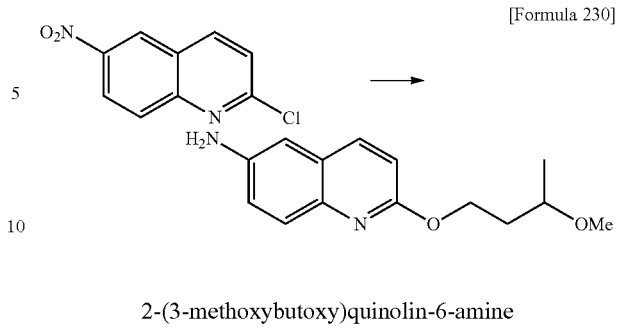

2-(3-methoxybutoxy)quinolin-6-amine

MS (ESI m/z): 247 (M+H)
RT (min): 1.68

Reference Example 197

The following compound was obtained as described in Reference Example 190.

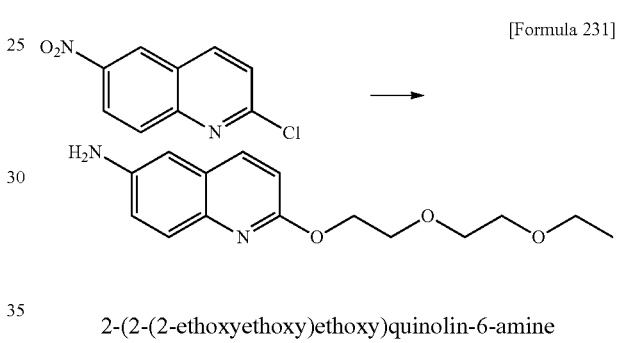

2-(2-(2-ethoxyethoxy)ethoxy)quinolin-6-amine

MS (ESI m/z): 277 (M+H)
RT (min): 0.82

Reference Example 198

The following compound was obtained as described in the 1st step of Reference Example 190.

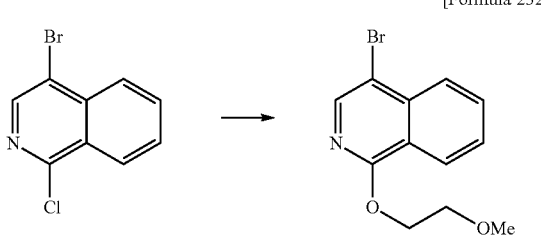

4-bromo-1-(2-methoxyethoxy)isoquinoline

MS (ESI m/z): 282, 284 (M+H)
RT (min): 2.25

Reference Example 199

The following compound was obtained as described in the 1st step of Reference Example 190.

[Formula 233]

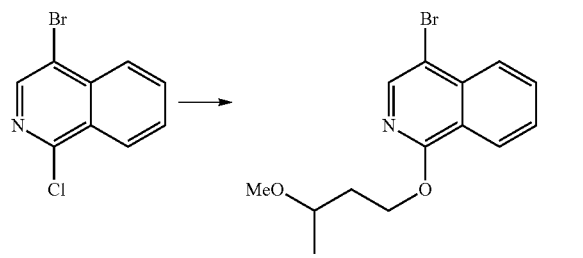

4-bromo-1-(3-methoxybutoxy)isoquinoline

MS (ESI m/z): 310 (M+H)
RT (min): 2.00

Reference Example 200

The following compound was obtained as described in the 1st step of Reference Example 190.

[Formula 234]

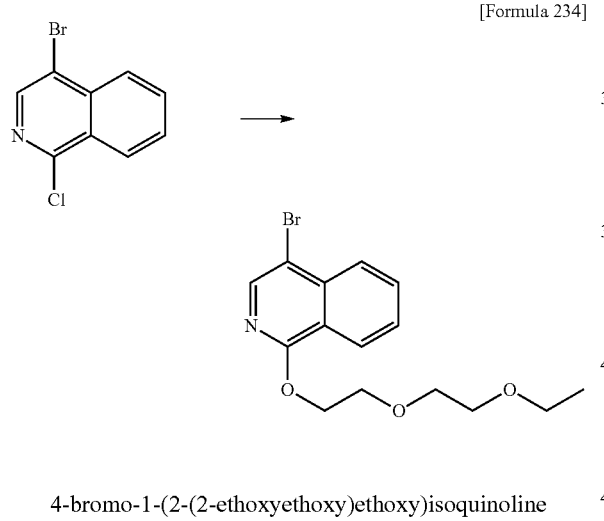

4-bromo-1-(2-(2-ethoxyethoxy)ethoxy)isoquinoline

MS (ESI m/z): 340, 342 (M+H)
RT (min): 1.82

Reference Example 201

The following compound was obtained as described in the 1st step of Reference Example 190.

[Formula 235]

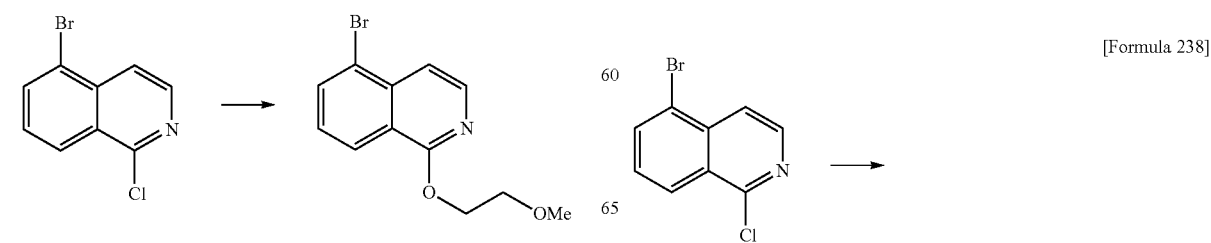

5-bromo-1-(2-methoxyethoxy)isoquinoline

MS (ESI m/z): 282, 284 (M+H)
RT (min): 1.67

Reference Example 202

The following compound was obtained as described in the 1st step of Reference Example 190.

[Formula 236]

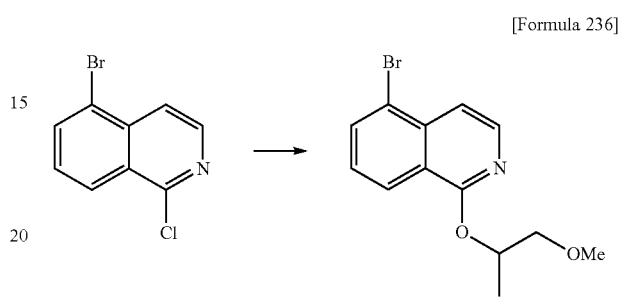

5-bromo-1-(2-methoxypropan-2-yl)oxy)isoquinoline

MS (ESI m/z): 296, 298 (M+H)
RT (min): 1.87

Reference Example 203

The following compound was obtained as described in the 1st step of Reference Example 190.

[Formula 237]

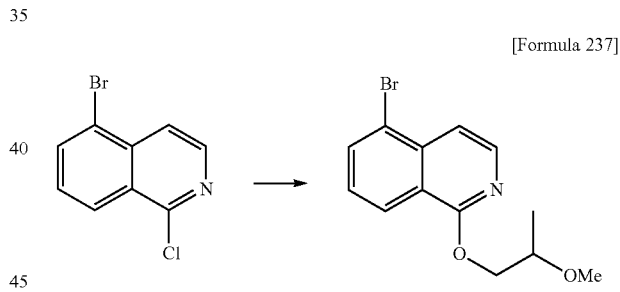

5-bromo-1-(2-methoxypropoxy)isoquinoline

MS (ESI m/z): 209, 210 (M+H)
RT (min): 1.37

Reference Example 204

The following compound was obtained as described in the 1st step of Reference Example 190.

[Formula 238]

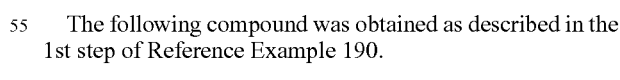

-continued

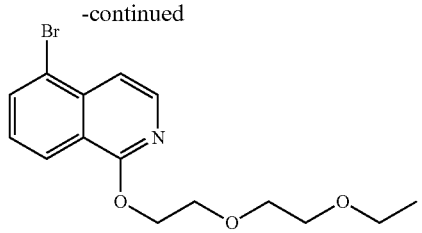

5-bromo-1-(2-(2-ethoxyethoxy)ethoxy)isoquinoline

MS (ESI m/z): 340, 342 (M+H)

Reference Example 205

The following compound was obtained as described in the 1st step of Reference Example 190.

[Formula 239]

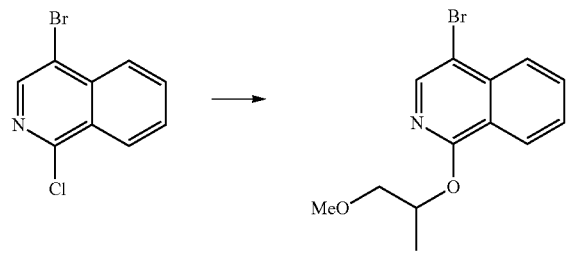

4-bromo-1-((1-methoxypropan-2-yl)oxy)isoquinoline

MS (ESI m/z): 296, 298 (M+H)
RT (min): 1.93

Reference Example 206

The following compound was obtained as described in the 1st step of Reference Example 190.

[Formula 240]

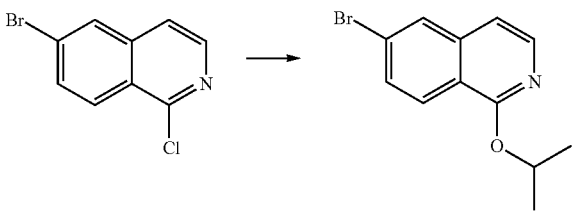

6-bromo-1-isopropoxyisoquinoline

MS (ESI m/z): 266, 268 (M+H)
RT (min): 2.07

Reference Example 207

The following compound was obtained as described in the 1st step of Reference Example 190.

[Formula 241]

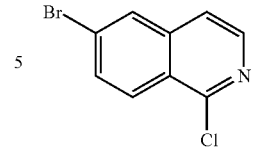

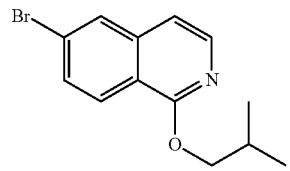

6-bromo-1-isobutoxyisoquinoline

MS (ESI m/z): 280, 282 (M+H)
RT (min): 2.18

Reference Example 208

The following compound was obtained as described in the 1st step of Reference Example 190.

[Formula 242]

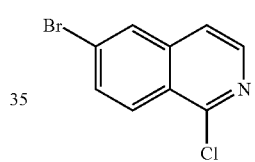

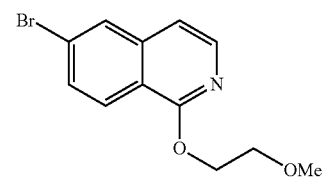

6-bromo-1-(2-methoxyethoxy)isoquinoline

MS (ESI m/z): 282, 284 (M+H)
RT (min): 1.64

Reference Example 209

The following compound was obtained as described in the 1st step of Reference Example 190.

[Formula 243]

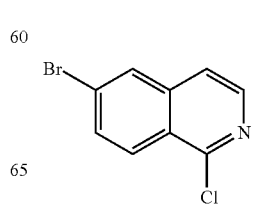

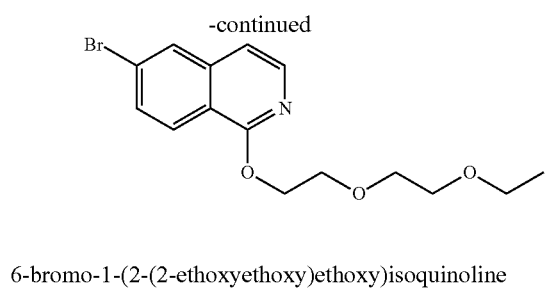

6-bromo-1-(2-(2-ethoxyethoxy)ethoxy)isoquinoline

MS (ESI m/z): 340, 342 (M+H)
RT (min): 1.73

Reference Example 210

The following compound was obtained as described in the 1st step of Reference Example 190.

[Formula 244]

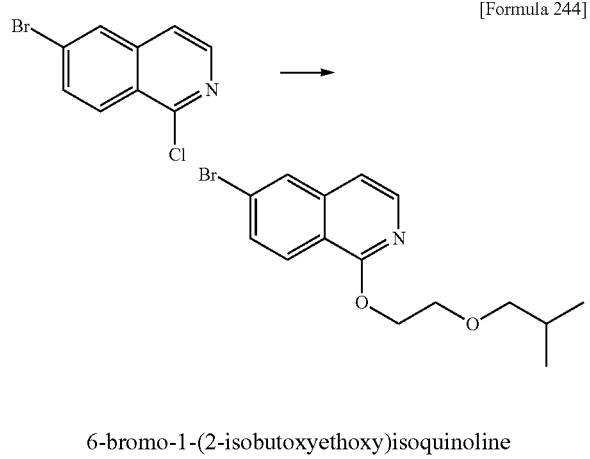

6-bromo-1-(2-isobutoxyethoxy)isoquinoline

MS (ESI m/z): 324, 326 (M+H)
RT (min): 2.11

Reference Example 211

The following compound was obtained as described in the 1st step of Reference Example 190.

[Formula 245]

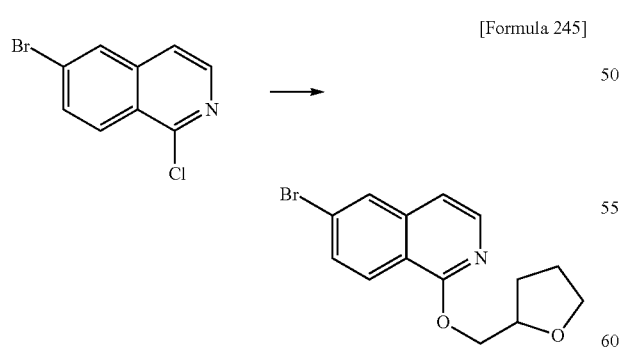

6-bromo-1-((tetrahydrofuran-2-yl)methoxy)isoquinoline

MS (ESI m/z): 308, 310 (M+H)
RT (min): 1.73

Reference Example 212

The following compound was obtained as described in Reference Example 190.

[Formula 246]

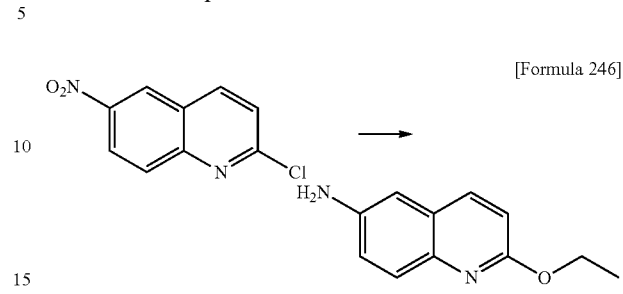

2-ethoxyquinolin-6-amine

MS (ESI m/z): 189 (M+H)
RT (min): 0.77

Reference Example 213

The following compound was obtained as described in Reference Example 190.

[Formula 247]

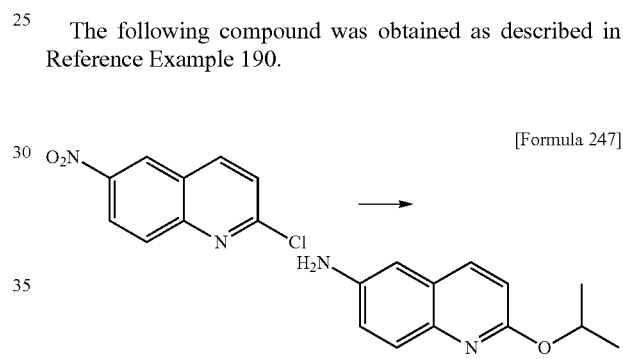

2-isopropoxyquinolin-6-amine

MS (ESI m/z): 203 (M+H)
RT (min): 0.92

Reference Example 214

The following compound was obtained as described in Reference Example 190.

[Formula 248]

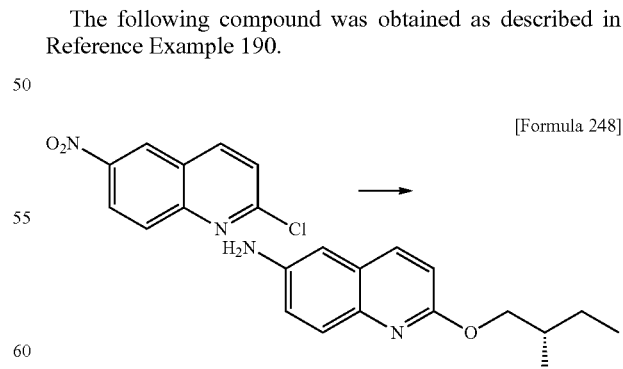

(S)-2-(2-methylbutoxy)quinolin-6-amine

MS (ESI m/z): 231 (M+H)
RT (min): 1.34

Reference Example 215

The following compound was obtained as described in Reference Example 190.

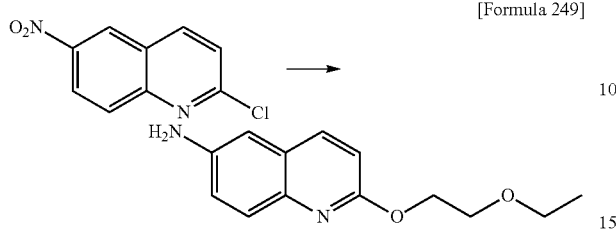

[Formula 249]

2-(2-ethoxyethoxy)quinolin-6-amine

MS (ESI m/z): 233 (M+H)
RT (min): 0.80

Reference Example 216

The following compound was obtained as described in Reference Example 190.

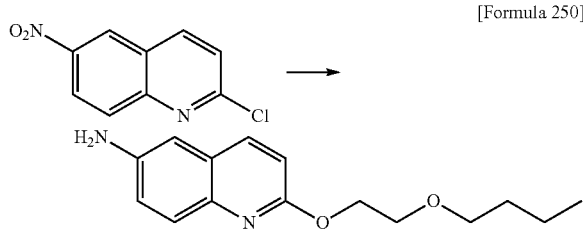

[Formula 250]

2-(2-butoxyethoxy)quinolin-6-amine

MS (ESI m/z): 261 (M+H)
RT (min): 1.19

Reference Example 217

The following compound was obtained as described in Reference Example 190.

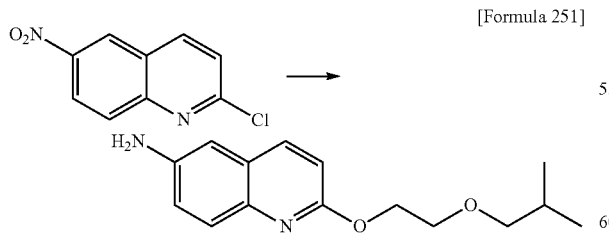

[Formula 251]

2-(2-isobutoxyethoxy)quinolin-6-amine

MS (ESI m/z): 261 (M+H)
RT (min): 1.21

Reference Example 218

The following compound was obtained as described in Reference Example 190.

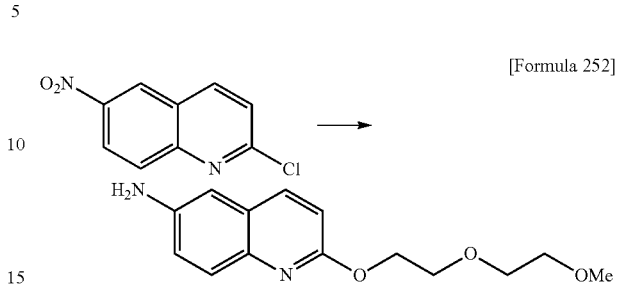

[Formula 252]

2-(2-(2-methoxyethoxy)ethoxy)quinolin-6-amine

MS (ESI m/z): 263 (M+H)
RT (min): 0.70

Reference Example 219

The following compound was obtained as described in Reference Example 190.

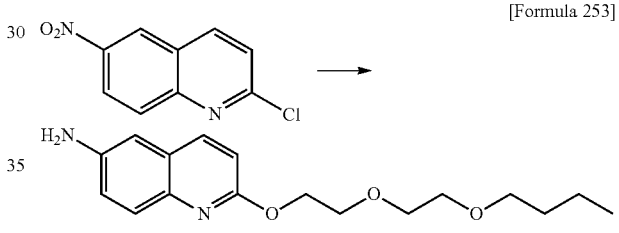

[Formula 253]

2-(2-(2-butoxyethoxy)ethoxy)quinolin-6-amine

MS (ESI m/z): 305 (M+H)
RT (min): 1.17

Reference Example 220

The following compound was obtained as described in Reference Example 190.

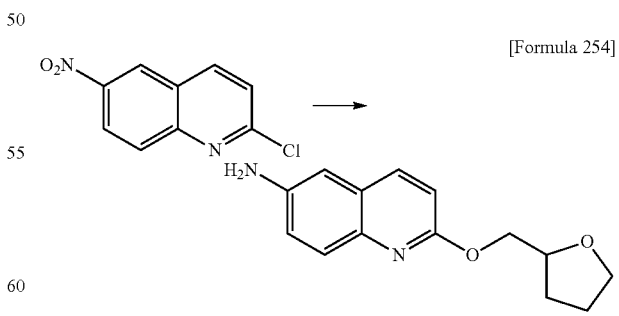

[Formula 254]

2-((tetrahydrofuran-2-yl)methoxy)quinolin-6-amine

MS (ESI m/z): 245 (M+H)
RT (min): 0.78

Reference Example 221

The following compound was obtained as described in Reference Example 190.

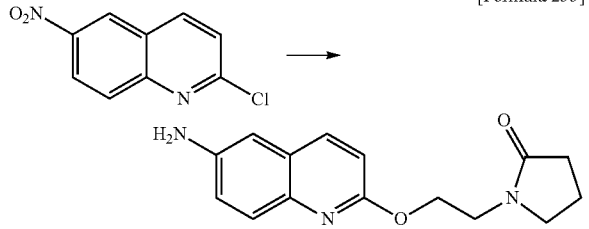

[Formula 255]

1-(2-((6-aminoquinolin-2-yl)oxy)ethyl)pyrrolidin-2-one

MS (ESI m/z): 272 (M+H)
RT (min): 0.64

Reference Example 222

The following compound was obtained as described in Reference Example 190.

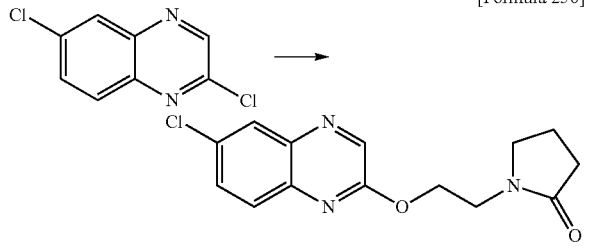

[Formula 256]

1-(2-((6-chloroquinoxalin-2-yl)oxy)ethyl)pyrrolidin-2-one

MS (ESI m/z): 292, 294 (M+H)
RT (min): 1.25

Reference Example 223

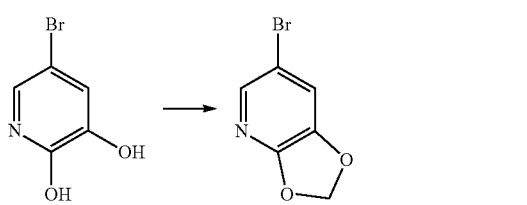

[Formula 257]

Dibromomethane (91 mg) and cesium carbonate (380 mg) were added to a tube containing a DMF (4 ml) solution containing 5-bromopyridin-2,3-diol (100 mg) and the tube was sealed, followed by stirring at 100° C.-110° C. for 8 hours. The reaction solution was adjusted to room temperature, and water was added, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane: ethyl acetate=50:1 to 4:1), and a brown solid of 5-bromo-[1,3]dioxolo[4,5-b]pyridine (13.8 mg) was thus obtained.

MS (ESI m/z): 202, 204 (M+H)
RT (min): 1.09

Reference Example 224

The following compound was obtained as described in Reference Example 223.

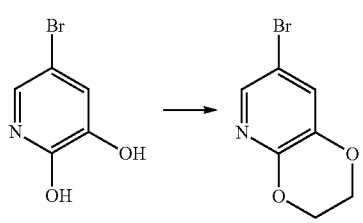

[Formula 258]

7-bromo-2,3-dihydro-[1,4]dioxino[2,3-b]pyridine

MS (ESI m/z): 216, 218 (M+H)
RT (min): 1.08

Reference Example 225

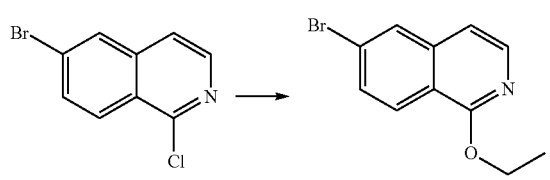

[Formula 259]

Sodium ethoxide (20% ethanol solution, 112 mg) was added to a DMF (0.5 ml) solution containing 6-bromo-1-chloroisoquinoline (40 mg), followed by stirring at room temperature for 2 hours. A saturated aqueous ammonium chloride solution was added to the reaction solution, followed by extraction with ethyl acetate. The resultant was washed with water and dried over anhydrous sodium sulfate. Subsequently, the solvent was distilled away under reduced pressure, the obtained residue was purified by silica gel chromatography, and 6-bromo-1-ethoxyisoquinoline (31 mg) was thus obtained.

MS (ESI m/z): 252, 254 (M+H)
RT (min): 1.91

Reference Example 226

The following compound was obtained with reference to Chem. Abstr. 1960, p. 17397.

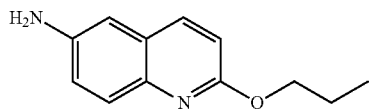

2-propoxyquinolin-6-amine

Reference Example 227

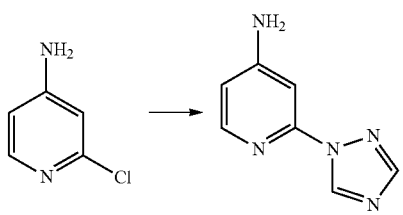

1H-1,2,4-triazole (540 mg), cesium carbonate (1.9 g), trans-N,N'-dimethylcyclohexane-1,2-diamine (74 mg), and copper iodide (50 mg) were added to a tube containing a DMF (5 ml) solution containing 2-chloropyridin-4-amine (500 mg) and the tube was sealed, followed by stirring at 150° C. for 14.5 hours. The reaction solution was adjusted to room temperature, and water was added, followed by extraction with ethyl acetate. The resultant was washed with saturated saline and dried over anhydrous sodium sulfate. Subsequently, the solvent was distilled away under reduced pressure, the obtained residue was purified by silica gel chromatography (chloroform:methanol=1:0 to 10:1), and a brown solid of 2-(1H-1,2,4-triazol-1-yl)pyridin-4-amine (25.8 mg) was thus obtained.

MS (ESI m/z): 162 (M+H)

RT (min): 0.30

$^1$H-NMR (DMSO-d$_6$, 300 MHz) δ:9.20 (s, 1H), 8.21 (s, 1H), 7.92 (d, 1H, J=5.1 Hz), 7.00 (d, 1H, J=1.8 Hz), 6.55 (br, 2H), 6.51 (dd, 1H, J=1.8, 5.1 Hz)

Reference Example 228

The following compound was obtained as described in Reference Example 227.

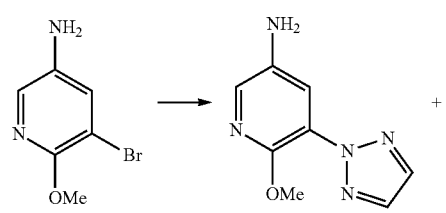

+

6-methoxy-5-(2H-1,2,3-triazol-2-yl)pyridin-3-amine

MS (ESI m/z): 192 (M+H)
RT (min): 0.58
$^1$H-NMR (CDCl$_3$, 300 MHz) δ: 7.87 (s, 2H), 7.77 (d, 1H, J=2.4 Hz), 7.39 (d, 1H, J=2.4 Hz), 3.98 (s, 3H), 3.53 (br, 2H)

6-methoxy-5-(1H-1,2,3-triazol-2-yl)pyridin-3-amine

MS (ESI m/z): 192 (M+H)
RT (min): 0.56
$^1$H-NMR (CDCl$_3$, 300 MHz) δ: 8.36-8.33 (m, 1H), 7.82 (s, 1H), 7.77-7.72 (m, 2H), 3.98 (s, 3H), 3.60 (br, 2H)

Reference Example 229

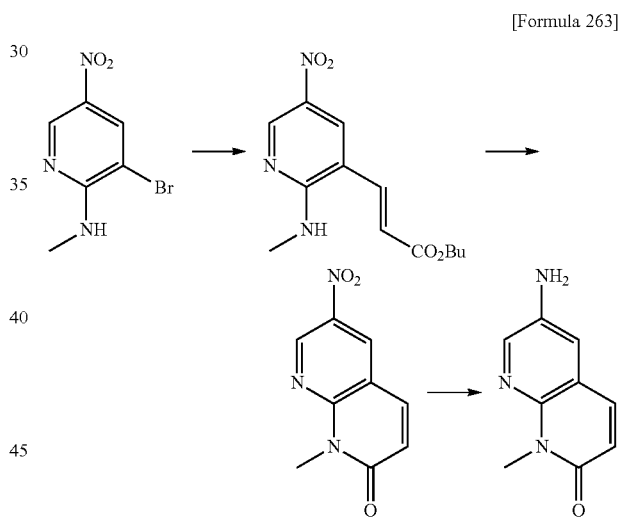

1st Step

Triethylamine (32 μl), n-butyl acrylate (33 μl), tri(o-toluoyl)phosphine (24 mg), and palladium acetate (5 mg) were added to a tube containing a DMF (3 ml) solution containing 3-bromo-N-methyl-5-nitropyridin-2-amine (45 mg) and the tube was sealed, followed by stirring at 100° C. for 8 hours. The reaction solution was adjusted to room temperature, and n-butyl acrylate (33 μl), tri(o-toluoyl)phosphine (24 mg), and palladium acetate (5 mg) were added again to the tube and the tube was sealed, followed by stirring at 100° C. for 9 hours. Further, the reaction solution was adjusted to room temperature, and water was added, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane: ethyl acetate=16:1 to 3:1), and a yellow solid of n-butyl 3-(2-(methylamino)-5-nitropyridin-3-yl)acrylate (44 mg) was thus obtained.

MS (ESI m/z): 280 (M+H), 278 (M–H)
RT (min): 1.62

2nd Step 5M sodium methoxide (methanol solution) (0.5 ml) was added to a methanol solution (2 ml) containing n-butyl 3-(2-(methylamino)-5-nitropyridin-3-yl)acrylate (43 mg) obtained in the 1st step, followed by reflux for 3.5 hours. Water was added to the reaction solution, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane:ethyl acetate=4:1 to 2:1), and a white solid of 1-methyl-6-nitro-1,8-naphthyridin-2(1H)-one (24 mg) was thus obtained.

MS (ESI m/z): 206 (M+H)
RT (min): 0.94

3rd Step

The following compound was obtained as described in the 3rd step of Reference Example 161.

MS (ESI m/z): 176 (M+H)
RT (min): 0.49

Reference Example 230

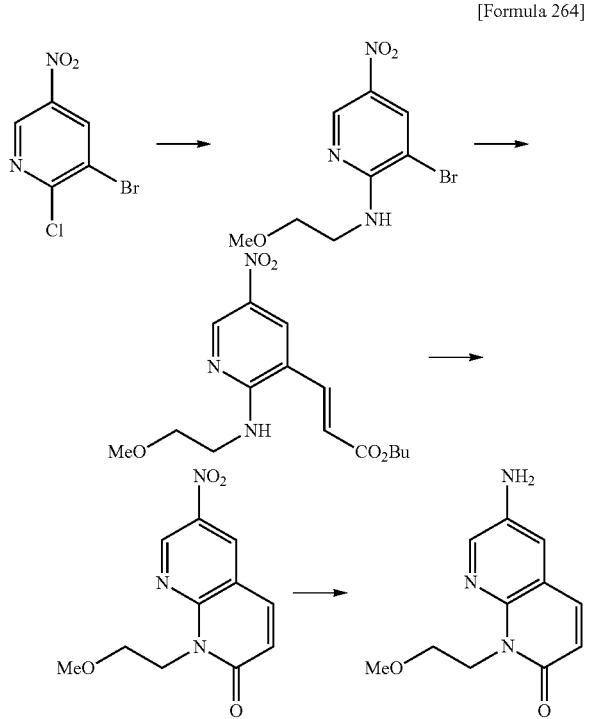

[Formula 264]

1st Step

Triethylamine (53 µl) and 2-methoxyethylamine (23 mg) were added to a tetrahydrofuran (2 ml) solution containing 3-bromo-2-chloro-5-nitropyridine (60 mg), followed by stirring at room temperature for 1 hour. Water was added to the reaction solution, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane:ethyl acetate=6:1 to 3:1), and a light yellow solid of 3-bromo-N-(2-methoxyethyl)-5-nitropyridin-2-amine (93.5 mg) was thus obtained.

MS (ESI m/z): 276, 278 (M+H)
RT (min): 1.30

2nd, 3rd, and 4th steps

The following compounds were obtained as described in the 1st, 2nd, and 3rd steps of Reference Example 229.

Butyl 3-(2-((2-methoxyethyl)amino)-5-nitropyridin-3-yl)acrylate

MS (ESI m/z): 324 (M+H)
RT (min): 1.67

1-(2-methoxyethyl)-6-nitro-1,8-naphthyridin-2(1H)-one

MS (ESI m/z): 250 (M+H)
RT (min): 1.01

6-amino-1-(2-methoxyethyl)-1,8-naphthyridin-2(1H)-one

MS (ESI m/z): 220 (M+H)
RT (min): 0.57

Reference Example 231

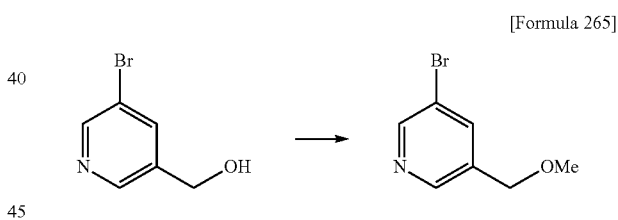

[Formula 265]

Sodium hydride (61% in oil) (11 mg) was added to a DMF (0.9 ml) solution containing (5-bromopyridin-3-yl)methanol (34 mg) under ice cooling, followed by stirring for 1 hour. Then, methyl iodide (17 µl) was added, followed by stirring at room temperature for 13 hours. Thereafter, water was added to the reaction solution, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane:ethyl acetate=4:1 to 1:1), and a light yellow solid of 3-bromo-5-(methoxymethyl)pyridine (26.5 mg) was thus obtained.

MS (ESI, m/z): 202, 204 (M+H)
RT (min): 0.97

Reference Example 232

The following compound was obtained with reference to Journal of the American Chemical Society, 2005, vol. 127, #1, pp. 74-75.

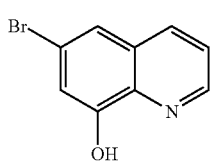

6-bromoquinolin-8-ol

Reference Example 233

The following compound was obtained as described in Reference Example 231.

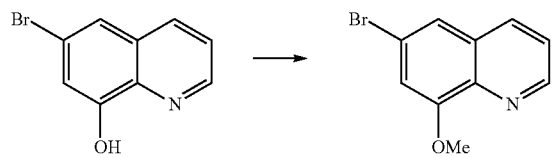

6-bromo-8-methoxyquinoline

MS (ESI m/z): 238, 240 (M+H)
RT (min): 1.68

Reference Example 234

The following compound was obtained as described in Reference Example 231.

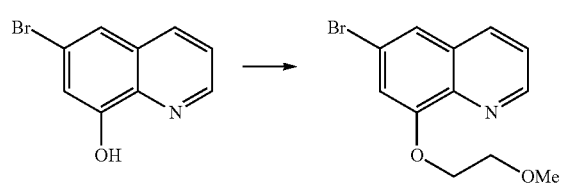

6-bromo-8-(2-methoxyethoxy)quinoline

MS (ESI m/z): 281, 283 (M+H)
RT (min): 0.98

Reference Example 235

The following compound was obtained as described in Reference Example 231.

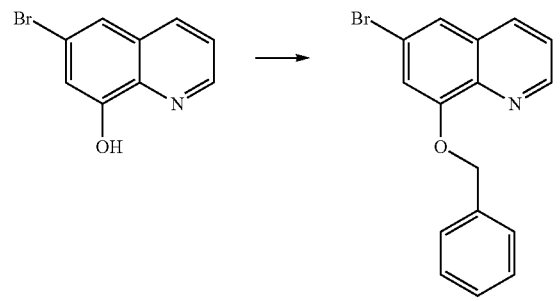

8-(benzyloxy)-6-bromoquinoline

MS (ESI m/z): 314, 316 (M+H)
RT (min): 1.49

Reference Example 236

The following compound was obtained as described in Reference Example 231.

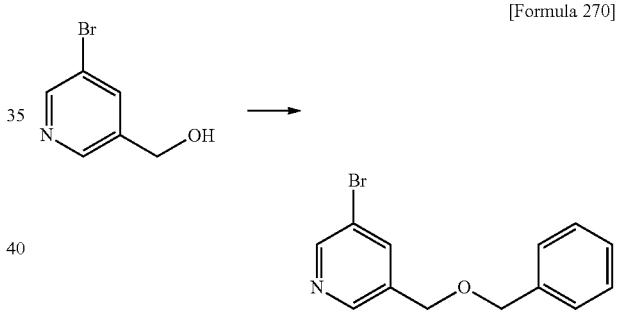

3-((benzyloxy)methyl)-5-bromopyridine

MS (ESI, m/z): 278, 280 (M+H)
RT (min): 1.55

Reference Example 237

The following compound was obtained as described in Reference Example 231.

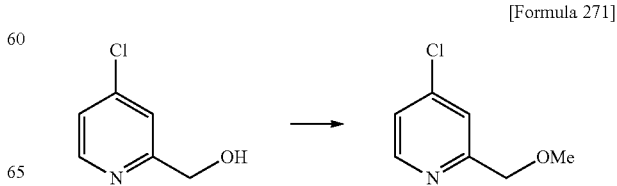

4-chloro-2-(methoxymethyl)pyridine

MS (ESI, m/z): 158, 160 (M+H)
RT (min): 0.84

Reference Example 238

[Formula 272]

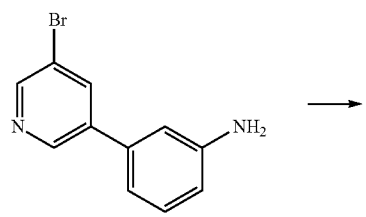

Triethylamine (70 μl) and bis(2-bromoethyl)ether (28 μl) were added to a DMF (2 ml) solution containing 3-(5-bromopyridin-3-yl)aniline (50 mg), followed by stirring at 80° C. for 3.5 hours. Bis(2-bromoethyl)ether (30 μl) was added, followed by stirring at 80° C. for 3 hours. Bis(2-bromoethyl)ether (30 μl) was added again, followed by stirring at 80° C. for 4.5 hours. Water was added to the reaction solution, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane:ethyl acetate=10:1 to 3:1), and colorless oily matter of 4-(3-(5-bromopyridin-3-yl)phenyl)morpholine (12.3 mg) was thus obtained.

MS (ESI m/z): 319, 321 (M+H)
RT (min): 1.47

Reference Example 239

The following compound was obtained as described in Reference Example 238.

[Formula 273]

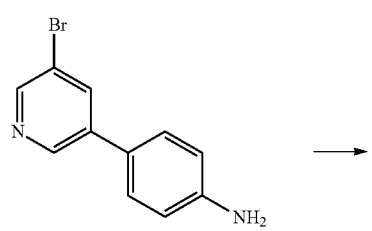

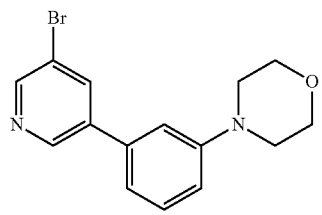

4-(4-(5-bromopyridin-3-yl)phenyl)morpholine

MS (ESI m/z): 319, 321 (M+H)
RT (min): 1.45

Reference Example 240

The following compound was obtained as described in Reference Example 231.

[Formula 274]

tert-Butyl(4-(5-bromopyridin-3-yl)phenyl)methylcarbamate

MS (ESI m/z): 363, 365 (M+H)
RT (min): 1.78

Reference Example 241

[Formula 275]

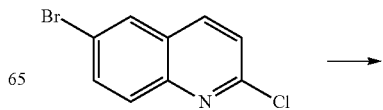

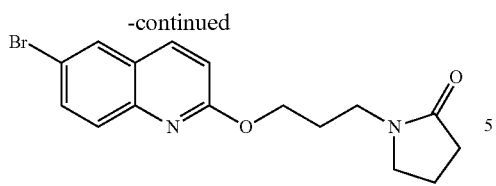

Sodium hydride (61% in oil, 14 mg) and 6-bromo-2-chloroquinoline (80 mg) were added to a DMF (0.5 ml) solution containing 1-(3-hydroxypropyl)-2-pyrrolidone (52 mg) in a nitrogen atmosphere, followed by stirring at room temperature for 6 hours. Water was added to the reaction solution, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane:ethyl acetate=1:0 to 0:1), and 1-(3-((6-bromoquinolin-2-yl)oxy)propyl)pyrrolidin-2-one (46 mg) was thus obtained.

MS (ESI m/z): 349, 351 (M+H)
RT (min): 1.48

Reference Example 242

The following compound was obtained as described in Reference Example 241.

[Formula 276]

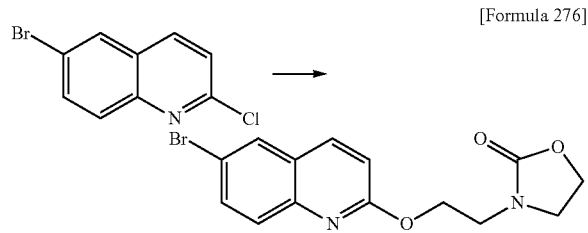

3-(2-(6-bromoquinolin-2-yl)oxy)ethyl)oxazolidin-2-one

MS (ESI m/z): 337, 339 (M+H)
RT (min): 1.42

Reference Example 243

[Formula 277]

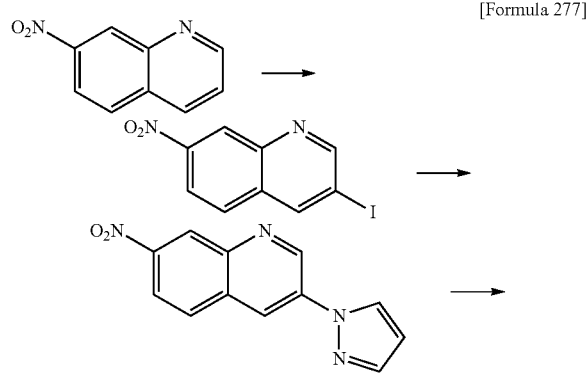

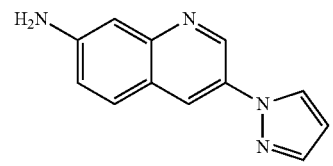

1st Step

An acetic acid (1 ml) solution containing 7-nitroquinoline (93 mg) was prepared, and N-iodosuccinimide (132 mg) was added thereto, followed by stirring at 110° C. for 1.5 hours. N-iodosuccinimide (400 mg) and acetic acid (1 ml) were added again, followed by stirring at 110° C. for 1 hour. Water and a 25% aqueous ammonia solution were added to the reaction solution, an insoluble precipitate was purified by silica gel chromatography (n-hexane:ethyl acetate=1:0 to 4:1), and 3-iodo-7-nitroquinoline (90 mg) was thus obtained.

MS (ESI m/z): 301 (M+H)
RT (min): 1.48

2nd Step

Pyrazole (20 mg), trans-N,N'-dimethylcyclohexane-1,2-diamine (24 μl), copper iodide (14 mg), and cesium carbonate (73 mg) were added to an N,N-dimethylpropyleneurea (2 ml) solution containing 3-iodo-7-nitroquinoline (45 mg), followed by stirring at 70° C. for 2.5 hours in a nitrogen atmosphere. Water was added to the reaction solution, an insoluble precipitate was purified by silica gel chromatography (n-hexane:ethyl acetate=1:0 to 0:1), and a light yellow solid of 7-nitro-3-(1H-pyrazol-1-yl)quinoline (36 mg) was thus obtained.

MS (ESI m/z): 241 (M+H)
RT (min): 1.26

3rd Step

A methanol (10 ml) solution containing 7-nitro-3-(1H-pyrazol-1-yl)quinoline (36 mg) was prepared and subjected to a hydrogenation reaction (80° C.; 50 bar; flow rate: 1 ml/min; 10% Pd/C) using H-cube™. Thereafter, the solvent was distilled away under reduced pressure, and a purple solid of 3-(1H-pyrazol-1-yl)quinolin-7-amine (20 mg) was thus obtained.

MS (ESI m/z): 211 (M+H)
RT (min): 0.61

Reference Example 244

The following compound was obtained as described in the 2nd step of Reference Example 243.

[Formula 278]

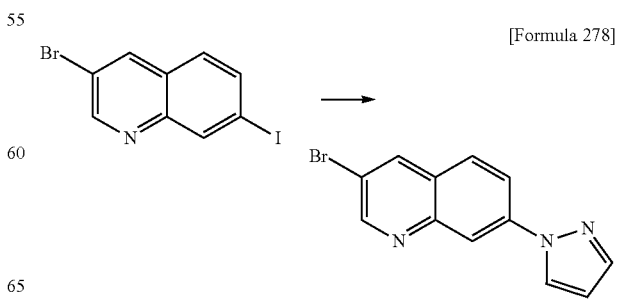

185

3-bromo-7-(1H-pyrazol-1-yl)quinoline

MS (ESI m/z): 274, 276 (M+H)
RT (min): 1.39

Reference Example 245

The following compound was obtained as described in the 3rd step of Reference Example 243.

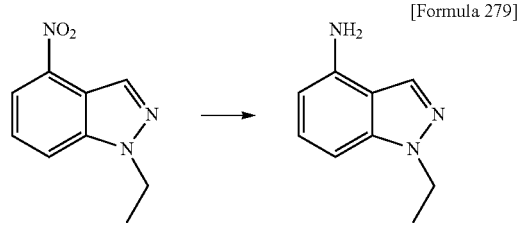

[Formula 279]

1-ethyl-1H-indazol-4-amine

MS (ESI m/z): 162 (M+H)
RT (min): 0.92

Reference Example 246

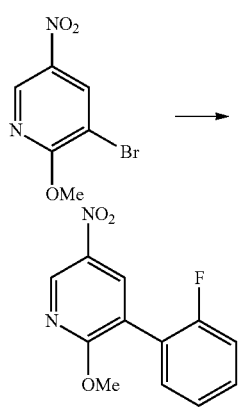

[Formula 280]

1st Step
The following compound was obtained as described in Reference Example 22.

3-(2-fluorophenyl)-2-methoxy-5-nitropyridine

MS (ESI m/z): 249 (M+H)
RT (min): 1.62
2nd Step
The following compound was obtained as described in the 2nd step of Reference Example 161.

5-(2-fluorophenyl)-6-methoxypyridin-3-amine

MS (ESI m/z): 219 (M+H)
RT (min): 0.96

Reference Example 247

The following compounds were obtained as described in Reference Example 246.

186

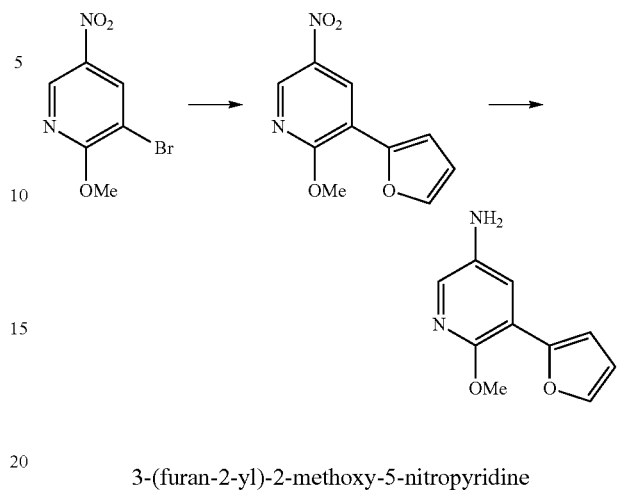

[Formula 281]

3-(furan-2-yl)-2-methoxy-5-nitropyridine

MS (ESI m/z): 221 (M+H)
RT (min): 1.60

5-(furan-2-yl)-6-methoxypyridin-3-amine

MS (ESI m/z): 191 (M+H)
RT (min): 0.85

Reference Example 248

The following compounds were obtained as described in Reference Example 246.

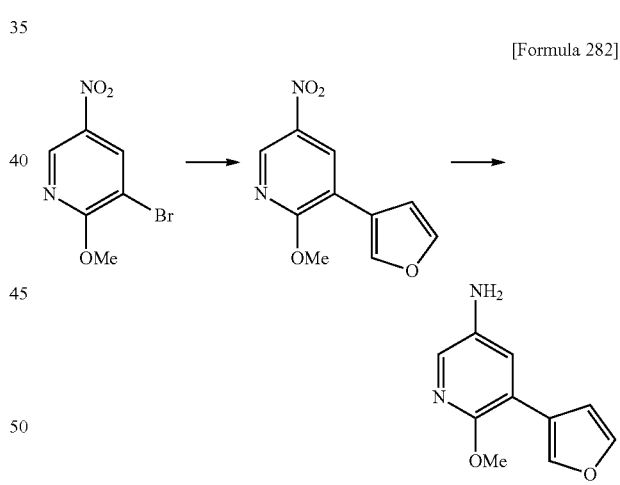

[Formula 282]

3-(furan-3-yl)-2-methoxy-5-nitropyridine

MS (ESI m/z): 221 (M+H)
RT (min): 1.53

5-(furan-3-yl)-6-methoxypyridin-3-amine

MS (ESI m/z): 191 (M+H)
RT (min): 0.85

Reference Example 249

The following compounds were obtained as described in Reference Example 246.

[Formula 283]

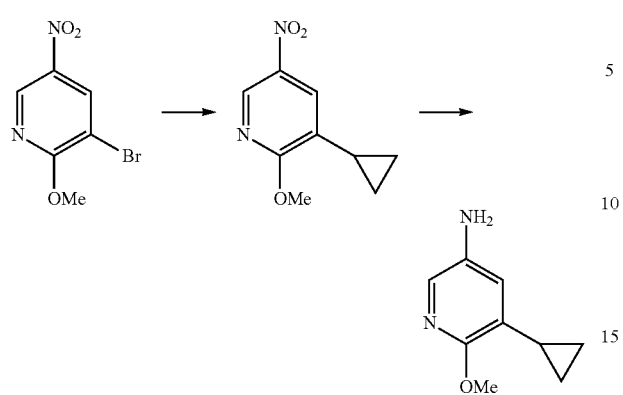

3-cyclopropyl-2-methoxy-5-nitropyridine

MS (ESI m/z): 195 (M+H)
RT (min): 1.53

5-cyclopropyl-6-methoxypyridin-3-amine

MS (ESI m/z): 165 (M+H)
RT (min): 0.67

Reference Example 250

[Formula 284]

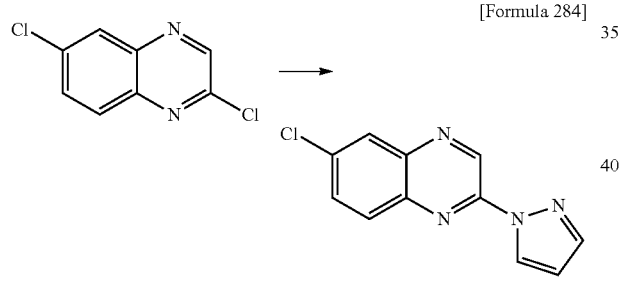

Sodium hydride (61% in oil, 30 mg) and pyrazole (68 mg) were added to a DMF (1 ml) solution containing 2,6-dichloroquinoxaline (100 mg) in a nitrogen atmosphere, followed by stirring at 100° C. for 30 minutes. Water was added to the reaction solution and an insoluble precipitate was collected by filtration, and 6-chloro-2-(1H-pyrazol-1-yl)quinoxaline (109 mg) was thus obtained.
MS (ESI m/z): 230, 232 (M+H)
RT (min): 1.62

Reference Example 251

The following compound was obtained as described in Reference Example 250.

[Formula 285]

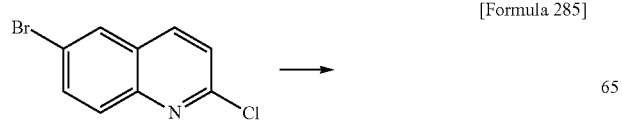

-continued

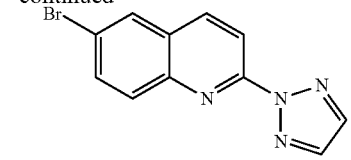

6-bromo-2-(2H-1,2,3-triazol-2-yl)quinoline

MS (ESI m/z): 275, 277 (M+H)
RT (min): 1.49

Reference Example 252

The following compound was obtained as described in Reference Example 250.

[Formula 286]

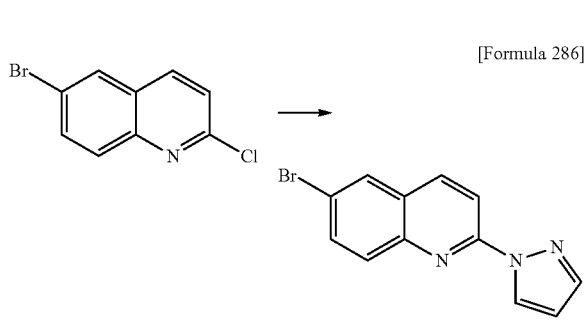

6-bromo-2-(1H-pyrazol-1-yl)quinoline

MS (ESI m/z): 274, 276 (M+H)
RT (min): 1.79

Reference Example 253

[Formula 287]

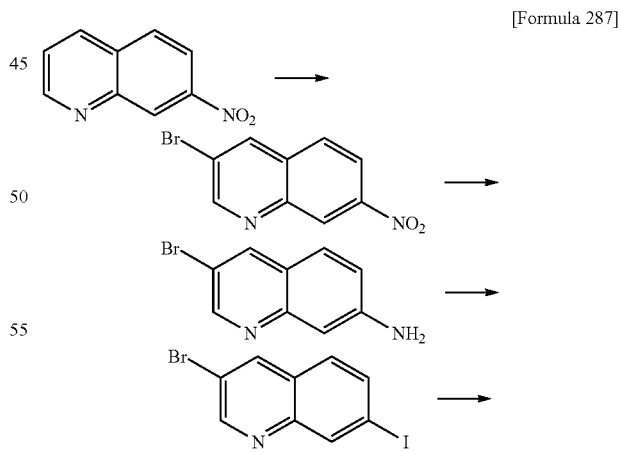

1st and 2nd steps

The following compounds were obtained as described in the 1st and 2nd steps of Reference Example 146.

3-bromo-7-nitroquinoline

MS (ESI m/z): 253, 255 (M+H)
RT (min): 1.42

3-bromoquinolin-7-amine

MS (ESI m/z): 223, 225 (M+H)
RT (min): 0.65

3rd Step

Cesium iodide (564 mg), copper iodide (94 mg), iodine (250 mg), and isoamyl nitrate (1.23 ml) were added to a 1,2-dimethoxyethane (5.6 ml) solution containing 3-bromoquinolin-7-amine (440 mg), followed by stirring at 65° C. for 1 hour. A saturated aqueous sodium hydrogen carbonate solution was added to the reaction solution, followed by extraction with ethyl acetate (×2). The resultant was washed with saturated saline and dried over anhydrous sodium sulfate. The solvent was distilled away under reduced pressure, the obtained residue was purified by silica gel chromatography (n-hexane:ethyl acetate=1:0 to 10:1), and 3-bromo-7-iodoquinoline (440 mg) was thus obtained.

MS (ESI m/z): 334, 336 (M+H)
RT (min): 1.75

4th Step

The following compound was obtained as described in the 2nd step of Reference Example 243.

3-bromo-7-(2H-1,2,3-triazol-2-yl)quinoline

MS (ESI m/z): 275, 277 (M+H)
RT (min): 1.50

Reference Example 254

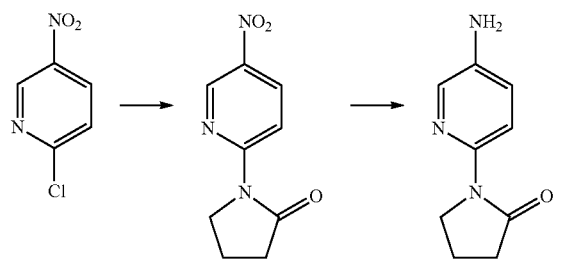

[Formula 288]

1st step

Pyrrolidin-2-one (129 mg), cesium carbonate (412 mg), Pd$_2$(dba)$_3$ (116 mg), and Xantphos (146 mg) were added to a 1,4-dioxane (10 ml) solution containing 2-chloro-5-nitropyridine (200 mg) in a nitrogen atmosphere, followed by stirring at 100° C. for 5 hour. Water was added to the reaction solution, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane:ethyl acetate=4:1 to 2:1), and a light red solid of 1-(5-nitropyridin-2-yl)pyrrolidin-2-one (261 mg) was thus obtained.

$^1$H-NMR (CDCl$_3$, 300 MHz) δ:9.23-9.20 (m, 1H), 8.67-8.62 (m, 1H), 8.46 (dd, 1H, J=2.8, 9.4 Hz), 4.17 (t, 2H, J=7.3 Hz), 2.73 (t, 2H, J=8.3 Hz), 2.26-2.13 (m, 2H)

2nd Step

A methanol (20 ml) solution containing 1-(5-nitropyridin-2-yl)pyrrolidin-2-one (31 mg) was prepared and subjected to a hydrogenation reaction (30° C.; 1 bar; flow rate: 1 ml/min; 10% Pd/C) using H-cube™. Then, the solvent was distilled away under reduced pressure, and a purple solid of 1-(5-aminopyridin-2-yl)pyrrolidin-2-one (29 mg) was thus obtained.

MS (ESI m/z): 178 (M+H)
RT (min): 0.38

Reference Example 255

The following compounds were obtained as described in Reference Example 254.

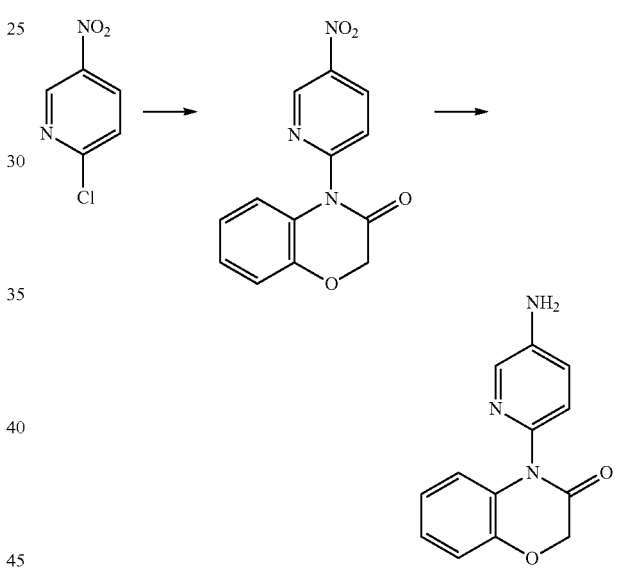

[Formula 289]

4-(5-nitropyridin-2-yl)-2H-benzo[b][1,4]oxazin-3(4H)-one $^1$H-NMR (CDCl$_3$, 300 MHz) δ:9.46-9.43 (m, 1H), 8.68 (dd, 1H, J=2.8, 8.8 Hz), 7.79-7.74 (m, 1H), 7.15-7.07 (m, 2H), 6.99-6.91 (m, 1H), 6.64-6.58 (m, 1H), 4.77 (s, 2H)

4-(5-aminopyridin-2-yl)-2H-benzo[b][1,4]oxazin-3(4H)-one

MS (ESI m/z): 242 (M+H)
RT (min): 0.88

Reference Example 256

The following compounds were obtained as described in Reference Example 254.

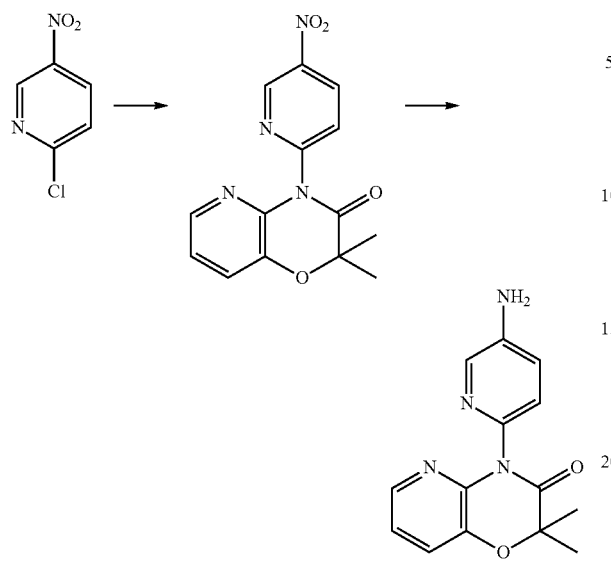

2,2-dimethyl-4-(5-nitropyridin-2-yl)-2H-pyrido[3,2-b][1,4]oxazin-3(4H)-one $^1$H-NMR (CDCl$_3$, 300 MHz) δ:9.49 (d, 1H, J=2.6 Hz), 8.67 (dd, 1H, J=3.0, 8.6 Hz), 7.96 (dd, 1H, J=1.7, 5.0 Hz), 7.57 (d, 1H, J=8.6 Hz), 7.02 (dd, 1H, J=5.0, 7.9 Hz), 1.66 (s, 6H)

4-(5-aminopyridin-2-yl)-2,2-dimethyl-2H-pyrido[3,2-b][1,4]oxazin-3(4H)-one

MS (ESI m/z): 271 (M+H)
RT (min): 0.85

Reference Example 257

The following compounds were obtained as described in Reference Example 254.

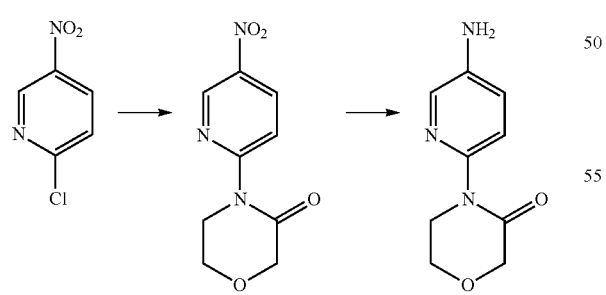

4-(5-nitropyridin-2-yl)morpholin-3-one $^1$H-NMR (CDCl$_3$, 300 MHz) δ:9.27-9.24 (m, 1H), 8.60-8.54 (m, 1H), 8.48 (dd, 1H, J=2.6, 9.2 Hz), 4.41 (s, 2H), 4.23-4.15 (m, 2H), 4.12-4.04 (m, 2H)

4-(5-aminopyridin-2-yl)morpholin-3-one

MS (ESI, m/z): 194 (M+H)
RT (min): 0.38

Reference Example 258

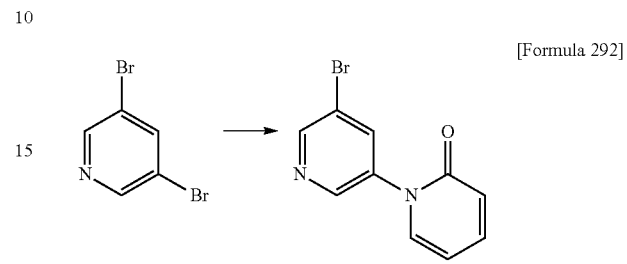

Pyridin-1-ol (96 mg), cesium carbonate (412 mg), and copper iodide (50 mg) were added to a tube containing a DMF (4 ml) solution containing 3,5-dibromopyridine (200 mg) and the tube was sealed in a nitrogen atmosphere, followed by stirring at 120° C. for 11 hours. Water was added to the reaction solution, followed by extraction with ethyl acetate. The resultant was washed with saturated saline and dried over anhydrous sodium sulfate, and the solvent was distilled away under reduced pressure. The obtained residue was purified by silica gel chromatography (n-hexane:ethyl acetate=1:5 to 1:1), and a brown solid of 5'-bromo-2H-[1,3'-bipyridine]-2-one (25.8 mg) was thus obtained.

MS (ESI m/z): 251, 253 (M+H)
RT (min): 0.76

Reference Example 259

The following compound was obtained with reference to Roczniki Chemii, 1967, vol. 41, #2, p. 279.

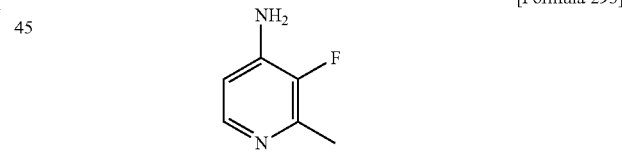

3-fluoro-2-methylpyridin-4-amine

Reference Example 260

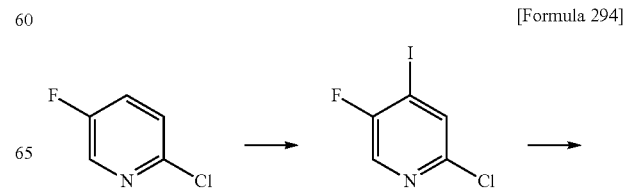

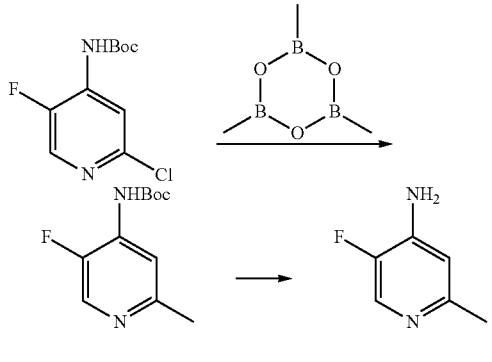

1st Step

A tetrahydrofuran (5 ml) solution containing 2-chloro-5-fluoropyridine (500 mg) was added to a tetrahydrofuran (20 ml) solution containing lithium-N,N-diisopropylamide (2M tetrahydrofuran/ethylbenzene/heptane solution) (2.9 ml) at −75° C. in a nitrogen atmosphere, followed by stirring at −75° C. for 3 hours. Subsequently, a tetrahydrofuran (5 ml) solution containing iodine (1.16 g) was added, followed by stirring at −75° C. for 1 hour. Then, water/tetrahydrofuran (2 ml/8 ml), water (10 ml), and 3M aqueous sodium thiosulfate were slowly added at −75° C., −50° C., and −35° C., respectively, to the reaction solution. The reaction solution was adjusted to room temperature, followed by extraction with ethyl acetate. The resultant was washed with saturated saline and dried over anhydrous sodium sulfate. Thereafter, the solvent was distilled away under reduced pressure, the obtained residue was purified by silica gel chromatography (n-hexane:ethyl acetate=20:1 to 10:1), and a white solid of 2-chloro-5-fluoro-4-iodopyridine (457 mg) was thus obtained.

$^1$H-NMR (CDCl$_3$, 300 MHz) δ:8.14 (s, 1H), 7.77 (d, 1H, J=4.3 Hz)

2nd Step

The following compound was obtained as described in Reference Example 124.

tert-Butyl(2-chloro-5-fluoropyridin-4-yl)carbamate

MS (ESI m/z): 247, 249 (M+H)
RT (min): 1.51

3rd Step

The following compound was obtained as described in Reference Example 22.

tert-Butyl(5-fluoro-2-methylpyridin-4-yl)carbamate

MS (ESI m/z): 227 (M+H)
RT (min): 0.79

4th Step

TFA (2 ml) was added to tert-butyl(5-fluoro-2-methylpyridin-4-yl)carbamate (20 mg) obtained in the 3rd step, followed by stirring at room temperature for 1 hour. The solvent was distilled away under reduced pressure, toluene was added for azeotropic boiling (×2), and 5-fluoro-2-methylpyridin-4-amine (32 mg) was thus obtained.

MS (ESI m/z): 127 (M+H)
RT (min): 0.23

Reference Example 261

The following compounds were obtained as described in Reference Example 124 and the 4th step of Reference Example 260.

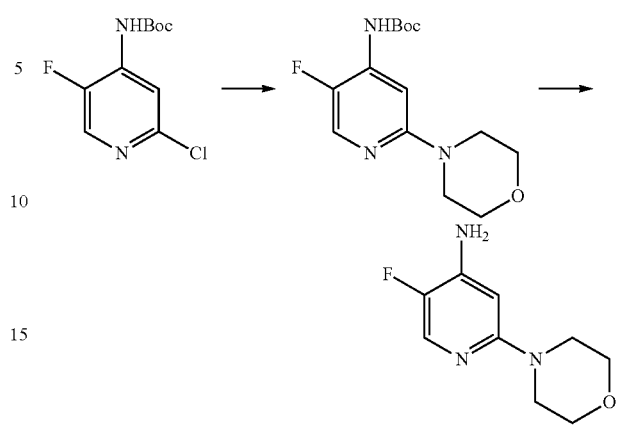

tert-Butyl(5-fluoro-2-morpholinopyridin-4-yl)carbamate

MS (ESI m/z): 298 (M+H)
RT (min): 1.08

5-fluoro-2-morpholinopyridin-4-amine

MS (ESI m/z): 198 (M+H)
RT (min): 0.40

Reference Example 262

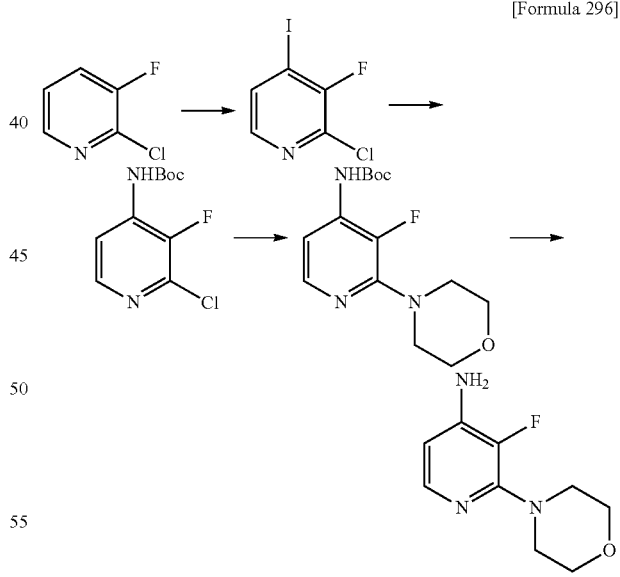

1st and 2nd steps

The following compounds were obtained as described in the 1st and 2nd steps of Reference Example 260

2-chloro-3-fluoro-4-iodopyridine $^1$H-NMR (CDCl$_3$, 300 MHz) δ:7.87 (d, 1H, J=5.3 Hz), 7.66 (dd, 1H, J=4.0, 5.0 Hz) tert-Butyl(2-chloro-3-fluoropyridin-4-yl)carbamate MS (ESI m/z): 247, 249 (M+H)
RT (min): 1.46
3rd Step
The following compound was obtained as described in Reference Example 124.

tert-Butyl(3-fluoro-2-morpholinopyridin-4-yl)carbamate

MS (ESI m/z): 298 (M+H)
RT (min): 1.21
4th Step
The following compound was obtained as described in the 4th step of Reference Example 260.

3-fluoro-2-morpholinopyridin-4-amine

MS (ESI m/z): 198 (M+H)
RT (min): 0.43

Reference Example 263

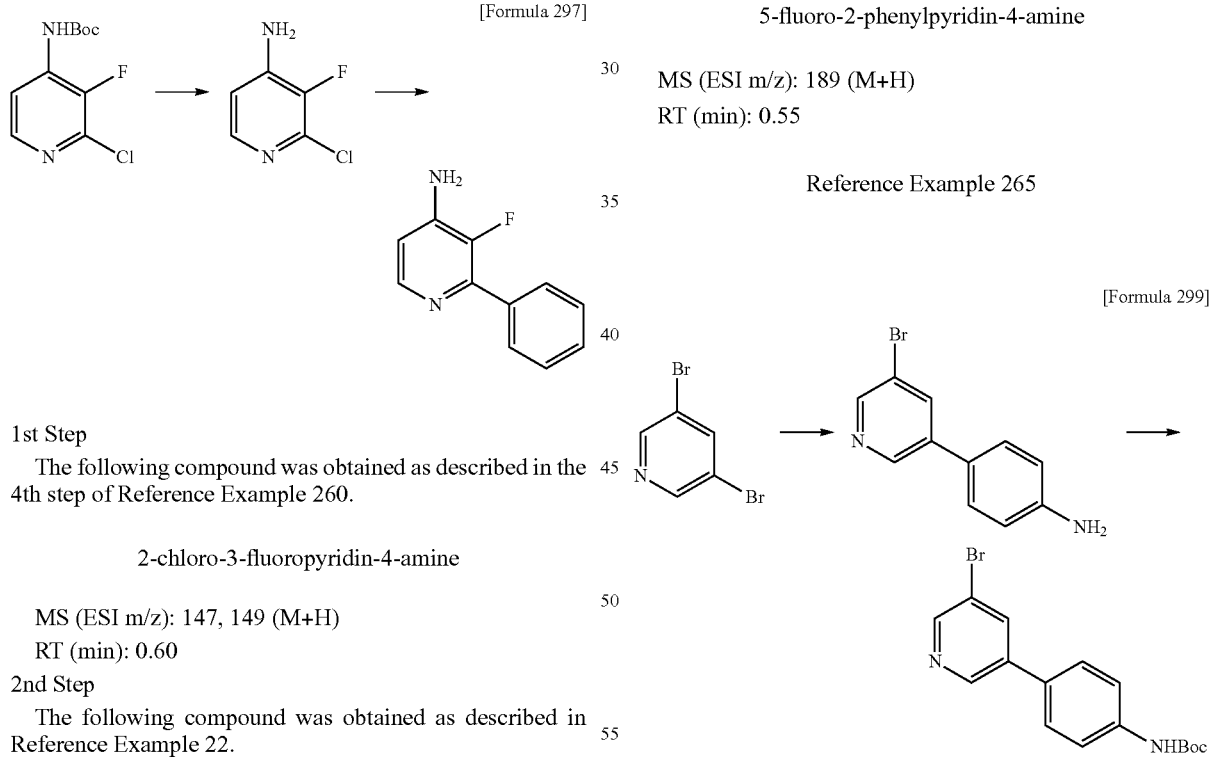

[Formula 297]

1st Step
The following compound was obtained as described in the 4th step of Reference Example 260.

2-chloro-3-fluoropyridin-4-amine

MS (ESI m/z): 147, 149 (M+H)
RT (min): 0.60
2nd Step
The following compound was obtained as described in Reference Example 22.

3-fluoro-2-phenylpyridin-4-amine

MS (ESI m/z): 189 (M+H)
RT (min): 0.61

Reference Example 264

The following compounds were obtained as described in Reference Example 263.

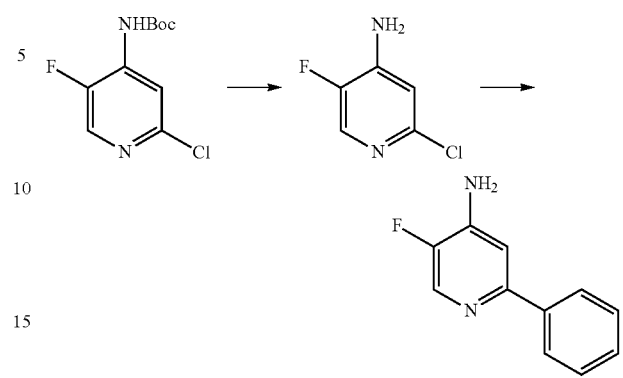

[Formula 298]

2-chloro-5-fluoropyridin-4-amine

MS (ESI m/z): 147, 149 (M+H)
RT (min): 0.56

5-fluoro-2-phenylpyridin-4-amine

MS (ESI m/z): 189 (M+H)
RT (min): 0.55

Reference Example 265

[Formula 299]

1st Step
The following compound was obtained as described in Reference Example 22.

4-(5-bromopyridin-3-yl)-aniline

MS (ESI m/z): 249, 251 (M+H)
RT (min): 1.02

2nd Step

The following compound was obtained as described in the 2nd step of Reference Example 2.

tert-Butyl (4-(5-bromopyridin-3-yl)phenyl)carbamate

MS (ESI m/z): 349, 351 (M+H)

RT (min): 1.71

Reference Example 266

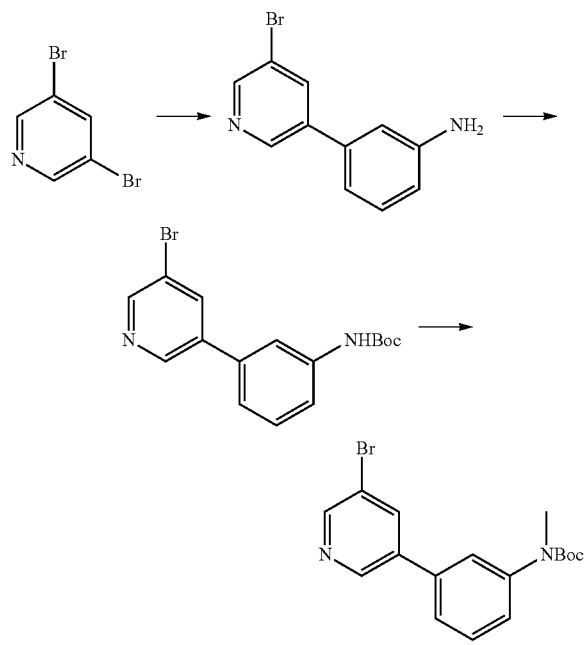

[Formula 300]

1st Step

The following compound was obtained as described in Reference Example 22.

3-(5-bromopyridin-3-yl)aniline

MS (ESI m/z): 249, 251 (M+H)

RT (min): 1.00

2nd Step

The following compound was obtained as described in the 2nd step of Reference Example 2.

tert-Butyl(3-(5-bromopyridin-3-yl)phenyl)carbamate

MS (ESI m/z): 349, 351 (M+H)

RT (min): 1.72

3rd Step

The following compound was obtained as described in Reference Example 231.

tert-Butyl(3-(5-bromopyridin-3-yl)phenyl)(methyl)carbamate

MS (ESI m/z): 363, 365 (M+H)

RT (min): 1.77

Reference Example 268

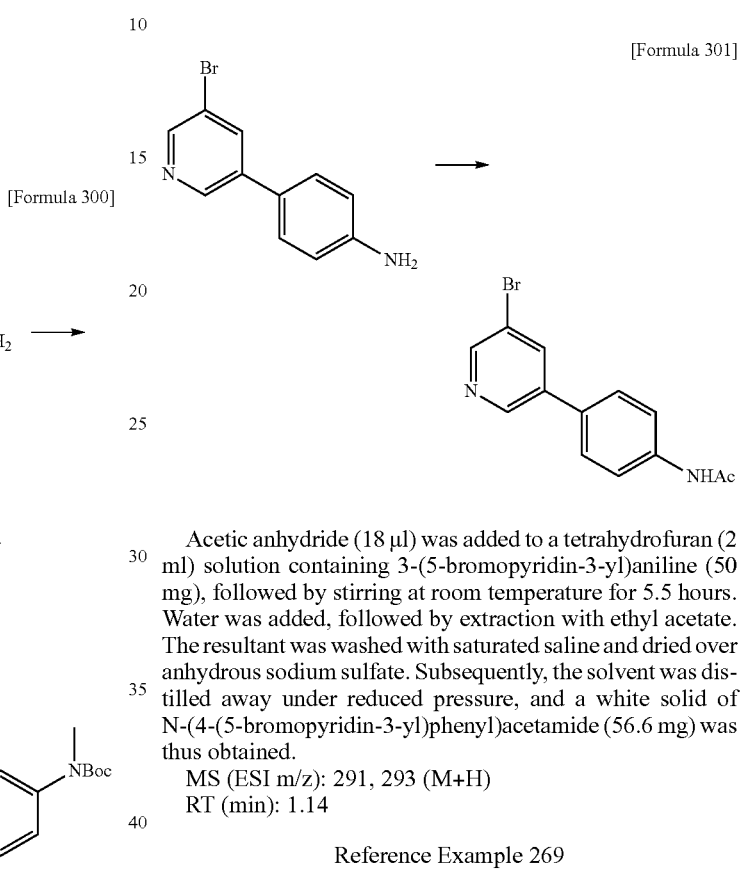

[Formula 301]

Acetic anhydride (18 μl) was added to a tetrahydrofuran (2 ml) solution containing 3-(5-bromopyridin-3-yl)aniline (50 mg), followed by stirring at room temperature for 5.5 hours. Water was added, followed by extraction with ethyl acetate. The resultant was washed with saturated saline and dried over anhydrous sodium sulfate. Subsequently, the solvent was distilled away under reduced pressure, and a white solid of N-(4-(5-bromopyridin-3-yl)phenyl)acetamide (56.6 mg) was thus obtained.

MS (ESI m/z): 291, 293 (M+H)

RT (min): 1.14

Reference Example 269

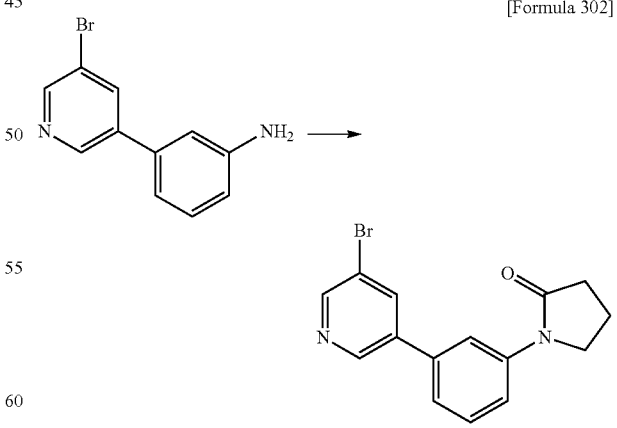

[Formula 302]

Triethylamine (70 μl) and 4-chlorobutyryl chloride (25 μl) were added to a tetrahydrofuran (2 ml) solution containing 3-(5-bromopyridin-3-yl)aniline (50 mg), followed by stirring at room temperature for 3.5 hours. Subsequently, sodium hydride (61% in oil, 12 mg) was added, followed by stirring for 3 hours. Sodium hydride (61% in oil, 12 mg) was again added, followed by stirring for 2 hours. Water was added, followed by extraction with ethyl acetate. The resultant was washed with saturated saline and dried over anhydrous sodium sulfate. Then, the solvent was distilled away under reduced pressure, the obtained residue was purified by silica gel chromatography (n-hexane:ethyl acetate=10:1 to 3:1), and colorless oily matter of 1-(3-(5-bromopyridin-3-yl)phenyl)pyrrolidin-2-one (12.3 mg) was thus obtained.

MS (ESI m/z): 317, 319 (M+H)
RT (min): 1.28

Reference Example 270

The following compound was obtained as described in Reference Example 269.

Potassium carbonate (83 mg) and methyl iodide (62 W) were added to an N,N-dimethylacetamide (1 ml) solution containing 3-(5-bromopyridin-3-yl)aniline (50 mg), followed by stirring at 80° C. for 4 hours. Water was added, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane:ethyl acetate=10:1 to 3:1), and a white solid of 3-(5-bromopyridin-3-yl)-N,N-dimethylaniline (7.1 mg) was thus obtained.

MS (ESI m/z): 277, 279 (M+H)
RT (min): 1.45

Reference Example 272

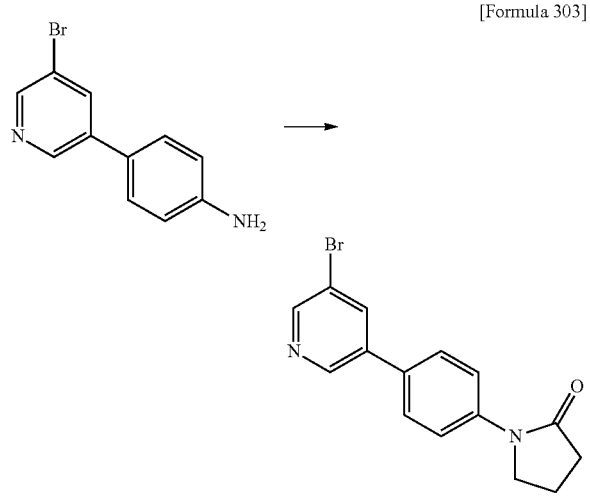

[Formula 303]

1-(4-(5-bromopyridin-3-yl)phenyl)pyrrolidin-2-one

MS (ESI m/z): 317, 319 (M+H)
RT (min): 1.28

Reference Example 271

[Formula 305]

N-bromosuccinimide (141 mg) was added to a DMF (3 ml) solution containing 2-morpholinonicotinonitrile (100 mg), followed by stirring at 80° C. for 5 hours. The reaction solution was adjusted to room temperature. Then, aqueous saturated sodium thiosulfate solution was added, followed by extraction with ethyl acetate. The organic layer was washed with saturated saline and dried over anhydrous sodium sulfate, and then the solvent was distilled away under reduced pressure. The obtained residue was purified by silica gel chromatography (n-hexane:ethyl acetate=10:1 to 7:3), and a light yellow solid of 5-bromo-2-morpholinonicotinonitrile (120 mg) was thus obtained.

MS (ESI m/z): 268, 270 (M+H)
RT (min): 1.37

Reference Example 273

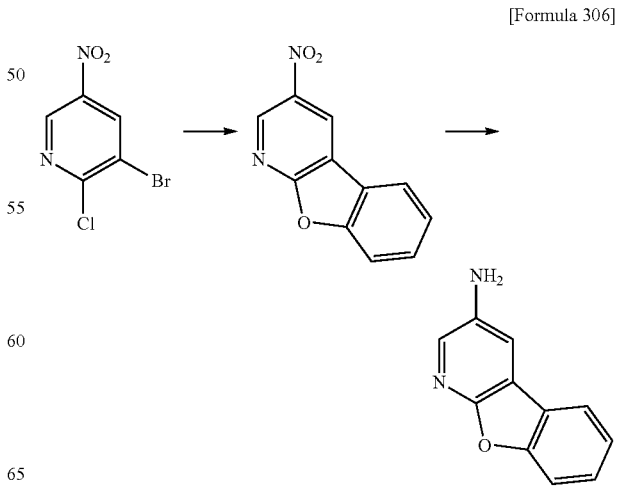

[Formula 304]

[Formula 306]

1st Step

Potassium carbonate (87 mg) and phenol (47 mg) were added to an N,N-dimethylacetamide (1 ml) solution containing 3-bromo-2-chloro-5-nitropyridine (100 mg), followed by stirring at 70° C. for 3 hours. Acetic acid palladium (20 mg) was added in a nitrogen atmosphere, followed by stirring at 100° C. for 3.5 hours. Water was added, followed by extraction with ethyl acetate. The resultant was washed with saturated saline and dried over anhydrous sodium sulfate. Subsequently, the solvent was distilled away under reduced pressure, hexane and ethyl acetate were added to the obtained residue, an insoluble precipitate was collected by filtration, and a light yellow solid of 3-nitrobenzofuro[2,3-b]pyridine (47.1 mg) was thus obtained.

MS (ESI m/z): 215 (M+H)
RT (min): 1.48

2nd Step

The following compound was obtained as described in the 2nd step of Reference Example 166.
Benzofuro[2,3-b]pyridin-3-amine
MS (ESI m/z): 185 (M+H)
RT (min): 0.94

Reference Example 274

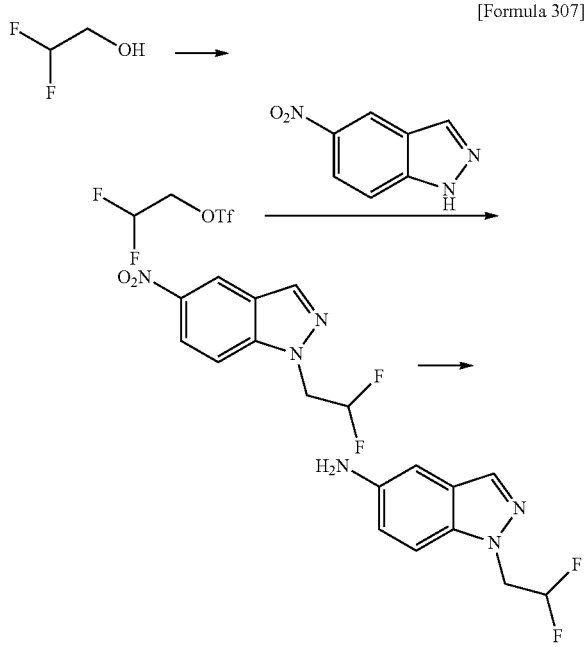

[Formula 307]

1st Step

A dichloromethane (10 ml) solution containing 2,2-difluoroethanol (5.0 g) and triethylamine (8.44 ml) was slowly added to a dichloromethane (10 ml) solution containing trifluoromethanesulfonic anhydride (10.2 ml) at −78° C. in a nitrogen atmosphere, followed by stirring for 45 minutes. The solvent was distilled away under reduced pressure, and colorless oily matter of 2,2-difluoroethyl trifluoromethane sulfonate (9.04 g) was thus obtained.

2nd Step

Calcium carbonate (517 mg) was added to a 1,4-dioxane (2.5 ml) solution containing 2,2-difluoroethyl trifluoromethane sulfonate (642 mg) obtained in the 1st step and 5-nitroindazole (407 mg) at room temperature in a nitrogen atmosphere, followed by stirring at 100° C. for 3 hours. Ethyl acetate was added, insoluble matter was removed, and the solvent was distilled away under reduced pressure. The obtained residue was purified by silica gel chromatography (n-hexane:ethyl acetate=5:1 to 1:1). Further, hexane and ethyl acetate were added and an insoluble precipitate was collected by filtration, and 1-(2,2-difluoroethyl)-5-nitro-1H-indazole (173 mg) was thus obtained.

MS (ESI m/z): 228 (M+H)
RT (min): 1.18

3rd Step

The following compound was obtained as described in the 3rd step of Reference Example 243.

1-(2,2-difluoro ethyl)-1H-indazol-5-amine

Reference Example 275

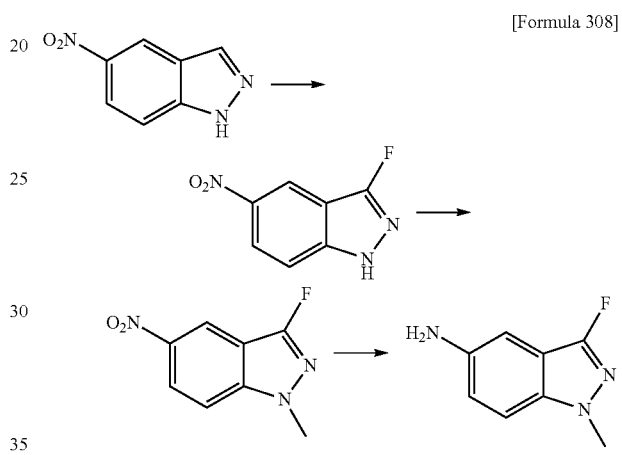

[Formula 308]

1st Step

Select flour (173 mg) and acetic acid (2.5 ml) were added to an acetonitrile (2.5 ml) solution containing 5-nitroindazole (615 mg) and irradiated with microwaves (Initiator™, 150° C., 0.5 hours, 2.45 GHz, 0-240 W). The obtained residue was purified by silica gel chromatography (n-hexane:ethyl acetate=1:0 to 1:1), and 3-fluoro-5-nitro-1H-indazole (404 mg) was thus obtained.

2nd Step

Methyl iodide (41 µl) and potassium carbonate (114 mg) were added to a 1,4-dioxane (2.5 ml) solution containing 3-fluoro-5-nitro-1H-indazole (100 mg), followed by stirring at 100° C. for 2 hours. Ethyl acetate was added, an insoluble precipitate was collected by filtration, and the solvent was distilled away under reduced pressure. The obtained residue was purified by silica gel chromatography (n-hexane:ethyl acetate=1:0 to 1:1), and 3-fluoro-1-methyl-5-nitro-1H-indazole was thus obtained.

3rd Step

The following compound was obtained as described in the 3rd step of Reference Example 243.

3-fluoro-1-methyl-1H-indazol-5-amine

MS (ESI m/z): 166 (M+H)
RT (min): 1.32

Reference Example 276

The following compound was obtained as described in the 2nd and 3rd steps of Reference Example 275.

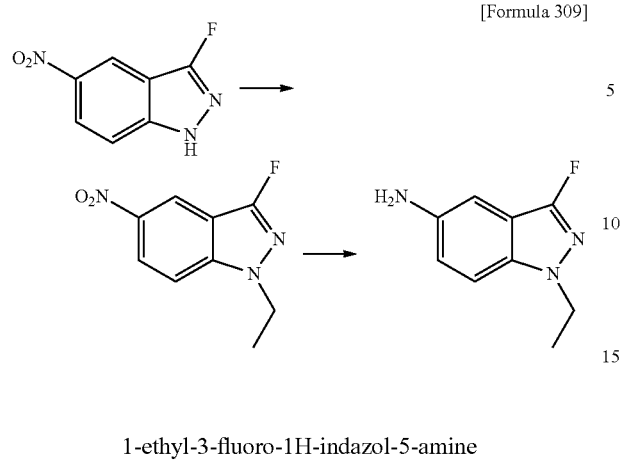

1-ethyl-3-fluoro-1H-indazol-5-amine

MS (ESI m/z): 180 (M+H)
RT (min): 0.57

Reference Example 277

The following compounds were obtained as described in the 2nd and 3rd steps of Reference Example 275.

[Formula 310]

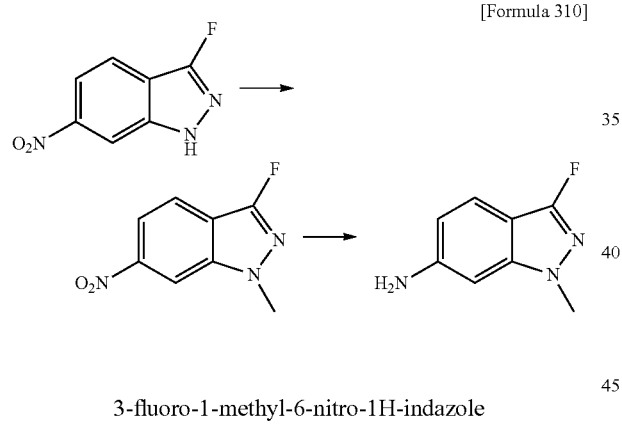

3-fluoro-1-methyl-6-nitro-1H-indazole

MS (ESI m/z): 196 (M+H)
RT (min): 1.38

3-fluoro-1-methyl-1H-indazol-6-amine

Reference Example 278

The following compounds were obtained as described in the 2nd and 3rd steps of Reference Example 275.

[Formula 311]

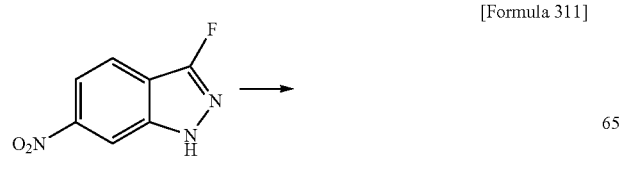

[Formula 309]

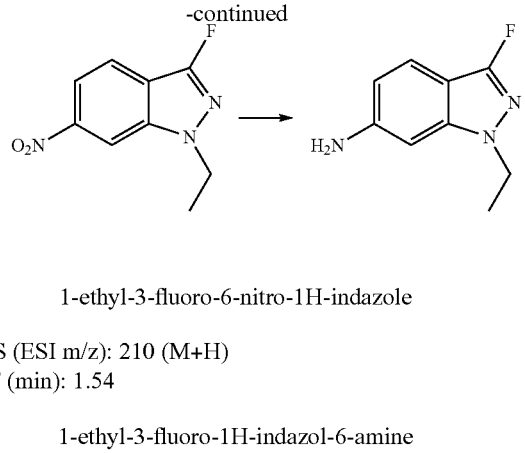

1-ethyl-3-fluoro-6-nitro-1H-indazole

MS (ESI m/z): 210 (M+H)
RT (min): 1.54

1-ethyl-3-fluoro-1H-indazol-6-amine

Reference Example 279

The following compound was obtained as described in the 2nd and 3rd steps of Reference Example 275.

[Formula 312]

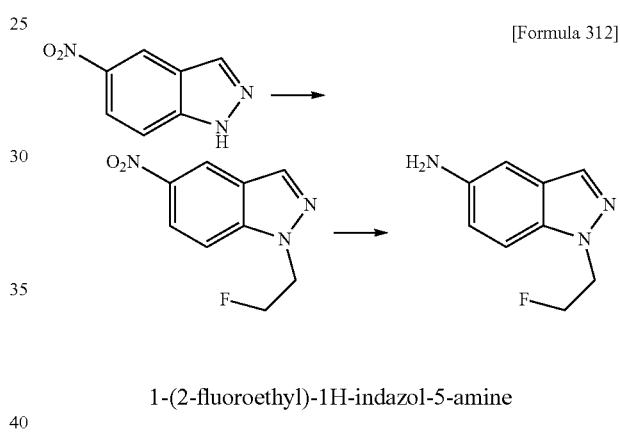

1-(2-fluoroethyl)-1H-indazol-5-amine

MS (ESI m/z): 180 (M+H)
RT (min): 0.28

Reference Example 280

The following compound was obtained as described in the 2nd and 3rd steps of Reference Example 275.

[Formula 313]

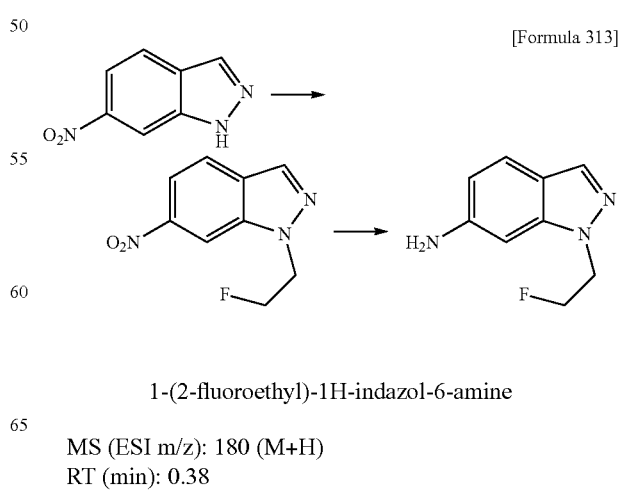

1-(2-fluoroethyl)-1H-indazol-6-amine

MS (ESI m/z): 180 (M+H)
RT (min): 0.38

Reference Example 281

The following compound was obtained as described in the 2nd and 3rd steps of Reference Example 275.

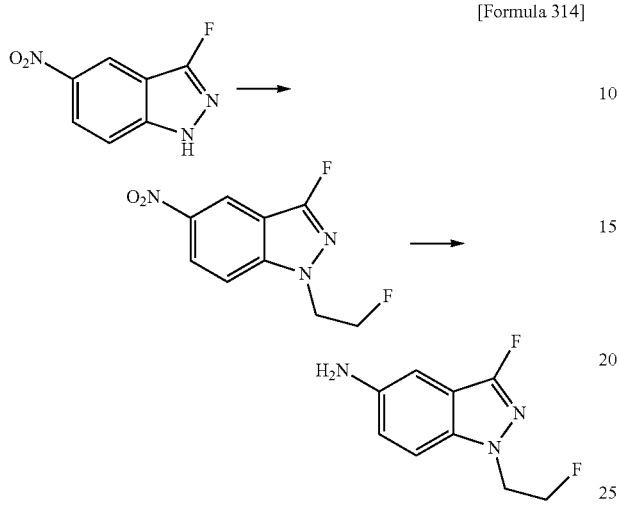

[Formula 314]

3-fluoro-1-(2-fluoroethyl)-1H-indazol-5-amine

MS (ESI m/z): 198 (M+H)
RT (min): 0.89

Reference Example 282

The following compound was obtained as described in the 2nd and 3rd steps of Reference Example 275.

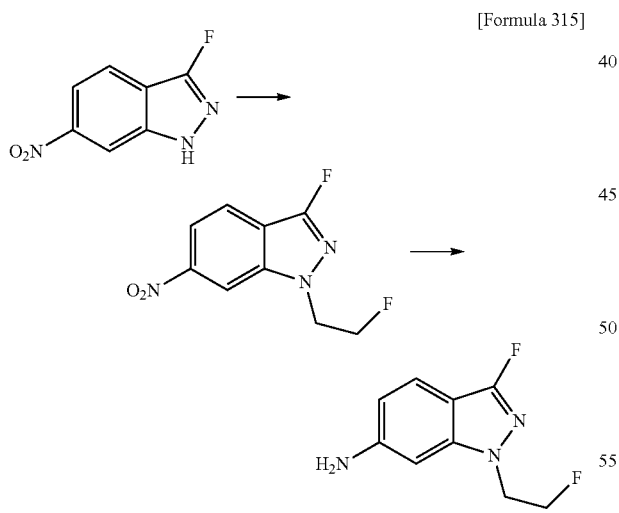

[Formula 315]

3-fluoro-1-(2-fluoroethyl)-1H-indazol-6-amine

MS (ESI m/z): 198 (M+H)
RT (min): 0.50

Reference Example 283

The following compound was obtained with reference to Journal of Organic Chemistry, 1966, vol. 31, pp. 677-681.

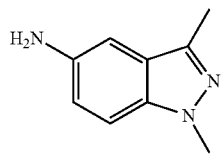

[Formula 316]

1,3-dimethyl-1H-indazol-5-amine

Reference Example 284-1

The following compound was obtained with reference to US2009/312314 A1.

[Formula 317]

1-ethyl-3-methyl-5-nitro-1H-indazole

Reference Example 284-2

The following compound was obtained as described in the 3rd step of Reference Example 275.

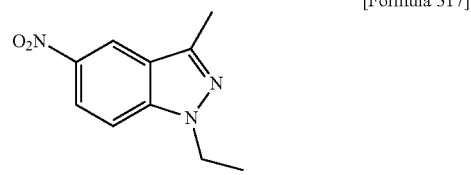

[Formula 318]

The following compound was obtained with reference to US2009/312314 A1.

1-ethyl-3-methyl-1H-indazol-5-amine

MS (ESI m/z): 176 (M+H)
RT (min): 0.51

Reference Example 285

The following compound was obtained as described in the 2nd and 3rd steps of Reference Example 275.

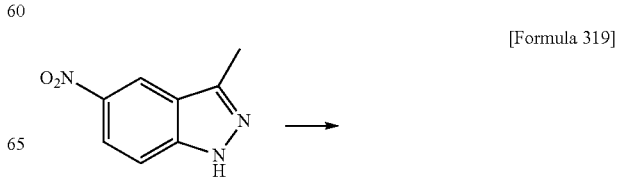

[Formula 319]

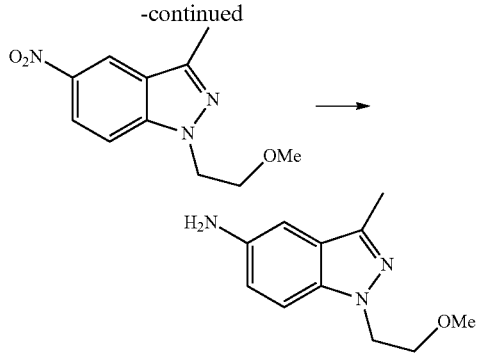

1-(2-methoxyethyl)-3-methyl-1H-indazol-5-amine

MS (ESI m/z): 206 (M+H)
RT (min): 0.79

Reference Example 286

The following compound was obtained as described in the 2nd and 3rd steps of Reference Example 275.

[Formula 320]

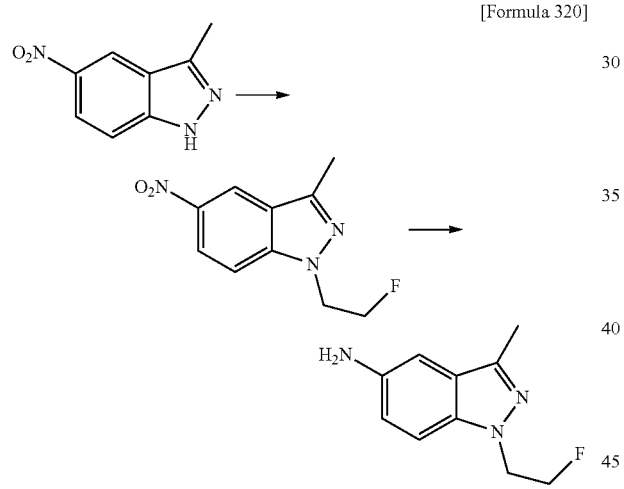

1-(2-fluoroethyl)-3-methyl-1H-indazol-5-amine

MS (ESI m/z): 194 (M+H)
RT (min): 0.45

Reference Example 287

The following compound was obtained with reference to Organic Letters, 2008, vol. 10, #5, pp. 1021-1023.

[Formula 321]

3-methyl-5-nitro-1H-indazole

Reference Example 288

The following compound was obtained as described in the 2nd and 3rd steps of Reference Example 275.

[Formula 322]

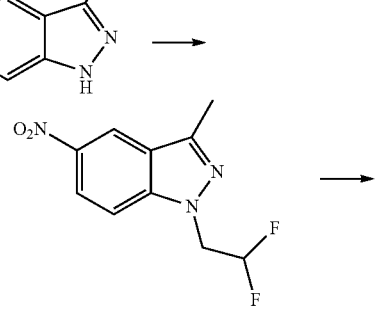

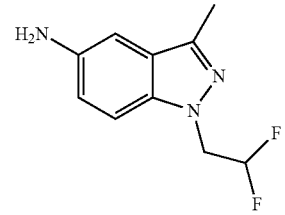

1-(2,2-difluoroethyl)-3-methyl-1H-indazol-5-amine

MS (ESI m/z): 212 (M+H)
RT (min): 0.49

Reference Example 289

The following compound was obtained with reference to Organic Letters, 2008, vol. 10, #5, pp. 1021-1023.

[Formula 323]

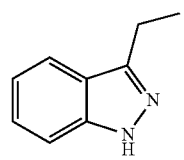

3-ethyl-1H-indazole

Reference Example 290

[Formula 324]

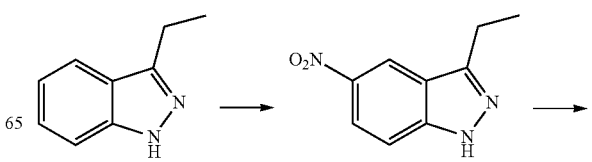

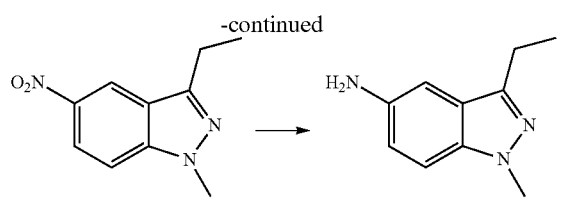

1st Step

Sodium nitrate (430 mg) was added to a 50% sulfuric acid aqueous solution (2.5 ml) containing 3-ethyl-1H-indazole (730 mg) under ice cooling, followed by stirring at 80° C. for 2 hours. Water and ethyl acetate were added to the reaction solution, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane:ethyl acetate=1:0 to 4:1), and 3-ethyl-5-nitro-1H-indazole (197 mg) was thus obtained.

2nd and 3rd Steps

The following compound was obtained as described in the 2nd and 3rd steps of Reference Example 275.

3-ethyl-1-methyl-1H-indazol-5-amine

MS (ESI m/z): 176 (M+H)
RT (min): 0.53

Reference Example 291

The following compound was obtained as described in the 2nd and 3rd steps of Reference Example 275.

[Formula 325]

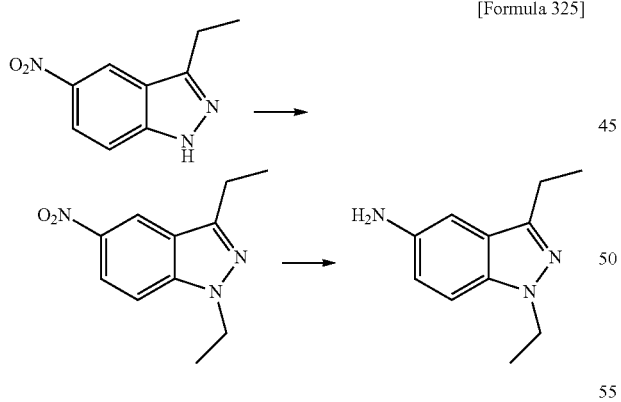

1,3-diethyl-1H-indazol-5-amine

MS (ESI m/z): 190 (M+H)
RT (min): 0.62

Reference Example 292

The following compound was obtained as described in the 2nd and 3rd steps of Reference Example 275.

[Formula 326]

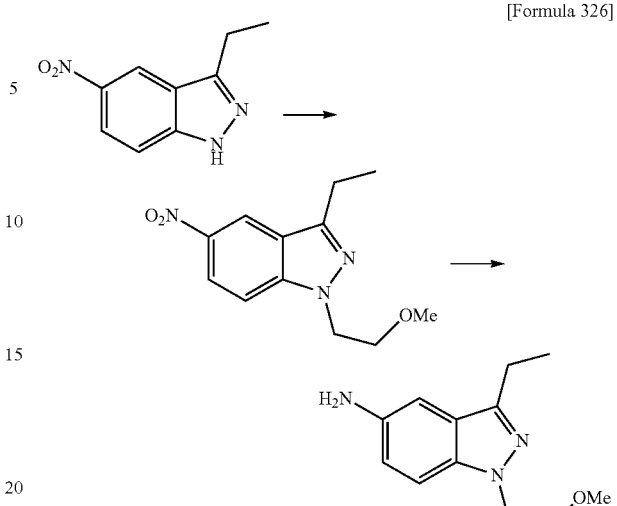

3-ethyl-1-(2-methoxyethyl)-1H-indazol-5-amine

MS (ESI m/z): 220 (M+H)
RT (min): 0.58

Reference Example 293

The following compound was obtained as described in the 2nd and 3rd steps of Reference Example 275.

[Formula 327]

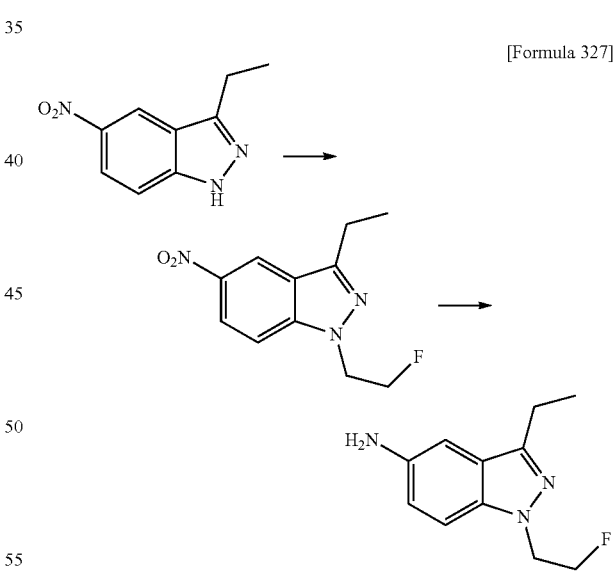

3-ethyl-1-(2-fluoroethyl)-1H-indazol-5-amine

MS (ESI m/z): 208 (M+H)
RT (min): 0.57

Reference Example 294

The following compound was obtained as described in the 2nd and 3rd steps of Reference Example 275.

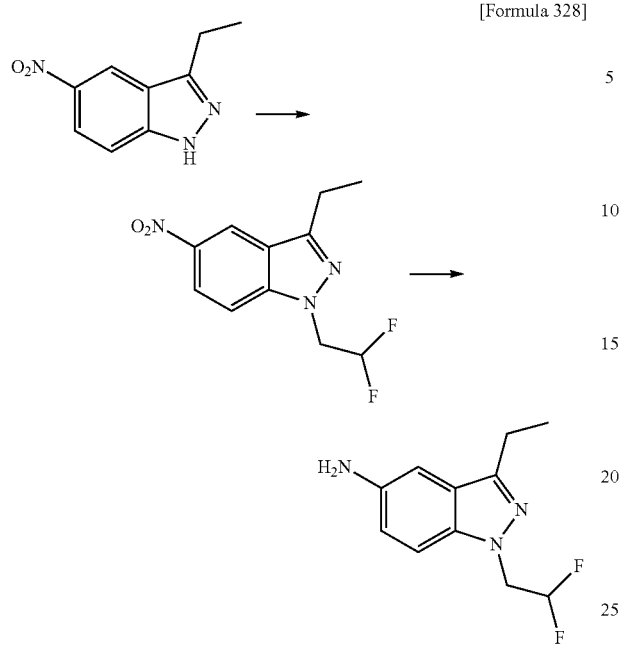

1-(2,2-difluoroethyl)-3-ethyl-1H-indazol-5-amine

MS (ESI m/z): 226 (M+H)
RT (min): 0.65

Reference Example 295

The following compound was obtained with reference to European Journal of Organic Chemistry, 2009, #19, pp. 3184-3188.

[Formula 329]

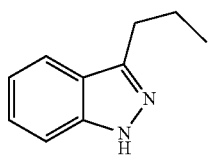

3-propyl-1H-indazole

Reference Example 296

[Formula 330]

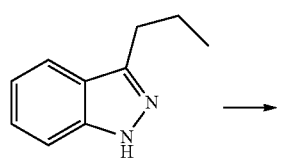

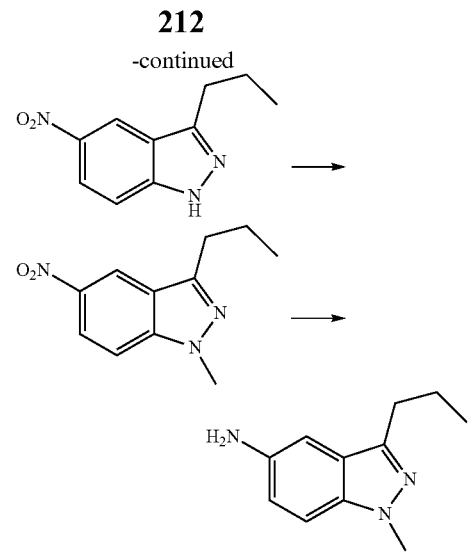

The following compound was obtained as described in Reference Example 290.

1-methyl-3-propyl-1H-indazol-5-amine

MS (ESI m/z): 190 (M+H)
RT (min): 0.62

Reference Example 297

The following compound was obtained as described in the 2nd and 3rd steps of Reference Example 275.

[Formula 331]

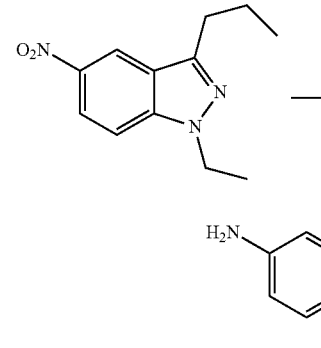

1-ethyl-3-propyl-1H-indazol-5-amine

MS (ESI m/z): 204 (M+H)
RT (min): 0.74

Reference Example 298

The following compound was obtained as described in the 2nd and 3rd steps of Reference Example 275.

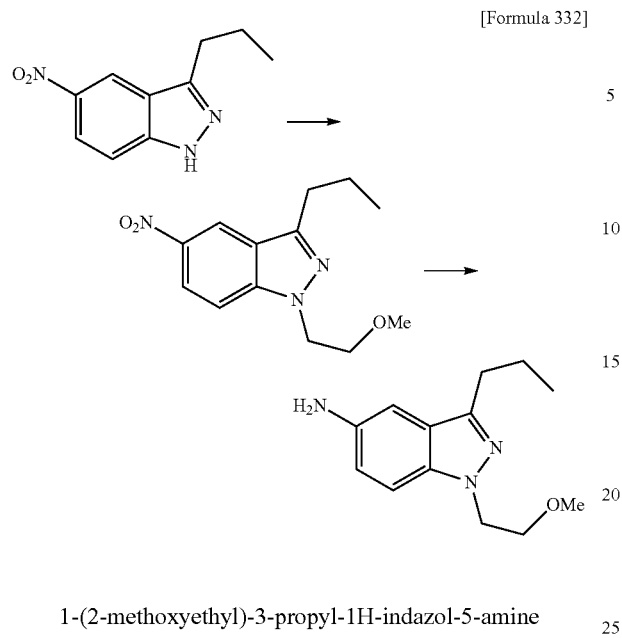

1-(2-methoxyethyl)-3-propyl-1H-indazol-5-amine

MS (ESI m/z): 234 (M+H)
RT (min): 0.70

Reference Example 299

The following compound was obtained as described in the 2nd and 3rd steps of Reference Example 275.

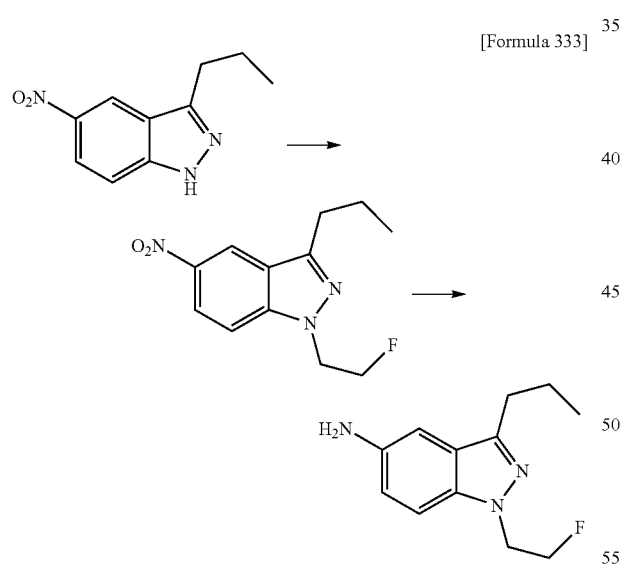

1-(2-fluoroethyl)-3-propyl-1H-indazol-5-amine

MS (ESI m/z): 222 (M+H)
RT (min): 0.69

Reference Example 300

1st Step
The following compound was obtained as described in the 2nd and 3rd steps of Reference Example 275.

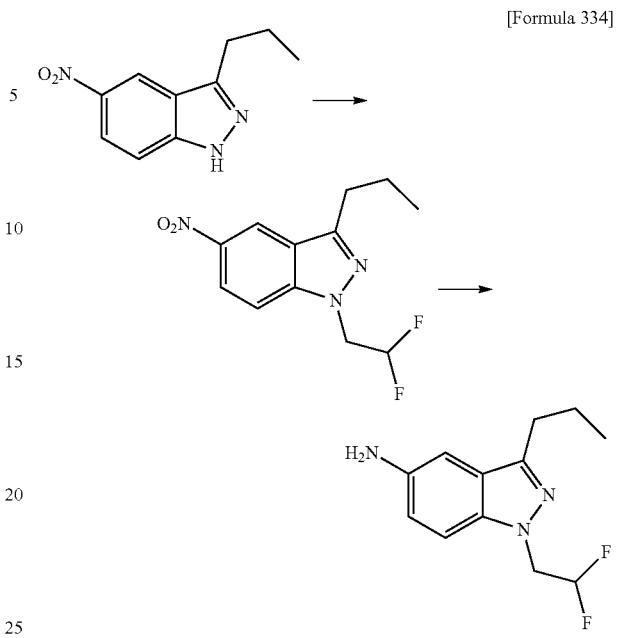

1-(2,2-difluoroethyl)-3-propyl-1H-indazol-5-amine

MS (ESI m/z): 240 (M+H)
RT (min): 0.76

Reference Example 301-1

The following compound was obtained with reference to US2008/139558 A1.

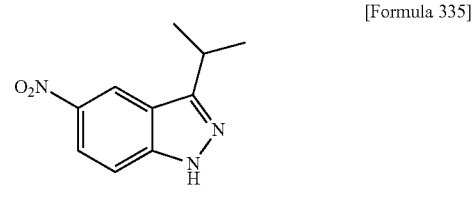

3-isopropyl-5-nitro-1H-indazole

Reference Example 301-2

The following compound was obtained as described in the 2nd and 3rd steps of Reference Example 275.

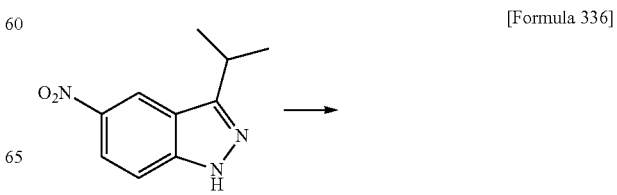

-continued

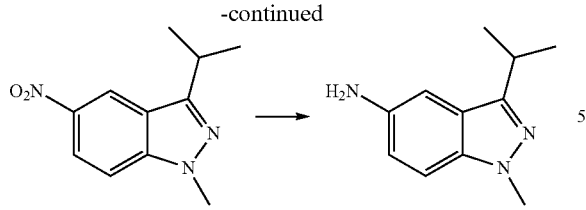

3-isopropyl-1-methyl-1H-indazol-5-amine

MS (ESI m/z): 190 (M+H)
RT (min): 0.63

Reference Example 302

The following compound was obtained as described in the 2nd and 3rd steps of Reference Example 275.

[Formula 337]

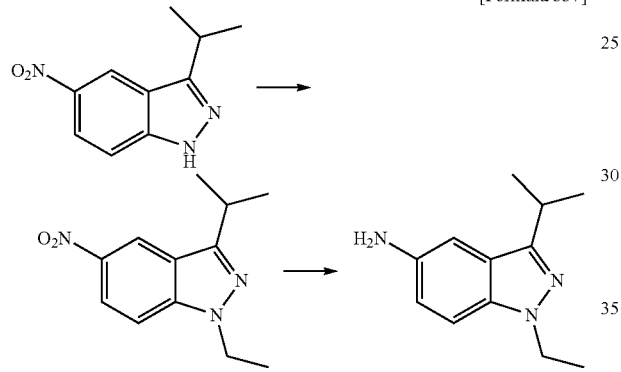

1-ethyl-3-isopropyl-1H-indazol-5-amine

MS (ESI m/z): 204 (M+H)
RT (min): 0.74

Reference Example 303

The following compound was obtained as described in the 2nd and 3rd steps of Reference Example 275.

[Formula 338]

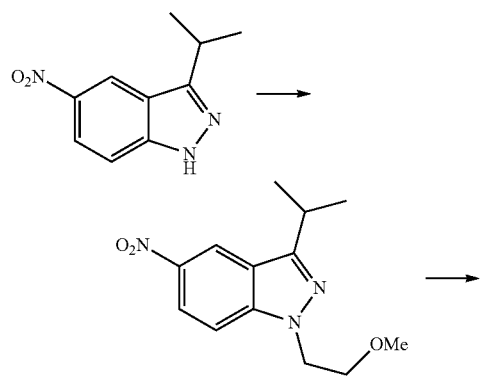

-continued

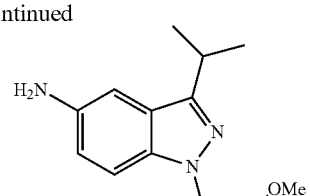

3-isopropyl-1-(2-methoxyethyl)-1H-indazol-5-amine

MS (ESI m/z): 234 (M+H)
RT (min): 0.70

Reference Example 304

The following compound was obtained with reference to Journal of Organic Chemistry, 2008, vol. 73, #16, pp. 6441-6444.

[Formula 339]

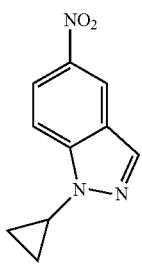

1-cyclopropyl-5-nitro-1H-indazole

Reference Example 305

[Formula 340]

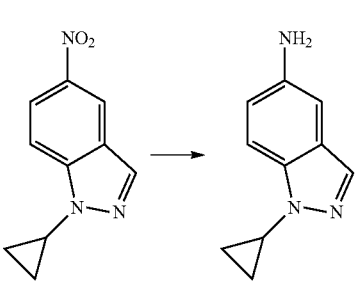

A methanol (15 ml) solution containing 1-cyclopropyl-5-nitro-1H-imidazole (60 mg) was prepared and subjected to hydrogenation reaction (80° C.; 50 bar; flow rate: 2 ml/min; 10% Pd/C) using H-cube™. Thereafter, the solvent was distilled away under reduced pressure, and a purple solid of 1-cyclopropyl-1H-imidazol-5-amine (20 mg) was thus obtained.

Reference Example 306

The following compound was obtained with reference to 2009/122180 A1, 2009.

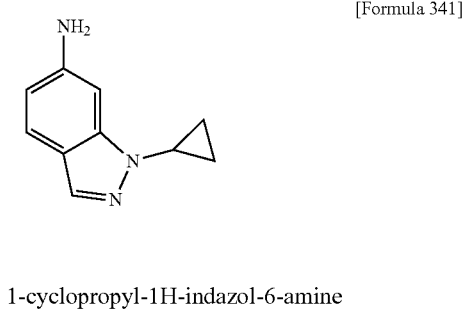

1-cyclopropyl-1H-indazol-6-amine

Reference Example 307

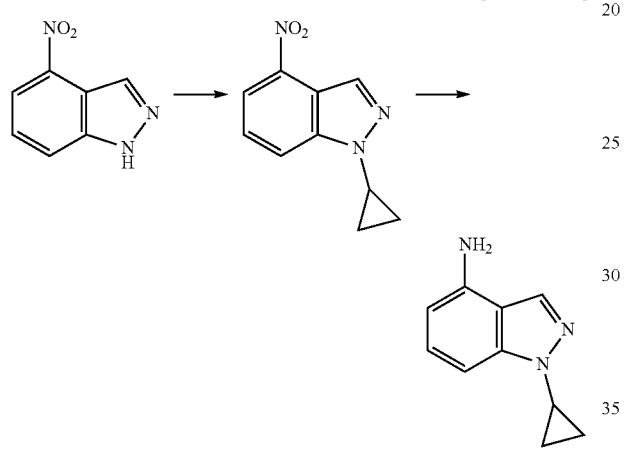

1st Step

Cyclopropylboronic acid monohydrate (52 mg), copper acetate (55 mg), sodium carbonate (64 mg), and pyridine (24 μl) were added to a dichloroethane (1 ml) solution containing 4-nitroindazole (50 mg) in a nitrogen atmosphere, followed by stirring at 70° C. for 3 hours. Ethyl acetate was added to the reaction solution, an insoluble precipitate was removed, and the solvent was distilled away under reduced pressure. Subsequently, the obtained residue was purified by silica gel chromatography (n-hexane:ethyl acetate=1:0 to 1:1), and 1-cyclopropyl-4-nitro-1H-indazole (30 mg) was thus obtained.

MS (ESI m/z): 204 (M+H)

RT (min): 1.37

2nd step

The following compound was obtained as described in Reference Example 305.

1-cyclopropyl-1H-indazol-4-amine

MS (ESI m/z): 174 (M+H)

RT (min): 0.87

Reference Example 308

The following compounds were obtained as described in Reference Example 307.

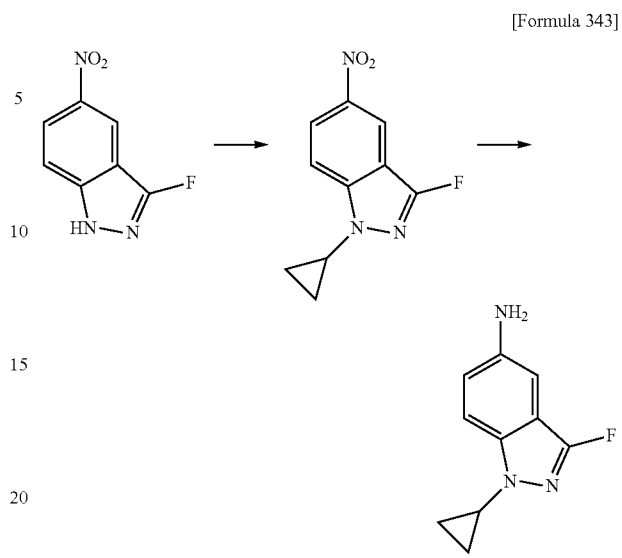

1-cyclopropyl-3-fluoro-5-nitro-1H-indazole

MS (ESI m/z): 222 (M+H)
RT (min): 1.46

1-cyclopropyl-3-fluoro-1H-indazol-5-amine

MS (ESI m/z): 192 (M+H)
RT (min): 0.63

Reference Example 309

The following compounds were obtained as described in Reference Example 307.

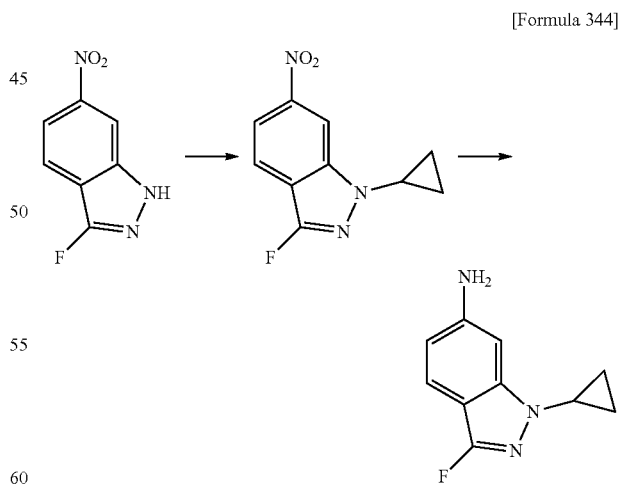

1-cyclopropyl-3-fluoro-6-nitro-1H-indazole

MS (ESI m/z): 222 (M+H)
RT (min): 1.50

1-cyclopropyl-3-fluoro-1H-indazol-6-amine

MS (ESI m/z): 192 (M+H)
RT (min): 0.97

Reference Example 311

The following compounds were obtained as described in Reference Example

[Formula 345]

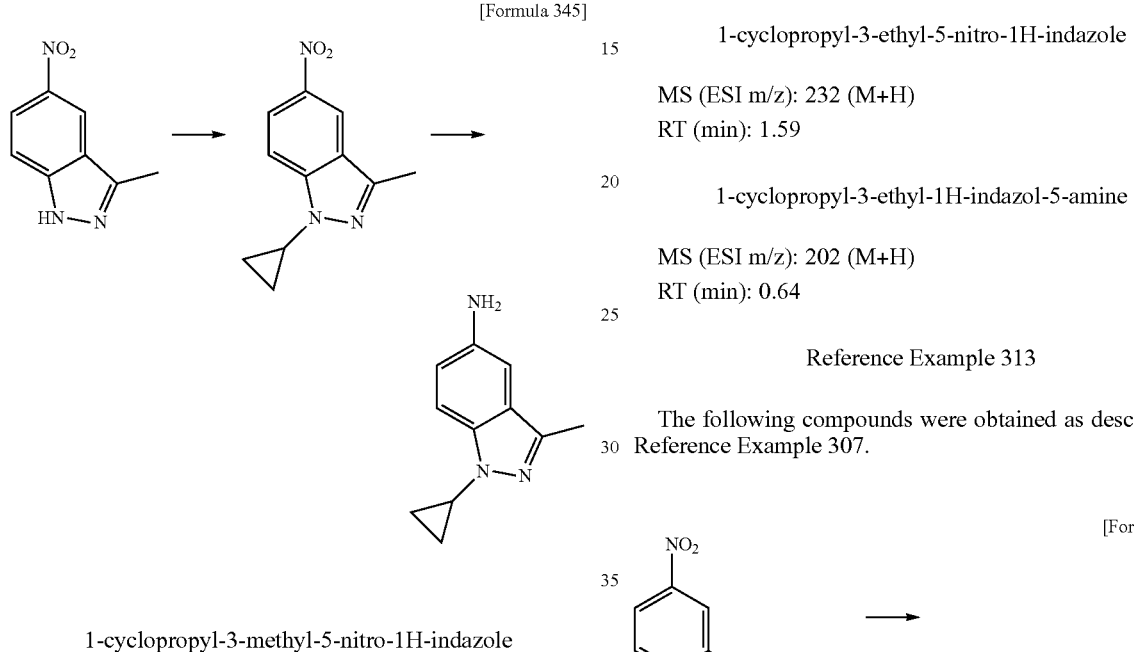

1-cyclopropyl-3-methyl-5-nitro-1H-indazole

MS (ESI m/z): 218 (M+H)
RT (min): 1.36

1-cyclopropyl-3-methyl-1H-indazol-5-amine

MS (ESI m/z): 188 (M+H)
RT (min): 0.54

Reference Example 312

The following compounds were obtained as described in Reference Example 307.

[Formula 346]

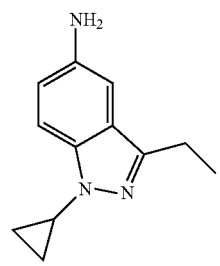

1-cyclopropyl-3-ethyl-5-nitro-1H-indazole

MS (ESI m/z): 232 (M+H)
RT (min): 1.59

1-cyclopropyl-3-ethyl-1H-indazol-5-amine

MS (ESI m/z): 202 (M+H)
RT (min): 0.64

Reference Example 313

The following compounds were obtained as described in Reference Example 307.

[Formula 347]

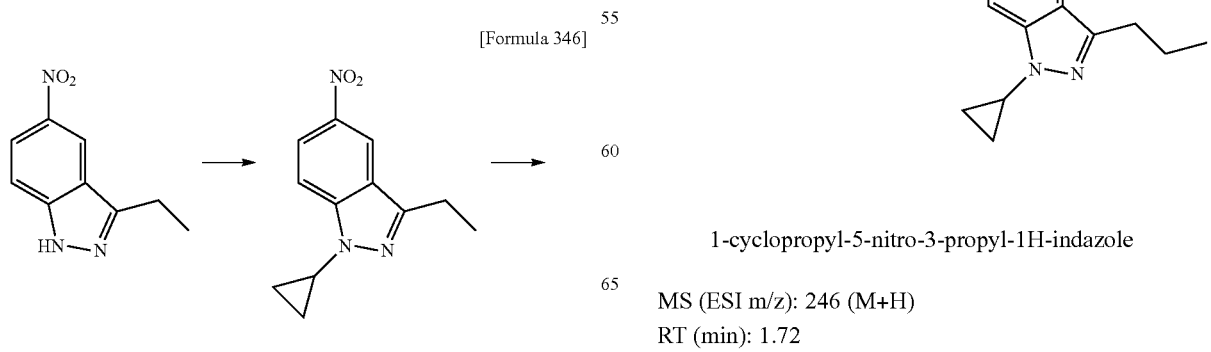

1-cyclopropyl-5-nitro-3-propyl-1H-indazole

MS (ESI m/z): 246 (M+H)
RT (min): 1.72

221

1-cyclopropyl-3-propyl-1H-indazol-5-amine

MS (ESI m/z): 216 (M+H)
RT (min): 0.73

Reference Example 314

The following compounds were obtained as described in the 2nd and 3rd steps of Reference Example 275.

[Formula 348]

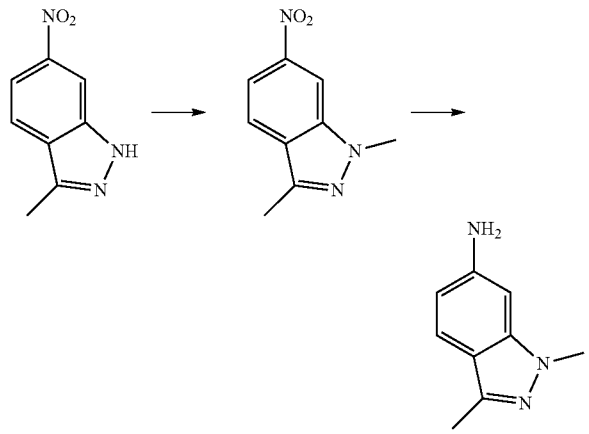

1,3-dimethyl-6-nitro-1H-indazole

MS (ESI m/z): 192 (M+H)
RT (min): 1.37

1,3-dimethyl-1H-indazol-6-amine

MS (ESI m/z): 162 (M+H)
RT (min): 0.52

Reference Example 315

The following compounds were obtained as described in the 2nd and 3rd steps of Reference Example 275.

[Formula 349]

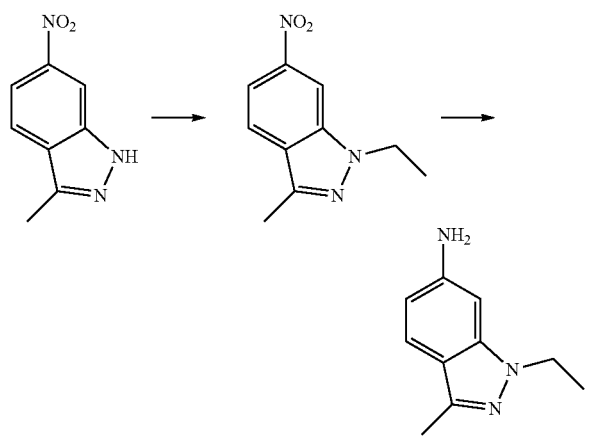

222

1-ethyl-3-methyl-6-nitro-1H-indazole

MS (ESI m/z): 206 (M+H)
RT (min): 1.34

1-ethyl-3-methyl-1H-indazol-6-amine

MS (ESI m/z): 176 (M+H)
RT (min): 0.60

Reference Example 316

The following compounds were obtained as described in the 2nd and 3rd steps of Reference Example 275.

[Formula 350]

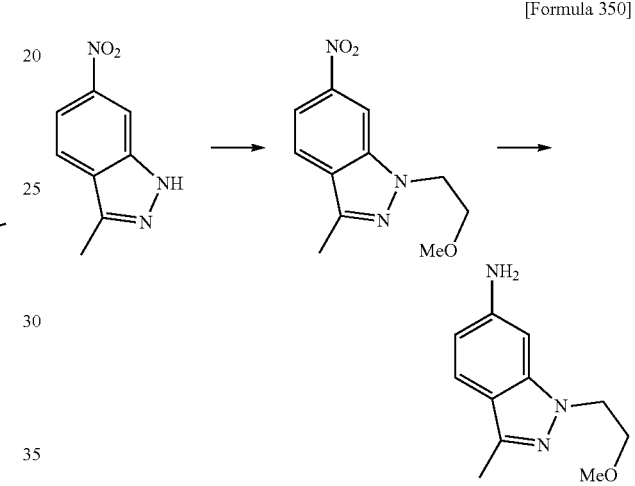

1-(2-methoxyethyl)-3-methyl-6-nitro-1H-indazole

MS (ESI m/z): 236 (M+H)
RT (min): 1.40

1-(2-methoxyethyl)-3-methyl-1H-indazol-6-amine

MS (ESI m/z): 206 (M+H)
RT (min): 0.58

Reference Example 317

The following compounds were obtained as described in the 2nd and 3rd steps of Reference Example 275.

[Formula 351]

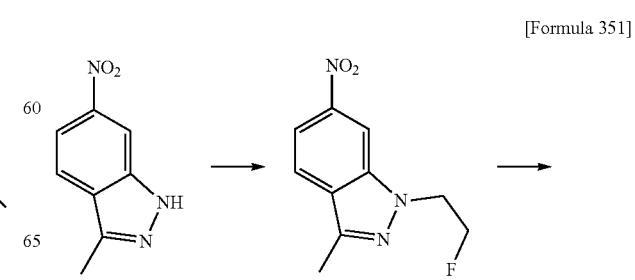

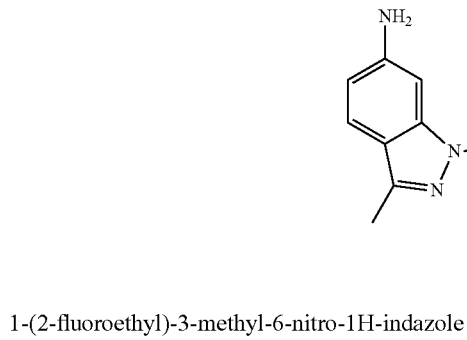

1-(2-fluoroethyl)-3-methyl-6-nitro-1H-indazole

MS (ESI m/z): 224 (M+H)
RT (min): 1.30

1-(2-fluoroethyl)-3-methyl-1H-indazol-6-amine

MS (ESI m/z): 194 (M+H)
RT (min): 0.59

Reference Example 318

The following compound was obtained as described in the 2nd and 3rd steps of Reference Example 275.

[Formula 352]

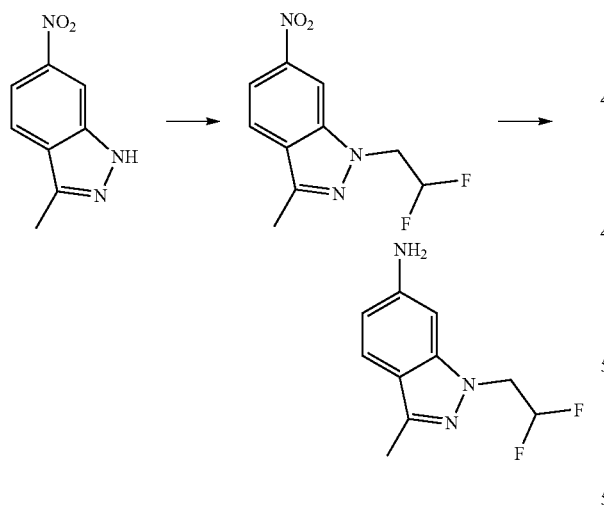

1-(2,2-difluoroethyl)-3-methyl-1H-indazol-6-amine

MS (ESI m/z): 212 (M+H)
RT (min): 0.75

Reference Example 319

The following compounds were obtained as described in Reference Example 275.

[Formula 353]

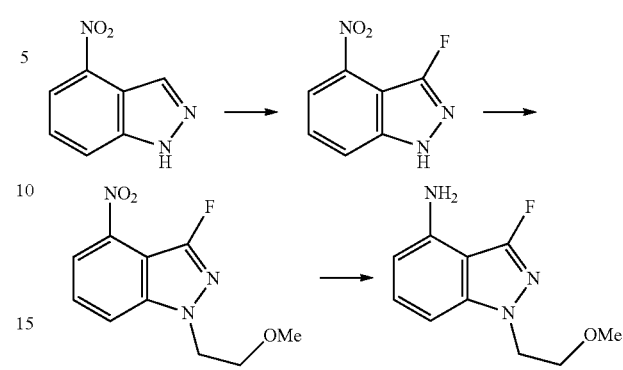

3-fluoro-1-(2-methoxyethyl)-4-nitro-1H-indazole

MS (ESI m/z): 240 (M+H)
RT (min): 1.39

3-fluoro-1-(2-methoxyethyl)-1H-indazol-4-amine

MS (ESI m/z): 210 (M+H)
RT (min): 0.93

Reference Example 320

The following compounds were obtained as described in Reference Example 319.

[Formula 354]

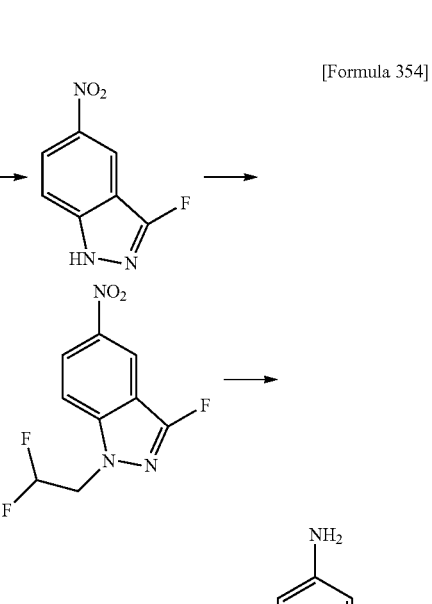

3-fluoro-5-nitro-1H-indazole

MS (ESI m/z): 182 (M+H)
RT (min): 1.30

1-(2,2-difluoroethyl)-3-fluoro-5-nitro-1H-indazole

MS (ESI m/z): 246 (M+H)
RT (min): 1.58

1-(2,2-difluoroethyl)-3-fluoro-1H-indazol-5-amine

MS (ESI m/z): 216 (M+H)
RT (min): 0.57

Reference Example 321

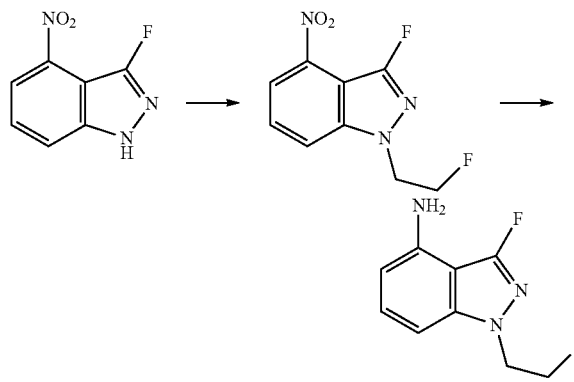

[Formula 355]

1st Step 2-fluoroethyltrifluoromethane sulfonate (30 µl) and potassium carbonate (31 mg) were added to a 1,4-dioxane (0.4 ml) solution containing 3-fluoro-4-nitro-1H-indazole (20 mg) in a nitrogen atmosphere, followed by stirring at 70° C. for 5 hours. Ethyl acetate was added to the reaction solution, an insoluble precipitate was removed, and the solvent was distilled away under reduced pressure. Subsequently, the obtained residue was purified by silica gel chromatography (n-hexane:ethyl acetate=1:0 to 1:1), and 3-fluoro-1-(2-fluoroethyl)-4-nitro-1H-indazole (13 mg) was thus obtained.

MS (ESI m/z): 228 (M+H)
RT (min): 1.40

2nd Step

The following compound was obtained as described in Reference Example 305.

3-fluoro-1-(2-fluoroethyl)-1H-indazol-4-amine

MS (ESI m/z): 198 (M+H)
RT (min): 0.95

Reference Example 322

The following compounds were obtained as described in Reference Example 321.

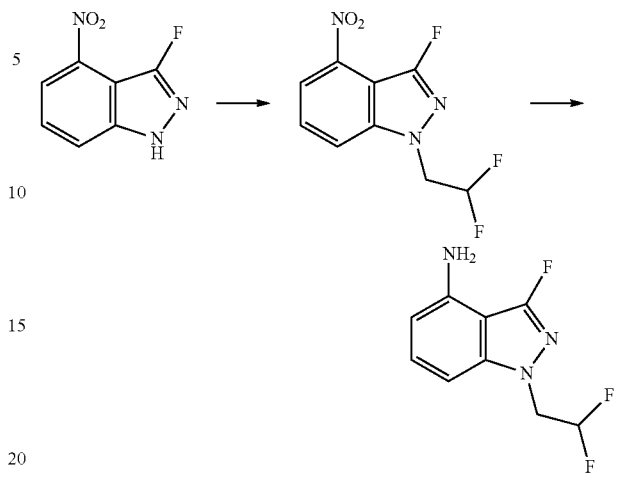

[Formula 356]

1-(2,2-difluoroethyl)-3-fluoro-4-nitro-1H-indazole

MS (ESI m/z): 246 (M+H)
RT (min): 1.45

1-(2,2-difluoroethyl)-3-fluoro-1H-indazol-4-amine

MS (ESI m/z): 216 (M+H)
RT (min): 1.06

Reference Example 323

The following compounds were obtained as described in Reference Example 22 and the 1st step of Reference Example 190.

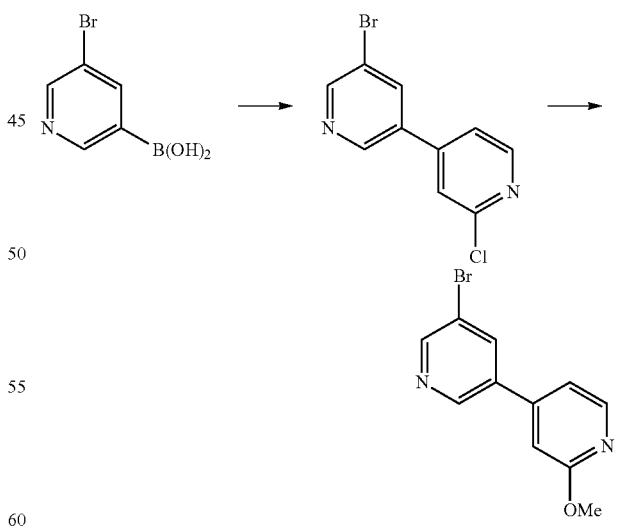

[Formula 357]

1st step 5-bromo-2'-chloro-3,4'-bipyridine

MS (ESI m/z): 269, 271, 273 (M+H)
RT (min): 1.33

2nd Step 5-bromo-2'-methoxy-3,4'-bipyridine

MS (ESI m/z): 265, 267 (M+H)
RT (min): 1.35

Reference Example 324

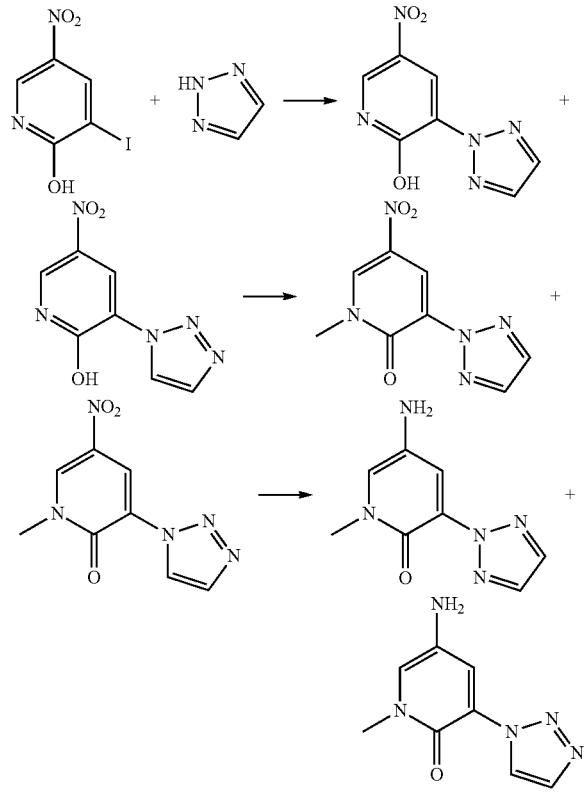

[Formula 358]

1st Step

Cesium carbonate (550 mg), L-proline (65 mg), and 1H-1,2,3-triazole (92 mg) were added to a dimethyl sulfoxide (3 ml) solution containing 2-hydroxy-3-iodo-5-nitropyridine (300 mg), and copper iodide (106 mg) was further added in a nitrogen atmosphere, followed by stirring at 100° C. for 3 hours. The reaction solution was adjusted to room temperature. Water and ethyl acetate were added. The pH was adjusted to pH 7 with 1M hydrochloric acid. Insoluble matter was filtered, followed by extraction with ethyl acetate (×3). The resultant was washed with saturated saline and dried over anhydrous sodium sulfate. Subsequently, the solvent was distilled away under reduced pressure, the obtained residue was purified by silica gel chromatography (chloroform:methanol=1:0 to 10:1), and an orange solid of a mixture (184 mg) of 5-nitro-3-(2H-1,2,3-triazol-2-yl)pyridin-2-ol and 5-nitro-3-(1H-1,2,3-triazol-1-yl)pyridin-2-ol was thus obtained.

2nd Step

Silver carbonate (377 mg) and methyl iodide (366 W) were added to a chloroform (10 ml) solution containing the mixture of 5-nitro-3-(2H-1,2,3-triazol-2-yl)pyridin-2-ol and 5-nitro-3-(1H-1,2,3-triazol-1-yl)pyridin-2-ol (184 mg) obtained in the 1st step while shielding light, followed by reflux for 2 hours. Water was added, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane:ethyl acetate=2:5 to 2:3), and a white solid of 1-methyl-5-nitro-3-(2H-1,2,3-triazol-2-yl)pyridin-2(1H)-one (28.1 mg) and a white solid of 1-methyl-5-nitro-3-(1H-1,2,3-triazol-1-yl)pyridin-2(1H)-one (23.3 mg) were thus obtained.

3rd Step

The following compounds were obtained as described in the 3rd step of Reference Example 161.

5-Amino-1-methyl-3-(2H-1,2,3-triazol-2-yl)pyridin-2(1H)-one

MS (ESI m/z): 129 (M+H)
RT (min): 0.21, 0.26
$^1$H-NMR (DMSO-$d_6$, 300 MHz) δ: 8.00 (s, 2H), 7.41 (d, 1H, J=2.4 Hz), 7.13 (d, 1H, J=2.4 Hz), 4.53 (br, 2H), 3.51 (s, 3H)

5-Amino-1-methyl-3-(1H-1,2,3-triazol-1-yl)pyridin-2(1H)-one

MS (ESI m/z): 192 (M+H)
RT (min): 0.29
$^1$H-NMR (DMSO-$d_6$, 300 MHz) δ: 8.85-8.83 (m, 1H), 7.89-7.87 (m, 1H), 7.85 (d, 1H, J=2.7 Hz), 7.12 (d, 1H, J=2.7 Hz), 1.82 (br, 2H), 3.51 (s, 3H)

Reference Example 325

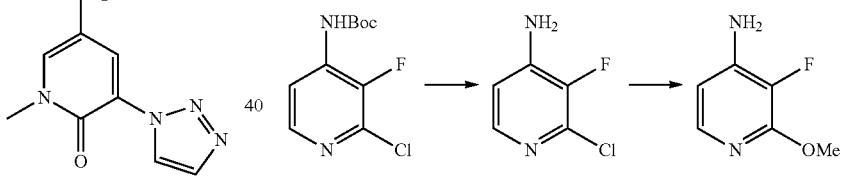

[Formula 359]

1st Step

TFA (1 ml) was added to tert-butyl(2-chloro-5-fluoropyridin-4-yl)carbamate (100 mg), followed by stirring at room temperature for 0.5 hours. The solvent was distilled away under reduced pressure. The residue was used in the next step.

2nd Step

The residue obtained in the 1st step and a sodium methoxide solution (5M methanol solution) (5 ml) were added to a tube and the tube was sealed, followed by stirring at 170° C. for 3 hours. The reaction solution was adjusted to room temperature. Sodium hydroxide (49 mg) was added, followed by stirring at 170° C. for 1 hour. The reaction solution was adjusted to room temperature, the solvent was distilled away under reduced pressure, and a saturated aqueous ammonium chloride solution was added, followed by extraction with ethyl acetate. Subsequently, the resultant was washed with saturated saline and dried over anhydrous sodium sulfate, and the solvent was distilled away under reduced pressure. The obtained residue was purified by silica gel chromatography (n-hexane:ethyl acetate=4:1 to 1:1), and yellow oily matter of 3-fluoro-2-methoxypyridin-4-amine (27 mg) was thus obtained.

MS (ESI m/z): 143 (M+H)
RT (min): 0.41

Reference Example 326

The following compound was obtained as described in Reference Example 325.

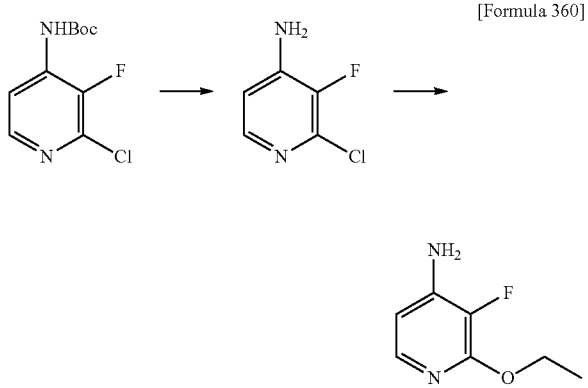
[Formula 360]

2-Ethoxy-3-fluoropyridin-4-amine

MS (ESI m/z): 157 (M+H)
RT (min): 0.53

Reference Example 327

The following compound was obtained with reference to Journal of Medicinal Chemistry, 2007, vol. 50, #15, pp. 3730-3742.

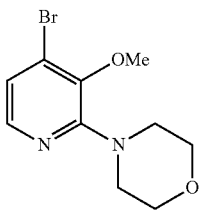
[Formula 361]

4-(5-Bromo-3-methoxypyridin-2-yl)morpholine

Reference Example 328

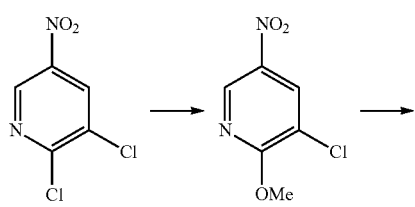
[Formula 362]

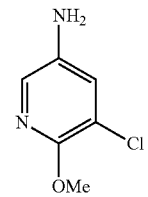

1st Step

Sodium methoxide (5M methanol solution) (0.5 ml) was added to a methanol (1 ml) solution of 2,3-dichloro-5-nitropyridine (50 mg), followed by stirring at room temperature for 1.5 hours. Water was added, followed by extraction with ethyl acetate. The resultant was washed with saturated saline and dried over anhydrous sodium sulfate, the solvent was distilled away under reduced pressure, and colorless oily matter of 3-chloro-2-methoxy-5-nitropyridine (45.8 mg) was thus obtained.

2nd Step

The following compound was obtained as described in the 2nd step of Reference Example 112.

5-Chloro-6-methoxypyridin-3-amine

MS (ESI m/z): 159, 161 (M+H)
RT (min): 0.74

Reference Example 329

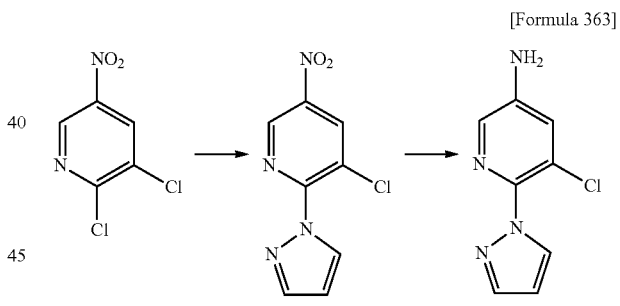
[Formula 363]

1st Step

The following compound was obtained as described in Reference Example 18.

3-Chloro-5-nitro-2-(1H-pyrazol-1-yl)pyridine

MS (ESI m/z): 225, 227 (M+H)
RT (min): 1.15

2nd Step

The following compound was obtained as described in the 2nd step of Reference Example 112.

5-Chloro-6-(1H-pyrazol-1-yl)pyridin-3-amine

MS (ESI m/z): 195, 197 (M+H)
RT (min): 0.80

Reference Example 330

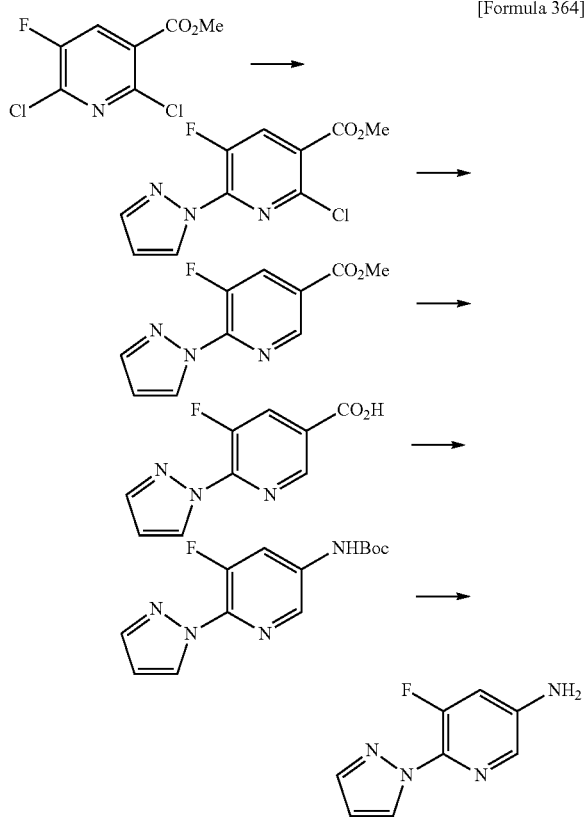

[Formula 364]

1st Step
The following compound was obtained as described in Reference Example 18.

Methyl 2-chloro-5-fluoro-6-(1H-pyrazol-1-yl)nicotinate

MS (ESI m/z): 256, 258 (M+H)
RT (min): 1.26

2nd Step
10% Pd/C (40 mg) and ammonium formate (210 mg) were added to a methanol (10 ml) solution containing methyl 2-chloro-5-fluoro-6-(1H-pyrazol-1-yl)nicotinate (42 mg) obtained in the 1st step, followed by stirring at 70° C. for 1.5 hours. Insoluble matter was removed and the solvent was distilled away under reduced pressure.

Methyl 5-fluoro-6-(1H-pyrazol-1-yl)nicotinate

MS (ESI m/z): 222 (M+H)
RT (min): 1.08

3rd Step
A 1M sodium hydroxide aqueous solution (1 ml) was added to a methanol/tetrahydrofuran (1 ml/1 ml) solution containing the residue obtained in the 2nd step, followed by reflux for 1.5 hours. Further, a 2M sodium hydroxide aqueous solution (1 ml) was added, followed by reflux for 0.5 hours. Insoluble matter was removed and the solvent was distilled away under reduced pressure. Water was added to the reaction solution, and the reaction solution was acidified with 1M hydrochloric acid, followed by extraction with ethyl acetate (×3). The resultant was washed with saturated saline and dried over anhydrous sodium sulfate, the solvent was distilled away under reduced pressure, and colorless oily matter of 5-fluoro-6-(1H-pyrazol-1-yl)nicotinic acid (45.8 mg) was thus obtained.

MS (ESI m/z): 208 (M+H)
RT (min): 1.08

4th Step
Triethylamine (193 µl), tert-butanol (227 µl), and DPPA (525 µl) were added to a toluene (5 ml) solution containing 5-fluoro-6-(1H-pyrazol-1-yl)nicotinic acid (330 mg), followed by reflux for 3 hours. Water was added to the reaction solution, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane:ethyl acetate=10:1 to 3:1), and a white solid of tert-butyl(5-fluoro-6-(1H-pyrazol-1-yl)pyridin-3-yl)carbamate (210 mg) was thus obtained.

MS (ESI m/z): 279 (M+H)
RT (min): 1.37
$^1$H-NMR (DMSO-$d_6$, 300 MHz) δ:10.03 (s, 1H), 8.37 (d, 1H, J=2.1 Hz), 8.30 (d, 1H, J=2.7 Hz), 8.05 (dd, 1H, J=2.1, 12.3 Hz), 7.79 (d, 1H, J=1.2 Hz), 6.57-6.53 (m, 1H), 1.50 (s, 3H)

5th step
The following compound was obtained as described in the 2nd step of Reference Example 141.

5-Fluoro-6-(1H-pyrazol-1-yl)pyridin-3-amine

MS (ESI m/z): 179 (M+H)
RT (min): 0.71

Reference Example 331

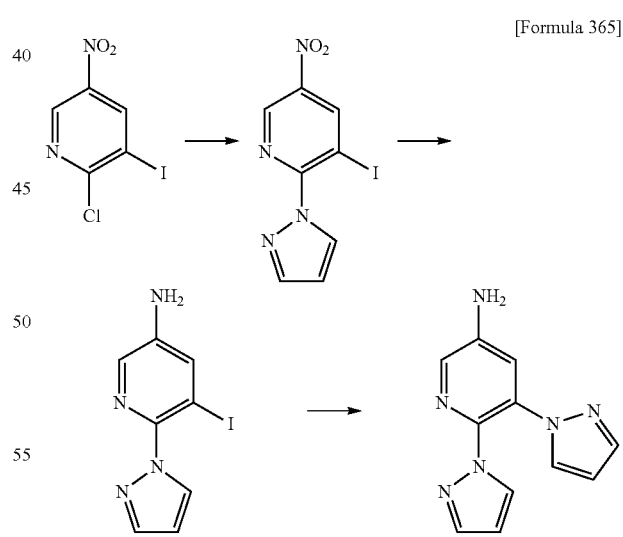

[Formula 365]

1st Step
The following compound was obtained as described in the 1st step of Reference Example 18.

3-Iodo-5-nitro-2-(1H-pyrazol-1-yl)pyridine

MS (ESI m/z): 317 (M+H)
RT (min): 1.30

2nd Step

Iron powder (160 mg) and ammonium chloride (50 mg) were added to an ethanol solution (4 ml) containing the residue obtained in the 1st step, followed by reflux for 5 hours. Insoluble matter was removed, and water was added, followed by extraction with ethyl acetate. The resultant was washed with saturated saline and dried over anhydrous sodium sulfate. Subsequently, the solvent was distilled away under reduced pressure, and a yellow solid of 5-Iodo-6-(1H-pyrazol-1-yl)pyridin-3-amine (210 mg) was thus obtained.

MS (ESI m/z): 287 (M+H)
RT (min): 0.86

3rd Step

L-proline (7 mg), cesium carbonate (60 mg), and copper iodide (12 mg) were added to a dimethyl sulfoxide (1 ml) solution containing 5-iodo-6-(1H-pyrazol-1-yl)pyridin-3-amine (35 mg) in a nitrogen atmosphere, followed by stirring at 100° C. for 5 hours. Water was added to the reaction solution, followed by extraction with ethyl acetate. The resultant was washed with saturated saline and dried over anhydrous sodium sulfate, and the solvent was distilled away under reduced pressure. The obtained residue was purified by silica gel chromatography (n-hexane:ethyl acetate=5:1 to 1:1), and a yellow solid of 5,6-di(1H-pyrazol-1-yl)pyridin-3-amine (4 mg) was obtained.

MS (ESI m/z): 227 (M+H)
RT (min): 0.75

Reference Example 332

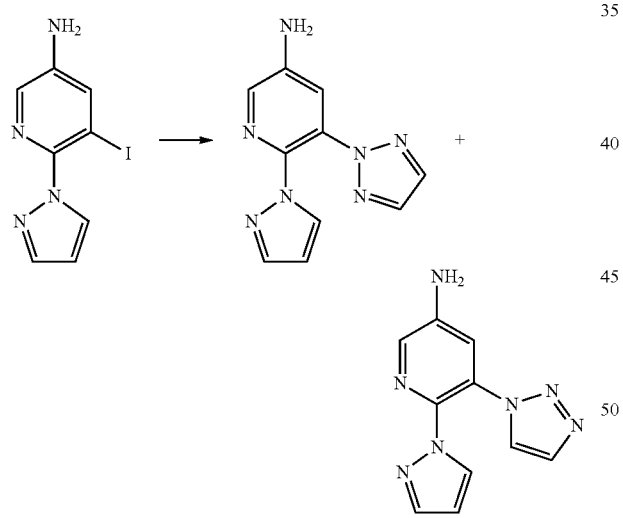

[Formula 366]

The following compounds were obtained as described in the 3rd step of Reference Example 331.

6-(1H-pyrazol-1-yl)-5-(2H-1,2,3-triazol-2-yl)pyridin-3-amine

MS (ESI m/z): 228 (M+H)
RT (min): 0.70
$^1$H-NMR (CDCl$_3$, 300 MHz) δ:8.10-8.00 (m, 1H), 7.90-7.80 (m, 1H), 7.76 (s, 2H), 7.55-7.47 (m, 1H), 7.44-7.36 (m, 1H), 6.41-6.33 (m, 1H), 4.06 (br, 2H)

6-(1H-pyrazol-1-yl)-5-(1H-1,2,3-triazol-1-yl)pyridin-3-amine

MS (ESI m/z): 228 (M+H)
RT (min): 0.59
$^1$H-NMR (CDCl$_3$, 300 MHz) δ:8.08 (d, 1H, J=2.7 Hz), 7.67 (d, 1H, J=1.5 Hz), 7.64-7.62 (m, 2H), 7.49 (d, 1H, J=2.7 Hz), 7.27-7.25 (m, 1H), 6.39-6.36

Reference Example 333

The following compound was obtained with reference to WO2006/95159 A1.

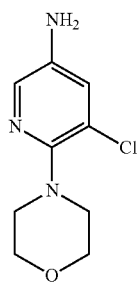

[Formula 367]

5-chloro-6-morpholinopyridin-3-amine

MS (ESI m/z): 214, 216 (M+H)
RT (min): 0.77

Reference Example 334

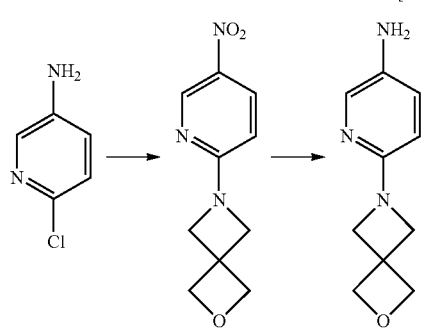

[Formula 368]

1st Step

Potassium carbonate (78 mg) and 2-oxa-6-azaspiro[3.3]heptane (30 mg) were added to a methanol/DMF (1 ml/2 ml) solution containing 2-chloro-5-nitropyridine (30 mg), followed by stirring at 80° C. for 3 hours. The reaction solution was adjusted to room temperature, and water was added, followed by extraction with ethyl acetate. The resultant was washed with saturated saline and dried over anhydrous sodium sulfate, the solvent was distilled away under reduced pressure, the obtained residue was purified by silica gel chromatography (n-hexane:ethyl acetate=1:1 to 1:4), and a white solid of 6-(5-nitropyridin-2-yl)-2-oxa-6-azaspiro[3.3]heptane (23 mg) was thus obtained.

MS (ESI m/z): 222 (M+H)
RT (min): 0.88

2nd Step

The following compound was obtained as described in the 1st step of Reference Example 263.

6-(2-oxa-6-azaspiro[3.3]heptane-6-yl)pyridin-3-amine

MS (ESI m/z): 192 (M+H)
RT (min): 0.30

Reference Example 335

The following compound was obtained as described in the 3rd step of Reference Example 347.

[Formula 369]

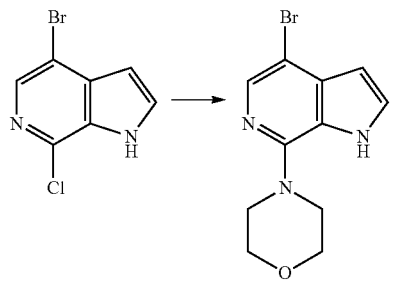

4-(4-bromo-1H-pyrrolo[2,3-c]pyridin-7-yl)morpholine

MS (ESI m/z): 282, 284 (M+H)
RT (min): 0.74

Reference Example 336

The following compound was obtained with reference to WO2007/120729 A2, 2007.

[Formula 370]

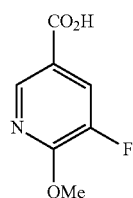

5-fluoro-6-methoxynicotinic acid

Reference Example 337

[Formula 371]

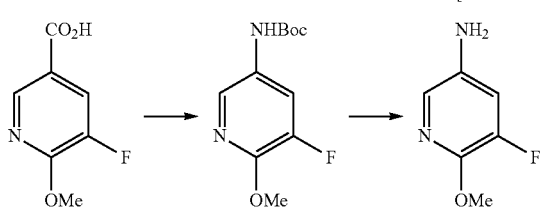

1st Step

Triethylamine (267 μl), tert-butanol (230 μl), and DPPA (413 μl) were added to a toluene (5 ml) solution containing 5-fluoro-6-methoxynicotinic acid (275 mg), followed by reflux for 3 hours. Water was added to the reaction solution, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane:ethyl acetate=10:1 to 3:1), and colorless oily matter of tert-butyl(5-fluoro-6-methoxypyridin-3-yl)carbamate (279 mg) was thus obtained.

MS (ESI m/z): 243 (M+H)
RT (min): 1.46

2nd Step

The following compound was obtained as described in the 2nd step of Reference Example 141.

5-fluoro-6-methoxypyridin-3-amine

MS (ESI m/z): 143 (M+H)
RT (min): 0.56

Reference Example 338

[Formula 372]

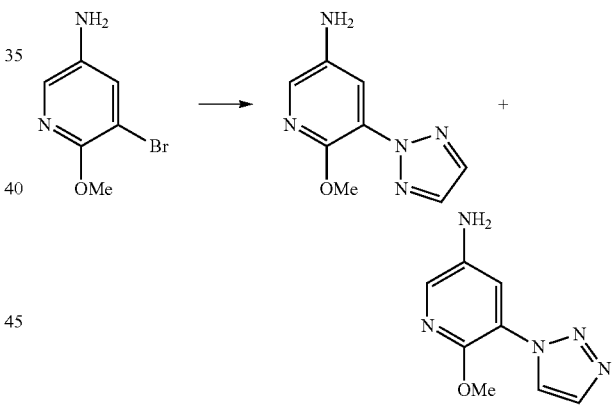

N,N-dimethylglycine (1.27 g), copper iodide (1.88 g), potassium tert-butoxide (4.1 g), and 1H-1,2,3,-triazole (1.7 g) were added to a dimethyl sulfoxide (25 ml) solution containing 5-bromo-6-methoxypyridin-3-amine (25 g), followed by stirring at 130° C. for 2 hours. Water was added to the reaction solution, and the pH was adjusted to pH 4 with 4M hydrochloric acid, followed by extraction with ethyl acetate (×5). The resultant was dried over anhydrous sodium sulfate. Then, the solvent was distilled away under reduced pressure, the obtained residue was purified by silica gel chromatography (n-hexane:ethyl acetate=1:1), and yellow oily matter of 6-methoxy-5-(2H-1,2,3-triazol-2-yl)pyridin-3-amine (1 g) and a light yellow solid of 6-methoxy-5-(1H-1,2,3-triazol-1-yl)pyridin-3-amine (525 mg) were thus obtained.

(Chemical data: See Reference Example 280)

Reference Example 339

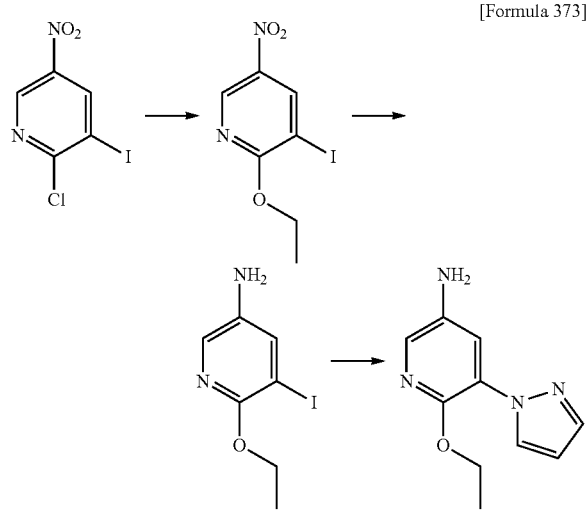

[Formula 373]

1st Step

The following compound was obtained as described in the 1st step of Reference Example 190.

2-Ethoxy-3-iodo-5-nitropyridine

MS (ESI m/z): 295 (M+H)
RT (min): 1.68

2nd Step

The following compound was obtained as described in the 2nd step of Reference Example 331.

6-Ethoxy-5-iodopyridin-3-amine

MS (ESI m/z): 265 (M+H)
RT (min): 1.09

3rd Step

The following compound was obtained as described in Reference Example 337.

6-Ethoxy-5-(1H-pyrazol-1-yl)pyridin-3-amine

MS (ESI m/z): 205 (M+H)
RT (min): 0.91

Reference Example 340

The following compounds were obtained as described in Reference Example 338.

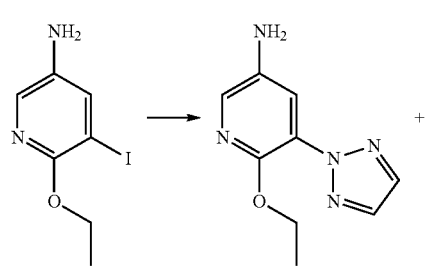

[Formula 374]

+

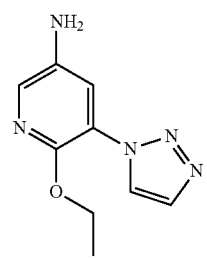

6-Ethoxy-5-(2H-1,2,3-triazol-2-yl)pyridin-3-amine

MS (ESI m/z): 206 (M+H)
RT (min): 0.75
$^1$H-NMR (CDCl$_3$, 300 MHz) δ:7.85 (s, 2H), 7.76 (d, 1H, J=3.3 Hz), 7.34 (d, 1H, J=3.3 Hz), 4.41 (q, 2H, J=7.2 Hz), 3.51 (br, 2H), 1.36 (t, 3H, J=7.2 Hz)

6-Ethoxy-5-(1H-1,2,3-triazol-1-yl)pyridin-3-amine

MS (ESI m/z): 206 (M+H)
RT (min): 0.78
$^1$H-NMR (CDCl$_3$, 300 MHz) δ:8.39 (s, 1H), 7.83-7.80 (m, 1H), 7.77 (d, 1H, J=2.7 Hz), 7.72 (d, 1H, J=2.7 Hz), 4.43 (q, 2H, J=7.2 Hz), 3.60 (br, 2H), 1.40 (t, 3H, J=7.2 Hz)

Reference Example 341

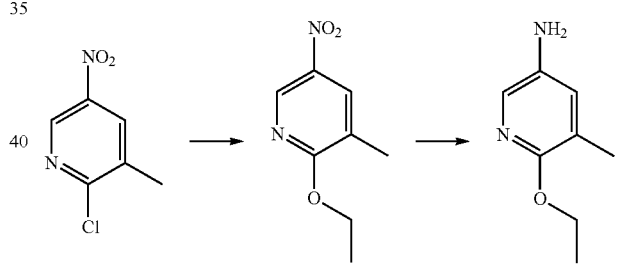

[Formula 375]

1st Step

The following compound was obtained as described in the 1st step of Reference Example 190.

2-Ethoxy-3-methyl-5-nitropyridine

MS (ESI m/z): 183 (M+H)
RT (min): 1.64

2nd Step

The following compound was obtained as described in the 3rd step of Reference Example 161.

6-Ethoxy-5-methylpyridin-3-amine

MS (ESI m/z): 153 (M+H)
RT (min): 0.67

Reference Example 342

The following compound was obtained as described in Reference Example 341.

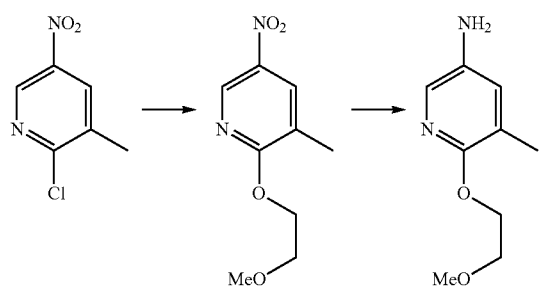

1st Step 2-(Methoxyethoxy)-3-methyl-5-nitropyridine

MS (ESI m/z): 213 (M+H)
RT (min): 1.38

2nd Step 6-(Methoxyethoxy)-5-methylpyridin-3-amine

MS (ESI m/z): 183 (M+H)
RT (min): 0.58

Reference Example 343

[Formula 377]

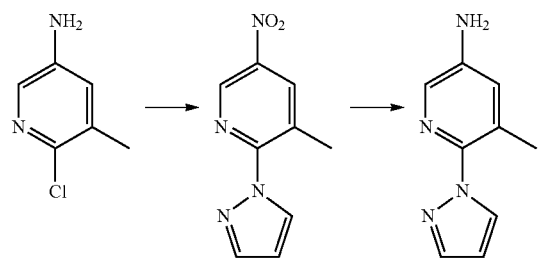

1st Step

Cesium carbonate (75 mg) and pyrazole (12 mg) were added to an N,N-dimethylacetamide (5 ml) solution containing 6-chloro-5-methylpyridin-3-amine (12 mg), followed by reflux for 3.5 hours. Water was added to the reaction solution, followed by extraction with ethyl acetate. The resultant was washed with saturated saline and dried over anhydrous sodium sulfate. Subsequently, the solvent was distilled away under reduced pressure, the obtained residue was purified by silica gel chromatography (n-hexane:ethyl acetate=1:0 to 10:1), and a light yellow solid of 3-methyl-5-nitro-2-(1H-pyrazol-1-yl)pyridine (12 mg) was obtained.

MS (ESI m/z): 205 (M+H)
RT (min): 1.39

2nd Step

The following compound was obtained as described in the 3rd step of Reference Example 161.

5-Methyl-6-(1H-pyrazol-1-yl)pyridin-3-amine

MS (ESI m/z): 175 (M+H)
RT (min): 0.71

Reference Example 344

The following compounds were obtained as described in Reference Example 343.

[Formula 378]

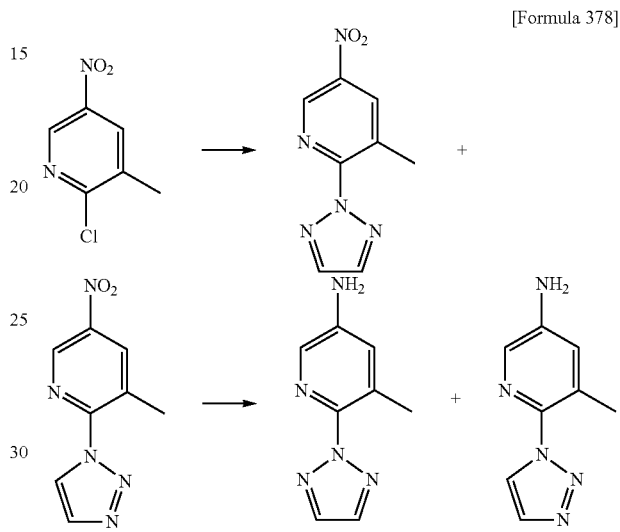

1st Step

3-Methyl-5-nitro-2-(2H-1,2,3-triazol-2-yl)pyridine

MS (ESI m/z): 206 (M+H)
RT (min): 1.08
$^1$H-NMR (CDCl$_3$, 300 MHz) δ:9.28 (d, 1H, J=2.7 Hz), 8.56 (d, 1H, J=2.7 Hz), 7.99 (s, 2H), 2.74 (s, 3H)

3-Methyl-5-nitro-2-(1H-1,2,3-triazol-1-yl)pyridine

MS (ESI m/z): 206 (M+H)
RT (min): 1.01
$^1$H-NMR (CDCl$_3$, 300 MHz) δ:9.21 (d, 1H, J=2.7 Hz), 8.59 (d, 1H, J=2.7 Hz), 8.57-8.54 (m, 1H), 7.89-7.86 (m, 1H), 2.87 (s, 3H)

2nd Step

5-Methyl-6-(2H-1,2,3-triazol-1-yl)pyridin-3-amine

MS (ESI m/z): 176 (M+H)
RT (min): 0.67

5-Methyl-6-(2H-1,2,3-triazol-2-yl)pyridin-3-amine

MS (ESI m/z): 176 (M+H)
RT (min): 0.58

Reference Example 345

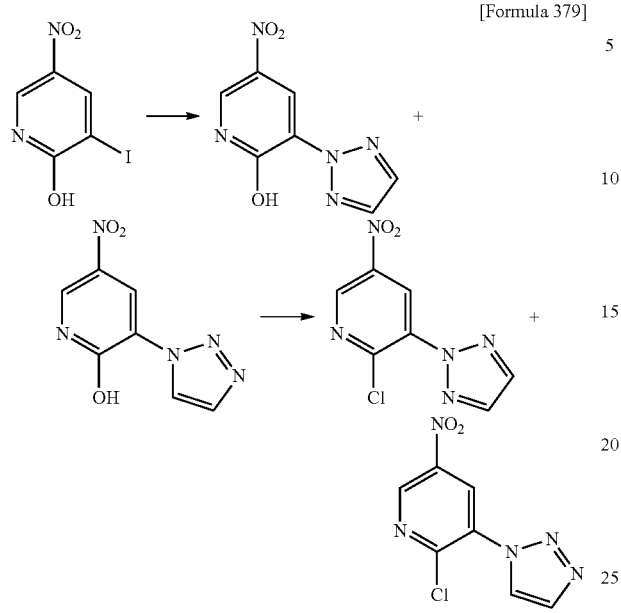

[Formula 379]

1st Step

Cesium carbonate (2.45 g), 1H-1,2,3-triazole (0.52 g), 2,2,6,6-tetramethylheptane-3,5-dione (0.39 ml), and copper iodide (I) (0.72 g) were added to an N-methylpyrrolidone (10 ml) solution containing 2-hydroxy-3-iodo-5-nitropyridine (1.00 g), followed by stirring at 170° C. for 30 minutes. The reaction solution was adjusted to room temperature, water was added, an insoluble precipitate was removed, and 6M hydrochloric acid (1.5 ml) and sodium chloride (10.0 g) were added, followed by extraction with ethyl acetate. Then, the resultant was washed with saturated saline and dried over anhydrous sodium sulfate, and the solvent was distilled away under reduced pressure. The obtained residue was subjected to silica gel chromatography (n-hexane:ethyl acetate=1:1 to 1:4) to remove initial point components, and a mixture of a yellow solid of 2-hydroxy-5-nitro-3-(2H-1,2,3-triazol-2-yl)pyridine and 2-hydroxy-5-nitro-3-(1H-1,2,3-triazol-1-yl)pyridine (385 mg) was thus obtained.

2nd Step

Thionyl chloride (3.9 ml) and DMF (0.39 ml) were added to a mixture of 2-hydroxy-5-nitro-3-(2H-1,2,3-triazol-2-yl)pyridine and 2-hydroxy-5-nitro-3-(1H-1,2,3-triazol-1-yl)pyridine (385 mg), followed by stirring at 90° C. for 2 hours. The reaction solution was adjusted to room temperature, slowly added to ice water, and stirred under ice cooling for 30 minutes, followed by extraction with ethyl acetate. Then, the resultant was washed with saturated saline and dried over anhydrous sodium sulfate. The solvent was distilled away under reduced pressure, the obtained residue was purified by silica gel chromatography (n-hexane:ethyl acetate=9:1 to 2:1), and a yellow solid of 2-chloro-5-nitro-3-(2H-1,2,3-triazol-2-yl)pyridine (177 mg) and a yellow solid of 2-chloro-5-nitro-3-(1H-1,2,3-triazol-1-yl)pyridine (83 mg) were thus obtained.

2-Chloro-5-nitro-3-(2H-1,2,3-triazol-2-yl)pyridine

MS (ESI m/z): 226, 228 (M+H)
RT (min): 1.10
$^1$H-NMR (DMSO-$d_6$, 300 MHz) δ:9.32 (d, 1H, J=2.5 Hz), 8.85 (d, 1H, J=2.5 Hz), 8.01 (s, 2H)

2-Chloro-5-nitro-3-(1H-1,2,3-triazol-1-yl)pyridine

MS (ESI m/z): 226, 228 (M+H)
RT (min): 0.84
$^1$H-NMR (DMSO-$d_6$, 300 MHz) δ:9.38 (d, 1H, J=2.3 Hz), 8.90 (d, 1H, J=2.3 Hz), 8.26 (d, 1H, J=1.0 Hz), 7.97 (d, 1H, J=1.0 Hz).

Reference Example 346

The following compound was obtained as described in Reference Example 341.

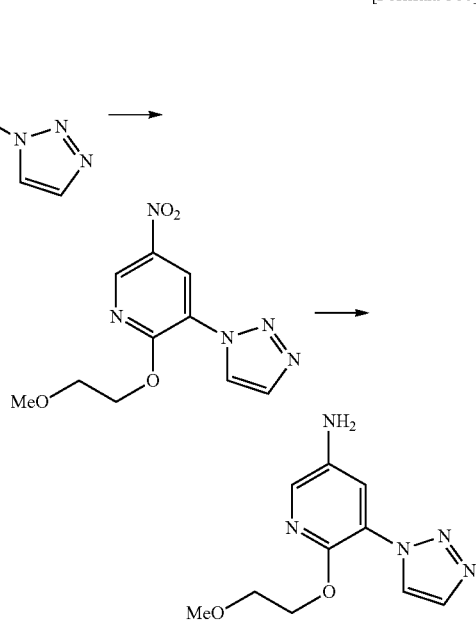

[Formula 380]

2-(2-Methoxyethoxy)-5-nitro-3-(1H-1,2,3-triazol-1-yl)pyridine

MS (ESI m/z): 266 (M+H)
RT (min): 1.26

6-(2-Methoxyethoxy)-5-(1H-1,2,3-triazol-1-yl)pyridin-3-amine

MS (ESI m/z): 236 (M+H)
RT (min): 0.69

Reference Example 347

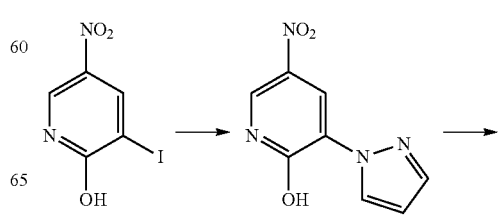

[Formula 381]

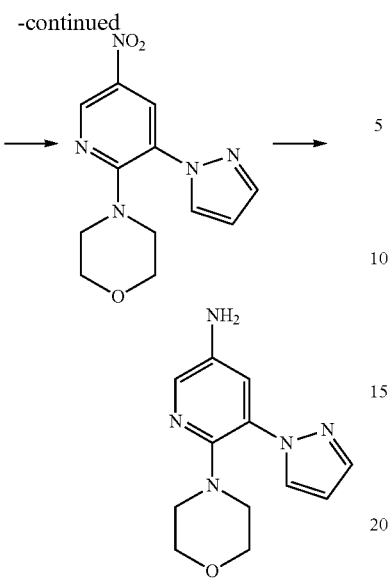

1st Step

Pyrazole (0.60 g), cesium carbonate (3.6 g), N,N-dimethylglycine (0.76 g), and copper iodide (I) (0.76 g) were added to an N,N-dimethylacetamide (20 ml) solution containing 2-hydroxy-3-iodo-5-nitropyridine (2.00 g) in a nitrogen atmosphere, followed by stirring at 90° C. for 2.5 hours. The reaction solution was adjusted to room temperature, water and ethyl acetate were added, and an insoluble precipitate was removed. The pH was adjusted to pH 2 with the addition of 6M hydrochloric acid. Then, organic layer was washed with saturated saline and dried over anhydrous sodium sulfate, the solvent was distilled away under reduced pressure. Ethyl acetate was added to the obtained residue, a solid precipitate was collected by filtration, and a green solid of 2-hydroxy-5-nitro-3-(1H-pyrazol-1-yl)pyridine (0.35 g) was thus obtained. Thereafter, the filtrate was collected, the solvent was distilled away under reduced pressure, the obtained residue was purified by silica gel chromatography (n-hexane:ethyl acetate=3:1 to 0:1), and a light green solid of 2-hydroxy-5-nitro-3-(1H-pyrazol-1-yl)pyridine (1.02 g) was thus obtained.

MS (ESI m/z): 207 (M+H)
RT (min): 0.94

2nd Step

Thionyl chloride (6 ml) and DMF (0.1 ml) were added to 2-hydroxy-5-nitro-3-(1H-pyrazol-1-yl)pyridine (1.37 g), followed by stirring at 80° C. for 2.5 hours. The reaction solution was adjusted to room temperature and slowly added to ice water, followed by extraction with ethyl acetate. The resultant was washed with saturated saline and dried over anhydrous sodium sulfate. Then, the solvent was distilled away under reduced pressure, the obtained residue was purified by silica gel chromatography (n-hexane:ethyl acetate=5:1 to 3:1), and a yellow solid of 2-chloro-5-nitro-3-(1H-pyrazol-1-yl)pyridine (0.12 g) was thus obtained.

MS (ESI m/z): 225, 227 (M+H)
RT (min): 1.14

3rd Step

Morpholine (50 μl) was added to a tetrahydrofuran solution (1 ml) containing 2-chloro-5-nitro-3-(1H-pyrazol-1-yl)pyridine (30 mg), followed by stirring at room temperature for 2 hours. Water was added to the reaction solution, followed by extraction with ethyl acetate. The organic layer was washed with saturated saline and dried over anhydrous sodium sulfate, the solvent was distilled away under reduced pressure, and a yellow solid of 2-morpholino-5-nitro-3-(1H-pyrazol-1-yl)pyridine (37 mg) was thus obtained.

MS (ESI m/z): 276 (M+H)
RT (min): 1.13

4th Step

A methanol (5 ml) solution containing 2-morpholino-5-nitro-3-(1H-pyrazol-1-yl)pyridine (37 mg) was prepared and was subjected to a hydrogenation reaction (room temperature; 1 bar; flow rate: 1 ml/min; 10% Pd/C) using H-cube™. Then, the solvent was distilled away under reduced pressure, and a white solid of 6-morpholino-5-(1H-pyrazol-1-yl)pyridin-3-amine (31 mg) was thus obtained.

MS (ESI m/z): 246 (M+H)
RT (min): 0.70

Reference Example 348

[Formula 382]

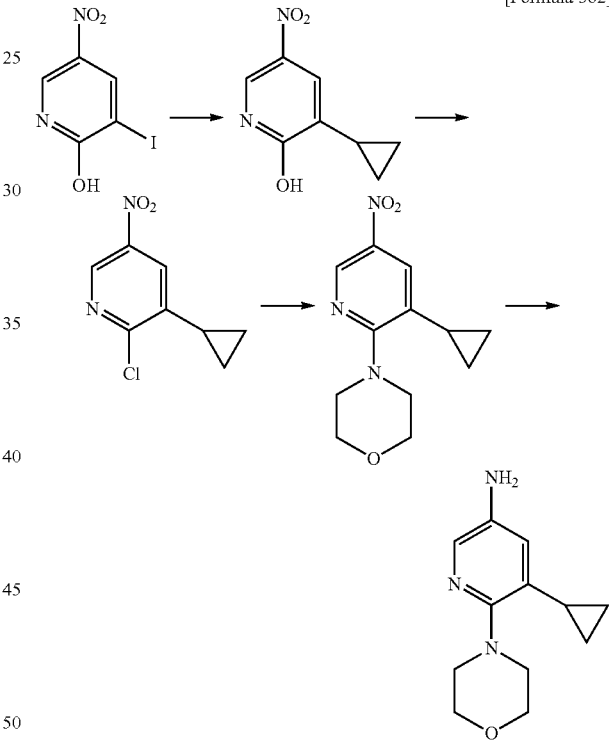

1st Step

Cesium carbonate (3.6 g), cyclopropylboronic acid·monohydrate (1.0 g), tetrakis(triphenylphosphine)palladium (0.87 g), and water (0.2 ml) were added to a 1,4-dioxane (20 ml) solution containing 2-hydroxy-3-iodo-5-nitropyridine (2.00 g) in a nitrogen atmosphere, followed by stirring for 10 hours. Then, N,N-dimethylacetamide (10 ml) was added to the reaction solution, followed by stirring at 120° C. for 7.5 hours. The reaction solution was adjusted to room temperature and the pH was adjusted to pH 2 with the addition of water and 6M hydrochloric acid, followed by extraction with ethyl acetate. The resultant was washed with saturated saline and dried over anhydrous sodium sulfate, the solvent was distilled away under reduced pressure, the obtained residue was purified by silica gel chromatography (n-hexane:

ethyl acetate=3:1 to 0:1), and a white solid of 2-hydroxy-5-nitro-3-cyclopropylpyridine (0.41 g) was thus obtained.
MS (ESI m/z): 181 (M+H)
RT (min): 1.04
2nd, 3rd, and 4th steps The following compounds were obtained as described in the 2nd, 3rd, and 4th steps of Reference Example 347.

2-Chloro-5-nitro-3-(1H-pyrazol-1-yl)pyridine

MS (ESI m/z): 199, 201 (M+H)
RT (min): 1.44

2-Morpholino-5-nitro-3-cyclopropylpyridine

MS (ESI m/z): 250 (M+H)
RT (min): 1.44

6-Morpholino-5-cyclopropylpyridin-3-amine

MS (ESI m/z): 220 (M+H)
RT (min): 0.63

Reference Example 349

[Formula 383]

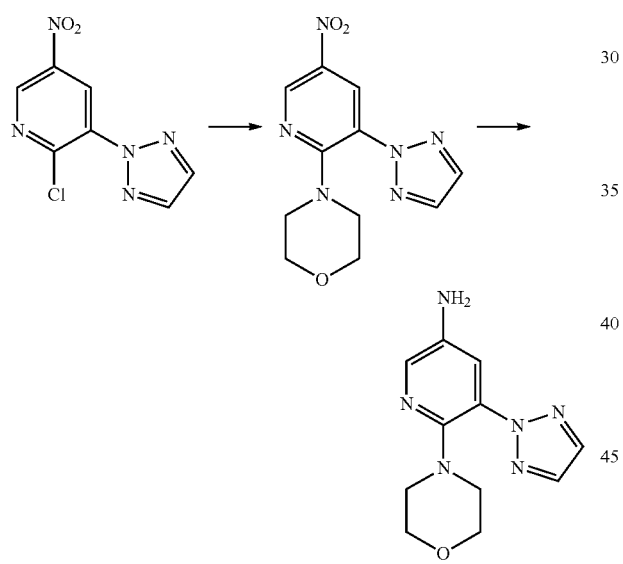

1st Step
Morpholine (0.5 ml) was added to a 1,4-dioxane solution (1 ml) containing 2-chloro-5-nitro-3-(2H-1,2,3-triazol-2-yl)pyridine (30 mg), followed by stirring at room temperature for 30 minutes. Water was added to the reaction solution, followed by extraction with ethyl acetate. The resultant was washed with saturated saline and dried over anhydrous sodium sulfate, the solvent was distilled away under reduced pressure, and a yellow solid of 5-nitro-2-morpholino-3-(2H-1,2,3-triazol-2-yl)pyridine (33 mg) was thus obtained.
MS (ESI m/z): 277 (M+H)
RT (min): 1.15
2nd Step
A methanol (15 ml) solution containing 5-nitro-2-morpholino-3-(2H-1,2,3-triazol-2-yl)pyridine (33 mg) was prepared and was subjected to a hydrogenation reaction (room temperature; 1 bar; flow rate: 1 ml/min; 10% Pd/C) using H-cube™. Then, the solvent was distilled away under reduced pressure, and colorless oily matter of 6-morpholino-3-(2H-1,2,3-triazol-2-yl)pyridin-4-amine (30 mg) was thus obtained.
MS (ESI m/z): 247 (M+H)
RT (min): 0.60

Reference Example 350

The following compounds were obtained as described in Reference Example 349.

[Formula 384]

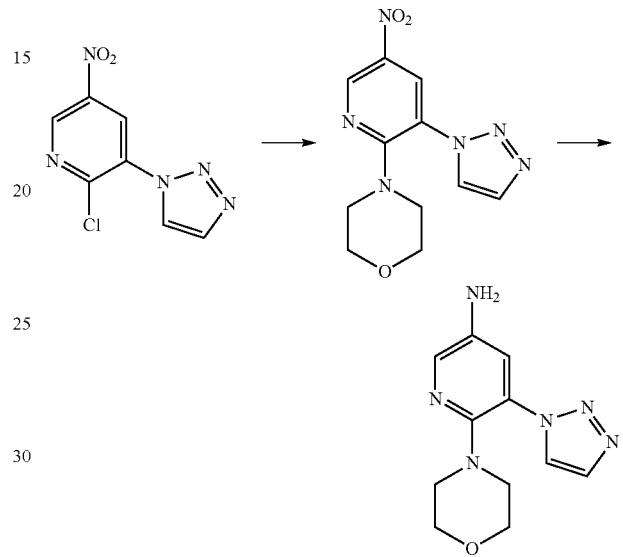

5-Nitro-2-morpholino-3-(1H-1,2,3-triazol-1-yl)pyridine

MS (ESI m/z): 277 (M+H)
RT (min): 0.97

6-Morpholino-3-(1H-1,2,3-triazol-1-yl)pyridin-4-amine

MS (ESI m/z): 247 (M+H)
RT (min): 0.61

Reference Example 351

The following compounds were obtained as described in Reference Example 254.

[Formula 385]

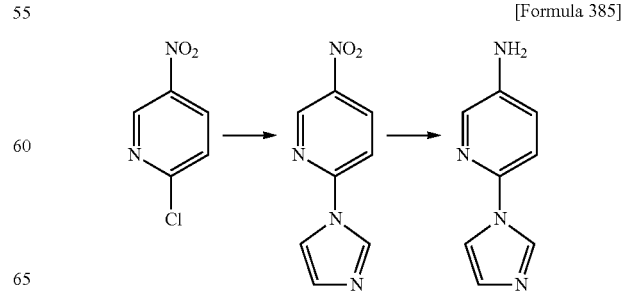

2-(Imidazol-1-yl)-5-nitropyridine

MS (ESI m/z): 191 (M+H)
RT (min): 0.48

6-(Imidazol-1-yl)-pyridin-3-amine

MS (ESI m/z): 161 (M+H)
RT (min): 0.28

Reference Example 352

The following compounds were obtained as described in Reference Example 254.

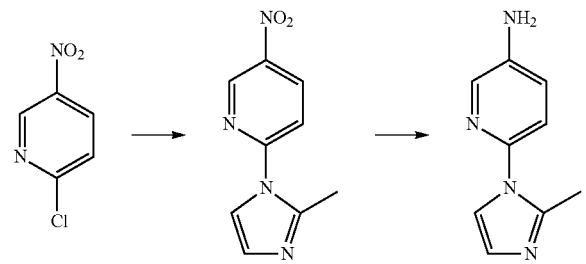

[Formula 386]

2-(2-Methylimidazol-1-yl)-5-nitropyridine

MS (ESI m/z): 205 (M+H)
RT (min): 0.44

6-(2-Methylimidazol-1-yl)-pyridin-3-amine

MS (ESI m/z): 175 (M+H)
RT (min): 0.28

Reference Example 353

The following compounds were obtained as described in Reference Example 254.

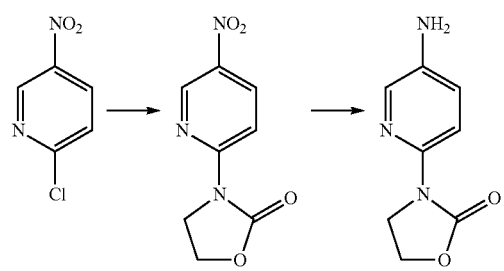

[Formula 387]

2-((Oxazolidine-2-one)-3-yl)-5-nitropyridine

MS (ESI m/z): 210 (M+H)
RT (min): 0.95

6-((Oxazolidine-2-one)-1-yl)-pyridin-3-amine

MS (ESI m/z): 180 (M+H)
RT (min): 0.36

Reference Example 354

The following compound was obtained as described in Reference Example 22.

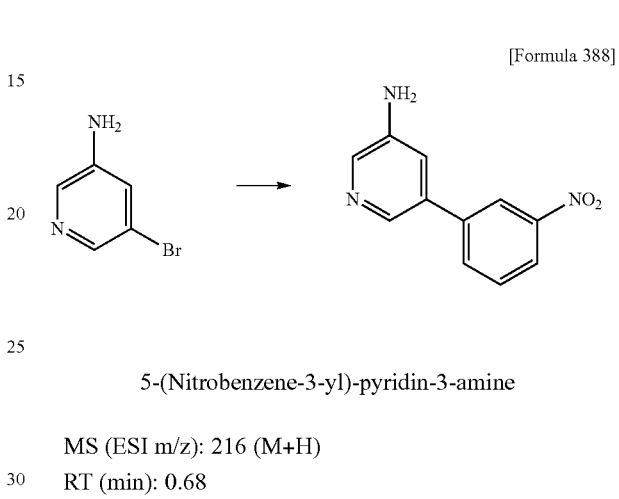

[Formula 388]

5-(Nitrobenzene-3-yl)-pyridin-3-amine

MS (ESI m/z): 216 (M+H)
RT (min): 0.68

Reference Example 355

The following compound was obtained with reference to Synthesis, 1990, #6, pp. 499-501.

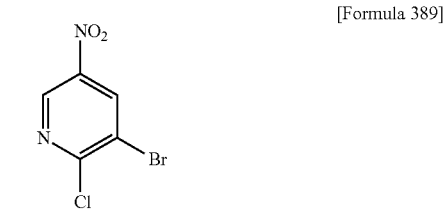 [SMILES: O=[N+]([O-])c1cnc(Cl)c(Br)c1]

[Formula 389]

3-Bromo-2-chloro-5-nitropyridine

Reference Example 356

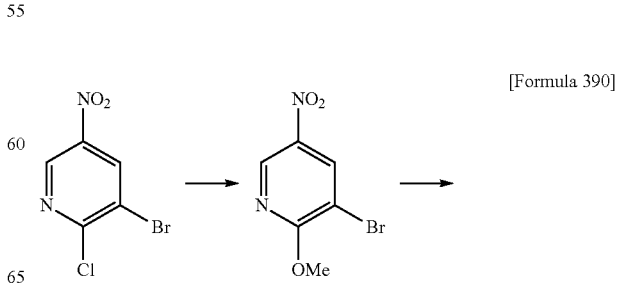

[Formula 390]

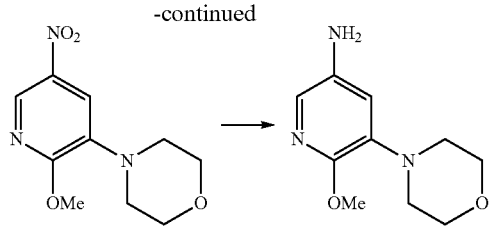
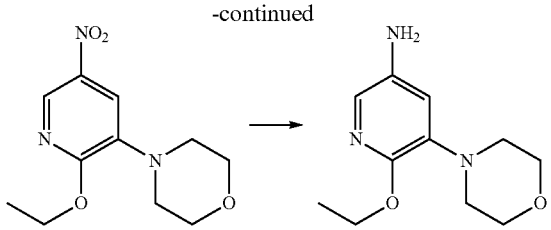

1st Step

Sodium methoxide (28% methanol solution) (2 ml) was added to a methanol (2 ml) solution containing 3-bromo-2-chloro-5-nitropyridine (100 mg), followed by stirring at room temperature for 1 hour. Water was added to the reaction solution, followed by extraction with ethyl acetate. The resultant was washed with saturated saline and dried over anhydrous sodium sulfate, the solvent was distilled away under reduced pressure, and a yellow solid of 3-bromo-2-methoxy-5-nitropyridine (96 mg) was thus obtained.

MS (ESI m/z): 233, 235 (M+H)
RT (min): 1.43

2nd Step

Morpholine (54 μl), cesium carbonate (336 mg), Pd$_2$(dba)$_3$ (57 mg), and Xantphos (72 mg) were added to a 1,4-dioxane (3 ml) solution containing 3-bromo-2-methoxy-5-nitropyridine (96 mg) in a nitrogen atmosphere, followed by stirring at 100° C. for 10 hours. The reaction solution was adjusted to room temperature, and water was added, followed by extraction with ethyl acetate. The resultant was washed with saturated saline and dried over anhydrous sodium sulfate, and the solvent was distilled away under reduced pressure. The obtained residue was purified by silica gel chromatography (n-hexane:ethyl acetate=4:1 to 2:1), and a yellow solid of 2-methoxy-3-morpholino-5-nitropyridine (54 mg) was thus obtained.

MS (ESI m/z): 240 (M+H)
RT (min): 1.21

3rd Step

A methanol (15 ml) solution containing 2-methoxy-3-morpholino-5-nitropyridine (27 mg) was prepared and was subjected to a hydrogenation reaction (room temperature; 1 bar; flow rate: 1 ml/min; 10% Pd/C) using H-cube™. Then, the solvent was distilled away under reduced pressure, and colorless oily matter of 6-methoxy-5-morpholinopyridin-3-amine (28 mg) was thus obtained.

MS (ESI m/z): 210 (M+H)
RT (min): 0.53

Reference Example 357

The following compounds were obtained as described in Reference Example 356.

[Formula 391]

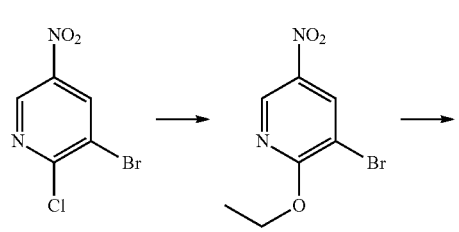

3-Bromo-2-ethoxy-5-nitropyridine

MS (ESI m/z): 247, 249 (M+H)
RT (min): 1.62

2-Ethoxy-3-morpholino-5-nitropyridine

MS (ESI m/z): 254 (M+H)
RT (min): 1.39

6-Ethoxy-5-morpholinopyridin-3-amine

MS (ESI m/z): 224 (M+H)
RT (min): 0.65

Reference Example 358

[Formula 392]

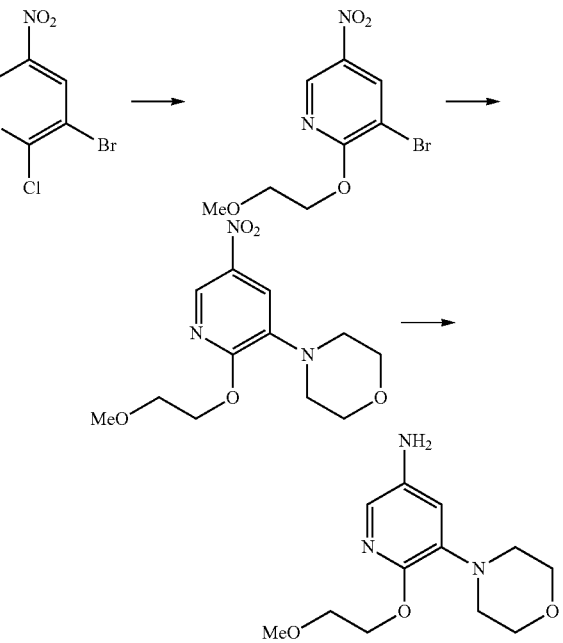

1st Step 2-methoxyethanol (133 μl) was added to a tetrahydrofuran solution (50 ml) containing sodium hydride (60% in oil, 51 mg) under ice cooling, followed by stirring at room temperature for 30 minutes. The reaction solution was ice-cooled again, and 3-bromo-2-chloro-5-nitropyridine (200 mg) was added, followed by stirring at room temperature for 1 hour. Water was added to the reaction solution, followed by extraction with ethyl acetate. The resultant was washed with saturated saline and dried over anhydrous sodium sulfate, and the solvent was distilled away under reduced pressure. The obtained residue was purified by silica gel chromatography (n-hexane:ethyl acetate=4:1 to 1:1), and a yellow solid of 2-(2-methoxyethoxy)-3-morpholino-5-nitropyridine (97 mg) was obtained.

MS (ESI, m/z): 277, 279 (M+H)

RT (min): 1.40

2nd and 3rd steps

The following compounds were obtained as described in the 2nd and 3rd steps of Reference Example 356.

2-(2-Methoxyethoxy)-3-morpholino-5-nitropyridine

MS (ESI m/z): 284 (M+H)

RT (min): 1.23

6-(2-Methoxyethoxy)-5-morpholinopyridin-3-amine

MS (ESI m/z): 254 (M+H)

RT (min): 0.58

Reference Example 359

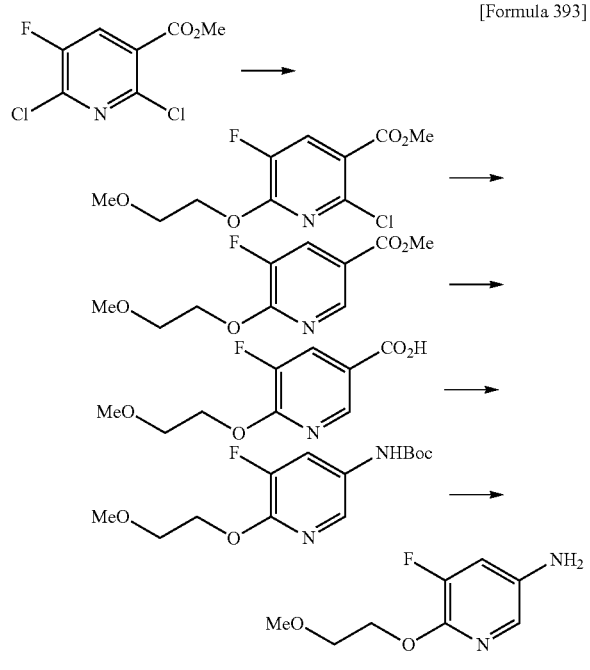

[Formula 393]

1st Step

The following compound was obtained as described in the 1st step of Reference Example 358.

Methyl 2-chloro-5-fluoro-6-(2-methoxyethoxy)-fluoronicotinate

MS (ESI m/z): 264, 266 (M+H)

RT (min): 1.38

2nd, 3rd, 4th, and 5th steps

The following compounds were obtained as described in the 2nd, 3rd, 4th, and 5th steps of Reference Example 330.

Methyl 6-(2-methoxyethoxy)-fluoronicotinate

MS (ESI m/z): 230 (M+H)

RT (min): 1.23

6-(2-Methoxyethoxy)-5-fluoronicotinate

MS (ESI m/z): 216 (M+H)

RT (min): 0.93 tert-Butyl(5-fluoro-6-(2-methoxyethoxy)pyridin-3-yl)carbamate

MS (ESI m/z): 287 (M+H)

RT (min): 1.45

6-(2-Methoxyethoxy)-5-fluoropyridin-3-amine

MS (ESI m/z): 187 (M+H)

RT (min): 0.64

Reference Example 360

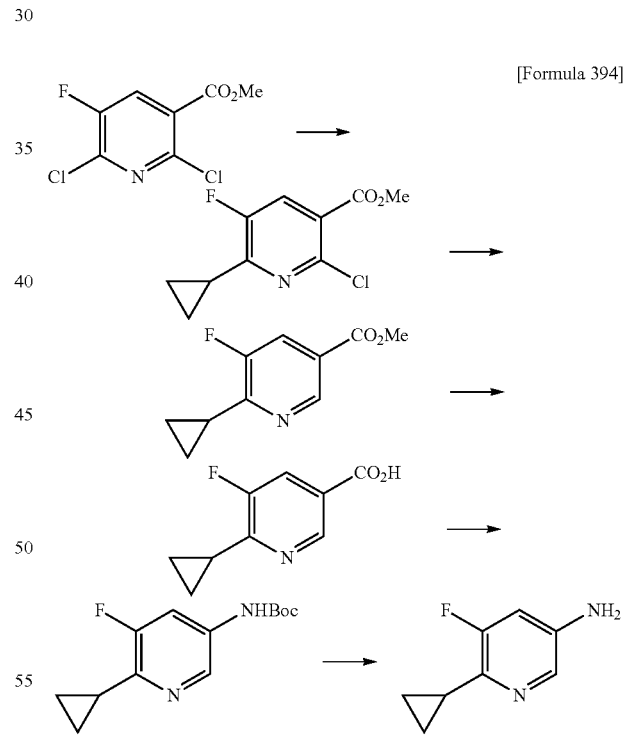

[Formula 394]

1st Step

The following compound was obtained as described in Reference Example 22.

Methyl 2-chloro-6-cyclopropyl-5-fluoronicotinate

MS (ESI m/z): 230, 232 (M+H)

RT (min): 1.62

2nd, 3rd, 4th, and 5th steps

The following compounds were obtained as described in the 2nd, 3rd, 4th, and 5th steps of Reference Example 330.

Methyl 6-cyclopropyl-5-fluoronicotinate

MS (ESI m/z): 196 (M+H)
RT (min): 1.46

6-Cyclopropyl-5-fluoronicotinic acid

MS (ESI m/z): 182 (M+H)
RT (min): 1.10 tert-Butyl(6-cyclopropyl-5-fluoropyridin-3-yl)carbamate

MS (ESI m/z): 253 (M+H)
RT (min): 1.64

6-Cyclopropyl-5-fluoropyridin-3-amine

MS (ESI m/z): 153 (M+H)
RT (min): 0.57

Reference Example 361

[Formula 395]

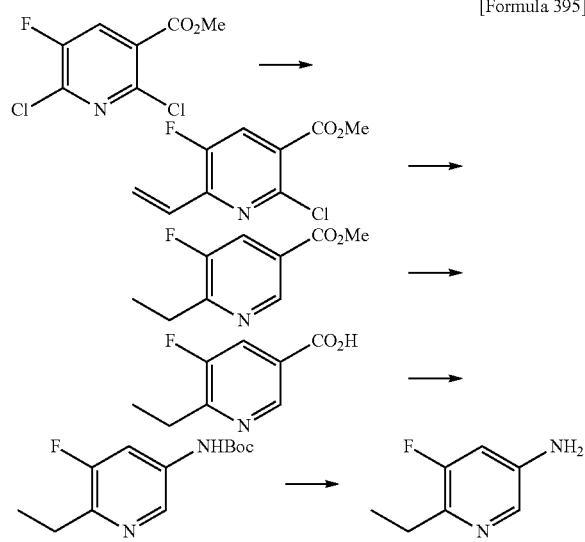

1st Step

The following compound was obtained as described in Reference Example 22.

Methyl 2-chloro-5-fluoro-6-vinylnicotinate

MS (ESI m/z): 216, 218 (M+H)
RT (min): 1.49

2nd, 3rd, 4th, and 5th steps

The following compounds were obtained as described in the 2nd, 3rd, 4th, and 5th steps of Reference Example 330.

Methyl 6-ethyl-5-fluoronicotinate

MS (ESI m/z): 184 (M+H)
RT (min): 1.27

6-Ethyl-5-fluoronicotinic acid

MS (ESI m/z): 170 (M+H)
RT (min): 0.93 tert-Butyl(6-ethyl-5-fluoropyridin-3-yl)carbamate

MS (ESI m/z): 241 (M+H)
RT (min): 1.48

6-Ethyl-5-fluoropyridin-3-amine

MS (ESI m/z): 141 (M+H)
RT (min): 0.46

Reference Example 362

[Formula 396]

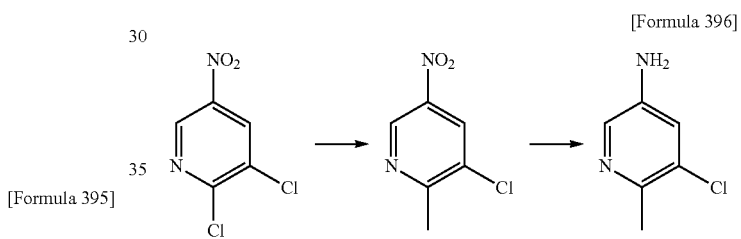

1st Step

Cesium carbonate (338 mg), methylboronic acid (47 mg), and tetrakis(triphenylphosphine)palladium (60 mg) were added to a 1,4-dioxane (3 ml) solution containing 2,3-dichloro-5-nitropyridine (100 mg), followed by stirring at 100° C. for 6 hours. The reaction solution was adjusted to room temperature, and water was added, followed by extraction with ethyl acetate. The resultant was washed with saturated saline and dried over anhydrous sodium sulfate, the solvent was distilled away under reduced pressure, and 3-chloro-2-methyl-5-nitropyridine (344 mg) was thus obtained.

2nd Step

Water (1 ml), iron powder (344 mg), and ammonium chloride (172 mg) were added to an ethanol solution (5 mL) containing the crude product (344 mg) obtained in the 1st step, followed by stirring at 90° C. for 1 hour. The reaction solution was adjusted to room temperature, water and ethyl acetate were added, and insoluble matter was removed by filtration. The obtained organic layer was washed with saturated saline and dried over anhydrous sodium sulfate, and the solvent was distilled away under reduced pressure. The obtained residue was purified by silica gel chromatography (hexane:ethyl acetate=4:1 to 1:1), and yellow oily matter of 5-chloro-6-methylpyridin-3-amine (53 mg) was thus obtained.

MS (ESI m/z): 143, 145 (M+H)
RT (min): 0.42

Reference Example 363

The following compound was obtained as described in Reference Example 362.

[Formula 397]

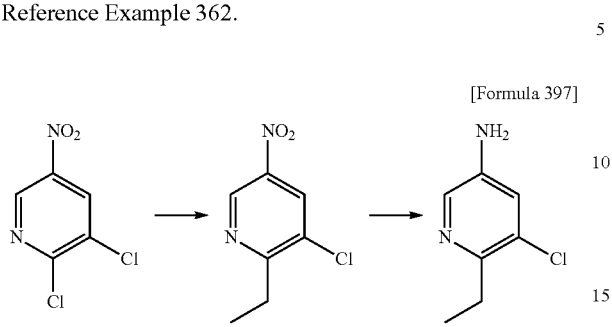

5-Chloro-6-ethylpyridin-3-amine

MS (ESI m/z): 157, 159 (M+H)
RT (min): 0.59

Reference Example 364

The following compound was obtained as described in Reference Example 362.

[Formula 398]

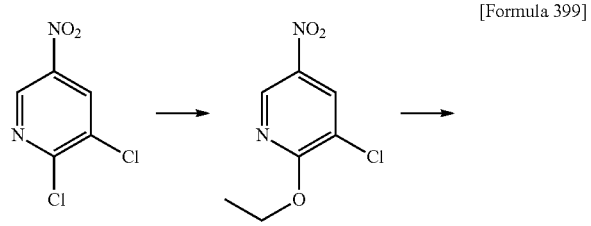

5-Chloro-6-cyclopropylpyridin-3-amine

MS (ESI m/z): 169, 171 (M+H)
RT (min): 0.75

Reference Example 365

The following compound was obtained as described in the 1st step of Reference Example 356 and the 2nd step of Reference Example 362.

[Formula 399]

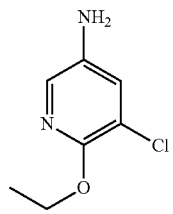

5-Chloro-6-ethoxypyridin-3-amine

MS (ESI m/z): 173, 175 (M+H)
RT (min): 1.08

Reference Example 366

The following compound was obtained as described in the 1st step of Reference Example 358 and the 2nd step of Reference Example 362.

[Formula 400]

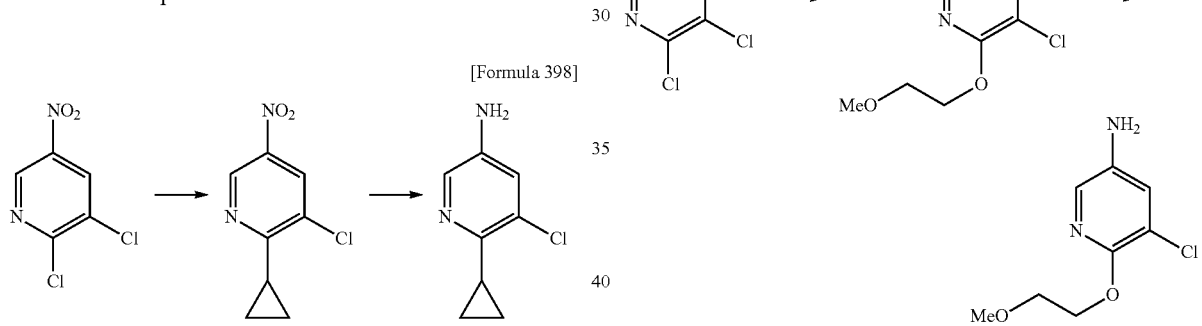

5-Chloro-6-(2-methoxyethoxy)pyridin-3-amine

MS (ESI m/z): 203, 205 (M+H)
RT (min): 0.83

Reference Example 367

[Formula 401]

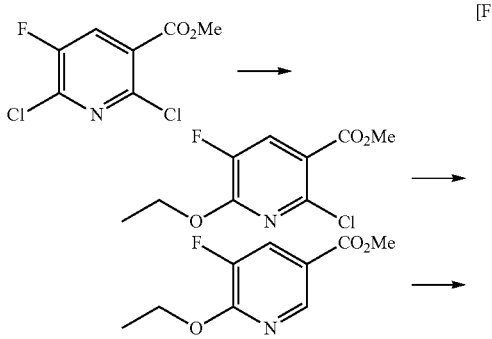

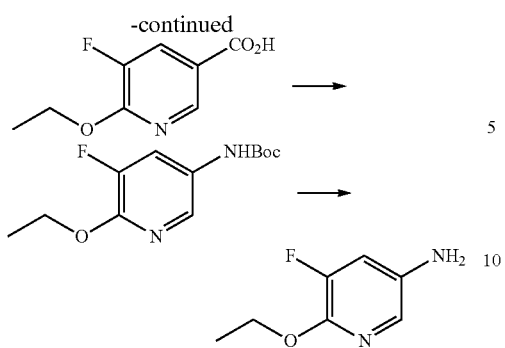

1st Step

The following compound was obtained as described in the 1st step of Reference Example 358.

Methyl 2-chloro-6-ethoxy-5-fluoronicotinate

MS (ESI, m/z): 234, 236 (M+H)
RT (min): 1.58

2nd, 3rd, 4th, and 5th steps

The following compounds were obtained as described in the 2nd, 3rd, 4th, and 5th steps of Reference Example 330.

Methyl 6-ethoxy-5-fluoronicotinate

MS (ESI m/z): 200 (M+H)
RT (min): 1.44

6-Ethoxy-5-fluoronicotinic acid

MS (ESI m/z): 1.10 (M+H)
RT (min): 186 tert-Butyl(6-ethoxy-5-fluoropyridin-3-yl)carbamate

MS (ESI m/z): 257 (M+H)
RT (min): 1.59

6-Ethoxy-5-fluoropyridin-3-amine

MS (ESI m/z): 157 (M+H)
RT (min): 0.76

Reference Example 368

[Formula 402]

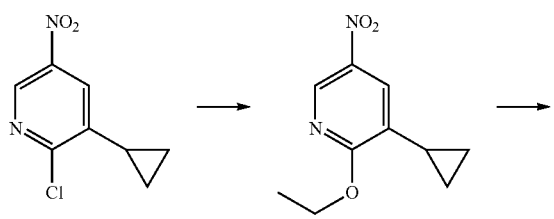

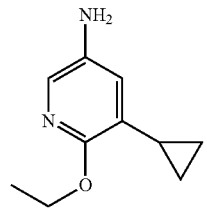

1st Step

The following compound was obtained as described in the 1st step of Reference Example 358.

3-Cyclopropyl-2-ethoxy-5-nitropyridine

MS (ESI m/z): 209 (M+H)
RT (min): 1.72

2nd Step

The following compound was obtained as described in the 2nd step of Reference Example 330.

6-Ethoxy-3-cyclopropylpyridin-3-amine

MS (ESI m/z): 179 (M+H)
RT (min): 0.83

Reference Example 369

The following compound was obtained as described in Reference Example 368.

[Formula 403]

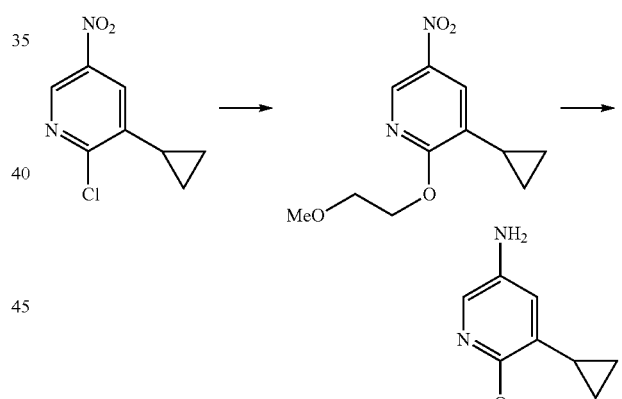

1st Step

3-Cyclopropyl-2-(2-methoxyethoxy)-5-nitropyridine

MS (ESI m/z): 239 (M+H)
RT (min): 1.50

2nd Step 6-(2-Methoxyethoxy)-3-cyclopropylpyridin-3-amine

MS (ESI m/z): 209 (M+H)
RT (min): 0.73

Reference Example 370

The following compounds were obtained as described in Reference Example 368.

[Formula 404]

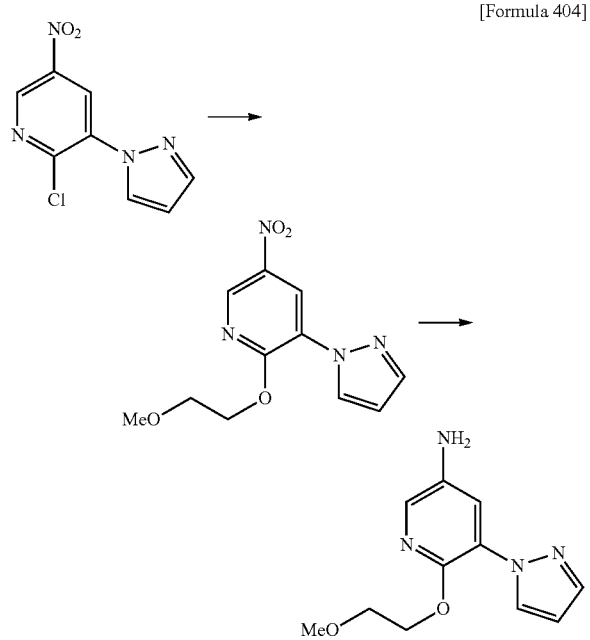

1st Step 2-(2-Methoxyethoxy)-5-nitro-3-(1H-pyrazol-1-yl)pyridine

MS (ESI m/z): 265 (M+H)
RT (min): 1.34

2nd Step 6-(2-Methoxyethoxy)-5-(1H-pyrazol-1-yl)pyridin-3-amine

MS (ESI m/z): 235 (M+H)
RT (min): 0.80

Reference Example 371

[Formula 405]

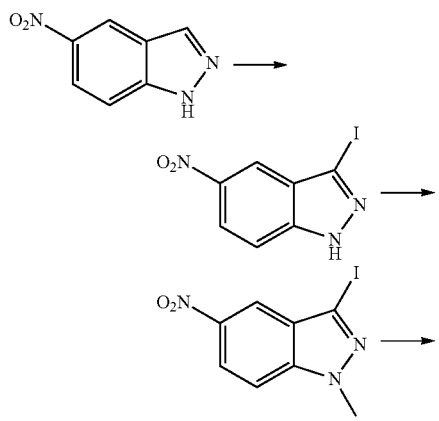

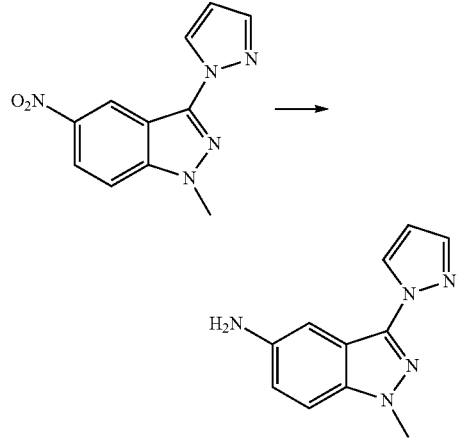

1st Step

Potassium hydroxide (6.45 g) and iodine (15.6 g) were added to a DMF (60 ml) solution containing 5-nitroindazole (5.0 g), followed by stirring at 65° C. for 1 hour. The reaction solution was adjusted to room temperature and poured into a saturated aqueous sodium hydrogen carbonate solution, a solid precipitate was collected by filtration, and a yellow solid of 3-iodo-5-nitro-1H-indazole (6.83 g) was thus obtained.

MS (ESI m/z): 290 (M+H)
RT (min): 1.28

2nd Step

The following compound was obtained as described in Reference Example 103.

3-Iodo-1-methyl-5-nitro-1H-indazole

MS (ESI m/z): 304 (M+H)
RT (min): 1.41

3rd Step

The following compound was obtained as described in Reference Example 338.

1-Methyl-5-nitro-3-(1H-pyrazol-1-yl)-1H-indazole

MS (ESI m/z): 244 (M+H)
RT (min): 1.41

4th Step

The following compound was obtained as described in the 2nd step of Reference Example 190.

1-Methyl-3-(1H-pyrazol-1-yl)-1H-indazol-5-amine

MS (ESI m/z): 214 (M+H)
RT (min): 1.61

Reference Example 372

[Formula 406]

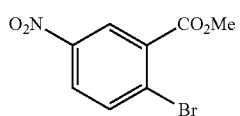

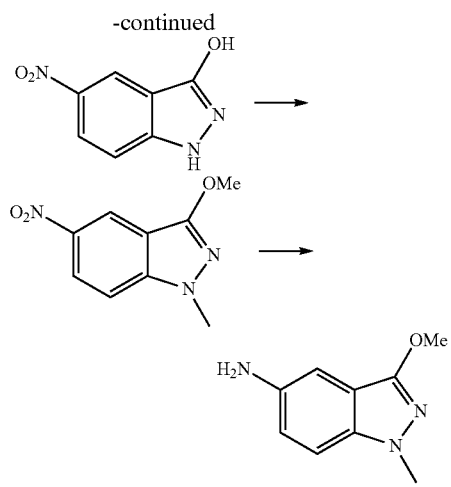

1st Step

Hydrazine•monohydrate (6.38 ml) was added to an ethanol (5 ml) solution containing methyl 2-bromo-5-nitrobenzoate (3.41 g), followed by reflux for 1 hour. The reaction solution was adjusted to room temperature, water and 1M hydrochloric acid were added, and an insoluble precipitate was collected by filtration. Thus, a light brown solid of 5-nitro-1H-indazol-3-ol (1.15 g) was obtained.

MS (ESI m/z): 180 (M+H)
RT (min): 0.73

2nd Step

The following compound was obtained as described in Reference Example 103.

3-Methoxy-1-methyl-5-nitro-1H-indazole

MS (ESI m/z): 208 (M+H)
RT (min): 1.33

3rd Step

The following compound was obtained as described in the 2nd step of Reference Example 190.

3-Methoxy-1-methyl-1H-indazol-5-amine

MS (ESI m/z): 178 (M+H)
RT (min): 0.44

Reference Example 373

[Formula 407]

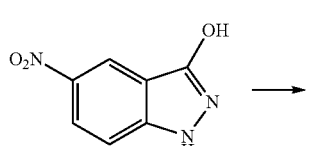

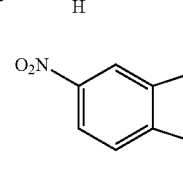

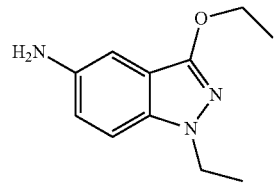

The following compounds were obtained as described in the 2nd and 3rd steps of Reference Example 372.

1st Step

3-Ethoxy-1-ethyl-5-nitro-1H-indazole

MS (ESI m/z): 236 (M+H)
RT (min): 1.66

2nd Step

3-Ethoxy-1-ethyl-1H-indazol-5-amine

MS (ESI m/z): 206 (M+H)
RT (min): 0.64

Reference Example 374-1

The following compound was synthesized with reference to WO2010/097248.

[Formula 408]

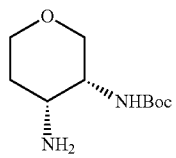

tert-Butyl((3R,4R)-4-aminotetrahydro-2H-pyran-3-yl)carbamate

Reference Example 374-2

The following compound was synthesized with reference to WO2010/097248.

[Formula 409]

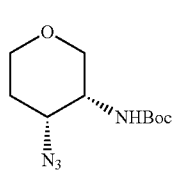

tert-Butyl((3R,4R)-4-azidotetrahydro-2H-pyran-3-yl)carbamate

Reference Example 375

[Formula 410]

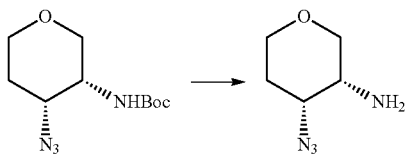

1st Step

TFA (1 ml) was added to a chloroform solution (1 ml) containing tert-butyl((3R,4R)-4-azidotetrahydro-2H-pyran-3-yl)carbamate (60 mg), followed by stirring at room temperature for 1 hour. The pH of the reaction solution was adjusted to pH 12 with the addition of water, chloroform, and a 5M sodium hydroxide aqueous solution. The organic layer was washed with saturated saline and dried over anhydrous sodium sulfate, the solvent was distilled away under reduced pressure, and colorless oily matter of (3R,4R)-4-azidotetrahydro-2H-pyran-3-amine (22 mg) was thus obtained.

Reference Example 376

The following compound was synthesized with reference to WO2005/066176.

[Formula 411]

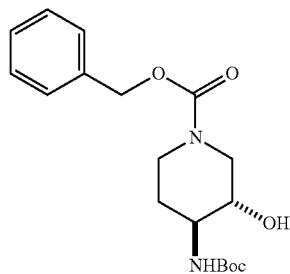

(trans)-Benzyl 4-((tert-butoxycarbonyl)amino)-3-hydroxypiperidin-1-carboxylate

Reference Example 377

[Formula 412]

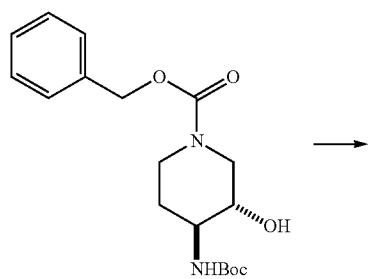

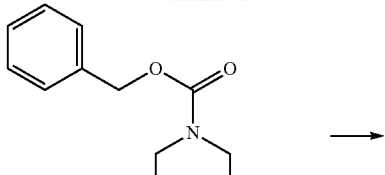

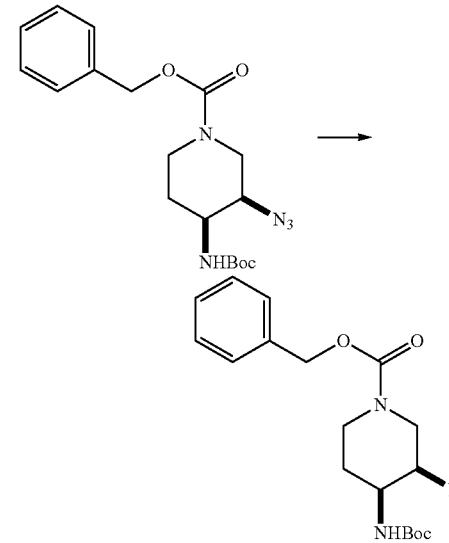

1st Step

Triethylamine (209 µl) and methanesulfonyl chloride (93 µl) were added to a dichloromethane (5 ml) solution containing (trans)-benzyl 4-((tert-butoxycarbonyl)amino)-3-hydroxypiperidin-1-carboxylate (350 mg) under ice cooling, followed by stirring at room temperature for 5 hours. The reaction solution was ice-cooled again, and water was added, followed by extraction with ethyl acetate. The organic layer was washed with saturated saline and dried over anhydrous sodium sulfate, the solvent was distilled away under reduced pressure, the obtained residue was purified by silica gel chromatography (n-hexane:ethyl acetate=4:1 to 3:2), and colorless oily matter of (trans)-benzyl 4-((tert-butoxycarbonyl)amino)-3-((methylsulfonyl)oxy)piperidin-1-carboxylate (535 mg) was thus obtained.

2nd Step

Sodium acetate (204 mg) and sodium azide (161 mg) were added to a DMF (5 mL) solution containing (trans)-benzyl 4-((tert-butoxycarbonyl)amino)-3-((methylsulfonyl)oxy)piperidin-1-carboxylate (532 mg), followed by stirring at 80° C. for 4 hours. The pH of the reaction solution was adjusted to pH 12 with the addition of water and a 2M sodium hydroxide aqueous solution, followed by extraction with ethyl acetate. The organic layer was washed with saturated saline and dried over anhydrous sodium sulfate, the solvent was distilled away under reduced pressure, the obtained residue was purified by silica gel chromatography (n-hexane:ethyl acetate=4:1 to 2:1), and a white solid of (cis)-benzyl 3-azido-4-((tert-butoxycarbonyl)amino)piperidin-1-carboxylate (124 mg) was thus obtained.

3rd Step

Triphenylphosphine (172 mg) was added to a tetrahydrofuran/water (4.95/0.05 ml) solution containing (cis)-benzyl 3-azido-4-((tert-butoxycarbonyl)amino)piperidin-1-carboxylate (123 mg), followed by stirring at 100° C. for 6 hours. The pH of the reaction solution was adjusted to pH 1 with the addition of water and 2M hydrochloric acid. The reaction solution was washed with ethyl acetate. The pH of the aqueous layer was adjusted to pH 13 with the addition of a 5M sodium hydroxide aqueous solution, followed by extraction with ethyl acetate. The obtained organic layer was washed with saturated saline and dried over anhydrous sodium sulfate, the solvent was distilled away under reduced pressure, and colorless oily matter of (cis)-benzyl 3-amino-4-((tert-butoxycarbonyl)amino)piperidin-1-carboxylate (61 mg) was thus obtained.

Reference Example 378

The following compounds were synthesized with reference to Reference Example 377.

[Formula 413]

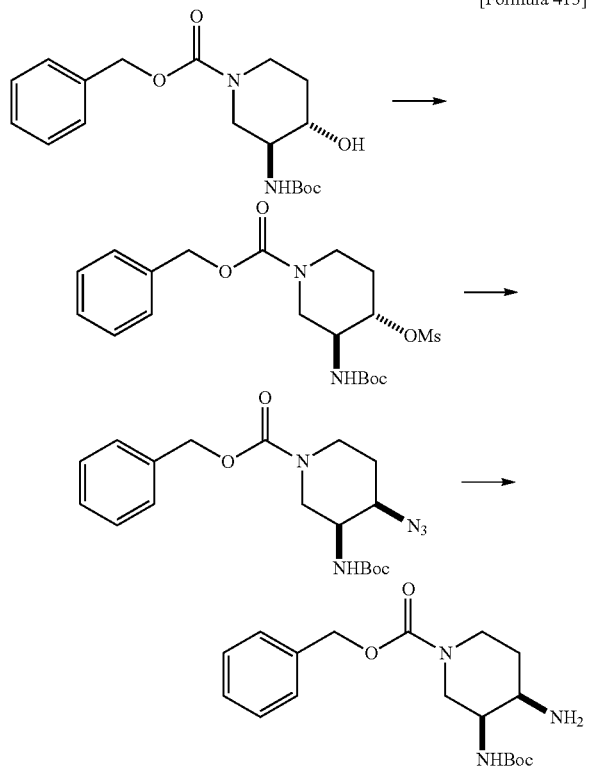

(trans)-Benzyl 3-((tert-butoxycarbonyl)amino)-4-((methylsulfonyl)oxy)piperidin-1-carboxylate (cis)-Benzyl 4-azido-3-((tert-butoxycarbonyl)amino) piperidin-1-carboxylate (cis)-Benzyl 4-amino-3-((tert-butoxycarbonyl) amino)piperidin-1-carboxylate Reference Example 379

[Formula 414]

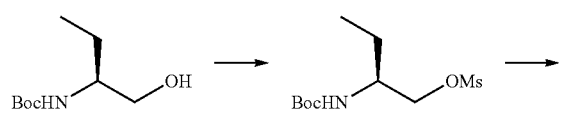

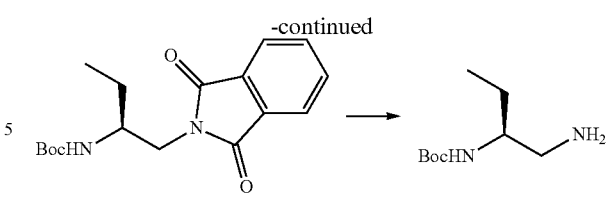

1st Step

Triethylamine (640 mg) and methanesulfonyl chloride (470 mg) were added to a tetrahydrofuran solution (10 ml) containing (S)-tert-butyl(1-hydroxybutan-2-yl)carbamate (600 mg) in an ice bath, followed by stirring at room temperature for 1.5 hours. A saturated aqueous sodium hydrogen carbonate solution was added to the reaction solution, followed by extraction with ethyl acetate. The resultant was dried over anhydrous sodium sulfate, the solvent was distilled away under reduced pressure, and (S)-2-((tert-butoxycarbonyl)amino)butyl methanesulfonate was thus obtained.

2nd Step

Potassium phthalimide (650 mg) was added to a DMF (10 ml) solution containing (S)-2-((tert-butoxycarbonyl)amino) butyl methanesulfonate obtained in the 1st step, followed by stirring at 70° C. for 1 hour. The reaction solution was adjusted to room temperature and added dropwise to a saturated aqueous sodium hydrogen carbonate solution (300 ml), and a solid precipitate was collected by filtration. Subsequently, the obtained solid was purified by silica gel chromatography (n-hexane:ethyl acetate=3:1), and a white solid of (S)-tert-butyl(2-((1,3-dioxoisoindolin-2-yl)butan-2-yl)carbamate (560 mg) was thus obtained.

MS (ESI m/z): 319 (M+H)

RT (min): 1.46

3rd Step

Hydrazine•monohydrate (0.076 ml) was added to an ethanol (6 ml) solution containing (S)-tert-butyl(24-(1,3-dioxoisoindolin-2-yl)butan-2-yl)carbamate (250 mg), followed by stirring at room temperature for 2 hours. The solvent was distilled away under reduced pressure, and diisopropylether was added, followed by stirring. Insoluble matter was removed. 4M hydrogen chloride/1,4-dioxane (1 ml) was added to the obtained solution, the solid precipitate was collected by filtration, and a white solid of (S)-tert-butyl(1-aminobutan-2-yl)carbamate (160 mg) was thus obtained.

MS (ESI m/z): 190 (M+H)

Reference Example 380

The following compounds were obtained as described in Reference Example 379.

[Formula 415]

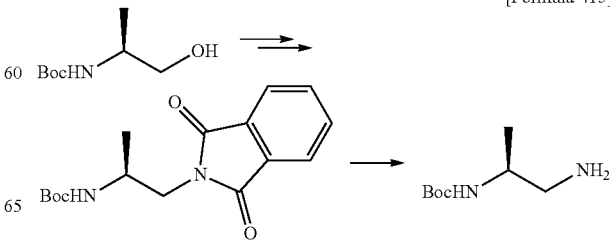

(S)-tert-butyl(1-(1,3-dioxoisoindolin-2-yl)propan-2-yl)carbamate

MS (ESI m/z): 306 (M+H)
RT (min): 1.35

(S)-tert-butyl(1-aminopropan-2-yl)carbamate

MS (ESI m/z): 175 (M+H)

Reference Example 381

The following compounds were obtained as described in Reference Example 379.

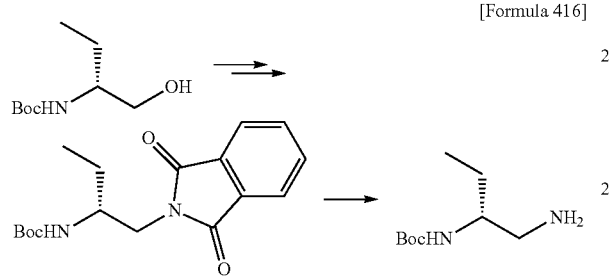

[Formula 416]

(R)-tert-butyl(2-((1,3-dioxoisoindolin-2-yl)butan-2-yl)carbamate

MS (ESI m/z): 319 (M+H)
RT (min): 1.46

(R)-tert-butyl(1-aminobutan-2-yl)carbamate

MS (ESI m/z): 190 (M+H)

Reference Example 382

The following compounds were obtained as described in Reference Example 379.

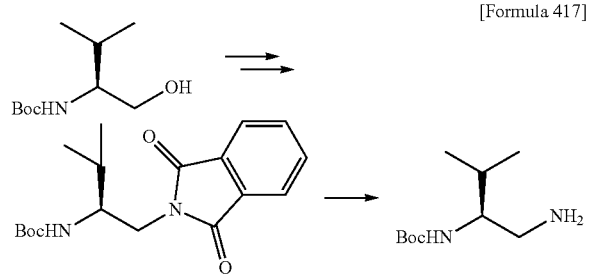

[Formula 417]

(S)-tert-butyl(1-(1,3-dioxoisoindolin-2-yl)-3-methylbutan-2-yl)carbamate

MS (ESI m/z): 333 (M+H)
RT (min): 1.56

(S)-tert-butyl(1-amino-3-methylbutan-2-yl)carbamate

MS (ESI m/z): 203 (M+H)

Reference Example 383

The following compounds were obtained as described in Reference Example 379.

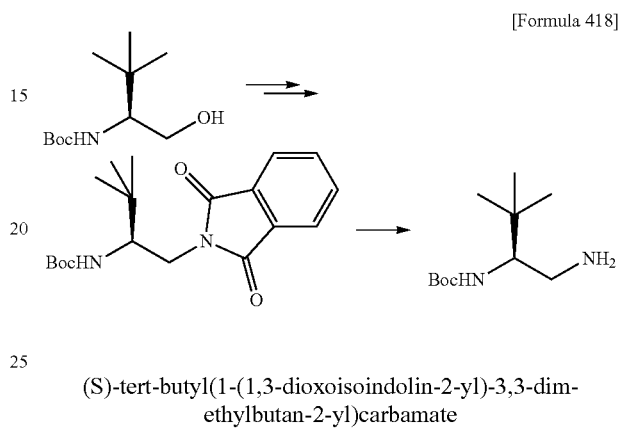

[Formula 418]

(S)-tert-butyl(1-(1,3-dioxoisoindolin-2-yl)-3,3-dimethylbutan-2-yl)carbamate

MS (ESI m/z): 347 (M+H)
RT (min): 1.65

(S)-tert-butyl(1-amino-3,3-dimethylbutan-2-yl)carbamate

MS (ESI m/z): 217 (M+H)
RT (min): 0.82

Reference Example 384

The following compounds were obtained as described in Reference Example 379.

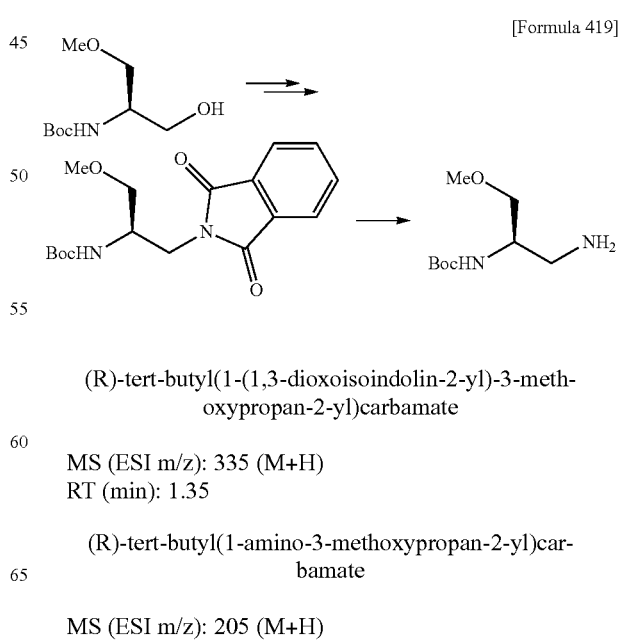

[Formula 419]

(R)-tert-butyl(1-(1,3-dioxoisoindolin-2-yl)-3-methoxypropan-2-yl)carbamate

MS (ESI m/z): 335 (M+H)
RT (min): 1.35

(R)-tert-butyl(1-amino-3-methoxypropan-2-yl)carbamate

MS (ESI m/z): 205 (M+H)

Reference Example 385

The following compound was obtained as described in Reference Example 379.

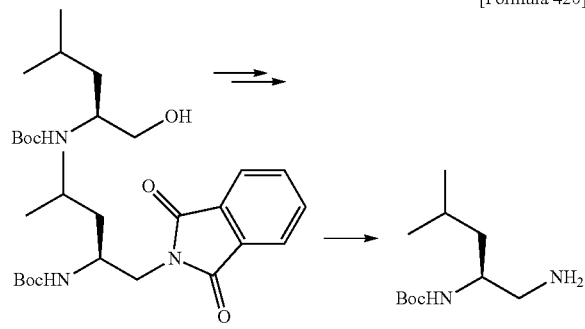

[Formula 420]

(S)-tert-butyl(1-(1,3-dioxoisoindolin-2-yl)-4-methyl-pentan-2-yl)carbamate

MS (ESI m/z): 347 (M+H)
RT (min): 1.67

Reference Example 386

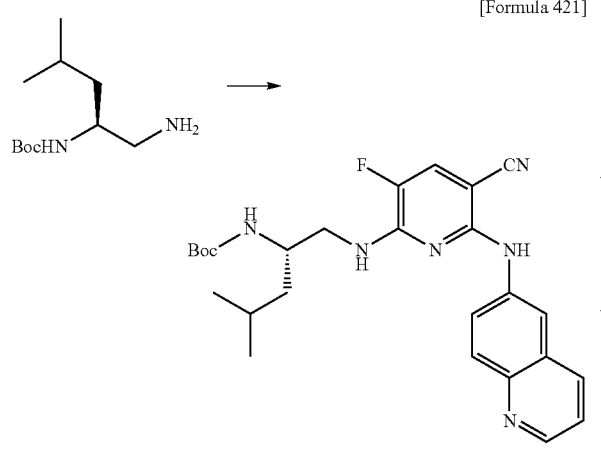

[Formula 421]

Potassium carbonate (139 mg) and 6-chloro-5-fluoro-2-(quinolin-6-ylamino)nicotinonitrile (60 mg) were added to a tube containing a 1,4-dioxane (2 ml) solution containing (S)-tert-butyl(1-amino-4-methylpentan-2-yl)carbamate (76 mg) and the tube was sealed, followed by stirring with heating at 140° C. for 13.5 hours. The reaction solution was adjusted to room temperature and an insoluble precipitate was removed. Subsequently, the solvent was distilled away under reduced pressure. The residue was purified by silica gel chromatography (hexane:ethyl acetate=1:1), and a white solid of (S)-tert-butyl(1-((5-cyano-3-fluoro-6-(quinolin-6-ylamino)pyridin-2-yl)amino)-4-methylpentan-2-yl)carbamate (50 mg) was thus obtained.

MS (ESI m/z): 479 (M+H)
RT (min): 1.39

Reference Example 387

The following compounds were obtained as described in Reference Example 379.

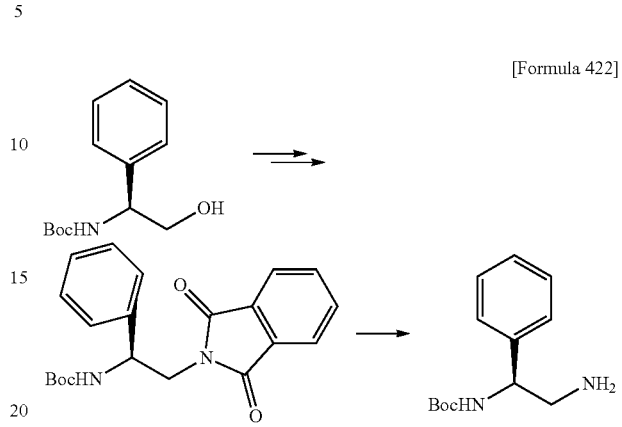

[Formula 422]

(S)-tert-butyl(2-(1,3-dioxoisoindolin-2-yl)-1-phenyl-ethyl)carbamate

MS (ESI m/z): 367 (M+H)
RT (min): 1.62

(S)-tert-butyl(2-amino-1-phenylethyl)carbamate

MS (ESI m/z): 237 (M+H)
RT (min): 0.79

Reference Example 388

The following compounds were obtained as described in Reference Example 379.

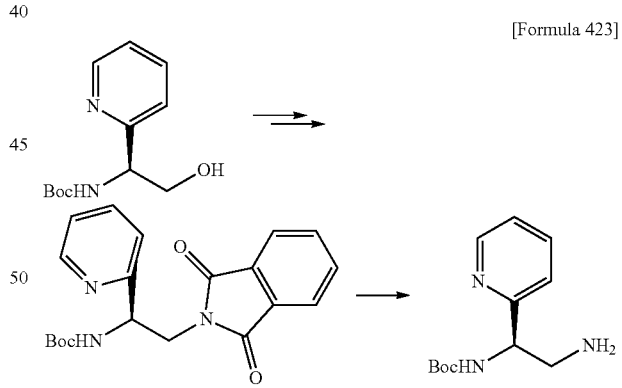

[Formula 423]

(R)-tert-butyl(2-(1,3-dioxoisoindolin-2-yl)-1-(pyridin-2-yl)ethyl)carbamate

MS (ESI m/z): 368 (M+H)
RT (min): 1.35

(R)-tert-butyl(2-amino-1-(pyridin-2-yl)ethyl)carbamate

MS (ESI m/z): 238 (M+H)
RT (min): 0.67

Reference Example 389

The following compounds were obtained as described in Reference Example 379.

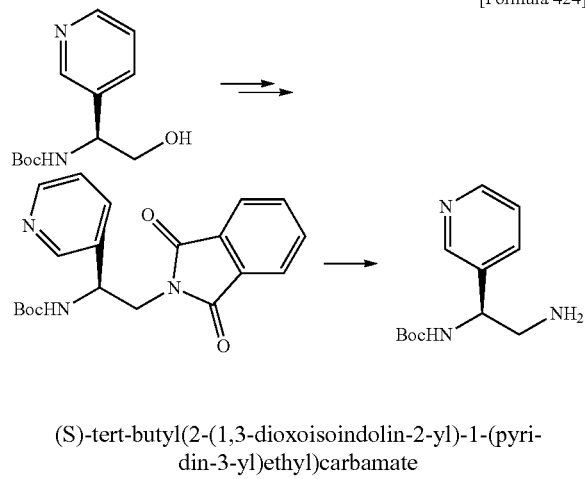

[Formula 424]

(S)-tert-butyl(2-(1,3-dioxoisoindolin-2-yl)-1-(pyridin-3-yl)ethyl)carbamate

MS (ESI m/z): 368 (M+H)
RT (min): 1.00

(S)-tert-butyl(2-amino-1-(pyridin-3-yl)ethyl)carbamate

MS (ESI m/z): 238 (M+H)
RT (min): 0.47

Reference Example 390

The following compounds were obtained as described in Reference Example 379.

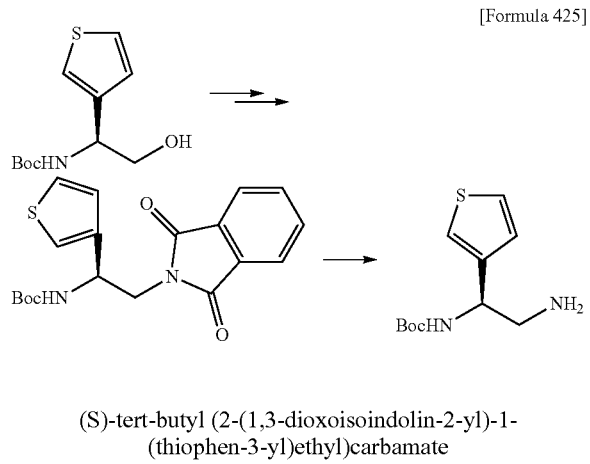

[Formula 425]

(S)-tert-butyl (2-(1,3-dioxoisoindolin-2-yl)-1-(thiophen-3-yl)ethyl)carbamate

MS (ESI m/z): 373 (M+H)
RT (min): 1.56

(S)-tert-butyl (2-amino-1-(thiophen-3-yl)ethyl)carbamate

MS (ESI m/z): 243 (M+H)
RT (min): 0.77

Reference Example 391

The following compounds were obtained as described in Reference Example 379.

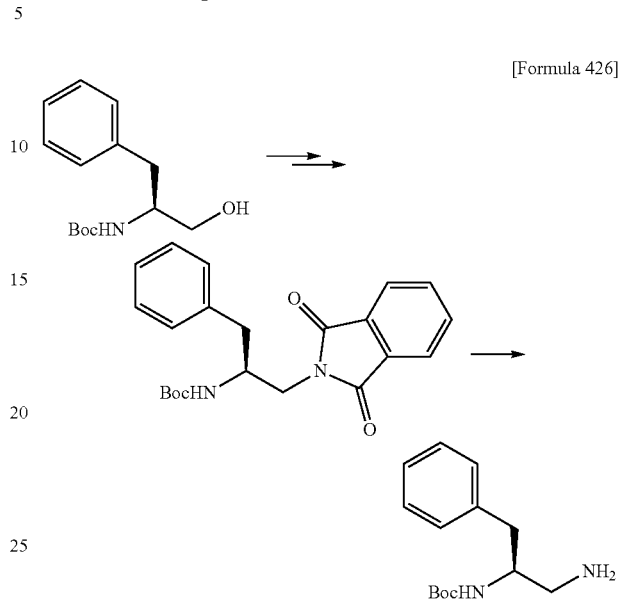

[Formula 426]

(S)-tert-butyl(1-(1,3-dioxoisoindolin-2-yl)-3-phenylpropan-2-yl)carbamate

MS (ESI m/z): 381 (M+H)
RT (min): 1.64

(S)-tert-butyl(1-amino-3-phenylpropan-2-yl)carbamate

MS (ESI m/z): 251 (M+H)

Reference Example 392

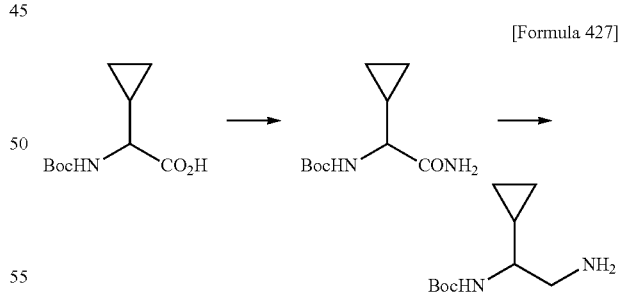

[Formula 427]

1st Step

HOBt.H$_2$O (353 mg), WSC.HCl (460 mg), diisopropylethylamine (986 mg), and ammonium chloride (500 mg) were added to a DMF (5 ml) solution containing 2-((tert-butoxycarbonyl)amino)-2-cyclopropyl acetic acid (500 mg) at room temperature, followed by stirring at room temperature for 3 hours. A saturated aqueous sodium hydrogen carbonate solution was added to the reaction mixture, followed by extraction with ethyl acetate. The resultant was dried over anhydrous sodium sulfate. Subsequently, the solvent was distilled away

273 under reduced pressure, and a white solid of tert-butyl(2-amino-1-cyclopropyl-2-oxoethyl)carbamate (500 mg) was thus obtained.

MS (ESI m/z): 215 (M+H)

2nd Step

A borane-tetrahydrofuran complex (1.1 M tetrahydrofuran, 1.69 ml) was slowly added to a tetrahydrofuran (5 ml) solution containing tert-butyl(2-amino-1-cyclopropyl-2-oxoethyl)carbamate (200 mg), followed by reflux for 2 hours. The reaction solution was adjusted to room temperature, and methanol was slowly added to the reaction solution until foaming stopped. Further, chloroform was added, the resultant was washed with a 1M sodium hydroxide aqueous solution and saturated saline and dried over sodium sulfate, the solvent was distilled away under reduced pressure, and the residue was directly used in the subsequent reaction.

MS (ESI m/z): 201 (M+H)

Reference Example 393

The following compounds were obtained as described in Reference Example 392.

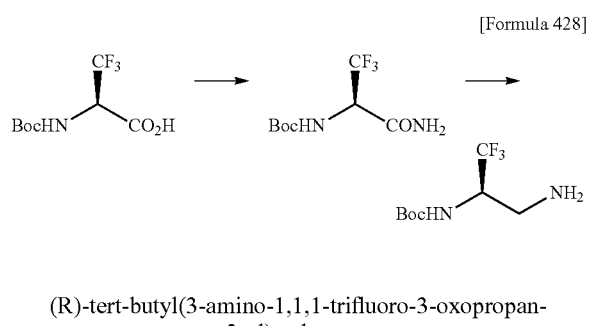

[Formula 428]

(R)-tert-butyl(3-amino-1,1,1-trifluoro-3-oxopropan-2-yl)carbamate

MS (ESI m/z): 241 (M−H)

(R)-tert-butyl (3-amino-1,1,1-trifluoropropan-2-yl) carbamate

MS (ESI m/z): 229 (M+H)

Reference Example 394

The following compound was obtained as described in Reference Example 392.

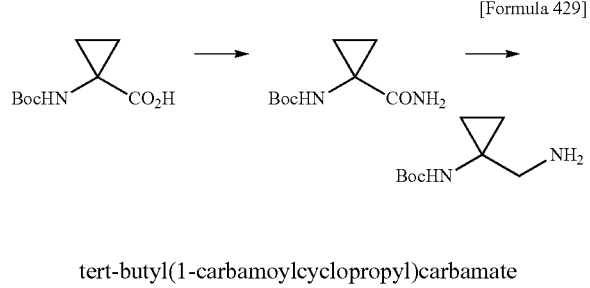

[Formula 429]

tert-butyl(1-carbamoylcyclopropyl)carbamate

MS (ESI m/z): 201 (M+H) tert-butyl(1-(aminomethyl)cyclopropyl)carbamate

MS (ESI m/z): 187 (M+H)

274

Reference Example 395

The following compound was obtained as described in the 1st step of Reference Example 2.

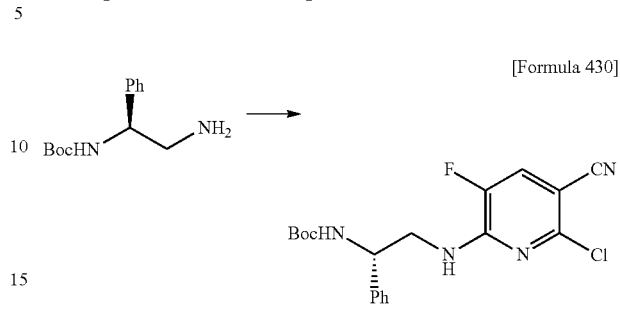

[Formula 430]

(S)-tert-butyl(2-((6-chloro-5-cyano-3-fluoropyridin-2-yl)amino)-1-phenylethyl)carbamate MS (ESI m/z): 391 (M+H)
RT (min): 1.71

Reference Example 396

The following compounds were obtained as described in the 1st and 2nd steps of Reference Example 379 and the 2nd step of Reference Example 97.

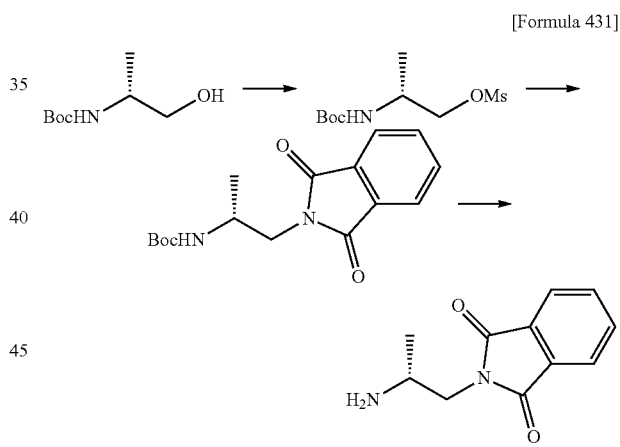

[Formula 431]

(R)-tert-butyl(1-(1,3-dioxoisoindolin-2-yl)propan-2-yl)carbamate

MS (ESI m/z): 306 (M+H)
RT (min): 1.35

(R)-2-(2-aminopropyl)isoindoline-1,3-dione

MS (ESI m/z): 206 (M+H)
RT (min): 0.49

Reference Example 397

The following compounds were obtained as described in Reference Example 396.

[Formula 432]

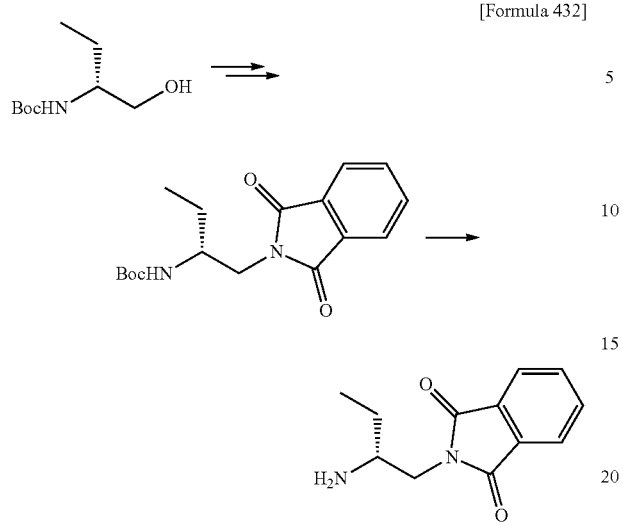

(R)-tert-butyl(1-(1,3-dioxoisoindolin-2-yl)butan-2-yl)carbamate

MS (ESI m/z): 319 (M+H)
RT (min): 1.46

(R)-2-(2-aminobutyl)isoindoline-1,3-dione

MS (ESI m/z): 219 (M+H)
RT (min): 0.59

Reference Example 398

[Formula 433]

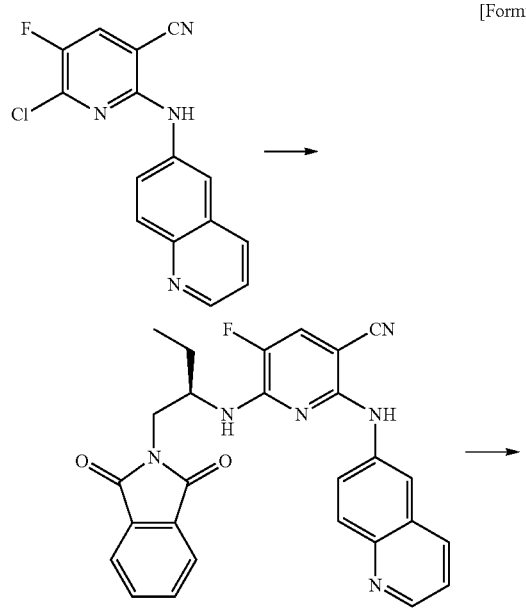

1st Step

Potassium carbonate (146 mg) and 6-chloro-5-fluoro-2-(quinolin-6-ylamino)nicotinonitrile (63 mg) were added to a tube containing a 1,4-dioxane (2 ml) solution containing (R)-2-(2-aminobutyl)isoindoline-1,3-dione (60 mg) and the tube was sealed, followed by stirring with heating at 140° C. for 13 hours. The reaction solution was cooled, and a saturated aqueous sodium hydrogen carbonate solution was added, followed by extraction with ethyl acetate. The organic layer was dried over anhydrous sodium sulfate, the solvent was distilled away under reduced pressure. The residue was purified by silica gel chromatography (n-hexane:ethyl acetate=3:2), and a yellow solid of (R)-6-((1-(1,3-dioxoisoindolin-2-yl)butan-2-yl)amino)-5-fluoro-2-(quinolin-6-ylamino)nicotinonitrile (20 mg) was thus obtained.

MS (ESI m/z): 481 (M+H)
RT (min): 1.13

2nd Step

The following compound was obtained as described in the 3rd step of Example 379.

(R)-6-((1-aminobutan-2-yl)amino)-5-fluoro-2-(quinolin-6-ylamino)nicotinonitrile

MS (ESI m/z): 351 (M+H)
RT (min): 0.68

3rd Step

The following compound was obtained as described in the 2nd step of Reference Example 2.

(R)-tert-butyl(2-((5-cyano-3-fluoro-6-(quinolin-6-ylamino)pyridin-2-yl)amino)butyl)carbamate MS (ESI m/z): 451 (M+H)
RT (min): 1.21

Reference Example 399

The following compounds were obtained as described in Reference Example 396.

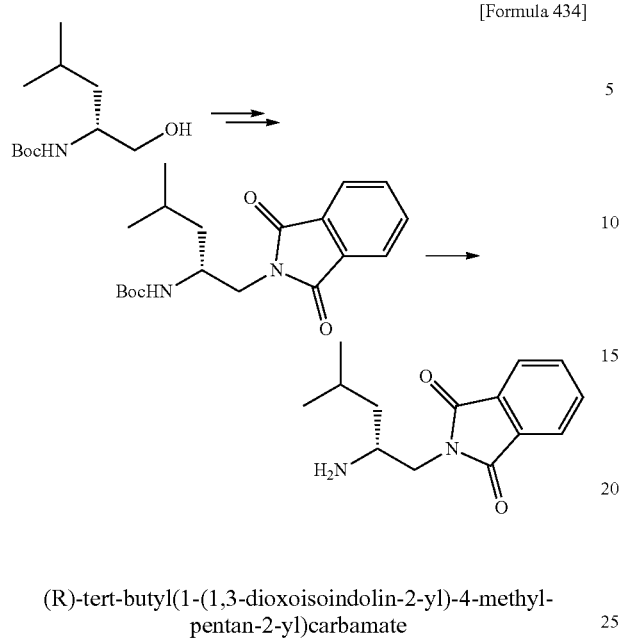

(R)-tert-butyl(1-(1,3-dioxoisoindolin-2-yl)-4-methyl-pentan-2-yl)carbamate

MS (ESI m/z): 347 (M+H)
RT (min): 1.65

(R)-2-(2-amino-4-methylpentyl)isoindoline-1,3-dione

MS (ESI m/z): 247 (M+H)
RT (min): 0.75

Reference Example 400

The following compounds were obtained as described in Reference Example 398.

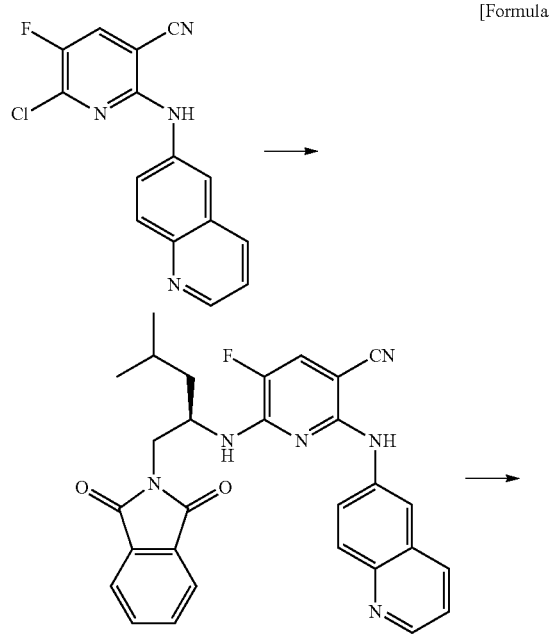

(R)-6-((1-(1,3-dioxoisoindolin-2-yl)-4-methylpentan-2-yl)amino)-5-fluoro-2-(quinolin-6-ylamino)nicotinonitrile MS (ESI m/z): 509 (M+H)
RT (min): 1.28

(R)-6-((1-amino-4-methylpentan-2-yl)amino)-5-fluoro-2-(quinolin-6-ylamino)nicotinonitrile MS (ESI m/z): 379 (M+H)
RT (min): 0.83

(R)-tert-butyl(2-((5-cyano-3-fluoro-6-(quinolin-6-ylamino)pyridin-2-yl)amino)-4-methylpentyl)carbamate MS (ESI m/z): 479 (M+H)
RT (min): 1.34

Reference Example 401

The following compounds were obtained as described in Reference Example 396.

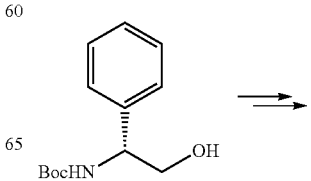

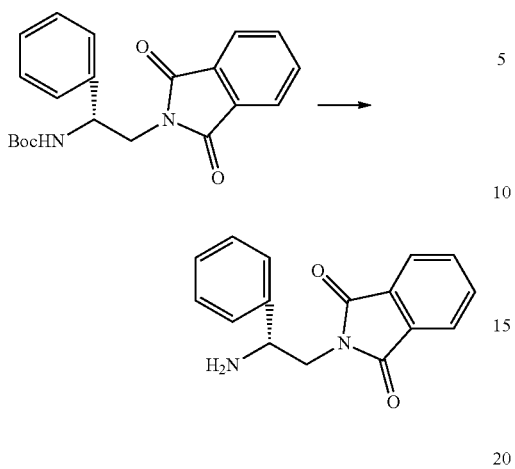

(R)-tert-butyl(2-(1,3-dioxoisoindolin-2-yl)-1-phenylethyl)carbamate

MS (ESI m/z): 367 (M+H)
RT (min): 1.61

(R)-2-(2-amino-2-phenylethyl)isoindoline-1,3-dione

MS (ESI m/z): 267 (M+H)
RT (min): 0.73

Reference Example 402

The following compounds were obtained as described in Reference Example 398.

[Formula 437]

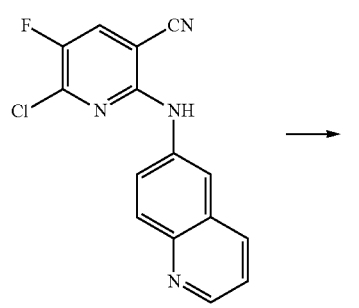

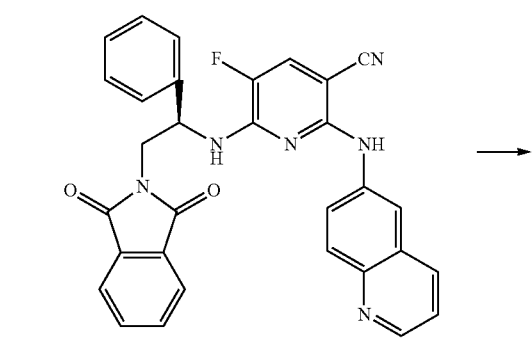

(R)-6-(2-(1,3-dioxoisoindolin-2-yl)-1-phenylethyl)amino)-5-fluoro-2-(quinolin-6-ylamino)nicotinonitrile MS (ESI m/z): 529 (M+H)
RT (min): 1.29

(R)-6-((2-amino-1-phenylethyl)amino)-5-fluoro-2-(quinolin-6-ylamino)nicotinonitrile MS (ESI m/z): 399 (M+H)
RT (min): 0.76

(R)-tert-butyl(2-((5-cyano-3-fluoro-6-(quinolin-6-ylamino)pyridin-2-yl)amino)-2-phenylethyl)carbamate MS (ESI m/z): 499 (M+H)
RT (min): 1.34

Reference Example 403

The following compounds were obtained as described in Reference Example 396.

[Formula 438]

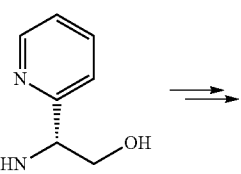

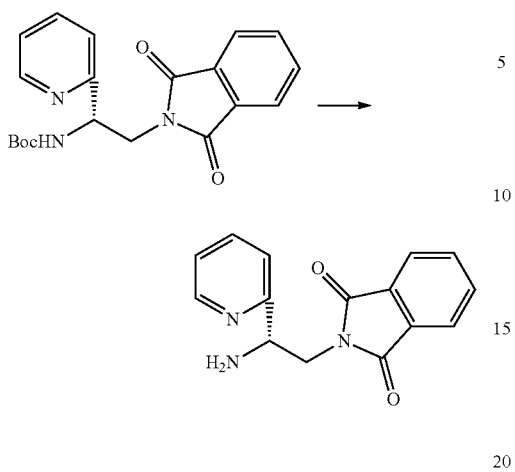

(S)-tert-butyl(2-(1,3-dioxoisoindolin-2-yl)-1-(pyridin-2-yl)ethyl)carbamate

MS (ESI m/z): 368 (M+H)
RT (min): 1.35

(S)-2-(2-amino-2-(pyridin-2-yl)ethyl)isoindoline-1,3-dione

MS (ESI m/z): 268 (M+H)
RT (min): 0.62

Reference Example 404

The following compounds were obtained as described in Reference Example 398.

[Formula 439]

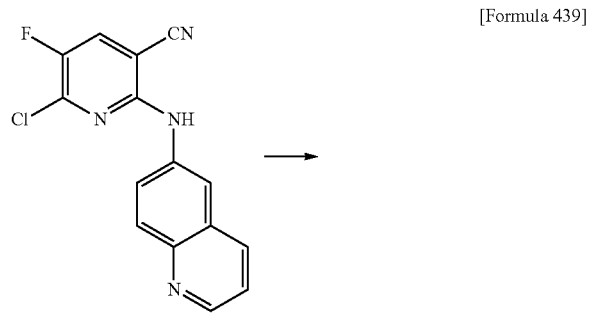

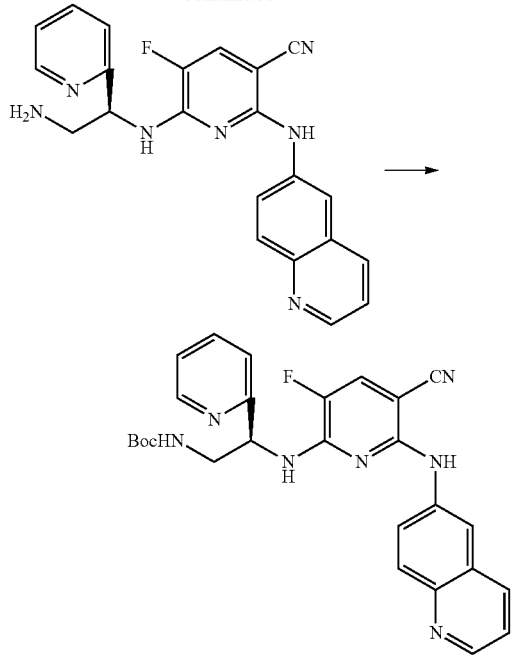

(S)-6-((2-(1,3-dioxoisoindolin-2-yl)-1-(pyridin-2-yl)ethyl)amino)-5-fluoro-2-(quinolin-6-ylamino)nicotinonitrile MS (ESI m/z): 530 (M+H)
RT (min): 1.14

(S)-6-((2-amino-1-(pyridin-2-yl)ethyl)amino)-5-fluoro-2-(quinolin-6-ylamino)nicotinonitrile MS (ESI m/z): 400 (M+H)
RT (min): 0.66

(S)-tert-butyl(2-((5-cyano-3-fluoro-6-(quinolin-6-ylamino)pyridin-2-yl)amino)-2-(pyridin-2-yl)ethyl)carbamate MS (ESI m/z): 500 (M+H)
RT (min): 1.15

Reference Example 405

[Formula 440]

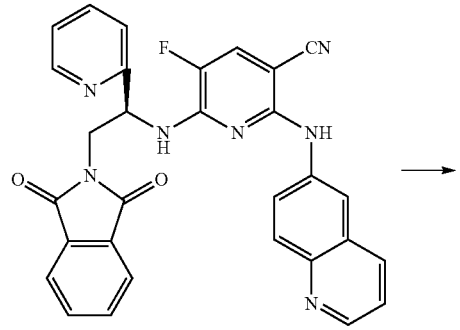

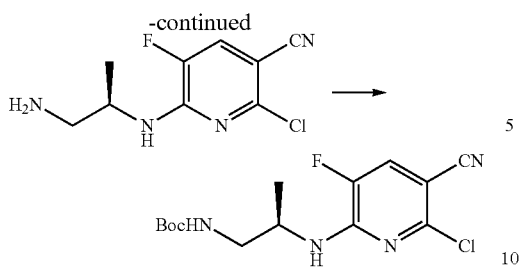

1st Step 2,6-dichloro-5-fluoro-3-pyridinecarbonitrile (3.3 g) and potassium carbonate (1.1 g) were added to a DMF (5 ml) solution containing (R)-2-(2-aminopropyl)isoindoline-1,3-dione•hydrochloride (690 mg), followed by stirring with heating at 60° C. for 5.5 hours. The reaction solution was adjusted to room temperature, and a saturated aqueous sodium hydrogen carbonate solution was added, followed by extraction with ethyl acetate. The obtained organic layer was dried over anhydrous sodium sulfate. Subsequently, the solvent was distilled away under reduced pressure, the residue was purified by silica gel chromatography (n-hexane:ethyl acetate=7:3, and a yellow solid of (R)-2-chloro-6-((1-(1,3-dioxoisoindolin-2-yl)propan-2-yl)amino)-5-fluoronicotinonitrile (300 mg) was thus obtained.

MS (ESI m/z): 359 (M+H)

RT (min.): 1.46

2nd Step

Hydrazine•monohydrate (0.124 ml) was added to an ethanol/tetrahydrofuran (5 ml/1 ml) solution containing (R)-2-chloro-6-((1-(1,3-dioxoisoindolin-2-yl)propan-2-yl)amino)-5-fluoronicotinonitrile (300 mg), followed by stirring at room temperature for 14 hours. Further, hydrazine•monohydrate (0.062 ml) was added, followed by stirring at room temperature for 8.5 hours. The solvent was distilled away under reduced pressure, chloroform was added, and insoluble matter was removed. Then, the solvent was distilled away under reduced pressure, and a yellow solid of (R)-6-((1-aminopropan-2-yl)amino)-2-chloro-5-fluoronicotinonitrile (38 mg) was thus obtained.

MS (ESI m/z): 229 (M+H)

RT (min.): 0.65

3rd Step

Potassium carbonate (127 mg) and di-tert-butyl dicarbonate (220 mg) were added to a tetrahydrofuran/water (8 ml/1.5 ml) solution containing (R)-6-((1-aminopropan-2-yl)amino)-2-chloro-5-fluoronicotinonitrile (190 mg), followed by stirring at room temperature for 30 minutes. The solvent was distilled away under reduced pressure, the residue was purified by silica gel chromatography (n-hexane:ethyl acetate=2:1), and yellow oily matter of (R)-tert-butyl(2-((6-chloro-5-cyano-3-fluoropyridin-2-yl)amino)propyl)carbamate (160 mg) was thus obtained.

MS (ESI m/z): 329 (M+H)

RT (min.): 1.54

Reference Example 406

The following compounds were obtained as described in Reference Examples 396 and 405.

[Formula 441]

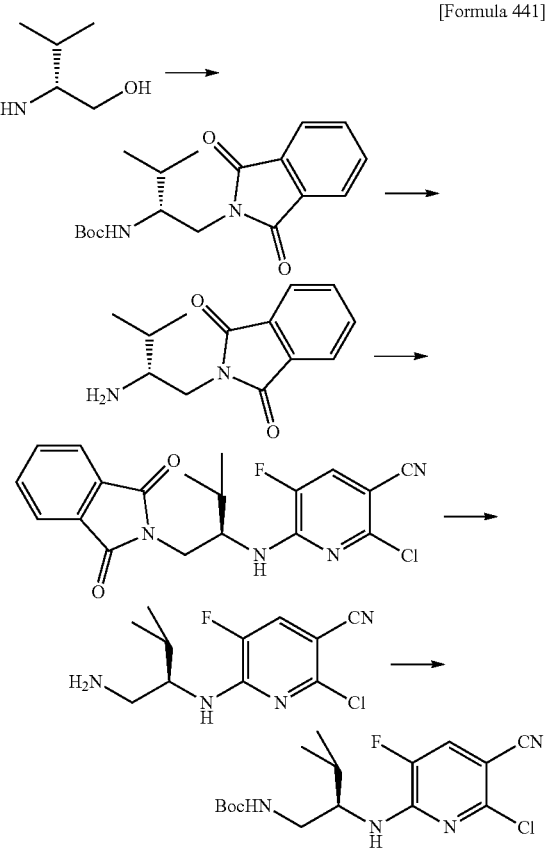

(R)-tert-butyl(1-(1,3-dioxoisoindolin-2-yl)-3-methylbutan-2-yl)carbamate

MS (ESI m/z): 333 (M+H)
RT (min): 1.54

(R)-2-(2-amino-3-methylbutyl)isoindoline-1,3-dione

MS (ESI m/z): 233 (M+H)
RT (min): 0.67

(R)-2-chloro-6-((1-(1,3-dioxoisoindolin-2-yl)-3-methylbutan-2-yl)amino)-5-fluoronicotinonitrile MS (ESI m/z): 387 (M+H)
RT (min): 1.63

(R)-6-((1-amino-3-methylbutan-2-yl)amino)-2-chloro-5-fluoronicotinonitrile

MS (ESI m/z): 257 (M+H)
RT (min): 0.88

(R)-tert-butyl(2-(((6-chloro-5-cyano-3-fluoropyridin-2-yl)amino)-3-methylbutyl)carbamate MS (ESI m/z): 357 (M+H)
RT (min): 1.71

Reference Example 407

The following compounds were obtained as described in Reference Examples 396 and 405.

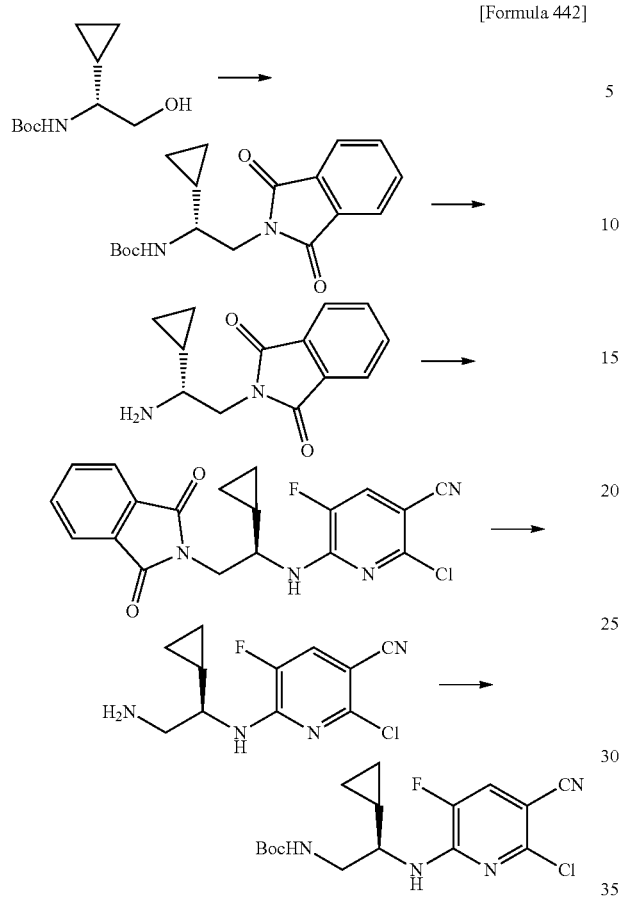

(R)-tert-butyl(1-cyclopropyl-2-(1,3-dioxoindolin-2-yl)ethyl)carbamate

MS (ESI m/z): 331 (M+H)
RT (min): 1.48

(R)-2-(2-amino-2-cyclopropylethyl)isoindoline-1,3-dione

MS (ESI m/z): 231 (M+H)
RT (min): 0.62

(R)-2-chloro-6-((1-cyclopropyl-2-(1,3-dioxoindolin-2-yl)ethyl)amino)-5-fluoronicotinonitrile MS (ESI m/z): 385 (M+H)
RT (min): 1.57

(R)-tert-butyl(2-((6-chloro-5-cyano-3-fluoropyridin-2-yl)amino)-2-cyclopropylethyl) carbamate MS (ESI m/z): 355 (M+H)
RT (min): 1.64

Reference Example 408

The following compounds were obtained as described in Reference Examples 396 and 405.

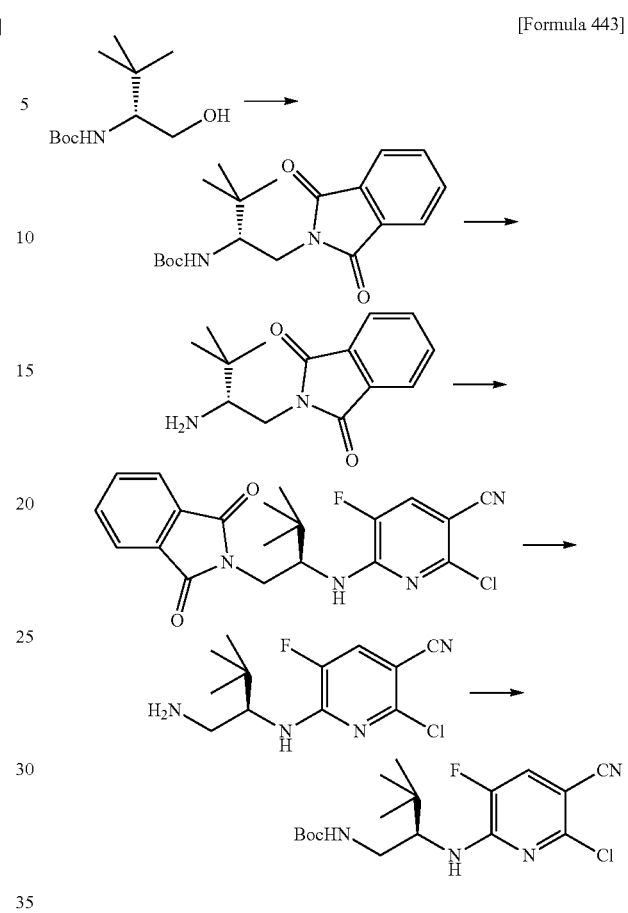

(R)-2-(2-amino-3,3-dimethylbutyl)isoindoline-1,3-dione

MS (ESI m/z): 347 (M+H)
RT (min): 1.63

(R)-tert-butyl(1-(1,3-dioxoindolin-2-yl)-3,3-dimethylbutan-2-yl)carbamate

MS (ESI m/z): 247 (M+H)
RT (min): 0.73

(R)-2-chloro-6-((1-(1,3-dioxoindolin-2-yl)-3,3-dimethylbutan-2-yl)amino)-5-fluoro nicotinonitrile MS (ESI m/z): 401 (M+H)
RT (min): 1.70

(R)-6-((1-amino-3,3-dimethylbutan-2-yl)amino)-2-chloro-5-fluoronicotinonitrile

MS (ESI m/z): 271 (M+H)
RT (min): 0.97

(R)-tert-butyl(2-((6-chloro-5-cyano-3-fluoropyridin-2-yl)amino)-3,3-dimethylbutyl) carbamate MS (ESI m/z): 371 (M+H)
RT (min): 1.78

Reference Example 409

The following compounds were obtained as described in Reference Examples 396 and 405.

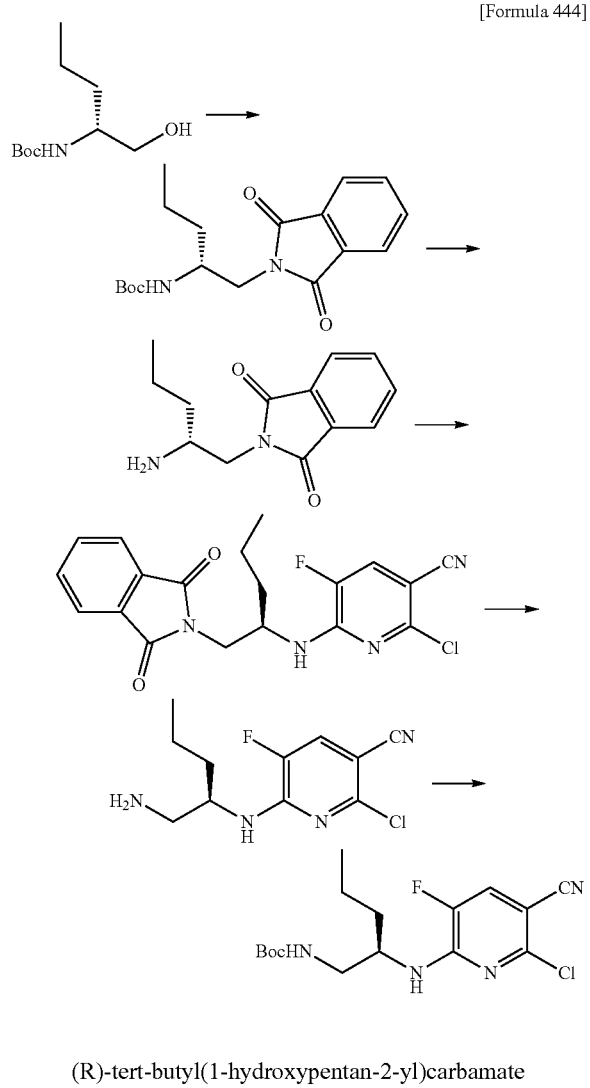

(R)-tert-butyl(1-hydroxypentan-2-yl)carbamate

MS (ESI m/z): 333 (M+H)
RT (min): 1.56

(R)-2-(2-aminopentyl)isoindoline-1,3-dione

MS (ESI m/z): 233 (M+H)
RT (min): 0.64

(R)-2-chloro-6-((1-(1,3-dioxoindolin-2-yl)pentan-2-yl)amino)-5-fluoronicotinonitrile MS (ESI m/z): 387 (M+H)
RT (min): 1.65

(R)-6-((1-aminopentan-2-yl)amino)-2-chloro-5-fluoronicotinonitrile

MS (ESI m/z): 257 (M+H)
RT (min): 0.86

(R)-tert-butyl(2-((6-chloro-5-cyano-3-fluoropyridin-2-yl)amino)pentyl)carbamate

MS (ESI m/z): 357 (M+H)
RT (min): 1.73

Reference Example 410

The following compounds were obtained as described in Reference Examples 396 and 405.

[Formula 445]

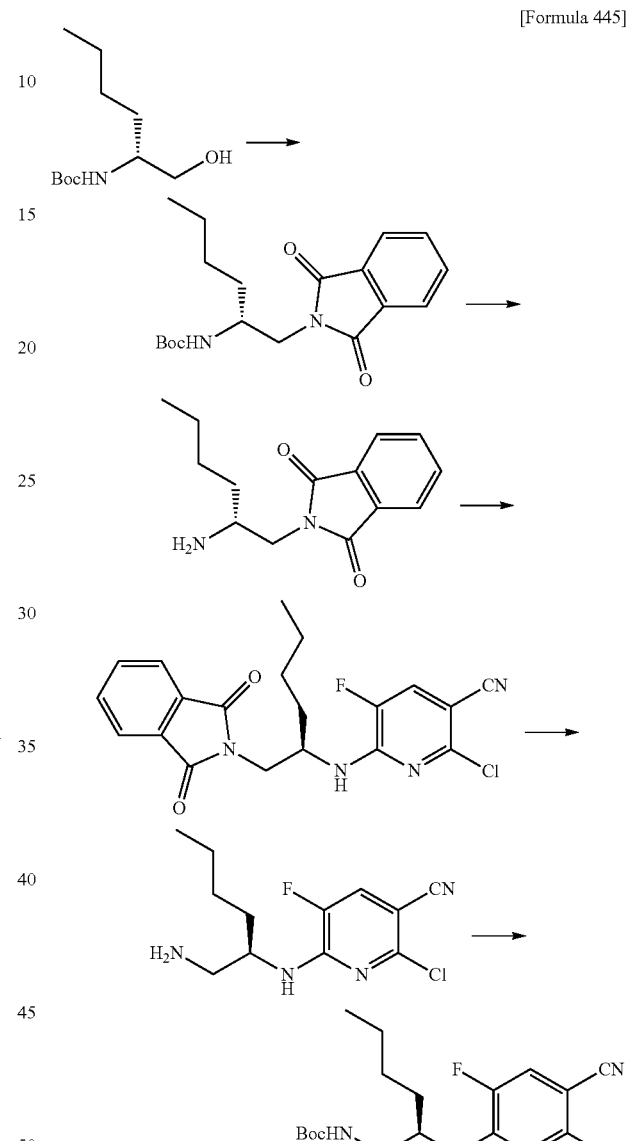

(R)-2-chloro-6-((1-(1,3-dioxoindolin-2-yl)hexan-2-yl)amino)-5-fluoronicotinonitrile MS (ESI m/z): 401 (M+H)
RT (min): 1.79

(R)-6-((1-aminohexan-2-yl)amino)-2-chloro-5-fluoronicotinonitrile

MS (ESI m/z): 271 (M+H)
RT (min): 1.02

(R)-tert-butyl(2-((6-chloro-5-cyano-3-fluoropyridin-2-yl)amino)hexyl)carbamate $^1$H-NMR (CDCl$_3$, 300 MHz) δ:7.27 (d, 1H, J=9.3 Hz), 5.90 (d, 1H, J=7.3 Hz), 4.79 (br, 1H), 4.30-4.13 (m, 1H), 3.45-3.26 (m, 2H), 1.51-1.28 (m, 15H), 0.99-0.80 (m, 3H)
MS (ESI m/z): 371 (M+H)
RT (min): 1.83

Reference Example 411

The following compounds were obtained as described in Reference Examples 396 and 405.

[Formula 446]

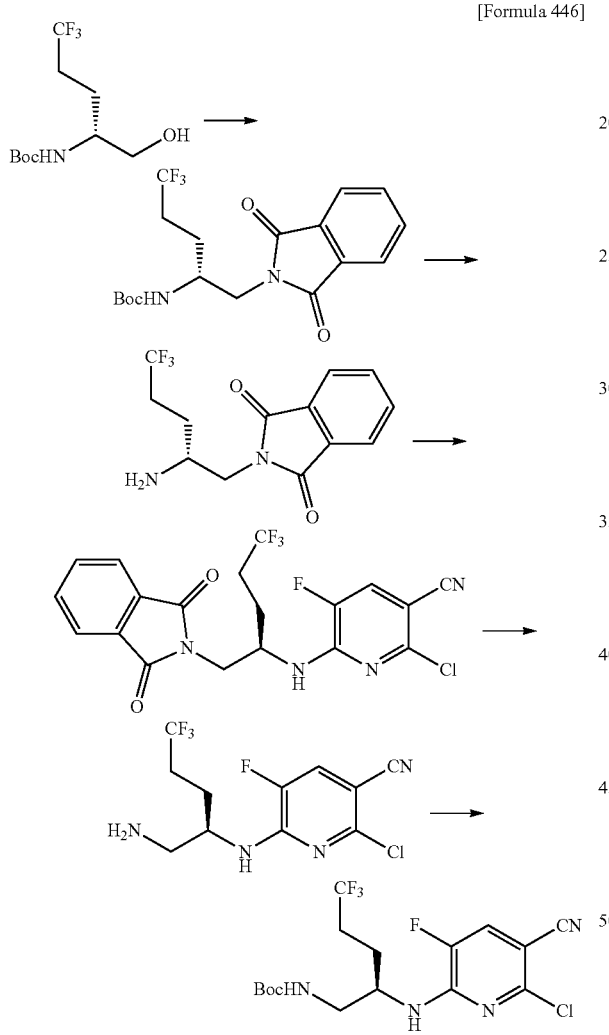

(R)-tert-butyl(1-(1,3-dioxoisoindolin-2-yl)-5,5,5-trifluoropentan-2-yl)carbamate MS (ESI m/z): 387 (M+H)
RT (min): 1.58

(R)-2-chloro-6-((1-(1,3-dioxoindolin-2-yl)-5,5,5-trifluoropentan-2-yl)amino)-5-fluoronicotinonitrile MS (ESI m/z): 441 (M+H)
RT (min): 1.64

(R)-tert-butyl(2-((6-chloro-5-cyano-3-fluoropyridin-2-yl)amino)-5,5,5-trifluoropentyl)carbamate MS (ESI m/z): 412 (M+H)
RT (min): 1.72

Reference Example 412

The following compounds were obtained as described in Reference Examples 396 and 405.

[Formula 447]

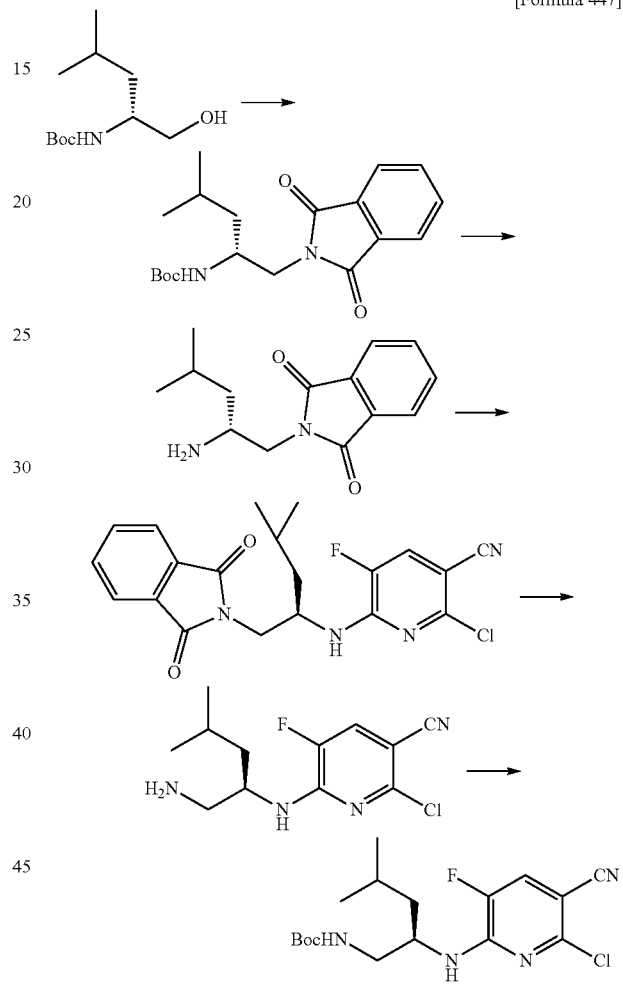

(R)-tert-butyl(1-(1,3-dioxoindolin-2-yl)-4-methylpentan-2-yl)carbamate

MS (ESI m/z): 347 (M+H)
RT (min): 1.65

(R)-2-(2-amino-4-methylpentyl)isoindoline-1,3-dione

MS (ESI m/z): 247 (M+H)
RT (min): 0.75

(R)-2-chloro-6-((1-(1,3-dioxoindolin-2-yl)-4-methylpentan-2-yl)amino)-5-fluoronicotinonitrile MS (ESI m/z): 401 (M+H)
RT (min): 1.73

(R)-6-(1-amino-4-methylpentan-2-yl)amino)-2-chloro-5-fluoronicotinonitrile

MS (ESI m/z): 271 (M+H)
RT (min): 0.96

(R)-tert-butyl(2-((6-chloro-5-cyano-3-fluoropyridin-2-yl)amino)-4-methylpentyl)carbamate $^1$H-NMR (CDCl$_3$, 300 MHz) δ:7.27 (d, 1H, J=9.3 Hz), 5.74 (d, 1H, J=5.9 Hz), 4.79 (br, 1H), 4.42-4.24 (m, 1H), 3.42-3.22 (m, 2H), 1.72-1.30 (m, 12H), 1.00-0.92 (m, 6H)
MS (ESI m/z): 371 (M+H)
RT (min): 1.81

Reference Example 413

The following compounds were obtained as described in Reference Examples 396 and 405.

[Formula 448]

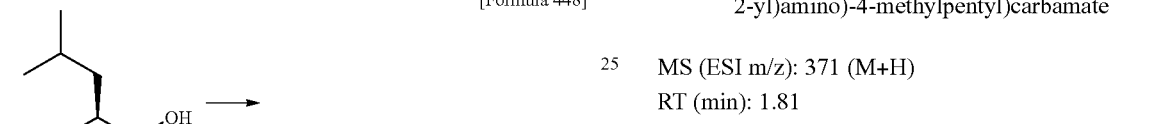

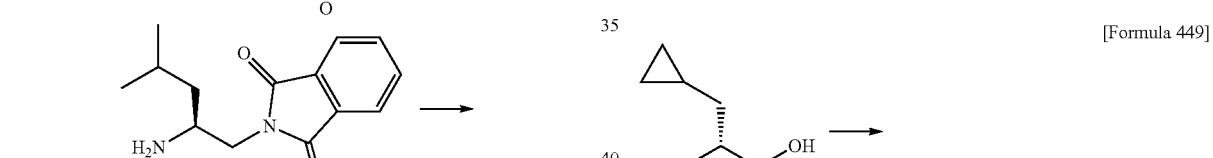

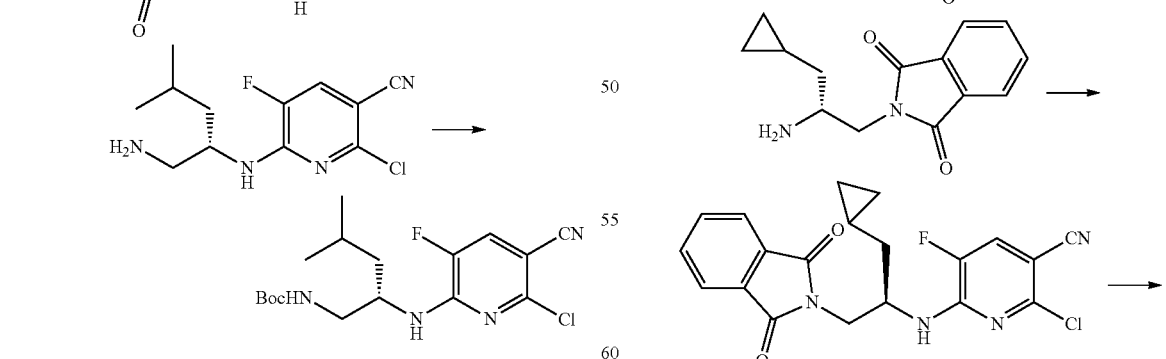

(S)-tert-butyl(1-(1,3-dioxoindolin-2-yl)-4-methylpentan-2-yl)carbamate

MS (ESI m/z): 347 (M+H)
RT (min): 1.67

(S)-2-(2-amino-4-methylpentyl)isoindoline-1,3-dione

MS (ESI m/z): 247 (M+H)
RT (min): 0.76

(S)-2-chloro-6-((1-(1,3-dioxoindolin-2-yl)-4-methylpentan-2-yl)amino)-5-fluoronicotinonitrile MS (ESI m/z): 401 (M+H)
RT (min): 1.73

(S)-6-((1-amino-4-methylpentan-2-yl)amino)-2-chloro-5-fluoronicotinonitrile

MS (ESI m/z): 271 (M+H)
RT (min): 0.98

(S)-tert-butyl(2-((6-chloro-5-cyano-3-fluoropyridin-2-yl)amino)-4-methylpentyl)carbamate MS (ESI m/z): 371 (M+H)
RT (min): 1.81

Reference Example 414

The following compounds were obtained as described in Reference Examples 396 and 405.

[Formula 449]

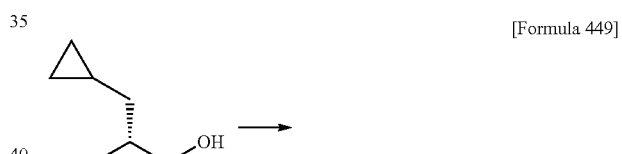

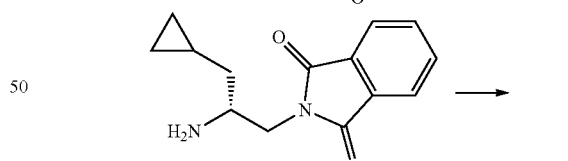

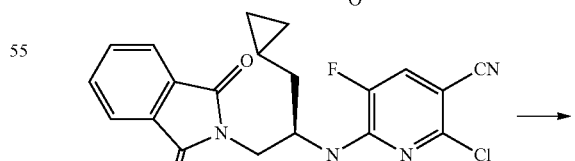

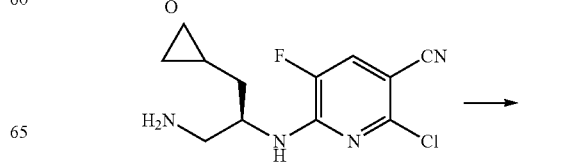

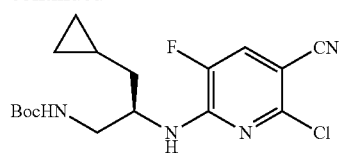

(R)-tert-butyl(1-cyclopropyl-3-(1,3-dioxoindolin-2-yl)propan-2-yl)carbamate

MS (ESI m/z): 345 (M+H)
RT (min): 1.57

(R)-2-(2-amino-3-cyclopropylpropyl)isoindolin-1,3-dione

MS (ESI m/z): 245 (M+H)
RT (min): 0.68

(R)-2-chloro-6-((1-cyclopropyl-3-(1,3-dioxoindolin-2-yl)propan-2-yl)amino)-5-fluoronicotinonitrile MS (ESI m/z): 399 (M+H)
RT (min): 1.66

(R)-tert-butyl(2-((6-chloro-5-cyano-3-fluoropyridin-2-yl)amino)-3-cyclopropylpropyl)carbamate MS (ESI m/z): 369 (M+H)
RT (min): 1.73

Reference Example 415

The following compounds were obtained as described in Reference Examples 396 and 405.

[Formula 450]

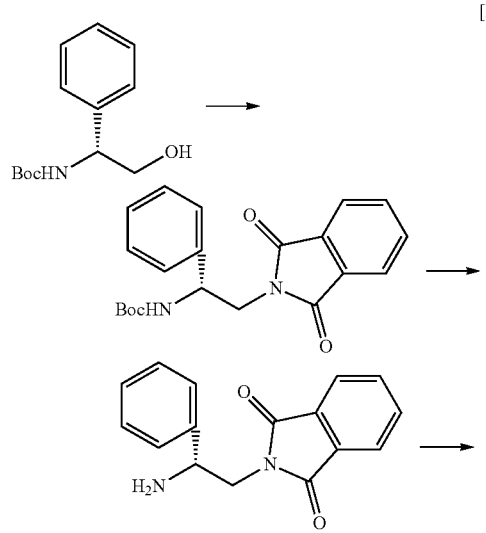

(R)-tert-butyl(2-(1,3-dioxoindolin-2-yl)-1-phenyl-ethyl)carbamate

MS (ESI m/z): 367 (M+H)
RT (min): 1.61

(R)-2-(2-amino-2-phenylethyl)isoindolin-1,3-dione

MS (ESI m/z): 267 (M+H)
RT (min): 0.73

(R)-2-chloro-6-((2-(1,3-dioxoindolin-2-yl)-1-phenyl-ethyl)amino)-5-fluoronicotinonitrile MS (ESI m/z): 421 (M+H)
RT (min): 1.68

(R)-6-((2-amino-1-phenylethyl)amino)-2-chloro-5-fluoronicotinonitrile

MS (ESI m/z): 291 (M+H)
RT (min): 0.93

(R)-tert-butyl(2-((6-chloro-5-cyano-3-fluoropyridin-2-yl)amino)-2-phenylethyl)carbamate MS (ESI m/z): 391 (M+H)
RT (min): 1.72

Reference Example 416

The following compounds were obtained as described in Reference Examples 396 and 405.

295

[Formula 451]

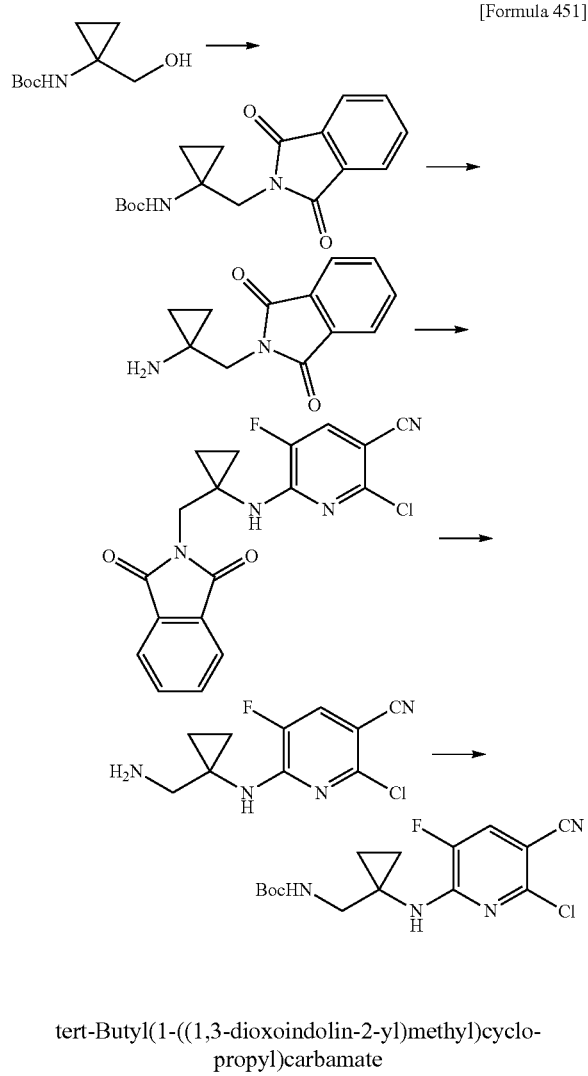

tert-Butyl(1-((1,3-dioxoindolin-2-yl)methyl)cyclo-
propyl)carbamate

MS (ESI m/z): 317 (M+H)

RT (min): 1.39

2-((1-aminocyclopropyl)methyl)isoindoline-1,3-
dione

MS (ESI m/z): 217 (M+H)

RT (min): 0.58

2-chloro-6-((1-((1,3-dioxoindolin-2-yl)methyl)cyclo-
propyl)amino)-5-fluoronicotinonitrile MS (ESI m/z): 371 (M+H)

RT (min): 1.52 tert-Butyl((1-((6-chloro-5-cyano-3-fluoropyridin-2-
yl)amino)cyclopropyl)methyl)carbamate MS (ESI m/z): 341 (M+H)

RT (min): 1.53

296

Reference Example 417

[Formula 452]

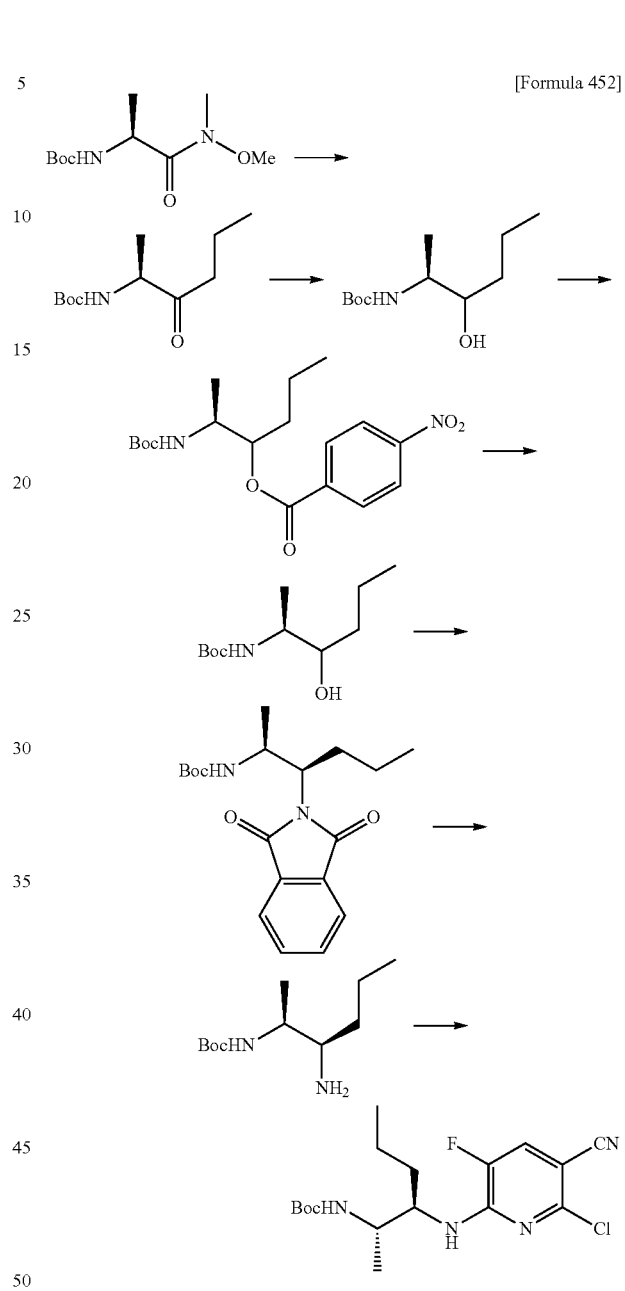

1st Step n-Propylmagnesium bromide (2M tetrahydrofuran solution) (100 ml) was added dropwise to a tetrahydrofuran solution (50 ml) containing (S)-tert-butyl(1-(methoxy(methyl)amino)-1-oxopropan-2-yl)carbamate (5 g) for 30 minutes under water cooling, followed by stirring at room temperature for 5 hours. The reaction solution was ice-cooled and added dropwise to 1M hydrochloric acid, followed by extraction with ethyl acetate. The organic layer was dried over anhydrous sodium sulfate. Then, the solvent was distilled away under reduced pressure, the obtained solid was purified by silica gel chromatography (n-hexane:ethyl acetate=4:1), and yellow oily matter of (S)-tert-butyl(3-oxohexan-2-yl)carbamate (3.7 g) was thus obtained.

MS (ESI m/z): 216 (M+H)

RT (min): 1.37

2nd Step

Sodium borohydride (3.7 g) was added in divided portions to a methanol/isopropanol (30 ml/30 ml) solution containing (S)-tert-butyl(3-oxohexan-2-yl)carbamate (17.5 g) at room temperature, followed by stirring for 1 hour. The solvent was distilled away under reduced pressure, and water was added, followed by extraction with ethyl acetate. The obtained organic layer was washed with saturated saline and dried over anhydrous sodium sulfate, the solvent was distilled away under reduced pressure, and a white solid of tert-butyl((2S)-3-hydroxyhexan-2-yl)carbamate (17 g) was obtained.

MS (ESI m/z): 218 (M+H)

RT (min): 1.27

3rd Step 4-nitrobenzoate (16.3 g), triphenylphosphine (32 g), and diisopropyl azodicarboxylate (40% toluene solution) (64 ml) were added dropwise to a tetrahydrofuran (50 ml) solution containing tert-butyl((2S)-3-hydroxyhexan-2-yl)carbamate (17 g) for 30 minutes, followed by stirring at room temperature for 14 hours. The solvent was distilled away from the reaction solution under reduced pressure, the obtained residue was purified by silica gel chromatography (n-hexane: ethyl acetate=5.5:1), and a yellow solid of (2S)-2-((tert-butoxycarbonyl)amino)hexane-3-yl 4-nitrobenzoate (17 g) was thus obtained.

MS (ESI m/z): 367 (M+H)

RT (min): 1.86

4th Step

A 1M lithium hydroxide aqueous solution (60 ml) was added to a tetrahydrofuran/methanol (50 ml/100 ml) solution containing (2S)-2-((tert-butoxycarbonyl)amino)hexane-3-yl 4-nitrobenzoate (17 g) at room temperature, followed by stirring for 30 minutes. The solvent was distilled away under reduced pressure, and water was added, followed by extraction with ethyl acetate. The obtained organic layer was washed with a saturated aqueous sodium hydrogen carbonate solution and saturated saline and dried over anhydrous sodium sulfate. The solvent was distilled away under reduced pressure, and colorless oily matter of tert-butyl((2S)-3-hydroxyhexan-2-yl)carbamate (9 g) was thus obtained.

MS (ESI m/z): 218 (M+H)

RT (min): 1.27

5th step

Phthalimide (8.2 g), triphenylphosphine (18 g), and diisopropyl azodicarboxylate (40% toluene solution) (37 ml) were added dropwise to a tetrahydrofuran (50 ml) solution containing tert-butyl((2S)-3-hydroxyhexan-2-yl)carbamate (17 g) for 30 minutes, followed by stirring at room temperature for 13.5 hours. The solvent was distilled away under reduced pressure, the obtained residue was purified by silica gel chromatography (n-hexane:ethyl acetate=5.5:1 and hexane:acetone=9:1), and yellow oily matter of tert-butyl((2S,3R)-3-(1,3-dioxoindoline-2-yl)hexan-2-yl)carbamate (6 g) was thus obtained.

¹H-NMR (CDCl₃, 300 MHz) δ:7.88-7.79 (m, 2H), 7.76-7.65 (m, 2H), 4.62-4.42 (m, 1H), 4.33-4.00 (m, 2H), 2.40-2.20 (m, 1H), 1.81-1.62 (m, 1H), 1.44 (s, 9H), 1.35-1.20 (m, 2H), 1.11 (d, 3H, J=6.6 Hz), 0.89 (t, 3H, J=7.3 Hz)

MS (ESI m/z): 347 (M+H)

RT (min): 1.70

6th step

Hydrazine•monohydrate (2.6 g) was added to an ethanol (20 ml) solution containing tert-butyl((2S,3R)-3-(1,3-dioxoindolin-2-yl)hexan-2-yl)carbamate (6 g), followed by stirring at 80° C. for 6 hours. Then, the solvent was distilled away under reduced pressure, chloroform was added, and insoluble matter was removed. Further, the solvent was distilled away under reduced pressure, and tert-butyl((2S,3R)-3-aminohexan-2-yl)carbamate (6 g) was thus obtained.

MS (ESI m/z): 217 (M+H)

RT (min): 0.79

7th step

Potassium carbonate (4.8 g) and 2,6-dichloro-5-fluoro-3-pyridinecarbonitrile (3.3 g) were added to a DMF (10 ml) solution containing tert-butyl((2S,3R)-3-aminohexan-2-yl)carbamate (6 g), followed by stirring at 60° C. for 1 hour. Water was added, followed by extraction with ethyl acetate. The organic layer was dried over anhydrous sodium sulfate. The solvent was distilled away under reduced pressure, the residue was purified by silica gel chromatography (n-hexane: ethyl acetate=9:1→4.5:1), and orange oily matter of tert-butyl((2S,3R)-3-((6-chloro-5-cyano-3-fluoropyridin-2-yl)amino)hexan-2-yl)carbamate (3.8 g) was thus obtained.

¹H-NMR (CDCl₃, 300 MHz) δ:7.29 (d, 1H, J=9.3 Hz), 5.76 (d, 1H, J=7.3 Hz), 4.67 (d, 1H, J=6.6 Hz), 4.36-4.20 (m, 1H), 3.96-3.80 (m, 1H), 1.70-1.29 (m, 13H), 1.17 (d, 3H, J=6.6 Hz), 0.94 (t, 3H, J=7.3 Hz)

MS (ESI m/z): 371 (M+H)

RT (min): 1.78

Reference Example 418

The following compounds were obtained with reference to Tetrahedron: Asymmetry, Vol. 8, No, 14, pp. 2381-2401, 1997.

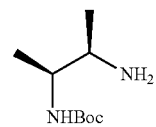

[Formula 453]

tert-Butyl((2S,3R)-3-aminobutan-2-yl)carbamate

MS (ESI m/z): 189 (M+H)

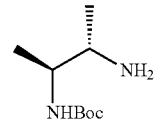

[Formula 454]

tert-Butyl((2S,3S)-3-aminobutan-2-yl)carbamate

MS (ESI m/z): 189 (M+H)

RT (min): 0.62

Reference Example 419

The following compound was obtained as described in the 7th step of Reference Example 417.

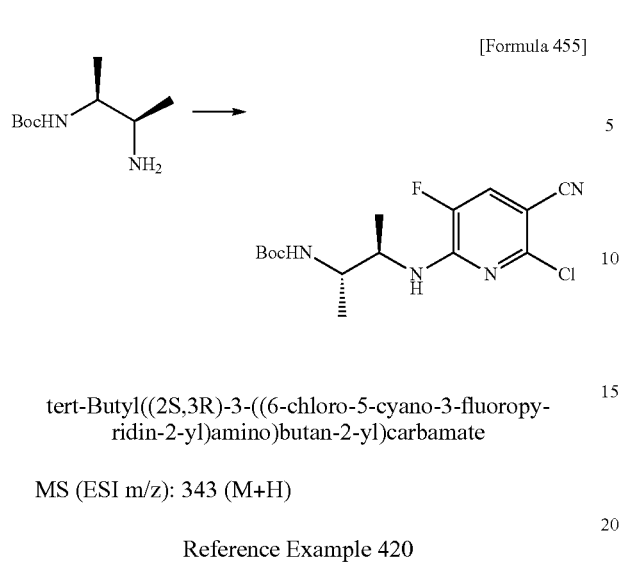

tert-Butyl((2S,3R)-3-((6-chloro-5-cyano-3-fluoropyridin-2-yl)amino)butan-2-yl)carbamate MS (ESI m/z): 343 (M+H)

Reference Example 420

The following compound was obtained as described in the 7th step of Reference Example 417.

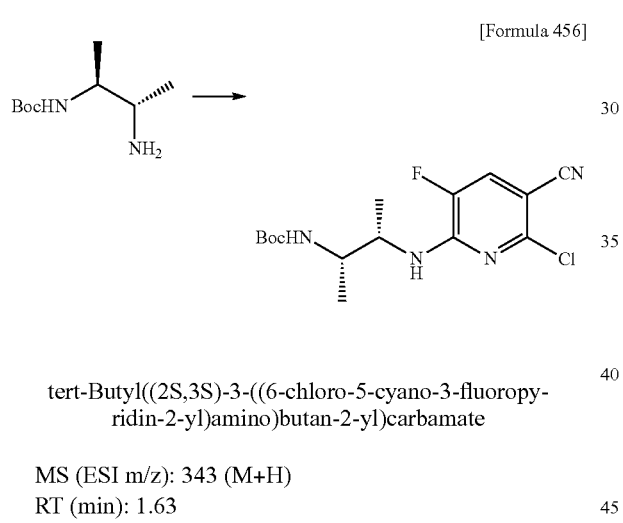

tert-Butyl((2S,3S)-3-((6-chloro-5-cyano-3-fluoropyridin-2-yl)amino)butan-2-yl)carbamate MS (ESI m/z): 343 (M+H)
RT (min): 1.63

Reference Example 421

The following compound was obtained as described in Reference Example 417.

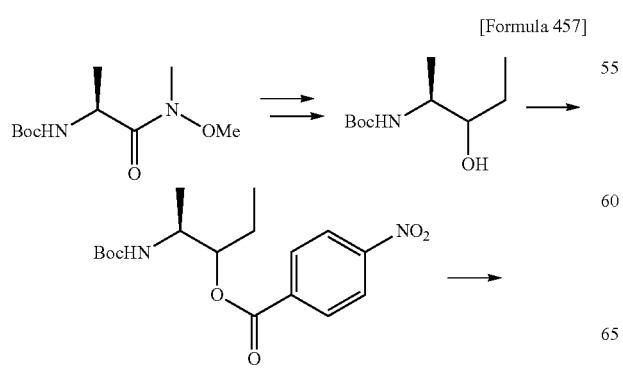

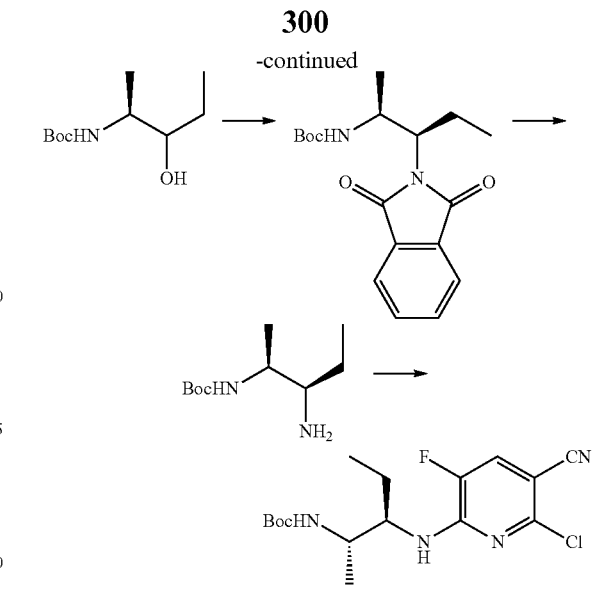

tert-Butyl((2S)-3-hydroxypentan-2-yl)carbamate

MS (ESI m/z): 204 (M+H)
RT (min): 1.12

(2S)-2-((tert-butoxycarbonyl)amino)pentan-3-yl 4-nitrobenzoate

MS (ESI m/z): 353 (M+H)
RT (min): 1.75 tert-Butyl((2S)-3-hydroxypentan-2-yl)carbamate

MS (ESI m/z): 204 (M+H)
RT (min): 1.13 tert-Butyl((2S,3R)-3-(1,3-dioxoindoline-2-yl)pentan-2-yl)carbamate $^1$H-NMR (CDCl$_3$, 300 MHz) δ:7.84 (dd, 2H, J=3.3, 5.4 Hz), 7.72 (dd, 2H, J=3.3, 5.4 Hz), 4.60-4.50 (m, 1H), 4.35-4.20 (m, 1H), 4.10-3.95 (m, 1H), 2.38-2.17 (m, 1H), 1.93-1.80 (m, 1H), 1.43 (s, 9H), 1.11 (d, 3H, J=6.6 Hz), 0.86 (d, 3H, J=7.3 Hz)
MS (ESI m/z): 333 (M+H)
RT (min): 1.56 tert-Butyl((2S,3R)-3-aminopentan-2-yl)carbamate

MS (ESI m/z): 203 (M+H)
RT (min): 0.69 tert-Butyl((2S,3R)-3-((6-chloro-5-cyano-3-fluoropyridin-2-yl)amino)pentan-2-yl)carbamate $^1$H-NMR (CDCl$_3$, 300 MHz) δ:7.29 (d, 1H, J=9.9 Hz), 5.76 (d, 1H, J=6.6 Hz), 4.68 (d, 1H, J=6.6 Hz), 4.26-4.14 (m, 1H), 3.98-3.84 (m, 1H), 1.80-1.62 (m, 1H), 1.49-1.36 (m, 10H), 1.17 (d, 3H, J=7.2 Hz), 0.97 (t, 3H, J=7.7 Hz)
MS (ESI m/z): 357 (M+H)
RT (min): 1.67

Reference Example 422

The following compounds were obtained as described in Reference Example 417.

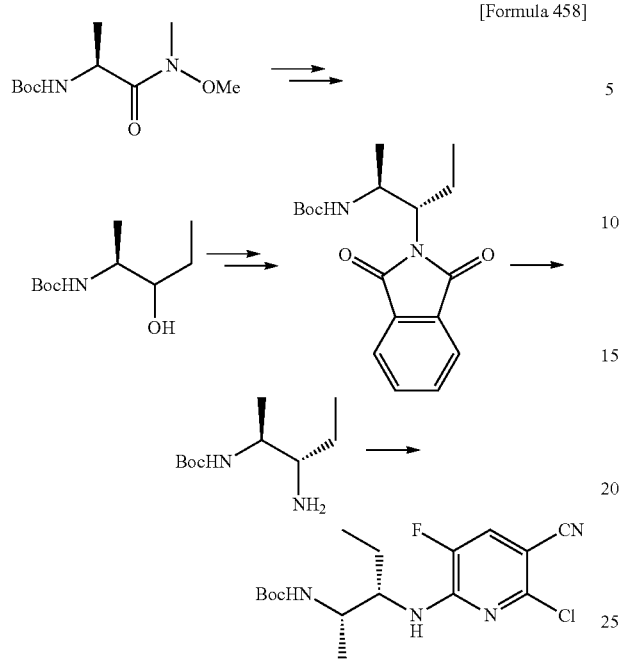

tert-Butyl((2S,3S)-3-(1,3-dioxoindolin-2-yl)pentan-2-yl)carbamate

¹H-NMR (CDCl₃, 300 MHz) δ:7.85 (dd, 2H, J=3.3, 5.4 Hz), 7.73 (dd, 2H, J=3.3, 5.4 Hz), 5.50 (d, 1H, J=9.3 Hz), 4.12-4.09 (m, 2H), 2.19-2.03 (m, 1H), 1.87-1.73 (m, 1H), 1.31 (s, 9H), 1.12 (d, 3H, J=6.6 Hz), 0.87 (d, 3H, J=7.3 Hz)
MS (ESI m/z): 333 (M+H)
RT (min): 1.56 tert-Butyl((2S,3S)-3-aminopentan-2-yl)carbamate

MS (ESI m/z): 203 (M+H)
RT (min): 0.67 tert-Butyl((2S,3S)-3-((6-chloro-5-cyano-3-fluoropyridin-2-yl)amino)pentan-2-yl)carbamate MS (ESI m/z): 357 (M+H)
RT (min): 1.72

Reference Example 423

The following compound was obtained as described in Reference Example 417.

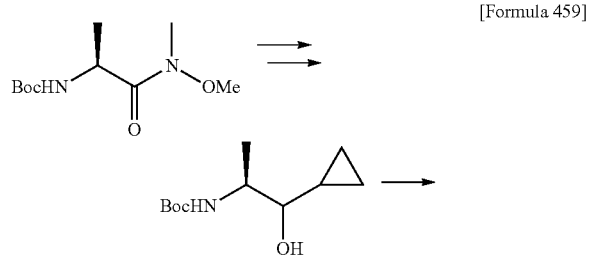

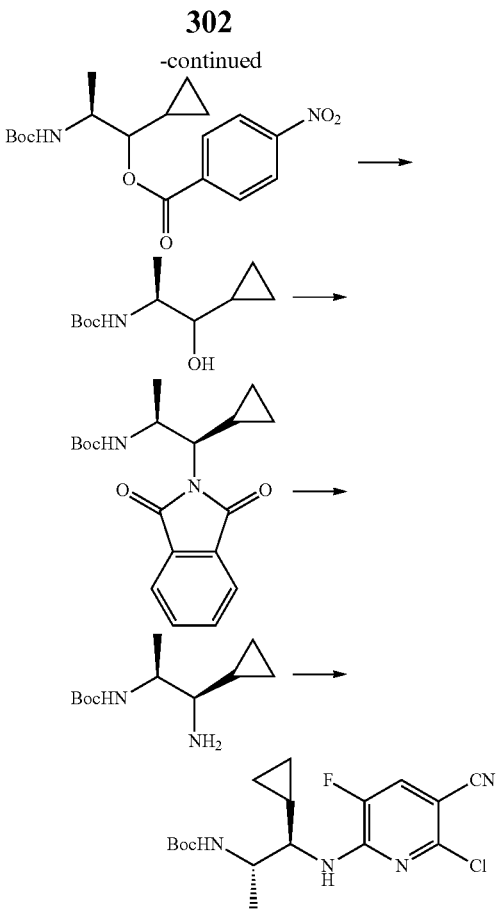

tert-Butyl((2S)-1-cyclopropyl-1-hydroxypropan-2-yl)carbamate

MS (ESI m/z): 216 (M+H)
RT (min): 1.14

(2S)-2-((tert-butoxycarbonyl)amino)-1-cyclopropylpropyl 4-nitrobenzoate

MS (ESI m/z): 365 (M+H)
RT (min): 1.76 tert-Butyl((2S)-1-cyclopropyl-1-hydroxypropan-2-yl)carbamate

MS (ESI m/z): 216 (M+H)
RT (min): 1.14 tert-Butyl((1R,2S)-1-cyclopropyl-1-(1,3-dioxoindolin-2-yl)propan-2-yl)carbamate

¹H-NMR (CDCl₃, 300 MHz) δ:7.87-7.68 (m, 4H), 4.62 (br, 1H), 4.45-4.28 (m, 1H), 3.31 (dd, 1H, J=10.7, 6.8 Hz), 2.25-1.75 (m, 1H), 1.40 (s, 9H), 1.18 (t, 3H, J=6.9 Hz), 0.85-0.72 (m, 1H), 0.52-0.38 (m, 2H), 0.16-0.04 (m, 1H)
MS (ESI m/z): 345 (M+H)
RT (min): 1.60 tert-Butyl((1R,2S)-1-((6-chloro-5-cyano-3-fluoropyridin-2-yl)amino)-1-cyclopropyl propan-2-yl)carbamate ¹H-NMR (CDCl₃, 300 MHz) δ:7.32-7.28 (m, 1H), 6.20 (br, 1H), 4.90-4.74 (m, 1H), 4.12-3.98 (m, 1H), 3.68-3.50 (m, 1H), 1.44 (s, 9H), 1.27 (t, 3H, J=3.3 Hz), 0.98-0.85 (m, 1H), 0.73-0.40 (m, 4H)

MS (ESI m/z): 369 (M+H)
RT (min): 1.72

Reference Example 424

The following compounds were obtained as described in Reference Example 417.

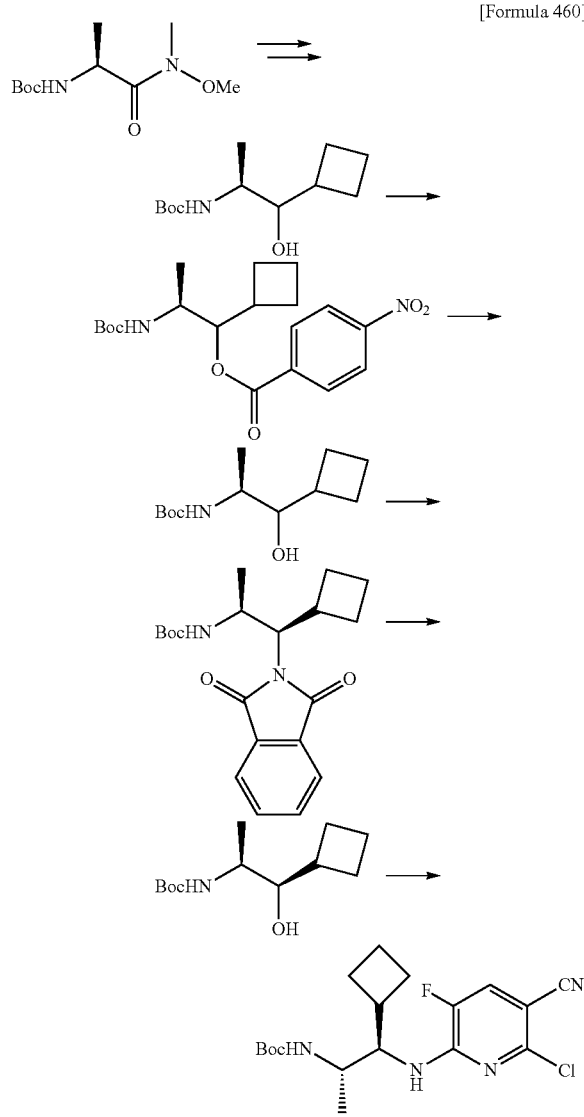

[Formula 460]

(2S)-2-((tert-butoxycarbonyl)amino)-1-cyclobutyl-propyl 4-nitrobenzoate

MS (ESI m/z): 379 (M+H)
RT (min): 1.91 tert-Butyl((1R,2S)-1-cyclobutyl-1-(1,3-dioxoisoindoline-2-yl)propan-2-yl)carbamate MS (ESI m/z): 359 (M+H)
RT (min): 1.71 tert-Butyl((1R,2S)-1-amino-1-cyclobutylpropan-2-yl)carbamate

MS (ESI m/z): 229 (M+H)
RT (min): 0.85 tert-Butyl((1R,2S)-1-((6-chloro-5-cyano-3-fluoropyridin-2-yl)amino)-1-cyclobutylpropan-2-yl)carbamate MS (ESI m/z): 384 (M+H)
RT (min): 1.83

Reference Example 425

The following compounds were obtained as described in Reference Example 417.

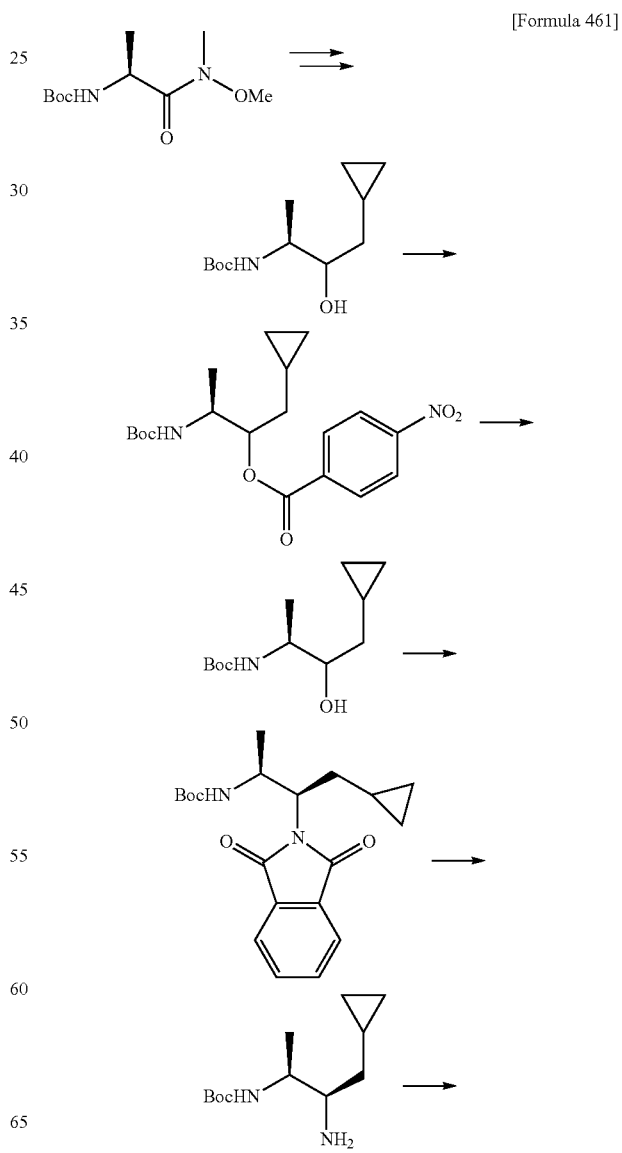

[Formula 461]

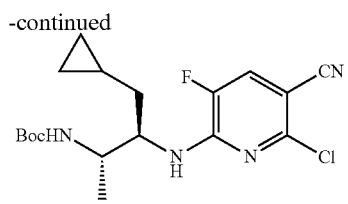

tert-Butyl((2S)-4-cyclopropyl-3-hydroxybutan-2-yl)carbamate

MS (ESI m/z): 230 (M+H)
RT (min): 1.32

(3S)-3-((tert-butoxycarbonyl)amino)-1-cyclopropylbutan-2-yl) 4-nitrobenzoate

MS (ESI m/z): 379 (M+H)
RT (min): 1.89 tert-Butyl((2S)-4-cyclopropyl-3-hydroxybutan-2-yl)carbamate

MS (ESI m/z): 230 (M+H)
RT (min): 1.32 tert-Butyl((2S,3R)-4-cyclopropyl-3-(1,3-dioxoindolin-2-yl)butan-2-yl)carbamate $^1$H-NMR (CDCl$_3$, 300 MHz) δ:7.87-7.69 (m, 4H), 5.81-5.66 (m, 1H), 5.00-4.82 (m, 2H), 4.58-4.46 (br, 1H), 4.33-4.06 (m, 2H), 2.55-1.80 (m, 2H), 1.44 (s, 9H), 1.34-1.26 (m, 2H), 1.11 (d, 3H, J=6.6 Hz)
MS (ESI m/z): 359 (M+H)
RT (min): 1.70 tert-Butyl((2S,3R)-3-amino-4-cyclopropylbutan-2-yl)carbamate

MS (ESI m/z): 229 (M+H)
RT (min): 0.89 tert-Butyl((2S,3R)-3-((6-chloro-5-cyano-3-fluoropyridin-2-yl)amino)-4-cyclopropyl butan-2-yl)carbamate $^1$H-NMR (CDCl$_3$, 300 MHz) δ:7.29 (d, 1H, J=9.9 Hz), 5.94-5.74 (m, 1H), 5.06-4.95 (m, 2H), 4.62 (br, 1H), 4.34-4.25 (m, 1H), 3.96-3.87 (m, 1H), 2.17-2.08 (m, 2H), 1.78-1.67 (m, 1H), 1.55-1.46 (m, 2H), 1.44 (s, 9H), 1.18 (d, 3H, J=7.3 Hz)
MS (ESI m/z): 383 (M+H)
RT (min): 1.77

Reference Example 426

The following compounds were obtained as described in Reference Example 417.

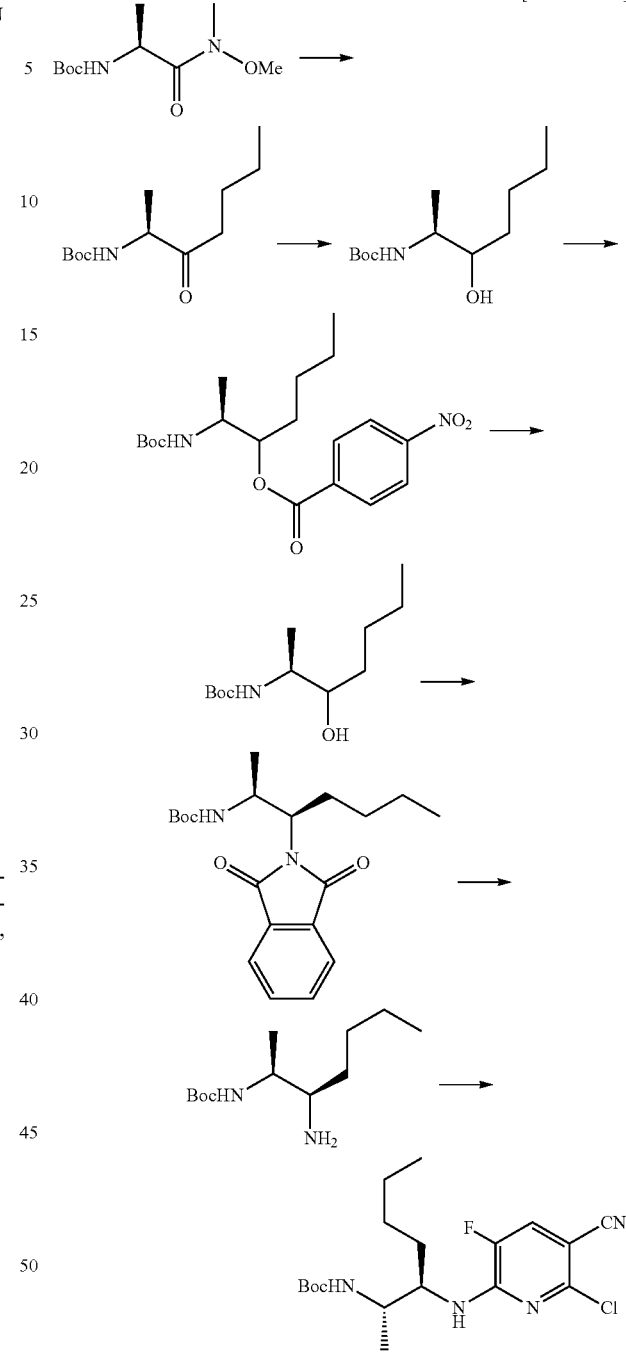

[Formula 462]

(S)-tert-butyl(3-oxoheptan-2-yl)carbamate

MS (ESI m/z): 230 (M+H)
RT (min): 1.53 tert-Butyl((2S)-3-hydroxyheptane-2-yl)carbamate

MS (ESI m/z): 232 (M+H)
RT (min): 1.40

307

(2S)-2-((tert-butoxycarbonyl)amino)heptan-3-yl 4-nitrobenzoate

MS (ESI m/z): 381 (M+H)
RT (min): 1.96 tert-Butyl((2S)-3-hydroxyheptan-2-yl)carbamate

MS (ESI m/z): 232 (M+H)
RT (min): 1.43 tert-Butyl((2S,3R)-3-(1,3-dioxoindolin-2-yl)heptan-2-yl)carbamate $^1$H-NMR (CDCl$_3$, 300 MHz) δ:7.87-7.79 (m, 2H), 7.76-7.68 (m, 2H), 4.53 (br, 1H), 4.32-3.99 (m, 2H), 2.40-2.17 (m, 1H), 1.86-1.69 (m, 1H), 1.44 (s, 9H), 1.36-1.04 (m, 7H), 0.83 (t, 3H, J=7.2 Hz)
MS (ESI m/z): 361 (M+H)
RT (min): 1.81 tert-Butyl((2S,3R)-3-aminoheptan-2-yl)carbamate

MS (ESI m/z): 231 (M+H)
RT (min): 0.89 tert-Butyl((2S,3R)-3-((6-chloro-5-cyano-3-fluoropyridin-2-yl)amino)heptan-2-yl)carbamate $^1$H-NMR (CDCl$_3$, 300 MHz) δ:7.29 (d, 1H, J=9.9 Hz), 5.74 (d, 1H, J=7.3 Hz), 4.68 (d, 1H, J=6.6 Hz), 4.34-4.18 (m, 1H), 3.97-3.80 (m, 1H), 1.71-1.22 (m, 15H), 1.17 (t, 3H, J=6.6 Hz), 0.89 (t, 3H, J=6.3 Hz)
MS (ESI m/z): 385 (M+H)
RT (min): 1.87

Reference Example 427

The following compounds were obtained as described in Reference Example 417.

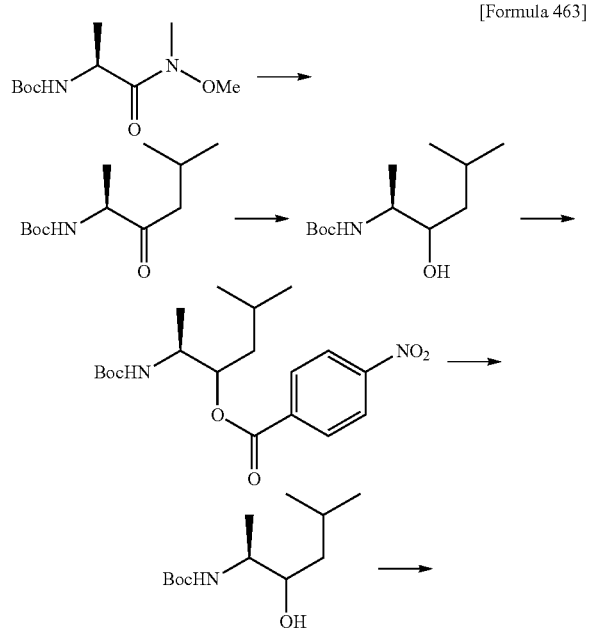

[Formula 463]

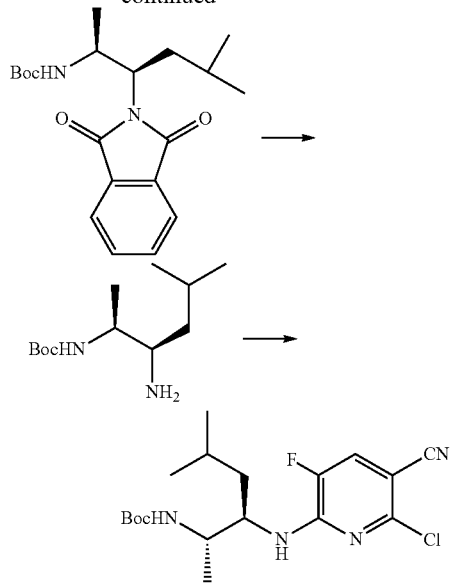

(S)-tert-butyl(5-methyl-3-oxohexan-2-yl)carbamate
MS (ESI m/z): 230 (M+H)
RT (min): 1.53 tert-Butyl((2S)-3-hydroxy-5-methylhexan-2-yl)carbamate

MS (ESI m/z): 232 (M+H)
RT (min): 1.42

(2S)-2-((tert-butoxycarbonyl)amino)-5-methylhexan-3-yl 4-nitrobenzoate

MS (ESI m/z): 381 (M+H)
RT (min): 1.95 tert-Butyl((2S)-3-hydroxy-5-methylhexan-2-yl)carbamate

MS (ESI m/z): 232 (M+H)
RT (min): 1.42 tert-Butyl((2S,3R)-3-(1,3-dioxoindolin-2-yl)-5-methylhexan-2-yl)carbamate $^1$H-NMR (CDCl$_3$, 300 MHz) δ:7.86-7.77 (m, 2H), 7.75-7.66 (m, 2H), 4.55 (br, 1H), 4.32-4.12 (m, 2H), 2.48-2.30 (m, 1H), 1.51-1.36 (s, 10H), 1.32-1.22 (m, 1H), 1.11 (d, 3H, J=6.6 Hz), 0.92-0.84 (m, 6H)
MS (ESI m/z): 361 (M+H)
RT (min): 1.80 tert-Butyl((2S,3R)-3-amino-5-methylhexan-2-yl)carbamate

MS (ESI m/z): 231 (M+H)
RT (min): 0.89 tert-Butyl((2S,3R)-3-((6-chloro-5-cyano-3-fluoropyridin-2-yl)amino)-5-methylhexan-2-yl)carbamate $^1$H-NMR (CDCl$_3$, 300 MHz) δ:7.29 (d, 1H, J=9.9 Hz), 5.69 (d, 1H, J=7.9 Hz), 4.67 (d, 1H, J=6.6 Hz), 4.46-4.28 (m, 1H), 3.96-3.80 (m, 1H), 1.70-1.32 (m, 12H), 1.16 (d, 3H, J=6.6 Hz), 0.94 (dd, 6H, J=6.6, 2.0 Hz)

MS (ESI m/z): 385 (M+H)

RT (min): 1.86

Reference Example 428

The following compounds were obtained as described in Reference Example 417.

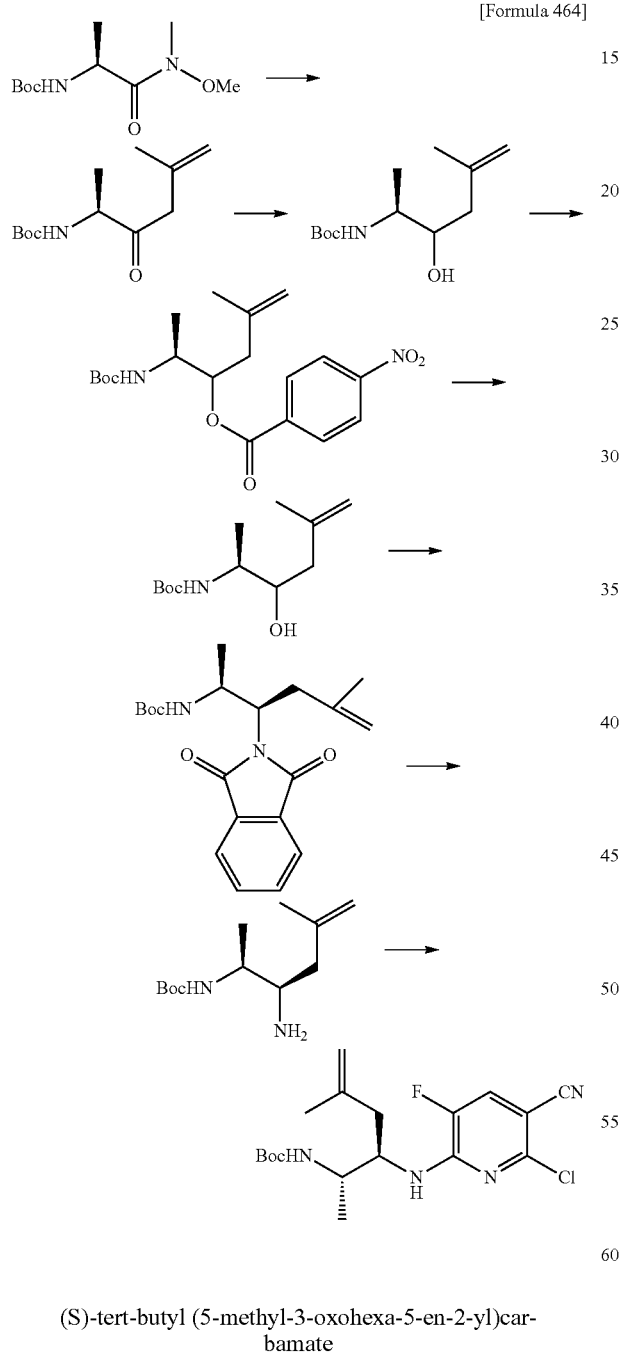

[Formula 464]

(S)-tert-butyl (5-methyl-3-oxohexa-5-en-2-yl)carbamate

MS (ESI, m/z): 228 (M+H)

RT (min): 1.40 tert-Butyl((2S)-3-hydroxy-5-methylhexa-5-en-2-yl)carbamate

MS (ESI m/z): 230 (M+H)

RT (min): 1.30

(2S)-2-((tert-butoxycarbonyl)amino)-5-methylhexane-3-yl 4-nitrobenzoate

MS (ESI m/z): 379 (M+H)

RT (min): 1.85 tert-Butyl((2S)-3-hydroxy-5-methylhexan-2-yl)carbamate

MS (ESI m/z): 230 (M+H)

RT (min): 1.30 tert-Butyl((2S,3R)-3-(1,3-dioxoindolin-2-yl)-5-methylhexa-5-en-2-yl)carbamate

MS (ESI m/z): 359 (M+H)

RT (min): 1.71 tert-Butyl((2S,3R)-3-amino-5-methylhexa-5-en-2-yl)carbamate

MS (ESI m/z): 229 (M+H)

RT (min): 0.90 tert-Butyl((2S,3R)-3-((6-chloro-5-cyano-3-fluoropyridin-2-yl)amino)-5-methylhexa-5-en-2-yl)carbamate MS (ESI m/z): 383 (M+H)

RT (min): 1.77

Reference Example 429

The following compounds were obtained as described in the 1st, 2nd, 5th, 6th, and 7th steps of Reference Example 417.

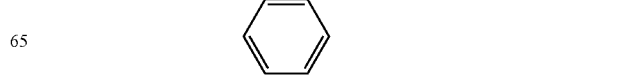

[Formula 465]

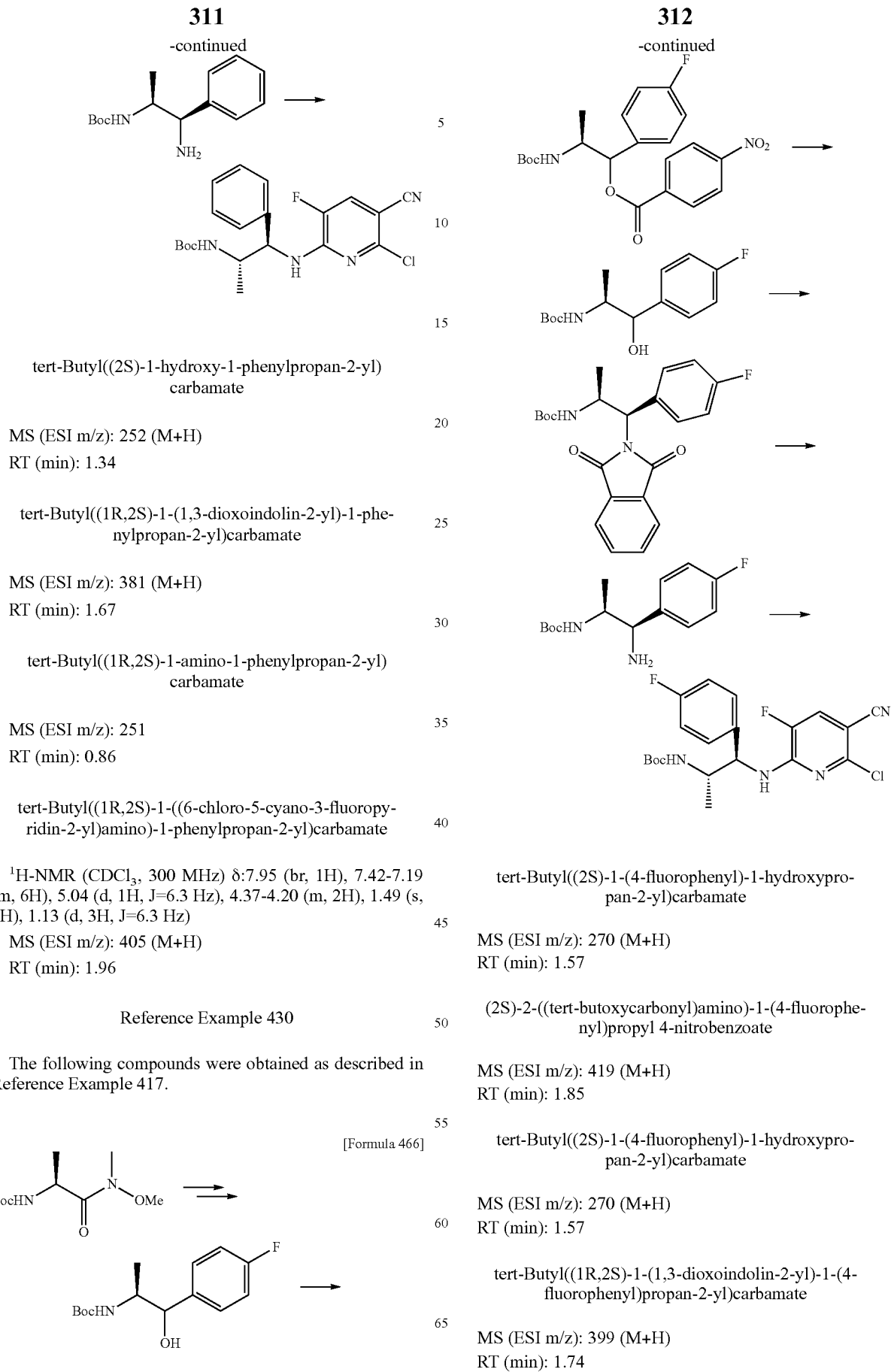

311 tert-Butyl((2S)-1-hydroxy-1-phenylpropan-2-yl)carbamate

MS (ESI m/z): 252 (M+H)
RT (min): 1.34 tert-Butyl((1R,2S)-1-(1,3-dioxoindolin-2-yl)-1-phenylpropan-2-yl)carbamate

MS (ESI m/z): 381 (M+H)
RT (min): 1.67 tert-Butyl((1R,2S)-1-amino-1-phenylpropan-2-yl)carbamate

MS (ESI m/z): 251
RT (min): 0.86 tert-Butyl((1R,2S)-1-((6-chloro-5-cyano-3-fluoropyridin-2-yl)amino)-1-phenylpropan-2-yl)carbamate $^1$H-NMR (CDCl$_3$, 300 MHz) δ:7.95 (br, 1H), 7.42-7.19 (m, 6H), 5.04 (d, 1H, J=6.3 Hz), 4.37-4.20 (m, 2H), 1.49 (s, 9H), 1.13 (d, 3H, J=6.3 Hz)
MS (ESI m/z): 405 (M+H)
RT (min): 1.96

Reference Example 430

The following compounds were obtained as described in Reference Example 417.

[Formula 466]

312 tert-Butyl((2S)-1-(4-fluorophenyl)-1-hydroxypropan-2-yl)carbamate

MS (ESI m/z): 270 (M+H)
RT (min): 1.57

(2S)-2-((tert-butoxycarbonyl)amino)-1-(4-fluorophenyl)propyl 4-nitrobenzoate

MS (ESI m/z): 419 (M+H)
RT (min): 1.85 tert-Butyl((2S)-1-(4-fluorophenyl)-1-hydroxypropan-2-yl)carbamate

MS (ESI m/z): 270 (M+H)
RT (min): 1.57 tert-Butyl((1R,2S)-1-(1,3-dioxoindolin-2-yl)-1-(4-fluorophenyl)propan-2-yl)carbamate MS (ESI m/z): 399 (M+H)
RT (min): 1.74

313 tert-Butyl((1R,2S)-1-amino-1-(4-fluorophenyl)propan-2-yl)carbamate

MS (ESI m/z): 269(M+H)
RT (min): 0.89 tert-Butyl((1R,2S)-1-((6-chloro-5-cyano-3-fluoropyridin-2-yl)amino)-1-(4-fluorophenyl)propan-2-yl)carbamate $^1$H-NMR (CDCl$_3$, 300 MHz) δ:8.07 (br, 1H), 7.25-7.16 (m, 3H), 7.09-6.98 (m, 2H), 4.99 (d, 1H, J=5.9 Hz), 4.36-4.16 (m, 2H), 1.50 (s, 9H), 1.12 (d, 3H, J=6.6 Hz)
MS (ESI m/z): 423 (M+H)
RT (min): 1.81

Reference Example 431

The following compounds were obtained as described in Reference Example 417.

[Formula 467]

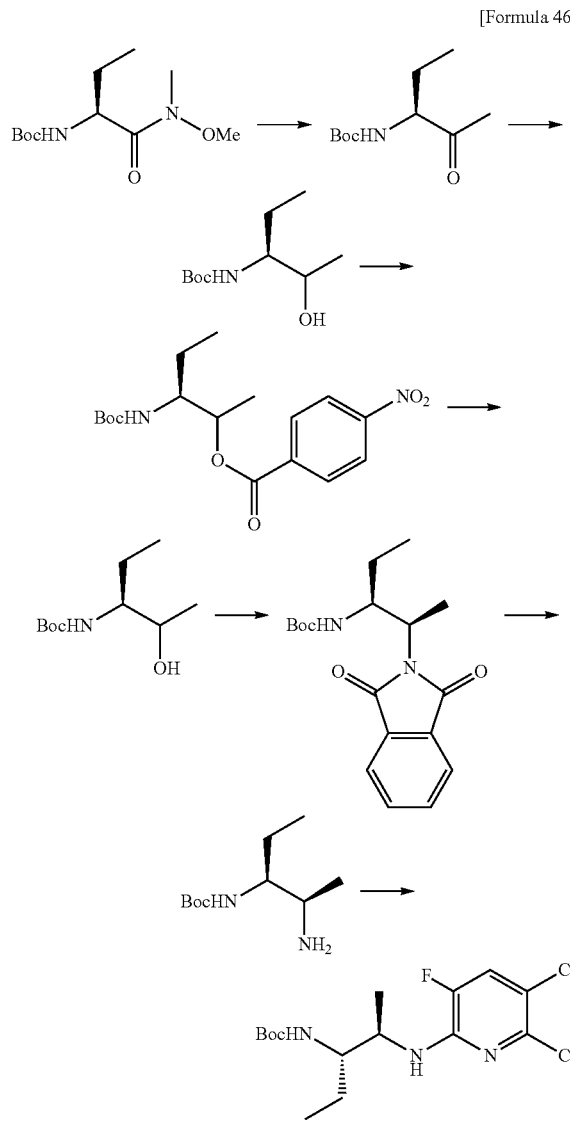

314

(S)-tert-butyl(2-oxopentan-3-yl)carbamate

MS (ESI m/z): 202 (M+H)
RT (min): 1.19 tert-Butyl((3S)-2-hydroxypentan-3-yl)carbamate

MS (ESI m/z): 204 (M+H)
RT (min): 1.09

(3S)-3-((tert-butoxycarbonyl)amino)pentan-2-yl 4-nitrobenzoate

MS (ESI m/z): 353 (M+H)
RT (min): 1.75 tert-Butyl((3S)-2-hydroxypentan-3-yl)carbamate

MS (ESI m/z): 204 (M+H)
RT (min): 1.09 tert-Butyl((2R,3S)-2-(1,3-dioxoindolin-2-yl)pentan-3-yl)carbamate $^1$H-NMR (CDCl$_3$, 300 MHz) δ:7.89-7.75 (m, 2H), 7.76-7.66 (m, 2H), 4.46 (d, 1H, J=8.6 Hz), 4.36-4.02 (m, 2H), 1.41 (s, 9H), 1.37-1.22 (m, 5H), 0.92 (t, 3H, J=7.2)
MS (ESI m/z): 333 (M+H)
RT (min): 1.58 tert-Butyl((2R,3S)-2-aminopentan-3-yl)carbamate

MS (ESI m/z): 203 (M+H)
RT (min): 0.69 tert-Butyl((2R,3S)-2-((6-chloro-5-cyano-3-fluoropyridin-2-yl)amino)pentan-3-yl)carbamate $^1$H-NMR (CDCl$_3$, 300 MHz) δ:7.25 (d, 1H, J=9.9 Hz), 6.79 (d, 1H, J=5.4 Hz), 4.46 (d, 1H, J=7.9 Hz), 4.30-4.15 (m, 1H), 3.80-3.68 (m, 1H), 1.71-1.30 (m, 11H), 1.17 (d, 3H, J=6.6 Hz), 1.02 (t, 3H, J=7.6 Hz)
MS (ESI m/z): 357 (M+H)
RT (min): 1.72

Reference Example 432

The following compounds were obtained as described in Reference Example 417.

[Formula 468]

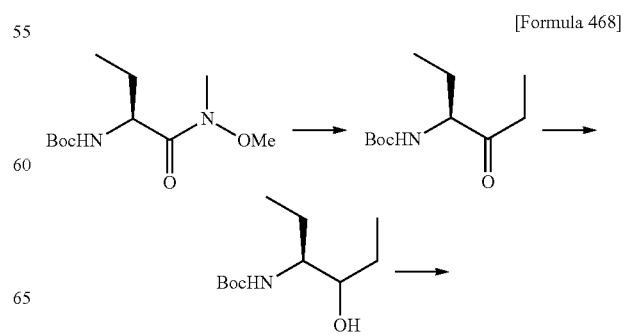

-continued

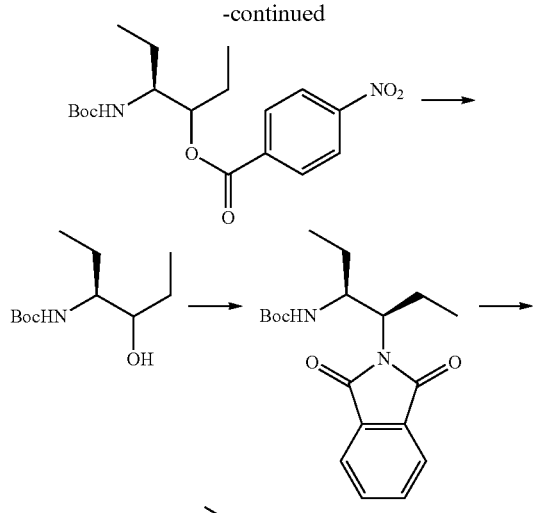

(S)-tert-butyl(4-oxohexan-3-yl)carbamate

MS (ESI m/z): 216 (M+H)
RT (min): 1.36 tert-Butyl((3S)-4-hydroxyhexan-3-yl)carbamate

MS (ESI m/z): 218 (M+H)
RT (min): 1.26

(4S)-4-((tert-butoxycarbonyl)amino)hexan-3-yl 4-nitrobenzoate

MS (ESI m/z): 367 (M+H)
RT (min): 1.85 tert-Butyl((3S)-4-hydroxyhexan-3-yl)carbamate

MS (ESI m/z): 218 (M+H)
RT (min): 1.26 tert-Butyl((3S,4R)-4-(1,3-dioxoindolin-2-yl)hexan-3-yl)carbamate $^1$H-NMR (CDCl$_3$, 300 MHz) δ:7.89-7.78 (m, 2H), 7.76-7.66 (m, 2H), 4.46 (d, 1H, J=8.6 Hz), 4.36-3.90 (m, 2H), 2.39-2.15 (m, 1H), 1.96-1.76 (m, 1H), 1.67-1.40 (m, 10H), 1.34-1.16 (m, 1H), 0.96-0.80 (m, 6H)
MS (ESI m/z): 347 (M+H)
RT (min): 1.68 tert-Butyl((3S,4R)-4-aminohexan-3-yl)carbamate

MS (ESI m/z): 217 (M+H)
RT (min): 0.75 tert-Butyl((3S,4R)-4-(6-chloro-5-cyano-3-fluoropyridin-2-yl)amino)hexan-3-yl)carbamate $^1$H-NMR (CDCl$_3$, 300 MHz) δ:7.28 (d, 1H, J=9.9 Hz), 5.80 (d, 1H, J=7.9 Hz), 4.43 (d, 1H, J=8.6 Hz), 4.29-4.05 (m, 1H), 3.74-3.60 (m, 1H), 1.78-1.27 (m, 13H), 1.00 (t, 3H, J=7.7 Hz), 0.96 (t, 3H, J=7.5 Hz)
MS (ESI m/z): 371 (M+H)
RT (min.): 1.77

Reference Example 433

The following compounds were obtained as described in Reference Example 417.

[Formula 469]

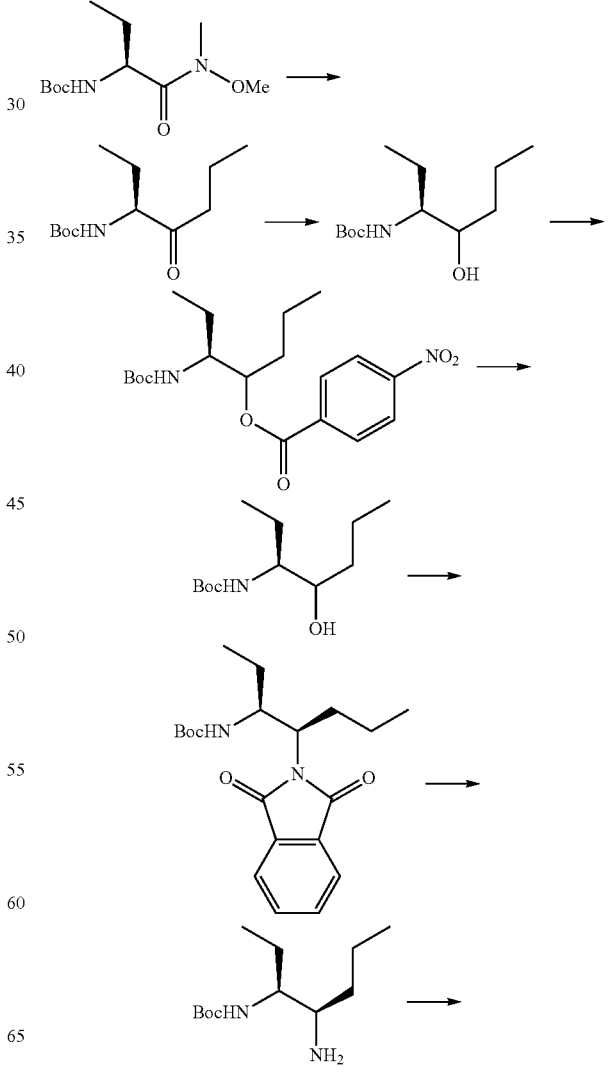

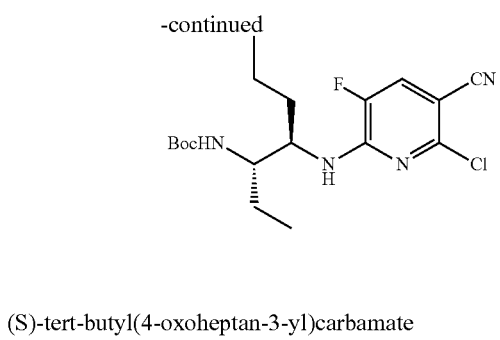

(S)-tert-butyl(4-oxoheptan-3-yl)carbamate

MS (ESI m/z): 230 (M+H)
RT (min): 1.53 tert-Butyl((3S)-4-hydroxyheptan-3-yl)carbamate

MS (ESI m/z): 232 (M+H)
RT (min): 1.39

(3S)-3-((tert-butoxycarbonyl)amino)heptan-4-yl 4-nitrobenzoate

MS (ESI m/z): 381 (M+H)
RT (min): 1.95 tert-Butyl((3S)-4-hydroxyheptan-3-yl)carbamate

MS (ESI m/z): 232 (M+H)
RT (min): 1.42 tert-Butyl((3S,4R)-4-(1,3-dioxoindolin-2-yl)heptan-3-yl)carbamate $^1$H-NMR (CDCl$_3$, 300 MHz) δ:7.86-7.78 (m, 2H), 7.77-7.65 (m, 2H), 4.42 (d, 1H, J=9.3 Hz), 4.20-4.00 (m, 2H), 2.42-2.12 (m, 1H), 1.80-1.58 (m, 1H), 1.43 (s, 9H), 1.38-1.08 (m, 4H), 0.96-0.84 (m, 6H)
MS (ESI m/z): 361 (M+H)
RT (min): 1.79 tert-Butyl((3S,4R)-4-aminoheptan-3-yl)carbamate

MS (ESI m/z): 231 (M+H)
RT (min): 0.89 tert-Butyl((3S,4R)-4-((6-chloro-5-cyano-3-fluoropyridin-2-yl)amino)heptan-3-yl)carbamate $^1$H-NMR (CDCl$_3$, 300 MHz) δ:7.27 (d, 1H, J=9.9 Hz), 5.80 (d, 1H, J=7.9 Hz), 4.43 (d, 1H, J=8.6 Hz), 4.37-4.21 (m, 1H), 3.75-3.61 (m, 1H), 1.70-1.19 (m, 15H), 1.05-0.87 (m, 6H)
MS (ESI m/z): 385 (M+H)
RT (min): 1.88

Reference Example 434

The following compounds were obtained as described in Reference Example 417.

[Formula 470]

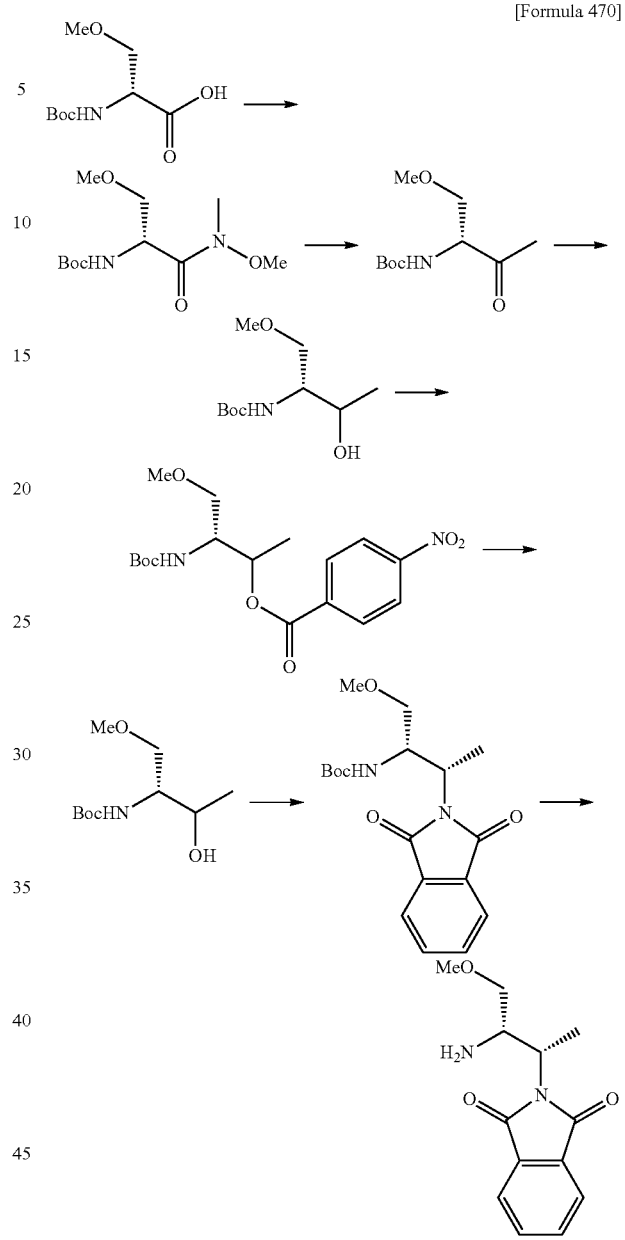

1st step 1,1'-carbonyldiimidazole (1.9 g) was added to a dichloromethane solution (10 ml) containing (R)-2-((tert-butoxycarbonyl)amino)-3-methoxypropionic acid (2 g) in an ice bath, followed by stirring for 30 minutes. Subsequently, triethylamine (1.2 g) and N,O-dimethylhydroxylamine (1.2 g) were added, followed by stirring at room temperature for 2.5 hours. The reaction solution was added dropwise to 4M hydrochloric acid, followed by extraction with ethyl acetate. The organic layer was washed with a saturated aqueous sodium hydrogen carbonate solution and water and dried over anhydrous sodium sulfate. Then, the solvent was distilled away under reduced pressure, and yellow oily matter of (R)-tert-butyl(1-(methoxy(methyl)amino)-1-oxobutan-2-yl)carbamate (1.8 g) was thus obtained.
MS (ESI m/z): 263 (M+H)
RT (min): 1.03

2nd, 3rd, 4th, 5th, 6th, and 7th steps

The following compounds were obtained as described in the 1st, 2nd, 3rd, 4th, and 5th steps of Reference Example 417 and the 2nd step of Reference Example 97.

(R)-tert-butyl(1-methoxy-3-oxobutan-2-yl)carbamate

MS (ESI m/z): 218 (M+H)
RT (min): 1.07 tert-Butyl((2R)-3-hydroxy-1-methoxybutan-2-yl)carbamate

MS (ESI, m/z): 220 (M+H)
RT (min): 0.92

(3R)-3-((tert-butoxycarbonyl)amino)-4-methoxybutan-2-yl 4-nitrobenzoate

MS (ESI m/z): 369 (M+H)
RT (min): 1.67 tert-Butyl((2R)-3-hydroxy-1-methoxybutan-2-yl)carbamate

MS (ESI m/z): 220(M+H)
RT (min): 0.92 tert-Butyl((2S,3S)-3-((1,3-dioxoisoindolin-2-yl)-1-methoxybutan-2-yl)carbamate $^1$H-NMR (CDCl$_3$, 300 MHz) δ:7.85-7.78 (m, 2H), 7.74-7.66 (m, 2H), 5.08-4.92 (m, 1H), 4.54-4.34 (m, 2H), 3.44-3.26 (m, 2H), 3.22 (s, 3H), 1.52 (d, 3H, J=6.6 Hz), 1.45 (s, 9H)
MS (ESI m/z): 349 (M+H)
RT (min): 1.50

2-((2S,3S)-3-amino-4-methoxybutan-2-yl)isoindolin-1,3-dione

MS (ESI m/z): 249 (M+H),
RT (min): 0.64

Reference Example 435

[Formula 471]

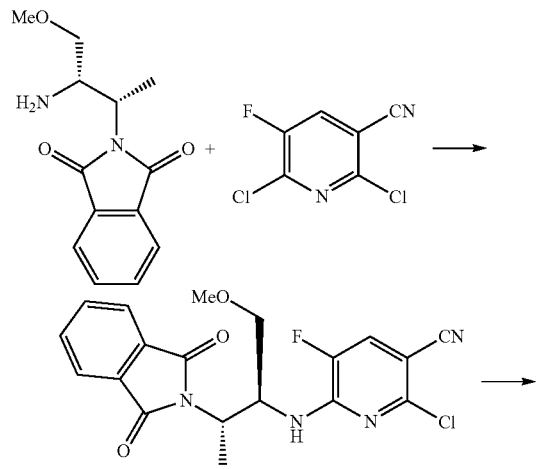

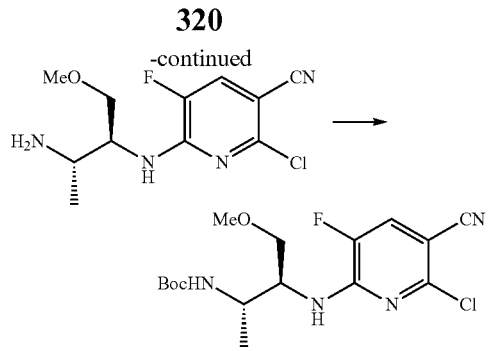

1st Step
The following compound was obtained as described in the 1st step of Reference Example 405.

2-chloro-6-(((2S,3S)-3-(1,3-dioxoindolin-2-yl)-1-methoxybutan-2-yl)amino)-5-fluoronicotinonitrile MS (ESI m/z): 403 (M+H),
RT (min): 1.59

2nd Step
The following compound was obtained as described in the 3rd step of Reference Example 379.

6-(((2S,3S)-3-amino-1-methoxybutan-2-yl)amino)-2-chloro-5-fluoronicotinonitrile

MS (ESI m/z): 273 (M+H),
RT (min): 0.72

3rd Step
The following compound was obtained as described in Reference Example 395.

tert-Butyl((2S,3S)-3-((6-chloro-5-cyano-3-fluoropyridin-2-yl)amino)-4-methoxybutan-2-yl)carbamate $^1$H-NMR (CDCl$_3$, 300 MHz) δ:7.31 (d, 1H, J=9.6 Hz), 6.10 (d, 1H, J=7.6 Hz), 5.17 (d 1H, J=8.9 Hz), 4.36-4.19 (m, 1H), 4.12-3.94 (m, 1H), 3.89 (s, 3H), 3.84-3.75 (m, 1H), 3.58-3.48 (m, 1H), 1.44 (s, 9H), 1.24 (d, 3H, J=7.2 Hz)
MS (ESI m/z): 373 (M+H)
RT (min): 1.60

Reference Example 436

[Formula 472]

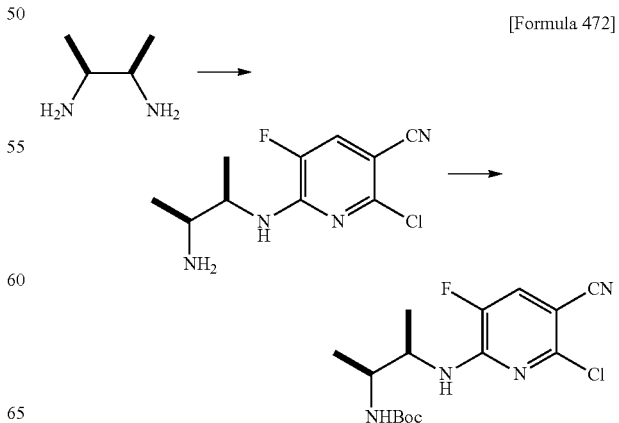

1st Step 2,6-dichloro-5-fluoro-3-pyridinecarbonitrile (300 mg) and potassium carbonate (1.1 g) were added to a DMF (6 ml) solution containing meso-2,3-diaminobutane (690 mg) at room temperature, followed by stirring for 3.5 hours. After cooling of the reaction solution, a saturated aqueous sodium hydrogen carbonate solution was added, followed by extraction with ethyl acetate. The organic layer was dried over anhydrous sodium sulfate. The solvent was distilled away under reduced pressure and the residue was purified by NH silica gel chromatography (n-hexane:ethyl acetate=4:1 to 3:2), and a yellow solid of 6-(((cis)-3-aminobutan-2-yl)amino)-2-chloro-5-fluoronicotinonitrile (150 mg) was thus obtained.

MS (ESI m/z): 243 (M+H) 2nd step

The following compound was obtained as described in Reference Example 395.

tert-Butyl((cis)-3-((6-chloro-5-cyano-3-fluoropyridin-2-yl)amino)butan-2-yl)carbamate $^1$H-NMR (CDCl$_3$, 300 MHz) δ:7.26 (d, 1H, J=9.9 Hz), 6.88 (br, 1H), 4.59 (d, 1H, J=6.6 Hz), 4.26-4.10 (m, 1H), 4.06-3.90 (m, 1H), 1.46 (s, 9H), 1.24-1.14 (m, 6H)

MS (ESI m/z): 343 (M+H)

RT (min): 1.62

Reference Example 437

The following compounds were obtained as described in Reference Example 436.

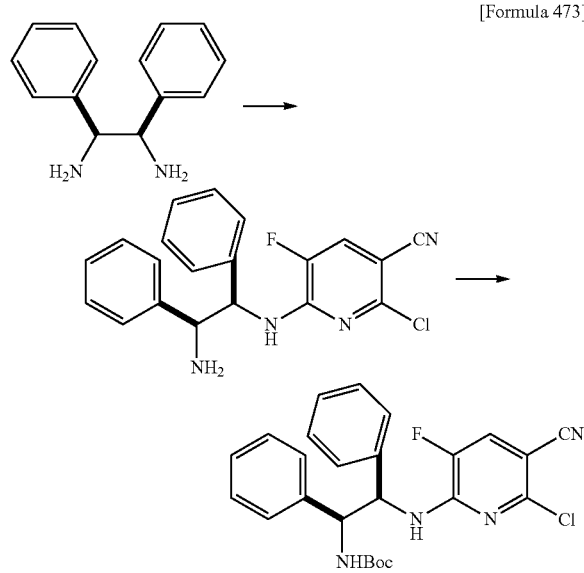

[Formula 473]

6-(((cis)-2-amino-1,2-diphenylethyl)amino)-2-chloro-5-fluoronicotinonitrile

MS (ESI m/z): 367 (M+H)
RT (min): 1.05.

tert-Butyl((cis)-2-((6-chloro-5-cyano-3-fluoropyridin-2-yl)amino)-1,2-diphenylethyl)carbamate MS (ESI m/z): 467 (M+H)
RT (min): 1.87

Reference Example 438

The following compounds were obtained as described in the 1st step of Reference Example 386 and the 3rd step of Reference Example 396.

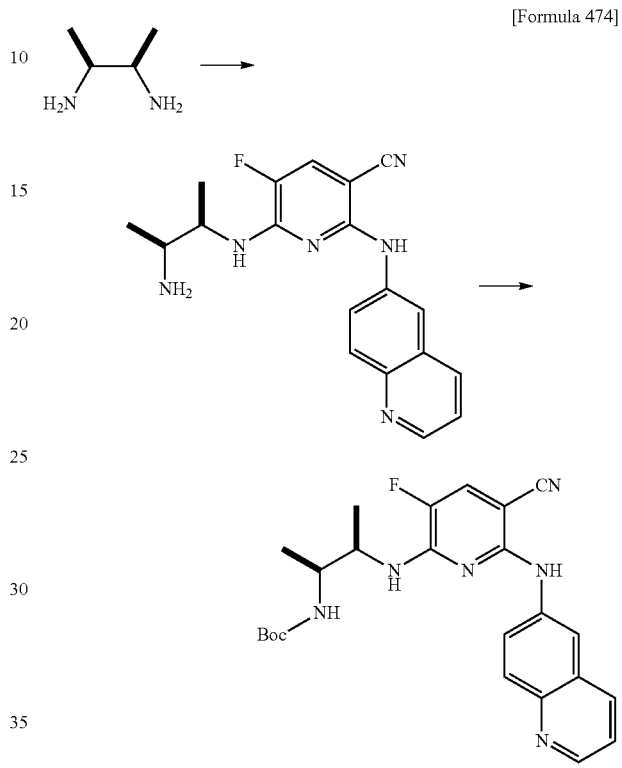

[Formula 474]

1st Step

The following compound was obtained as described in Reference Example 386.

6-(((cis)-3-aminobutan-2-yl)amino)-5-fluoro-2-(quinolin-6-ylamino)nicotinonitrile MS (ESI m/z): 351 (M+H)
RT (min): 0.59

2nd Step

The following compound was obtained as described in Reference Example 395.

tert-Butyl((cis)-3-((5-cyano-3-fluoro-6-(quinolin-6-ylamino)pyridin-2-yl)amino)butan-2-yl)carbamate MS (ESI m/z): 451 (M+H)
RT (min): 1.21

Reference Example 439-1

The following compounds were obtained with reference to Tetrahedron: Asymmetry, Vol. 8, No, 14, pp. 2381-2401, 1997.

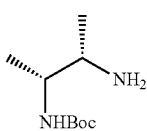

tert-Butyl((2R,3S)-3-aminobutan-2-yl)carbamate

MS (ESI m/z): 343 (M+H), 341 (M−H)

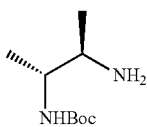

tert-Butyl((2R,3R)-3-aminobutan-2-yl)carbamate

MS (ESI m/z): 343 (M+H), 341 (M−H)

Reference Example 439-2

The following compound was obtained as described in the 7th step of Reference Example 417.

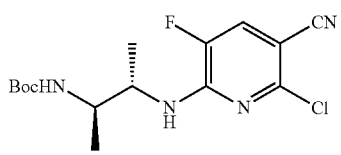

tert-Butyl((2R,3S)-3-((6-chloro-5-cyano-3-fluoropyridin-2-yl)amino)butan-2-yl)carbamate MS (ESI m/z): 343 (M+H), 341 (M−H)

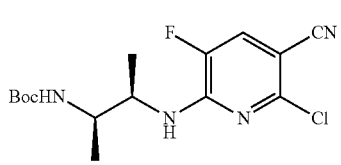

tert-Butyl((2R,3R)-3-((6-chloro-5-cyano-3-fluoropyridin-2-yl)amino)butan-2-yl)carbamate MS (ESI m/z): 343 (M+H), 341 (M−H)

Reference Example 440

The following compound was obtained with reference to Archiv der Pharmazie (Weinheim, Germany), 2004, vol. 337, #12, pp. 654-667.

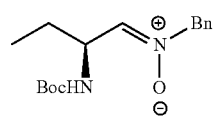

(S,Z)-N-(2-((tert-butoxycarbonyl)amino)butylidyne)-1-phenylmethaneamineoxide

Reference Example 441

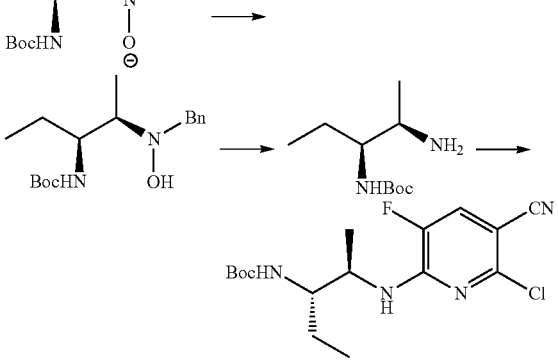

1st Step

Methylmagnesium bromide (3M diethylether solution, 0.86 ml) was added dropwise to a tetrahydrofuran (5 ml) solution containing (S,Z)-N-(2-((tert-butoxycarbonyl)amino)butylidyne)-1-phenylmethaneamineoxide (250 mg) at −50° C., followed by stirring at −50° C. to −35° C. for 2 hours. Further, methylmagnesium bromide (3M diethylether solution, 0.86 ml) was added dropwise to the reaction solution, followed by stirring at −45° C. to −40° C. for 1 hour. A saturated aqueous ammonium chloride solution was added to the reaction solution, followed by extraction with ethyl acetate. The organic layer was washed with saturated saline and dried over anhydrous sodium sulfate, the solvent was distilled away under reduced pressure, the obtained residue was purified by silica gel chromatography (n-hexane:ethyl acetate=19:1 to 4:1), and tert-butyl((3S,4R)-4-(benzyl(hydroxy)amino)pentan-3-yl)carbamate (39 mg) was thus obtained.

$^1$H-NMR (CDCl$_3$, 300 MHz) δ:7.39-7.18 (m, 5H), 6.70 (s, 1H), 4.43 (d, 1H, J=10.2 Hz), 4.11 (d, 1H, J=13.9 Hz), 4.10-3.97 (m, 1H), 3.64 (d, 1H, J=13.9 Hz), 2.78-2.68 (m, 1H), 1.47 (s, 9H), 1.44-1.26 (m, 2H), 1.03-0.94 (m, 9H)

2nd Step

A methanol (20 ml) solution containing tert-butyl((3S,4R)-4-(benzyl(hydroxy)amino)pentan-3-yl)carbamate (39 mg) was prepared and was subjected to a hydrogenation reaction (45° C.; 100 bar; flow rate: 1 ml/min; 20% Pd(OH)$_2$/C) using H-cube™. Then, the solvent was distilled away under reduced pressure, and colorless oily matter of tert-butyl ((3S,4R)-4-aminopentan-3-yl)carbamate (27 mg) was thus obtained.

3rd Step

The following compound was obtained as described in the 7th step of Reference Example 417.

325 tert-Butyl((2R,3S)-2-((6-chloro-5-cyano-3-fluoropyridin-2-yl)amino)pentan-3-yl)carbamate MS (ESI m/z): 357 (M+H), 355 (M−H)

Reference Example 442

The following compounds were obtained as described in Reference Example 441.

[Formula 481]

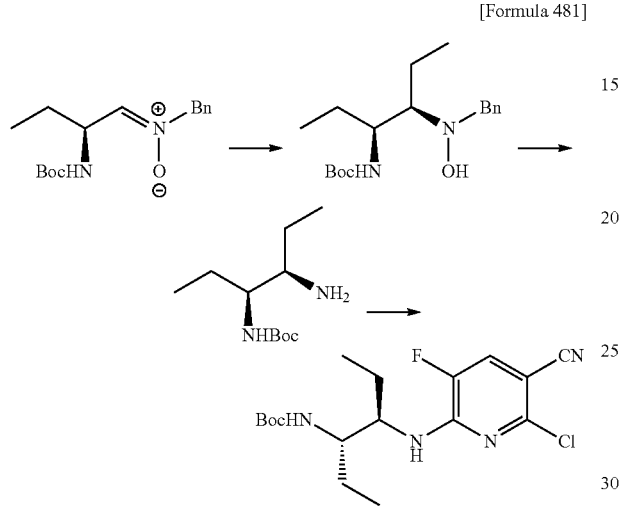

tert-Butyl((3S,4R)-4-(benzyl(hydroxy)amino)hexan-3-yl)carbamate

¹H-NMR (CDCl₃, 300 MHz) δ:7.40-7.20 (m, 5H), 5.88 (s, 1H), 4.62 (d, 1H, J=9.6 Hz), 4.07 (d, 1H, J=13.9 Hz), 4.01-3.88 (m, 1H), 3.73 (d, 1H, J=13.9 Hz), 2.59-2.50 (m, 1H), 1.69-1.32 (m, 4H), 1.45 (s, 9H), 1.05 (t, 3H, J=7.6 Hz), 0.98 (t, 3H, J=7.3 Hz)

tert-Butyl((3S,4R)-4-((6-chloro-5-cyano-3-fluoropyridin-2-yl)amino)hexan-3-yl)carbamate MS (ESI m/z): 371 (M+H), 369 (M−H)

Reference Example 443

The following compounds were obtained as described in Reference Example 441.

[Formula 482]

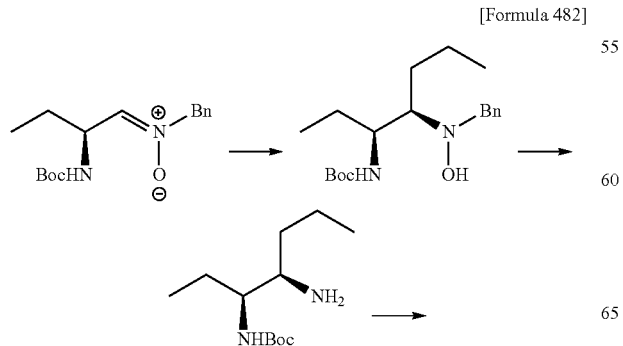

326

-continued

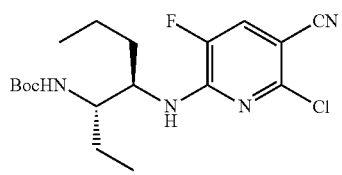

tert-Butyl((3S,4R)-4-(benzyl(hydroxy)amino)heptan-3-yl)carbamate

¹H-NMR (CDCl₃, 300 MHz) δ:7.39-7.20 (m, 5H), 5.96 (s, 1H), 4.60 (d, 1H, J=9.9 Hz), 4.05 (d, 1H, J=13.9 Hz), 4.01-3.88 (m, 1H), 3.72 (d, 1H, J=13.9 Hz), 2.63-2.55 (m, 1H), 1.69-1.20 (m, 1H), 1.46 (s, 9H), 0.97 (t, 3H, J=7.6 Hz), 0.93 (t, 3H, J=6.9 Hz)

tert-Butyl((3S,4R)-4-((6-chloro-5-cyano-3-fluoropyridin-2-yl)amino)heptan-3-yl)carbamate MS (ESI m/z): 385 (M+H), 383 (M−H)

Reference Example 444

The following compounds were obtained as described in Reference Example 441.

[Formula 483]

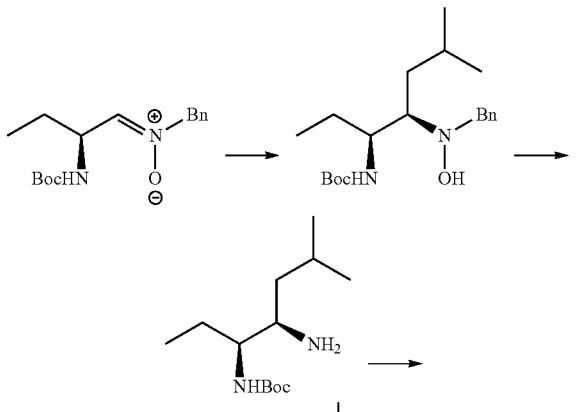

tert-Butyl((3S,4R)-4-(benzyl(hydroxy)amino)-6-methylheptan-3-yl)carbamate

¹H-NMR (CDCl₃, 300 MHz) δ:7.39-7.23 (m, 5H), 5.85 (s, 1H), 4.59 (d, 1H, J=9.9 Hz), 4.04 (d, 1H, J=13.5 Hz), 4.01-

3.88 (m, 1H), 3.73 (d, 1H, J=13.5 Hz), 2.72-2.63 (m, 1H), 1.81-1.69 (m, 1H), 1.50-1.13 (m, 4H), 1.46 (s, 9H), 1.02-0.89 (m, 9H)

tert-Butyl((3S,4R)-4-((6-chloro-5-cyano-3-fluoropyridin-2-yl)amino)-6-methylheptan-3-yl)carbamate MS (ESI m/z): 399 (M+H), 397 (M−H)

Reference Example 445

[Formula 484]

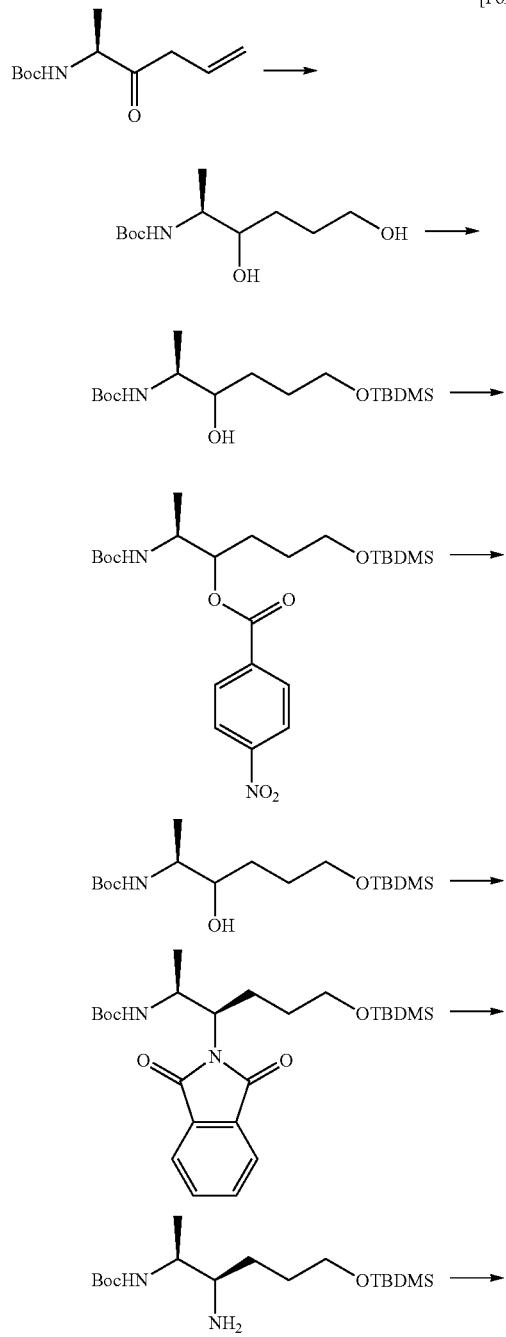

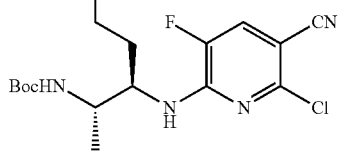

1st Step

A tetrahydrofuran solution (50 ml) containing (S)-tert-butyl(3-oxohexa-5-en-2-yl)carbamate (8 g) was added dropwise to 9-borabicyclo[3,3,1]nonane (0.5 M tetrahydrofuran solution) (225 ml) in an ice bath, followed by stirring at room temperature for 4 hours. A 6M sodium hydroxide aqueous solution (50 ml) and then a 30% hydrogen peroxide solution (50 ml) were added to the reaction solution in an ice bath. An insoluble precipitate was removed, followed by extraction with ethyl acetate. The obtained organic layer was washed with water and saturated saline and dried over anhydrous sodium sulfate. Subsequently, the solvent was distilled away under reduced pressure, and colorless oily matter of tert-butyl ((2S)-3,6-dihydroxyhexan-2-yl)carbamate (4.4 g) was thus obtained.

MS (ESI m/z): 232 (M+H)
RT (min): 0.85

2nd Step

A DMF solution (5 ml) containing imidazole (1.4 g) and tert-butyldimethylsilyl chloride (3 g) was added to a DMF (10 ml) solution containing tert-butyl((2S)-3,6-dihydroxyhexan-2-yl)carbamate (4.4 g), followed by stirring at room temperature for 40 minutes. Water was added to the reaction solution, followed by extraction with ethyl acetate. The obtained organic layer was washed with a 1M citric acid aqueous solution and dried over anhydrous sodium sulfate. The solvent was distilled away under reduced pressure. The residue was purified by silica gel chromatography (n-hexane:ethyl acetate=7:3), and colorless oily matter of tert-butyl((2S)-6-((tert-butyldimethylsilyl)oxy)-3-hydroxyhexan-2-yl)carbamate (4.9 g) was thus obtained.

MS (ESI m/z): 348 (M+H)
RT (min): 1.94

3rd, 4th, 5th, 6th, and 7th steps

The following compounds were obtained as described in the 3rd, 4th, 5th, 6th, and 7th steps of Reference Example 417.

tert-Butyl((2S)-6-((tert-butyldimethylsilyl)oxy)-3-(4-nitrobenzoyl)oxyhexan-2-yl)carbamate MS (ESI m/z): 497 (M+H)
RT (min): 2.29 tert-Butyl((2S,3R)-6-((tert-butyldimethylsilyl)oxo)-3-(1,3-dioxoisoindolin-2-yl)hexan-2-yl)carbamate MS (ESI m/z): 477 (M+H)
RT (min): 2.22 tert-Butyl((2S,3R)-6-((tert-butyldimethylsilyl)oxo)-3-((6-chloro-5-cyano-3-fluoropyridin-2-yl)amino)hexan-2-yl)carbamate MS (ESI m/z): 502 (M+H)
RT (min): 2.26

Reference Example 446

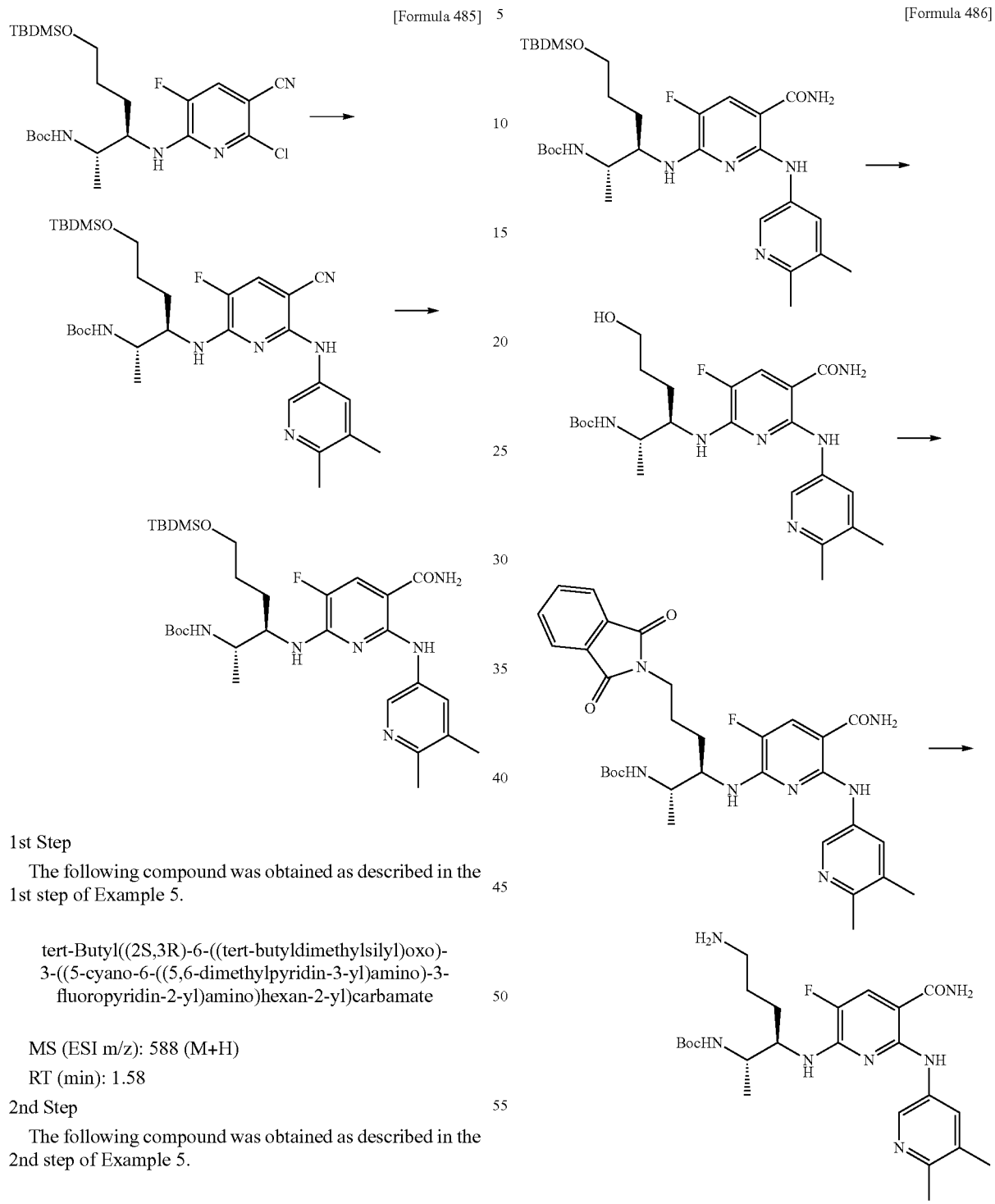

1st Step

The following compound was obtained as described in the 1st step of Example 5.

tert-Butyl((2S,3R)-6-((tert-butyldimethylsilyl)oxo)-3-((5-cyano-6-((5,6-dimethylpyridin-3-yl)amino)-3-fluoropyridin-2-yl)amino)hexan-2-yl)carbamate MS (ESI m/z): 588 (M+H)

RT (min): 1.58

2nd Step

The following compound was obtained as described in the 2nd step of Example 5.

tert-Butyl((2S,3R)-6-((tert-butyldimethylsilyl)oxy)-3-((5-carbamoyl-6-((5,6-dimethylpyridin-3-yl)amino)-3-fluoropyridin-2-yl)amino)hexan-2-yl)carbamate MS (ESI m/z): 606 (M+H)

RT (min): 1.57

Reference Example 447

1st Step

Tetrabutylammonium fluoride (1M tetrahydrofuran solution, 150 μl) was added to a tetrahydrofuran solution (2 ml) containing tert-butyl((2S,3R)-6-((tert-butyldimethylsilyl)oxy)-3-((5-carbamoyl-6-((5,6-dimethylpyridin-3-yl)amino)-3-fluoropyridin-2-yl)amino)hexan-2-yl)carbamate (60 mg), followed by stirring for 30 minutes. Further, tetrabutylammonium fluoride (1M in tetrahydrofuran, 300 μl) was added, followed by stirring for 1 hour. Water was added to the reaction solution, followed by extraction with ethyl acetate. The obtained organic layer was dried over anhydrous sodium sulfate. The solvent was distilled away under reduced pressure. The residue was purified by silica gel chromatography (ethyl acetate:methanol=1:0 to 97:3) and used in the subsequent reaction.

2nd and 3rd Steps

The following compounds were obtained as described in the 5th and 6th steps of Reference Example 417.

tert-Butyl((2S,3R)-3-(5-carbamoyl-6-((5,6-dimethylpyridin-3-yl)amino)-3-fluoropyridin-2-yl)amino)-6-(1,3-dioxoisoindolin-2-yl)hexan-2-yl)carbamate MS (ESI m/z): 621 (M+H)
RT (min): 1.16 tert-Butyl((2S,3R)-6-amino-3-((5-carbamoyl-6-((5,6-dimethylpyridin-3-yl)amino)-3-fluoropyridin-2-yl)amino)hexan-2-yl)carbamate MS (ESI m/z): 491 (M+H)
RT (min): 0.80

Reference Example 447

The following compound was obtained as described in Reference Example 386.

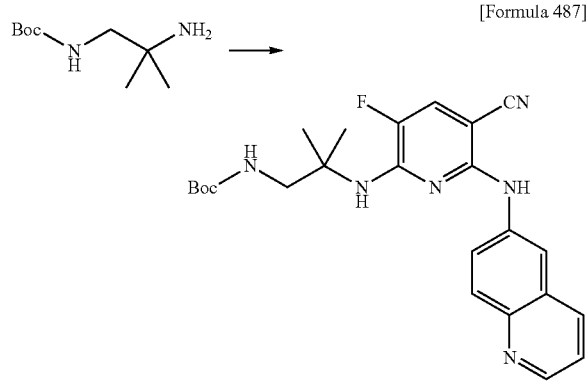

[Formula 487]

tert-Butyl(2-((5-cyano-6-(quinolin-6-ylamino)pyridin-2-yl)amino)-2-methylpropyl)carbamate MS (ESI m/z): 451 (M+H)
RT (min): 1.27

Reference Example 448

The following compound was obtained as described in Reference Example 386.

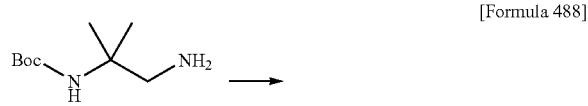

[Formula 488]

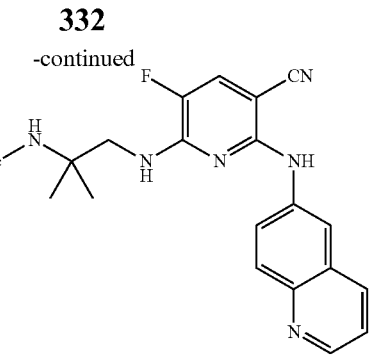

tert-Butyl(1-((5-cyano-3-fluoro-6-(quinolin-6-ylamino)pyridin-2-yl)amino)-2-methylpropan-2-yl)carbamate MS (ESI m/z): 451 (M+H)
RT (min): 1.26

Example 1

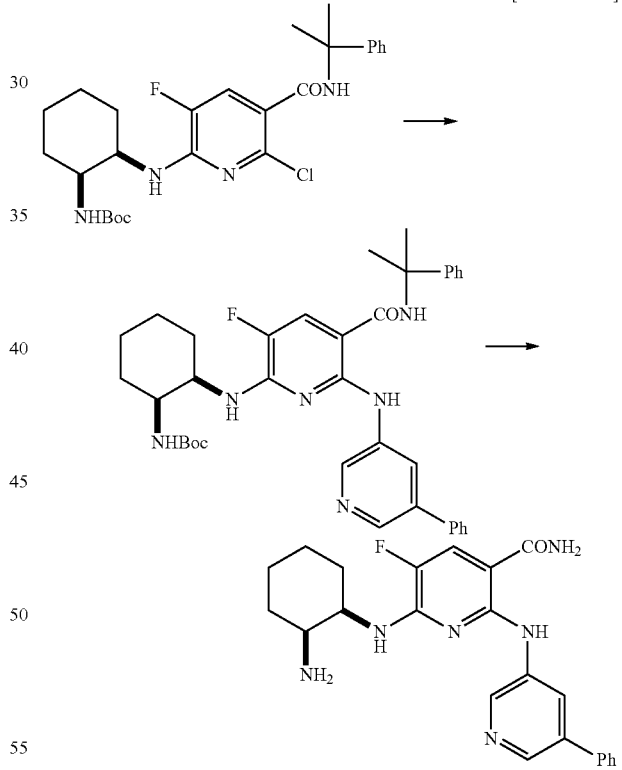

[Formula 489]

1st Step 5-phenylpyridin-3-amine (10 mg), cesium carbonate (32 mg), Pd$_2$(dba)$_3$ (5 mg), and Xantphos (7 mg) were added to a 1,4-dioxane (0.8 ml) solution containing tert-butyl cis-2-(6-chloro-3-fluoro-5-(2-phenylpropan-2-ylaminocarbonyl)pyridin-2-ylamino)cyclohexylcarbamate (20 mg), followed by stirring at 100° C. for 2 hours in a nitrogen atmosphere. The reaction mixture was cooled to room temperature. Then, water and ethyl acetate were added. Insoluble matter was removed by filtration, and the filter cake was washed with ethyl acetate and water. The filtrate was mixed with the washing solution. The organic layer was collected, washed with saturated saline, and dried over anhydrous magnesium sulfate, and the solvent was distilled away under reduced pressure. The obtained residue was purified using a PLC glass plate (hexane:ethyl acetate=1:1), diisopropylether and hexane were added, solid matter was collected by filtration, and light yellow oily matter of tert-butyl cis-2-(3-fluoro-5-(2-phenylpropan-2-ylaminocarbonyl)-6-(5-phenylpyridin-3-ylamino)pyridin-2-ylamino)cyclohexylcarbamate (11 mg) was thus obtained.

$^1$H-NMR (DMSO-$d_6$, 400 MHz) δ:11.30 (s, 1H), 8.59 (d, 1H, J=2.3 Hz), 8.38 (d, 1H, J=2.0 Hz), 8.35 (s, 1H), 8.19 (d, 1H, J=13.3 Hz), 8.14 (s, 1H), 7.72-7.66 (m, 2H), 7.52-7.45 (m, 2H), 7.44-7.36 (m, 3H), 7.32-7.26 (m, 2H), 7.20-7.14 (m, 1H), 6.67-6.60 (m, 2H), 4.03-3.94 (m, 1H), 3.84-3.76 (m, 1H), 1.74-1.10 (m, 23H)

MS (ESI, m/z): 639 (M+H), 637 (M−H)

2nd Step

A mixture of tert-butyl cis-2-(3-fluoro-5-(2-phenylpropan-2-ylaminocarbonyl)-6-(5-phenylpyridin-3-ylamino)pyridin-2-ylamino)cyclohexylcarbamate (10 mg) and TFA (0.2 ml) was stirred at room temperature for 30 minutes. The solvent was distilled away under reduced pressure (at 40° C. or less), and ethyl acetate and 4N hydrogen chloride/1,4-dioxane (20 µl) were added, followed by stirring at room temperature for 30 minutes. Solid matter was collected by filtration and washed with ethyl acetate, and a yellow solid of 6-(cis-2-amino cyclohexylamino)-5-fluoro-2-(5-phenylpyridin-3-ylamino)nicotinamide•hydrochloride (8 mg) was thus obtained.

($^1$H-NMR data and MS data are shown in table 1.)

Example 2

The compounds listed in table 1 were obtained as described in Example 1.

TABLE 1

| Number | Structure |
| --- | --- |
| Example 2-1 (Example 1) HCl salt | 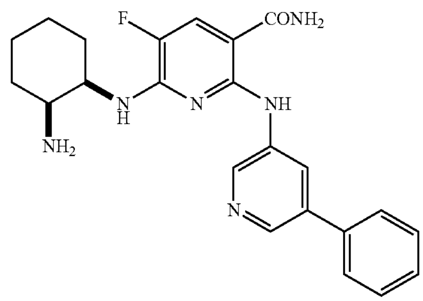 |
| Example 2-2 HCl salt | 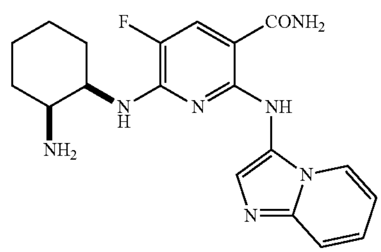 |
| Example 2-3 HCl salt | 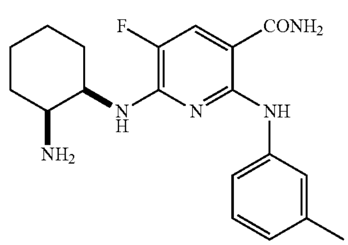 |
| Example 2-4 HCl salt | 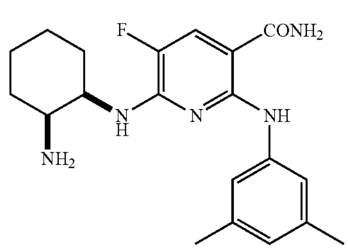 |

TABLE 1-continued
| | |
|---|---|
| Example 2-5<br>HCl salt | 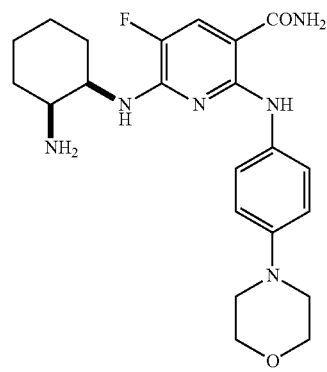 |
| Example 2-6<br>HCl salt | 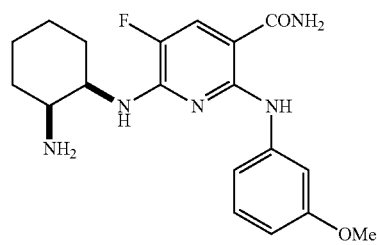 |
| Example 2-7<br>HCl salt | 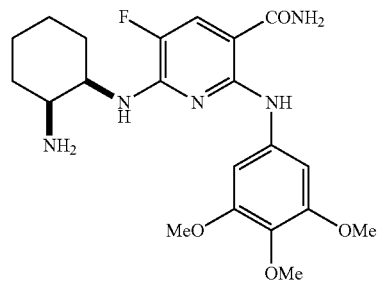 |
| Example 2-8<br>HCl salt | 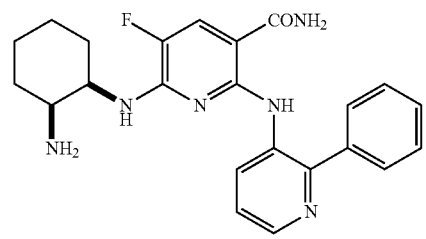 |
| Example 2-9<br>HCl salt | 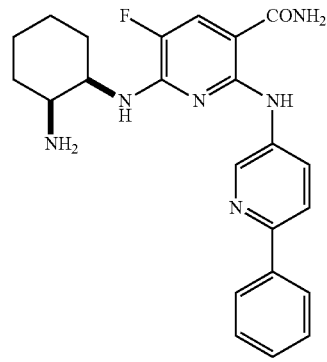 |

TABLE 1-continued
| | |
|---|---|
| Example 2-10<br>HCl salt | 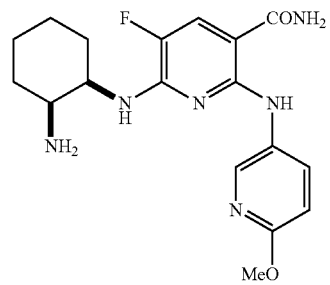 |
| Example 2-11<br>HCl salt | 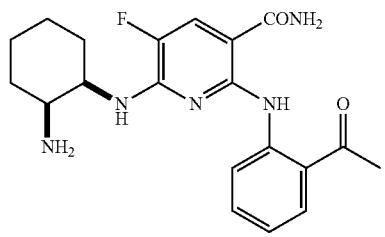 |
| Example 2-12<br>HCl salt | 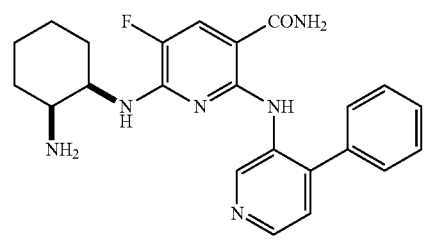 |
| Example 2-13<br>HCl salt | 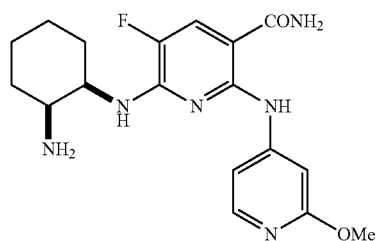 |
| Example 2-14<br>HCl salt | 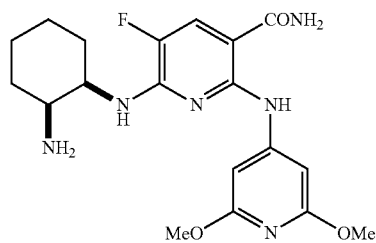 |
| Example 2-15<br>HCl salt | 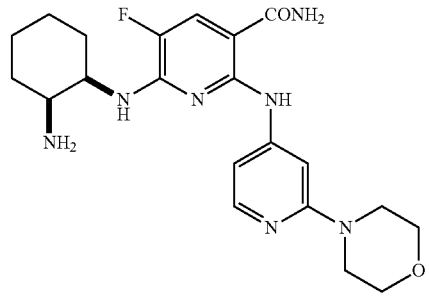 |

TABLE 1-continued
| | | |
|---|---|---|
| Example 2-16
2HCl salt | | 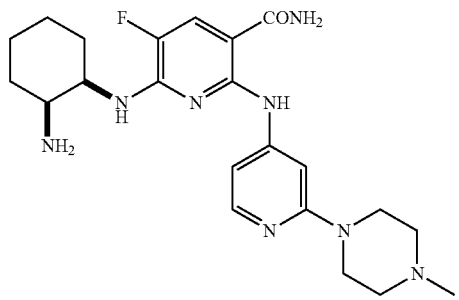 |
| Example 2-17
HCl salt | | 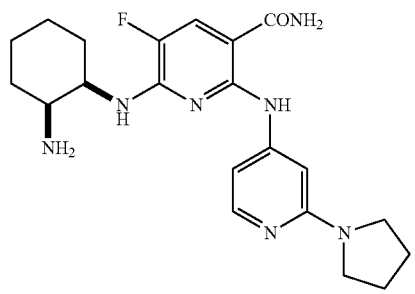 |
| Example 2-18
HCl salt | | 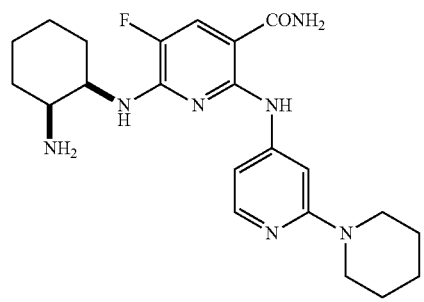 |
| Example 2-19
HCl salt | | 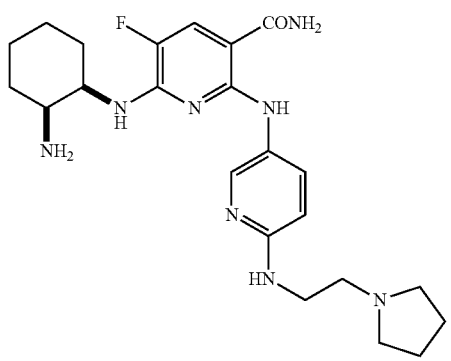 |
| Example 2-20
HCl salt | | 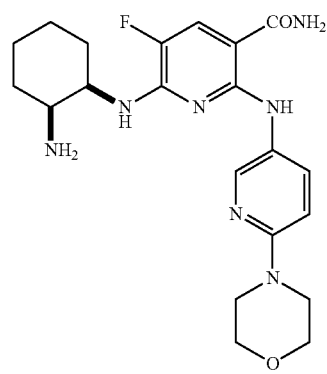 |

TABLE 1-continued

| | | |
|---|---|---|
| Example 2-21<br>2HCl salt | 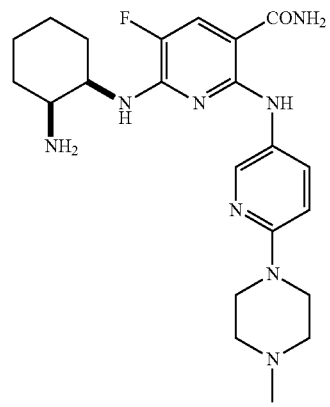 | |
| Example 2-22 | 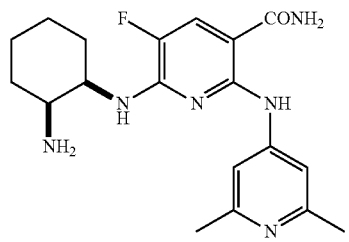 | 6-((cis-2-aminocyclo-hexyl)amino)-2-((2,6-dimethylpyridin-4-yl)amino)-5-fluoronicotinamide |
| Example 2-23 | 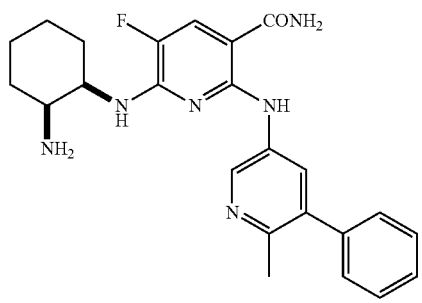 | 6-(cis-2-aminocyclohexyl-amino)-5-fluoro-2-((6-methyl-5-phenylpyridin-3-yl)amino)nicotinamide |
| Example 2-24 | 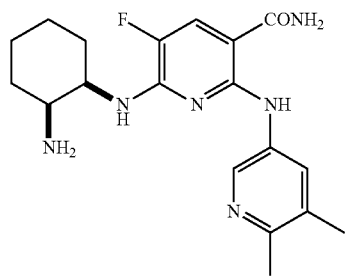 | 6-(cis-2-aminocyclohexylamino)-2-((5,6-dimethylpyridin-3-yl)amino)-5-fluoronicotinamide |
| Example 2-25 | 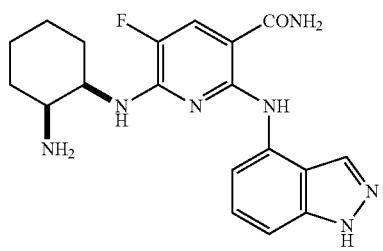 | 2-(1H-indazol-4-yl)amino)-6-(cis-2-aminocyclohexylamino)-5-fluoronicotinamide |

| | | |
|---|---|---|
| Example 2-26 | 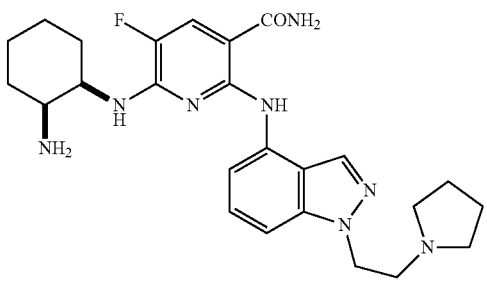 | 6-(cis-2-aminocyclohexyl-amino)-5-fluoro-2-((1-(2-(pyrrolidin-1-yl)ethyl)-1H-indazol-4-yl)amino)nicotinamide |
| Example 2-27 | 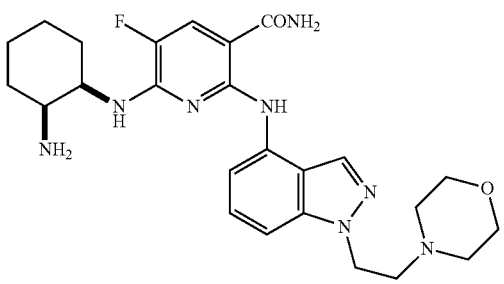 | 6-(cis-2-aminocyclohexyl-amino)-5-fluoro-2-((1-(2-morpholinoethyl)-1H-indazol-4-yl)amino)nicotinamide |
| Example 2-28 | 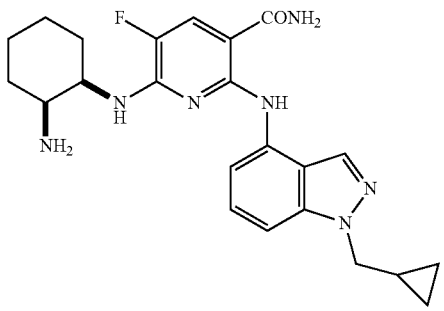 | 6-(cis-2-aminocyclohexyl-amino)-2-((1-(cyclopropylmethyl)-1H-indazol-4-yl)amino)-5-fluoronicotinamide |
| Example 2-29 | 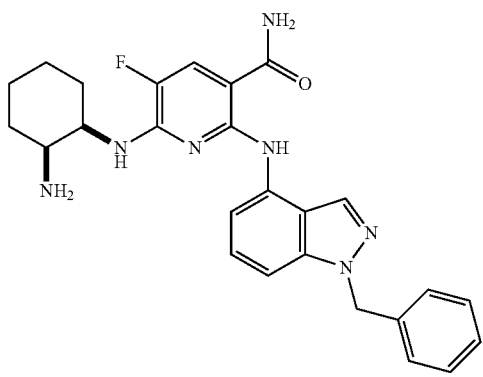 | 6-(cis-2-aminocyclohexyl-amino)-2-((1-benzyl-1H-indazol-4-yl)amino)-5-fluoronicotinamide |
| Example 2-30 | 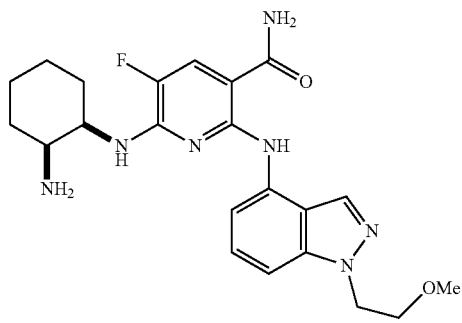 | 6-(cis-2-aminocyclohexyl-amino)-5-fluoro-2-((1-(2-methoxyethyl)-1H-indazol-4-yl)amino)nicotinamide |

TABLE 1-continued

| Example 2-31 | 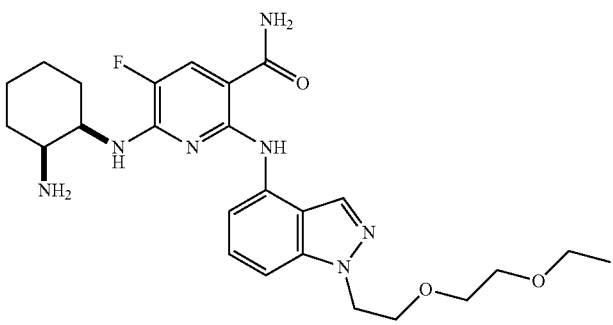 | 6-(cis-2-aminocyclohexyl-amino)-2-((1-(2-(2-ethoxyethoxy)ethyl)-1H-indazol-4-yl)amino)-5-fluoronicotinamide |
| --- | --- | --- |
| Example 2-32 | 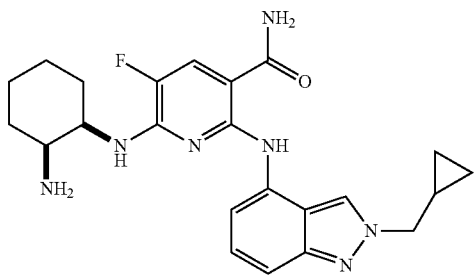 | 6-(cis-2-aminocyclohexyl-amino)-2-((2-(cyclopropylmethyl)-2H-indazol-4-yl)amino)-5-fluoronicotinamide |
| Example 2-33 | 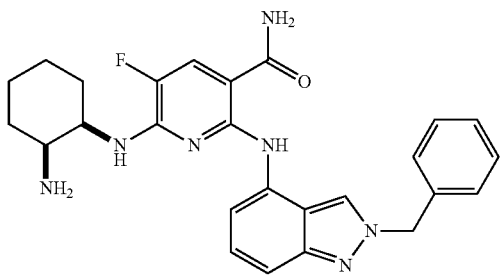 | 6-(cis-2-aminocyclohexyl-amino)-2-((2-benzyl-2H-indazol-4-yl)amino)-5-fluoronicotinamide |
| Example 2-34 | 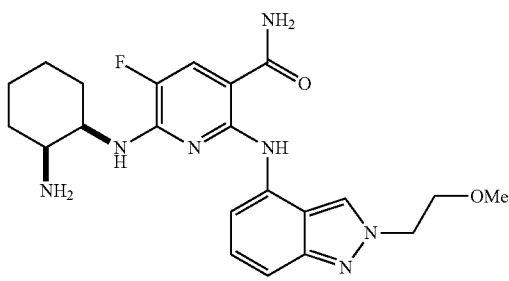 | 6-(cis-2-aminocyclohexyl-amino)-5-fluoro-2-((2-(2-methoxyethyl)-2H-indazol-4-yl)amino)nicotinamide |
| Example 2-35 | 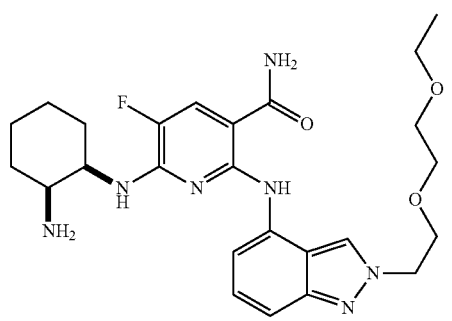 | 6-(cis-2-aminocyclohexyl-amino)-2-((2-(2-(2-ethoxyethoxy)ethyl)-2H-indazol-4-yl)amino)-5-fluoronicotinamide |

TABLE 1-continued

| Example 2-36 | 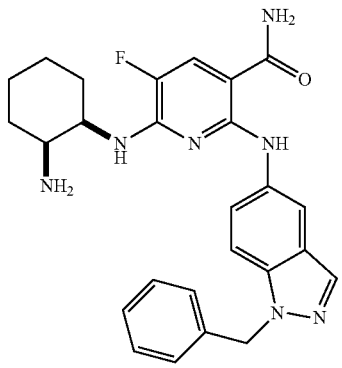 | 6-(cis-2-aminocyclohexyl-amino)-2-((1-benzyl-1H-indazol-5-yl)amino)-5-fluoronicotinamide |
| Example 2-37 | 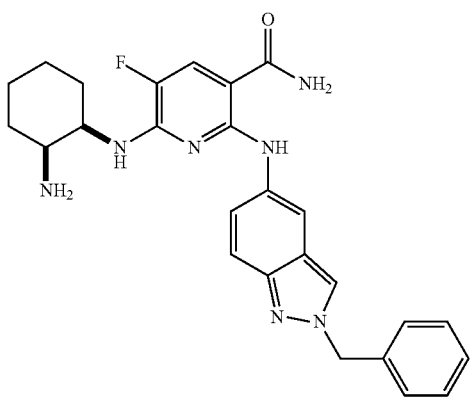 | 6-(cis-2-aminocyclohexyl-amino)-2-((2-benzyl-2H-indazol-5-yl)amino)-5-fluoronicotinamide |
| Example 2-38 | 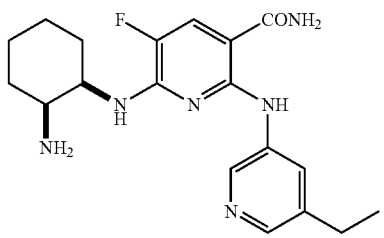 | 6-(cis-2-aminocyclohexyl-amino)-2-((5-ethylpyridin-3-yl)amino)-5-fluoronicotinamide |
| Example 2-39 | 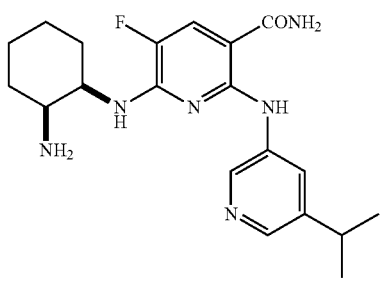 | 6-(cis-2-aminocyclohexyl-amino)-5-fluoro-2-((5-isopropylpyridin-3-yl)amino)nicotinamide |
| Example 2-40 | 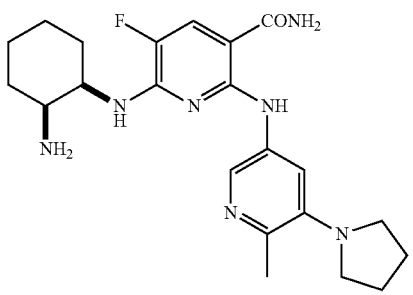 | 6-(cis-2-aminocyclohexyl-amino)-5-fluoro-2-((6-methyl-5-(pyrrolidin-1-yl)pyridin-3-yl)amino)nicotinamide |

TABLE 1-continued

| Example | | |
|---|---|---|
| Example 2-41 | 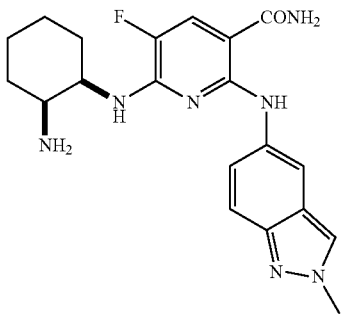 | 6-(cis-2-aminocyclohexyl-amino)-5-fluoro-2-((2-methyl-2H-indazol-5-yl)amino)nicotinamide |
| Example 2-42 | 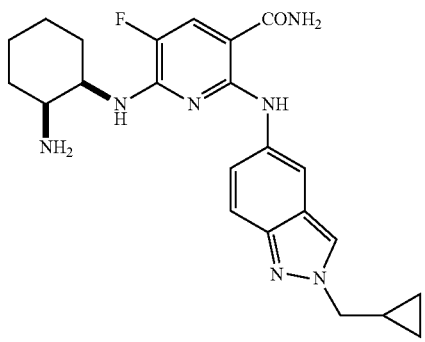 | 6-(cis-2-aminocyclohexyl-amino)-2-((2-(cyclopropylmethyl)-2H-indazol-6-yl)amino)-5-fluoronicotinamide |
| Example 2-43 | 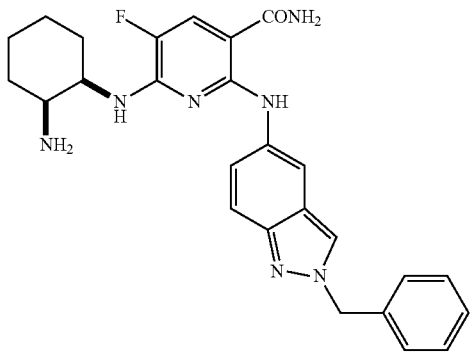 | 6-(cis-2-aminocyclohexyl-amino)-2-((2-benzyl-2H-indazol-6-yl)amino)-5-fluoronicotinamide |
| Example 2-44 | 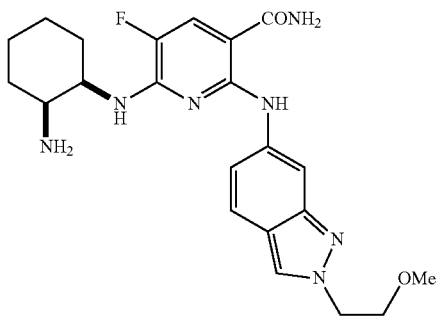 | 6-(cis-2-aminocyclohexyl-amino)-5-fluoro-2-((2-(2-methoxyethyl)-2H-indazol-6-yl)amino)nicotinamide |
| Example 2-45 | 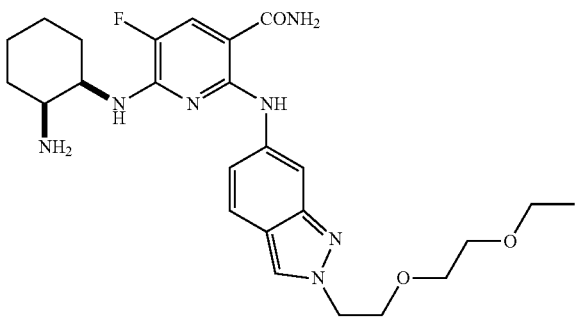 | 6-(cis-2-aminocyclohexyl-amino)-2-((2-(2-(2-ethoxyethoxy)ethyl)-2H-indazol-6-yl)amino)-5-fluoronicotinamide |

TABLE 1-continued

| | | |
|---|---|---|
| Example 2-46 | 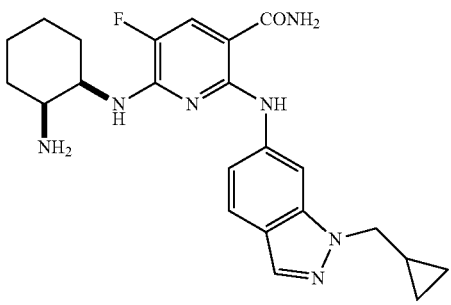 | 6-(cis-2-aminocyclohexyl-amino)-2-((1-(cyclopropylmethyl)-1H-indazol-6-yl)amino)-5-fluoronicotinamide |
| Example 2-47 | 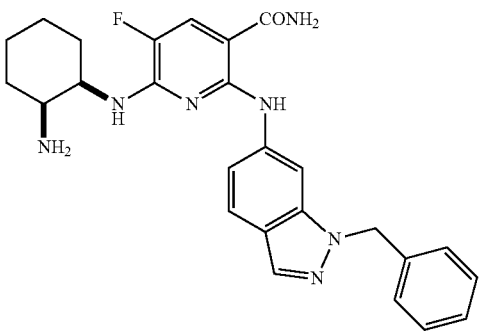 | 6-(cis-2-aminocyclohexyl-amino)-2-((1-benzyl-1H-indazol-6-yl)amino)-5-fluoronicotinamide |
| Example 2-48 | 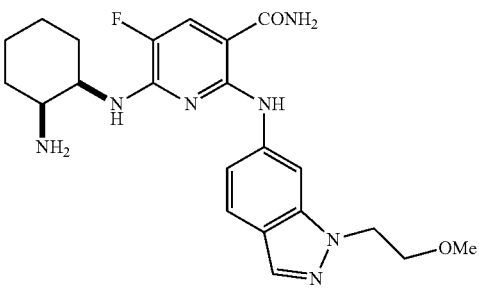 | 6-(cis-2-aminocyclohexyl-amino)-5-fluoro-2-((1-(2-methoxyethyl)-1H-indazol-6-yl)amino)nicotinamide |
| Example 2-49 | 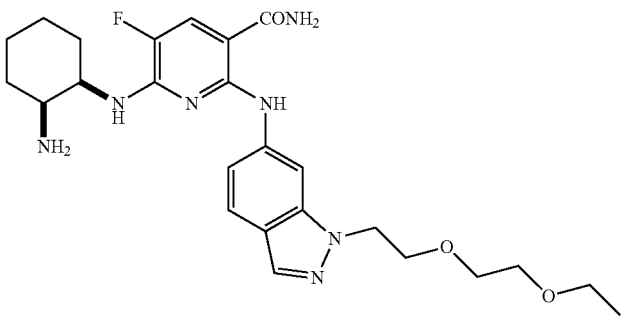 | 6-(cis-2-aminocyclo-hexylamino)-2-((1-(2-(2-ethoxyethoxy)ethyl)-1H-indazol-6-yl)amino)-5-fluoronicotinamide |
| Example 2-50 | 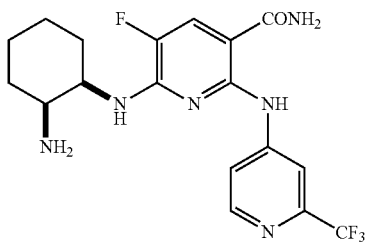 | 6-(cis-2-aminocyclohexyl-amino)-5-fluoro-2-((2-(trifluoromethyl)pyridin-4-yl)amino)nicotinamide |

TABLE 1-continued

| Example 2-51 | 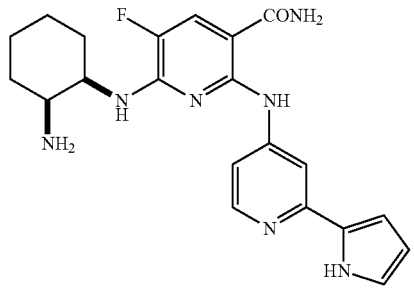 | 2-(2-(1H-pyrrol-2-yl)pyridin-4-yl)amino)-6-(cis-2-aminocyclohexylamino)-5-fluoronicotinamide |
| Example 2-52 | 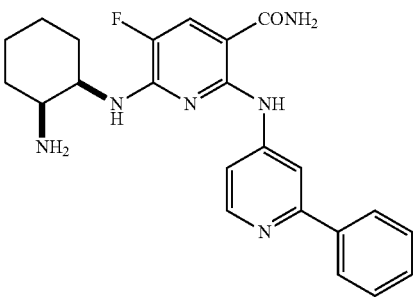 | 6-(cis-2-aminocyclohexyl-amino)-5-fluoro-2-((2-phenylpyridin-4-yl)amino)nicotinamide |
| Example 2-53 | 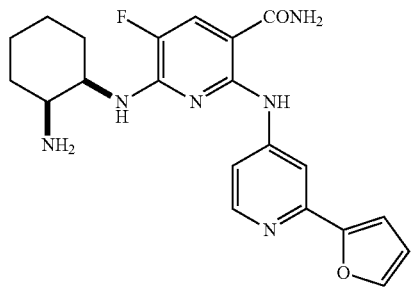 | 6-(cis-2-aminocyclo-hexylamino)-5-fluoro-2-((2-(furan-2-yl)pyridin-4-yl)amino)nicotinamide |
| Example 2-54 | 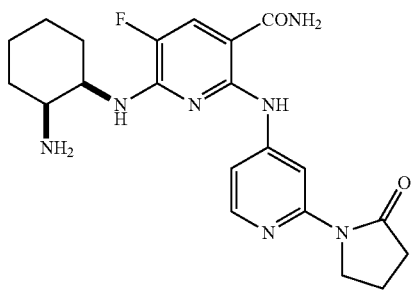 | 6-(cis-2-aminocyclohexyl-amino)-5-fluoro-2-((2-(2-oxopyrrolidin-1-yl)pyridin-4-yl)amino)nicotinamide |
| Example 2-55 | 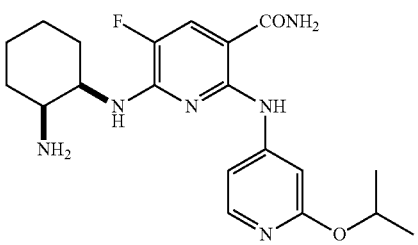 | 6-(cis-2-aminocyclohexyl-amino)-5-fluoro-2-((2-isopropoxypyridin-4-yl)amino)nicotinamide |

TABLE 1-continued

| | | |
|---|---|---|
| Example 2-56 | 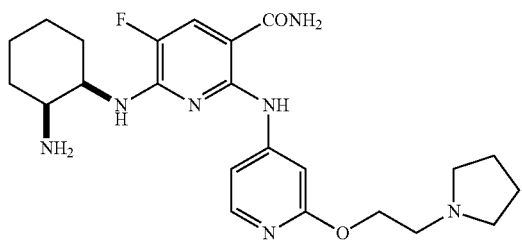 | 6-(cis-2-aminocyclohexyl-amino)-5-fluoro-2-((2-(2-(pyrrolidin-1-yl)ethoxy)pyridin-4-yl)amino)nicotinamide |
| Example 2-57 | 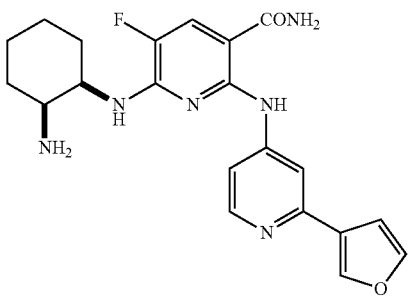 | 6-(cis-2-aminocyclo-hexylamino)-5-fluoro-2-((2-(furan-3-yl)pyridin-4-yl)amino)nicotinamide |
| Example 2-58 | 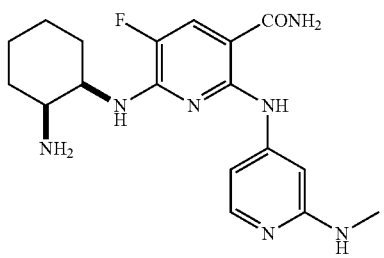 | 6-(cis-2-aminocyclohexyl-amino)-5-fluoro-2-((2-(methylamino)pyridin-4-yl)amino)nicotinamide |
| Example 2-59 | 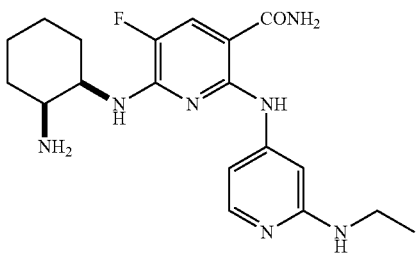 | 6-(cis-2-aminocyclo-hexylamino)-2-(2-(ethylamino)pyridin-4-yl)amino)-5-fluoronicotinamide |
| Example 2-60 | 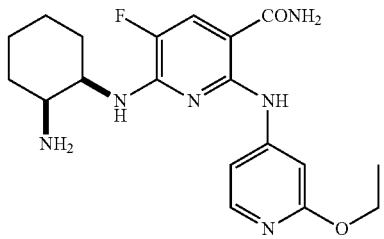 | 6-(cis-2-aminocyclo-hexylamino)-2-(2-ethoxypyridin-4-yl)amino)-5-fluoronicotinamide |
| Example 2-61 | 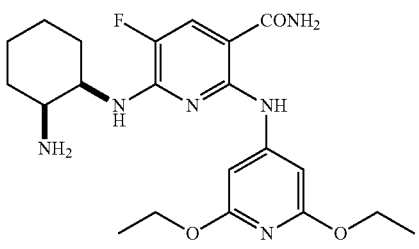 | 6-(cis-2-aminocyclo-hexylamino)-2-(2,6-diethoxypyridin-4-yl)amino)-5-fluoronicotinamide |

TABLE 1-continued

| Example 2-62 | 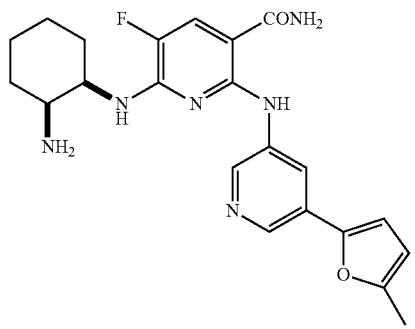 | 6-(cis-2-aminocyclohexyl-amino)-5-fluoro-2-((5-(5-methylfuran-2-yl)pyridin-3-yl)amino)nicotinamide |
| Example 2-63 | 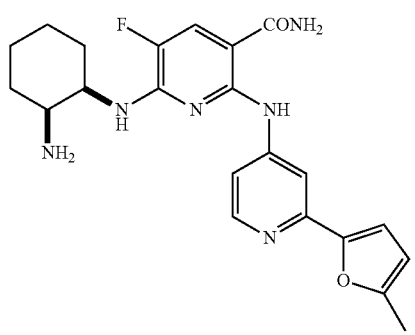 | 6-(cis-2-aminocyclohexyl-amino)-5-fluoro-2-((2-((5-methylfuran-2-yl)pyridin-4-yl)amino)nicotinamide |
| Example 2-64 | 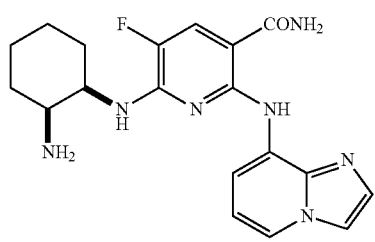 | 6-(cis-2-aminocyclohexyl-amino)-5-fluoro-2-((imidazo[1,2-a]pyridin-8-yl)amino)nicotinamide |
| Example 2-65 | 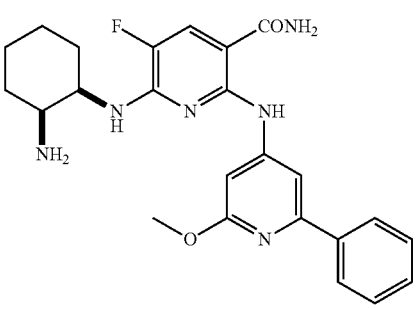 | 6-(cis-2-aminocyclo-hexylamino)-5-fluoro-2-((2-methoxy-6-phenylpyridin-4-yl)amino)nicotinamide |
| Example 2-66 | 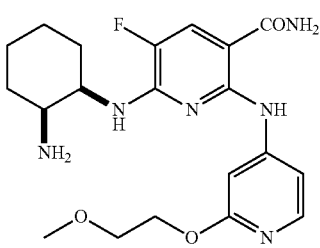 | 6-(cis-2-aminocyclo-hexylamino)-5-fluoro-2-((2-(2-methoxyethoxy)pyridin-4-yl)amino)nicotinamide |

TABLE 1-continued

| Example | | |
|---|---|---|
| Example 2-67 | 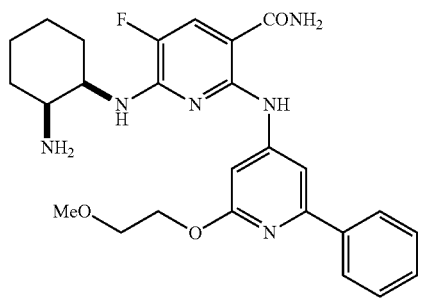 | 6-(cis-2-aminocyclo-hexylamino)-5-fluoro-2-((2-(2-methoxyethoxy)-6-phenylpyridin-4-yl)amino)nicotinamide |
| Example 2-68 | 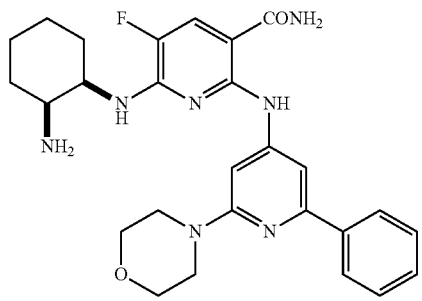 | 6-(cis-2-aminocyclo-hexylamino)-5-fluoro-2-((2-morpholino-6-phenylpyridin-4-yl)amino)nicotinamide |
| Example 2-69 | 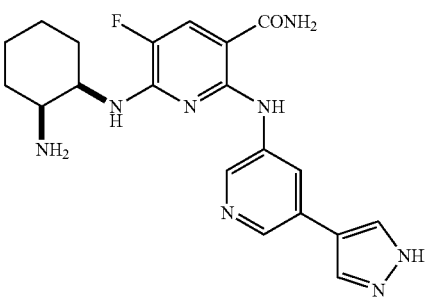 | 2-((5-(1H-pyrazol-4-yl)pyridin-3-yl)amino)-6-(cis-2-aminocyclohexylamino)-5-fluoronicotinamide |
| Example 2-70 | 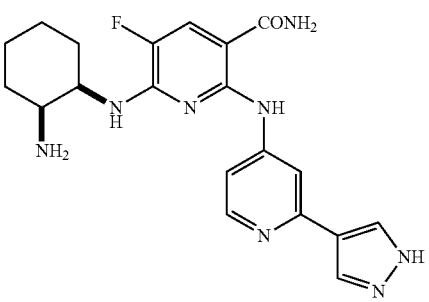 | 2-(2-(1H-pyrazol-4-yl)pyridin-4-yl)amino)-6-(cis-2-aminocyclohexylamino)-5-fluoronicotinamide |
| Example 2-71 | 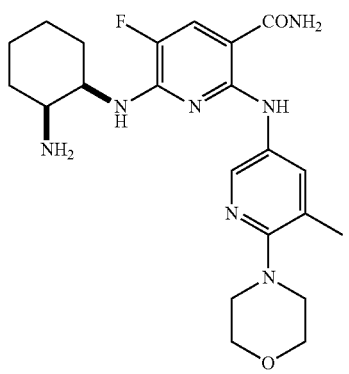 | 6-(cis-2-aminocyclo-hexylamino)-5-fluoro-2-((5-methyl-6-morpholinopyridin-3-yl)amino)nicotinamide |

TABLE 1-continued

| Example | Structure | Name |
|---|---|---|
| Example 2-72 | 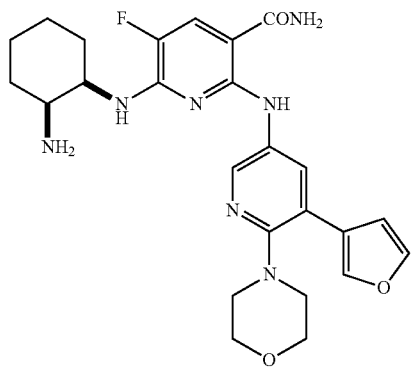 | 6-(cis-2-aminocyclohexylamino)-5-fluoro-2-((5-(furan-3-yl)-6-morpholinopyridin-3-yl)amino)nicotinamide |
| Example 2-73 | 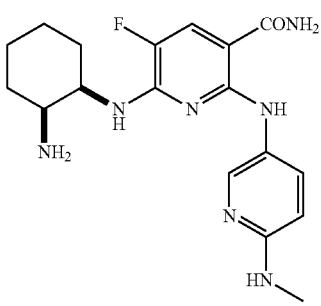 | 6-(cis-2-aminocyclohexylamino)-5-fluoro-2-((6-methylaminopyridin-3-yl)amino)nicotinamide |
| Example 2-74 | 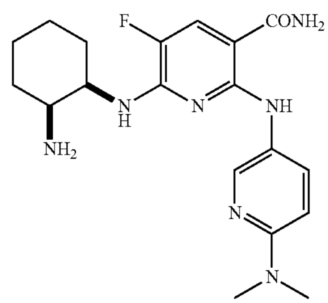 | 6-(cis-2-aminocyclohexylamino)-2-(6-dimethylaminopyridin-3-yl)amino)-5-fluoronicotinamide |
| Example 2-75 | 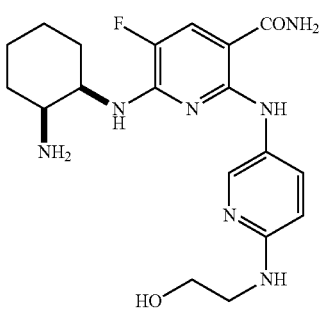 | 6-(cis-2-aminocyclohexylamino)-5-fluoro-2-((6-(2-hydroxyethylamino)pyridin-3-yl)amino)nicotinamide |
| Example 2-76 | 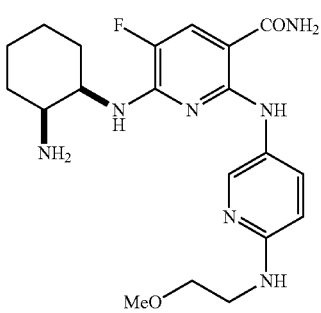 | 6-(cis-2-aminocyclohexylamino)-5-fluoro-2-((6-(2-methoxyethylamino)pyridin-3-yl)amino)nicotinamide |

TABLE 1-continued

| Example 2-77 | 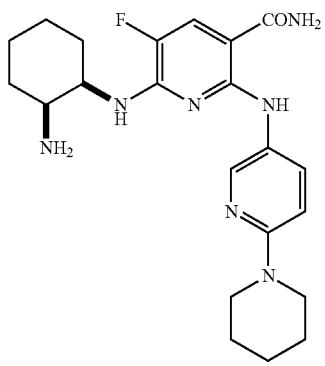 | 6-(cis-2-aminocyclo-hexylamino)-5-fluoro-2-((6-(piperidin-1-yl)pyridin-3-yl)amino)nicotinamide |
| Example 2-78 | 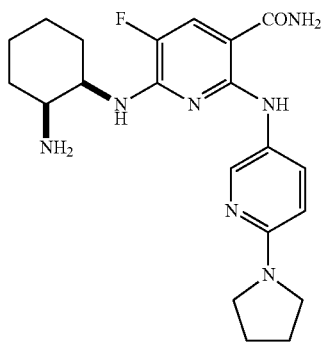 | 6-(cis-2-aminocyclohexyl-amino)-5-fluoro-2-((6-(pyrrolidin-1-yl)pyridin-3-yl)amino)nicotinamide |
| Example 2-79 | 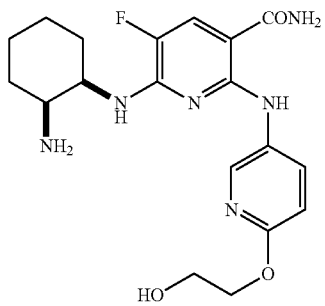 | 6-(cis-2-aminocyclohexyl-amino)-5-fluoro-2-((6-(2-hydroxyethoxy)pyridin-3-yl)amino)nicotinamide |
| Example 2-80 | 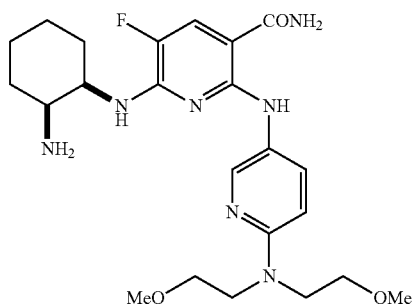 | 6-(cis-2-aminocyclo-hexylamino)-2-(6-(bis(2-methoxyethylamino)pyridin-3-yl)amino)-5-fluoronicotinamide |
| Example 2-81 | 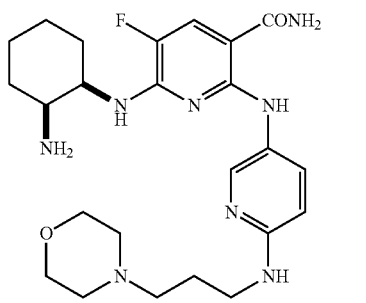 | 6-(cis-2-aminocyclo-hexylamino)-5-fluoro-2-((6-(3-morpholinopropyl-amino)pyridin-3-yl)amino)nicotinamide |

TABLE 1-continued

| Example 2-82 | 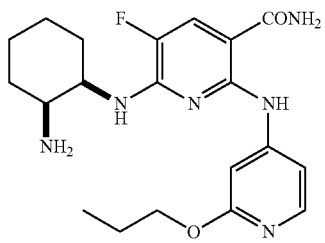 | 6-(cis-2-aminocyclohexylamino)-5-fluoro-2-((2-propoxypyridin-4-yl)amino)nicotinamide |
| Example 2-83 | 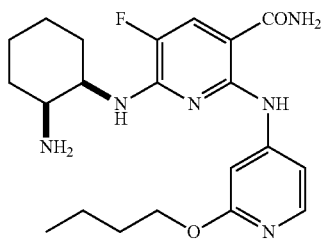 | 6-(cis-2-aminocyclohexylamino)-2-((2-butoxypyridin-4-yl)amino)-5-fluoronicotinamide |
| Example 2-84 | 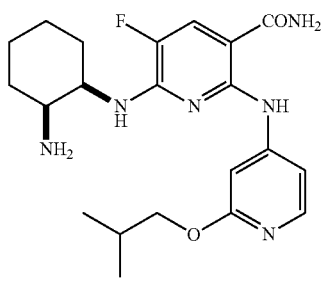 | 6-(cis-2-aminocyclohexylamino)-5-fluoro-2-((2-isobutoxypyridin-4-yl)amino)nicotinamide |
| Example 2-85 | 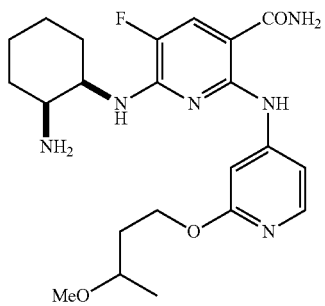 | 6-(cis-2-aminocyclohexylamino)-5-fluoro-2-((2-(3-methoxybutoxy)pyridin-4-yl)amino)nicotinamide |
| Example 2-86 | 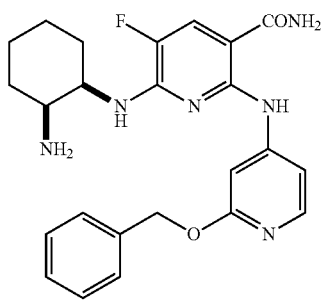 | 6-(cis-2-aminocyclohexylamino)-2-((2-(benzyloxy)pyridin-4-yl)amino)-5-fluoronicotinamide |

TABLE 1-continued

| Example 2-87 | 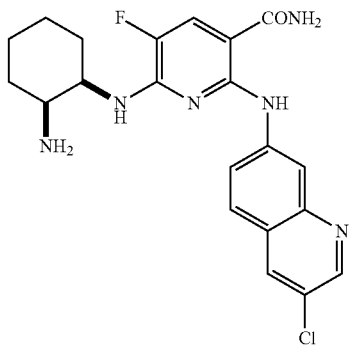 | 6-(cis-2-aminocyclo-hexylamino)-2-((3-chloroquinolin-7-yl)amino)-5-fluoronicotinamide |
| Example 2-88 | 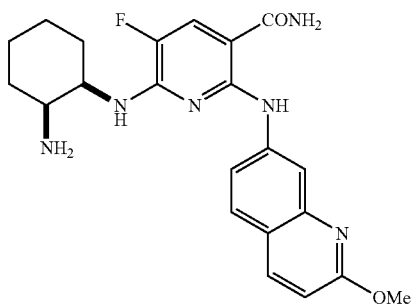 | 6-(cis-2-aminocyclo-hexylamino)-5-fluoro-2-((2-methoxyquinolin-7-yl)amino)nicotinamide |
| Example 2-89 | 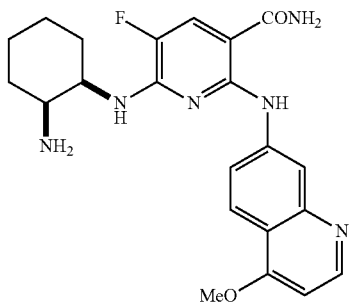 | 6-(cis-2-aminocyclo-hexylamino)-5-fluoro-2-((4-methoxyquinolin-7-yl)amino)nicotinamide |
| Example 2-90 | 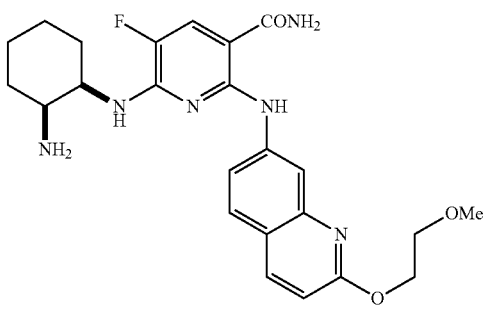 | 6-(cis-2-aminocyclo-hexylamino)-5-fluoro-2-((2-(2-methoxyethoxy)quinolin-7-yl)amino)nicotinamide |
| Example 2-91 | 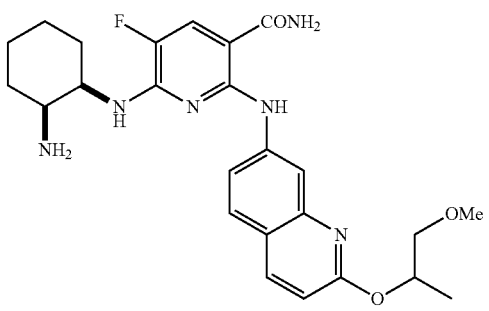 | 6-(cis-2-aminocyclo-hexylamino)-5-fluoro-2-((2-((1-methoxypropan-2-yl)oxy)quinolin-7-yl)amino)nicotinamide |

TABLE 1-continued

| Example 2-92 | 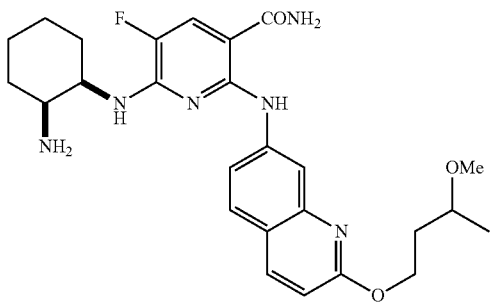 | 6-(cis-2-aminocyclo-hexylamino)-5-fluoro-2-((2-(3-methoxybutoxy)quinolin-7-yl)amino)nicotinamide |
| Example 2-93 | 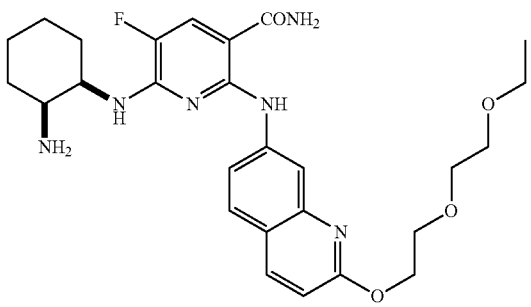 | 6-(cis-2-aminocyclo-hexylamino)-2-((2-(2-(2-ethoxy-ethoxy)ethoxy)quinolin-7-yl)amino)-5-fluoronicotinamide |
| Example 2-94 | 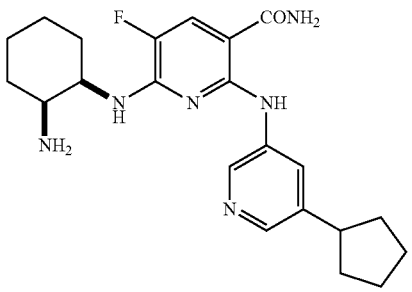 | 6-(cis-2-aminocyclo-hexylamino)-2-((5-cyclopentylpyridin-3-yl)amino)-5-fluoronicotinamide |
| Example 2-95 | 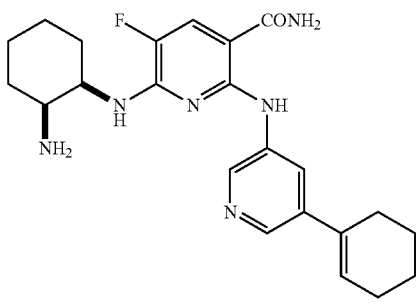 | 6-(cis-2-aminocyclo-hexylamino)-2-((5-(1-cyclohexen-1-yl)pyridin-3-yl)amino)-5-fluoronicotinamide |
| Example 2-96 | 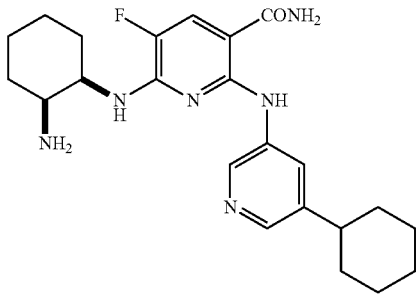 | 6-(cis-2-aminocyclo-hexylamino)-2-((5-cyclohexylpyridin-3-yl)amino)-5-fluoronicotinamide |

TABLE 1-continued

| Example 2-97 | 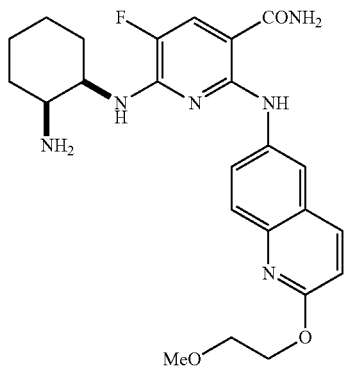 | 6-(cis-2-aminocyclo-hexylamino)-5-fluoro-2-((2-(2-methoxyethoxy)quinolin-6-yl)amino)nicotinamide |
| --- | --- | --- |
| Example 2-98 | 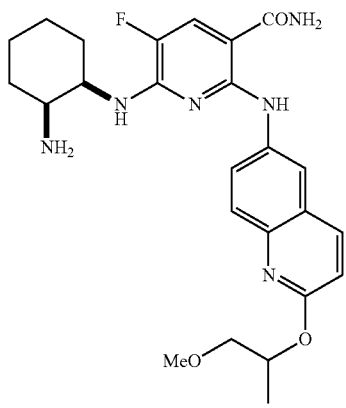 | 6-(cis-2-aminocyclo-hexylamino)-5-fluoro-2-((2-((1-methoxypropan-2-yl)oxy)quinolin-6-yl)amino)nicotinamide |
| Example 2-99 | 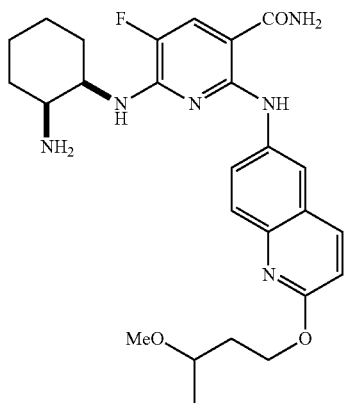 | 6-(cis-2-aminocyclo-hexylamino)-5-fluoro-2-((2-(3-methoxybutoxy)quinolin-6-yl)amino)nicotinamide |
| Example 2-100 | 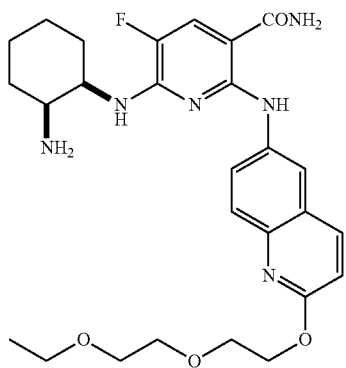 | 6-(cis-2-amino-cyclohexylamino)-2-((2-(2-(2-ethoxyethoxy)ethoxy)quinolin-6-yl)amino)-5-fluoronicotinamide |

| | | |
|---|---|---|
| Example 2-101 | 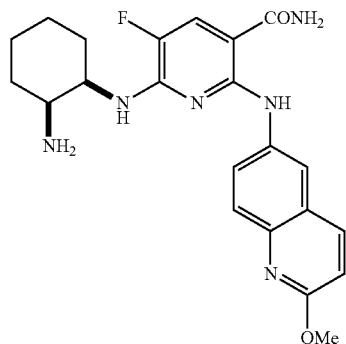 | 6-(cis-2-aminocyclo-hexylamino)-5-fluoro-2-((2-methoxyquinolin-6-yl)amino)nicotinamide |
| Example 2-102 | 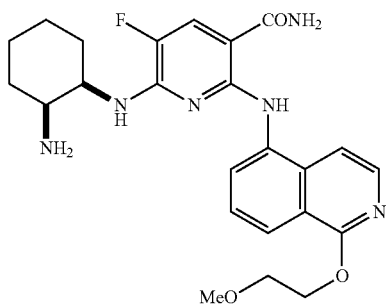 | 6-(cis-2-aminocyclo-hexylamino)-5-fluoro-2-((1-(2-methoxyethoxy)isoquinolin-5-yl)amino)nicotinamide |
| Example 2-103 | 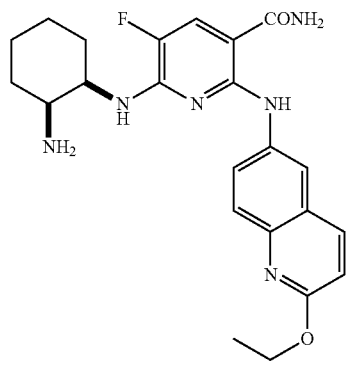 | 6-(cis-2-aminocyclo-hexylamino)-2-((2-ethoxyquinolin-6-yl)amino)-5-fluoronicotinamide |
| Example 2-104 | 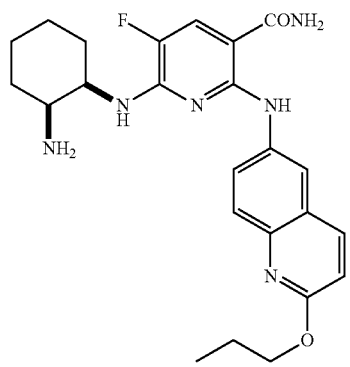 | 6-(cis-2-aminocyclo-hexylamino)-5-fluoro-2-((2-propoxyquinolin-6-yl)amino)nicotinamide |

TABLE 1-continued

| Example 2-105 | 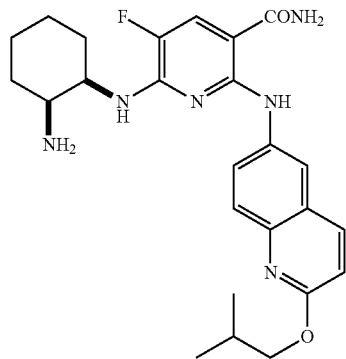 | 6-(cis-2-aminocyclo-hexylamino)-5-fluoro-2-((2-isobutoxyquinolin-6-yl)amino)nicotinamide |
| Example 2-106 | 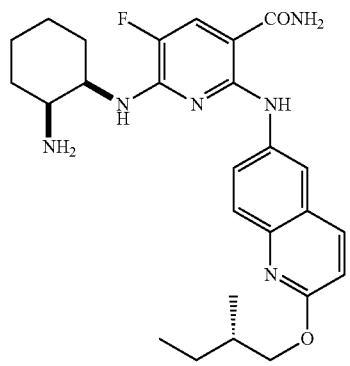 | 6-(cis-2-aminocyclo-hexylamino)-5-fluoro-2-((2-((S)-2-methylbutoxy)quinolin-6-yl)amino)nicotinamide |
| Example 2-107 | 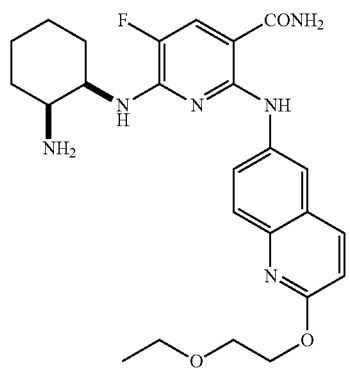 | 6-(cis-2-aminocyclo-hexylamino)-2-((2-(2-ethoxyethoxy)quinolin-6-yl)amino)-5-fluoronicotinamide |
| Example 2-108 | 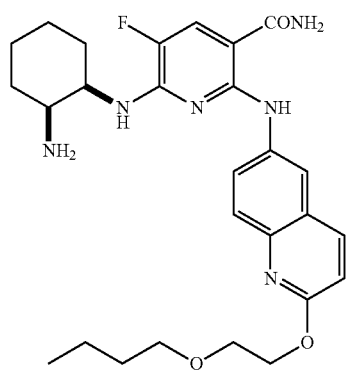 | 6-(cis-2-aminocyclo-hexylamino)-2-((2-(2-butoxyethoxy)quinolin-6-yl)amino)-5-fluoronicotinamide |

| | | |
|---|---|---|
| Example 2-109 | 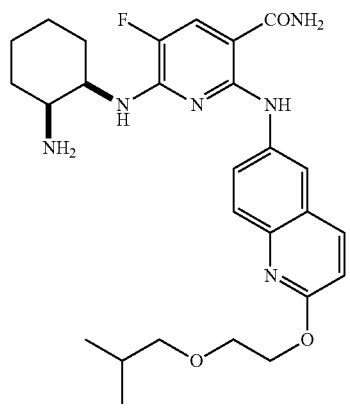 | 6-(cis-2-aminocyclo-hexylamino)-5-fluoro-2-((2-(2-isobutoxyethoxy)quinolin-6-yl)amino)nicotinamide |
| Example 2-110 | 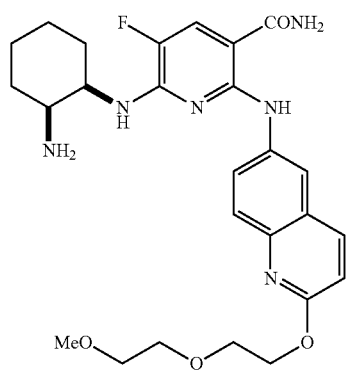 | 6-(cis-2-aminocyclohexylamino)-5-fluoro-2-((2-(2-(2-methoxyethoxy)ethoxy)quinolin-6-yl)amino)nicotinamide |
| Example 2-111 | 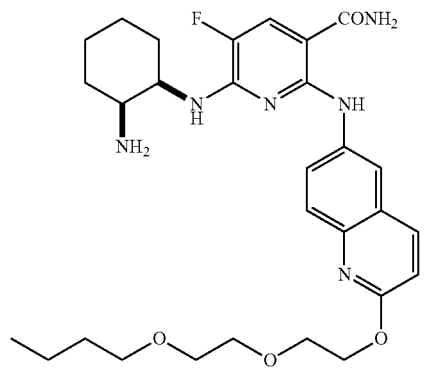 | 6-(cis-2-aminocyclohexylamino)-2-((2-(2-(2-butoxyethoxy)ethoxy)quinolin-6-yl)amino)-5-fluoronicotinamide |
| Example 2-112 | 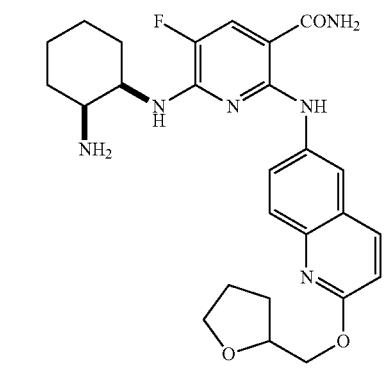 | 6-(cis-2-aminocyclohexylamino)-5-fluoro-2-((2-((tetrahydrofuran-2-yl)methoxy)quinolin-6-yl)amino)nicotinamide |

TABLE 1-continued

| Example 2-113 | 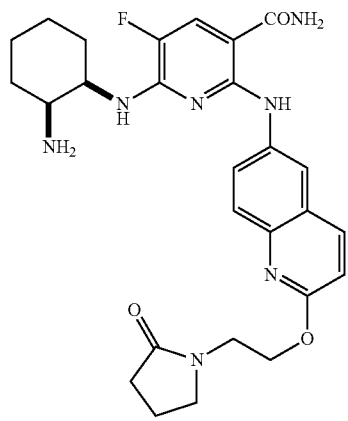 | 6-(cis-2-aminocyclohexylamino)-5-fluoro-2-((2-(2-(2-oxopyrrolidin-1-yl)ethoxy)quinolin-6-yl)amino)nicotinamide |
| Example 2-114 | 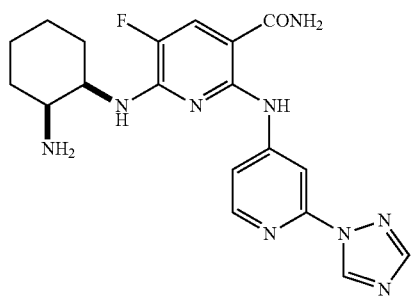 | 2-((2-(1H-1,2,4-triazol-1-yl)pyridin-4-yl)amino)-6-(cis-2-aminocyclohexylamino)-5-fluoronicotinamide |
| Example 2-115 | 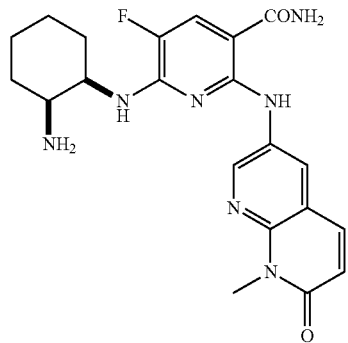 | 6-(cis-2-aminocyclohexylamino)-5-fluoro-2-((8-methyl-7-oxo-7,8-dihydro-1,8-naphthyridin-3-yl)amino)nicotinamide |
| Example 2-116 | 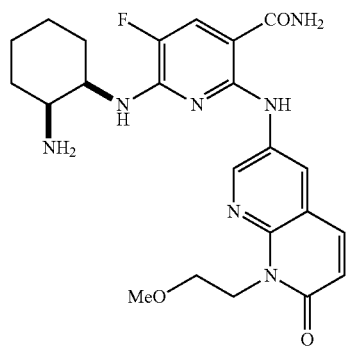 | 6-(cis-2-aminocyclohexylamino)-5-fluoro-2-((8-(2-methoxyethyl)-7-oxo-7,8-dihydro-1,8-naphthyridin-3-yl)amino)nicotinamide |

TABLE 1-continued

| Example | Structure | Name |
|---|---|---|
| Example 2-117 | 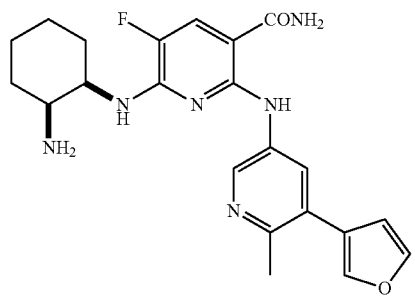 | 6-(cis-2-aminocyclohexylamino)-5-fluoro-2-((5-(furan-3-yl)-6-methylpyridin-3-yl)amino)nicotinamide |
| Example 2-118 | 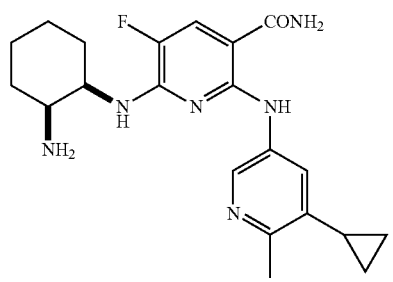 | 6-(cis-2-aminocyclohexylamino)-2-((5-cyclopropyl-6-methylpyridin-3-yl)amino)-5-fluoronicotinamide |
| Example 2-119 | 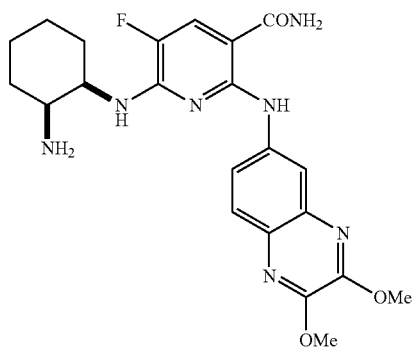 | 6-(cis-2-aminocyclo-hexylamino)-2-((2,3-dimethoxyquinoxalin-6-yl)amino)-5-fluoronicotinamide |
| Example 2-120 | 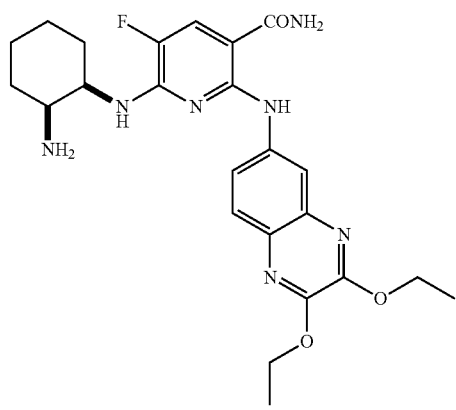 | 6-(cis-2-aminocyclo-hexylamino)-2-((2,3-diethoxyquinoxalin-6-yl)amino)-5-fluoronicotinamide |

TABLE 1-continued

| Example 2-121 | 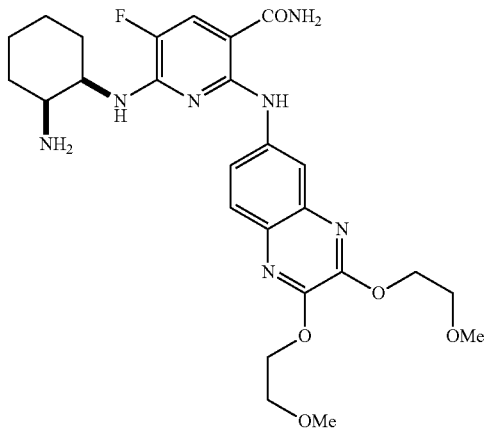 | 6-(cis-2-aminocyclo-hexylamino)-2-((2,3-bis(2-methoxy-ethoxy)quinoxalin-6-yl)amino)-5-fluoronicotinamide |
| Example 2-122 | 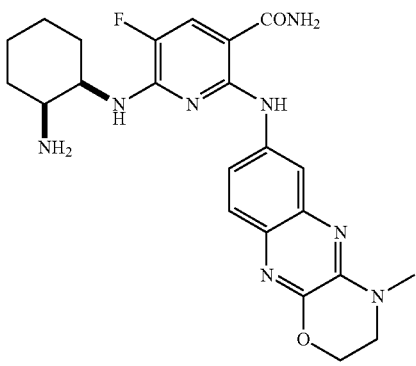 | 6-(cis-2-aminocyclo-hexylamino)-5-fluoro-2-((4-methyl-3,4-dihydro-2H-[1,4]oxazino[2,3-b]quinoxalin-7-yl)amino)nicotinamide |
| Example 2-123 | 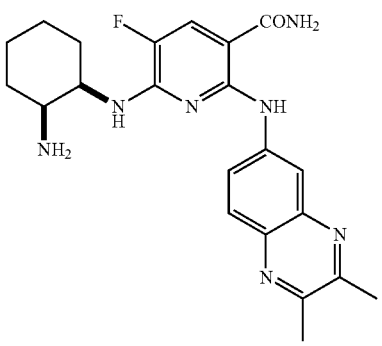 | 6-(cis-2-aminocyclo-hexylamino)-2-((2,3-dimethylquinoxalin-6-yl)amino)-5-fluoronicotinamide |
| Example 2-124 | 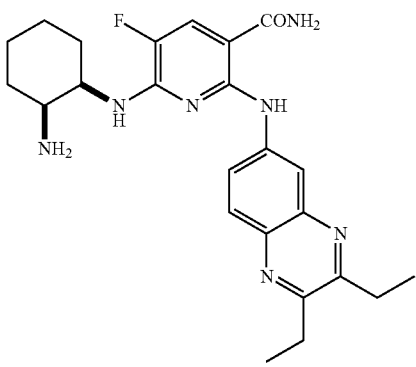 | 6-(cis-2-aminocyclo-hexylamino)-2-((2,3-diethylquinoxalin-6-yl)amino)-5-fluoronicotinamide |

TABLE 1-continued

| Example 2-125 | 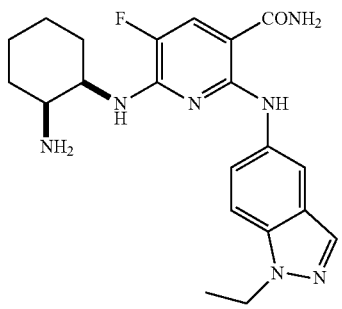 | 6-(cis-2-aminocyclo-hexylamino)-2-((1-ethyl-1H-indazol-5-yl)amino)-5-fluoronicotinamide |
| Example 2-126 | 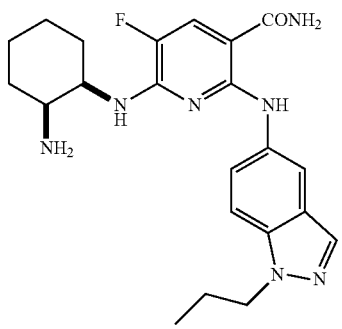 | 6-(cis-2-aminocyclo-hexylamino)-5-fluoro-2-((1-propyl-1H-indazol-5-yl)amino)nicotinamide |
| Example 2-127 | 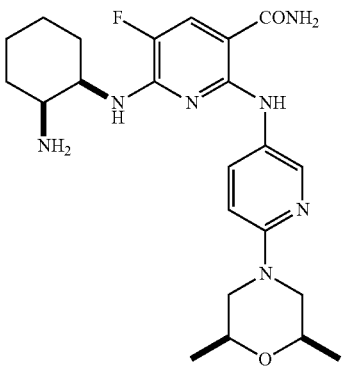 | 6-(cis-2-aminocyclo-hexylamino)-2-((6-((cis)-2,6-dimethyl-morpholino)pyridin-3-yl)amino)-5-fluoronicotinamide |
| Example 2-128 | 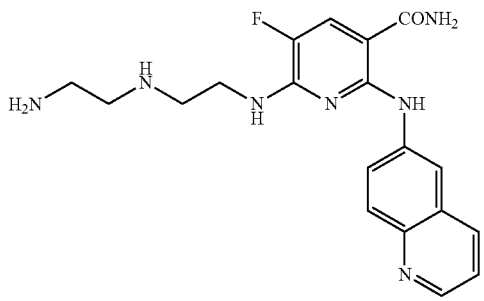 [SMILES: NCCNCCNc1nc(Nc2ccc3ncccc3c2)c(C(N)=O)cc1F] | 6-((2-((2-aminoethyl)amino)ethyl)amino)-5-fluoro-2-((quinolin-6-yl)amino)nicotinamide |
| Example 2-129 | 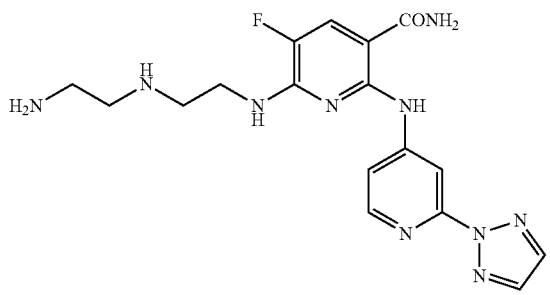 [SMILES: NCCNCCNc1nc(Nc2ccnc(-n3nccn3)c2)c(C(N)=O)cc1F] | 2-((2-(2H-1,2,3-triazol-2-yl)pyridin-4-yl)amino)-6-((2-((2-aminoethyl)amino)ethyl)amino)-5-fluoronicotinamide |

| | | |
|---|---|---|
| Example 2-130 | 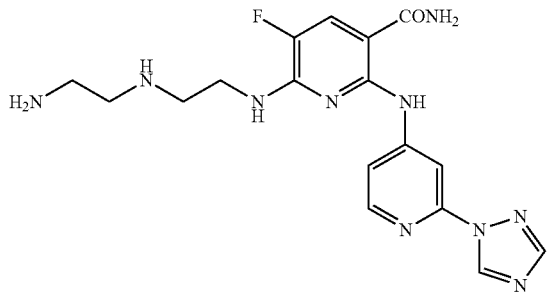 [SMILES: NCCNCCNc1nc(Nc2ccnc(-n3cncn3)c2)c(C(N)=O)cc1F] | 2-((2-(1H-1,2,4-triazol-1-yl)pyridin-4-yl)amino)-6-((2-((2-aminoethyl)amino)ethyl)amino)-5-fluoronicotinamide |
| Example 2-131 | 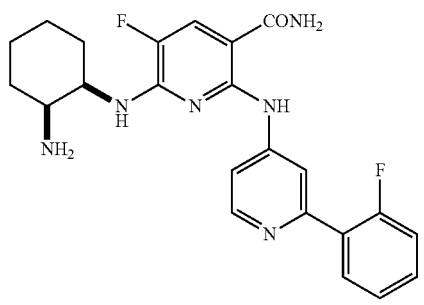 | 6-(cis-2-aminocyclohexylamino)-5-fluoro-2-((2-(2-fluorophenyl)pyridin-4-yl)amino)nicotinamide |
| Example 2-132 | 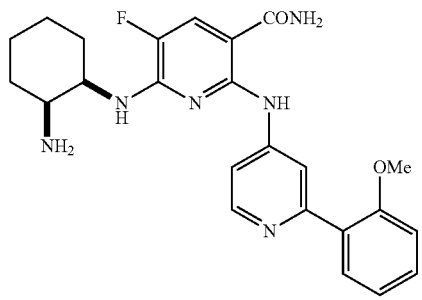 | 6-(cis-2-aminocyclo-hexylamino)-5-fluoro-2-((2-(2-methoxyphenyl)pyridin-4-yl)amino)nicotinamide |
| Example 2-133 | 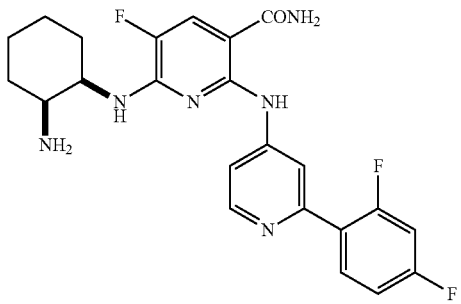 | 6-(cis-2-aminocyclohexylamino)-2-((2-(2,4-difluorophenyl)pyridin-4-yl)amino)-5-fluoronicotinamide |
| Example 2-134 | 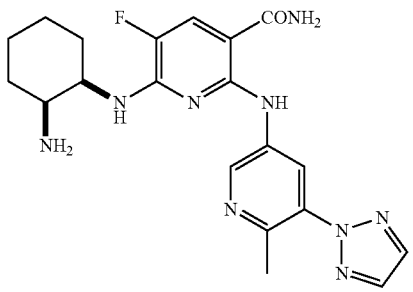 | 6-(cis-2-aminocyclohexylamino)-5-fluoro-2-((6-methyl-5-(2H-1,2,3-triazol-2-yl)pyridin-3-yl)amino)nicotinamide |

TABLE 1-continued

| Example 2-135 | 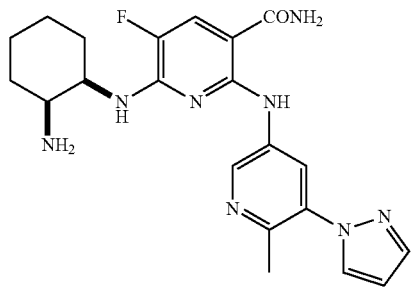 | 6-(cis-2-aminocyclohexylamino)-5-fluoro-2-((6-methyl-5-(1H-pyrazol-1-yl)pyridin-3-yl)amino)nicotinamide |
| Example 2-136 | 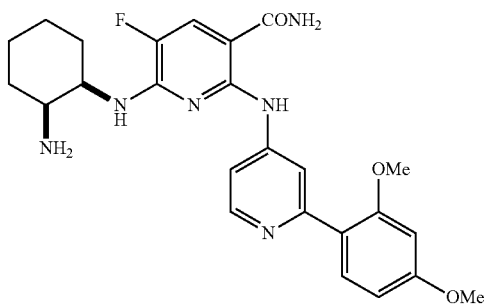 | 6-(cis-2-aminocyclohexylamino)-2-((2-(2,4-dimethoxyphenyl)pyridin-4-yl)amino)-5-fluoronicotinamide |
| Example 2-137 | 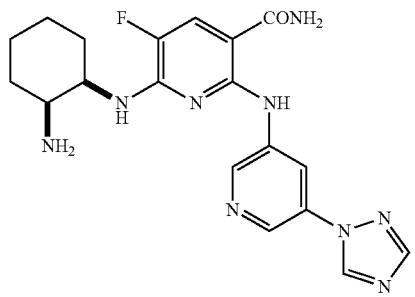 | 2-((5-(1H-1,2,4-triazol-1-yl)pyridin-3-yl)amino)-6-(cis-2-aminocyclohexylamino)-5-fluoronicotinamide |
| Example 2-138 | 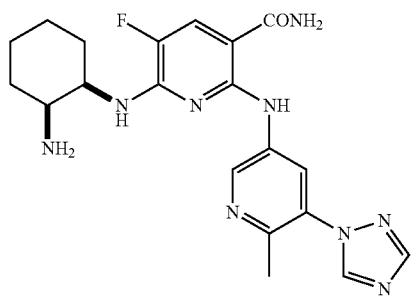 | 6-(cis-2-aminocyclohexylamino)-5-fluoro-2-((6-methyl-5-(1H-1,2,4-triazol-1-yl)pyridin-3-yl)amino)nicotinamide |
| Example 2-139 | 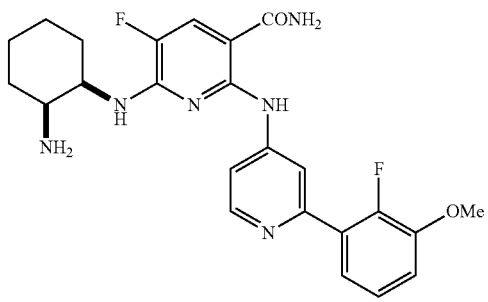 | 6-(cis-2-aminocyclohexylamino)-5-fluoro-2-((2-(2-fluoro-3-methoxyphenyl)pyridin-4-yl)amino)nicotinamide |

TABLE 1-continued

| Example 2-140 | 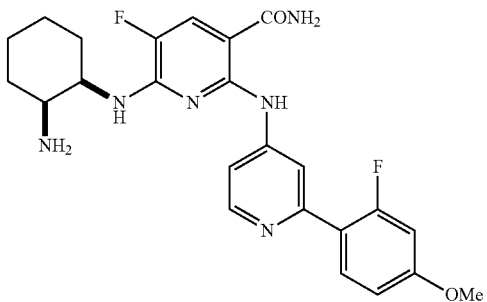 | 6-(cis-2-aminocyclohexylamino)-5-fluoro-2-((2-(2-fluoro-4-methoxyphenyl)pyridin-4-yl)amino)nicotinamide |
| Example 2-141 | 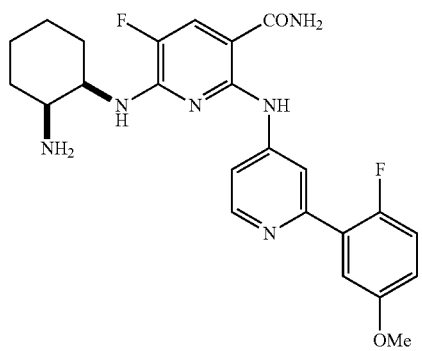 | 6-(cis-2-aminocyclohexylamino)-5-fluoro-2-((2-(2-fluoro-5-methoxyphenyl)pyridin-4-yl)amino)nicotinamide |
| Example 2-142 | 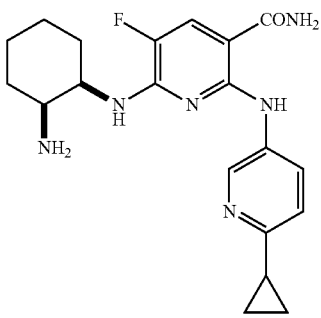 | 6-(cis-2-aminocyclohexylamino)-2-((6-cyclopropylpyridin-3-yl)amino)-5-fluoronicotinamide |
| Example 2-143 | 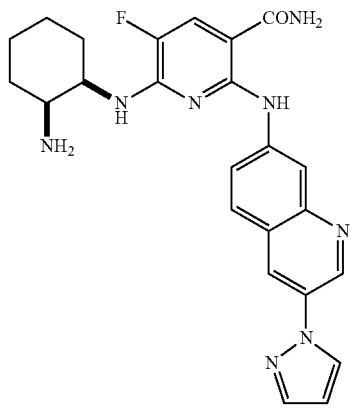 | 2-((3-(1H-pyrazol-1-yl)quinolin-7-yl)amino)-6-(cis-2-aminocyclohexylamino)-5-fluoronicotinamide |

TABLE 1-continued

| Example 2-144 | 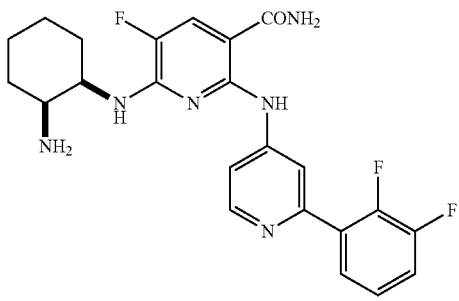 | 6-(cis-2-aminocyclohexylamino)-2-((2-(2,3-difluorophenyl)pyridin-4-yl)amino)-5-fluoronicotinamide |
| --- | --- | --- |
| Example 2-145 | 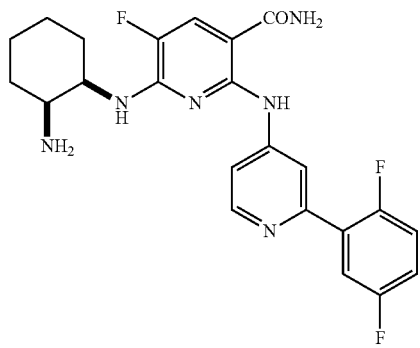 | 6-(cis-2-aminocyclohexylamino)-2-((2-(2,5-difluorophenyl)pyridin-4-yl)amino)-5-fluoronicotinamide |
| Example 2-146 | 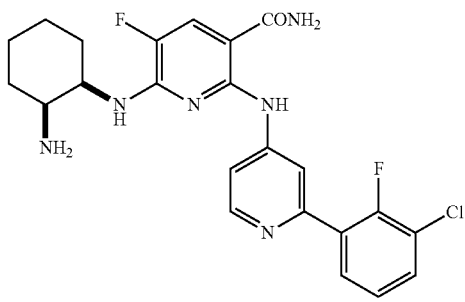 | 6-(cis-2-aminocyclohexylamino)-2-((2-(3-chloro-2-fluorophenyl)pyridin-4-yl)amino)-5-fluoronicotinamide |
| Example 2-147 | 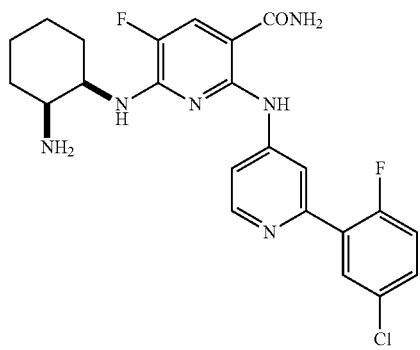 | 6-(cis-2-aminocyclohexylamino)-2-((2-((5-chloro-2-fluorophenyl)pyridin-4-yl)amino)-5-fluoronicotinamide |
| Example 2-148 | 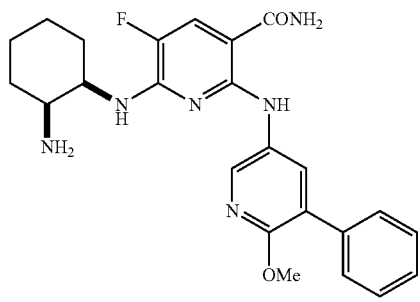 | 6-(cis-2-aminocyclohexylamino)-5-fluoro-2-((6-methoxy-5-phenylpyridin-3-yl)amino)nicotinamide |

TABLE 1-continued

| Example 2-149 | 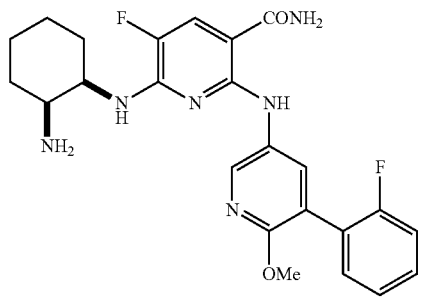 | 6-(cis-2-aminocyclohexylamino)-5-fluoro-2-((5-(2-fluorophenyl)-6-methoxypyridin-3-yl)amino)nicotinamide |
| --- | --- | --- |
| Example 2-150 | 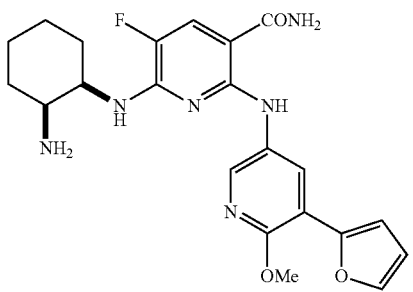 | 6-(cis-2-aminocyclohexylamino)-5-fluoro-2-((5-(furan-2-yl)-6-methoxypyridin-3-yl)amino)nicotinamide |
| Example 2-151 | 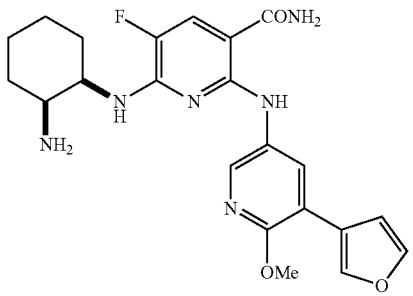 | 6-(cis-2-aminocyclohexylamino)-5-fluoro-2-((5-(furan-3-yl)-6-methoxypyridin-3-yl)amino)nicotinamide |
| Example 2-152 | 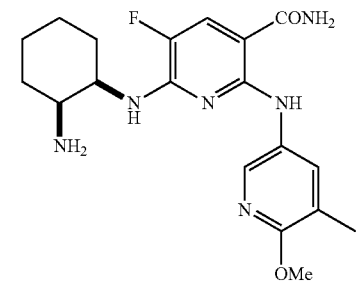 | 6-(cis-2-aminocyclohexylamino)-5-fluoro-2-((6-methoxy-5-methylpyridin-3-yl)amino)nicotinamide |
| Example 2-153 | 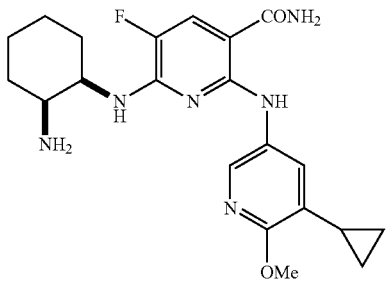 | 6-(cis-2-aminocyclohexylamino)-2-((5-cyclopropyl-6-methoxypyridin-3-yl)amino)-5-fluoronicotinamide |

| Example | | |
|---|---|---|
| Example 2-154 | 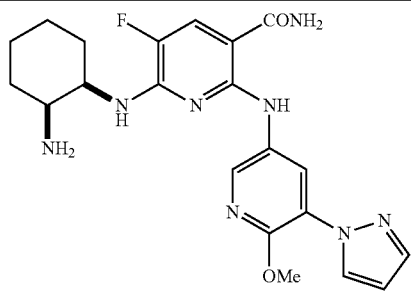 | 6-(cis-2-aminocyclohexylamino)-5-fluoro-2-((6-methoxy-5-(1H-pyrazol-1-yl)pyridin-3-yl)amino)nicotinamide |
| Example 2-155 | 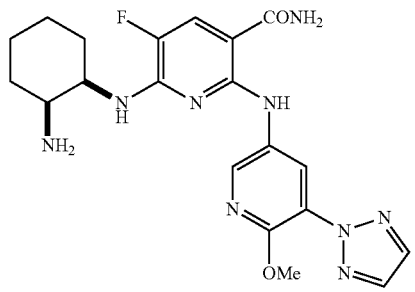 | 6-(cis-2-aminocyclohexylamino)-5-fluoro-2-((6-methoxy-5-(2H-1,2,3-triazol-2-yl)pyridin-3-yl)amino)nicotinamide |
| Example 2-156 | 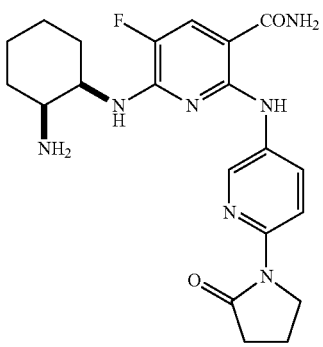 | 6-(cis-2-aminocyclohexylamino)-5-fluoro-2-((6-(2-oxopyrrolidin-1-yl)pyridin-3-yl)amino)nicotinamide |
| Example 2-157 | 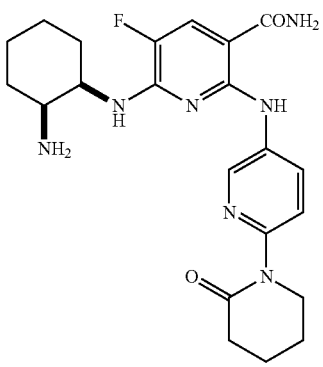 | 6-(cis-2-aminocyclohexylamino)-5-fluoro-2-((6-(2-oxopiperidin-1-yl)pyridin-3-yl)amino)nicotinamide |
| Example 2-158 | 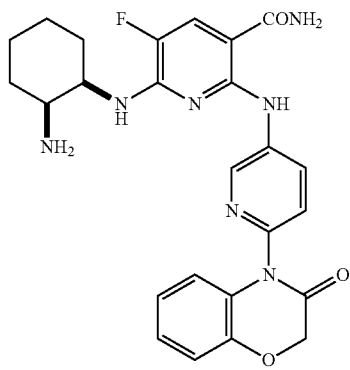 | 6-(cis-2-aminocyclohexylamino)-5-fluoro-2-((6-(3-oxo-2H-benzo[b][1,4]oxazin-4(3H)-yl)pyridin-3-yl)amino)nicotinamide |

| | | |
|---|---|---|
| Example 2-159 | 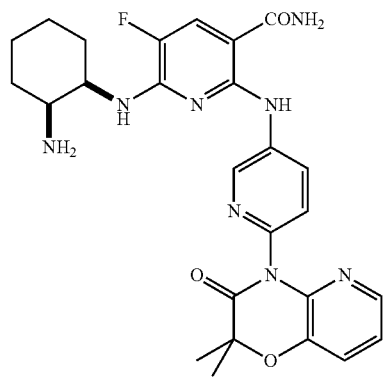 | 6-(cis-2-aminocyclohexylamino)-2-((6-(2,2-dimethyl-3-oxo-2H-pyrido[3,2-b][1,4]oxazin-4(3H)-yl)pyridin-3-yl)amino)-5-fluoronicotinamide |
| Example 2-160 | 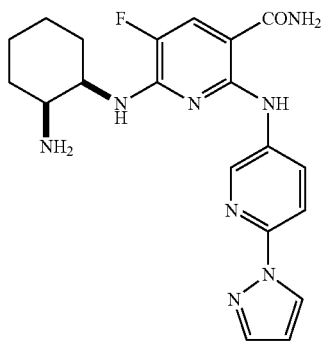 | 2-((6-(1H-pyrazol-1-yl)pyridin-3-yl)amino)-6-(cis-2-aminocyclohexylamino)-5-fluoronicotinamide |
| Example 2-161 | 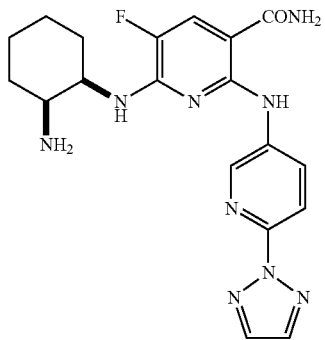 | 2-((6-(2H-1,2,3-triazol-2-yl)pyridin-3-yl)amino)-6-(cis-2-aminocyclohexylamino)-5-fluoronicotinamide |
| Example 2-162 | 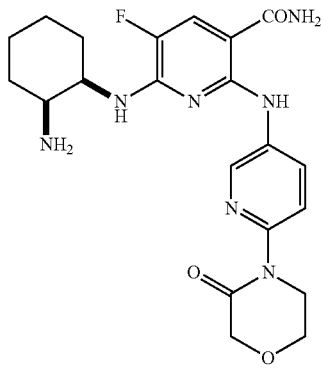 | 6-(cis-2-aminocyclohexylamino)-5-fluoro-2-((6-(3-oxomorpholino)pyridin-3-yl)amino)nicotinamide |

TABLE 1-continued

| Example 2-163 | 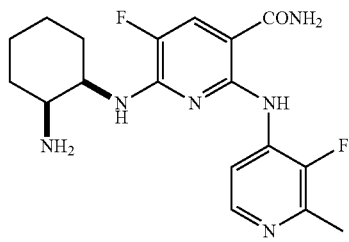 | 6-(cis-2-aminocyclohexylamino)-5-fluoro-2-((3-fluoro-2-methylpyridin-4-yl)amino)nicotinamide |
| Example 2-164 | 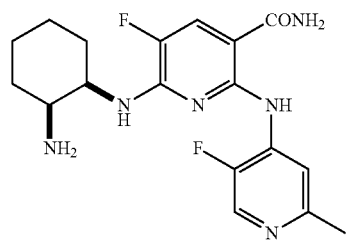 | 6-(cis-2-aminocyclohexylamino)-5-fluoro-2-((5-fluoro-2-methylpyridin-4-yl)amino)nicotinamide |
| Example 2-165 | 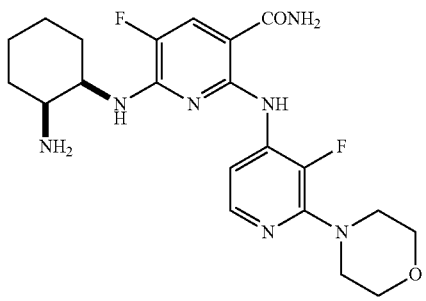 | 6-(cis-2-aminocyclohexylamino)-5-fluoro-2-((3-fluoro-2-morpholinopyridin-4-yl)amino)nicotinamide |
| Example 2-166 | 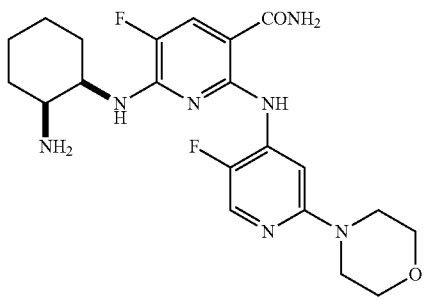 | 6-(cis-2-aminocyclohexylamino)-5-fluoro-2-((5-fluoro-2-morpholinopyridin-4-yl)amino)nicotinamide |
| Example 2-167 | 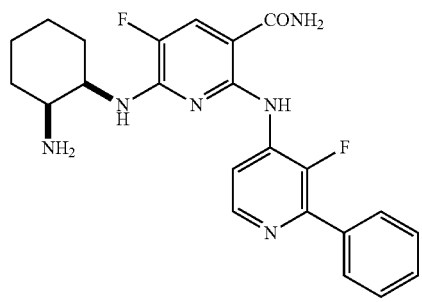 | 6-(cis-2-aminocyclohexylamino)-5-fluoro-2-((3-fluoro-2-phenylpyridin-4-yl)amino)nicotinamide |

TABLE 1-continued

| Example 2-168 | 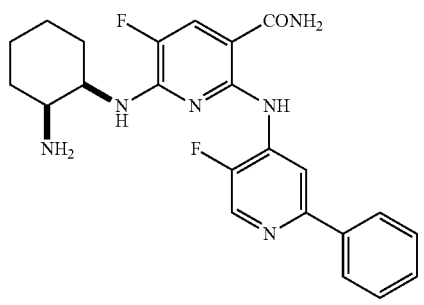 | 6-(cis-2-aminocyclohexylamino)-5-fluoro-2-((5-fluoro-2-phenylpyridin-4-yl)amino)nicotinamide |
| Example 2-169 | 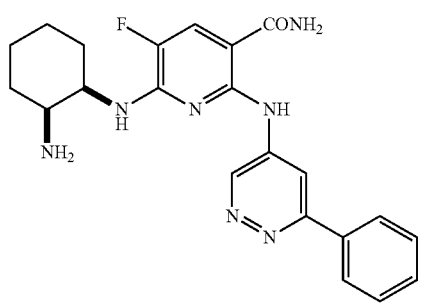 | 6-(cis-2-aminocyclohexylamino)-5-fluoro-2-((6-phenylpyridazin-4-yl)amino)nicotinamide |
| Example 2-170 | 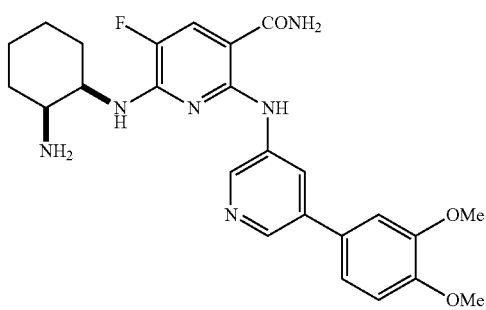 | 6-(cis-2-aminocyclohexylamino)-2-((5-(3,4-dimethoxyphenyl)pyridin-3-yl)amino)-5-fluoronicotinamide |
| Example 2-171 | 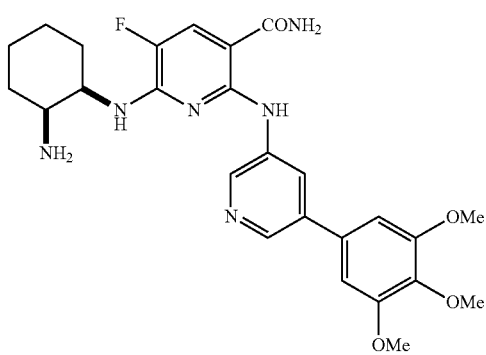 | 6-(cis-2-aminocyclohexylamino)-5-fluoro-2-((5-(3,4,5-trimethoxyphenyl)pyridin-3-yl)amino)nicotinamide |
| Example 2-172 | 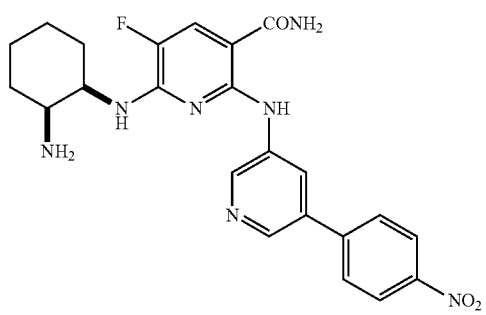 | 6-(cis-2-aminocyclohexylamino)-5-fluoro-2-((5-(4-nitrophenyl)pyridin-3-yl)amino)nicotinamide |

TABLE 1-continued

| Example 2-173 | 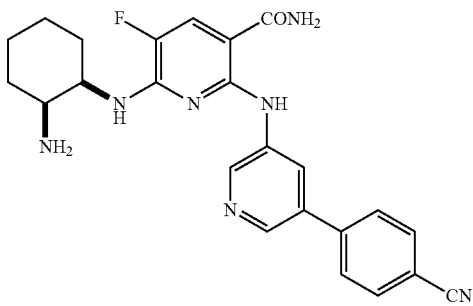 | 6-(cis-2-aminocyclohexylamino)-2-((5-(4-cyanophenyl)pyridin-3-yl)amino)-5-fluoronicotinamide |
| Example 2-174 | 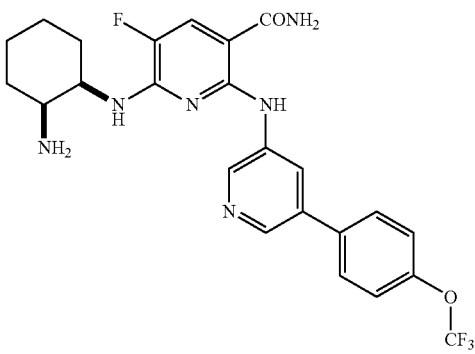 | 6-(cis-2-aminocyclohexylamino)-5-fluoro-2-((5-(4-(trifluoromethoxy)phenyl)pyridin-3-yl)amino)nicotinamide |
| Example 2-175 | 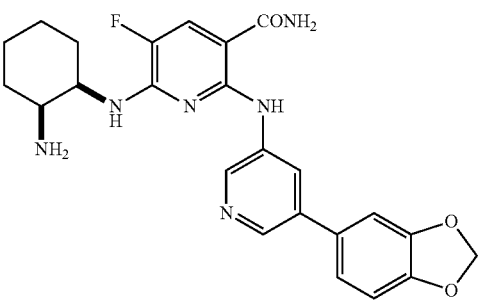 | 6-(cis-2-aminocyclohexylamino)-2-((5-(benzo[d][1,3]dioxol-5-yl)pyridin-3-yl)amino)-5-fluoronicotinamide |
| Example 2-176 | 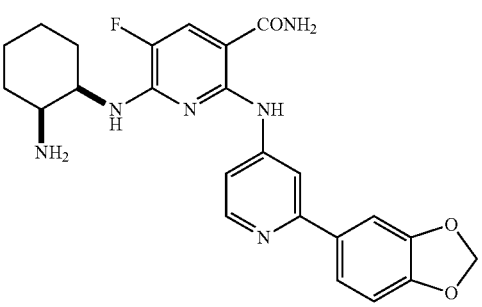 | 6-(cis-2-aminocyclohexylamino)-2-((2-(benzo[d][1,3]dioxol-5-yl)pyridin-4-yl)amino)-5-fluoronicotinamide |
| Example 2-177 | 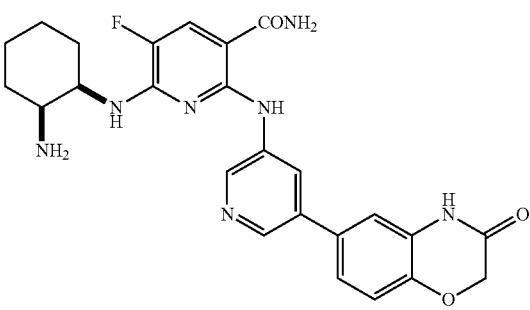 | 6-(cis-2-aminocyclohexylamino)-5-fluoro-2-((5-(3-oxo-3,4-dihydro-2H-benzo[b][1,4]oxazin-6-yl)pyridin-3-yl)amino)nicotinamide |

TABLE 1-continued

| Example 2-178 | 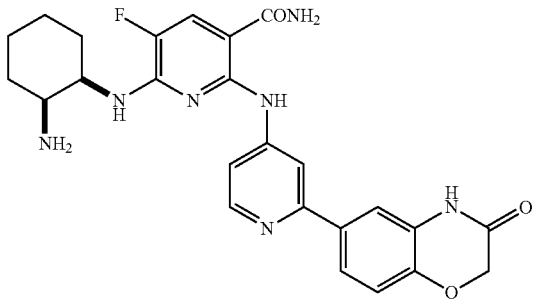 | 6-(cis-2-aminocyclohexylamino)-5-fluoro-2-((2-(3-oxo-3,4-dihydro-2H-benzo[b][1,4]oxazin-6-yl)pyridin-4-yl)amino)nicotinamide |
| --- | --- | --- |
| Example 2-179 | 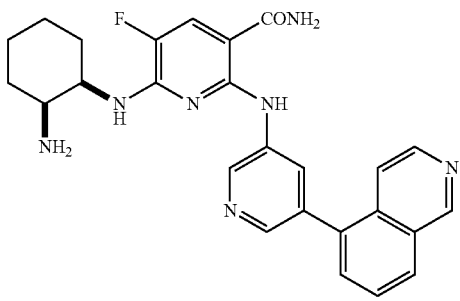 | 6-(cis-2-aminocyclohexylamino)-5-fluoro-2-((5-(isoquinolin-5-yl)pyridin-3-yl)amino)nicotinamide |
| Example 2-180 | 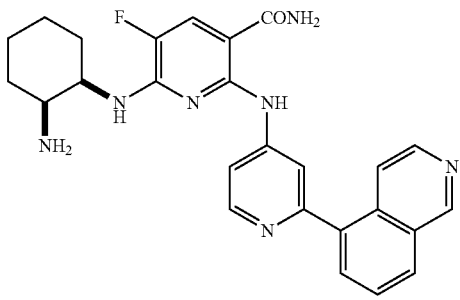 | 6-(cis-2-aminocyclohexylamino)-5-fluoro-2-((2-(isoquinolin-5-yl)pyridin-4-yl)amino)nicotinamide |
| Example 2-181 | 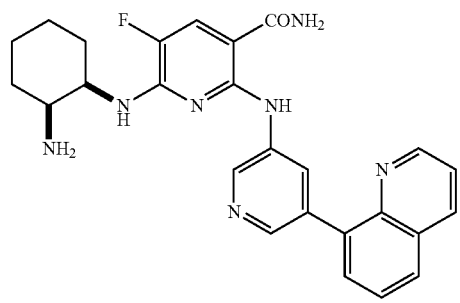 | 6-(cis-2-aminocyclo-hexylamino)-5-fluoro-2-((5-(quinolin-8-yl)pyridin-3-yl)amino)nicotinamide |
| Example 2-182 | 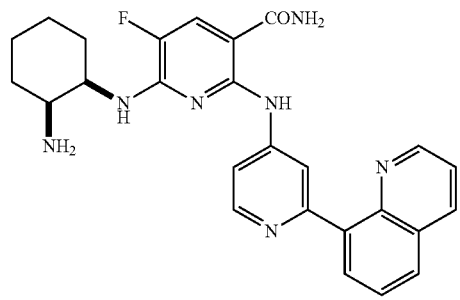 | 6-(cis-2-aminocyclo-hexylamino)-5-fluoro-2-((2-(quinolin-8-yl)pyridin-4-yl)amino)nicotinamide |

| Example 2-183 | 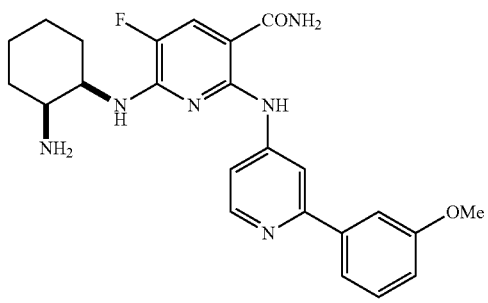 | 6-(cis-2-aminocyclo-hexylamino)-5-fluoro-2-((2-(3-methoxyphenyl)pyridin-4-yl)amino)nicotinamide |
| Example 2-184 | 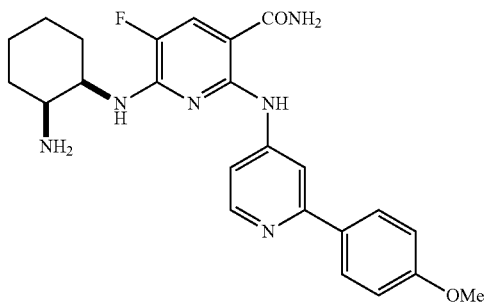 | 6-(cis-2-aminocyclo-hexylamino)-5-fluoro-2-((2-(4-methoxyphenyl)pyridin-4-yl)amino)nicotinamide |
| Example 2-185 | 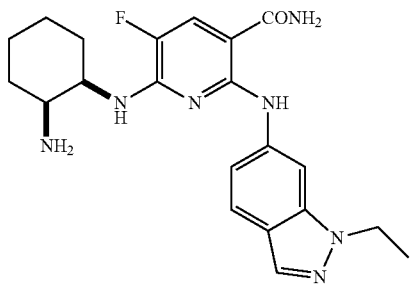 | 6-((cis-2-aminocyclo-hexyl)amino)-2-((1-ethyl-1H-indazol-6-yl)amino)-5-fluoronicotinamide |
| Example 2-186 | 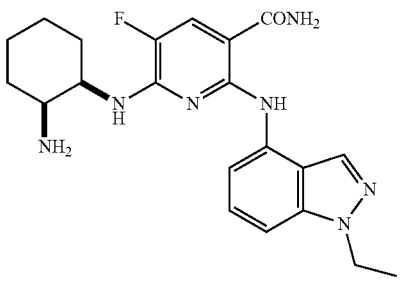 | 6-((cis-2-aminocyclo-hexyl)amino)-2-((1-ethyl-1H-indazol-4-yl)amino)-5-fluoronicotinamide |
| Example 2-187 | 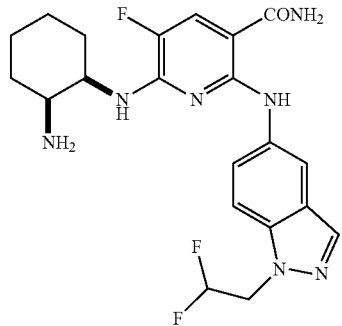 | 6-((cis-2-aminocyclo-hexyl)amino)-2-((1-(2,2-difluoroethyl)-1H-indazol-5-yl)amino)-5-fluoronicotinamide |

TABLE 1-continued

| Example 2-188 | 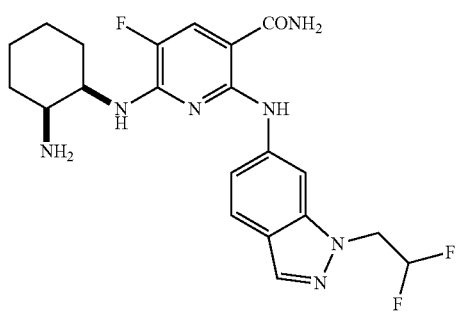 | 6-((cis-2-aminocyclohexyl)amino)-2-((1-(2,2-difluoroethyl)-1H-indazol-6-yl)amino)-5-fluoronicotinamide |
| --- | --- | --- |
| Example 2-189 | 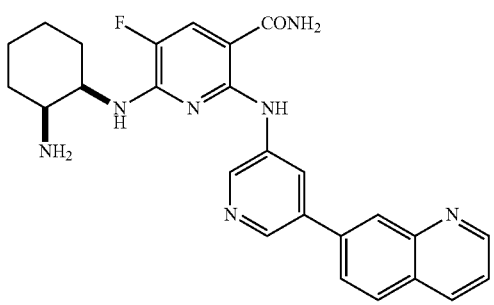 | 6-((cis-2-aminocyclohexyl)amino)-5-fluoro-2-((5-(quinolin-7-yl)pyridin-3-yl)amino)nicotinamide |
| Example 2-190 | 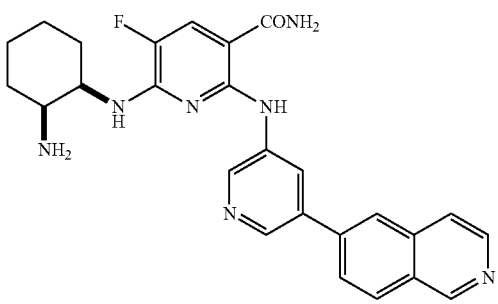 | 6-((cis-2-aminocyclohexyl)amino)-5-fluoro-2-((5-(isoquinolin-6-yl)pyridin-3-yl)amino)nicotinamide |
| Example 2-191 | 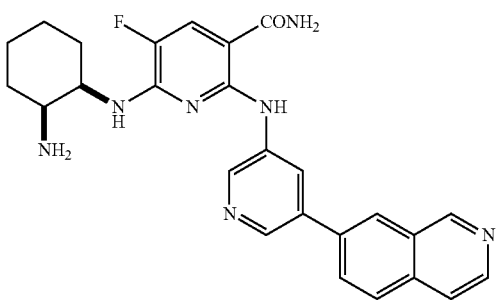 | 6-((cis-2-aminocyclohexyl)amino)-5-fluoro-2-((5-(isoquinolin-7-yl)pyridin-3-yl)amino)nicotinamide |
| Example 2-192 | 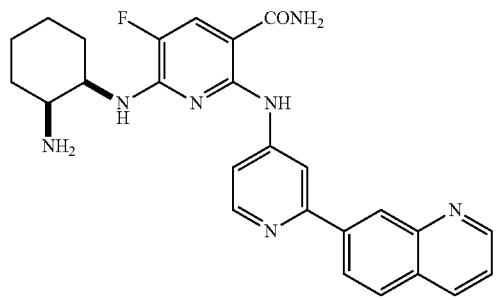 | 6-((cis-2-aminocyclohexyl)amino)-5-fluoro-2-((2-(quinolin-7-yl)pyridin-4-yl)amino)nicotinamide |

TABLE 1-continued

| Example | | |
|---|---|---|
| Example 2-193 | 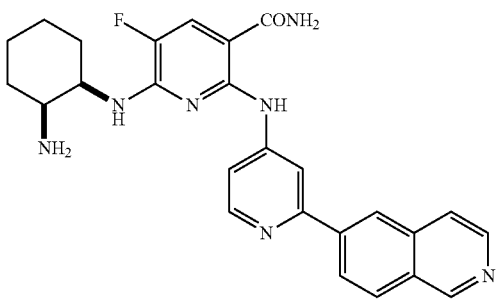 | 6-((cis-2-aminocyclo-hexyl)amino)-5-fluoro-2-((2-(isoquinolin-6-yl)pyridin-4-yl)amino)nicotinamide |
| Example 2-194 | 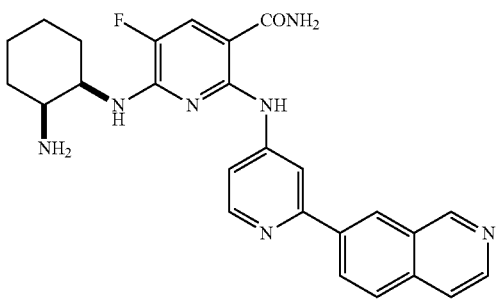 | 6-((cis-2-aminocyclo-hexyl)amino)-5-fluoro-2-((2-(isoquinolin-7-yl)pyridin-4-yl)amino)nicotinamide |
| Example 2-195 | 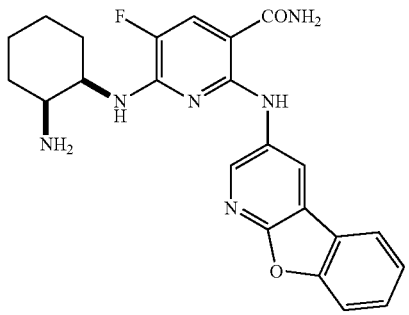 | 6-(((cis)-2-aminocyclo-hexyl)amino)-2-((benzofuro[2,3-b]pyridin-3-yl)amino)-5-fluoronicotinamide |
| Example 2-196 | 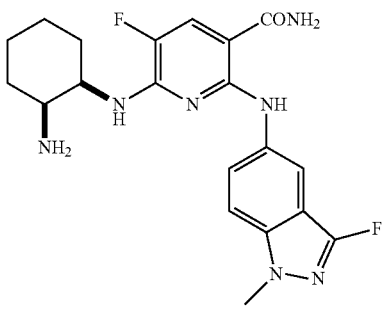 | 6-((cis-2-aminocyclo-hexyl)amino)-5-fluoro-2-((3-fluoro-1-methyl-1H-indazol-5-yl)amino)nicotinamide |
| Example 2-197 | 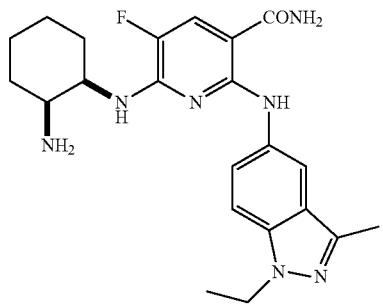 | 6-((cis-2-aminocyclo-hexyl)amino)-2-((1-ethyl-3-fluoro-1H-indazol-5-yl)amino)-5-fluoronicotinamide |

TABLE 1-continued

| | | |
|---|---|---|
| Example 2-198 | 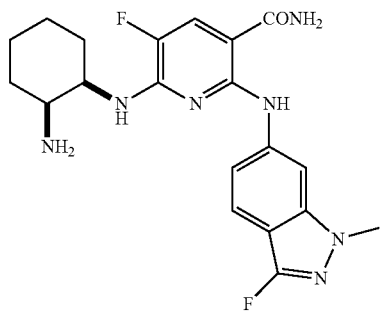 | 6-((cis-2-aminocyclo-hexyl)amino)-5-fluoro-2-((3-fluoro-1-methyl-1H-indazol-6-yl)amino)nicotinamide |
| Example 2-199 | 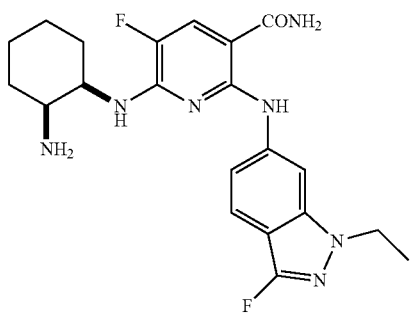 | 6-((cis-2-aminocyclo-hexyl)amino)-2-((1-ethyl-3-fluoro-1H-indazol-6-yl)amino)-5-fluoronicotinamide |
| Example 2-200 | 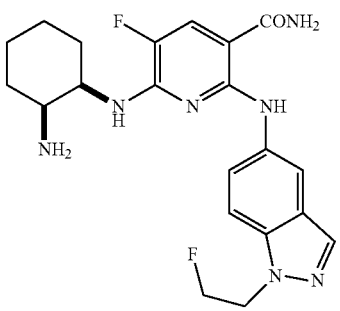 | 6-((cis-2-aminocyclo-hexyl)amino)-5-fluoro-2-((1-(2-fluoroethyl)-1H-indazol-5-yl)amino)nicotinamide |
| Example 2-201 | 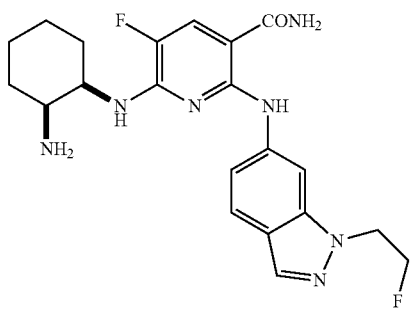 | 6-((cis-2-aminocyclo-hexyl)amino)-5-fluoro-2-((1-(2-fluoroethyl)-1H-indazol-6-yl)amino)nicotinamide |
| Example 2-202 | 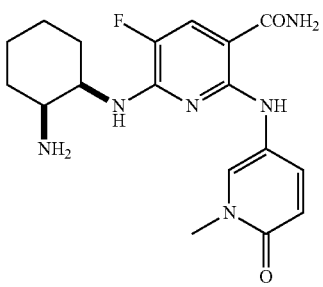 | 6-((cis-2-aminocyclo-hexyl)amino)-5-fluoro-2-((1-methyl-6-oxo-1,6-dihydropyridin-3-yl)amino)nicotinamide |

TABLE 1-continued

| Example 2-203 | 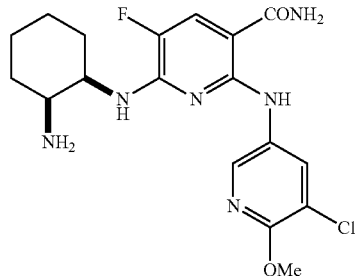 | 6-((cis-2-aminocyclohexyl)amino)-2-((5-chloro-6-methoxypyridin-3-yl)amino)-5-fluoronicotinamide |
| Example 2-204 | 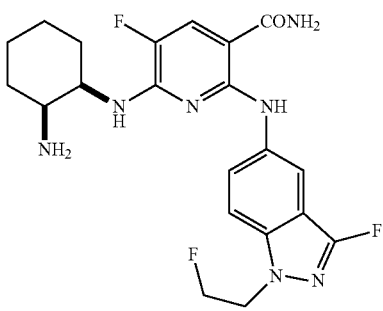 | 6-((cis-2-aminocyclohexyl)amino)-5-fluoro-2-((3-fluoro-1-(2-fluoroethyl)-1H-indazol-5-yl)amino)nicotinamide |
| Example 2-205 | 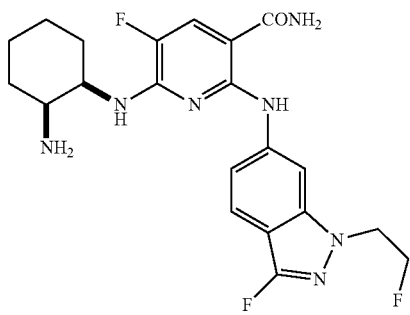 | 6-((cis-2-aminocyclohexyl)amino)-5-fluoro-2-((3-fluoro-1-(2-fluoroethyl)-1H-indazol-6-yl)amino)nicotinamide |
| Example 2-206 | 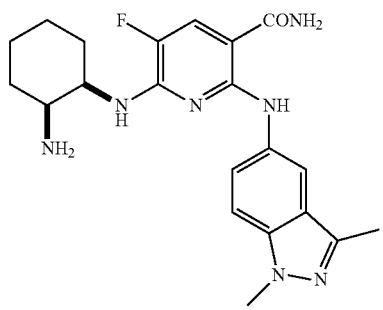 | 6-((cis-2-aminocyclohexyl)amino)-2-((1,3-dimethyl-1H-indazol-5-yl)amino)-5-fluoronicotinamide |
| Example 2-207 | 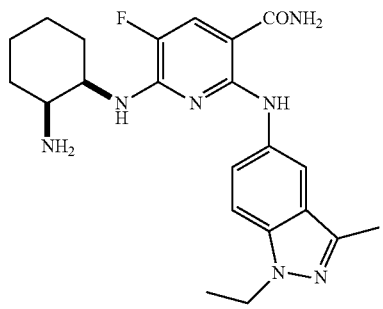 | 6-((cis-2-aminocyclohexyl)amino)-2-((1-ethyl-3-methyl-1H-indazol-5-yl)amino)-5-fluoronicotinamide |

TABLE 1-continued

| Example 2-208 | 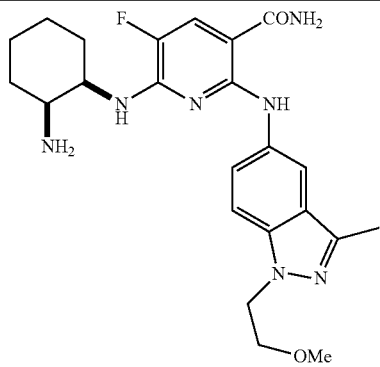 | 6-((cis-2-aminocyclo-hexyl)amino)-5-fluoro-2-((1-(2-methoxyethyl)-3-methyl-1H-indazol-5-yl)amino)nicotinamide |
| Example 2-209 | 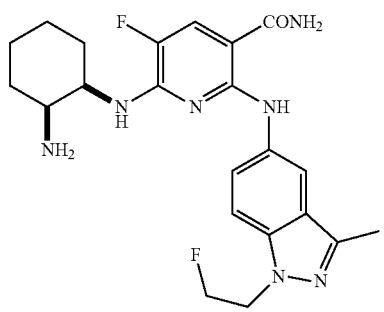 | 6-((cis-2-aminocyclo-hexyl)amino)-5-fluoro-2-((1-(2-fluoroethyl)-3-methyl-1H-indazol-5-yl)amino)nicotinamide |
| Example 2-210 | 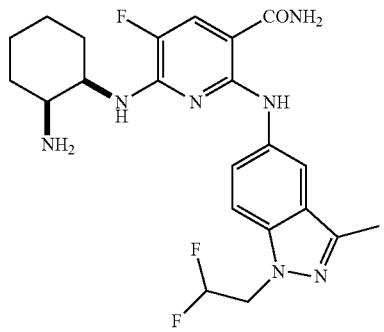 | 6-((cis-2-aminocyclo-hexyl)amino)-2-((1-(2,2-difluoroethyl)-3-methyl-1H-indazol-5-yl)amino)-5-fluoronicotinamide |

| Number | Compound name | $^1$H-NMR | MS (ESI, m/z) |
| --- | --- | --- | --- |
| Example 2-1 HCl salt | 6-(cis-2-aminocyclohexylamino)-5-fluoro-2-((5-phenylpyridin-3-yl)amino)nicotinamide | $^1$H-NMR (DMSO-d$_6$, 400 MHz) δ: 12.14 (s, 1H), 9.09 (s, 1H), 8.74-8.67 (m, 2H), 8.08-7.90 (m, 5H), 7.88-7.83 (m, 2H), 7.62-7.43 (m, 4H), 7.13-7.06 (m, 1H), 4.28-4.17 (m, 1H), 1.87-1.15 (m, 8H). | 421 (M + H) |
| Example 2-2 HCl salt | 6-(cis-2-aminocyclohexylamino)-5-fluoro-2-((imidazo[1,2-a]pyridin-3-yl)amino)nicotinamide | $^1$H-NMR (CD$_3$OD), 300 MHz) δ: 8.47 (d, 1H, J = 6.8 Hz), 8.07-7.98 (m, 3H), 7.88 (d, 1H, J = 11.7 Hz), 7.56-7.46 (m, 1H), 3.58-3.52 (m, 1H), 3.13-3.10 (m, 1H), 1.70-1.06 (m, 8H). | 384 (M + H) |
| Example 2-3 HCl salt | 6-(cis-2-aminocyclohexylamino)-5-fluoro-2-((3-methyl-phenyl)amino)nicotinamide | $^1$H-NMR (DMSO-d$_6$, 400 MHz) δ: 11.53 (s, 1H), 7.95-7.70 (m, 5H), 7.43-7.33 (m, 2H), 7.33-7.13 (m, 2H), 6.84 (d, 1H, J = 5.8 Hz), 6.77 (d, 1H, J = 7.6 Hz), 4.30-4.20 (m, 1H), 3.71-3.62 (m, 1H), 2.30 (s, 3H), 1.95-1.36 (m, 8H). | 358 (M + H) |
| Example 2-4 HCl salt | 6-(cis-2-aminocyclohexylamino)-2-((3,5-dimethylphenyl)amino)-5-fluoronicotinamide | $^1$H-NMR (DMSO-d6, 400 MHz) δ: 11.49 (s, 1H), 8.00-7.65 (m, 5H), 7.30-7.16 (m, 3H), 6.80 (d, 1H, J = 6.8 Hz), 6.59 (s, 1H), 4.34-4.25 (m, 1H), 3.66-3.56 (m, 1H), 2.25 (s, 6H), 1.96-1.85 (m, 2H), 1.72-1.56 (m, 2H), 1.52-1.35 (m, 2H). | 372 (M + H) |
| Example 2-5 HCl salt | 6-(cis-2-aminocyclohexylamino)-5-fluoro-2-((4-(morpholin-4-yl)phenyl)amino)nicotinamide | $^1$H-NMR (DMSO-d$_6$, 400 MHz) δ: 11.60-11.40 (br, 1H), 8.00-7.60 (m, 5H), 7.60-7.46 (m, 2H), 7.40-7.00 (br, 3H), 6.90-6.83 (m, 1H), 4.23-4.13 (m, 1H), 3.90-3.80 (m, 4H), 3.72-3.62 (m, 1H), 3.32-3.10 (m, 4H), 1.96-1.37 (m, 8H). | 429 (M + H) |
| Example 2-6 | 6-(cis-2-aminocyclohexylamino)-5-fluoro-2-((3-methoxy- | $^1$H-NMR (DMSO-d$_6$, 400 MHz) δ: 11.59 (s, 1H), 7.96-7.70 (m, 5H), 7.34-7.15 (m, 3H), | 374 (M + H) |

TABLE 1-continued

| | | | |
|---|---|---|---|
| HCl salt | phenyl)amino)nicotinamide | 7.07-7.03 (m, 1H), 6.89 (d, 1H, J = 6.6 Hz), 6.54 (dd, 1H, J = 2.2, 7.8 Hz), 4.28-4.20 (m, 1H), 3.75 (s, 3H), 3.72-3.63 (m, 1H), 1.95-1.36 (m, 8H). | |
| Example 2-7 HCl salt | 6-(cis-2-aminocyclohexylamino)-5-fluoro-2-((3,4,5-trimethoxy-phenyl)amino)nicotinamide | $^1$H-NMR (DMSO-d$_6$, 400 MHz) δ: 11.43 (s, 1H), 8.00-7.66 (m, 5H), 7.35-7.10 (br, 1H), 6.82 (s, 2H), 6.72 (d, 1H, J = 6.8 Hz), 4.42-4.31 (m, 1H), 3.79 (s, 6H), 3.62 (s, 3H), 3.56-3.45 (m, 1H), 1.95-1.80 (m, 2H), 1.69-1.54 (, 4H), 1.47-1.28 (m, 2H). $^1$H-NMR (DMSO-d$_6$ + D$_2$O, 400 MHz) δ: 7.90 (d, 1H, J = 12.4 Hz), 6.84 (s, 2H), 4.42-4.32 (m, 1H), 3.79 (s, 6H), 3.62 (s, 3H), 3.56-3.46 (m, 1H), 1.90-1.30 (m, 8H). | 434 (M + H) |
| Example 2-8 HCl salt | 6-(cis-2-aminocyclohexylamino)-5-fluoro-2-((2-phenylpyridin-3-yl)amino)nicotinamide | $^1$H-NMR (DMSO-d$_6$, 400 MHz) δ: 11.72 (s, 1H), 9.08 (s, 1H), 8.42-8.37 (m, 1H), 8.03 (brs, 3H), 7.92 (d, 1H, J = 12.3 Hz), 7.84-7.61 (m, 4H), 7.58-7.52 (m, 3H), 7.27 (brs, 1H), 7.02 (d, 1H, J = 5.9 Hz), 4.25-4.16 (m, 1H), 3.10-3.90 (1H, overlapping with H$_2$O), 1.97-1.78 (m, 2H), 1.72-1.57 (m, 4H), 1.51-1.38 (m, 2H). | 421 (M + H), 419 (M − H) |
| Example 2-9 HCl salt | 6-(cis-2-aminocyclohexylamino)-5-fluoro-2-((6-phenylpyridin-3-yl)amino)nicotinamide | $^1$H-NMR (DMSO-d$_6$, 400 MHz) δ: 11.89 (s, 1H), 8.95 (s, 1H), 8.27-8.21 (m, 1H), 8.08-7.85 (m, 8H), 7.54-7.48 (m, 2H), 7.47-7.36 (m, 2H), 6.99 (d, 1H, J = 6.4 Hz), 4.36-4.27 (m, 1H), 3.71-3.64 (m, 1H), 1.96-1.40 (m, 8H). | 421 (M + H), 419 (M − H) |
| Example 2-10 HCl salt | 6-(cis-2-aminocyclohexylamino)-5-fluoro-2-((6-methoxypyridin-3-yl)amino)nicotinamide | $^1$H-NMR (DMSO-d$_6$, 400 MHz) δ: 11.21 (s, 1H), 8.29-8.27 (m, 1H), 7.94-7.66 (m, 6H), 7.24 (brs, 1H), 6.84 (d, 1H, J = 5.8 Hz), 6.82-6.78 (m, 1H), 4.15-4.06 (m, 1H), 3.82 (s, 3H), 3.60-3.54 (m, 1H), 1.91-1.33 (m, 8H). | 375 (M + H), 373 (M − H) |
| Example 2-11 HCl salt | 2-((2-acetylphenyl)amino)-6-(cis-2-aminocyclohexylamino)-5-fluoronicotinamide | $^1$H-NMR (CD$_3$OD, 400 MHz) δ: 8.10-8.05 (m, 1H), 7.89-7.84 (m, 1H), 7.71 (d, 1H, J = 11.7 Hz), 7.52-7.46 (m, 1H), 7.11-7.03 (m, 1H), 4.26-4.17 (m, 1H), 3.78-3.70 (m, 1H), 2.54 (s, 3H), 1.88-1.38 (m, 8H). | 386 (M + H), 384 (M − H) |
| Example 2-12 HCl salt | 6-(cis-2-aminocyclohexylamino)-5-fluoro-2-((4-phenylpyridin-3-yl)amino)nicotinamide | $^1$H-NMR (DMSO-d$_6$, 400 MHz) δ: 11.94 (s, 1H), 9.80 (s, 1H), 8.50 (d, 1H, J = 5.5 Hz), 8.08-7.96 (m, 3H), 7.95 (d, 1H, J = 12.3 Hz), 7.85-7.71 (m, 2H), 7.58-7.51 (m, 5H), 7.33 (brs, 1H), 7.05 (d, 1H, J = 6.2 Hz), 4.37-4.28 (m, 1H), 3.62-3.53 (m, 1H), 1.94-1.37 (m, 8H). | 421 (M + H), 419 (M − H) |
| Example 2-13 HCl salt | 6-(cis-2-aminocyclohexylamino)-5-fluoro-2-((2-methoxypyridin-4-yl)amino)nicotinamide | $^1$H-NMR (DMSO-d$_6$, 400 MHz) δ: 12.51 (s, 1H), 8.16-7.99 (m, 6H), 7.58 (brs, 1H), 7.40 (s, 1H), 7.30 (brs, 1H), 7.14 (d, 1H, J = 6.5 Hz), 4.38-4.26 (m, 1H), 3.99 (s, 3H), 3.67-3.55 (m, 1H), 2.00-1.36 (m, 8H). | 375 (M + H), 373 (M − H) |
| Example 2-14 HCl salt | 6-(cis-2-aminocyclohexylamino)-2-((2,6-dimethoxypyridin-4-yl)amino)-5-fluoronicotinamide | $^1$H-NMR (DMSO-d$_6$, 400 MHz) δ: 11.93 (s, 1H), 8.01-7.85 (m, 5H), 7.38 (brs, 1H), 7.05 (d, 1H, J = 6.0 Hz), 6.59 (s, 2H), 4.25-4.16 (m, 1H), 3.80 (s, 6H), 3.72-3.64 (m, 1H), 1.98-1.35 (m, 8H). | 405 (M + H), 403 (M − H) |
| Example 2-15 HCl salt | 6-(cis-2-aminocyclohexylamino)-5-fluoro-2-((2-morpholin-4-yl)pyridin-4-yl)amino)nicotinamide | $^1$H-NMR (DMSO-d$_6$, 400 MHz) δ: 12.52 (s, 1H), 8.16-7.99 (m, 5H), 7.91 (d, 1H, J = 7.1 Hz), 7.62 (s, 1H), 7.38-7.27 (m, 1H), 7.20 (s, 1H), 7.12-7.03 (m, 1H), 4.39-4.30 (m, 1H), 3.86-3.70 (m, 4H), 3.62-3.50 (m, 5H), 1.98-1.35 (m, 8H). | 430 (M + H), 428 (M − H) |
| Example 2-16 2HCl salt | 6-(cis-2-aminocyclohexylamino)-5-fluoro-2-((2-(4-methylpiperazin-1-yl)pyridin-4-yl)amino)nicotinamide | $^1$H-NMR (D$_2$O, 400 MHz) δ: 7.88 (d, 1H, J = 7.1 Hz), 7.74 (d, 1H, J = 11.5 Hz), 7.57-7.51 (m, 1H), 6.94-6.89 (m, 1H), 4.55-4.46 (m, 1H), 4.19-3.10 (m, 9H), 2.99 (s, 3H), 1.95-1.47 (m, 8H). | 443 (M − H), 441 (M − H) |
| Example 2-17 HCl salt | 6-(cis-2-aminocyclohexylamino)-5-fluoro-2-((2-(pyrrolidin-1-yl)pyridin-4-yl)amino)nicotinamide | $^1$H-NMR (DMSO-d$_6$ + D$_2$O, 400 MHz) δ: 8.00 (d, 1H, J = 11.8 Hz), 7.73 (d, 1H, J = 7.2 Hz), 7.14 (s, 1H), 7.02-6.97 (m, 1H), 4.47-4.41 (m, 1H), 3.56-3.42 (m, 5H), 2.09-2.01 (m, 4H), 1.92-1.40 (m, 8H). | 415 (M + H) |
| Example 2-18 HCl salt | 6-(cis-2-aminocyclohexylamino)-5-fluoro-2-((2-(piperidin-1-yl)pyridin-4-yl)amino)nicotinamide | $^1$H-NMR (DMSO-d$_6$ + D$_2$O, 400 MHz) δ: 8.03-7.96 (m, 1H), 7.81-7.76 (m, 1H), 7.29 (s, 1H), 7.18-7.12 (m, 1H), 4.42-4.35 (m, 1H), 3.59-3.50 (m, 5H), 1.92-1.38 (m, 14H). | 428 (M + H), 426 (M − H) |
| Example 2-19 HCl salt | 6-(cis-2-aminocyclohexylamino)-5-fluoro-2-((6-((2-(pyrrolidin-1-yl)ethyl)amino)pyridin-3-yl)amino)nicotinamide | $^1$H-NMR (DMSO-d$_6$ + D$_2$O, 400 MHz) δ: 8.32 (d, 1H, J = 2.3 Hz), 7.93 (dd, 1H, J = 2.3, 9.3 Hz), 7.90 (d, 1H, J = 12.2 Hz), 6.93 (d, 1H, J = 9.4 Hz), 4.24-4.17 (m, 1H), 3.72-3.65 (m, 2H), 3.60-3.54 (m, 1H), 3.43-3.35 (m, | 457 (M + H) |

TABLE 1-continued

| | | |
|---|---|---|
| Example 2-20 HCl salt | 6-(cis-2-aminocyclohexylamino)-5-fluoro-2-((6-(morpholin-4-yl)pyridin-3-yl)amino)nicotinamide | 2H), 2.60-2.50 (1H, overlapping with H₂O), 2.05-1.92 (m, 4H), 1.88-1.37 (m, 8H). ¹H-NMR (DMSO-d₆ + D₂O, 400 MHz) δ: 8.36 (d, 1H, J = 2.6 Hz), 7.96 (dd, 1H, J = 2.6, 9.4 Hz), 7.88 (d, 1H, J = 12.2 Hz), 7.12 (d, 1H, J = 9.4 Hz), 4.21-4.14 (m, 1H), 3.78-3.72 (m, 4H), 3.60-3.54 (m, 1H), 3.49-3.43 (m, 4H), 1.88-1.38 (m, 8H). 430 (M + H), 428 (M − H) |
| Example 2-21 2HCl salt | 6-(cis-2-aminocyclohexylamino)-5-fluoro-2-((6-(4-methylpiperazin-1-yl)pyridin-3-yl)amino)nicotinamide | ¹H-NMR (DMSO-d₆ + D₂O, 400 MHz) δ: 8.41 (d, 1H, J = 2.7 Hz), 7.94 (dd, 1H, J = 2.7, 9.2 Hz), 7.88 (d, 1H, J = 12.2 Hz), 7.06 (d, 1H, J = 9.2 Hz), 4.36-4.12 (m, 2H), 3.63-3.48 (m, 4H), 3.22-3.06 (m, 4H), 2.86 (s, 3H), 1.89-1.38 (m, 8H). 443 (M + H) |

| Number | Salt | Solvent | NMR | 1HNMR | Mass (M + H) | Mass (M − H) | rt(min) |
|---|---|---|---|---|---|---|---|
| Example 2-22 | HCl | DMSO-d6 | 400 MHz | δ: 14.04 (s, 1H), 12.84 (s, 1H), 8.18-8.12 (m, 1H), 8.09 (d, 1H, J = 12.2 Hz), 8.08-7.86 (m, 3H), 7.80-7.70 (m, 3H), 7.28-7.21 (m, 1H), 4.40-4.30 (m, 1H), 3.67-3.58 (m, 1H), 2.57 (s, 6H), 2.05-1.35 (m, 8H). | 373 | 371 | 8.31 |
| Example 2-23 | HCl | DMSO-d6 | 400 MHz | δ: 12.15 (s, 1H), 9.02-8.90 (m, 1H), 8.51 (s, 1H), 8.02 (d, 1H, J = 12.2 Hz), 8.00-7.87 (m, 4H), 7.58-7.45 (m, 6H), 7.06 (d, 1H, J = 7.1 Hz), 4.15-4.06 (m, 1H), 3.43-3.35 (m, 1H), 2.54 (s, 3H), 1.80-1.10 (m, 8H). | 435 | 433 | 8.45 |
| Example 2-24 | HCl | DMSO-d6 | 400 MHz | δ: 12.02 (s, 1H), 9.02 (s, 1H), 8.24 (s, 1H), 8.02 (d, 1H, J = 12.2 Hz), 8.02-7.90 (m, 4H), 7.48 (s, 1H), 7.04 (d, 1H, J = 6.3 Hz), 4.36-4.28 (m, 1H), 3.60-3.50 (m, 1H), 2.58 (s, 3H), 2.38 (s, 3H), 1.95-1.35 (m, 8H). | 373 | 371 | 10.61 |
| Example 2-25 | free | | | | 384 | 382 | 0.8 |
| Example 2-26 | free | | | | 481 | 479 | 0.68 |
| Example 2-27 | free | | | | 497 | 495 | 0.67 |
| Example 2-28 | free | | | | 438 | 436 | 1.05 |
| Example 2-29 | free | | | | 474 | 472 | 1.12 |
| Example 2-30 | free | | | | 442 | 440 | 0.9 |
| Example 2-31 | free | | | | 500 | 498 | 0.97 |
| Example 2-32 | HCl | | | | 438 | 436 | 0.95 |
| Example 2-33 | HCl | | | | 474 | 472 | 1.05 |
| Example 2-34 | HCl | | | | 442 | 440 | 0.86 |
| Example 2-35 | HCl | | | | 500 | 498 | 0.92 |
| Example 2-36 | free | | | | 474 | 472 | 1.08 |
| Example 2-37 | free | | | | 474 | 472 | 1.02 |
| Example 2-38 | HCl | DMSO-d6 | 300 MHz | δ: 12.12 (s, 1H), 9.18 (s, 1H), 8.35 (s, 1H), 8.25 (s, 1H), 8.06-7.90 (m, 5H), 7.48 (br, 1H), 7.06 (d, 1H, J = 7.2 Hz), 4.40-4.28 (m, 1H), 3.60-3.48 (m, 1H), 2.76 (q, 2H, J = 7.5 Hz), 2.00-1.35 (m, 8H), 1.25 (t, 3H, J = 7.5 Hz). | 373 | 371 | 7.28 |
| Example 2-39 | HCl | DMSO-d6 | 300 MHz | δ: 12.12 (s, 1H), 9.24 (s , 1H), 8.39 (s, 1H), 8.22 (s, 1H), 8.26-7.88 (m, 5H), 7.49 (br, 1H), 7.05 (d, 1H, J = 7.2 Hz), 4.40-4.29 (m, 1H), 3.60-3.46 (m, 1H), 3.15-3.06 (m, 1H), 2.00-1.35 (m, 8H), 1.29 (d, 6H, J = 6.6 Hz). | 387 | 385 | 7.87 |
| Example 2-40 | free | DMSO-d6 | 300 MHz | δ: 11.92 (s, 1H), 8.69 (s, 1H), 8.04-7.86 (m, 5H), 7.43 (br, 1H), 7.24 (s, 1H), 6.99 (d, 1H, J = 6.6 Hz), 4.36-4.24 (m, 1H), 3.60-3.40 (m, 5H), 2.72 (s, 3H), 2.00-1.35 (m, 12H). | 428 | 426 | 7.83 |
| Example 2-41 | free | | | | 398 | 396 | 0.77 |
| Example 2-42 | free | | | | 438 | 436 | 0.98 |
| Example 2-43 | free | | | | 474 | 472 | 1.07 |
| Example 2-44 | free | | | | 442 | 440 | 0.85 |
| Example 2-45 | free | | | | 500 | 498 | 0.93 |
| Example 2-46 | free | | | | 438 | 436 | 0.98 |
| Example 2-47 | free | | | | 474 | 472 | 1.06 |
| Example 2-48 | free | | | | 442 | 440 | 0.88 |
| Example 2-49 | free | | | | 500 | 498 | 0.94 |
| Example 2-50 | HCl | DMSO-d6 | 300 MHz | δ: 12.32 (s, 1H), 8.48 (d, 1H, J = 5.6 Hz), 8.24 (d, 1H, J = 2.0 Hz), 8.03 (d, 1H, J = 12.2 Hz), 8.02-7.80 (m, 4H), 7.62 (dd, 1H, J = 2.0, 5.6 Hz), 7.59-7.46 (m, 1H), 7.04 (d, 1H, J = 6.6 Hz), | 413 | 411 | |

TABLE 1-continued

| | | | | | | | |
|---|---|---|---|---|---|---|---|
| Example 2-51 | HCl | DMSO-d6 | 300 MHz | 4.40-4.29 (m, 1H), 3.63-3.54 (m, 1H), 2.01-1.82 (m, 2H), 1.80-1.32 (m, 6H).<br>δ: 14.35 (br, 1H), 12.89 (s, 1H), 12.31 (s, 1H), 8.39-8.28 (m, 1H), 8.22-8.05 (m, 6H), 7.80-7.65 (m, 1H), 7.35-7.20 (m, 3H), 6.38-6.33 (m, 1H), 4.40-4.26 (m, 1H), 3.70-3.55 (m, 1H), 2.00-1.40 (m, 8H). | 410 | 408 | 0.67 |
| Example 2-52 | HCl | DMSO-d6 | 300 MHz | δ: 13.02 (s, 1H), 8.54 (d, 1H, J = 6.6 Hz), 8.46-8.38 (m, 1H), 8.25-7.60 (m, 12H), 7.34-7.26 (m, 1H), 4.32-4.20 (m, 1H), 3.72-3.59 (m, 1H), 1.95-1.15 (m, 8H). | 421 | 419 | 0.71 |
| Example 2-53 | HCl | DMSO-d6 | 300 MHz | δ: 12.85 (br, 1H), 8.45-8.33 (m, 2H), 8.18-7.96 (m, 6H), 7.76-7.60 (m, 3H), 7.27-7.18 (m, 1H), 6.88-6.82 (m, 1H), 4.47-4.35 (m, 1H), 3.70-3.58 (m, 1H), 2.00-1.35 (m, 8H). | 411 | 409 | 0.67 |
| Example 2-54 | HCl | DMSO-d6 | 300 MHz | δ: 12.54 (s, 1H), 8.25-7.95 (m, 7H), 7.70-7.50 (m, 2H), 7.13 (d, 1H, J = 7.4 Hz), 4.50-4.36 (m, 1H), 4.14-3.92 (m, 2H), 3.70-3.58 (m, 1H), 2.70-2.60 (m, 2H), 2.20-2.05 (m, 2H), 2.00-1.35 (m, 8H). | 428 | 426 | 0.65 |
| Example 2-55 | HCl | DMSO-d6 | 300 MHz | δ: 12.30 (s, 1H), 8.10-7.93 (m, 5H), 7.92-7.83 (m, 1H), 7.53-7.47 (m, 1H), 7.45-7.40 (m, 1H), 7.22 (d, 1H, J = 6.3 Hz), 7.20-7.05 (m, 1H), 5.22-5.11 (m, 1H), 4.29-4.18 (m, 1H), 3.74-3.66 (m, 1H), 2.05-1.35 (m, 8H), 1.35-1.29 (m, 6H). | 403 | 401 | |
| Example 2-56 | 2HCl | DMSO-d6 | 300 MHz | δ: 12.16 (s, 1H), 10.68-10.05 (m, 1H), 8.10-7.92 (m, 6H), 7.55-7.40 (m, 1H), 7.35-7.30 (m, 1H), 7.15-7.05 (m, 1H), 4.69-4.50 (m, 2H), 4.36-4.24 (m, 1H), 3.73-3.63 (m, 1H), 3.62-3.48 (m, 4H), 3.22-3.00 (m, 2H), 2.08-1.37 (m, 12H). | 459 | 457 | |
| Example 2-57 | HCl | DMSO-d6 | 300 MHz | δ: 12.88 (s, 1H), 8.83 (s, 1H), 8.48 (d, 1H, J = 6.6 Hz), 8.25-7.95 (m, 8H), 7.73 (br, 1H), 7.40 (s, 1H), 7.30 (d, 1H, J = 5.7 Hz), 4.40-4.24 (m, 1H), 3.68-3.54 (m, 1H), 2.00-1.30 (m, 8H). | 411 | 409 | 0.68 |
| Example 2-58 | HCl | DMSO-d6 | 300 MHz | δ: 12.62-12.52 (m, 1H), 12.43 (s, 1H), 8.35-8.23 (m, 1H), 8.13-7.96 (m, 4H), 8.05 (d, 1H, J = 12.2 Hz), 7.80-7.73 (m, 1H), 7.68-7.59 (m, 1H), 7.26-7.20 (m, 1H), 7.01 (d, 1H, J = 6.6 Hz), 6.90 (d, 1H, J = 5.9 Hz), 4.50-4.38 (m, 1H), 3.66-3.55 (m, 1H), 2.92 (d, 3H, J = 5.0 Hz), 1.98-1.32 (m, 8H). | 374 | 372 | |
| Example 2-59 | HCl | DMSO-d6 | 300 MHz | δ: 12.58-12.50 (m, 1H), 12.37 (s, 1H), 8.36-8.27 (m, 1H), 8.12-7.98 (m, 4H), 8.04 (d, 1H, J = 12.2 Hz), 7.80-7.71 (m, 1H), 7.67-7.58 (m, 1H), 7.20 (s, 1H), 7.06 (d, 1H, J = 6.6 Hz), 6.96 (d, 1H, J = 5.9 Hz), 4.47-4.35 (m, 1H), 3.63-3.56 (m, 1H), 3.39-3.26 (m, 2H), 2.02-1.36 (m, 8H), 1.21 (t, 3H, J = 7.1 Hz). | 388 | 386 | |
| Example 2-60 | HCl | DMSO-d6 | 300 MHz | δ: 12.54 (s, 1H), 8.16-8.00 (m, 6H), 7.66-7.55 (m, 1H), 7.45 (s, 1H), 7.36-7.25 (m, 1H), 7.22 (d, 1H, J = 6.6 Hz), 4.44-4.25 (m, 3H), 3.67-3.57 (m, 1H), 2.05-1.38 (m, 8H), 1.37 (t, 3H, J = 6.9 Hz). | 389 | 387 | |
| Example 2-61 | HCl | DMSO-d6 | 300 MHz | δ: 11.92 (s, 1H), 8.02-7.80 (m, 4H), 7.96 (d, 1H, J = 12.6 Hz), 7.46-7.32 (m, 1H), 7.17 (d, 1H, J = 5.9 Hz), 6.57 (s, 2H), 4.28-4.17 (m, 1H), 4.23 (q, 4H, J = 6.9 Hz), 3.77-3.66 (m, 1H), 2.00-1.37 (m, 8H), 1.29 (t, 6H, J = 6.9 Hz). | 433 | 431 | |
| Example 2-62 | HCl | DMSO-d6 | 300 MHz | δ: 11.98 (s, 1H), 8.93-8.88 (m, 1H), 8.64-8.61 (m, 1H), 8.42-8.37 (m, 1H), 8.02 (d, 1H, J = 12.3 Hz), 8.00-7.88 (m, 4H), 7.45 (br, 1H), 7.20 (d, 1H, J = 3.0 Hz), 7.04 (d, 1H, J = 6.6 Hz), 6.33 (d, 1H, J = 3.0 Hz), 4.32-4.25 (m, 1H), | 425 | 423 | 0.88 |

TABLE 1-continued

| | | | | | | | |
|---|---|---|---|---|---|---|---|
| Example 2-63 | HCl | DMSO-d6 | 300 MHz | δ: 12.83 (br, 1H), 8.38 (d, 1H, J = 7.2 Hz), 8.20-7.98 (m, 6H), 7.88-7.56 (m, 3H), 7.26-7.16 (m, 1H), 6.49 (d, 1H, J = 2.7 Hz), 4.45-4.33 (m, 1H), 3.65-3.53 (m, 1H), 2.46 (s, 3H), 2.05-1.30 (m, 8H). [preceded by: 3.63-3.43 (m, 1H), 2.40 (s, 3H), 1.95-1.25 (m, 8H).] | 425 | 423 | 0.74 |
| Example 2-64 | HCl | DMSO-d6-D2O | 300 MHz | δ: 8.50 (d, 1H, J = 6.3 Hz), 8.24 (d, 1H, J = 1.7 Hz), 8.05 (d, 1H, J = 7.3 Hz), 7.96 (d, 1H, J = 12.2 Hz), 7.96 (d, 1H, J = 1.7 Hz), 7.36-7.28 (m, 1H), 3.84-3.77 (m, 1H), 3.41-3.30 (m, 1H), 1.84-1.20 (m, 8H). | 384 | 382 | |
| Example 2-65 | HCl | DMSO-d6-D2O | 300 MHz | δ: 8.64-8.00 (m, 2H), 7.95 (d, 1H, J = 12.2 Hz), 7.57-7.42 (m, 4H), 7.24 (d, 1H, J = 1.7 Hz), 4.32-4.22 (m, 1H), 3.96 (s, 3H), 3.71-3.61 (m, 1H), 1.92-1.32 (m, 8H). | 452 | 450 | |
| Example 2-66 | HCl | DMSO-d6-D2O | 300 MHz | δ: 8.01 (d, 1H, J = 6.6 Hz), 7.98 (d, 1H, J = 11.9 Hz), 7.52-7.48 (m, 1H), 7.33-7.25 (m, 1H), 4.46-4.38 (m, 2H), 4.36-4.26 (m, 1H), 3.76-3.69 (m, 2H), 3.71-3.63 (m, 1H), 3.33 (s, 3H), 1.98-1.40 (m, 8H). | 419 | 417 | |
| Example 2-67 | HCl | DMSO-d6 | 300 MHz | δ: 8.06-7.99 (m, 2H), 7.95 (d, 1H, J = 11.9 Hz), 7.56-7.44 (m, 3H), 7.44-7.37 (m, 2H), 4.55-4.43 (m, 2H), 4.30-4.18 (m, 1H), 3.77-3.67 (m, 3H), 3.33 (s, 3H), 1.96-1.33 (m, 8H). | 496 | 494 | |
| Example 2-68 | HCl | DMSO-d6 | 300 MHz | δ: 7.98 (d, 1H, J = 12.2 Hz), 7.92-7.84 (m, 2H), 7.79 (s, 1H), 7.62-7.53 (m, 3H), 6.89 (s, 1H), 4.30-4.20 (m, 1H), 3.82-3.73 (m, 4H), 3.62-3.52 (m, 4H), 3.51-3.44 (m, 1H), 1.87-1.05 (m, 8H). | 507 | 505 | |
| Example 2-69 | HCl | DMSO-d6 | 300 MHz | δ: 12.02 (s, 1H), 9.05 (s, 1H), 8.70 (s, 1H), 8.56 (s, 1H), 8.38 (s, 2H), 8.02 (d, 1H, J = 12.6 Hz), 8.01-7.94 (m, 4H), 7.48 (br, 1H), 7.08 (d, 1H, J = 6.6 Hz), 4.33-4.22 (m, 1H), 3.65-3.50 (m, 1H), 1.90-1.25 (m, 8H). | 411 | 409 | 0.6 |
| Example 2-70 | HCl | DMSO-d6 | 300 MHz | δ: 14.50 (br, 1H), 12.83 (s, 1H), 8.46-8.37 (m, 1H), 8.20-7.86 (m, 9H), 7.71 (s, 1H), 7.34-7.22 (m, 1H), 4.38-4.26 (m, 1H), 3.66-3.54 (m, 1H), 1.95-1.20 (m, 8H). | 411 | 409 | 0.6 |
| Example 2-71 | HCl | DMSO-d6 | 300 MHz | δ: 11.47 (s, 1H), 8.50-8.42 (m, 1H), 7.97-7.70 (m, 6H), 7.30 (br, 1H), 6.85 (d, 1H, J = 6.6 Hz), 4.32-4.21 (m, 1H), 3.78-3.70 (m, 4H), 3.70-3.50 (m, 1H), 3.14-3.06 (m, 4H), 2.30 (s, 3H), 1.95-1.35 (m, 8H). | 444 | 442 | 0.77 |
| Example 2-72 | HCl | DMSO-d6 | 300 MHz | δ: 11.35 (s, 1H), 8.32 (d, 1H, J = 2.7 Hz), 8.27-8.24 (m, 1H), 8.08 (d, 1H, J = 2.7 Hz), 7.92 (d, 1H, J = 12.3 Hz), 7.82-7.70 (m, 5H), 7.26 (br, 1H), 7.09 (d, 1H, J = 1.2 Hz), 6.89 (d, 1H, 5.1 Hz), 4.12-4.00 (m, 1H), 3.73-3.66 (m, 4H), 3.55-3.40 (m, 1H), 3.04-2.90 (m, 4H), 1.85-1.15 (m, 8H). | 496 | 494 | 0.96 |
| Example 2-73 | HCl | DMSO-d6 | 300 MHz | δ: 11.38 (s, 1H), 8.64 (br, 1H), 8.42 (d, 1H, J = 2.0 Hz), 8.10-7.75 (m, 4H), 7.96 (d, 1H, J = 12.6 Hz), 7.92 (dd, 1H, J = 2.0, 9.6 Hz), 7.32 (br, 1H), 7.04 (d, 1H, J = 9.6 Hz), 6.83 (d, 1H, J = 6.6 Hz), 4.37-4.26 (m, 1H), 3.62-3.43 (m, 1H), 2.99 (d, 3H, J = 4.3 Hz), 1.95-1.30 (m, 8H). | 374 | 372 | |
| Example 2-74 | HCl | DMSO-d6 | 300 MHz | δ: 11.38 (s, 1H), 8.52 (s, 1H), 8.05-7.70 (m, 5H), 7.95 (d, 1H, J = 12.6 Hz), 7.45-7.05 (m, 2H), 6.79 (d, 1H, J = 6.6 Hz), 4.39-4.26 (m, 1H), 3.62-3.51 (m, 1H), 3.20 (s, 6H), 1.92-1.31 (m, 8H). | 388 | 386 | |
| Example 2-75 | HCl | DMSO-d6-D2O | 300 MHz | δ: 8.22 (d, 1H, J = 2.3 Hz), 7.98 (dd, 1H, J = 2.3, 9.6 Hz), 7.90 (d, 1H, J = 9.6 Hz), 7.10 (d, 1H, J = 9.6 Hz), 4.24-4.15 (m, 1H), 3.65 (t, 2H, J = | 404 | 402 | |

TABLE 1-continued

| | | | | | | |
|---|---|---|---|---|---|---|
| Example 2-76 | HCl | DMSO-d6-D2O | 300 MHz | δ: 8.22 (d, 1H, J = 2.1 Hz), 7.98 (dd, 1H, J = 2.1, 9.5 Hz), 7.90 (d, 1H, J = 12.2 Hz), 7.08 (d, 1H, J = 9.5 Hz), 4.24-4.14 (m, 1H), 3.61-3.46 (m, 5H), 3.31 (s, 3H), 1.92-1.36 (m, 8H). | 418 | 416 | |
| | | | | 5.3 Hz), 3.59-3.51 (m, 1H), 3.42 (t, 2H, J = 5.3 Hz), 1.90-1.37 (m, 8H). | | | |
| Example 2-77 | HCl | DMSO-d6-D2O | 300 MHz | δ: 8.32 (d, 1H, J = 2.6 Hz), 8.02 (dd, 1H, J = 2.6, 9.7 Hz), 7.90 (d, 1H, J = 12.2 Hz), 7.32 (d, 1H, J = 9.7 Hz), 4.26-4.17 (m, 1H), 3.64-3.45 (m, 5H), 1.90-1.37 (m, 14H). | 429 | 427 | |
| Example 2-78 | HCl | DMSO-d6 | 300 MHz | δ: 11.37 (s, 1H), 8.46 (s, 1H), 8.03-7.70 (m, 5H), 7.95 (d, 1H, J = 12.2 Hz), 7.43-7.23 (m, 1H), 7.13-6.95 (m, 1H), 6.80 (d, 1H, J = 7.3 Hz), 4.36-4.25 (m, 1H), 3.60-3.48 (m, 5H), 2.10-1.97 (m, 4H), 1.93-1.32 (m, 8H). | 414 | 412 | |
| Example 2-79 | HCl | DMSO-d6-D2O | 300 MHz | δ: 8.29 (d, 1H, J = 2.6 Hz), 7.90 (dd, 1H, J = 2.6, 8.8 Hz), 7.86 (d, 1H, J = 12.2 Hz), 6.86 (d, 1H, J = 5.1 Hz), 4.24 (t, 2H, J = 5.1 Hz), 4.18-4.09 (m, 1H), 3.73 (t, 2H, J = 5.1 Hz), 3.64-3.57 (m, 1H), 1.90-1.36 (m, 8H). | 405 | 403 | |
| Example 2-80 | HCl | CD3OD | 300 MHz | δ: 8.48 (d, 1H, J = 2.6 Hz), 8.04 (dd, 1H, J = 2.6, 9.9 Hz), 7.82 (d, 1H, J = 11.9 Hz), 7.39 (d, 1H, J = 9.9 Hz), 4.57-4.47 (m, 1H), 3.89 (t, 4H, J = 5.0 Hz), 3.80-3.75 (m, 1H), 3.70 (t, 4H, J = 5.0 Hz), 3.37 (s, 6H), 1.94-1.52 (m, 8H). | 477 | 475 | |
| Example 2-81 | 2HCl | DMSO-d6-D2O | 300 MHz | δ: 8.29 (d, 1H, J = 2.5 Hz), 7.95 (dd, 1H, J = 2.5, 9.5 Hz), 7.91 (d, 1H, J = 12.2 Hz), 6.98 (d, 1H, J = 9.5 Hz), 4.28-4.18 (m, 1H), 3.95-3.80 (m, 6H), 3.62-3.52 (m, 1H), 3.45-3.37 (m, 2H), 3.35-3.51 (m, 4H), 2.08-1.94 (m, 2H), 1.92-1.34 (m, 8H). | 487 | 485 | |
| Example 2-82 | HCl | DMSO-d6 | 300 MHz | δ: 12.60 (s, 1H), 8.22-8.02 (m, 6H), 7.62 (s, 1H), 7.48 (s, 1H), 7.33 (s, 1H), 7.23 (d, 1H, J = 6.9 Hz), 4.39-4.21 (m, 3H), 3.60-3.50 (m, 1H), 2.05-1.58 (m, 8H), 1.54-1.36 (m, 2H), 1.01 (t, 3H, J = 7.4 Hz). | 403 | 401 | 0.74 |
| Example 2-83 | HCl | DMSO-d6 | 300 MHz | δ: 12.63 (s, 1H), 8.25-8.02 (m, 6H), 7.62 (s, 1H), 7.48 (s, 1H), 7.37 (s, 1H), 7.25 (d, 1H, J = 6.6 Hz), 4.44-4.26 (m, 3H), 3.60-3.50 (m, 1H), 2.05-1.61 (m, 8H), 1.55-1.36 (m, 4H), 0.95 (t, 3H, J = 7.3 Hz). | 417 | 415 | 0.83 |
| Example 2-84 | HCl | DMSO-d6 | 300 MHz | δ: 12.67 (s, 1H), 8.33-8.03 (m, 6H), 7.64 (s, 1H), 7.50 (s, 1H), 7.37 (s, 1H), 7.24 (d, 1H, J = 6.6 Hz), 4.41-4.29 (m, 1H), 4.25-4.05 (m, 2H), 3.60-3.50 (m, 1H), 2.15-1.58 (m, 7H), 1.55-1.35 (m, 2H), 1.04-0.99 (m, 6H). | 417 | 415 | 0.82 |
| Example 2-85 | HCl | DMSO-d6-D2O | 300 MHz | δ: 8.02 (d, 1H, J = 6.6 Hz), 8.00 (d, 1H, J = 11.9 Hz), 7.52 (s, 1H), 7.28 (d, 1H, J = 5.9 Hz), 4.43-4.27 (m, 3H), 3.69-3.59 (m, 1H), 3.59-3.47 (m, 1H), 3.24 (s, 3H), 2.02-1.35 (m, 10H), 1.16 (d, 3H, J = 6.3 Hz). | 447 | 445 | 0.75 |
| Example 2-86 | HCl | DMSO-d6 | 300 MHz | δ: 12.46 (s, 1H), 8.15-7.97 (m, 6H), 7.62-7.12 (m, 9H), 5.46-5.34 (m, 2H) 4.31-4.19 (m, 1H), 3.60-3.50 (m, 1H), 1.92-1.47 (m, 6H), 1.43-1.17 (m, 2H). | 451 | 449 | 0.94 |
| Example 2-87 | free | | | | 429 | 427 | 1.07 |
| Example 2-88 | HCl | | | | 425 | 423 | 1.06 |
| Example 2-89 | HCl | | | | 425 | 423 | 0.69 |
| Example 2-90 | HCl | | | | 469 | 467 | 1.05 |
| Example 2-91 | HCl | | | | 483 | 481 | 1.15 |
| Example 2-92 | HCl | | | | 497 | 495 | 1.19 |
| Example 2-93 | HCl | | | | 527 | 525 | 1.12 |
| Example 2-94 | HCl | DMSO-d6 | 300 MHz | δ: 12.04 (s, 1H), 9.20-9.13 (m, 1H), 8.37-8.16 (m, 1H), 8.20-8.14 (m, 1H), 8.01 (d, 1H, J = 12.6 Hz), 8.00-7.80 (m, 4H), 7.48 (br, 1H), 7.05 (d, 1H, J = 6.6 Hz), 4.36-4.26 (m, 1H), 3.60-3.45 (m, 1H), 3.20-3.02 (m, 1H), 2.16-2.02 (m, 2H), 1.95-1.35 (m, 14H). | 413 | 411 | 0.86 |

TABLE 1-continued

| | | | | | | | |
|---|---|---|---|---|---|---|---|
| Example 2-95 | HCl | DMSO-d6 | 300 MHz | δ: 11.98 (s, 1H), 9.02-8.86 (m, 1H), 8.42-8.38 (m, 1H), 8.31-8.26 (m, 1H), 8.00 (d, 1H, J = 12.0 Hz), 8.00-7.80 (m, 4H), 7.45 (br, 1H), 7.06 (d, 1H, J = 7.2 Hz), 6.50-6.43 (m, 1H), 4.30-4.18 (m, 1H), 3.63-3.43 (m, 1H), 2.50-2.37 (m, 2H), 2.30-2.18 (m, 2H), 1.90-1.35 (m, 12H). | 425 | 423 | 0.9 |
| Example 2-96 | HCl | DMSO-d6 | 300 MHz | δ: 12.01 (s, 1H), 9.10-9.02 (m, 1H), 8.32-8.28 (m, 1H), 8.20-8.09 (m, 1H), 8.00 (d, 1H, J = 11.7 Hz), 8.00-7.78 (m, 4H), 7.46 (br, 1H), 7.04 (d, 1H, J = 7.5 Hz), 4.38-4.26 (m, 1H), 3.60-3.55 (m, 1H), 2.75-2.62 (m, 1H), 1.90-1.15 (m, 18H). | 427 | 425 | 0.88 |
| Example 2-97 | HCl | | | | 469 | 467 | 1 |
| Example 2-98 | HCl | | | | 483 | 481 | 1.1 |
| Example 2-99 | HCl | | | | 497 | 495 | 1.14 |
| Example 2-100 | HCl | | | | 527 | 525 | 1.07 |
| Example 2-101 | HCl | | | | 425 | 423 | 1.02 |
| Example 2-102 | HCl | | | | 469 | 467 | 1.01 |
| Example 2-103 | HCl | | | | 439 | 437 | 1.1 |
| Example 2-104 | HCl | | | | 453 | 451 | 1.21 |
| Example 2-105 | HCl | | | | 467 | 465 | 1.3 |
| Example 2-106 | HCl | | | | 481 | 479 | 1.39 |
| Example 2-107 | HCl | | | | 483 | 481 | 1.09 |
| Example 2-108 | HCl | | | | 511 | 509 | 1.29 |
| Example 2-109 | HCl | | | | 511 | 509 | 1.3 |
| Example 2-110 | HCl | | | | 513 | 511 | 1 |
| Example 2-111 | HCl | | | | 555 | 553 | 1.26 |
| Example 2-112 | HCl | | | | 495 | 493 | 1.07 |
| Example 2-113 | HCl | | | | 522 | 520 | 0.93 |
| Example 2-114 | HCl | DMSO-d6 | 300 MHz | δ: 12.36 (s, 1H), 9.35 (s, 1H), 8.57-8.53 (m, 1H), 8.33 (s, 1H), 8.29-8.24 (m, 1H), 8.80-7.94 (m, 2H), 7.94-7.80 (m, 3H), 7.54 (br, 1H), 7.28-7.21 (m, 1H), 7.09 (d, 1H, J = 6.6 Hz), 4.59-4.45 (m, 1H), 3.73-3.60 (m, 1H), 2.00-1.35 (m, 8H). | 412 | 410 | 0.82 |
| Example 2-115 | HCl | DMSO-d6 | 300 MHz | δ: 11.57 (s, 1H), 8.78 (d, 1H, J = 1.8 Hz), 8.42 (d, 1H, J = 1.8 Hz), 7.95 (d, 1H, J = 12.6 Hz), 7.92 (d, 1H, J = 9.6 Hz), 7.86-7.64 (m, 4H), 7.34 (br, 1H), 6.86 (d, 1H, J = 7.2 Hz), 6.73 (d, 1H, J = 9.6 Hz), 4.30-4.18 (m, 1H), 3.68 (s, 3H), 3.65-3.56 (m, 1H), 1.90-1.35 (m, 8H). | 426 | 424 | 0.8 |
| Example 2-116 | HCl | DMSO-d6 | 300 MHz | δ: 11.58 (s, 1H), 8.79 (d, 1H, J = 1.8 Hz), 8.40 (d, 1H, J = 1.8 Hz), 8.05-7.75 (m, 6H), 7.33 (br, 1H), 6.91 (d, 1H, J = 6.0 Hz), 6.71 (d, 1H, J = 9.3 Hz), 4.58 (t, 2H, J = 6.0 Hz), 4.32-4.16 (m, 1H), 3.61 (t, 2H, J = 6.0 Hz), 3.55-3.40 (m, 1H), 3.27 (s, 3H), 1.95-1.35 (m, 8H). | 470 | 468 | 0.83 |
| Example 2-117 | HCl | DMSO-d6 | 300 MHz | δ: 12.02 (s, 1H), 8.99 (s, 1H), 8.51 (s, 1H), 8.23 (s, 1H), 8.01 (d, 1H, J = 12.6 Hz), 8.00-7.86 (m, 5H), 7.46 (br, 1H), 7.09-7.03 (m, 2H), 4.28-4.16 (m, 1H), 3.50-3.30 (m, 1H), 2.69 (s, 3H), 1.85-1.25 (m, 8H),. | 425 | 423 | 0.74 |
| Example 2-118 | HCl | DMSO-d6 | 300 MHz | δ: 11.89 (s, 1H), 9.08-9.01 (m, 1H), 8.04-7.78 (m, 6H), 7.44 (br, 1H), 7.01 (d, 1H, J = 7.5 Hz), 4.36-4.24 (m, 1H), 3.60-3.45 (m, 1H), 2.71 (s, 3H), 2.10-1.98 (m, 1H), 1.95-1.35 (m, 8H), 1.10-1.00 (m, 2H), 0.92-0.80 (m, 2H). | 399 | 397 | 0.69 |
| Example 2-119 | HCl | | | | 456 | 454 | 1.05 |
| Example 2-120 | HCl | | | | 484 | 482 | 1.21 |
| Example 2-121 | HCl | | | | 544 | 542 | 1.36 |
| Example 2-122 | HCl | | | | 467 | 465 | 1.12 |
| Example 2-123 | HCl | | | | 424 | 422 | 0.91 |
| Example 2-124 | HCl | | | | 452 | 450 | 1.12 |
| Example 2-125 | HCl | | | | 412 | 410 | 0.91 |
| Example 2-126 | HCl | | | | 426 | 424 | 0.98 |
| Example 2-127 | HCl | DMSO-d6-D2O | 300 MHz | δ: 8.40 (d, 1H, J = 2.6 Hz), 8.03 (dd, 1H, J = 2.6, 9.6 Hz), 7.91 (d, 1H, J = 12.2 Hz), 7.27 (d, 1H, J = 9.6 Hz), 4.29-4.18 (m, 1H), 4.06-3.95 (m, 2H), 3.76-3.62 (m, 2H), 3.60-3.50 (m, 1H), | 458 | 456 | 0.76 |

TABLE 1-continued

| | | | | | | | |
|---|---|---|---|---|---|---|---|
| | | | | 2.74-2.62 (m, 2H), 1.92-1.36 (m, 8H), 1.19 (d, 6H, J = 5.9 Hz). | | | |
| Example 2-128 | HCl | | | | 384 | 382 | 0.46 |
| Example 2-129 | HCl | | | | 401 | 399 | 0.55 |
| Example 2-130 | HCl | | | | 401 | 399 | 0.58 |
| Example 2-131 | HCl | DMSO-d6 | 300 MHz | δ: 12.94 (br, 1H), 8.62-8.55 (m, 1H), 8.40-8.28 (m, 1H), 8.20-8.02 (m, 2H), 8.00-7.62 (m, 7H), 7.58-7.42 (m, 2H), 7.34-7.24 (m, 1H), 4.22-4.10 (m, 1H), 3.60-3.40 (m, 1H), 1.90-1.15 (m, 8H). | 439 | 437 | 0.69 |
| Example 2-132 | HCl | DMSO-d6 | 300 MHz | δ: 13.08 (s, 1H), 8.52 (d, 1H, J = 5.4 Hz), 8.46-8.34 (m, 1H), 8.24-8.12 (m, 1H), 8.10 (d, 1H, J = 12.6 Hz), 8.00-7.86 (m, 3H), 7.82-7.70 (m, 2H), 7.70-7.60 (m, 2H), 7.40-7.25 (m, 2H), 7.25-7.16 (m, 1H), 4.14-4.00 (m, 1H), 3.86 (s, 3H), 3.60-3.40 (m, 1H), 1.90-1.00 (m, 8H). | 451 | 449 | 0.7 |
| Example 2-133 | HCl | DMSO-d6 | 300 MHz | δ: 12.84 (br, 1H), 8.57 (d, 1H, J = 6.6 Hz), 8.28-8.16 (m, 1H), 8.16-8.06 (m, 1H), 8.07 (d, 1H, J = 12.6 Hz), 8.00-7.50 (m, 7H), 7.42-7.32 (m, 1H), 7.30-7.21 (m, 1H), 4.25-4.13 (m, 1H), 3.60-3.48 (m, 1H), 1.90-1.15 (m, 8H). | 457 | 455 | 0.73 |
| Example 2-134 | HCl | DMSO-d6 | 300 MHz | δ: 11.95 (s, 1H), 8.65 (d, 1H, J = 2.4 Hz), 8.54 (d, 1H, J = 2.4 Hz), 8.22 (s, 2H), 7.98 (d, 1H, J = 12.6 Hz), 7.94-7.64 (m, 4H), 7.40 (br, 1H), 6.96 (d, 1H, J = 6.6 Hz), 4.24-4.12 (m, 1H), 3.60-3.48 (m, 1H), 2.48 (s, 3H), 1.85-1.15 (m, 8H). | 426 | 424 | 0.85 |
| Example 2-135 | HCl | DMSO-d6 | 300 MHz | δ: 12.00 (s, 1H), 8.62 (d, 1H, J = 2.7 Hz), 8.53 (d, 1H, J = 2.7 Hz), 8.26 (d, 1H, J = 1.8 Hz), 7.98 (d, 1H, J = 12.0 Hz), 7.96-7.76 (m, 5H), 7.41 (br, 1H), 7.03 (d, 1H, J = 6.6 Hz), 6.60-6.57 (m, 1H), 4.18-4.06 (m, 1H), 3.60-3.46 (m, 1H), 2.43 (s, 3H), 1.85-1.10 (m, 8H). | 425 | 423 | 0.81 |
| Example 2-136 | HCl | DMSO-d6 | 300 MHz | δ: 14.09 (br, 1H), 13.03 (s, 1H), 8.46 (d, 1H, J = 6.6 Hz), 8.39-8.30 (m, 1H), 8.20-8.12 (m, 1H), 8.09 (d, 1H, J = 12.0 Hz), 7.90-7.68 (m, 5H), 7.62 (d, 1H, J = 10.4 Hz), 7.33 (d, 1H, J = 7.2 Hz), 6.84-6.75 (m, 2H), 4.14-4.02 (m, 1H), 3.88 (s, 3H), 3.87 (s, 3H), 3.56-3.40 (m, 1H), 1.90-1.40 (m, 5H), 1.25-1.00 (m, 3H). | 481 | 479 | 0.78 |
| Example 2-137 | HCl | DMSO-d6 | 300 MHz | δ: 12.03 (s, 1H), 9.45 (s, 1H), 8.81-8.77 (m, 1H), 8.71 (d, 1H, J = 2.7 Hz), 8.68 (d, 1H, J = 21 Hz), 8.35 (s, 1H), 8.01 (d, 1H, J = 12.6 Hz), 8.00-7.80 (m, 4H), 7.50-7.36 (m, 1H), 7.05 (d, 1H, J = 7.2 Hz), 4.40-4.24 (m, 1H), 3.62-3.50 (m, 1H), 1.90-1.25 (m, 8H). | 412 | 410 | 0.73 |
| Example 2-138 | HCl | DMSO-d6 | 300 MHz | δ: 11.95 (s, 1H), 9.05 (s, 1H), 8.61 (d, 1H, J = 1.8 Hz), 8.45 (d, 1H, J = 1.8 Hz), 8.31 (s, 1H), 7.98 (d, 1H, J = 12.6 Hz), 7.87 (br, 1H), 7.82-7.66 (m, 3H), 7.41 (br, 1H), 7.00 (d, 1H, J = 6.6 Hz), 4.20-4.04 (m, 1H), 3.65-3.50 (m, 1H), 2.35 (s, 3H), 1.80-1.05 (m, 8H). | 426 | 424 | 0.73 |
| Example 2-139 | HCl | DMSO-d6 | 300 MHz | δ: 12.96 (s, 1H), 8.57 (d, 1H, J = 6.6 Hz), 8.36 (s, 1H), 8.14 (s, 1H), 8.08 (d, 1H, J = 12.0 Hz), 8.00-7.80 (m, 3H), 7.80-7.64 (m, 2H), 7.48-7.22 (m, 4H), 4.20-4.08 (m, 1H), 3.93 (s, 3H), 3.60-3.46 (m, 1H), 1.90-1.10 (m, 8H). | 469 | 467 | 0.73 |
| Example 2-140 | HCl | DMSO-d6 | 300 MHz | δ: 12.99 (br, 1H), 8.54 (d, 1H, J = 6.6 Hz), 8.34-8.24 (m, 1H), 8.20-8.13 (m, 1H), 8.00 (d, 1H, J = 12.0 Hz), 8.05-7.90 (m, 3H), 7.84-7.64 (m, 3H), 7.31 (d, 1H, J = 5.7 Hz), 7.20-7.10 (m, 1H), 7.10-7.02 (m, 1H), 4.23-4.10 (m, 1H), 3.88 (s, 3H), 3.60-3.46 (m, 1H), 1.90-1.15 (m, 8H). | 469 | 467 | 0.76 |
| Example 2-141 | HCl | DMSO-d6 | 300 MHz | δ: 12.97 (s, 1H), 8.58 (d, 1H, J = 6.6 Hz), 8.40-8.28 (m, 1H), 8.20-8.10 (m, 1H), 8.09 (d, 1H, J = 11.7 Hz), 8.00-7.65 (m, 5H), 7.50-7.37 (m, 2H), 7.36-7.10 (m, 2H), 4.22-4.10 (m, 1H), 3.83 | 469 | 467 | 0.74 |

TABLE 1-continued

| | | | | | | | |
|---|---|---|---|---|---|---|---|
| | | | | (s, 3H), 3.60-3.46 (m, 1H), 1.90-1.10 (m, 8H). | | | |
| Example 2-142 | HCl | DMSO-d6 | 300 MHz | δ: 11.74 (s, 1H), 8.90-8.70 (m, 1H), 8.20-8.04 (m, 1H), 7.97 (d, 1H, J = 12.0 Hz), 7.95-7.75 (m, 4H), 7.46-7.30 (m, 2H), 7.00-6.92 (m, 1H), 4.30-4.18 (m, 1H), 3.66-3.50 (m, 1H), 2.28-2.12 (m, 1H), 1.90-1.40 (m, 8H), 1.16-0.92 (m, 4H). | 385 | 383 | 0.67 |
| Example 2-143 | HCl | | | | 461 | 459 | 0.93 |
| Example 2-144 | HCl | DMSO-d6 | 300 MHz | δ: 12.87 (br, 1H), 8.60 (d, 1H, J = 6.6 Hz), 8.30-8.23 (m, 1H), 8.18-8.04 (m, 1H), 8.08 (d, 1H, J = 12.0 Hz), 8.00-7.76 (m, 4H), 7.76-7.60 (m, 3H), 7.51-7.40 (m, 1H), 7.28 (d, 1H, J = 5.4 Hz), 4.24-4.12 (m, 1H), 3.56-3.48 (m, 1H), 1.90-1.15 (m, 8H). | 457 | 455 | 0.75 |
| Example 2-145 | HCl | DMSO-d6 | 300 MHz | δ: 12.90 (s, 1H), 8.60 (d, 1H, J = 6.6 Hz), 8.32-8.20 (m, 1H), 8.17-8.07 (m, 1H), 8.08 (d, 1H, J = 12.0 Hz), 8.00-7.75 (m, 5H), 7.75-7.65 (m, 1H), 7.60-7.50 (m, 2H), 7.29 (d, 1H, J = 6.6 Hz), 4.24-4.14 (m, 1H), 3.56-3.48 (m, 1H), 1.90-1.15 (m, 8H). | 457 | 455 | 0.73 |
| Example 2-146 | HCl | DMSO-d6 | 300 MHz | δ: 12.84 (br, 1H), 8.59 (d, 1H, J = 6.6 Hz), 8.33-8.23 (m, 1H), 8.15-8.05 (m, 1H), 8.08 (d, 1H, J = 11.7 Hz), 8.02-7.88 (m, 3H), 7.88-7.60 (m, 4H), 7.51-7.43 (m, 1H), 7.30-7.20 (m, 1H), 4.25-4.14 (m, 1H), 3.56-3.40 (m, 1H), 1.90-1.15 (m, 8H). | 475<br>473 | 473<br>471 | 0.8 |
| Example 2-147 | HCl | DMSO-d6 | 300 MHz | δ: 12.82 (br, 1H), 8.58 (d, 1H, 6.6 Hz), 8.30-8.20 (m, 1H), 8.15-8.00 (m, 2H), 8.00-7.62 (m, 7H), 7.60-7.50 (m, 1H), 7.25 (d, 1H, J = 6.0 Hz), 4.28-4.14 (m, 1H), 4.56-4.40 (m, 1H), 1.90-1.20 (m, 8H). | 475<br>473 | 473<br>471 | 0.79 |
| Example 2-148 | HCl | DMSO-d6 | 300 MHz | δ: 11.45 (s, 1H), 8.20-8.15 (m, 2H), 8.02 (d, 1H, J = 12.6 Hz), 7.80-7.66 (m, 4H), 7.62-7.56 (m, 2H), 7.50-7.42 (m, 2H), 7.40-7.33 (m, 1H), 7.26 (br, 1H), 6.86 (d, 1H, J = 6.0 Hz), 4.20-3.92 (m, 1H), 3.86 (s, 3H), 3.46-3.35 (m, 1H), 1.74-1.34 (m, 5H), 1.19-0.92 (m, 3H). | 451 | 449 | 1.13 |
| Example 2-149 | HCl | DMSO-d6 | 300 MHz | δ: 11.52 (s, 1H), 8.22 (d, 1H, J = 2.7 Hz), 8.16 (d, 1H, J = 2.7 Hz), 7.93 (d, 1H, J = 12.3 Hz), 7.93-7.70 (m, 4H), 7.51-7.41 (m, 2H), 7.34-7.24 (m, 3H), 6.92 (d, 1H, J = 6.6 Hz), 4.04-3.92 (m, 1H), 3.82 (s, 3H), 3.46-3.36 (m, 1H), 1.80-1.30 (m, 5H), 1.20-0.90 (m, 3H). | 469 | 467 | 1.11 |
| Example 2-150 | HCl | DMSO-d6 | 300 MHz | δ: 11.37 (s, 1H), 8.44 (d, 1H, J = 2.7 Hz), 8.08 (d, 1H, J = 2.7 Hz), 8.00-7.78 (m, 6H), 7.27 (br, 1H), 7.02 (d, 1H, J = 3.3 Hz), 6.87 (d, 1H, J = 6.0 Hz), 6.65 (dd, 1H, J = 1.5, 3.3 Hz), 4.22-4.06 (m, 1H), 3.97 (s, 3H), 3.60-3.44 (m, 1H), 2.00-1.20 (m, 8H). | 441 | 439 | 1.09 |
| Example 2-151 | HCl | DMSO-d6 | 300 MHz | δ: 11.16 (s, 1H), 8.22-8.19 (m, 1H), 8.20-8.16 (m, 2H), 7.91 (d, 1H, J = 12.6 Hz), 7.82-7.64 (m, 5H), 7.23 (br, 1H), 7.16-7.12 (m, 1H), 6.84 (d, 1H, J = 6.0 Hz), 4.12-4.00 (m, 1H), 3.96 (s, 3H), 3.56-3.40 (m, 1H), 1.82-1.15 (m, 8H). | 441 | 439 | 1.05 |
| Example 2-152 | HCl | DMSO-d6 | 300 MHz | δ: 11.18 (s, 1H), 8.12 (d, 1H, J = 2.4 Hz), 8.00-7.84 (m, 4H), 7.78-7.60 (m, 1H), 7.25 (br, 1H), 6.83 (d, 1H, J = 6.0 Hz), 4.22-4.08 (m, 1H), 3.85 (s, 3H), 3.62-3.50 (m, 1H), 2.16 (s, 3H), 1.95-1.78 (m, 2H), 1.70-1.50 (m, 4H), 1.50-1.30 (m, 2H). | 389 | 387 | 0.95 |
| Example 2-153 | HCl | DMSO-d6 | 300 MHz | δ: 11.08 (s, 1H), 8.14 (d, 1H, J = 2.7 Hz), 7.96-7.60 (m, 4H), 7.30 (d, 1H, J = 2.7 Hz), 7.30-7.10 (m, 1H), 6.81 (d, 1H, J = 6.6 Hz), 4.22-4.04 (m, 1H), 3.87 (s, 3H), 3.58-3.44 (m, 1H), 2.05-1.94 (m, 1H), 1.92-1.76 (m, 2H), 1.70- | 415 | 413 | 1.03 |

TABLE 1-continued

| | | | | | | | |
|---|---|---|---|---|---|---|---|
| | | | | | 1.52 (m, 4H), 1.50-1.30 (m, 2H), 0.96-0.80 (m, 3H), 0.80-0.60 (m, 2H). | | | |
| Example 2-154 | HCl | DMSO-d6 | 300 MHz | δ: 11.56 (s, 1H), 8.69 (d, 1H, J = 2.1 Hz), 8.39 (d, 1H, J = 2.7 Hz), 8.11 (d, 1H, J = 2.7 Hz), 7.93 (d, 1H, J = 12.0 Hz), 7.79 (d, 1H, J = 2.1 Hz), 7.80-7.60 (m, 4H), 7.31 (br, 1H), 6.89 (d, 1H, J = 7.2 Hz), 6.57-6.53 (m, 1H), 4.26-4.15 (m, 1H), 3.98 (s, 3H), 3.58-3.42 (m, 1H), 1.80-1.20 (m, 8H). | 441 | 439 | 1 |
| Example 2-155 | HCl | DMSO-d6 | 300 MHz | δ: 11.59 (s, 1H), 8.52 (d, 1H, J = 2.4 Hz), 8.28 (d, 1H, J = 2.4 Hz), 8.13 (s, 2H), 7.94 (d, 1H, J = 12.3 Hz), 7.88-7.67 (m, 4H), 7.31 (br, 1H), 6.91 (d, 1H, J = 6.6 Hz), 4.17-4.05 (m, 1H), 3.89 (s, 3H), 3.51-3.41 (m, 1H), 1.82-1.13 (m, 8H). | 442 | 440 | 0.88 |
| Example 2-156 | HCl | DMSO-d6-D2O | 300 MHz | δ: 8.54 (d, 1H, J = 2.3 Hz), 8.19 (d, 1H, J = 9.2 Hz), 8.08 (dd, 1H, J = 2.6, 9.2 Hz), 7.88 (d, 1H, J = 12.2 Hz) 4.27-4.17 (m, 1H), 4.01-3.93 (m, 2H), 3.69-3.61 (m, 1H), 2.60-2.52 (m, 2H), 2.15-2.00 (m, 2H), 1.93-1.35 (m, 8H). | 428 | 426 | 0.83 |
| Example 2-157 | HCl | DMSO-d6-D2O | 300 MHz | δ: 8.63 (d, 1H, J = 2.6 Hz), 8.07 (dd, 1H, J = 2.8, 8.8 Hz), 7.90 (d, 1H, J = 12.2 Hz), 7.50 (d, 1H, J = 8.9 Hz), 4.30-4.20 (m, 1H), 3.82-3.75 (m, 2H), 3.78-3.70 (m, 2H), 3.69-3.62 (m, 1H), 2.45 (t, 2H, J = 6.3 Hz), 1.95-1.38 (m, 10H). | 442 | 440 | 0.82 |
| Example 2-158 | HCl | DMSO-d6-D2O | 300 MHz | δ: 8.88 (d, 1H, J = 2.6 Hz), 8.25 (dd, 1H, J = 2.6, 8.6 Hz), 7.93 (d, 1H, J = 12.2 Hz), 7.47 (d, 1H, J = 8.6 Hz), 7.15-7.03 (m, 2H), 6.97-6.90 (m, 1H), 6.36 (dd, 1H, J = 1.3, 8.3 Hz), 4.81 (s, 2H), 4.33-4.22 (m, 1H), 3.73-3.63 (m, 1H), 1.93-1.35 (m, 8H). | 493 | 491 | 0.99 |
| Example 2-159 | HCl | DMSO-d6-D2O | 300 MHz | δ: 8.84 (d, 1H, J = 2.6 Hz), 8.24 (dd, 1H, J = 2.6, 8.6 Hz), 7.93 (d, 1H, J = 11.9 Hz), 7.84 (dd, 1H, J = 1.3, 4.6 Hz), 7.51 (dd, 1H, J = 1.5, 8.1 Hz) 7.39 (d, 1H, J = 8.9 Hz), 7.12 (dd, 1H, J = 4.6, 7.9 Hz), 4.33-4.23 (m, 1H), 3.71-3.62 (m, 1H), 1.92-1.36 (m, 8H), 1.56 (s, 6H). | 521 | 519 | 0.97 |
| Example 2-160 | HCl | DMSO-d6 | 300 MHz | δ: 11.70 (s, 1H), 8.60 (d, 1H, J = 2.7 Hz), 8.53 (d, 1H, J = 2.7 Hz), 8.27 (dd, 1H, J = 2.7, 5.7 Hz), 7.96 (d, 1H, J = 12.6 Hz), 7.90-7.74 (m, 6H), 7.35 (br, 1H), 6.94 (d, 1H, J = 5.7 Hz), 6.57-6.54 (m, 1H), 4.30-4.20 (m, 1H), 3.72-3.60 (m, 1H), 1.94-1.40 (m, 8H). | 411 | 409 | 0.93 |
| Example 2-161 | HCl | DMSO-d6 | 300 MHz | δ: 11.88 (s, 1H), 8.78 (d, 1H, J = 2.4 Hz), 8.28 (dd, 1H, J = 2.4, 8.7 Hz), 8.13 (s, 2H), 7.99 (d, 1H, J = 12.0 Hz), 7.94 (d, 1H, J = 8.7 Hz), 7.90-7.75 (m, 4H), 7.41 (br, 1H), 6.95 (d, 1H, J = 6.6 Hz), 4.36-4.24 (m, 1H), 3.72-3.60 (m, 1H), 1.94-1.40 (m, 8H). | 412 | 410 | 0.84 |
| Example 2-162 | HCl | DMSO-d6-D2O | 300 MHz | δ: 8.64 (d, 1H, J = 2.6 Hz), 8.11 (dd, 1H, J = 2.6, 8.9 Hz), 7.90 (d, 1H, J = 12.2 Hz), 7.76 (d, 1H, J = 8.9 Hz), 4.27-4.20 (m, 1H), 4.26 (s, 2H), 4.02-3.95 (m, 2H), 3.94-3.86 (m, 2H), 3.70-3.62 (m, 1H), 1.94-1.39 (m, 8H). | 444 | 442 | 0.76 |
| Example 2-163 | HCl | DMSO-d6-D2O | 300 MHz | δ: 8.68 (dd, 1H, J = 6.9, 6.9 Hz), 8.35 (d, 1H, J = 6.9 Hz), 8.05 (d, 1H, J = 11.9 Hz), 4.39-4.29 (m, 1H), 3.74-3.66 (m, 1H), 2.57 (d, 3H, J = 2.6 Hz), 1.98-1.42 (m, 8H). | 377 | 375 | 0.61 |
| Example 2-164 | HCl | DMSO-d6-D2O | 300 MHz | δ: 8.62 (d, 1H, J = 7.3 Hz), 8.61 (d, 1H, J = 5.0 Hz), 8.05 (d, 1H, J = 11.9 Hz), 4.46-4.36 (m, 1H), 3.72-3.63 (m, 1H), 2.59 (s, 3H), 2.03-1.40 (m, 8H). | 377 | 375 | 0.62 |
| Example 2-165 | HCl | DMSO-d6-D2O | 300 MHz | δ: 8.10 (dd, 1H, J = 5.6, 5.9 Hz), 7.96 (d, 1H, J = 12.2 Hz), 7.90 (d, 1H, J = 5.9 Hz), 4.33-4.24 (m, 1H), 3.79-3.72 (m, 4H), 3.76-3.68 (m, 1H), 3.41-3.33 (m, 4H), 1.98-1.42 (m, 8H). | 448 | 446 | 0.78 |

TABLE 1-continued

| Example | Salt | Solvent | Freq | NMR | | | |
|---|---|---|---|---|---|---|---|
| Example 2-166 | HCl | DMSO-d6-D2O | 300 MHz | δ: 8.06 (d, 1H, J = 3.3 Hz), 8.00 (d, 1H, J = 11.9 Hz), 7.86 (d, 1H, J = 5.9 Hz), 4.51-4.43 (m, 1H), 3.80-3.72 (m, 4H), 3.54-3.45 (m, 1H), 3.44-3.36 (m, 4H), 1.96-1.33 (m, 8H). | 448 | 446 | 0.72 |
| Example 2-167 | HCl | DMSO-d6-D2O | 300 MHz | δ: 8.70 (dd, 1H, J = 6.3, 6.6 Hz), 8.45 (d, 1H, J = 6.3 Hz), 8.04 (d, 1H, J = 11.9 Hz), 7.87-7.78 (m, 2H), 7.68-7.60 (m, 3H), 4.44-4.33 (m, 1H), 3.79-3.70 (m, 1H), 2.02-1.44 (m, 8H). | 439 | 437 | 0.89 |
| Example 2-168 | HCl | DMSO-d6-D2O | 300 MHz | δ: 9.00 (d, 1H, J = 6.9 Hz), 8.65 (d, 1H, J = 4.0 Hz), 8.04 (d, 1H, J = 11.9 Hz), 7.93-7.86 (m, 2H), 7.68-7.54 (m, 3H), 4.33-4.22 (m, 1H), 3.53-3.44 (m, 1H), 1.85-0.83 (m, 8H). | 439 | 437 | 0.85 |
| Example 2-169 | HCl | DMSO-d6 | 300 MHz | δ: 12.74 (br, 1H), 9.34-9.30 (m, 1H), 8.64-8.56 (m, 1H), 8.14-8.02 (m, 4H), 7.90-7.80 (m, 3H), 7.74-7.58 (m, 4H), 7.18-7.10 (m, 1H), 4.32-4.24 (m, 1H), 3.60-3.45 (m, 1H), 2.00-1.10 (m, 8H). | 422 | 420 | 0.73 |
| Example 2-170 | HCl | DMSO-d6 | 300 MHz | δ: 11.96 (s, 1H), 8.95 (s, 1H), 8.65-8.55 (m, 2H), 8.00 (d, 1H, J = 12.6 Hz), 7.96-7.75 (m, 4H), 7.50-7.32 (m 3H), 7.17-7.00 (m, 2H), 4.23-4.12 (m, 1H), 3.87 (s, 3H), 3.82 (s, 3H), 3.6-3.46 (m, 1H), 1.85-1.15 (m, 8H). | 481 | 479 | 0.78 |
| Example 2-171 | HCl | DMSO-d6 | 300 MHz | δ: 11.93 (s, 1H), 8.96 (s, 1H), 8.64 (s, 2H), 8.00 (d, 1H, J = 12.6 Hz), 8.00-7.75 (m, 4H), 7.42 (br, 1H), 7.10-7.04 (m, 3H), 4.20-4.08 (m, 1H), 3.88 (s, 6H), 3.70 (s, 3H), 3.60-3.46 (m, 1H), 1.85-1.10 (m, 8H). | 511 | 509 | 0.82 |
| Example 2-172 | HCl | DMSO-d6 | 300 MHz | δ: 11.99 (s, 1H), 9.02-8.95 (m, 1H), 8.68-8.64 (m, 1H), 8.62-8.58 (m, 1H), 8.40-8.34 (m, 2H), 8.14-8.08 (m, 2H), 8.00 (d, 1H, J = 12.6 Hz), 7.96-7.80 (m, 4H), 7.44 (br, 1H), 7.02 (d, 1H, J = 6.6 Hz), 4.26-4.15 (m, 1H), 3.60-3.48 (m, 1H), 1.86-1.14 (m, 8H). | 466 | 464 | 0.95 |
| Example 2-173 | HCl | DMSO-d6 | 300 MHz | δ: 12.00 (s, 1H), 8.98 (s, 1H), 8.65 (s, 1H), 8.61 (s, 1H), 8.04-7.97 (m, 5H), 7.97-7.70 (m, 4H), 7.44 (br, 1H), 7.03 (d, 1H, J = 6.6 Hz), 4.25-4.14 (m, 1H), 3.62-3.50 (m, 1H), 1.90-1.12 (m, 8H). | 446 | 444 | 0.88 |
| Example 2-174 | HCl | DMSO-d6 | 300 MHz | δ: 12.09 (s, 1H), 9.04-8.96 (m, 1H), 8.74-8.66 (m, 1H), 8.66-8.62 (m, 1H), 8.05-7.85 (m, 7H), 7.56 (d, 2H, J = 5.8 Hz), 7.46 (br, 1H), 7.08 (d, 1H, J = 6.6 Hz), 4.24-4.10 (m, 1H), 3.62-3.50 (m, 1H), 1.86-1.45 (m, 5H), 1.36-1.10 (m, 3H). | 505 | 503 | 1.08 |
| Example 2-175 | HCl | DMSO-d6-D2O | 300 MHz | δ: 9.00 (d, 1H, J = 2.3 Hz), 8.80 (dd, 1H, J = 2.0, 2.0 Hz), 8.60 (d, 1H, J = 2.0 Hz), 7.98 (d, 1H, J = 12.2 Hz), 7.45 (d, 1H, J = 2.0 Hz), 7.35 (dd, 1H, J = 1.8, 8.1 Hz), 7.13 (d, 1H, J = 7.9 Hz), 6.11 (d, 2H, J = 2.6 Hz), 4.28-4.17 (m, 1H), 3.55-3.46 (m, 1H), 1.90-1.20 (m, 8H). | 465 | 463 | 0.93 |
| Example 2-176 | HCl | DMSO-d6-D2O | 300 MHz | δ: 8.46 (s, 1H), 8.39 (d, 1H, J = 7.3 Hz), 8.04 (d, 1H, J = 11.9 Hz), 7.76 (s, 1H), 7.50 (d, 1H, J = 2.0 Hz), 7.44 (dd, 1H, J = 2.0, 8.3 Hz), 7.21 (d, 1H, J = 8.3 Hz), 6.17 (d, 2H, J = 5.6 Hz), 4.34-4.23 (m, 1H), 3.62-3.51 (m, 1H), 1.90-1.22 (m, 8H). | 465 | 463 | 0.83 |
| Example 2-177 | HCl | DMSO-d6-D2O | 300 MHz | δ: 8.90-8.85 (m, 1H), 8.64 (s, 1H), 8.50 (d, 1H, J = 1.7 Hz), 7.95 (d, 1H, J = 11.9 Hz), 7.42-7.35 (m, 1H), 7.28 (d, 1H, J = 2.3 Hz), 7.18 (d, 1H, J = 8.3 Hz), 4.66 (s, 2H), 4.20-4.10 (m, 1H), 3.55-3.47 (m, 1H), 1.95-1.15 (m, 8H). | 492 | 490 | 0.85 |
| Example 2-178 | HCl | DMSO-d6-D2O | 300 MHz | δ: 8.41 (d, 1H, J = 6.9 Hz), 8.40 (s, 1H), 8.03 (d, 1H, J = 11.9 Hz), 7.78 (s, 1H), 7.49 (dd, 1H, J = 2.3, 8.3 Hz), 7.38 (d, 1H, J = 2.0 Hz), 7.26 (d, 1H, J = 8.3 Hz), 4.72 (s, 2H), 4.26-4.13 (m, 1H), 3.63-3.53 (m, 1H), 1.90-1.16 (m, 8H). | 492 | 490 | 0.76 |

TABLE 1-continued

| Example 2-179 | HCl | DMSO-d6-D2O | 300 MHz | δ: 9.72 (s, 1H), 8.97 (d, 1H, J = 2.3 Hz), 8.69-8.64 (m, 1H), 8.59 (d, 1H, J = 6.6 Hz), 8.52 (d, 1H, J = 7.9 Hz), 8.43 (d, 1H, J = 2.0 Hz), 8.19-8.13 (m, 1H), 8.10-8.02 (m, 2H), 7.95 (d, 1H, J = 12.2 Hz), 3.97-3.89 (m, 1H), 3.38-3.30 (m, 1H), 1.75-0.55 (m, 8H). | 472 | 470 | 0.69 |
| --- | --- | --- | --- | --- | --- | --- | --- |
| Example 2-180 | HCl | DMSO-d6-D2O | 300 MHz | δ: 9.61 (s, 1H), 8.64 (d, 1H, J = 6.3 Hz), 8.61-8.54 (m, 1H), 8.58 (d, 1H, J = 6.9 Hz), 8.54 (d, 1H, J = 5.9 Hz), 8.24-8.18 (m, 1H), 8.05-7.98 (m, 1H), 8.04 (d, 1H, J = 11.9 Hz), 7.94 (d, 1H, J = 5.9 Hz), 7.81 (s, 1H), 3.86-3.76 (m, 1H), 3.34-3.25 (m, 1H), 1.70-0.40 (m, 8H). | 472 | 470 | 0.59 |
| Example 2-181 | HCl | DMSO-d6-D2O | 300 MHz | δ: 9.11-9.00 (m, 2H), 8.99-8.93 (m, 1H), 8.71 (s, 1H), 8.60-8.52 (m, 1H), 8.21 (d, 1H, J = 8.9 Hz), 8.05 (d, 1H, J = 7.3 Hz), 7.98 (d, 1H, J = 12.2 Hz), 7.84 (dd, 1H, J = 7.6, 7.9 Hz), 7.69 (dd, 1H, J = 4.3, 8.3 Hz), 3.96-3.88 (m, 1H), 3.39-3.31 (m, 1H), 1.75-0.65 (m, 8H). | 472 | 470 | 0.8 |
| Example 2-182 | HCl | DMSO-d6-D2O | 300 MHz | δ: 9.02 (dd, 1H, J = 1.7, 4.3 Hz), 8.70 (s, 1H), 8.61 (dd, 1H, J = 1.7, 8.6 Hz), 8.57 (d, 1H, J = 6.9 Hz), 8.37-8.30 (m, 1H), 8.28-8.22 (m, 1H), 8.04 (d, 1H, J = 11.9 Hz), 7.89 (dd, 1H, J = 7.6, 7.9 Hz), 7.85-7.76 (m, 1H), 7.75 (dd, 1H, J = 4.3, 8.6 Hz), 3.97-3.92 (m, 1H), 3.44-3.33 (m, 1H), 1.75-0.83 (m, 8H). | 472 | 470 | 0.76 |
| Example 2-183 | HCl | DMSO-d6 | 300 MHz | δ: 12.97 (s, 1H), 8.53 (d, 1H, J = 6.6 Hz), 8.48-8.36 (m, 1H), 8.25-8.10 (m, 1H), 8.10 (d, 1H, J = 12.6 Hz), 8.05-7.80 (m, 4H), 7.80-7.70 (m, 1H), 7.61-7.50 (m, 3H), 7.32-7.20 (m, 2H), 4.32-4.20 (m, 1H), 3.88 (s, 3H), 3.60-3.48 (m, 1H), 1.90-1.10 (m, 8H). | 451 | 449 | 0.75 |
| Example 2-184 | HCl | DMSO-d6 | 300 MHz | δ: 12.96 (s, 1H), 8.48 (d, 1H, J = 6.6 Hz), 8.40-8.30 (m, 1H), 8.20-8.10 (m, 1H), 8.10 (d, 1H, J = 11.7 Hz), 8.05-7.65 (m, 7H), 7.28 (d, 1H, J = 5.4 Hz), 7.21 (d, 2H, J = 9.0 Hz), 4.32-4.20 (m, 1H), 3.87 (s, 3H), 3.60-3.48 (m, 1H), 1.95-1.15 (m, 8H). | 451 | 449 | 0.75 |
| Example 2-185 | HCl | | | | 412 | 410 | 0.9 |
| Example 2-186 | HCl | CD3OD | 300 MHz | δ: 8.09 (s, 1H), 7.90 (d, 1H, J = 7.3 Hz), 7.82 (d, 1H, J = 12.6 Hz), 7.38 (t, 1H, J = 7.9 Hz), 7.17 (d, 1H, J = 7.9 Hz), 4.45 (q, 2H, J = 7.0 Hz), 4.36 (br, 1H), 3.87 (br, 1H), 1.85-1.61 (m, 8H), 1.47 (t, 3H, J = 7.3 Hz). | 412 | 410 | 0.94 |
| Example 2-187 | HCl | | | | 448 | 446 | 0.87 |
| Example 2-188 | HCl | | | | 448 | 446 | 0.89 |
| Example 2-189 | HCl | DMSO-d6-D2O | 300 MHz | δ: 9.14-9.07 (m, 2H), 8.99-8.92 (m, 1H), 8.81 (d, 1H, J = 1.7 Hz), 8.76 (d, 1H, J = 7.9 Hz), 8.50 (s, 1H), 8.34 (d, 1H, J = 8.9 Hz), 8.17 (dd, 1H, J = 1.7, 8.6 Hz), 7.98 (d, 1H, J = 11.9 Hz), 7.83 (dd, 1H, J = 4.6, 8.3 Hz), 4.33-4.21 (m, 1H), 3.59-3.50 (m, 1H), 1.82-0.96 (m, 8H). | 472 | 470 | 0.78 |
| Example 2-190 | HCl | DMSO-d6-D2O | 300 MHz | δ: 9.72 (s, 1H), 9.05 (d, 1H, J = 2.3 Hz), 8.75 (d, 1H, J = 2.0 Hz), 8.69 (dd, 1H, J = 2.0, 2.0 Hz), 8.67-8.63 (m, 1H), 8.64 (d, 1H, J = 6.6 Hz), 8.59 (d, 1H, J = 8.6 Hz), 8.40 (d, 1H, J = 6.6 Hz), 8.37-8.31 (m, 1H), 7.96 (d, 1H, J = 12.2 Hz), 4.28-4.15 (m, 1H), 3.54-3.46 (m, 1H), 1.82-0.97 (m, 8H). | 472 | 470 | 0.67 |
| Example 2-191 | HCl | DMSO-d6-D2O | 300 MHz | δ: 9.77 (s, 1H), 9.16 (d, 1H, J = 2.3 Hz), 8.87 (s, 1H), 8.80 (d, 1H, J = 1.7 Hz), 8.75 (dd, 1H, J = 2.0, 2.3 Hz), 8.66 (d, 1H, J = 6.6 Hz), 8.54 (dd, 1H, J = 1.8, 8.8 Hz), 8.47-8.40 (m, 2H), 7.98 (d, 1H, J = 12.2 Hz), 4.27-4.16 (m, 1H), 3.56-3.46 (m, 1H), 1.85-1.02 (m, 8H). | 472 | 470 | 0.68 |
| Example 2-192 | HCl | DMSO-d6-D2O | 300 MHz | δ: 9.11 (dd, 1H, J = 1.5, 4.5 Hz), 8.70 (s, 1H), 8.67-8.59 (m, 2H), 8.55 (d, | 472 | 470 | 0.7 |

TABLE 1-continued

| | | | | | | | |
|---|---|---|---|---|---|---|---|
| | | | | 1H, J = 6.9 Hz), 8.35 (d, 1H, J = 8.6 Hz), 8.12 (dd, 1H, J = 1.8, 8.4 Hz), 8.06 (d, 1H, J = 11.9 Hz), 7.93-7.83 (m, 1H), 7.80 (dd, 1H, J = 4.3, 8.3 Hz), 4.39-4.28 (m, 1H), 3.66-3.55 (m, 1H), 1.87-0.83 (m, 8H). | | | |
| Example 2-193 | HCl | DMSO-d6-D2O | 300 MHz | δ: 9.59 (s, 1H), 8.70 (m, 2H), 8.58 (d, 1H, J = 6.9 Hz), 8.55-8.47 (m, 2H), 8.30-8.24 (m, 1H), 8.20 (d, 1H, J = 5.9 Hz), 8.05 (d, 1H, J = 11.9 Hz), 7.98-7.90 (m, 1H), 4.30-4.19 (m, 1H), 3.57-3.48 (m, 1H), 1.90-0.90 (m, 8H). | 472 | 470 | 0.63 |
| Example 2-194 | HCl | DMSO-d6-D2O | 300 MHz | δ: 9.64 (s, 1H), 8.84 (s, 1H), 8.69 (d, 1H, J = 5.9 Hz), 8.57 (d, 1H, J = 6.6 Hz), 8.52 (s, 1H), 8.40-8.35 (m, 2H), 8.21 (d, 1H, J = 6.3 Hz), 8.05 (d, 1H, J = 11.9 Hz), 8.03-7.95 (m, 1H), 4.30-4.19 (m, 1H), 3.59-3.50 (m, 1H), 1.90-0.90 (m, 8H). | 472 | 470 | 0.64 |
| Example 2-195 | HCl | DMSO-d6 | 300 MHz | δ: 11.59 (s, 1H), 8.82 (d, 1H, J = 2.4 Hz), 8.56 (d, 1H, J = 2.4 Hz), 8.21 (d, 1H, J = 7.2 Hz), 7.97 (d, 1H, J = 12.6 Hz), 7.90-7.70 (m, 5H), 7.63-7.55 (m, 1H), 7.48-7.40 (m, 1H), 7.35 (br, 1H), 6.92 (d, 1H, J = 5.1 Hz), 4.32-4.21 (m, 1H), 3.60-3.50 (m, 1H), 1.92-1.25 (m, 8H). | 435 | 433 | 1.06 |
| Example 2-196 | HCl | | | | 416 | 414 | 0.94 |
| Example 2-197 | HCl | | | | 430 | 428 | 1.02 |
| Example 2-198 | HCl | | | | 416 | 414 | 0.97 |
| Example 2-199 | HCl | | | | 430 | 428 | 1.03 |
| Example 2-200 | HCl | | | | 430 | 428 | 0.81 |
| Example 2-201 | HCl | | | no data | 430 | 428 | 0.86 |
| Example 2-202 | HCl | DMSO-d6 | 300 MHz | δ: 10.73 (s, 1H), 7.90-7.70 (m, 6H), 7.55 (dd, 1H, J = 3.0, 9.6 Hz), 7.20 (br, 1H), 6.76 (d, 1H, J = 6.0 Hz), 6.38 (d, 1H, J = 12.3 Hz), 4.14-4.03 (m, 1H), 3.60-3.48 (m, 1H), 3.43 (s, 3H), 1.90-1.25 (m, 8H). | 375 | 373 | 0.66 |
| Example 2-203 | HCl | DMSO-d6 | 300 MHz | δ: 11.40 (s, 1H), 8.31 (d, 1H, J = 2.4 Hz), 8.13 (d, 1H, J = 2.4 Hz), 7.93 (d, 1H, J = 12.3 Hz), 7.90-7.70 (m, 4H), 7.29 (br, 1H), 6.90 (d, 1H, J = 6.0 Hz), 4.22-4.10 (m, 1H), 3.91 (s, 3H), 3.61-3.50 (m, 1H), 1.95-1.45 (m, 8H). | 409 411 | 407 409 | 1.02 |
| Example 2-204 | HCl | CD3OD | 300 MHz | δ: 8.10 (s, 1H), 7.76 (d, 1H, J = 11.9 Hz), 7.49 (d, 1H, J = 9.2 Hz), 7.38 (dd, 1H, J = 9.2, 2.0 Hz), 4.84-4.82 (m, 1H), 4.69-4.67 (m, 1H), 4.59-4.57 (m, 1H), 4.50-4.49 (m, 1H), 4.36-4.33 (m, 1H), 3.81-3.78 (m, 1H), 1.90-1.50 (m, 8H). | 448 | 446 | 0.97 |
| Example 2-205 | HCl | | | no data | 448 | 446 | 1.02 |
| Example 2-206 | HCl | CD3OD | 300 MHz | δ: 7.85 (s, 1H), 7.75 (d, 1H, J = 11.9 Hz), 7.48 (s, 1H), 7.47 (t, 1H, J = 7.9 Hz), 4.35-4.32 (m, 1H), 3.99 (s, 3H), 3.65-3.61 (m, 1H), 2.55 (s, 3H), 1.99-1.50 (m, 8H). | 412 | 410 | 0.98 |
| Example 2-207 | HCl | | | no data | 426 | 424 | 0.95 |
| Example 2-208 | HCl | CD3OD | 300 MHz | δ: 7.81 (s, 1H), 7.75 (d, 1H, J = 11.9 Hz), 7.49 (s, 1H), 7.49 (s, 1H), 4.48 (t, 2H, J = 5.3 Hz), 4.30 (s, 1H), 3.78 (t, 2H, J = 5.3 Hz), 3.64 (s, 1H), 3.27 (s, 3H), 2.54 (s, 3H), 1.98-1.50 (m, 8H). | 456 | 454 | 0.91 |
| Example 2-209 | HCl | CD3OD | 300 MHz | δ: 7.80 (s, 1H), 7.74 (d, 1H, J = 11.9 Hz), 7.49 (s, 1H), 7.48 (s, 1H), 4.85-4.83 (m, 1H), 4.71-4.65 (m, 2H), 4.58-4.56 (m, 1H), 4.29-4.26 (m, 1H), 3.65-3.61 (m, 1H), 2.54 (s, 3H), 1.90-1.51 (m, 8H). | 444 | 442 | 0.92 |
| Example 2-210 | HCl | | | no data | 462 | 460 | 0.95 |

Example 3

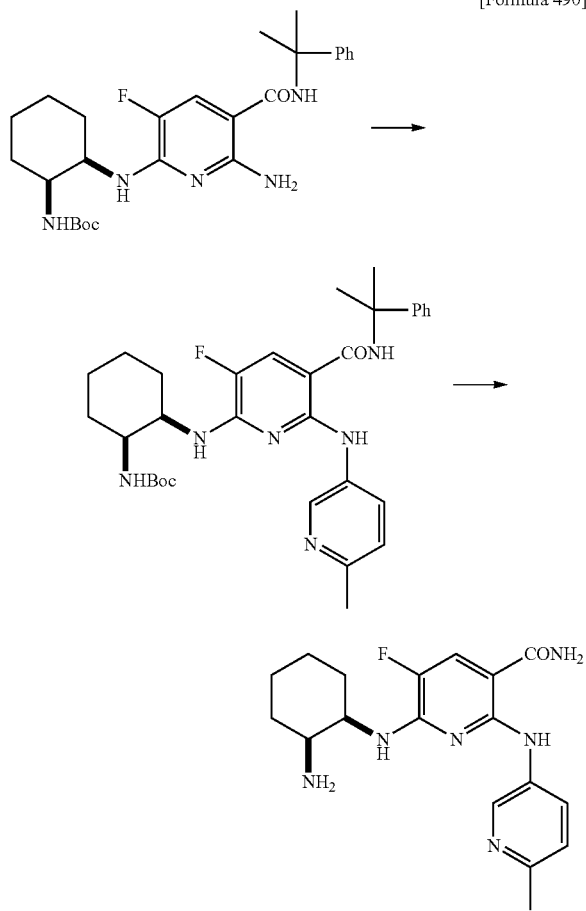

[Formula 490]

1st Step 5-bromo-2-picoline (13 mg), cesium carbonate (42 mg), Pd$_2$(dba)$_3$ (7 mg) and Xantphos (9 mg) were added to a 1,4-dioxane (0.5 ml) solution containing tert-butyl cis-2-(6-amino-3-fluoro-5-(2-phenylpropan-2-ylaminocarbonyl)pyridin-2-ylamino)cyclohexylcarbamate (25 mg), followed by stirring at 100° C. for 2 hours in a nitrogen atmosphere. The reaction mixture was cooled to room temperature, and water and ethyl acetate were added. Insoluble matter was removed by filtration, and the filter cake was washed with water and ethyl acetate. The filtrate was mixed with the washing solution, the organic layer was collected, washed with saturated saline, and dried over anhydrous magnesium sulfate, and the solvent was distilled away under reduced pressure. The obtained residue was purified using a PLC glass plate (hexane:ethyl acetate=1:1), diisopropylether and hexane were added, solid matter was collected by filtration, and a light yellow solid of tert-butyl cis-2-(3-fluoro-5-(2-phenylpropan-2-ylaminocarbonyl)-6-(6-methylpyridin-3-ylamino)pyridin-2-ylamino)cyclohexylcarbamate (14 mg) was thus obtained.

$^1$H-NMR (DMSO-d$_6$, 400 MHz) δ:11.07 (s, 1H), 8.50 (d, 1H, J=2.5 Hz), 8.15 (d, 1H, J=12.7 Hz), 8.08 (s, 1H), 7.92 (dd, 1H, J=2.5 Hz, 8.4 Hz), 7.40-7.34 (m, 2H), 7.31-7.25 (m, 2H), 7.19-7.13 (m, 1H), 7.10 (d, 1H, J=8.4 Hz), 6.72-6.60 (m, 2H), 4.06-3.87 (m, 2H), 2.37 (s, 3H), 1.88-1.10 (m, 23H)

MS (ESI, m/z): 577 (M+H), 575 (M−H)

2nd Step

A mixture of tert-butyl cis-2-(3-fluoro-5-(2-phenylpropan-2-ylaminocarbonyl)-6-(6-methylpyridin-3-ylamino)pyridin-2-ylamino)cyclohexylcarbamate (13 mg) and TFA (0.26 ml) was stirred at room temperature for 30 minutes. The solvent was distilled away under reduced pressure (at 40° C. or less), and ethyl acetate and 4N hydrogen chloride/1,4-dioxane (28 μl) were added, followed by stirring at room temperature for 30 minutes. Solid matter was collected by filtration, washed with ethyl acetate, and a yellow solid of 6-(cis-2-aminocyclohexylamino)-5-fluoro-2-(6-methylpyridin-3-ylamino)nicotinamide•hydrochloride (11 mg) was thus obtained.

($^1$H-NMR data and MS data are shown in table 2.)

Example 4

The compounds listed in table 2 were obtained as described in Example 3.

TABLE 2

| Number | Structure | Number | Structure |
|---|---|---|---|
| Example 4-1 | 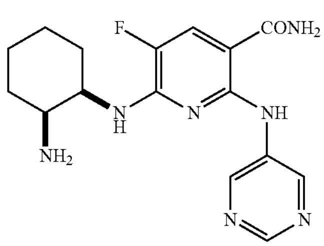 | Example 4-2 | 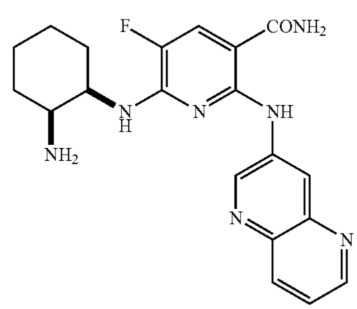 |

TABLE 2-continued
| Example 4-3 | 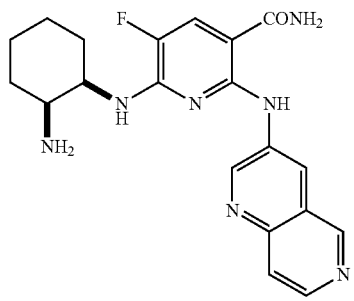 [SMILES: NC(=O)c1cc(F)c(N[C@@H]2CCCC[C@@H]2N)nc1Nc1cnc2ccncc2c1] | Example 4-4 | 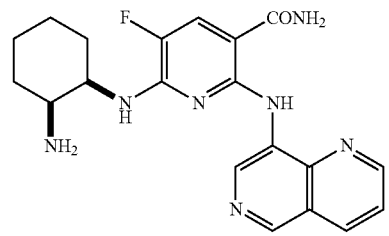 [SMILES: NC(=O)c1cc(F)c(N[C@@H]2CCCC[C@@H]2N)nc1Nc1cncc2cccnc12] |
| Example 4-5 | 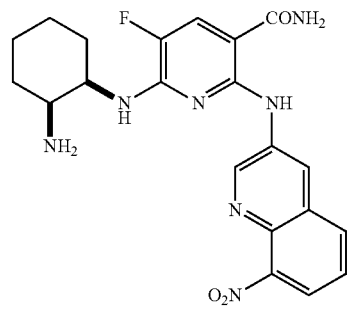 | Example 4-6 | 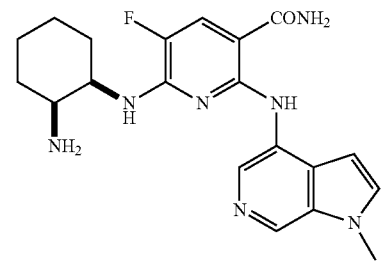 [SMILES: Cn1ccc2c(Nc3nc(N[C@@H]4CCCC[C@@H]4N)c(F)cc3C(N)=O)cncc21] |
| Example 4-7 | 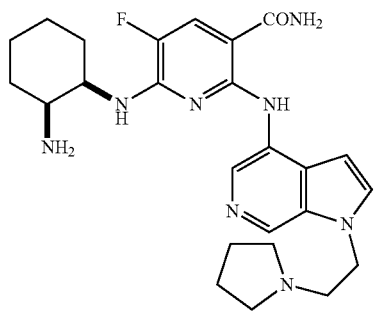 [SMILES: NC(=O)c1cc(F)c(N[C@@H]2CCCC[C@@H]2N)nc1Nc1cncc2c1ccn2CCN1CCCC1] | Example 4-8 | 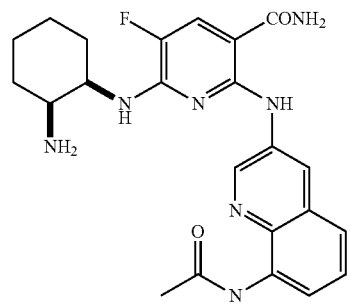 [SMILES: CC(=O)Nc1cccc2cc(Nc3nc(N[C@@H]4CCCC[C@@H]4N)c(F)cc3C(N)=O)cnc12] |
| Example 4-9 | 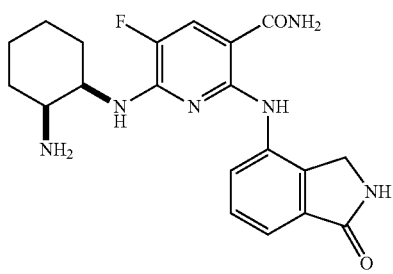 [SMILES: NC(=O)c1cc(F)c(N[C@@H]2CCCC[C@@H]2N)nc1Nc1cccc2c1CNC2=O] | Example 4-10 HCl salt | 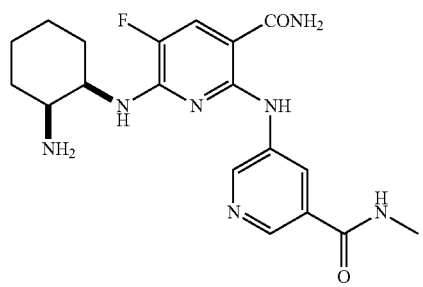 |
| Example 4-11 HCl salt | 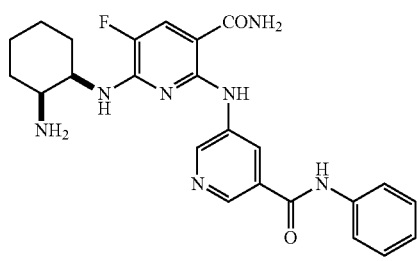 [SMILES: NC(=O)c1cc(F)c(N[C@@H]2CCCC[C@@H]2N)nc1Nc1cncc(C(=O)Nc2ccccc2)c1] | Example 4-12 | 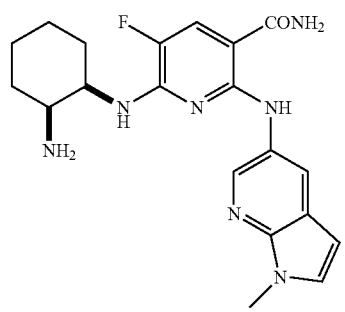 |

TABLE 2-continued
| Example 4-13 | 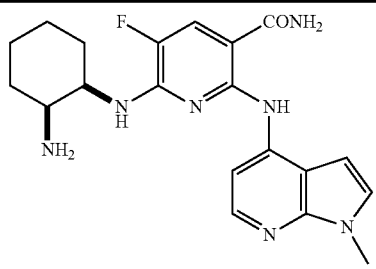 | Example 4-14 | 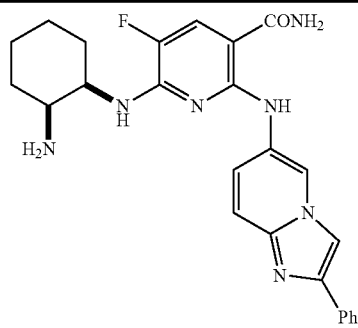 |
| Example 4-15 HCl salt | 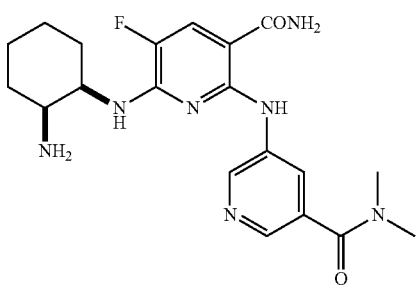 [SMILES: CN(C)C(=O)c1cncc(Nc2nc(N[C@@H]3CCCC[C@@H]3N)c(F)cc2C(N)=O)c1] | Example 4-16 HCl salt | 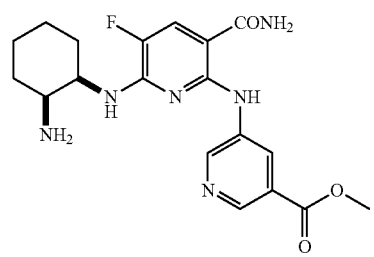 [SMILES: COC(=O)c1cncc(Nc2nc(N[C@@H]3CCCC[C@@H]3N)c(F)cc2C(N)=O)c1] |
| Example 4-17 (Example 3) HCl salt | 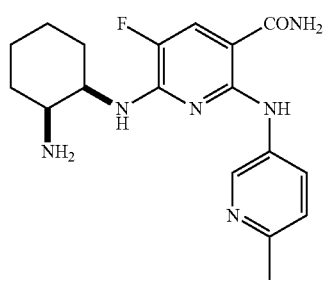 [SMILES: Cc1ccc(Nc2nc(N[C@@H]3CCCC[C@@H]3N)c(F)cc2C(N)=O)cn1] | Example 4-18 HCl salt | 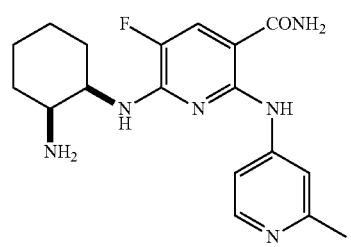 [SMILES: Cc1cc(Nc2nc(N[C@@H]3CCCC[C@@H]3N)c(F)cc2C(N)=O)ccn1] |
| Example 4-19 HCl salt | 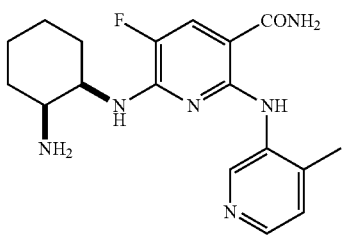 [SMILES: Cc1ccncc1Nc1nc(N[C@@H]2CCCC[C@@H]2N)c(F)cc1C(N)=O] | Example 4-20 | 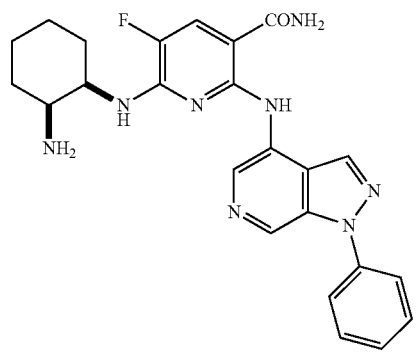 [SMILES: NC(=O)c1cc(F)c(N[C@@H]2CCCC[C@@H]2N)nc1Nc1cncc2c1cnn2-c1ccccc1] |
| Example 4-21 | 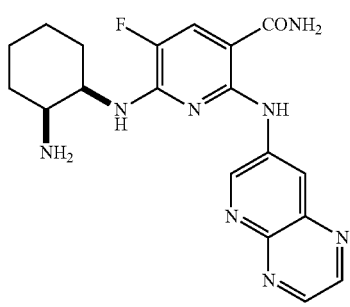 [SMILES: NC(=O)c1cc(F)c(N[C@@H]2CCCC[C@@H]2N)nc1Nc1cnc2nccnc2c1] | Example 4-22 | 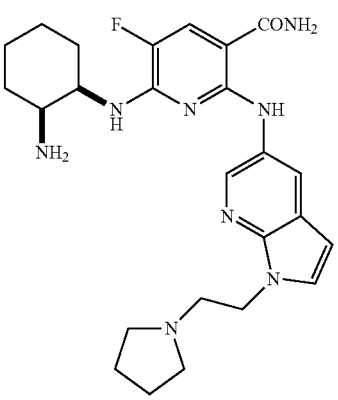 [SMILES: NC(=O)c1cc(F)c(N[C@@H]2CCCC[C@@H]2N)nc1Nc1cnc2c(ccn2CCN2CCCC2)c1] |

TABLE 2-continued
| Example 4-23 | 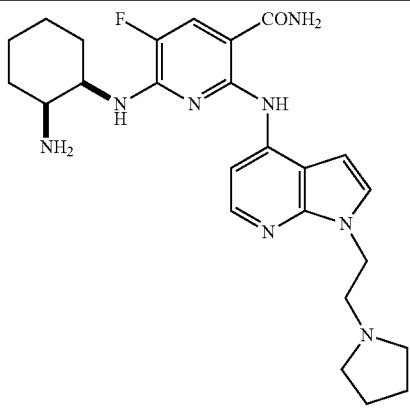 | Example 4-24 | 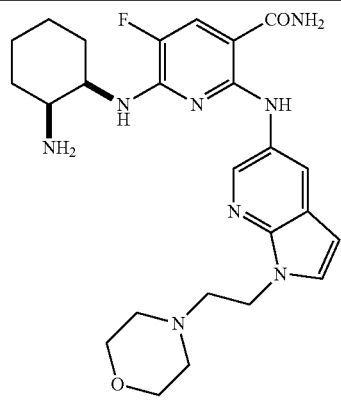 |
| Example 4-25 | 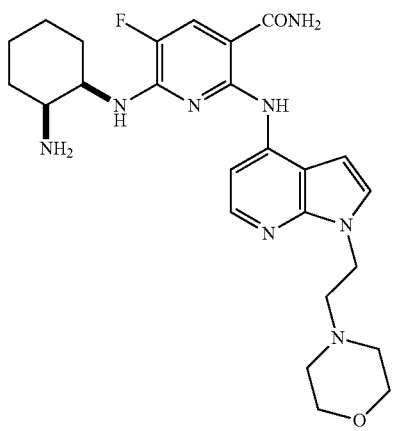 [SMILES: NC(=O)c1cc(F)c(N[C@@H]2CCCC[C@@H]2N)nc1Nc1ccnc2c1ccn2CCN1CCOCC1] | Example 4-26 HCl salt | 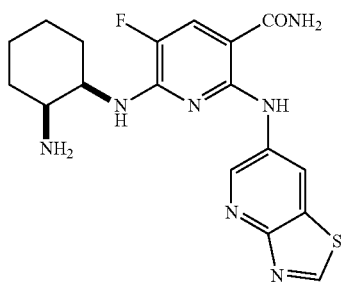 [SMILES: NC(=O)c1cc(F)c(N[C@@H]2CCCC[C@@H]2N)nc1Nc1cnc2ncsc2c1] |
| Example 4-27 | 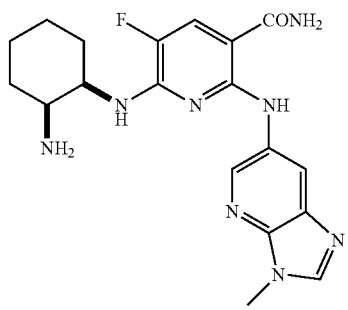 [SMILES: Cn1cnc2cc(Nc3nc(N[C@@H]4CCCC[C@@H]4N)c(F)cc3C(N)=O)cnc21] | Example 4-28 | 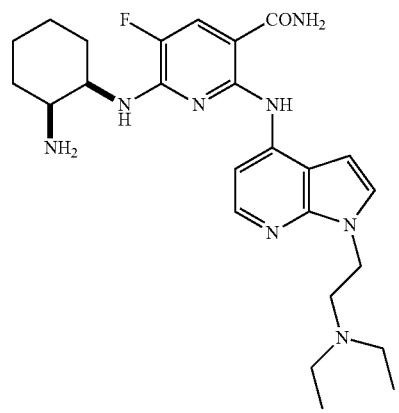 [SMILES: CCN(CC)CCn1ccc2c(Nc3nc(N[C@@H]4CCCC[C@@H]4N)c(F)cc3C(N)=O)ccnc21] |
| Example 4-29 | 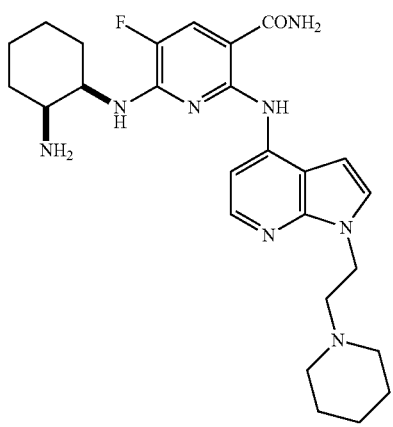 [SMILES: NC(=O)c1cc(F)c(N[C@@H]2CCCC[C@@H]2N)nc1Nc1ccnc2c1ccn2CCN1CCCCC1] | Example 4-30 | 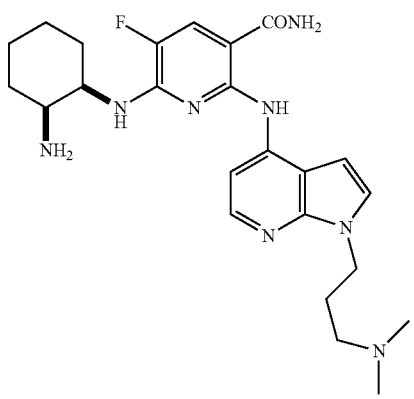 [SMILES: CN(C)CCCn1ccc2c(Nc3nc(N[C@@H]4CCCC[C@@H]4N)c(F)cc3C(N)=O)ccnc21] |

TABLE 2-continued
| | | | |
|---|---|---|---|
| Example 4-31 HCl salt | 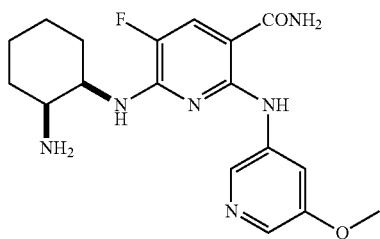 [SMILES: COc1cncc(Nc2nc(N[C@@H]3CCCC[C@@H]3N)c(F)cc2C(N)=O)c1] | Example 4-32 | 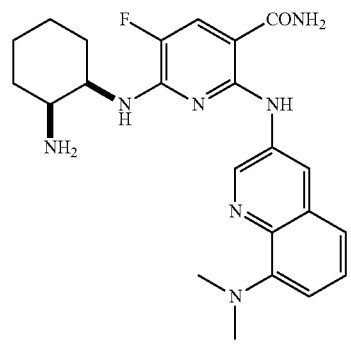 [SMILES: CN(C)c1cccc2cc(Nc3nc(N[C@@H]4CCCC[C@@H]4N)c(F)cc3C(N)=O)cnc12] |
| Example 4-33 HCl salt | 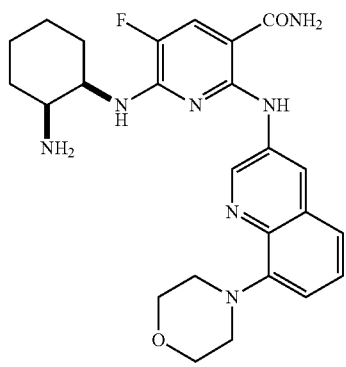 [SMILES: NC(=O)c1cc(F)c(N[C@@H]2CCCC[C@@H]2N)nc1Nc1cnc2c(N3CCOCC3)cccc2c1] | Example 4-34 | 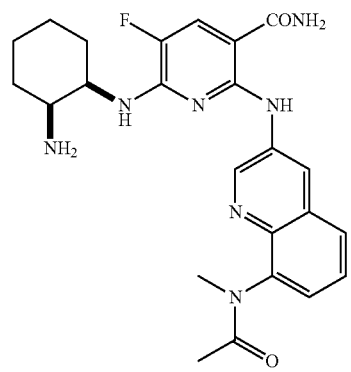 [SMILES: CC(=O)N(C)c1cccc2cc(Nc3nc(N[C@@H]4CCCC[C@@H]4N)c(F)cc3C(N)=O)cnc12] |
| Example 4-35 | 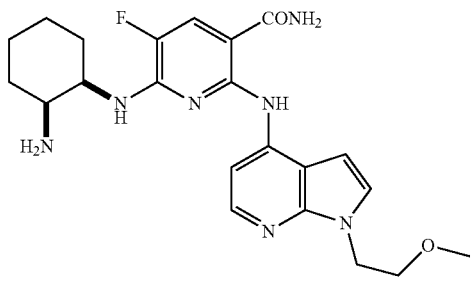 [SMILES: COCCn1ccc2c(Nc3nc(N[C@@H]4CCCC[C@@H]4N)c(F)cc3C(N)=O)ccnc21] | Example 4-36 | 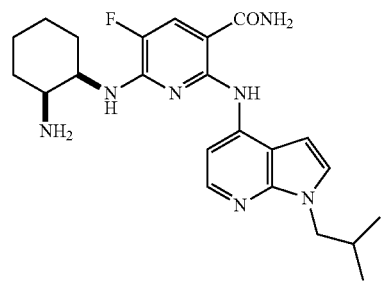 [SMILES: CC(C)Cn1ccc2c(Nc3nc(N[C@@H]4CCCC[C@@H]4N)c(F)cc3C(N)=O)ccnc21] |
| Example 4-37 | 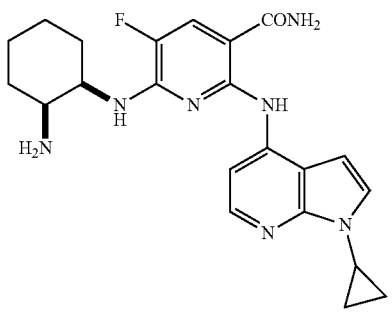 [SMILES: NC(=O)c1cc(F)c(N[C@@H]2CCCC[C@@H]2N)nc1Nc1ccnc2c1ccn2C1CC1] | Example 4-38 | 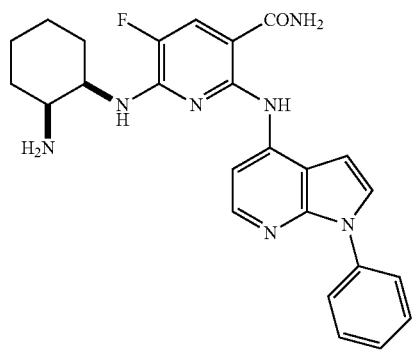 [SMILES: NC(=O)c1cc(F)c(N[C@@H]2CCCC[C@@H]2N)nc1Nc1ccnc2c1ccn2-c1ccccc1] |

TABLE 2-continued
| Example 4-39 HCl salt | 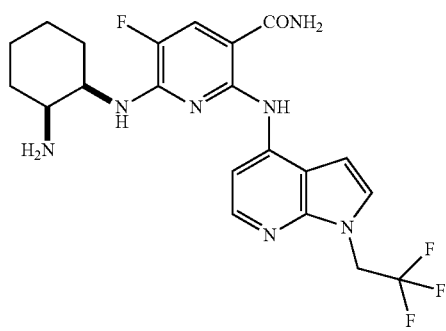 [SMILES: NC(=O)c1cc(F)c(N[C@@H]2CCCC[C@@H]2N)nc1Nc1ccnc2c1ccn2CC(F)(F)F] | Example 4-40 | 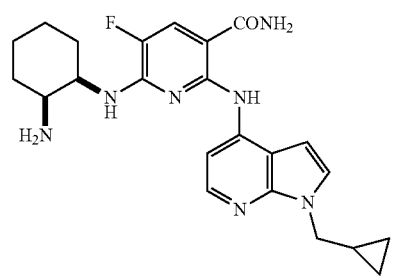 [SMILES: NC(=O)c1cc(F)c(N[C@@H]2CCCC[C@@H]2N)nc1Nc1ccnc2c1ccn2CC1CC1] |
|---|---|---|---|
| Example 4-41 HCl salt | 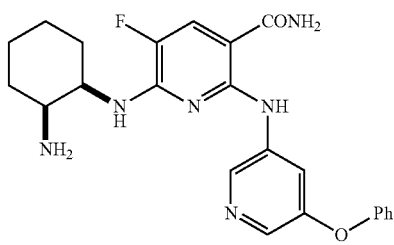 [SMILES: NC(=O)c1cc(F)c(N[C@@H]2CCCC[C@@H]2N)nc1Nc1cncc(Oc2ccccc2)c1] | Example 4-42 HCl salt | 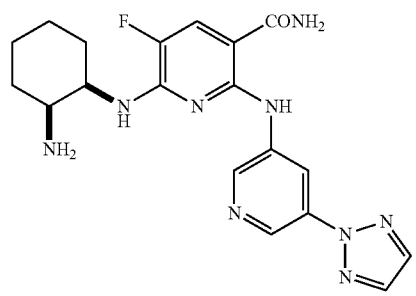 |
| Example 4-43 HCl salt | 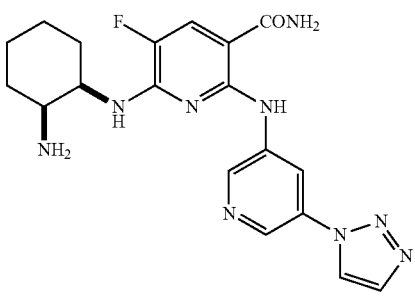 | Example 4-44 | 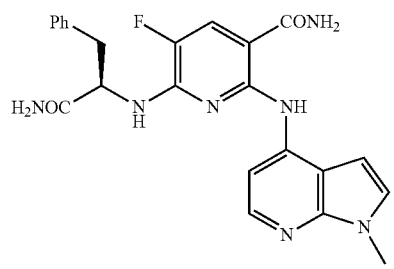 [SMILES: Cn1ccc2c(Nc3nc(N[C@H](Cc4ccccc4)C(N)=O)c(F)cc3C(N)=O)ccnc21] |
| Example 4-45 | 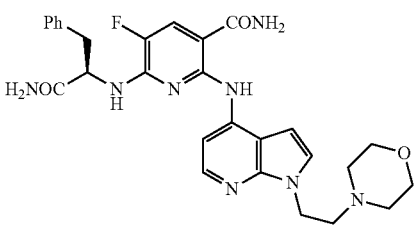 [SMILES: NC(=O)c1cc(F)c(N[C@H](Cc2ccccc2)C(N)=O)nc1Nc1ccnc2c1ccn2CCN1CCOCC1] | Example 4-46 | 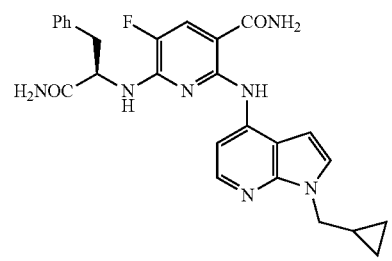 [SMILES: NC(=O)c1cc(F)c(N[C@H](Cc2ccccc2)C(N)=O)nc1Nc1ccnc2c1ccn2CC1CC1] |
| Example 4-47 | 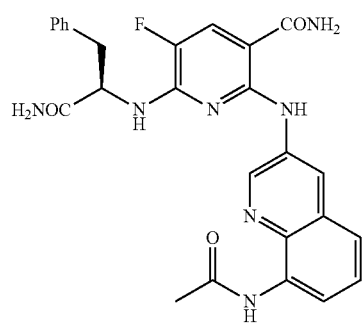 [SMILES: CC(=O)Nc1cccc2cc(Nc3nc(N[C@H](Cc4ccccc4)C(N)=O)c(F)cc3C(N)=O)cnc12] | Example 4-48 | 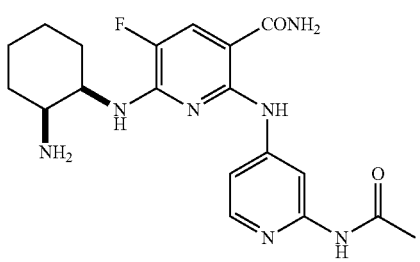 |

TABLE 2-continued
| Example 4-49 HCl salt | 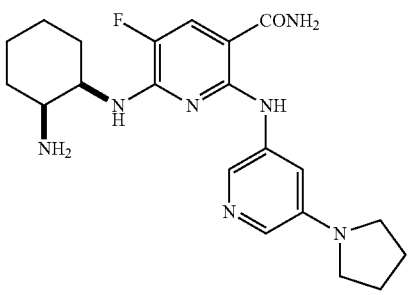 | Example 4-50 HCl salt | 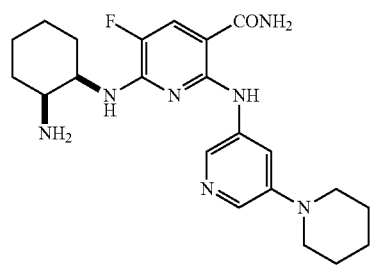 |
| Example 4-51 HCl salt | 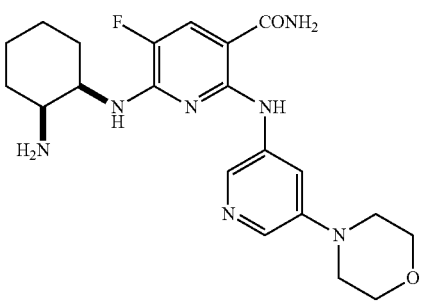 | Example 4-52 2HCl salt | 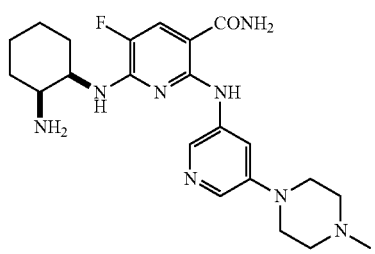 |
| Example 4-53 HCl salt | 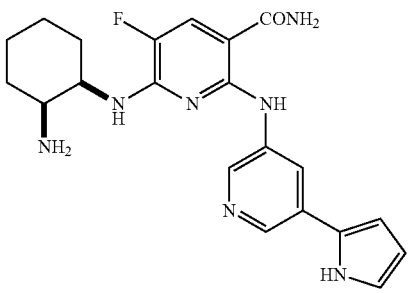 | Example 4-54 HCl salt | 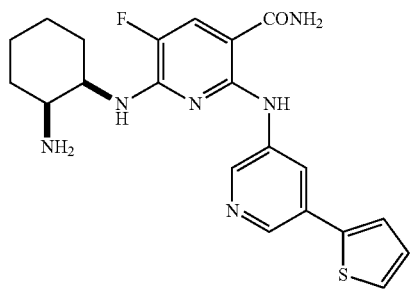 |
| Example 4-55 HCl salt | 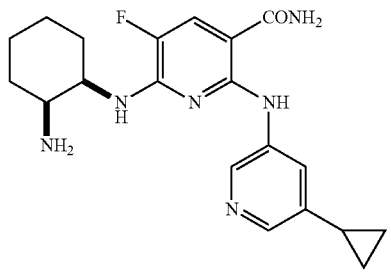 | Example 4-56 HCl salt | 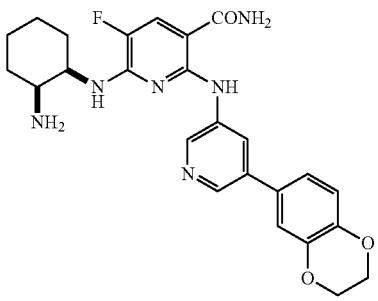 |
| Example 4-57 HCl salt | 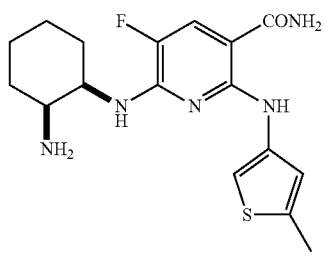 | Example 4-58 HCl salt | 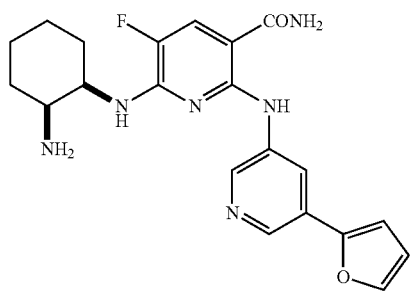 |

TABLE 2-continued
| | | | |
|---|---|---|---|
| Example 4-59 | 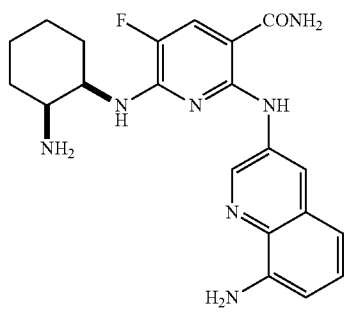 | Example 4-60 | 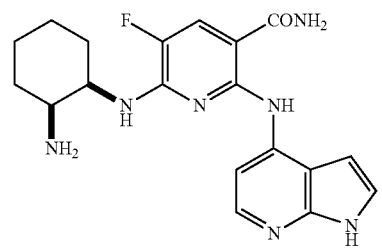 |
| Example 4-61 | 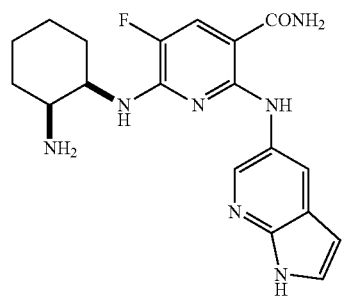 | Example 4-62 | 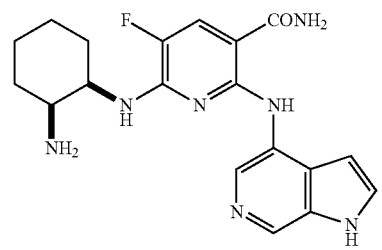 |
| Example 4-63 | 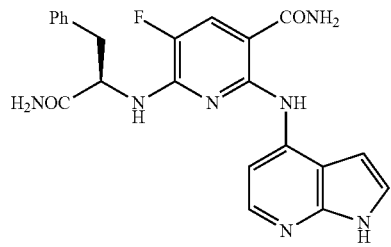 [SMILES: NC(=O)c1cc(F)c(N[C@H](Cc2ccccc2)C(N)=O)nc1Nc1ccnc2[nH]ccc12] | Example 4-64 | 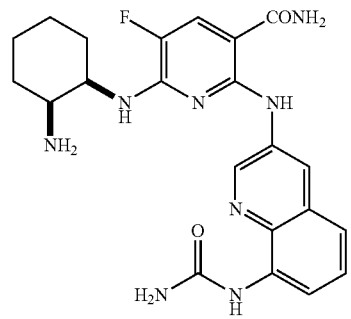 |
| Number | Structure | Compound name |
|---|---|---|
| Example 4-65 | 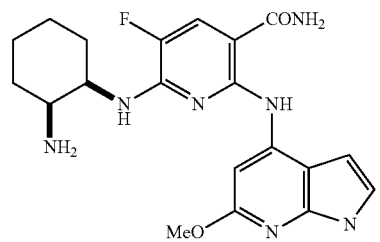 | 6-(cis-2-aminocyclohexylamino)-5-fluoro-2-((6-methoxy-1H-pyrrolo[2,3-b]pyridin-4-yl)-amino)nicotinamide |
| Example 4-66 | 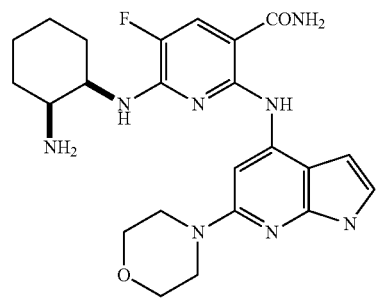 | 6-(cis-2-aminocyclohexylamino)-5-fluoro-2-((6-morpholino-1H-pyrrolo[2,3-b]pyridin-4-yl)-amino)nicotinamide |

TABLE 2-continued

| Example 4-67 | 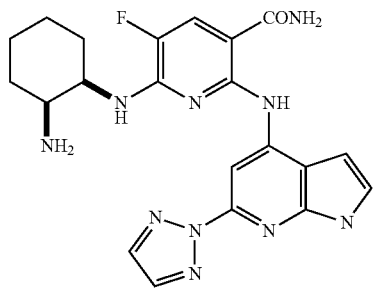 | 2-((6-(2H-1,2,3-triazol-2-yl)-1H-pyrrolo[2,3-b]pyridin-4-yl)amino)-6-(cis-2-aminocyclohexylamino)-5-fluoronicotinamide |
| --- | --- | --- |
| Example 4-68 | 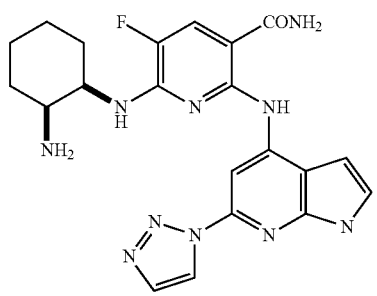 | 2-((6-(1H-1,2,3-triazol-1-yl)-1H-pyrrolo[2,3-b]pyridin-4-yl)amino)-6-(cis-2-aminocyclohexylamino)-5-fluoronicotinamide |
| Example 4-69 | 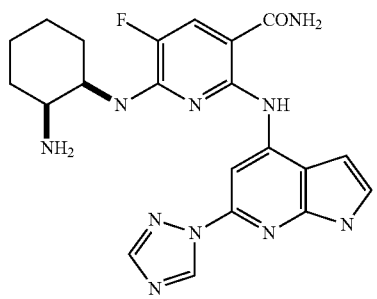 | 2-((6-(1H-1,2,4-triazol-1-yl)-1H-pyrrolo[2,3-b]pyridin-4-yl)amino)-6-(cis-2-aminocyclohexylamino)-5-fluoronicotinamide |
| Example 4-70 | 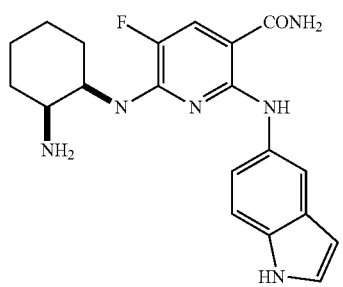 | 2-((1H-indol-5-yl)amino)-6-(cis-2-aminocyclohexylamino)-5-fluoronicotinamide |
| Example 4-71 | 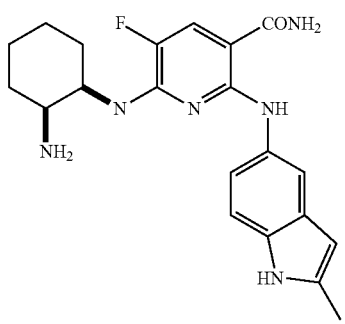 | 6-(cis-2-aminocyclohexylamino)-5-fluoro-2-((2-methyl-1H-indol-5-yl)amino)nicotinamide |

TABLE 2-continued

| Example 4-72 | 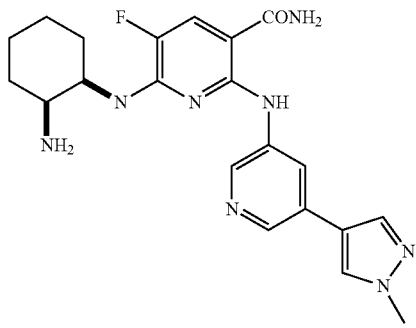 | 6-(cis-2-aminocyclohexylamino)-5-fluoro-2-((5-(1-methyl-1H-pyrazol-4-yl)pyridin-3-yl)-amino)nicotinamide |
| Example 4-73 | 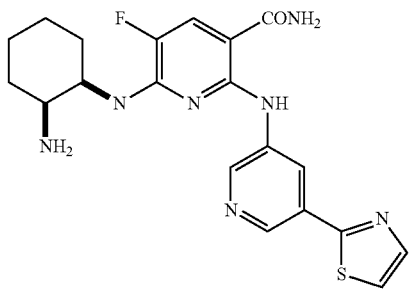 | 6-(cis-2-aminocyclohexylamino)-5-fluoro-2-((5-(thiazol-5-yl)pyridin-3-yl)amino)-nicotinamide |
| Example 4-74 | 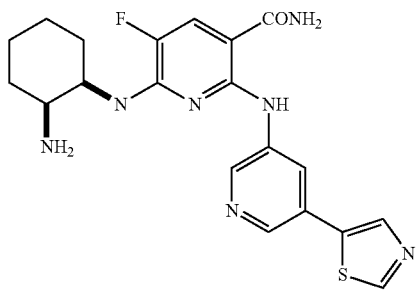 | 6-(cis-2-aminocyclohexylamino)-5-fluoro-2-((5-(thiazol-5-yl)pyridin-3-yl)amino)-nicotinamide |
| Example 4-75 | 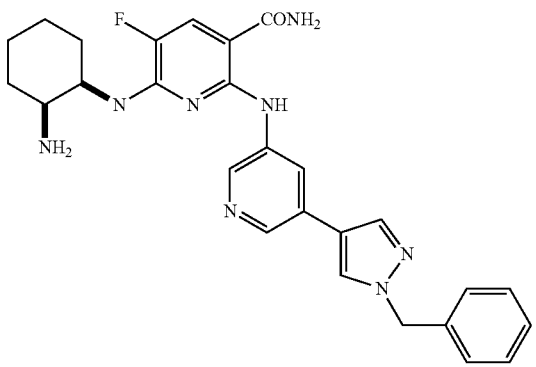 | 6-(cis-2-aminocyclohexylamino)-2-((5-(1-benzyl-1H-pyrazol-4-yl)pyridin-3-yl)amino)-5-fluoronicotinamide |
| Example 4-76 | 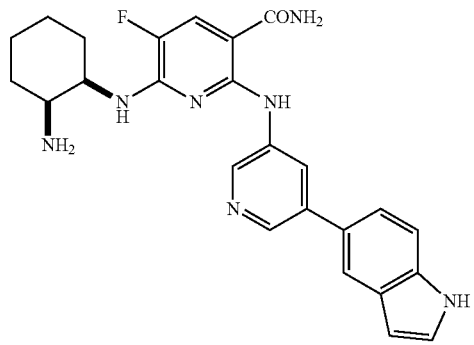 | 2-((5-(1H-indol-5-yl)pyridin-3-yl)amino)-6-(cis-2-aminocyclohexylamino)-5-fluoronicotinamide |

TABLE 2-continued

| Example | | |
|---|---|---|
| Example 4-77 | 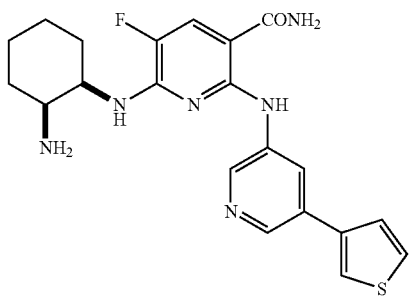 | 6-(cis-2-aminocyclohexylamino)-5-fluoro-2-((5-(thiophene-3-yl)pyridin-3-yl)amino)-nicotinamide |
| Example 4-78 | 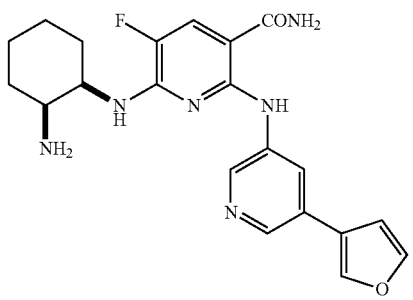 | 6-(cis-2-aminocyclohexylamino)-5-fluoro-2-((5-(furan-3-yl)pyridin-3-yl)amino)-nicotinamide |
| Example 4-79 | 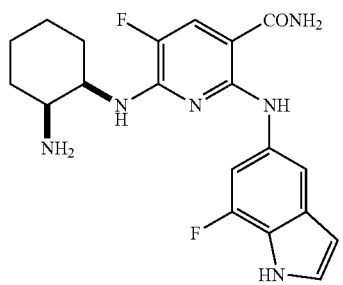 | 6-(cis-2-aminocyclohexylamino)-5-fluoro-2-((7-fluoro-1H-indol-5-yl)amino)nicotinamide |
| Example 4-80 | 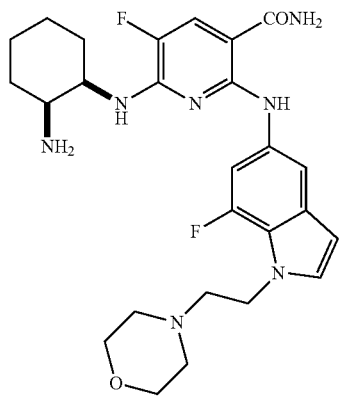 | 6-(cis-2-aminocyclohexylamino)-5-fluoro-2-((7-fluoro-1-(2-morpholinoethyl)-1H-indol-5-yl)amino)nicotinamide |
| Example 4-81 | 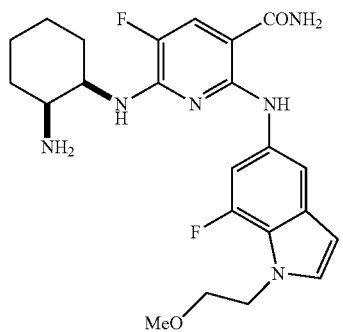 | 6-(cis-2-aminocyclohexylamino)-5-fluoro-2-((7-fluoro-1-(2-methoxyethyl)-1H-indol-5-yl)-amino)nicotinamide |

| | | |
|---|---|---|
| Example 4-82 | 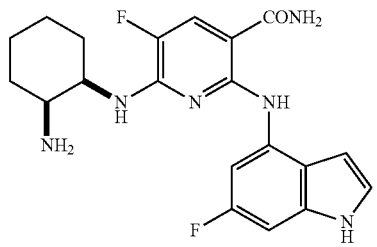 | 6-(cis-2-aminocyclohexylamino)-5-fluoro-2-((6-fluoro-1H-indol-4-yl)amino)nicotinamide |
| Example 4-83 | 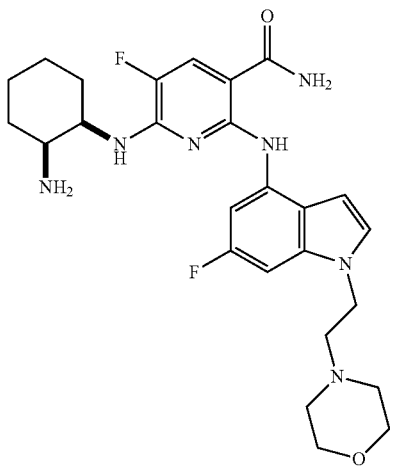 | 6-(cis-2-aminocyclohexylamino)-5-fluoro-2-((6-fluoro-1-(2-morpholinoethyl)-1H-indol-4-yl)amino)nicotinamide |
| Example 4-84 | 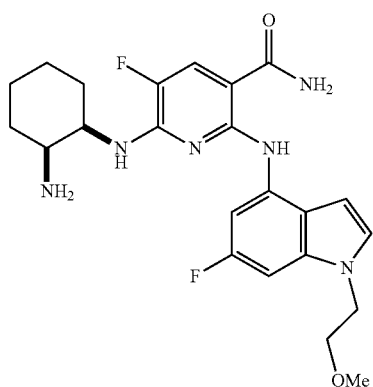 | 6-(cis-2-aminocyclohexylamino)-5-fluoro-2-((6-fluoro-1-(2-methoxyethyl)-1H-indol-4-yl)amino)nicotinamide |
| Example 4-85 | 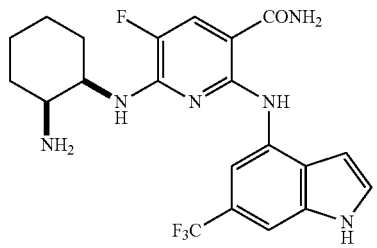 | 6-(cis-2-aminocyclohexylamino)-5-fluoro-2-((6-(trifluoromethyl)-1H-indol-4-yl)amino)-nicotinamide |
| Example 4-86 | 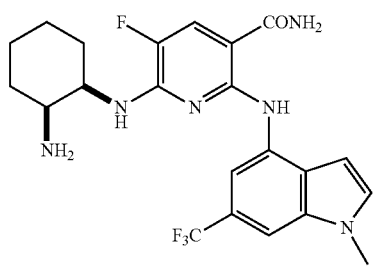 [SMILES: Cn1ccc2c(Nc3nc(N[C@@H]4CCCC[C@@H]4N)c(F)cc3C(N)=O)cc(C(F)(F)F)cc21] | 6-(cis-2-aminocyclohexylamino)-5-fluoro-2-((1-methyl-6-trifluoromethyl)-1H-indol-4-yl)-amino)nicotinamide |

TABLE 2-continued

| Example 4-87 | 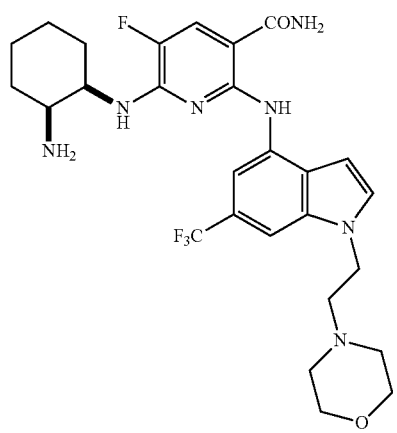 [SMILES: NC(=O)c1cc(F)c(N[C@@H]2CCCC[C@@H]2N)nc1Nc1cc(C(F)(F)F)cc2c1ccn2CCN1CCOCC1] | 6-(cis-2-aminocyclohexylamino)-5-fluoro-2-((1-2-morpholinoethyl)-6-(trifluoromethyl)-1H-indol-4-yl)amino)nicotinamide |
| Example 4-88 | 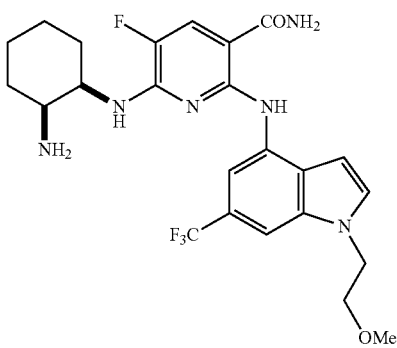 [SMILES: COCCn1ccc2c(Nc3nc(N[C@@H]4CCCC[C@@H]4N)c(F)cc3C(N)=O)cc(C(F)(F)F)cc21] | 6-(cis-2-aminocyclohexylamino)-5-fluoro-2-((1-(2-methoxyethyl)-6-(trifluoromethyl)-1H-indol-4-yl)nicotinamide |
| Example 4-89 | 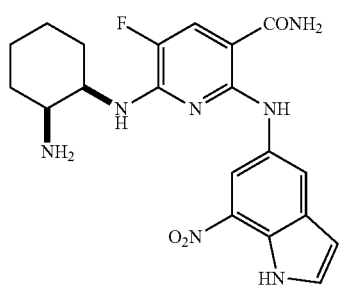 | 6-(cis-2-aminocyclohexylamino)-5-fluoro-2-((7-nitro-1H-indol-5-yl)amino)nicotinamide |
| Example 4-90 | 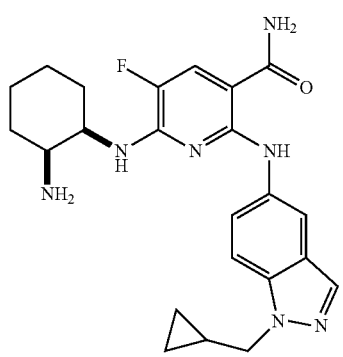 [SMILES: NC(=O)c1cc(F)c(N[C@@H]2CCCC[C@@H]2N)nc1Nc1ccc2c(cnn2CC2CC2)c1] | 6-(cis-2-aminocyclohexylamino)-2-((1-(cyclopropylmethyl)-1H-indazol-5-yl)amino)-5-fluoronicotinamide |

TABLE 2-continued

| Example | | |
|---|---|---|
| Example 4-91 | 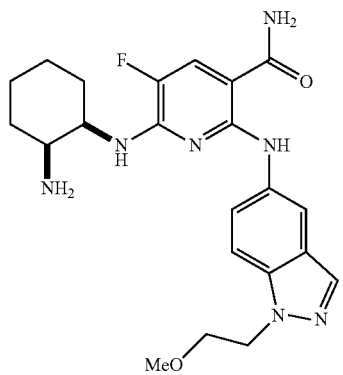 [SMILES: COCCn1ncc2cc(Nc3nc(N[C@@H]4CCCC[C@@H]4N)c(F)cc3C(N)=O)ccc21] | 6-(cis-2-aminocyclohexylamino)-5-fluoro-2-((1-(2-methoxyethyl)-1H-indazol-5-yl)amino)-nicotinamide |
| Example 4-92 | 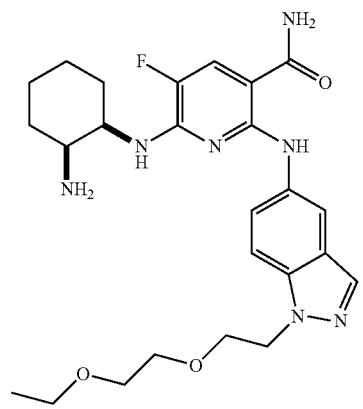 [SMILES: CCOCCOCCn1ncc2cc(Nc3nc(N[C@@H]4CCCC[C@@H]4N)c(F)cc3C(N)=O)ccc21] | 6-(cis-2-aminocyclohexylamino)-2-((1-(2-(2-ethoxyethoxy)ethyl)-1H-indazol-5-yl)amino)-5-fluoronicotinamide |
| Example 4-93 | 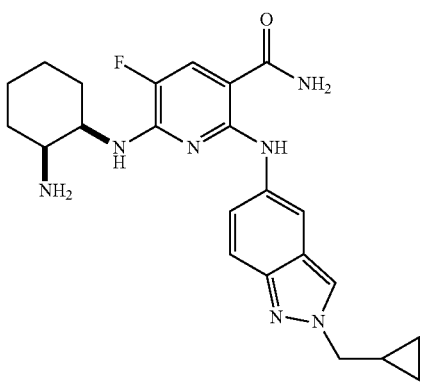 [SMILES: NC(=O)c1cc(F)c(N[C@@H]2CCCC[C@@H]2N)nc1Nc1ccc2nn(CC3CC3)cc2c1] | 6-(cis-2-aminocyclohexylamino)-2-((2-(cyclopropylmethyl)-2H-indazol-5-yl)amino)-5-fluoronicotinamide |
| Example 4-94 | 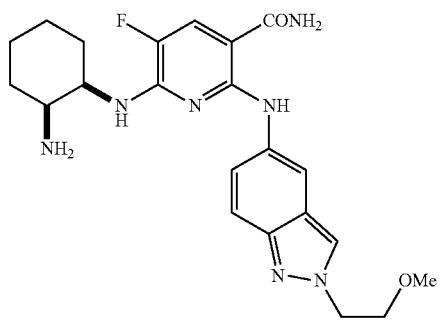 | 6-(cis-2-aminocyclohexylamino)-5-fluoro-2-((2-(2-methoxyethyl)-2H-indazol-5-yl)amino)-nicotinamide |

TABLE 2-continued

| Example 4-95 | 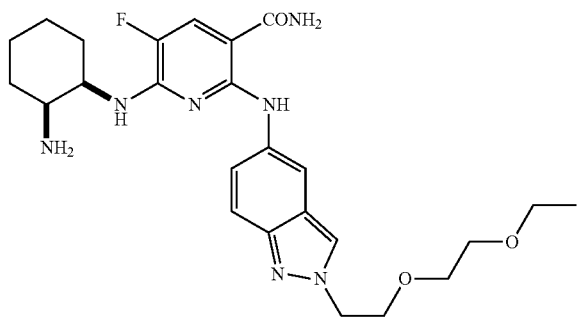 [SMILES: CCOCCOCCn1cc2cc(Nc3nc(N[C@@H]4CCCC[C@@H]4N)c(F)cc3C(N)=O)ccc2n1] | 6-(cis-2-aminocyclohexylamino)-2-((2-(2-(2-ethoxyethoxy)ethyl)-2H-indazol-5-yl)amino)-5-fluoronicotinamide |
| --- | --- | --- |
| Example 4-96 | 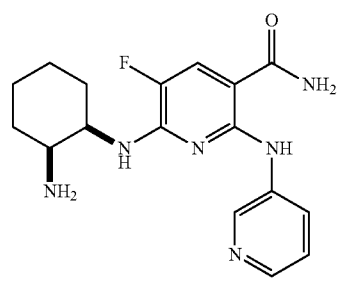 [SMILES: NC(=O)c1cc(F)c(N[C@@H]2CCCC[C@@H]2N)nc1Nc1cccnc1] | 6-(cis-2-aminocyclohexylamino)-5-fluoro-2-((pyridin-3-yl)amino)nicotinamide |
| Example 4-97 | 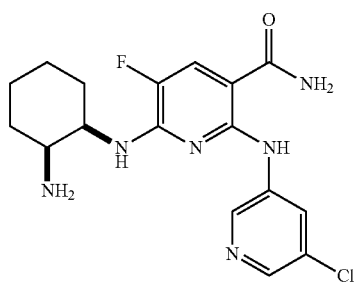 [SMILES: NC(=O)c1cc(F)c(N[C@@H]2CCCC[C@@H]2N)nc1Nc1cncc(Cl)c1] | 6-(cis-2-aminocyclohexylamino)-2-((5-chloropyridin-3-yl)amino)-5-fluoronicotinamide |
| Example 4-98 | 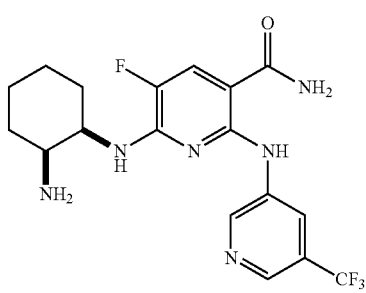 [SMILES: NC(=O)c1cc(F)c(N[C@@H]2CCCC[C@@H]2N)nc1Nc1cncc(C(F)(F)F)c1] | 6-(cis-2-aminocyclohexylamino)-5-fluoro-2-((5-(trifluoromethyl)pyridin-3-yl)amino)-nicotinamide |
| Example 4-99 | 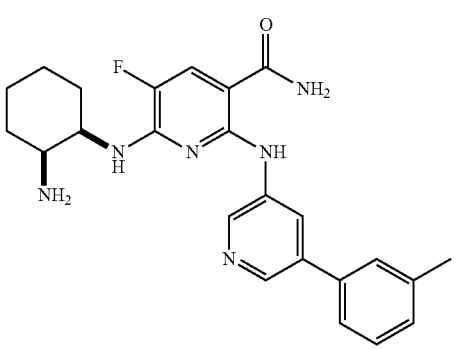 [SMILES: Cc1cccc(-c2cncc(Nc3nc(N[C@@H]4CCCC[C@@H]4N)c(F)cc3C(N)=O)c2)c1] | 6-(cis-2-aminocyclohexylamino)-5-fluoro-2-((5-(3-methylphenyl)pyridin-3-yl)amino)-nicotinamide |

TABLE 2-continued

| Example 4-100 | 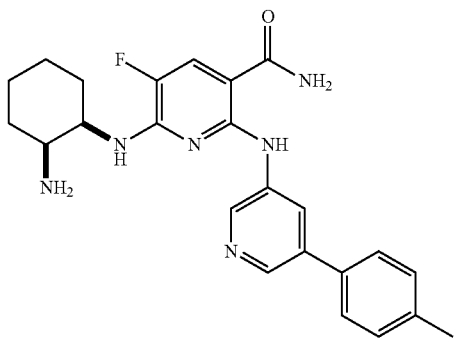 [SMILES: Cc1ccc(-c2cncc(Nc3nc(N[C@@H]4CCCC[C@@H]4N)c(F)cc3C(N)=O)c2)cc1] | 6-(cis-2-aminocyclohexylamino)-5-fluoro-2-((5-(4-methylphenyl)pyridin-3-yl)amino)-nicotinamide |
| Example 4-101 | 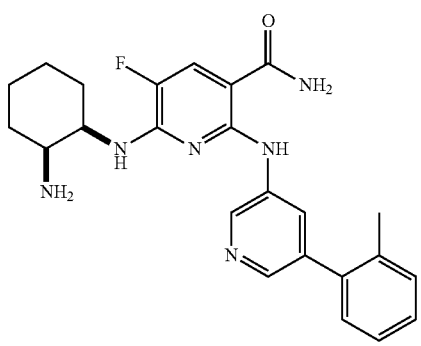 [SMILES: Cc1ccccc1-c1cncc(Nc2nc(N[C@@H]3CCCC[C@@H]3N)c(F)cc2C(N)=O)c1] | 6-(cis-2-aminocyclohexylamino)-5-fluoro-2-((5-(2-methylphenyl)pyridin-3-yl)amino)-nicotinamide |
| Example 4-102 | 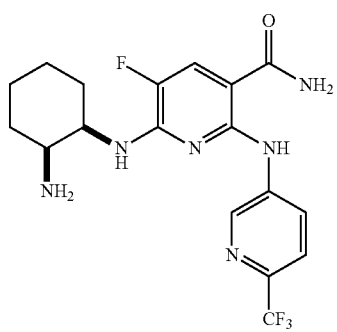 [SMILES: NC(=O)c1cc(F)c(N[C@@H]2CCCC[C@@H]2N)nc1Nc1ccc(C(F)(F)F)nc1] | 6-(cis-2-aminocyclohexylamino)-5-fluoro-2-((6-(trifluoromethyl)pyridin-3-yl)amino)-nicotinamide |
| Example 4-103 | 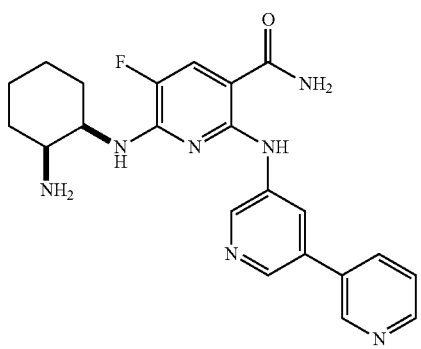 [SMILES: NC(=O)c1cc(F)c(N[C@@H]2CCCC[C@@H]2N)nc1Nc1cncc(-c2cccnc2)c1] | 2-([3,3'-bipyridine]-5-yl)amino)-6-(cis-2-aminocyclohexylamino)-5-fluoronicotinamide |

TABLE 2-continued

| Example 4-104 | 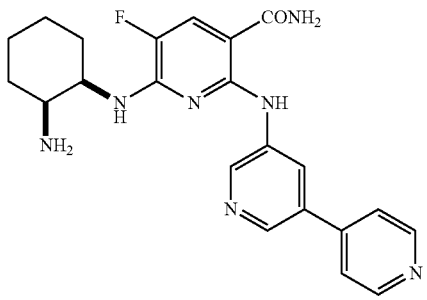 [SMILES: NC(=O)c1cc(F)c(N[C@@H]2CCCC[C@@H]2N)nc1Nc1cncc(-c2ccncc2)c1] | 2-([3,4'-bipyridine]-5-yl)amino)-6-(cis-2-aminocyclohexylamino)-5-fluoronicotinamide |
| Example 4-105 | 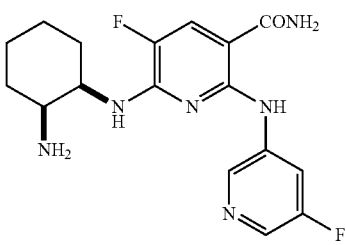 [SMILES: NC(=O)c1cc(F)c(N[C@@H]2CCCC[C@@H]2N)nc1Nc1cncc(F)c1] | 6-(cis-2-aminocyclohexylamino)-5-fluoro-2-((5-fluoropyridin-3-yl)amino)nicotinamide |
| Example 4-106 | 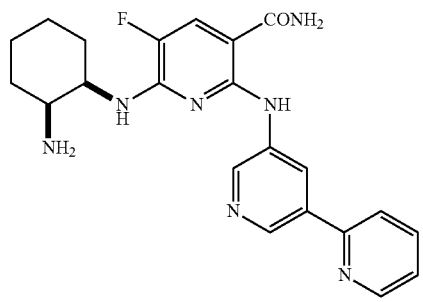 | 2-([2,3'-bipyridine]-5'-yl)amino)-6-(cis-2-aminocyclohexylamino)-5-fluoronicotinamide |
| Example 4-107 | 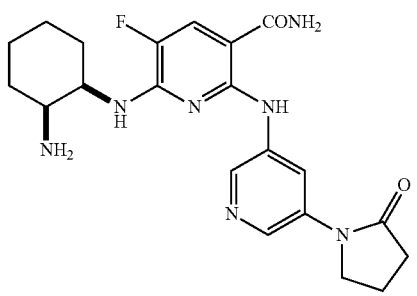 [SMILES: NC(=O)c1cc(F)c(N[C@@H]2CCCC[C@@H]2N)nc1Nc1cncc(N2CCCC2=O)c1] | 6-(cis-2-aminocyclohexylamino)-5-fluoro-2-((5-(2-oxopyrolidin-1-yl)pyridin-3-yl)amino)-nicotinamide |
| Example 4-108 | 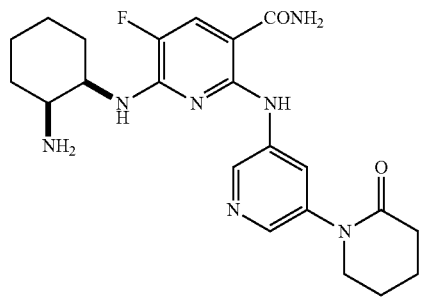 [SMILES: NC(=O)c1cc(F)c(N[C@@H]2CCCC[C@@H]2N)nc1Nc1cncc(N2CCCCC2=O)c1] | 6-(cis-2-aminocyclohexylamino)-5-fluoro-2-((5-(2-oxopiperidine-1-yl)pyridin-3-yl)amino)-nicotinamide |

TABLE 2-continued

| Example 4-109 | 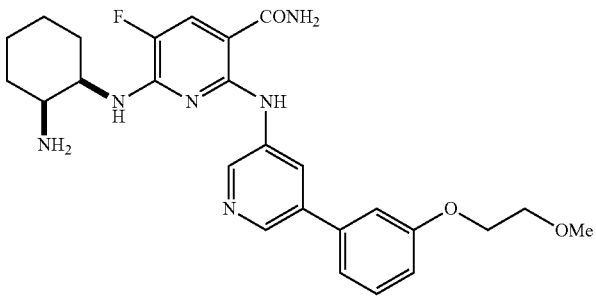 [SMILES: COCCOc1cccc(-c2cncc(Nc3nc(N[C@@H]4CCCC[C@@H]4N)c(F)cc3C(N)=O)c2)c1] | 6-(cis-2-aminocyclohexylamino)-5-fluoro-2-((5-(3-(2-methoxyethoxy)phenyl)pyridin-3-yl)-amino)nicotinamide |
| Example 4-110 | 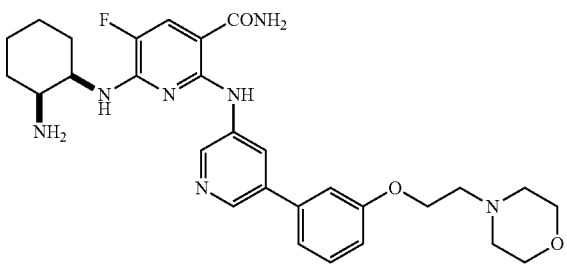 [SMILES: NC(=O)c1cc(F)c(N[C@@H]2CCCC[C@@H]2N)nc1Nc1cncc(-c2cccc(OCCN3CCOCC3)c2)c1] | 6-(cis-2-aminocyclohexylamino)-5-fluoro-2-((5-(3-(2-morpholinoethoxy)phenyl)pyridin-3-yl)amino)nicotinamide |
| Example 4-111 | 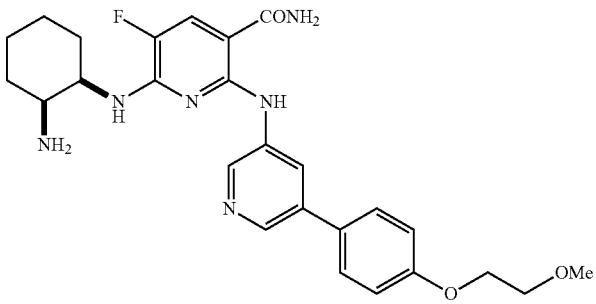 [SMILES: COCCOc1ccc(-c2cncc(Nc3nc(N[C@@H]4CCCC[C@@H]4N)c(F)cc3C(N)=O)c2)cc1] | 6-(cis-2-aminocyclohexylamino)-5-fluoro-2-((5-(4-(2-methoxyethoxy)phenyl)pyridin-3-yl)-amino)nicotinamide |
| Example 4-112 | 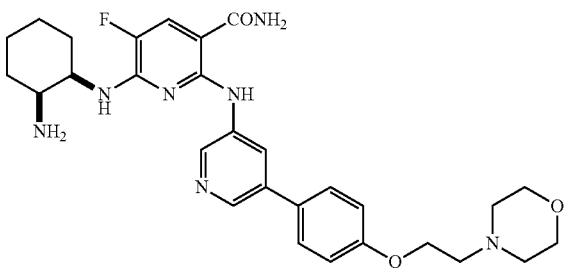 [SMILES: NC(=O)c1cc(F)c(N[C@@H]2CCCC[C@@H]2N)nc1Nc1cncc(-c2ccc(OCCN3CCOCC3)cc2)c1] | 6-(cis-2-aminocyclohexylamino)-5-fluoro-2-((5-(4-(2-morpholinoethoxy)phenyl)pyridin-3-yl)amino)nicotinamide |
| Example 4-113 | 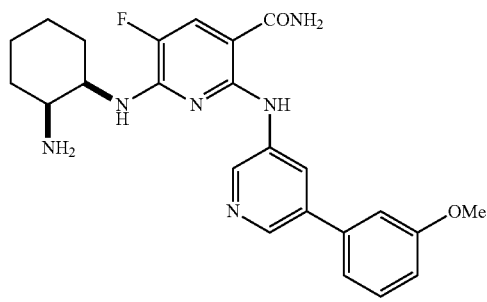 [SMILES: COc1cccc(-c2cncc(Nc3nc(N[C@@H]4CCCC[C@@H]4N)c(F)cc3C(N)=O)c2)c1] | 6-(cis-2-aminocyclohexylamino)-5-fluoro-2-((5-(3-methoxyphenyl)pyridin-3-yl)amino)-nicotinamide |

TABLE 2-continued

| Example | Structure | Name |
|---|---|---|
| Example 4-114 | 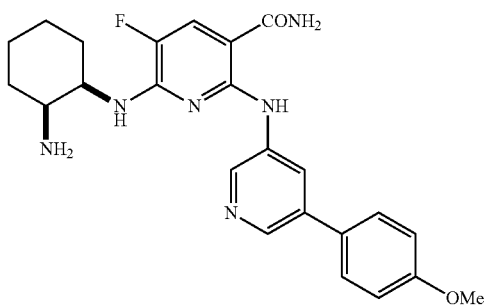 [SMILES: COc1ccc(-c2cncc(Nc3nc(N[C@@H]4CCCC[C@@H]4N)c(F)cc3C(N)=O)c2)cc1] | 6-(cis-2-aminocyclohexylamino)-5-fluoro-2-((5-(4-methoxyphenyl)pyridin-3-yl)amino)-nicotinamide |
| Example 4-115 | 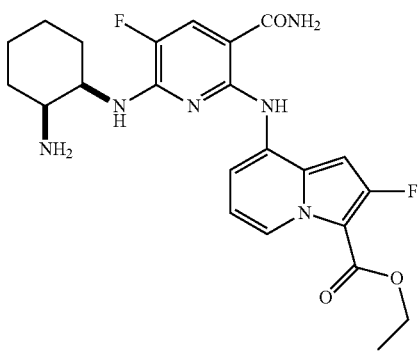 [SMILES: CCOC(=O)c1c(F)cc2c(Nc3nc(N[C@@H]4CCCC[C@@H]4N)c(F)cc3C(N)=O)cccn12] | ethyl 8-(6-(cis-2-aminocyclohexylamino)-3-carbamoyl-5-fluoropyridin-2-yl)amino)-2-fluoroindolizine-3-carboxylate |
| Example 4-116 | 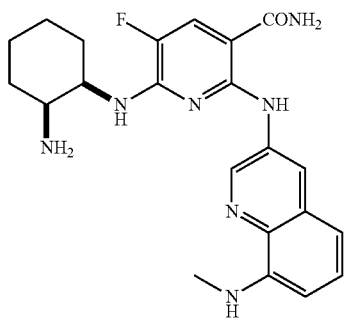 [SMILES: CNc1cccc2cc(Nc3nc(N[C@@H]4CCCC[C@@H]4N)c(F)cc3C(N)=O)cnc12] | 6-(cis-2-aminocyclohexylamino)-5-fluoro-2-((8-(methylamino)quinolin-3-yl)amino)-nicotinamide |
| Example 4-117 | 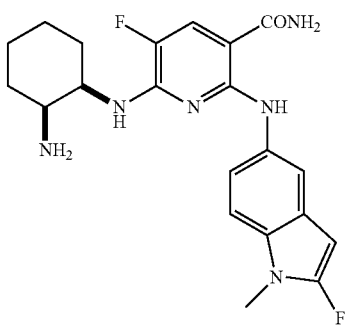 [SMILES: Cn1c(F)cc2cc(Nc3nc(N[C@@H]4CCCC[C@@H]4N)c(F)cc3C(N)=O)ccc21] | 6-(cis-2-aminocyclohexylamino)-5-fluoro-2-((2-fluoro-1-methyl-1H-indol-5-yl)amino)-nicotinamide |
| Example 4-118 | 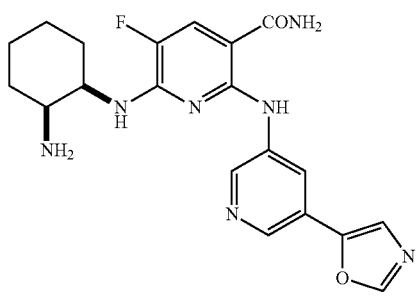 [SMILES: NC(=O)c1cc(F)c(N[C@@H]2CCCC[C@@H]2N)nc1Nc1cncc(-c2cnco2)c1] | 6-(cis-2-aminocyclohexylamino)-5-fluoro-2-((5-(oxazol-5-yl)pyridin-3-yl)amino)-nicotinamide |

TABLE 2-continued

| Example 4-119 | 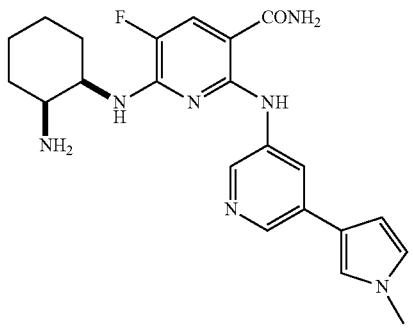 [SMILES: Cn1ccc(-c2cncc(Nc3nc(N[C@@H]4CCCC[C@@H]4N)c(F)cc3C(N)=O)c2)c1] | 6-(cis-2-aminocyclohexylamino)-5-fluoro-2-((5-(1-methyl-1H-pyrrol-3-yl)pyridin-3-yl)amino)nicotinamide |
| Example 4-120 | 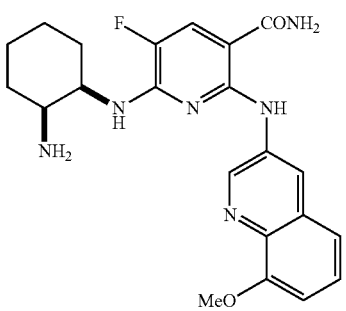 [SMILES: COc1cccc2cc(Nc3nc(N[C@@H]4CCCC[C@@H]4N)c(F)cc3C(N)=O)cnc12] | 6-(cis-2-aminocyclohexylamino)-5-fluoro-2-((8-methoxyquinolin-3-yl)amino)nicotinamide |
| Example 4-121 | 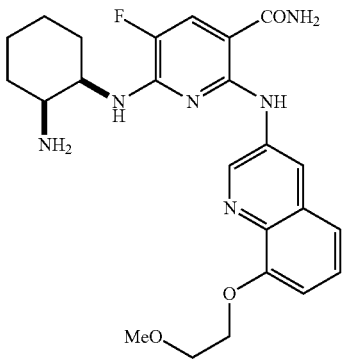 [SMILES: COCCOc1cccc2cc(Nc3nc(N[C@@H]4CCCC[C@@H]4N)c(F)cc3C(N)=O)cnc12] | 6-(cis-2-aminocyclohexylamino)-5-fluoro-2-((8-(2-methoxyethoxy)quinolin-3-yl)amino)-nicotinamide |
| Example 4-122 | 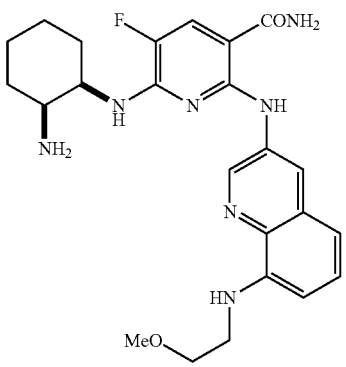 [SMILES: COCCNc1cccc2cc(Nc3nc(N[C@@H]4CCCC[C@@H]4N)c(F)cc3C(N)=O)cnc12] | 6-(cis-2-aminocyclohexylamino)-5-fluoro-2-((8-(2-methoxyethyl)amino)quinolin-3-yl)amino)nicotinamide |

TABLE 2-continued

| Example 4-123 | 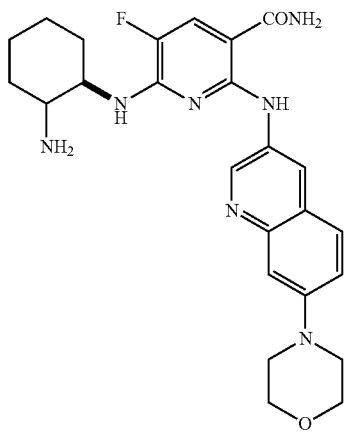 [SMILES: NC(=O)c1cc(F)c(N[C@@H]2CCCCC2N)nc1Nc1cnc2cc(N3CCOCC3)ccc2c1] | 6-(cis-2-aminocyclohexylamino)-5-fluoro-2-((7-morpholinoquinolin-3-yl)amino)-nicotinamide |
| --- | --- | --- |
| Example 4-124 | 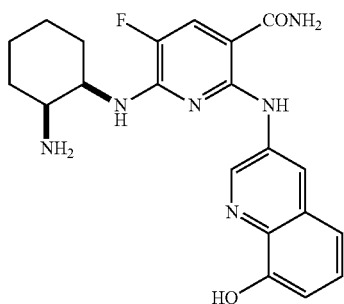 [SMILES: NC(=O)c1cc(F)c(N[C@@H]2CCCC[C@@H]2N)nc1Nc1cnc2c(O)cccc2c1] | 6-(cis-2-aminocyclohexylamino)-5-fluoro-2-((8-hydroxyquinolin-3-yl)amino)nicotinamide |
| Example 4-125 | 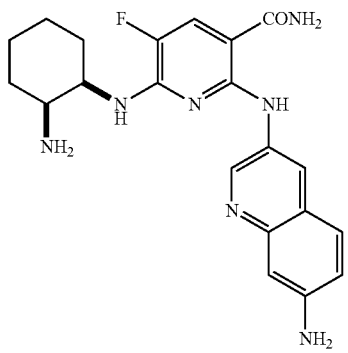 [SMILES: NC(=O)c1cc(F)c(N[C@@H]2CCCC[C@@H]2N)nc1Nc1cnc2cc(N)ccc2c1] | 6-(cis-2-aminocyclohexylamino)-2-((7-aminoquinolin-3-yl)amino)-5-fluoronicotinamide |
| Example 4-126 | 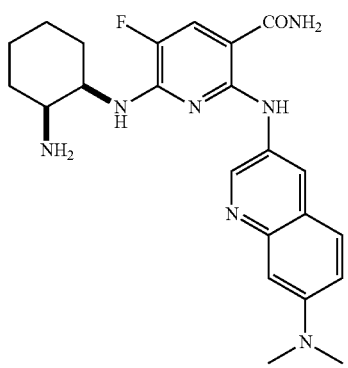 [SMILES: CN(C)c1ccc2cc(Nc3nc(N[C@@H]4CCCC[C@@H]4N)c(F)cc3C(N)=O)cnc2c1] | 6-(cis-2-aminocyclohexylamino)-2-(7-(dimethylamino)quinolin-3-yl)amino)-5-fluoronicotinamide |

TABLE 2-continued

| Example 4-127 | 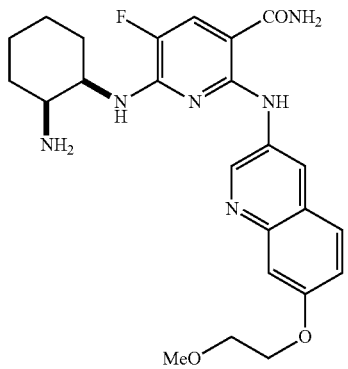 [SMILES: COCCOc1ccc2cc(Nc3nc(N[C@@H]4CCCC[C@@H]4N)c(F)cc3C(N)=O)cnc2c1] | 6-(cis-2-aminocyclohexylamino)-5-fluoro-2-((7-(2-methoxyethoxy)quinolin-3-yl)amino)-nicotinamide |
| Example 4-128 | 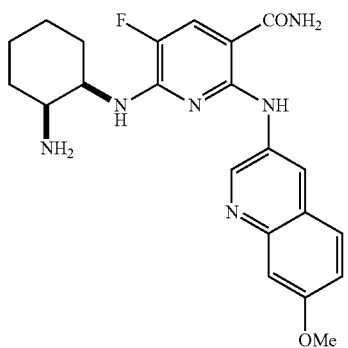 [SMILES: COc1ccc2cc(Nc3nc(N[C@@H]4CCCC[C@@H]4N)c(F)cc3C(N)=O)cnc2c1] | 6-(cis-2-aminocyclohexylamino)-5-fluoro-2-((7-methoxyquinolin-3-yl)amino)nicotinamide |
| Example 4-129 | 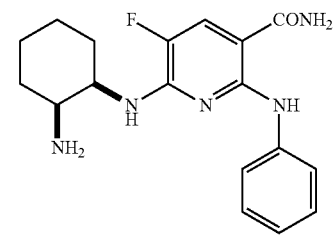 [SMILES: NC(=O)c1cc(F)c(N[C@@H]2CCCC[C@@H]2N)nc1Nc1ccccc1] | 6-(cis-2-aminocyclohexylamino)-5-fluoro-2-(phenylamino)nicotinamide |
| Example 4-130 | 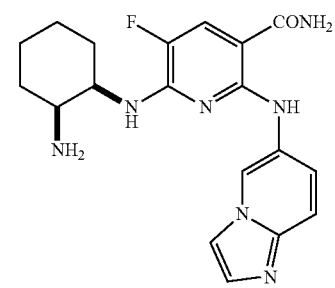 [SMILES: NC(=O)c1cc(F)c(N[C@@H]2CCCC[C@@H]2N)nc1Nc1ccc2nccn2c1] | 6-(cis-2-aminocyclohexylamino)-5-fluoro-2-((imidazo[1,2-a]pyridin-6-yl)amino)-nicotinamide |
| Example 4-131 | 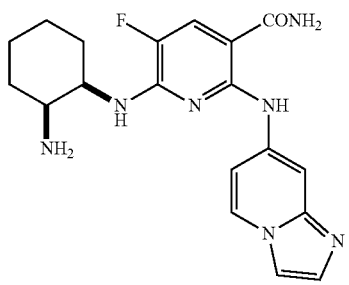 [SMILES: NC(=O)c1cc(F)c(N[C@@H]2CCCC[C@@H]2N)nc1Nc1ccn2ccnc2c1] | 6-(cis-2-aminocyclohexylamino)-5-fluoro-2-((imidazo[1,2-a]pyridin-7-yl)amino)-nicotinamide |

TABLE 2-continued

| Example 4-132 | 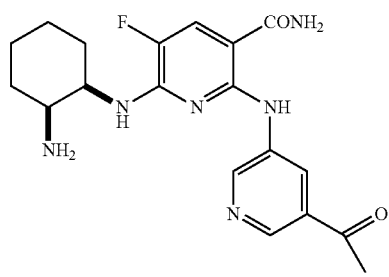 [SMILES: CC(=O)c1cncc(Nc2nc(N[C@@H]3CCCC[C@@H]3N)c(F)cc2C(N)=O)c1] | 2-((5-acetylpyridin-3-yl)amino)-6-(cis-2-aminocyclohexylamino)-5-fluoronicotinamide |
| --- | --- | --- |
| Example 4-133 | 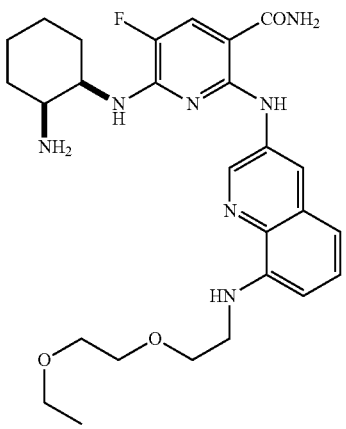 [SMILES: CCOCCOCCNc1cccc2cc(Nc3nc(N[C@@H]4CCCC[C@@H]4N)c(F)cc3C(N)=O)cnc12] | 6-(cis-2-aminocyclohexylamino)-2-(8-(2-(2-ethoxyethoxy)ethylamino)quinolin-3-yl)amino)-5-fluoronicotinamide |
| Example 4-134 | 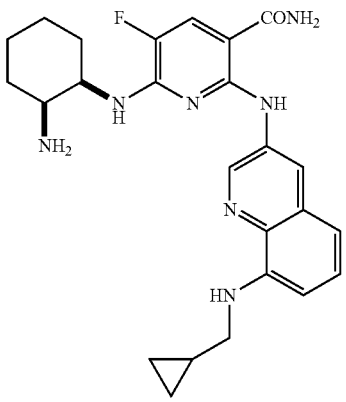 [SMILES: NC(=O)c1cc(F)c(N[C@@H]2CCCC[C@@H]2N)nc1Nc1cnc2c(NCC3CC3)cccc2c1] | 6-(cis-2-aminocyclohexylamino)-2-(8-(cyclopropylmethylamino)quinolin-3-yl)amino)-5-fluoronicotinamide |
| Example 4-135 | 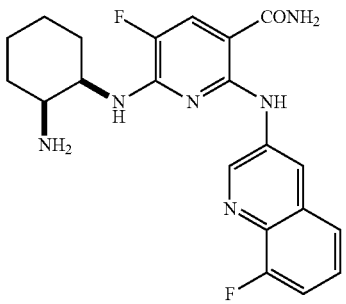 [SMILES: NC(=O)c1cc(F)c(N[C@@H]2CCCC[C@@H]2N)nc1Nc1cnc2c(F)cccc2c1] | 6-(cis-2-aminocyclohexylamino)-5-fluoro-2-((8-fluoroquinolin-3-yl)amino)nicotinamide |

TABLE 2-continued

| Example 4-136 | 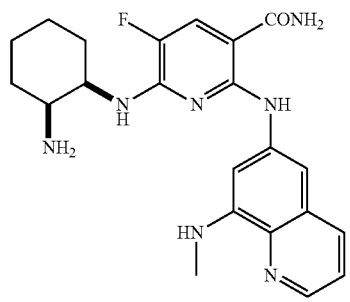 [SMILES: CNc1cc(Nc2nc(N[C@@H]3CCCC[C@@H]3N)c(F)cc2C(N)=O)cc2cccnc12] | 6-(cis-2-aminocyclohexylamino)-5-fluoro-2-((8-(methylamino)quinolin-6-yl)amino)-nicotinamide |
| Example 4-137 | 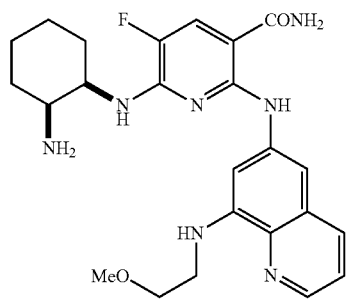 [SMILES: COCCNc1cc(Nc2nc(N[C@@H]3CCCC[C@@H]3N)c(F)cc2C(N)=O)cc2cccnc12] | 6-(cis-2-aminocyclohexylamino)-5-fluoro-2-((8-(2-methoxyethylamino)quinolin-6-yl)-amino)nicotinamide |
| Example 4-138 | 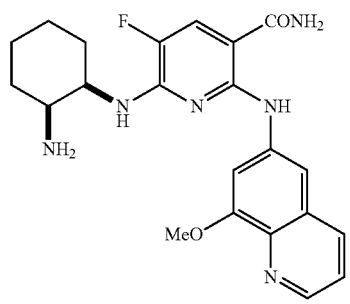 [SMILES: COc1cc(Nc2nc(N[C@@H]3CCCC[C@@H]3N)c(F)cc2C(N)=O)cc2cccnc12] | 6-(cis-2-aminocyclohexylamino)-5-fluoro-2-((8-methoxyquinolin-6-yl)amino)nicotinamide |
| Example 4-139 | 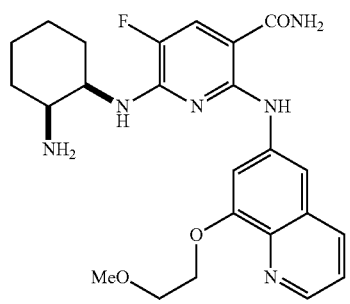 [SMILES: COCCOc1cc(Nc2nc(N[C@@H]3CCCC[C@@H]3N)c(F)cc2C(N)=O)cc2cccnc12] | 6-(cis-2-aminocyclohexylamino)-5-fluoro-2-((8-(2-methoxyethoxy)quinolin-6-yl)amino)-nicotinamide |
| Example 4-140 | 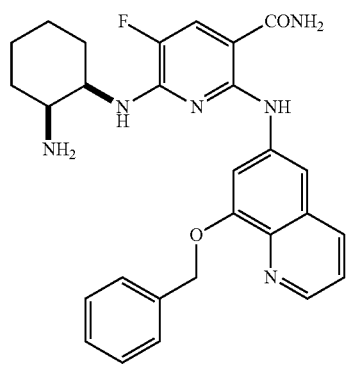 [SMILES: NC(=O)c1cc(F)c(N[C@@H]2CCCC[C@@H]2N)nc1Nc1cc(OCc2ccccc2)c2ncccc2c1] | 6-(cis-2-aminocyclohexylamino)-2-((8-(benzyloxy)quinolin-6-yl)amino)-5-fluoronicotinamide |

TABLE 2-continued

| Example | | |
|---|---|---|
| Example 4-141 | 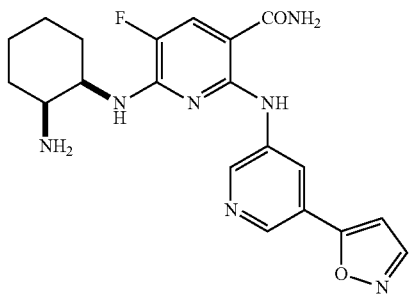 [SMILES: NC(=O)c1cc(F)c(N[C@@H]2CCCC[C@@H]2N)nc1Nc1cncc(-c2ccno2)c1] | 6-(cis-2-aminocyclohexylamino)-5-fluoro-2-((5-(isoxazol-5-yl)pyridin-3-yl)amino)-nicotinamide |
| Example 4-142 | 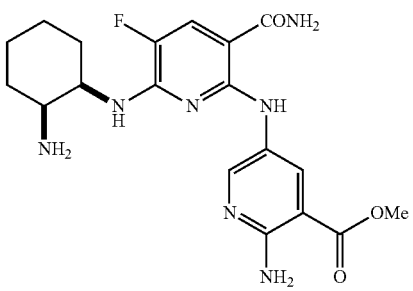 [SMILES: COC(=O)c1cc(Nc2nc(N[C@@H]3CCCC[C@@H]3N)c(F)cc2C(N)=O)cnc1N] | methyl 2-amino-5-((6-(cis-2-aminocyclohexylamino)-3-carbamoyl-5-fluoropyridin-2-yl)amino)nicotinate |
| Example 4-143 | 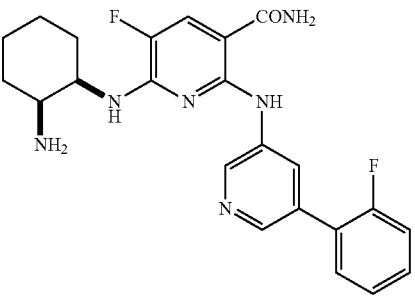 [SMILES: NC(=O)c1cc(F)c(N[C@@H]2CCCC[C@@H]2N)nc1Nc1cncc(-c2ccccc2F)c1] | 6-(cis-2-aminocyclohexylamino)-5-fluoro-2-((5-(2-fluorophenyl)pyridin-3-yl)amino)-nicotinamide |
| Example 4-144 | 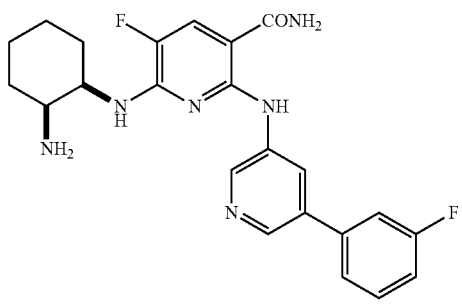 [SMILES: NC(=O)c1cc(F)c(N[C@@H]2CCCC[C@@H]2N)nc1Nc1cncc(-c2cccc(F)c2)c1] | 6-(cis-2-aminocyclohexylamino)-5-fluoro-2-((5-(3-fluorophenyl)pyridin-3-yl)amino)-nicotinamide |
| Example 4-145 | 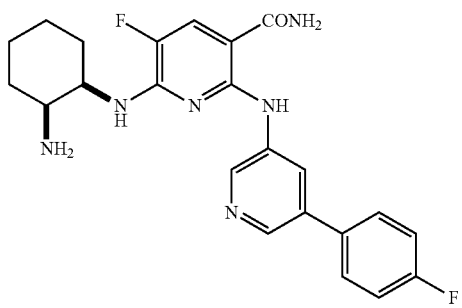 [SMILES: NC(=O)c1cc(F)c(N[C@@H]2CCCC[C@@H]2N)nc1Nc1cncc(-c2ccc(F)cc2)c1] | 6-(cis-2-aminocyclohexylamino)-5-fluoro-2-((5-(4-fluorophenyl)pyridin-3-yl)amino)-nicotinamide |

TABLE 2-continued

| Example | | |
|---|---|---|
| Example 4-146 | 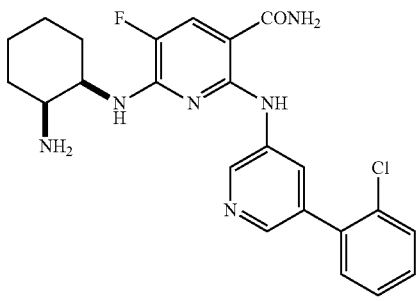 [SMILES: NC(=O)c1cc(F)c(N[C@@H]2CCCC[C@@H]2N)nc1Nc1cncc(-c2ccccc2Cl)c1] | 6-(cis-2-aminocyclohexylamino)-2-((5-(2-chlorophenyl)pyridin-3-yl)amino)-5-fluoronicotinamide |
| Example 4-147 | 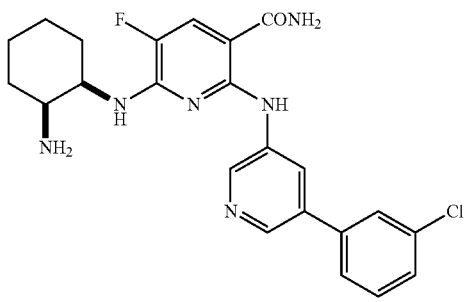 [SMILES: NC(=O)c1cc(F)c(N[C@@H]2CCCC[C@@H]2N)nc1Nc1cncc(-c2cccc(Cl)c2)c1] | 6-(cis-2-aminocyclohexylamino)-2-((5-(3-chlorophenyl)pyridin-3-yl)amino)-5-fluoronicotinamide |
| Example 4-148 | 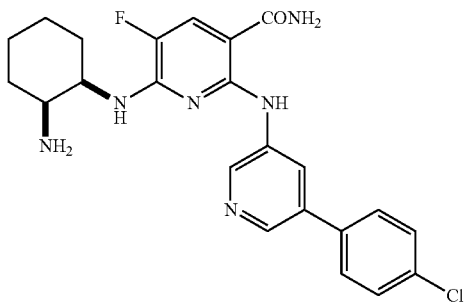 [SMILES: NC(=O)c1cc(F)c(N[C@@H]2CCCC[C@@H]2N)nc1Nc1cncc(-c2ccc(Cl)cc2)c1] | 6-(cis-2-aminocyclohexylamino)-2-((5-(4-chlorophenyl)pyridin-3-yl)amino)-5-fluoronicotinamide |
| Example 4-149 | 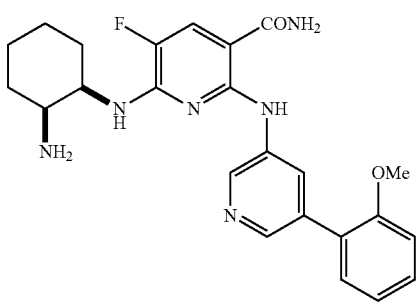 [SMILES: COc1ccccc1-c1cncc(Nc2nc(N[C@@H]3CCCC[C@@H]3N)c(F)cc2C(N)=O)c1] | 6-(cis-2-aminocyclohexylamino)-5-fluoro-2-((5-(2-methoxyphenyl)pyridin-3-yl)amino)-nicotinamide |
| Example 4-150 | 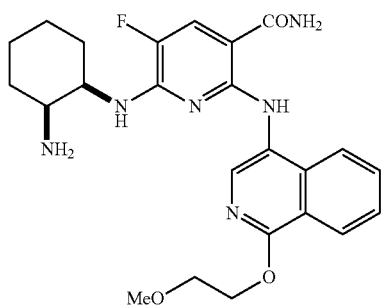 [SMILES: COCCOc1ncc(Nc2nc(N[C@@H]3CCCC[C@@H]3N)c(F)cc2C(N)=O)c2ccccc12] | 6-(cis-2-aminocyclohexylamino)-5-fluoro-2-((1-(2-methoxyethoxy)isoquinolin-4-yl)amino)-nicotinamide |

TABLE 2-continued

| Example | | |
|---|---|---|
| Example 4-151 | 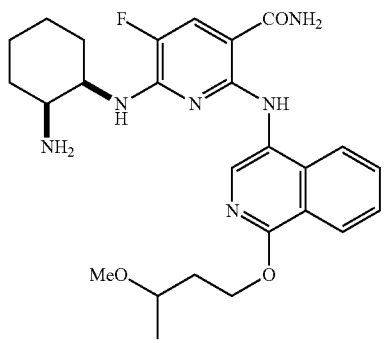 [SMILES: COC(C)CCOc1ncc(Nc2nc(N[C@@H]3CCCC[C@@H]3N)c(F)cc2C(N)=O)c2ccccc12] | 6-(cis-2-aminocyclohexylamino)-5-fluoro-2-((1-(3-methoxybutoxy)isoquinolin-4-yl)amino)-nicotinamide |
| Example 4-152 | 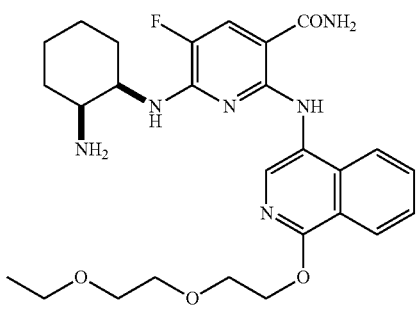 [SMILES: CCOCCOCCOc1ncc(Nc2nc(N[C@@H]3CCCC[C@@H]3N)c(F)cc2C(N)=O)c2ccccc12] | 6-(cis-2-aminocyclohexylamino)-2-((1-(2-(2-ethoxyethoxy)ethoxy)isoquinolin-4-yl)amino)-5-fluoronicotinamide |
| Example 4-153 | 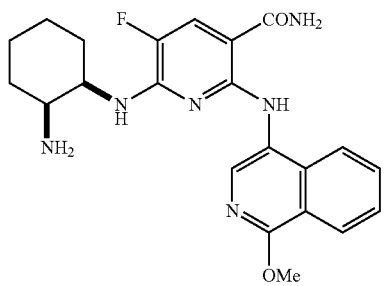 [SMILES: COc1ncc(Nc2nc(N[C@@H]3CCCC[C@@H]3N)c(F)cc2C(N)=O)c2ccccc12] | 6-(cis-2-aminocyclohexylamino)-5-fluoro-2-((1-methoxyisoquinolin-4-yl)amino)-nicotinamide |
| Example 4-154 | 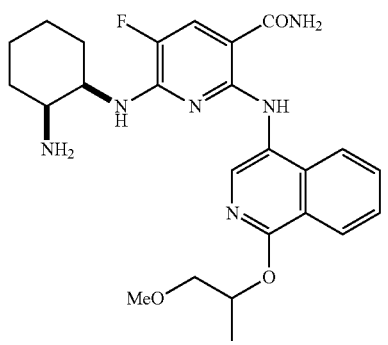 [SMILES: COCC(C)Oc1ncc(Nc2nc(N[C@@H]3CCCC[C@@H]3N)c(F)cc2C(N)=O)c2ccccc12] | 6-(cis-2-aminocyclohexylamino)-5-fluoro-2-((1-((1-methoxypropan-2-yl)oxy)isoquinolin-4-yl)amino)nicotinamide |
| Example 4-155 | 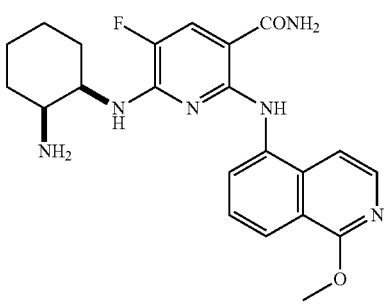 [SMILES: COc1nccc2c(Nc3nc(N[C@@H]4CCCC[C@@H]4N)c(F)cc3C(N)=O)cccc12] | 6-(cis-2-aminocyclohexylamino)-5-fluoro-2-((1-methoxyisoquinolin-5-yl)amino)-nicotinamide |

TABLE 2-continued

| Example 4-156 | 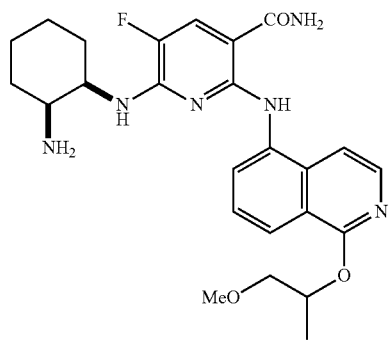 [SMILES: COCC(C)Oc1nccc2c(Nc3nc(N[C@@H]4CCCC[C@@H]4N)c(F)cc3C(N)=O)cccc12] | 6-(cis-2-aminocyclohexylamino)-5-fluoro-2-((1-((1-methoxypropan-2-yl)oxy)isoquinolin-5-yl)amino)nicotinamide |
| --- | --- | --- |
| Example 4-157 | 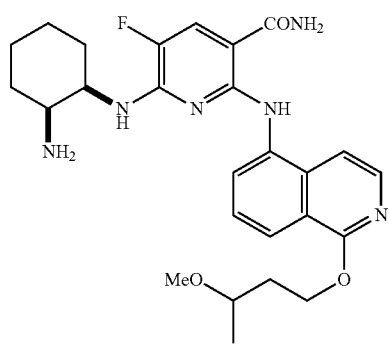 [SMILES: COC(C)CCOc1nccc2c(Nc3nc(N[C@@H]4CCCC[C@@H]4N)c(F)cc3C(N)=O)cccc12] | 6-(cis-2-aminocyclohexylamino)-5-fluoro-2-((1-(3-methoxybutoxy)isoquinolin-5-yl)amino)-nicotinamide |
| Example 4-158 | 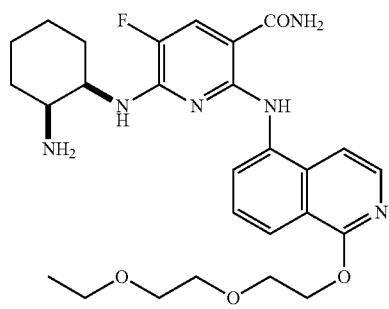 [SMILES: CCOCCOCCOc1nccc2c(Nc3nc(N[C@@H]4CCCC[C@@H]4N)c(F)cc3C(N)=O)cccc12] | 6-(cis-2-aminocyclohexylamino)-2-((1-(2-(2-ethoxyethoxy)ethoxy)isoquinolin-5-yl)amino)-5-fluoronicotinamide |
| Example 4-159 | 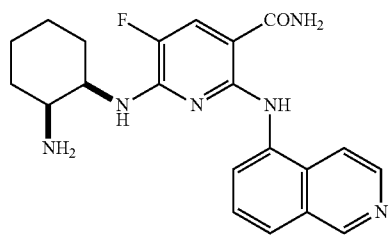 [SMILES: NC(=O)c1cc(F)c(N[C@@H]2CCCC[C@@H]2N)nc1Nc1cccc2cnccc12] | 6-(cis-2-aminocyclohexylamino)-5-fluoro-2-((isoquinolin-5-yl)amino)nicotinamide |
| Example 4-160 | 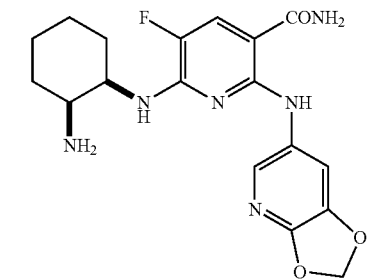 [SMILES: NC(=O)c1cc(F)c(N[C@@H]2CCCC[C@@H]2N)nc1Nc1cnc2c(c1)OCO2] | 2-([1,3]dioxolo[4,5-b]pyridin-6-yl)amino)-6-(cis-6-aminocyclohexylamino)-5-fluoronicotinamide |

TABLE 2-continued

| Example 4-161 | 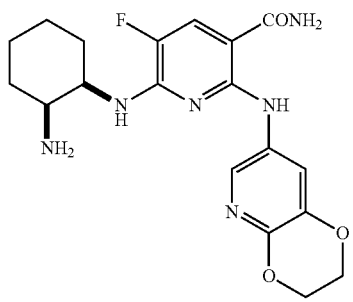 [SMILES: NC(=O)c1cc(F)c(N[C@@H]2CCCC[C@@H]2N)nc1Nc1cnc2c(c1)OCCO2] | 6-(cis-2-aminocyclohexylamino)-2-((2,3-dihydro-[1,4]dioxino[2,3-b]pyridin-7-yl)amino)-5-fluoronicotinamide |
| Example 4-162 | 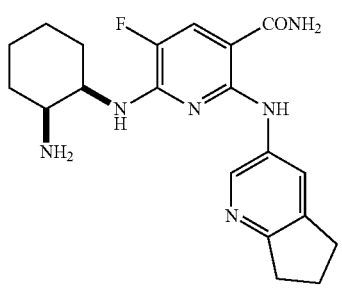 [SMILES: NC(=O)c1cc(F)c(N[C@@H]2CCCC[C@@H]2N)nc1Nc1cnc2c(c1)CCC2] | 6-(cis-2-aminocyclohexylamino)-2-((6,7-dihydro-5H-cyclopenta[b]pyridin-3-yl)amino)-5-fluoronicotinamide |
| Example 4-163 | 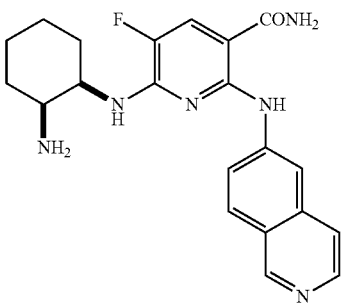 [SMILES: NC(=O)c1cc(F)c(N[C@@H]2CCCC[C@@H]2N)nc1Nc1ccc2cnccc2c1] | 6-(cis-2-aminocyclohexylamino)-5-fluoro-2-((isoquinolin-6-yl)amino)nicotinamide |
| Example 4-164 | 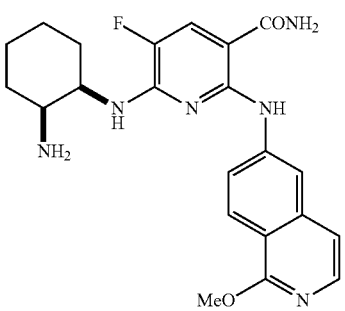 | 6-(cis-2-aminocyclohexylamino)-5-fluoro-2-((1-methoxyisoquinolin-6-yl)amino)-nicotinamide |
| Example 4-165 | 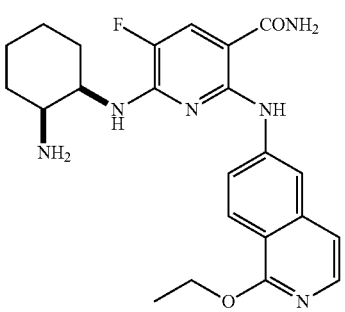 [SMILES: CCOc1nccc2cc(Nc3nc(N[C@@H]4CCCC[C@@H]4N)c(F)cc3C(N)=O)ccc12] | 6-(cis-2-aminocyclohexylamino)-2-((1-ethoxyisoquinolin-6-yl)amino)-5-fluoronicotinamide |

TABLE 2-continued

| Example 4-166 | 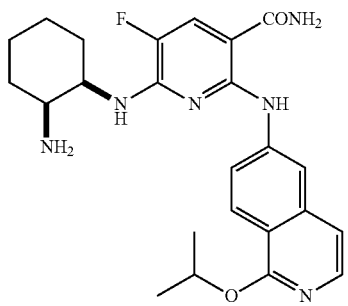 [SMILES: CC(C)Oc1nccc2cc(Nc3nc(N[C@@H]4CCCC[C@@H]4N)c(F)cc3C(N)=O)ccc12] | 6-(cis-2-aminocyclohexylamino)-5-fluoro-2-((1-isopropoxyisoquinolin-6-yl)amino)-nicotinamide |
| Example 4-167 | 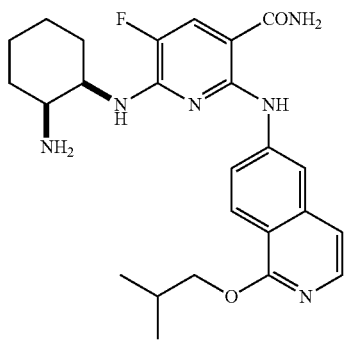 [SMILES: CC(C)COc1nccc2cc(Nc3nc(N[C@@H]4CCCC[C@@H]4N)c(F)cc3C(N)=O)ccc12] | 6-(cis-2-aminocyclohexylamino)-5-fluoro-2-((1-isobutoxyisoquinolin-6-yl)amino)-nicotinamide |
| Example 4-168 | 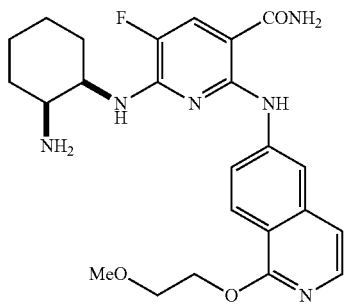 [SMILES: COCCOc1nccc2cc(Nc3nc(N[C@@H]4CCCC[C@@H]4N)c(F)cc3C(N)=O)ccc12] | 6-(cis-2-aminocyclohexylamino)-5-fluoro-2-((1-(2-methoxyethoxy)isoquinolin-6-yl)amino)-nicotinamide |
| Example 4-169 | 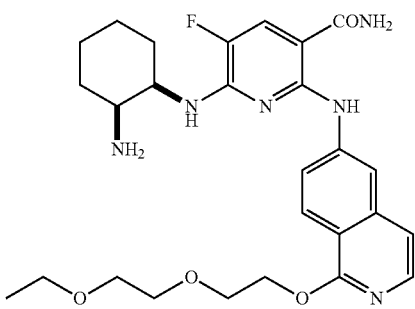 [SMILES: CCOCCOCCOc1nccc2cc(Nc3nc(N[C@@H]4CCCC[C@@H]4N)c(F)cc3C(N)=O)ccc12] | 6-(cis-2-aminocyclohexylamino)-2-((1-(2-(2-ethoxyethoxy)ethoxy)isoquinolin-6-yl)amino)-5-fluoronicotinamide |
| Example 4-170 | 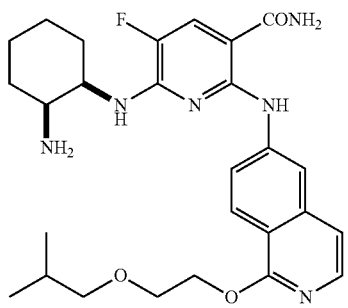 [SMILES: CC(C)COCCOc1nccc2cc(Nc3nc(N[C@@H]4CCCC[C@@H]4N)c(F)cc3C(N)=O)ccc12] | 6-(cis-2-aminocyclohexylamino)-5-fluoro-2-((1-(2-isobutoxyethoxy)isoquinolin-6-yl)amino)-nicotinamide |

TABLE 2-continued

| Example 4-171 | 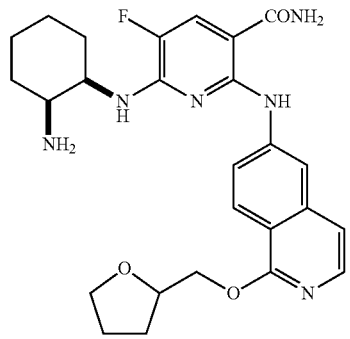 [SMILES: NC(=O)c1cc(F)c(N[C@@H]2CCCC[C@@H]2N)nc1Nc1ccc2c(OCC3CCCO3)nccc2c1] | 6-(cis-2-aminocyclohexylamino)-5-fluoro-2-((1-((tetrahydrofuran-2-yl)-methoxy)isoquinolin-6-yl)amino)nicotinamide |
| --- | --- | --- |
| Example 4-172 | 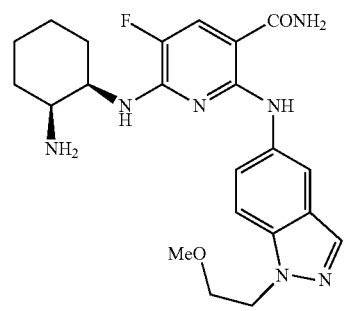 [SMILES: COCCn1ncc2cc(Nc3nc(N[C@@H]4CCCC[C@@H]4N)c(F)cc3C(N)=O)ccc21] | 6-((1R,2S)-2-aminocyclohexylamino)-5-fluoro-2-((1-(2-methoxyethyl)-1H-indazol-5-yl)-amino)nicotinamide |
| Example 4-173 | 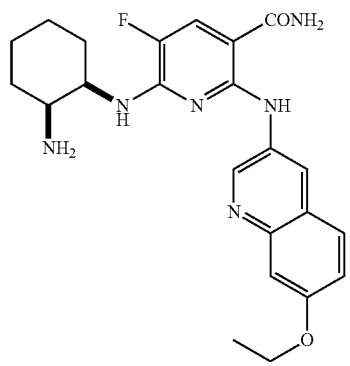 | 6-(cis-2-aminocyclohexylamino)-2-((7-ethoxyquinolin-3-yl)amino)-5-fluoronicotinamide |
| Example 4-174 | 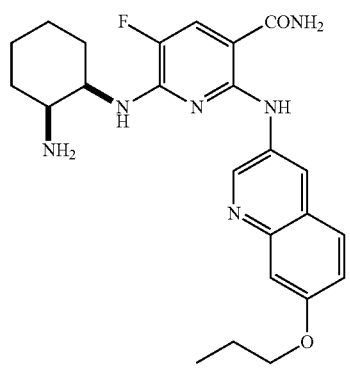 | 6-(cis-2-aminocyclohexylamino)-5-fluoro-2-((7-propoxyquinolin-3-yl)amino)nicotinamide |

TABLE 2-continued

| Example 4-175 | 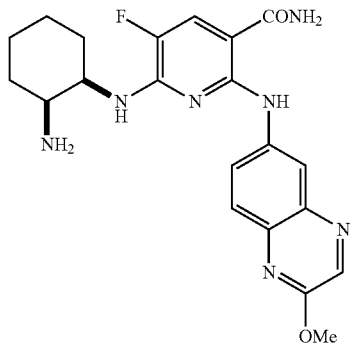 [SMILES: COc1cnc2cc(Nc3nc(N[C@@H]4CCCC[C@@H]4N)c(F)cc3C(N)=O)ccc2n1] | 6-(cis-2-aminocyclohexylamino)-5-fluoro-2-((2-methoxyquinolin-6-yl)amino)-nicotinamide |
| Example 4-176 | 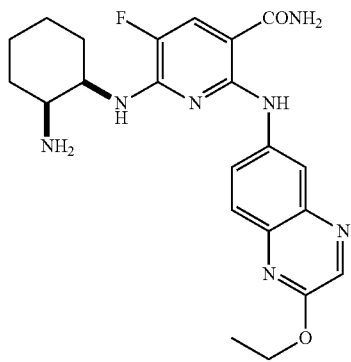 [SMILES: CCOc1cnc2cc(Nc3nc(N[C@@H]4CCCC[C@@H]4N)c(F)cc3C(N)=O)ccc2n1] | 6-(cis-2-aminocyclohexylamino)-2-((2-ethoxyquinoxalin-6-yl)amino)-5-fluoronicotinamide |
| Example 4-177 | 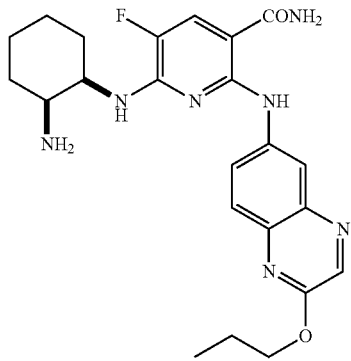 [SMILES: CCCOc1cnc2cc(Nc3nc(N[C@@H]4CCCC[C@@H]4N)c(F)cc3C(N)=O)ccc2n1] | 6-(cis-2-aminocyclohexylamino)-5-fluoro-2-((2-propoxyquinoxalin-6-yl)amino)nicotinamide |
| Example 4-178 | 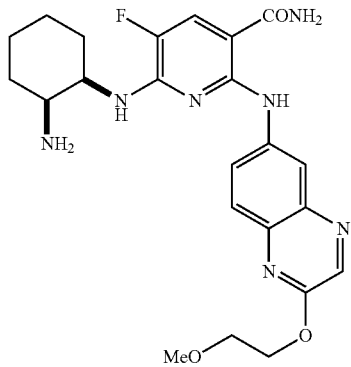 [SMILES: COCCOc1cnc2cc(Nc3nc(N[C@@H]4CCCC[C@@H]4N)c(F)cc3C(N)=O)ccc2n1] | 6-(cis-2-aminocyclohexylamino)-5-fluoro-2-((2-(2-methoxyethoxy)quinoxalin-6-yl)amino)-nicotinamide |

TABLE 2-continued

| Example 4-179 | 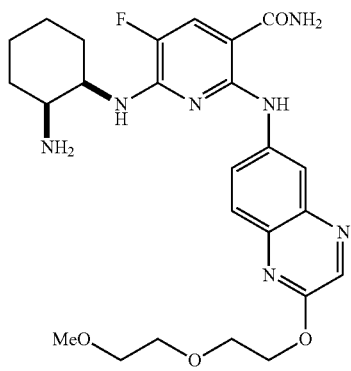 [SMILES: COCCOCCOc1cnc2cc(Nc3nc(N[C@@H]4CCCC[C@@H]4N)c(F)cc3C(N)=O)ccc2n1] | 6-(cis-2-aminocyclohexylamino)-5-fluoro-2-((2-(2-(2-methoxyethoxy)ethoxy)quinoxalin-6-yl)amino)nicotinamide |
| Example 4-180 | 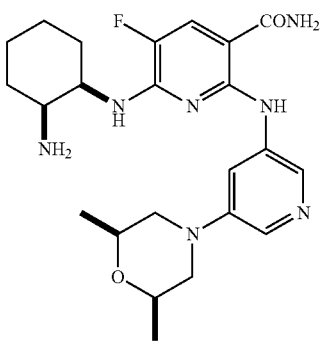 [SMILES: C[C@@H]1CN(c2cncc(Nc3nc(N[C@@H]4CCCC[C@@H]4N)c(F)cc3C(N)=O)c2)C[C@H](C)O1] | 6-(cis-2-aminocyclohexylamino)-2-((5-cis-2,6-dimethylmorpholino)pyridin-3-yl)amino)-5-fluoronicotinamide |
| Example 4-181 | 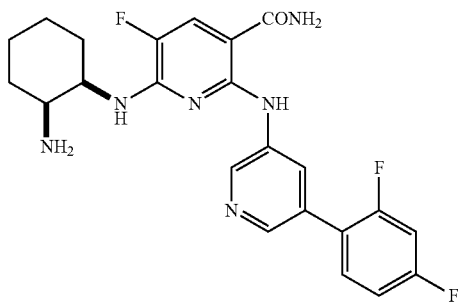 | 6-(cis-2-aminocyclohexylamino)-2-((5-(2,4-difluorophenyl)pyridin-3-yl)amino)-5-fluoronicotinamide |
| Example 4-182 | 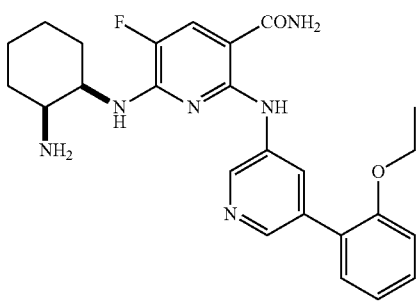 [SMILES: CCOc1ccccc1-c1cncc(Nc2nc(N[C@@H]3CCCC[C@@H]3N)c(F)cc2C(N)=O)c1] | 6-(cis-2-aminocyclohexylamino)-2-((5-(2-ethoxyphenyl)pyridin-3-yl)amino)-5-fluoronicotinamide |
| Example 4-183 | 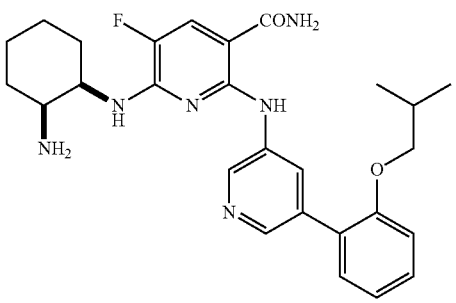 [SMILES: CC(C)COc1ccccc1-c1cncc(Nc2nc(N[C@@H]3CCCC[C@@H]3N)c(F)cc2C(N)=O)c1] | 6-(cis-2-aminocyclohexylamino)-5-fluoro-2-((5-(2-isobutoxyphenyl)pyridin-3-yl)amino)-nicotinamide |

TABLE 2-continued

| Example 4-184 | 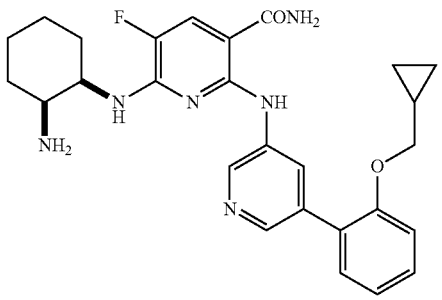 [SMILES: NC(=O)c1cc(F)c(N[C@@H]2CCCC[C@@H]2N)nc1Nc1cncc(-c2ccccc2OCC2CC2)c1] | 6-(cis-2-aminocyclohexylamino)--2-((5-(2-(cyclopropylmethoxy)phenyl)pyridin-3-yl)amino)-5-fluoronicotinamide |
| Example 4-185 | 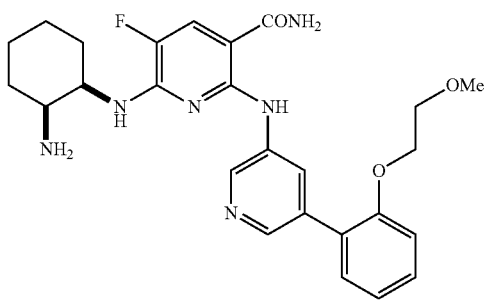 [SMILES: COCCOc1ccccc1-c1cncc(Nc2nc(N[C@@H]3CCCC[C@@H]3N)c(F)cc2C(N)=O)c1] | 6-(cis-2-aminocyclohexylamino)-5-fluoro-2-((5-(2-(2-methoxyethoxy)phenyl)pyridin-3-yl)amino)nicotinamide |
| Example 4-186 | 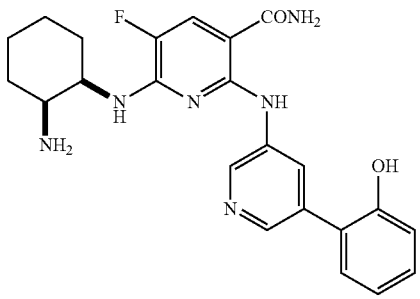 | 6-(cis-2-aminocyclohexylamino)-5-fluoro-2-((5-(2-hydroxyphenyl)pyridin-3-yl)amino)nicotinamide |
| Example 4-187 | 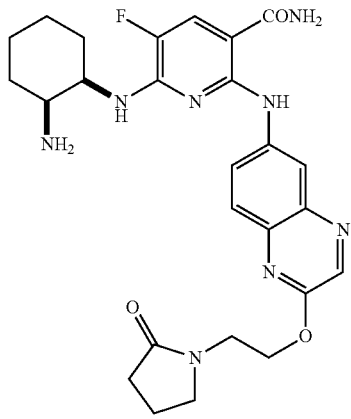 [SMILES: NC(=O)c1cc(F)c(N[C@@H]2CCCC[C@@H]2N)nc1Nc1ccc2nc(OCCN3CCCC3=O)cnc2c1] | 6-(cis-2-aminocyclohexylamino)-5-fluoro-2-((2-(2-(2-oxopyridin-1-yl)ethoxy)quinoxalin-6-yl)amino)nicotinamide |
| Example 4-188 | 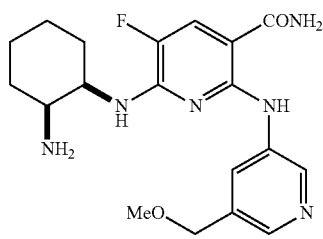 [SMILES: COCc1cncc(Nc2nc(N[C@@H]3CCCC[C@@H]3N)c(F)cc2C(N)=O)c1] | 6-(cis-2-aminocyclohexylamino)-5-fluoro-2-((5-(methoxymethyl)pyridin-3-yl)amino)nicotinamide |

TABLE 2-continued

| | | |
|---|---|---|
| Example 4-189 | 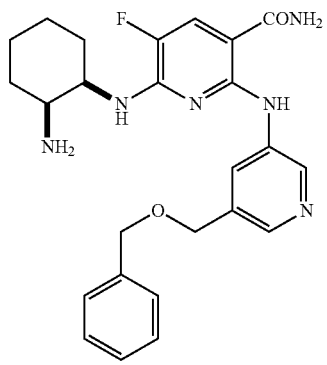 [SMILES: NC(=O)c1cc(F)c(N[C@@H]2CCCC[C@@H]2N)nc1Nc1cncc(COCc2ccccc2)c1] | 6-(cis-2-aminocyclohexylamino)-2-((5-((benzyloxy)methyl)pyridin-3-yl)amino)-5-fluoronicotinamide |
| Example 4-190 | 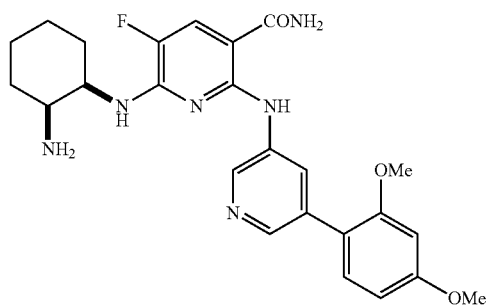 [SMILES: COc1ccc(-c2cncc(Nc3nc(N[C@@H]4CCCC[C@@H]4N)c(F)cc3C(N)=O)c2)c(OC)c1] | 6-(cis-2-aminocyclohexylamino)-2-((5-(2,4-dimethoxyphenyl)pyridin-3-yl)amino)-5-fluoronicotinamide |
| Example 4-191 | 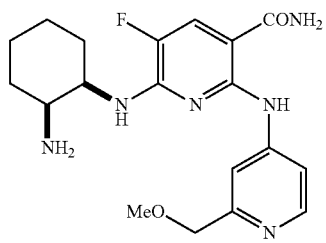 [SMILES: COCc1cc(Nc2nc(N[C@@H]3CCCC[C@@H]3N)c(F)cc2C(N)=O)ccn1] | 6-(cis-2-aminocyclohexylamino)-5-fluoro-2-((2-(methoxymethyl)pyridin-4-yl)amino)nicotinamide |
| Example 4-192 | 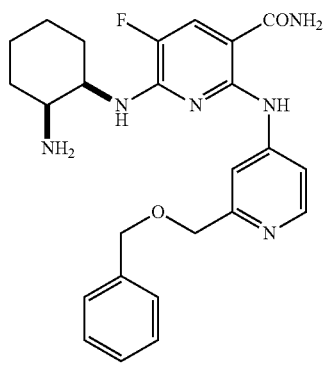 [SMILES: NC(=O)c1cc(F)c(N[C@@H]2CCCC[C@@H]2N)nc1Nc1ccnc(COCc2ccccc2)c1] | 6-(cis-2-aminocyclohexylamino)-2-((2-((benzyloxy)methyl)pyridin-4-yl)amino)-5-fluoronicotinamide |
| Example 4-193 | 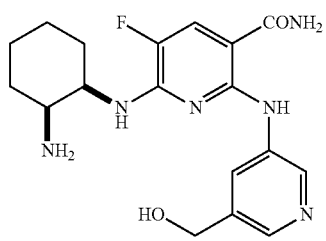 [SMILES: NC(=O)c1cc(F)c(N[C@@H]2CCCC[C@@H]2N)nc1Nc1cncc(CO)c1] | 6-(cis-2-aminocyclohexylamino)-5-fluoro-2-((5-(hydroxymethyl)pyridin-3-yl)amino)nicotinamide |

TABLE 2-continued

| Example | | |
|---|---|---|
| Example 4-194 | 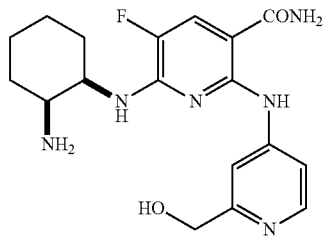 [SMILES: NC(=O)c1cc(F)c(N[C@@H]2CCCC[C@@H]2N)nc1Nc1ccnc(CO)c1] | 6-(cis-2-aminocyclohexylamino)-5-fluoro-2-((2-(hydroxymethyl)pyridin-4-yl)amino)nicotinamide |
| Example 4-195 | 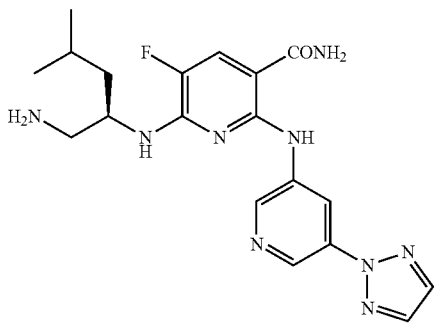 [SMILES: CC(C)C[C@H](CN)Nc1nc(Nc2cncc(-n3nccn3)c2)c(C(N)=O)cc1F] | (R)-2-((5-(2H-1,2,3-triazol-2-yl)pyridin-3-yl)amino)-6-((1-amino-4-methylpentan-2-yl)amino)-5-fluoronicotinamide |
| Example 4-196 | 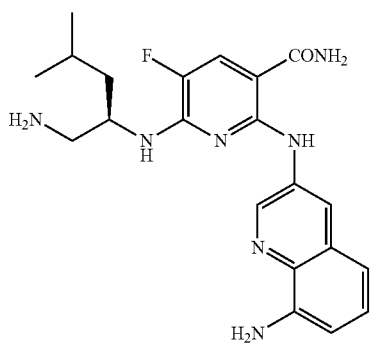 [SMILES: CC(C)C[C@H](CN)Nc1nc(Nc2cnc3c(N)cccc3c2)c(C(N)=O)cc1F] | (R)-6-((1-amino-4-methylpentan-2-yl)amino)-2-((8-aminoquinolin-3-yl)amino)-5-fluoronicotinamide |
| Example 4-197 | 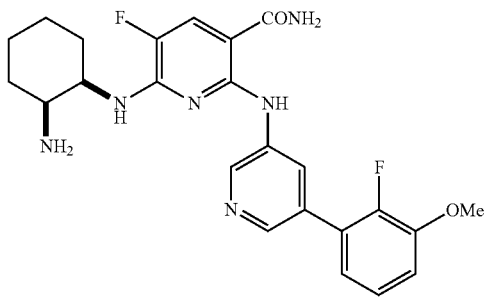 [SMILES: COc1cccc(-c2cncc(Nc3nc(N[C@@H]4CCCC[C@@H]4N)c(F)cc3C(N)=O)c2)c1F] | 6-(cis-2-aminocyclohexylamino)-5-fluoro-2-((5-(2-fluoro-3-methoxyphenyl)pyridin-3-yl)amino)nicotinamide |
| Example 4-198 | 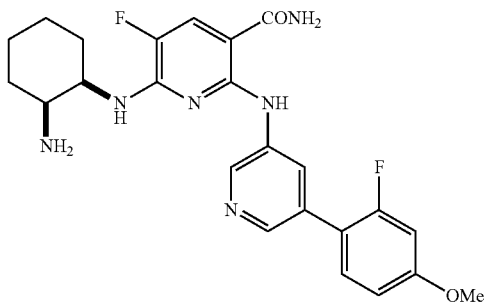 [SMILES: COc1ccc(-c2cncc(Nc3nc(N[C@@H]4CCCC[C@@H]4N)c(F)cc3C(N)=O)c2)c(F)c1] | 6-(cis-2-aminocyclohexylamino)-5-fluoro-2-((5-(2-fluoro-4-methoxyphenyl)pyridin-3-yl)amino)nicotinamide |

TABLE 2-continued

| Example | | |
|---|---|---|
| Example 4-199 | 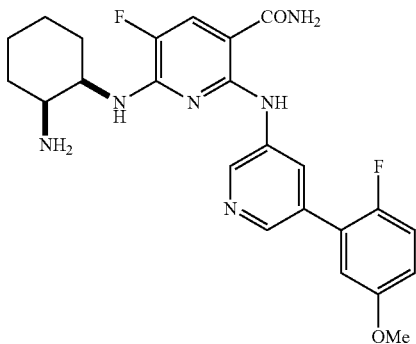 | 6-(cis-2-aminocyclohexylamino)-5-fluoro-2-((5-(2-fluoro-5-methoxyphenyl)pyridin-3-yl)amino)nicotinamide |
| Example 4-200 | 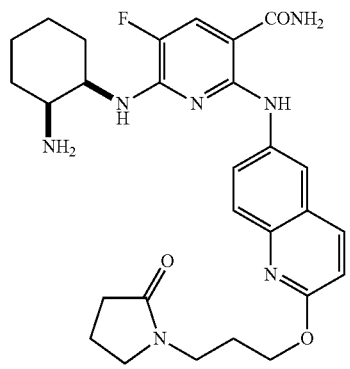 [SMILES: NC(=O)c1cc(F)c(N[C@@H]2CCCC[C@@H]2N)nc1Nc1ccc2nc(OCCCN3CCCC3=O)ccc2c1] | 6-(cis-2-aminocyclohexylamino)-5-fluoro-2-((2-(3-(2-oxopyrrolidin-1-yl)propoxy)quinolin-6-yl)amino)nicotinamide |
| Example 4-201 | 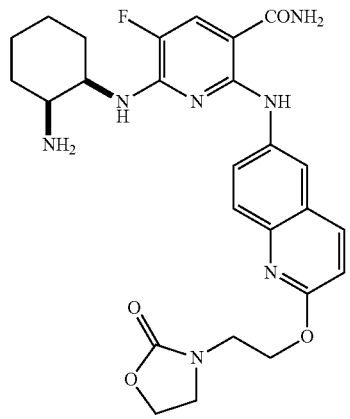 | 6-(cis-2-aminocyclohexylamino)-5-fluoro-2-((2-(2-(2-oxooxazolidin-3-yl)ethoxy)quinolin-6-yl)amino)nicotinamide |
| Example 4-202 | 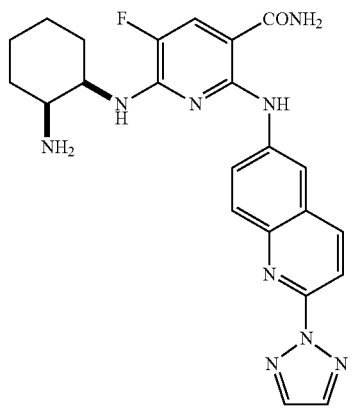 [SMILES: NC(=O)c1cc(F)c(N[C@@H]2CCCC[C@@H]2N)nc1Nc1ccc2nc(-n3nccn3)ccc2c1] | 2-((2-(2H-1,2,3-triazol-2-yl)quinolin-6-yl)amino)-6-(cis-2-aminocyclohexylamino)-5-fluoronicotinamide |

TABLE 2-continued

| Example 4-203 | 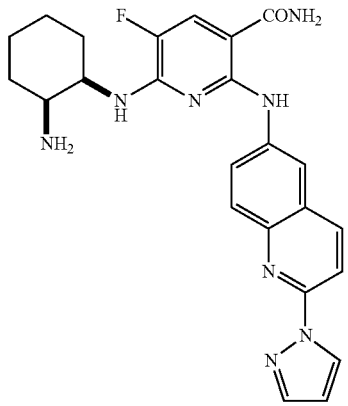 [SMILES: NC(=O)c1cc(F)c(N[C@@H]2CCCC[C@@H]2N)nc1Nc1ccc2nc(-n3cccn3)ccc2c1] | 2-((2-(1H-pyrazol-1-yl)quinolin-6-yl)amino)-6-(cis-2-aminocyclohexylamino)-5-fluoronicotinamide |
| Example 4-204 | 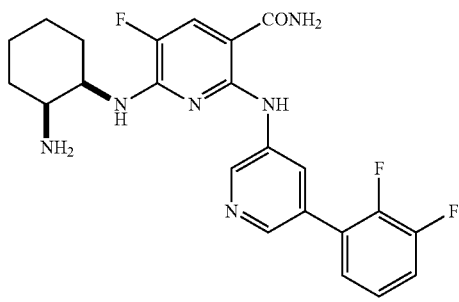 | 6-(cis-2-aminocyclohexylamino)-2-((5-(2,3-difluorophenyl)pyridin-3-yl)amino)-5-fluoronicotinamide |
| Example 4-205 | 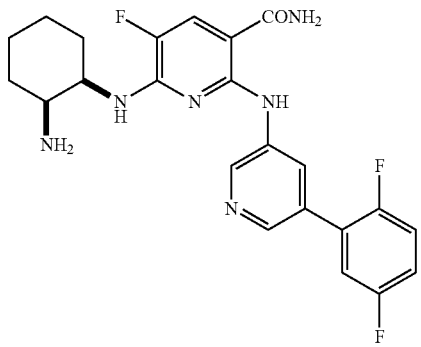 | 6-(cis-2-aminocyclohexylamino)-2-((5-(2,5-difluorophenyl)pyridin-3-yl)amino)-5-fluoronicotinamide |
| Example 4-206 | 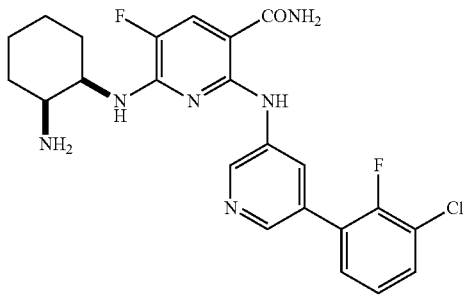 | 6-(cis-2-aminocyclohexylamino)-2-((5-(3-chloro-2-fluorophenyl)pyridin-3-yl)amino)-5-fluoronicotinamide |

| Example 4-207 | 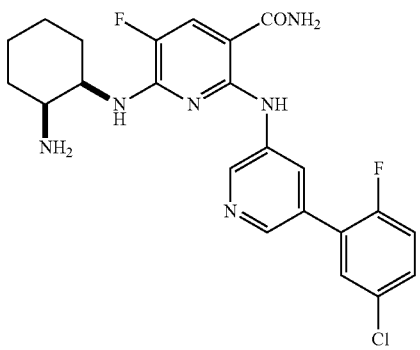 | 6-(cis-2-aminocyclohexylamino)-2-((5-(5-chloro-2-fluorophenyl)pyridin-3-yl)amino)-5-fluoronicotinamide |
| Example 4-208 | 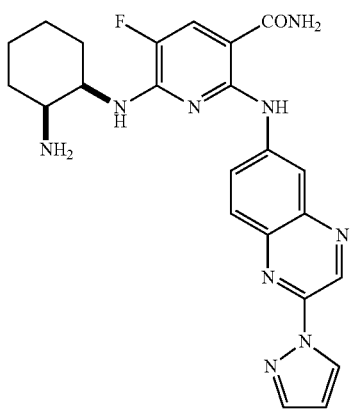 | 2-((2-(1H-pyrazol-1-yl)quinoxalin-6-yl)amino)-6-(cis-2-aminocyclohexylamino)-5-fluoronicotinamide |
| Example 4-209 | 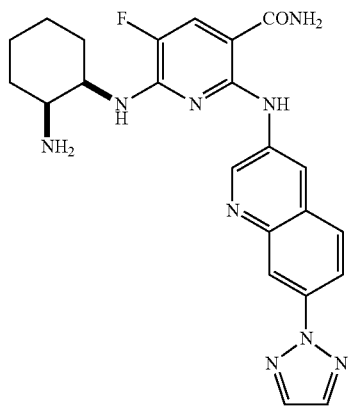 [SMILES: NC(=O)c1cc(F)c(N[C@@H]2CCCC[C@@H]2N)nc1Nc1cnc2cc(-n3nccn3)ccc2c1] | 2-((7-(2H-1,2,3-triazol-2-yl)quinolin-3-yl)amino)-6-(cis-2-aminocyclohexylamino)-5-fluoronicotinamide |
| Example 4-210 | 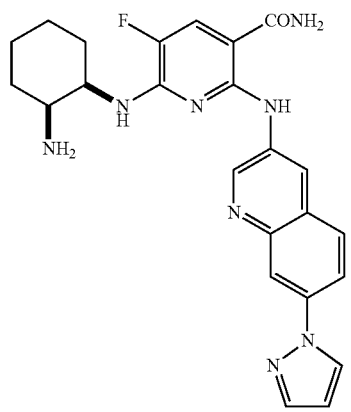 [SMILES: NC(=O)c1cc(F)c(N[C@@H]2CCCC[C@@H]2N)nc1Nc1cnc2cc(-n3cccn3)ccc2c1] | 2-((7-(1H-pyrazol-1-yl)quinolin-3-yl)amino)-6-(cis-2-aminocyclohexylamino)-5-fluoronicotinamide |

TABLE 2-continued

| | | |
|---|---|---|
| Example 4-211 | 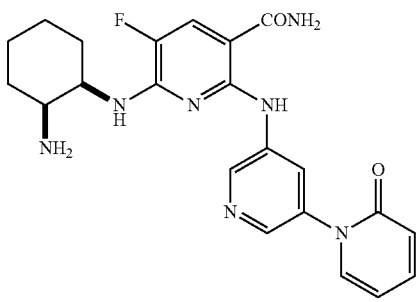 [SMILES: NC(=O)c1cc(F)c(N[C@@H]2CCCC[C@@H]2N)nc1Nc1cncc(-n2ccccc2=O)c1] | 6-(cis-2-aminocyclohexylamino)-5-fluoro-2-((2-oxo-2H-[1,3'-bipyridin]-5'-yl)amino)nicotinamide |
| Example 4-212 | 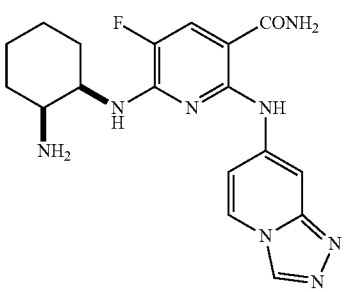 [SMILES: NC(=O)c1cc(F)c(N[C@@H]2CCCC[C@@H]2N)nc1Nc1ccn2cnnc2c1] | 2-([1,2,4]triazol[4,3-a]pyridin-7-yl)amino)-6-(cis-2-aminocyclohexylamino)-5-fluoronicotinamide |
| Example 4-213 | 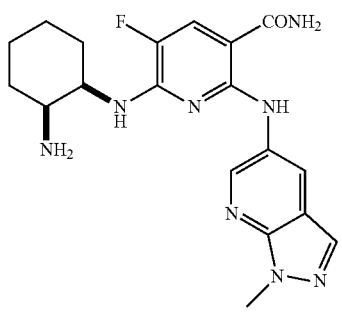 [SMILES: Cn1ncc2cc(Nc3nc(N[C@@H]4CCCC[C@@H]4N)c(F)cc3C(N)=O)cnc21] | 6-(cis-2-aminocyclohexylamino)-5-fluoro-2-((1-methyl-1H-pyrazole[3,4-b]pyridin-5-yl)amino)nicotinamide |
| Example 4-214 | 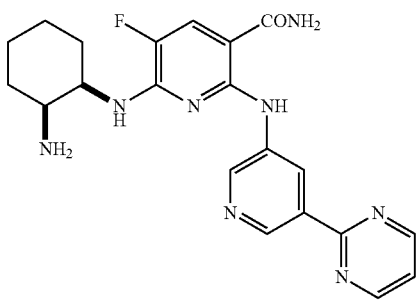 | 6-(cis-2-aminocyclohexylamino)-5-fluoro-2-((5-(pyrimidin-2-yl)pyridin-3-yl)amino)nicotinamide |
| Example 4-215 | 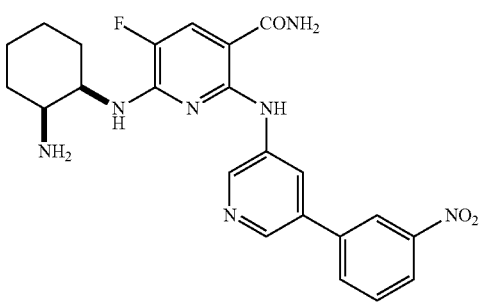 [SMILES: NC(=O)c1cc(F)c(N[C@@H]2CCCC[C@@H]2N)nc1Nc1cncc(-c2cccc([N+](=O)[O-])c2)c1] | 6-(cis-2-aminocyclohexylamino)-5-fluoro-2-((5-(3-nitrophenyl)pyridin-3-yl)amino)nicotinamide |

TABLE 2-continued

| Example 4-216 | 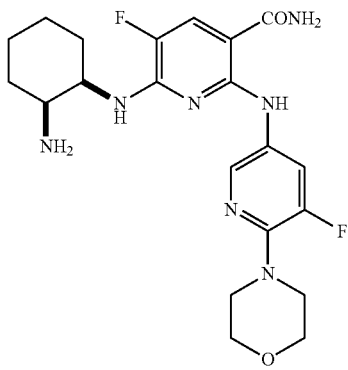 [SMILES: NC(=O)c1cc(F)c(N[C@@H]2CCCC[C@@H]2N)nc1Nc1cnc(N2CCOCC2)c(F)c1] | 6-(cis-2-aminocyclohexylamino)-5-fluoro-2-((5-fluoro-6-morpholinopyridin-3-yl)amino)nicotinamide |
| Example 4-217 | 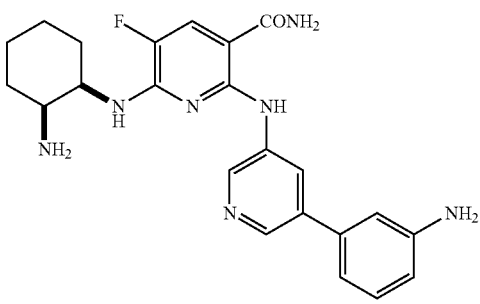 | 6-(cis-2-aminocyclohexylamino)-2-((5-(3-aminophenyl)pyridin-3-yl)amino)-5-fluoronicotinamide |
| Example 4-218 | 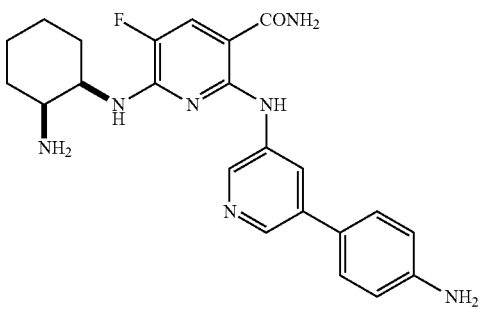 | 6-(cis-2-aminocyclohexylamino)-2-((5-(4-aminophenyl)pyridin-3-yl)amino)-5-fluoronicotinamide |
| Example 4-219 | 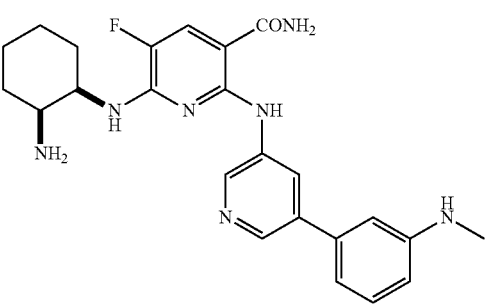 [SMILES: CNc1cccc(-c2cncc(Nc3nc(N[C@@H]4CCCC[C@@H]4N)c(F)cc3C(N)=O)c2)c1] | 6-(cis-2-aminocyclohexylamino)-5-fluoro-2-((5-(3-(methylamino)phenyl)pyridin-3-yl)amino)nicotinamide |
| Example 4-220 | 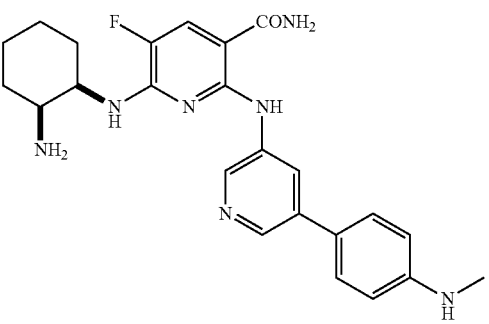 [SMILES: CNc1ccc(-c2cncc(Nc3nc(N[C@@H]4CCCC[C@@H]4N)c(F)cc3C(N)=O)c2)cc1] | 6-(cis-2-aminocyclohexylamino)-5-fluoro-2-((5-(4-(methylamino)phenyl)pyridin-3-yl)amino)nicotinamide |

TABLE 2-continued

| | | |
|---|---|---|
| Example 4-221 | 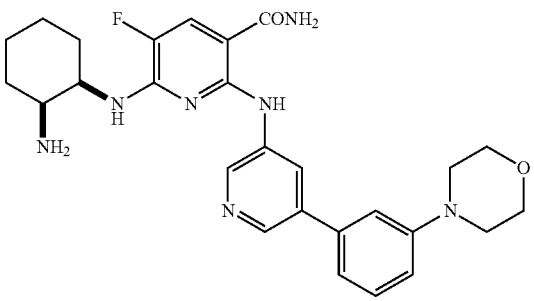 [SMILES: NC(=O)c1cc(F)c(N[C@@H]2CCCC[C@@H]2N)nc1Nc1cncc(-c2cccc(N3CCOCC3)c2)c1] | 6-(cis-2-aminocyclohexylamino)-5-fluoro-2-((5-(3-morpholinophenyl)pyridin-3-yl)amino)nicotinamide |
| Example 4-222 | 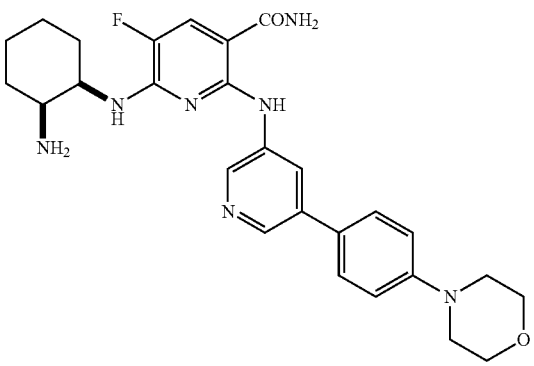 [SMILES: NC(=O)c1cc(F)c(N[C@@H]2CCCC[C@@H]2N)nc1Nc1cncc(-c2ccc(N3CCOCC3)cc2)c1] | 6-(cis-2-aminocyclohexylamino)-5-fluoro-2-((5-(4-morpholinophenyl)pyridin-3-yl)amino)nicotinamide |
| Example 4-223 | 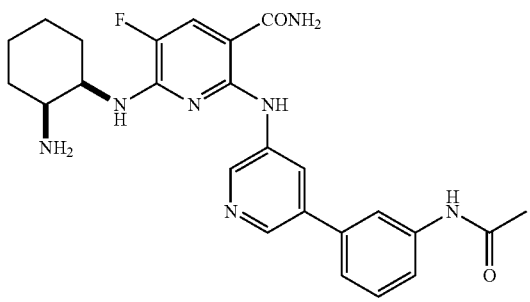 [SMILES: CC(=O)Nc1cccc(-c2cncc(Nc3nc(N[C@@H]4CCCC[C@@H]4N)c(F)cc3C(N)=O)c2)c1] | 2-((5-(3-acetamidephenyl)pyridin-3-yl)amino)-6-(cis-2-aminocyclohexylamino)-5-fluoronicotinamide |
| Example 4-224 | 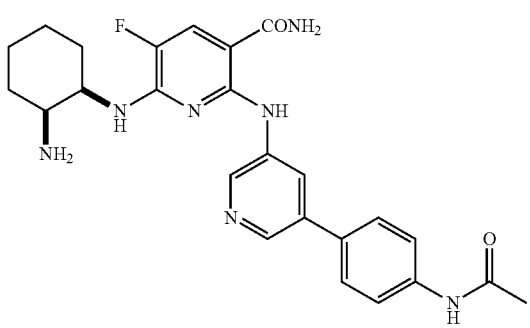 [SMILES: CC(=O)Nc1ccc(-c2cncc(Nc3nc(N[C@@H]4CCCC[C@@H]4N)c(F)cc3C(N)=O)c2)cc1] | 2-((5-(4-acetamidephenyl)pyridin-3-yl)amino)-6-(cis-2-aminocyclohexylamino)-5-fluoronicotinamide |
| Example 4-225 | 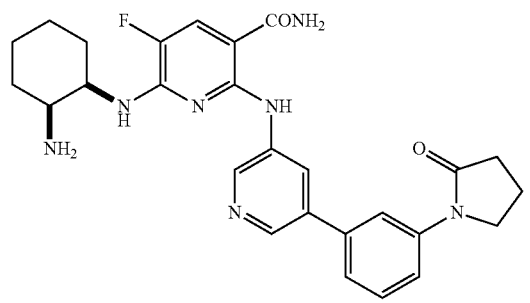 [SMILES: NC(=O)c1cc(F)c(N[C@@H]2CCCC[C@@H]2N)nc1Nc1cncc(-c2cccc(N3CCCC3=O)c2)c1] | 6-(cis-2-aminocyclohexylamino)-5-fluoro-2-((5-(3-(2-oxopyrrolidin-1-yl)phenyl)pyridin-3-yl)amino)nicotinamide |

TABLE 2-continued

| Example | Structure | Name |
|---|---|---|
| Example 4-226 | 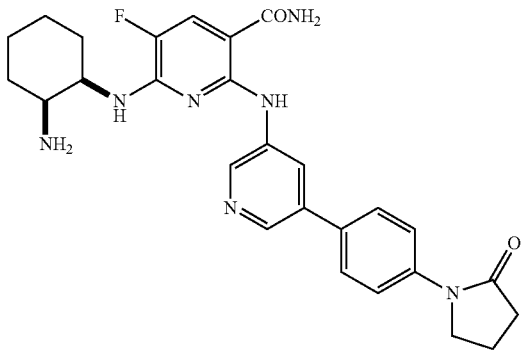 [SMILES: NC(=O)c1cc(F)c(N[C@@H]2CCCC[C@@H]2N)nc1Nc1cncc(-c2ccc(N3CCCC3=O)cc2)c1] | 6-(cis-2-aminocyclohexylamino)-5-fluoro-2-((5-(4-(2-oxopyrrolidin-1-yl)phenyl)pyridin-3-yl)amino)nicotinamide |
| Example 4-227 | 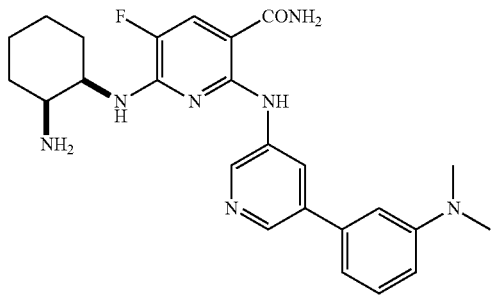 [SMILES: CN(C)c1cccc(-c2cncc(Nc3nc(N[C@@H]4CCCC[C@@H]4N)c(F)cc3C(N)=O)c2)c1] | 6-(cis-2-aminocyclohexylamino)-2-((5-(3-(dimethylamino)phenyl)pyridin-3-yl)amino)-5-fluoronicotinamide |
| Example 4-228 | 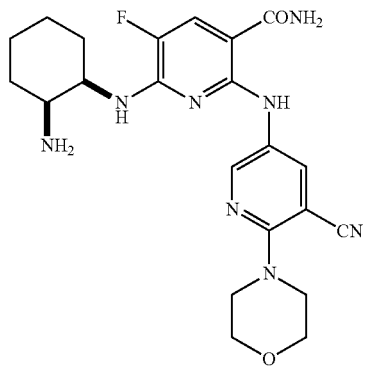 [SMILES: N#Cc1cc(Nc2nc(N[C@@H]3CCCC[C@@H]3N)c(F)cc2C(N)=O)cnc1N1CCOCC1] | 6-((cis-2-aminocyclohexyl)amino)-2-((5-cyano-6-morpholinopyridin-3-yl)amino)-5-fluoronicotinamide |
| Example 4-229 | 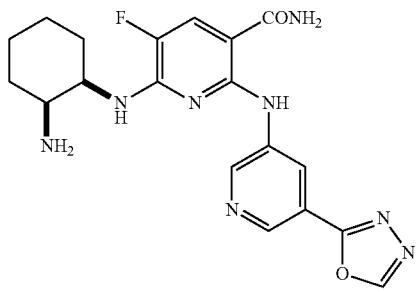 [SMILES: NC(=O)c1cc(F)c(N[C@@H]2CCCC[C@@H]2N)nc1Nc1cncc(-c2nnco2)c1] | 2-((5-(1,3,4-oxadiazol-2-yl)pyridin-3-yl)amino)-6-((cis-2-aminocyclohexyl)amino)-5-fluoronicotinamide |
| Example 4-230 | 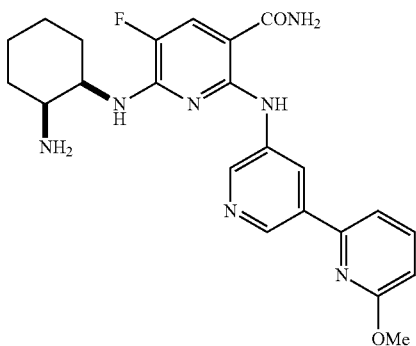 [SMILES: COc1cccc(-c2cncc(Nc3nc(N[C@@H]4CCCC[C@@H]4N)c(F)cc3C(N)=O)c2)n1] | 6-((cis-2-aminocyclohexyl)amino)-5-fluoro-2-((6-methoxy-[2,3'-bipyridin]-5'-yl)amino)nicotinamide |

TABLE 2-continued

| Example 4-231 | 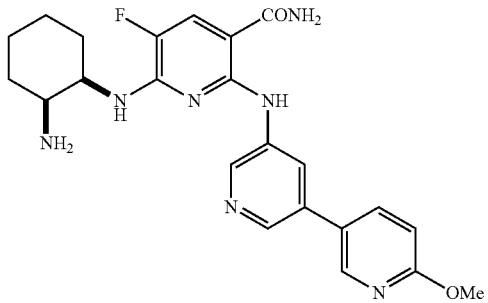 [SMILES: COc1ccc(-c2cncc(Nc3nc(N[C@@H]4CCCC[C@@H]4N)c(F)cc3C(N)=O)c2)cn1] | 6-((cis-2-aminocyclohexyl)amino)-5-fluoro-2-((6'-methoxy-[3,3'-bipyridin]-5-yl)amino)nicotinamide |
| --- | --- | --- |
| Example 4-232 | 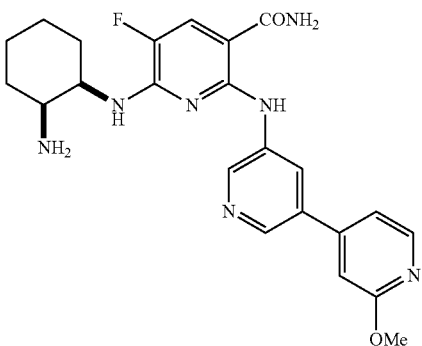 [SMILES: COc1cc(-c2cncc(Nc3nc(N[C@@H]4CCCC[C@@H]4N)c(F)cc3C(N)=O)c2)ccn1] | 6-((cis-2-aminocyclohexyl)amino)-5-fluoro-2-((2'-methoxy-[3,4'-bipyridine]-5-yl)amino)nicotinamide |
| Example 4-233 | 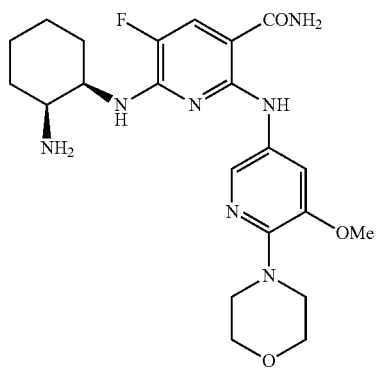 [SMILES: COc1cc(Nc2nc(N[C@@H]3CCCC[C@@H]3N)c(F)cc2C(N)=O)cnc1N1CCOCC1] | 6-(((1R,2S)-2-aminocyclohexyl)amino)-5-fluoro-2-((5-methoxy-6-morpholinopyridin-3-yl)amino)nicotinamide |
| Example 4-234 | 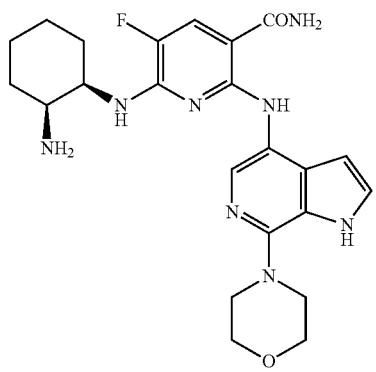 [SMILES: NC(=O)c1cc(F)c(N[C@@H]2CCCC[C@@H]2N)nc1Nc1cnc(N2CCOCC2)c2[nH]ccc12] | 6-(((1R,2S)-2-aminocyclohexyl)amino)-5-fluoro-2-((7-morpholino-1H-pyrrolo[2,3-c]pyridin-4-yl)amino)nicotinamide |

TABLE 2-continued

| Example 4-235 | 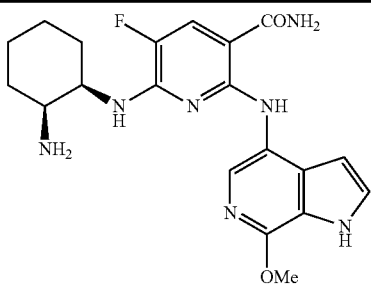 | 6-(((1R,2S)-2-aminocyclohexylamino)-5-fluoro-2-((7-methoxy-1H-pyrrolo[2,3-c]pyridin-4-yl)amino)nicotinamide |
|---|---|---|

| Number | Compound name | $^1$H-NMR | MS (ESI, m/z) |
|---|---|---|---|
| Example 4-1 | 6-(cis-2-aminocyclohexylamino)-5-fluoro-2-((pyrimidin-5-yl)amino)nicotinamide | $^1$H-NMR (DMSO-$d_6$, 300 MHz) δ: 11.71 (s, 1H), 9.08 (s, 2H), 8.73 (s, 1H), 7.92 (d, 1H, J = 12.5 Hz), 7.86-7.58 (br, 1H), 7.58-7.00 (br, 1H), 6.72-6.66 (m, 1H), 3.92-3.88 (m, 1H), 3.15-3.13 (m, 1H), 1.78-1.17 (m, 8H). | 347 (M + H) |
| Example 4-2 | 6-(cis-2-aminocyclohexylamino)-5-fluoro-2-((1,5-naphthyridin-3-yl)amino)nicotinamide | $^1$H-NMR (DMSO-$d_6$, 300 MHz) δ: 12.28 (s, 1H), 8.98 (d, 1H, J = 2.4 Hz), 8.89 (dd, 1H, J = 1.7, 4.2 Hz), 8.86 (d, 1H, J = 2.6 Hz), 8.29 (d, 1H, J = 7.6 Hz), 7.98 (d, 1H, J = 12.5 Hz), 7.92-7.76 (br, 1H), 7.55 (dd, 1H, J = 4.2, 8.4 Hz), 7.48-7.25 (br, 1H), 6.85-6.62 (m, 1H), 4.20-4.16 (m, 1H), 3.20-3.16 (m, 1H), 1.94-1.30 (m, 8H). | 396 (M + H) |
| Example 4-3 | 6-(cis-2-aminocyclohexylamino)-5-fluoro-2-((1,6-naphthyridin-3-yl)amino)nicotinamide | $^1$H-NMR (DMSO-$d_6$, 300 MHz) δ: 12.23 (s, 1H), 9.21 (s, 1H), 9.07 (d, 1H, J = 2.6 Hz), 8.93 (d, 1H, J = 2.2 Hz), 8.56 (d, 1H, J = 5.8 Hz), 7.96 (d, 1H, J = 12.6 Hz), 7.92-7.74 (br, 1H), 7.82 (d, 1H, J = 5.7 Hz), 7.57-7.08 (br, 1H), 6.74-6.59 (m, 1H), 4.09-4.05 (m, 1H), 3.20-3.16 (m, 1H), 1.86-1.26 (m, 8H). | 396 (M + H) |
| Example 4-4 | 6-(cis-2-aminocyclohexylamino)-5-fluoro-2-((1,6-naphthyridin-8-yl)amino)nicotinamide | $^1$H-NMR (DMSO-$d_6$, 300 MHz) δ 12.79 (s, 1H), 10.04 (s, 1H), 9.11 (dd, 1H, J = 1.7, 4.2 Hz), 8.91 (s, 1H), 8.53 (dd, 1H, J = 1.7, 8.3 Hz), 7.93 (d, 1H, J = 12.5 Hz), 7.73 (dd, 1H, J = 4.3, 8.2 Hz), 7.86-7.47 (br, 1H), 7.40-6.80 (br, 1H), 6.66 (d, 1H, J = 7.0 Hz), 4.12-4.08 (m, 1H), 3.27-3.25 (m, 1H), 1.86-1.33 (m, 8H). | 396 (M + H) |
| Example 4-5 | 6-(cis-2-aminocyclohexylamino)-5-fluoro-2-((8-nitroquinolin-3-yl)amino)nicotinamide | $^1$H-NMR (CD$_3$OD, 300 MHz) δ: 9.23 (d, 1H, J = 2.5 Hz), 8.54 (d, 1H, J = 2.5 Hz), 8.07 (dd, 1H, J = 1.2, 8.4 Hz), 7.92 (dd, 1H, J = 1.3, 7.5 Hz), 7.83 (d, 1H, J = 11.9 Hz), 7.64 (t, 1H, J = 7.9 Hz), 4.49-4.45 (m, 1H), 3.74-3.70 (m, 1H), 1.95-1.47 (m, 8H). | 440 (M + H) |
| Example 4-6 | 6-(cis-2-aminocyclohexylamino)-5-fluoro-2-((1-methyl-1H-pyrrolo[2,3-c]pyridin-4-yl)amino)nicotinamide | $^1$H-NMR (DMSO-$d_6$, 300 MHz) δ: 12.03 (s, 1H), 9.26 (s, 1H), 8.46 (s, 1H), 8.31 (s, 1H), 7.91 (d, 1H, J = 12.7 Hz), 7.86-7.57 (br, 1H), 7.49 (d, 1H, J = 3.0 Hz), 7.46-7.04 (br, 1H), 6.62 (d, 1H, J = 6.9 Hz), 6.49 (d, 1H, J = 2.9 Hz), 4.06-4.02 (m, 1H), 3.89 (s, 3H), 3.21-3.17 (m, 1H), 1.77-1.27 (m, 8H). | 398 (M + H) |
| Example 4-7 | 6-(cis-2-aminocyclohexylamino)-5-fluoro-2-((1-(2-(pyrrolidin-1-yl)ethyl)-1H-pyrrolo[2,3-c]pyridin-4-yl)amino)nicotinamide | $^1$H-NMR (CD$_3$OD, 300 MHz) δ: 9.22 (s, 1H), 8.45 (s, 1H), 7.73 (d, 1H, J = 12.2 Hz), 7.49 (d, 1H, J = 3.2 Hz), 6.70 (d, 1H, J = 3.2 Hz), 4.42 (t, 2H, J = 7.0 Hz), 4.35-4.30 (m, 1H), 3.32-3.28 (1H, overlapping with CH$_3$OH peak), 2.95 (t, 2H, J = 7.0), 2.64-2.48 (m, 4H), 1.96-1.41 (m, 12H). | 481 (M + H) |
| Example 4-8 | 2-((8-acetylaminoquinolin-3-yl)amino)-6-(cis-2-aminocyclohexyl-amino)-5-fluoronicotinamide | | 452 (M + H) |
| Example 4-9 | 6-(cis-2-aminocyclohexylamino)-5-fluoro-2-((1-oxoisoindolin-4-yl)amino)nicotinamide | | 399 (M + H) |
| Example 4-10 HCl salt | 6-(cis-2-aminocyclohexylamino)-5-fluoro-2-((5-(methylaminocarbonyl)pyridin-3-yl)amino)nicotinamide | $^1$H-NMR (DMSO-$d_6$, 400 MHz) δ: 11.93 (s, 1H), 8.91 (d, 1H, J = 2.1 Hz), 8.80-8.73 (m, 1H), 8.67-8.63 (m, 1H), 8.62 (d, 1H, J = 1.7 Hz), 7.99 (d, 1H, J = 12.3 Hz), 7.96-7.82 (m, 4H), 7.49-7.37 (m, 1H), 7.08-7.02 (m, 1H), 4.36-4.27 (m, 1H), 3.60-3.53 (1H, overlapping with H$_2$O peak), 2.81 (d, 3H, J = 4.5 Hz), 1.90-1.37 (m, 8H). | 400 (M − H) |

TABLE 2-continued

| | | | |
|---|---|---|---|
| Example 4-11 HCl salt | 6-(cis-2-aminocyclohexylamino)-5-fluoro-2-((5-(anilinocarbonyl)pyridin-3-yl)amino)nicotinamide | $^1$H-NMR (DMSO-d$_6$, 400 MHz) δ: 11.95 (s, 1H), 10.51 (s, 1H), 8.88-8.84 (m, 1H), 8.80-8.76 (m, 1H), 8.74-8.69 (m, 1H), 7.99 (d, 1H, J = 12.2 Hz), 7.96-7.75 (m, 5H), 7.50-7.27 (m, 3H), 7.18-7.10 (m, 2H), 7.09-7.01 (m, 1H), 4.34-4.24 (m, 1H), 3.60-3.53 (1H, overlapping with H$_2$O peak), 1.88-1.16 (m, 8H). | 464 (M + H) |
| Example 4-12 | 6-(cis-2-aminocyclohexylamino)-5-fluoro-2-((1-methyl-1H-pyrrolo[2,3-b]pyridin-5-yl)amino)nicotinamide | $^1$H-NMR (DMSO-d$_6$, 300 MHz) δ: 11.48 (s, 1H), 8.47 (d, 1H, J = 2.4 Hz), 8.18 (d, 1H, J = 2.4 Hz), 7.85 (d, 1H, J = 12.7 Hz), 7.72-7.48 (br, 1H), 7.46 (d, 1H, J = 3.4 Hz), 7.36-6.92 (br, 1H), 6.55-6.45 (m, 1H), 6.32 (d, 1H, J = 3.4 Hz), 3.92-3.88 (m, 1H), 3.79 (s, 3H), 3.13-3.09 (m, 1H), 1.74-1.18 (m, 8H). | 398 (M + H) |
| Example 4-13 | 6-(cis-2-aminocyclohexylamino)-5-fluoro-2-((1-methyl-1H-pyrrolo[2,3-b]pyridin-4-yl)amino)nicotinamide | $^1$H-NMR (DMSO-d$_6$, 300 MHz) δ: 12.46 (s, 1H), 8.17 (d, 1H, J = 5.5 Hz), 8.07 (d, 1H, J = 5.5 Hz), 7.95 (d, 1H, J = 12.7 Hz), 7.90-7.70 (br, 1H), 7.54-7.19 (m, 2H), 6.76-6.64 (m, 1H), 6.46 (d, 1H, J = 3.5 Hz), 4.05-4.01 (m, 1H), 3.79 (s, 3H), 3.24-3.20 (m, 1H), 1.82-1.27 (m, 8H). | 398 (M + H) |
| Example 4-14 | 6-(cis-2-aminocyclohexylamino)-5-fluoro-2-((2-phenylimidazo[1,2-a]pyridin-6-yl)amino)nicotinamide | $^1$H-NMR (CDCl$_3$, 300 MHz) δ: 10.90 (s, 1H), 8.96 (s, 1H), 7.94-7.89 (m, 2H), 7.77 (s, 1H), 7.55 (d, 1H, J = 9.3 Hz), 7.46-7.41 (m, 2H), 7.34-7.30 (m, 1H), 7.23-7.22 (m, 2H), 4.13-4.03 (m, 1H), 3.26-3.18 (m, 1H), 1.96-0.80 (m, 8H). | 458 (M − H) |
| Example 4-15 HCl salt | 2-((5-(dimethylaminocarbonyl)pyridin-3-yl)amino)-5-fluoronicotinamide | $^1$H-NMR (DMSO-d$_6$, 400 MHz) δ: 12.01 (s, 1H), 8.84 (d, 1H, J = 2.1 Hz), 8.38-8.34 (m, 1H), 8.28 (d, 1H, J = 1.6 Hz), 8.00 (d, 1H, J = 12.3 Hz), 7.97-7.88 (m, 4H), 7.50-7.37 (m, 1H), 7.13-7.07 (m, 1H), 4.26-4.16 (m, 1H), 3.58-3.50 (1H, overlapping with H$_2$O peak), 3.00 (s, 3H), 2.96 (s, 3H), 1.94-1.36 (m, 8H). | 416 (M + H) |
| Example 4-16 HCl salt | Methyl 5-(3-carbamoyl-6-(cis-2-amino-cyclohexylamino)-5-fluoropyridin-2-ylamino)nicotinamide | $^1$H-NMR (DMSO-d$_6$, 400 MHz) δ: 11.97 (s, 1H), 8.90 (d, 1H, J = 2.6 Hz), 8.74-8.71 (m, 1H), 8.68 (d, 1H, J = 1.8 Hz), 8.04-7.86 (m, 4H), 8.00 (d, 1H, J = 12.4 Hz), 7.50-7.36 (m, 1H), 7.05-6.98 (m, 1H), 4.37-4.27 (m, 1H), 3.91 (s, 3H), 3.52-3.46 (1H, overlapping with H$_2$O peak), 1.94-1.83 (m, 2H), 1.73-1.57 (m, 4H), 1.50-1.37 (m, 2H). | 403 (M + H) |
| Example 4-17 HCl salt | 6-(cis-2-aminocyclohexylamino)-5-fluoro-2-((6-methylpyridin-3-yl)amino)nicotinamide | $^1$H-NMR (DMSO-d$_6$, 400 MHz) δ: 12.07 (s, 1H), 9.17 (s, 1H), 8.40-8.32 (m, 1H), 8.10-7.92 (m, 5H), 7.77-7.69 (m, 1H), 7.54-7.42 (m, 1H), 7.11-7.03 (m, 1H), 4.36-4.26 (m, 1H), 3.60-3.50 (m, 1H), 2.65 (s, 3H), 1.95-1.35 (m, 8H) | 359 (M + H) |
| Example 4-18 HCl salt | 6-(cis-2-aminocyclohexylamino)-5-fluoro-2-((2-methylpyridin-4-yl)amino)nicotinamide | $^1$H-NMR (DMSO-d$_6$, 400 MHz) δ: 12.92 (s, 1H), 8.48-8.41 (m, 1H), 8.26-8.14 (m, 4H), 8.11 (d, 1H, J = 12.1 Hz), 8.00-7.91 (m, 1H), 7.83 (s, 1H), 7.74 (s, 1H), 7.35-7.28 (m, 1H), 4.38-4.28 (m, 1H), 3.68-3.58 (m, 1H), 2.60 (s, 3H), 2.05-1.38 (m, 8H) | 359 (M + H) |
| Example 4-19 HCl salt | 6-(cis-2-aminocyclohexylamino)-5-fluoro-2-((4-methylpyridin-3-yl)amino)nicotinamide | $^1$H-NMR (DMSO-d$_6$, 400 MHz) δ: 12.35 (s, 1H), 9.74 (s, 1H), 8.41 (d, 1H, J = 5.6 Hz), 8.12-7.99 (m, 4H), 7.92-7.88 (m, 1H), 7.60-7.51 (m, 1H), 7.18-7.12 (m, 1H), 4.42-4.32 (m, 1H), 3.60-3.51 (m, 1H), 2.54 (s, 3H), 1.94-1.36 (m, 8H). | 359 (M + H) |
| Example 4-20 | 6-(cis-2-aminocyclohexylamino)-5-fluoro-2-((1-phenyl-1H-pyrazolo[3,4-c]pyridin-4-yl)amino)nicotinamide | $^1$H-NMR (DMSO-d$_6$, 300 MHz) δ: 12.56 (s, 1H), 9.37 (s, 1H), 8.88 (s, 1H), 8.34 (s, 1H), 7.99 (d, 1H, J = 12.6 Hz), 7.87 (d, 2H, J = 7.6 Hz), 7.64 (t, 2H, J = 7.9 Hz), 7.47 (t, 1H, J = 7.3 Hz), 7.45-7.20 (br, 1H), 7.20-6.95 (br, 1H), 6.80-6.70 (m, 1H), 4.03-3.99 (m, 1H), 3.27-3.23 (1H, overlapping with H$_2$O peak), 1.79-1.20 (m, 8H). | 461 (M + H) |
| Example 4-21 | 6-(cis-2-aminocyclohexylamino)-5-fluoro-2-((pyrido[2,3-b]pyrazin-7-yl)amino)nicotinamide | $^1$H-NMR (CD$_3$OD, 300 MHz) δ: 9.13 (d, 1H, J = 2.8 Hz), 9.09 (d, 1H, J = 2.8 Hz), 8.92 (d, 1H, J = 1.9 Hz), 8.84 (d, 1H, J = 1.9 Hz), 7.85 (d, 1H, J = 12.0 Hz), 4.54-4.50 (m, 1H), 3.64-3.60 (m, 1H), 1.94-1.20 (m, 8H). | 397 (M + H) |
| Example 4-22 | 6-(cis-2-aminocyclohexylamino)-5-fluoro-2-((1-(2-(pyrrolidin-1-yl)ethyl)-1H-pyrrolo[2,3-b]pyridin-5-yl)amino)nicotinamide | $^1$H-NMR (DMSO-d$_6$, 300 MHz) δ: 11.39 (s, 1H), 8.33 (d, 1H, J = 2.6 Hz), 8.21 (d, 1H, J = 2.3 Hz), 7.86 (d, 1H, J = 12.7 Hz), 7.80-7.55 (br, 1H), 7.52 (d, 1H, J = 3.4 Hz), 7.35-6.92 (br, 1H), 6.66-6.50 (m, 1H), 6.33 (d, 1H, J = 3.7 Hz), 4.33 (t, 2H, J = | 481 (M + H) |

TABLE 2-continued

| | | | |
|---|---|---|---|
| | | 6.6 Hz), 3.92-3.88 (m, 1H), 3.27-3.23 (m, 1H), 2.83 (t, 2H, J = 6.6 Hz), 2.69-2.34 (4H, overlapping with DMSO peak), 1.77-1.21 (m, 12H). | |
| Example 4-23 | 6-(cis-2-aminocyclohexylamino)-5-fluoro-2-((1-(2-(pyrrolidin-1-yl)ethyl)-1H-pyrrolo[2,3-b]pyridin-4-yl)amino)nicotinamide | $^1$H-NMR (DMSO-$d_6$, 300 MHz) δ: 12.44 (s, 1H), 8.14 (d, 1H, J = 5.5 Hz), 8.06 (d, 1H, J = 5.5 Hz), 7.95 (d, 1H, J = 12.7 Hz), 7.90-7.69 (br, 1H), 7.44 (d, 1H, J = 3.5 Hz), 7.42-7.20 (br, 1H), 6.76-6.60 (m, 1H), 6.45 (d, 1H, J = 3.5 Hz), 4.33 (t, 2H, J = 6.7 Hz), 4.06-4.02 (m, 1H), 3.26-3.22 (m, 1H), 2.81 (t, 2H, J = 6.7 Hz), 2.6-2.43 (4H, overlapping with DMSO peak), 1.80-1.25 (m, 12H). | 481 (M + H) |
| Example 4-24 | 6-(cis-2-aminocyclohexylamino)-5-fluoro-2-((1-(2-(morpholin-4-yl)ethyl)-1H-pyrrolo[2,3-b]pyridin-5-yl)amino)nicotinamide | $^1$H-NMR (DMSO-$d_6$, 300 MHz) δ: 11.43 (s, 1H), 8.39 (d, 1H, J = 2.3 Hz), 8.18 (d, 1H, J = 2.3 Hz), 7.85 (d, 1H, J = 12.7 Hz), 7.8-7.52 (br, 1H), 7.53 (d, 1H, J = 3.4 Hz), 7.40-6.80 (br, 1H), 6.56-6.46 (m, 1H), 6.32 (d, 1H, J = 3.4 Hz), 4.34 (t, 2H, J = 6.7 Hz), 3.90-3.86 (m, 1H), 3.53 (t, 4H, J = 4.5 Hz), 3.12-3.08 (m, 1H), 2.70 (t, 2H, J = 6.7 Hz), 2.43 (t, 4H, J = 4.5 Hz), 1.70-1.21 (m, 8H). | 497 (M + H) |
| Example 4-25 | 6-(cis-2-aminocyclohexylamino)-5-fluoro-2-((1-(2-(morpholin-4-yl)ethyl)-1H-pyrrolo[2,3-b]pyridin-4-yl)amino)nicotinamide | $^1$H-NMR (DMSO-$d_6$, 300 MHz) δ: 12.45 (s, 1H), 8.15 (d, 1H, J = 5.5 Hz), 8.06 (d, 1H, J = 5.5 Hz), 7.95 (d, 1H, J = 12.7 Hz), 7.90-7.53 (br, 1H), 7.44 (d, 1H, J = 3.6 Hz), 7.42-7.02 (br, 1H), 6.73-6.65 (m, 1H), 6.45 (d, 1H, J = 3.6 Hz), 4.34 (t, 2H, J = 6.5 Hz), 4.04-4.00 (m, 1H), 3.53 (t, 4H, J = 4.5 Hz), 3.24-3.20 (m, 1H), 2.69 (t, 2H, J = 6.4 Hz), 2.43 (t, 4H, J = 4.4 Hz), 1.75-1.39 (m, 8H). | 497 (M + H) |
| Example 4-26 HCl salt | 6-(cis-2-aminocyclohexylamino)-5-fluoro-2-(([1,3]thiazolo[4,5-b]pyridin-6-yl)amino)nicotinamide | $^1$H-NMR (DMSO-$d_6$, 400 MHz) δ: 11.91 (s, 1H), 9.48 (s, 1H), 8.96 (d, 1H, J = 2.4 Hz), 8.76 (d, 1H, J = 2.6 Hz), 8.62-7.84 (m, 5H), 7.46-7.32 (m, 1H), 7.04-6.99 (m, 1H), 4.33-4.34 (m, 1H), 3.68-3.60 (m, 1H), 1.94-1.38 (m, 8H). | 402 (M + H) |
| Example 4-27 | 6-(cis-2-aminocyclohexylamino)-5-fluoro-2-((3-methyl-3H-imidazo[4,5-b]pyridin-6-yl)amino)nicotinamide | | 477 (M + H) |
| Example 4-28 | 6-(cis-2-aminocyclohexylamino)-2-((1-(2-(diethylamino)ethyl)-1H-pyrrolo[2,3-b]pyridin-4-yl)amino)-5-fluoronicotinamide | | 488 (M + H) |
| Example 4-29 | 6-(cis-2-aminocyclohexylamino)-5-fluoro-2-((1-(2-(piperidin-1-yl)ethyl)-1H-pyrrolo[2,3-b]pyridin-4-yl)amino)nicotinamide | | 496 (M + H) |
| Example 4-30 | 6-(cis-2-aminocyclohexylamino)-2-((1-(3-(dimethylamino)propyl)-1H-pyrrolo[2,3-b]pyridin-4-yl)amino)-5-fluoronicotinamide | | 470 (M + H) |
| Example 4-31 HCl salt | 6-(cis-2-aminocyclohexylamino)-5-fluoro-2-((5-methoxypyridin-3-yl)amino)nicotinamide | $^1$H-NMR (DMSO-$d_6$, 400 MHz) δ: 12.03 (s, 1H), 8.77 (s, 1H), 8.14 (d, 1H, J = 2.2 Hz), 8.03-7.92 (m, 6H), 7.45 (brs, 1H), 7.05 (d, 1H, J = 6.5 Hz), 4.33-4.24 (m, 1H), 3.93 (s, 3H), 3.60-3.52 (m, 1H), 1.95-1.37 (m, 8H). | 375 (M + H), 373 (M − H) |
| Example 4-32 | 6-(cis-2-aminocyclohexylamino)-2-((8-(dimethylamino)quinolin-3-yl)amino)-5-fluoronicotinamide | | 438 (M + H) |
| Example 4-33 HCl salt | 6-(cis-2-aminocyclohexylamino)-5-fluoro-2-((8-(morpholin-4-yl)quinolin-3-yl)amino)nicotinamide | | 480 (M + H) |
| Example 4-34 | 2-(8-(acetyl(methyl)amino)quinolin-3-yl)amino)-6-(cis-2-amino-cyclohexylamino)-5-fluoronicotinamide | | 466 (M + H) |
| Example 4-35 | 6-(cis-2-aminocyclohexylamino)-5-fluoro-2-((1-(2-methoxyethyl)-1H-pyrrolo[2,3-b]pyridin-4-yl)amino)nicotinamide | | 442 (M + H) |
| Example 4-36 | 6-(cis-2-aminocyclohexylamino)-5-fluoro-2-((1-isobutyl-1H-pyrrolo[2,3-b]pyridin-4-yl)amino)nicotinamide | | 440 (M + H) |

TABLE 2-continued

| | | | |
|---|---|---|---|
| Example 4-37 | 6-(cis-2-aminocyclohexylamino)-2-((1-cyclopropyl-1H-pyrrolo[2,3-b]pyridin-4-yl)amino)-5-fluoronicotinamide | | 424 (M + H) |
| Example 4-38 | 6-(cis-2-aminocyclohexylamino)-5-fluoro-2-((1-phenyl-1H-pyrrolo[2,3-b]pyridin-4-yl)amino)nicotinamide | | 460 (M + H) |
| Example 4-39 HCl salt | 6-(cis-2-aminocyclohexylamino)-5-fluoro-2-((1-(2,2,2-trifluoroethyl)-1H-pyrrolo[2,3-b]pyridin-4-yl)amino)nicotinamide | | 424 (M + H) |
| Example 4-40 | 6-((1-(cyclopropylmethyl)-1H-pyrrolo[2,3-b]pyridin-4-yl)amino)-5-fluoronicotinamide | | 466 (M + H) |
| Example 4-41 HCl salt | 6-(cis-2-aminocyclohexylamino)-5-fluoro-2-((5-phenoxypyridin-3-yl)amino)nicotinamide | $^1$H-NMR (DMSO-$d_6$, 400 MHz) δ: 12.07 (s, 1H), 8.70 (d, 1H, J = 1.6 Hz), 8.13-7.90 (m, 7H), 7.49-7.41 (m, 3H), 7.25-7.19 (m, 1H), 7.15-7.10 (m, 2H), 7.05 (d, 1H, J = 6.7 Hz), 4.17-4.08 (m, 1H), 3.52-3.43 (m, 1H), 1.92-1.21 (m, 8H). | 437 (M + H), 435 (M − H) |
| Example 4-42 HCl salt | 6-(cis-2-aminocyclohexylamino)-5-fluoro-2-((5-(2H-1,2,3-triazol-2-yl)pyridin-3-yl)amino)nicotinamide | $^1$H-NMR (DMSO-$d_6$, 400 MHz) δ: 12.09 (s, 1H), 9.07-9.04 (m, 1H), 8.80 (d, 1H, J = 2.1 Hz), 8.56 (d, 1H, J = 2.1 Hz), 8.24 (s, 2H), 8.01 (d, 1H, J = 12.3 Hz), 7.96-7.82 (m, 4H), 7.43 (brs, 1H), 7.02 (d, 1H, J = 6.5 Hz), 4.47-4.38 (m, 1H), 3.63-3.56 (m, 1H), 1.93-1.32 (m, 8H). | 412 (M + H), 410 (M − H) |
| Example 4-43 HCl salt | 6-(cis-2-aminocyclohexylamino)-5-fluoro-2-((5-(1H-1,2,3-triazol1-yl)pyridin-3-yl)amino)nicotinamide | | 412 (M + H), 410 (M − H) |
| Example 4-44 | 6-(((2R)-1-amino-1-oxo-3-phenyl-propan-2-yl)amino)-5-fluoro-2-(1-methyl-1H-pyrrolo[2,3-b]pyridin-4-ylamino)nicotinamide | | 448 (M + H) |
| Example 4-45 | 6-(((2R)-1-amino-1-oxo-3-phenyl-propan-2-yl)amino)-5-fluoro-2-(1-(2-(morpholin-4-yl)ethyl)-1H-pyrrolo[2,3-b]pyridin-4-ylamino)nicotinamide | | 547 (M + H) |
| Example 4-46 | 6-(((2R)-1-amino-1-oxo-3-phenyl-propan-2-yl)amino)-2-((1-(cyclopropylmethyl)-1H-pyrrolo[2,3-b]pyridin-4-yl)amino)-5-fluoronicotinamide | | 488 (M + H) |
| Example 4-47 | 2-((8-acetylaminoquinolin-3-yl)amino)-6-(((2R)-1-amino-1-oxo-3-phenylpropan-2-yl)amino)-5-fluoronicotinamide | | 502 (M + H) |
| Example 4-48 | 2-((2-acetylaminopyridin-4-yl)amino)-6-(cis-2-aminocyclohexylamino)-5-fluoronicotinamide | | 402 (M + H) |
| Example 4-49 HCl salt | 6-(cis-2-aminocyclohexylamino)-5-fluoro-2-((5-(pyrrolidin-1-yl)pyridin-3-yl)amino)nicotinamide | $^1$H-NMR (DMSO-$d_6$, 400 MHz) δ: 11.98 (s, 1H), 8.64 (s, 1H), 8.03-7.90 (m, 5H), 7.72 (d, 1H, J = 2.1 Hz), 7.75 (brs, 1H), 7.27 (s, 1H), 7.02 (d, 1H, J = 6.5 Hz), 4.33-4.24 (m, 1H), 3.56-3.46 (m, 1H), 3.32-3.26 (4H, overlapping with H$_2$O peak), 2.04-1.93 (m, 4H), 1.92-1.34 (m, 8H). | 414 (M + H) |
| Example 4-50 HCl salt | 6-(cis-2-aminocyclohexylamino)-5-fluoro-2-((5-(piperidin-1-yl)pyridin-3-yl)amino)nicotinamide | $^1$H-NMR (DMSO-$d_6$, 400 MHz) δ: 11.98 (s, 1H), 8.79 (s, 1H), 8.17-7.90 (m, 6H), 7.70 (s, 1H), 7.46 (brs, 1H), 7.11-7.02 (m, 1H), 4.34-4.25 (m, 1H), 3.56-3.36 (5H, overlapping with H$_2$O peak), 1.94-1.22 (m, 14H). | 428 (M + H), 426 (M − H) |
| Example 4-51 HCl salt | 6-(cis-2-aminocyclohexylamino)-5-fluoro-2-((5-(morpholin-4-yl)pyridin-3-yl)amino)nicotinamide | $^1$H-NMR (DMSO-$d_6$ + D$_2$O, 400 MHz) δ: 8.74-8.71 (m, 1H), 8.04 (d, 1H, J = 2.3 Hz), 7.96 (d, 1H, J = 12.1 Hz), 7.72 (s, 1H), 4.30-4.23 (m, 1H), 3.81-3.72 (m, 4H), 3.58-3.52 (m, 1H), 3.35-3.27 (m, 4H), 1.90-1.41 (m, 8H). | 430 (M + H), 428 (M − H) |
| Example 4-52 2HCl salt | 6-(cis-2-aminocyclohexylamino)-5-fluoro-2-((5-(4-methylpiperazin-1-yl)pyridin-3-yl)amino)nicotinamide | $^1$H-NMR (D$_2$O, 400 MHz) δ: 8.90 (d, 1H, J = 1.7 Hz), 8.02 (d, 1H, J = 2.4 Hz), 7.80-7.77 (m, 1H), 7.72 (d, 1H, J = 11.6 Hz), 4.47-4.40 (m, 1H), 3.81-3.75 (m, 1H), 3.42-3.24 (m, 8H), 3.00 (s, 3H), 1.90-1.51 (m, 8H). | 443 (M + H), 441 (M − H) |
| Example 4-53 HCl salt | 6-(cis-2-aminocyclohexylamino)-5-fluoro-2-((5-(1H-pyrrol-2-yl)pyridin-3-yl)amino)nicotinamide | $^1$H-NMR (DMSO-$d_6$, 400 MHz) δ: 12.10 (s, 1H), 11.85 (s, 1H), 9.04-8.98 (m, 1H), 8.73-8.69 (m, 1H), 8.57-8.52 (m, 1H), 8.07-7.90 (m, 5H), 7.55-7.45 (br, 1H), 7.11 (d, 1H, J = 6.6 Hz), 7.09-7.04 (m, 1H), 6.94-6.88 (m, | 410 (M + H) |

TABLE 2-continued

|  |  |  |  |
|---|---|---|---|
| | | 1H), 6.25-6.22 (m, 1H), 4.34-4.25 (m, 1H), 3.60-3.50 (1H, overlapping with H$_2$O peak), 1.90-1.25 (m, 8H).<br>$^1$H-NMR (DMSO-d$_6$ + D$_2$O, 400 MHz) δ: 8.90-8.85 (m, 1H), 8.63-8.55 (m, 2H), 7.98 (d, 1H, J = 12.2 Hz), 7.09-7.04 (m, 1H), 6.90-6.82 (m, 1H), 6.30-6.24 (m, 1H), 4.30-4.20 (m, 1H), 3.60-3.50 (m, 1H), 1.90-1.30 (m, 8H). | |
| Example 4-54 HCl salt | 6-(cis-2-aminocyclohexylamino)-5-fluoro-2-((5-(2-thienyl)pyridin-3-yl)amino)nicotinamide | $^1$H-NMR (DMSO-d$_6$, 400 MHz) δ: 11.98 (s, 1H), 8.92-8.87 (m, 1H), 8.67-8.60 (m, 1H), 8.54-8.05 (m, 1H), 8.04-7.88 (m, 5H), 7.79 (d, 1H, J = 3.6 Hz), 7.78-7.73 (m, 1H), 7.52-7.37 (br, 1H), 7.24 (dd, 1H, J = 3.6, 5.0 Hz), 7.05 (d, 1H, J = 6.8 Hz), 4.32-4.23 (m, 1H), 3.60-3.50 (1H, overlapping with H$_2$O peak), 1.90-1.20 (m, 8H).<br>$^1$H-NMR (DMSO-d$_6$ + D$_2$O, 400 MHz) δ: 8.81-8.78 (m, 1H), 8.60-8.56 (m, 2H), 7.95 (d, 1H, J = 12.2 Hz), 7.74-7.70 (m, 2H), 7.26 (dd, 1H, J = 4.0, 4.8 Hz), 4.32-4.24 (m, 1H), 3.60-3.50 (m, 1H), 1.85-1.25 (m, 8H). | 427 (M + H) |
| Example 4-55 HCl salt | 6-(cis-2-aminocyclohexylamino)-2-((5-cyclopropylpyridin-3-yl)amino)-5-fluoronicotinamide | $^1$H-NMR (DMSO-d$_6$, 400 MHz) δ: 12.01 (s, 1H), 9.15-9.08 (m, 1H), 8.26-8.20 (m, 1H), 8.10-7.90 (m, 6H), 7.55-7.40 (br, 1H), 7.06 (d, 1H, J = 6.6 Hz), 4.37-4.26 (m, 1H), 3.58-3.46 (m, 1H), 2.18-2.08 (m, 1H), 1.94-1.36 (m, 8H), 1.16-1.06 (m, 2H), 1.00-0.90 (m, 2H). | 385 (M + H) |
| Example 4-56 HCl salt | 6-(cis-2-aminocyclohexylamino)-2-((5-(2,3-dihydro[1,4]benzo-dioxin-6-yl)pyridin-3-yl)amino)-5-fluoronicotinamide | $^1$H-NMR (DMSO-d$_6$, 400 MHz) δ: 12.07 (s, 1H), 9.00-8.90 (m, 1H), 8.68-8.62 (m, 1H), 8.62-8.56 (m, 1H), 8.02 (d, 1H, J = 12.2 Hz), 8.00-7.85 (m, 4H), 7.50-7.42 (br, 1H), 7.40 (d, 1H, J = 2.0), 7.32 (dd, 1H, J = 2.0, 8.5 Hz), 7.08-7.00 (m, 2H), 4.35-4.20 (m, 5H), 3.55-3.46 (1H, overlapping with H$_2$O peak), 1.85-1.20 (m, 8H).<br>$^1$H-NMR (DMSO-d$_6$ + D$_2$O, 400 MHz) δ: 8.85-8.82 (m, 1H), 8.74-8.68 (m, 1H), 8.55-8.50 (m, 1H), 7.97 (d, 1H, J = 12.2 Hz), 7.34 (d, 1H, J = 2.2 Hz), 7.28 (dd, 1H, J = 2.2, 8.6 Hz), J = 7.06 (d, 1H, J = 8.3 Hz), 4.35-4.18 (m, 5H), 3.55-3.46 (m, 1H), 1.84-1.20 (m, 8H). | 479 (M + H) |
| Example 4-57 HCl salt | 6-(cis-2-aminocyclohexylamino)-5-fluoro-2-((5-methyl-3-thienyl)amino)nicotinamide | $^1$H-NMR (DMSO-d$_6$, 400 MHz) δ: 11.58 (s, 1H), 8.00-7.60 (m, 5H), 7.32-7.12 (m, 2H), 6.85-6.76 (m, 2H), 4.32-4.22 (m, 1H), 3.75-3.66 (m, 1H), 2.42-2.38 (m, 3H), 1.96-1.38 (m, 8H). | 364 (M + H) |
| Example 4-58 HCl salt | 6-(cis-2-aminocyclohexylamino)-5-fluoro-2-((5-(2-furyl)pyridin-3-yl)amino)nicotinamide | $^1$H-NMR (DMSO-d$_6$, 400 MHz) δ: 11.96 (s, 1H), 8.82-8.77 (m, 1H), 8.68-8.64 (m, 1H), 8.60-8.55 (m, 1H), 8.04-7.88 (m, 6H), 7.50-7.38 (br, 1H), 7.29 (d, 1H, J = 3.6 Hz), 7.02 (d, 1H, J = 6.8 Hz), 6.72-6.69 (m, 1H), 4.36-4.26 (m, 1H), 3.61-3.54 (1H, overlapping with H$_2$O peak), 1.92-1.30 (m, 8H).<br>$^1$H-NMR (DMSO-d$_6$ + D$_2$O, 400 MHz) δ: 8.71 (d, 1H, J = 2.2 Hz), 8.65-8.60 (m, 2H), 7.97 (d, 1H, J = 12.2 Hz), 7.89 (d, 1H, J = 1.7 Hz), 7.23 (d, 1H, J = 3.4 Hz), 6.71 (dd, 1H, J = 1.7, 3.4 Hz), 4.36-4.27 (m, 1H), 3.61-3.54 (m, 1H), 1.90-1.30 (m, 8H). | 411 (M + H) |
| Example 4-59 | 6-(cis-2-aminocyclohexylamino)-2-((8-aminoquinolin-3-yl)amino)-5-fluoronicotinamide | $^1$H-NMR (CD$_3$OD, 300 MHz) δ: 8.80 (d, 1H, J = 2.4 Hz), 8.40 (d, 1H, J = 2.7 Hz), 7.79 (d, 1H, J = 11.8 Hz), 7.28 (t, 1H, J = 7.9 Hz), 7.07 (dd, 1H, J = 0.9, 8.1 Hz), 6.85 (dd, 1H, J = 1.17, 7.4 Hz), 4.44-4.40 (m, 1H), 3.79-3.75 (m, 1H), 1.96-1.43 (m, 8H). | 410 (M + H) |
| Example 4-60 | 6-(cis-2-aminocyclohexylamino)-5-fluoro-2-((1H-pyrrolo[2,3-b]pyridin-4-yl)amino)nicotinamide | $^1$H-NMR (DMSO-d$_6$, 300 MHz) δ: 12.42 (s, 1H), 11.50 (br, 1H), 8.14 (d, 1H, J = 5.3 Hz), 8.03 (d, 1H, J = 5.6 Hz), 7.94 (d, 1H, J = 12.8 Hz), 7.84 (br, 1H), 7.55 (dd, 1H, J = 4.22, 8.4 Hz), 7.34 (br, 1H), 7.32 (t, 1H, J = 2.9 Hz), 6.69 (br, 1H), 6.46 (dd, 1H, J = 2.0, 3.60 Hz), 4.05-4.01 (m, 1H), 3.23-3.19 (m, 1H), 1.84-1.31 (m, 8H). | 384 (M + H) |
| Example 4-61 | 6-(cis-2-aminocyclohexylamino)-5-fluoro-2-((1H-pyrrolo[2,3-b]pyridin-5-yl)amino)nicotinamide | $^1$H-NMR (DMSO-d$_6$, 300 MHz) δ: 12.02 (s, 1H), 11.55 (br, 1H), 9.22 (s, 1H), 8.39 (s, 1H), 7.91 (d, 1H, J = 12.7 Hz), 7.75 (br, 1H), 7.53 (t, 1H, J = 2.5 Hz), 7.26 (br, 1H), 6.62 | 384 (M + H) |

TABLE 2-continued

| | | |
|---|---|---|
| Example 4-62 | 6-(cis-2-aminocyclohexylamino)-5-fluoro-2-((1H-pyrrolo[2,3-c]pyridin-4-yl)amino)nicotinamide | (br, 1H), 6.52 (br, 1H), 4.08-4.04 (m, 1H), 3.22-3.18 (m, 1H), 1.81-1.30 (m, 8H). <sup>1</sup>H-NMR (DMSO-d<sub>6</sub>, 300 MHz) δ: 11.50 (br, 1H), 11.45 (s, 1H), 8.37 (d, 1H, J = 2.3 Hz), 8.22 (d, 1H, J = 2.4 Hz), 7.84 (d, 1H, J = 12.7 Hz), 7.63 (br, 1H), 7.41 (t, 1H, J = 2.9 Hz), 7.16 (br, 1H), 6.51 (br, 1H), 6.52 (dd, 1H, J = 1.8, 3.4 Hz), 3.93-3.91 (m, 1H), 3.14-3.10 (m, 1H), 1.76-1.27 (m, 8H). | 384 (M + H) |
| Example 4-63 | 6-(((2R)-1-amino-1-oxo-3-phenyl-propan-2-yl)amino)-5-fluoro-2-((1H-pyrrolo[2,3-b]pyridin-4-yl)amino)nicotinamide | | 434 (M + H) |
| Example 4-64 | 2-((8-(aminocarbonyl)amino-quinolin-3-yl)amino)-6-(cis-2-amino-cyclohexylamino)-5-fluoronicotinamide | | 481 (M + H) |

| Number | Salt | Solvent | NMR | 1HNMR | Mass (M + H) | Mass (M − H) | rt (min) |
|---|---|---|---|---|---|---|---|
| Example 4-65 | free | | | | 414 | 412 | 0.86 |
| Example 4-66 | free | | | | 469 | 467 | 0.74 |
| Example 4-67 | free | | | | 451 | 449 | 0.89 |
| Example 4-68 | free | | | | 451 | 449 | 0.91 |
| Example 4-69 | free | | | | 451 | 449 | 0.86 |
| Example 4-70 | free | | | | 383 | 381 | 0.89 |
| Example 4-71 | free | | | | 397 | 395 | 0.96 |
| Example 4-72 | HCl | DMSO-d6 | 400 MHz | δ: 12.05 (s, 1H), 9.08 (s, 1H), 8.67 (s, 1H), 8.55-8.48 (m, 2H), 8.16 (s, 1H), 8.03 (d, 1H, J = 12.2 Hz), 8.02-7.90 (m, 4H), 7.48 (br, 1H), 7.09 (d, 1H, J = 6.8 Hz), 4.32-4.22 (m, 1H), 3.90 (s, 3H), 3.60-3.48 (m, 1H), 1.90-1.28 (m, 8H). | 425 | 423 | 8.17 |
| Example 4-73 | HCl | DMSO-d6 | 400 MHz | δ: 11.95 (s, 1H), 8.87-8.84 (m, 1H), 8.73-8.69 (m, 2H), 8.03 (d, 1H, J = 5.6 Hz), 8.00 (d, 1H, J = 12.0 Hz), 7.93 (d, 1H, J = 5.6 Hz), 7.90-7.78 (m, 4H), 7.41 (br, 1H), 7.00 (d, 1H, J = 3.1 Hz), 4.42-4.31 (m, 1H), 3.63-3.52 (m, 1H), 1.90-1.25 (m, 8H). | 428 | 426 | 9.83 |
| Example 4-74 | HCl | DMSO-d6 | 400 MHz | δ: 11.98 (s, 1H), 9.24 (s, 1H), 8.95 (s, 1H), 8.60 (s, 1H), 8.56 (s, 2H), 8.01 (d, 1H, J = 12.4 Hz), 8.01-7.88 (m, 4H), 7.45 (br, 1H), 7.04 (d, 1H, J = 5.6 Hz), 4.32-4.22 (m, 1H), 3.60-3.48 (m, 1H), 1.90-1.20 (m, 8H). | 428 | 426 | 8.67 |
| Example 4-75 | HCl | DMSO-d6 | 400 MHz | δ: 11.97 (br, 1H), 8.99 (s, 1H), 8.68-8.59 (m, 2H), 8.51 (s, 1H), 8.20 (s, 1H), 8.01 (d, 1H, J = 12.4 Hz), 8.00-7.82 (m, 4H), 7.46 (br, 1H), 7.40-7.26 (m, 5H), 7.06 (d, 1H, J = 6.1 Hz), 5.40 (s, 2H), 4.30-4.20 (m, 1H), 3.55-3.40 (m, 1H), 1.85-1.10 (m, 8H). | 501 | 499 | 10.92 |
| Example 4-76 | HCl | | | | 460 | 458 | 10.23 |
| Example 4-77 | HCl | DMSO-d6 | 400 MHz | δ: 12.00 (s, 1H), 9.01 (s, 1H), 8.76-8.72 (m, 1H), 8.67 (s, 1H), 8.27 (s, 1H), 8.02 (d, 1H, J = 12.4 Hz), 8.00-7.85 (m, 4H), 7.79-7.74 (m, 2H), 7.46 (br, 1H), 7.07 (d, 1H, J = 6.3 Hz), 4.28-4.18 (m, 1H), 3.60-3.48 (m, 1H), 1.85-1.20 (m, 8H). | 427 | 425 | 9.98 |
| Example 4-78 | HCl | DMSO-d6 | 400 MHz | δ: 11.98 (s, 1H), 9.06 (s, 1H), 8.67 (s, 1H), 8.55-8.50 (m, 2H), 8.02 (d, 1H, J = 12.1 Hz), 8.01-7.88 (m, 4H), 7.88-7.85 (m, 1H), 7.46 (br, 1H), 7.21 (s, 1H), 7.07 (d, 1H, J = 6.1 Hz), 4.31-4.22 (m, 1H), 3.59-3.50 (m, 1H), 1.90-1.25 (m, 8H). | 411 | 409 | 9.43 |
| Example 4-79 | free | | | | 401 | 399 | 0.94 |
| Example 4-80 | free | | | | 514 | 512 | 0.82 |

TABLE 2-continued

| | | | | | | | |
|---|---|---|---|---|---|---|---|
| Example 4-81 | free | | | | 459 | 457 | 1.07 |
| Example 4-82 | free | | | | 401 | 399 | 0.98 |
| Example 4-83 | free | | | | 514 | 512 | 0.77 |
| Example 4-84 | free | | | | 459 | 457 | 1.09 |
| Example 4-85 | free | | | | 451 | 449 | 1.09 |
| Example 4-86 | free | | | | 465 | 463 | 1.21 |
| Example 4-87 | free | | | | 564 | 562 | 0.88 |
| Example 4-88 | free | | | | 509 | 507 | 1.2 |
| Example 4-89 | free | | | | 428 | 426 | 0.98 |
| Example 4-90 | free | | | | 438 | 436 | 1 |
| Example 4-91 | free | CD3OD | 300 MHz | δ: 8.15 (d, 1H, J = 1.3 Hz), 7.90 (s, 1H), 7.65 (d, 1H, J = 11.9 Hz), 7.51 (d, 1H, J = 9.2 Hz), 7.42 (dd, 1H, J = 9.2, 2.0 Hz), 4.83-4.82 (m, 1H), 4.54 (t, 2H, J = 5.3 Hz), 4.18 (dd, 1H, J = 9.2, 4.0 Hz), 3.81 (t, 2H, J = 5.3 Hz), 3.27 (s, 3H), 1.74-1.51 (m, 8H). | 442 | 440 | 0.86 |
| Example 4-92 | free | CD3OD | 300 MHz | δ: 8.17 (d, 1H, J = 1.3 Hz), 7.91 (d, 1H, J = 2.0 Hz), 7.66 (d, 1H, J = 12.6 Hz), 7.55 (d, 1H, J = 8.6 Hz), 7.41 (dd, 1H, J = 8.6, 2.0 Hz), 4.85-4.77 (m, 1H), 4.56 (t, 2H, J = 5.3 Hz), 4.26-4.15 (m, 1H), 3.90 (t, 2H, J = 5.3 Hz), 3.47 (m, 4H), 3.37 (q, 2H, J = 6.9 Hz), 1.80-1.50 (m, 8H), 1.08 (t, 3H, J = 6.9 Hz). | 500 | 498 | 0.93 |
| Example 4-93 | free | | | | 438 | 436 | 0.93 |
| Example 4-94 | free | | | | 442 | 440 | 0.81 |
| Example 4-95 | HCl | | | | 500 | 498 | 0.88 |
| Example 4-96 | HCl | DMSO-d6 | 300 MHz | δ: 12.10 (s, 1H), 9.23 (s, 1H), 8.44-8.35 (m, 2H), 8.08-7.90 (m, 5H), 7.86-7.74 (m, 1H), 7.47 (br, 1H), 7.07 (d, 1H, J = 6.6 Hz), 4.36-4.24 (m, 1H), 3.66-3.54 (m, 1H), 2.00-1.35 (m, 8H). | 345 | 343 | 0.55 |
| Example 4-97 | HCl | DMSO-d6 | 300 MHz | δ: 11.92 (s, 1H), 8.55 (d, 1H, J = 2.1 Hz), 8.44-8.40 (m, 1H), 8.19 (d, 1H, J = 2.1 Hz), 8.05-7.80 (m, 5H), 7.40 (br, 1H), 7.05 (d, 1H, J = 6.6 Hz), 4.32-4.20 (m, 1H), 3.75-3.55 (m, 1H), 2.00-1.35 (m, 8H). | 381 379 | 379 377 | 0.89 |
| Example 4-98 | HCl | DMSO-d6 | 300 MHz | δ: 12.03 (s, 1H), 8.91 (d, 1H, J = 2.7 Hz), 8.60-8.54 (m, 1H), 8.54-8.49 (m, 1H), 8.10-7.80 (m, 5H), 7.43 (br, 1H), 7.01 (d, 1H, J = 6.6 Hz), 4.36-4.23 (m, 1H), 3.56-3.44 (m, 1H), 2.00-1.30 (m, 8H). | 413 | 411 | 0.97 |
| Example 4-99 | HCl | DMSO-d6 | 300 MHz | δ: 12.02 (s, 1H), 8.97 (s, 1H), 8.60 (s, 2H), 8.01 (d, 1H, J = 12.0 Hz), 7.96-7.78 (m, 4H), 7.67-7.66 (m, 2H), 7.48-7.39 (m, 2H), 7.34-7.28 (m, 1H), 7.02 (d, 1H, J = 6.0 Hz), 4.26-4.15 (m, 1H), 3.75-3.55 (m, 1H), 2.41 (s, 3H), 1.85-1.15 (m, 8H). | 435 | 433 | 0.92 |
| Example 4-100 | HCl | DMSO-d6 | 300 MHz | δ: 12.02 (s, 1H), 8.95 (s, 1H), 8.60 (s, 2H), 8.01 (d, 1H, J = 12.6 Hz), 8.00-7.78 (m, 4H), 7.76-7.68 (m, 2H), 7.52-7.32 (m, 3H), 7.03 (d, 1H, J = 6.6 Hz), 4.28-4.16 (m, 1H), 3.75-3.55 (m, 1H), 2.38 (s, 3H), 1.90-1.15 (m, 8H). | 435 | 433 | 0.91 |
| Example 4-101 | HCl | DMSO-d6 | 300 MHz | δ: 12.15 (s, 1H), 8.87 (s, 1H), 8.47 (s, 1H), 8.33 (s, 1H), 8.00 (d, 1H, J = 12.3 Hz), 8.00-7.78 (m, 4H), 7.54-7.30 (m, 5H), 7.08 (d, 1H, J = 6.0 Hz), 4.14-4.00 (m, 1H), 3.75-3.55 (m, 1H), 2.28 (s, 3H), 1.85-1.00 (m, 8H). | 435 | 433 | 0.89 |

TABLE 2-continued

| Example 4-102 | HCl | DMSO-d6 | 300 MHz | δ: 12.07 (s, 1H), 8.91 (d, 1H, J = 2.4 Hz), 8.29 (dd, 1H, J = 2.4, 8.7 Hz), 8.00 (d, 1H, J = 11.7 Hz), 8.00-7.80 (m, 4H), 7.81 (d, 1H, J = 8.7 Hz), 7.45 (br, 1H), 7.01 (d, 1H, J = 6.0 Hz), 4.34-4.23 (m, 1H), 3.70-3.58 (m, 1H), 2.00-1.40 (m, 8H). | 413 | 411 | 1 |
|---|---|---|---|---|---|---|---|
| Example 4-103 | HCl | DMSO-d6 | 300 MHz | δ: 12.09 (s, 1H), 9.18-9.12 (m, 2H), 8.81-8.76 (m, 1H), 8.76-8.71 (m, 1H), 8.69-8.64 (m, 1H), 8.50 (d, 1H, J = 8.1 Hz), 8.02 (d, 1H, J = 11.7 Hz), 8.02-7.90 (m, 4H), 7.81-7.72 (m, 1H), 7.46 (br, 1H), 7.07 (d, 1H, J = 6.6 Hz), 4.32-4.18 (m, 1H), 3.56-3.40 (m, 1H), 1.90-1.20 (m, 8H). | 422 | 420 | 0.66 |
| Example 4-104 | HCl | DMSO-d6 | 300 MHz | δ: 11.96 (s, 1H), 9.15-9.14 (m, 1H), 8.92 (d, 2H, J = 6.0 Hz), 8.79-8.74 (m, 1H), 8.63-8.58 (m, 1H), 8.25 (d, 2H, J = 6.0 Hz), 8.01 (d, 1H, J = 12.6 Hz), 8.00-7.86 (m, 4H), 7.44 (br, 1H), 7.03 (d, 1H, J = 6.6 Hz), 4.29-4.18 (m, 1H), 3.56-3.45 (m, 1H), 1.90-1.15 (m, 8H). | 422 | 420 | 0.62 |
| Example 4-105 | HCl | DMSO-d6 | 300 MHz | δ: 11.95 (s, 1H), 8.48-8.45 (m, 1H), 8.24-8.16 (m, 1H), 8.15 (d, 1H, J = 2.7 Hz), 7.99 (d, 1H, J = 12.6 Hz), 7.96-7.80 (m, 4H), 7.40 (br, 1H), 7.04 (d, 1H, J = 6.6 Hz), 4.31-4.20 (m, 1H), 3.72-3.59 (m, 1H), 2.00-1.35 (m, 8H). | 363 | 361 | 0.82 |
| Example 4-106 | HCl | DMSO-d6 | 300 MHz | δ: 12.23 (s, 1H), 9.24-9.20 (m, 1H), 9.13-9.08 (m, 1H), 9.05-9.02 (m, 1H), 8.82-8.78 (m, 1H), 8.27 (d, 1H, J = 7.8 Hz), 8.08-7.96 (m, 6H), 7.60-7.45 (m, 2H), 7.10 (d, 1H, J = 7.2 Hz), 4.40-4.28 (m, 1H), 3.75-3.55 (m, 1H), 1.95-1.20 (m, 8H). | 422 | 420 | 0.75 |
| Example 4-107 | HCl | DMSO-d6 | 300 MHz | δ: 12.05 (s, 1H), 8.95 (s, 1H), 8.64-8.56 (m, 2H), 8.10-7.90 (m, 5H), 7.47 (br, 1H), 7.06 (d, 1H, J = 6.6 Hz), 4.40-4.26 (m, 1H), 4.20-3.86 (m, 2H), 3.72-3.59 (m, 1H), 2.62-2.50 (m, 2H), 2.20-2.06 (m, 2H), 1.95-1.35 (m, 8H). | 428 | 426 | 0.68 |
| Example 4-108 | HCl | DMSO-d6 | 300 MHz | δ: 12.03 (s, 1H), 8.91-8.84 (m, 1H), 8.35-8.31 (m, 1H), 8.31-8.24 (m, 1H), 8.04-7.86 (m, 5H), 7.44 (br, 1H), 7.04 (d, 1H, J = 6.6 Hz), 4.36-4.24 (m, 1H), 3.80-3.64 (m, 2H), 3.56-3.45 (m, 1H), 2.48-2.41 (m, 2H), 1.95-1.35 (m, 12H). | 443 | 441 | 0.74 |
| Example 4-109 | HCl | DMSO-d6 | 300 MHz | δ: 12.02 (s, 1H), 8.94 (s, 1H), 8.70-8.59 (m, 2H), 8.01 (d, 1H, J = 12.0 Hz), 8.00-7.80 (m, 4H), 7.52-7.34 (m, 4H), 7.14-6.98 (m, 2H), 4.30-4.16 (m, 3H), 3.76-3.66 (m, 2H), 3.56-3.45 (m, 1H), 3.33 (s, 3H), 1.90-1.10 (m, 8H). | 495 | 493 | 0.87 |
| Example 4-110 | 2HCl | DMSO-d6 | 300 MHz | δ: 11.98 (s, 1H), 11.02-10.84 (m, 1H), 8.97 (s, 1H), 8.59 (s, 1H), 8.53-8.47 (m, 1H), 8.00 (d, 1H, J = 11.7 Hz), 7.98-7.84 (m, 4H), 7.54-7.36 (m, 4H), 7.16-7.08 (m, 1H), 7.07-6.96 (m, 1H), 4.56-4.49 (m, 2H), 4.28-4.16 (m, 1H), 4.04-3.94 (m, 2H), 3.88-3.76 (m, 2H), 3.64-3.20 (m, 7H), 1.90-1.15 (m, 8H). | 550 | 548 | 0.64 |

TABLE 2-continued

| | | | | | | | |
|---|---|---|---|---|---|---|---|
| Example 4-111 | HCl | DMSO-d6 | 300 MHz | δ: 11.93 (s, 1H), 8.85-8.77 (m, 1H), 8.55-8.48 (m, 2H), 7.99 (d, 1H, J = 12.6 Hz), 7.94-7.68 (m, 6H), 7.50-7.30 (m, 1H), 7.14-7.07 (m, 2H), 7.02-6.94 (m, 1H), 4.26-4.13 (m, 3H), 3.71-3.66 (m, 2H), 3.54-3.44 (m, 1H), 3.33 (s, 3H), 1.85-1.10 (m, 8H). | 495 | 493 | 0.84 |
| Example 4-112 | 2HCl | DMSO-d6 | 300 MHz | δ: 11.85 (s, 1H), 1.74-10.50 (m, 1H), 8.86 (s, 1H), 8.50 (s, 1H), 8.38-8.32 (m, 1H), 7.98 (d, 1H, J = 12.6 Hz), 7.92-7.72 (m, 6H), 7.46-7.33 (m, 1H), 7.21-7.12 (m, 2H), 7.03-6.95 (m, 1H), 4.52-4.41 (m, 2H), 4.30-4.14 (m, 1H), 4.06-3.94 (m, 2H), 3.86-3.72 (m, 2H), 3.65-3.48 (m, 3H), 3.48-3.20 (m, 4H), 1.90-1.15 (m, 8H). | 550 | 549 | 0.6 |
| Example 4-113 | HCl | DMSO-d6 | 300 MHz | δ: 12.11 (s, 1H), 9.09-9.03 (m, 1H), 8.75-8.60 (m, 2H), 8.08-7.86 (m, 5H), 7.52-7.36 (m, 4H), 7.12-7.03 (m, 2H), 4.30-4.16 (m, 1H), 3.85 (s, 3H), 3.65-3.55 (m, 1H), 1.90-1.15 (m, 8H). | 451 | 449 | 0.87 |
| Example 4-114 | HCl | DMSO-d6 | 300 MHz | δ: 12.11 (s, 1H), 9.08-9.03 (m, 1H), 8.65 (s, 2H), 8.03 (d, 1H, J = 11.7 Hz), 8.02-7.88 (m, 4H), 7.85-7.78 (m, 2H), 7.46 (br, 1H), 7.15-7.03 (m, 3H), 4.30-4.17 (m, 1H), 3.83 (s, 3H), 3.66-3.54 (m, 1H), 1.90-1.15 (m, 8H). | 451 | 449 | 0.83 |
| Example 4-115 | HCl | DMSO-d6 | 300 MHz | δ: 12.26 (s, 1H), 8.96 (d, 1H, J = 7.2 Hz), 8.20-7.85 (m, 6H), 7.49 (br, 1H), 7.12-7.00 (m, 2H), 6.44 (s, 1H), 4.40-4.22 (m, 3H), 3.78-3.66 (m, 1H), 2.05-1.40 (m, 8H), 1.33 (t, 3H, J = 6.9 Hz). | 473 | 471 | 1.23 |
| Example 4-116 | HCl | | | | 424 | 422 | 1.02 |
| Example 4-117 | free | | | | 415 | 413 | 1.03 |
| Example 4-118 | HCl | DMSO-d6 | 300 MHz | δ: 11.92 (s, 1H), 8.80 (d, 1H, J = 1.8 Hz), 8.66-8.62 (m, 2H), 8.57-8.52 (m, 1H), 8.00 (d, 1H, J = 12.6 Hz), 8.00-7.86 (m, 5H), 7.56-7.30 (m, 1H), 7.00 (d, 1H, J = 6.6 Hz), 4.38-4.26 (m, 1H), 3.64-3.44 (m, 1H), 1.95-1.25 (m, 8H). | 412 | 410 | 0.73 |
| Example 4-119 | HCl | | | | 424 | 422 | 0.73 |
| Example 4-120 | HCl | | | | 425 | 423 | 0.79 |
| Example 4-121 | HCl | | | | 469 | 467 | 0.82 |
| Example 4-122 | HCl | | | | 468 | 466 | 1.07 |
| Example 4-123 | HCl | | | | 480 | 478 | 0.71 |
| Example 4-124 | HCl | | | | 411 | 409 | 0.77 |
| Example 4-125 | HCl | | | | 410 | 408 | 0.61 |
| Example 4-126 | HCl | | | | 438 | 436 | 1 |
| Example 4-127 | HCl | | | | 469 | 467 | 0.79 |
| Example 4-128 | HCl | | | | 425 | 423 | 0.78 |
| Example 4-129 | HCl | DMSO-d6 | 300 MHz | δ: 7.89 (d, 1H, J = 12.6 Hz), 7.59-7.53 (m, 2H), 7.35-7.27 (m, 2H), 7.01-6.94 (m, 1H), 4.27-4.15 (m, 1H), 3.76-3.67 (m, 1H), 1.97-1.35 (m, 8H). | 344 | 342 | |
| Example 4-130 | HCl | | | | 384 | 382 | |
| Example 4-131 | HCl | DMSO-d6 | 300 MHz | δ: 8.57 (d, 1H, J = 7.3 Hz), 8.37-8.32 (m, 1H), 7.98-7.93 (m, 1H), 7.92 (d, 1H, J = 11.9 Hz), 7.79 (d, 1H, J = 3.0 Hz), 7.44 (dd, 1H, J = 2.0, 7.6 Hz), 4.70-4.62 (m, 1H), 3.92-3.83 (m, 1H), 2.05-1.50 (m, 8H). | 384 | 382 | |
| Example 4-132 | HCl | DMSO-d6 | 300 MHz | δ: 11.92 (s, 1H), 8.94 (d, 1H, J = 2.7 Hz), 8.78 (d, 1H, J = 2.1 Hz), 8.64-8.60 (m, 1H), 7.99 (d, 1H, J = 12.6 Hz), 7.98-7.76 (m, 4H), 7.41 (br, | 387 | 385 | 0.75 |

TABLE 2-continued

| | | | | | | | |
|---|---|---|---|---|---|---|---|
| | | | | 1H), 6.99 (d, 1H, 6.6 Hz), 4.41-4.30 (m, 1H), 3.64-3.48 (m, 1H), 2.66 (s, 3H), 1.95-1.35 (m, 8H). | | | |
| Example 4-133 | HCl | | | | 526 | 524 | 1.12 |
| Example 4-134 | HCl | | | | 464 | 462 | 1.21 |
| Example 4-135 | HCl | | | | 413 | 411 | 0.94 |
| Example 4-136 | HCl | | | | 424 | 422 | 0.92 |
| Example 4-137 | HCl | | | | 468 | 466 | 0.97 |
| Example 4-138 | HCl | | | | 425 | 423 | 0.66 |
| Example 4-139 | HCl | | | | 469 | 467 | 0.69 |
| Example 4-140 | HCl | | | | 501 | 499 | 0.85 |
| Example 4-141 | HCl | DMSO-d6 | 300 MHz | δ: 11.94 (s, 1H), 8.77-8.70 (m, 4H), 8.00 (d, 1H, J = 12.0 Hz), 8.00-7.80 (m, 4H), 7.42 (br, 1H), 7.25 (d, 1H, J = 2.1 Hz), 7.03 (d, 1H, J = 5.4 Hz), 4.40-4.29 (m, 1H), 3.60-3.50 (m, 1H), 1.95-1.25 (m, 8H). | 412 | 410 | 0.81 |
| Example 4-142 | HCl | DMSO-d6 | 300 MHz | δ: 11.24 (s, 1H), 8.51-8.42 (m, 2H), 8.00-7.88 (m, 3H), 7.93 (d, 1H, J = 12.2 Hz), 7.88-7.68 (m, 1H), 7.40-7.20 (m, 1H), 6.87 (d, 1H, J = 6.3 Hz), 4.20-4.09 (m, 1H), 3.88 (s, 3H), 3.60-3.50 (m, 1H), 1.92-1.73 (m, 2H), 1.70-1.50 (m, 4H), 1.48-1.28 (m, 2H). | 418 | 416 | 0.72 |
| Example 4-143 | HCl | DMSO-d6 | 300 MHz | δ: 12.05 (s, 1H), 8.87 (d, 1H, J = 2.1 Hz), 8.56-8.51 (m, 1H), 8.46-8.42 (m, 1H), 8.00 (d, 1H, J = 12.6 Hz), 8.00-7.76 (m, 4H), 7.74-7.65 (m, 1H), 7.59-7.50 (m, 1H), 7.46-7.35 (m, 3H), 7.06 (d, 1H, J = 6.6 Hz), 4.20-4.08 (m, 1H), 3.60-3.50 (m, 1H), 1.85-1.05 (m, 8H). | 439 | 437 | 0.89 |
| Example 4-144 | HCl | DMSO-d6 | 300 MHz | δ: 12.00 (s, 1H), 8.95 (s, 1H), 8.62 (s, 2H), 8.00 (d, 1H, J = 12.3 Hz), 8.00-7.78 (m, 4H), 7.77-7.64 (m, 2H), 7.64-7.53 (m, 1H), 7.44 (br, 1H), 7.38-7.28 (m, 1H), 7.04 (d, 1H, J = 6.6 Hz), 4.28-4.14 (m, 1H), 3.55-3.40 (m, 1H), 1.90-1.15 (m, 8H). | 439 | 437 | 0.92 |
| Example 4-145 | HCl | DMSO-d6 | 300 MHz | δ: 12.09 (s, 1H), 9.06 (s, 1H), 8.67-8.63 (m, 2H), 8.02 (d, 1H, J = 12.6 Hz), 8.02-7.86 (m, 6H), 7.54-7.36 (m, 3H), 7.07 (d, 1H, J = 7.5 Hz), 4.28-4.16 (m, 1H), 3.55-3.40 (m, 1H), 1.90-1.20 (m, 8H). | 439 | 437 | 0.89 |
| Example 4-146 | HCl | DMSO-d6 | 300 MHz | δ: 12.12 (s, 1H), 8.80-8.74 (m, 1H), 8.57-8.52 (m, 1H), 8.35-8.30 (m, 1H), 8.00 (d, 1H, J = 12.6 Hz), 8.00-7.70 (m, 4H), 7.70-7.61 (m, 1H), 7.61-7.35 (m, 4H), 7.09 (d, 1H, J = 6.0 Hz), 4.14-4.00 (m, 1H), 3.55-3.40 (m, 1H), 1.90-0.95 (m, 8H). | 457 455 | 455 453 | 0.94 |
| Example 4-147 | HCl | DMSO-d6 | 300 MHz | δ: 11.98 (s, 1H), 8.91 (s, 1H), 8.62-8.57 (m, 2H), 8.00 (d, 1H, J = 12.6 Hz), 8.00-7.74 (m, 6H), 7.62-7.36 (m, 3H), 7.01 (d, 1H, J = 6.6 Hz), 4.28-4.16 (m, 1H), 3.50-3.35 (m, 1H), 1.90-1.15 (m, 8H). | 457 455 | 455 453 | 1.03 |
| Example 4-148 | HCl | DMSO-d6 | 300 MHz | δ: 11.99 (s, 1H), 8.94-8.89 (m, 1H), 8.60-8.56 (m, 2H), 8.00 (d, 1H, J = 12.6 Hz), 8.00-7.75 (m, 6H), 7.64-7.58 (m, 2H), 7.43 (br, 1H), 7.03 (d, 1H, J = 6.6 Hz), 4.24-4.13 (m, 1H), 3.63-3.43 (m, 1H), 1.85-1.15 (m, 8H). | 457 455 | 455 453 | 1.01 |
| Example 4-149 | HCl | DMSO-d6 | 300 MHz | δ: 12.03 (s, 1H), 8.86-8.80 (m, 1H), 8.55-8.50 (m, 1H), 8.43-8.38 (m, 1H), 8.00 (d, 1H, | 451 | 449 | 0.82 |

TABLE 2-continued

| | | | | | | | |
|---|---|---|---|---|---|---|---|
| | | | | J = 12.6 Hz), 8.00-7.70 (m, 4H), 7.50-7.36 (m, 3H), 7.23-7.17 (m, 1H), 7.14-7.04 (m, 2H), 4.12-4.01 (m, 1H), 3.80 (s, 3H), 3.63-3.43 (m, 1H), 1.85-1.00 (m, 8H). | | | |
| Example 4-150 | HCl | | | | 469 | 467 | 1.01 |
| Example 4-151 | HCl | | | | 497 | 495 | 1.13 |
| Example 4-152 | HCl | | | | 527 | 525 | 1.08 |
| Example 4-153 | HCl | | | | 425 | 423 | 1.01 |
| Example 4-154 | HCl | | | | 483 | 481 | 1.1 |
| Example 4-155 | HCl | | | | 425 | 423 | 1.02 |
| Example 4-156 | HCl | | | | 483 | 481 | 1.08 |
| Example 4-157 | HCl | | | | 497 | 495 | 1.13 |
| Example 4-158 | HCl | | | | 527 | 525 | 1.07 |
| Example 4-159 | HCl | | | | 395 | 393 | 0.66 |
| Example 4-160 | HCl | DMSO-d6 | 300 MHz | δ: 11.35 (s, 1H), 7.91 (d, 1H, J = 12.0 Hz), 7.90-7.70 (m, 4H), 7.68 (d, 1H, J = 1.8 Hz), 7.62 (d, 1H, J = 1.8 Hz), 7.26 (br, 1H), 6.89 (d, 1H, J = 6.0 Hz), 6.13 (s, 2H), 4.18-4.08 (m, 1H), 3.68-3.54 (m, 1H), 1.95-1.30 (m, 8H). | 389 | 387 | 0.8 |
| Example 4-161 | HCl | DMSO-d6 | 300 MHz | δ: 11.40 (s, 1H), 7.91 (d, 1H, J = 12.6 Hz), 7.82 (d, 1H, J = 2.4 Hz), 7.80-7.68 (m, 4H), 7.67 (d, 1H, J = 2.4 Hz), 7.27 (br, 1H), 6.88 (d, 1H, J = 6.6 Hz), 4.38-4.32 (m, 2H), 4.26-4.21 (m, 2H), 4.20-4.10 (m, 1H), 3.68-3.56 (m, 1H), 1.95-1.30 (m, 8H). | 403 | 401 | 0.78 |
| Example 4-162 | HCl | DMSO-d6 | 300 MHz | δ: 12.09 (s, 1H), 9.07-9.01 (m, 1H), 8.35-8.30 (m, 1H), 8.10-7.84 (m, 5H), 7.48 (br, 1H), 7.09 (d, 1H, J = 6.6 Hz), 4.34-4.22 (m, 1H), 3.66-3.50 (m, 1H), 3.20-3.10 (m, 2H), 3.08-2.98 (m, 2H), 2.30-2.14 (m, 2H), 2.00-1.37 (m, H). | 385 | 383 | 0.66 |
| Example 4-163 | HCl | | | | 395 | 393 | 0.62 |
| Example 4-164 | HCl | | | | 425 | 423 | 0.95 |
| Example 4-165 | HCl | | | | 439 | 437 | 1.02 |
| Example 4-166 | HCl | | | | 453 | 451 | 1.09 |
| Example 4-167 | HCl | | | | 467 | 465 | 1.2 |
| Example 4-168 | HCl | | | | 469 | 467 | 0.97 |
| Example 4-169 | HCl | | | | 527 | 525 | 1.03 |
| Example 4-170 | HCl | | | | 511 | 509 | 1.24 |
| Example 4-171 | HCl | | | | 495 | 493 | 1.02 |
| Example 4-172 | HCl | DMSO-d6 | 300 MHz | δ: 8.08 (d, 1H, J = 1.7 Hz), 7.98 (s, 1H), 7.87 (d, 1H, J = 12.2 Hz), 7.60 (d, 1H, J = 8.9 Hz), 7.38 (dd, 1H, J = 1.8, 9.1 Hz), 4.52 (t, 2H, J = 5.1 Hz), 4.22-4.15 (m, 1H), 3.76 (t, 2H, J = 5.1 Hz), 3.75-3.66 (m, 1H), 3.19 (s, 3H), 1.91-1.38 (m, 8H). | 443 | 441 | 0.87 |
| Example 4-173 | HCl | | | | 439 | 437 | 0.86 |
| Example 4-174 | HCl | | | | 453 | 451 | 0.95 |
| Example 4-175 | HCl | | | | 426 | 424 | 0.99 |
| Example 4-176 | HCl | | | | 440 | 438 | 1.09 |
| Example 4-177 | HCl | | | | 454 | 452 | 1.19 |
| Example 4-178 | HCl | | | | 470 | 468 | 0.98 |
| Example 4-179 | HCl | | | | 514 | 512 | 0.98 |
| Example 4-180 | HCl | DMSO-d6 | 300 MHz | δ: 8.77 (d, 1H, J = 1.3 Hz), 8.06 (d, 1H, J = 2.0 Hz), 7.96 (d, 1H, J = 12.2 Hz), 7.73 (s, 1H), 4.33-4.23 (m, 1H), 3.91-3.81 (m, 2H), 3.83-3.63 (m, 2H), 3.63-3.51 (m, 1H), 2.57-2.45 (m, 2H), 1.93-1.39 (m, 8H), 1.19 (d, 6H, J = 5.9 Hz). | 458 | 456 | 0.75 |
| Example 4-181 | HCl | DMSO-d6 | 300 MHz | δ: 11.99 (s, 1H), 8.87-8.81 (m, 1H), 8.48-8.36 (m, 2H), 7.99 (d, 1H, J = 12.3 Hz), 8.00-7.68 (m, 5H), 7.55-7.36 (m, 2H), 7.35-7.25 (m, 1H), 7.10-7.00 (m, 1H), 4.20-4.08 (m, | 457 | 455 | 0.93 |

TABLE 2-continued

| | | | | | | | |
|---|---|---|---|---|---|---|---|
| | | | | 1H), 4.60-4.45 (m, 1H), 1.85-1.10 (m, 8H). | | | |
| Example 4-182 | HCl | DMSO-d6 | 300 MHz | δ: 12.15 (s, 1H), 8.98-8.93 (m, 1H), 8.67-8.62 (m, 1H), 8.54-8.50 (m, 1H), 8.02 (d, 1H, J = 12.3 Hz), 8.00-7.75 (m, 4H), 7.56-7.42 (m, 3H), 7.22-7.06 (m, 3H), 4.16-4.06 (m, 3H), 3.60-3.46 (m, 1H), 1.85-1.40 (m, 5H), 1.32-1.10 (m, 6H). | 465 | 463 | 0.87 |
| Example 4-183 | HCl | DMSO-d6 | 300 MHz | δ: 12.12 (s, 1H), 8.94-8.87 (m, 1H), 8.71-8.63 (m, 1H), 8.49-8.43 (m, 1H), 8.01 (d, 1H, J = 11.7 Hz), 7.98-7.80 (m, 4H), 7.54-7.40 (m, 3H), 7.21-7.07 (m, 3H), 4.14-4.00 (m, 1H), 3.86-3.76 (m, 2H), 3.60-3.46 (m, 1H), 2.00-1.87 (m, 1H), 1.85-1.40 (m, 5H), 1.22-1.04 (m, 3H), 0.89 (d, 3H, J = 2.7 Hz), 0.87 (d, 3H, J = 2.7 Hz). | 493 | 491 | 0.99 |
| Example 4-184 | HCl | | | | 491 | 489 | 0.95 |
| Example 4-185 | HCl | DMSO-d6 | 300 MHz | δ: 12.06 (s, 1H), 8.93-8.84 (m, 1H), 8.74-8.64 (m, 1H), 8.52-8.46 (m, 1H), 8.00 (d, 1H, J = 12.0 Hz), 8.00-7.72 (m, 4H), 7.57-7.40 (m, 3H), 7.24-7.06 (m, 3H), 4.24-4.02 (m, 3H), 3.64-3.54 (m, 2H), 3.54-3.40 (m, 1H), 3.18 (s, 3H), 1.85-1.35 (m, 5H), 1.25-1.05 (m, 3H). | 495 | 493 | 0.8 |
| Example 4-186 | HCl | | | | 437 | 435 | 0.75 |
| Example 4-187 | HCl | | | | 523 | 521 | 0.9 |
| Example 4-188 | HCl | DMSO-d6-D2O | 300 MHz | δ: 8.92 (d, 1H, J = 2.6 Hz), 8.33-8.30 (m, 1H), 8.27-8.23 (m, 1H), 7.96 (d, 1H, J = 12.2 Hz), 4.54 (s, 2H), 4.35-4.25 (m, 1H), 3.63-3.53 (m, 1H), 3.38 (s, 3H), 1.93-1.39 (m, 8H). | 389 | 387 | 0.63 |
| Example 4-189 | HCl | DMSO-d6-D2O | 300 MHz | δ: 9.02 (d, 1H, J = 2.3 Hz), 8.44-8.39 (m, 1H), 8.33 (d, 1H, J = 1.3 Hz), 7.97 (d, 1H, J = 12.2 Hz), 7.43-7.30 (m, 5H), 4.69 (s, 2H), 4.63 (s, 2H), 4.33-4.22 (m, 1H), 3.55-3.49 (m, 1H), 1.93-1.29 (m, 8H). | 465 | 463 | 0.88 |
| Example 4-190 | HCl | DMSO-d6 | 300 MHz | δ: 11.97 (s, 1H), 8.79-8.71 (m, 1H), 8.47-8.42 (m, 1H), 8.35 (s, 1H), 7.98 (d, 1H, J = 11.7 Hz), 7.90 (br, 1H), 7.82-7.66 (m, 3H), 7.45-7.35 (m, 2H), 7.05 (d, 1H, J = 7.2 Hz), 6.75-6.65 (m, 2H), 4.11-3.98 (m, 1H), 3.82 (s, 3H), 3.80 (s, 3H), 3.60-3.45 (m, 1H), 1.85-1.35 (m, 5H), 1.25-1.05 (m, 3H). | 481 | 479 | 0.83 |
| Example 4-191 | HCl | DMSO-d6-D2O | 300 MHz | δ: 8.40 (d, 1H, J = 6.9 Hz), 8.06-7.98 (m, 1H), 8.02 (d, 1H, J = 11.9 Hz), 7.92-7.83 (m, 1H), 4.67 (s, 2H), 4.40-4.31 (m, 1H), 3.70-3.61 (m, 1H), 3.45 (s, 3H), 1.98-1.41 (m, 8H). | 389 | 387 | 0.59 |
| Example 4-192 | HCl | DMSO-d6-D2O | 300 MHz | δ: 8.42 (d, 1H, J = 6.9 Hz), 8.08-8.01 (m, 1H), 8.04 (d, 1H, J = 11.9 Hz), 7.93-7.82 (m, 1H), 7.43-7.33 (m, 5H), 4.76 (d, 2H, J = 3.0 Hz), 4.68 (s, 2H), 4.32-4.22 (m, 1H), 3.60-3.51 (m, 1H), 1.96-1.29 (m, 8H). | 465 | 463 | 0.78 |
| Example 4-193 | HCl | DMSO-d6-D2O | 300 MHz | δ: 8.94 (d, 1H, J = 2.3 Hz), 8.36 (s, 1H), 8.27-8.23 (m, 1H), 7.96 (d, 1H, J = 11.9 Hz), 4.65 (s, 2H), 4.38-4.28 (m, 1H), 3.63-3.55 (m, 1H), 1.95-1.37 (m, 8H). | 375 | 373 | 0.55 |
| Example 4-194 | HCl | DMSO-d6-D2O | 300 MHz | δ: 8.37 (d, 1H, J = 6.9 Hz), 8.10 (s, 1H), 8.03 (d, 1H, J = 11.9 Hz), 7.24 (d, 1H, J = 9.6 | 375 | 373 | 0.55 |

TABLE 2-continued

| | | | | Hz), 7.83-7.73 (m, 1H), 4.75 (s, 2H), 4.44-4.34 (m, 1H), 3.68-3.60 (m, 1H), 1.95-1.43 (m, 8H). | | | |
|---|---|---|---|---|---|---|---|
| Example 4-195 | HCl | | | | 414 | 412 | 0.95 |
| Example 4-196 | HCl | | | | 412 | 410 | 0.96 |
| Example 4-197 | HCl | DMSO-d6 | 300 MHz | δ: 12.10 (s, 1H), 8.90-8.84 (m, 1H), 8.58 (s, 1H), 8.43 (s, 1H), 8.00 (d, 1H, J = 12.0 Hz), 8.00-7.80 (m, 4H), 7.45 (br, 1H), 7.34-7.26 (m, 2H), 7.24-7.16 (m, 1H), 7.07 (d, 1H, J = 6.6 Hz), 4.20-4.08 (m, 1H), 3.90 (s, 3H), 3.54-3.40 (m, 1H), 1.85-1.10 (m, 8H). | 469 | 467 | 0.89 |
| Example 4-198 | HCl | DMSO-d6 | 300 MHz | δ: 12.07 (s, 1H), 8.93-8.87 (m, 1H), 8.53-8.48 (m, 1H), 8.60-8.42 (m, 1H), 8.01 (d, 1H, J = 12.6 Hz), 8.00-7.80 (m, 4H), 7.70-7.60 (m, 1H), 7.44 (br, 1H), 7.10-7.01 (m, 2H), 6.98 (dd, 1H, J = 2.4, 8.4 Hz), 4.20-4.08 (m, 1H), 3.84 (s, 3H), 3.60-3.46 (m, 1H), 1.85-1.10 (m, 8H). | 469 | 467 | 0.9 |
| Example 4-199 | HCl | DMSO-d6 | 300 MHz | δ: 12.03 (s, 1H), 8.86-8.81 (m, 1H), 8.56-8.51 (m, 1H), 8.45-8.41 (m, 1H), 8.00 (d, 1H), 8.00-7.76 (m, 4H), 7.42 (br, 1H), 7.38-7.28 (m, 1H), 7.21 (dd, 1H, J = 3.3, 6.0 Hz), 7.10-7.02 (m, 2H), 4.20-4.08 (m, 1H), 3.81 (s, 3H), 3.60-3.46 (m, 1H), 1.85-1.10 (m, 8H). | 469 | 467 | 0.93 |
| Example 4-200 | HCl | | | | 536 | 534 | 0.96 |
| Example 4-201 | HCl | | | | 524 | 522 | 0.91 |
| Example 4-202 | HCl | | | | 462 | 460 | 0.96 |
| Example 4-203 | HCl | | | | 461 | 459 | 1.09 |
| Example 4-204 | HCl | DMSO-d6 | 300 MHz | δ: 12.10 (s, 1H), 8.97-8.92 (m, 1H), 8.54 (s, 1H), 8.48 (s, 1H), 8.01 (d, 1H, J = 12.6 Hz), 8.00-7.82 (m, 4H), 7.64-7.34 (m, 4H), 7.08 (d, 1H, J = 6.6 Hz), 4.22-4.10 (m, 1H), 3.54-3.40 (m, 1H), 1.90-1.10 (m, 8H). | 457 | 455 | 0.96 |
| Example 4-205 | HCl | DMSO-d6 | 300 MHz | δ: 12.04 (s, 1H), 8.91-8.96 (m, 1H), 8.54-8.48 (m, 1H), 8.46-8.42 (m, 1H), 8.00 (d, 1H, J = 12.6 Hz), 7.95-7.80 (m, 4H), 7.70-7.60 (m, 1H), 7.53-7.32 (m, 3H), 7.06 (d, 1H, J = 6.6 Hz), 4.22-4.10 (m, 1H), 3.54-3.40 (m, 1H), 1.85-1.10 (m, 8H). | 457 | 455 | 0.95 |
| Example 4-206 | HCl | DMSO-d6 | 300 MHz | δ: 12.07 (s, 1H), 8.92-8.86 (m, 1H), 8.54 (s, 1H), 8.45 (s, 1H), 8.00 (d, 1H, J = 12.6 Hz), 8.00-7.80 (m, 4H), 7.76-7.62 (m, 2H), 7.50-7.36 (m, 2H), 7.06 (d, 1H, J = 6.6 Hz), 4.21-4.10 (m, 1H), 3.54-3.40 (m, 1H), 1.85-1.10 (m, 8H). | 475 473 | 473 471 | 1.02 |
| Example 4-207 | HCl | DMSO-d6 | 300 MHz | δ: 11.94 (s, 1H), 8.76 (d, 1H, J = 1.8 Hz), 8.43 (s, 1H), 8.39-8.35 (m, 1H), 7.98 (d, 1H, J = 12.6 Hz), 7.96-7.65 (m, 5H), 7.62-7.54 (m, 1H), 7.52-7.30 (m, 2H), 7.00 (d, 1H, J = 5.4 Hz), 4.22-4.10 (m, 1H), 4.54-4.40 (m, 1H), 1.85-1.10 (m, 8H). | 475 473 | 473 471 | 1.04 |
| Example 4-208 | HCl | | | | 462 | 460 | 1.07 |
| Example 4-209 | HCl | | | | 462 | 460 | 0.96 |
| Example 4-210 | HCl | | | | 461 | 459 | 0.92 |
| Example 4-211 | HCl | DMSO-d6 | 300 MHz | δ: 12.08 (s, 1H), 8.64 (d, 1H, J = 1.8 Hz), 8.48-8.44 (m, 1H), 8.22 (d, 1H, J = 2.1 Hz), 7.99 (d, 1H, J = 12.3 Hz), 7.90-7.74 (m, 5H), 7.60-7.52 (m, 1H), 7.43 (br, 1H), 7.07 (d, 1H, J = 6.6 Hz), 6.54 (d, 1H, J = 9.3 | 438 | 436 | 0.73 |

TABLE 2-continued

| | | | | | | | |
|---|---|---|---|---|---|---|---|
| Example 4-212 | HCl | | | Hz), 6.42-6.34 (m, 1H), 4.22-4.08 (m, 1H), 3.54-3.44 (m, 1H), 1.84-1.20 (m, 8H). | 385 | 383 | 0.58 |
| Example 4-213 | HCl | | | | 399 | 397 | 0.77 |
| Example 4-214 | HCl | DMSO-d6 | 300 MHz | δ: 11.94 (s, 1H), 9.13-9.09 (m, 2H), 9.01 (s, 1H), 8.99 (s, 1H), 8.85 (d, 1H, J = 2.7 Hz), 8.00 (d, 1H, J = 12.6 Hz), 7.85-7.70 (m, 4H), 7.60-7.54 (m, 1H), 7.42 (br, 1H), 6.97 (d, 1H, J = 7.2 Hz), 4.44-4.32 (m, 1H), 3.64-3.50 (m, 1H), 1.95-1.25 (m, 8H). | 423 | 421 | 0.74 |
| Example 4-215 | HCl | DMSO-d6 | 300 MHz | δ: 12.04 (s, 1H), 9.09 (s, 1H), 8.72 (s, 1H), 8.68-8.60 (m, 2H), 8.36-8.28 (m, 2H), 8.02 (d, 1H, J = 12.6 Hz), 8.00-7.80 (m, 5H), 7.45 (br, 1H), 7.04 (d, 1H, J = 6.0 Hz), 4.30-4.16 (m, 1H), 3.54-3.40 (m, 1H), 1.90-1.15 (m, 8H). | 466 | 464 | 0.92 |
| Example 4-216 | HCl | DMSO-d6 | 300 MHz | δ: 11.49 (s, 1H), 8.08 (s, 1H), 8.05 (dd, 1H, J = 2.0, 12.9 Hz), 7.98-7.72 (m, 4H), 7.93 (d, 1H, J = 12.6 Hz), 7.41-7.17 (m, 1H), 6.69-6.90 (m, 1H), 4.23-4.11 (m, 1H), 3.78-3.70 (m, 4H), 3.68-3.59 (m, 1H), 3.28-3.20 (m, 4H), 1.97-1.32 (m, 8H). | 448 | 446 | 0.93 |
| Example 4-217 | HCl | DMSO-d6 | 300 MHz | δ: 12.12 (s, 1H), 9.03-8.98 (m, 1H), 8.63-8.58 (m, 1H), 8.58-8.53 (m, 1H), 8.02 (d, 1H, J = 12.6 Hz), 8.00-7.84 (m, 4H), 7.55-7.17 (m, 4H), 7.17-7.95 (m, 2H), 4.26-4.14 (m, 1H), 3.62-3.50 (m, 1H), 1.88-1.15 (m, 8H). | 436 | 434 | 0.69 |
| Example 4-218 | HCl | DMSO-d6 | 300 MHz | δ: 12.05 (s, 1H), 8.97 (s, 1H), 8.60-8.51 (m, 2H), 8.01 (d, 1H, J = 12.0 Hz), 8.00-7.76 (m, 4H), 7.64-7.57 (m, 2H), 7.47 (br, 1H), 7.06 (d, 1H, J = 6.6 Hz), 6.85-6.73 (m, 2H), 4.28-4.18 (m, 1H), 4.63-4.52 (m, 1H), 1.90-1.20 (m, 8H). | 436 | 434 | 0.65 |
| Example 4-219 | HCl | DMSO-d6 | 300 MHz | δ: 12.15 (s, 1H), 9.08-9.04 (m, 1H), 8.73-8.68 (m, 1H), 8.64-8.61 (m, 1H), 8.03 (d, 1H, J = 12.6 Hz), 8.02-7.84 (m, 4H), 7.49 (br, 1H), 7.34-7.26 (m, 1H), 7.17-6.96 (m, 3H), 6.77 (d, 1H, J = 6.6 Hz), 4.25-4.14 (m, 1H), 3.60-3.48 (m, 1H), 2.78 (s, 3H), 1.85-1.15 (m, 8H). | 450 | 448 | 0.77 |
| Example 4-220 | HCl | DMSO-d6 | 300 MHz | δ: 12.11 (s, 1H), 9.04-8.98 (m, 1H), 8.64-8.59 (m, 2H), 8.02 (d, 1H, J = 12.6 Hz), 8.01-7.80 (m, 4H), 7.67 (d, 2H, J = 8.4 Hz), 7.49 (br, 1H), 7.09 (d, 1H, J = 6.0 Hz), 6.70 (d, 2H, J = 8.4 Hz), 4.30-4.18 (m, 1H), 3.62-3.50 (m, 1H), 2.74 (s, 3H), 1.95-1.15 (m, 8H). | 450 | 448 | 0.77 |
| Example 4-221 | HCl | DMSO-d6 | 300 MHz | δ: 12.11 (s, 1H), 9.12-9.08 (m, 1H), 8.75-8.68 (m, 2H), 8.02 (d, 1H, J = 11.7 Hz), 8.02-7.80 (m, 4H), 7.48 (br, 1H), 7.44-7.32 (m, 2H), 7.28-7.22 (m, 1H), 7.12-7.05 (m, 2H), 4.24-4.12 (m, 1H), 3.80-3.73 (m, 4H), 3.60-3.48 (m, 1H), 3.26-3.19 (m, 4H), 1.85-1.15 (m, 8H). | 506 | 504 | 0.85 |
| Example 4-222 | HCl | DMSO-d6 | 300 MHz | δ: 11.96 (s, 1H), 8.86-8.79 (m, 1H), 8.58-8.52 (m, 2H), 8.00 (d, 1H, J = 12.6 Hz), 7.89 (br, 1H), 7.82-7.60 (m, 5H), 7.43 (br, 1H), 7.09 (d, 2H, J = | 506 | 504 | 0.82 |

TABLE 2-continued

| | | | | | | | |
|---|---|---|---|---|---|---|---|
| | | | | 8.7 Hz), 7.06-6.99 (m, 1H), 4.22-4.12 (m, 1H), 3.80-3.73 (m, 4H), 3.56-3.44 (m, 1H), 3.23-3.15 (m, 4H), 1.90-1.15 (m, 8H). | | | |
| Example 4-223 | HCl | DMSO-d6 | 300 MHz | δ: 12.11 (s, 1H), 10.21 (s, 1H), 8.94-8.90 (m, 1H), 8.66-8.60 (m, 1H), 8.56-8.52 (m, 1H), 8.05-7.80 (m, 6H), 7.70-7.61 (m, 1H), 7.50-7.40 (m, 3H), 7.06 (d, 1H, J = 6.6 Hz), 4.24-4.12 (m, 1H), 3.52-3.40 (m, 1H), 2.08 (s, 3H), 1.85-1.10 (m, 8H). | 478 | 476 | 0.72 |
| Example 4-224 | HCl | DMSO-d6 | 300 MHz | δ: 12.05 (s, 1H), 10.19 (s, 1H), 8.89-8.93 (m, 1H), 8.62-8.52 (m, 2H), 8.01 (d, 1H, J = 12.6 Hz), 8.00-7.70 (m, 8H), 7.56-7.34 (m, 1H), 7.06 (d, 1H, J = 6.0 Hz), 4.28-4.16 (m, 1H), 3.60-3.48 (m, 1H), 2.09 (s, 3H), 1.90-1.15 (m, 8H). | 478 | 476 | 0.69 |
| Example 4-225 | HCl | DMSO-d6 | 300 MHz | δ: 11.94 (s, 1H), 8.85-8.80 (m, 1H), 8.54-8.50 (m, 2H), 8.02-7.95 (m, 2H), 7.90 (br, 1H), 7.80-7.65 (m, 3H), 7.56-7.60 (m, 2H), 7.41 (br, 1H), 7.03-6.97 (m, 2H), 4.21-4.10 (m, 1H), 3.98-3.86 (m, 2H), 3.58-3.46 (m, 1H), 2.58-2.50 (m, 2H), 2.16-2.04 (m, 2H), 1.85-1.10 (m, 8H). | 504 | 502 | 0.81 |
| Example 4-226 | HCl | DMSO-d6 | 300 MHz | δ: 11.98 (s, 1H), 8.92-8.87 (m, 1H), 8.61-8.53 (m, 2H), 8.00 (d, 1H, J = 12.6 Hz), 8.00-7.70 (m, 8H), 7.42 (br, 1H), 7.05-7.69 (m, 1H), 4.28-4.16 (m, 1H), 3.94-3.85 (m, 2H), 3.60-3.48 (m, 1H), 2.58-2.48 (m, 2H), 2.16-2.03 (m, 2H), 1.85-1.15 (m, 8H). | 504 | 502 | 0.78 |
| Example 4-227 | HCl | DMSO-d6 | 300 MHz | δ: 11.98 (s, 1H), 8.92-8.86 (m, 1H), 8.65-8.55 (m, 2H), 8.00 (d, 1H, J = 12.6 Hz), 7.93 (br, 1H), 7.82-7.68 (m, 3H), 7.45 (br, 1H), 7.39-7.30 (m, 1H), 7.07-7.00 (m, 3H), 6.88-6.82 (m, 1H), 4.20-4.08 (m, 1H), 3.60-3.48 (m, 1H), 2.98 (s, 6H), 1.85-1.10 (m, 8H). | 464 | 462 | 0.87 |
| Example 4-228 | HCl | DMSO-d6-D2O | 300 MHz | δ: 8.50-8.46 (m, 2H), 7.89 (d, 1H, J = 12.2 Hz), 4.23-4.13 (m, 1H), 3.80-3.72 (m, 4H), 3.62-3.53 (m, 1H), 3.48-3.40 (m, 4H), 1.95-1.36 (m, 8H). | 455 | 453 | 0.92 |
| Example 4-229 | HCl | DMSO-d6 | 300 MHz | δ: 12.04 (s, 1H), 9.50 (s, 1H), 8.98-8.95 (m, 1H), 8.78 (d, 1H, J = 2.7 Hz), 8.74 (d, 1H, J = 1.8 Hz), 8.01 (d, 1H, J = 12.6 Hz), 8.00-7.76 (m, 4H), 7.44 (br, 1H), 7.02 (d, 1H, J = 6.0 Hz), 4.48-4.37 (m, 1H), 3.66-3.50 (m, 1H), 1.95-1.30 (m, 8H). | 413 | 411 | 0.75 |
| Example 4-230 | HCl | DMSO-d6 | 300 MHz | δ: 11.87 (s, 1H), 9.00-8.94 (m, 1H), 8.94-8.90 (m, 1H), 8.76-8.72 (m, 1H), 7.99 (d, 1H, J = 12.3 Hz), 7.94-7.68 (m, 6H), 7.42 (br, 1H), 7.03 (d, 1H, J = 6.0 Hz), 6.91 (d, 1H, J = 7.8 Hz), 4.24-4.12 (m, 1H), 3.96 (s, 3H), 3.60-3.48 (m, 1H), 1.90-1.15 (m, 8H). | 452 | 450 | 0.93 |
| Example 4-231 | HCl | DMSO-d6 | 300 MHz | δ: 11.93 (s, 1H), 8.57-8.52 (m, 1H), 8.61 (d, 1H, J = 2.7 Hz), 8.52-8.48 (m, 2H), 8.15 (dd, 1H, J = 2.7, 8.7 Hz), 7.99 (d, 1H, J = 12.6 Hz), 7.98-7.64 (m, 4H), 7.42 (br, 1H), 7.05-6.95 (m, 2H), 4.25-4.14 (m, | 452 | 450 | 0.88 |

TABLE 2-continued

| | | | | | | | |
|---|---|---|---|---|---|---|---|
| Example 4-232 | HCl | DMSO-d6 | 300 MHz | δ: 12.04 (s, 1H), 9.04-9.00 (m, 1H), 8.70-8.66 (m, 2H), 8.32 (d, 1H, J = 5.1 Hz), 8.01 (d, 1H, J = 12.6 Hz), 8.00-7.80 (m, 4H), 7.48-7.40 (m, 2H), 7.32-7.28 (m, 1H), 7.05 (d, 1H, J = 6.6 Hz), 4.34-4.20 (m, 1H), 3.92 (s, 3H), 3.62-3.50 (m, 1H), 1.90-1.20 (m, 8H). | 452 | 450 | 0.88 |
| Example 4-233 | HCl | DMSO-d6-D2O | 300 MHz | δ: 8.18-8.12 (m, 1H), 7.88 (d, 1H, J = 12.2 Hz), 7.47-7.40 (m, 1H), 4.29-4.19 (m, 1H), 3.85 (s, 3H), 3.80-3.68 (m, 4H), 3.60-3.52 (m, 1H), 3.30-3.18 (m, 4H), 1.95-1.05 (m, 8H). | 460 | 458 | 0.8 |
| Example 4-234 | HCl | DMSO-d6-D2O | 300 MHz | δ: 8.47 (s, 1H), 7.99 (d, 1H, J = 12.2 Hz), 7.93-7.89 (m, 1H), 6.82-6.78 (m, 1H), 4.42-4.33 (m, 1H), 4.00-3.90 (m, 4H), 3.71-3.65 (m, 1H), 3.63-3.53 (m, 4H), 1.93-1.38 (m, 8H). | 469 | 467 | 0.71 |
| Example 4-235 | HCl | DMSO-d6-D2O | 300 MHz | δ: 8.39 (s, 1H), 7.93 (d, 1H, J = 12.2 Hz), 7.61 (d, 1H, J = 3.0 Hz), 6.59 (d, 1H, J = 3.0 Hz), 4.33-4.21 (m, 1H), 4.10 (s, 3H), 3.66-3.57 (m, 1H), 1.95-1.37 (m, 8H). | 414 | 412 | 0.74 |

Example 5

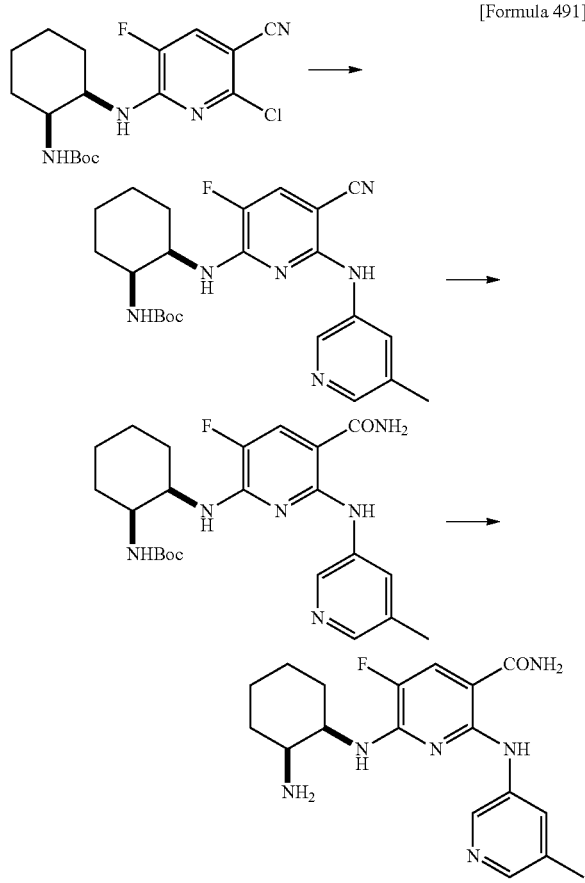

[Formula 491]

1st Step 5-methyl-3-pyridineamine (191 mg), cesium carbonate (1.10 g), Pd$_2$(dba)$_3$ (186 mg), and Xantphos (235 mg) were added to a 1,4-dioxane (14 ml) solution containing tert-butyl cis-2-(6-chloro-5-cyano-3-fluoropyridin-2-ylamino)cyclohexylcarbamate (500 mg), followed by stirring at 100° C. for 2 hours in a nitrogen atmosphere. The reaction mixture was cooled to room temperature, and water and ethyl acetate were added. Insoluble matter was removed by filtration, the filter cake was washed with water and ethyl acetate, the organic layer was collected, washed with saturated saline, and dried over anhydrous magnesium sulfate, and the solvent was distilled away under reduced pressure. The obtained residue was purified by silica gel column chromatography (hexane:ethyl acetate=10:0 to 1:4), diisopropylether was added, solid matter was collected by filtration, and a light yellow solid of tert-butyl cis-2-(6-(5-methylpyridin-3-ylamino)-5-cyano-3-fluoropyridin-2-ylamino)cyclohexylcarbamate (523 mg) was thus obtained.

$^1$H-NMR (DMSO-d$_6$, 400 MHz) δ:8.90 (s, 1H), 8.55-8.51 (m, 1H), 8.05-8.02 (m, 1H), 7.78 (s, 1H), 7.67 (d, 1H, J=11.1 Hz), 7.00-6.94 (m, 1H), 6.67-6.62 (m, 1H), 3.95-3.80 (m, 2H), 2.28 (s, 3H), 1.82-1.10 (m, 17H)

MS (ESI, m/z): 441 (M+H), 439 (M−H)

2nd step

A 5N sodium hydroxide aqueous solution (1.18 ml) and 30% hydrogen peroxide solution (0.70 ml) were added to a solution of dimethyl sulfoxide (10 ml) and ethanol (10 ml) containing tert-butyl cis-2-(6-(5-methylpyridin-3-ylamino)-5-cyano-3-fluoropyridin-2-ylamino)cyclohexylcarbamate (520 mg), followed by stirring at 34° C. for 30 minutes. The reaction mixture was cooled to room temperature, and water was added. Solid matter was collected by filtration, dissolved in ethyl acetate and tetrahydrofuran, washed with water and then with saturated saline, and dried over anhydrous magnesium sulfate. The solvent was distilled away under reduced pressure. The obtained residue was added to diisopropylether, solid matter was collected by filtration and washed with diisopropylether and hexane, and a light yellow solid of tert-butyl cis-2-(5-aminocarbonyl-3-fluoro-6-(5-methylpyridin-3-ylamino)pyridin-2-ylamino)cyclohexylcarbamate (506 mg) was thus obtained.

$^1$H-NMR (DMSO-$d_6$, 400 MHz) δ:11.72 (s, 1H), 8.59 (d, 1H, J=2.2 Hz), 8.01 (s, 1H), 7.97 (s, 1H), 7.89 (d, 1H, J=12.6 Hz), 7.76 (brs, 1H), 7.26 (brs, 1H), 6.74-6.64 (m, 2H), 4.14-4.04 (m, 1H), 3.95-3.86 (m, 1H), 2.31 (s, 3H), 1.87-1.10 (m, 17H)

MS (ESI, m/z): 459 (M+H), 457 (M−H)

3rd Step

A mixture of tert-butyl cis-2-(5-aminocarbonyl-3-fluoro-6-(5-methylpyridin-3-ylamino)-pyridin-2-ylamino)cyclohexylcarbamate (500 mg) and TFA (5 ml) was stirred at room temperature for 30 minutes. The solvent was distilled away under reduced pressure (at 40° C. or less). 4N hydrogen chloride/1,4-dioxane (1.36 ml) was added to a tetrahydrofuran/methanol (10/1) (50 ml) suspension containing the obtained residue, followed by stirring at room temperature for 30 minutes. Solid matter was collected by filtration, washed with tetrahydrofuran/methanol (10/1), and a light yellow solid of 6-(cis-2-aminocyclohexylamino)-5-fluoro-2-(5-methylpyridin-3-ylamino)nicotinamide•hydrochloride (498 mg) was obtained.

($^1$H-NMR data and MS data are shown in table 3.)

Example 6

The compounds listed in table 3 were obtained as described in Example 5.

TABLE 3

| Number | Structure | Compound Name | $^1$H-NMR | MS (ESI, m/z) |
|---|---|---|---|---|
| Example 6-1 HCl salt | 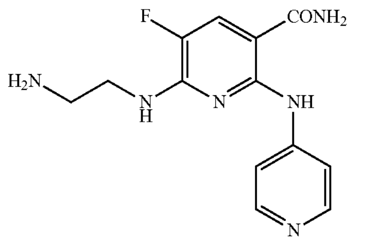 [SMILES: NCCNc1nc(Nc2ccncc2)c(C(N)=O)cc1F] | 6-((2-aminoethyl)amino)-5-fluoro-2-(pyridin-4-ylamino)nicotinamide | $^1$H-NMR (DMSO-d$_6$, 400 MHz) δ: 13.04 (s, 1H), 8.59 (d, 2H, J = 7.1 Hz), 8.23 (brs, 3H), 8.16 (brs, 1H), 8.12-8.02 (m, 3H), 7.81-7.75 (m, 1H), 7.70 (brs, 1H), 3.78-3.70 (m, 2H), 3.13-3.04 (m, 2H). | 291 (M + H), 289 (M − H) |
| Example 6-2 HCl salt | 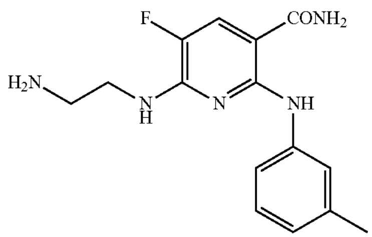 [SMILES: Cc1cccc(Nc2nc(NCCN)c(F)cc2C(N)=O)c1] | 6-((2-aminoethyl)amino)-5-fluoro-2-(3-methylphenylamino)nicotinamide | $^1$H-NMR (CD$_3$OD, 400 MHz) δ: 7.72 (d, 1H, J = 12.0 Hz), 7.39 (d, 1H, J = 8.0 Hz), 7.35 (s, 1H), 7.18 (t, 1H, J = 8.0 Hz), 6.82 (d, 1H, J = 8.0 Hz), 3.73 (t, 2H, J = 5.2 Hz), 3.22 (t, 2H, J = 5.2 Hz), 2.32 (s, 3H). | 304 (M + H) |
| Example 6-3 HCl salt | 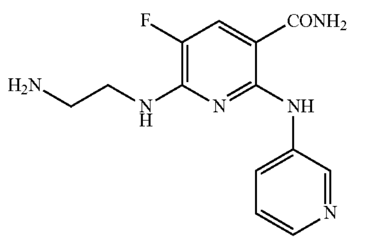 [SMILES: NCCNc1nc(Nc2cccnc2)c(C(N)=O)cc1F] | 6-((2-aminoethyl)amino)-5-fluoro-2-(pyridin-3-ylamino)nicotinamide | $^1$H-NMR (CD$_3$OD, 400 MHz) δ: 9.51 (d, 1H, J = 2.7 Hz), 8.59 (ddd, 1H, J = 1.2, 2.7, 8.7 Hz), 8.40-8.37 (m, 1H), 7.97 (dd, 1H, J = 5.3, 8.7 Hz), 7.89 (d, 1H, J = 11.7 Hz), 3.88 (t, 2H, J = 5.9 Hz), 3.48-3.21 (2H, overlapping with CH$_3$OH peak). | 291 (M + H) |
| Example 6-4 HCl salt | 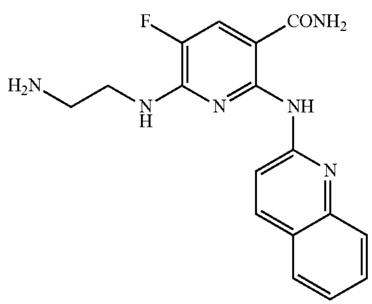 | 6-((2-aminoethyl)amino)-5-fluoro-2-(quinolin-2-ylamino)nicotinamide | $^1$H-NMR (CD$_3$OD, 400 MHz) δ: 9.96 (d, 1H, J = 2.3 Hz), 9.03 (d, 1H, J = 2.3 Hz), 8.23-8.15 (m, 2H), 7.97-7.93 (m, 1H), 7.90-7.80 (m, 2H), 3.92 (t, 2H, J = 6.1 Hz), 3.35 (t, 2H, J = 6.1 Hz). | 341 (M + H) |

TABLE 3-continued

| | Structure | Name | ¹H NMR | MS |
|---|---|---|---|---|
| Example 6-5 HCl salt | F, CONH₂, NH-(4-methylphenyl), H₂N-CH₂CH₂-NH (pyridine) | 6-((2-aminoethyl)amino)-5-fluoro-2-(4-methylphenylamino)nicotinamide | ¹H-NMR (CD₃OD, 300 MHz) δ: 7.71 (d, 1H, J = 12.0 Hz), 7.41 (d, 2H, J = 8.4 Hz), 7.12 (d, 2H, J = 8.4 Hz), 3.70 (t, 2H, J = 5.2 Hz), 3.19 (t, 2H, J = 5.2 Hz), 2.30 (s, 3H). | 304 (M + H) |
| Example 6-6 | F, CONH₂, NH-(3-chlorophenyl), H₂N-CH₂CH₂-NH (pyridine) | 6-((2-aminoethyl)amino)-2-(3-chlorophenylamino)-5-fluoronicotinamide | ¹H-NMR (CD₃OD, 300 MHz) δ: 8.00 (s, 1H), 7.75 (d, 1H, J = 12.0 Hz), 7.26-7.24 (m, 2H), 6.97-6.94 (m, 1H), 3.79 (t, 2H, J = 5.2 Hz), 3.33 (t, 2H, J = 5.2 Hz). | 324 (M + H) |
| Example 6-7 | F, CONH₂, NH-(3,5-dichlorophenyl), H₂N-CH₂CH₂-NH (pyridine) | 6-((2-aminoethyl)amino)-2-(3,5-dichlorophenyl)amino)-5-fluoronicotinamide | ¹H NMR (CD₃OD, 300 MHz) δ: 7.77 (d, 1H, J = 12.0 Hz), 7.68-7.67 (m, 2H), 6.98-6.97 (m, 1H), 3.79 (t, 2H, J = 5.2 Hz), 3.33 (t, 2H, J = 5.2 Hz). | 358 (M + H) |
| Example 6-8 HCl salt | F, CONH₂, NH-(3-trifluoromethylphenyl), H₂N-CH₂CH₂-NH (pyridine) | 6-((2-aminoethyl)amino)-5-fluoro-2-(3-trifluoromethyl)phenyl)amino)nicotinamide | ¹H-NMR (CD₃OD, 300 MHz) δ: 8.32 (s, 1H), 7.77 (d, 1H, J = 12.0 Hz), 7.54 (d, 1H, J = 8.4 Hz), 7.45 (t, 1H, J = 8.4 Hz), 7.22 (d, 1H, J = 8.4 Hz), 3.80 (t, 2H, J = 5.7 Hz), 3.24 (t, 2H, J = 5.7 Hz). | 358 (M + H) |

TABLE 3-continued

| | Structure | Name | ¹H-NMR | MS |
|---|---|---|---|---|
| Example 6-9 HCl salt | [structure] | 6-((2-aminoethyl)amino)-2-(3,5-bis(trifluoromethyl)phenyl)amino)-5-fluoronicotinamide | ¹H-NMR (CD₃OD, 300 MHz) δ: 8.27 (s, 2H), 7.82 (d, 1H, J = 12.0 Hz), 7.46 (s, 1H), 3.82 (t, 2H, J = 5.7 Hz), 3.24 (t, 2H, J = 5.7 Hz). | 426 (M + H) |
| Example 6-10 HCl salt | [structure] | 6-((2-aminoethyl)amino)-5-fluoro-2-((1H-indazol-6-yl)amino)nicotinamide | ¹H-NMR (CD₃OD, 300 MHz) δ: 8.51 (s, 1H), 8.46-8.45 (m, 1H), 7.83 (d, 1H, J = 9.0 Hz), 7.82 (d, 1H, J = 12.0 Hz), 7.23 (dd, 1H, J = 1.8, 9.0 Hz), 3.93 (t, 2H, J = 5.7 Hz), 3.37 (t, 2H, J = 5.7 Hz). | 330 (M + H) |
| Example 6-11 HCl salt | [structure] | 6-((2-aminoethyl)amino)-2-((3,4-dichlorophenyl)amino)-5-fluoronicotinamide | ¹H-NMR (CD₃OD, 400 MHz) δ: 8.15 (d, 1H, J = 2.4 Hz), 7.76 (d, 1H, J = 12 Hz), 7.39 (d, 1H, J = 8.8 Hz), 7.29 (dd, 1H, J = 2.4, 8.8 Hz), 3.78 (t, 2H, J = 6.0 Hz), 3.28 (t, 2H, J = 6.0 Hz). | 358 (M + H) |
| Example 6-12 HCl salt | [structure] | 6-((2-aminoethyl)amino)-5-fluoro-2-((1,3-thiazol-2-yl)amino)nicotinamide | | 297 (M + H) |

TABLE 3-continued

| | Structure | Name | NMR | MS |
|---|---|---|---|---|
| Example 6-13 HCl salt | 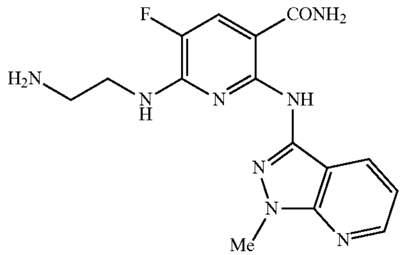 [SMILES: Cn1nc(Nc2nc(NCCN)c(F)cc2C(N)=O)c2cccnc21] | 6-(2-aminoethyl)amino)-5-fluoro-2-((1-methyl-1H-pyrazolo[3,4-b]pyridin-3-yl)amino)nicotinamide | | 345 (M + H) |
| Example 6-14 HCl salt | 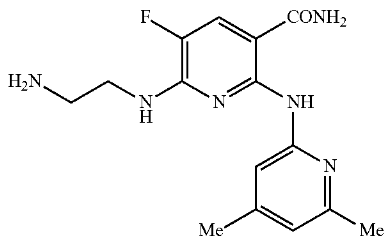 [SMILES: Cc1cc(C)nc(Nc2nc(NCCN)c(F)cc2C(N)=O)c1] | 6-((2-aminoethyl)amino)-2-((4,6-dimethylpyridin-2-yl)amino)-5-fluoronicotinamide | $^1$H-NMR (CD$_3$OD, 400 MHz) δ: 8.02 (d, 1H, J = 11.7 Hz), 7.50-7.44 (m, 2H), 3.72 (t, 2H, J = 5.7 Hz), 3.23 (t, 2H, J = 5.7 Hz), 2.67 (s, 6H). | 319 (M + H) |
| Example 6-15 HCl salt | 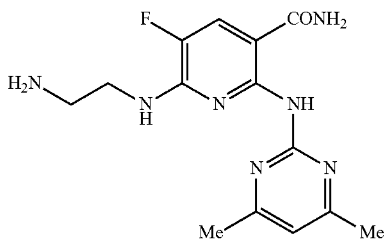 [SMILES: Cc1cc(C)nc(Nc2nc(NCCN)c(F)cc2C(N)=O)n1] | 6-((2-aminoethyl)amino)-2-((4,6-dimethylpyrimidin-2-yl)amino)-5-fluoronicotinamide | $^1$H-NMR (CD$_3$OD, 400 MHz) δ: 8.06 (d, 1H, J = 11.7 Hz), 7.22 (s, 1H), 3.94 (t, 2H, J = 5.7 Hz), 3.39 (t, 2H, J = 5.7 Hz), 2.67 (s, 6H). | 320 (M + H) |
| Example 6-16 HCl salt | 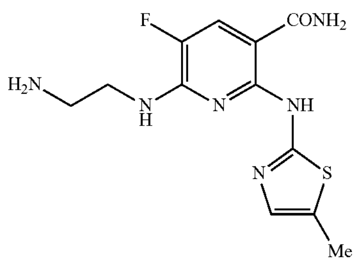 [SMILES: Cc1cnc(Nc2nc(NCCN)c(F)cc2C(N)=O)s1] | 6-((2-aminoethyl)amino)-5-fluoro-2-((5-methyl-1,3-thiazol-2-yl)amino)nicotinamide | $^1$H-NMR (CD$_3$OD, 400 MHz) δ: 8.00 (d, 1H, J = 11.5 Hz), 7.35 (d, 1H, J = 1.3 Hz), 3.99 (t, 2H, J = 5.8 Hz), 3.37 (t, 2H, J = 5.8 Hz), 2.47 (d, 3H, J = 1.3 Hz). | 311 (M + H), 309 (M − H) |

TABLE 3-continued

| | | | |
|---|---|---|---|
| Example 6-17 HCl salt | 6-((2-aminoethyl)amino)-2-((2,2-dimethyl-3-oxo-3,4-dihydro-2H-pyrido[3,2-b][1,4]oxazin-6-yl)amino)-5-fluoronicotinamide | $^1$H-NMR (CD$_3$OD, 400 MHz) δ: 7.82 (d, 1H, J = 11.7 Hz), 7.77-7.68 (m, 1H), 7.32 (d, 1H, J = 8.8 Hz), 3.83 (t, 2H, J = 6.0 Hz), 3.38-3.15 (2H, overlapping with CH$_3$OH peak), 1.48 (s, 6H). | 390 (M + H), 388 (M − H) |
| Example 6-18 | 6-(ethylamino)-5-fluoro-2-((1H-indazol-6-yl)amino)nicotinamide | $^1$H-NMR (CD$_3$OD, 400 MHz) δ: 8.46 (s, 1H), 7.92 (s, 1H), 7.65 (d, 1H, J = 12 Hz), 7.61 (d, 1H, J = 9.2 Hz), 7.04 (dd, 1H, J = 9.2 Hz), 3.65 (q, 2H, J = 7.2 Hz), 1.34 (t, 3H, J = 7.2 Hz). | 313 (M − H) |
| Example 6-19 | 6-(ethylamino)-5-fluoro-2-((3-(trifluoromethyl)phenyl)amino)nicotinamide | $^1$H-NMR (CDCl$_3$, 300 MHz) δ: 11.2 (s, 1H), 8.56 (s, 1H), 7.48 (s, 1H, J = 8.7 Hz), 7.36 (t, 1H, J = 8.7 Hz), 7.23-7.19 (m, 2H), 5.41 (brs, 2H), 5.01 (brs, 1H), 3.60 (dq, 2H, J = 5.4, 9.6 Hz), 1.31 (t, 3H, J = 5.4 Hz). | 343 (M + H) |

TABLE 3-continued

| Example | Structure | Name | NMR | MS |
|---|---|---|---|---|
| Example 6-20 | 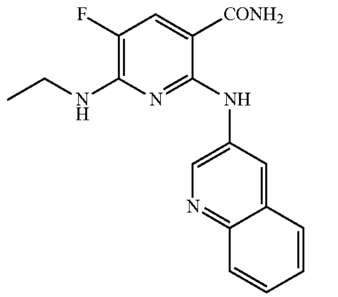 [SMILES: CCNc1nc(Nc2cnc3ccccc3c2)c(C(N)=O)cc1F] | 6-(ethylamino)-5-fluoro-2-(quinolin-3-ylamino)nicotinamide | $^1$H-NMR (CD$_3$OD, 300 MHz) δ: 8.96 (d, 1H, J = 2.4 Hz), 8.89 (d, 1H, J = 2.4 Hz), 7.95-7.88 (m, 1H), 7.80-7.75 (m, 1H), 7.69 (d, 1H, J = 12.0 Hz), 7.61-7.49 (m, 2H), 3.63 (q, 2H, J = 7.2 Hz), 1.36 (t, 3H, J = 7.2 Hz). | 326 (M + H) |
| Example 6-21 HCl salt | 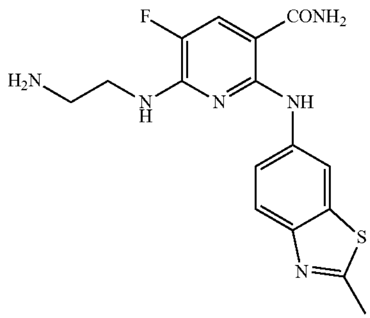 | 6-((2-aminoethyl)amino)-5-fluoro-2-((2-methylbenzo[d]thiazol-6-yl)amino)nicotinamide | $^1$H-NMR (DMSO-d$_6$, 300 MHz) δ: 11.82 (s, 1H), 8.38 (d, 1H, J = 2.1 Hz), 8.00-7.85 (m, 6H), 7.45-7.35 (m, 3H), 3.76-3.65 (m, 2H), 3.20-3.08 (2H, m), 2.80 (s, 3H). | 361 (M + H) |
| Example 6-22 HCl salt | 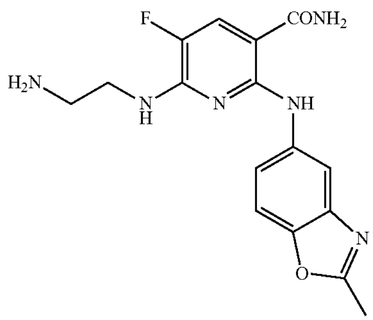 [SMILES: Cc1nc2cc(Nc3nc(NCCN)c(F)cc3C(N)=O)ccc2o1] | 6-(2-aminoethylamino)-5-fluoro-2-((2-methylbenzo[d]oxazol-5-yl)amino)nicotinamide | $^1$H-NMR (CD$_3$OD, 400 MHz) δ: 8.31 (d, 1H, J = 2.0 Hz), 7.75 (d, 1H, J = 12.0 Hz), 7.48 (d, 1H, J = 8.8 Hz), 7.19 (dd, 1H, J = 2.0, 8.8 Hz), 3.79 (t, 2H, J = 6.0 Hz), 3.25 (t, 2H, J = 6.0 Hz), 2.64 (s, 3H). | 345 (M + H) |

TABLE 3-continued

| | Structure | Name | NMR | MS |
|---|---|---|---|---|
| Example 6-23 HCl salt | (structure) | 6-((2-aminoethyl)amino)-5-fluoro-2-((2-methylbenzo[d]oxazol-6-yl)amino)nicotinamide | $^1$H-NMR (CD$_3$OD, 300 MHz) δ: 8.12 (d, 1H, J = 2.0 Hz), 7.76 (d, 1H, J = 12.0 Hz) 7.51 (d, 1H, J = 8.4 Hz), 7.34 (dd, 1H, J = 2.0, 8.4 Hz), 3.79 (t, 2H, J = 6.0 Hz), 3.25 (t, 2H, J = 6.0 Hz), 2.64 (s, 3H). | 345 (M + H) |
| Example 6-24 HCl salt | (structure) | 2-((3-acetylaminophenyl)amino)-6-((2-aminoethyl)amino)-5-fluoronicotinamide | $^1$H-NMR (CD$_3$OD, 300 MHz) δ: 8.56 (s, 1H), 7.73 (d, 1H, J = 12.0 Hz), 7.24-7.17 (m, 1H), 6.99-6.88 (m, 1H), 6.80-6.74 (m, 1H), 3.91 (t, 2H, J = 6.0 Hz), 3.18 (t, 2H, J = 6.0 Hz), 2.15 (s, 3H). | 347 (M + H) |
| Example 6-25 HCl salt | (structure) | 6-((2-aminoethyl)amino)-5-fluoro-2-((3-(methylsulfonyl)phenyl)amino)nicotinamide | $^1$H-NMR (CD$_3$OD, 300 MHz) δ: 9.07-9.05 (m, 1H), 7.77 (d, 1H, J = 12.0 Hz), 7.53-7.51 (m, 2H), 7.37-7.33 (m, 1H), 3.89 (t, 2H, J = 6.0 Hz), 3.26 (t, 2H, J = 6.0 Hz), 3.15 (s, 3H). | 368 (M + H) |
| Example 6-26 HCl salt | (structure) | 6-((2-aminoethyl)amino)-5-fluoro-2-(quinolin-6-ylamino)nicotinamide | $^1$H-NMR (DMSO-d$_6$, 300 MHz) δ: 12.30 (s, 1H), 8.99-8.98 (m, 1H), 8.94 (d, 1H, J = 8.7 Hz), 8.66 (d, 1H, J = 2.1 Hz), 8.26 (d, 1H, J = 9.0 Hz), 8.21-8.08 (m, 4H), 8.02 (d, 1H, J = 12.0 Hz), 7.99-7.90 (m, 1H), 7.87 (dd, 1H, J = 5.1, 8.4 Hz), 7.55-7.35 (m, 2H), 3.79 (q, 2H, J = 5.4 Hz), 3.21 (q, 2H, J = 6.0 Hz). | 341 (M + H) |

TABLE 3-continued

| Example | Structure | Name | ¹H-NMR | MS |
|---|---|---|---|---|
| Example 6-27 HCl salt | 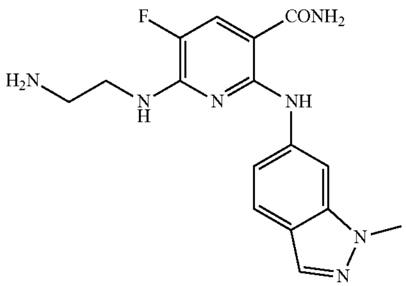 [SMILES: Cn1ncc2ccc(Nc3nc(NCCN)c(F)cc3C(N)=O)cc21] | 6-((2-aminoethyl)amino)-5-fluoro-2-((1-methyl-1H-indazol-6-yl)amino)nicotinamide | ¹H-NMR (DMSO-d₆, 300 MHz) δ: 11.90 (s, 1H), 8.21 (s, 1H), 8.08-7.88 (m, 5H), 7.63 (d, 1H, J = 8.7 Hz), 7.38-7.32 (m, 2H), 6.99 (dd, 1H, J = 1.8, 8.7 Hz), 3.97 (s, 3H), 3.83-3.75 (m, 2H), 3.19-3.10 (m, 2H). | 344 (M + H) |
| Example 6-28 HCl salt | 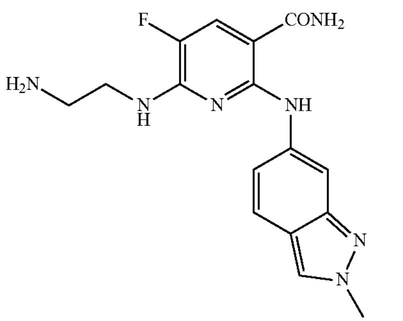 [SMILES: Cn1cc2ccc(Nc3nc(NCCN)c(F)cc3C(N)=O)cc2n1] | 6-((2-aminoethyl)amino)-5-fluoro-2-((2-methyl-2H-indazol-6-yl)amino)nicotinamide | ¹H-NMR (DMSO-d₆, 300 MHz) δ: 11.83 (s, 1H), 8.31 (s, 1H), 8.25 (s, 1H), 8.00-7.93 (m, 4H), 7.64 (d, 1H, J = 9.0 Hz), 7.38-7.32 (m, 2H), 6.91 (dd, 1H, J = 1.8, 9.0 Hz), 4.13 (s, 3H), 3.73-3.71 (m, 2H), 3.21-3.18 (m, 2H). | 344 (M + H) |
| Example 6-29 HCl salt | 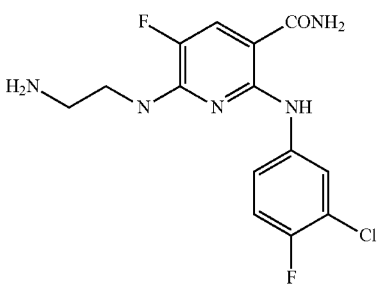 [SMILES: NCCNc1nc(Nc2ccc(F)c(Cl)c2)c(C(N)=O)cc1F] | 6-((2-aminoethyl)amino)-2-((3-chloro-4-fluorophenyl)amino)-5-fluoronicotinamide | ¹H-NMR (CD₃OD, 300 MHz) δ: 8.01 (dd, 1H, J = 2.7, 6.9 Hz), 7.75 (d, 1H, J = 12.0 Hz), 7.33-7.27 (m, 1H), 7.18-7.13 (m, 1H), 3.77-3.73 (m, 2H), 3.28-3.23 (m, 2H). | 342 (M + H) |

TABLE 3-continued

| Example | Structure | Name | ¹H-NMR | MS |
|---|---|---|---|---|
| Example 6-30 HCl salt | (pyridine with F, CONH₂, NH-phenyl-Ph, NH-CH₂CH₂NH₂) | 6-((2-aminoethyl)amino)-2-(biphenyl-3-yl)amino)-5-fluoronicotinamide | ¹H-NMR (CD₃OD, 300 MHz) δ: 7.96 (t, 1H, J = 1.8 Hz), 7.75 (d, 1H, J = 12.0 Hz), 7.64-7.58 (m, 2H), 7.57-7.52 (m, 1H), 7.48-7.31 (m, 4H), 7.256-7.22 (m, 1H), 3.73-3.72 (m, 2H), 3.11-3.07 (m, 2H). | 366 (M + H) |
| Example 6-31 HCl salt | (pyridine with F, CONH₂, NH-phenyl-CN, NH-CH₂CH₂NH₂) | 6-((2-aminoethyl)amino)-2-((3-cyanophenyl)amino)-5-fluoronicotinamide | ¹H-NMR (CD₃OD, 300 MHz) δ: 8.38-8.36 (m, 1H), 7.78 (d, 1H, J = 12.0 Hz), 7.64-7.58 (m, 1H), 7.44 (t, 1H, 8.1 Hz), 7.30-7.28 (m, 1H), 3.83-3.78 (m, 2H), 3.35-3.22 (m, 2H). | 315 (M + H) |
| Example 6-32 HCl salt | (pyridine with F, CONH₂, NH-phenyl-CONH₂, NH-CH₂CH₂NH₂) | 2-(3-aminocarbonyl)phenyl)amino)-6-((2-aminoethyl)amino)-5-fluoronicotinamide | ¹H-NMR (CD₃OD, 300 MHz) δ: 8.99-8.98 (m, 1H), 7.75 (d, 1H, J = 12.0 Hz), 7.45-7.33 (m, 2H), 7.35-7.32 (m, 1H), 3.90 (t, 2H, J = 6.9 Hz), 3.23 (t, 2H, J = 6.9 Hz). | 333 (M + H) |
| Example 6-33 HCl salt | (pyridine with F, CONH₂, NH-phenyl-COMe, NH-CH₂CH₂NH₂) | 2-((3-acetylphenyl)amino)-6-((2-aminoethyl)amino)-5-fluoronicotinamide | ¹H-NMR (CD₃OD, 300 MHz) δ: 8.85-8.40 (m, 1H), 7.75 (d, 1H, J = 12.0 Hz), 7.65-7.63 (m, 1H), 7.45-7.38 (m, 2H), 3.90 (t, 2H, J = 6.3 Hz), 3.35 (t, 2H, J = 6.3 Hz), 2.63 (s, 3H). | 332 (M + H) |

TABLE 3-continued

| Example | Name | Structure | NMR | MS |
|---|---|---|---|---|
| Example 6-34 HCl salt | 6-(cis-2-aminocyclohexylamino)-2-((benzo[c][1,2,5]thiadiazol-5-yl)amino)-5-fluoronicotinamide | | $^1$H-NMR (CD$_3$OD, 300 MHz) δ: 8.79 (d, 1H, J = 2.0 Hz), 7.88 (d, 1H, J = 9.3 Hz), 7.84 (d, 1H, J = 11.9 Hz), 7.47 (dd, 1H, J = 2.0, 9.3 Hz), 4.56-4.53 (m, 1H), 4.04-4.00 (m, 1H), 1.95-1.56 (m, 8H). | 402 (M + H) |
| Example 6-35 HCl salt | 6-(cis-2-aminocyclohexylamino)-2-((benzo[d]thiazol-6-yl)amino)-5-fluoronicotinamide | | $^1$H-NMR (CD$_3$OD, 300 MHz) δ: 9.19 (s, 1H), 8.52 (d, 1H, J = 2.1 Hz), 7.98 (d, 1H, J = 8.9 Hz), 7.79 (d, 1H, J = 12.0 Hz), 7.60 (dd, 1H, J = 2.1, 8.9 Hz), 4.46-4.33 (m, 1H), 3.92-3.79 (m, 1H), 1.86-1.62 (m, 8H). | 401 (M + H), 399 (M − H) |
| Example 6-36 HCl salt | 6-((2-aminoethyl)amino)-5-fluoro-2-(3-(methylamino-carbonyl)phenyl)amino)nicotinamide | | $^1$H-NMR (CD$_3$OD, 300 MHz) δ: 8.97-8.95 (m, 1H), 7.75 (d, 1H, J = 12.0 Hz), 7.35-7.33 (m, 2H), 7.24-7.17 (m, 1H), 3.90 (t, 2H, J = 6.3 Hz), 3.25 (t, 2H, J = 6.3 Hz), 2.94 (s, 3H). | 347 (M + H) |
| Example 6-37 HCl salt | 6-((2-aminoethyl)amino)-5-fluoro-2-(1-naphthyl)amino)nicotinamide | | $^1$H-NMR (DMSO-d$_6$, 300 MHz) δ: 8.46 (dd, 1H, J = 2.7, 6.0 Hz), 8.22 (d, 1H, J = 7.8 Hz), 8.02-7.89 (m, 6H), 7.61-7.49 (m, 4H), 7.42-7.32 (m, 2H), 3.67-3.59 (m, 2H), 3.12-3.05 (m, 2H). | 340 (M + H) |

TABLE 3-continued

| | | | |
|---|---|---|---|
| Example 6-38 HCl salt | 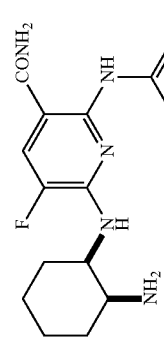 | 6-(cis-2-aminocyclohexylamino)-2-((benzo[d][1,3]dioxol-5-yl)amino)-5-fluoronicotinamide | $^1$H-NMR (CD$_3$OD, 300 MHz) δ: 7.72 (d, 1H, J = 12.1 Hz), 7.33-7.29 (m, 1H), 6.79-6.75 (m, 2H), 5.95-5.90 (m, 2H), 4.30-4.20 (m, 1H), 3.90-3.80 (m, 1H), 1.90-1.50 (m, 8H). | 388 (M + H) |
| Example 6-39 HCl salt | 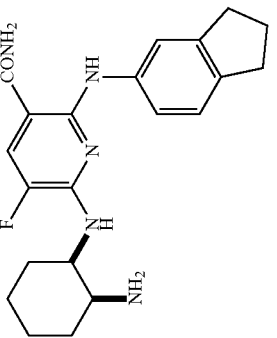 | 6-(cis-2-aminocyclohexylamino)-2-((2,3-dihydro-1H-inden-5-yl)amino)-5-fluoronicotinamide | $^1$H-NMR (CD$_3$OD, 300 MHz) δ: 7.72 (d, 1H, J = 12.0 Hz), 7.39 (brs, 1H), 7.24 (dd, 1H, J = 1.9, 8.0 Hz), 7.14 (d, 1H, J = 8.0 Hz), 4.38-4.25 (m, 1H), 3.88-3.75 (m, 1H), 3.00-2.71 (m, 4H), 2.18-2.00 (m, 2H), 1.92-1.50 (m, 8H). | 384 (M + H) |
| Example 6-40 HCl salt | 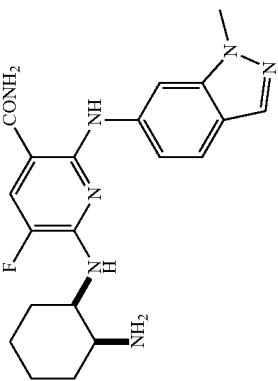 | 6-(cis-2-aminocyclohexylamino)-5-fluoro-2-((1-methyl-1H-indazol-6-yl)amino)nicotinamide | $^1$H-NMR (CD$_3$OD, 300 MHz) δ: 8.47 (s, 1H), 8.24 (s, 1H), 7.84 (d, 1H, J = 11.9 Hz), 7.77 (d, 1H, J = 9.0 Hz), 7.25 (dd, 1H, J = 1.7, 9.0 Hz), 4.68-4.54 (m, 1H), 4.28 (s, 3H), 3.96-3.84 (m, 1H), 2.00-1.50 (m, 8H). | 398 (M + H), 396 (M − H) |

| Example | Structure | Name | NMR | MS |
|---|---|---|---|---|
| Example 6-41 HCl salt | 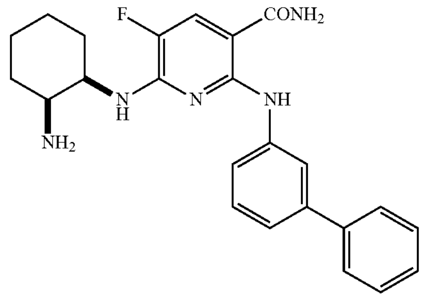 | 6-(cis-2-aminocyclohexylamino)-2-(biphenyl-3-ylamino)-5-fluoronicotinamide | ¹H-NMR (CD₃OD, 300 MHz) δ: 8.13-8.07 (m, 1H), 7.76 (d, 1H, J = 12.0 Hz), 7.70-7.20 (m, 8H), 4.30-4.17 (m, 1H), 3.76-3.65 (m, 1H), 1.88-1.11 (m, 8H). | 420 (M + H), 418 (M − H) |
| Example 6-42 | 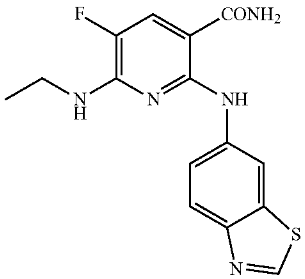 | 2-(benzo[d]thiazol-6-yl)amino)-6-(ethylamino)-5-fluoronicotinamide | ¹H-NMR (DMSO-d₆, 300 MHz) δ: 11.9 (s, 1H), 9.17 (s, 1H), 8.75 (d, 1H, J = 2.1 Hz), 7.95 (d, 1H, J = 9.0 Hz), 7.88 (d, 1H, J = 12.0 Hz), 7.54 (dd, 1H, J = 2.1, 9.0 Hz), 3.46 (q, 2H, J = 7.2 Hz), 1.22 (t, 3H, J = 7.2 Hz). | 361 (M + H) |
| Example 6-43 | 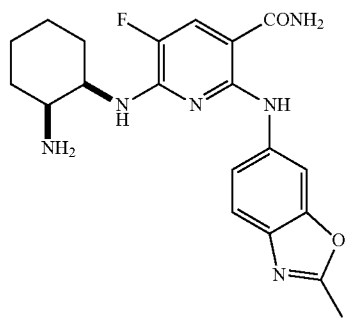 | 6-(cis-2-aminocyclohexylamino)-5-fluoro-2-((2-methylbenzo[d]oxazol-6-yl)amino)nicotinamide | ¹H-NMR (CD₃OD, 300 MHz) δ: 8.34 (d, 1H, J = 2.0 Hz), 7.69 (d, 1H, J = 12.2 Hz), 7.46 (d, 1H, J = 8.6 Hz), 7.23 (dd, 1H, J = 2.0, 8.6 Hz), 4.31-4.19 (m, 1H), 3.44-3.37 (m, 1H), 2.61 (s, 3H), 1.87-1.44 (m, 8H). | 399 (M + H), 397 (M − H) |

| | | | |
|---|---|---|---|
| Example 6-44 TFA salt | 6-(2-aminoethylamino)-2-((benzo[d]thiazol-6-yl)amino)-5-fluoro-nicotinamide | 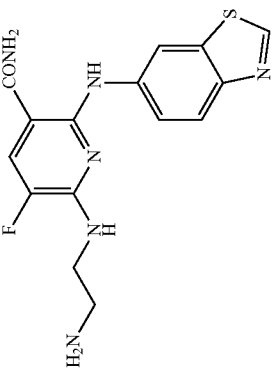 | ¹H-NMR (CD₃OD, 300 MHz) δ: 9.07 (s, 1H), 8.40 (d, 1H, J = 2.1 Hz), 7.97 (d, 1H, J = 8.9 Hz), 7.77 (d, 1H, J = 12.0 Hz), 7.69 (dd, 1H, J = 2.1, 8.9 Hz), 3.79 (t, 2H, J = 5.7 Hz), 3.25 (t, 2H, J = 5.7 Hz). | 347 (M + H), 345 (M − H) |
| Example 6-45 HCl salt | 6-(cis-2-aminocyclohexylamino)-5-fluoro-2-((4-(2-(pyrrolidin-1-yl)ethoxy)phenyl)amino)nicotinamide | 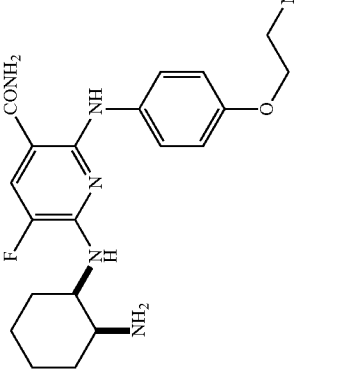 | ¹H-NMR (CD₃OD, 300 MHz) δ: 7.73 (d, 1H, J = 12.0 Hz), 7.48 (d, 2H, J = 8.3 Hz), 7.02 (d, 2H, J = 8.3 Hz), 4.50-4.20 (m, 3H), 3.93-3.50 (m, 5H), 3.39-3.15 (2H, overlapping with CH₃OH peak), 2.30-2.00 (m, 4H), 2.00-1.45 (m, 8H). | 455 (M − H) |
| Example 6-46 HCl salt | 6-(cis-2-aminocyclohexylamino)-5-fluoro-2-((2-methylbenzo[d]oxazol-5-yl)amino)nicotinamide | 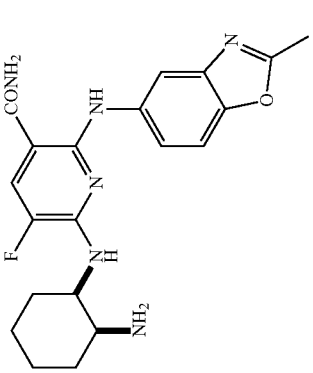 | ¹H-NMR (CD₃OD, 300 MHz) δ: 8.10 (d, 1H, J = 2.1 Hz), 7.77 (d, 1H, J = 12.0 Hz), 7.49 (d, 1H, J = 8.7 Hz), 7.25 (dd, 1H, J = 2.1, 8.7 Hz), 4.46-4.30 (m, 1H), 3.89-3.76 (m, 1H), 2.64 (s, 3H), 1.94-1.50 (m, 8H). | 399 (M + H), 397 (M − H) |

TABLE 3-continued

| Example | Structure | Name | NMR | MS |
|---|---|---|---|---|
| Example 6-47 HCl salt | 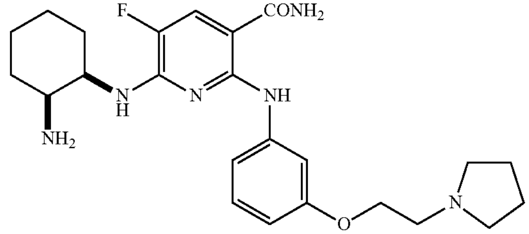 | 6-((cis-2-aminocyclohexyl)amino)-5-fluoro-2-((3-(2-(pyrrolidin-1-yl)ethoxy)phenyl)amino)nicotinamide | ¹H-NMR (CD₃OD, 300 MHz) δ: 7.76 (d, 1H, J = 12.0 Hz), 7.60-7.51 (m, 1H), 7.27 (t, 1H, J = 8.2 Hz), 7.00-6.94 (m, 1H), 6.68 (dd, 1H, J = 2.2, 8.0 Hz), 4.43-4.30 (m, 3H), 3.94-3.84 (m, 1H), 3.80-3.60 (m, 4H), 3.30-3.17 (m, 2H), 2.25-1.97 (m, 4H), 1.95-1.40 (m, 8H). | 457 (M + H), 455 (M − H) |
| Example 6-48 HCl salt | 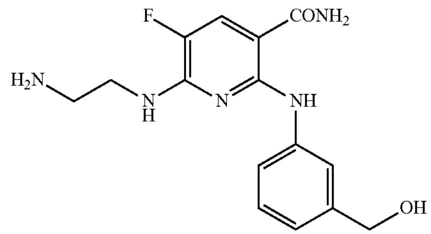 [SMILES: NCCNc1nc(Nc2cccc(CO)c2)c(C(N)=O)cc1F] | 6-((2-aminoethyl)amino)-5-fluoro-2-((3-(hydroxymethyl)phenyl)amino)nicotinamide | ¹H-NMR (CD₃OD, 300 MHz) δ: 8.04 (brs, 1H), 7.74 (d, 1H, J = 12.0 Hz), 7.28-7.16 (m, 2H), 6.92 (d, 1H, J = 7.5 Hz), 4.63 (s, 2H), 3.79 (t, 2H, J = 6.3 Hz), 3.21 (t, 2H, J = 6.3 Hz). | 319 (M + H) |
| Example 6-49 (Example 5) HCl salt | 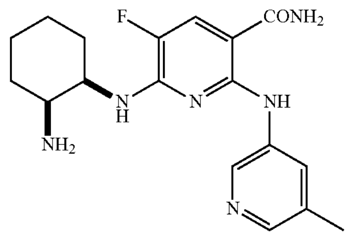 | 6-((cis-2-aminocyclohexyl)amino)-5-fluoro-2-((5-methylpyridin-3-yl)amino)nicotinamide | ¹H-NMR (DMSO-d₆, 400 MHz) δ: 12.09 (s, 1H), 9.10 (s, 1H), 8.29 (s, 1H), 8.25 (s, 1H), 8.02 (d, 1H, J = 12.3 Hz), 8.02-7.92 (m, 3H), 7.54-7.44 (m, 1H), 7.10-7.04 (m, 1H), 4.36-4.27 (m, 1H), 3.60-3.53 (m, 1H), 2.42 (s, 3H), 1.95-1.38 (m, 8H) | 359 (M + H), 357 (M − H) |
| Example 6-50 HCl salt | 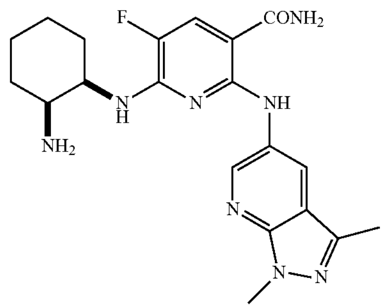 | 6-((cis-2-aminocyclohexyl)amino)-2-((1,3-dimethyl-1H-pyrazolo[3,4-b]pyridin-5-yl)amino)-5-fluoronicotinamide | ¹H-NMR (CD₃OD, 300 MHz) δ: 8.77 (d, 1H, J = 2.3 Hz), 8.36 (d, 1H, J = 2.3 Hz), 7.79 (d, 1H, J = 11.9 Hz), 4.35-4.23 (m, 1H), 4.05 (s, 3H), 3.65-3.54 (m, 1H), 2.57 (s, 3H), 1.92-1.42 (m, 8H). | 413 (M + H), 411 (M − H) |

TABLE 3-continued

| | | | |
|---|---|---|---|
| Example 6-51 HCl salt | 6-(cis-2-aminocyclohexylamino)-2-((2,3-dihydrobenzo[b][1,4]dioxin-6-yl)amino)-5-fluoronicotinamide | ¹H-NMR (CD₃OD, 300 MHz) δ: 7.71 (d, 1H, J = 12.0 Hz), 7.32-7.27 (m, 1H), 6.77-6.74 (m, 2H), 4.32-4.14 (m, 5H), 3.94-3.85 (m, 1H), 1.88-1.52 (m, 8H). | 402 (M + H) |
| Example 6-52 HCl salt | 6-(cis-2-aminocyclohexylamino)-5-fluoro-2-((3-(2H-1,2,3-triazol-2-yl)phenyl)amino)nicotinamide | ¹H-NMR (CD₃OD, 300 MHz) δ: 8.86 (t, 1H, J = 2.1 Hz), 7.96 (s, 2H), 7.79 (d, 1H, J = 12.0 Hz), 7.72-7.64 (m, 1H), 7.42 (t, 1H, J = 8.1 Hz), 7.22-7.13 (m, 1H), 4.77-4.61 (m, 1H), 3.88-3.73 (m, 1H), 2.00-1.42 (m, 8H). | 411 (M + H) |
| Example 6-53 HCl salt | 6-(cis-2-aminocyclohexylamino)-5-fluoro-2-((6-methoxyquinolin-3-yl)amino)nicotinamide | ¹H-NMR (CD₃OD, 300 MHz) δ: 9.49 (d, 1H, J = 2.3 Hz), 9.00 (d, 1H, J = 2.3 Hz), 8.06 (d, 1H, J = 9.3 Hz), 7.90 (d, 1H, J = 11.8 Hz), 7.59 (dd, 1H, J = 2.6, 9.3 Hz), 7.51 (d, 1H, J = 2.6 Hz), 4.67-4.50 (m, 1H), 4.02 (s, 3H), 3.83-3.69 (m, 1H), 2.00-1.50 (m, 8H). | 425 (M + H), 423 (M − H) |

| Example | Structure | Name | 1H-NMR | MS |
|---|---|---|---|---|
| Example 6-55 HCl salt | | 6-(cis-2-aminocyclohexylamino)-5-fluoro-2-(quinolin-5-ylamino)nicotinamide | 1H-NMR (CD3OD, 300 MHz) δ: 9.41 (d, 1H, J = 8.7 Hz), 9.19 (dd, 1H, J = 1.4, 5.4 Hz), 8.82 (d, 1H, J = 8.3 Hz), 8.17 (t, 1H, J = 8.3 Hz), 8.09 (dd, 1H, J = 5.4, 8.7 Hz), 7.93 (d, 1H, J = 11.9 Hz), 7.81 (d, 1H, J = 8.3 Hz), 4.46-4.35 (m, 1H), 3.88-3.75 (m, 1H), 2.00-1.50 (m, 8H). | 395 (M + H), 393 (M − H) |
| Example 6-55 HCl salt | | 6-(cis-2-aminocyclohexylamino)-5-fluoro-2-(quinoxalin-6-ylamino)nicotinamide | 1H-NMR (CD3OD, 300 MHz) δ: 8.87 (d, 1H, J = 2.1 Hz), 8.79-8.78 (m, 2H), 8.05 (d, 1H, J = 9.3 Hz), 7.87 (d, 1H, J = 12.0 Hz), 7.85-7.82 (m, 1H), 4.73-4.60 (m, 1H), 4.02-3.95 (m, 1H), 2.20-1.60 (m, 8H). | 396 (M + H) |
| Example 6-56 HCl salt | 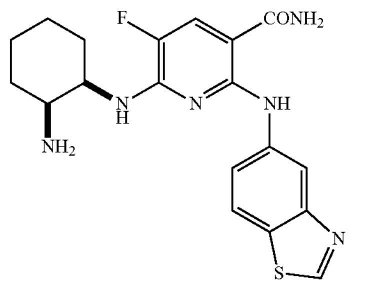 | 6-(cis-2-aminocyclohexylamino)-2-((benzo[d]thiazol-5-yl)amino)-5-fluoronicotinamide | 1H-NMR (CD3OD, 300 MHz) δ: 9.36 (brs, 1H), 8.67 (brs, 1H), 8.05-7.92 (m, 1H), 7.86-7.73 (m, 1H), 7.51-7.40 (m, 1H), 4.63-4.38 (m, 1H), 4.40-3.79 (m, 1H), 1.87-1.61 (m, 8H). | 401 (M + H), 399 (M − H) |
| Example 6-57 HCl salt | 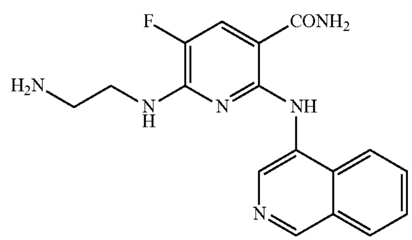 [SMILES: NCCNc1nc(Nc2cncc3ccccc23)c(C(N)=O)cc1F] | 6-((2-aminoethyl)amino)-5-fluoro-2-(isoquinolin-4-ylamino)nicotinamide | 1H-NMR (DMSO-d6, 400 MHz) δ: 9.71 (s, 1H), 9.43-9.35 (m, 1H), 8.50-8.35 (m, 2H), 8.28-8.18 (m, 1H), 8.11 (d, 1H, J = 12.1 Hz), 8.07-7.95 (m, 4H), 7.73-7.57 (m, 2H), 3.83-3.74 (m, 2H), 3.21-3.10 (m, 2H) | 341 (M + H), 339 (M − H) |

TABLE 3-continued

| Example | Structure | Name | ¹H-NMR | MS |
|---|---|---|---|---|
| Example 6-58 HCl salt | 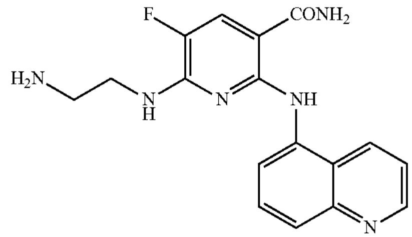 [SMILES: NCCNc1nc(Nc2cccc3ncccc23)c(C(N)=O)cc1F] | 6-((2-aminoethyl)amino)-5-fluoro-2-(quinolin-5-ylamino)nicotinamide | ¹H-NMR (DMSO-d₆, 400 MHz) δ: 12.79 (s, 1H), 9.14-9.09 (m, 1H), 8.93-8.85 (m, 1H), 8.65 (d, 1H, J = 7.8 Hz), 8.04 (d, 1H, J = 12.4 Hz), 8.00-7.83 (m, 6H), 7.53-7.43 (m, 2H), 3.78-3.61 (m, 2H), 3.12-3.03 (m, 2H) | 341 (M + H), 339 (M − H) |
| Example 6-59 | 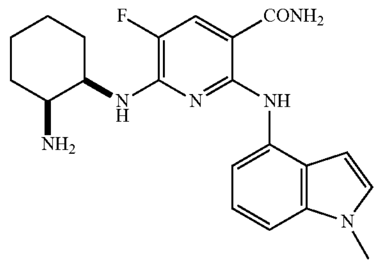 | 6-(cis-2-aminocyclohexylamino)-5-fluoro-2-((1-methyl-1H-indol-4-yl)amino)nicotinamide | ¹H-NMR (CD₃OD, 300 MHz) δ: 8.08 (d, 1H, J = 7.6 Hz), 7.68 (d, 1H, J = 12.3 Hz), 7.15-7.06 (m, 2H), 7.01 (d, 1H, J = 8.2 Hz), 6.61 (dd, 1H, J = 0.6, 3.2 Hz), 4.33-4.21 (m, 1H), 3.78 (s, 3H), 3.42-3.33 (m, 1H), 1.85-1.42 (m, 8H). | 397 (M + H), 395 (M − H) |
| Example 6-60 HCl salt | 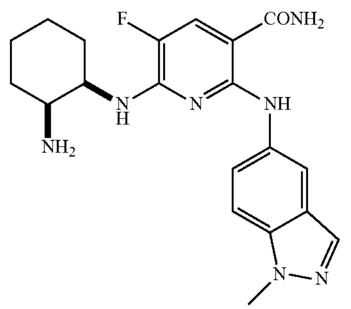 | 6-(cis-2-aminocyclohexylamino)-5-fluoro-2-((1-methyl-1H-indazol-5-yl)amino)nicotinamide | ¹H-NMR (CD₃OD, 300 MHz) δ: 8.03-7.98 (m, 1H), 7.97-7.94 (m, 1H), 7.75 (d, 1H, J = 12.0 Hz), 7.53 (d, 1H, J = 9.0 Hz), 7.45 (dd, 1H, J = 1.9, 9.0 Hz), 4.33-4.22 (m, 1H), 4.06 (s, 3H), 3.81-3.70 (m, 1H), 1.91-1.46 (m, 8H). | 398 (M + H), 396 (M − H) |
| Example 6-61 HCl salt | 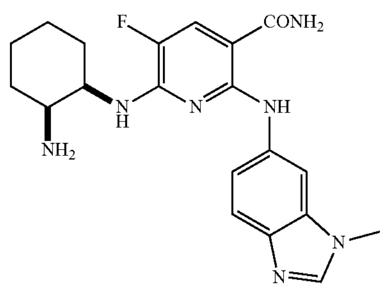 | 6-(cis-2-aminocyclohexylamino)-5-fluoro-2-((1-methyl-1H-benzo[d]imidazol-6-yl)amino)nicotinamide | ¹H-NMR (CD₃OD, 300 MHz) δ: 9.25 (s, 1H), 8.15 (d, 1H, J = 1.7 Hz), 7.86 (dd, 1H, J = 1.7, 9.0 Hz), 7.84 (d, 1H, J = 11.9 Hz), 7.75 (d, 1H, J = 9.0 Hz), 4.66-4.50 (m, 1H), 4.12 (s, 3H), 3.77-3.68 (m, 1H), 1.92-1.45 (m, 8H). | 398 (M + H), 396 (M − H) |

| | Structure | Name | ¹H-NMR | MS |
|---|---|---|---|---|
| Example 6-62 | 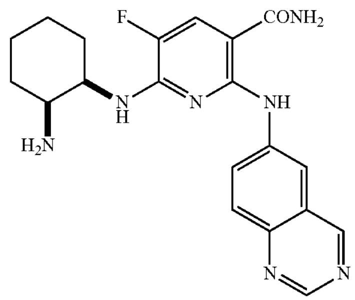 | 6-(cis-2-aminocyclohexylamino)-5-fluoro-2-(quinazolin-6-ylamino)nicotinamide | ¹H-NMR (DMSO-d₆, 300 MHz) δ: 12.10 (s, 1H), 9.36 (s, 1H), 9.12 (s, 1H), 8.56 (d, 1H, J = 2.4 Hz), 8.02 (dd, 1H, J = 2.4, 9.0 Hz), 7.94 (d, 1H, J = 12.0 Hz), 7.91 (d, 1H, J = 9.0 Hz), 7.88-7.75 (m, 1H), 7.40-7.25 (m, 1H), 6.64 (d, 1H, 6.9 Hz), 4.13-4.03 (m, 1H), 3.22-3.15 (m, 1H), 1.87-1.30 (m, 8H). | 396 (M + H) |
| Example 6-63 HCl salt | 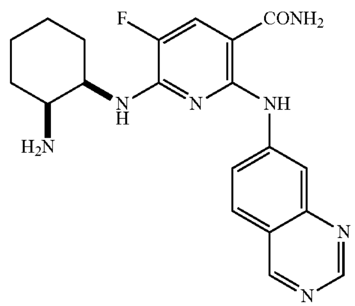 | 6-(cis-2-aminocyclohexylamino)-5-fluoro-2-(quinazolin-7-ylamino)nicotinamide | ¹H-NMR (DMSO-d₆, 300 MHz) δ: 12.60 (s, 1H), 9.46 (s, 1H), 9.18 (s, 1H), 8.69 (d, 1H, J = 2.4 Hz), 8.13-8.00 (m, 6H), 7.63 (dd, 1H, J = 2.4, 9.0 Hz), 7.60-7.53 (m, 1H), 7.22 (d, 1H, J = 6.3 Hz), 4.50-4.40 (m, 1H), 3.83-3.73 (m, 1H), 2.12-1.46 (m, 8H). | 396 (M + H) |
| Example 6-64 HCl salt | 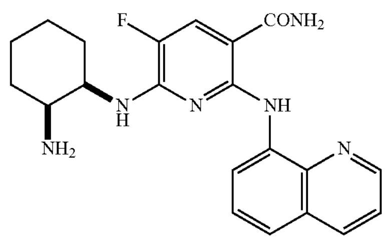 | 6-(cis-2-aminocyclohexylamino)-5-fluoro-2-(quinolin-8-ylamino)nicotinamide | ¹H-NMR (CD₃OD, 300 MHz) δ: 9.24 (d, 1H, J = 7.5 Hz), 9.16-9.08 (m, 1H), 8.24-8.08 (m, 3H), 7.98 (dd, 1H, J = 7.9, 8.0 Hz), 7.85 (d, 1H, J = 11.7 Hz), 3.40-3.26 (2H, overlapping with CH₃OH peak), 3.13-2.96 (m, 1H), 1.68-1.39 (m, 8H). | 395 (M + H) |

TABLE 3-continued

| Example | Structure | Name | ¹H-NMR | MS |
|---|---|---|---|---|
| Example 6-65 HCl salt | 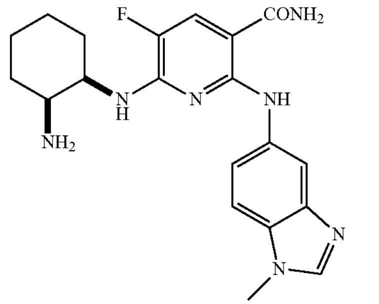 | 6-(cis-2-aminocyclohexylamino)-5-fluoro-2-((1-methyl-1H-benzo[d]imidazol-5-yl)amino)nicotinamide | ¹H-NMR (CD$_3$OD, 300 MHz) δ: 9.28 (s, 1H), 8.21 (d, 1H, J = 1.6 Hz), 7.88-7.73 (m, 3H), 4.58-4.46 (m, 1H), 4.13 (s, 3H), 3.92-3.77 (m, 1H), 2.00-1.50 (m, 8H). | 398 (M + H) |
| Example 6-66 HCl salt | 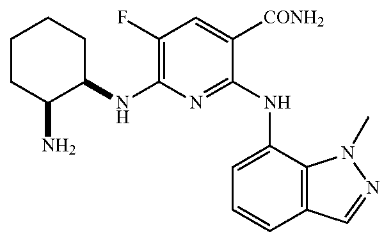 | 6-(cis-2-aminocyclohexylamino)-5-fluoro-2-((1-methyl-1H-indazol-7-yl)amino)nicotinamide | ¹H-NMR (CD$_3$OD, 300 MHz) δ: 8.04 (s, 1H), 7.78 (d, 1H, J = 11.9 Hz), 7.64 (dd, 1H, J = 1.0, 8.0 Hz), 7.24 (dd, 1H, J = 1.0, 7.3 Hz), 7.18-7.11 (m, 1H), 4.01 (s, 3H), 3.34-3.26 (m, 1H), 2.96-2.86 (m, 1H), 1.70-1.28 (m, 8H). | 398 (M + H), 396 (M − H) |
| Example 6-67 HCl salt | 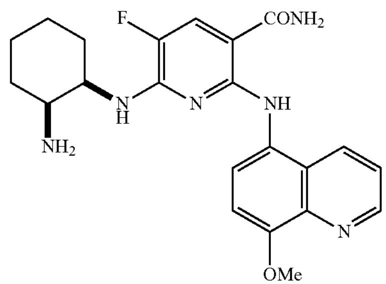 | 6-(cis-2-aminocyclohexylamino)-5-fluoro-2-((8-methoxyquinolin-5-yl)amino)nicotinamide | ¹H-NMR (CD$_3$OD, 300 MHz) δ: 9.29 (d, 1H, J = 8.7 Hz), 9.12 (d, 1H, J = 4.9 Hz), 8.36 (d, 1H, J = 8.7 Hz), 8.17-8.09 (m, 1H), 7.86 (d, 1H, J = 11.9 Hz), 7.73 (d, 1H, J = 8.7 Hz), 4.24 (s, 3H), 4.08-3.92 (m, 1H), 3.56-3.44 (m, 1H), 1.88-1.33 (m, 8H). | 425 (M + H), 423 (M − H) |
| Example 6-68 HCl salt | 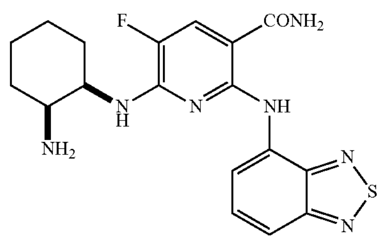 | 6-(cis-2-aminocyclohexylamino)-2-(benzo[c][1,2,5]thiadiazol-4-ylamino)-5-fluoronicotinamide | ¹H-NMR (CD$_3$OD, 300 MHz) δ: 8.45 (dd, 1H, J = 0.8, 7.5 Hz), 7.82 (d, 1H, J = 12.0 Hz), 7.57-7.48 (m, 1H), 7.43 (dd, 1H, J = 0.8, 8.7 Hz), 4.56-4.46 (m, 1H), 4.16-4.04 (m, 1H), 2.12-1.54 (m, 8H). | 402 (M + H), 400 (M − H) |

TABLE 3-continued

| Example | Name | Structure | NMR / MS |
|---|---|---|---|
| Example 6-69 | 6-(cis-2-aminocyclohexylamino)-5-fluoro-2-((1-methyl-1H-indol-5-yl)amino)nicotinamide | | 397 (M + H) |
| Example 6-70 HCl salt | 6-(cis-2-aminocyclohexylamino)-5-fluoro-2-((2-methylquinolin-6-yl)amino)nicotinamide | | ¹H-NMR (DMSO-d₆, 300 MHz) δ: 12.10 (s, 1H), 8.83-8.73 (m, 1H), 8.55 (s, 1H), 8.22 (d, 1H, J = 9.3 Hz), 8.15-7.90 (m, 6H), 7.81 (d, 1H, J = 8.1 Hz), 7.49-7.38 (m, 1H), 6.99 (d, 1H, J = 6.3 Hz), 4.50-4.43 (m, 1H), 3.76-3.66 (m, 1H), 2.88 (s, 3H), 2.00-1.38 (m, 8H). 409 (M + H) |
| Example 6-71 HCl salt | 6-(cis-2-aminocyclohexylamino)-5-fluoro-2-(isoquinolin-7-ylamino)nicotinamide | | ¹H-NMR (DMSO-d₆, 300 MHz) δ: 12.20 (s, 1H), 9.65 (s, 1H), 8.71 (s, 1H), 8.48 (d, 1H, J = 6.3 Hz), 8.32 (d, 1H, J = 6.3 Hz), 8.27-8.19 (m, 2H), 8.18-8.08 (m, 3H), 8.03 (d, 1H, J = 12.6 Hz), 8.02-7.93 (m, 1H), 7.53-7.43 (m, 1H), 7.01 (d, 1H, J = 6.6 Hz), 4.54-4.46 (m, 1H), 3.76-3.66 (m, 1H), 2.02-1.38 (m, 8H). 395 (M + H) |

| | | | |
|---|---|---|---|
| Example 6-72 HCl salt | 6-(cis-2-aminocyclohexylamino)-5-fluoro-2-(quinolin-7-ylamino)nicotinamide | $^1$H-NMR (DMSO-d$_6$, 300 MHz) δ: 12.40 (s, 1H), 9.01 (d, 1H, J = 5.1 Hz), 8.96-8.83 (m, 1H), 8.70 (s, 1H), 8.19 (d, 1H, J = 8.7 Hz), 8.06 (d, 1H, J = 12.3 Hz), 8.05-7.97 (m, 4H), 7.82 (d, 1H, J = 9.6 Hz), 7.78-7.68 (m, 1H), 7.60-7.53 (m, 1H), 6.94 (d, 1H, J = 6.9 Hz), 4.73-4.62 (m, 1H), 3.86-3.77 (m, 1H), 1.97-1.35 (m, 8H). | 395 (M + H) |
| Example 6-73 HCl salt | 6-(cis-2-aminocyclohexylamino)-5-fluoro-2-(quinazolin-6-ylamino)nicotinamide | $^1$H-NMR (CD$_3$OD, 300 MHz) δ: 7.80-7.72 (m, 2H), 7.25-7.14 (m, 2H), 4.46-4.31 (m, 3H), 3.87-3.80 (m, 1H), 3.51 (t, 2H, J = 6.3 Hz), 3.14-3.09 (m, 2H), 2.00-1.50 (m, 8H). | 399 (M + H) |
| Example 6-74 | 6-(cis-2-aminocyclohexylamino)-5-fluoro-2-((2-methyl-2H-indazol-7-yl)amino)nicotinamide | $^1$H-NMR (CD$_3$OD, 300 MHz) δ: 8.21 (d, 1H, J = 7.3 Hz), 8.07 (s, 1H), 7.71 (d, 1H, J = 12.2 Hz), 7.22 (d, 1H, J = 8.3 Hz), 7.01-6.94 (m, 1H), 4.37-4.25 (m, 1H), 4.21 (s, 3H), 3.48-3.40 (m, 1H), 1.93-1.47 (m, 8H). | 398 (M + H) |
| Example 6-75 HCl salt | 6-(cis-2-aminocyclohexylamino)-5-fluoro-2-((1-methyl-1H-indazol-4-yl)amino)nicotinamide | $^1$H-NMR (CD$_3$OD, 300 MHz) δ: 8.07 (d, 1H, J = 0.8 Hz), 7.90 (d, 1H, J = 7.5 Hz), 7.82 (d, 1H, J = 12.0 Hz), 7.39 (t, 1H, J = 8.2 Hz), 7.16 (d, 1H, J = 8.5 Hz), 4.42-4.33 (m, 1H), 4.05 (s, 3H), 3.93-3.85 (m, 8H), 1.93-1.51 (m, 8H). | 398 (M + H) |

TABLE 3-continued

| Example | Structure | Name | NMR | MS |
|---|---|---|---|---|
| Example 6-76 HCl salt | 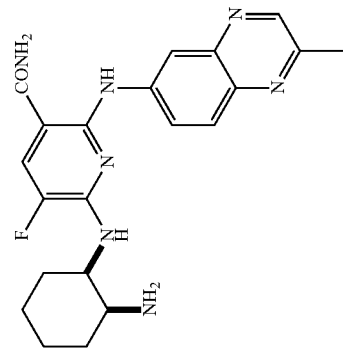 | 6-(cis-2-aminocyclohexylamino)-5-fluoro-2-((2-methylquinoxalin-6-yl)amino)nicotinamide | ¹H-NMR (DMSO-d₆, 300 MHz) δ: 12.10 (s, 1H), 8.76 (s, 1H), 8.62 (d, 1H, J = 2.4 Hz), 8.00 (d, 1H, J = 12.6 hz), 7.97-7.90 (m, 4H), 7.87 (d, 1H, J = 9.0 Hz), 7.65 (dd, 1H, J = 2.4, 9.0 Hz), 7.50-7.34 (m, 1H), 7.07 (d, 1H, J = 6.3 Hz), 4.44-4.35 (m, 1H), 3.80-3.60 (m, 1H), 2.65 (s, 3H), 2.10-1.45 (m, 8H). | 410 (M + H) |
| Example 6-77 | 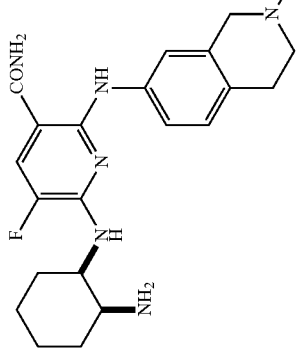 | 6-(cis-2-aminocyclohexylamino)-5-fluoro-2-((2-methyl-1,2,3,4-tetrahydroisoquinolin-7-yl)amino)nicotinamide | ¹H-NMR (CDCl₃, 300 MHz) δ: 10.80 (s, 1H), 7.49-7.43 (m, 1H), 7.35-7.34 (m, 1H), 7.17 (d, 1H, J = 11.7 Hz), 7.01 (d, 1H, J = 8.4 Hz), 5.65 (brd, 1H, J = 9.0 Hz), 5.38 (brs, 2H), 4.14-4.03 (m, 1H), 3.60-3.54 (m, 2H), 3.18 (q, 1H, J = 3.9 Hz), 2.93-2.85 (m, 2H), 2.72-2.65 (m, 2H), 2.46 (s, 3H), 1.90-1.35 (m, 8H). | 413 (M + H) |
| Example 6-78 HCl salt | 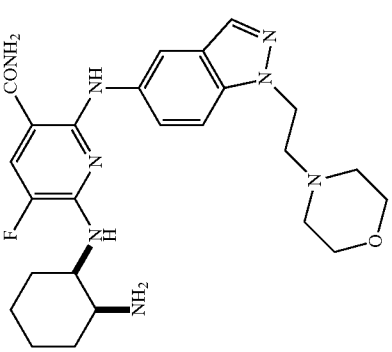 | 6-(cis-2-aminocyclohexylamino)-5-fluoro-2-((1-(2-(morpholin-4-yl)ethyl)-1H-indazol-5-yl)amino)nicotinamide | | 497 (M + H) |

TABLE 3-continued

| Example 6-79 HCl salt | [structure] | 6-(cis-2-aminocyclohexylamino)-5-fluoro-2-((1-(2-(morpholin-4-yl)ethyl)-1H-indazol-6-yl)amino)nicotinamide | 497 (M + H) |
| --- | --- | --- | --- |
| Example 6-80 HCl salt | [structure] | 6-(cis-2-aminocyclohexylamino)-5-fluoro-2-((2-(2-(morpholin-4-yl)ethyl)-2H-indazol-5-yl)amino)nicotinamide | 497 (M + H) |

| Example 6-81 HCl salt | 6-((cis-2-aminocyclohexylamino)-5-fluoro-2-((2-(2-(morpholin-4-yl)ethyl)-2H-indazol-6-yl)amino)nicotinamide | 497 (M + H) |
|---|---|---|
| Example 6-82 HCl salt | 6-((cis-2-aminocyclohexylamino)-5-fluoro-2-((1-(2-(pyrrolidin-1-yl)ethyl)-1H-indazol-5-yl)amino)nicotinamide | 481 (M + H) |

| Example | | | |
|---|---|---|---|
| Example 6-83 HCl salt |  | 6-(cis-2-aminocyclohexylamino)-5-fluoro-2-(2-(2-(pyrrolidin-1-yl)ethyl)-2H-indazol-5-yl)amino)nicotinamide | 481 (M + H) |
| Example 6-84 HCl salt | 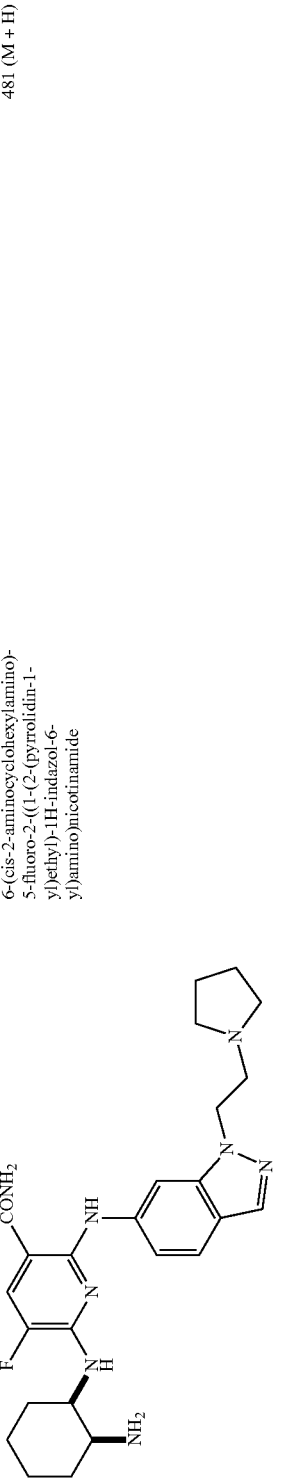 | 6-(cis-2-aminocyclohexylamino)-5-fluoro-2-((1-(2-(pyrrolidin-1-yl)ethyl)-1H-indazol-6-yl)amino)nicotinamide | 481 (M + H) |
| Example 6-85 HCl salt | 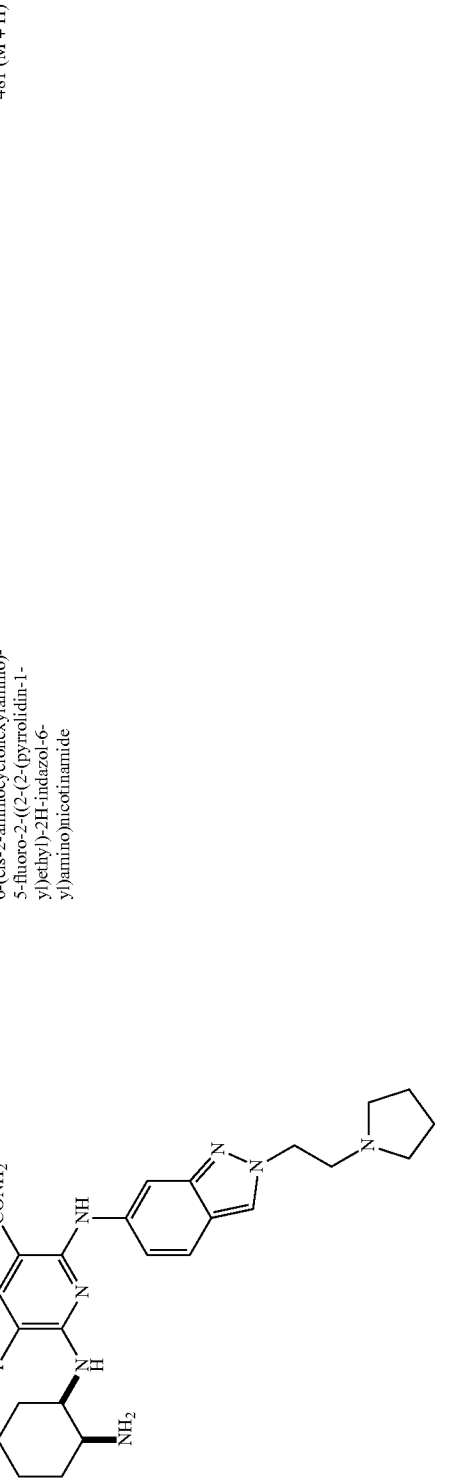 | 6-(cis-2-aminocyclohexylamino)-5-fluoro-2-(2-(2-(pyrrolidin-1-yl)ethyl)-2H-indazol-6-yl)amino)nicotinamide | 481 (M + H) |

TABLE 3-continued

| Example | Structure | Name | NMR | MS |
|---|---|---|---|---|
| Example 6-86 | 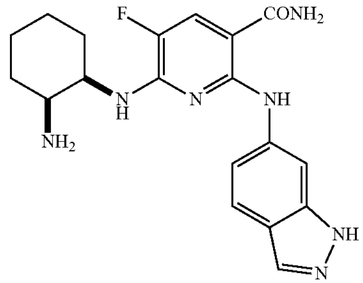 [SMILES: NC(=O)c1cc(F)c(N[C@@H]2CCCC[C@@H]2N)nc1Nc1ccc2cn[nH]c2c1] | 6-(cis-2-aminocyclohexylamino)-5-fluoro-2-((1H-indazol-6-yl)amino)nicotinamide | ¹H-NMR (CD₃OD, 300 MHz) δ: 8.04 (s, 1H), 7.92 (d, 1H, J = 1.0 Hz), 7.68 (d, 1H, J = 12.2 Hz), 7.63 (d, 1H, J = 8.7 Hz), 7.17 (dd, 1H, J = 1.7, 8.7 Hz), 4.38-4.23 (m, 1H), 3.36-3.24 (2H, overlapping with CH₃OH peak), 1.86-1.47 (m, 8H). | 384 (M + H), 382 (M − H) |
| Example 6-87 HCl salt | 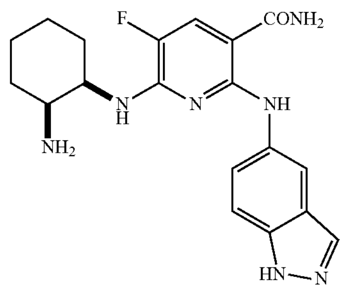 [SMILES: NC(=O)c1cc(F)c(N[C@@H]2CCCC[C@@H]2N)nc1Nc1ccc2[nH]ncc2c1] | 6-(cis-2-aminocyclohexylamino)-5-fluoro-2-((1H-indazol-5-yl)amino)nicotinamide | ¹H-NMR (CD₃OD, 300 MHz) δ: 8.08 (d, 1H, J = 0.8 Hz), 8.04 (d, 1H, J = 1.1 Hz), 7.76 (d, 1H, J = 12.0 Hz), 7.54 (d, 1H, J = 8.9 Hz), 7.45 (dd, 1H, J = 1.9, 8.9 Hz), 4.32-4.27 (m, 1H), 3.80-3.76 (m, 1H), 1.83-1.56 (m, 8H). | 384 (M + H) |
| Example 6-88 HCl salt | 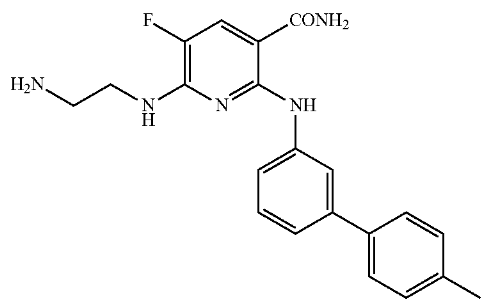 [SMILES: Cc1ccc(-c2cccc(Nc3nc(NCCN)c(F)cc3C(N)=O)c2)cc1] | 6-((2-aminoethyl)amino)-5-fluoro-2-((4'-methylbiphenyl-3-yl)amino)nicotinamide | ¹H-NMR (DMSO-d₆, 300 MHz) δ: 11.70 (s, 1H), 7.92 (d, 1H, J = 12.0 Hz), 7.89-7.82 (m, 5H), 7.63-7.52 (m, 3H), 7.41-7.26 (m, 5H), 7.21-7.18 (m, 1H), 3.70-3.64 (m, 2H), 3.07-3.00 (m, 2H), 2.35 (s, 3H). | 380 (M + H) |

TABLE 3-continued

| Example | Structure | Compound name | Salt | Solvent | NMR | 1HNMR | Mass (M + H) | Mass (M − H) | rt (min) |
|---|---|---|---|---|---|---|---|---|---|
| Example 6-89 | 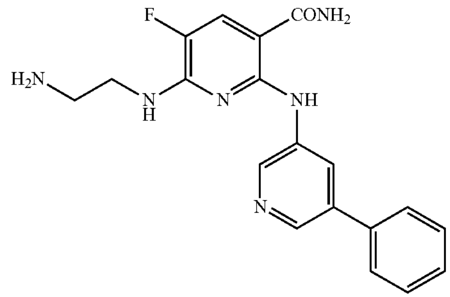 [SMILES: NCCNc1nc(Nc2cncc(-c3ccccc3)c2)c(C(N)=O)cc1F] | 6-((2-aminoethyl)amino)-5-fluoro-2-((5-phenylpyridin-3-yl)amino)nicotinamide | HCl | DMSO-d6 | 400 MHz | δ: 12.20 (s, 1H), 9.35-9.25 (m, 1H), 8.74 (s, 1H), 8.57 (s, 1H), 8.02 (d, 1H, J = 12.4 Hz), 8.02-7.90 (m, 4H), 7.88-7.83 (m, 2H), 7.60-7.83 (m, 5H), 3.75-3.68 (m, 2H), 3.12-3.03 (m, 2H). | 367 | 365 | 8.61 |
| Example 6-90 | 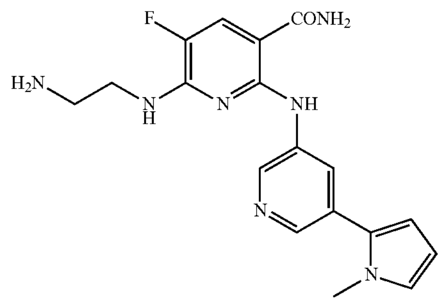 [SMILES: Cn1cccc1-c1cncc(Nc2nc(NCCN)c(F)cc2C(N)=O)c1] | 6-((2-aminoethyl)amino)-5-fluoro-2-((5-(1-methyl-1H-pyrrol-2-yl)pyridin-3-yl)amino)nicotinamide | HCl | DMSO-d6 | 400 MHz | δ: 12.18 (s, 1H), 9.33 (s, 1H), 8.55 (s, 1H), 8.24 (s, 1H), 8.10-7.90 (m, 5H), 7.60-7.54 (m, 1H), 7.46 (br, 1H), 7.03-7.00 (m, 1H), 6.55-6.50 (m, 1H), 6.18-6.15 (m, 1H), 3.77 (s, 3H), 3.75-3.67 (m, 2H), 3.12-3.04 (m, 2H). | 370 | 368 | 8.17 |
| Example 6-91 | 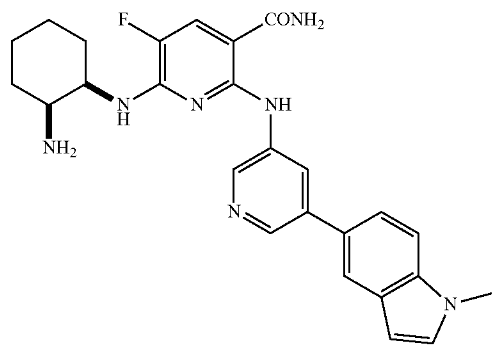 [SMILES: Cn1ccc2cc(-c3cncc(Nc4nc(N[C@@H]5CCCC[C@@H]5N)c(F)cc4C(N)=O)c3)ccc21] | 6-((cis-2-aminocyclohexyl)amino)-5-fluoro-2-((5-(1-methyl-1H-indol-5-yl)pyridin-3-yl)amino)nicotinamide | HCl | | | | 474 | 472 | 11.39 |

TABLE 3-continued

| Example | Structure | Name | Salt | Solvent | Freq | NMR | MS1 | MS2 | MS3 |
|---|---|---|---|---|---|---|---|---|---|
| Example 6-92 | 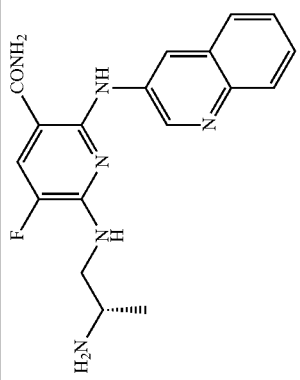 | (S)-6-((2-aminopropyl)amino)-5-fluoro-2-((quinolin-3-yl)amino)nicotinamide | HCl | DMSO-d6-D2O | 400 MHz | δ: 9.31 (d, 1H, J = 2.4 Hz), 8.96-8.89 (m, 1H), 8.12-8.03 (m, 2H), 7.96 (d, 1H, J = 12.2 Hz), 7.87-7.70 (m, 2H), 3.77-3.66 (m, 1H), 3.58-3.45 (m, 2H), 1.21 (d, 3H, J = 5.9 Hz) | 355 | 353 | ND |
| Example 6-93 | 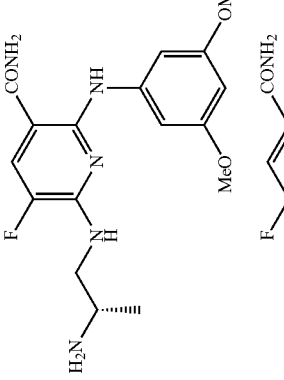 | (S)-6-((2-aminopropyl)amino)-2-(3,5-dimethoxyphenylamino)-5-fluoronicotinamide | HCl | DMSO-d6 | 400 MHz | δ: 11.64 (s, 1H), 7.97-7.70 (m, 5H), 7.43-7.17 (m, 2H), 6.79 (d, 2H, J = 2.2 Hz), 6.13 (t, 1H, J = 2.2 Hz), 3.73 (s, 6H), 3.68-3.49 (m, 2H), 3.50-3.30 (m, 1H), 1.24 (d, 3H, J = 6.6 Hz) | 364 | 362 | ND |
| Example 6-94 | 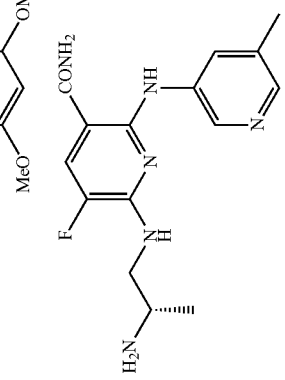 | (S)-6-((2-aminopropyl)amino)-5-fluoro-2-((5-methylpyridin-3-yl)amino)nicotinamide | HCl | CD3OD | 400 MHz | δ: 9.39 (d, 1H, J = 2.2 Hz), 8.34-8.29 (m, 1H), 8.28-8.23 (m, 1H), 7.87 (d, 1H, J = 11.7 Hz), 3.85-3.60 (m, 3H), 2.53 (s, 3H), 1.39 (d, 3H, J = 6.3 Hz) | 319 | 317 | ND |
| Example 6-95 | 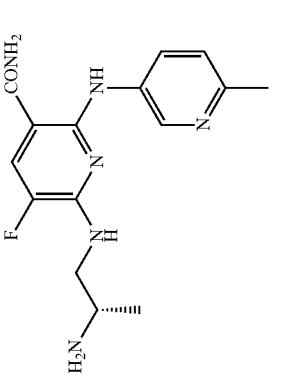 | (S)-6-((2-aminopropyl)amino)-5-fluoro-2-((6-methylpyridin-3-yl)amino)nicotinamide | HCl | CD3OD | 400 MHz | δ: 9.32 (d, 1H, J = 2.3 Hz), 8.43 (dd, 1H, J = 2.3, 8.9 Hz), 7.86 (d, 1H, J = 12.0 Hz), 7.78 (d, 1H, J = 8.9 Hz), 3.84-3.59 (m, 3H), 2.72 (s, 3H), 1.39 (d, 3H, J = 6.6 Hz) | 319 | 317 | ND |

TABLE 3-continued

| Example | Structure | Name | Salt | Solvent | Freq | NMR | MS1 | MS2 | IC50 |
|---|---|---|---|---|---|---|---|---|---|
| Example 6-96 | [structure with F, CONH2, NH, OMe pyridine, H2N-propyl] | (S)-6-((2-aminopropyl)amino)-5-fluoro-2-((2-methoxypyridin-4-yl)amino)nicotinamide | HCl | DMSO-d6-D2O | 400 MHz | δ: 8.10-7.98 (m, 2H), 7.58-7.50 (m, 1H), 7.46-7.36 (m, 1H), 4.04 (s, 3H), 3.72-3.50 (m, 3H), 1.27 (d, 3H, J = 6.1 Hz) | 335 | 333 | ND |
| Example 6-97 | [structure with F, CONH2, NH, triazolyl-phenyl, H2N-propyl] | (S)-2-((3-(2H-1,2,3-triazol-2-yl)phenyl)amino)-6-((2-aminopropyl)amino)-5-fluoronicotinamide | HCl | DMSO-d6 | 400 MHz | δ: 11.94 (s, 1H), 8.12 (s, 2H), 8.04-7.77 (m, 5H), 7.64-7.56 (m, 1H), 7.52-7.27 (m, 4H), 3.79-3.68 (m, 1H), 3.67-3.47 (m, 2H), 1.13 (d, 3H, J = 6.6 Hz) | 371 | 369 | ND |
| Example 6-98 | [structure with F, CONH2, NH, 2,6-dimethoxypyridin-4-yl, H2N-propyl] | (S)-6-((2-aminopropyl)amino)-2-((2,6-dimethoxypyridin-4-yl)amino)-5-fluoronicotinamide | HCl | DMSO-d6-D2O | 400 MHz | δ: 7.92 (d, 1H, J = 12.0 Hz), 6.64 (s, 2H), 3.82 (s, 6H), 3.73-3.51 (m, 2H), 3.45-3.34 (m, 1H), 1.30 (d, 3H, J = 6.6 Hz) | 365 | 363 | ND |
| Example 6-99 | [structure with F, CONH2, NH, 3-methylphenyl, H2N-propyl] | (S)-6-((2-aminopropyl)amino)-5-fluoro-2-((3-methylphenylamino)nicotinamide | HCl | DMSO-d6 | 400 MHz | δ: 11.55 (s, 1H), 8.00-7.66 (m, 5H), 7.50-7.42 (m, 1H), 7.41-7.12 (m, 4H), 6.77 (d, 1H, J = 7.3 Hz), 3.67-3.35 (m, 3H), 2.29 (s, 3H), 1.22 (d, 3H, J = 6.3 Hz) | 318 | 316 | ND |

TABLE 3-continued

| | | | | | | |
|---|---|---|---|---|---|---|
| Example 6-100 | 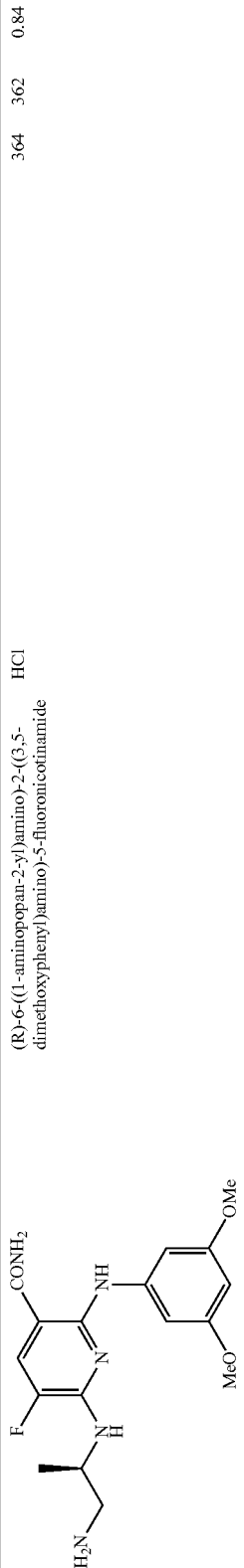 | (R)-6-((1-aminopropan-2-yl)amino)-2-((3,5-dimethoxyphenyl)amino)-5-fluoronicotinamide | HCl | | 364 362 | 0.84 |
| Example 6-101 | 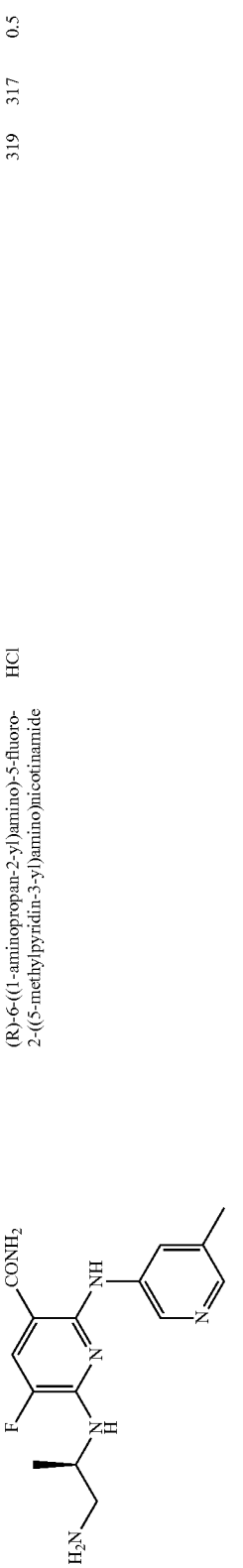 | (R)-6-((1-aminopropan-2-yl)amino)-5-fluoro-2-((5-methylpyridin-3-yl)amino)nicotinamide | HCl | | 319 317 | 0.5 |
| Example 6-102 | 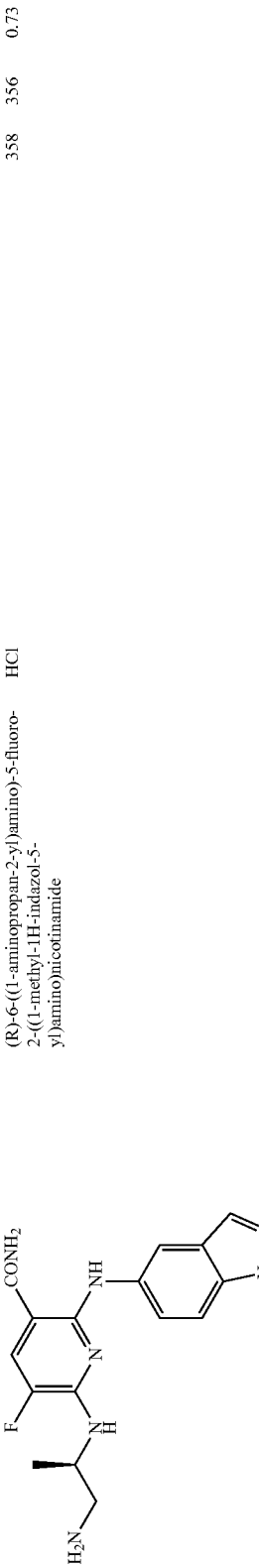 | (R)-6-((1-aminopropan-2-yl)amino)-5-fluoro-2-((1-methyl-1H-indazol-5-yl)amino)nicotinamide | HCl | | 358 356 | 0.73 |
| Example 6-103 | 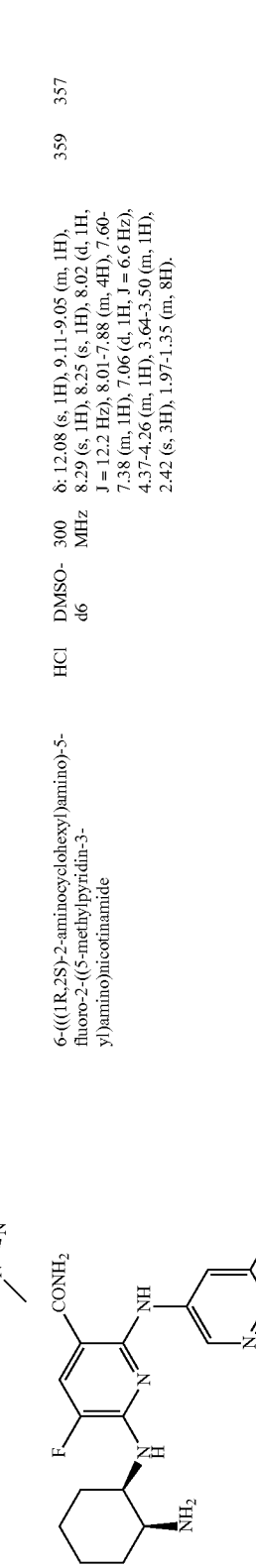 | 6-(((1R,2S)-2-aminocyclohexyl)amino)-5-fluoro-2-((5-methylpyridin-3-yl)amino)nicotinamide | HCl | DMSO-d6 | 300 MHz | δ: 12.08 (s, 1H), 9.11-9.05 (m, 1H), 8.29 (s, 1H), 8.25 (s, 1H), 8.02 (d, 1H, J = 12.2 Hz), 8.01-7.88 (m, 4H), 7.60-7.38 (m, 1H), 7.06 (d, 1H, J = 6.6 Hz), 4.37-4.26 (m, 1H), 3.64-3.50 (m, 1H), 2.42 (s, 3H), 1.97-1.35 (m, 8H). | 359 357 |

TABLE 3-continued

| Example | Structure | Salt | Solvent | Freq | NMR | M+1 | M-1 | |
|---|---|---|---|---|---|---|---|---|
| Example 6-104 | 6-(((1R,2S)-2-aminocyclohexyl)amino)-5-fluoro-2-((6-methylpyridin-3-yl)amino)nicotinamide 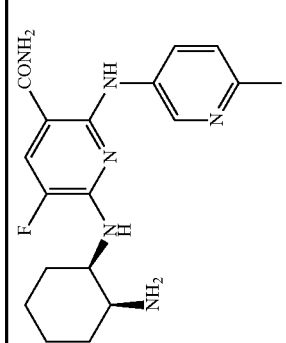 | HCl | DMSO-d6 | 300 MHz | δ: 12.02 (s, 1H), 9.12 (s, 1H), 8.34 (d, 1H, J = 8.6 Hz), 8.02 (d, 1H, J = 11.9 Hz), 8.02-7.88 (m, 4H), 7.70 (d, 1H, J = 8.3 Hz), 7.55-7.37 (m, 1H), 7.04 (d, 1H, J = 6.6 Hz), 4.35-4.24 (m, 1H), 3.60-3.52 (m, 1H), 2.63 (s, 3H), 1.97-1.33 (m, 8H). | 359 | 357 | |
| Example 6-105 | 6-(((1R,2S)-2-aminocyclohexyl)amino)-5-fluoro-2-((5-methylpyridin-3-yl)amino)nicotinamide 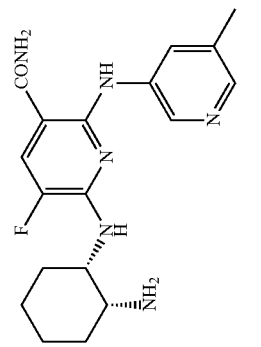 | HCl | DMSO-d6 | 300 MHz | δ: 12.11 (s, 1H), 9.11 (s, 1H), 8.30 (s, 1H), 8.26 (s, 1H), 8.08-7.87 (m, 4H), 8.02 (d, 1H, J = 12.2 Hz), 7.55-7.43 (m, 1H), 7.07 (d, 1H, J = 6.9 Hz), 4.38-4.26 (m, 1H), 3.62-3.52 (m, 1H), 2.43 (s, 3H), 1.98-1.35 (m, 8H). | 359 | 357 | |
| Example 6-106 | 6-(((1R,2S)-2-aminocyclohexyl)amino)-5-fluoro-2-((6-methylpyridin-3-yl)amino)nicotinamide 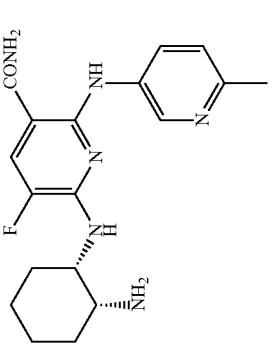 | HCl | DMSO-d6 | 300 MHz | δ: 12.03 (s, 1H), 9.12 (s, 1H), 8.41-8.31 (m, 1H), 8.02-7.85 (m, 4H), 8.02 (d, 1H, J = 12.2 Hz), 7.71 (d, 1H, J = 8.6 Hz), 7.53-7.40 (m, 1H), 7.08-7.00 (m, 1H), 4.35-4.24 (m, 1H), 3.60-3.51 (m, 1H), 2.63 (s, 3H), 1.95-1.36 (m, 8H). | 359 | 357 | |
| Example 6-107 | 6-(((2R,3S)-3-aminobutan-2-yl)amino)-2-(3,5-dimethoxyphenyl)amino)-5-fluoronicotinamide 6-(((2S,3R)-3-aminobutan-2-yl)amino)-2-(3,5-dimethoxyphenyl)amino)-5-fluoronicotinamide 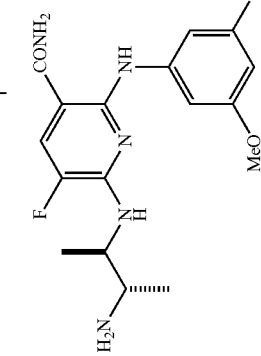 | HCl | | | | 378 | 376 | 0.88 |

TABLE 3-continued

| Example | Structure | Name | Salt | | | |
|---|---|---|---|---|---|---|
| Example 6-108 | 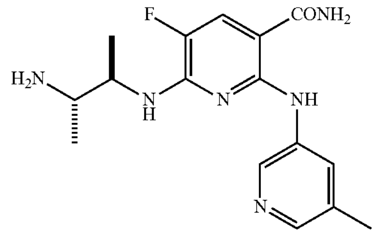 [SMILES: Cc1cncc(Nc2nc(N[C@H](C)[C@H](C)N)c(F)cc2C(N)=O)c1] | 6-(((2R,3S)-3-aminobutan-2-yl)amino)-2-((5-methylpyridin-3-yl)amino)-5-fluoronicotinamide  6-(((2S,3R)-3-aminobutan-2-yl)amino)-2-((5-methylpyridin-3-yl)amino)-5-fluoronicotinamide | HCl | 333 | 331 | 0.51 |
| Example 6-109 | 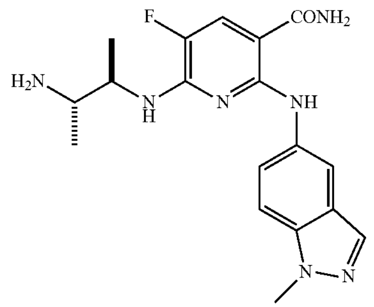 [SMILES: C[C@H](N)[C@@H](C)Nc1nc(Nc2ccc3c(cnn3C)c2)c(C(N)=O)cc1F] | 6-(((2R,3S)-3-aminobutan-2-yl)amino)-5-fluoro-2-((1-methyl-1H-indazol-5-yl)amino)nicotinamide  6-(((2S,3R)-3-aminobutan-2-yl)amino)-5-fluoro-2-((1-methyl-1H-indazol-5-yl)amino)nicotinamide | HCl | 372 | 370 | 0.76 |
| Example 6-110 | 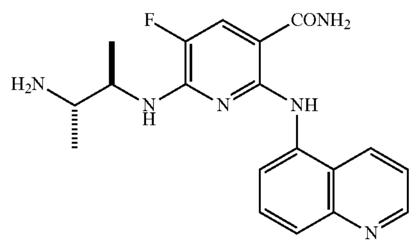 [SMILES: C[C@H](N)[C@@H](C)Nc1nc(Nc2cccc3ncccc23)c(C(N)=O)cc1F] | 6-(((2R,3S)-3-aminobutan-2-yl)amino)-5-fluoro-2-(quinolin-5-ylamino)nicotinamide  6-(((2S,3R)-3-aminobutan-2-yl)amino)-5-fluoro-2-(quinolin-5-ylamino)nicotinamide | HCl | 369 | 367 | 0.59 |
| Example 6-111 | 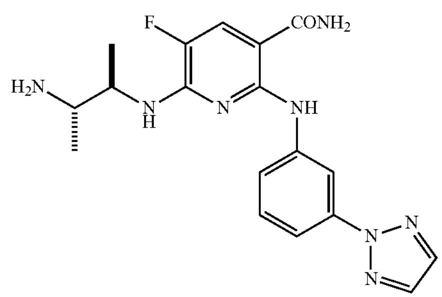 [SMILES: C[C@H](N)[C@@H](C)Nc1nc(Nc2cccc(-n3nccn3)c2)c(C(N)=O)cc1F] | 2-((3-(2H-1,2,3-triazol-2-yl)phenyl)amino)-6-(((2R,3S)-3-aminobutan-2-yl)amino)-5-fluoronicotinamide  2-((3-(2H-1,2,3-triazol-2-yl)phenyl)amino)-6-(((2S,3R)-3-aminobutan-2-yl)amino)-5-fluoronicotinamide | HCl | 385 | 383 | 0.95 |

TABLE 3-continued

| Example | Structure | Name | Salt | Solvent | Freq | NMR | | | |
|---|---|---|---|---|---|---|---|---|---|
| Example 6-112 | | 6-(((2R,3S)-3-aminobutan-2-yl)amino)-2-((2,6-dimethoxypyridin-4-yl)amino)-5-fluoronicotinamide 6-(((2S,3R)-3-aminobutan-2-yl)amino)-2-((2,6-dimethoxypyridin-4-yl)amino)-5-fluoronicotinamide | HCl | | | 379 | 377 | 0.9 |
| Example 6-113 | 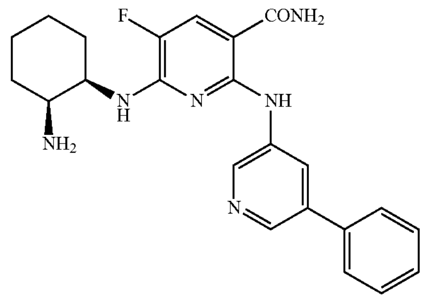 [SMILES: NC(=O)c1cc(F)c(N[C@@H]2CCCC[C@@H]2N)nc1Nc1cncc(-c2ccccc2)c1] | 6-(((1R,2S)-2-aminocyclohexyl)amino)-5-fluoro-2-((5-phenylpyridin-3-yl)amino)nicotinamide | HCl | DMSO-d6 | 300 MHz | δ: 12.13 (s, 1H), 9.08 (s, 1H), 8.73-8.65 (m, 2H), 8.03 (d, 1H, J = 12.6 Hz), 8.02-7.90 (m, 4H), 7.88-7.82 (m, 2H), 7.61-7.48 (m, 4H), 7.08 (d, 1H, J = 7.2 Hz), 4.28-4.16 (m, 1H), 3.54-3.34 (m, 1H), 1.90-1.15 (m, 8H). | 421 | 419 | 0.86 |
| Example 6-114 | 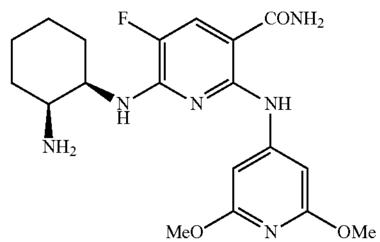 | 6-(((1R,2S)-2-aminocyclohexyl)amino)-2-((2,6-dimethoxypyridin-4-yl)amino)-5-fluoronicotinamide | HCl | DMSO-d6 | 300 MHz | δ: 11.94 (s, 1H), 7.96 (d, 1H, J = 12.6 Hz), 7.94-7.80 (m, 4H), 7.48-7.30 (m, 1H), 7.03 (d, 1H, J = 6.3 Hz), 6.60 (s, 2H), 4.29-4.17 (m, 1H), 3.82 (s, 6H), 3.74-3.65 (m, 1H), 2.02-1.36 (m, 8H). | 405 | 403 | |
| Example 6-115 | 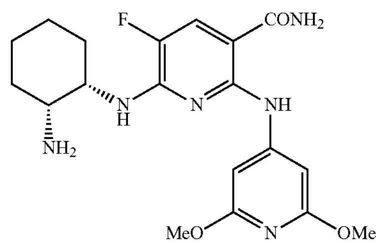 [SMILES: COc1cc(Nc2nc(N[C@H]3CCCC[C@H]3N)c(F)cc2C(N)=O)cc(OC)n1] | 6-(((1S,2R)-2-aminocyclohexylamino)-2-((2,6-dimethoxypyridin-4-yl)amino)-5-fluoronicotinamide | HCl | DMSO-d6 | 300 MHz | δ: 11.94 (s, 1H), 8.02-7.85 (m, 4H), 7.96 (d, 1H, J = 12.2 Hz), 7.48-7.28 (m, 1H), 7.05 (d, 1H, J = 6.3 Hz), 6.60 (s, 2H), 4.28-4.17 (m, 1H), 3.82 (s, 6H), 3.75-3.64 (m, 1H), 2.02-1.35 (m, 8H). | 405 | 403 | |

TABLE 3-continued

| Example | Structure | Name | Salt | Solvent | Freq | NMR | MS+1 | MS | Value |
|---|---|---|---|---|---|---|---|---|---|
| Example 6-116 | 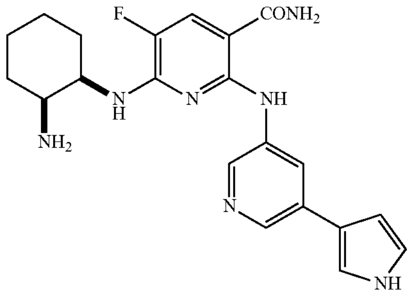 [SMILES: NC(=O)c1cc(F)c(N[C@@H]2CCCC[C@@H]2N)nc1Nc1cncc(-c2cc[nH]c2)c1] | 2-((5-((1H-pyrrol-3-yl)pyridin-3-yl)amino)-6-((cis-2-aminocyclohexyl)amino)-5-fluoronicotinamide | HCl | DMSO-d6 | 300 MHz | δ: 11.98 (s, 1H), 11.34 (s, 1H), 8.96 (s, 1H), 8.62 (s, 1H), 8.48 (s, 1H), 8.02 (d, 1H, J = 12.3 Hz), 8.00-7.80 (m, 4H), 7.64-7.69 (m, 1H), 7.47 (br, 1H), 7.06 (d, 1H, J = 6.6 Hz), 6.94-6.89 (m, 1H), 6.72-6.68 (m, 1H), 4.34-4.20 (m, 1H), 3.60-3.46 (m, 1H), 1.90-1.20 (m, 8H). | 410 | 408 | 0.65 |
| Example 6-117 | 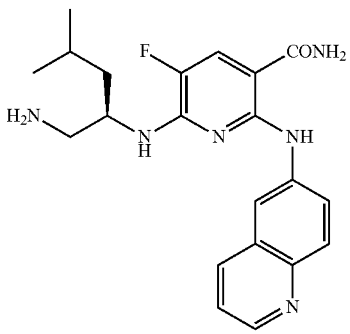 [SMILES: CC(C)C[C@H](CN)Nc1nc(Nc2ccc3ncccc3c2)c(C(N)=O)cc1F] | (R)-6-((1-amino-4-methylpentan-2-yl)amino)-5-fluoro-2-((quinolin-6-yl)amino)nicotinamide | HCl | CD3OD | 300 MHz | δ: 9.07 (d, 1H, J = 7.9 Hz), 8.94 (dd, 1H, J = 5.3, 1.3 Hz), 8.71 (d, 1H, J = 2.6 Hz), 8.30 (dd, 1H, J = 9.2, 2.0 Hz), 8.17 (d, 1H, J = 9.2 Hz), 8.03-7.95 (m, 1H), 7.86 (d, 1H, J = 11.9 Hz), 4.82-4.67 (m, 1H), 3.41-3.33 (m, 1H), 3.17-3.05 (m, 1H), 1.81-1.45 (m, 3H), 0.96-0.86 (m, 6H). | 397 | 395 | 0.77 |
| Example 6-118 | 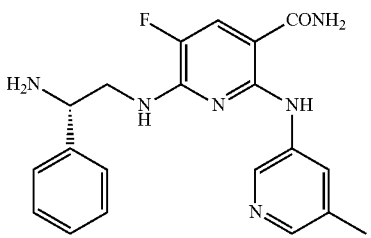 [SMILES: Cc1cncc(Nc2nc(NC[C@@H](N)c3ccccc3)c(F)cc2C(N)=O)c1] | (S)-6-((2-amino-2-phenylethyl)amino)-5-fluoro-2-((5-methylpyridin-3-yl)amino)nicotinamide | HCl | | | | 381 | 379 | 0.58 |

TABLE 3-continued

| Example | Structure | Name | Salt | | | |
|---|---|---|---|---|---|---|
| Example 6-119 | 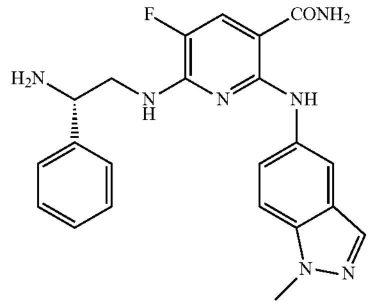 [SMILES: Cn1ncc2cc(Nc3nc(NC[C@@H](N)c4ccccc4)c(F)cc3C(N)=O)ccc21] | (S)-6-((2-amino-2-phenylethyl)amino)-5-fluoro-2-((1-methyl-1H-indazol-5-yl)amino)nicotinamide | HCl | 420 | 418 | 0.86 |
| Example 6-120 | 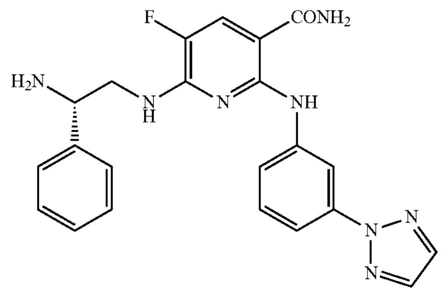 [SMILES: NC(=O)c1cc(F)c(NC[C@@H](N)c2ccccc2)nc1Nc1cccc(-n2nccn2)c1] | (S)-2-((3-(2H-1,2,3-triazol-2-yl)phenyl)amino)-6-((2-amino-2-phenylethyl)amino)-5-fluoronicotinamide | HCl | 433 | 431 | 1 |
| Example 6-121 | 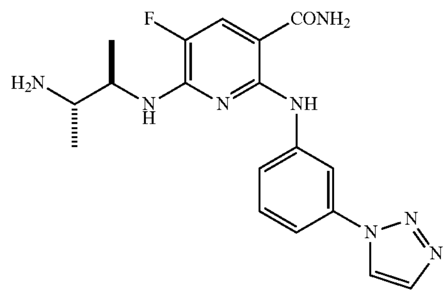 [SMILES: C[C@H](N)[C@@H](C)Nc1nc(Nc2cccc(-n3ccnn3)c2)c(C(N)=O)cc1F] | 2-((3-(1H-1,2,3-triazol-1-yl)phenyl)amino)-6-(((2R,3S)-3-aminobutan-2-yl)amino)-5-fluoronicotinamide 2-((3-(1H-1,2,3-triazol-1-yl)phenyl)amino)-6-(((2S,3R)-3-aminobutan-2-yl)amino)-5-fluoronicotinamide | HCl | 385 | 383 | 0.79 |

TABLE 3-continued

| Example | Name | Salt | Solvent | Freq | NMR | M | M+1 | RT |
|---|---|---|---|---|---|---|---|---|
| Example 6-122 | 2-(3-(1H-1,2,3-triazol-1-yl)phenylamino)-6-(((cis-2-aminocyclohexyl)amino)-5-fluoronicotinamide | HCl | | | | 411 | 409 | 0.87 |
| Example 6-123 | 2-((5-(1H-pyrrol-1-yl)pyridin-3-yl)amino)-6-(cis-2-aminocyclohexylamino)-5-fluoronicotinamide | HCl | DMSO-d6 | 300 MHz | δ: 11.95 (s, 1H), 8.75-8.70 (m, 1H), 8.57-8.53 (m, 1H), 8.53-8.49 (m, 1H), 8.00 (d, 1H, J = 12.6 Hz), 8.00-7.80 (m, 4H), 7.55-7.51 (m, 2H), 7.43 (br, 1H), 7.06 (d, 1H, J = 6.0 Hz), 6.36-6.32 (m, 2H), 4.27-4.15 (m, 1H), 3.70-3.50 (m, 1H), 1.90-1.15 (m, 8H). | 410 | 408 | 0.9 |
| Example 6-124 | 2-((2-(1H-pyrrol-1-yl)pyridin-4-yl)amino)-6-(((cis-2-aminocyclohexyl)amino)-5-fluoronicotinamide | HCl | DMSO-d6 | 300 MHz | δ: 12.13 (s, 1H), 8.21 (d, 1H, J = 5.7 Hz), 8.01 (d, 1H, J = 12.6 Hz), 8.00-7.80 (m, 5H), 7.66-7.62 (m, 2H), 7.56-7.38 (m, 2H), 7.07 (d, 1H, J = 6.6 Hz), 6.30-6.27 (m, 2H), 4.37-4.25 (m, 1H), 3.65-3.50 (m, 1H), 1.95-1.25 (m, 8H). | 410 | 408 | 0.92 |

TABLE 3-continued

| | | | | | | | |
|---|---|---|---|---|---|---|---|
| Example 6-125 | 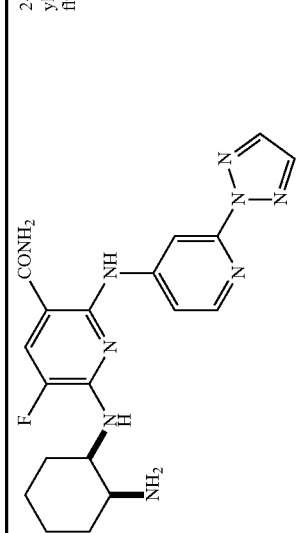 | 2-((2-(2H-1,2,3-triazol-2-yl)pyridin-4-yl)amino)-6-((cis-2-aminocyclohexyl)amino)-5-fluoronicotinamide | HCl | DMSO-d6 | 300 MHz | δ: 12.37 (s, 1H), 8.70-8.60 (m, 1H), 8.36-8.24 (m, 1H), 8.19 (s, 2H), 8.03 (d, 1H, J = 12.0 Hz), 8.02-7.84 (m, 4H), 7.60-7.44 (m, 1H), 7.34-7.24 (m, 1H), 7.10 (d, 1H, J = 7.2 Hz), 4.52-4.40 (m, 1H), 3.70-3.55 (m, 1H), 2.00-1.35 (m, 8H). | 412 410 0.79 |
| Example 6-126 | 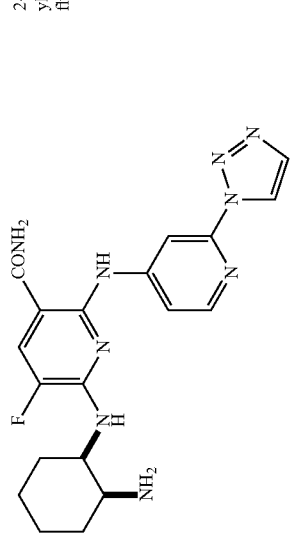 | 2-((2-(1H-1,2,3-triazol-1-yl)pyridin-4-yl)amino)-6-((cis-2-aminocyclohexyl)amino)-5-fluoronicotinamide | HCl | DMSO-d6 | 300 MHz | δ: 12.41 (s, 1H), 8.90 (d, 1H, J = 1.8 Hz), 8.84 (d, 1H, J = 1.5 Hz), 8.32 (d, 1H, J = 6.0 Hz), 8.10-7.86 (m, 6H), 7.54 (br, 1H), 7.25 (dd, 1H, J = 1.8, 6.0 Hz), 7.14 (d, 1H, J = 7.2 Hz), 4.58-4.46 (m, 1H), 3.69-3.57 (m, 1H), 1.95-1.25 (m, 8H). | 412 410 0.86 |
| Example 6-127 | 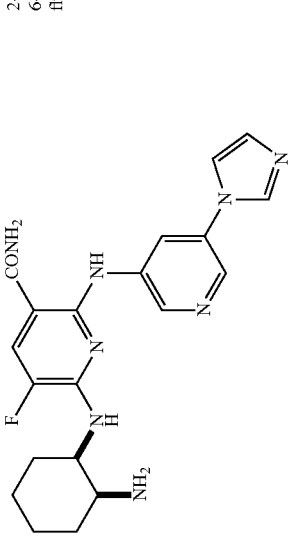 | 2-((5-(1H-imidazol-1-yl)pyridin-3-yl)amino)-6-((cis-2-aminocyclohexyl)amino)-5-fluoronicotinamide | HCl | DMSO-d6 | 300 MHz | δ: 12.03 (s, 1H), 9.75-9.70 (m, 1H), 9.07 (d, 1H, J = 2.1 Hz), 8.59 (d, 1H, J = 2.1 Hz), 8.48-8.44 (m, 1H), 8.39-8.36 (m, 1H), 8.10-7.85 (m, 6H), 7.45 (br, 1H), 7.11 (d, 1H, J = 6.0 Hz), 4.28-4.16 (m, 1H), 3.60-3.40 (m, 1H), 1.90-1.50 (m, 8H). | 411 409 0.57 |

TABLE 3-continued

| | | | | | | | |
|---|---|---|---|---|---|---|---|
| Example 6-128 | [structure] | 2-((2-((1-imidazol-1-yl)pyridin-4-yl)amino)-6-((cis-2-aminocyclohexyl)amino)-5-fluoronicotinamide | HCl | DMSO-d6 | 300 MHz | δ: 12.35 (s, 1H), 9.85 (s, 1H), 8.47 (s, 1H), 8.40 (d, 1H, J = 6.0 Hz), 8.08-7.94 (m, 7H), 7.87 (s, 1H), 7.55 (br, 1H), 7.16 (d, 1H, J = 6.0 Hz), 4.36-4.24 (m, 1H), 3.70-3.58 (m, 1H), 2.00-1.30 (m, 8H). | 411 409 0.63 |
| Example 6-129 | [structure] | 2-((5-((1H-pyrazol-1-yl)pyridin-3-yl)amino)-6-((cis-2-aminocyclohexyl)amino)-5-fluoronicotinamide | HCl | DMSO-d6 | 300 MHz | δ: 11.97 (s, 1H), 8.84-8.80 (m, 1H), 8.74-8.66 (m, 1H), 8.67 (d, 1H, J = 2.4 Hz), 8.62-8.54 (m, 1H), 8.00 (d, 1H, J = 11.7 Hz), 8.00-7.77 (m, 5H), 7.42 (br, 1H), 7.03 (d, 1H, J = 6.6 Hz), 6.64-6.61 (m, 1H), 4.40-4.28 (m, 1H), 3.62-3.48 (m, 1H), 1.90-1.25 (m, 8H). | 411 409 0.82 |
| Example 6-130 | [structure] | 2-((2-(1H-pyrazol-1-yl)pyridin-4-yl)amino)-6-((cis-2-aminocyclohexyl)amino)-5-fluoronicotinamide | HCl | DMSO-d6 | 300 MHz | δ: 12.26 (s, 1H), 8.62-8.58 (m, 2H), 8.21 (d, 1H, J = 6.0 Hz), 8.01 (d, 1H, J = 12.6 Hz), 8.01-7.92 (m, 1H), 7.86-7.74 (m, 4H), 7.60-7.44 (m, 1H), 7.13 (dd, 1H, J = 1.4, 6.0 Hz), 7.06 (d, 1H, J = 7.2 Hz), 6.59-6.55 (m, 1H), 4.60-4.46 (m, 1H), 3.73-3.60 (m, 1H), 1.95-1.35 (m, 8H). | 411 409 0.93 |

TABLE 3-continued

| Example | Structure | Name | Salt | Solvent | NMR freq | NMR | MW calc | MW obs | RT |
|---|---|---|---|---|---|---|---|---|---|
| Example 6-131 | 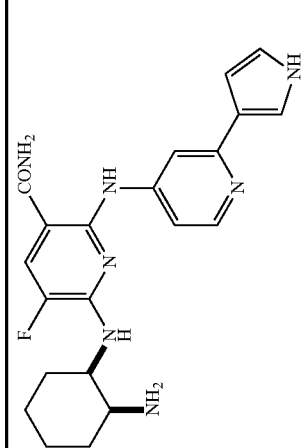 | 2-((2-((1H-pyrrol-3-yl)pyridin-4-yl)amino)-6-(((cis-2-aminocyclohexyl)amino)-5-fluoronicotinamide | HCl | DMSO-d6 | 300 MHz | δ: 13.99 (br, 1H), 12.76 (s, 1H), 11.78-11.68 (m, 1H), 8.29 (d, 1H, J = 6.6 Hz), 8.20-8.04 (m, 3H), 8.00-7.86 (m, 4H), 7.82-7.64 (m, 2H), 7.25 (d, 1H, J = 6.0 Hz), 7.04-7.00 (m, 1H), 6.88-6.84 (m, 1H), 4.40-4.28 (m, 1H), 3.68-3.52 (m, 1H), 1.95-1.25 (m, 8H). | 410 | 408 | 0.65 |
| Example 6-132 | 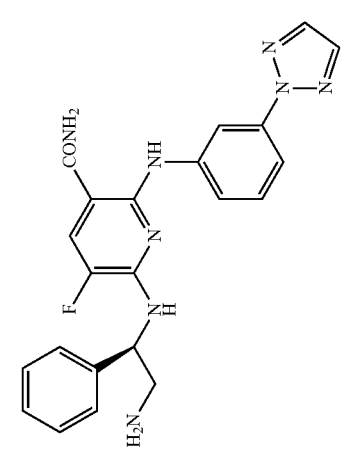 | (R)-2-((3-(2H-1,2,3-triazol-2-yl)phenyl)amino)-6-((2-amino-1-phenylethyl)amino)-5-fluoronicotinamide | HCl | | | | 433 | 431 | 1.03 |
| Example 6-133 | 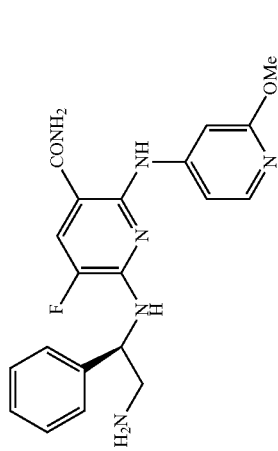 | (R)-6-((2-amino-1-phenylethyl)amino)-5-fluoro-2-((2-methoxypyridin-4-yl)amino)nicotinamide | HCl | | | | 397 | 395 | 0.66 |

TABLE 3-continued

| Example | Structure | Name | Salt | Solvent | Freq | NMR | MS1 | MS2 | RT |
|---|---|---|---|---|---|---|---|---|---|
| Example 6-134 | | (R)-6-((2-amino-1-phenylethyl)amino)-5-fluoro-2-(quinolin-7-ylamino)nicotinamide | HCl | CD3OD | 300 MHz | δ: 8.92 (d, 2H, J = 5.9 Hz), 8.69 (s, 1H), 8.10 (d, 1H, J = 9.2 Hz), 7.92-7.73 (m, 3H), 7.48 (d, 2H, J = 6.6 Hz), 7.34-7.16 (m, 3H), 5.94 (d, 1H, J = 8.1 Hz), 3.59-3.40 (2H, m). | 417 | 415 | 0.77 |
| Example 6-135 | | 6-(((1R,2S)-2-amino-1,2-diphenylethyl)amino)-5-fluoro-2-(quinolin-6-ylamino)nicotinamide 6-(((1S,2R)-2-amino-1,2-diphenylethyl)amino)-5-fluoro-2-(quinolin-6-ylamino)nicotinamide | HCl | | | | 493 | 491 | 0.81 |
| Example 6-136 | | 6-(((1R,2S)-2-amino-1,2-diphenylethyl)amino)-5-fluoro-2-((1-methyl-1H-indazol-5-yl)amino)nicotinamide 6-(((1S,2R)-2-amino-1,2-diphenylethyl)amino)-5-fluoro-2-((1-methyl-1H-indazol-5-yl)amino)nicotinamide | HCl | | | | 496 | 494 | 0.97 |

TABLE 3-continued

| Example | Structure | Name | Salt | | | |
|---|---|---|---|---|---|---|
| Example 6-137 | 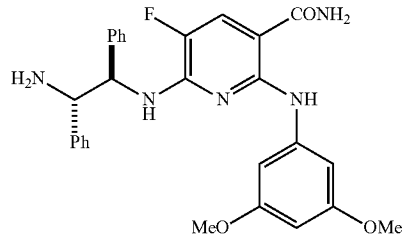 [SMILES: COc1cc(Nc2nc(N[C@H](c3ccccc3)[C@@H](N)c3ccccc3)c(F)cc2C(N)=O)cc(OC)c1] | 6-(((1R,2S)-2-amino-1,2-diphenylethyl)amino)-2-((3,5-dimethoxyphenyl)amino)-5-fluoronicotinamide 6-(((1S,2R)-2-amino-1,2-diphenylethyl)amino)-2-((3,5-dimethoxyphenyl)amino)-5-fluoronicotinamide | HCl | 502 | 501 | 1.08 |
| Example 6-138 | 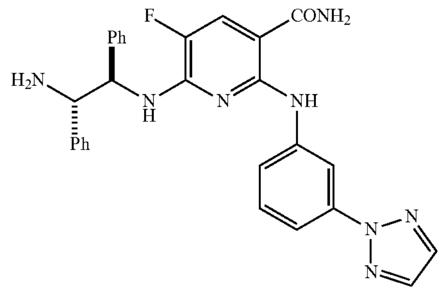 [SMILES: NC(=O)c1cc(F)c(N[C@H](c2ccccc2)[C@@H](N)c2ccccc2)nc1Nc1cccc(-n2nccn2)c1] | 2-(3-(2H-1,2,3-triazol-2-yl)phenyl)amino)-6-(((1R,2S)-2-amino-1,2-diphenylethyl)amino)-5-fluoronicotinamide 2-(3-(2H-1,2,3-triazol-2-yl)phenyl)amino)-6-(((1S,2R)-2-amino-1,2-diphenylethyl)amino)-5-fluoronicotinamide | HCl | 509 | 507 | 1.13 |
| Example 6-139 | 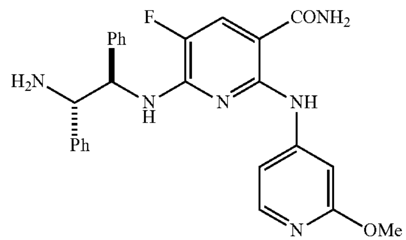 [SMILES: COc1cc(Nc2nc(N[C@H](c3ccccc3)[C@@H](N)c3ccccc3)c(F)cc2C(N)=O)ccn1] | 6-(((1R,2S)-2-amino-1,2-diphenylethyl)amino)-5-fluoro-2-((2-methoxypyridin-4-yl)amino)nicotinamide 6-(((1S,2R)-2-amino-1,2-diphenylethyl)amino)-5-fluoro-2-((2-methoxypyridin-4-yl)amino)nicotinamide | HCl | 473 | 471 | 0.77 |
| Example 6-140 | 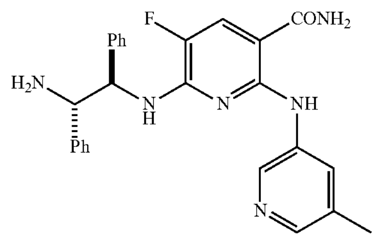 [SMILES: Cc1cncc(Nc2nc(N[C@H](c3ccccc3)[C@@H](N)c3ccccc3)c(F)cc2C(N)=O)c1] | 6-(((1R,2S)-2-amino-1,2-diphenylethyl)amino)-5-fluoro-2-((5-methylpyridin-3-yl)amino)nicotinamide 6-(((1S,2R)-2-amino-1,2-diphenylethyl)amino)-5-fluoro-2-((5-methylpyridin-3-yl)amino)nicotinamide | HCl | 458 | 456 | 0.79 |

TABLE 3-continued

| Example | Structure | Name | Salt | NMR | MS calc | MS obs | RT |
|---|---|---|---|---|---|---|---|
| Example 6-141 | | 6-(((1R,2S)-2-amino-1,2-diphenylethyl)amino)-5-fluoro-2-(quinolin-7-ylamino)nicotinamide 6-(((1S,2R)-2-amino-1,2-diphenylethyl)amino)-5-fluoro-2-(quinolin-7-ylamino)nicotinamide | HCl | CD3OD 300 MHz δ: 9.02-8.95 (m, 2H), 8.52 (s, 1H), 8.24 (d, 1H, J = 8.9 Hz), 8.02 (dd, 1H, J = 9.1, 1.8 Hz), 7.85-7.60 (m, 6H), 7.46-7.30 (m, 6H), 6.11 (d, 1H, J = 9.2 Hz), 4.85-4.83 (m, 1H). | 493 | 491 | 0.88 |
| Example 6-142 | | (R)-6-((1-amino-4-methylpentan-2-yl)amino)-5-fluoro-2-((1-methyl-1H-indazol-5-yl)amino)nicotinamide | HCl | | 400 | 398 | 0.95 |
| Example 6-143 | | (R)-2-((2-(1H-1,2,3-triazol-1-yl)pyridin-4-yl)amino)-6-((1-amino-4-methylpentan-2-yl)amino)-5-fluoronicotinamide | HCl | | 414 | 412 | 0.97 |

TABLE 3-continued

| Example | Structure | Name | Salt | Solvent | Freq | NMR | | | |
|---|---|---|---|---|---|---|---|---|---|
| Example 6-144 | 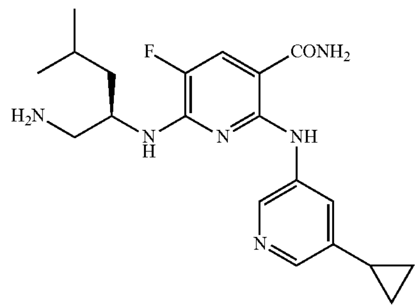 [SMILES: CC(C)C[C@H](CN)Nc1nc(Nc2cncc(C3CC3)c2)c(C(N)=O)cc1F] | (R)-6-((1-amino-4-methylpentan-2-yl)amino)-2-((5-cyclopropylpyridin-3-yl)amino)-5-fluoronicotinamide | HCl | | | | 387 | 385 | 0.84 |
| Example 6-145 | 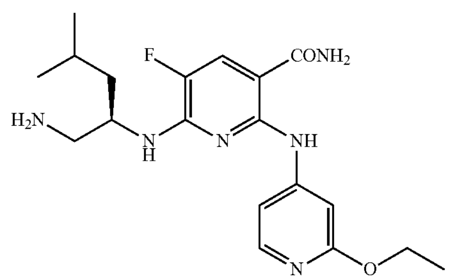 [SMILES: CCOc1cc(Nc2nc(N[C@@H](CN)CC(C)C)c(F)cc2C(N)=O)ccn1] | (R)-6-((1-amino-4-methylpentan-2-yl)amino)-2-((2-ethoxypyridin-4-yl)amino)-5-fluoronicotinamide | HCl | | | | 391 | 389 | 0.79 |
| Example 6-146 | 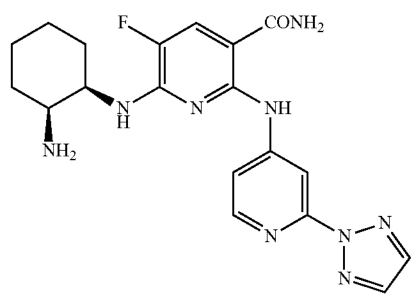 [SMILES: NC(=O)c1cc(F)c(N[C@@H]2CCCC[C@@H]2N)nc1Nc1ccnc(-n2nccn2)c1] | 2-((2-(2H-1,2,3-triazol-2-yl)pyridin-4-yl)amino)-6-(((1R,2S)-2-aminocyclohexyl)amino)-5-fluoronicotinamide | HCl | DMSO-d6 | 300 MHz | δ: 12.37 (s, 1H), 8.70-8.60 (m, 1H), 8.36-8.24 (m, 1H), 8.19 (s, 2H), 8.03 (d, 1H, J = 12.0 Hz), 8.02-7.84 (m, 4H), 7.60-7.44 (m, 1H), 7.34-7.24 (m, 1H), 7.10 (d, 1H, J = 7.2 Hz), 4.52-4.40 (m, 1H), 3.70-3.55 (m, 1H), 2.00-1.35 (m, 8H). | 412 | 410 | 0.79 |

TABLE 3-continued

| Example | Structure | Name | Salt | | | |
|---|---|---|---|---|---|---|
| Example 6-147 | 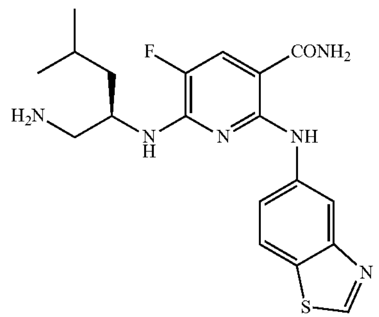 [SMILES: CC(C)C[C@H](CN)Nc1nc(Nc2ccc3scnc3c2)c(C(N)=O)cc1F] | (R)-6-((1-amino-4-methylpentan-2-yl)amino)-2-(benzo[d]thiazol-5-ylamino)-5-fluoronicotinamide | HCl | 403 | 401 | 1.01 |
| Example 6-148 | 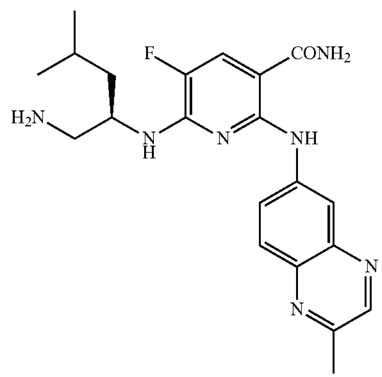 [SMILES: Cc1cnc2cc(Nc3nc(N[C@@H](CN)CC(C)C)c(F)cc3C(N)=O)ccc2n1] | (R)-6-((1-amino-4-methylpentan-2-yl)amino)-5-fluoro-2-((2-methylquinoxalin-6-yl)amino)nicotinamide | HCl | 412 | 410 | 0.98 |
| Example 6-149 | 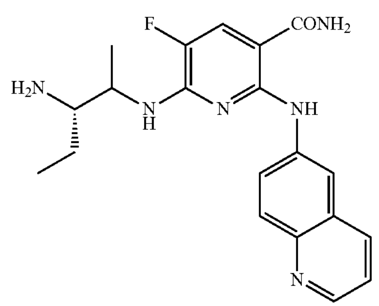 [SMILES: CC[C@H](N)C(C)Nc1nc(Nc2ccc3ncccc3c2)c(C(N)=O)cc1F] | 6-(((3S)-4-aminopentan-2-yl)amino)-5-fluoro-2-(quinolin-6-ylamino)nicotinamide | HCl | 383 | 381 | 0.61 |

TABLE 3-continued

| Example | Structure | Name | Salt | Solvent | MHz | NMR | | | |
|---|---|---|---|---|---|---|---|---|---|
| Example 6-150 | | 6-(((4S)-4-aminohexan-3-yl)amino)-5-fluoro-2-(quinolin-6-ylamino)nicotinamide | HCl | | | | 397 | 395 | 0.66 |
| Example 6-151 | | 6-(((5S)-5-amino-2-methylheptan-4-yl)amino)-5-fluoro-2-(quinolin-6-ylamino)nicotinamide | HCl | | | | 425 | 423 | 0.79 |
| Example 6-152 | | 6-((cis-2-aminocyclohexyl)amino)-5-fluoro-2-(((6-methyl-5-(1H-1,2,3-triazol-1-yl)pyridin-3-yl)amino)nicotinamide | HCl | DMSO-d6 | 300 MHz | δ: 12.00 (s, 1H), 8.68-8.66 (m, 1H), 8.63 (d, 1H, J = 2.7 Hz), 8.50 (d, 1H, J = 2.7 Hz), 8.03 (s, 1H), 7.98 (d, 1H, J = 12.6 Hz), 7.94-7.70 (m, 4H), 7.41 (br, 1H), 7.01 (d, 1H, J = 6.6 Hz), 4.16-4.04 (m, 1H), 3.50-3.36 (m, 1H), 2.31 (s, 3H), 1.80-1.00 (m, 8H). | 426 | 424 | 0.75 |

TABLE 3-continued
| Example | | | | |
|---|---|---|---|---|
| Example 6-153 | 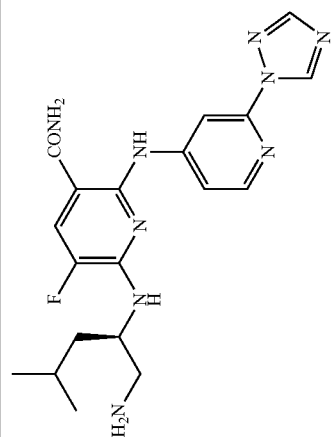 | (R)-2-((2-(1H-1,2,4-triazol-1-yl)pyridin-4-yl)amino)-6-((1-amino-4-methylpentan-2-yl)amino)-5-fluoronicotinamide | HCl | 414 412 0.96 |
| Example 6-154 | 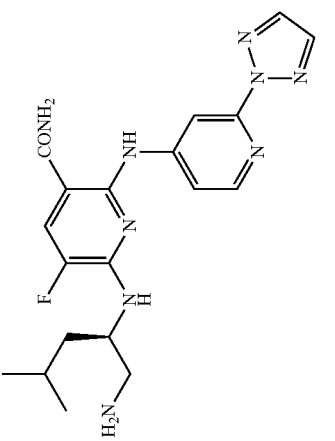 | (R)-2-((2-(2H-1,2,3-triazol-2-yl)pyridin-4-yl)amino)-6-((1-amino-4-methylpentan-2-yl)amino)-5-fluoronicotinamide | HCl | 414 412 0.93 |
| Example 6-155 | 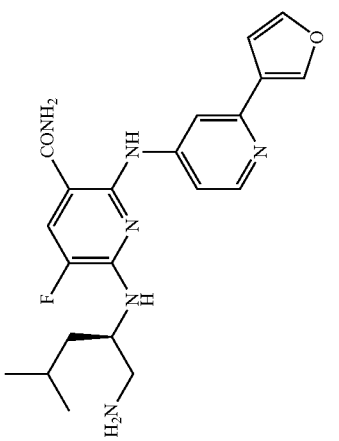 | (R)-6-((1-amino-4-methylpentan-2-yl)amino)-5-fluoro-2-((2-(furan-3-yl)pyridin-4-yl)amino)nicotinamide | HCl | 413 411 0.87 |

TABLE 3-continued

| Example | Structure | Name | Salt | | | |
|---|---|---|---|---|---|---|
| Example 6-156 | 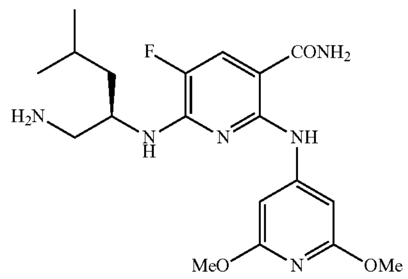 [SMILES: COc1cc(Nc2nc(N[C@@H](CN)CC(C)C)c(F)cc2C(N)=O)cc(OC)n1] | (R)-6-((1-amino-4-methylpentan-2-yl)amino)-2-((2,6-dimethoxypyridin-4-yl)amino)-5-fluoronicotinamide | HCl | 407 | 405 | 1.09 |
| Example 6-157 | 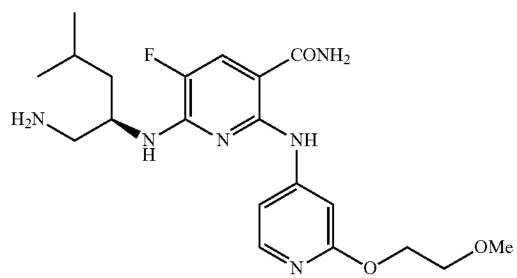 [SMILES: COCCOc1cc(Nc2nc(N[C@@H](CN)CC(C)C)c(F)cc2C(N)=O)ccn1] | (R)-6-((1-amino-4-methylpentan-2-yl)amino)-5-fluoro-2-((2-(2-methoxyethoxy)pyridin-4-yl)amino)nicotinamide | HCl | 421 | 419 | 0.82 |
| Example 6-158 | 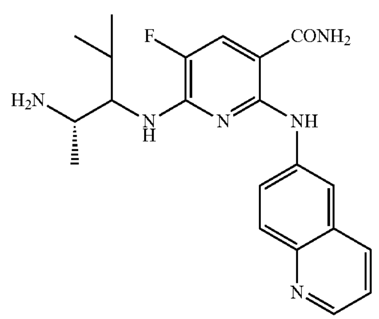 [SMILES: CC(C)C(Nc1nc(Nc2ccc3ncccc3c2)c(C(N)=O)cc1F)[C@H](C)N] | 6-(((2S)-2-amino-4-methylpentan-3-yl)amino)-5-fluoro-2-(quinolin-6-ylamino)nicotinamide | HCl | 397 | 395 | 0.72 |

TABLE 3-continued

| Example | Structure | Name | Salt | | | |
|---|---|---|---|---|---|---|
| Example 6-159 | 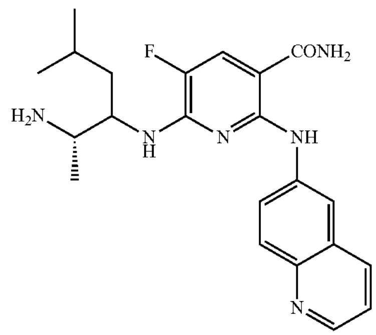 [SMILES: CC(C)CC(Nc1nc(Nc2ccc3ncccc3c2)c(C(N)=O)cc1F)[C@H](C)N] | 6-(((2S)-2-amino-5-methylhexan-3-yl)amino)-5-fluoro-2-(quinolin-6-ylamino)nicotinamide | HCl | 411 | 409 | 0.8 |
| Example 6-160 | 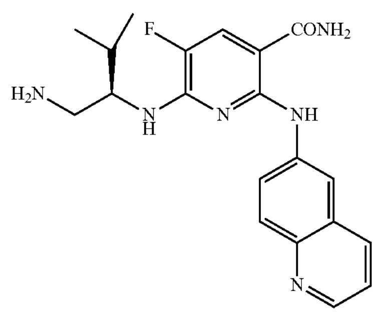 [SMILES: CC(C)[C@H](CN)Nc1nc(Nc2ccc3ncccc3c2)c(C(N)=O)cc1F] | (R)-6-((1-amino-3-methylbutan-2-yl)amino)-5-fluoro-2-(quinolin-6-ylamino)nicotinamide | HCl | 383 | 381 | 0.69 |
| Example 6-161 | 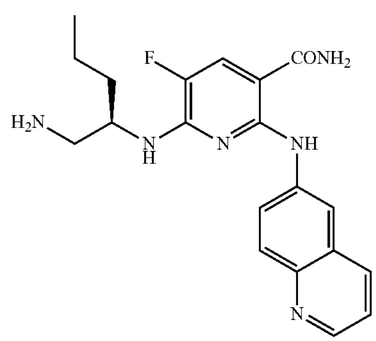 [SMILES: CCC[C@H](CN)Nc1nc(Nc2ccc3ncccc3c2)c(C(N)=O)cc1F] | (R)-6-((1-aminopentan-2-yl)amino)-5-fluoro-2-(quinolin-6-ylamino)nicotinamide | HCl | 383 | 381 | 0.71 |

TABLE 3-continued

| Example | Structure | Name | Salt | Solvent | Freq | NMR | MS | MS | MS | LC |
|---|---|---|---|---|---|---|---|---|---|---|
| Example 6-162 | | (R)-6-((1-amino-3,3-dimethylbutan-2-yl)amino)-5-fluoro-2-(quinolin-6-ylamino)nicotinamide | HCl | | | | 397 | 395 | | 0.75 |
| Example 6-163 | | 6-((cis-2-aminocyclohexyl)amino)-2-((2-chloropyridin-4-yl)amino)-5-fluoronicotinamide | HCl | | | | 379 381 | 377 379 | | 0.84 |
| Example 6-164 | | 6-((cis-2-aminocyclohexyl)amino)-5-fluoro-2-((6-(phenylamino)pyridin-3-yl)amino)nicotinamide | HCl | DMSO-d6-D2O | 300 MHz | δ: 8.37 (d, 1H, J = 2.6 Hz), 7.92 (dd, 1H, J = 2.5, 8.8 Hz), 7.88 (d, 1H, J = 11.9 Hz), 7.54-7.46 (m, 2H), 7.41-7.32 (m, 2H), 7.11-6.99 (m, 2H), 4.22-4.10 (m, 1H), 3.66-3.58 (m, 1H), 1.93-1.36 (m, 8H). | 436 | 434 | | 0.83 |

TABLE 3-continued

| Example | Structure | Name | Salt | Solvent | Freq | ¹H NMR | MS (M+) | MS (M+1) | RT |
|---|---|---|---|---|---|---|---|---|---|
| Example 6-165 | 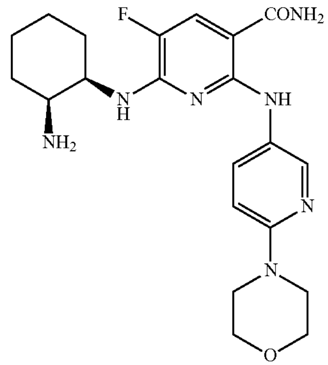 [SMILES: NC(=O)c1cc(F)c(N[C@@H]2CCCC[C@@H]2N)nc1Nc1ccc(N2CCOCC2)nc1] | 6-(((1R,2S)-2-aminocyclohexyl)amino)-5-fluoro-2-((6-morpholinopyridin-3-yl)amino)nicotinamide | HCl | DMSO-d6-D2O | 300 MHz | δ: 8.43 (d, 1H, J = 2.6 Hz), 8.03 (dd, 1H, J = 2.5 Hz, 9.4 Hz), 7.91 (d, 1H, J = 12.2 Hz), 7.24 (d, 1H, J = 9.6 Hz), 4.29-4.17 (m, 1H), 3.81-3.73 (m, 4H), 3.61-3.51 (m, 1H), 3.59-3.47 (m, 4H), 1.93-1.36 (m, 8H). | 430 | 428 | 0.67 |
| Example 6-166 | 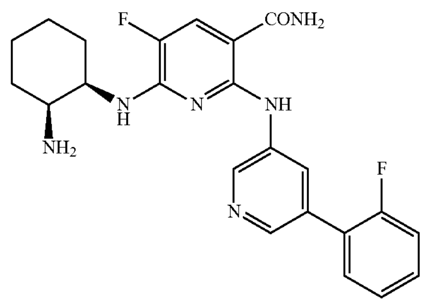 [SMILES: NC(=O)c1cc(F)c(N[C@@H]2CCCC[C@@H]2N)nc1Nc1cncc(-c2ccccc2F)c1] | 6-(((1R,2S)-2-aminocyclohexyl)amino)-5-fluoro-2-((5-(2-fluorophenyl)pyridin-3-yl)amino)nicotinamide | HCl | DMSO-d6 | 300 MHz | δ: 12.05 (s, 1H), 8.87 (d, 1H, J = 2.1 Hz), 8.56-8.51 (m, 1H), 8.46-8.42 (m, 1H), 8.00 (d, 1H, J = 12.6 Hz), 7.76 (m, 4H), 7.74-7.65 (m, 1H), 7.59-7.50 (m, 1H), 7.46-7.35 (m, 3H), 7.06 (d, 1H, J = 6.6 Hz), 4.20-4.08 (m, 1H), 3.60-3.50 (m, 1H), 1.85-1.05 (m, 8H). | 439 | 437 | 0.88 |
| Example 6-167 | 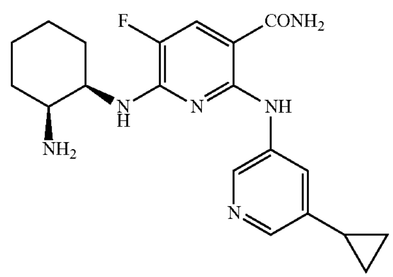 [SMILES: NC(=O)c1cc(F)c(N[C@@H]2CCCC[C@@H]2N)nc1Nc1cncc(C2CC2)c1] | 6-(((1R,2S)-2-aminocyclohexyl)amino)-2-((5-cyclopropylpyridin-3-yl)amino)-5-fluoronicotinamide | HCl | DMSO-d6 | 300 MHz | δ: 12.01 (s, 1H), 9.15-9.08 (m, 1H), 8.26-8.20 (m, 1H), 8.10-7.90 (m, 6H), 7.55-7.40 (br, 1H), 7.06 (d, 1H, J = 6.6 Hz), 4.37-4.26 (m, 1H), 3.58-3.46 (m, 1H), 2.18-2.08 (m, 1H), 1.94-1.36 (m, 8H), 1.16-1.06 (m, 2H), 1.00-0.90 (m, 2H). | 385 | 383 | 0.65 |

TABLE 3-continued

| Example | Name | Salt | Solvent | Freq | NMR | MS+1 | MS-1 | RT |
|---|---|---|---|---|---|---|---|---|
| Example 6-168 | 2-((5-(1H-pyrazol-1-yl)pyridin-3-yl)amino)-6-(((1R,2S)-2-aminocyclohexyl)amino)-5-fluoronicotinamide 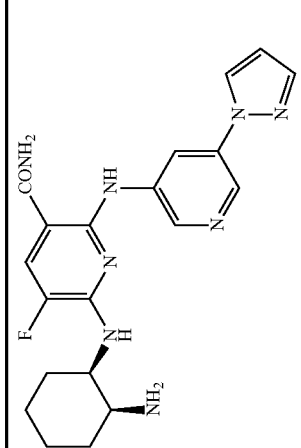 | HCl | DMSO-d6 | 300 MHz | δ: 11.97 (s, 1H), 8.84-8.80 (m, 1H), 8.74-8.66 (m, 1H), 8.67 (d, 1H, J = 2.4 Hz), 8.62-8.54 (m, 1H), 8.00 (d, 1H, J = 11.7 Hz), 8.00-7.77 (m, 5H), 7.42 (br, 1H), 7.03 (d, 1H, J = 6.6 Hz), 6.64-6.61 (m, 1H), 4.40-4.28 (m, 1H), 3.62-3.48 (m, 1H), 1.90-1.25 (m, 8H). | 411 | 409 | 0.82 |
| Example 6-169 | 6-(((1R,2S)-2-aminocyclohexyl)amino)-5-fluoro-2-((2-propoxypyridin-4-yl)amino)nicotinamide 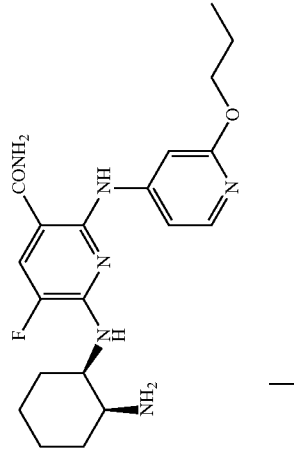 | HCl | | | | 403 | 401 | 0.72 |
| Example 6-170 | (R)-2-((5-(1H-pyrazol-1-yl)pyridin-3-yl)amino)-6-((1-amino-4-methylpentan-2-yl)amino)-5-fluoronicotinamide 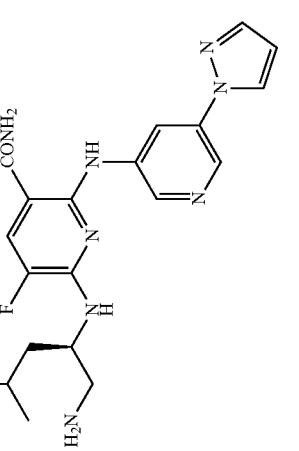 | HCl | | | | 413 | 411 | 0.94 |

TABLE 3-continued

| Example | Structure | Name | Salt | | | |
|---|---|---|---|---|---|---|
| Example 6-171 | 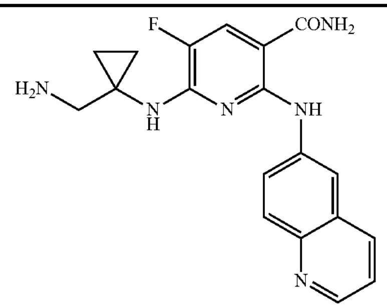 | 6-((1-(aminomethyl)cyclopropyl)amino)-5-fluoro-2-((quinolin-6-yl)amino)nicotinamide | HCl | 367 | 365 | 0.61 |
| Example 6-172 | 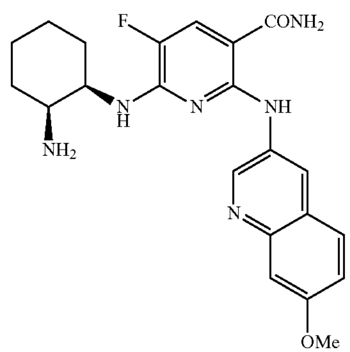 [SMILES: COc1ccc2cc(Nc3nc(N[C@@H]4CCCC[C@@H]4N)c(F)cc3C(N)=O)cnc2c1] | 6-(((1R,2S)-2-aminocyclohexyl)amino)-5-fluoro-2-((7-methoxyquinolin-3-yl)amino)nicotinamide | HCl | 425 | 423 | 0.78 |
| Example 6-173 | 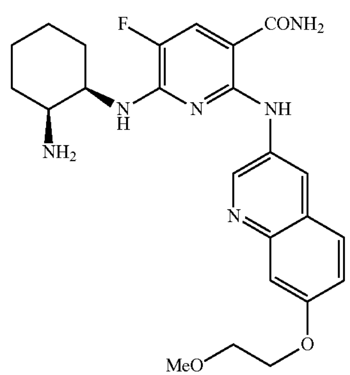 [SMILES: COCCOc1ccc2cc(Nc3nc(N[C@@H]4CCCC[C@@H]4N)c(F)cc3C(N)=O)cnc2c1] | 6-(((1R,2S)-2-aminocyclohexyl)amino)-5-fluoro-2-((7-(2-methoxyethoxy)quinolin-3-yl)amino)nicotinamide | HCl | 469 | 467 | 0.79 |

TABLE 3-continued

| Example | Structure | Name | Salt | | | |
|---|---|---|---|---|---|---|
| Example 6-174 | 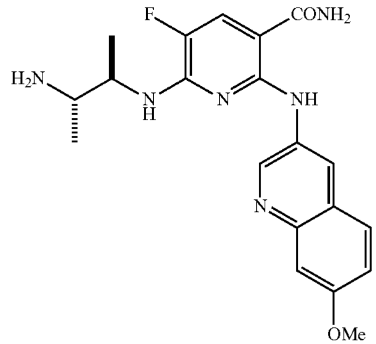 [SMILES: COc1ccc2cc(Nc3nc(N[C@H](C)[C@H](C)N)c(F)cc3C(N)=O)cnc2c1] | 6-(((2R,3S)-3-aminobutan-2-yl)amino)-5-fluoro-2-((7-methoxyquinolin-3-yl)amino)nicotinamide 6-(((2S,3R)-3-aminobutan-2-yl)amino)-5-fluoro-2-((7-methoxyquinolin-3-yl)amino)nicotinamide | HCl | 399 | 397 | 0.7 |
| Example 6-175 | 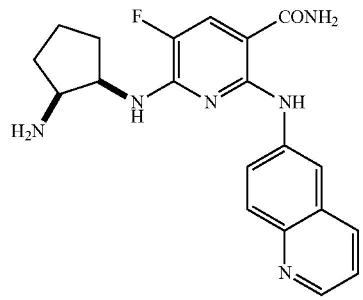 | 6-((cis-2-aminocyclopentyl)amino)-5-fluoro-2-(quinolin-6-ylamino)nicotinamide | HCl | 381 | 379 | 0.62 |
| Example 6-176 | 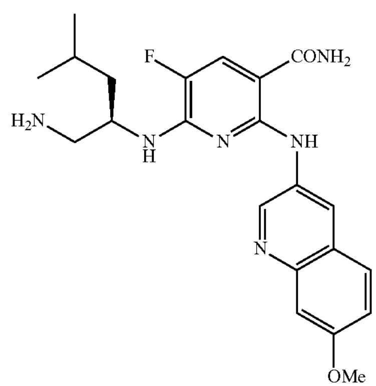 [SMILES: COc1ccc2cc(Nc3nc(N[C@@H](CN)CC(C)C)c(F)cc3C(N)=O)cnc2c1] | (R)-6-((1-amino-4-methylpentan-2-yl)amino)-5-fluoro-2-((7-methoxyquinolin-3-yl)amino)nicotinamide | HCl | 427 | 425 | 0.94 |

TABLE 3-continued

| Example | Structure | Name | Salt | Solvent | Freq | NMR | MS | MS | Rf |
|---|---|---|---|---|---|---|---|---|---|
| Example 6-177 | 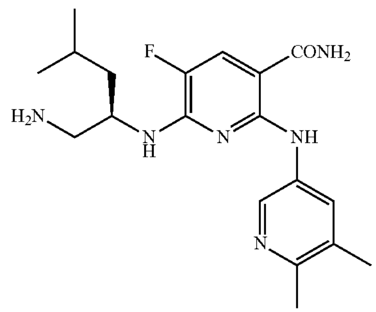 [SMILES: Cc1cc(Nc2nc(N[C@@H](CN)CC(C)C)c(F)cc2C(N)=O)cnc1C] | (R)-6-((1-amino-4-methylpentan-2-yl)amino)-2-((5,6-dimethylpyridin-3-yl)amino)-5-fluoronicotinamide | HCl | DMSO-d6 | 300 MHz | δ: 12.06 (s, 1H), 9.21 (s, 1H), 8.19 (s, 1H), 8.06-7.88 (m, 4H), 7.44 (s, 1H), 7.29-7.20 (m, 2H), 4.45-4.36 (m, 1H), 3.02 (s, 2H), 2.59 (s, 3H), 2.38 (s, 3H), 1.68-1.50 (m, 2H), 1.45-1.35 (m, 1H), 0.80 (dd, 6H, J = 12.9, 6.3 Hz). | 375 | 373 | 0.72 |
| Example 6-178 | 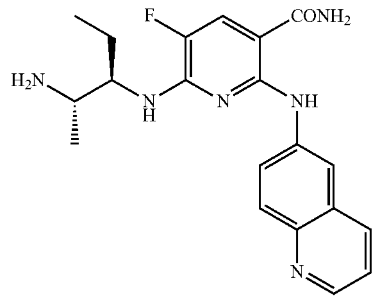 [SMILES: CC[C@@H](Nc1nc(Nc2ccc3ncccc3c2)c(C(N)=O)cc1F)[C@H](C)N] | 6-(((2S,3R)-2-aminopentan-3-yl)amino)-5-fluoro-2-((quinolin-6-yl)amino)nicotinamide | HCl | | | | 383 | 381 | 0.65 |
| Example 6-179 | 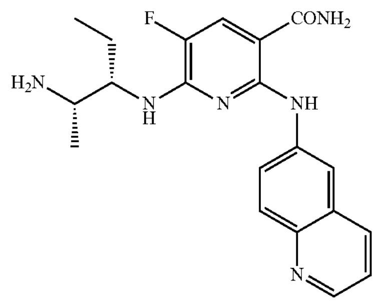 [SMILES: CC[C@H](Nc1nc(Nc2ccc3ncccc3c2)c(C(N)=O)cc1F)[C@H](C)N] | 6-(((2S,3S)-2-aminopentan-3-yl)amino)-5-fluoro-2-((quinolin-6-yl)amino)nicotinamide | HCl | | | | 383 | 381 | 0.65 |

TABLE 3-continued

| Example | Structure | Name | Salt | Solvent | Freq | NMR | M+H | M | Activity |
|---|---|---|---|---|---|---|---|---|---|
| Example 6-180 | 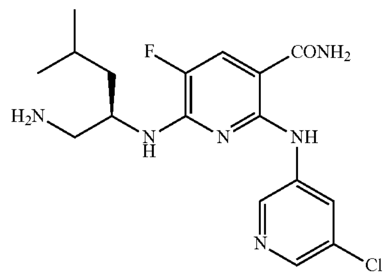 [SMILES: CC(C)C[C@H](CN)Nc1nc(Nc2cncc(Cl)c2)c(C(N)=O)cc1F] | (R)-6-((1-amino-4-methylpentan-2-yl)amino)-2-((5-chloropyridin-3-yl)amino)-5-fluoronicotinamide | HCl | DMSO-d6 | 300 MHz | δ: 11.92 (br, 1H), 8.67 (d, 1H, J = 2.0 Hz), 8.29 (t, 1H, J = 2.0 Hz), 8.18 (1H, d, J = 2.0 Hz), 7.95 (d, 1H, J = 12.6 Hz), 7.90-7.80 (m, 3H), 7.37 (s, 1H), 7.19-7.10 (m, 1H), 4.37 (s, 2H), 3.04 (s, 2H), 1.68-1.50 (m, 2H), 1.45-1.35 (m, 1H), 0.85 (6H, dd, J = 12.9, 6.3 Hz). | 382 | 380 | 1 |
| Example 6-181 | 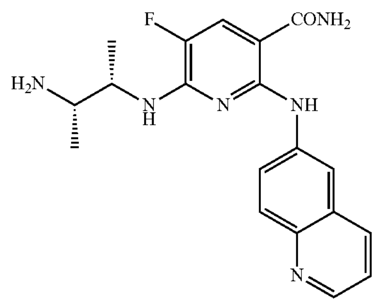 [SMILES: C[C@H](N)[C@H](C)Nc1nc(Nc2ccc3ncccc3c2)c(C(N)=O)cc1F] | 6-(((2S,3S)-3-aminobutan-2-yl)amino)-5-fluoro-2-((quinolin-6-yl)amino)nicotinamide | HCl | | | | 369 | 367 | 0.59 |
| Example 6-182 | 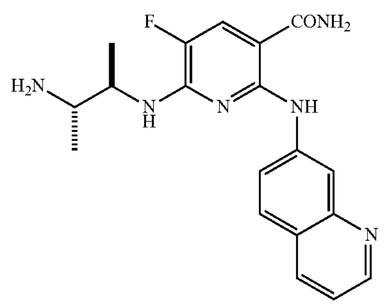 [SMILES: C[C@H](N)[C@@H](C)Nc1nc(Nc2ccc3cccnc3c2)c(C(N)=O)cc1F] | 6-(((2R,3S)-3-aminobutan-2-yl)amino)-5-fluoro-2-((quinolin-7-yl)amino)nicotinamide 6-(((2S,3R)-3-aminobutan-2-yl)amino)-5-fluoro-2-((quinolin-7-yl)amino)nicotinamide | HCl | | | | 369 | 367 | 0.56 |

TABLE 3-continued

| Example | Structure | Name | Salt | MW | Obs | RT |
|---|---|---|---|---|---|---|
| Example 6-183 | 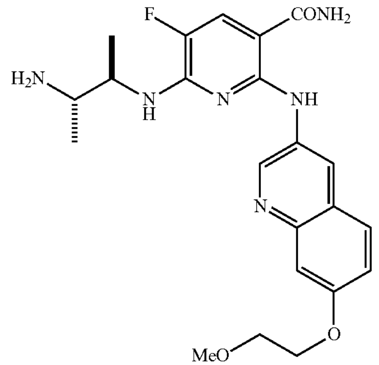 [SMILES: COCCOc1ccc2cc(Nc3nc(N[C@H](C)[C@H](C)N)c(F)cc3C(N)=O)cnc2c1] | 6-(((2R,3S)-3-aminobutan-2-yl)amino)-5-fluoro-2-((7-(2-methoxyethoxy)quinolin-3-yl)amino)nicotinamide 6-(((2S,3R)-3-aminobutan-2-yl)amino)-5-fluoro-2-((7-(2-methoxyethoxy)quinolin-3-yl)amino)nicotinamide | HCl | 443 | 441 | 0.71 |
| Example 6-184 | 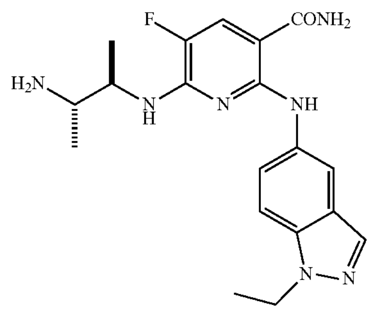 [SMILES: CCn1ncc2cc(Nc3nc(N[C@H](C)[C@H](C)N)c(F)cc3C(N)=O)ccc21] | 6-(((2R,3S)-3-aminobutan-2-yl)amino)-2-((1-ethyl-1H-indazol-5-yl)amino)-5-fluoronicotinamide 6-(((2S,3R)-3-aminobutan-2-yl)amino)-2-((1-ethyl-1H-indazol-5-yl)amino)-5-fluoronicotinamide | HCl | 386 | 384 | 0.82 |
| Example 6-185 | 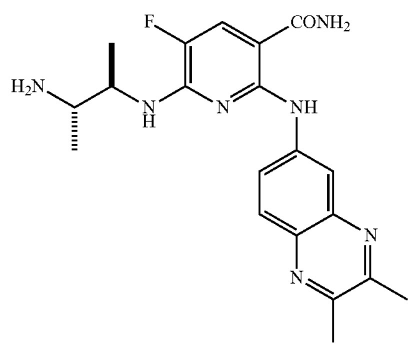 [SMILES: Cc1nc2ccc(Nc3nc(N[C@H](C)[C@H](C)N)c(F)cc3C(N)=O)cc2nc1C] | 6-(((2R,3S)-3-aminobutan-2-yl)amino)-2-((2,3-dimethylquinoxalin-6-yl)amino)-5-fluoronicotinamide 6-(((2S,3R)-3-aminobutan-2-yl)amino)-2-((2,3-dimethylquinoxalin-6-yl)amino)-5-fluoronicotinamide | HCl | 398 | 396 | 0.81 |

TABLE 3-continued

| Example | Structure | Name | Salt | MS1 | MS2 | RT |
|---|---|---|---|---|---|---|
| Example 6-186 | 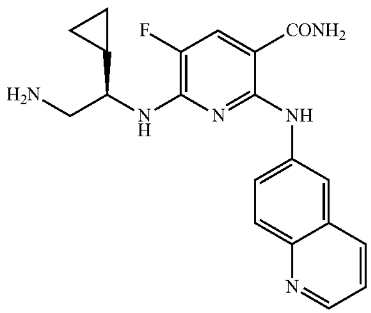 [SMILES: NC[C@H](Nc1nc(Nc2ccc3ncccc3c2)c(C(N)=O)cc1F)C1CC1] | (R)-6-((2-amino-1-cyclopropylethyl)amino)-5-fluoro-2-((quinolin-6-yl)amino)nicotinamide | HCl | 381 | 379 | 0.65 |
| Example 6-187 | 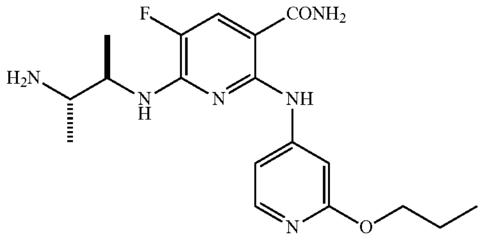 [SMILES: CCCOc1cc(Nc2nc(N[C@H](C)[C@H](C)N)c(F)cc2C(N)=O)ccn1] | 6-(((2R,3S)-3-aminobutan-2-yl)amino)-5-fluoro-2-((2-propoxypyridin-4-yl)amino)nicotinamide 6-(((2S,3R)-3-aminobutan-2-yl)amino)-5-fluoro-2-((2-propoxypyridin-4-yl)amino)nicotinamide | HCl | 377 | 375 | 0.65 |
| Example 6-188 | 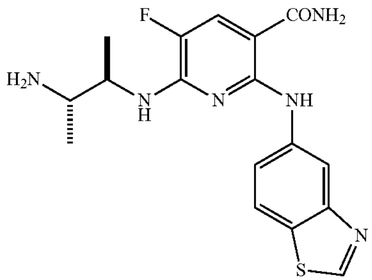 [SMILES: C[C@H](N)[C@@H](C)Nc1nc(Nc2ccc3scnc3c2)c(C(N)=O)cc1F] | 6-(((2R,3S)-3-aminobutan-2-yl)amino)-2-(benzo[d]thiazol-5-ylamino)-5-fluoronicotinamide 6-(((2S,3R)-3-aminobutan-2-yl)amino)-2-(benzo[d]thiazol-5-ylamino)-5-fluoronicotinamide | HCl | 375 | 373 | 0.82 |

TABLE 3-continued

| | | | | | |
|---|---|---|---|---|---|
| Example 6-189 | 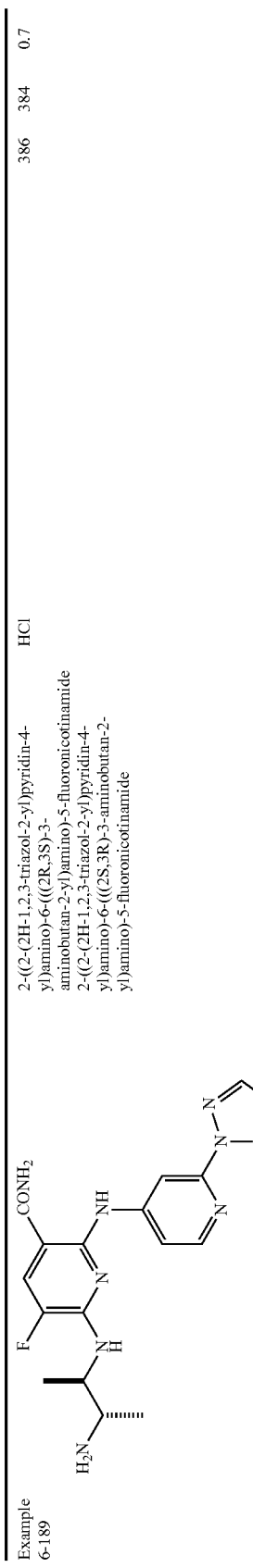 | 2-((2-(2H-1,2,3-triazol-2-yl)pyridin-4-yl)amino)-6-(((2R,3S)-3-aminobutan-2-yl)amino)-5-fluoronicotinamide 2-((2-(2H-1,2,3-triazol-2-yl)pyridin-4-yl)amino)-6-(((2S,3R)-3-aminobutan-2-yl)amino)-5-fluoronicotinamide | HCl | | 386 384 0.7 |
| Example 6-190 | 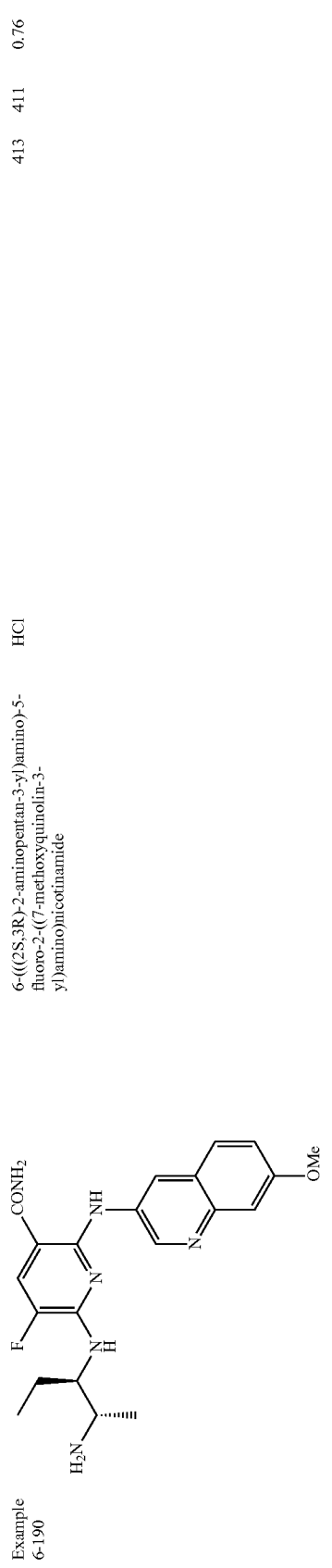 | 6-(((2S,3R)-2-aminopentan-3-yl)amino)-5-fluoro-2-((7-methoxyquinolin-3-yl)amino)nicotinamide | HCl | | 413 411 0.76 |
| Example 6-191 | 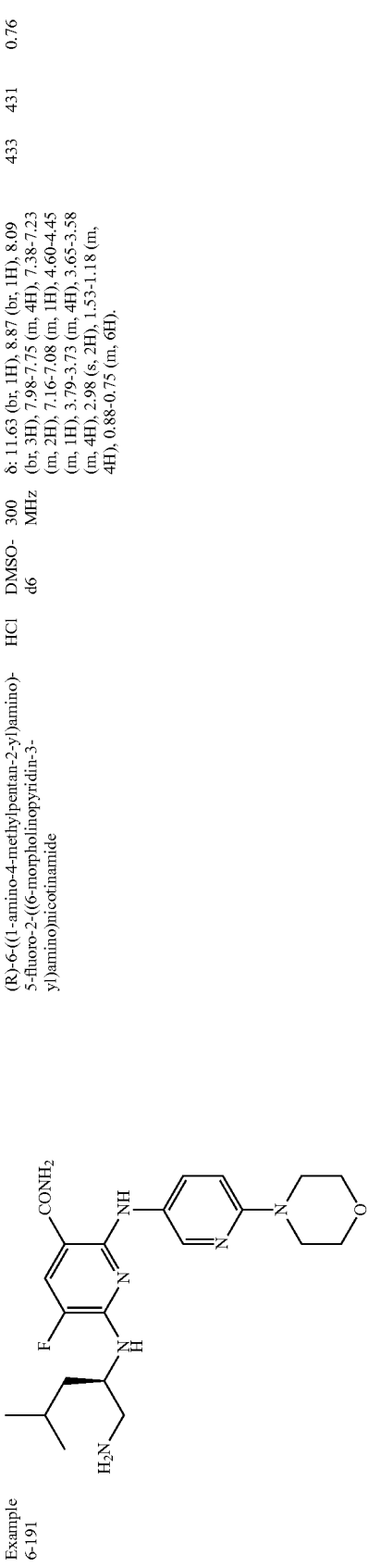 | (R)-6-((1-amino-4-methylpentan-2-yl)amino)-5-fluoro-2-((6-morpholinopyridin-3-yl)amino)nicotinamide | HCl | DMSO-d6 300 MHz | 433 431 0.76 δ: 11.63 (br, 1H), 8.87 (br, 1H), 8.09 (br, 3H), 7.98-7.75 (m, 4H), 7.38-7.23 (m, 2H), 7.16-7.08 (m, 1H), 4.60-4.45 (m, 1H), 3.79-3.73 (m, 4H), 3.65-3.58 (m, 4H), 2.98 (s, 2H), 1.53-1.18 (m, 4H), 0.88-0.75 (m, 6H). |

TABLE 3-continued

| Example | Structure | Name | Salt | Solvent | Freq | NMR | MS | Rf |
|---|---|---|---|---|---|---|---|---|
| Example 6-192 | | 2-((5-(1H-pyrazol-1-yl)pyridin-3-yl)amino)-6-(((2R,3S)-3-aminobutan-2-yl)amino)-5-fluoronicotinamide 2-((5-(1H-pyrazol-1-yl)pyridin-3-yl)amino)-6-(((2S,3R)-3-aminobutan-2-yl)amino)-5-fluoronicotinamide | HCl | DMSO-d6 | 300 MHz | δ: 12.19 (br, 1H), 8.87 (s, 2H), 8.84 (s, 1H), 8.72 (d, 1H, J = 2.6 Hz), 8.12-8.00 (m, 5H), 7.89 (d, 1H, J = 1.3 Hz), 7.54-7.40 (m, 1H), 7.33 (d, 1H, J = 7.9 Hz), 6.66 (t, 1H, J = 2.3 Hz), 4.54-4.42 (m, 1H), 3.47-3.36 (m, 1H), 1.29-1.16 (m, 6H). | 385 | 383 | 0.73 |
| Example 6-193 | | 6-(((2R,3S)-3-aminobutan-2-yl)amino)-2-((5-cyclopropylpyridin-3-yl)amino)-5-fluoronicotinamide 6-(((2S,3R)-3-aminobutan-2-yl)amino)-2-((5-cyclopropylpyridin-3-yl)amino)-5-fluoronicotinamide | HCl | DMSO-d6 | 300 MHz | δ: 12.21 (br, 1H), 9.42 (d, 1H, J = 2.0 Hz), 8.35 (d, 1H, J = 1.3 Hz), 8.22 (br, 3H), 8.06-7.95 (m, 3H), 7.52-7.44 (m, 1H), 7.41 (d, 2H, J = 9.2 Hz), 4.46-4.35 (m, 1H), 3.65-3.56 (m, 1H), 2.21-2.12 (m, 2H), 1.32-1.26 (m, 3H), 1.20-1.05 (m, 3H), 1.00-0.95 (m, 2H). | 359 | 357 | 0.57 |
| Example 6-194 | | 6-(((2R,3S)-3-aminobutan-2-yl)amino)-2-((5,6-dimethylpyridin-3-yl)amino)-5-fluoronicotinamide 6-(((2S,3R)-3-aminobutan-2-yl)amino)-2-((5,6-dimethylpyridin-3-yl)amino)-5-fluoronicotinamide | HCl | DMSO-d6 | 300 MHz | δ: 12.15 (br, 1H), 8.16 (br, 3H), 8.06-7.90 (m, 2H), 7.54-7.42 (m, 3H), 4.44-4.30 (m, 1H), 3.64-3.54 (m, 1H), 2.59 (s, 3H), 2.38 (s, 3H), 1.35-1.22 (m, 6H). | 347 | 345 | 0.52 |

TABLE 3-continued

| Example | Structure | Name | Salt | Solvent | Freq | NMR | MW1 | MW2 | Val |
|---|---|---|---|---|---|---|---|---|---|
| Example 6-195 | 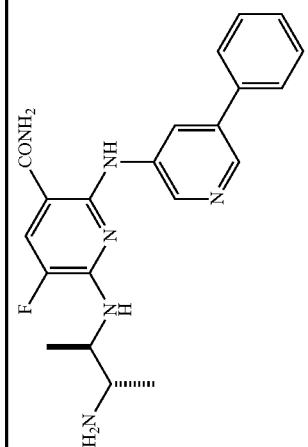 | 6-(((2R,3S)-3-aminobutan-2-yl)amino)-5-fluoro-2-((5-phenylpyridin-3-yl)amino)nicotinamide 6-(((2S,3R)-3-aminobutan-2-yl)amino)-5-fluoro-2-((5-phenylpyridin-3-yl)amino)nicotinamide | HCl | DMSO-d6 | 300 MHz | δ: 12.14 (br, 1H), 9.23 (s, 1H), 8.72 (s, 1H), 8.55 (s, 1H), 8.05-7.97 (m, 6H), 7.87-7.82 (m, 1H), 7.58-7.50 (m, 4H), 7.28 (d, 1H, J = 8.6 Hz), 4.36 (s, 1H), 3.62-3.54 (m, 1H), 1.21 (t, 3H, J = 9.9 Hz), 1.14 (dd, 3H, J = 11.6, 6.9 Hz). | 395 | 393 | 0.75 |
| Example 6-196 | 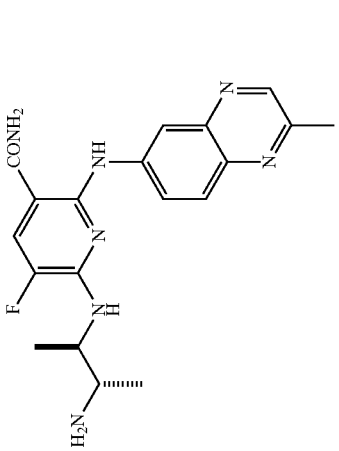 | 6-(((2R,3S)-3-aminobutan-2-yl)amino)-5-fluoro-2-((2-methylquinoxalin-6-yl)amino)nicotinamide 6-(((2S,3R)-3-aminobutan-2-yl)amino)-5-fluoro-2-((2-methylquinoxalin-6-yl)amino)nicotinamide | HCl | DMSO-d6 | 300 MHz | δ: 12.14 (br, 1H), 8.74 (s, 1H), 8.52 (t, 1H, J = 4.3 Hz), 8.03-7.87 (m, 7H), 7.74-7.68 (m, 1H), 7.46-7.30 (m, 1H), 7.19 (d, 1H, J = 8.6 Hz), 4.41 (t, 1H, J = 5.6 Hz), 3.60 (s, 1H), 2.65 (s, 3H), 1.37-1.30 (m, 6H). | 384 | 382 | 0.78 |
| Example 6-197 | 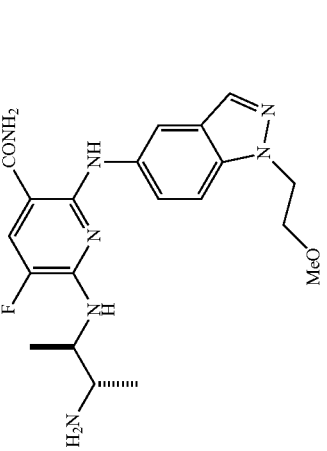 | 6-(((2R,3S)-3-aminobutan-2-yl)amino)-5-fluoro-2-((1-(2-methoxyethyl)-1H-indazol-5-yl)amino)nicotinamide 6-(((2S,3R)-3-aminobutan-2-yl)amino)-5-fluoro-2-((1-(2-methoxyethyl)-1H-indazol-5-yl)amino)nicotinamide | HCl | | | | 416 | 414 | 0.79 |

TABLE 3-continued

| Example | Structure | Name | Salt | Solvent | Freq | NMR | M+1 | M-1 | Rf |
|---|---|---|---|---|---|---|---|---|---|
| Example 6-198 | 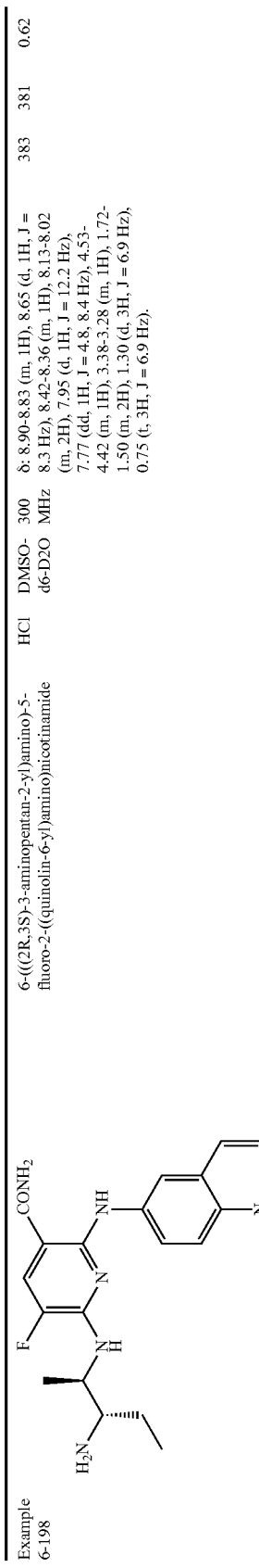 | 6-(((2R,3S)-3-aminopentan-2-yl)amino)-5-fluoro-2-((quinolin-6-yl)amino)nicotinamide | HCl | DMSO-d6-D2O | 300 MHz | δ: 8.90-8.83 (m, 1H), 8.65 (d, 1H, J = 8.3 Hz), 8.42-8.36 (m, 1H), 8.13-8.02 (m, 2H), 7.95 (d, 1H, J = 12.2 Hz), 7.77 (dd, 1H, J = 4.8, 8.4 Hz), 4.53-4.42 (m, 1H), 3.38-3.28 (m, 1H), 1.72-1.50 (m, 2H), 1.30 (d, 3H, J = 6.9 Hz), 0.75 (t, 3H, J = 6.9 Hz). | 383 | 381 | 0.62 |
| Example 6-199 | 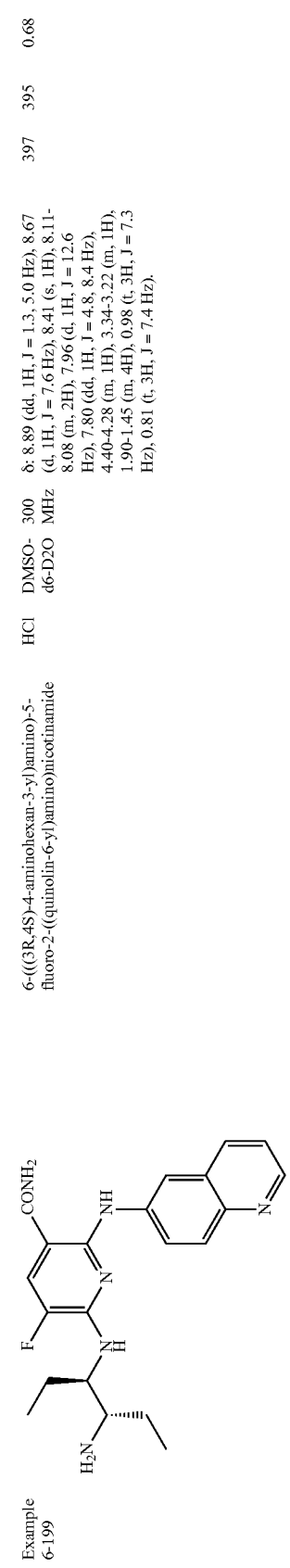 | 6-(((3R,4S)-4-aminohexan-3-yl)amino)-5-fluoro-2-((quinolin-6-yl)amino)nicotinamide | HCl | DMSO-d6-D2O | 300 MHz | δ: 8.89 (dd, 1H, J = 1.3, 5.0 Hz), 8.67 (d, 1H, J = 7.6 Hz), 8.41 (s, 1H), 8.11-8.08 (m, 2H), 7.96 (d, 1H, J = 12.6 Hz), 7.80 (dd, 1H, J = 4.8, 8.4 Hz), 4.40-4.28 (m, 1H), 3.34-3.22 (m, 1H), 1.90-1.45 (m, 4H), 0.98 (t, 3H, J = 7.3 Hz), 0.81 (t, 3H, J = 7.4 Hz). | 397 | 395 | 0.68 |
| Example 6-200 | 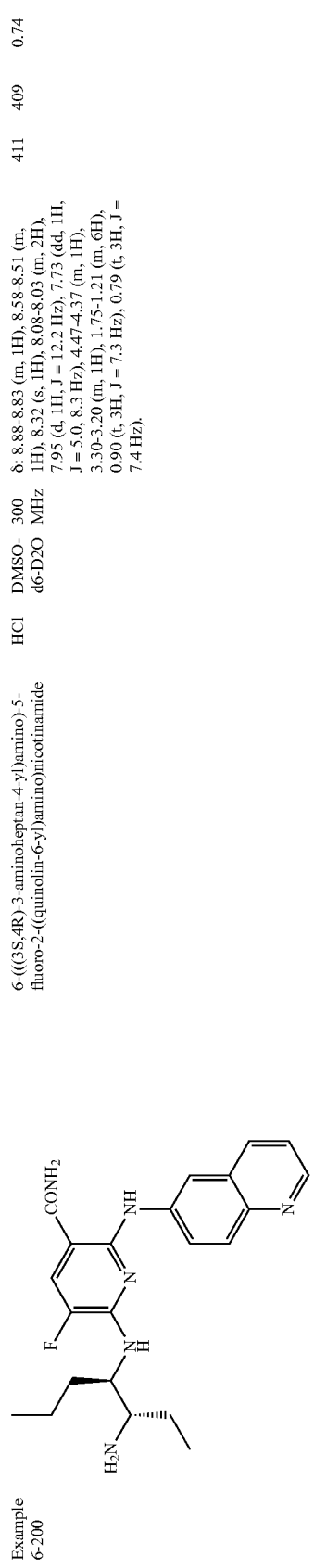 | 6-(((3S,4R)-3-aminoheptan-4-yl)amino)-5-fluoro-2-((quinolin-6-yl)amino)nicotinamide | HCl | DMSO-d6-D2O | 300 MHz | δ: 8.88-8.83 (m, 1H), 8.58-8.51 (m, 1H), 8.32 (s, 1H), 8.08-8.03 (m, 2H), 7.95 (d, 1H, J = 12.2 Hz), 7.73 (dd, 1H, J = 5.0, 8.3 Hz), 4.47-4.37 (m, 1H), 3.30-3.20 (m, 1H), 1.75-1.21 (m, 6H), 0.90 (t, 3H, J = 7.3 Hz), 0.79 (t, 3H, J = 7.4 Hz). | 411 | 409 | 0.74 |

TABLE 3-continued

| Example | Structure | Name | Salt | Solvent | Freq | NMR | | | |
|---|---|---|---|---|---|---|---|---|---|
| Example 6-201 | 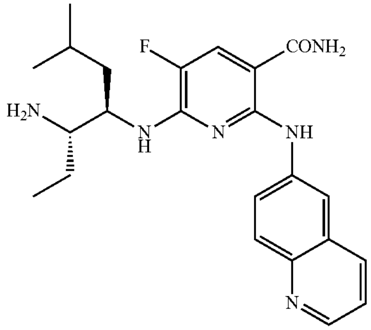 [SMILES: CC[C@H](N)[C@@H](CC(C)C)Nc1nc(Nc2ccc3ncccc3c2)c(C(N)=O)cc1F] | 6-(((4R,5S)-5-amino-2-methylheptan-4-yl)amino)-5-fluoro-2-((quinolin-6-yl)amino)nicotinamide | HCl | DMSO-d6-D2O | 300 MHz | δ: 8.85-8.79 (m, 1H), 8.48-8.40 (m, 1H), 8.24 (s, 1H), 8.05-8.00 (m, 2H), 7.94 (d, 1H, J = 12.2 Hz), 7.73-7.63 (m, 1H), 4.52-4.38 (m, 1H), 3.29-3.13 (m, 1H), 1.74-1.20 (m, 5H), 1.02-0.83 (m, 6H), 0.74 (t, 3H, J = 7.4 Hz). | 425 | 423 | 0.85 |
| Example 6-202 | 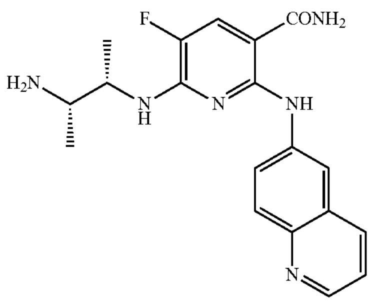 [SMILES: C[C@H](N)[C@H](C)Nc1nc(Nc2ccc3ncccc3c2)c(C(N)=O)cc1F] | 6-(((2S,3S)-3-aminobutan-2-yl)amino)-5-fluoro-2-((quinolin-6-yl)amino)nicotinamide | HCl | DMSO-d6-D2O | 300 MHz | δ: 8.91 (dd, 1H, J = 1.3, 5.0 Hz), 8.70-8.61 (m, 2H), 8.15-8.10 (m, 1H), 8.02 (dd, 1H, J = 2.5, 9.1 Hz), 7.97 (d, 1H, J = 12.2 Hz), 7.85 (dd, 1H, J = 5.1, 8.4 Hz), 4.43-4.30 (m, 1H), 3.56-3.42 (m, 1H), 1.32 (d, 6H, J = 6.6 Hz). | 369 | 367 | 0.61 |
| Example 6-203 | 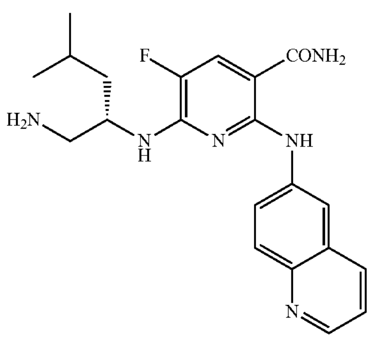 [SMILES: CC(C)C[C@@H](CN)Nc1nc(Nc2ccc3ncccc3c2)c(C(N)=O)cc1F] | (S)-6-((1-amino-4-methylpentan-2-yl)amino)-5-fluoro-2-((quinolin-6-yl)amino)nicotinamide | HCl | | | | 397 | 395 | 0.78 |

TABLE 3-continued

| Example | Structure | Name | Salt | | | |
|---|---|---|---|---|---|---|
| Example 6-204 | 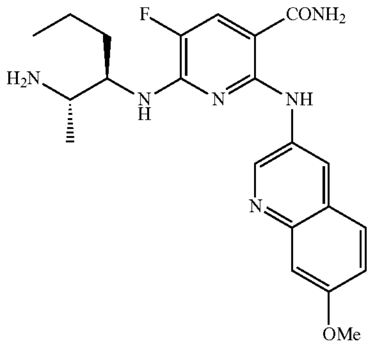 [SMILES: CCC[C@@H](Nc1nc(Nc2cnc3cc(OC)ccc3c2)c(C(N)=O)cc1F)[C@H](C)N] | 6-(((2S,3R)-2-aminohexan-3-yl)amino)-5-fluoro-2-((7-methoxyquinolin-3-yl)amino)nicotinamide | HCl | 427 | 425 | 0.84 |
| Example 6-205 | 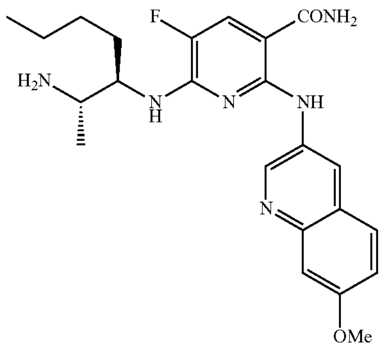 [SMILES: CCCC[C@@H](Nc1nc(Nc2cnc3cc(OC)ccc3c2)c(C(N)=O)cc1F)[C@H](C)N] | 6-(((2S,3R)-2-aminoheptan-3-yl)amino)-5-fluoro-2-((7-methoxyquinolin-3-yl)amino)nicotinamide | HCl | 441 | 439 | 0.92 |
| Example 6-206 | 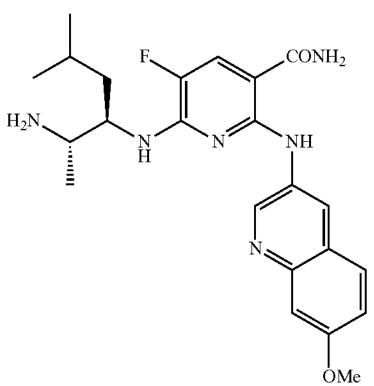 [SMILES: COc1ccc2cc(Nc3nc(N[C@H](CC(C)C)[C@H](C)N)c(F)cc3C(N)=O)cnc2c1] | 6-(((2S,3R)-2-amino-5-methylhexan-3-yl)amino)-5-fluoro-2-((7-methoxyquinolin-3-yl)amino)nicotinamide | HCl | 441 | 439 | 0.92 |

TABLE 3-continued

| Example | Structure | Name | Salt | Solvent | Freq | NMR | MS+1 | MS | Activity |
|---|---|---|---|---|---|---|---|---|---|
| Example 6-207 | (structure) | 6-(((2S,3R)-2-aminohexan-3-yl)amino)-5-fluoro-2-((quinolin-6-yl)amino)nicotinamide | HCl | CD3OD | 300 MHz | δ: 9.03-8.93 (m, 2H), 8.62 (d, J = 2.0 Hz), 8.30 (dd, 1H, J = 9.2, 2.3 Hz), 8.18 (d, 1H, J = 9.6 Hz), 7.99 (dd, 1H, J = 8.4, 5.4 Hz), 7.88 (d, 1H, J = 12.3 Hz), 4.66-4.57 (m, 1H), 3.71-3.60 (m, 1H), 1.84-1.41 (m, 4H), 1.37 (d, 3H, J = 6.9 Hz), 1.00 (t, 3H, J = 7.3 Hz). | 397 | 395 | 0.71 |
| Example 6-208 | (structure) | 6-(((2S,3R)-2-aminoheptan-3-yl)amino)-5-fluoro-2-((quinolin-6-yl)amino)nicotinamide | HCl | CD3OD | 300 MHz | δ: 9.01 (d, 1H, J = 8.3 Hz), 8.95 (dd, 1H, J = 5.3, 1.0 Hz), 8.61 (d, 1H, J = 2.3 Hz), 8.30 (dd, 1H, J = 9.4, 2.1 Hz), 8.18 (d, 1H, J = 9.2 Hz), 8.00 (dd, 1H, J = 8.4, 5.4 Hz), 7.88 (d, 1H, J = 12.0 Hz), 4.67-4.55 (m, 1H), 3.7-3.60 (m, 1H), 1.90-1.32 (m, 9H), 0.88 (t, 3H, J = 6.9 Hz). | 411 | 409 | 0.8 |
| Example 6-209 | (structure) | 6-(((2S,3R)-2-amino-5-methylhexan-3-yl)amino)-5-fluoro-2-((quinolin-6-yl)amino)nicotinamide | HCl | CD3OD | 300 MHz | δ: 9.03-8.93 (m, 2H), 8.58 (d, 1H, J = 2.3 Hz), 8.33 (dd, 1H, J = 9.2, 2.3 Hz), 8.19 (d, 1H, J = 9.2 Hz), 8.00 (dd, 1H, J = 8.4, 5.4 Hz), 7.88 (d, 1H, J = 12.0 Hz), 4.73-4.63 (m, 1H), 3.69-3.57 (m, 1H), 1.84-1.31 (m, 6H), 0.99 (dd, 6H, J = 13.5, 6.6 Hz). | 411 | 409 | 0.79 |

TABLE 3-continued

| Example | Name | Structure | Salt | Solvent | Freq | NMR | MS1 | MS2 | RT |
|---|---|---|---|---|---|---|---|---|---|
| Example 6-210 | 6-(((2S,3R)-2-aminopentan-3-yl)amino)-5-fluoro-2-((1-methyl-1H-indazol-5-yl)amino)nicotinamide | | HCl | | | | 386 | 384 | 0.81 |
| Example 6-211 | 6-(((2S,3R)-2-aminopentan-3-yl)amino)-2-((1-ethyl-1H-indazol-5-yl)amino)-5-fluoronicotinamide | | HCl | CD3OD | 300 MHz | δ: 7.97 (s, 1H), 7.93 (d, 1H, J = 2.0 Hz), 7.76 (d, 1H, J = 11.9 Hz), 7.57 (d, 1H, J = 8.6 Hz), 7.43 (dd, 1H, J = 8.6, 2.0 Hz), 4.85-4.75 (m, 1H), 4.46 (q, 2H, J = 7.3 Hz), 4.18-4.12 (m, 1H), 1.75-1.56 (m, 2H), 1.47 (dd, 3H, J = 13.2, 6.6 Hz), 1.20 (d, 3H, J = 6.6 Hz), 1.05 (t, 3H, J = 7.3 Hz). | 400 | 398 | 0.88 |
| Example 6-212 | (R)-6-((1-amino-4-methylpentan-2-yl)amino)-5-fluoro-2-((quinoxalin-6-yl)amino)nicotinamide | | HCl | | | | 398 | 396 | 0.91 |

TABLE 3-continued

| Example | Structure | Name | Salt | Solvent | MHz | NMR | M | M+1 | Rt |
|---|---|---|---|---|---|---|---|---|---|
| Example 6-213 | (structure with F, CONH2, NH, ethoxypyridine, H2N-butyl) | 6-(((2R,3S)-3-aminobutan-2-yl)amino)-2-((2-ethoxypyridin-4-yl)amino)-5-fluoronicotinamide 6-(((2S,3R)-3-aminobutan-2-yl)amino)-2-((2-ethoxypyridin-4-yl)amino)-5-fluoronicotinamide | HCl | | | | 363 | 361 | 0.56 |
| Example 6-214 | (structure with cyclopropyl, F, CONH2, NH, quinoline) | (R)-6-((1-amino-3-cyclopropylpropan-2-yl)amino)-5-fluoro-2-((quinolin-6-yl)amino)nicotinamide | HCl | DMSO-d6 | 300 MHz | δ: 12.24 (br, 1H), 8.93 (d, 1H, J = 4.0 Hz), 8.76 (s, 1H), 8.63 (s, 1H), 8.16-7.96 (m, 9H), 7.82-7.76 (m, 1H), 7.45-7.35 (m, 1H), 7.26 (d, 1H, J = 8.6 Hz), 4.65-4.55 (m, 1H), 3.40-3.35 (m, 2H), 1.59-1.50 (m, 2H), 0.74-0.64 (m, 1H), 0.28 (d, 2H, J = 7.9 Hz). | 395 | 393 | 0.69 |
| Example 6-215 | (structure with cyclopropyl, F, CONH2, NH, 7-methoxyquinoline) | (R)-6-((1-amino-3-cyclopropylpropan-2-yl)amino)-5-fluoro-2-((7-methoxyquinolin-3-yl)amino)nicotinamide | HCl | | | | 425 | 423 | 0.83 |

TABLE 3-continued

| Example | Structure | Name | Salt | | | |
|---|---|---|---|---|---|---|
| Example 6-216 | 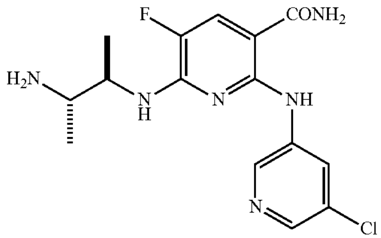 [SMILES: C[C@H](N)[C@@H](C)Nc1nc(Nc2cncc(Cl)c2)c(C(N)=O)cc1F] | 6-(((2R,3S)-3-aminobutan-2-yl)amino)-2-((5-chloropyridin-3-yl)amino)-5-fluoronicotinamide | HCl | 354 | 352 | 0.78 |
| Example 6-217 | 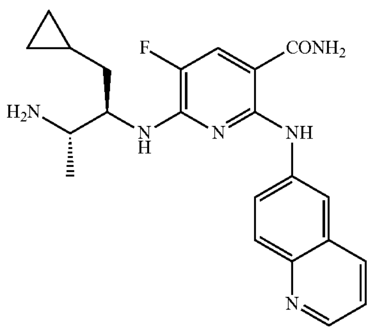 [SMILES: C[C@H](N)[C@@H](CC1CC1)Nc1nc(Nc2ccc3ncccc3c2)c(C(N)=O)cc1F] | 6-(((2R,3S)-3-amino-1-cyclopropylbutan-2-yl)amino)-5-fluoro-2-((quinolin-6-yl)amino)nicotinamide | HCl | 409 | 407 | 0.79 |
| Example 6-218 | 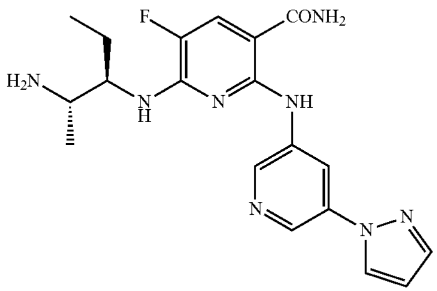 [SMILES: CC[C@@H](Nc1nc(Nc2cncc(-n3cccn3)c2)c(C(N)=O)cc1F)[C@H](C)N] | 2-((5-(1H-pyrazol-1-yl)pyridin-3-yl)amino)-6-(((2S,3R)-2-aminopentan-3-yl)amino)-5-fluoronicotinamide | HCl | 399 | 397 | 0.82 |

TABLE 3-continued

| Example | Name | Structure | Salt | Solvent | Freq | NMR | MS | MS | Act |
|---|---|---|---|---|---|---|---|---|---|
| Example 6-219 | 2-((5-(1H-pyrazol-1-yl)pyridin-3-yl)amino)-6-(((2S,3R)-2-aminohexan-3-yl)amino)-5-fluoronicotinamide | | HCl | DMSO-d6 | 300 MHz | δ: 12.03 (br, 1H), 8.92 (s, 1H), 8.73 (d, 1H, J = 2.0 Hz), 8.68-8.62 (m, 2H), 7.99 (d, 1H, J = 12.6 Hz), 7.87-7.75 (m, 5H), 7.48-7.35 (m, 1H), 7.15 (d, 1H, J = 8.6 Hz), 6.64 (t, 1H, J = 2.3 Hz), 4.56-4.45 (m, 1H), 3.55-3.48 (m, 1H), 1.64-1.56 (m, 2H), 1.44-1.36 (m, 2H), 1.21-1.12 (m, 3H), 0.83 (t, 3H, J = 7.3 Hz). | 413 | 411 | 0.9 |
| Example 6-220 | 6-(((2S,3R)-2-aminohexan-3-yl)amino)-5-fluoro-2-((2-(furan-2-yl)pyridin-4-yl)amino)nicotinamide | | HCl | DMSO-d6 | 300 MHz | δ: 12.94 (br, 1H), 8.47 (d, 1H, J = 7.3 Hz), 8.31 (s, 1H), 8.16-8.04 (m, 3H), 8.00-7.94 (m, 3H), 7.84-7.78 (m, 1H), 7.72-7.60 (m, 2H), 7.45-7.38 (m, 1H), 6.87-6.85 (m, 1H), 4.56-4.46 (m, 1H), 3.55-3.49 (m, 1H), 1.78-1.60 (m, 2H), 1.42-1.36 (m, 2H), 1.22-1.18 (m, 3H), 0.87 (t, 3H, J = 7.3 Hz). | 413 | 411 | 0.72 |
| Example 6-221 | 2-(2-(2H-1,2,3-triazol-2-yl)pyridin-4-yl)amino)-6-(((2S,3R)-2-aminohexan-3-yl)amino)-5-fluoronicotinamide | | HCl | DMSO-d6 | 300 MHz | δ: 12.33 (br, 1H), 8.77 (d, 1H, J = 1.3 Hz), 8.30 (d, 1H, J = 1.3 Hz), 8.27 (s, 1H), 8.02-7.97 (m, 3H), 7.77 (3H, br), 7.56-7.46 (m, 1H), 7.30-7.20 (m, 2H), 4.68-4.58 (m, 1H), 3.65-3.59 (m, 1H), 1.72-1.58 (m, 2H), 1.46-1.30 (m, 2H), 1.19 (d, 3H, J = 6.6 Hz), 0.86 (t, 3H, J = 7.3 Hz). | 414 | 412 | 0.84 |

TABLE 3-continued

| Example | Name | Salt | Solvent | NMR | MS | | | |
|---|---|---|---|---|---|---|---|---|
| 6-222 | 6-(((2S,3R)-2-aminohexan-3-yl)amino)-5-fluoro-2-((5-(2-fluorophenyl)pyridin-3-yl)amino)nicotinamide | HCl | | | 441 | 439 | | 0.94 |
| 6-223 | 6-(((2S,3R)-2-aminohexan-3-yl)amino)-2-((5-cyclopropylpyridin-3-yl)amino)-5-fluoronicotinamide | HCl | | | 387 | 385 | | 0.73 |
| 6-224 | 6-(((2R,3R)-3-aminobutan-2-yl)amino)-5-fluoro-2-((quinolin-6-yl)amino)nicotinamide | HCl | DMSO-d6-D2O | 300 MHz | δ: 8.88 (d, 1H, J = 5.0 Hz), 8.68-8.62 (m, 2H), 8.12 (d, 1H, J = 9.2 Hz), 8.02 (dd, 1H, J = 2.1, 9.1 Hz), 7.94 (d, 1H, J = 12.2 Hz), 7.84 (dd, 1H, J = 5.1, 8.4 Hz), 4.42-4.30 (m, 1H), 3.56-3.42 (m, 1H), 1.32 (d, 6H, J = 6.6 Hz). | 369 | 367 | 0.6 |

TABLE 3-continued

| Example | Structure | Name | Salt | Solvent | Freq | NMR | | | |
|---|---|---|---|---|---|---|---|---|---|
| Example 6-225 | | 6-(((2S,3R)-3-aminobutan-2-yl)amino)-5-fluoro-2-((quinolin-6-yl)amino)nicotinamide | HCl | DMSO-d6-D2O | 300 MHz | δ: 8.91 (dd, 1H, J = 1.4, 5.1 Hz), 8.77 (d, 1H, J = 7.9 Hz), 8.54 (d, 1H, J = 2.0 Hz), 8.17-8.06 (m, 2H), 7.95 (d, 1H, J = 11.9 Hz), 7.86 (dd, 1H, J = 5.1, 8.4 Hz), 4.48-4.36 (m, 1H), 3.61-3.50 (m, 1H), 1.34 (d, 3H, J = 6.9 Hz), 1.26 (d, 3H, J = 6.9 Hz). | 369 | 367 | 0.6 |
| Example 6-226 | | (R)-6-((1-amino-4-methylpentan-2-yl)amino)-5-fluoro-2-((1-methyl-1H-indazol-6-yl)amino)nicotinamide | HCl | | | | 400 | 398 | 0.93 |
| Example 6-227 | | (R)-6-((1-amino-4-methylpentan-2-yl)amino)-5-fluoro-2-((1-methyl-1H-indazol-4-yl)amino)nicotinamide | HCl | | | | 400 | 398 | 0.97 |

TABLE 3-continued

| Example | | | | | |
|---|---|---|---|---|---|
| Example 6-228 | (R)-6-((1-amino-4-methylpentan-2-yl)amino)-5-fluoro-2-((quinolin-7-yl)amino)nicotinamide | HCl | 397 | 395 | 0.76 |
| Example 6-229 | (R)-6-((1-amino-4-methylpentan-2-yl)amino)-5-fluoro-2-((quinolin-5-yl)amino)nicotinamide | HCl | 397 | 395 | 0.75 |
| Example 6-230 | (R)-6-((1-amino-4-methylpentan-2-yl)amino)-5-fluoro-2-((quinolin-8-yl)amino)nicotinamide | HCl | 397 | 395 | 1.02 |

TABLE 3-continued

| Example | Structure | Name | Salt | | | |
|---|---|---|---|---|---|---|
| Example 6-231 | 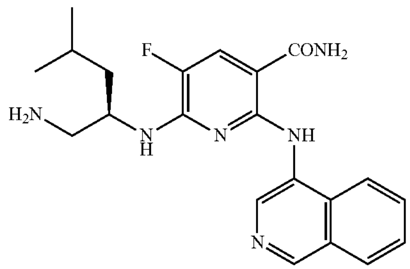 [SMILES: CC(C)C[C@H](CN)Nc1nc(Nc2cncc3ccccc23)c(C(N)=O)cc1F] | (R)-6-((1-amino-4-methylpentan-2-yl)amino)-5-fluoro-2-(isoquinolin-4-yl)aminonicotinamide | HCl | 397 | 395 | 0.78 |
| Example 6-232 | 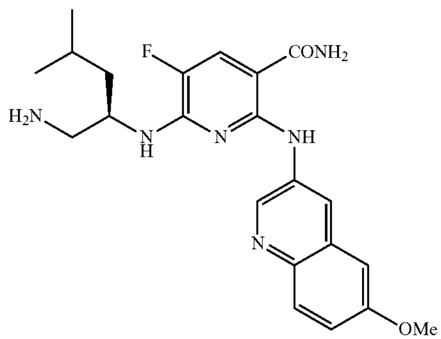 [SMILES: COc1ccc2ncc(Nc3nc(N[C@@H](CN)CC(C)C)c(F)cc3C(N)=O)cc2c1] | (R)-6-((1-amino-4-methylpentan-2-yl)amino)-5-fluoro-2-((6-methoxyquinolin-3-yl)amino)nicotinamide | HCl | 427 | 425 | 0.93 |
| Example 6-233 | 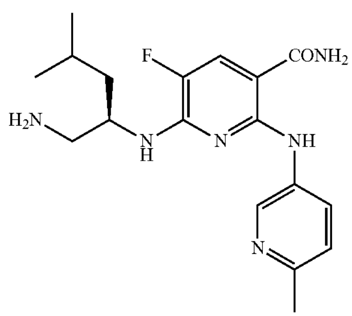 [SMILES: Cc1ccc(Nc2nc(N[C@@H](CN)CC(C)C)c(F)cc2C(N)=O)cn1] | (R)-6-((1-amino-4-methylpentan-2-yl)amino)-5-fluoro-2-((6-methylpyridin-3-yl)amino)nicotinamide | HCl | 361 | 359 | 0.65 |

TABLE 3-continued

| Example | Name | Salt | | | |
|---|---|---|---|---|---|
| Example 6-234 | (R)-6-((1-amino-4-methylpentan-2-yl)amino)-5-fluoro-2-((2-methoxypyridin-4-yl)amino)nicotinamide | HCl | 377 | 375 | 0.94 |
| Example 6-235 | (R)-6-((1-amino-4-methylpentan-2-yl)amino)-5-fluoro-2-((5-phenylpyridin-3-yl)amino)nicotinamide | HCl | 423 | 421 | 0.69 |
| Example 6-236 | 6-(((2S,3R)-2-aminohexan-3-yl)amino)-5-fluoro-2-((1-methyl-1H-indazol-5-yl)amino)nicotinamide | HCl | 400 | 398 | 0.91 |

| Example 6-237 | 6-(((2S,3R)-2-aminohexan-3-yl)amino)-2-((1-ethyl-1H-indazol-5-yl)amino)-5-fluoronicotinamide | HCl | DMSO-d6 | 300 MHz | δ: 11.54 (br, 1H), 8.09 (s, 1H), 7.93-7.87 (m, 3H), 7.79-7.70 (m, 3H), 7.59 (d, 1H, J = 9.2 Hz), 7.35-7.10 (t, 1H, J = 5.6 Hz), 6.89 (d, 1H, J = 7.3 Hz), 4.48-4.36 (m, 2H), 4.26-4.16 (m, 1H), 3.55-3.50 (m, 1H), 1.63-1.54 (m, 2H), 1.44-1.36 (m, 4H), 1.19 (t, 4H, J = 5.0 Hz), 0.87 (t, 3H, J = 6.9 Hz). | 414 | 412 | 0.98 |
|---|---|---|---|---|---|---|---|---|
| Example 6-238 | 6-(((2S,3R)-2-aminohexan-3-yl)amino)-5-fluoro-2-((7-(2-methoxyethoxy)quinolin-3-yl)amino)nicotinamide | HCl | DMSO-d6 | 300 MHz | δ: 11.87 (br, 1H), 8.96 (s, 1H), 8.55 (s, 1H), 7.98-7.70 (m, 5H), 7.38-7.24 (m, 3H), 7.14-6.98 (m, 1H), 4.30-4.20 (m, 3H), 3.76-3.72 (m, 2H), 3.55-3.20 (m, 5H), 1.62-1.58 (m, 2H), 1.46-1.30 (m, 2H), 1.19 (d, 3H, J = 6.6 Hz), 0.85 (t, 3H, J = 7.3 Hz). | 472 | 470 | 0.88 |
| Example 6-239 | 6-(((2S,3R)-2-aminohexan-3-yl)amino)-5-fluoro-2-((1-methoxyisoquinolin-6-yl)amino)nicotinamide | HCl | | | | 427 | 425 | 1.02 |

TABLE 3-continued

| Example | Structure | Name | Salt | | | |
|---|---|---|---|---|---|---|
| Example 6-240 | 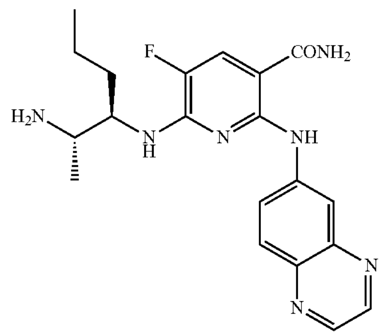 [SMILES: CCC[C@@H](Nc1nc(Nc2ccc3nccnc3c2)c(C(N)=O)cc1F)[C@H](C)N] | 6-(((2S,3R)-2-aminohexan-3-yl)amino)-5-fluoro-2-((quinoxalin-6-yl)amino)nicotinamide | HCl | 398 | 396 | 0.89 |
| Example 6-241 | 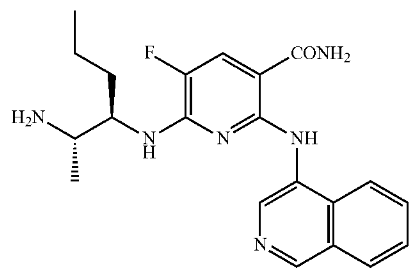 [SMILES: CCC[C@@H](Nc1nc(Nc2cncc3ccccc23)c(C(N)=O)cc1F)[C@H](C)N] | 6-(((2S,3R)-2-aminohexan-3-yl)amino)-5-fluoro-2-((isoquinolin-4-yl)amino)nicotinamide | HCl | 397 | 395 | 0.76 |
| Example 6-242 | 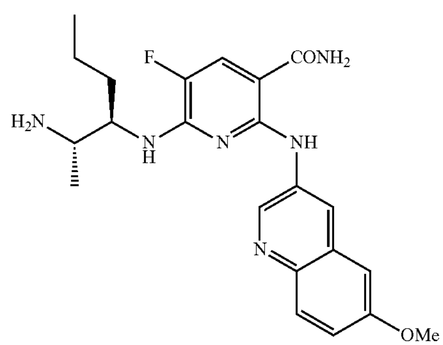 [SMILES: CCC[C@@H](Nc1nc(Nc2cnc3ccc(OC)cc3c2)c(C(N)=O)cc1F)[C@H](C)N] | 6-(((2S,3R)-2-aminohexan-3-yl)amino)-5-fluoro-2-((6-methoxyquinolin-3-yl)amino)nicotinamide | HCl | 427 | 425 | 0.91 |

TABLE 3-continued

| Example 6-243 | 6-(((2S,3R)-2-aminohexan-3-yl)amino)-5-fluoro-2-((quinolin-8-yl)amino)nicotinamide | HCl | 397 | 395 | 0.99 |
| Example 6-244 | 6-(((2S,3R)-2-aminohexan-3-yl)amino)-5-fluoro-2-((quinolin-7-yl)amino)nicotinamide | HCl | 397 | 395 | 0.74 |
| Example 6-245 | 6-(((2S,3R)-2-aminohexan-3-yl)amino)-5-fluoro-2-((2-methylquinoxalin-6-yl)amino)nicotinamide | HCl | 412 | 410 | 0.92 |

TABLE 3-continued

| Example | Structure | Name | Salt | Solvent | Freq | NMR | | | |
|---|---|---|---|---|---|---|---|---|---|
| 6-246 | (structure with morpholinopyridine) | 6-(((2S,3R)-2-aminohexan-3-yl)amino)-5-fluoro-2-((6-mopholinopyridin-3-yl)amino)nicotinamide | HCl | | | | 433 | 431 | 0.71 |
| 6-247 | (structure with phenylpyridine) | 6-(((2S,3R)-2-aminohexan-3-yl)amino)-5-fluoro-2-((5-phenylpyridin-3-yl)amino)nicotinamide | HCl | | | | 424 | 422 | 0.91 |
| 6-248 | (structure with 2,6-dimethoxypyridine) | 6-(((2S,3R)-2-aminohexan-3-yl)amino)-2-((2,6-dimethoxypyridin-4-yl)amino)-5-fluoronicotinamide | HCl | DMSO-d6 | 300 MHz | δ: 11.92 (br, 1H), 7.99-7.80 (m, 5H), 7.44-7.30 (m, 1H), 7.13 (d, 1H, J = 8.6 Hz), 6.57 (s, 2H), 4.26-4.16 (m, 1H), 3.81 (s, 6H), 3.52-3.41 (m, 1H), 1.68-1.56 (m, 2H), 1.55-1.40 (m, 2H), 1.30 (d, 3H, J = 6.6 Hz), 0.89 (t, 3H, J = 7.3 Hz). | 407 | 405 | 1.02 |

| Example 6-249 | 6-(((2S,3R)-2-aminohexan-3-yl)amino)-5-fluoro-2-((2-methoxypyridin-4-yl)amino)nicotinamide | HCl | DMSO-d6 | 300 MHz | δ: 12.32 (br, 2H), 8.10-7.78 (m, 6H), 7.63-7.43 (m, 1H), 7.30-7.08 (m, 2H), 4.33-4.22 (m, 1H), 3.84 (s, 3H), 3.53-3.45 (m, 1H), 1.67-1.55 (m, 2H), 1.51-1.18 (m, 5H), 0.95-0.78 (m, 3H). | 377 | 375 | 0.65 |
| --- | --- | --- | --- | --- | --- | --- | --- | --- |
| Example 6-250 | 6-(((2S,3R)-2-aminohexan-3-yl)amino)-2-((5-cyclopropyl-6-methylpyridin-3-yl)amino)-5-fluoronicotinamide | HCl | | | | 401 | 399 | 0.76 |
| Example 6-251 | 6-(((2S,3R)-2-aminohexan-3-yl)amino)-5-fluoro-2-((1-methyl-1H-indazol-4-yl)amino)nicotinamide | HCl | | | | 400 | 398 | 0.94 |

TABLE 3-continued

| Example | Structure | Name | Salt | | | |
|---|---|---|---|---|---|---|
| Example 6-252 | 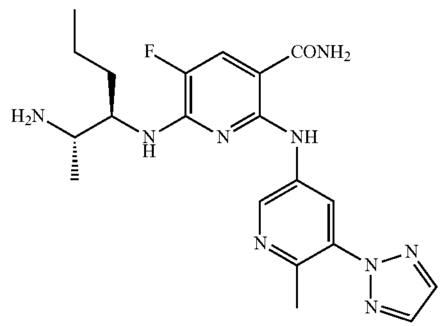 [SMILES: CCC[C@@H](Nc1nc(Nc2cnc(C)c(-n3nccn3)c2)c(C(N)=O)cc1F)[C@H](C)N] | 6-(((2S,3R)-2-aminohexan-3-yl)amino)-5-fluoro-2-((6-methyl-5-(2H-1,2,3-triazol-2-yl)pyridin-3-yl)amino)nicotinamide | HCl | 428 | 426 | 0.92 |
| Example 6-253 | 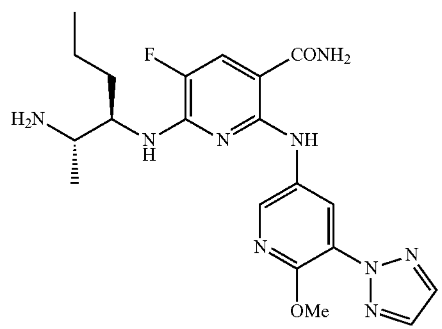 [SMILES: CCC[C@@H](Nc1nc(Nc2cnc(OC)c(-n3nccn3)c2)c(C(N)=O)cc1F)[C@H](C)N] | 6-(((2S,3R)-2-aminohexan-3-yl)amino)-5-fluoro-2-((6-methoxy-5-(2H-1,2,3-triazol-2-yl)pyridin-3-yl)amino)nicotinamide | HCl | 444 | 442 | 0.94 |
| Example 6-254 | 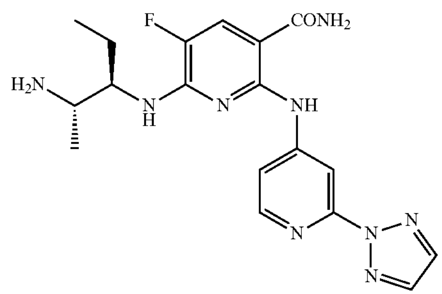 [SMILES: CC[C@@H](Nc1nc(Nc2ccnc(-n3nccn3)c2)c(C(N)=O)cc1F)[C@H](C)N] | 2-((2-(2H-1,2,3-triazol-2-yl)pyridin-4-yl)amino)-6-(((2S,3R)-2-aminopentan-3-yl)amino)-5-fluoronicotinamide | HCl | 400 | 398 | 0.77 |

TABLE 3-continued

| Example | Structure | Name | Salt | Solvent | Freq | NMR | M+2 | M | RT |
|---|---|---|---|---|---|---|---|---|---|
| Example 6-255 | 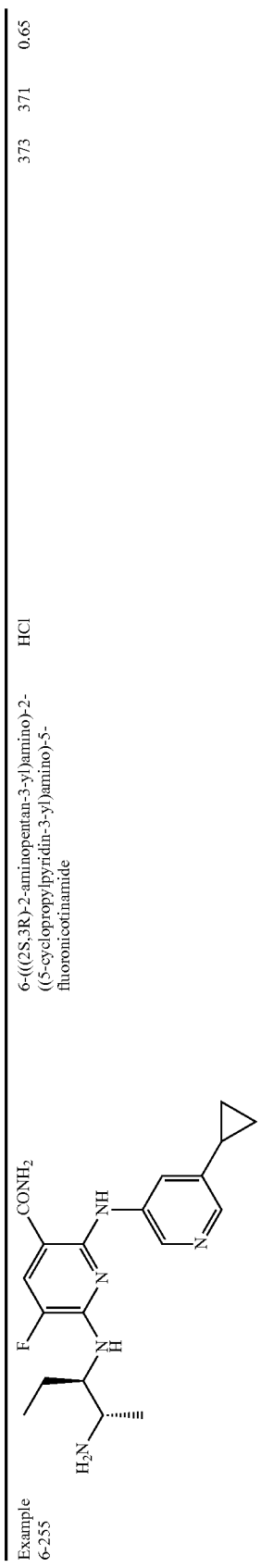 | 6-(((2S,3R)-2-aminopentan-3-yl)amino)-2-((5-cyclopropylpyridin-3-yl)amino)-5-fluoronicotinamide | HCl | | | | 373 | 371 | 0.65 |
| Example 6-256 | 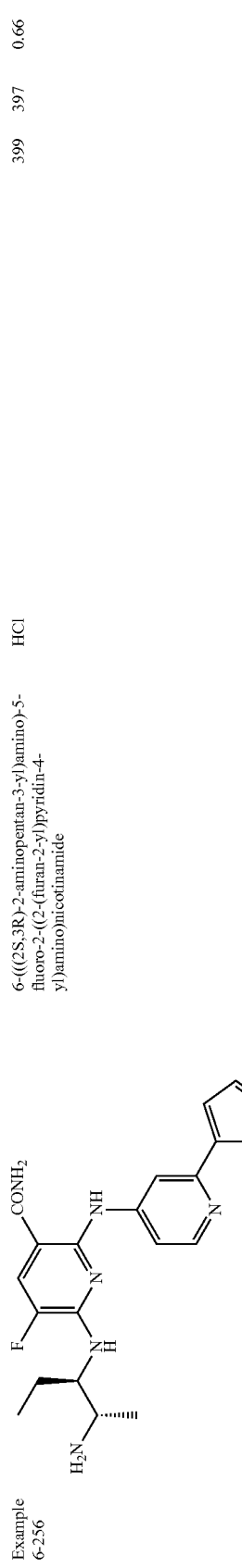 | 6-(((2S,3R)-2-aminopentan-3-yl)amino)-5-fluoro-2-((2-(furan-2-yl)pyridin-4-yl)amino)nicotinamide | HCl | | | | 399 | 397 | 0.66 |
| Example 6-257 | 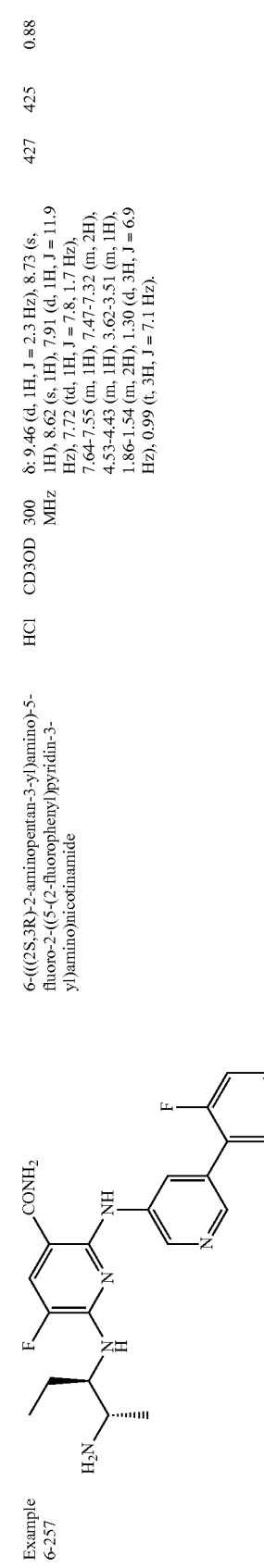 | 6-(((2S,3R)-2-aminopentan-3-yl)amino)-5-fluoro-2-((5-(2-fluorophenyl)pyridin-3-yl)amino)nicotinamide | HCl | CD3OD | 300 MHz | δ: 9.46 (d, 1H, J = 2.3 Hz), 8.73 (s, 1H), 8.62 (s, 1H), 7.91 (d, 1H, J = 11.9 Hz), 7.72 (td, 1H, J = 7.8, 1.7 Hz), 7.64-7.55 (m, 1H), 7.47-7.32 (m, 2H), 4.53-4.43 (m, 1H), 3.62-3.51 (m, 1H), 1.86-1.54 (m, 2H), 1.30 (d, 3H, J = 6.9 Hz), 0.99 (t, 3H, J = 7.1 Hz). | 427 | 425 | 0.88 |
| Example 6-258 | 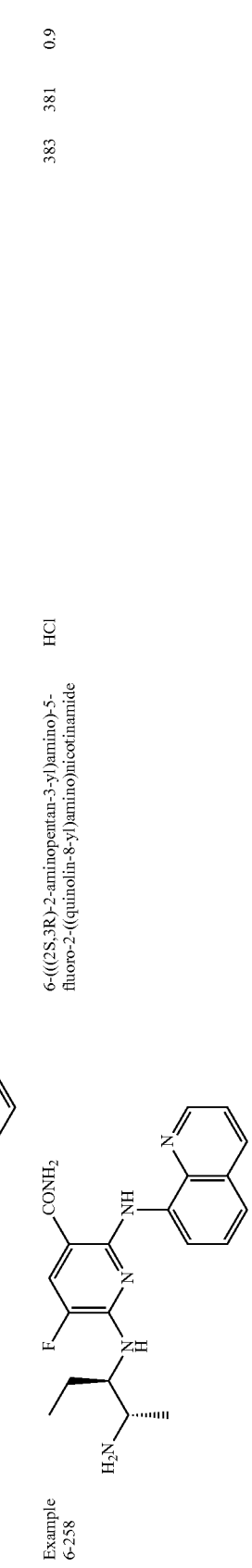 | 6-(((2S,3R)-2-aminopentan-3-yl)amino)-5-fluoro-2-((quinolin-8-yl)amino)nicotinamide | HCl | | | | 383 | 381 | 0.9 |

TABLE 3-continued

| Example | Structure | Name | Salt | | | |
|---|---|---|---|---|---|---|
| Example 6-259 | 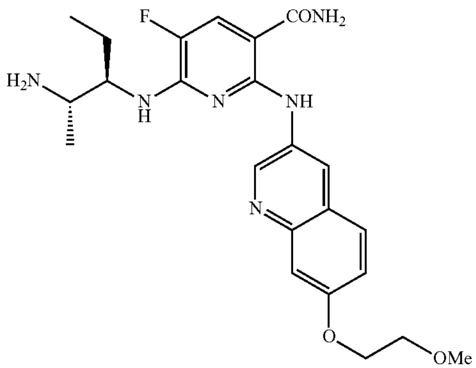 [SMILES: CC[C@@H](Nc1nc(Nc2cnc3cc(OCCOC)ccc3c2)c(C(N)=O)cc1F)[C@H](C)N] | 6-(((2S,3R)-2-aminopentan-3-yl)amino)-5-fluoro-2-((7-(2-methoxyethoxy)quinolin-3-yl)amino)nicotinamide | HCl | 458 | 456 | 0.8 |
| Example 6-260 | 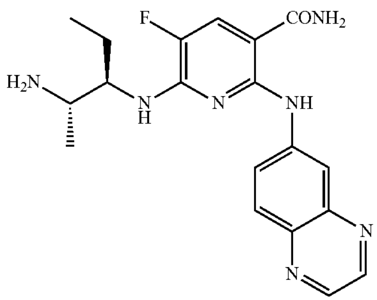 [SMILES: CC[C@@H](Nc1nc(Nc2ccc3nccnc3c2)c(C(N)=O)cc1F)[C@H](C)N] | 6-(((2S,3R)-2-aminopentan-3-yl)amino)-5-fluoro-2-((quinoxalin-6-yl)amino)nicotinamide | HCl | 384 | 382 | 0.81 |
| Example 6-261 | 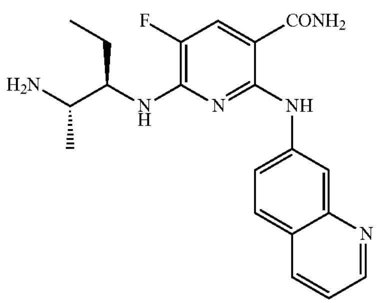 [SMILES: CC[C@@H](Nc1nc(Nc2ccc3cccnc3c2)c(C(N)=O)cc1F)[C@H](C)N] | 6-(((2S,3R)-2-aminopentan-3-yl)amino)-5-fluoro-2-((quinolin-7-yl)amino)nicotinamide | HCl | 383 | 381 | 0.64 |

| Example | Name | Structure | Salt | Solvent | NMR | MS | RT |
|---|---|---|---|---|---|---|---|
| Example 6-262 | 6-(((2S,3R)-2-aminopentan-3-yl)amino)-5-fluoro-2-((isoquinolin-4-yl)amino)nicotinamide | | HCl | | | 383 381 | 0.67 |
| Example 6-263 | 6-(((2S,3R)-2-aminopentan-3-yl)amino)-5-fluoro-2-((1-methoxyisoquinolin-6-yl)amino)nicotinamide | | HCl | CD3OD 300 MHz | δ: 8.38 (d, 1H, J = 9.3 Hz), 8.31 (d, 1H, J = 2.1 Hz), 8.01 (dd, 1H, J = 9.1, 2.1 Hz), 7.88 (d, 1H, J = 12.0 Hz), 7.78 (d, 1H, J = 6.9 Hz), 7.57 (d, 1H, J = 6.9 Hz), 4.56-4.47 (m, 1H), 4.45 (s, 1H), 3.73-3.59 (m, 1H), 1.96-1.62 (m, 2H), 1.36 (d, 3H, J = 6.6 Hz), 1.11 (t, 3H, J = 7.4 Hz). | 413 411 | 0.93 |
| Example 6-264 | 6-(((2S,3R)-2-aminopentan-3-yl)amino)-5-fluoro-2-((6-methoxyquinolin-3-yl)amino)nicotinamide | | HCl | CD3OD 300 MHz | δ: 9.66 (d, 1H, J = 2.3 Hz), 8.78 (d, 1H, J = 2.0 Hz), 8.06 (d, 1H, J = 9.2 Hz), 7.89 (d, 1H, J = 12.0 Hz), 7.58 (dd, 1H, J = 9.2, 2.6 Hz), 7.49 (d, 1H, J = 2.6 Hz), 4.52-4.44 (m, 1H), 4.02 (s, 3H), 3.64-3.54 (m, 1H), 1.92-1.58 (m, 2H), 1.32 (d, 3H, J = 6.9 Hz), 1.07 (t, 3H, J = 7.4 Hz). | 413 411 | 0.84 |

TABLE 3-continued

| Example | Structure | Name | Salt | | | |
|---|---|---|---|---|---|---|
| Example 6-265 | 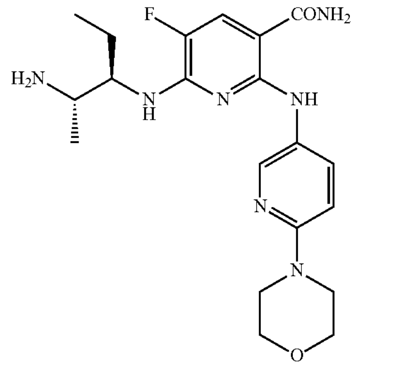 [SMILES: CC[C@@H](Nc1nc(Nc2ccc(N3CCOCC3)nc2)c(C(N)=O)cc1F)[C@H](C)N] | 6-(((2S,3R)-2-aminopentan-3-yl)amino)-5-fluoro-2-((6-morpholinopyridin-3-yl)amino)nicotinamide | HCl | 418 | 416 | 0.64 |
| Example 6-266 | 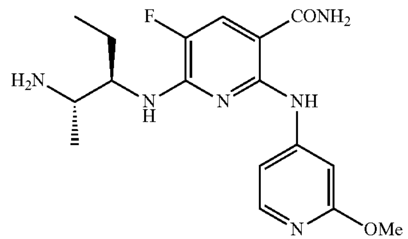 [SMILES: CC[C@@H](Nc1nc(Nc2ccnc(OC)c2)c(C(N)=O)cc1F)[C@H](C)N] | 6-(((2S,3R)-2-aminopentan-3-yl)amino)-5-fluoro-2-((2-methoxypyridin-4-yl)amino)nicotinamide | HCl | 363 | 361 | 0.58 |
| Example 6-267 | 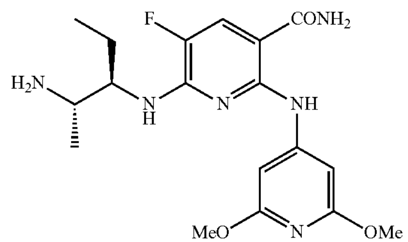 [SMILES: CC[C@@H](Nc1nc(Nc2cc(OC)nc(OC)c2)c(C(N)=O)cc1F)[C@H](C)N] | 6-(((2S,3R)-2-aminopentan-3-yl)amino)-2-((2,6-dimethoxypyridin-4-yl)amino)-5-fluoronicotinamide | HCl | 393 | 391 | 0.94 |

TABLE 3-continued

| Example | Name | Salt | Solvent | Freq | NMR | MS | RT |
|---|---|---|---|---|---|---|---|
| Example 6-268 | 6-(((2S,3R)-2-aminopentan-3-yl)amino)-5-fluoro-2-((1-methyl-1H-indazol-4-yl)amino)nicotinamide | HCl | CD3OD | 300 MHz | δ: 8.08 (s, 1H), 7.87 (d, 1H, J = 7.6 Hz), 7.83 (d, 1H, J = 11.9 Hz), 7.45-7.38 (m, 1H), 7.17 (d, 1H, J = 8.3 Hz), 4.37-4.27 (m, 1H), 4.06 (s, 1H), 3.36-3.35 (m, 1H), 1.84-1.57 (m, 2H), 1.30 (d, 3H, J = 6.9 Hz), 1.07 (t, 3H, J = 7.3 Hz). | 386 384 | 0.87 |
| Example 6-269 | 6-(((2S,3R)-2-aminopentan-3-yl)amino)-5-fluoro-2-((5-fluoropyridin-3-yl)amino)nicotinamide | HCl | CD3OD | 300 MHz | δ: 9.14 (d, 1H, J = 2.0 Hz), 8.55 (dt, 1H, J = 10.8, 2.1 Hz), 8.43 (s, 1H), 7.89 (d, 1H, J = 11.9 Hz), 4.48-4.38 (m, 1H), 3.68-3.56 (m, 1H), 1.92-1.57 (m, 2H), 1.37 (d, 3H, J = 6.9 Hz), 1.05 (t, 3H, J = 7.4 Hz). | 351 349 | 0.78 |
| Example 6-270 | 6-(((2S,3R)-2-aminopentan-3-yl)amino)-5-fluoro-2-((5-phenylpyridin-3-yl)amino)nicotinamide | HCl | CD3OD | 300 MHz | δ: 9.29 (d, 1H, J = 2.3 Hz), 8.80 (s, 1H), 8.65 (d, 1H, J = 1.3 Hz), 7.90 (d, 1H, J = 11.9 Hz), 7.82-7.76 (m, 2H), 7.63-7.56 (m, 3H), 4.47-4.38 (m, 1H), 3.60-3.48 (m, 1H), 1.84-1.56 (m, 2H), 1.25 (d, 3H, J = 6.9 Hz), 1.00 (t, 3H, J = 7.4 Hz). | 409 407 | 0.83 |

TABLE 3-continued

| Example | Structure | Name | Salt | | | |
|---|---|---|---|---|---|---|
| Example 6-271 | 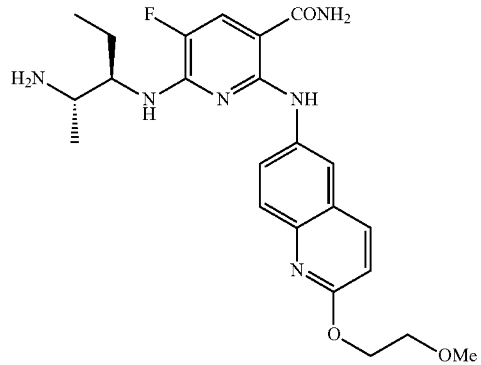 [SMILES: CC[C@@H](Nc1nc(Nc2ccc3nc(OCCOC)ccc3c2)c(C(N)=O)cc1F)[C@H](C)N] | 6-(((2S,3R)-2-aminopentan-3-yl)amino)-5-fluoro-2-((2-(2-methoxyethoxy)quinolin-6-yl)amino)nicotinamide | HCl | 458 | 456 | 1 |
| Example 6-272 | 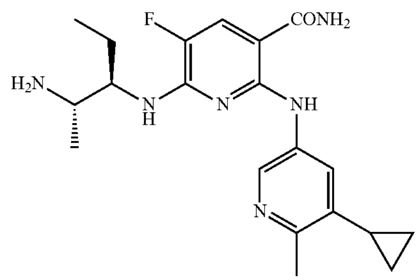 [SMILES: CC[C@@H](Nc1nc(Nc2cnc(C)c(C3CC3)c2)c(C(N)=O)cc1F)[C@H](C)N] | 6-(((2S,3R)-2-aminopentan-3-yl)amino)-2-(((5-cyclopropyl-6-methylpyridin-3-yl)amino)-5-fluoronicotinamide | HCl | 387 | 385 | 0.68 |
| Example 6-273 | 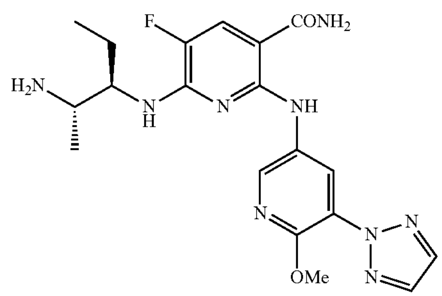 [SMILES: CC[C@@H](Nc1nc(Nc2cnc(OC)c(-n3nccn3)c2)c(C(N)=O)cc1F)[C@H](C)N] | 6-(((2S,3R)-2-aminopentan-3-yl)amino)-5-fluoro-2-(((6-methoxy-5-(2H-1,2,3-triazol-2-yl)pyridin-3-yl)amino)nicotinamide | HCl | 430 | 428 | 0.86 |

TABLE 3-continued

| Example | Structure | Name | Salt | Solvent | Freq | NMR | M+2 | M+ | M- | RT |
|---|---|---|---|---|---|---|---|---|---|---|
| Example 6-274 | | (R)-6-((1-aminohexan-2-yl)amino)-5-fluoro-2-(quinolin-6-ylamino)nicotinamide | HCl | | | | 397 | 395 | | 0.78 |
| Example 6-275 | | 6-(((2R,3S)-3-aminobutan-2-yl)amino)-5-fluoro-2-((quinolin-6-yl)amino)nicotinamide | HCl | DMSO-d6-D2O | 300 MHz | δ: 8.90 (dd, 1H, J = 1.5, 5.1 Hz), 8.74 (d, 1H, J = 8.3 Hz), 8.53 (d, 1H, J = 2.0 Hz), 8.16-8.05 (m, 2H), 7.95 (d, 1H, J = 12.2 Hz), 7.84 (dd, 1H, J = 5.0, 8.3 Hz), 4.49-4.35 (m, 1H), 3.62-3.48 (m, 1H), 1.34 (d, 3H, J = 6.6 Hz), 1.26 (d, 3H, J = 6.9 Hz). | 369 | 367 | | 0.59 |
| Example 6-276 | | 6-(((2S,3R)-2-aminopentan-3-yl)amino)-5-fluoro-2-((5-(3-methoxyphenyl)pyridin-3-yl)amino)nicotinamide | HCl | | | | 439 | 437 | | 0.83 |

TABLE 3-continued

| Example | Structure | Name | Salt | Solvent | Freq | NMR | MS1 | MS2 | Val |
|---|---|---|---|---|---|---|---|---|---|
| Example 6-277 | 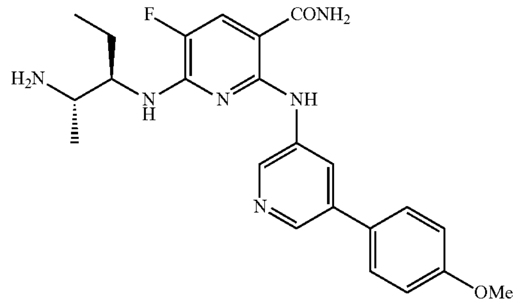 [SMILES: CC[C@@H](Nc1nc(Nc2cncc(-c3ccc(OC)cc3)c2)c(C(N)=O)cc1F)[C@H](C)N] | 6-(((2S,3R)-2-aminopentan-3-yl)amino)-5-fluoro-2-((5-(4-methoxyphenyl)pyridin-3-yl)amino)nicotinamide | HCl | | | | 439 | 437 | 0.8 |
| Example 6-278 | 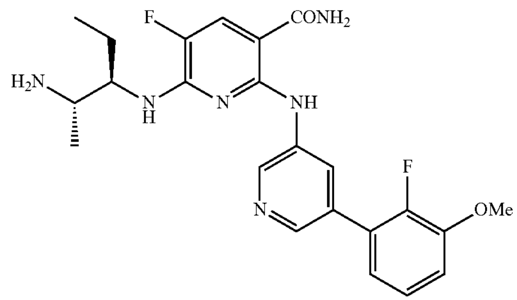 [SMILES: CC[C@@H](Nc1nc(Nc2cncc(-c3cccc(OC)c3F)c2)c(C(N)=O)cc1F)[C@H](C)N] | 6-(((2S,3R)-2-aminopentan-3-yl)amino)-5-fluoro-2-((5-(2-fluoro-3-methoxyphenyl)pyridin-3-yl)amino)nicotinamide | HCl | CD3OD | 300 MHz | δ: 9.26 (d, 1H, J = 2.0 Hz), 8.93 (s, 1H), 8.58 (s, 1H), 7.91 (t, 1H, J = 5.9 Hz), 7.33 (dd, 2H, J = 5.3, 3.3 Hz), 7.25-7.18 (m, 1H), 4.47 (ddd, 1H, J = 21.1, 11.6, 5.3 Hz), 3.96 (s, 3H), 3.56 (ddd, 1H, J = 15.4, 8.4, 5.1 Hz), 1.80-1.58 (m, 2H), 1.28 (d, 3H, J = 6.6 Hz), 0.96 (t, 3H, J = 7.3 Hz). | 457 | 455 | 0.85 |
| Example 6-279 | 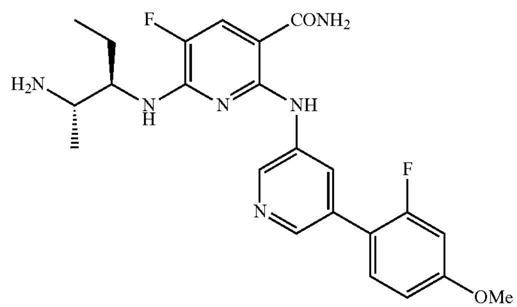 | 6-(((2S,3R)-2-aminopentan-3-yl)amino)-5-fluoro-2-((5-(2-fluoro-4-methoxyphenyl)pyridin-3-yl)amino)nicotinamide | HCl | | | | 457 | 455 | 0.86 |

TABLE 3-continued

| Example 6-280 | 6-(((2S,3R)-2-aminopentan-3-yl)amino)-5-fluoro-2-((5-(2-fluoro-5-methoxyphenyl)pyridin-3-yl)amino)nicotinamide 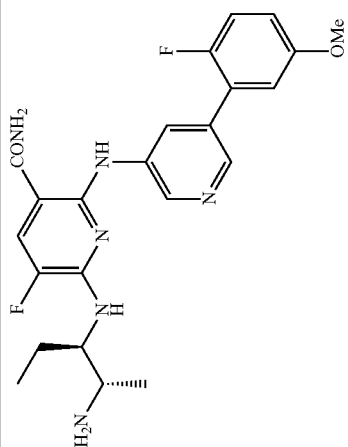 | HCl | | | 457 | 455 | 0.99 |
|---|---|---|---|---|---|---|---|
| Example 6-281 | 6-(((2S,3R)-2-aminopentan-3-yl)amino)-5-fluoro-2-((2-(2-fluoro-3-methoxyphenyl)pyridin-4-yl)amino)nicotinamide 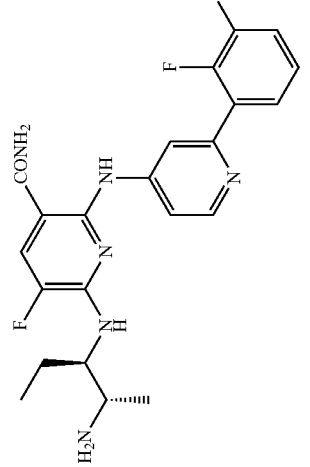 | HCl | CD3OD | 300 MHz | δ: 8.47 (d, 1H, J = 7.3 Hz), 8.43 (s, 1H), 7.96 (d, 1H, J = 11.2 Hz), 7.91 (s, 1H), 7.47-7.38 (m, 2H), 7.26 (td, 1H, J = 6.8, 2.4 Hz), 4.49-4.43 (m, 1H), 3.99 (s, 3H), 3.59-3.53 (m, 1H), 2.02-1.58 (m, 2H), 1.27 (t, 3H, J = 5.9 Hz), 0.94 (t, 3H, J = 7.6 Hz). | 457 | 455 | 0.69 |
| Example 6-282 | (R)-6-((1-amino-3-cyclopropylpropan-2-yl)amino)-5-fluoro-2-((1-methyl-1H-indazol-5-yl)amino)nicotinamide 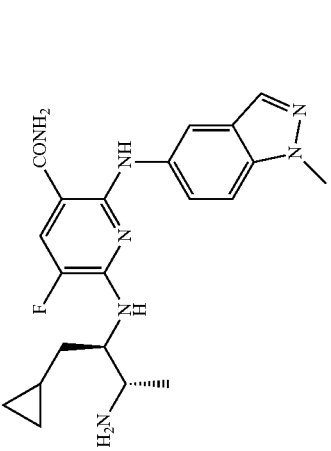 | HCl | | | 398 | 396 | 0.88 |

TABLE 3-continued

| Example | Name | Structure | Salt | Solvent | Freq | MS1 | MS2 | RT |
|---|---|---|---|---|---|---|---|---|
| Example 6-283 | (R)-6-((1-amino-3-cyclopropylpropan-2-yl)amino)-5-fluoro-2-((5-phenylpyridin-3-yl)amino)nicotinamide | | HCl | | | 421 | 419 | 0.88 |
| Example 6-284 | 6-(((2S,3R)-2-aminohexan-3-yl)amino)-5-fluoro-2-((5-(3-methoxyphenyl)pyridin-3-yl)amino)nicotinamide | | HCl | | | 453 | 451 | 0.91 |
| Example 6-285 | 6-(((2S,3R)-2-aminohexan-3-yl)amino)-5-fluoro-2-((5-(4-methoxyphenyl)pyridin-3-yl)amino)nicotinamide | | HCl | CD3OD | 300 MHz | 453 | 451 | 0.87 |

Example 6-285 NMR: δ: 9.32 (d, 1H, J = 2.0 Hz), 8.71 (t, 1H, J = 2.0 Hz), 8.63 (d, 1H, J = 1.3 Hz), 7.90 (d, 1H, J = 11.9 Hz), 7.75 (d, 2H, J = 9.2 Hz), 7.14 (d, 2H, J = 8.6 Hz), 4.51 (dd, 1H, J = 9.9, 4.6 Hz), 3.87 (d, 3H, J = 5.3 Hz), 3.56 (td, 1H, J = 8.1, 4.4 Hz), 1.66-1.38 (m, 4H), 1.27 (d, 3H, J = 6.6 Hz), 0.93 (q, 3H, J = 6.6 Hz).

| Example | Name | Structure | Salt | Solvent | Freq | NMR | M+1 | M-1 | RT |
|---|---|---|---|---|---|---|---|---|---|
| Example 6-286 | 6-(((2S,3R)-2-aminohexan-3-yl)amino)-5-fluoro-2-((5-(2-fluoro-3-methoxyphenyl)pyridin-3-yl)amino)nicotinamide | | HCl | CD3OD | 300 MHz | δ: 9.23 (s, 1H), 8.95 (s, 1H), 8.57 (s, 1H), 7.90 (d, 1H, J = 11.9 Hz), 7.34 (d, 2H, J = 5.3 Hz), 7.21 (t, 1H, J = 6.6 Hz), 4.56-4.53 (m, 1H), 3.97 (s, 3H), 3.56-3.52 (m, 1H), 1.64-1.62 (m, ,2H), 1.43-1.33 (m, 2H), 1.27 (d, 3H, J = 6.6 Hz), 0.89 (t, 3H, J = 7.3 Hz). | 471 | 469 | 0.92 |
| Example 6-287 | 6-(((2S,3R)-2-aminohexan-3-yl)amino)-5-fluoro-2-((5-(2-fluoro-4-methoxyphenyl)pyridin-3-yl)amino)nicotinamide | | HCl | | | | 471 | 469 | 0.93 |
| Example 6-288 | 6-(((2S,3R)-2-aminohexan-3-yl)amino)-5-fluoro-2-((5-(2-fluoro-5-methoxyphenyl)pyridin-3-yl)amino)nicotinamide | | HCl | | | | 471 | 469 | 1.06 |

TABLE 3-continued

| Example | Structure | Name | Salt | Solvent | NMR | MS+1 | MS-1 | Rf |
|---|---|---|---|---|---|---|---|---|
| Example 6-289 | | 6-(((2S,3R)-2-aminohexan-3-yl)amino)-5-fluoro-2-((2-(2-fluoro-3-methoxyphenyl)pyridin-4-yl)amino)nicotinamide | HCl | | | 471 | 469 | 0.76 |
| Example 6-290 | | 6-(((2S,3R)-2-aminohexan-3-yl)amino)-5-fluoro-2-((2-(2-fluoro-5-methoxyphenyl)pyridin-4-yl)amino)nicotinamide | HCl | CD3OD 300 MHz | δ: 8.50 (d, 1H, J = 7.3 Hz), 8.33 (s, 1H), 8.03 (br, 1H), 7.95 (d, 1H, J = 11.9 Hz), 7.37 (t, 1H, J = 9.6 Hz), 7.32-7.23 (m, 2H), 4.54-4.51 (m, 1H), 3.89 (s, 3H), 3.59-3.54 (m, 1H), 1.64 (q, 2H, J = 7.5 Hz), 1.42 (dq, 2H, J = 30.9, 7.9 Hz), 1.27 (d, 3H, J = 6.6 Hz), 0.89 (t, 3H, J = 7.3 Hz). | 471 | 469 | 0.92 |
| Example 6-291 | | (R)-6-((1-amino-4-methylpentan-2-yl)amino)-5-fluoro-2-((5-(4-methoxyphenyl)pyridin-3-yl)amino)nicotinamide | HCl | | | 453 | 451 | 0.93 |

TABLE 3-continued
| Example | Structure | Name | Salt | | | |
|---|---|---|---|---|---|---|
| Example 6-292 | 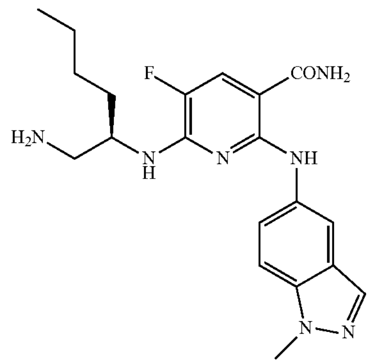 [SMILES: CCCC[C@H](CN)Nc1nc(Nc2ccc3c(cnn3C)c2)c(C(N)=O)cc1F] | (R)-6-((1-aminohexan-2-yl)amino)-5-fluoro-2-((1-methyl-1H-indazol-5-yl)amino)nicotinamide | HCl | 400 | 398 | 0.94 |
| Example 6-293 | 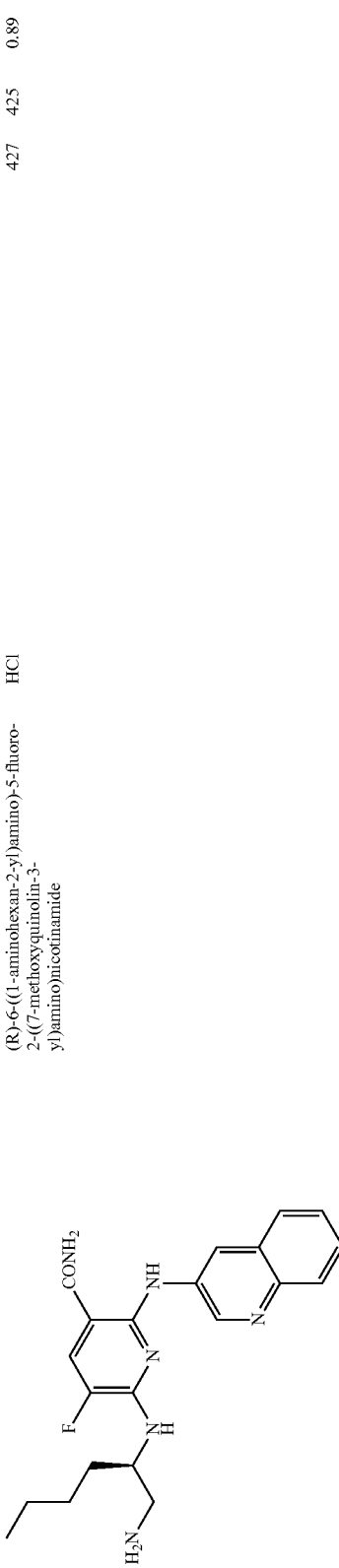 | (R)-6-((1-aminohexan-2-yl)amino)-5-fluoro-2-((7-methoxyquinolin-3-yl)amino)nicotinamide | HCl | 427 | 425 | 0.89 |
| Example 6-294 | 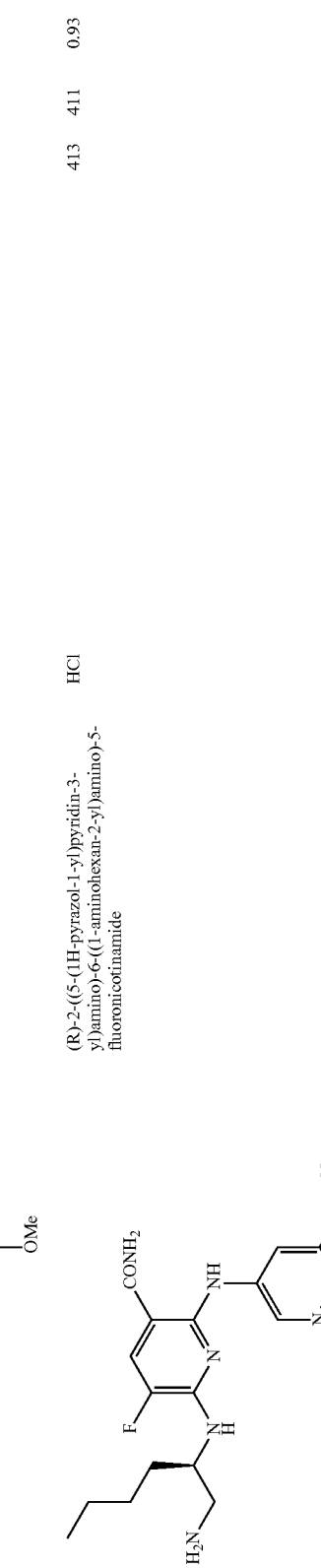 | (R)-2-((5-(1H-pyrazol-1-yl)pyridin-3-yl)amino)-6-((1-aminohexan-2-yl)amino)-5-fluoronicotinamide | HCl | 413 | 411 | 0.93 |

TABLE 3-continued

| Example | Structure | Name | Salt | Solvent | Freq | NMR | MS1 | MS2 | Value |
|---|---|---|---|---|---|---|---|---|---|
| Example 6-295 | 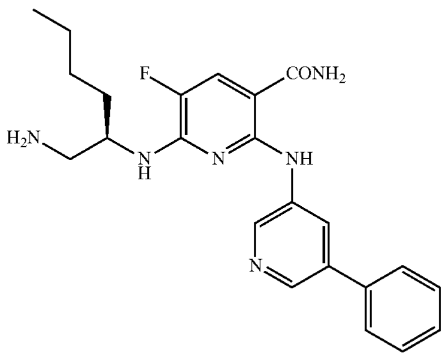 [SMILES: CCCC[C@H](CN)Nc1nc(Nc2cncc(-c3ccccc3)c2)c(C(N)=O)cc1F] | (R)-6-((1-aminohexan-2-yl)amino)-5-fluoro-2-((5-phenylpyridin-3-yl)amino)nicotinamide | HCl | | | | 423 | 421 | 0.94 |
| Example 6-296 | 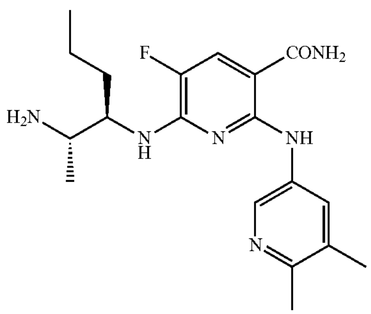 [SMILES: CCC[C@@H](Nc1nc(Nc2cnc(C)c(C)c2)c(C(N)=O)cc1F)[C@H](C)N] | 6-(((2S,3R)-2-aminohexan-3-yl)amino)-2-((5,6-dimethylpyridin-3-yl)amino)-5-fluoronicotinamide | HCl | DMSO-d6 | 300 MHz | δ: 12.20 (br, 1H), 9.39 (s, 1H), 8.13 (br, 3H), 8.05-7.88 (m, 3H), 7.53-7.42 (m, 1H), 7.29 (d, 1H, J = 9.2 Hz), 4.43-4.30 (m, 1H), 3.56-3.48 (m, 1H), 2.59 (s, 3H), 2.38 (s, 3H), 1.75-1.50 (m, 2H), 1.43-1.21 (m, 5H), 0.82 (dt, 3H, J = 21.8, 7.3 Hz). | 375 | 373 | 0.66 |
| Example 6-297 | 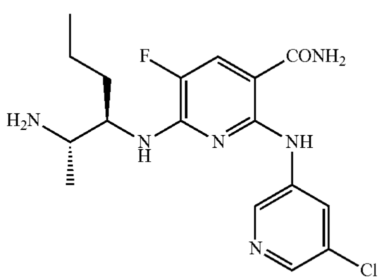 [SMILES: CCC[C@@H](Nc1nc(Nc2cncc(Cl)c2)c(C(N)=O)cc1F)[C@H](C)N] | 6-(((2S,3R)-2-aminohexan-3-yl)amino)-2-((5-chloropyridin-3-yl)amino)-5-fluoronicotinamide | HCl | | | | 382 | 380 | 0.94 |

TABLE 3-continued

| Example | Structure | Name | Salt | | | |
|---|---|---|---|---|---|---|
| Example 6-298 | 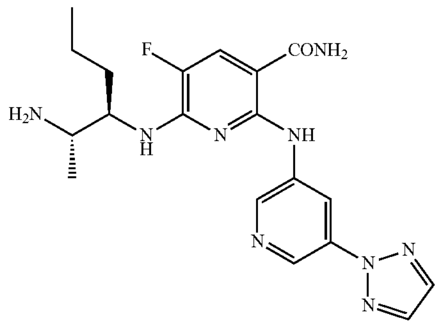 [SMILES: CCC[C@@H](Nc1nc(Nc2cncc(-n3nccn3)c2)c(C(N)=O)cc1F)[C@H](C)N] | 2-((5-(2H-1,2,3-triazol-2-yl)pyridin-3-yl)amino)-6-(((2S,3R)-2-aminohexan-3-yl)amino)-5-fluoronicotinamide | HCl | 414 | 412 | 0.92 |
| Example 6-299 | 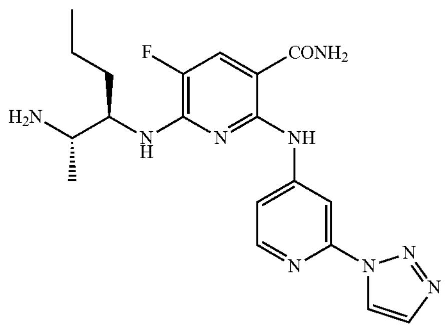 [SMILES: CCC[C@@H](Nc1nc(Nc2ccnc(-n3ccnn3)c2)c(C(N)=O)cc1F)[C@H](C)N] | 2-((2-(1H-1,2,3-triazol-1-yl)pyridin-4-yl)amino)-6-(((2S,3R)-2-aminohexan-3-yl)amino)-5-fluoronicotinamide | HCl | 414 | 412 | 0.91 |
| Example 6-300 | 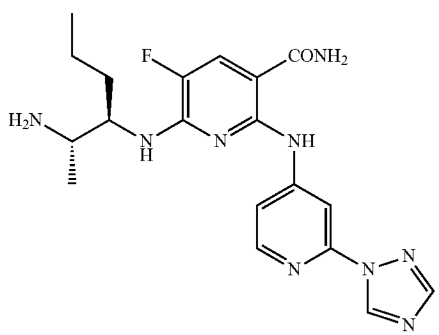 [SMILES: CCC[C@@H](Nc1nc(Nc2ccnc(-n3cncn3)c2)c(C(N)=O)cc1F)[C@H](C)N] | 2-((2-(1H-1,2,4-triazol-1-yl)pyridin-4-yl)amino)-6-(((2S,3R)-2-aminohexan-3-yl)amino)-5-fluoronicotinamide | HCl | 414 | 412 | 0.87 |

TABLE 3-continued
| | | | | | | | | |
|---|---|---|---|---|---|---|---|---|
| Example 6-301 | 6-(((2S,3R)-2-aminohexan-3-yl)amino)-5-fluoro-2-((5-fluoropyridin-3-yl)amino)nicotinamide | 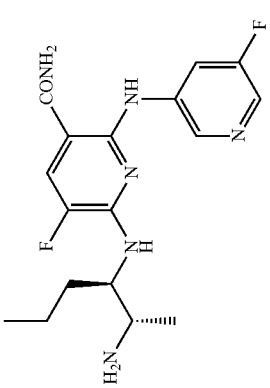 | HCl | DMSO-d6 | 300 MHz | δ: 11.96 (br, 1H), 8.51 (s, 1H), 8.17-8.13 (m, 2H), 7.97 (d, 1H, J = 12.6 Hz), 7.90-7.80 (m, 4H), 7.45-7.30 (m, 1H), 7.09 (d, 1H, J = 9.2 Hz), 4.30-4.14 (m, 1H), 3.54-3.45 (m, 1H), 1.64-1.53 (m, 2H), 1.48-1.20 (m, 5H), 0.87 (t, 3H, J = 6.9 Hz). | 365 363 | 0.87 |
| Example 6-302 | 6-(((2S,3R)-2-aminohexan-3-yl)amino)-5-fluoro-2-((6-methylpyridin-3-yl)amino)nicotinamide | 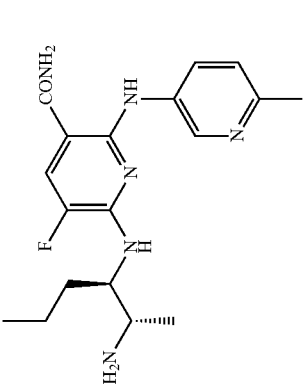 | HCl | | | | 361 359 | 0.61 |
| Example 6-303 | 6-(((2S,3R)-2-aminohexan-3-yl)amino)-5-fluoro-2-((2-(2-methoxyethoxy)quinolin-6-yl)amino)nicotinamide | 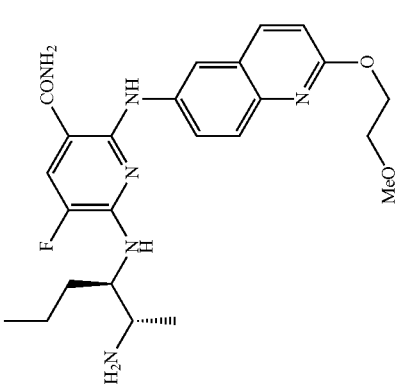 | HCl | | | | 472 470 | 1.08 |

TABLE 3-continued

| Example 6-304 | [structure: pyridine with CONH2, F, CF3-pentyl-CH2NH2 chain, and quinolin-6-yl amino] | 6-((1-amino-5,5,5-trifluoropentan-2-yl)amino)-5-fluoro-2-((quinolin-6-yl)amino)nicotinamide | HCl | 437 | 435 | 0.73 |
|---|---|---|---|---|---|---|
| Example 6-305 | [structure: pyridine with CONH2, F, CF3-pentyl-CH2NH2 chain, and 5-phenylpyridin-3-yl amino] | 6-((1-amino-5,5,5-trifluoropentan-2-yl)amino)-5-fluoro-2-((5-phenylpyridin-3-yl)amino)nicotinamide | HCl | 463 | 461 | 0.96 |
| Example 6-306 | [structure: pyridine with CONH2, F, 2-aminohexyl chain, and 2,3-dimethylquinoxalin-6-yl amino] | 6-(((2S,3R)-2-aminohexan-3-yl)amino)-2-((2,3-dimethylquinoxalin-6-yl)amino)-5-fluoronicotinamide | HCl | 426 | 424 | 0.97 |

TABLE 3-continued

| Example | Name | Salt | | | | |
|---|---|---|---|---|---|---|
| Example 6-307 | 6-(((2S,3R)-2-aminohexan-3-yl)amino)-5-fluoro-2-(quinolin-5-ylamino)nicotinamide | HCl | 397 | 395 | 0.73 | |
| Example 6-308 | 6-(((2S,3R)-2-aminohexan-3-yl)amino)-2-(benzo[d]thiazol-5-ylamino)-5-fluoronicotinamide | HCl | 403 | 401 | 0.98 | |
| Example 6-309 | 6-(((2S,3R)-2-aminohexan-3-yl)amino)-2-((2-ethoxypyridin-4-yl)amino)-5-fluoronicotinamide | HCl | 391 | 389 | 0.72 | |

TABLE 3-continued

| Example | Structure | Name | Salt | Solvent | Freq | NMR | | | |
|---|---|---|---|---|---|---|---|---|---|
| Example 6-310 | 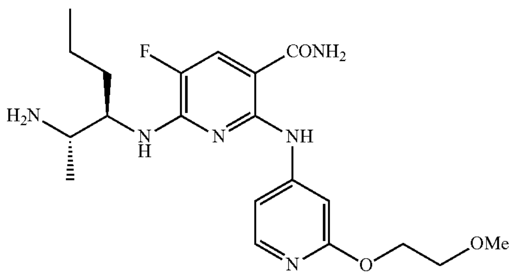 [SMILES: CCC[C@@H](Nc1nc(Nc2ccnc(OCCOC)c2)c(C(N)=O)cc1F)[C@H](C)N] | 6-(((2S,3R)-2-aminohexan-3-yl)amino)-5-fluoro-2-((2-(2-methoxyethoxy)pyridin-4-yl)amino)nicotinamide | HCl | | | | 421 | 419 | 0.72 |
| Example 6-311 | 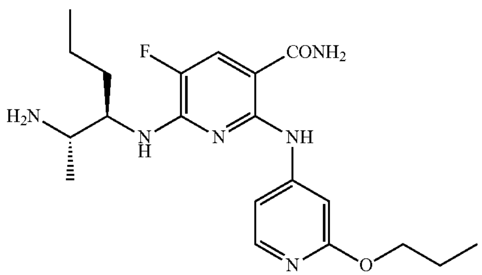 [SMILES: CCCOc1cc(Nc2nc(N[C@H](CCC)[C@H](C)N)c(F)cc2C(N)=O)ccn1] | 6-(((2S,3R)-2-aminohexan-3-yl)amino)-5-fluoro-2-((2-propoxypyridin-4-yl)amino)nicotinamide | HCl | | | | 405 | 403 | 0.78 |
| Example 6-312 | 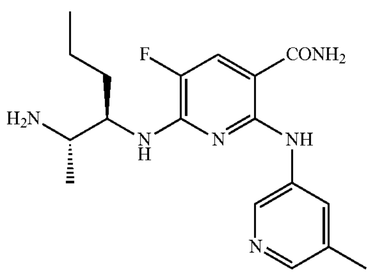 [SMILES: CCC[C@@H](Nc1nc(Nc2cncc(C)c2)c(C(N)=O)cc1F)[C@H](C)N] | 6-(((2S,3R)-2-aminohexan-3-yl)amino)-5-fluoro-2-((5-methylpyridin-3-yl)amino)nicotinamide | HCl | CD3OD | 300 MHz | δ: 9.39 (d, 1H, J = 1.7 Hz), 8.26 (s, 2H), 7.88 (d, 1H, J = 11.9 Hz), 4.59-4.50 (m, 1H), 3.63-3.51 (m, 1H), 2.53 (s, 3H), 1.8-1.36 (m, 7H), 0.97 (t, 3H, J = 7.3 Hz). | 361 | 359 | 0.64 |

TABLE 3-continued

| Example | Structure | Name | Salt | Solvent | Freq | NMR | M+H | M-H | Activity |
|---|---|---|---|---|---|---|---|---|---|
| Example 6-313 | 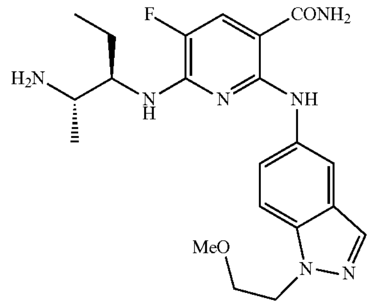 [SMILES: CC[C@@H](Nc1nc(Nc2ccc3c(cnn3CCOC)c2)c(C(N)=O)cc1F)[C@H](C)N] | 6-(((2S,3R)-2-aminopentan-3-yl)amino)-5-fluoro-2-((1-(2-methoxyethyl)-1H-indazol-5-yl)amino)nicotinamide | HCl | CD3OD | 300 MHz | δ: 8.46 (s, 1H), 8.38 (d, 1H, J = 2.0 Hz), 8.24 (d, 1H, J = 11.9 Hz), 8.07 (d, 1H, J = 9.2 Hz), 7.90 (dd, 1H, J = 9.2, 2.0 Hz), 5.05 (t, 2H, J = 5.0 Hz), 4.66-4.60 (m, 1H), 4.31 (t, 2H, J = 5.0 Hz), 3.76 (s, 3H), 3.96-3.94 (m, 1H), 2.23-2.04 (m, 2H), 1.68 (d, 3H, J = 7.3 Hz), 1.55 (t, 3H, J = 6.8 Hz). | 430 | 428 | 0.83 |
| Example 6-314 | 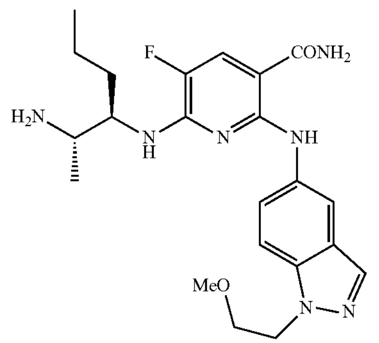 [SMILES: CCC[C@@H](Nc1nc(Nc2ccc3c(cnn3CCOC)c2)c(C(N)=O)cc1F)[C@H](C)N] | 6-(((2S,3R)-2-aminohexan-3-yl)amino)-5-fluoro-2-((1-(2-methoxyethyl)-1H-indazol-5-yl)amino)nicotinamide | HCl | | | | 444 | 442 | 0.91 |
| Example 6-315 | 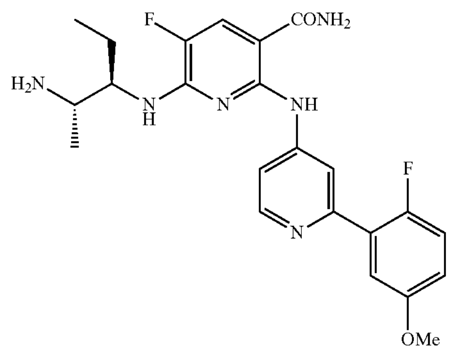 [SMILES: CC[C@@H](Nc1nc(Nc2ccnc(-c3cc(OC)ccc3F)c2)c(C(N)=O)cc1F)[C@H](C)N] | 6-(((2S,3R)-2-aminopentan-3-yl)amino)-5-fluoro-2-((2-fluoro-5-methoxyphenyl)pyridin-4-yl)amino)nicotinamide | HCl | | | | 457 | 455 | 0.7 |

TABLE 3-continued

| Example 6-316 | (R)-6-((1-amino-4-methylpentan-2-yl)amino)-5-fluoro-2-((5-(2-fluorophenyl)pyridin-3-yl)amino)nicotinamide | HCl | 441 | 439 | 0.99 |
| --- | --- | --- | --- | --- | --- |
| Example 6-317 | (R)-6-((1-amino-4-methylpentan-2-yl)amino)-5-fluoro-2-((5-(3-methoxyphenyl)pyridin-3-yl)amino)nicotinamide | HCl | 453 | 451 | 0.96 |
| Example 6-318 | (R)-6-((1-amino-4-methylpentan-2-yl)amino)-5-fluoro-2-((5-(2-fluoro-3-methoxyphenyl)pyridin-3-yl)amino)nicotinamide | HCl | 471 | 469 | 0.98 |

TABLE 3-continued

| Example | Structure | Name | Salt | | | |
|---|---|---|---|---|---|---|
| Example 6-319 | 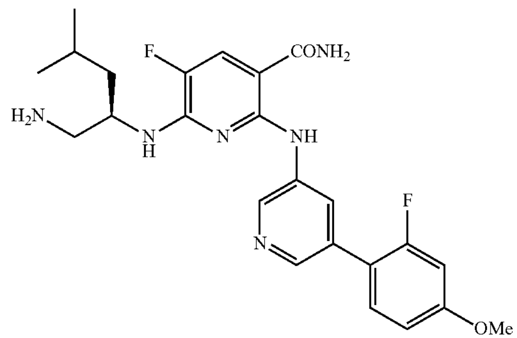 [SMILES: COc1ccc(-c2cncc(Nc3nc(N[C@@H](CN)CC(C)C)c(F)cc3C(N)=O)c2)c(F)c1] | (R)-6-((1-amino-4-methylpentan-2-yl)amino)-5-fluoro-2-((5-(2-fluoro-4-methoxyphenyl)pyridin-3-yl)amino)nicotinamide | HCl | 471 | 469 | 0.99 |
| Example 6-320 | 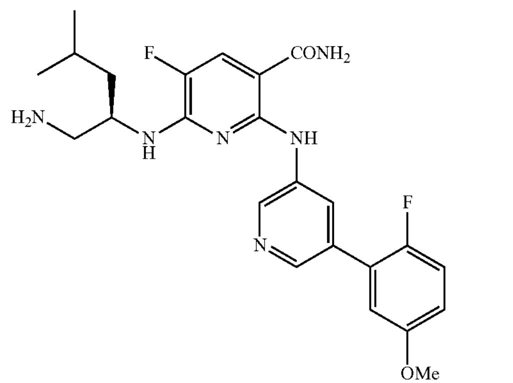 [SMILES: COc1ccc(F)c(-c2cncc(Nc3nc(N[C@@H](CN)CC(C)C)c(F)cc3C(N)=O)c2)c1] | (R)-6-((1-amino-4-methylpentan-2-yl)amino)-5-fluoro-2-((5-(2-fluoro-5-methoxyphenyl)pyridin-3-yl)amino)nicotinamide | HCl | 471 | 469 | 0.95 |
| Example 6-321 | 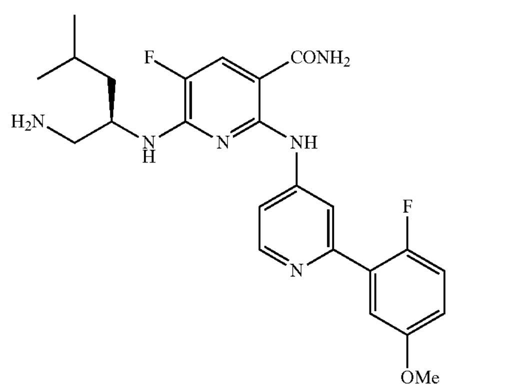 [SMILES: COc1ccc(F)c(-c2cc(Nc3nc(N[C@@H](CN)CC(C)C)c(F)cc3C(N)=O)ccn2)c1] | (R)-6-((1-amino-4-methylpentan-2-yl)amino)-5-fluoro-2-((2-(2-fluoro-5-methoxyphenyl)pyridin-4-yl)amino)nicotinamide | HCl | 471 | 469 | 0.81 |

TABLE 3-continued

| Example | Structure | Name | Salt | Solvent | Freq | NMR | | | |
|---|---|---|---|---|---|---|---|---|---|
| Example 6-322 | 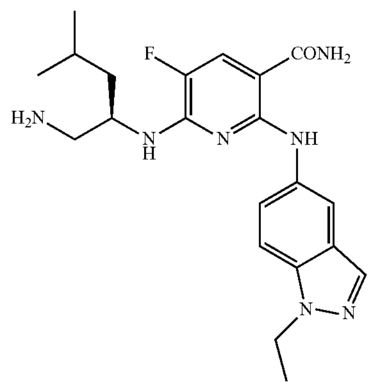 [SMILES: CCn1ncc2cc(Nc3nc(N[C@@H](CN)CC(C)C)c(F)cc3C(N)=O)ccc21] | (R)-6-((1-amino-4-methylpentan-2-yl)amino)-2-((1-ethyl-1H-indazol-5-yl)amino)-5-fluoronicotinamide | HCl | CD3OD | 300 MHz | δ: 8.02 (s, 1H), 7.93 (s, 1H), 7.74 (d, 1H, J = 11.9 Hz), 7.53 (d, 1H, J = 9.2 Hz), 7.43 (d, 1H, J = 9.2 Hz), 4.45 (q, 2H, J = 7.3 Hz), 3.05 (tt, 1H, J = 18.8, 6.4 Hz), 1.65 (tt, 2H, J = 16.8, 5.7 Hz), 1.47 (t, 3H, J = 7.3 Hz), 1.37 (dd, 1H, J = 13.5, 7.6 Hz), 0.91 (t, 6H, J = 7.3 Hz). | 414 | 412 | 0.99 |
| Example 6-323 | 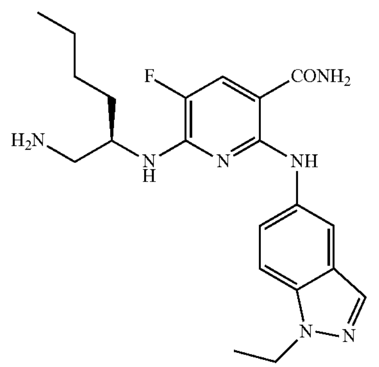 [SMILES: CCCC[C@H](CN)Nc1nc(Nc2ccc3c(cnn3CC)c2)c(C(N)=O)cc1F] | (R)-6-((1-aminohexan-2-yl)amino)-2-((1-ethyl-1H-indazol-5-yl)amino)-5-fluoronicotinamide | HCl | | | | 414 | 412 | 1 |
| Example 6-324 | 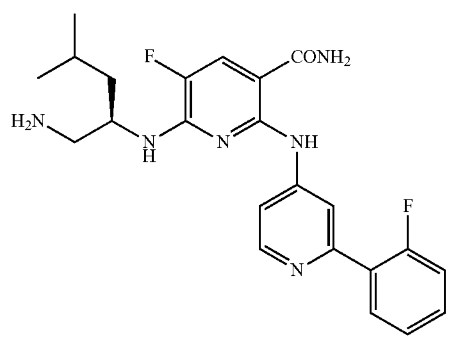 [SMILES: CC(C)C[C@H](CN)Nc1nc(Nc2ccnc(-c3ccccc3F)c2)c(C(N)=O)cc1F] | (R)-6-((1-amino-4-methylpentan-2-yl)amino)-5-fluoro-2-((2-(2-fluorophenyl)pyridin-4-yl)amino)nicotinamide | HCl | | | | 441 | 439 | 0.78 |

TABLE 3-continued

| Example 6-325 | [structure with CONH2, F, NH, pyridine, 3-methoxyphenyl, H2N-isobutyl chain] | (R)-6-((1-amino-4-methylpentan-2-yl)amino)-5-fluoro-2-((2-(3-methoxyphenyl)pyridin-4-yl)amino)nicotinamide | HCl | 453 | 451 | 0.82 |
|---|---|---|---|---|---|---|
| Example 6-326 | [structure with CONH2, F, NH, pyridine, 4-methoxyphenyl, H2N-isobutyl chain] | (R)-6-((1-amino-4-methylpentan-2-yl)amino)-5-fluoro-2-((2-(4-methoxyphenyl)pyridin-4-yl)amino)nicotinamide | HCl | 453 | 451 | 0.82 |
| Example 6-327 | [structure with CONH2, F, NH, pyridine, 2-fluoro-3-methoxyphenyl, H2N-isobutyl chain] | (R)-6-((1-amino-4-methylpentan-2-yl)amino)-5-fluoro-2-((2-(2-fluoro-3-methoxyphenyl)pyridin-4-yl)amino)nicotinamide | HCl | 471 | 469 | 0.8 |

TABLE 3-continued

| Example | Name | Structure | Salt | Solvent | NMR | MS1 | MS2 | Activity |
|---|---|---|---|---|---|---|---|---|
| Example 6-328 | (R)-6-((1-amino-4-methylpentan-2-yl)amino)-5-fluoro-2-((2-(2-fluoro-4-methoxyphenyl)pyridin-4-yl)amino)nicotinamide | | HCl | | | 471 | 469 | 0.83 |
| Example 6-329 | 6-(((2S,3R)-2-aminopentan-3-yl)amino)-5-fluoro-2-((2-(2-fluorophenyl)pyridin-4-yl)amino)nicotinamide | | HCl | | | 427 | 425 | 0.66 |
| Example 6-330 | 6-(((2S,3R)-2-aminopentan-3-yl)amino)-5-fluoro-2-((2-(3-methoxyphenyl)pyridin-4-yl)amino)nicotinamide | | HCl | CD3OD 300 MHz | δ: 8.94 (d, 1H, J = 6.6 Hz), 8.84 (s, 1H), 8.51 (br, 1H), 8.44 (d, 1H J = 11.9 Hz), 8.08 (t, 1H, J = 8.3 Hz), 7.91 (s, 2H), 7.75 (d, 1H, J = 7.3 Hz), 4.97-4.94 (m, 1H), 4.41 (s, 3H), 4.07-4.04 (m, 1H), 2.23-2.17 (m, 2H), 1.76 (d, 3H, J = 6.6 Hz), 1.46 (t, 3H, J = 7.3 Hz). | 439 | 437 | 0.7 |

TABLE 3-continued

| Example | Name | Structure | Salt | Solvent | Freq | NMR | MS obs | MS calc | RT |
|---|---|---|---|---|---|---|---|---|---|
| Example 6-331 | 6-(((2S,3R)-2-aminopentan-3-yl)amino)-5-fluoro-2-((2-(4-methoxyphenyl)pyridin-4-yl)amino)nicotinamide | | HCl | | | | 439 | 437 | 0.71 |
| Example 6-332 | 6-(((2S,3R)-2-aminopentan-3-yl)amino)-5-fluoro-2-((2-(2-fluoro-4-methoxyphenyl)pyridin-4-yl)amino)nicotinamide | | HCl | CD3OD | 300 MHz | δ: 8.45 (d, 1H, J = 7.3 Hz), 8.20 (s, 1H), 8.02 (br, 1H), 7.95 (d, 1H, J = 11.9 Hz), 7.70 (t, 1H, J = 8.9 Hz), 7.04 (dd, 2H, J = 8.9, 5.6 Hz), 4.46-4.44 (m, 1H), 3.92 (s, 3H), 3.59-3.57 (m, 1H), 1.69 (ddt, 2H, J = 31.7, 13.9, 5.7 Hz), 1.29 (d, 3H, J = 6.6 Hz), 0.97 (t, 3H, J = 7.3 Hz). | 457 | 455 | 0.72 |
| Example 6-333 | 6-(((2S,3R)-2-aminohexan-3-yl)amino)-5-fluoro-2-((2-(2-fluorophenyl)pyridin-4-yl)amino)nicotinamide | | HCl | | | | 441 | 439 | 0.73 |

TABLE 3-continued

| Example | Structure | Name | Salt | | | |
|---|---|---|---|---|---|---|
| Example 6-334 | 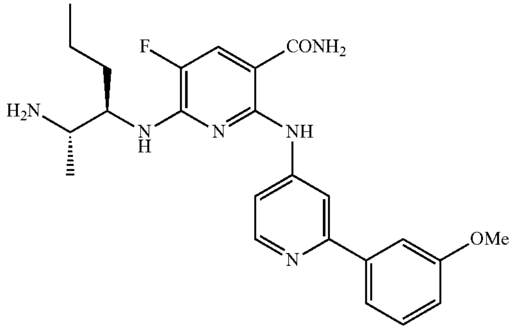 [SMILES: CCC[C@@H](Nc1nc(Nc2ccnc(-c3cccc(OC)c3)c2)c(C(N)=O)cc1F)[C@H](C)N] | 6-(((2S,3R)-2-aminohexan-3-yl)amino)-5-fluoro-2-((2-(3-methoxyphenyl)pyridin-4-yl)amino)nicotinamide | HCl | 453 | 451 | 0.76 |
| Example 6-335 | 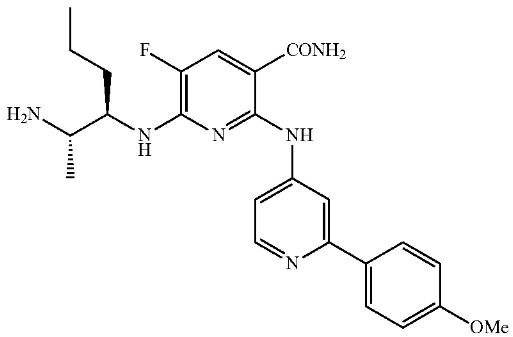 [SMILES: CCC[C@@H](Nc1nc(Nc2ccnc(-c3ccc(OC)cc3)c2)c(C(N)=O)cc1F)[C@H](C)N] | 6-(((2S,3R)-2-aminohexan-3-yl)amino)-5-fluoro-2-((2-(4-methoxyphenyl)pyridin-4-yl)amino)nicotinamide | HCl | 453 | 451 | 0.76 |
| Example 6-336 | 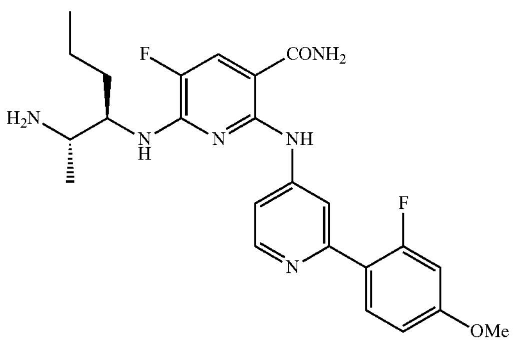 [SMILES: CCC[C@@H](Nc1nc(Nc2ccnc(-c3ccc(OC)cc3F)c2)c(C(N)=O)cc1F)[C@H](C)N] | 6-(((2S,3R)-2-aminohexan-3-yl)amino)-5-fluoro-2-((2-(2-fluoro-4-methoxyphenyl)pyridin-4-yl)amino)nicotinamide | HCl | 471 | 469 | 0.77 |

TABLE 3-continued

| Example | Structure | Name | Salt | Solvent | NMR | MS calc | MS found | RT |
|---|---|---|---|---|---|---|---|---|
| Example 6-337 | | (R)-6-((2-amino-1-cyclopropylethyl)amino)-5-fluoro-2-((5-phenylpyridin-3-yl)amino)nicotinamide | HCl | | | 407 | 405 | 0.82 |
| Example 6-338 | | (R)-6-((1-aminohexan-2-yl)amino)-5-fluoro-2-((1-(2-methoxyethyl)-1H-indazol-5-yl)amino)nicotinamide | HCl | CD3OD 300 MHz | δ: 8.04 (d, 1H, J = 1.3 Hz), 7.98 (s, 1H), 7.74 (d, 1H, J = 12.6 Hz), 7.56 (d, 1H, J = 9.2 Hz), 7.43 (dd, 1H, J = 8.9, 2.3 Hz), 4.56 (t, 2H, J = 5.3 Hz), 4.40-4.30 (m, 2H), 3.81 (t, 2H, J = 5.3 Hz), 3.57-3.53 (m, 1H), 3.27 (s, 3H), 1.65 (tt, 2H, J = 22.5, 7.6 Hz), 1.35 (dq, 4H, J = 22.1, 5.8 Hz), 0.86 (t, 3H, J = 6.9 Hz). | 444 | 442 | 0.96 |
| Example 6-339 | | (R)-6-((1-aminohexan-2-yl)amino)-5-fluoro-2-((1-methyl-1H-indazol-4-yl)amino)nicotinamide | HCl | | | 400 | 398 | 0.98 |

TABLE 3-continued

| Example | Structure | Name | Salt | NMR solvent | NMR freq | NMR data | | | |
|---|---|---|---|---|---|---|---|---|---|
| Example 6-340 | 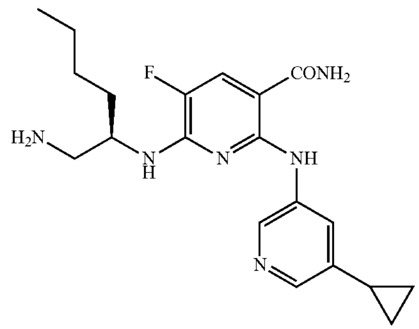 [SMILES: CCCC[C@H](CN)Nc1nc(Nc2cncc(C3CC3)c2)c(C(N)=O)cc1F] | (R)-6-((1-aminohexan-2-yl)amino)-2-((5-cyclopropylpyridin-3-yl)amino)-5-fluoronicotinamide | HCl | | | | 387 | 385 | 0.76 |
| Example 6-341 | 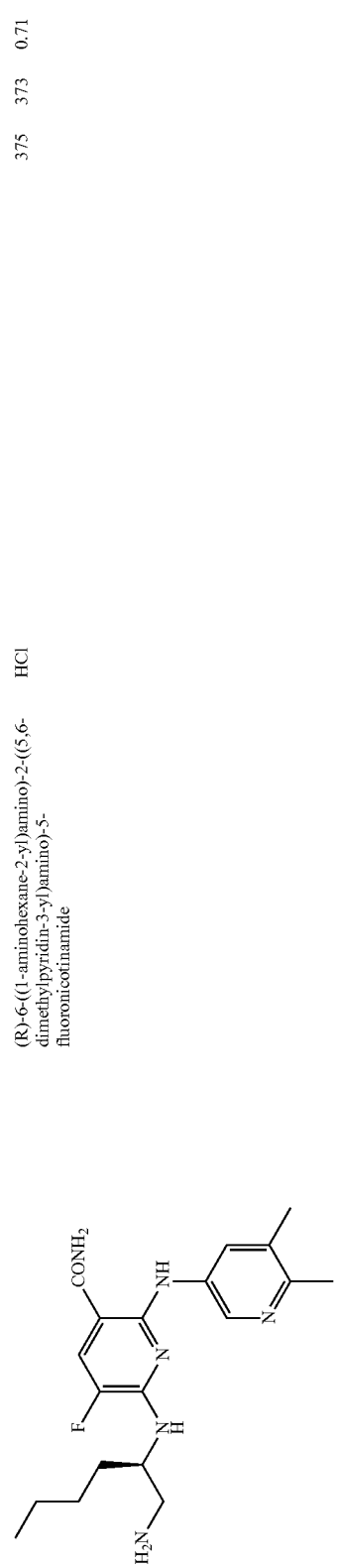 | (R)-6-((1-aminohexane-2-yl)amino)-2-((5,6-dimethylpyridin-3-yl)amino)-5-fluoronicotinamide | HCl | | | | 375 | 373 | 0.71 |
| Example 6-342 | 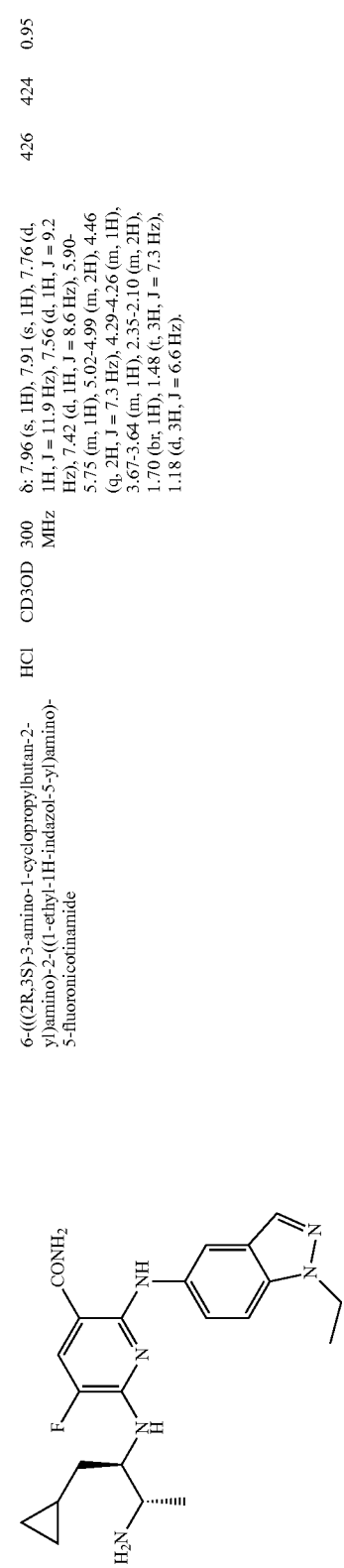 | 6-(((2R,3S)-3-amino-1-cyclopropylbutan-2-yl)amino)-2-((1-ethyl-1H-indazol-5-yl)amino)-5-fluoronicotinamide | HCl | CD3OD | 300 MHz | δ: 7.96 (s, 1H), 7.91 (s, 1H), 7.76 (d, 1H, J = 11.9 Hz), 7.56 (d, 1H, J = 9.2 Hz), 7.42 (d, 1H, J = 8.6 Hz), 5.90-5.75 (m, 1H), 5.02-4.99 (m, 2H), 4.46 (q, 2H, J = 7.3 Hz), 4.29-4.26 (m, 1H), 3.67-3.64 (m, 1H), 2.35-2.10 (m, 2H), 1.70 (br, 1H), 1.48 (t, 3H, J = 7.3 Hz), 1.18 (d, 3H, J = 6.6 Hz). | 426 | 424 | 0.95 |

TABLE 3-continued

| Example | Structure | Name | Salt | Solvent | Freq | NMR | | | |
|---|---|---|---|---|---|---|---|---|---|
| Example 6-343 | 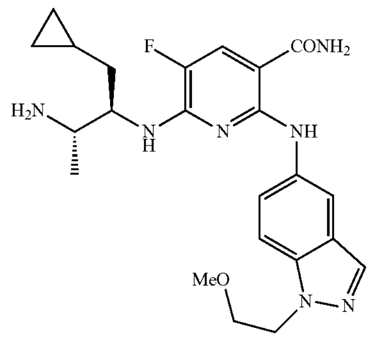 [SMILES: COCCn1ncc2cc(Nc3nc(N[C@H](CC4CC4)[C@H](C)N)c(F)cc3C(N)=O)ccc21] | 6-(((2R,3S)-3-amino-1-cyclopropylbutan-2-yl)amino)-5-fluoro-2-((1-(2-methoxyethyl)-1H-indazol-5-yl)amino)nicotinamide | HCl | CD3OD | 300 MHz | δ: 7.97 (s, 1H), 7.86 (t, 1H, J = 7.3 Hz), 7.76 (d, 1H, J = 11.9 Hz), 7.58 (d, 1H, J = 9.2 Hz), 7.42 (dd, 1H, J = 9.2, 2.0 Hz), 5.91-5.78 (m, 1H), 5.04-4.96 (m, 2H), 4.57 (t, 2H, J = 5.3 Hz), 4.30-4.24 (m, 1H), 3.83 (t, 3H, J = 5.3 Hz), 3.45-3.43 (m, 1H), 2.31-2.08 (m, 2H), 1.72 (ddd, 2H, J = 22.5, 14.5, 7.9 Hz), 1.17 (t, 3H, J = 7.3 Hz). | 456 | 454 | 0.92 |
| Example 6-344 | 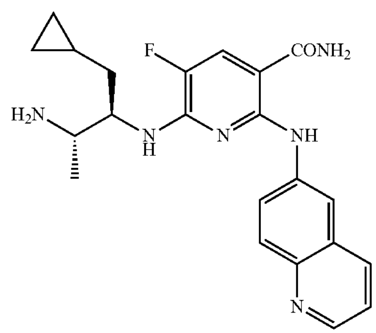 [SMILES: C[C@H](N)[C@@H](CC1CC1)Nc1nc(Nc2ccc3ncccc3c2)c(C(N)=O)cc1F] | 6-(((2R,3S)-3-amino-1-cyclopropylbutan-2-yl)amino)-5-fluoro-2-((quinolin-6-yl)amino)nicotinamide | HCl | DMSO-d6 | 300 MHz | δ: 12.11 (s, 1H), 8.85 (s, 1H), 8.55-8.40 (m, 1H), 8.33 (s, 1H), 8.06-7.95 (m, 3H), 7.87 (br, 3H), 7.70-7.62 (m, 1H), 7.50-7.40 (m, 2H), 7.15-7.10 (m, 1H), 5.88-5.74 (m, 1H), 5.00-4.85 (m, 2H), 4.45-4.30 (m, 1H), 3.55-3.48 (m, 1H), 2.25-1.65 (m, 4H), 1.25-1.15 (m, 3H). | 409 | 407 | 0.73 |
| Example 6-345 | 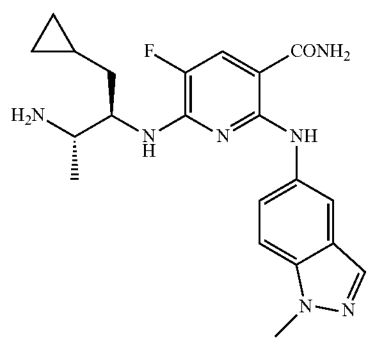 [SMILES: C[C@H](N)[C@@H](CC1CC1)Nc1nc(Nc2ccc3c(cnn3C)c2)c(C(N)=O)cc1F] | 6-(((2R,3S)-3-amino-1-cyclopropylbutan-2-yl)amino)-5-fluoro-2-((1-methyl-1H-indazol-5-yl)amino)nicotinamide | HCl | | | | 412 | 410 | 0.93 |

TABLE 3-continued

| Example | Structure | Name | Salt | | | |
|---|---|---|---|---|---|---|
| Example 6-346 | 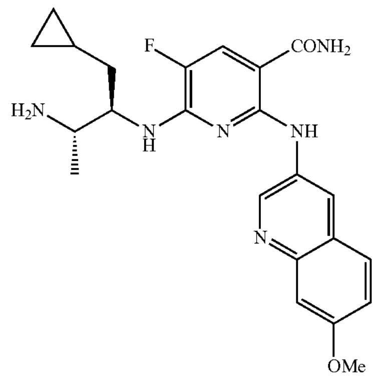 [SMILES: COc1ccc2cc(Nc3nc(N[C@H](CC4CC4)[C@H](C)N)c(F)cc3C(N)=O)cnc2c1] | 6-(((2R,3S)-3-amino-1-cyclopropylbutan-2-yl)amino)-5-fluoro-2-((7-methoxyquinolin-3-yl)amino)nicotinamide | HCl | 440 | 438 | 0.9 |
| Example 6-347 | 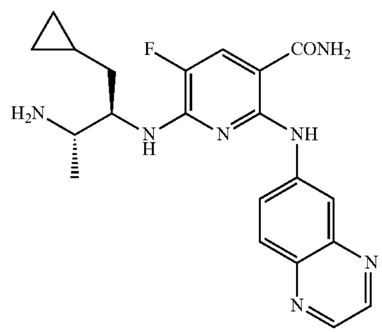 [SMILES: C[C@H](N)[C@@H](CC1CC1)Nc1nc(Nc2ccc3nccnc3c2)c(C(N)=O)cc1F] | 6-(((2R,3S)-3-amino-1-cyclopropylbutan-2-yl)amino)-5-fluoro-2-((quinoxalin-6-yl)amino)nicotinamide | HCl | 410 | 408 | 0.9 |
| Example 6-348 | 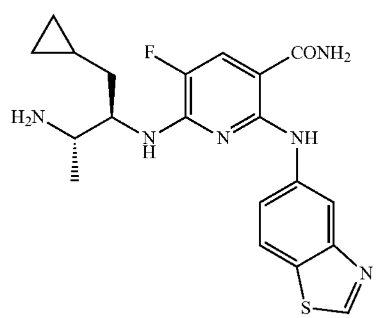 [SMILES: C[C@H](N)[C@@H](CC1CC1)Nc1nc(Nc2ccc3scnc3c2)c(C(N)=O)cc1F] | 6-(((2R,3S)-3-amino-1-cyclopropylbutan-2-yl)amino)-2-(benzo[d]thiazol-5-ylamino)-5-fluoronicotinamide | HCl | 416 | 414 | 0.98 |

| Example 6-349 | 6-(((2R,3S)-3-amino-1-cyclopropylbutan-2-yl)amino)-2-((2,6-dimethoxypyridin-4-yl)amino)-5-fluoronicotinamide | HCl | | | 419 | 417 | 1.05 |
|---|---|---|---|---|---|---|---|
| Example 6-350 | 6-(((2R,3S)-3-amino-1-cyclopropylbutan-2-yl)amino)-2-((5-cyclopropylpyridin-3-yl)amino)-5-fluoronicotinamide | HCl | DMSO-d6 | 300 MHz | δ: 11.87 (br, 1H), 8.95 (s, 1H), 8.20-7.70 (m, 8H), 7.44-7.00 (m, 2H), 5.84-5.70 (m, 1H), 5.00-4.85 (m, 2H), 4.32-4.22 (m, 1H), 3.45-3.38 (m, 1H), 2.25-1.65 (m, 4H), 1.26-1.12 (m, 5H), 0.90-0.82 (m, 2H). | 399 | 397 | 0.76 |
| Example 6-351 | 6-(((2R,3S)-3-amino-1-cyclopropylbutan-2-yl)amino)-5-fluoro-2-((5-phenylpyridin-3-yl)amino)nicotinamide | HCl | DMSO-d6 | 300 MHz | δ: 12.07 (1H, br, 1H), 9.13 (1H, s, 1H), 8.67 (1H, s, 1H), 8.47 (1H, s, 1H), 8.05-7.77 (6H, m, 6H), 7.57-7.40 (2H, m), 7.24-7.18 (2H, m), 5.80-5.65 (1H, m), 4.94-4.81 (2H, m), 4.36-4.27 (1H, m), 3.45-3.38 (1H, m), 2.20-1.60 (5H, m), 1.20-1.04 (3H, m). | 436 | 434 | 0.95 |

TABLE 3-continued

| Example | Structure | Name | Salt | Solvent | Freq | NMR | MS1 | MS2 | Val |
|---|---|---|---|---|---|---|---|---|---|
| Example 6-352 | 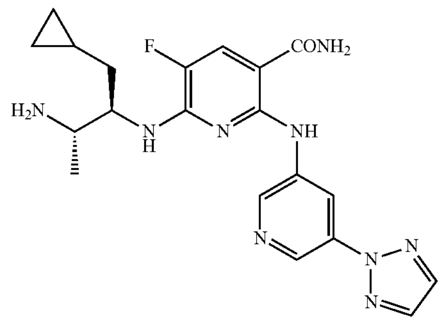 [SMILES: C[C@H](N)[C@@H](CC1CC1)Nc1nc(Nc2cncc(-n3nccn3)c2)c(C(N)=O)cc1F] | 2-((5-(2H-1,2,3-triazol-2-yl)pyridin-3-yl)amino)-6-(((2R,3S)-3-amino-1-cyclopropylbutan-2-yl)amino)-5-fluoronicotinamide | HCl | | | | 426 | 424 | 0.93 |
| Example 6-353 | 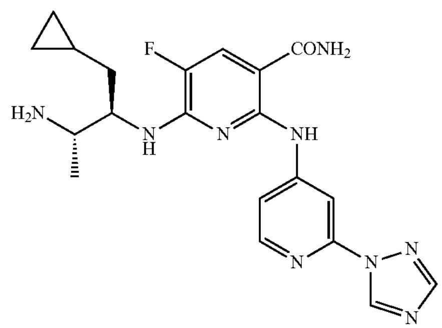 [SMILES: C[C@H](N)[C@@H](CC1CC1)Nc1nc(Nc2ccnc(-n3cncn3)c2)c(C(N)=O)cc1F] | 2-(2-(1H-1,2,4-triazol-1-yl)pyridin-4-yl)amino)-6-(((2R,3S)-3-amino-1-cyclopropylbutan-2-yl)amino)-5-fluoronicotinamide | HCl | DMSO-d6 | 300 MHz | δ: 12.34 (s, 1H), 9.35 (s, 1H), 8.65 (s, 1H), 8.47 (s, 1H), 8.30 (s, 1H), 8.28 (t, 1H, J = 7.9 Hz), 8.04-7.90 (m, 2H), 7.73 (br, 3H), 7.32-7.22 (m, 2H), 5.86-5.75 (m, 1H), 4.98-4.83 (m, 2H), 4.68-4.57 (m, 1H), 3.35-3.28 (m, 1H), 2.20-1.60 (m, 4H), 1.24-1.16 (m, 3H). | 426 | 424 | 0.88 |
| Example 6-354 | 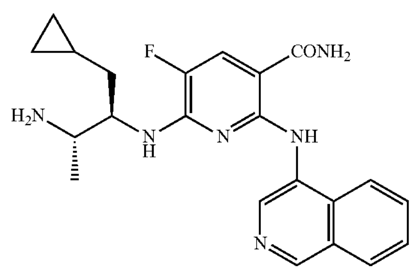 [SMILES: C[C@H](N)[C@@H](CC1CC1)Nc1nc(Nc2cncc3ccccc23)c(C(N)=O)cc1F] | 6-(((2R,3S)-3-amino-1-cyclopropylbutan-2-yl)amino)-5-fluoro-2-(isoquinolin-4-yl)amino)nicotinamide | HCl | | | | 409 | 407 | 0.79 |

TABLE 3-continued

| Example | Name | Salt | Solvent | Freq | NMR | | | |
|---|---|---|---|---|---|---|---|---|
| Example 6-355 | 6-(((2R,3S)-3-amino-1-cyclopropylbutan-2-yl)amino)-5-fluoro-2-((2-methoxypyridin-4-yl)amino)nicotinamide | HCl | | | | 389 | 387 | 0.68 |
| Example 6-356 | 6-(((2R,3S)-3-amino-1-cyclopropylbutan-2-yl)amino)-5-fluoro-2-((1-methyl-1H-indazol-4-yl)amino)nicotinamide | HCl | DMSO-d6 | 300 MHz | δ: 12.39 (s, 1H), 8.02-7.92 (m, 2H), 7.91-7.68 (m, 3H), 7.47-7.00 (m, 6H), 5.90-5.76 (m, 1H), 5.05-4.90 (m, 2H), 4.37-4.25 (m, 1H), 4.03 (s, 3H), 3.49-3.34 (m, 1H), 2.20-1.60 (m, 4H), 1.30-1.16 (m, 3H). | 412 | 410 | 0.97 |
| Example 6-357 | 6-(((2R,3S)-3-amino-1-cyclopropylbutan-2-yl)amino)-5-fluoro-2-((5-fluoropyridin-3-yl)amino)nicotinamide | HCl | | | | 379 | 377 | 0.88 |

TABLE 3-continued

| Example | Structure | Name | Salt | | | |
|---|---|---|---|---|---|---|
| Example 6-358 | 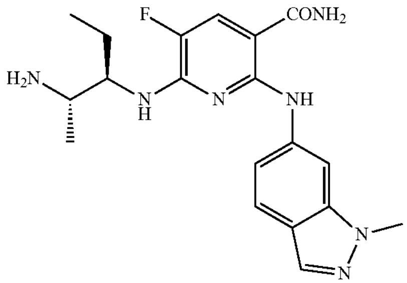 [SMILES: CC[C@@H](Nc1nc(Nc2ccc3cnn(C)c3c2)c(C(N)=O)cc1F)[C@H](C)N] | 6-(((2S,3R)-2-aminopentan-3-yl)amino)-5-fluoro-2-((1-methyl-1H-indazol-6-yl)amino)nicotinamide | HCl | 386 | 384 | 0.82 |
| Example 6-359 | 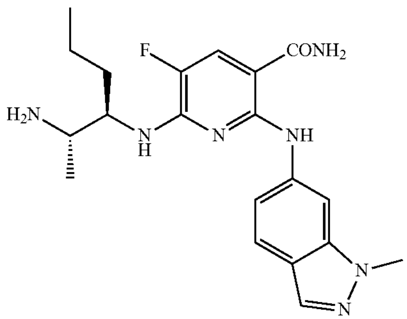 [SMILES: CCC[C@@H](Nc1nc(Nc2ccc3cnn(C)c3c2)c(C(N)=O)cc1F)[C@H](C)N] | 6-(((2S,3R)-2-aminohexan-3-yl)amino)-5-fluoro-2-((1-methyl-1H-indazol-6-yl)amino)nicotinamide | HCl | 400 | 398 | 0.89 |
| Example 6-360 | 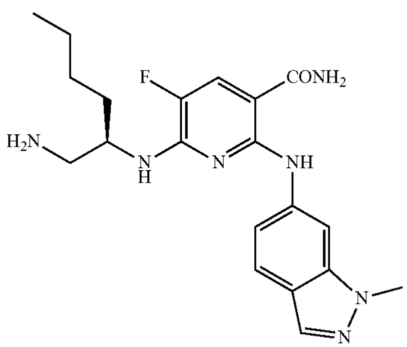 [SMILES: CCCC[C@H](CN)Nc1nc(Nc2ccc3cnn(C)c3c2)c(C(N)=O)cc1F] | (R)-6-((1-aminohexan-2-yl)amino)-5-fluoro-2-((1-methyl-1H-indazol-6-yl)amino)nicotinamide | HCl | 400 | 398 | 0.89 |

TABLE 3-continued

| Example | Structure | Name | Salt | | | |
|---|---|---|---|---|---|---|
| Example 6-361 | 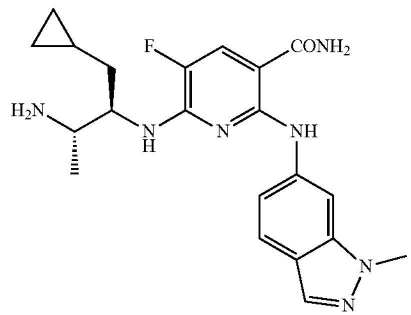 [SMILES: C[C@H](N)[C@@H](CC1CC1)Nc1nc(Nc2ccc3cnn(C)c3c2)c(C(N)=O)cc1F] | 6-(((2R,3S)-3-amino-1-cyclopropylbutan-2-yl)amino)-5-fluoro-2-((1-methyl-1H-indazol-6-yl)amino)nicotinamide | HCl | 412 | 410 | 0.86 |
| Example 6-362 | 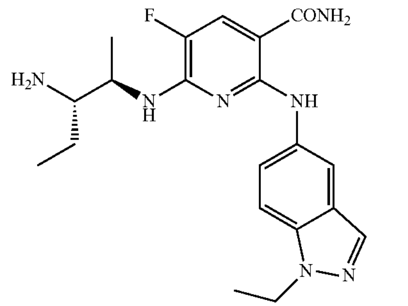 [SMILES: CC[C@H](N)[C@@H](C)Nc1nc(Nc2ccc3c(cnn3CC)c2)c(C(N)=O)cc1F] | 6-(((2R,3S)-3-aminopentan-2-yl)amino)-2-((1-ethyl-1H-indazol-5-yl)amino)-5-fluoronicotinamide | HCl | 400 | 398 | 0.91 |
| Example 6-363 | 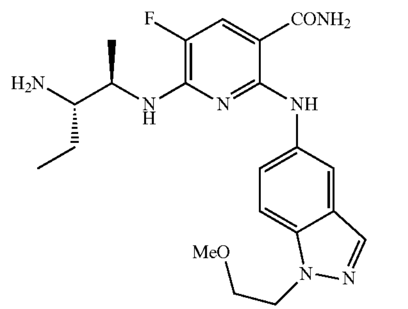 [SMILES: CC[C@H](N)[C@@H](C)Nc1nc(Nc2ccc3c(cnn3CCOC)c2)c(C(N)=O)cc1F] | 6-(((2R,3S)-3-aminopentan-2-yl)amino)-5-fluoro-2-((1-(2-methoxyethyl)-1H-indazol-5-yl)amino)nicotinamide | HCl | 430 | 428 | 0.84 |

TABLE 3-continued

| Example | Structure | Name | Salt | | | |
|---|---|---|---|---|---|---|
| Example 6-364 | 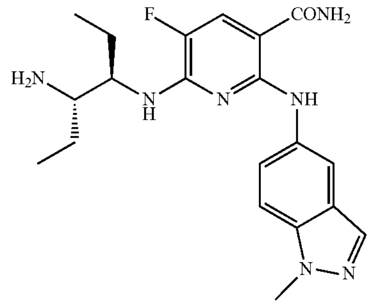 [SMILES: CC[C@H](N)[C@@H](CC)Nc1nc(Nc2ccc3c(cnn3C)c2)c(C(N)=O)cc1F] | 6-(((3R,4S)-4-aminohexan-3-yl)amino)-5-fluoro-2-((1-methyl-1H-indazol-5-yl)amino)nicotinamide | HCl | 400 | 398 | 0.81 |
| Example 6-365 | 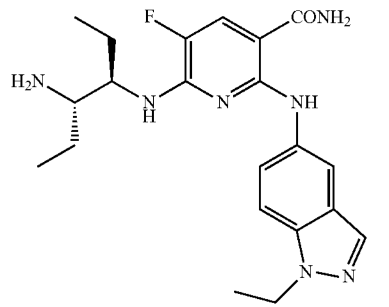 [SMILES: CC[C@H](N)[C@@H](CC)Nc1nc(Nc2ccc3c(cnn3CC)c2)c(C(N)=O)cc1F] | 6-(((3R,4S)-4-aminohexan-3-yl)amino)-2-((1-ethyl-1H-indazol-5-yl)amino)-5-fluoronicotinamide | HCl | 414 | 412 | 0.85 |
| Example 6-366 | 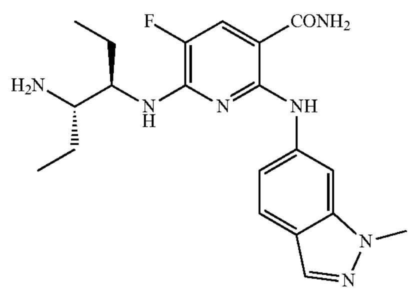 [SMILES: CC[C@H](N)[C@@H](CC)Nc1nc(Nc2ccc3cnn(C)c3c2)c(C(N)=O)cc1F] | 6-(((3R,4S)-4-aminohexan-3-yl)amino)-5-fluoro-2-((1-methyl-1H-indazol-6-yl)amino)nicotinamide | HCl | 400 | 398 | 0.91 |

TABLE 3-continued

| Example | Structure | Name | Salt | Solvent | Freq | NMR | MS1 | MS2 | Value |
|---|---|---|---|---|---|---|---|---|---|
| Example 6-367 | 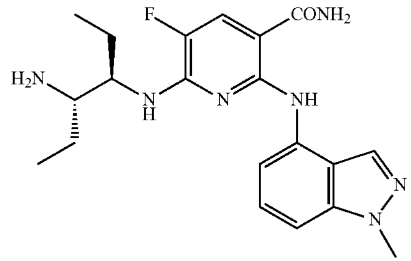 [SMILES: CC[C@H](N)[C@@H](CC)Nc1nc(Nc2cccc3c2cnn3C)c(C(N)=O)cc1F] | 6-(((3R,4S)-4-aminohexan-3-yl)amino)-5-fluoro-2-((1-methyl-1H-indazol-4-yl)amino)nicotinamide | HCl | | | | 400 | 398 | 0.96 |
| Example 6-368 | 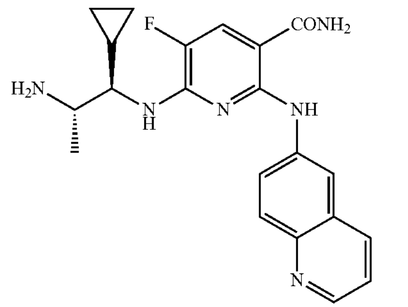 [SMILES: C[C@H](N)[C@H](Nc1nc(Nc2ccc3ncccc3c2)c(C(N)=O)cc1F)C1CC1] | 6-(((1R,2S)-2-amino-1-cyclopropylpropyl)amino)-5-fluoro-2-((quinolin-6-yl)amino)nicotinamide | HCl | DMSO-d6 | 300 MHz | δ: 12.25 (s, 1H), 8.86 (d, 1H, J = 6.0 Hz), 8.77 (d, 1H, J = 6.0 Hz), 8.42 (s, 1H), 8.22-7.80 (m, 8H), 7.47-7.35 (m, 1H), 7.31 (d, 1H, J = 8.6 Hz), 3.91-3.80 (m, 1H), 3.41-3.33 (m, 1H), 1.31 (d, 3H, J = 6.6 Hz), 1.20-1.11 (m, 1H), 0.78-0.33 (m, 4H). | 395 | 393 | 0.64 |
| Example 6-369 | 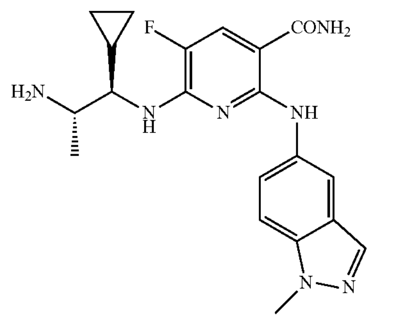 [SMILES: C[C@H](N)[C@H](Nc1nc(Nc2ccc3c(cnn3C)c2)c(C(N)=O)cc1F)C1CC1] | 6-(((1R,2S)-2-amino-1-cyclopropylpropyl)amino)-5-fluoro-2-((1-methyl-1H-indazol-5-yl)amino)nicotinamide | HCl | | | | 398 | 396 | 0.84 |

TABLE 3-continued

| Example | Structure | Name | Salt | | | |
|---|---|---|---|---|---|---|
| Example 6-370 | 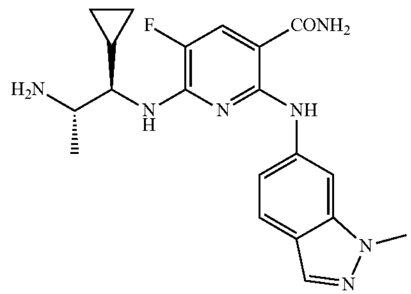 [SMILES: C[C@H](N)[C@H](Nc1nc(Nc2ccc3cnn(C)c3c2)c(C(N)=O)cc1F)C1CC1] | 6-(((1R,2S)-2-amino-1-cyclopropylpropyl)amino)-5-fluoro-2-((1-methyl-1H-indazol-6-yl)amino)nicotinamide | HCl | 398 | 396 | 0.85 |
| Example 6-371 | 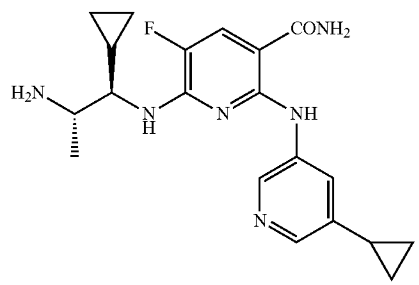 [SMILES: C[C@H](N)[C@H](Nc1nc(Nc2cncc(C3CC3)c2)c(C(N)=O)cc1F)C1CC1] | 6-(((1R,2S)-2-amino-1-cyclopropylpropyl)amino)-2-((5-cyclopropylpyridin-3-yl)amino)-5-fluoronicotinamide | HCl | 385 | 383 | 0.67 |
| Example 6-372 | 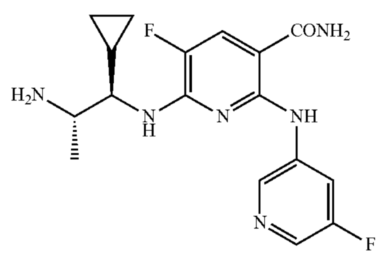 [SMILES: C[C@H](N)[C@H](Nc1nc(Nc2cncc(F)c2)c(C(N)=O)cc1F)C1CC1] | 6-(((1R,2S)-2-amino-1-cyclopropylpropyl)amino)-5-fluoro-2-((5-fluoropyridin-3-yl)amino)nicotinamide | HCl | 363 | 361 | 0.8 |

TABLE 3-continued

| Example | Structure | Name | Salt | Solvent | Freq | NMR | | | |
|---|---|---|---|---|---|---|---|---|---|
| Example 6-373 | 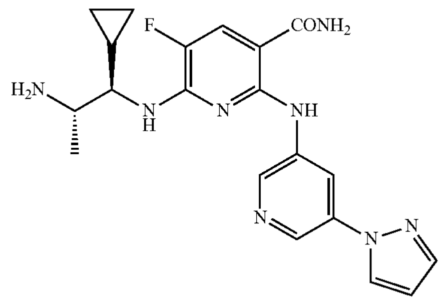 [SMILES: C[C@H](N)[C@H](Nc1nc(Nc2cncc(-n3cccn3)c2)c(C(N)=O)cc1F)C1CC1] | 2-((5-((1H-pyrazol-1-yl)pyridin-3-yl)amino)-6-(((1R,2S)-2-amino-1-cyclopropylpropyl)amino)-5-fluoronicotinamide | HCl | DMSO-d6 | 300 MHz | δ: 11.98 (dd, 1H, J = 26.1, 18.2 Hz), 8.76-8.53 (m, 4H), 8.02-7.74 (m, 6H), 7.48-7.25 (m, 2H), 6.64 (dq, 1H, J = 27.1, 9.5 Hz), 3.82-3.72 (m, 1H), 3.41-3.33 (m, 1H), 1.25-1.05 (m, 4H), 0.63-0.24 (m, 4H). | 411 | 409 | 0.84 |
| Example 6-374 | 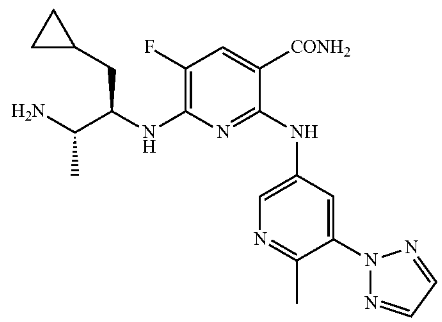 [SMILES: Cc1ncc(Nc2nc(N[C@H](CC3CC3)[C@H](C)N)c(F)cc2C(N)=O)cc1-n1nccn1] | 6-(((2R,3S)-3-amino-1-cyclopropylbutan-2-yl)amino)-5-fluoro-2-((6-methyl-5-(2H-1,2,3-triazol-2-yl)pyridin-3-yl)amino)nicotinamide | HCl | | | | 440 | 438 | 0.96 |
| Example 6-375 | 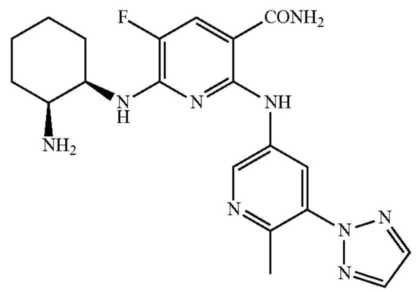 [SMILES: Cc1ncc(Nc2nc(N[C@@H]3CCCC[C@@H]3N)c(F)cc2C(N)=O)cc1-n1nccn1] | 6-(((1R,2S)-2-aminocyclohexyl)amino)-5-fluoro-2-((6-methyl-5-(2H-1,2,3-triazol-2-yl)pyridin-3-yl)amino)nicotinamide | HCl | DMSO-d6 | 300 MHz | δ: 11.96 (s, 1H), 8.65 (d, 1H, J = 2.4 Hz), 8.55 (d, 1H, J = 2.4 Hz), 8.22 (s, 2H), 7.98 (d, 1H, J = 12.6 Hz), 7.94-7.66 (m, 4H), 7.41 (br, 1H), 6.97 (d, 1H, J = 5.4 Hz), 4.24-4.12 (m, 1H), 2.50 (s, 3H), 3.58-3.45 (m, 1H), 1.90-1.10 (m, 8H). | 426 | 424 | 0.86 |

TABLE 3-continued

| Example | Structure | Name | Salt | Solvent | NMR Freq | NMR | MW+1 | MW | ret |
|---|---|---|---|---|---|---|---|---|---|
| Example 6-376 | 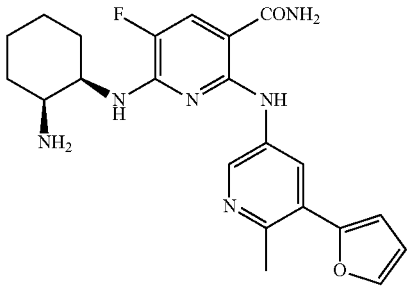 [SMILES: Cc1ncc(Nc2nc(N[C@@H]3CCCC[C@@H]3N)c(F)cc2C(N)=O)cc1-c1ccco1] | 6-(((1R,2S)-2-aminocyclohexyl)amino)-5-fluoro-2-((5-(furan-2-yl)-6-methylpyridin-3-yl)amino)nicotinamide | HCl | DMSO-d6 | 300 MHz | δ: 12.00 (s, 1H), 8.88-8.82 (m, 1H), 8.68-8.62 (m, 1H), 8.04-7.84 (m, 6H), 7.45 (br, 1H), 7.12 (d, 1H, J = 3.9 Hz), 7.02 (d, 1H, J = 6.6 Hz), 6.78-6.74 (m, 1H), 4.34-4.22 (m, 1H), 3.60-3.56 (m, 1H), 2.76 (s, 3H), 1.90-1.25 (m, 8H). | 425 | 423 | 0.76 |
| Example 6-377 | 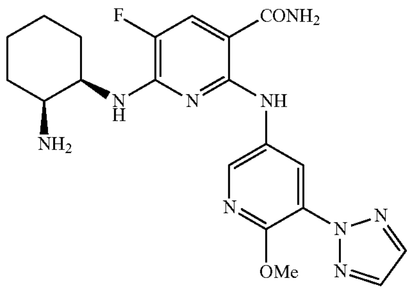 [SMILES: COc1ncc(Nc2nc(N[C@@H]3CCCC[C@@H]3N)c(F)cc2C(N)=O)cc1-n1nccn1] | 6-(((1R,2S)-2-aminocyclohexyl)amino)-5-fluoro-2-((6-methoxy-5-(2H-1,2,3-triazol-2-yl)pyridin-3-yl)amino)nicotinamide | HCl | DMSO-d6 | 300 MHz | δ: 11.59 (s, 1H), 8.52 (d, 1H, J = 2.4 Hz), 8.28 (d, 1H, J = 2.4 Hz), 8.13 (s, 2H), 7.94 (d, 1H, J = 12.3 Hz), 7.88-7.67 (m, 4H), 7.33 (br, 1H), 6.91 (d, 1H, J = 7.2 Hz), 4.17-4.05 (m, 1H), 3.89 (s, 3H), 3.51-3.40 (m, 1H), 1.80-1.15 (m, 8H). | 442 | 440 | 0.88 |
| Example 6-378 | 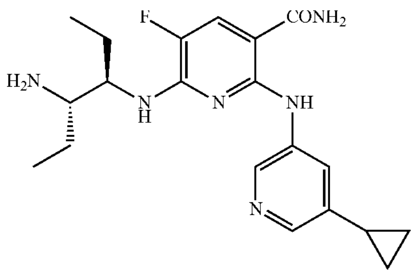 [SMILES: CC[C@H](N)[C@@H](CC)Nc1nc(Nc2cncc(C3CC3)c2)c(C(N)=O)cc1F] | 6-(((3R,4S)-4-aminohexan-3-yl)amino)-2-((5-cyclopropylpyridin-3-yl)amino)-5-fluoronicotinamide | HCl | | | | 387 | 385 | 0.68 |
| Example 6-379 | 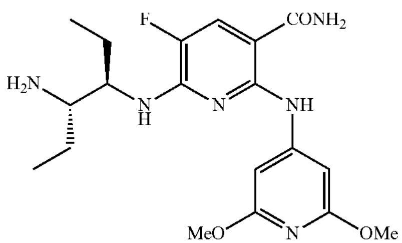 [SMILES: CC[C@H](N)[C@@H](CC)Nc1nc(Nc2cc(OC)nc(OC)c2)c(C(N)=O)cc1F] | 6-(((3R,4S)-4-aminohexan-3-yl)amino)-2-((2,6-dimethoxypyridin-4-yl)amino)-5-fluoronicotinamide | HCl | | | | 407 | 405 | 0.98 |

TABLE 3-continued

| Example | Structure | Name | Salt | | | |
|---|---|---|---|---|---|---|
| Example 6-380 | 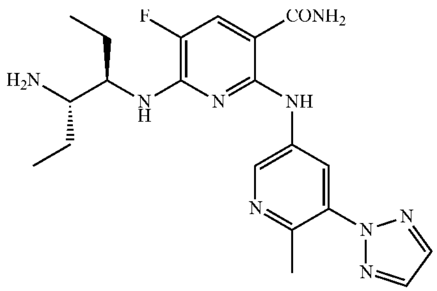 [SMILES: CC[C@H](N)[C@@H](CC)Nc1nc(Nc2cnc(C)c(-n3nccn3)c2)c(C(N)=O)cc1F] | 6-(((3R,4S)-4-aminohexan-3-yl)amino)-5-fluoro-2-((6-methyl-5-(2H-1,2,3-triazol-2-yl)pyridin-3-yl)amino)nicotinamide | HCl | 428 | 426 | 0.85 |
| Example 6-381 | 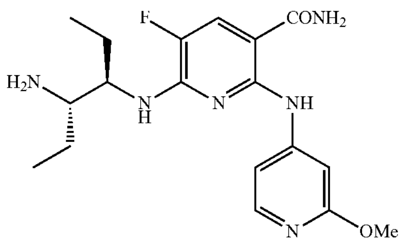 [SMILES: CC[C@H](N)[C@@H](CC)Nc1nc(Nc2ccnc(OC)c2)c(C(N)=O)cc1F] | 6-(((3R,4S)-4-aminohexan-3-yl)amino)-5-fluoro-2-((2-methoxypyridin-4-yl)amino)nicotinamide | HCl | 377 | 375 | 0.62 |
| Example 6-382 | 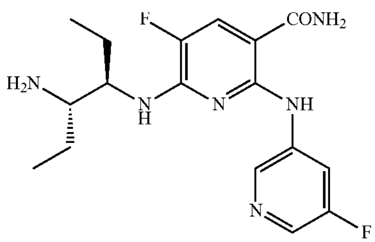 [SMILES: CC[C@H](N)[C@@H](CC)Nc1nc(Nc2cncc(F)c2)c(C(N)=O)cc1F] | 6-(((3R,4S)-4-aminohexan-3-yl)amino)-5-fluoro-2-((5-fluoropyridin-3-yl)amino)nicotinamide | HCl | 365 | 363 | 0.82 |

TABLE 3-continued

| Example | Structure | Name | Salt | Solvent | Freq | NMR | MS1 | MS2 | MS3 |
|---|---|---|---|---|---|---|---|---|---|
| Example 6-383 | 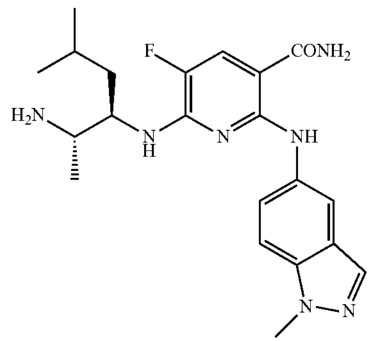 [SMILES: CC(C)C[C@@H](Nc1nc(Nc2ccc3c(cnn3C)c2)c(C(N)=O)cc1F)[C@H](C)N] | 6-(((2S,3R)-2-amino-5-methylhexan-3-yl)amino)-2-((1-methyl-1H-indazol-5-yl)amino)nicotinamide | HCl | CD3OD | 300 MHz | δ: 7.93 (s, 1H), 7.90 (s, 1H), 7.75 (d, 1H, J = 11.9 Hz), 7.55 (d, 1H, J = 8.6 Hz), 7.43 (dd, 1H, J = 8.9, 1.7 Hz), 4.32-4.28 (m, 1H), 4.07 (s, 3H), 3.38-3.35 (m, 1H), 1.72-1.57 (m, 1H), 1.35-1.30 (m, 2H), 1.17 (d, 3H, J = 6.6 Hz), 0.99 (d, 3H, J = 5.9 Hz), 0.91 (d, 3H, J = 5.9 Hz). | 414 | 412 | 0.95 |
| Example 6-384 | 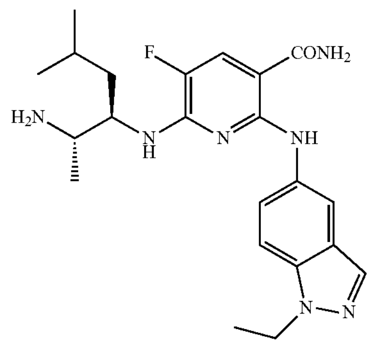 [SMILES: CCn1ncc2cc(Nc3nc(N[C@H](CC(C)C)[C@H](C)N)c(F)cc3C(N)=O)ccc21] | 6-(((2S,3R)-2-amino-5-methylhexan-3-yl)amino)-2-((1-ethyl-1H-indazol-5-yl)amino)-5-fluoronicotinamide | HCl | CD3OD | 300 MHz | δ: 7.93 (s, 1H), 7.91 (d, 1H, J = 2.0 Hz), 7.76 (d, 1H, J = 11.9 Hz), 7.56 (d, 1H, J = 8.6 Hz), 7.42 (dd, 1H, J = 9.2, 2.0 Hz), 4.46 (q, 2H, J = 7.3 Hz), 4.36-4.31 (m, 1H), 3.41-3.39 (m, 1H), 1.73-1.56 (m, 1H), 1.47 (t, 3H, J = 7.3 Hz), 1.36-1.30 (m, 2H), 1.17 (d, 3H, J = 6.6 Hz), 0.99 (d, 3H, J = 6.6 Hz), 0.92 (d, 3H, J = 6.6 Hz). | 428 | 426 | 1 |
| Example 6-385 | 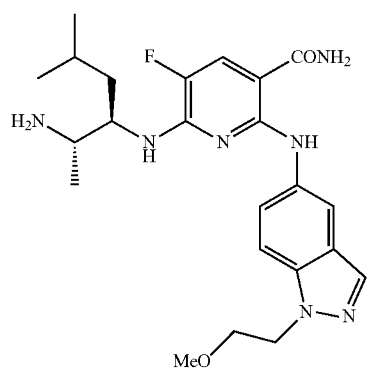 [SMILES: COCCn1ncc2cc(Nc3nc(N[C@H](CC(C)C)[C@H](C)N)c(F)cc3C(N)=O)ccc21] | 6-(((2S,3R)-2-amino-5-methylhexan-3-yl)amino)-5-fluoro-2-((1-(2-methoxyethyl)-1H-indazol-5-yl)amino)nicotinamide | HCl | | | | 458 | 456 | 0.96 |

TABLE 3-continued

| Example 6-386 | [structure] | 6-(((2S,3R)-2-amino-5-methylhexan-3-yl)amino)-5-fluoro-2-((6-methyl-5-(2H-1,2,3-triazol-2-yl)pyridin-3-yl)amino)nicotinamide | HCl | 442 | 440 | 0.94 |
| --- | --- | --- | --- | --- | --- | --- |
| Example 6-387 | [structure] | 6-(((2S,3R)-2-aminoheptane-3-yl)amino)-5-fluoro-2-((1-methyl-1H-indazol-5-yl)amino)nicotinamide | HCl | 414 | 412 | 0.95 |
| Example 6-388 | [structure] | 6-(((2S,3R)-2-aminoheptane-3-yl)amino)-2-((1-ethyl-1H-indazol-5-yl)amino)-5-fluoronicotinamide | HCl | 428 | 426 | 1 |

TABLE 3-continued
| Example 6-389 | 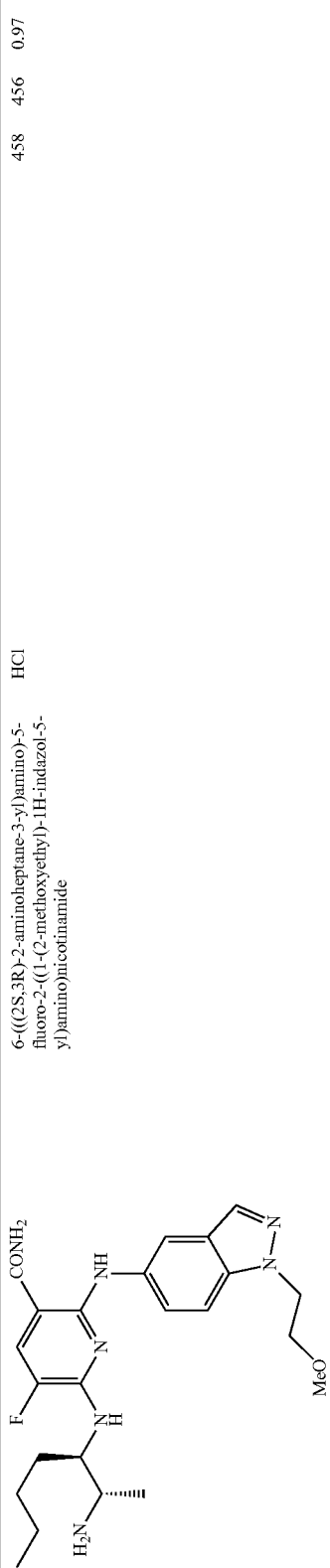 | 6-(((2S,3R)-2-aminoheptane-3-yl)amino)-5-fluoro-2-((1-(2-methoxyethyl)-1H-indazol-5-yl)amino)nicotinamide | HCl | 458 | 456 | 0.97 |
| --- | --- | --- | --- | --- | --- | --- |
| Example 6-390 | 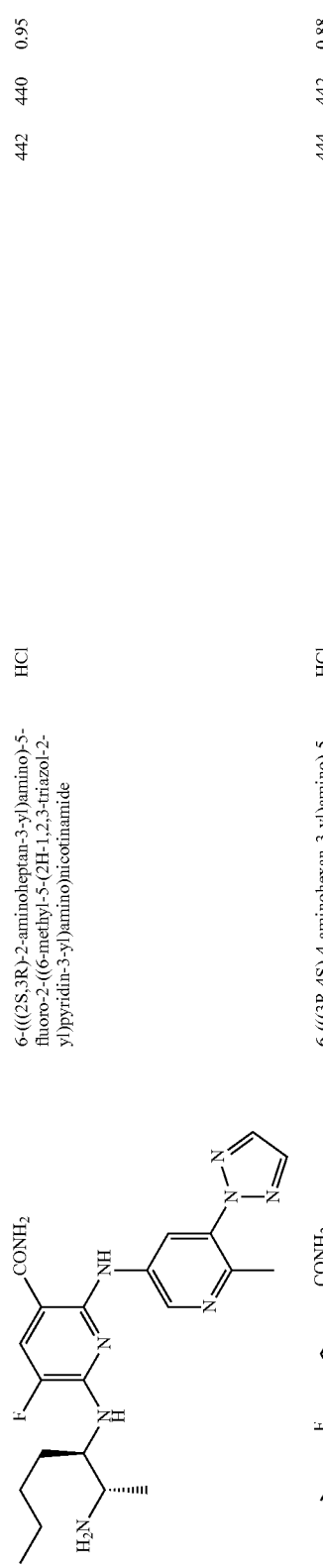 | 6-(((2S,3R)-2-aminoheptan-3-yl)amino)-5-fluoro-2-((6-methyl-5-(2H-1,2,3-triazol-2-yl)pyridin-3-yl)amino)nicotinamide | HCl | 442 | 440 | 0.95 |
| Example 6-391 | 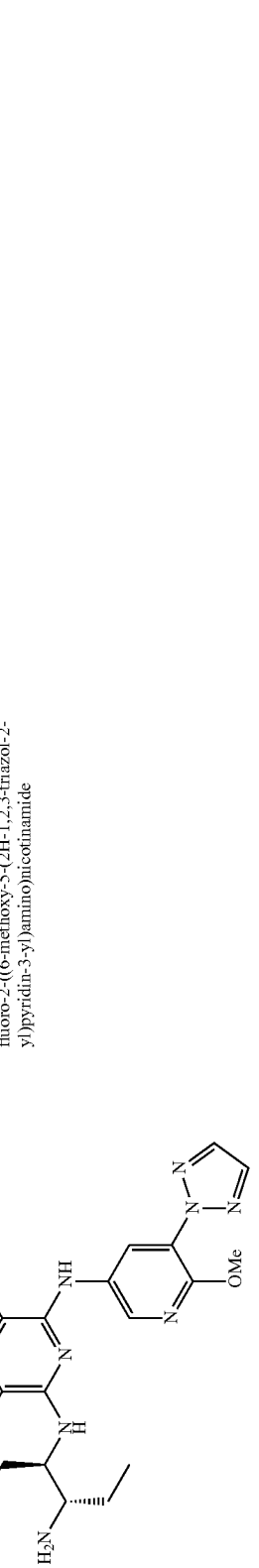 | 6-(((3R,4S)-4-aminohexan-3-yl)amino)-5-fluoro-2-((6-methoxy-5-(2H-1,2,3-triazol-2-yl)pyridin-3-yl)amino)nicotinamide | HCl | 444 | 442 | 0.88 |

TABLE 3-continued

| Example 6-392 | 2-((5-(1H-pyrazol-1-yl)pyridin-3-yl)amino)-6-(((2R,3S)-3-amino-1-cyclopropylbutan-2-yl)amino)-5-fluoronicotinamide | HCl | DMSO-d6 | 300 MHz | δ: 11.98 (s, 1H), 8.89-8.54 (m, 3H), 8.01-7.70 (m, 6H), 7.50-7.30 (m, 1H), 7.20-7.00 (m, 2H), 6.62 (t, 1H, J = 2.3 Hz), 5.87-5.30 (m, 1H), 4.95-4.82 (m, 2H), 4.56-4.45 (m, 1H), 3.51-3.43 (m, 1H), 2.25-1.62 (m, 4H), 1.21-1.11 (m, 3H). | 425 | 423 | 0.91 |
| --- | --- | --- | --- | --- | --- | --- | --- | --- |
| Example 6-393 | 6-(((2R,3S)-3-amino-1-cyclopropylbutan-2-yl)amino)-5-fluoro-2-((6-methoxy-5-(2H-1,2,3-triazol-2-yl)pyridin-3-yl)amino)nicotinamide | HCl | | | | 456 | 454 | 0.95 |
| Example 6-394 | 6-(((2R,3S)-3-amino-1-cyclopropylbutan-2-yl)amino)-5-fluoro-2-((2-(2-methoxyethoxy)pyridin-4-yl)amino)nicotinamide | HCl | | | | 433 | 431 | 0.74 |

TABLE 3-continued

| Example | Structure | Name | Salt | Solvent | MHz | NMR | M+1 | M-1 | RT |
|---|---|---|---|---|---|---|---|---|---|
| Example 6-395 | 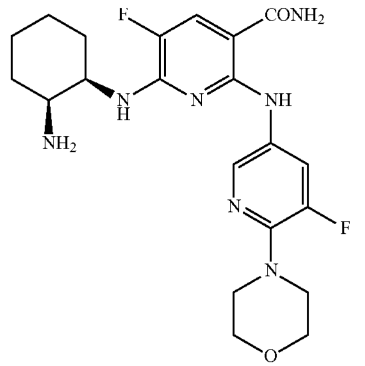 [SMILES: NC(=O)c1cc(F)c(N[C@@H]2CCCC[C@@H]2N)nc1Nc1cnc(N2CCOCC2)c(F)c1] | 6-(((1R,2S)-2-aminocyclohexyl)amino)-5-fluoro-2-((5-fluoro-6-morpholinopyridin-3-yl)amino)nicotinamide | HCl | DMSO-d6 | 300 MHz | δ: 11.48 (s, 1H), 8.10-8.00 (m, 1H), 8.08 (s, 1H), 7.92 (d, 1H, J = 12.2 Hz), 7.87-7.66 (m, 4H), 7.36-7.21 (m, 1H), 6.97-6.88 (m, 1H), 4.23-4.12 (m, 1H), 3.77-3.69 (m, 4H), 3.68-3.59 (m, 1H), 3.28-3.20 (m, 4H), 1.96-1.34 (m, 8H). | 448 | 446 | 0.91 |
| Example 6-396 | 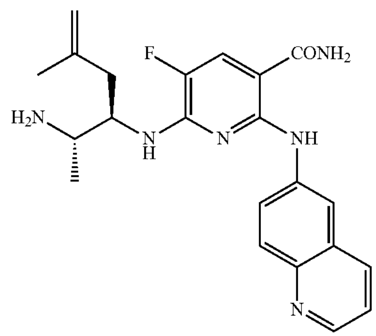 [SMILES: C=C(C)C[C@@H](Nc1nc(Nc2ccc3ncccc3c2)c(C(N)=O)cc1F)[C@H](C)N] | 6-(((2S,3R)-2-amino-5-methylhex-5-en-3-yl)amino)-5-fluoro-2-(quinolin-6-yl)amino)nicotinamide | HCl | | | | 409 | 407 | 0.74 |
| Example 6-397 | 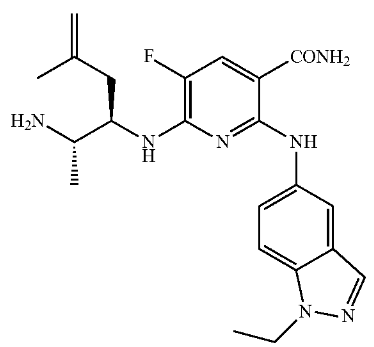 [SMILES: C=C(C)C[C@@H](Nc1nc(Nc2ccc3c(cnn3CC)c2)c(C(N)=O)cc1F)[C@H](C)N] | 6-(((2S,3R)-2-amino-5-methylhex-5-en-3-yl)amino)-2-((1-ethyl-1H-indazol-5-yl)amino)-5-fluoronicotinamide | HCl | | | | 427 | 425 | |

TABLE 3-continued

| Example | Name | Salt | NMR | MS | MS | RT |
|---|---|---|---|---|---|---|
| Example 6-398 | 6-(((3S,4R)-3-aminoheptan-4-yl)amino)-5-fluoro-2-((1-methyl-1H-indazol-5-yl)amino)nicotinamide | HCl | | 414 | 412 | 0.97 |
| Example 6-399 | 6-(((3S,4R)-3-aminoheptan-4-yl)amino)-2-(((1-ethyl-1H-indazol-5-yl)amino)-5-fluoronicotinamide | HCl | | 428 | 426 | 1.01 |
| Example 6-400 | 6-(((3S,4R)-3-aminoheptan-4-yl)amino)-5-fluoro-2-((1-(2-methoxyethyl)-1H-indazol-5-yl)amino)nicotinamide | HCl | CD3OD 300 MHz δ: 7.95 (s, 1H), 7.86 (d, 1H, J = 1.3 Hz), 7.75 (d, 1H, J = 11.9 Hz), 7.57 (d, 1H, J = 8.9 Hz), 7.40 (dd, 1H, J = 9.1, 1.8 Hz), 4.56 (t, 2H, J = 5.1 Hz), 4.31-4.21 (m, 1H), 3.82 (t, 2H, J = 5.1 Hz), 3.28 (s, 3H), 3.26-3.18 (m, 1H), 1.68-1.32 (m, 6H), 0.99 (t, 3H, J = 6.9 Hz), 0.75 (t, 3H, J = 7.6 Hz). | 458 | 456 | 0.96 |

TABLE 3-continued

| | Structure | Name | Salt | | | |
|---|---|---|---|---|---|---|
| Example 6-401 | 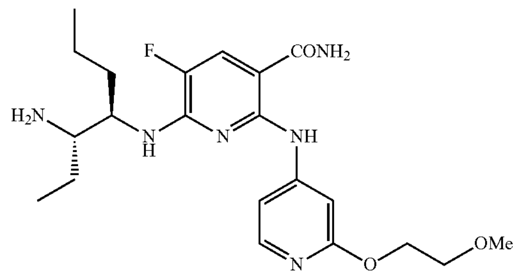 [SMILES: CCC[C@@H](Nc1nc(Nc2ccnc(OCCOC)c2)c(C(N)=O)cc1F)[C@@H](N)CC] | 6-(((3S,4R)-3-aminoheptan-4-yl)amino)-5-fluoro-2-((2-(2-methoxyethoxy)pyridin-4-yl)amino)nicotinamide | HCl | 435 | 433 | 0.76 |
| Example 6-402 | 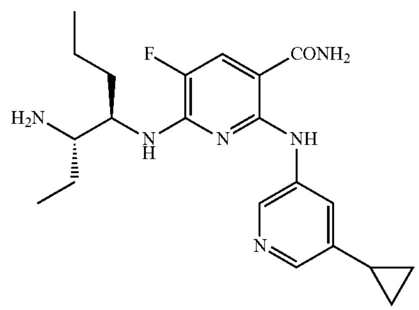 [SMILES: CCC[C@@H](Nc1nc(Nc2cncc(C3CC3)c2)c(C(N)=O)cc1F)[C@@H](N)CC] | 6-(((3S,4R)-3-aminoheptan-4-yl)amino)-2-((5-cyclopropylpyridin-3-yl)amino)-5-fluoronicotinamide | HCl | 401 | 399 | 0.77 |
| Example 6-403 | 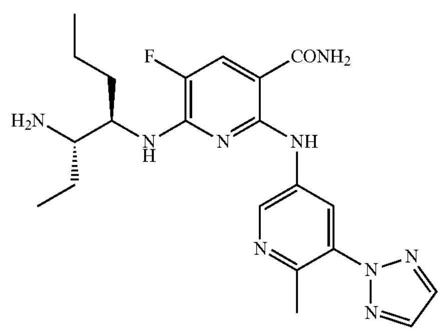 [SMILES: CCC[C@@H](Nc1nc(Nc2cnc(C)c(-n3nccn3)c2)c(C(N)=O)cc1F)[C@@H](N)CC] | 6-(((3S,4R)-3-aminoheptan-4-yl)amino)-5-fluoro-2-((6-methyl-5-(2H-1,2,3-triazol-2-yl)pyridin-3-yl)amino)nicotinamide | HCl | 442 | 440 | 0.94 |

TABLE 3-continued

| Example | Structure | Name | Salt | | | |
|---|---|---|---|---|---|---|
| Example 6-404 | 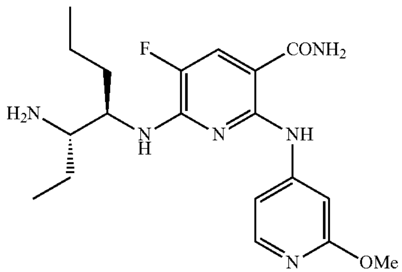 [SMILES: CCC[C@@H](Nc1nc(Nc2ccnc(OC)c2)c(C(N)=O)cc1F)[C@@H](N)CC] | 6-(((3S,4R)-3-aminoheptan-4-yl)amino)-5-fluoro-2-((2-methoxypyridin-4-yl)amino)nicotinamide | HCl | 391 | 389 | 0.71 |
| Example 6-405 | 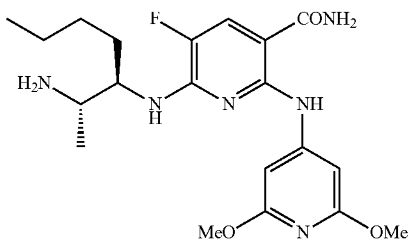 [SMILES: CCCC[C@@H](Nc1nc(Nc2cc(OC)nc(OC)c2)c(C(N)=O)cc1F)[C@H](C)N] | 6-(((2S,3R)-2-aminoheptan-3-yl)amino)-2-((2,6-dimethoxypyridin-4-yl)amino)-5-fluoronicotinamide | HCl | 421 | 419 | 1.07 |
| Example 6-406 | 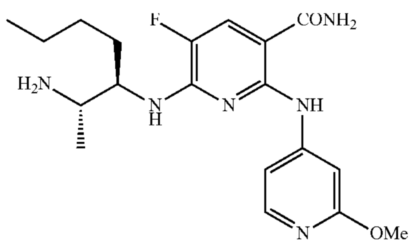 [SMILES: CCCC[C@@H](Nc1nc(Nc2ccnc(OC)c2)c(C(N)=O)cc1F)[C@H](C)N] | 6-(((2S,3R)-2-aminoheptan-3-yl)amino)-5-fluoro-2-((2-methoxypyridin-4-yl)amino)nicotinamide | HCl | 391 | 389 | 0.72 |
| Example 6-407 | 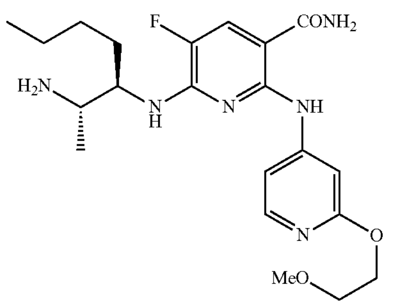 [SMILES: CCCC[C@@H](Nc1nc(Nc2ccnc(OCCOC)c2)c(C(N)=O)cc1F)[C@H](C)N] | 6-(((2S,3R)-2-aminoheptan-3-yl)amino)-5-fluoro-2-((2-(2-methoxyethoxy)pyridin-4-yl)amino)nicotinamide | HCl | 435 | 433 | 0.78 |

TABLE 3-continued

| Example | Structure | Name | Salt | | | |
|---|---|---|---|---|---|---|
| Example 6-408 | 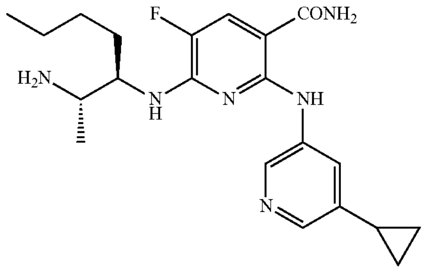 [SMILES: CCCC[C@@H](Nc1nc(Nc2cncc(C3CC3)c2)c(C(N)=O)cc1F)[C@H](C)N] | 6-(((2S,3R)-2-aminoheptan-3-yl)amino)-2-((5-cyclopropylpyridin-3-yl)amino)-5-fluoronicotinamide | HCl | 401 | 399 | 0.77 |
| Example 6-409 | 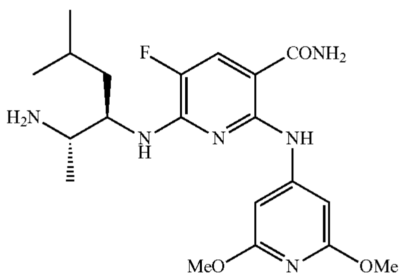 [SMILES: COc1cc(Nc2nc(N[C@H](CC(C)C)[C@H](C)N)c(F)cc2C(N)=O)cc(OC)n1] | 6-(((2S,3R)-2-amino-5-methylhexan-3-yl)amino)-2-((2,6-dimethoxypyridin-4-yl)amino)-5-fluoronicotinamide | HCl | 421 | 419 | 1.07 |
| Example 6-410 | 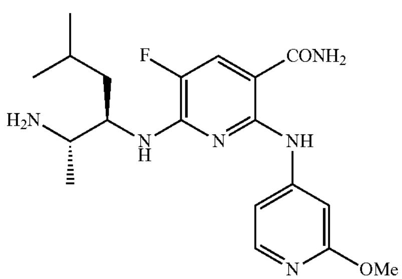 [SMILES: COc1cc(Nc2nc(N[C@H](CC(C)C)[C@H](C)N)c(F)cc2C(N)=O)ccn1] | 6-(((2S,3R)-2-amino-5-methylhexan-3-yl)amino)-5-fluoro-2-((2-methoxypyridin-4-yl)amino)nicotinamide | HCl | 391 | 389 | 0.71 |

TABLE 3-continued

| Example | Structure | Name | Salt | | | |
|---|---|---|---|---|---|---|
| Example 6-411 | 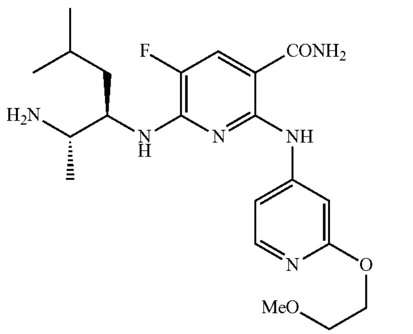 [SMILES: COCCOc1cc(Nc2nc(N[C@H](CC(C)C)[C@H](C)N)c(F)cc2C(N)=O)ccn1] | 6-(((2S,3R)-2-amino-5-methylhexan-3-yl)amino)-5-fluoro-2-((2-(2-methoxyethoxy)pyridin-4-yl)amino)nicotinamide | HCl | 435 | 433 | 0.77 |
| Example 6-412 | 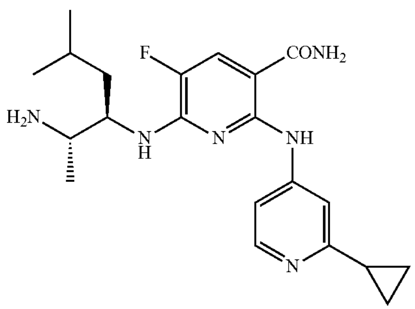 [SMILES: CC(C)C[C@@H](Nc1nc(Nc2ccnc(C3CC3)c2)c(C(N)=O)cc1F)[C@H](C)N] | 6-(((2S,3R)-2-amino-5-methylhexan-3-yl)amino)-2-((5-cyclopropylpyridin-3-yl)amino)-5-fluoronicotinamide | HCl | 401 | 399 | 0.76 |
| Example 6-413 | 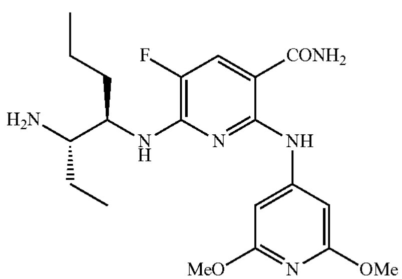 [SMILES: CCC[C@@H](Nc1nc(Nc2cc(OC)nc(OC)c2)c(C(N)=O)cc1F)[C@@H](N)CC] | 6-(((3S,4R)-3-aminoheptan-4-yl)amino)-2-((2,6-dimethoxypyridin-4-yl)amino)-5-fluoronicotinamide | HCl | 421 | 419 | 1.07 |

TABLE 3-continued

| Example | Structure | Name | Salt | | | |
|---|---|---|---|---|---|---|
| Example 6-414 | 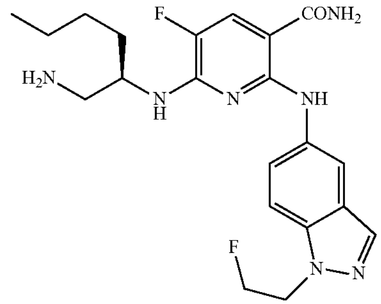 [SMILES: CCCC[C@H](CN)Nc1nc(Nc2ccc3c(cnn3CCF)c2)c(C(N)=O)cc1F] | (R)-6-((1-aminohexan-2-yl)amino)-5-fluoro-2-(1-(2-fluoroethyl)-1H-indazol-5-yl)amino)nicotinamide | HCl | 432 | 430 | 0.92 |
| Example 6-415 | 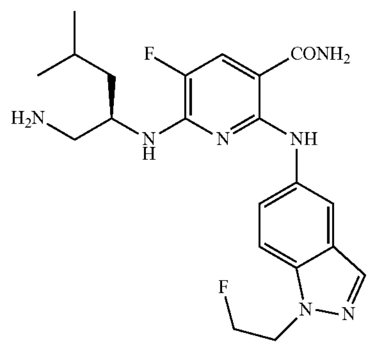 [SMILES: CC(C)C[C@H](CN)Nc1nc(Nc2ccc3c(cnn3CCF)c2)c(C(N)=O)cc1F] | (R)-6-((1-amino-4-methylpentan-2-yl)amino)-5-fluoro-2-((1-(2-fluoroethyl)-1H-indazol-5-yl)amino)nicotinamide | HCl | 432 | 430 | 0.91 |
| Example 6-416 | 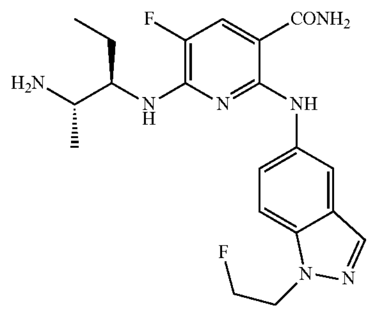 [SMILES: CC[C@@H](Nc1nc(Nc2ccc3c(cnn3CCF)c2)c(C(N)=O)cc1F)[C@H](C)N] | 6-(((2S,3R)-2-aminopentan-3-yl)amino)-5-fluoro-2-((1-(2-fluoroethyl)-1H-indazol-5-yl)amino)nicotinamide | HCl | 418 | 416 | 0.79 |

TABLE 3-continued

| Example | Structure | Name | Salt | | | |
|---|---|---|---|---|---|---|
| Example 6-417 | 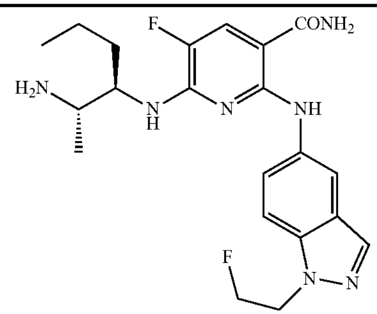 | 6-(((2S,3R)-2-aminohexan-3-yl)amino)-5-fluoro-2-((1-(2-fluoroethyl)-1H-indazol-5-yl)amino)nicotinamide | HCl | 432 | 430 | 0.87 |
| Example 6-418 | 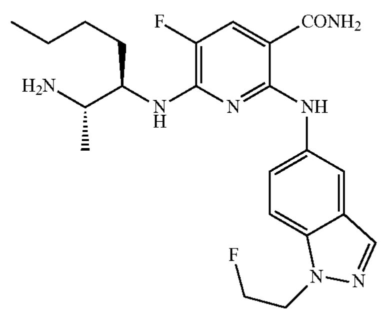 [SMILES: CCCC[C@@H](Nc1nc(Nc2ccc3c(cnn3CCF)c2)c(C(N)=O)cc1F)[C@H](C)N] | 6-(((2S,3R)-2-aminoheptan-3-yl)amino)-5-fluoro-2-((1-(2-fluoroethyl)-1H-indazol-5-yl)amino)nicotinamide | HCl | 446 | 444 | 0.94 |
| Example 6-419 | 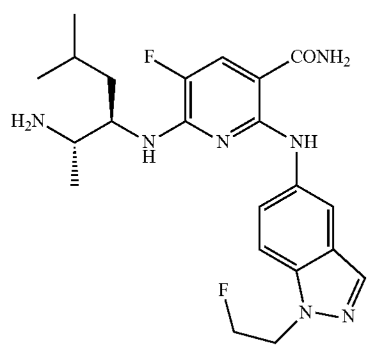 [SMILES: CC(C)C[C@@H](Nc1nc(Nc2ccc3c(cnn3CCF)c2)c(C(N)=O)cc1F)[C@H](C)N] | 6-(((2S,3R)-2-amino-5-methylhexan-3-yl)amino)-5-fluoro-2-((1-(2-fluoroethyl)-1H-indazol-5-yl)amino)nicotinamide | HCl | 446 | 444 | 0.93 |

TABLE 3-continued

| Example | Structure | Name | Salt | | | |
|---|---|---|---|---|---|---|
| Example 6-420 | 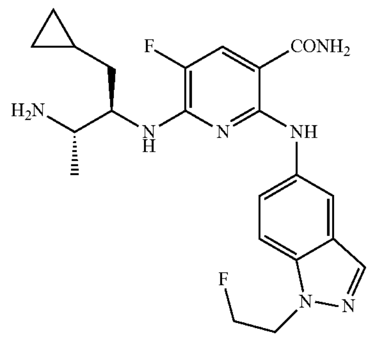 [SMILES: C[C@H](N)[C@@H](CC1CC1)Nc1nc(Nc2ccc3c(cnn3CCF)c2)c(C(N)=O)cc1F] | 6-(((2R,3S)-3-amino-1-cyclopropylbutan-2-yl)amino)-5-fluoro-2-((1-(2-fluoroethyl)-1H-indazol-5-yl)amino)nicotinamide | HCl | 444 | 442 | 0.88 |
| Example 6-421 | 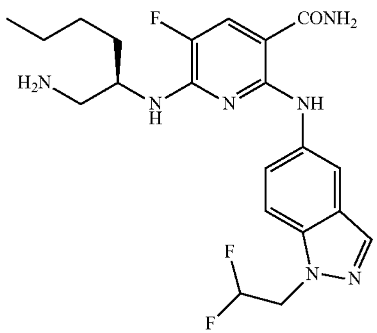 [SMILES: CCCC[C@H](CN)Nc1nc(Nc2ccc3c(cnn3CC(F)F)c2)c(C(N)=O)cc1F] | (R)-6-((1-aminohexan-2-yl)amino)-2-((1-(2,2-difluoroethyl)-1H-indazol-5-yl)amino)-5-fluoronicotinamide | HCl | 450 | 448 | 0.96 |
| Example 6-422 | 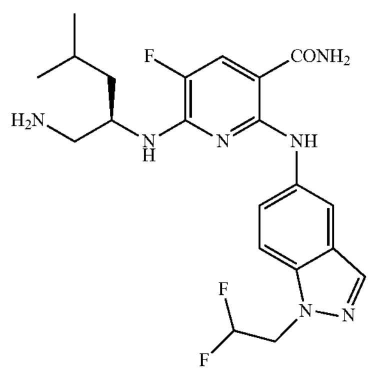 [SMILES: CC(C)C[C@H](CN)Nc1nc(Nc2ccc3c(cnn3CC(F)F)c2)c(C(N)=O)cc1F] | (R)-6-((1-amino-4-methylpentan-2-yl)amino)-2-((1-(2,2-difluoroethyl)-1H-indazol-5-yl)amino)-5-fluoronicotinamide | HCl | 450 | 448 | 0.96 |

TABLE 3-continued

| Example | Structure | Name | Salt | | | |
|---|---|---|---|---|---|---|
| Example 6-423 | 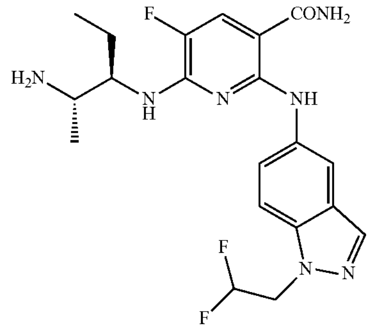 [SMILES: CC[C@@H](Nc1nc(Nc2ccc3c(cnn3CC(F)F)c2)c(C(N)=O)cc1F)[C@H](C)N] | 6-(((2S,3R)-2-aminopentan-3-yl)amino)-2-((1-(2,2-difluoroethyl)-1H-indazol-5-yl)amino)-5-fluoronicotinamide | HCl | 436 | 434 | 0.85 |
| Example 6-424 | 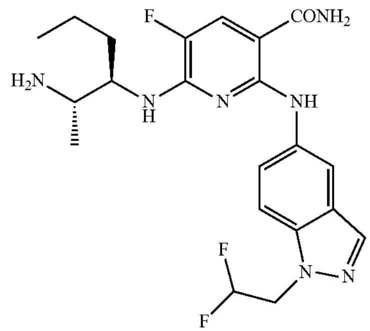 [SMILES: CCC[C@@H](Nc1nc(Nc2ccc3c(cnn3CC(F)F)c2)c(C(N)=O)cc1F)[C@H](C)N] | 6-(((2S,3R)-2-aminohexan-3-yl)amino)-2-((1-(2,2-difluoroethyl)-1H-indazol-5-yl)amino)-5-fluoronicotinamide | HCl | 450 | 448 | 0.76 |
| Example 6-425 | 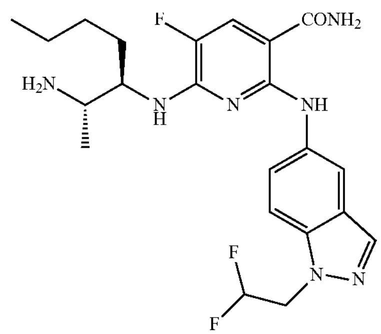 [SMILES: CCCC[C@@H](Nc1nc(Nc2ccc3c(cnn3CC(F)F)c2)c(C(N)=O)cc1F)[C@H](C)N] | 6-(((2S,3R)-2-aminoheptan-3-yl)amino)-2-((1-(2,2-difluoroethyl)-1H-indazol-5-yl)amino)-5-fluoronicotinamide | HCl | 464 | 462 | 0.99 |

TABLE 3-continued

| Example | Name | Salt | Solvent | Freq | NMR | m/z | | |
|---|---|---|---|---|---|---|---|---|
| Example 6-426 | 6-(((2R,3S)-3-amino-1-cyclopropylbutan-2-yl)amino)-2-((1-(2,2-difluoroethyl)-1H-indazol-5-yl)amino)-5-fluoronicotinamide | HCl | | | | 462 | 460 | 0.93 |
| Example 6-427 | 6-((cis-2-aminocyclohexyl)amino)-5-fluoro-2-(((1-methyl-6-oxo-5-(2H-1,2,3-triazol-2-yl)-1,6-dihydropyridin-3-yl)amino)nicotinamide | HCl | DMSO-d6 | 300 MHz | δ: 10.86 (s, 1H), 8.09 (d, 1H, J = 2.7 Hz), 8.04 (s, 2H), 8.01 (d, 1H, J = 2.7 Hz), 7.88 (d, 1H, J = 11.7 Hz), 7.80-7.60 (m, 4H), 7.25 (br, 1H), 6.79 (d, 1H, J = 7.2 Hz), 4.16-4.05 (m, 1H), 3.62-3.50 (m, 1H), 3.55 (s, 3H), 1.80-1.15 (m, 8H). | 442 | 440 | 0.72 |
| Example 6-428 | 6-((cis-2-aminocyclohexyl)amino)-5-fluoro-2-(((1-methyl-6-oxo-5-(1H-1,2,3-triazol-1-yl)-1,6-dihydropyridin-3-yl)amino)nicotinamide | HCl | DMSO-d6 | 300 MHz | δ: 11.00 (s, 1H), 8.85 (s, 1H), 8.54 (d, 1H, J = 2.7 Hz), 8.03 (d, 1H, J = 2.7 Hz), 7.95-7.60 (m, 6H), 7.30 (br, 1H), 6.83 (d, 1H, J = 6.6 Hz), 4.28-4.14 (m, 1H), 3.61 (s, 3H), 3.54-3.40 (m, 8H), 2.00-1.15 (m, 8H). | 442 | 440 | 0.74 |

TABLE 3-continued

| Example | Name | Structure | Salt | Solvent | Freq | NMR | MS | MS | Rt |
|---|---|---|---|---|---|---|---|---|---|
| Example 6-429 | 6-(((1R,2S)-2-amino-1-cyclopropylpropyl)amino)-2-((2,6-dimethoxypyridin-4-yl)amino)-5-fluoronicotinamide | | HCl | DMSO-d6 | 300 MHz | δ: 11.86 (s, 1H), 7.97-7.80 (m, 5H), 7.40-7.22 (m, 3H), 7.26 (d, 1H, J = 8.6 Hz), 6.51 (s, 2H), 3.84-3.78 (s, 6H), 3.70-3.50 (m, 2H), 1.33 (d, 3H, J = 6.6 Hz), 1.24-1.08 (m, 1H), 0.74-0.30 (m, 3H). | 405 | 403 | 0.98 |
| Example 6-430 | 6-(((1R,2S)-2-amino-1-cyclopropylpropyl)amino)-5-fluoro-2-((2-methoxypyridin-4-yl)amino)nicotinamide | | HCl | | | | 375 | 373 | 0.62 |
| Example 6-431 | 6-(((1R,2S)-2-amino-1-cyclopropylpropyl)amino)-5-fluoro-2-((2-(2-methoxyethoxy)pyridin-4-yl)amino)nicotinamide | | HCl | DMSO-d6 | 300 MHz | δ: 12.51 (s, 1H), 8.30-7.70 (m, 6H), 7.60-7.40 (m, 3H), 7.16 (s, 1H), 4.46-4.40 (m, 2H), 3.78-3.66 (m, 3H), 3.40-3.36 (m, 1H), 3.25 (s, 3H), 1.33 (d, 3H, J = 6.6Hz), 1.20-1.08 (m, 1H), 0.70-0.24 (m, 4H). | 419 | 417 | 0.69 |
| Example 6-432 | 6-(((1R,2S)-2-aminocyclohexyl)amino)-5-fluoro-2-((3-fluoro-2-methoxypyridin-4-yl)amino)nicotinamide | | HCl | DMSO-d6-D2O | 300 MHz | δ: 8.10 (dd, 1H, J = 5.6, 5.6 Hz), 7.93 (d, 1H, J = 12.2 Hz), 7.85 (d, 1H, J = 5.9 Hz), 4.35-4.23 (m, 1H), 3.93 (s, 3H), 3.79-3.66 (m, 1H), 1.98-1.41 (m, 8H). | 393 | 391 | 0.92 |

TABLE 3-continued

| Example | Structure | Name | Salt | Solvent | Freq | NMR | MW1 | MW2 | Val |
|---|---|---|---|---|---|---|---|---|---|
| Example 6-433 | 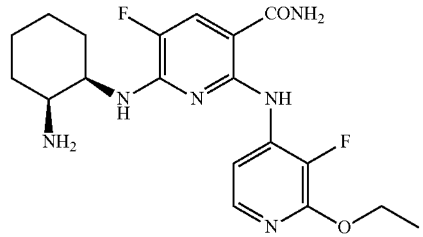 [SMILES: CCOc1nccc(Nc2nc(N[C@@H]3CCCC[C@@H]3N)c(F)cc2C(N)=O)c1F] | 6-(((1R,2S)-2-aminocyclohexyl)amino)-2-((2-ethoxy-3-fluoropyridin-4-yl)amino)-5-fluoronicotinamide | HCl | DMSO-d6-D2O | 300 MHz | δ: 8.07 (dd, 1H, J = 5.3, 5.6 Hz), 7.95 (d, 1H, J = 12.2 Hz), 7.83 (d, 1H, J = 5.6 Hz), 4.38 (q, 2H, J = 6.9 Hz), 4.33-4.23 (m, 1H), 3.76-3.67 (m, 1H), 2.00-1.40 (m, 8H), 1.35 (t, 3H, J = 6.9 Hz). | 407 | 405 | 0.98 |
| Example 6-434 | 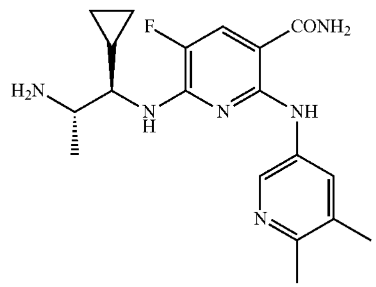 [SMILES: Cc1cc(Nc2nc(N[C@H](C3CC3)[C@H](C)N)c(F)cc2C(N)=O)cnc1C] | 6-(((1R,2S)-2-amino-1-cyclopropylpropyl)amino)-2-((5,6-dimethylpyridin-3-yl)amino)-5-fluoronicotinamide | HCl | | | | 373 | 371 | 0.64 |
| Example 6-435 | 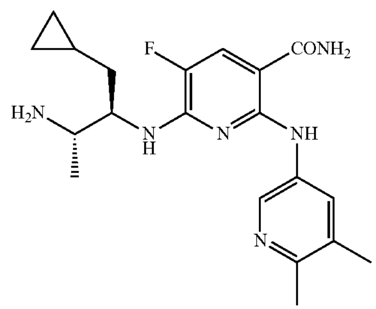 [SMILES: Cc1cc(Nc2nc(N[C@H](CC3CC3)[C@H](C)N)c(F)cc2C(N)=O)cnc1C] | 6-(((2R,3S)-3-amino-1-cyclopropylbutan-2-yl)amino)-2-((5,6-dimethylpyridin-3-yl)amino)-5-fluoronicotinamide | HCl | DMSO-d6 | 300 MHz | δ: 12.20 (s, 1H), 9.40 (s, 1H), 8.22-7.95 (m, 6H), 7.47 (s, 1H), 7.34 (d, 1H, J = 8.6 Hz), 5.85-5.70 (m, 1H), 4.97-4.78 (m, 2H), 4.44-4.30 (m, 1H), 3.50-3.44 (m, 1H), 2.62 (s, 3H), 2.39 (s, 3H), 2.25-1.62 (m, 4H), 1.21-1.11 (m, 3H). | 387 | 385 | 0.73 |

TABLE 3-continued

| Example | Structure | Name | Salt | | | |
|---|---|---|---|---|---|---|
| Example 6-436 | 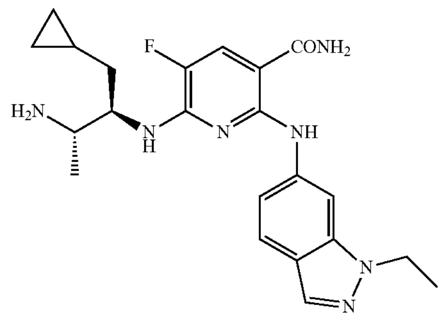 [SMILES: CCn1ncc2ccc(Nc3nc(N[C@H](CC4CC4)[C@H](C)N)c(F)cc3C(N)=O)cc21] | 6-(((2R,3S)-3-amino-1-cyclopropylbutan-2-yl)amino)-2-(1-ethyl-1H-indazol-6-yl)amino)-5-fluoronicotinamide | HCl | 426 | 424 | 0.96 |
| Example 6-437 | 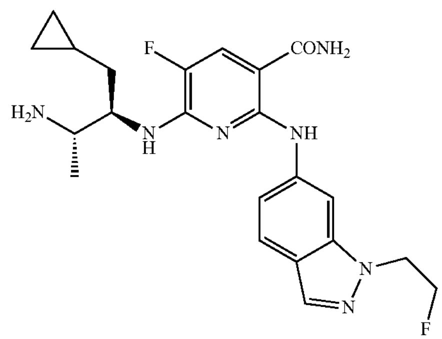 [SMILES: C[C@H](N)[C@@H](CC1CC1)Nc1nc(Nc2ccc3cnn(CCF)c3c2)c(C(N)=O)cc1F] | 6-(((2R,3S)-3-amino-1-cyclopropylbutan-2-yl)amino)-5-fluoro-2-((1-(2-fluoroethyl)-1H-indazol-6-yl)amino)nicotinamide | HCl | 444 | 442 | N.D |
| Example 6-438 | 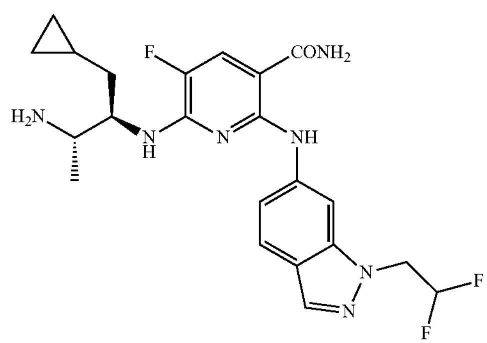 [SMILES: C[C@H](N)[C@@H](CC1CC1)Nc1nc(Nc2ccc3cnn(CC(F)F)c3c2)c(C(N)=O)cc1F] | 6-(((2R,3S)-3-amino-1-cyclopropylbutan-2-yl)amino)-2-((1-(2,2-difluoroethyl)-1H-indazol-6-yl)amino)-5-fluoronicotinamide | HCl | 462 | 460 | N.D |

TABLE 3-continued

| Example | Structure | Name | Salt | | | |
|---|---|---|---|---|---|---|
| Example 6-439 | 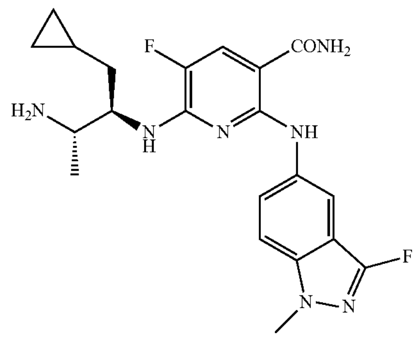 [SMILES: C[C@H](N)[C@@H](CC1CC1)Nc1nc(Nc2ccc3c(c2)c(F)nn3C)c(C(N)=O)cc1F] | 6-(((2R,3S)-3-amino-1-cyclopropylbutan-2-yl)amino)-5-fluoro-2-((3-fluoro-1-methyl-1H-indazol-5-yl)amino)nicotinamide | HCl | 430 | 428 | 0.99 |
| Example 6-440 | 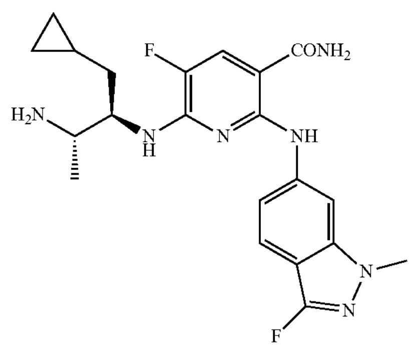 [SMILES: C[C@H](N)[C@@H](CC1CC1)Nc1nc(Nc2ccc3c(F)nn(C)c3c2)c(C(N)=O)cc1F] | 6-(((2R,3S)-3-amino-1-cyclopropylbutan-2-yl)amino)-5-fluoro-2-((3-fluoro-1-methyl-1H-indazol-6-yl)amino)nicotinamide | HCl | 430 | 428 | 1.04 |
| Example 6-441 | 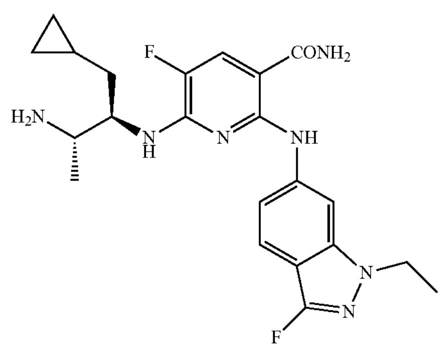 [SMILES: CCn1nc(F)c2ccc(Nc3nc(N[C@H](CC4CC4)[C@H](C)N)c(F)cc3C(N)=O)cc21] | 6-(((2R,3S)-3-amino-1-cyclopropylbutan-2-yl)amino)-2-((1-ethyl-3-fluoro-1H-indazol-6-yl)amino)-5-fluoronicotinamide | HCl | 444 | 442 | N.D |

TABLE 3-continued

| Example 6-442 | [structure] | 6-(((2R,3S)-3-amino-1-cyclopropylbutan-2-yl)amino)-2-((1,3-dimethyl-1H-indazol-5-yl)amino)-5-fluoronicotinamide | HCl | 426 | 424 | 0.95 |
| Example 6-443 | [structure] | 6-(((2R,3S)-3-amino-1-cyclopropylbutan-2-yl)amino)-2-((1-ethyl-3-methyl-1H-indazol-5-yl)amino)-5-fluoronicotinamide | HCl | 440 | 438 | 1.01 |
| Example 6-444 | [structure] | 6-(((2R,3S)-3-amino-1-cyclopropylbutan-2-yl)amino)-5-fluoro-2-((1-(2-methoxyethyl)-3-methyl-1H-indazol-5-yl)amino)nicotinamide | HCl | 470 | 468 | N.D |

TABLE 3-continued

| Example | Structure | Name | Salt | Solvent | Freq | NMR | MS | RT |
|---|---|---|---|---|---|---|---|---|
| Example 6-445 | | 6-(((2R,3S)-3-amino-1-cyclopropylbutan-2-yl)amino)-2-((1-(2,2-difluoroethyl)-3-methyl-1H-indazol-5-yl)amino)-5-fluoronicotinamide | HCl | | | | 476 474 | 0.95 |
| Example 6-446 | | 6-(((1R,2S)-2-aminocyclohexyl)amino)-2-((5-chloro-6-(1H-pyrazol-1-yl)pyridin-3-yl)amino)-5-fluoronicotinamide | HCl | DMSO-d6 | 300 MHz | δ: 12.06 (s, 1H), 8.65 (d, 1H, J = 2.7 Hz), 8.54 (d, 1H, J = 2.7 Hz), 8.15 (s, 1H, J = 2.7 Hz), 8.01 (d, 1H, J = 12.6 Hz), 8.00-7.77 (m, 4H), 7.76 (d, 1H, J = 2.1 Hz), 7.47 (br, 1H), 7.03 (d, 1H, J = 6.6 Hz), 6.54-6.50 (m, 1H), 4.35-4.25 (m, 1H), 3.68-3.56 (m, 1H), 2.00-1.35 (m, 8H). | 445 447 443 445 | 0.95 |
| Example 6-447 | | 6-(((1R,2S)-2-aminocyclohexyl)amino)-5-fluoro-2-((5-fluoro-6-(1H-pyrazol-1-yl)pyridin-3-yl)amino)nicotinamide | HCl | DMSO-d6 | 300 MHz | δ: 12.07 (s, 1H), 8.48 (dd, 1H, J = 2.1, 13.2 Hz), 8.39 (d, 1H, J = 2.1 Hz), 8.29 (d, 1H, J = 2.7 Hz), 8.01 (d, 1H, J = 12.6 Hz), 8.00-7.82 (m, 4H), 7.79 (d, 1H, J = 1.5 Hz), 7.44 (br, 1H), 7.09 (d, 1H, J = 6.6 Hz), 6.57-6.54 (m, 1H), 4.34-4.22 (m, 1H), 3.74-3.60 (m, 1H), 2.00-1.35 (m, 8H). | 429 427 | 0.9 |

TABLE 3-continued

| Example | Structure | Name | Salt | Solvent | Freq | NMR | MS | RT |
|---|---|---|---|---|---|---|---|---|
| Example 6-448 | | 6-(((1R,2S)-2-aminocyclohexyl)amino)-2-((5,6-di(1H-pyrazol-1-yl)pyridin-3-yl)amino)-5-fluoronicotinamide | HCl | DMSO-d6 | 300 MHz | δ: 12.20 (s, 1H), 8.88 (d, 1H, J = 2.7 Hz), 8.50 (d, 1H, J = 2.7 Hz), 7.94 (br, 1H), 8.05-7.92 (m, 2H), 7.62 (d, 1H, J = 1.8 Hz), 7.47 (m, 4H), 7.13 (d, 1H, J = 2.7 Hz), 7.03 (br, 1H), 7.03 (d, 1H, J = 5.7 Hz), 6.50-6.46 (m, 1H), 6.40-6.37 (m, 1H), 4.34-4.20 (m, 1H), 3.60-3.50 (m, 1H), 1.90-1.20 (m, 8H). | 477 475 | 0.93 |
| Example 6-449 | | 2-((6-(1H-pyrazol-1-yl)-5-(2H-1,2,3-triazol-2-yl)pyridin-3-yl)amino)-6-(((1R,2S)-2-aminocyclohexyl)amino)-5-fluoronicotinamide | HCl | DMSO-d6 | 300 MHz | δ: 12.19 (s, 1H), 8.86 (d, 1H, J = 1.8 Hz), 8.59 d, 1H, J = 2.7 Hz), 8.16 (d, 1H, J = 2.7 Hz), 8.04-7.88 (m, 4H), 7.82-7.70 (m, 3H), 7.55-7.42 (m, 2H), 7.02 (d, 1H, J = 6.6 Hz), 6.44-6.41 (m, 1H), 4.30-4.16 (m, 1H), 3.57-3.45 (m, 1H), 1.85-1.15 (m, 8H). | 478 476 | 0.9 |
| Example 6-450 | | 2-((6-((1H-pyrazol-1-yl)pyridin-3-yl)amino)-5-(1H-1,2,3-triazol-1-yl)amino)-6-(((1R,2S)-2-aminocyclohexyl)amino)-5-fluoronicotinamide | HCl | DMSO-d6 | 300 MHz | δ: 12.24 (s, 1H), 8.88 (d, 1H, J = 2.7 Hz), 8.65 (d, 1H, J = 2.4 Hz), 8.20 (d, 1H, J = 2.1 Hz), 8.05-7.88 (m, 3H), 7.84 (d, 1H, J = 1.2 Hz), 7.83-7.68 (m, 3H), 7.53 (d, 1H, J = 1.2 Hz), 7.49 (br, 1H), 7.05 (d, 1H, J = 7.5 Hz), 6.49-6.45 (m, 1H), 4.28-4.14 (m, 1H), 3.54-3.40 (m, 1H), 1.85-1.15 (m, 8H). | 478 476 | 0.85 |

TABLE 3-continued

| Example | Structure | Name | Salt | | | |
|---|---|---|---|---|---|---|
| Example 6-451 | 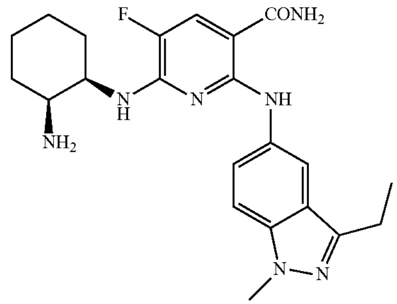 [SMILES: CCc1nn(C)c2ccc(Nc3nc(N[C@@H]4CCCC[C@@H]4N)c(F)cc3C(N)=O)cc12] | 6-(((1R,2S)-2-aminocyclohexyl)amino)-2-((3-ethyl-1-methyl-1H-indazol-5-yl)amino)-5-fluoronicotinamide | HCl | 426 | 424 | 0.92 |
| Example 6-452 | 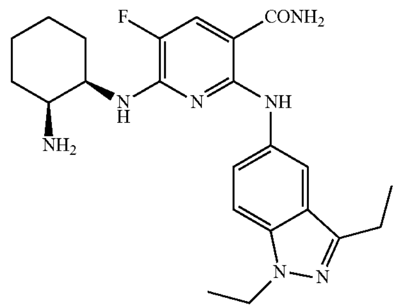 [SMILES: CCc1nn(CC)c2ccc(Nc3nc(N[C@@H]4CCCC[C@@H]4N)c(F)cc3C(N)=O)cc12] | 6-(((1R,2S)-2-aminocyclohexyl)amino)-2-((1,3-diethyl-1H-indazol-5-yl)amino)-5-fluoronicotinamide | HCl | 440 | 438 | 0.96 |
| Example 6-453 | 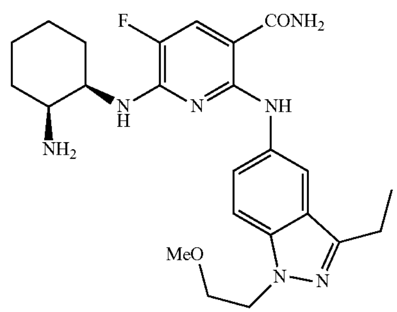 [SMILES: CCc1nn(CCOC)c2ccc(Nc3nc(N[C@@H]4CCCC[C@@H]4N)c(F)cc3C(N)=O)cc12] | 6-(((1R,2S)-2-aminocyclohexyl)amino)-2-((3-ethyl-1-(2-methoxyethyl)-1H-indazol-5-yl)amino)-5-fluoronicotinamide | HCl | 470 | 468 | 0.94 |

TABLE 3-continued

| | | | | | |
|---|---|---|---|---|---|
| Example 6-454 | [structure] | 6-(((1R,2S)-2-aminocyclohexyl)amino)-2-((3-ethyl-1-(2-fluoroethyl)-1H-indazol-5-yl)amino)-5-fluoronicotinamide | HCl | 458 456 | 0.94 |
| Example 6-455 | [structure] | 6-(((1R,2S)-2-aminocyclohexyl)amino)-2-((1-(2,2-difluoroethyl)-3-ethyl-1H-indazol-5-yl)amino)-5-fluoronicotinamide | HCl | 476 474 | 0.99 |
| Example 6-456 | [structure] | 6-(((1R,2S)-2-aminocyclohexyl)amino)-5-fluoro-2-((1-methyl-3-propyl-1H-indazol-5-yl)amino)nicotinamide | HCl | 440 438 | 0.98 |

TABLE 3-continued

| Example | Structure | Name | Salt | | | |
|---|---|---|---|---|---|---|
| Example 6-457 | 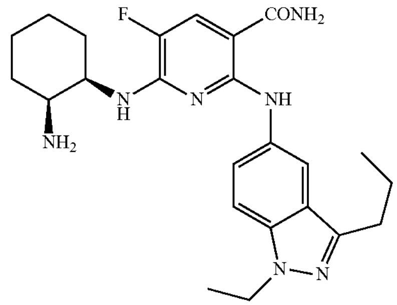 [SMILES: CCCc1nn(CC)c2ccc(Nc3nc(N[C@@H]4CCCC[C@@H]4N)c(F)cc3C(N)=O)cc12] | 6-(((1R,2S)-2-aminocyclohexyl)amino)-2-((1-ethyl-3-propyl-1H-indazol-5-yl)amino)-5-fluoronicotinamide | HCl | 454 | 452 | 1.04 |
| Example 6-458 | 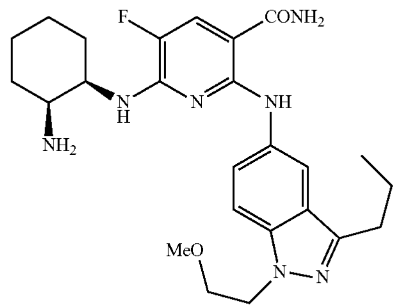 [SMILES: CCCc1nn(CCOC)c2ccc(Nc3nc(N[C@@H]4CCCC[C@@H]4N)c(F)cc3C(N)=O)cc12] | 6-(((1R,2S)-2-aminocyclohexyl)amino)-5-fluoro-2-((1-(2-methoxyethyl)-3-propyl-1H-indazol-5-yl)amino)nicotinamide | HCl | 484 | 482 | 1 |
| Example 6-459 | 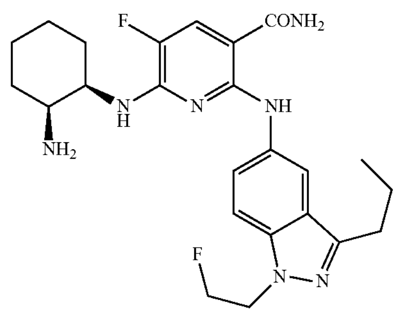 [SMILES: CCCc1nn(CCF)c2ccc(Nc3nc(N[C@@H]4CCCC[C@@H]4N)c(F)cc3C(N)=O)cc12] | 6-(((1R,2S)-2-aminocyclohexyl)amino)-5-fluoro-2-((1-(2-fluoroethyl)-3-propyl-1H-indazol-5-yl)amino)nicotinamide | HCl | 472 | 470 | 1.02 |

TABLE 3-continued

| Example | Structure | Name | Salt | | | |
|---|---|---|---|---|---|---|
| Example 6-460 | 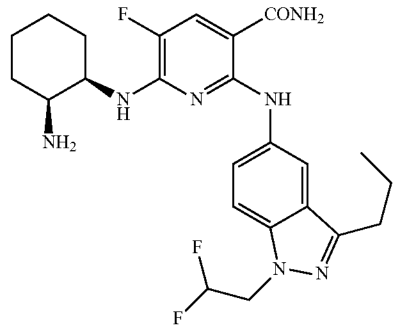 [SMILES: CCCc1nn(CC(F)F)c2ccc(Nc3nc(N[C@@H]4CCCC[C@@H]4N)c(F)cc3C(N)=O)cc12] | 6-(((1R,2S)-2-aminocyclohexyl)amino)-2-((1-(2,2-difluoroethyl)-3-propyl-1H-indazol-5-yl)amino)-5-fluoronicotinamide | HCl | 490 | 488 | 1.04 |
| Example 6-461 | 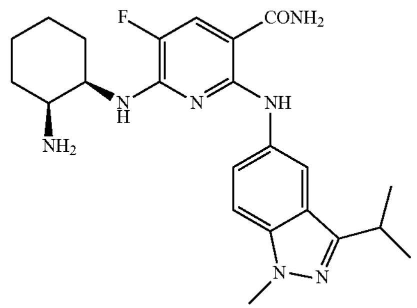 [SMILES: CC(C)c1nn(C)c2ccc(Nc3nc(N[C@@H]4CCCC[C@@H]4N)c(F)cc3C(N)=O)cc12] | 6-(((1R,2S)-2-aminocyclohexyl)amino)-5-fluoro-2-((3-isopropyl-1-methyl-1H-indazol-5-yl)amino)nicotinamide | HCl | 440 | 438 | 0.98 |
| Example 6-462 | 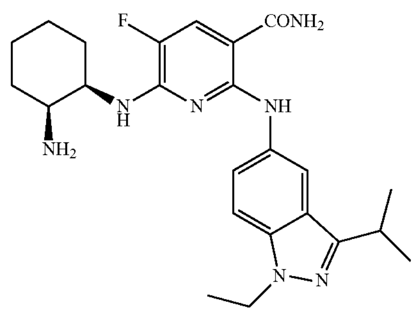 [SMILES: CCn1nc(C(C)C)c2cc(Nc3nc(N[C@@H]4CCCC[C@@H]4N)c(F)cc3C(N)=O)ccc21] | 6-(((1R,2S)-2-aminocyclohexyl)amino)-2-((1-ethyl-3-isopropyl-1H-indazol-5-yl)amino)-5-fluoronicotinamide | HCl | 454 | 452 | 1.05 |

TABLE 3-continued

| Example | Structure | Name | Salt | | | |
|---|---|---|---|---|---|---|
| Example 6-463 | 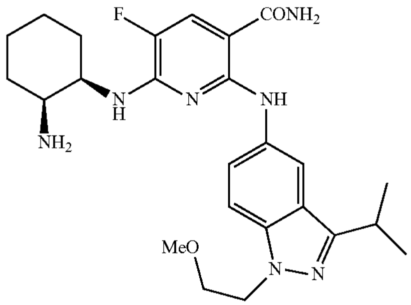 [SMILES: COCCn1nc(C(C)C)c2cc(Nc3nc(N[C@@H]4CCCC[C@@H]4N)c(F)cc3C(N)=O)ccc21] | 6-(((1R,2S)-2-aminocyclohexyl)amino)-5-fluoro-2-((3-isopropyl-1-(2-methoxyethyl)-1H-indazol-5-yl)amino)nicotinamide | HCl | 484 | 482 | 1.01 |
| Example 6-464 | 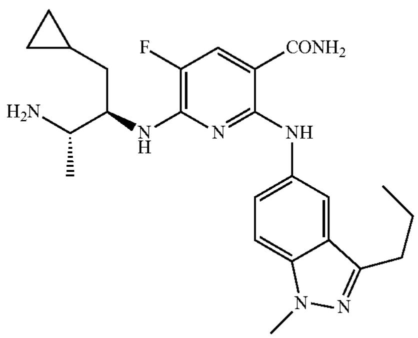 [SMILES: CCCc1nn(C)c2ccc(Nc3nc(N[C@H](CC4CC4)[C@H](C)N)c(F)cc3C(N)=O)cc12] | 6-(((2R,3S)-3-amino-1-cyclopropylbutan-2-yl)amino)-5-fluoro-2-((1-methyl-3-propyl-1H-indazol-5-yl)amino)nicotinamide | HCl | 454 | 452 | 1.02 |
| Example 6-465 | 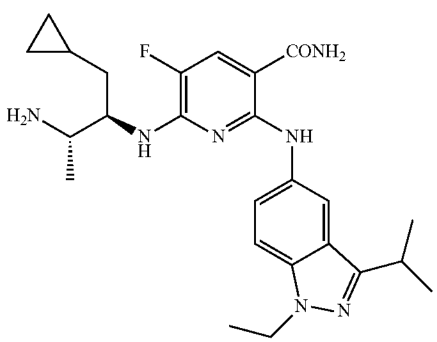 [SMILES: CCn1nc(C(C)C)c2cc(Nc3nc(N[C@H](CC4CC4)[C@H](C)N)c(F)cc3C(N)=O)ccc21] | 6-(((2R,3S)-3-amino-1-cyclopropylbutan-2-yl)amino)-2-((1-ethyl-3-isopropyl-1H-indazol-5-yl)amino)-5-fluoronicotinamide | HCl | 468 | 466 | 1.1 |

TABLE 3-continued

| Example | Structure | Name | Salt | Solvent | Freq | NMR | MS | MS | MS | ret |
|---|---|---|---|---|---|---|---|---|---|---|
| Example 6-466 | 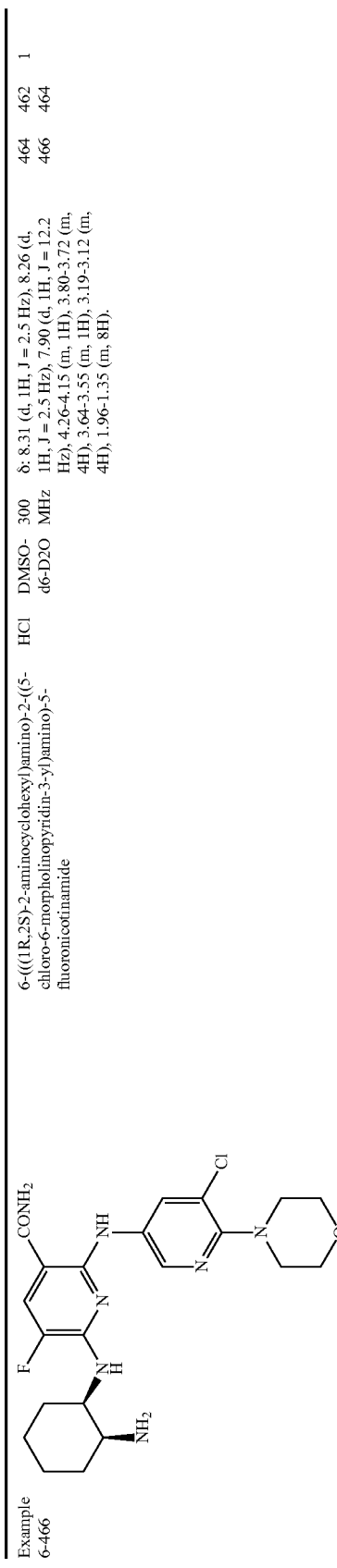 | 6-(((1R,2S)-2-aminocyclohexyl)amino)-2-((5-chloro-6-morpholinopyridin-3-yl)amino)-5-fluoronicotinamide | HCl | DMSO-d6-D2O | 300 MHz | δ: 8.31 (d, 1H, J = 2.5 Hz), 8.26 (d, 1H, J = 2.5 Hz), 7.90 (d, 1H, J = 12.2 Hz), 4.26-4.15 (m, 1H), 3.80-3.72 (m, 4H), 3.64-3.55 (m, 1H), 3.19-3.12 (m, 4H), 1.96-1.35 (m, 8H). | 464 466 | 462 464 | 1 |
| Example 6-467 | 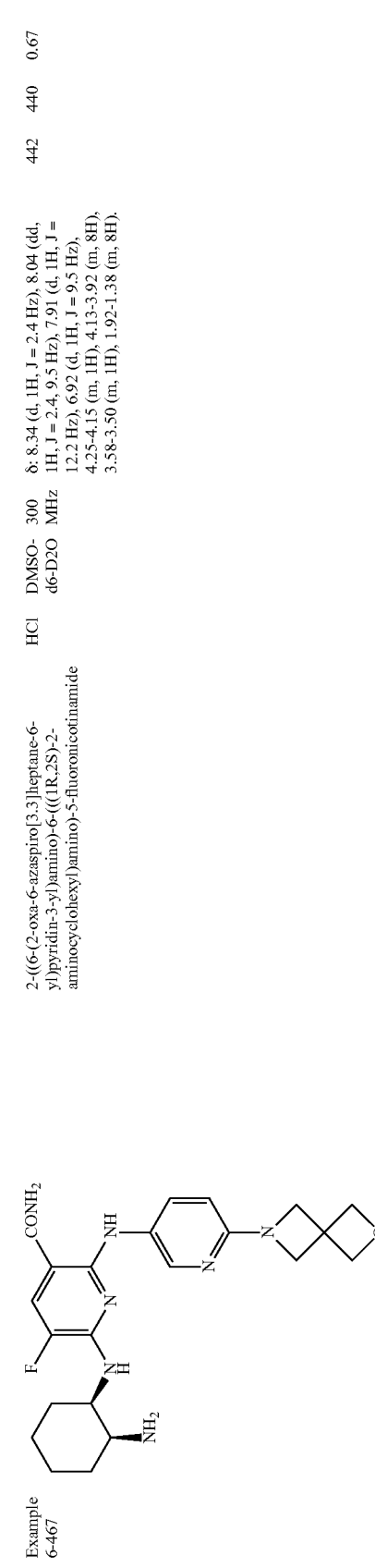 | 2-((6-(2-oxa-6-azaspiro[3.3]heptane-6-yl)pyridin-3-yl)amino)-6-(((1R,2S)-2-aminocyclohexyl)amino)-5-fluoronicotinamide | HCl | DMSO-d6-D2O | 300 MHz | δ: 8.34 (d, 1H, J = 2.4 Hz), 8.04 (dd, 1H, J = 2.4, 9.5 Hz), 7.91 (d, 1H, J = 12.2 Hz), 6.92 (d, 1H, J = 9.5 Hz), 4.25-4.15 (m, 1H), 4.13-3.92 (m, 8H), 3.58-3.50 (m, 1H), 1.92-1.38 (m, 8H). | 442 | 440 | 0.67 |
| Example 6-468 | 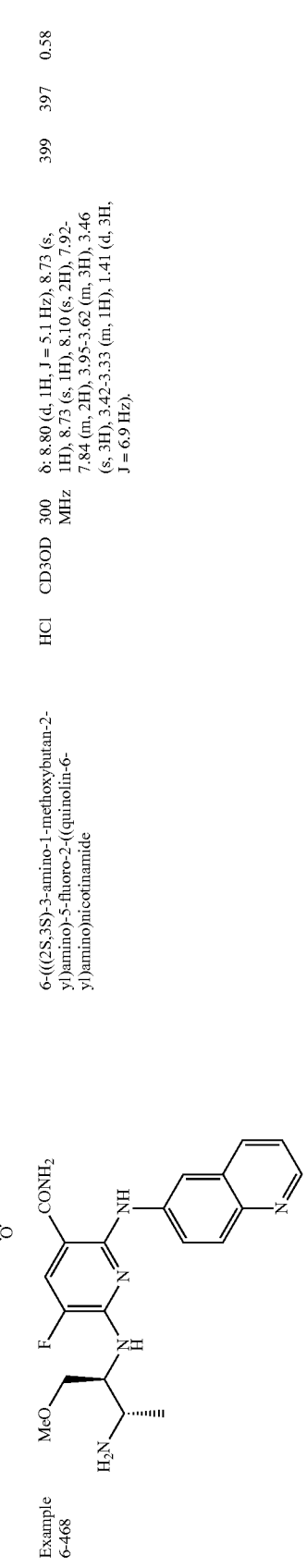 | 6-(((2S,3S)-3-amino-1-methoxybutan-2-yl)amino)-5-fluoro-2-((quinolin-6-yl)amino)nicotinamide | HCl | CD3OD | 300 MHz | δ: 8.80 (d, 1H, J = 5.1 Hz), 8.73 (s, 1H), 8.73 (s, 1H), 8.10 (s, 2H), 7.92-7.84 (m, 2H), 3.95-3.62 (m, 3H), 3.46 (s, 3H), 3.42-3.33 (m, 1H), 1.41 (d, 3H, J = 6.9 Hz). | 399 | 397 | 0.58 |

TABLE 3-continued

| Example | Structure | Name | Salt | Solvent | Freq | NMR | [M+H]+ | [M–H]– | tR |
|---|---|---|---|---|---|---|---|---|---|
| Example 6-469 | 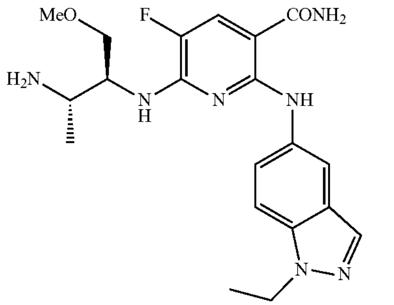 [SMILES: CCn1ncc2cc(Nc3nc(N[C@H](COC)[C@H](C)N)c(F)cc3C(N)=O)ccc21] | 6-(((2S,3S)-3-amino-1-methoxybutan-2-yl)amino)-2-((1-ethyl-1H-indazol-5-yl)amino)-5-fluoronicotinamide | HCl | CD3OD | 300 MHz | δ: 8.01 (s, 1H), 7.94 (s, 1H), 7.77 (d, 1H, J = 12.2 Hz), 7.54 (d, 1H, J = 8.9 Hz), 7.40 (dd, 1H, J = 9.1, 1.8 Hz), 4.45 (q, 2H, J = 7.3 Hz), 4.38-4.31 (m, 1H), 3.86-3.78 (m, 1H), 3.74-3.55 (m, 2H), 3.42 (s, 3H), 1.47 (t, 3H, J = 7.1 Hz), 1.26 (d, 3H, J = 6.9 Hz). | 416 | 414 | 0.83 |
| Example 6-470 | 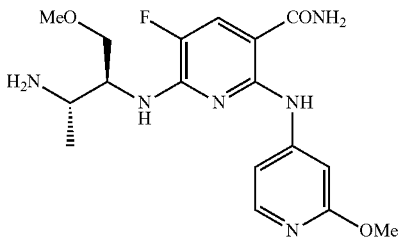 [SMILES: COC[C@@H](Nc1nc(Nc2ccnc(OC)c2)c(C(N)=O)cc1F)[C@H](C)N] | 6-(((2S,3S)-3-amino-1-methoxybutan-2-yl)amino)-5-fluoro-2-((2-methoxypyridin-4-yl)amino)nicotinamide | HCl | | | | 379 | 377 | 0.52 |
| Example 6-471 | 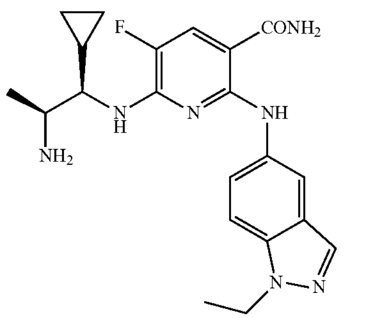 [SMILES: CCn1ncc2cc(Nc3nc(N[C@H](C4CC4)[C@H](C)N)c(F)cc3C(N)=O)ccc21] | 6-(((1R,2S)-2-amino-1-cyclopropylpropyl)amino)-2-((1-ethyl-1H-indazol-5-yl)amino)-5-fluoronicotinamide | HCl | DMSO-d6 | 300 MHz | δ: 11.55 (s, 1H), 8.09-7.85 (m, 5H), 7.90 (d, 1H, J = 12.6 Hz), 7.85-7.67 (m, 1H), 7.58 (d, 1H, J = 8.9 Hz), 7.30-7.08 (m, 2H), 7.29 (dd, 1H, J = 2.0, 8.1 Hz), 4.40 (q, 2H, J = 7.3 Hz), 3.72-3.54 (m, 2H), 1.39 (t, 3H, J = 7.3 Hz), 1.27 (d, 3H, J = 6.6 Hz), 1.17-1.02 (m, 1H), 0.72-0.27 (m, 4H). | 412 | 410 | 0.94 |

TABLE 3-continued

| Example | Structure | Name | Salt | | | |
|---|---|---|---|---|---|---|
| Example 6-472 | 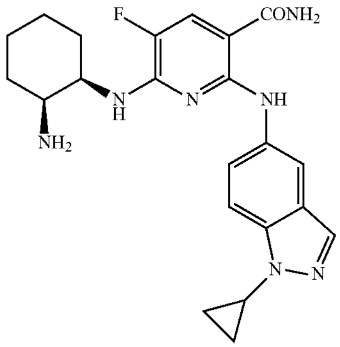 [SMILES: NC(=O)c1cc(F)c(N[C@@H]2CCCC[C@@H]2N)nc1Nc1ccc2c(cnn2C2CC2)c1] | 6-(((1R,2S)-2-aminocyclohexyl)amino)-2-((1-cyclopropyl-1H-indazol-5-yl)amino)-5-fluoronicotinamide | HCl | 424 | 422 | 0.95 |
| Example 6-473 | 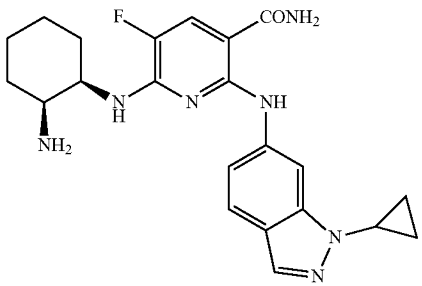 [SMILES: NC(=O)c1cc(F)c(N[C@@H]2CCCC[C@@H]2N)nc1Nc1ccc2cnn(C3CC3)c2c1] | 6-(((1R,2S)-2-aminocyclohexyl)amino)-2-((1-cyclopropyl-1H-indazol-6-yl)amino)-5-fluoronicotinamide | HCl | 424 | 422 | 0.93 |
| Example 6-474 | 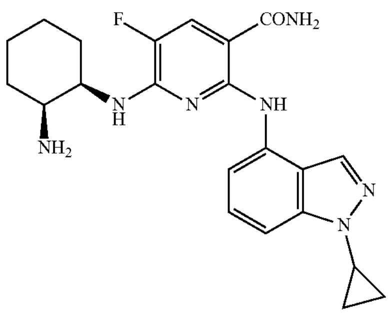 [SMILES: NC(=O)c1cc(F)c(N[C@@H]2CCCC[C@@H]2N)nc1Nc1cccc2c1cnn2C1CC1] | 6-(((1R,2S)-2-aminocyclohexyl)amino)-2-((1-cyclopropyl-1H-indazol-4-yl)amino)-5-fluoronicotinamide | HCl | 424 | 422 | 1.03 |

TABLE 3-continued

| Example 6-475 | 6-(((1R,2S)-2-aminocyclohexyl)amino)-2-((1-cyclopropyl-3-fluoro-1H-indazol-5-yl)amino)-5-fluoronicotinamide | HCl | 442 | 440 | 1.11 |
| Example 6-476 | 6-(((1R,2S)-2-aminocyclohexyl)amino)-2-((1-cyclopropyl-3-fluoro-1H-indazol-6-yl)amino)-5-fluoronicotinamide | HCl | 442 | 440 | 1.1 |
| Example 6-477 | 6-(((1R,2S)-2-aminocyclohexyl)amino)-2-((1-cyclopropyl-3-methyl-1H-indazol-5-yl)amino)-5-fluoronicotinamide | HCl | 438 | 436 | 1 |

TABLE 3-continued

| Example | Structure | Name | Salt | MS | | |
|---|---|---|---|---|---|---|
| Example 6-478 | 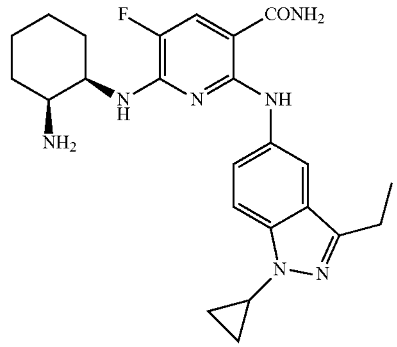 [SMILES: CCc1nn(C2CC2)c2ccc(Nc3nc(N[C@@H]4CCCC[C@@H]4N)c(F)cc3C(N)=O)cc12] | 6-(((1R,2S)-2-aminocyclohexyl)amino)-2-((1-cyclopropyl-3-ethyl-1H-indazol-5-yl)amino)-5-fluoronicotinamide | HCl | 452 | 450 | 1.06 |
| Example 6-479 | 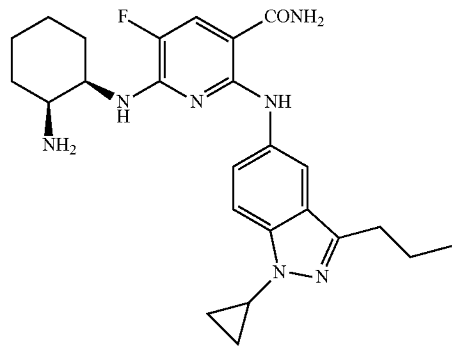 [SMILES: CCCc1nn(C2CC2)c2ccc(Nc3nc(N[C@@H]4CCCC[C@@H]4N)c(F)cc3C(N)=O)cc12] | 6-(((1R,2S)-2-aminocyclohexyl)amino)-2-((1-cyclopropyl-3-propyl-1H-indazol-5-yl)amino)-5-fluoronicotinamide | HCl | 466 | 464 | 1.13 |
| Example 6-480 | 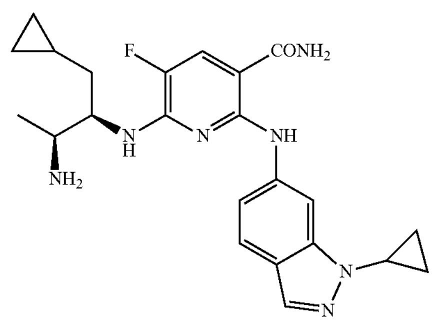 [SMILES: C[C@H](N)[C@@H](CC1CC1)Nc1nc(Nc2ccc3cnn(C4CC4)c3c2)c(C(N)=O)cc1F] | 6-(((2R,3S)-3-amino-1-cyclopropylbutan-2-yl)amino)-2-((1-cyclopropyl-1H-indazol-6-yl)amino)-5-fluoronicotinamide | HCl | 438 | 436 | 1.02 |

TABLE 3-continued

| Example | Name | Structure | Salt | Solvent | Freq | NMR | M+1 | M-1 | RT |
|---|---|---|---|---|---|---|---|---|---|
| Example 6-481 | 6-(((2R,3S)-3-amino-1-cyclopropylbutan-2-yl)amino)-2-((1-cyclopropyl-3-fluoro-1H-indazol-6-yl)amino)-5-fluoronicotinamide | | HCl | | | | 456 | 454 | 1.2 |
| Example 6-482 | 6-(((2R,3S)-3-amino-1-cyclopropylbutan-2-yl)amino)-2-((1-cyclopropyl-3-propyl-1H-indazol-5-yl)amino)-5-fluoronicotinamide | | HCl | | | | 480 | 478 | 1.19 |
| Example 6-483 | 6-(((1R,2S)-2-amino-1-cyclopropylpropyl)amino)-5-fluoro-2-((6-methyl-5-(2H-1,2,3-triazol-2-yl)pyridin-3-yl)amino)nicotinamide | | HCl | DMSO-d6 | 300 MHz | δ: 11.96 (s, 1H), 8.67 (d, 1H, J = 2.0 Hz), 8.48 (d, 1H, J = 2.6 Hz), 8.22 (s, 2H), 8.01-7.80 (m, 5H), 7.46-7.24 (m, 2H), 3.75-3.65 (m, 1H), 3.40-3.36 (m, 1H), 2.53 (s, 3H), 1.22-1.00 (m, 4H), 0.60-0.16 (m, 4H). | 426 | 424 | 0.86 |

TABLE 3-continued

| Example | Structure | Name | Salt | Solvent | Freq | NMR | | | |
|---|---|---|---|---|---|---|---|---|---|
| Example 6-484 | 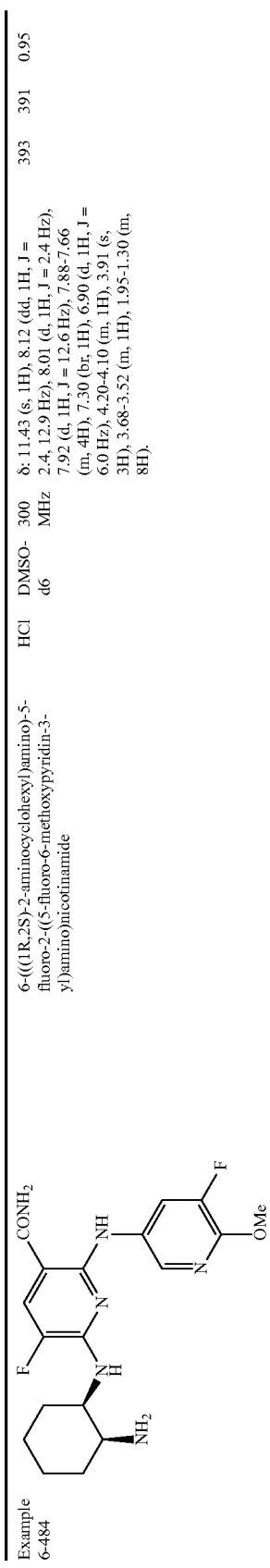 | 6-(((1R,2S)-2-aminocyclohexyl)amino)-5-fluoro-2-((5-fluoro-6-methoxypyridin-3-yl)amino)nicotinamide | HCl | DMSO-d6 | 300 MHz | δ: 11.43 (s, 1H), 8.12 (dd, 1H, J = 2.4, 12.9 Hz), 8.01 (d, 1H, J = 2.4 Hz), 7.92 (d, 1H, J = 12.6 Hz), 7.88-7.66 (m, 4H), 7.30 (br, 1H), 6.90 (d, 1H, J = 6.0 Hz), 4.20-4.10 (m, 1H), 3.91 (s, 3H), 3.68-3.52 (m, 1H), 1.95-1.30 (m, 8H). | 393 | 391 | 0.95 |
| Example 6-485 | 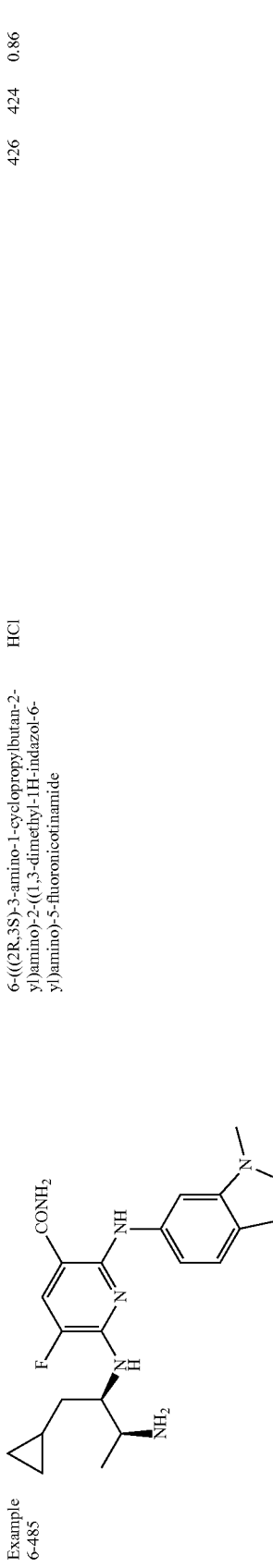 | 6-(((2R,3S)-3-amino-1-cyclopropylbutan-2-yl)amino)-2-((1,3-dimethyl-1H-indazol-6-yl)amino)-5-fluoronicotinamide | HCl | | | | 426 | 424 | 0.86 |
| Example 6-486 | 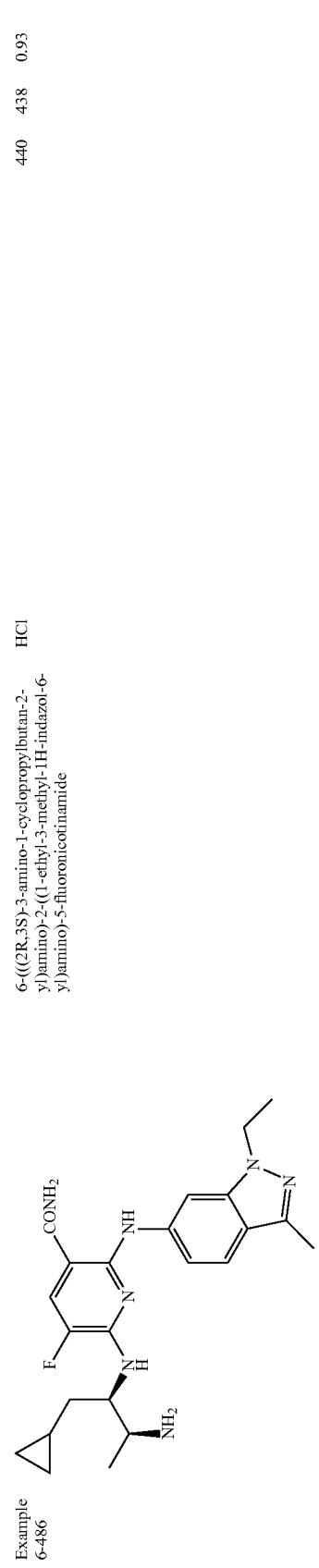 | 6-(((2R,3S)-3-amino-1-cyclopropylbutan-2-yl)amino)-2-((1-ethyl-3-methyl-1H-indazol-6-yl)amino)-5-fluoronicotinamide | HCl | | | | 440 | 438 | 0.93 |

TABLE 3-continued

| Example | Structure | Name | Salt | | | |
|---|---|---|---|---|---|---|
| 6-487 | | 6-(((2R,3S)-3-amino-1-cyclopropylbutan-2-yl)amino)-5-fluoro-2-((1-(2-methoxyethyl))-3-methyl-1H-indazol-6-yl)amino)nicotinamide | HCl | 470 | 468 | 0.89 |
| 6-488 | | 6-(((2R,3S)-3-amino-1-cyclopropylbutan-2-yl)amino)-5-fluoro-2-((1-(2-fluoroethyl))-3-methyl-1H-indazol-6-yl)amino)nicotinamide | HCl | 458 | 456 | 0.92 |
| 6-489 | | 6-(((2R,3S)-3-amino-1-cyclopropylbutan-2-yl)amino)-2-((1-(2,2-difluoroethyl)-3-methyl-1H-indazol-6-yl)amino)-5-fluoronicotinamide | HCl | 476 | 474 | 0.97 |

TABLE 3-continued

| Example | Name | Salt | | | |
|---|---|---|---|---|---|
| Example 6-490 | 6-(((2R,3S)-3-amino-1-cyclopropylbutan-2-yl)amino)-5-fluoro-2-((3-fluoro-1-(2-methoxyethyl)-1H-indazol-4-yl)amino)nicotinamide | HCl | 474 | 472 | 0.98 |
| Example 6-491 | 6-(((2R,3S)-3-amino-1-cyclopropylbutan-2-yl)amino)-5-fluoro-2-((3-fluoro-1-(2-fluoroethyl)-1H-indazol-4-yl)amino)nicotinamide | HCl | 462 | 460 | 1.14 |
| Example 6-492 | 6-(((2R,3S)-3-amino-1-cyclopropylbutan-2-yl)amino)-2-((1-(2,2-difluoroethyl)-3-fluoro-1H-indazol-4-yl)amino)-5-fluoronicotinamide | HCl | 480 | 478 | 1.03 |

TABLE 3-continued

| Example | Name | Salt | Solvent | Freq | NMR | | | |
|---|---|---|---|---|---|---|---|---|
| Example 6-493 | 6-(((1R,2S)-2-aminocyclohexyl)amino)-5-fluoro-2-((6-methoxy-5-(1H-1,2,3-triazol-1-yl)pyridin-3-yl)amino)nicotinamide | HCl | DMSO-d6 | 300 MHz | δ: 11.67 (s, 1H), 8.78 (d, 1H, J = 1.8 Hz), 8.64 (d, 1H, J = 1.2 Hz), 8.27 (d, 1H, J = 2.7 Hz), 8.00-7.60 (m, 6H), 7.33 (br, 1H), 6.92 (d, 1H, J = 7.2 Hz), 4.30-4.18 (m, 1H), 3.95 (s, 3H), 3.52-3.40 (m, 1H), 1.85-1.15 (m, 8H). | 442 | 440 | 1.01 |
| Example 6-494 | 6-(((1R,2S)-2-aminocyclohexyl)amino)-2-((6-ethoxy-5-(1H-pyrazol-1-yl)pyridin-3-yl)amino)-5-fluoronicotinamide | HCl | DMSO-d6 | 300 MHz | δ: 11.55 (s, 1H), 8.70 (d, 1H, J = 2.4 Hz), 8.41 (d, 1H, J = 2.4 Hz), 8.08 (d, 1H, J = 2.7 Hz), 7.93 (d, 1H, J = 12.6 Hz), 7.90-7.70 (m, 5H), 7.29 (br, 1H), 6.90 (d, 1H, J = 6.0 Hz), 6.58-6.54 (m, 1H), 4.43 (q, 2H, J = 7.2 Hz), 4.14-4.00 (m, 1H), 3.62-3.40 (m, 1H), 1.95-1.10 (m, 8H), 1.38 (t, 3H, J = 7.2 Hz). | 455 | 453 | 1.24 |
| Example 6-495 | 6-(((1R,2S)-2-aminocyclohexyl)amino)-2-((6-ethoxy-5-(2H-1,2,3-triazol-2-yl)pyridin-3-yl)amino)-5-fluoronicotinamide | HCl | DMSO-d6 | 300 MHz | δ: 11.57 (s, 1H), 8.49 (d, 1H, J = 2.7 Hz), 8.26 (d, 1H, J = 2.4 Hz), 8.13 (s, 2H), 7.93 (d, 1H, J = 12.6 Hz), 7.88-7.64 (m, 4H), 7.26 (br, 1H), 6.90 (d, 1H, J = 6.6 Hz), 4.37 (q, 2H, J = 7.2 Hz), 4.16-4.04 (m, 1H), 3.50-3.40 (m, 1H), 1.80-1.10 (m, 8H), 1.25 (t, 3H, J = 7.2 Hz). | 456 | 454 | 1.1 |

| Example | Structure (name) | Salt | Solvent | Freq | NMR | MS1 | MS2 | RT |
|---|---|---|---|---|---|---|---|---|
| Example 6-496 | 6-(((1R,2S)-2-aminocyclohexyl)amino)-2-((6-ethoxy-5-(1H-1,2,3-triazol-1-yl)pyridin-3-yl)amino)-5-fluoronicotinamide | HCl | DMSO-d6 | 300 MHz | δ: 11.66 (s, 1H), 8.79 (d, 1H, J = 2.7 Hz), 8.64 (s, 1H), 8.25 (d, 1H, J = 1.8 Hz), 7.99 (s, 1H), 7.95 (d, 1H, J = 12.6 Hz), 7.90-7.60 (m, 4H), 7.33 (br, 1H), 6.92 (d, 1H, J = 6.6 Hz), 4.41 (q, 2H, J = 7.2 Hz), 4.30-4.18 (m, 1H), 3.52-3.40 (m, 1H), 1.80-1.20 (m, 8H), 1.33 (t, 3H, J = 7.2 Hz). | 456 | 454 | 1.11 |
| Example 6-497 | 6-(((1R,2S)-2-aminocyclohexyl)amino)-2-((6-ethoxy-5-methylpyridin-3-yl)amino)-5-fluoronicotinamide | HCl | DMSO-d6 | 300 MHz | δ: 11.15 (s, 1H), 8.10 (d, 1H, J = 2.7 Hz), 7.99 (d, 1H, J = 12.6 Hz), 7.80-7.60 (m, 5H), 7.20 (br, 1H), 6.79 (d, 1H, J = 6.0 Hz), 4.28 (q, 2H, J = 7.2 Hz), 4.20-4.08 (m, 1H), 3.64-3.50 (m, 1H), 2.14 (s, 3H), 1.95-1.25 (m, 8H), 1.31 (t, 3H, J = 7.2 Hz). | 403 | 401 | 1.18 |
| Example 6-498 | 6-(((1R,2S)-2-aminocyclohexyl)amino)-5-fluoro-2-((6-(2-methoxyethoxy)-5-methylpyridin-3-yl)amino)nicotinamide | HCl | DMSO-d6 | 300 MHz | δ: 11.18 (s, 1H), 8.11 (d, 1H, J = 2.7 Hz), 7.90 (d, 1H, J = 12.6 Hz), 7.86-7.60 (m, 5H), 7.23 (br, 1H), 6.81 (d, 1H, J = 6.6 Hz), 4.38-4.32 (m, 2H), 4.20-4.08 (m, 1H), 3.70-3.64 (m, 2H), 3.60-3.48 (m, 1H), 3.31 (s, 3H), 2.16 (s, 3H), 1.90-1.30 (m, 8H). | 433 | 431 | 1.08 |

TABLE 3-continued

| Example | Structure | Name | Salt | Solvent | Freq | NMR | MS | MS | RT |
|---|---|---|---|---|---|---|---|---|---|
| Example 6-499 | 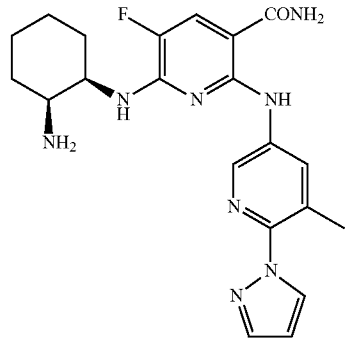 [SMILES: Cc1cc(Nc2nc(N[C@@H]3CCCC[C@@H]3N)c(F)cc2C(N)=O)cnc1-n1cccn1] | 6-(((1R,2S)-2-aminocyclohexyl)amino)-5-fluoro-2-((5-methyl-6-(1H-pyrazol-1-yl)pyridin-3-yl)amino)nicotinamide | HCl | DMSO-d6 | 300 MHz | δ: 11.76 (s, 1H), 8.58 (d, 1H, J = 1.8 Hz), 8.20 (d, 1H, J = 2.1 Hz), 8.07 (d, 1H, J = 2.7 Hz), 7.98 (d, 1H, J = 12.6 Hz), 7.98-7.80 (m, 4H), 7.73 (d, 1H, J = 1.2 Hz), 7.37 (br, 1H), 6.94 (d, 1H, J = 6.6 Hz), 6.52-6.48 (m, 1H), 4.36-4.25 (m, 1H), 3.70-3.58 (m, 1H), 2.38 (s, 3H), 2.00-1.34 (m, 8H). | 425 | 423 | 1.03 |
| Example 6-500 | 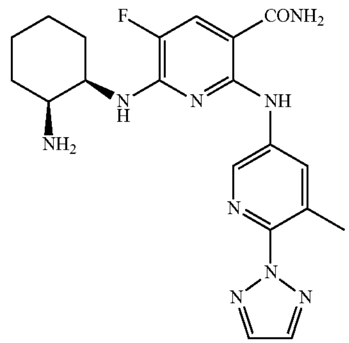 [SMILES: Cc1cc(Nc2nc(N[C@@H]3CCCC[C@@H]3N)c(F)cc2C(N)=O)cnc1-n1nccn1] | 6-(((1R,2S)-2-aminocyclohexyl)amino)-5-fluoro-2-((5-methyl-6-(2H-1,2,3-triazol-2-yl)pyridin-3-yl)amino)nicotinamide | HCl | DMSO-d6 | 300 MHz | δ: 11.91 (s, 1H), 8.73-8.69 (m, 1H), 8.12-8.10 (m, 1H), 8.09 (s, 2H), 7.99 (d, 1H, J = 12.3 Hz), 7.94-7.70 (m, 4H), 7.43 (br, 1H), 6.94 (d, 1H, J = 6.6 Hz), 4.38-4.26 (m, 1H), 3.68-3.58 (m, 1H), 2.17 (s, 3H), 1.95-1.35 (m, 8H). | 426 | 424 | 0.98 |
| Example 6-501 | 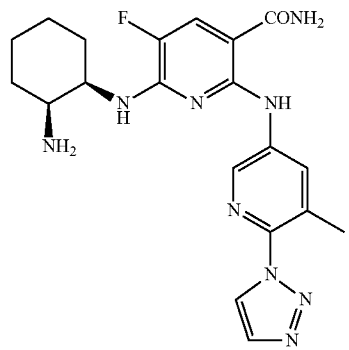 [SMILES: Cc1cc(Nc2nc(N[C@@H]3CCCC[C@@H]3N)c(F)cc2C(N)=O)cnc1-n1ccnn1] | 6-(((1R,2S)-2-aminocyclohexyl)amino)-5-fluoro-2-((5-methyl-6-(1H-1,2,3-triazol-1-yl)pyridin-3-yl)amino)nicotinamide | HCl | DMSO-d6 | 300 MHz | δ: 11.92 (s, 1H), 8.70 (d, 1H, J = 2.1 Hz), 8.53 (s, 1H), 8.18 (d, 1H, J = 12.3 Hz), 7.95 (s, 1H), 7.99 (d, 1H, J = 2.1 Hz), 7.42 (br, 1H), 7.95-7.70 (m, 4H), 6.97-6.90 (m, 1H), 4.38-4.28 (m, 1H), 3.70-3.58 (m, 1H), 2.29 (s, 3H), 2.00-1.35 (m, 8H). | 426 | 424 | 0.89 |

TABLE 3-continued

| Example | Structure | Name | Salt | Solvent | Freq | NMR | M1 | M2 | M3 |
|---|---|---|---|---|---|---|---|---|---|
| Example 6-502 | 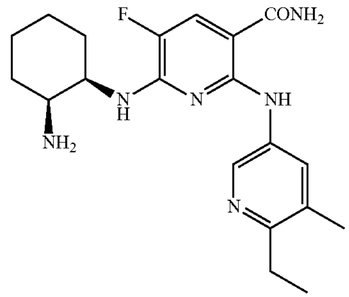 [SMILES: CCc1ncc(Nc2nc(N[C@@H]3CCCC[C@@H]3N)c(F)cc2C(N)=O)cc1C] | 6-(((1R,2S)-2-aminocyclohexyl)amino)-2-((6-ethyl-5-methylpyridin-3-yl)amino)-5-fluoronicotinamide | HCl | DMSO-d6 | 300 MHz | δ: 11.97 (br, 1H), 9.10-8.90 (m, 1H), 8.30-8.14 (m, 1H), 8.00 (d, 1H, J = 12.3 Hz), 8.00-7.80 (m, 4H), 7.56-7.36 (m, 1H), 7.05-6.95 (m, 1H), 4.37-4.26 (m, 1H), 3.61-3.50 (m, 1H), 2.98-2.84 (m, 2H), 2.42 (s, 3H), 1.95-1.35 (m, 8H), 1.24 (t, 3H, J = 7.5 Hz). | 387 | 385 | 0.69 |
| Example 6-503 | 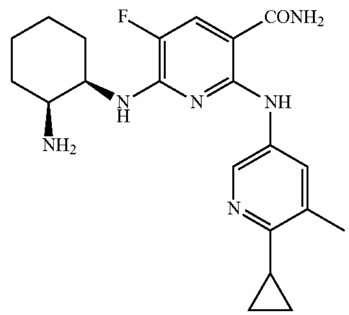 [SMILES: Cc1cc(Nc2nc(N[C@@H]3CCCC[C@@H]3N)c(F)cc2C(N)=O)cnc1C1CC1] | 6-(((1R,2S)-2-aminocyclohexyl)amino)-2-((6-cyclopropyl-5-methylpyridin-3-yl)amino)-5-fluoronicotinamide | HCl | DMSO-d6 | 300 MHz | | 399 | 397 | 0.73 |
| Example 6-504 | 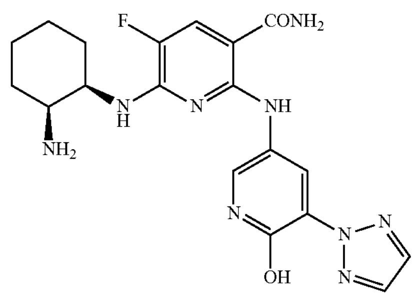 [SMILES: NC(=O)c1cc(F)c(N[C@@H]2CCCC[C@@H]2N)nc1Nc1cnc(O)c(-n2nccn2)c1] | 6-(((1R,2S)-2-aminocyclohexyl)amino)-5-fluoro-2-((6-hydroxy-5-(2H-1,2,3-triazol-2-yl)pyridin-3-yl)amino)nicotinamide | | | | | 428 | 426 | 0.7 |

TABLE 3-continued

| Example | Structure | Name | Salt | | | |
|---|---|---|---|---|---|---|
| Example 6-505 | 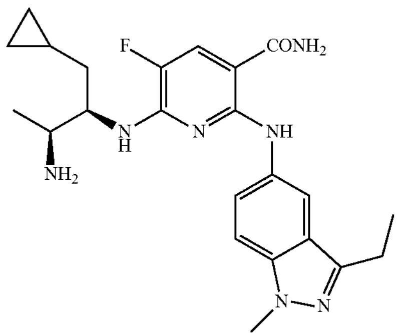 [SMILES: CCc1nn(C)c2ccc(Nc3nc(N[C@H](CC4CC4)[C@H](C)N)c(F)cc3C(N)=O)cc12] | 6-(((2R,3S)-3-amino-1-cyclopropylbutan-2-yl)amino)-2-((3-ethyl-1-methyl-1H-indazol-5-yl)amino)-5-fluoronicotinamide | HCl | 440 | 438 | 1.01 |
| Example 6-506 | 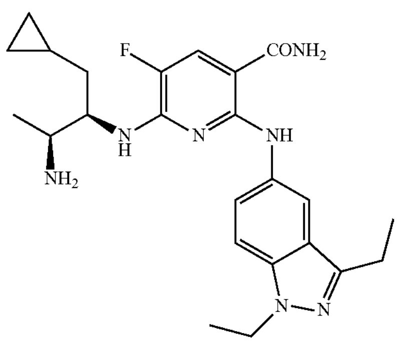 [SMILES: CCc1nn(CC)c2ccc(Nc3nc(N[C@H](CC4CC4)[C@H](C)N)c(F)cc3C(N)=O)cc12] | 6-(((2R,3S)-3-amino-1-cyclopropylbutan-2-yl)amino)-2-((1,3-diethyl-1H-indazol-5-yl)amino)-5-fluoronicotinamide | HCl | 454 | 452 | 1.07 |
| Example 6-507 | 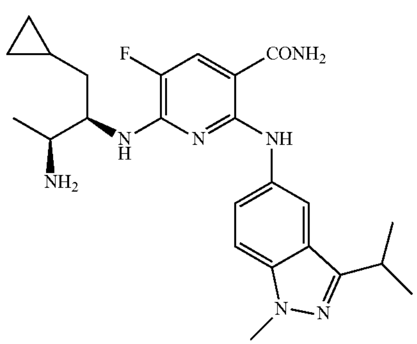 [SMILES: CC(C)c1nn(C)c2ccc(Nc3nc(N[C@H](CC4CC4)[C@H](C)N)c(F)cc3C(N)=O)cc12] | 6-(((2R,3S)-3-amino-1-cyclopropylbutan-2-yl)amino)-5-fluoro-2-((3-isopropyl-1-methyl-1H-indazol-5-yl)amino)nicotinamide | HCl | 454 | 452 | 1.07 |

TABLE 3-continued

| Example | Structure | Name | Salt | | | |
|---|---|---|---|---|---|---|
| Example 6-508 | 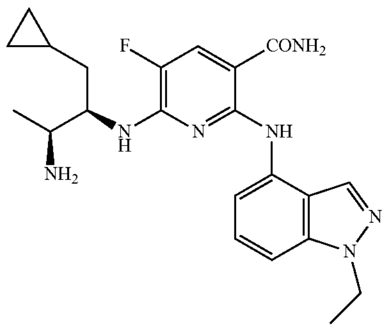 [SMILES: CCn1ncc2c(Nc3nc(N[C@H](CC4CC4)[C@H](C)N)c(F)cc3C(N)=O)cccc21] | 6-(((2R,3S)-3-amino-1-cyclopropylbutan-2-yl)amino)-2-((1-ethyl-1H-indazol-4-yl)amino)-5-fluoronicotinamide | HCl | 426 | 424 | 1 |
| Example 6-509 | 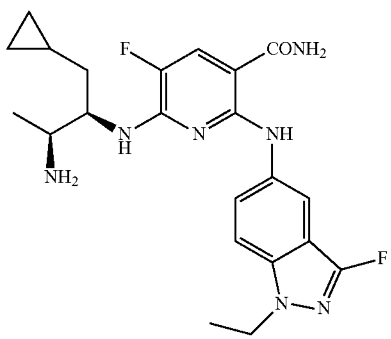 [SMILES: CCn1nc(F)c2cc(Nc3nc(N[C@H](CC4CC4)[C@H](C)N)c(F)cc3C(N)=O)ccc21] | 6-(((2R,3S)-3-amino-1-cyclopropylbutan-2-yl)amino)-2-((1-ethyl-3-fluoro-1H-indazol-5-yl)amino)-5-fluoronicotinamide | HCl | 444 | 442 | 0.99 |
| Example 6-510 | 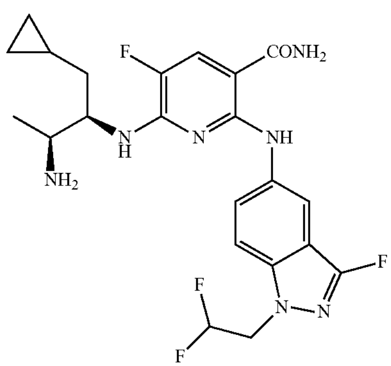 [SMILES: C[C@H](N)[C@@H](CC1CC1)Nc1nc(Nc2ccc3c(c2)c(F)nn3CC(F)F)c(C(N)=O)cc1F] | 6-(((2R,3S)-3-amino-1-cyclopropylbutan-2-yl)amino)-2-((1-(2,2-difluoroethyl)-3-fluoro-1H-indazol-5-yl)amino)-5-fluoronicotinamide | HCl | 480 | 478 | 1.03 |

TABLE 3-continued

| Example 6-511 | 6-(((2S,3R)-2-amino-5-methylhexan-3-yl)amino)-5-fluoro-2-((3-fluoro-1-methyl-1H-indazol-5-yl)amino)nicotinamide | HCl | 432 | 430 | 1.08 |
| Example 6-512 | 6-(((2S,3R)-2-amino-5-methylhexan-3-yl)amino)-2-((1-ethyl-3-fluoro-1H-indazol-5-yl)amino)-5-fluoronicotinamide | HCl | 446 | 444 | 1.13 |
| Example 6-513 | 6-(((2S,3R)-2-amino-5-methylhexan-3-yl)amino)-2-((1-(2,2-difluoroethyl)-3-fluoro-1H-indazol-5-yl)amino)-5-fluoronicotinamide | HCl | 482 | 480 | 1.09 |

TABLE 3-continued

| | | | | | | | |
|---|---|---|---|---|---|---|---|
| Example 6-514 | [structure] | 2-(([1,3]dioxolo[4,5-b]pyridin-6-ylamino)-6-(((1R,2S)-2-amino-1-cyclopropylpropyl)amino)-5-fluoronicotinamide | HCl | | | 389 387 | 0.8 |
| Example 6-515 | [structure] | 6-(((1R,2S)-2-amino-1-cyclopropylpropyl)amino)-5-fluoro-2-((6-morpholinopyridin-3-yl)amino)nicotinamide | HCl | | | 430 428 | 0.67 |
| Example 6-516 | [structure] | 6-(((1R,2S)-2-amino-1-phenylpropyl)amino)-2-((1-ethyl-1H-indazol-5-yl)amino)-5-fluoronicotinamide | HCl | CD3OD | 300 MHz | δ: 7.95 (s, 1H), 7.84 (d, 1H, J = 2.0 Hz), 7.76 (d, 1H, J = 12.2 Hz), 7.51-7.33 (dtd, 6H, J = 40.5, 14.5, 4.3 Hz), 7.27 (dd, 1H, J = 8.9, 2.0 Hz), 5.50 (d, 1H, J = 5.9 Hz), 4.46 (q, 2H, J = 7.3 Hz), 3.87-3.75 (s, 1H), 1.49 (t, 3H, J = 7.3 Hz), 1.30 (d, 3H, J = 6.9 Hz). | 448 446 | 0.92 |

TABLE 3-continued

| Example | Structure | Name | Salt | Solvent | MHz | NMR | MS | MS | Rt |
|---|---|---|---|---|---|---|---|---|---|
| Example 6-517 | 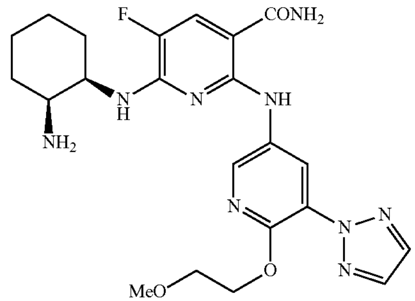 [SMILES: COCCOc1ncc(Nc2nc(N[C@@H]3CCCC[C@@H]3N)c(F)cc2C(N)=O)cc1-n1nccn1] | 6-(((1R,2S)-2-aminocyclohexyl)amino)-5-fluoro-2-((6-(2-methoxyethoxy)-5-(2H-1,2,3-triazol-2-yl)pyridin-3-yl)amino)nicotinamide | HCl | DMSO-d6 | 300 MHz | δ: 11.59 (s, 1H), 8.51 (d, 1H, J = 2.7 Hz), 8.26 (d, 1H, J = 2.7 Hz), 8.13 (s, 2H), 7.93 (d, 1H, J = 12.6 Hz), 7.90-7.60 (m, 4H), 7.32 (br, 1H), 6.90 (d, 1H, J = 6.6 Hz), 4.57-4.41 (m, 2H), 4.16-4.06 (m, 1H), 3.63-3.58 (m, 2H), 3.50-3.40 (m, 1H), 3.22 (s, 3H), 1.80-1.10 (m, 8H). | 486 | 484 | 0.92 |
| Example 6-518 | 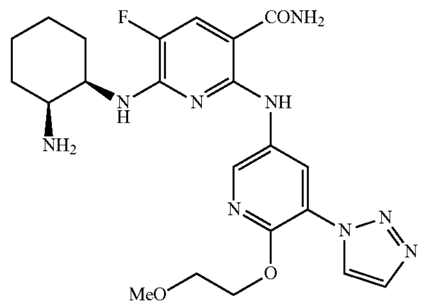 [SMILES: COCCOc1ncc(Nc2nc(N[C@@H]3CCCC[C@@H]3N)c(F)cc2C(N)=O)cc1-n1ccnn1] | 6-(((1R,2S)-2-aminocyclohexyl)amino)-5-fluoro-2-((6-(2-methoxyethoxy)-5-(1H-1,2,3-triazol-1-yl)pyridin-3-yl)amino)nicotinamide | HCl | | | | 486 | 484 | 0.94 |
| Example 6-519 | 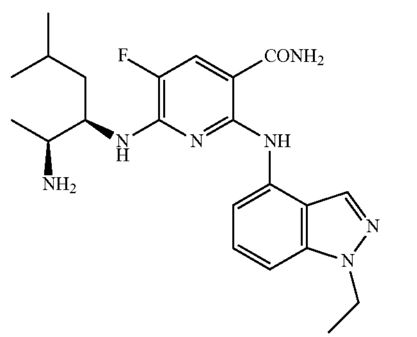 [SMILES: CCn1ncc2c(Nc3nc(N[C@H](CC(C)C)[C@H](C)N)c(F)cc3C(N)=O)cccc21] | 6-(((2S,3R)-2-amino-5-methylhexan-3-yl)amino)-2-((1-ethyl-1H-indazol-4-yl)amino)-5-fluoronicotinamide | HCl | | | | 428 | 426 | 1.05 |

TABLE 3-continued

| Example 6-520 | 6-(((2S,3R)-2-amino-5-methylhexan-3-yl)amino)-2-((1,3-dimethyl-1H-indazol-5-yl)amino)-5-fluoronicotinamide | HCl | | 428 | 426 | 1 |
| --- | --- | --- | --- | --- | --- | --- |
| Example 6-521 | 6-(((2S,3R)-2-amino-5-methylhexan-3-yl)amino)-2-((1-ethyl-3-methyl-1H-indazol-5-yl)amino)-5-fluoronicotinamide | HCl | | 442 | 440 | 1.03 |
| Example 6-522 | 6-(((2S,3R)-2-amino-5-methylhexan-3-yl)amino)-2-((1-(2,2-difluoroethyl)-3-methyl-1H-indazol-5-yl)amino)-5-fluoronicotinamide | HCl | | 478 | 476 | 1.05 |

TABLE 3-continued

| Example | Structure | Name | Salt | | | |
|---|---|---|---|---|---|---|
| Example 6-523 | 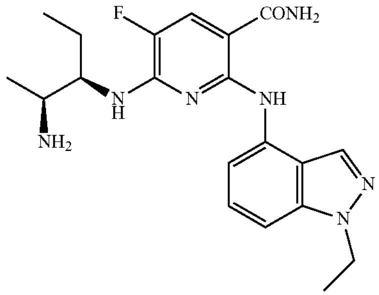 [SMILES: CC[C@@H](Nc1nc(Nc2cccc3c2cnn3CC)c(C(N)=O)cc1F)[C@H](C)N] | 6-(((2S,3R)-2-aminopentan-3-yl)amino)-2-((1-ethyl-1H-indazol-4-yl)amino)-5-fluoronicotinamide | HCl | 400 | 398 | 0.94 |
| Example 6-524 | 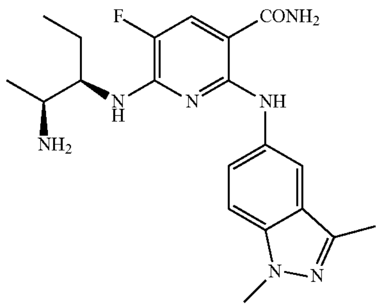 [SMILES: CC[C@@H](Nc1nc(Nc2ccc3c(c2)c(C)nn3C)c(C(N)=O)cc1F)[C@H](C)N] | 6-(((2S,3R)-2-aminopentan-3-yl)amino)-2-((1,3-dimethyl-1H-indazol-5-yl)amino)-5-fluoronicotinamide | HCl | 400 | 398 | 0.87 |
| Example 6-525 | 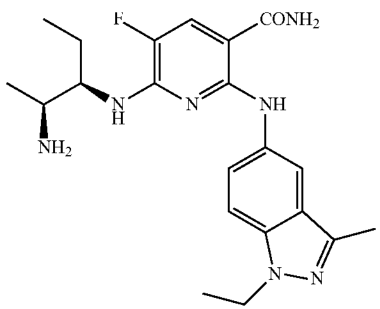 [SMILES: CC[C@@H](Nc1nc(Nc2ccc3c(c2)c(C)nn3CC)c(C(N)=O)cc1F)[C@H](C)N] | 6-(((2S,3R)-2-aminopentan-3-yl)amino)-2-((1-ethyl-3-methyl-1H-indazol-5-yl)amino)-5-fluoronicotinamide | HCl | 414 | 412 | 0.94 |

TABLE 3-continued

| Example 6-526 | 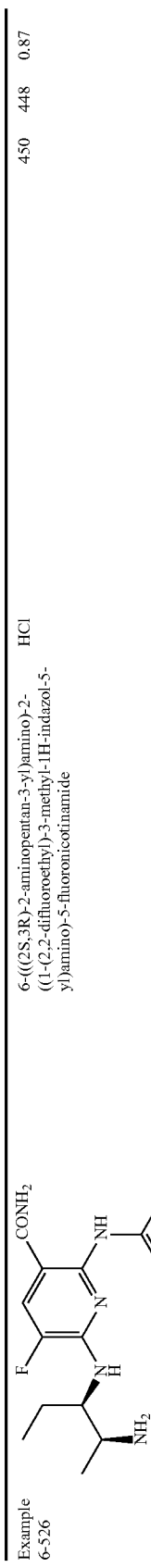 | 6-(((2S,3R)-2-aminopentan-3-yl)amino)-2-(((1-(2,2-difluoroethyl)-3-methyl-1H-indazol-5-yl)amino)-5-fluoronicotinamide | HCl | | | 450 | 448 | 0.87 |
| --- | --- | --- | --- | --- | --- | --- | --- | --- |
| Example 6-527 | 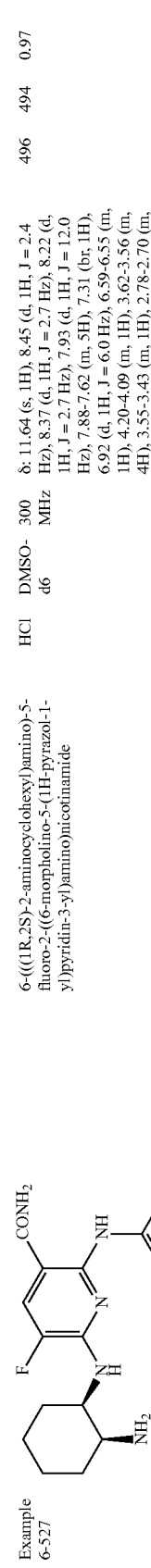 | 6-(((1R,2S)-2-aminocyclohexyl)amino)-5-fluoro-2-((6-morpholino-5-(1H-pyrazol-1-yl)pyridin-3-yl)amino)nicotinamide | HCl | DMSO-d6 | 300 MHz | δ: 11.64 (s, 1H), 8.45 (d, 1H, J = 2.4 Hz), 8.37 (d, 1H, J = 2.7 Hz), 8.22 (d, 1H, J = 2.7 Hz), 7.93 (d, 1H, J = 12.0 Hz), 7.88-7.62 (m, 5H), 7.31 (br, 1H), 6.92 (d, 1H, J = 6.0 Hz), 6.59-6.55 (m, 1H), 4.20-4.09 (m, 1H), 3.62-3.56 (m, 4H), 3.55-3.43 (m, 1H), 2.78-2.70 (m, 4H), 1.80-1.20 (m, 8H). | 496 | 494 | 0.97 |
| Example 6-528 | 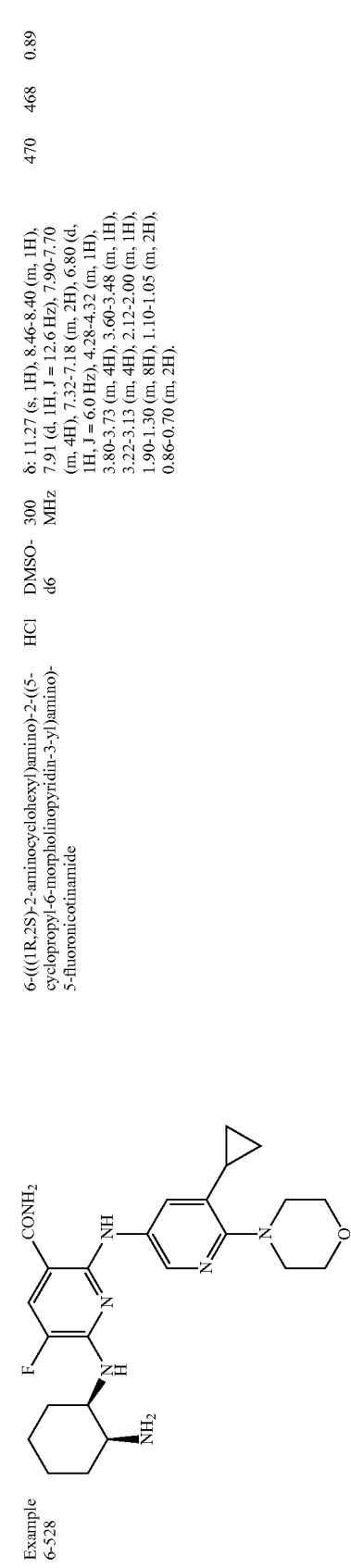 | 6-(((1R,2S)-2-aminocyclohexyl)amino)-2-((5-cyclopropyl-6-morpholinopyridin-3-yl)amino)-5-fluoronicotinamide | HCl | DMSO-d6 | 300 MHz | δ: 11.27 (s, 1H), 8.46-8.40 (m, 1H), 7.91 (d, 1H, J = 12.6 Hz), 7.90-7.70 (m, 4H), 7.32-7.18 (m, 2H), 6.80 (d, 1H, J = 6.0 Hz), 4.28-4.32 (m, 1H), 3.80-3.73 (m, 4H), 3.60-3.48 (m, 1H), 3.22-3.13 (m, 4H), 2.12-2.00 (m, 1H), 1.90-1.30 (m, 8H), 1.10-1.05 (m, 2H), 0.86-0.70 (m, 2H). | 470 | 468 | 0.89 |

| Example | Name | Salt | Solvent | Freq | NMR | M+1 | M | RT |
|---|---|---|---|---|---|---|---|---|
| Example 6-529 | (3R,4S)-benzyl 4-amino-3-((5-carbamoyl-3-fluoro-6-((2-methoxypyridin-4-yl)amino)pyridin-2-yl)amino)piperidine-1-carboxylate and (3S,4R)-benzyl-4-amino-3-((5-carbamoyl-3-fluoro-6-((2-methoxypyridin-4-yl)amino)pyridin-2-yl)amino)piperidine-1-carboxylate(=1:1) | HCl | CD3OD | 300 MHz | δ: 8.01 (d, 1H, J = 6.9 Hz), 7.95-7.75 (m, 1H), 7.58-6.90 (m, 7H), 4.57-4.40 (m, 1H), 4.37-4.15 (m, 2H), 4.11 (s, 3H), 3.92-3.80 (m, 1H), 3.46-2.99 (m, 4H), 2.14-1.88 (m, 2H). | 510 | 508 | 0.78 |
| Example 6-530 | (3S,4R)-benzyl 3-amino-4-((5-carbamoyl-3-fluoro-6-((2-methoxypyridin-2-yl)amino)pyridin-2-yl)amino)piperidine-1-carboylate and (3R,4S)-benzyl 3-amino-4-((5-carbamoyl-3-fluoro-6-((2-methoxypyridin-4-yl)amino)pyridin-2-yl)amino)piperidine-1-carboxylate(=1:1) | HCl | CD3OD | 300 MHz | δ: 8.07 (d, 1H, J = 6.6 Hz), 7.92 (d, 1H, J = 11.6 Hz), 7.80-7.71 (m, 1H), 7.44-7.30 (m, 5H), 7.23 (s, 1H), 5.25-5.10 (m, 2H), 4.54-4.42 (m, 1H), 4.40-4.21 (m, 2H), 4.10 (s, 3H), 4.04-3.97 (m, 1H), 3.62-3.35 (m, 1H), 2.06-1.94 (m, 2H). | 510 | 508 | 0.88 |
| Example 6-531 | 6-(((3R,4R)-3-aminotetrahydro-2H-pyran-4-yl)amino)-5-fluoro-2-((2-methoxypyridin-4-yl)amino)nicotinamide | HCl | CD3OD | 300 MHz | δ: 8.04 (d, 1H, J = 6.6 Hz), 7.91 (d, 1H, J = 11.6 Hz), 7.67-7.58 (m, 1H), 7.31-7.28 (m, 1H), 4.56-4.46 (m, 1H), 4.20-3.38 (m, 5H), 4.09 (s, 3H), 2.26-1.87 (m, 2H). | 377 | 375 | 0.57 |

TABLE 3-continued

| Example | Structure | Name | Salt | Solvent | Freq | MS | MS | RT |
|---|---|---|---|---|---|---|---|---|
| Example 6-532 | | 6-(((3S,4S)-4-aminotetrahydro-2H-pyran-3-yl)amino)-5-fluoro-2-((2-methoxypyridin-4-yl)amino)nicotinamide | HCl | CD3OD | 300 MHz | δ: 8.02-7.92 (m, 1H), 7.95 (d, 1H, J = 11.6 Hz), 7.46-7.40 (m, 1H), 7.37-7.30 (m, 1H), 4.75-4.68 (m, 1H), 4.12-3.98 (m, 2H), 4.07 (s, 3H), 3.90-3.51 (m, 3H), 2.20-1.86 (m, 2H). | 377 | 375 | 0.52 |
| Example 6-533 | | 6-(((1R,2S)-2-aminocyclohexyl)amino)-5-fluoro-2-((6-morpholino-5-(2H-1,2,3-triazol-2-yl)pyridin-3-yl)amino)nicotinamide | HCl | DMSO-d6-D2O | 300 MHz | δ: 8.41 (d, 1H, J = 2.6 Hz), 8.32 (d, 1H, J = 2.6 Hz), 8.16 (s, 2H), 7.90 (d, 1H, J = 12.2 Hz), 4.15-4.04 (m, 1H), 3.57-3.50 (m, 4H), 3.50-3.43 (m, 1H), 2.83-2.66 (m, 4H), 1.80-1.16 (m, 8H). | 497 | 495 | 0.89 |
| Example 6-534 | | 6-(((1R,2S)-2-aminocyclohexyl)amino)-5-fluoro-2-((6-morpholino-5-(1H-1,2,3-triazol-1-yl)pyridin-3-yl)amino)nicotinamide | HCl | DMSO-d6-D2O | 300 MHz | δ: 8.71 (d, 1H, J = 1.0 Hz), 8.61 (d, 1H, J = 2.6 Hz), 8.34 (d, 1H, J = 2.6 Hz), 8.03 (d, 1H, J = 1.0 Hz), 7.91 (d, 1H, J = 12.2 Hz), 4.26-4.14 (m, 1H), 3.62-3.54 (m, 4H), 3.52-3.44 (m, 1H), 2.78-2.69 (m, 4H), 1.80-1.21 (m, 8H). | 497 | 495 | 0.88 |

TABLE 3-continued

| Example | Structure | Name | Salt | Solvent | Freq | NMR | MS+1 | MS-1 | RT |
|---|---|---|---|---|---|---|---|---|---|
| Example 6-535 | 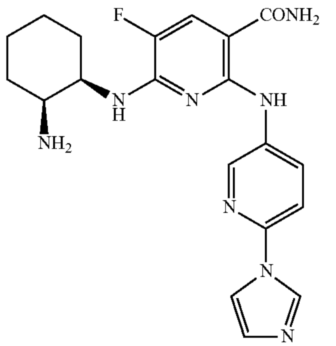 [SMILES: NC(=O)c1cc(F)c(N[C@@H]2CCCC[C@@H]2N)nc1Nc1ccc(-n2ccnc2)nc1] | 2-((6-((1H-imidazole-1-yl)pyridin-3-yl)amino)-6-(((1R,2S)-2-aminocyclohexyl)amino)-5-fluoronicotinamide | HCl | DMSO-d6-D2O | 300 MHz | δ: 9.68-9.65 (m, 1H), 8.80 (d, 1H, J = 2.8 Hz), 8.39 (dd, 1H, J = 2.8, 8.8 Hz), 8.34-8.30 (m, 1H), 8.02-7.90 (m, 2H), 7.81-7.77 (m, 1H), 4.34-4.23 (m, 1H), 3.70-3.62 (m, 1H), 1.98-1.37 (m, 8H). | 411 | 409 | 0.65 |
| Example 6-536 | 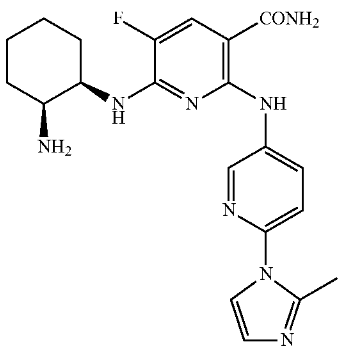 [SMILES: Cc1nccn1-c1ccc(Nc2nc(N[C@@H]3CCCC[C@@H]3N)c(F)cc2C(N)=O)cn1] | 6-(((1R,2S)-2-aminocyclohexyl)amino)-5-fluoro-2-((6-(2-methyl-1H-imidazol-1-yl)pyridin-3-yl)amino)nicotinamide | HCl | DMSO-d6-D2O | 300 MHz | δ: 8.89 (d, 1H, J = 2.7 Hz), 8.36 (dd, 1H, J = 2.7, 8.7 Hz), 7.97 (d, 1H, J = 11.9 Hz), 7.95 (d, 1H, J = 2.3 Hz), 7.75 (d, 1H, J = 8.37 Hz), 7.69 (d, 1H, J = 2.3 Hz), 4.35-4.24 (m, 1H), 3.72-3.64 (m, 1H), 2.71 (s, 3H), 2.00-1.38 (m, 8H). | 425 | 423 | 0.63 |
| Example 6-537 | 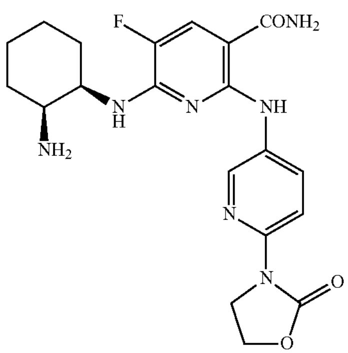 [SMILES: NC(=O)c1cc(F)c(N[C@@H]2CCCC[C@@H]2N)nc1Nc1ccc(N2CCOC2=O)nc1] | 6-(((1R,2S)-2-aminocyclohexyl)amino)-5-fluoro-2-((6-(2-oxoxazolidin-3-yl)pyridin-3-yl)amino)nicotinamide | HCl | DMSO-d6-D2O | 300 MHz | δ: 8.51 (d, 1H, J = 2.5 Hz), 8.11 (dd, 1H, J = 2.5, 8.8 Hz), 8.01 (d, 1H, J = 8.8 Hz), 7.91 (d, 1H, J = 12.2 Hz), 4.51-4.42 (m, 2H), 4.25-4.11 (m, 3H), 3.68-3.50 (m, 1H), 1.93-1.35 (m, 8H). | 430 | 428 | 0.83 |

TABLE 3-continued

| Example | Structure | Name | Salt | | | |
|---|---|---|---|---|---|---|
| Example 6-538 | 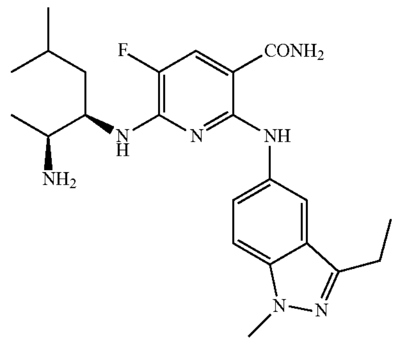 [SMILES: CCc1nn(C)c2ccc(Nc3nc(N[C@H](CC(C)C)[C@H](C)N)c(F)cc3C(N)=O)cc12] | 6-(((2S,3R)-2-amino-5-methylhexan-3-yl)amino)-2-((3-ethyl-1-methyl-1H-indazol-5-yl)amino)-5-fluoronicotinamide | HCl | 442 | 440 | 1.06 |
| Example 6-539 | 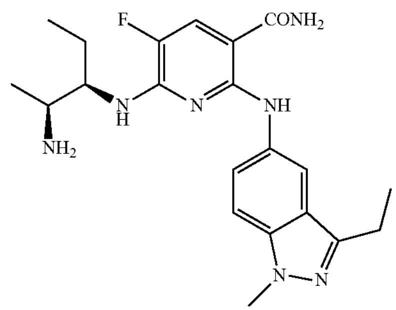 [SMILES: CCc1nn(C)c2ccc(Nc3nc(N[C@H](CC)[C@H](C)N)c(F)cc3C(N)=O)cc12] | 6-(((2S,3R)-2-aminopentan-3-yl)amino)-2-((3-ethyl-1-methyl-1H-indazol-5-yl)amino)-5-fluoronicotinamide | HCl | 414 | 412 | 0.93 |
| Example 6-540 | 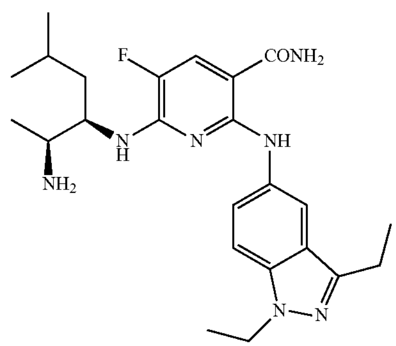 [SMILES: CCc1nn(CC)c2ccc(Nc3nc(N[C@H](CC(C)C)[C@H](C)N)c(F)cc3C(N)=O)cc12] | 6-(((2S,3R)-2-amino-5-methylhexan-3-yl)amino)-2-((1,3-diethyl-1H-indazol-5-yl)amino)-5-fluoronicotinamide | HCl | 456 | 454 | 1.13 |

TABLE 3-continued

| Example | Structure | Name | Salt | | | |
|---|---|---|---|---|---|---|
| Example 6-541 | 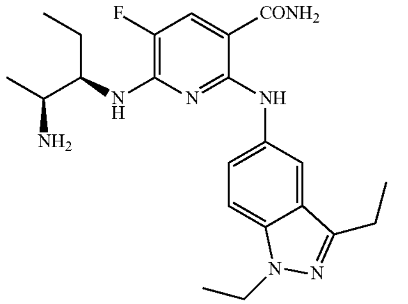 [SMILES: CCc1nn(CC)c2ccc(Nc3nc(N[C@H](CC)[C@H](C)N)c(F)cc3C(N)=O)cc12] | 6-(((2S,3R)-2-aminopentan-3-yl)amino)-2-(((1,3-diethyl-1H-indazol-5-yl)amino)-5-fluoronicotinamide | HCl | 428 | 426 | 0.98 |
| Example 6-542 | 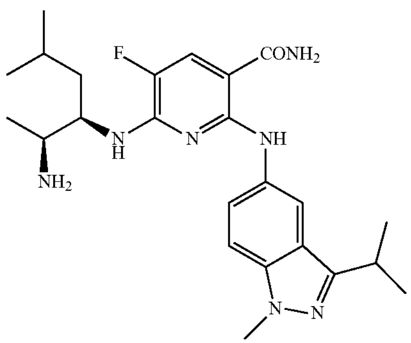 [SMILES: CC(C)C[C@@H](Nc1nc(Nc2ccc3c(c2)c(C(C)C)nn3C)c(C(N)=O)cc1F)[C@H](C)N] | 6-(((2S,3R)-2-amino-5-methylhexan-3-yl)amino)-5-fluoro-2-((3-isopropyl-1-methyl-1H-indazol-5-yl)amino)nicotinamide | HCl | 456 | 454 | 1.12 |
| Example 6-543 | 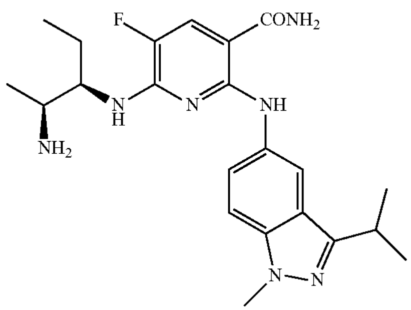 [SMILES: CC[C@@H](Nc1nc(Nc2ccc3c(c2)c(C(C)C)nn3C)c(C(N)=O)cc1F)[C@H](C)N] | 6-(((2S,3R)-2-aminopentan-3-yl)amino)-5-fluoro-2-((3-isopropyl-1-methyl-1H-indazol-5-yl)amino)nicotinamide | HCl | 428 | 426 | 0.99 |

TABLE 3-continued

| Example | Structure | Name | Salt | | | |
|---|---|---|---|---|---|---|
| Example 6-544 | 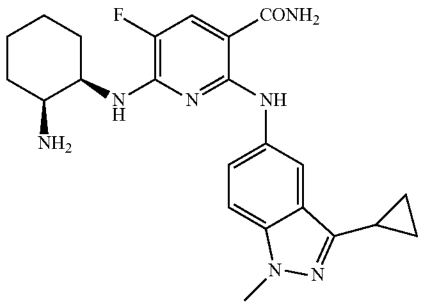 [SMILES: Cn1nc(C2CC2)c2cc(Nc3nc(N[C@@H]4CCCC[C@@H]4N)c(F)cc3C(N)=O)ccc21] | 6-(((1R,2S)-2-aminocyclohexyl)amino)-2-((3-cyclopropyl-1-methyl-1H-indazol-5-yl)amino)-5-fluoronicotinamide | HCl | 438 | 436 | 0.95 |
| Example 6-545 | 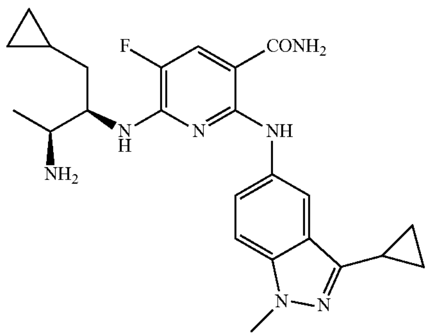 [SMILES: C[C@H](N)[C@@H](CC1CC1)Nc1nc(Nc2ccc3c(c2)c(C2CC2)nn3C)c(C(N)=O)cc1F] | 6-(((2R,3S)-3-amino-1-cyclopropylbutan-2-yl)amino)-2-((3-cyclopropyl-1-methyl-1H-indazol-5-yl)amino)-5-fluoronicotinamide | HCl | 452 | 450 | 1.05 |
| Example 6-546 | 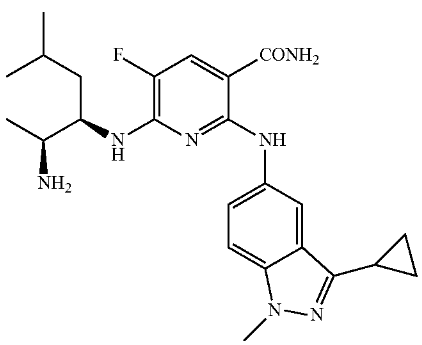 [SMILES: CC(C)C[C@@H](Nc1nc(Nc2ccc3c(c2)c(C2CC2)nn3C)c(C(N)=O)cc1F)[C@H](C)N] | 6-(((2S,3R)-2-amino-5-methylhexan-3-yl)amino)-2-((3-cyclopropyl-1-methyl-1H-indazol-5-yl)amino)-5-fluoronicotinamide | HCl | 454 | 452 | 1.05 |

TABLE 3-continued

| Example | Name | Salt | | | |
|---|---|---|---|---|---|
| Example 6-547 | 6-(((2S,3R)-2-aminopentan-3-yl)amino)-2-((3-cyclopropyl-1-methyl-1H-indazol-5-yl)amino)-5-fluoronicotinamide | HCl | 426 | 424 | 0.97 |
| Example 6-548 | 6-(((1R,2S)-2-aminocyclohexyl)amino)-2-((3-cyclopropyl-1-ethyl-1H-indazol-5-yl)amino)-5-fluoronicotinamide | HCl | 452 | 450 | 1.06 |
| Example 6-549 | 6-(((2R,3S)-3-amino-1-cyclopropylbutan-2-yl)amino)-2-((3-cyclopropyl-1-ethyl-1H-indazol-5-yl)amino)-5-fluoronicotinamide | HCl | 466 | 464 | 1.11 |

TABLE 3-continued

| Example 6-550 | 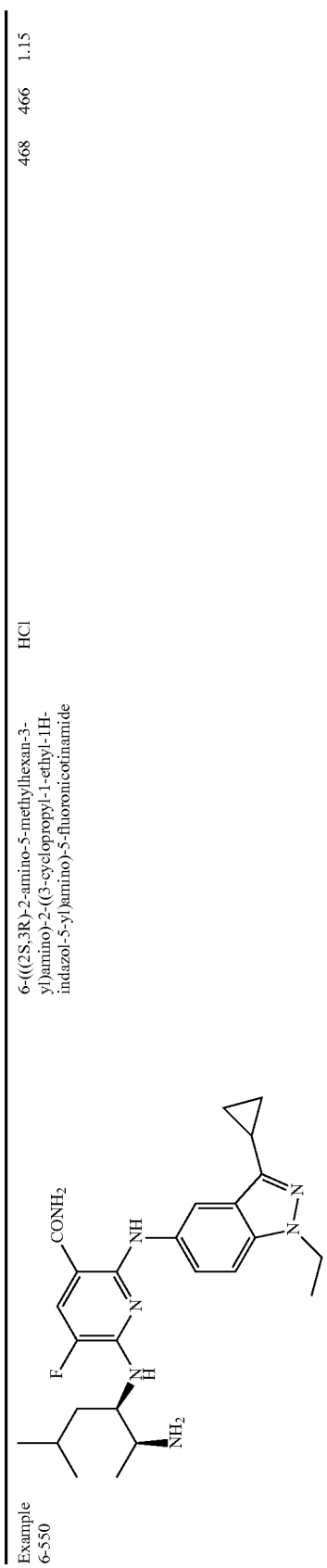 | 6-(((2S,3R)-2-amino-5-methylhexan-3-yl)amino)-2-((3-cyclopropyl-1-ethyl-1H-indazol-5-yl)amino)-5-fluoronicotinamide | HCl | | | 468 | 466 | 1.15 |
| --- | --- | --- | --- | --- | --- | --- | --- | --- |
| Example 6-551 | 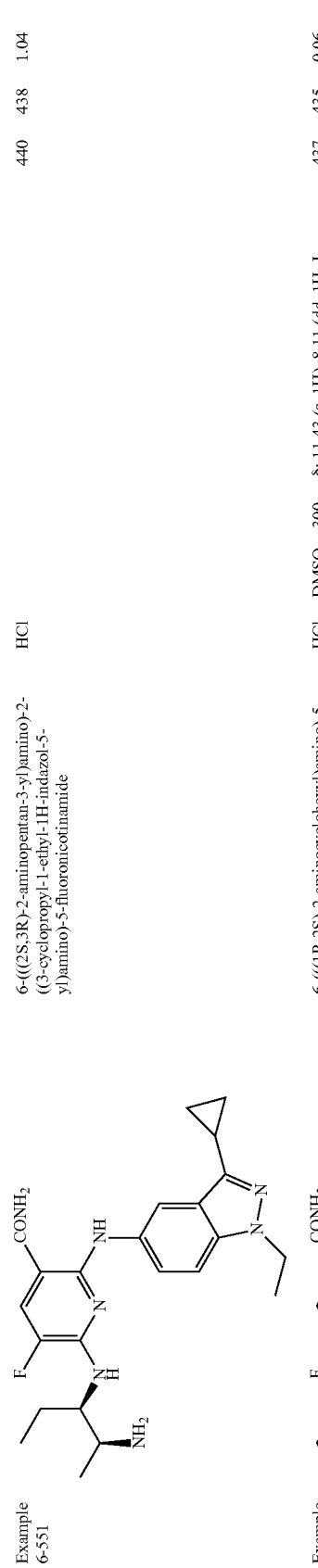 | 6-(((2S,3R)-2-aminopentan-3-yl)amino)-2-((3-cyclopropyl-1-ethyl-1H-indazol-5-yl)amino)-5-fluoronicotinamide | HCl | | | 440 | 438 | 1.04 |
| Example 6-552 |  | 6-(((1R,2S)-2-aminocyclohexyl)amino)-5-fluoro-2-((5-fluoro-6-(2-methoxyethoxy)pyridin-3-yl)amino)nicotinamide | HCl | DMSO-d6 | 300 MHz | δ: 11.43 (s, 1H), 8.11 (dd, 1H, J = 2.1, 12.3 Hz), 7.93 (d, 1H, J = 12.3 Hz), 7.90-7.70 (m, 4H), 7.29 (br, 1H), 6.92 (d, 1H, J = 6.6 Hz), 4.44-4.39 (m, 2H), 4.20-4.10 (m, 1H), 3.70-3.65 (m, 2H), 3.65-3.55 (m, 1H), 3.30 (s, 3H), 1.95-1.75 (m, 2H), 1.75-1.50 (m, 4H), 1.50-1.20 (m, 2H). | 437 | 435 | 0.96 |

TABLE 3-continued

| Example | | | | | | |
|---|---|---|---|---|---|---|
| Example 6-553 | 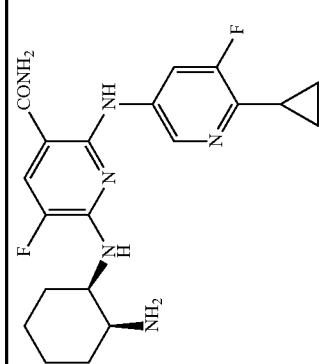 | 6-(((1R,2S)-2-aminocyclohexyl)amino)-2-((6-cyclopropyl-5-fluoropyridin-3-yl)amino)-5-fluoronicotinamide | HCl | DMSO-d6 300 MHz | δ: 11.74 (s, 1H), 8.26-8.23 (m, 1H), 8.13 (dd, 1H, J = 2.1, 12.6 Hz), 7.96 (dd, 1H, J = 12.6 Hz), 7.95-7.80 (m, 4H), 7.34 (br, 1H), 7.00 (d, 1H, J = 6.0 Hz), 4.26-4.15 (m, 1H), 3.7-3.60 (m, 1H), 2.26-2.16 (m, 1H), 2.00-1.35 (m, 8H), 0.98-0.90 (m, 4H). | 403 401 1.04 |
| Example 6-554 | 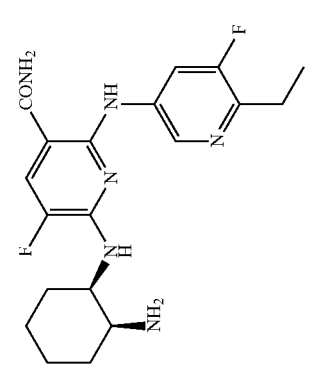 | 6-(((1R,2S)-2-aminocyclohexyl)amino)-2-((6-ethyl-5-fluoropyridin-3-yl)amino)-5-fluoronicotinamide | HCl | DMSO-d6 300 MHz | δ: 11.83 (s, 1H), 8.40-8.36 (m, 1H), 8.17 (dd, 1H, J = 2.1, 12.6 Hz), 7.97 (d, 1H, J = 12.3 Hz), 7.96-7.80 (m, 4H), 7.37 (br, 1H), 7.02 (d, 1H, J = 5.7 Hz), 4.30-4.18 (m, 1H), 3.70-3.60 (m, 1H), 2.80-2.69 (m, 2H), 2.00-1.35 (m, 8H), 1.21 (t, 3H, J = 7.5 Hz). | 391 389 0.95 |
| Example 6-555 | 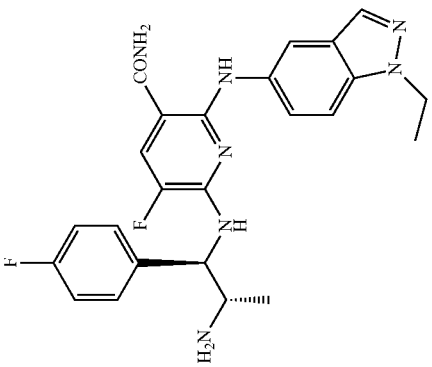 | 6-(((1R,2S)-2-amino-1-(4-fluorophenyl)propyl)amino)-2-((1-ethyl-1H-indazol-5-yl)amino)-5-fluoronicotinamide | HCl | | | 466 464 1.01 |

TABLE 3-continued

| Example | Name | Salt | MW calc | MW obs | RT |
|---|---|---|---|---|---|
| Example 6-556 | 6-(((1R,2S)-2-amino-1-(4-fluorophenyl)propyl)amino)-5-fluoro-2-((2-methoxypyridin-4-yl)amino)nicotinamide | HCl | 429 | 427 | 0.73 |
| Example 6-557 | 6-(((1R,2S)-2-amino-1-(4-fluorophenyl)propyl)amino)-2-((2,6-dimethoxypyridin-4-yl)amino)-5-fluoronicotinamide | HCl | 459 | 457 | 1.05 |

TABLE 3-continued

| Example | Name | Salt | | | |
|---|---|---|---|---|---|
| Example 6-558 | 6-(((1R,2S)-2-amino-1-(4-fluorophenyl)propyl)amino)-2-((5,6-dimethylpyridin-3-yl)amino)-5-fluoronicotinamide | HCl | 427 | 425 | 0.68 |
| Example 6-559 | 6-(((1R,2S)-2-amino-1-(4-fluorophenyl)propyl)amino)-5-fluoro-2-((2-(2-methoxyethoxy)pyridin-4-yl)amino)nicotinamide | HCl | 473 | 471 | 0.81 |
| Example 6-560 | 6-(((1R,2S)-2-aminocyclohexyl)amino)-5-fluoro-2-((1-methyl-3-morpholino-1H-indazol-5-yl)amino)nicotinamide | HCl | 483 | 481 | 0.9 |

TABLE 3-continued

| Example | Structure | Name | Salt | | | |
|---|---|---|---|---|---|---|
| Example 6-561 | 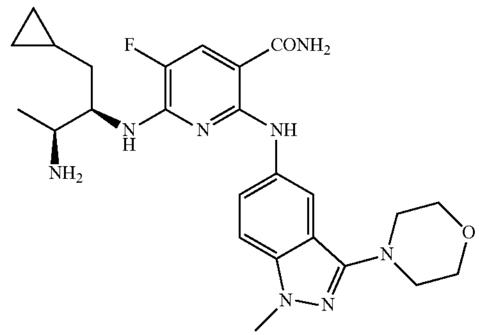 [SMILES: C[C@H](N)[C@@H](CC1CC1)Nc1nc(Nc2ccc3c(c2)c(N2CCOCC2)nn3C)c(C(N)=O)cc1F] | 6-(((2R,3S)-3-amino-1-cyclopropylbutan-2-yl)amino)-5-fluoro-2-((1-methyl-3-morpholino-1H-indazol-5-yl)amino)nicotinamide | HCl | 497 | 495 | 0.94 |
| Example 6-562 | 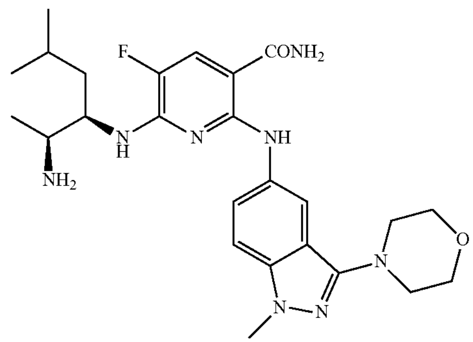 [SMILES: CC(C)C[C@@H](Nc1nc(Nc2ccc3c(c2)c(N2CCOCC2)nn3C)c(C(N)=O)cc1F)[C@H](C)N] | 6-(((2S,3R)-2-amino-5-methylhexan-3-yl)amino)-5-fluoro-2-((1-methyl-3-morpholino-1H-indazol-5-yl)amino)nicotinamide | HCl | 499 | 497 | 0.99 |
| Example 6-563 | 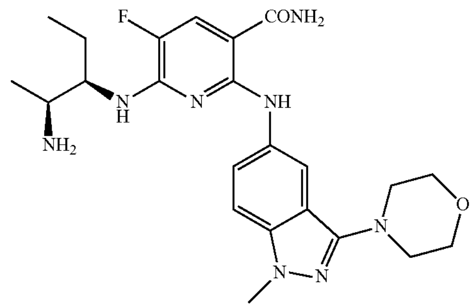 [SMILES: CC[C@@H](Nc1nc(Nc2ccc3c(c2)c(N2CCOCC2)nn3C)c(C(N)=O)cc1F)[C@H](C)N] | 6-(((2S,3R)-2-aminopentan-3-yl)amino)-5-fluoro-2-((1-methyl-3-morpholino-1H-indazol-5-yl)amino)nicotinamide | HCl | 471 | 469 | 0.87 |

TABLE 3-continued

| Example | Name | Structure | Salt | Solvent | MHz | NMR | | | |
|---|---|---|---|---|---|---|---|---|---|
| Example 6-564 | 6-(((1R,2S)-2-aminocyclohexyl)amino)-5-fluoro-2-((6-methoxy-5-morpholinopyridin-3-yl)amino)nicotinamide | | HCl | DMSO-d6-D2O | 300 MHz | δ: 8.07 (d, 1H, J = 2.1 Hz), 7.86 (d, 1H, J = 12.2 Hz), 7.22 (d, 1H, J = 2.1 Hz), 4.26-4.17 (m, 1H), 3.86 (s, 3H), 3.79-3.70 (m, 4H), 3.59-3.50 (m, 1H), 3.06-2.98 (m, 4H), 1.90-1.33 (m, 8H). | 460 | 458 | 0.88 |
| Example 6-565 | 6-(((1R,2S)-2-aminocyclohexyl)amino)-2-((6-ethoxy-5-morpholinopyridin-3-yl)amino)-5-fluoronicotinamide | | HCl | DMSO-d6-D2O | 300 MHz | δ: 8.05 (d, 1H, J = 2.1 Hz), 7.86 (d, 1H, J = 12.2 Hz), 7.20 (d, 1H, J = 2.1 Hz), 4.30 (q, 2H, J = 6.9 Hz), 4.25-4.17 (m, 1H), 3.79-3.72 (m, 4H), 3.58-3.50 (m, 1H), 3.12-2.97 (m, 4H), 1.92-1.34 (m, 8H), 1.33 (t, 3H, J = 6.9 Hz). | 474 | 472 | 0.95 |
| Example 6-566 | 6-(((1R,2S)-2-aminocyclohexyl)amino)-5-fluoro-2-((6-(2-methoxyethoxy)-5-morpholinopyridin-3-yl)amino)nicotinamide | | HCl | CD3OD | 300 MHz | δ: 8.16 (d, 1H, J = 2.1 Hz), 7.74 (d, 1H, J = 11.9 Hz), 7.18 (d, 1H, J = 2.1 Hz), 4.53-4.43 (m, 1H), 3.95-3.70 (m, 7H), 3.42 (s, 3H), 3.40-3.35 (m, 4H), 3.19-3.08 (m, 2H), 1.97-1.35 (m, 8H). | 504 | 502 | 0.91 |

TABLE 3-continued

| Example | Structure | Name | Salt | Solvent | MHz | NMR | | | |
|---|---|---|---|---|---|---|---|---|---|
| Example 6-567 | 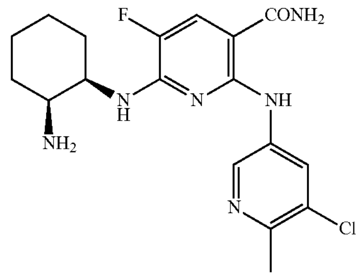 [SMILES: Cc1ncc(Nc2nc(N[C@@H]3CCCC[C@@H]3N)c(F)cc2C(N)=O)cc1Cl] | 6-(((1R,2S)-2-aminocyclohexyl)amino)-2-((5-chloro-6-methylpyridin-3-yl)amino)-5-fluoronicotinamide | HCl | CD3OD | 300 MHz | δ: 8.98 (d, 1H, J = 2.3 Hz), 8.72 (d, 1H, J = 2.3 Hz), 7.87 (d, 1H, J = 11.9 Hz), 4.57-4.47 (m, 1H), 3.83-3.71 (m, 1H), 3.01 (s, 3H), 2.08-1.54 (m, 8H). | 393 | 391 | 0.94 |
| Example 6-568 | 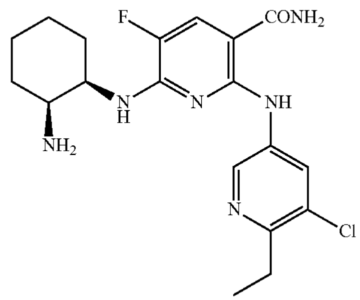 [SMILES: CCc1ncc(Nc2nc(N[C@@H]3CCCC[C@@H]3N)c(F)cc2C(N)=O)cc1Cl] | 6-(((1R,2S)-2-aminocyclohexyl)amino)-2-((5-chloro-6-ethylpyridin-3-yl)amino)-5-fluoronicotinamide | HCl | CD3OD | 300 MHz | δ: 8.86 (d, 1H, J = 2.3 Hz), 8.72 (d, 1H, J = 2.3 Hz), 7.87 (d, 1H, J = 11.9 Hz), 4.53-4.44 (m, 1H), 3.81-3.73 (m, 1H), 3.04 (q, 2H, J = 7.6 Hz), 2.05-1.50 (m, 8H), 1.34 (t, 3H, J = 7.6 Hz). | 407 | 405 | 1.06 |
| Example 6-569 | 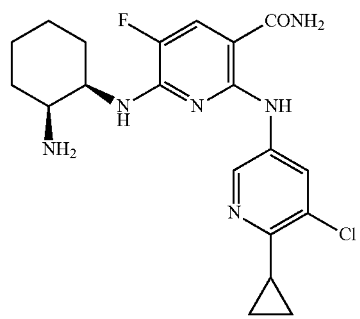 [SMILES: NC(=O)c1cc(F)c(N[C@@H]2CCCC[C@@H]2N)nc1Nc1cnc(C2CC2)c(Cl)c1] | 6-(((1R,2S)-2-aminocyclohexyl)amino)-2-((5-chloro-6-cyclopropylpyridin-3-yl)amino)-5-fluoronicotinamide | HCl | DMSO-d6-D2O | 300 MHz | δ: 8.37-8.33 (m, 2H), 7.91 (d, 1H, J = 12.2 Hz), 4.28-4.19 (m, 1H), 3.65-3.57 (m, 1H), 2.46-2.34 (m, 1H), 1.97-1.37 (m, 8H), 1.05-0.87 (m, 4H). | 419 | 417 | 1.14 |

TABLE 3-continued

| Example | Structure | Name | Salt | Solvent | Freq | | | |
|---|---|---|---|---|---|---|---|---|
| Example 6-570 | (structure) | 6-(((1R,2S)-2-aminocyclohexyl)amino)-2-((5-chloro-6-ethoxypyridin-3-yl)amino)-5-fluoronicotinamide | HCl | DMSO-d6-D2O | 300 MHz | δ: 8.30 (d, 1H, J = 2.5 Hz), 8.11 (d, 1H, J = 2.5 Hz), 7.89 (d, 1H, J = 12.2 Hz), 4.35 (q, 2H, J = 6.9 Hz), 4.21-4.12 (m, 1H), 3.63-3.53 (m, 1H), 1.94-1.34 (m, 8H), 1.34 (t, 3H, J = 6.9 Hz). | 423 | 421 | 1.11 |
| Example 6-571 | (structure) | 6-(((1R,2S)-2-aminocyclohexyl)amino)-2-((5-chloro-6-(2-methoxyethoxy)pyridin-3-yl)amino)-5-fluoronicotinamide | HCl | CD3OD | 300 MHz | δ: 8.19 (d, 1H, J = 2.5 Hz), 8.10 (d, 1H, J = 2.5 Hz), 7.75 (d, 1H, J = 11.9 Hz), 4.50-4.44 (m, 2H), 4.34-4.24 (m, 1H), 3.81-3.74 (m, 3H), 3.44 (s, 3H), 1.93-1.48 (m, 8H). | 453 | 451 | 1.04 |
| Example 6-572 | (structure) | 6-(((1R,2S)-2-aminocyclohexyl)amino)-2-((6-ethoxy-5-fluoropyridin-3-yl)amino)-5-fluoronicotinamide | HCl | DMSO-d6 | 300 MHz | δ: 11.43 (s, 1H), 8.10 (dd, 1H, J = 2.1, 12.9 Hz), 7.99 (d, 1H, J = 2.1 Hz), 7.93 (d, 1H, J = 12.6 Hz), 7.92-7.70 (m, 4H), 7.29 (br, 1H), 6.92 (d, 1H, J = 6.6 Hz), 4.35 (q, 2H, J = 7.2 Hz), 4.20-4.10 (m, 1H), 3.66-3.54 (m, 1H), 1.95-1.30 (m, 8H), 1.34 (t, 3H, J = 7.2 Hz). | 407 | 405 | 1.04 |

TABLE 3-continued

| Example | Structure | Name | Salt | Solvent | Freq | NMR | | | |
|---|---|---|---|---|---|---|---|---|---|
| Example 6-573 | 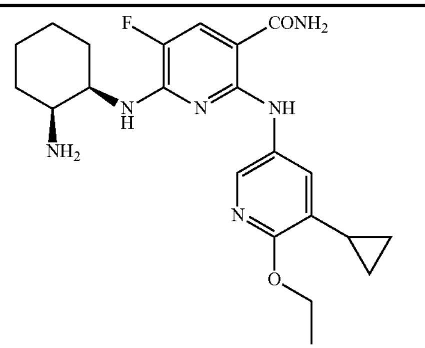 | 6-(((1R,2S)-2-aminocyclohexyl)amino)-2-((5-cyclopropyl-6-ethoxypyridin-3-yl)amino)-5-fluoronicotinamide | HCl | DMSO-d6 | 300 MHz | δ: 11.07 (s, 1H), 8.13 (d, 1H, J = 1.8 Hz), 7.96-7.84 (m, 5H), 7.27 (d, 1H, J = 2.7 Hz), 7.20 (br, 1H), 6.81 (d, 1H, J = 5.1 Hz), 4.31 (q, 2H, J = 7.2 Hz), 4.16-4.06 (m, 1H), 3.58-3.46 (m, 1H), 2.06-1.96 (m, 1H), 1.92-1.75 (m, 2H), 1.70-1.50 (m, 4H), 1.50-1.30 (m, 2H), 1.33 (t, 3H, J = 7.2 Hz), 0.96-0.80 (m, 2H), 0.80-0.64 (m, 2H). | 429 | 427 | 1.15 |
| Example 6-574 | 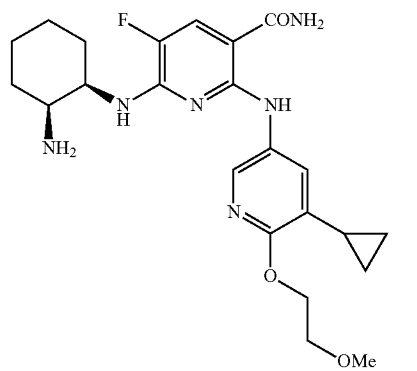 [SMILES: COCCOc1ncc(Nc2nc(N[C@@H]3CCCC[C@@H]3N)c(F)cc2C(N)=O)cc1C1CC1] | 6-(((1R,2S)-2-aminocyclohexyl)amino)-2-((5-cyclopropyl-6-(2-methoxyethoxy)pyridin-3-yl)amino)-5-fluoronicotinamide | HCl | DMSO-d6 | 300 MHz | δ: 11.07 (s, 1H), 8.13 (d, 1H, J = 2.7 Hz), 7.98 (d, 1H, J = 12.6 Hz), 7.84-7.64 (m, 4H), 7.27 (d, 1H, J = 1.8 Hz), 7.20 (br, 1H), 6.79 (d, 1H, J = 5.7 Hz), 4.40-4.34 (m, 2H), 4.16-4.04 (m, 1H), 3.70-3.65 (m, 2H), 3.60-3.50 (m, 1H), 3.32 (s, 3H), 2.07-1.96 (m, 1H), 1.90-1.70 (m, 2H), 1.70-1.50 (m, 4H), 1.50-1.30 (m, 2H), 0.95-0.88 (m, 2H), 0.82-0.64 (m, 2H). | 459 | 457 | 1.07 |
| Example 6-575 | 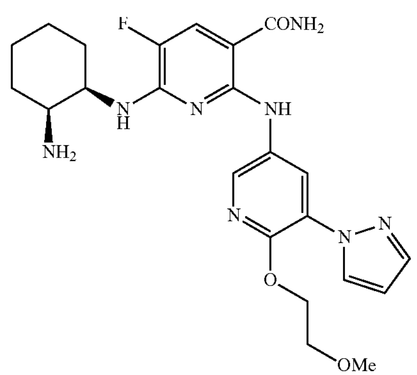 [SMILES: COCCOc1ncc(Nc2nc(N[C@@H]3CCCC[C@@H]3N)c(F)cc2C(N)=O)cc1-n1cccn1] | 6-(((1R,2S)-2-aminocyclohexyl)amino)-2-((6-(2-methoxyethoxy)-5-(1H-pyrazol-1-yl)pyridin-3-yl)amino)-5-fluoronicotinamide | HCl | DMSO-d6 | 300 MHz | δ: 11.57 (s, 1H), 8.73 (d, 1H, J = 2.7 Hz), 8.45 (d, 1H, J = 1.8 Hz), 8.08 (d, 1H, J = 1.5 Hz), 7.93 (d, 1H, J = 12.0 Hz), 7.80 (d, 1H, J = 1.5 Hz), 7.70 (m, 4H), 7.31 (br, 1H), 6.88 (d, 1H, J = 6.6 Hz), 6.59-6.56 (m, 1H), 4.53-4.47 (m, 2H), 4.28-4.16 (m, 1H), 3.75-3.70 (m, 2H), 3.55-3.45 (m, 1H), 3.31 (s, 3H), 1.85-1.15 (m, 8H). | 485 | 483 | 1.03 |

TABLE 3-continued

| Example | Name | | | | |
|---|---|---|---|---|---|
| Example 6-576 | 6-(((1R,2S)-2-amino-1-cyclopropylpropyl)amino)-2-((1-ethyl-1H-indazol-4-yl)amino)-5-fluoronicotinamide | HCl | 412 | 410 | 0.96 |
| Example 6-577 | 6-(((1R,2S)-2-amino-1-cyclopropylpropyl)amino)-2-((3-fluoro-1-methyl-1H-indazol-5-yl)amino)-5-fluoronicotinamide | HCl | 416 | 414 | 0.97 |
| Example 6-578 | 6-(((1R,2S)-2-amino-1-cyclopropylpropyl)amino)-2-((3-ethyl-1-methyl-1H-indazol-5-yl)amino)-5-fluoronicotinamide | HCl | 426 | 424 | 0.94 |

TABLE 3-continued

| Example | Structure | Name | Salt | | | |
|---|---|---|---|---|---|---|
| Example 6-579 | 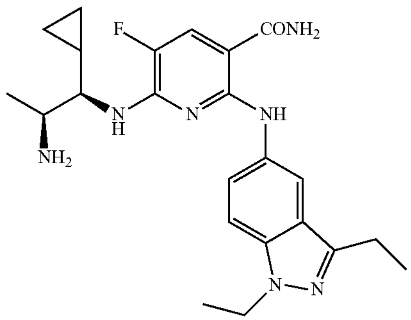 [SMILES: CCc1nn(CC)c2ccc(Nc3nc(N[C@H](C4CC4)[C@H](C)N)c(F)cc3C(N)=O)cc12] | 6-(((1R,2S)-2-amino-1-cyclopropylpropyl)amino)-2-((1,3-diethyl-1H-indazol-5-yl)amino)-5-fluoronicotinamide | HCl | 440 | 438 | 0.99 |
| Example 6-580 | 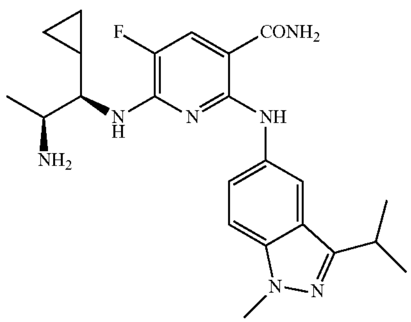 [SMILES: CC(C)c1nn(C)c2ccc(Nc3nc(N[C@H](C4CC4)[C@H](C)N)c(F)cc3C(N)=O)cc12] | 6-(((1R,2S)-2-amino-1-cyclopropylpropyl)amino)-5-fluoro-2-((3-isopropyl-1-methyl-1H-indazol-5-yl)amino)nicotinamide | HCl | 440 | 438 | 1 |
| Example 6-581 | 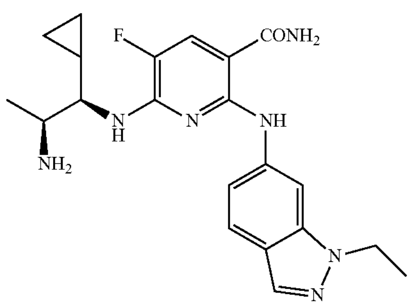 [SMILES: CCn1ncc2ccc(Nc3nc(N[C@H](C4CC4)[C@H](C)N)c(F)cc3C(N)=O)cc21] | 6-(((1R,2S)-2-amino-1-cyclopropylpropyl)amino)-2-((1-ethyl-1H-indazol-6-yl)amino)-5-fluoronicotinamide | HCl | 412 | 410 | 0.9 |

TABLE 3-continued

| Example | Structure | Name | Salt | | | |
|---|---|---|---|---|---|---|
| Example 6-582 | 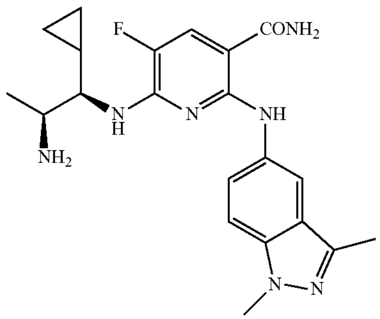 [SMILES: Cc1nn(C)c2ccc(Nc3nc(N[C@H](C4CC4)[C@H](C)N)c(F)cc3C(N)=O)cc12] | 6-(((1R,2S)-2-amino-1-cyclopropylpropyl)amino)-2-((1,3-dimethyl-1H-indazol-5-yl)amino)-5-fluoronicotinamide | HCl | 412 | 410 | 0.9 |
| Example 6-583 | 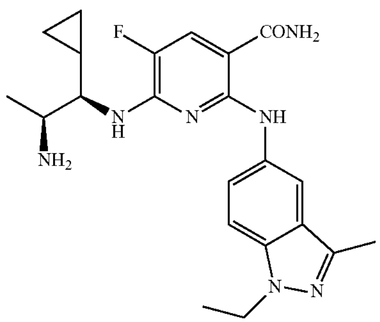 [SMILES: CCn1nc(C)c2cc(Nc3nc(N[C@H](C4CC4)[C@H](C)N)c(F)cc3C(N)=O)ccc21] | 6-(((1R,2S)-2-amino-1-cyclopropylpropyl)amino)-2-((1-ethyl-3-methyl-1H-indazol-5-yl)amino)-5-fluoronicotinamide | HCl | 426 | 424 | 0.95 |
| Example 6-584 | 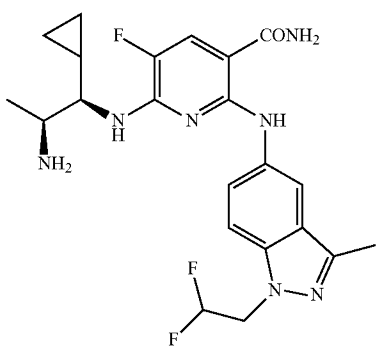 [SMILES: Cc1nn(CC(F)F)c2ccc(Nc3nc(N[C@H](C4CC4)[C@H](C)N)c(F)cc3C(N)=O)cc12] | 6-(((1R,2S)-2-amino-1-cyclopropylpropyl)amino)-2-((1-(2,2-difluoroethyl)-3-methyl-1H-indazol-5-yl)amino)-5-fluoronicotinamide | HCl | 462 | 460 | 0.97 |

TABLE 3-continued

| Example | Structure | Name | Salt | MS1 | MS2 | RT |
|---|---|---|---|---|---|---|
| Example 6-585 | 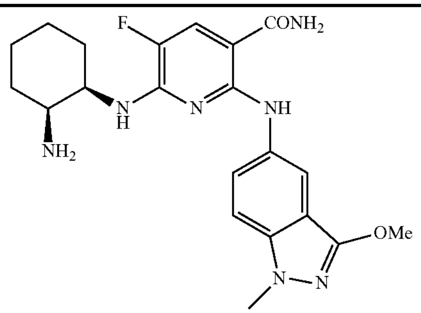 | 6-(((1R,2S)-2-aminocyclohexyl)amino)-5-fluoro-2-((3-methoxy-1-methyl-1H-indazol-5-yl)amino)nicotinamide | HCl | 428 | 426 | 0.95 |
| Example 6-586 | 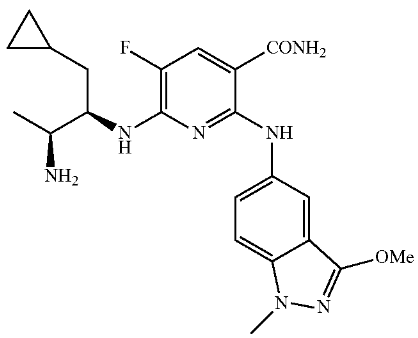 [SMILES: COc1nn(C)c2ccc(Nc3nc(N[C@H](CC4CC4)[C@H](C)N)c(F)cc3C(N)=O)cc12] | 6-(((2R,3S)-3-amino-1-cyclopropylbutan-2-yl)amino)-5-fluoro-2-((3-methoxy-1-methyl-1H-indazol-5-yl)amino)nicotinamide | HCl | 442 | 440 | 0.96 |
| Example 6-587 | 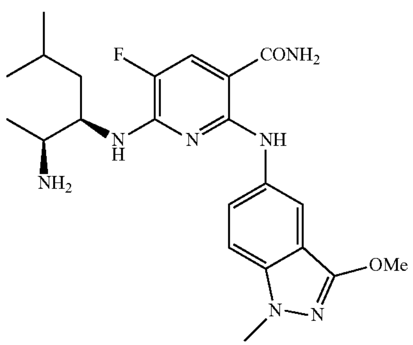 [SMILES: COc1nn(C)c2ccc(Nc3nc(N[C@H](CC(C)C)[C@H](C)N)c(F)cc3C(N)=O)cc12] | 6-(((2S,3R)-2-amino-5-methylhexan-3-yl)amino)-5-fluoro-2-((3-methoxy-1-methyl-1H-indazol-5-yl)amino)nicotinamide | HCl | 444 | 442 | 1.03 |

TABLE 3-continued

| Example | Structure | Name | Salt | | | |
|---|---|---|---|---|---|---|
| Example 6-588 | 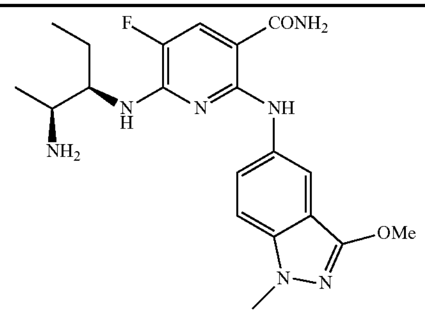 | 6-(((2S,3R)-2-aminopentan-3-yl)amino)-5-fluoro-2-((3-methoxy-1-methyl-1H-indazol-5-yl)amino)nicotinamide | HCl | 416 | 414 | 0.92 |
| Example 6-589 | 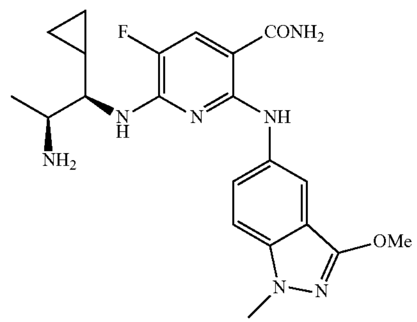 [SMILES: COc1nn(C)c2ccc(Nc3nc(N[C@H](C4CC4)[C@H](C)N)c(F)cc3C(N)=O)cc12] | 6-(((1R,2S)-2-amino-1-cyclopropylpropyl)amino)-5-fluoro-2-((3-methoxy-1-methyl-1H-indazol-5-yl)amino)nicotinamide | HCl | 428 | 426 | 0.95 |
| Example 6-590 | 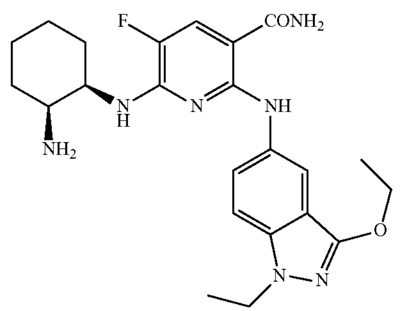 [SMILES: CCOc1nn(CC)c2ccc(Nc3nc(N[C@@H]4CCCC[C@@H]4N)c(F)cc3C(N)=O)cc12] | 6-(((1R,2S)-2-aminocyclohexyl)amino)-2-((3-ethoxy-1-ethyl-1H-indazol-5-yl)amino)-5-fluoronicotinamide | HCl | 456 | 454 | 1.05 |

TABLE 3-continued

| Example 6-591 | 6-(((2R,3S)-3-amino-1-cyclopropylbutan-2-yl)amino)-2-((3-ethoxy-1-ethyl-1H-indazol-5-yl)amino)-5-fluoronicotinamide | HCl | 470 | 468 | 1.12 |
| --- | --- | --- | --- | --- | --- |
| Example 6-592 | 6-(((2S,3R)-2-amino-5-methylhexan-3-yl)amino)-2-((3-ethoxy-1-ethyl-1H-indazol-5-yl)amino)-5-fluoronicotinamide | HCl | 472 | 470 | 1.18 |
| Example 6-593 | 6-(((2S,3R)-2-aminopentan-3-yl)amino)-2-((3-ethoxy-1-ethyl-1H-indazol-5-yl)amino)-5-fluoronicotinamide | HCl | 444 | 442 | 1.03 |

TABLE 3-continued

| Example | Structure | Name | Salt | | | |
|---|---|---|---|---|---|---|
| Example 6-594 | 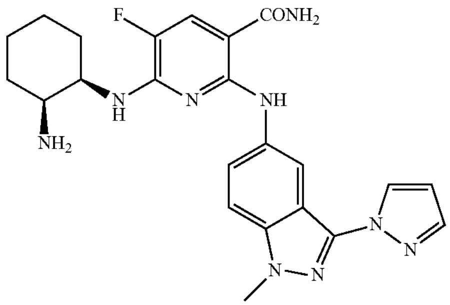 [SMILES: Cn1nc(-n2cccn2)c2cc(Nc3nc(N[C@@H]4CCCC[C@@H]4N)c(F)cc3C(N)=O)ccc21] | 6-(((1R,2S)-2-aminocyclohexyl)amino)-5-fluoro-2-((1-methyl-3-(1H-pyrazol-1-yl)-1H-indazol-5-yl)amino)nicotinamide | HCl | 464 | 462 | 1.02 |
| Example 6-595 | 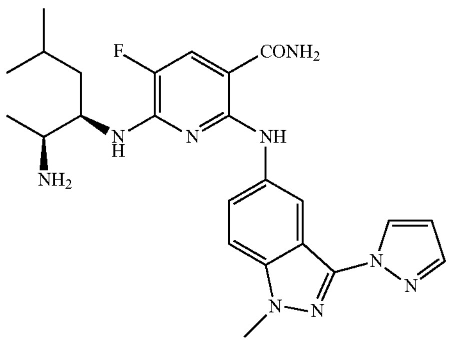 [SMILES: CC(C)C[C@@H](Nc1nc(Nc2ccc3c(c2)c(-n2cccn2)nn3C)c(C(N)=O)cc1F)[C@H](C)N] | 6-(((2S,3R)-2-amino-5-methylhexan-3-yl)amino)-5-fluoro-2-((1-methyl-3-(1H-pyrazol-1-yl)-1H-indazol-5-yl)amino)nicotinamide | HCl | 480 | 478 | 1.15 |
| Example 6-596 | 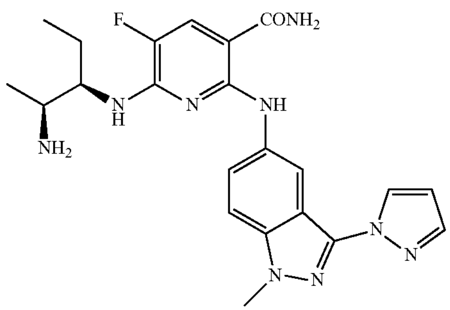 [SMILES: CC[C@@H](Nc1nc(Nc2ccc3c(c2)c(-n2cccn2)nn3C)c(C(N)=O)cc1F)[C@H](C)N] | 6-(((2S,3R)-2-aminopentan-3-yl)amino)-5-fluoro-2-((1-methyl-3-(1H-pyrazol-1-yl)-1H-indazol-5-yl)amino)nicotinamide | HCl | 452 | 450 | 0.99 |

TABLE 3-continued
| Example 6-597 | 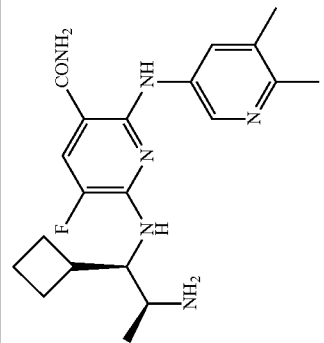 6-(((1R,2S)-2-amino-1-cyclobutylpropyl)amino)-2-((5,6-dimethylpyridin-3-yl)amino)-5-fluoronicotinamide | HCl | 387 | 385 | 0.74 |
| --- | --- | --- | --- | --- | --- |
| Example 6-598 | 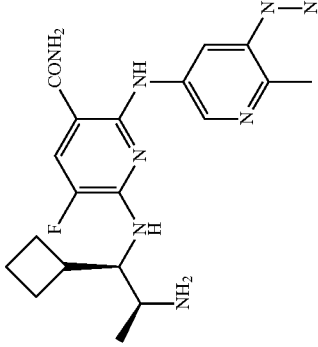 6-(((1R,2S)-2-amino-1-cyclobutylpropyl)amino)-5-fluoro-2-((6-methyl-5-(2H-1,2,3-triazol-2-yl)pyridin-3-yl)amino)nicotinamide | HCl | 440 | 438 | 0.96 |

Example 7

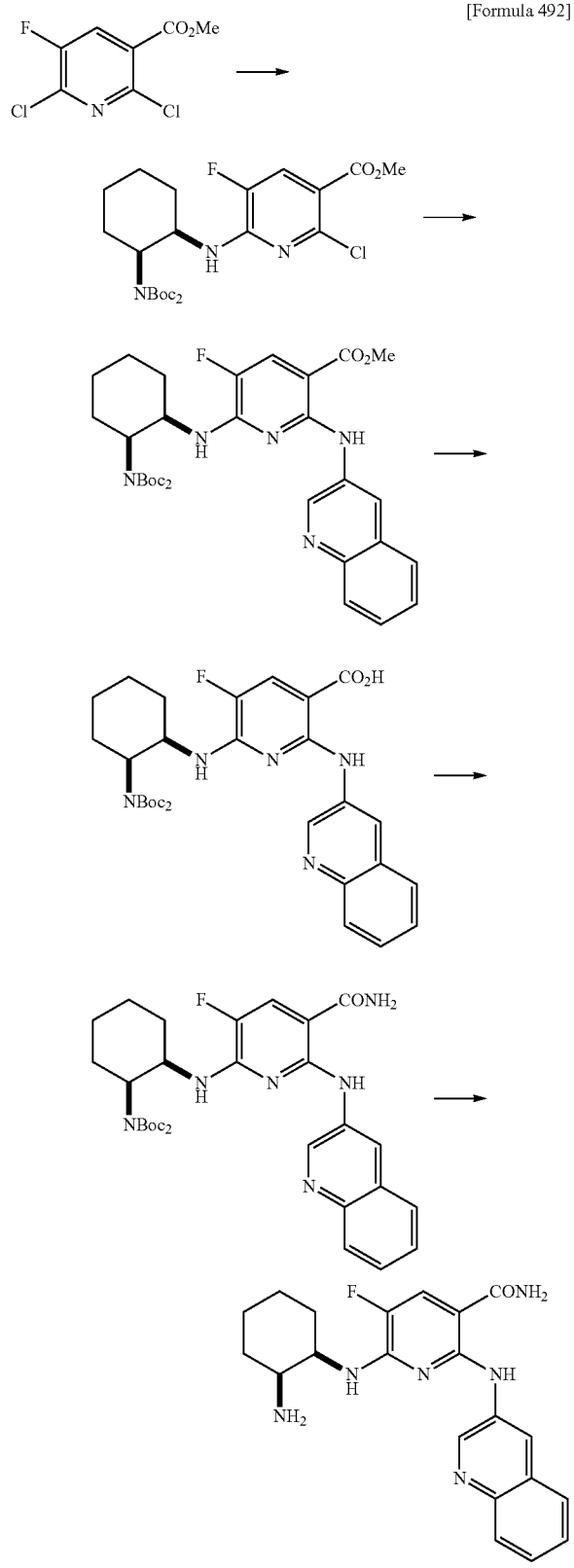

1st Step

The following compound was obtained as described in Reference Example 2. Methyl 6-(cis-2-(bis(tert-butoxycarbonyl)amino)cyclohexylamino)-2-chloro-5-fluoro nicotinate $^1$H-NMR (CDCl$_3$, 400 MHz) δ:7.69 (d, 1H, J=10.7 Hz), 7.32 (brs, 1H), 4.34 (dt, 1H, J=3.7 Hz, 13.0 Hz), 4.30-4.24 (m, 1H), 3.86 (s, 3H), 2.51-2.43 (m, 1H), 2.31-2.17 (m, 1H), 1.90-1.82 (m, 1H), 1.65-1.30 (m, 5H), 1.47 (s, 18H)

2nd Step

The following compound was obtained as described in the 1st step of Example 1.

Methyl 6-(cis-2-(bis(tert-butoxycarbonyl)amino) cyclohexylamino)-5-fluoro-2-(quinolin-3-ylamino) nicotinate MS (ESI, m/z): 610 (M+H), 608 (M−H)

3rd Step

The following compound was obtained as described in the 1st step of Reference Example 3.

6-(cis-2-(bis(tert-butoxycarbonyl)amino)cyclohexylamino)-5-fluoro-2-(quinolin-3-ylamino)nicotinic acid MS (ESI, m/z): 596 (M+H), 594 (M−H)

4th Step

A mixture of 6-(cis-2-(bis(tert-butoxycarbonyl)amino)cyclohexylamino)-5-fluoro-2-(quinolin-3-ylamino)nicotinic acid (65 mg), HOBt.H$_2$O (67 mg), WSC.HCl (84 mg), and DMF (3 ml) was stirred at room temperature for 2 hours, and 25% ammonia water (1 ml) was added, followed by stirring at 40° C. for 30 minutes. Ethyl acetate was added to the reaction mixture, the reaction mixture was washed with water and then with saturated saline and dried over anhydrous magnesium sulfate, and the solvent was distilled away under reduced pressure. The obtained residue was purified by silica gel column chromatography (hexane:ethyl acetate=10:0 to 1:1), and a light yellow solid of di-tert-butyl cis-2-(5-aminocarbonyl-3-fluoro-6-(quinolin-3-ylamino)pyridin-2-ylamino)cyclohexylimidedicarbamate (41 mg) was thus obtained.

MS (ESI, m/z): 595 (M+H)

5th step

The following compound was obtained as described in the 2nd step of Example 1.

6-(cis-2-aminocyclohexylamino)-5-fluoro-2-(quinolin-3-ylamino)nicotinamide ($^1$H-NMR data and MS data are shown in table 4.)

Example 8

The compounds listed in table 4 were obtained as described in Example 7.

TABLE 4

| Number | Structure | Number | Structure |
|---|---|---|---|
| Example 8-1 HCl salt | 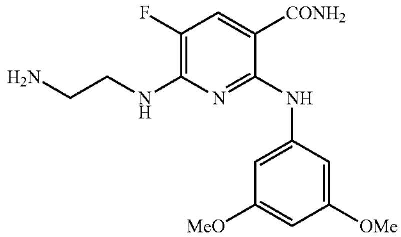 [SMILES: COc1cc(Nc2nc(NCCN)c(F)cc2C(N)=O)cc(OC)c1] | Example 8-2 HCl salt | 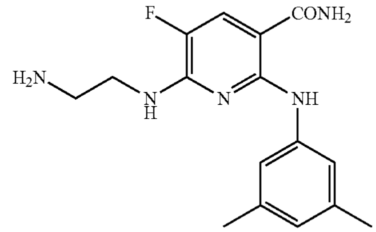 [SMILES: Cc1cc(C)cc(Nc2nc(NCCN)c(F)cc2C(N)=O)c1] |
| Example 8-3 HCl salt | 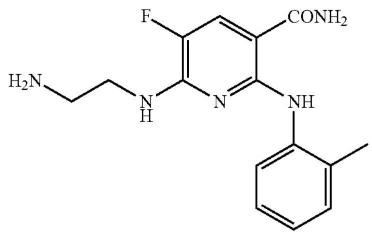 [SMILES: Cc1ccccc1Nc1nc(NCCN)c(F)cc1C(N)=O] | Example 8-4 (Example 7) HCl salt | 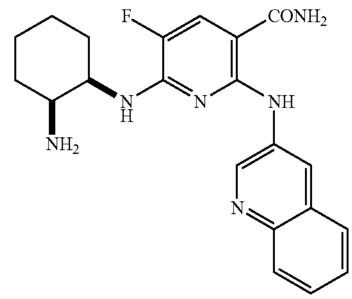 |
| Example 8-5 HCl salt | 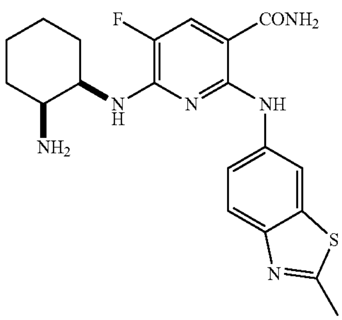 | Example 8-6 HCl salt | 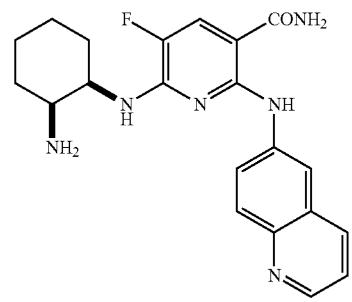 |
| Example 8-7 HCl salt | 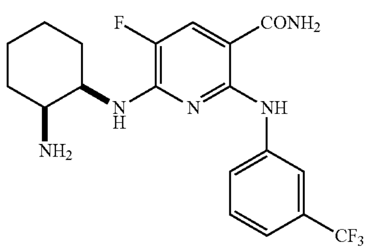 | Example 8-8 HCl salt | 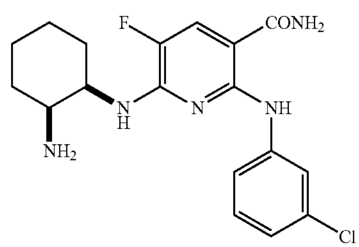 |
| Example 8-9 HCl salt | 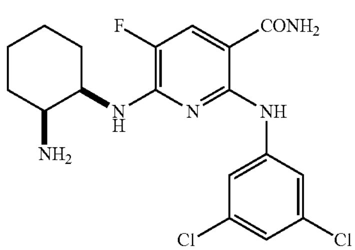 | Example 8-10 HCl salt | 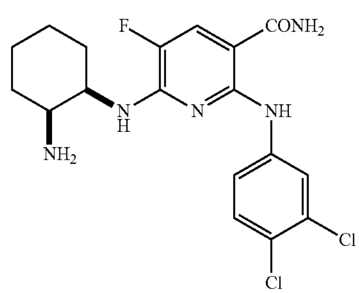 |

TABLE 4-continued

Example 8-11 HCl salt

| Number | Compound name | ¹H-NMR | MS (ESI, m/z) |
|---|---|---|---|
| Example 8-1 HCl salt | 6-((2-aminoethyl)amino)-2-((3,5-dimethoxyphenyl)amino)-5-fluoro-nicotinamide | ¹H-NMR (DMSO-d$_6$, 400 MHz) δ: 11.66 (s, 1H), 8.00-7.88 (m, 5H), 7.40-7.12 (m, 2H), 6.81 (d, 2H, J = 2.3 Hz), 6.11 (t, 1H, J = 2.3 Hz), 3.73 (s, 6H), 3.70-3.64 (m, 2H), 3.14-3.06 (m, 2H). | 350 (M + H) 348 (M − H) |
| Example 8-2 HCl salt | 6-((2-aminoethyl)amino)-2-((3,5-dimethylphenyl)amino)-5-fluoro-nicotinamide | ¹H-NMR (DMSO-d$_6$, 400 MHz) δ: 11.51 (s, 1H), 7.88 (d, 1H, J = 12.7 Hz), 7.82-7.60 (m, 4H), 7.25-7.20 (m, 4H), 6.60-6.56 (m, 1H), 3.66-3.57 (m, 2H), 3.18-3.08 (m, 2H), 2.24 (s, 6H). | 318 (M + H) |
| Example 8-3 HCl salt | 6-((2-aminoethyl)amino)-5-fluoro-2-(2-methylphenylamino)-nicotinamide | ¹H-NMR (CD$_3$OD, 300 MHz) δ: 7.90 (d, 1H, J = 8.1 Hz), 7.73 (d, 1H, J = 12.0 Hz), 7.25-7.16 (m, 2H), 6.99 (t, 1H, J = 8.1 Hz), 3.61 (t, 2H, J = 5.2 Hz), 3.10 (t, 2H, J = 5.2 Hz), 2.30 (s, 3H). | 304 (M + H) |
| Example 8-4 HCl salt | 6-((cis-2-aminocyclohexyl)amino)-5-fluoro-2-(quinolin-3-ylamino)-nicotinamide | ¹H-NMR (DMSO-d$_6$, 400 MHz) δ: 12.12 (s, 1H), 9.35-9.30 (m, 1H), 8.99-8.95 (m, 1H), 8.15-8.01 (m, 7H), 7.80-7.70 (m, 2H), 7.45 (brs, 1H), 7.01 (d, 1H, J = 6.8 Hz), 4.45-4.38 (m, 1H), 3.64-3.58 (m, 1H), 1.98-1.84 (m, 2H), 1.78-1.57 (m, 4H), 1.52-1.36 (m, 2H). | 395 (M + H) |
| Example 8-5 HCl salt | 6-(cis-2-aminocyclohexylamino)-5-fluoro-2-((2-methyl-1,3-benzo-thiazol-6-yl)amino)nicotinamide | ¹H-NMR (DMSO-d$_6$, 300 MHz) δ: 11.78 (s, 1H), 8.40 (d, 1H, J = 2.1 Hz), 7.95-8.00 (m, 6H), 7.36 (dd, 1H, J = 2.1, 8.7 Hz), 7.33-7.18 (m, 1H), 6.93 (d, 1H, J = 6.0 Hz), 4.33-4.23 (m, 1H), 3.77-3.66 (m, 1H), 2.77 (s, 3H), 1.95-1.38 (m, 8H). | 413 (M + H) |
| Example 8-6 HCl salt | 6-(cis-2-aminocyclohexylamino)-5-fluoro-2-(quinolin-6-ylamino)-nicotinamide | ¹H-NMR (CD$_3$OD, 300 MHz) δ: 9.00 (d, 1H, J = 8.4 Hz), 8.95 (dd, 1H, J = 1.4, 5.4 Hz), 8.72 (d, 1H, J = 2.3 Hz), 8.25 (dd, 1H, J = 2.4, 9.3 Hz), 8.16 (d, 1H, J = 9.3 Hz), 8.03-7.96 (m, 1H), 7.89 (d, 1H, J = 11.9 Hz), 4.75-4.60 (m, 1H), 3.89-3.86 (m, 1H), 2.15-1.55 (m, 8H). | 395 (M + H) |
| Example 8-7 HCl salt | 6-(cis-2-aminocyclohexylamino)-5-fluoro-2-((3-(trifluoromethyl)-phenyl)amino)nicotinamide | ¹H-NMR (DMSO-d$_6$, 400 MHz) δ: 11.88 (s, 1H), 8.15-8.12 (m, 1H), 7.95 (d, 1H, J = 12.7 Hz), 7.86-7.70 (m, 3H), 7.65-7.59 (m, 1H), 7.52-7.47 (m, 1H), 7.40-7.30 (m, 1H), 7.29-7.24 (m, 1H), 6.89-6.83 (m, 1H), 4.33-4.25 (m, 1H), 3.56-3.48 (m, 1H), 1.94-1.32 (m, 8H). | 412 (M + H) |
| Example 8-8 HCl salt | 6-(cis-2-aminocyclohexylamino)-2-((3-chlorophenyl)amino)-5-fluoro-nicotinamide | ¹H-NMR (DMSO-d$_6$, 400 MHz) δ•: 11.77 (s, 1H), 8.01-7.97 (m, 1H), 7.93 (d, 1H, J = 12.4 Hz), 7.87-7.72 (m, 3H), 7.35-7.25 (m, 2H), 7.24-7.19 (m, 1H), 7.00-6.90 (m, 2H), 4.29-4.21 (m, 1H), 3.66-3.59 (m, 1H), 1.94-1.37 (m, 8H). | 376 (M − H) |
| Example 8-9 HCl salt | 6-(cis-2-aminocyclohexylamino)-2-((3,5-dichlorophenyl)amino)-5-fluoronicotinamide | ¹H-NMR (DMSO-d$_6$, 400 MHz) δ: 11.91 (s, 1H), 7.96 (d, 1H, J = 12.4 Hz), 7.93-7.82 (m, 4H), 7.66 (d, 2H, J = 1.8 Hz), 7.46-7.32 (m, 1H), 7.09 (t, 1H, J = 1.8 Hz), 4.29-4.21 (m, 1H), 3.64-3.54 (m, 1H), 1.96-1.36 (m, 8H). | 413 (M + H), 415 (M + H) |
| Example 8-10 HCl salt | 6-(cis-2-aminocyclohexylamino)-2-((3,4-dichlorophenyl)amino)-5-fluoronicotinamide | ¹H-NMR (DMSO-d$_6$, 400 MHz) δ: 11.86 (s, 1H), 8.18 (d, 1H, J = 2.6 Hz), 8.00-7.81 (m, 4H), 7.96 (d, 1H, J = 12.3 Hz), 7.49 (d, 1H, J = 8.8 Hz), 7.44-7.32 (m, 1H), 7.30 (dd, 1H, J = 2.4, 8.8 Hz), 7.01-6.94 (m, 1H), 4.31-4.22 (m, 1H), 3.66-3.57 (m, 1H), 1.98-1.38 (m, 8H). | 413 (M + H), 415 (M + H) |

TABLE 4-continued

| Example | | | |
|---|---|---|---|
| 8-11 HCl salt | 6-(2-aminoethylamino)-5-fluoro-2-(quinolin-3-ylamino)nicotinamide | $^1$H-NMR (DMSO-$d_6$, 400 MHz) δ: 12.20 (s, 1H), 9.40-9.34 (m, 1H), 8.97-8.92 (m, 1H), 8.10-7.96 (m, 7H), 7.78-7.66 (m, 2H), 7.56-7.48 (m, 1H), 7.44 (brs, 1H), 3.78-3.72 (m, 2H), 3.20-3.12 (m, 2H). | 341 (M + H), 339 (M − H) |

Example 9

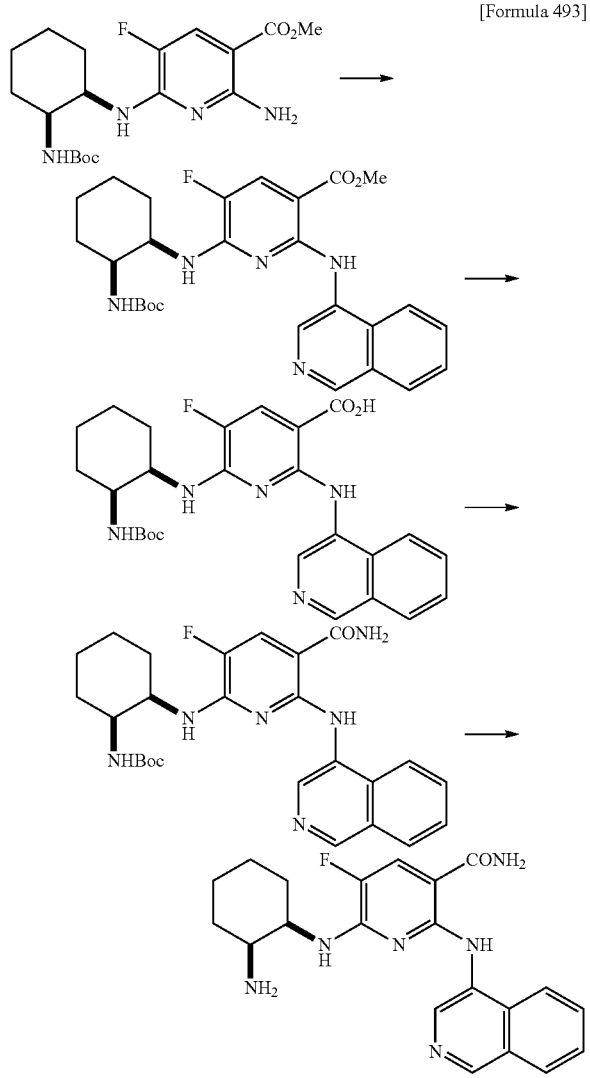

[Formula 493]

1st Step 4-bromoisoquinoline (65 mg), cesium carbonate (170 mg), Pd$_2$(dba)$_3$ (29 mg), and Xantphos (36 mg) were added to a 1,4-dioxane (2.1 ml) solution containing methyl 2-amino-6-(cis-2-(tert-butoxycarbonylamino)cyclohexylamino)-5-fluoronicotinate (80 mg), followed by stirring at 100° C. for 3 hours in a nitrogen atmosphere. The reaction mixture was cooled to room temperature, and water and ethyl acetate were added. Insoluble matter was removed by filtration, and the filter cake was washed with water and ethyl acetate. The organic layer was collected, washed with saturated saline, and dried over anhydrous magnesium sulfate, and the solvent was distilled away under reduced pressure. The obtained residue was purified by silica gel column chromatography (hexane:ethyl acetate=10:0 to 1:2), diisopropylether was added, solid matter was collected by filtration, and a light yellow solid of methyl 6-(cis-2-(tert-butoxycarbonylamino)cyclohexylamino)-5-fluoro-2-(isoquinoline 4-ylamino)nicotinate (77 mg) was obtained.

MS (ESI, m/z): 510 (M+H), 508 (M−H)

2nd Step

A 1N sodium hydroxide aqueous solution (2 ml) was added to a solution of tetrahydrofuran (2 ml) and methanol (2 ml) containing methyl 6-(cis-2-(tert-butoxycarbonylamino)cyclohexylamino)-5-fluoro-2-(isoquinoline 4-ylamino)nicotinate (75 mg), followed by stirring at 65° C. for 2 hours. The reaction mixture was cooled to room temperature, and the solvent was distilled away under reduced pressure. A saturated aqueous ammonium chloride solution was added to the obtained residue, solid matter was collected by filtration and washed with water and ethyl acetate, and a yellow solid of 6-(cis-2-(tert-butoxycarbonylamino)cyclohexylamino)-5-fluoro-2-(isoquinoline 4-ylamino)nicotinic acid (67 mg) was thus obtained.

MS (ESI, m/z): 496 (M+H), 494 (M−H)

3rd Step

Ammonium chloride (28 mg), WSC.HCl (75 mg), HOBt.H$_2$O (60 mg), and diisopropylethylamine (180 μl) were added to a DMF (1.3 ml) suspension containing 6-(cis-2-(tert-butoxycarbonylamino)cyclohexylamino)-5-fluoro-2-(isoquinoline 4-ylamino)nicotinic acid (65 mg), followed by stirring at room temperature for 3 hours. A saturated aqueous ammonium chloride solution and ethyl acetate were added to the reaction mixture. Solid matter was collected by filtration and washed with water and ethyl acetate, and a light yellow solid of tert-butyl cis-2-(5-aminocarbonyl-3-fluoro-6-(isoquinolin-4-ylamino)pyridin-2-ylamino)cyclohexylcarbamate (47 mg) was thus obtained.

$^1$H-NMR (DMSO-$d_6$, 400 MHz) δ:12.39 (s, 1H), 9.56 (s, 1H), 8.95 (s, 1H), 8.18 (d, 1H, J=8.8 Hz), 8.13 (d, 1H, J=8.2 Hz), 7.96 (d, 1H, J=12.6 Hz), 7.91-7.81 (m, 2H), 7.74-7.68 (m, 1H), 7.40-7.28 (br, 1H), 6.82-6.75 (m, 1H), 6.72-6.65 (m, 1H), 4.12-4.01 (m, 1H), 3.99-3.92 (m, 1H), 1.89-1.03 (m, 17H)

MS (ESI, m/z): 495 (M+H), 493 (M−H)

4th Step

A mixture of tert-butyl cis-2-(5-aminocarbonyl-3-fluoro-6-(isoquinoline 4-ylamino)pyridin-2-ylamino)cyclohexylcarbamate (45 mg) and TFA (0.9 ml) was stirred at room temperature for 30 minutes. The solvent was distilled away under reduced pressure (at 40° C. or less), and ethyl acetate and 4N hydrogen chloride/1,4-dioxane (34 μl) were added to the obtained residue, followed by stirring at room temperature for 30 minutes. Solid matter was collected by filtration and washed with ethyl acetate, and a yellow solid of 6-(cis-2-aminocyclohexylamino)-5-fluoro-2-(isoquinolin-4-ylamino)nicotinamide•hydrochloride (47 mg) was thus obtained.

($^1$H-NMR data and MS data are shown in table 5.)

Example 10

The compounds listed in table 5 were obtained as described in Example 9.

TABLE 5

| Number | Structure | Number | Structure |
|---|---|---|---|
| Example 10-1 (Example 9) HCl salt | 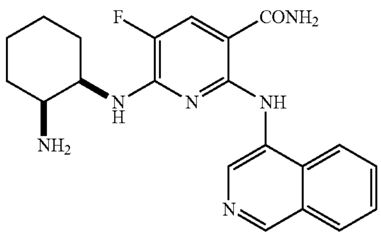 | Example 10-2 HCl salt | 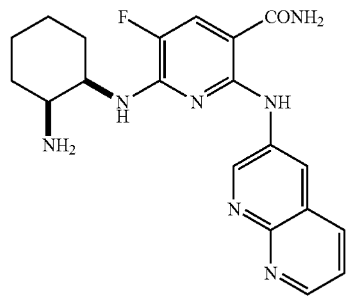 |

| Number | Compound name | ¹H-NMR | MS (ESI, m/z) |
|---|---|---|---|
| Example 10-1 HCl salt | 6-(cis-2-aminocyclohexylamino)-5-fluoro-2-(isoquinolin-4-ylamino)nicotinamide | ¹H-NMR (DMSO-$d_6$, 400 MHz) δ: 9.56 (s, 1H), 9.39-9.33 (m, 1H), 8.48-8.41 (m, 1H), 8.39-8.33 (m, 1H), 8.24-8.09 (m, 3H), 8.04-7.91 (m, 4H), 7.67-7.58 (m, 1H), 7.23-7.16 (m, 1H), 4.41-4.31 (m, 1H), 3.65-3.57 (m, 1H), 1.95-1.40 (m, 8H). | 393 (M − H) |
| Example 10-2 HCl salt | 6-(cis-2-aminocyclohexylamino)-5-fluoro-2-((1,8-naphthyridin-3-yl)amino)nicotinamide | ¹H-NMR (DMSO-$d_6$, 400 MHz) δ: 12.15 (s, 1H), 9.17 (d, 1H, J = 2.9 Hz), 8.95 (dd, 1H, J = 1.6, 4.3 Hz), 8.77 (d, 1H, J = 2.9 Hz), 8.50-8.45 (m, 1H), 8.02 (d, 1H, J = 12.6 Hz), 7.98-7.84 (m, 4H), 7.69 (dd, 1H, J = 4.4, 8.2 Hz), 7.52-7.42 (m, 1H), 7.01-6.96 (m, 1H), 4.48-4.39 (m, 1H), 3.71-3.61 (m, 1H), 1.98-1.40 (m, 8H). | 396 (M + H) |

Example 11

[Formula 494]

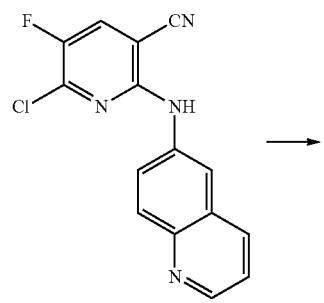

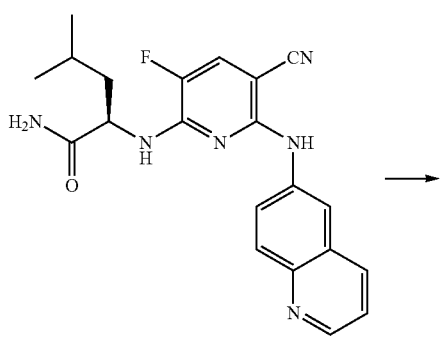

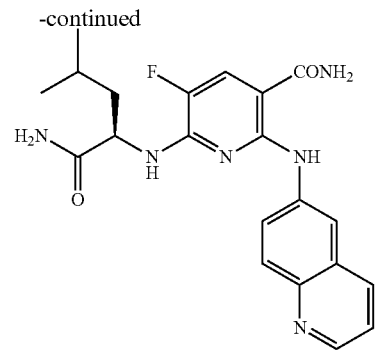

-continued

1st Step

Calcium carbonate (138 mg) and D-leucinamide•hydrochloride (83 mg) were added to a 1,4-dioxane (1 ml) solution containing 6-chloro-5-fluoro-2-(quinolin-6-ylamino)nicotinonitrile (30 mg), followed by reflux for 15 hours. The reaction mixture was cooled to room temperature, and water, sodium chloride, and ethyl acetate were added. The organic layer was collected and dried over anhydrous magnesium sulfate, and the solvent was distilled away under reduced pressure. Diisopropylether was added to the obtained residue, solid matter was collected by filtration, and a yellow solid of (2R)-2-(5-cyano-3-fluoro-6-(quinolin-6-ylamino)pyridin-2-ylamino)-4-methylpentanamide (33 mg) was thus obtained.

MS (ESI, m/z): 393 (M+H), 391 (M−H)

2nd Step

Potassium carbonate (35 mg) and a 30% hydrogen peroxide solution (29 μl) were added to an ethanol (1 ml) solution containing (2R)-2-(5-cyano-3-fluoro-6-(quinolin-6-ylamino)pyridin-2-ylamino)-4-methylpentanamide (20 mg), followed by stirring at room temperature for 1 hour. A 30% hydrogen peroxide solution (29 μl) was added to the reaction mixture, followed by stirring at room temperature for 1 hour. Water, sodium chloride, and ethyl acetate were added to the reaction mixture. The organic layer was collected and dried over anhydrous magnesium sulfate, and the solvent was distilled away under reduced pressure. The obtained residue was dissolved in ethyl acetate, and diisopropylether was added. Solid matter was collected by filtration and washed with diisopropylether, and a yellow solid of 6-((2R)-1-amino-4-methyl-1-oxopentan-2-ylamino)-5-fluoro-2-(quinolin-6-ylamino)nicotinamide (8 mg) was thus obtained.

($^1$H-NMR data and MS data are shown in table 6.)

Example 12

The compounds listed in table 6 below were obtained as described in Example 11.

TABLE 6

| Number | Structure | Number | Structure |
| --- | --- | --- | --- |
| Example 12-1 | 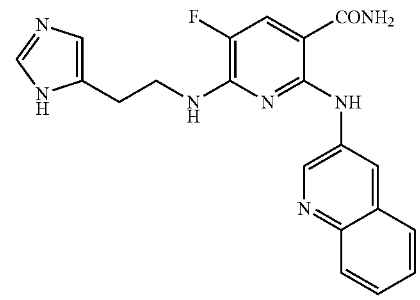 [SMILES: NC(=O)c1cc(F)c(NCCc2cnc[nH]2)nc1Nc1cnc2ccccc2c1] | Example 12-2 | 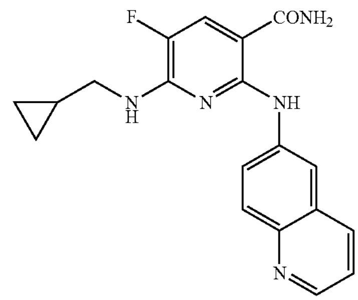 [SMILES: NC(=O)c1cc(F)c(NCC2CC2)nc1Nc1ccc2ncccc2c1] |
| Example 12-3 | 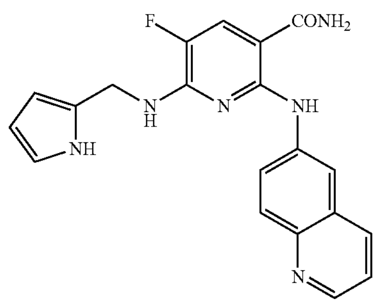 [SMILES: NC(=O)c1cc(F)c(NCc2ccc[nH]2)nc1Nc1ccc2ncccc2c1] | Example 12-4 | 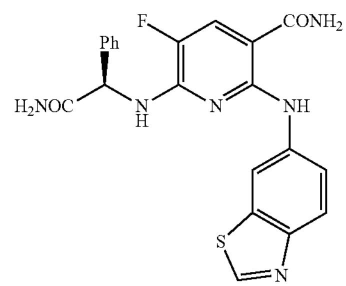 [SMILES: NC(=O)c1cc(F)c(N[C@@H](C(N)=O)c2ccccc2)nc1Nc1ccc2ncsc2c1] |
| Example 12-5 | 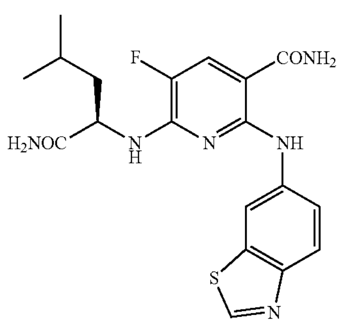 [SMILES: CC(C)C[C@@H](Nc1nc(Nc2ccc3ncsc3c2)c(C(N)=O)cc1F)C(N)=O] | Example 12-6 | 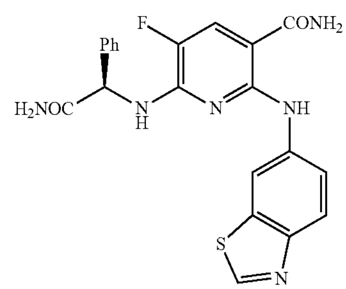 [SMILES: NC(=O)c1cc(F)c(N[C@@H](C(N)=O)c2ccccc2)nc1Nc1ccc2ncsc2c1] |
| Example 12-7 | 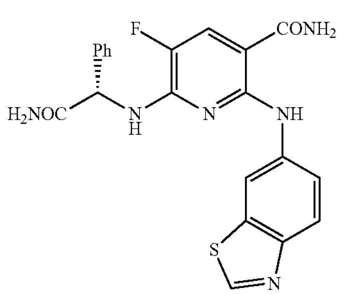 [SMILES: NC(=O)c1cc(F)c(N[C@H](C(N)=O)c2ccccc2)nc1Nc1ccc2ncsc2c1] | Example 12-8 | 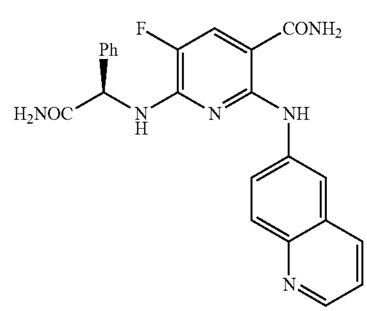 [SMILES: NC(=O)c1cc(F)c(N[C@@H](C(N)=O)c2ccccc2)nc1Nc1ccc2ncccc2c1] |

TABLE 6-continued
| Example 12-9 (Example 11) | 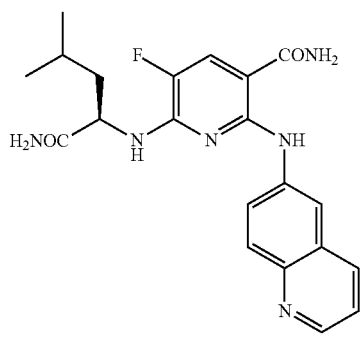 [SMILES: CC(C)C[C@@H](Nc1nc(Nc2ccc3ncccc3c2)c(C(N)=O)cc1F)C(N)=O] | Example 12-10 | 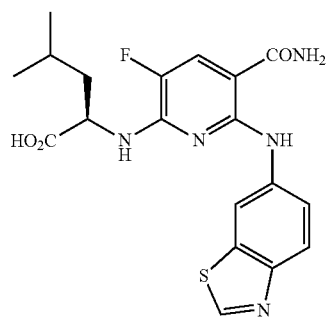 [SMILES: CC(C)C[C@@H](Nc1nc(Nc2ccc3ncsc3c2)c(C(N)=O)cc1F)C(=O)O] |
| --- | --- | --- | --- |
| Example 12-11 | 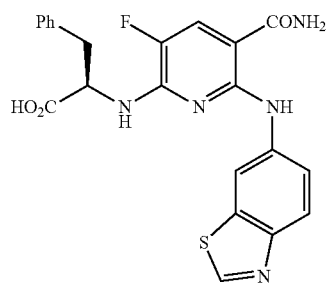 [SMILES: NC(=O)c1cc(F)c(N[C@H](Cc2ccccc2)C(=O)O)nc1Nc1ccc2ncsc2c1] | Example 12-12 | 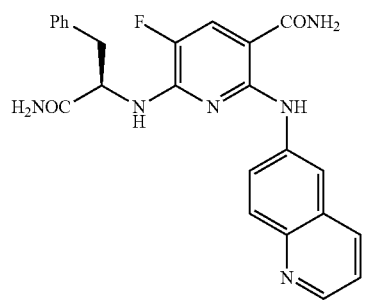 [SMILES: NC(=O)c1cc(F)c(N[C@H](Cc2ccccc2)C(N)=O)nc1Nc1ccc2ncccc2c1] |
| Example 12-13 | 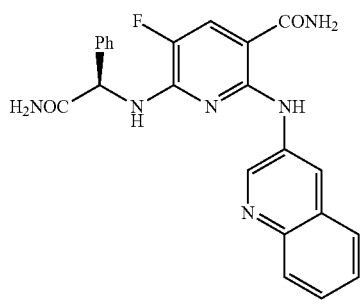 [SMILES: NC(=O)c1cc(F)c(N[C@@H](C(N)=O)c2ccccc2)nc1Nc1cnc2ccccc2c1] | Example 12-14 | 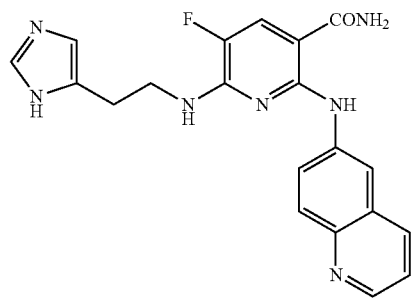 [SMILES: NC(=O)c1cc(F)c(NCCc2cnc[nH]2)nc1Nc1ccc2ncccc2c1] |
| Example 12-15 | 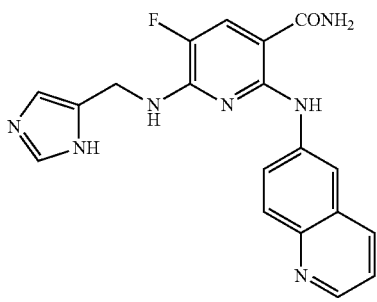 [SMILES: NC(=O)c1cc(F)c(NCc2cnc[nH]2)nc1Nc1ccc2ncccc2c1] | Example 12-16 | 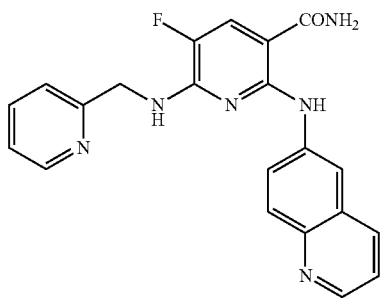 [SMILES: NC(=O)c1cc(F)c(NCc2ccccn2)nc1Nc1ccc2ncccc2c1] |
| Example 12-17 | 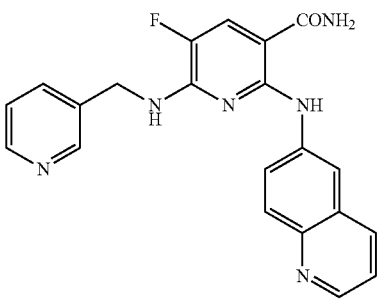 [SMILES: NC(=O)c1cc(F)c(NCc2cccnc2)nc1Nc1ccc2ncccc2c1] | Example 12-18 | 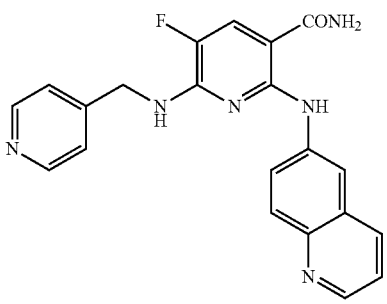 [SMILES: NC(=O)c1cc(F)c(NCc2ccncc2)nc1Nc1ccc2ncccc2c1] |

TABLE 6-continued
| Example 12-19 | 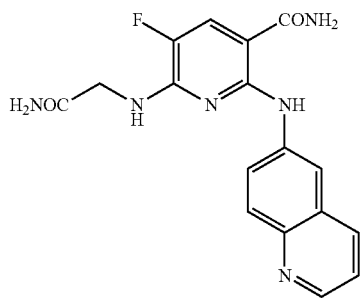 [SMILES: NC(=O)CNc1nc(Nc2ccc3ncccc3c2)c(C(N)=O)cc1F] | Example 12-20 | 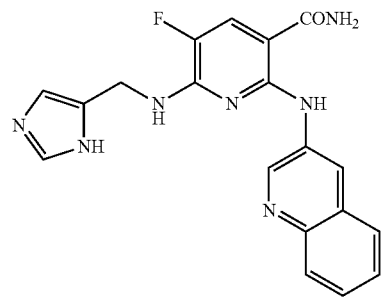 [SMILES: NC(=O)c1cc(F)c(NCc2cnc[nH]2)nc1Nc1cnc2ccccc2c1] |
| Example 12-21 | 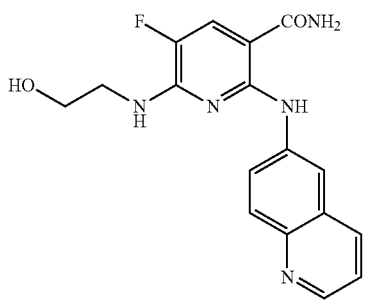 [SMILES: NC(=O)c1cc(F)c(NCCO)nc1Nc1ccc2ncccc2c1] | Example 12-22 | 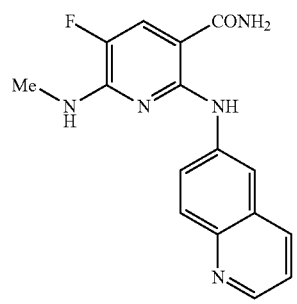 [SMILES: CNc1nc(Nc2ccc3ncccc3c2)c(C(N)=O)cc1F] |
| Example 12-23 | 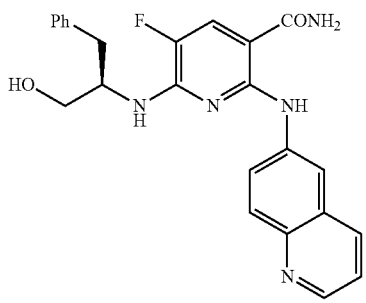 [SMILES: NC(=O)c1cc(F)c(N[C@@H](CO)Cc2ccccc2)nc1Nc1ccc2ncccc2c1] | Example 12-24 | 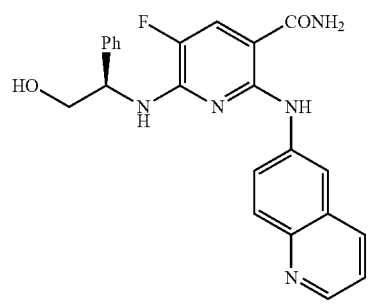 [SMILES: NC(=O)c1cc(F)c(N[C@@H](CO)c2ccccc2)nc1Nc1ccc2ncccc2c1] |
| Example 12-25 | 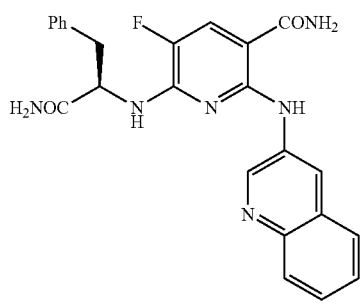 [SMILES: NC(=O)c1cc(F)c(N[C@H](Cc2ccccc2)C(N)=O)nc1Nc1cnc2ccccc2c1] | Example 12-26 | 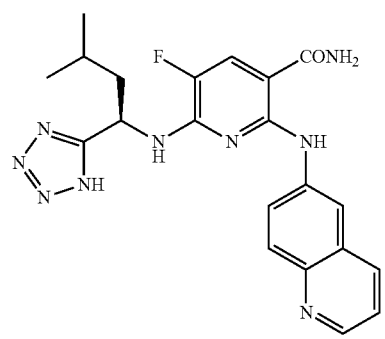 [SMILES: CC(C)C[C@@H](Nc1nc(Nc2ccc3ncccc3c2)c(C(N)=O)cc1F)c1nnn[nH]1] |
| Example 12-27 | 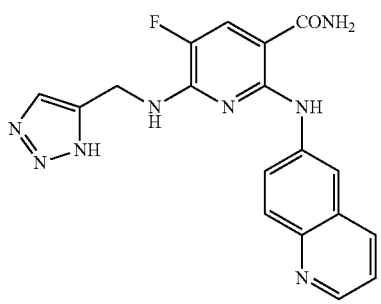 [SMILES: NC(=O)c1cc(F)c(NCc2cnn[nH]2)nc1Nc1ccc2ncccc2c1] | Example 12-28 | 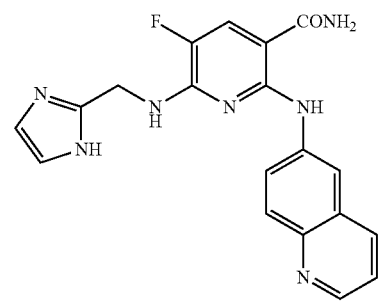 [SMILES: NC(=O)c1cc(F)c(NCc2ncc[nH]2)nc1Nc1ccc2ncccc2c1] |

TABLE 6-continued
| Example 12-29 | 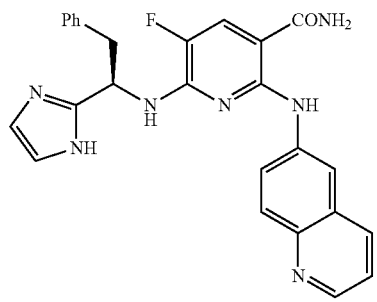 [SMILES: NC(=O)c1cc(F)c(N[C@H](Cc2ccccc2)c2ncc[nH]2)nc1Nc1ccc2ncccc2c1] | Example 12-30 | 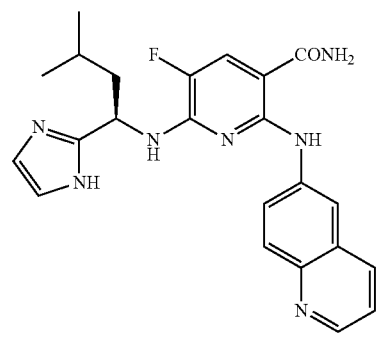 [SMILES: CC(C)C[C@@H](Nc1nc(Nc2ccc3ncccc3c2)c(C(N)=O)cc1F)c1ncc[nH]1] |
|---|---|---|---|
| Example 12-31 | 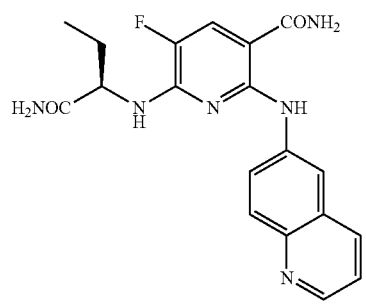 [SMILES: CC[C@@H](Nc1nc(Nc2ccc3ncccc3c2)c(C(N)=O)cc1F)C(N)=O] | Example 12-32 | 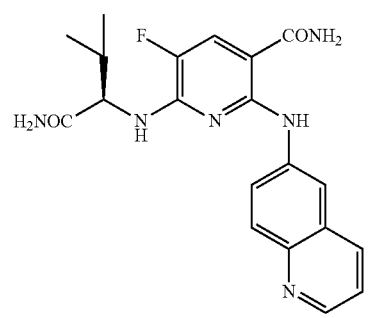 [SMILES: CC(C)[C@@H](Nc1nc(Nc2ccc3ncccc3c2)c(C(N)=O)cc1F)C(N)=O] |
| Example 12-33 | 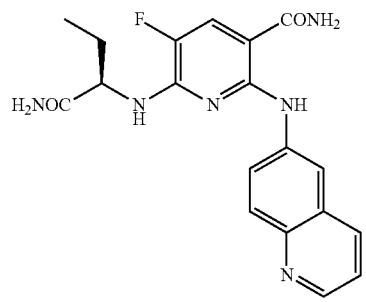 [SMILES: CC[C@@H](Nc1nc(Nc2ccc3ncccc3c2)c(C(N)=O)cc1F)C(N)=O] | Example 12-34 | 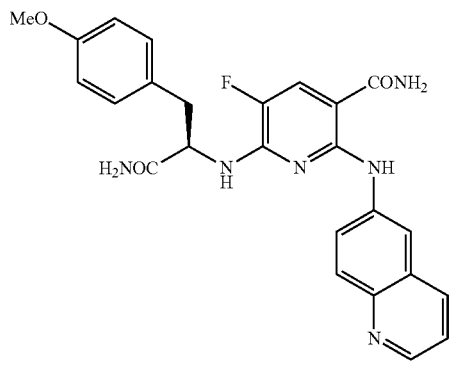 [SMILES: COc1ccc(C[C@@H](Nc2nc(Nc3ccc4ncccc4c3)c(C(N)=O)cc2F)C(N)=O)cc1] |
| Number | Structure | Compound name |
|---|---|---|
| Example 12-35 | 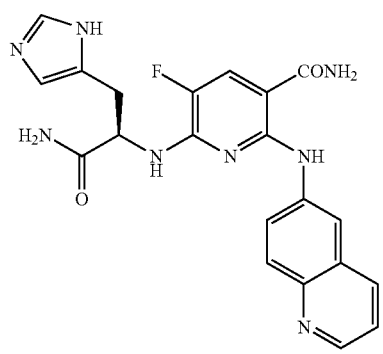 [SMILES: NC(=O)c1cc(F)c(N[C@H](Cc2cnc[nH]2)C(N)=O)nc1Nc1ccc2ncccc2c1] | (R)-6-((1-amino-3-(1H-imidazol-5-yl)-1-oxopropan-2-yl)amino)-5-fluoro-2-((quinolin-6-yl)amino)nicotinamide |

TABLE 6-continued

| | | |
|---|---|---|
| Example 12-36 | [structure] | (R)-6-((1-amino-1-oxopropan-2-yl)amino)-5-fluoro-2-((quinolin-6-yl)amino)nicotinamide |
| Example 12-37 | [structure] | (R)-6-(1-amino-3,3-dimethyl-1-oxobutan-2-yl)amino)-5-fluoro-2-((quinolin-6-yl)amino)-nicotinamide |
| Example 12-38 | [structure] | (R)-6-(1-amino-1-oxopentan-2-yl)amino)-5-fluoro-2-((quinolin-6-yl)amino)nicotinamide |

| Number | Compound | $^1$H-NMR | MS (ESI, m/z) |
|---|---|---|---|
| Example 12-1 | 5-fluoro-6-((2-(1H-imidazol-5-yl)ethyl)amino)-2-(quinolin-3-ylamino)nicotinamide | $^1$H-NMR (DMSO-$d_6$, 400 MHz) δ: 12.14 (s, 1H), 11.86 (brs, 1H), 9.02-8.71 (m, 2H), 8.03-7.75 (m, 3H), 7.73-7.21 (m, 6H), 7.00-6.86 (m, 1H), 3.85-3.70 (m, 2H), 2.97-2.80 (m, 2H). | 392 (M + H), 390 (M − H) |
| Example 12-2 | 6-((cyclopropylmethyl)amino)-5-fluoro-2-(quinolin-6-ylamino)-nicotinamide | $^1$H-NMR (DMSO-$d_6$, 400 MHz) δ: 12.01 (s, 1H), 8.70 (dd, 1H, J = 1.6, 4.0 Hz), 8.65 (d, 1H, J = 2.2 Hz), 8.16-8.07 (m, 1H), 8.00-7.64 (m, 4H), 7.61-7.52 (m, 1H), 7.46 (dd, 1H, J = 4.3, 8.2 Hz), 7.25 (brs, 1H), 3.46-3.38 (m, 2H), 1.35-1.21 (m, 1H), 0.55-0.41 (m, 2H), 0.39-0.25 (m, 2H). | 352 (M + H), 350 (M − H) |
| Example 12-3 | 5-fluoro-6-(((1H-pyrrol-2-yl)methyl)amino)-2-(quinolin-6-ylamino)nicotinamide | | 377 (M + H), 375 (M − H) |
| Example 12-4 | 6-(((1R)-2-amino-2-oxo-1-phenyl-ethyl)amino)-2-(1,3-benzothiazol-6-ylamino)-5-fluoronicotinamide | $^1$H-NMR (DMSO-$d_6$, 400 MHz) δ: 11.92 (s, 1H), 9.19 (s, 1H), 8.39 (d, 1H, J = 2.2 Hz), 8.02-7.88 (m, 3H), 7.64-7.58 (m, 2H), 7.42-7.26 (m, 7H), 6.98-6.92 (m, 1H), 5.63 (d, 1H, J = 7.3 Hz). | 437 (M + H), 435 (M − H) |
| Example 12-5 | 6-(((2R)-1-amino-4-methyl-1-oxo-pentan-2-yl)amino)-2-(1,3-benzo-thiazol-6-ylamino)-5-fluoronicotinamide | $^1$H-NMR (CD$_3$OD, 400 MHz) δ: 8.94 (s, 1H), 8.59 (d, 1H, J = 2.3 Hz), 7.83 (d, 1H, J = 8.9 Hz), 7.66 (d, 1H, J = 12.2 Hz), 7.39 (dd, 1H, J = 2.3, 8.9 Hz), 4.53-4.48 (m, 1H), 1.77-1.66 (m, 3H), 0.91 (d, 3H, J = 6.3 Hz), 0.82 (d, 3H, J = 6.3 Hz). | 417 (M + H), 439 (M + Na), 415 (M − H) |
| Example 12-6 | 6-(((2R)-1-amino-1-oxo-3-phenyl-propan-2-yl)amino)-2-(1,3-benzo-thiazol-6-ylamino)-5-fluoronicotinamide | $^1$H-NMR (CD$_3$OD, 400 MHz) δ: 9.05 (s, 1H), 8.54 (d, 1H, J = 1.9 Hz), 7.94 (d, 1H, J = 8.8 Hz), 7.69 (d, 1H, J = 12.0 Hz), 7.49 (dd, 1H, J = 1.9, 8.8 Hz), 7.29-7.10 (m, 5H), | 451 (M + H), 449 (M − H) |

TABLE 6-continued

| | | 5.10-4.40 (1H, overlapping with H₂O peak), 3.14-3.04 (m, 2H). | |
|---|---|---|---|
| Example 12-7 | 6-(((1S)-2-amino-2-oxo-1-phenyl-ethyl)amino)-2-(1,3-benzothiazol-6-ylamino)-5-fluoronicotinamide | ¹H-NMR (CD₃OD, 400 MHz) δ: 9.04 (s, 1H), 8.44 (d, 1H, J = 1.9 Hz), 7.90 (d, 1H, J = 8.5 Hz), 7.77 (d, 1H, J = 11.9 Hz), 7.58-7.54 (m, 2H), 7.48-7.28 (m, 4H), 5.66 (s, 1H). | 437 (M + H), 435 (M − H) |
| Example 12-8 | 6-(((1R)-2-amino-2-oxo-1-phenyl-ethyl)amino)-5-fluoro-2-(quinolin-6-ylamino)nicotinamide | ¹H-NMR (DMSO-d₆, 400 MHz) δ: 12.00 (s, 1H), 8.74-8.67 (m, 1H), 8.37-8.28 (m, 1H), 8.19 (d, 1H, J = 2.4 Hz), 8.07-7.80 (m, 4H), 7.70 (dd, 1H, J = 2.4, 9.3 Hz), 7.58 (d, 2H, J = 7.3 Hz), 7.52-7.24 (m, 6H), 7.07-6.96 (m, 1H), 5.67 (d, 1H, J = 7.3 Hz). | 431 (M + H), 429 (M − H) |
| Example 12-9 | 6-(((2R)-1-amino-4-methyl-1-oxo-pentan-2-yl)amino)-5-fluoro-2-(quinolin-6-ylamino)nicotinamide | ¹H-NMR (DMSO-d₆, 400 MHz) δ: 12.03 (s, 1H), 8.68 (dd, 1H, J = 1.6, 4.3 Hz), 8.58 (d, 1H, J = 2.3 Hz), 8.47-8.41 (m, 1H), 7.94 (d, 1H, J = 12.4 Hz), 7.91-7.76 (m, 2H), 7.60 (dd, 1H, J = 2.3, 9.0 Hz), 7.52-7.13 (m, 5H), 4.61-4.51 (m, 1H), 1.89-1.64 (m, 3H), 0.92 (d, 3H, J = 6.1 Hz), 0.82 (d, 3H, J = 6.1 Hz). | 411 (M + H), 409 (M − H) |
| Example 12-10 | ((2R)-2-(5-aminocarbonyl-6-(1,3-benzothiazol-6-ylamino)-3-fluoropyridin-2-yl)amino)-4-methylvaleric acid | ¹H-NMR (CD₃OD, 400 MHz) δ: 9.02 (s, 1H), 8.83 (d, 1H, J = 2.0 Hz), 7.90 (d, 1H, J = 8.9 Hz), 7.72 (d, 1H, J = 12.0 Hz), 7.40 (dd, 1H, J = 2.0, 8.9 Hz), 4.78-4.74 (m, 1H), 1.92-1.72 (m, 3H), 1.01 (d, 3H, J = 6.3 Hz), 0.93 (d, 3H, J = 6.3 Hz). | 418 (M + H), 416 (M − H) |
| Example 12-11 | (2R)-2-((5-aminocarbonyl-6-(1,3-benzothiazol-6-ylamino)-3-fluoropyridin-2-yl)amino)-3-phenylpropionic acid | ¹H-NMR (CD₃OD, 400 MHz) δ: 9.28 (s, 1H), 8.80 (d, 1H, J = 2.2 Hz), 7.93 (d, 1H, J = 8.8 Hz), 7.71 (d, 1H, J = 12.0 Hz), 7.45 (dd, 1H, J = 2.2, 8.8 Hz), 7.28-7.16 (m, 5H), 4.85-4.80 (m, 1H), 3.24-3.16 (m, 2H). | 452 (M + H), 450 (M − H) |
| Example 12-12 | 6-((2R)-1-amino-1-oxo-3-phenyl-propan-2-ylamino)-5-fluoro-2-(quinolin-6-ylamino)nicotinamide | ¹H-NMR (DMSO-d₆, 400 MHz) δ: 12.03 (s, 1H), 8.82-8.72 (m, 1H), 8.59-8.45 (m, 2H), 8.00-7.85 (m, 3H), 7.75-7.46 (m, 3H), 7.43-7.10 (m, 8H), 4.76-4.65 (m, 1H), 3.60-3.22 (1H, overlapping with H₂O peak), 3.22-3.10 (m, 2H). | 445 (M + H), 443 (M − H) |
| Example 12-13 | 6-(((1R)-2-amino-2-oxo-1-phenyl-ethyl)amino)-5-fluoro-2-(quinolin-3-ylamino)nicotinamide | ¹H-NMR (DMSO-d₆, 400 MHz) δ: 12.12 (s, 1H), 8.74-8.67 (m, 2H), 8.10-7.84 (m, 5H), 7.66-7.23 (m, 9H), 7.14-7.04 (m, 1H), 5.68 (d, 1H, J = 7.3 Hz). | 431 (M + H), 429 (M − H) |
| Example 12-14 | 5-fluoro-6-((2-(1H-imidazol-5-yl)ethyl)amino)-2-(quinolin-6-ylamino)nicotinamide | ¹H-NMR (DMSO-d₆, 400 MHz) δ: 12.10-12.04 (m, 1H), 11.96-11.80 (m, 1H), 8.70-8.58 (m, 2H), 8.02-8.52 (m, 7H), 7.40-7.16 (m, 2H), 6.91 (s, 1H), 3.85-3.75 (m, 2H), 2.90 (t, 2H, J = 7.6 Hz). | 392 (M + H), 390 (M − H) |
| Example 12-15 | 5-fluoro-6-(((1H-imidazol-5-yl)methyl)amino)-2-(quinolin-6-ylamino)nicotinamide | ¹H-NMR (DMSO-d₆, 400 MHz) δ: 11.97 (s, 1H), 11.82 (brs, 1H), 8.66 (dd, 1H, J = 1.5, 4.1 Hz), 8.57 (d, 1H, J = 2.2 Hz), 8.09 (d, 1H, J = 7.8 Hz), 7.95-7.55 (m, 6H), 7.39 (dd, 1H, J = 4.1, 8.3 Hz), 7.35-7.15 (brs, 1H), 6.89 (s, 1H), 4.67-4.60 (m, 2H). | 378 (M + H), 376 (M − H) |
| Example 12-16 | 5-fluoro-6-((pyridin-2-ylmethyl)-amino)-2-(quinolin-6-ylamino)-nicotinamide | ¹H-NMR (DMSO-d₆, 400 MHz) δ: 11.97 (s, 1H), 8.69-8.63 (m, 1H), 8.61-8.56 (m, 1H), 8.35-8.30 (m, 1H), 8.14-7.94 (m, 3H), 7.90-7.68 (m, 3H), 7.53-7.19 (m, 5H), 4.83 (d, 2H, J = 5.9 Hz). | 389 (M + H), 387 (M − H) |
| Example 12-17 | 5-fluoro-6-((pyridin-3-ylmethyl)-amino)-2-(quinolin-6-ylamino)-nicotinamide | ¹H-NMR (DMSO-d₆, 400 MHz) δ: 11.95 (s, 1H), 8.66 (dd, 1H, J = 1.7, 4.2 Hz), 8.60 (d, 1H, J = 1.7 Hz), 8.45-8.39 (m, 1H), 8.20 (d, 1H, J = 2.4 Hz), 8.03 (t, 1H, 6.1 Hz), 7.97 (d, 1H, J = 12.7 Hz), 7.88-7.72 (m, 4H), 7.65 (dd, 1H, J = 2.4, 9.0 Hz), 7.42-7.24 (m, 3H), 4.75 (d, 2H, J = 6.1 Hz). | 389 (M + H), 387 (M − H) |
| Example 12-18 | 5-fluoro-6-((pyridin-4-ylmethyl)-amino)-2-(quinolin-6-ylamino)-nicotinamide | ¹H-NMR (DMSO-d₆, 400 MHz) δ: 11.93 (s, 1H), 8.65 (dd, 1H, J = 1.7, 4.1 Hz), 8.54-8.46 (m, 2H), 8.07 (d, 1H, J = 2.4 Hz), 8.04 (t, 1H, J = 6.1 Hz), 7.99 (d, 1H, J = 12.4 Hz), 7.88-7.76 (m, 1H), 7.76-7.68 (m, 2H), 7.59 (dd, 1H, J = 2.4, 9.3 Hz), 7.42-7.24 (m, 4H), 4.74 (d, 2H, J = 6.1 Hz). | 389 (M + H), 387 (M − H) |
| Example 12-19 | 6-((2-amino-2-oxo-ethyl)amino)-5-fluoro-2-(quinolin-6-ylamino)-nicotinamide | ¹H-NMR (DMSO-d₆, 400 MHz) δ: 12.02 (s, 1H), 8.70-8.66 (m, 1H), 8.52 (d, 1H, J = 2.4 Hz), 8.36 (d, 1H, J = 7.8 Hz), 7.98-7.75 (m, 3H), 7.61 (dd, 1H, J = 2.4, 9.0 Hz), 7.58-7.48 (m, 2H), 7.41 (dd, 1H, J = 4.3, 8.4 Hz), 7.38-7.19 (m, 2H), 4.00 (d, 2H, J = 6.1 Hz). | 355 (M + H), 353 (M − H) |
| Example 12-20 | 5-fluoro-6-(((1H-imidazol-5-yl)methyl)amino)-2-(quinolin-3-ylamino)nicotinamide | ¹H-NMR (DMSO-d₆, 400 MHz) δ: 12.04 (s, 1H), 8.84-8.77 (m, 2H), 7.96 (d, 1H, J = 12.7 Hz), 7.92-7.73 (m, 4H), 7.72-7.66 (m, 1H), | 378 (M + H), 376 (M − H) |

TABLE 6-continued

| | | | |
|---|---|---|---|
| | | 7.56-7.44 (m, 2H), 7.30 (brs, 1H), 6.99 (s, 1H), 4.66 (d, 2H, J = 5.6 Hz). | |
| Example 12-21 | 5-fluoro-6-((2-hydroxyethyl)-amino)-2-(quinolin-6-ylamino)-nicotinamide | $^1$H-NMR (CD$_3$OD, 400 MHz) δ: 8.65 (d, 1H, J = 2.4 Hz), 8.62 (dd, 1H, J = 1.7, 4.4 Hz), 8.30-8.24 (m, 1H), 7.90 (d, 1H, J = 9.2 Hz), 7.75 (dd, 1H, J = 2.4, 9.2 Hz), 7.70 (d, 1H, J = 12.4 Hz), 7.44 (dd, 1H, J = 4.4, 8.3 Hz), 3.88-3.83 (m, 2H), 3.78-3.73 (m, 2H). | 342 (M + H), 340 (M − H) |
| Example 12-22 | 5-fluoro-6-(methylamino)-2-(quinolin-6-ylamino)nicotinamide | $^1$H-NMR (CD$_3$OD, 400 MHz) δ: 8.57 (d, 1H, J = 2.3 Hz), 8.55-8.49 (m, 1H), 8.10-8.06 (m, 1H), 7.80 (d, 1H, J = 9.1 Hz), 7.73 (dd, 1H, J = 2.3, 9.1 Hz), 7.57 (d, 1H, J = 12.2 Hz), 7.34 (dd, 1H, J = 4.4, 8.3 Hz), 3.06 (s, 3H). | 312 (M + H), 310 (M − H) |
| Example 12-23 | 6-(((2R)-1-hydroxy-3-phenyl-propan-2-yl)amino)-5-fluoro-2-(quinolin-6-ylamino)nicotinamide | $^1$H-NMR (CD$_3$OD, 400 MHz) δ: 8.64 (dd, 1H, J = 1.7, 4.4 Hz), 8.44 (d, 1H, J = 2.4 Hz), 8.17-8.13 (m, 1H), 7.91 (d, 1H, J = 9.1 Hz), 7.76 (dd, 1H, J = 2.3, 9.1 Hz), 7.67 (d, 1H, J = 12.2 Hz), 7.41 (dd, 1H, 4.4, 8.3 Hz), 7.32-7.14 (m, 4H), 7.10-7.06 (m, 1H), 4.66-4.58 (m, 1H), 3.70 (d, 2H, J = 5.4 Hz), 3.02 (dd, 1H, J = 7.1, 13.4 Hz), 2.90 (dd, 1H, J = 7.3, 13.4 Hz). | 430 (M − H) |
| Example 12-24 | 5-fluoro-6-(((1R)-2-hydroxy-1-phenylethyl)amino)-2-(quinolin-6-ylamino)nicotinamide | $^1$H-NMR (CD$_3$OD, 400 MHz) δ: 8.63-8.60 (m, 1H), 8.13-8.08 (m, 1H), 8.06 (d, 1H, J = 2.2 Hz), 7.81 (d, 1H, J = 9.0 Hz), 7.75-7.70 (m, 2H), 7.46-7.30 (m, 5H), 7.26-7.20 (m, 1H), 5.42-5.36 (m, 1H), 3.98-3.86 (m, 2H). | 418 (M + H), 416 (M − H) |
| Example 12-25 | 6-(((2R)-1-amino-1-oxo-3-phenyl-propan-2-yl)amino)-5-fluoro-2-quinolin-3-ylamino)nicotinamide | $^1$H-NMR (DMSO-d$_6$, 400 MHz) δ: 12.08 (s, 1H), 8.85 (d, 1H, J = 2.6 Hz), 8.70 (d, 1H, J = 2.6 Hz), 8.13-8.03 (m, 1H), 8.00-7.75 (m, 3H), 7.67-7.50 (m, 3H), 7.40-7.10 (m, 8H), 4.77-4.67 (m, 1H), 3.40-3.21 (1H, overlapping with H$_2$O peak), 3.21-3.09 (m, 1H). | 445 (M + H), 443 (M − H) |
| Example 12-26 | 5-fluoro-6-(((1R)-3-methyl-1-(1H-tetrazol-5-yl)butyl)amino)-2-(quinolin-6-ylamino)nicotinamide | $^1$H-NMR (DMSO-d$_6$, 400 MHz) δ: 11.93 (s, 1H), 8.67 (dd, 1H, J = 1.7, 4.2 Hz), 8.28-8.16 (m, 2H), 8.04-7.67 (m, 5H), 7.50 (dd, 1H, J = 2.3, 8.9 Hz), 7.43 (dd, 1H, J = 4.2, 8.3 Hz), 7.39-7.23 (m, 1H), 5.75-5.65 (m, 1H), 2.11-1.98 (m, 1H), 1.94-1.82 (m, 1H), 1.80-1.65 (m, 1H), 0.91 (d, 3H, J = 6.5 Hz), 0.84 (d, 3H, J = 6.5 Hz). | 436 (M + H), 434 (M − H) |
| Example 12-27 | 5-fluoro-2-(quinolin-6-ylamino)-6-(((1H-1,2,3-triazol-5-yl)methyl)amino)nicotinamide | $^1$H-NMR (DMSO-d$_6$, 400 MHz) δ: 11.97 (s, 1H), 10.24-10.15 (m, 1H), 8.71-8.62 (m, 1H), 8.48-8.40 (m, 1H), 8.10-7.53 (m, 7H), 7.44-7.18 (m, 2H), 4.78 (d, 2H, J = 5.6 Hz). | 379 (M + H), 377 (M − H) |
| Example 12-28 | 5-fluoro-6-(((1H-imidazol-2-yl)methyl)amino)-2-(quinolin-6-ylamino)nicotinamide | $^1$H-NMR (DMSO-d$_6$, 400 MHz) δ: 11.96 (s, 1H), 11.76 (brs, 1H), 8.64 (dd, 1H, J = 1.5, 4.2 Hz), 8.39 (d, 1H, J = 2.4 Hz), 8.22-8.14 (m, 1H), 7.94 (d, 1H, J = 12.7 Hz), 7.86-7.66 (m, 3H), 7.51 (dd, 1H, J = 2.4, 9.0 Hz), 7.38 (dd, 1H, J = 4.2, 8.3 Hz), 7.28 (brs, 1H), 7.01 (s, 1H), 6.87 (s, 1H), 4.73 (d, 2H, J = 5.9 Hz). | 378 (M + H), 376 (M − H) |
| Example 12-29 | 5-fluoro-6-(((1R)-1-(1H-imidazol-2-yl)-2-phenylethyl)amino)-2-(quinolin-6-ylamino)nicotinamide | | 468 (M + H), 466 (M − H) |
| Example 12-30 | 5-fluoro-6-(((1R)-1-(1H-imidazol-2-yl)-3-methylbutyl)amino)-2-(quinolin-6-ylamino)nicotinamide | $^1$H-NMR (DMSO-d$_6$, 400 MHz) δ: 11.95 (s, 1H), 11.69 (brs, 1H), 8.74-8.47 (m, 2H), 8.39 (d, 1H, J = 8.3 Hz), 8.00-7.71 (m, 3H), 7.68-7.19 (m, 4H), 7.12-6.76 (m, 2H), 5.64-5.47 (m, 1H), 1.94-1.77 (m, 2H), 1.70-1.51 (m, 1H), 0.87 (d, 3H, J = 6.4 Hz), 0.80 (d, 3H, J = 6.4 Hz). | 434 (M + H), 432 (M − H) |
| Example 12-31 | 6-(((2R)-1-amino-1-oxobutan-2-yl)amino)-5-fluoro-2-(quinolin-6-ylamino)nicotinamide | $^1$H-NMR (CD$_3$OD, 400 MHz) δ: 8.56-8.50 (m, 1H), 8.43 (d, 1H, J = 2.2 Hz), 8.41-8.37 (m, 1H), 7.81 (d, 1H, J = 9.0 Hz), 7.69 (d, 1H, J = 12.2 Hz), 7.62 (dd, 1H, J = 2.4, 9.0 Hz), 7.36 (dd, 1H, J = 4.2, 8.3 Hz), 4.44 (dd, 1H, J = 4.2, 8.3 Hz), 2.06-1.76 (m, 2H), 1.02-0.96 (m, 3H). | 383 (M + H), 381 (M − H) |
| Example 12-32 | 6-(((2R)-1-amino-3-methyl-1-oxo-butan-2-yl)amino)-5-fluoro-2-(quinolin-6-ylamino)nicotinamide | $^1$H-NMR (CD$_3$OD, 400 MHz) δ: 8.56-8.52 (m, 1H), 8.44-8.40 (m, 1H), 8.40-8.36 (m, 1H), 7.85-7.80 (m, 1H), 7.70 (d, 1H, J = 12.0 Hz), 7.67-7.62 (m, 1H), 7.39-7.34 (m, 1H), 4.50-4.46 (m, 1H), 2.30-2.20 (m, 1H), 1.04-0.90 (m, 6H). | 397 (M + H), 395 (M − H) |
| Example 12-33 | 6-(((2R)-1-amino-3-(4-fluoro-phenyl)-1-oxopropan-2-yl)amino)-5-fluoro-2-(quinolin-6-ylamino)-nicotinamide | $^1$H-NMR (CD$_3$OD, 400 MHz) δ: 8.66-8.62 (m, 1H), 8.47-8.37 (m, 1H), 7.90 (d, 1H, J = 9.0 Hz), 7.76-7.66 (m, 1H), 7.50-7.40 (m, 1H), 7.29-7.20 (m, 3H), 7.04-6.98 (m, 2H), | 485 (M + Na), 461 (M − H) |

TABLE 6-continued

| | | | | | | Mass | Mass | |
|---|---|---|---|---|---|---|---|---|
| Example 12-34 | 6-(((2R)-1-amino-3-(4-methoxy-phenyl)-1-oxopropan-2-yl)amino)-5-fluoro-2-(quinolin-6-ylamino)-nicotinamide | | | | 6.96-6.88 (m, 1H), 3.55-3.49 (m, 1H), 2.97 (dd, 1H, J = 6.0, 13.5 Hz), 2.79 (dd, 1H, J = 7.3, 13.5 Hz).<br>$^1$H-NMR (CD$_3$OD, 400 MHz) δ: 8.64 (dd, 1H, J = 1.6, 4.4 Hz), 8.48 (d, 1H, J = 2.4 Hz), 8.42 (d, 1H, J = 8.5 Hz), 7.92 (d, 1H, J = 9.0 Hz), 7.76-7.67 (m, 2H), 7.45 (dd, 1H, J = 4.4, 8.5 Hz), 7.19-7.13 (m, 2H), 6.79-6.74 (m, 2H), 5.00-4.70 (1H, overlapping with H$_2$O peak), 3.71 (s, 3H), 3.34-3.20 (m, 1H), 3.30-3.20 (1H, overlapping with CH$_3$OH peak). | 475 (M + H), 473 (M − H) | | |

| Number | salt | solvent | NMR | 1HNMR | Mass (M + H) | Mass (M − H) | rt (min) |
|---|---|---|---|---|---|---|---|
| Example 12-35 | free | | | | 435 | 433 | |
| Example 12-36 | free | | | | 369 | 367 | |
| Example 12-37 | free | | | | 411 | 409 | |
| Example 12-38 | free | | | | 397 | 395 | |

Example 13

[Formula 495]

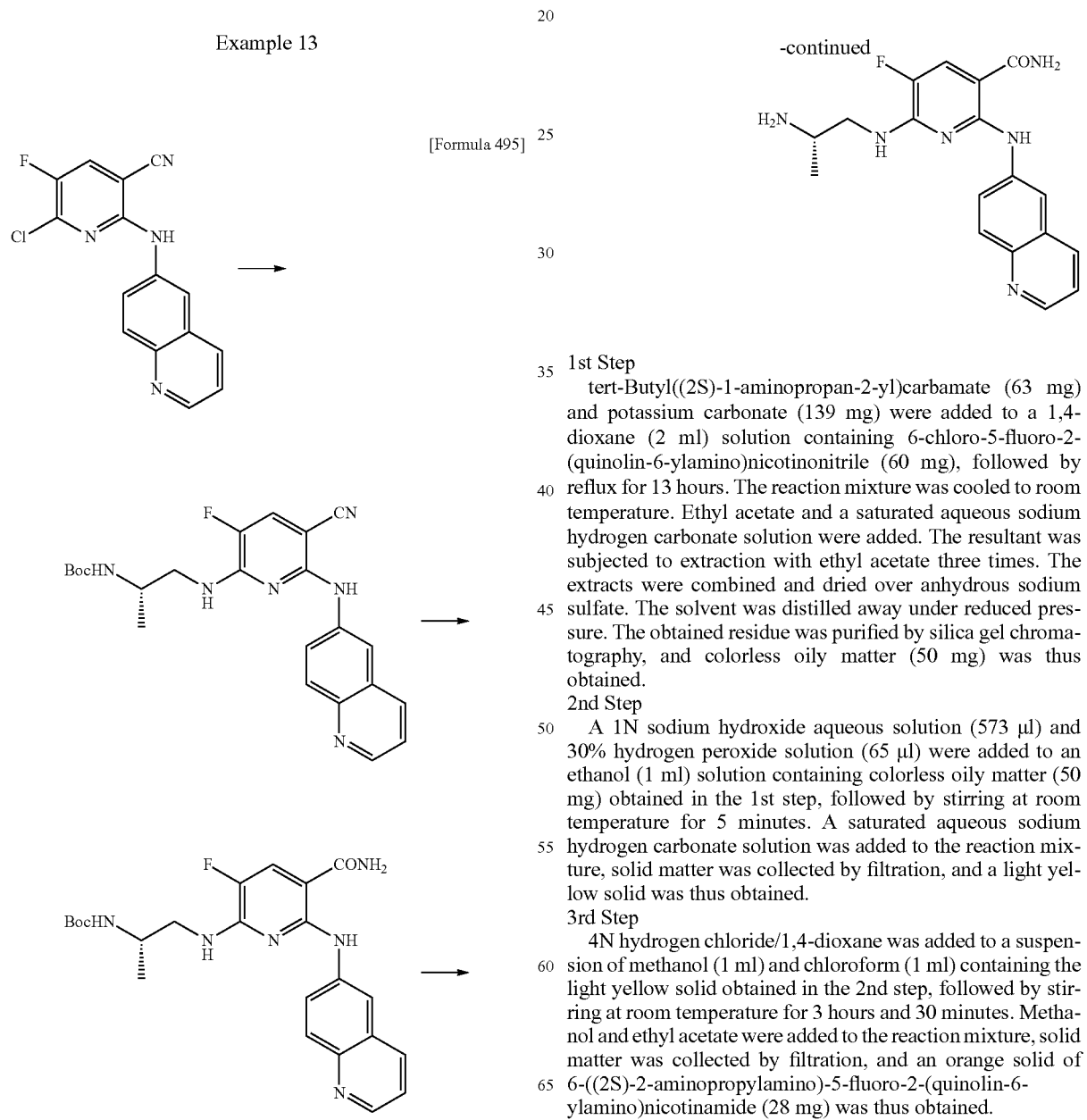

1st Step tert-Butyl((2S)-1-aminopropan-2-yl)carbamate (63 mg) and potassium carbonate (139 mg) were added to a 1,4-dioxane (2 ml) solution containing 6-chloro-5-fluoro-2-(quinolin-6-ylamino)nicotinonitrile (60 mg), followed by reflux for 13 hours. The reaction mixture was cooled to room temperature. Ethyl acetate and a saturated aqueous sodium hydrogen carbonate solution were added. The resultant was subjected to extraction with ethyl acetate three times. The extracts were combined and dried over anhydrous sodium sulfate. The solvent was distilled away under reduced pressure. The obtained residue was purified by silica gel chromatography, and colorless oily matter (50 mg) was thus obtained.

2nd Step

A 1N sodium hydroxide aqueous solution (573 µl) and 30% hydrogen peroxide solution (65 µl) were added to an ethanol (1 ml) solution containing colorless oily matter (50 mg) obtained in the 1st step, followed by stirring at room temperature for 5 minutes. A saturated aqueous sodium hydrogen carbonate solution was added to the reaction mixture, solid matter was collected by filtration, and a light yellow solid was thus obtained.

3rd Step 4N hydrogen chloride/1,4-dioxane was added to a suspension of methanol (1 ml) and chloroform (1 ml) containing the light yellow solid obtained in the 2nd step, followed by stirring at room temperature for 3 hours and 30 minutes. Methanol and ethyl acetate were added to the reaction mixture, solid matter was collected by filtration, and an orange solid of 6-((2S)-2-aminopropylamino)-5-fluoro-2-(quinolin-6-ylamino)nicotinamide (28 mg) was thus obtained.

($^1$H-NMR data and MS data are shown in table 7.)

Example 14

The compounds listed in table 7 were obtained as described in Example 13.

TABLE 7

| Number | Structure |
|---|---|
| Example 14-1 HCl salt | (5-fluoro-6-[((2S)-2-aminobutyl)amino]-2-(isoquinolin-6-ylamino)pyridine-3-carboxamide) |
| Example 14-2 HCl salt | (5-fluoro-6-[((2S)-2-amino-3-methylbutyl)amino]-2-(isoquinolin-6-ylamino)pyridine-3-carboxamide) |
| Example 14-3 HCl salt | (5-fluoro-6-[((2S)-2-amino-3-phenylpropyl)amino]-2-(quinolin-6-ylamino)pyridine-3-carboxamide) |
| Example 14-4 HCl salt | (5-fluoro-6-[((2S)-2-aminobutyl)amino]-2-(quinolin-6-ylamino)pyridine-3-carboxamide) |

TABLE 7-continued
| Example 14-5 HCl salt | 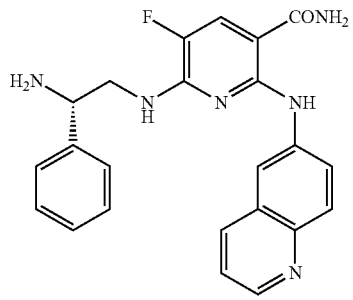 [SMILES: NC(=O)c1cc(F)c(NC[C@@H](N)c2ccccc2)nc1Nc1ccc2ncccc2c1] |
| --- | --- |
| Example 14-6 HCl salt | 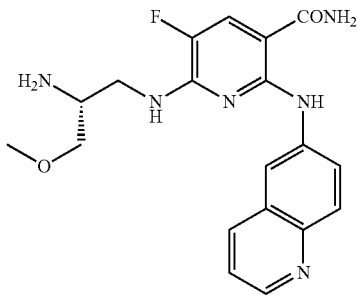 [SMILES: COC[C@H](N)CNc1nc(Nc2ccc3ncccc3c2)c(C(N)=O)cc1F] |
| Example 14-7 HCl salt | 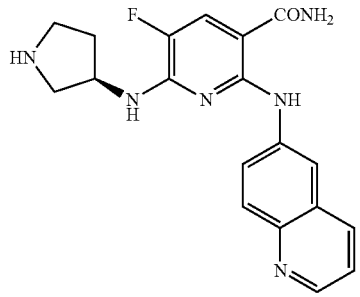 [SMILES: NC(=O)c1cc(F)c(N[C@@H]2CCNC2)nc1Nc1ccc2ncccc2c1] |
| Example 14-8 HCl salt | 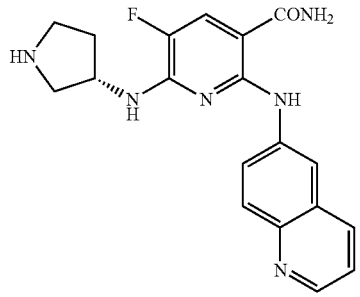 [SMILES: NC(=O)c1cc(F)c(N[C@H]2CCNC2)nc1Nc1ccc2ncccc2c1] |
| Example 14-9 (Example 13) HCl salt | 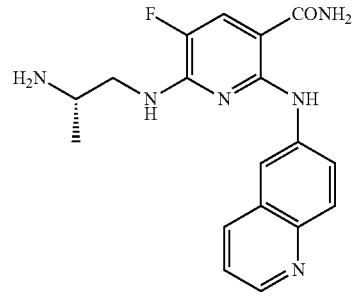 [SMILES: C[C@H](N)CNc1nc(Nc2ccc3ncccc3c2)c(C(N)=O)cc1F] |

TABLE 7-continued

| Example 14-10 HCl salt | 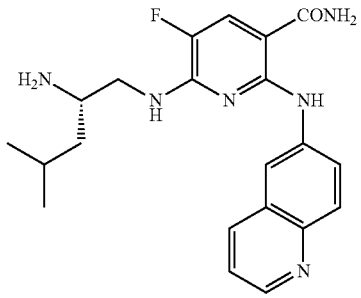 [SMILES: CC(C)C[C@H](N)CNc1nc(Nc2ccc3ncccc3c2)c(C(N)=O)cc1F] | |

| Number | Structure | Compound name |
| --- | --- | --- |
| Example 14-11 | 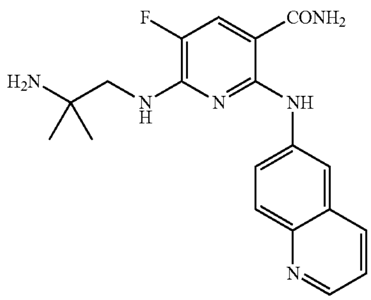 [SMILES: CC(C)(N)CNc1nc(Nc2ccc3ncccc3c2)c(C(N)=O)cc1F] | 6-((2-amino-2-methylpropyl)amino)-5-fluoro-2-((quinolin-6-yl)amino)nicotinamide |
| Example 14-12 | 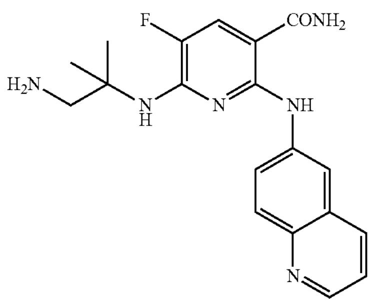 [SMILES: CC(C)(CN)Nc1nc(Nc2ccc3ncccc3c2)c(C(N)=O)cc1F] | 6-((1-amino-2-methylpropan-2-yl)amino)-5-fluoro-2-((quinolin-6-yl)amino)nicotinamide |
| Example 14-13 | 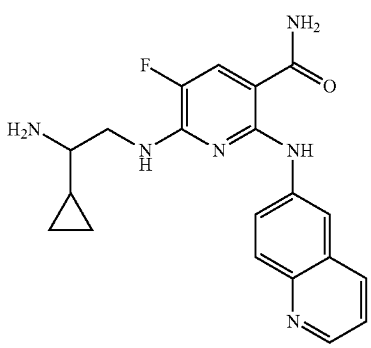 [SMILES: NC(=O)c1cc(F)c(NCC(N)C2CC2)nc1Nc1ccc2ncccc2c1] | 6-((2-amino-2-cyclopropylethyl)amino)-5-fluoro-2-((quinolin-6-yl)amino)nicotinamide |
| Example 14-14 | 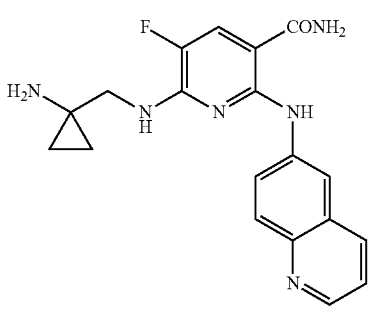 [SMILES: NC(=O)c1cc(F)c(NCC2(N)CC2)nc1Nc1ccc2ncccc2c1] | 6-((1-aminocyclopropylmethyl)amino)-5-fluoro-2-((quinolin-6-yl)amino)nicotinamide |

TABLE 7-continued

| | | |
|---|---|---|
| Example 14-15 | 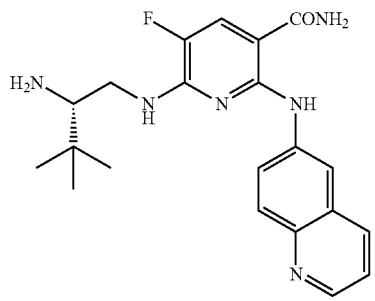 [SMILES: CC(C)(C)[C@H](N)CNc1nc(Nc2ccc3ncccc3c2)c(C(N)=O)cc1F] | (S)-6-((2-amino-3,3-dimethylbutyl)amino)-5-fluoro-2-((quinolin-6-yl)amino)nicotinamide |
| Example 14-16 | 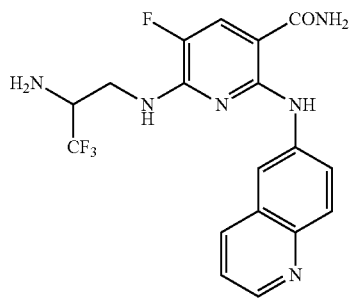 [SMILES: NC(=O)c1cc(F)c(NCC(N)C(F)(F)F)nc1Nc1ccc2ncccc2c1] | 6-((2-amino-3,3,3-trifluoropropyl)amino)-5-fluoro-2-((quinolin-6-yl)amino)nicotinamide |
| Example 14-17 | 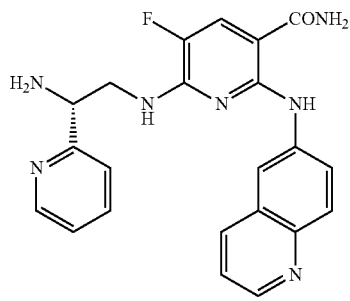 [SMILES: NC(=O)c1cc(F)c(NC[C@@H](N)c2ccccn2)nc1Nc1ccc2ncccc2c1] | (R)-6-((2-amino-2-(pyridin-2-yl)ethyl)amino)-5-fluoro-2-((quinolin-6-yl)amino)nicotinamide |
| Example 14-18 | 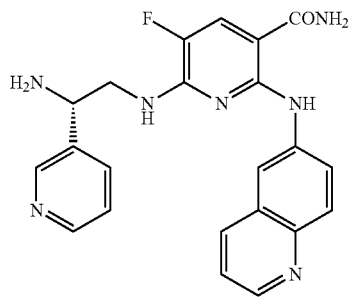 | (S)-6-((2-amino-2-(pyridin-3-yl)ethyl)amino)-5-fluoro-2-((quinolin-6-yl)amino)nicotinamide |
| Example 14-19 | 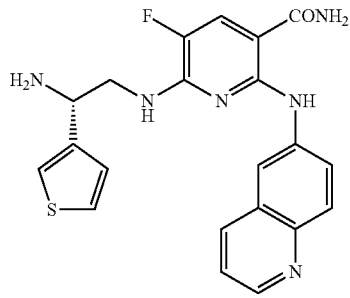 [SMILES: NC(=O)c1cc(F)c(NC[C@@H](N)c2ccsc2)nc1Nc1ccc2ncccc2c1] | (S)-6-((2-amino-2-(thiophene-3-yl)ethyl)amino)-5-fluoro-2-((quinolin-6-yl)amino)nicotinamide |

TABLE 7-continued

| | | |
|---|---|---|
| Example 14-20 | 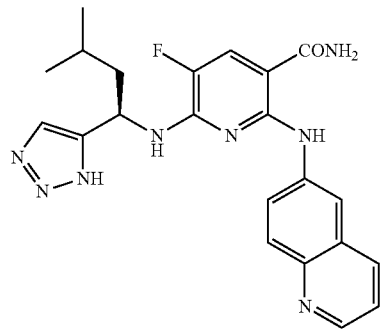 | (R)-5-fluoro-6-((3-methyl-1-(1H-1,2,3-triazol-5-yl)butyl)amino)-2-(quinolin-6-yl)amino)-nicotinamide |
| Example 14-21 | 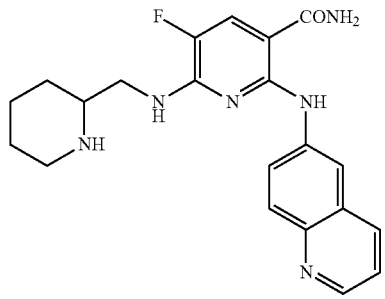 [SMILES: NC(=O)c1cc(F)c(NCC2CCCCN2)nc1Nc1ccc2ncccc2c1] | 5-fluoro-6-((2-piperidin-2-ylmethyl)amino)-2-(quinolin-6-yl)amino)nicotinamide |

| Number | Compound name | $^1$H-NMR | MS (ESI, m/z) |
|---|---|---|---|
| Example 14-1 HCl salt | 6-(((2S)-2-aminobutyl)amino)-5-fluoro-2-(quinolin-6-ylamino)-nicotinamide | $^1$H-NMR (CD$_3$OD, 300 MHz) δ: 9.00 (d, 1H, J = 8.4 Hz), 8.94 (dd, 1H, J = 1.4, 5.3 Hz), 8.65 (d, 1H, J = 2.3 Hz), 8.29 (dd, 1H, J = 2.3, 9.3 Hz), 8.15 (d, 1H, J = 9.3 Hz), 8.00-7.95 (m, 1H), 7.87 (d, 1H, J = 11.9 Hz), 4.01 (dd, 1H, J = 4.0, 14.6 Hz), 3.74-3.63 (m, 1H), 3.56-3.43 (m, 1H), 1.85-1.62 (m, 2H), 0.99 (t, 3H, J = 7.6 Hz). | 369 (M + H) |
| Example 14-2 HCl salt | 6-(((2S)-2-amino-3-methylbutyl)-amino)-5-fluoro-2-(quinolin-6-yl-amino)nicotinamide | $^1$H-NMR (CD$_3$OD, 300 MHz) δ: 9.03 (d, 1H, J = 8.0 Hz), 8.96 (dd, 1H, J = 1.4, 5.5 Hz), 8.64 (d, 1H, J = 2.2 Hz), 8.31 (dd, 1H, J = 2.4, 9.3 Hz), 8.16 (d, 1H, J = 9.1 Hz), 8.02-7.97 (m, 1H), 7.87 (d, 1H, J = 11.9 Hz), 4.02 (dd, 1H, J = 3.7, 14.4 Hz), 3.81-3.70 (m, 1H), 3.46-3.37 (m, 1H), 2.12-1.97 (m, 1H), 1.05-1.00 (m, 6H). | 383 (M + H) |
| Example 14-3 HCl | 6-(((2S)-2-amino-3-phenylpropyl)-amino)-5-fluoro-2-(quinolin-6-ylamino)nicotinamide | $^1$H-NMR (CD$_3$OD, 300 MHz) δ: 8.96-8.89 (m, 2H), 8.57 (d, 1H, J = 2.3 Hz), 8.27 (dd, 1H, J = 2.3, 9.3 Hz), 8.13 (d, 1H, J = 9.3 Hz), 7.98-7.93 (m, 1H), 7.87 (d, 1H, J = 11.9 Hz), 7.16-7.01 (m, 5H), 4.02-3.74 (m, 3H), 3.11-2.89 (m, 2H). | 431 (M + H) |
| Example 14-4 HCl salt | 6-(((2R)-2-aminobutyl)amino)-5-fluoro-2-(quinolin-6-ylamino)-nicotinamide | $^1$H-NMR (CD$_3$OD, 300 MHz) δ: 9.03 (d, 1H, J = 8.1 Hz), 8.95 (dd, 1H, J = 1.3, 5.4 Hz), 8.67 (d, 1H, J = 2.3 Hz), 8.30 (dd, 1H, J = 2.3, 9.3 Hz), 8.17 (d, 1H, J = 9.3 Hz), 8.02-7.97 (m, 1H), 7.87 (d, 1H, J = 11.9 Hz), 4.01 (dd, 1H, J = 4.0, 14.4 Hz), 3.76-3.64 (m, 1H), 3.57-3.46 (m, 1H), 1.87-1.62 (m, 2H), 0.99 (t, 3H, J = 7.6 Hz). | 369 (M + H) |
| Example 14-5 HCl salt | 6-(((2S)-2-amino-2-phenylethyl)-amino)-5-fluoro-2-(quinolin-6-yl-amino)nicotinamide | $^1$H-NMR (CD$_3$OD, 300 MHz) δ: 8.89 (dd, 1H, J = 1.4, 5.4 Hz), 8.70 (d, 1H, J = 2.1 Hz), 8.20-8.00 (m, 3H), 7.89 (d, 1H, J = 11.9 Hz), 7.78-7.73 (m, 1H), 7.47-7.26 (m, 5H), 4.70 (dd, 1H, J = 3.3, 10.0 Hz), 4.33 (dd, 1H, J = 3.6, 14.5 Hz), 4.09-4.00 (m, 1H). | 417 (M + H) |
| Example 14-6 HCl salt | 6-(((2R)-2-amino-3-methoxypropyl)-amino)-5-fluoro-2-(quinolin-6-ylamino)nicotinamide | $^1$H-NMR (CD$_3$OD, 300 MHz) δ: 9.03 (d, 1H, J = 8.4 Hz), 8.95 (dd, 1H, J = 1.4, 5.4 Hz), 8.83 (d, 1H, J = 2.2 Hz), 8.22 (dd, 1H, J = 2.3, 9.3 Hz), 8.15 (d, 1H, J = 9.2 Hz), 8.02-7.98 (m, 1H), 7.88 (d, 1H, J = 11.9 Hz), 3.92-3.59 (m, 5H), 3.38 (s, 3H). | 385 (M + H) |
| Example 14-7 HCl salt | 5-fluoro-6-((3R)-pyrrolidin-3-yl-amino)-2-(quinolin-6-ylamino)-nicotinamide | $^1$H-NMR (DMSO-d$_6$, 400 MHz) δ: 12.12 (s, 1H), 8.92-8.84 (m, 1H), 8.72-8.56 (m, 2H), 8.30-8.14 (m, 3H), 8.10-8.00 (m, 3H), 7.98-7.88 (m, 1H), 7.76-7.66 (m, 1H), | 367 (M + H), 365 (M − H) |

TABLE 7-continued

| | | |
|---|---|---|
| Example 14-8 HCl salt | 5-fluoro-6-((3S)-pyrrolidin-3-yl-amino)-2-(quinolin-6-ylamino)-nicotinamide | 7.52-7.36 (m, 1H), 4.08-3.80 (m, 5H), 2.36-2.30 (m, 1H), 2.20-2.10 (m, 1H). $^1$H-NMR (DMSO-d$_6$, 400 MHz) δ: 12.21 (s, 1H), 9.00-8.92 (m, 1H), 8.89-8.78 (m, 1H), 8.78-8.72 (m, 1H), 8.40-8.23 (m, 3H), 8.20-7.90 (m, 4H), 7.88-7.76 (m, 1H), 7.56-7.37 (m, 1H), 4.10-3.80 (m, 5H), 2.38-2.28 (m, 1H), 2.20-2.09 (m, 1H). | 367 (M + H), 365 (M − H) |
| Example 14-9 HCl salt | 6-(((2S)-2-aminopropyl)amino-5-fluoro-2-(quinolin-6-ylamino)-nicotinamide | $^1$H-NMR (CD$_3$OD, 300 MHz) δ: 9.01 (d, 1H, J = 8.5 Hz), 8.94 (dd, 1H, J = 1.3, 5.4 Hz), 8.69 (d, 1H, J = 2.2 Hz), 8.28 (dd, 1H, J = 2.3, 9.3 Hz), 8.16 (d, 1H, J = 9.3 Hz), 8.01-7.96 (m, 1H), 7.86 (d, 1H, J = 11.9 Hz), 3.95 (dd, 1H, J = 2.8, 12.8 Hz), 3.78-3.62 (m, 2H), 1.37 (d, 3H, J = 6.3 Hz). | 355 (M + H) |
| Example 14-10 HCl salt | 6-(((2S)-2-amino-4-methyl-pentyl)amino)-5-fluoro-2-(quinolin-6-ylamino)nicotinamide | $^1$H-NMR (CD$_3$OD, 300 MHz) δ: 9.04 (d, 1H, J = 8.3 Hz), 8.96 (dd, 1H, J = 1.3, 5.4 Hz), 8.65 (d, 1H, J = 2.2 Hz), 8.26 (dd, 1H, J = 2.3, 9.2 Hz), 8.16 (d, 1H, J = 9.3 Hz), 8.02-7.97 (m, 1H), 7.87 (d, 1H, J = 11.9 Hz), 4.03 (dd, 1H, J = 3.0, 14 Hz), 3.68-3.53 (m, 2H), 1.72-1.41 (m, 3H), 0.70 (d, 3H, J = 6.5 Hz), 0.63 (d, 3H, J = 6.5 Hz). | 397 (M + H) |

| Number | Salt | Solvent | NMR | 1HNMR | Mass (M + H) | Mass (M − H) | rt(min) |
|---|---|---|---|---|---|---|---|
| Example 14-11 | HCl | | | | 369 | 367 | 0.53 |
| Example 14-12 | HCl | | | | 369 | 367 | 0.59 |
| Example 14-13 | HCl | | | | 381 | 379 | 0.57 |
| Example 14-14 | HCl | | | | 367 | 365 | 0.54 |
| Example 14-15 | HCl | | | | 397 | 395 | 0.62 |
| Example 14-16 | free | | | | 410 | 408 | 0.82 |
| Example 14-17 | HCl | | | | 418 | 416 | 0.59 |
| Example 14-18 | HCl | | | | 418 | 416 | 0.55 |
| Example 14-19 | HCl | | | | 423 | 421 | 0.63 |
| Example 14-20 | free | CD3OD | 400 MHz | δ: 8.62 (dd, 1H, J = 1.6, 4.4 Hz), 8.56-8.18 (m, 2H), 7.87 (d, 1H, J = 9.3 Hz), 7.80-7.58 (m, 3H), 7.44 (dd, 1H, J = 4.4, 8.3 Hz), 5.80-5.70 (m, 1H), 2.02-1.70 (m, 3H), 0.97 (d, 3H, J = 6.5 Hz), 0.92 (d, 3H, J = 6.5 Hz) | 436 | 433 | |
| Example 14-21 | HCl | CD3OD | 400 MHz | δ: 9.06 (d, 1H, J = 8.5 Hz), 8.98-8.92 (m, 1H), 8.66 (d, 1H, J = 2.2 Hz), 8.32 (dd, 1H, J = 2.2, 9.3 Hz), 8.18 (d, 1H, J = 9.3 Hz), 8.00 (dd, 1H, J = 5.4, 8.5 Hz), 7.87 (d, 1H, J = 12.0 Hz), 4.00-3.91 (m, 1H), 3.80-3.70 (m, 1H), 3.58-3.46 (m, 1H), 2.96-2.84 (m, 1H), 2.10-1.30 (m, 7H) | 395 | 393 | |

Example 15

[Formula 496]

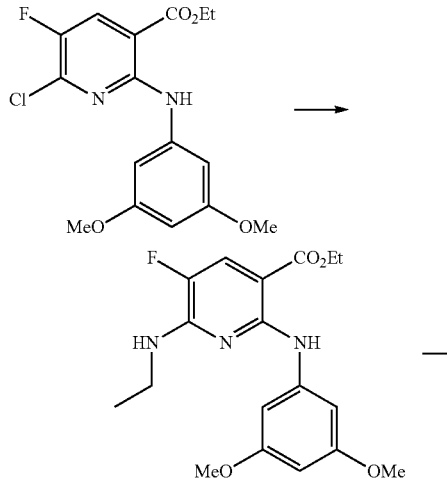

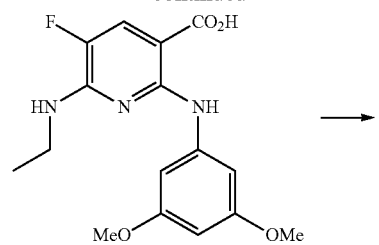

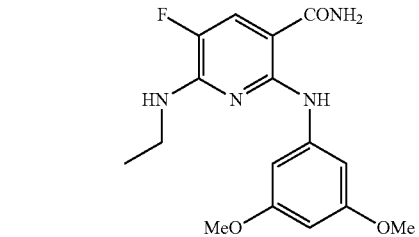

1st Step

The following compound was obtained as described in the 1st step of Reference Example 2.

Ethyl 2-(3,5-dimethoxyphenylamino)-6-ethylamino-5-fluoronicotinate

¹H-NMR (CDCl₃, 400 MHz) δ:10.47 (s, 1H), 7.67 (d, 1H, J=11.7 Hz), 6.99 (d, 2H, J=2.3 Hz), 6.16 (t, 1H, J=2.3 Hz), 5.02-4.96 (m, 1H), 4.30 (q, 2H, J=7.2 Hz), 3.79 (s, 6H), 3.68-3.59 (m, 2H), 1.37 (t, 3H, J=7.2 Hz), 1.31 (d, 3H, J=7.2 Hz)

2nd and 3rd Steps

The following compound was obtained as described in the 3rd and 4th steps of Example 7.

2-(3,5-dimethoxyphenylamino)-6-(ethylamino)-5-fluoronicotinamide (¹H-NMR and ESI-MS data are shown in table 8.)

Example 16

The compounds listed in table 8 were obtained as described in Example 15.

TABLE 8

| Number | Structure |
| --- | --- |
| Example 16-1 (Example 15) | 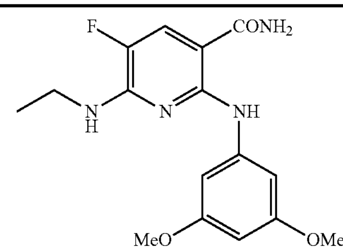 |
| Example 16-2 | 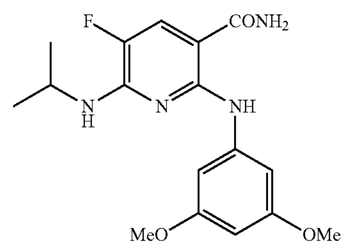 [SMILES: COc1cc(Nc2nc(NC(C)C)c(F)cc2C(N)=O)cc(OC)c1] |
| Example 16-3 | 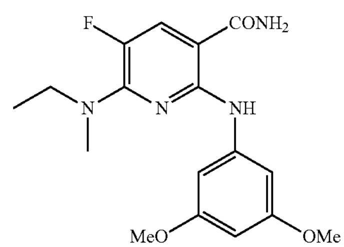 [SMILES: CCN(C)c1nc(Nc2cc(OC)cc(OC)c2)c(C(N)=O)cc1F] |
| Example 16-4 | 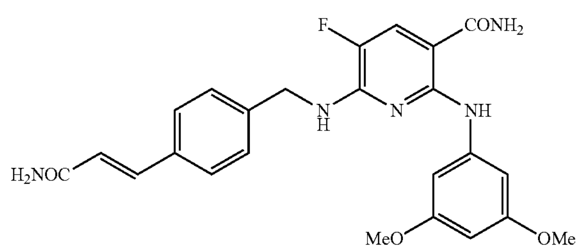 [SMILES: COc1cc(Nc2nc(NCc3ccc(/C=C/C(N)=O)cc3)c(F)cc2C(N)=O)cc(OC)c1] |
| Example 16-5 | 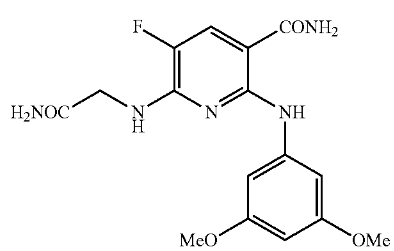 [SMILES: COc1cc(Nc2nc(NCC(N)=O)c(F)cc2C(N)=O)cc(OC)c1] |

TABLE 8-continued
Example 16-6 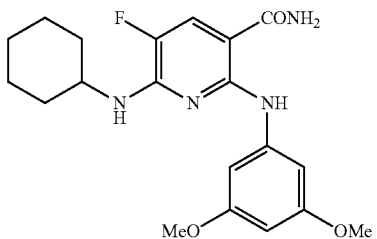 [SMILES: COc1cc(Nc2nc(NC3CCCCC3)c(F)cc2C(N)=O)cc(OC)c1]
Example 16-7 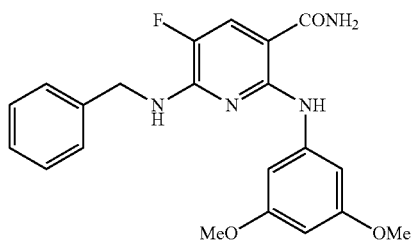 [SMILES: COc1cc(Nc2nc(NCc3ccccc3)c(F)cc2C(N)=O)cc(OC)c1]
Example 16-8 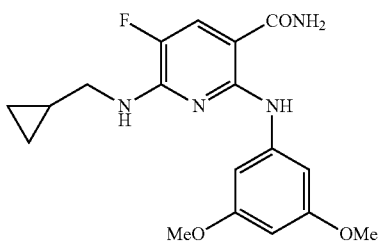 [SMILES: COc1cc(Nc2nc(NCC3CC3)c(F)cc2C(N)=O)cc(OC)c1]
Example 16-9 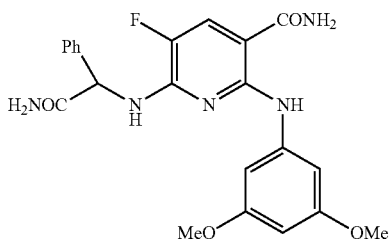 [SMILES: COc1cc(Nc2nc(NC(C(N)=O)c3ccccc3)c(F)cc2C(N)=O)cc(OC)c1]
Example 16-10 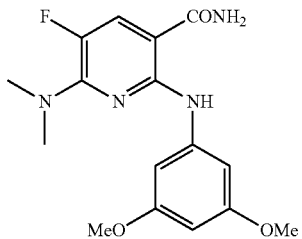 [SMILES: COc1cc(Nc2nc(N(C)C)c(F)cc2C(N)=O)cc(OC)c1]
Example 16-11 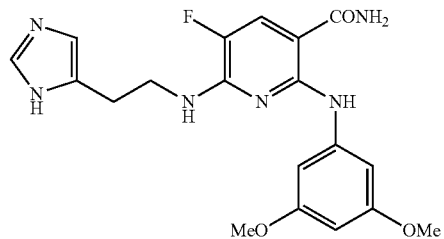 [SMILES: COc1cc(Nc2nc(NCCc3cnc[nH]3)c(F)cc2C(N)=O)cc(OC)c1]

TABLE 8-continued
| Example 16-12 | 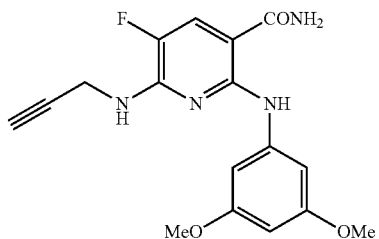 [SMILES: C#CCNc1nc(Nc2cc(OC)cc(OC)c2)c(C(N)=O)cc1F] |
| Example 16-13 | 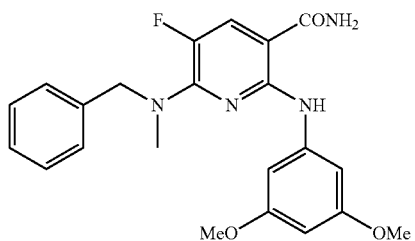 [SMILES: COc1cc(Nc2nc(N(C)Cc3ccccc3)c(F)cc2C(N)=O)cc(OC)c1] |
| Example 16-14 | 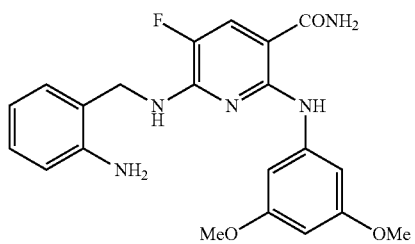 [SMILES: COc1cc(Nc2nc(NCc3ccccc3N)c(F)cc2C(N)=O)cc(OC)c1] |
| Example 16-15 | 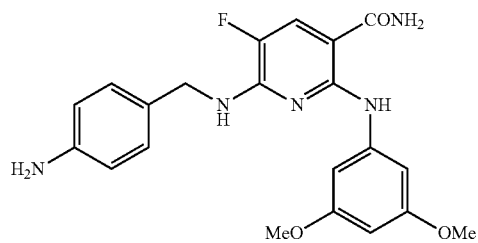 [SMILES: COc1cc(Nc2nc(NCc3ccc(N)cc3)c(F)cc2C(N)=O)cc(OC)c1] |
| Example 16-16 | 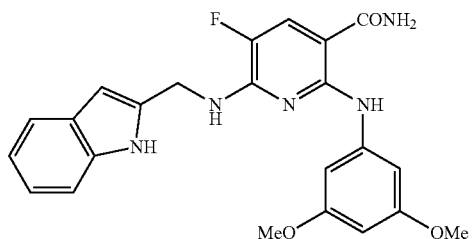 [SMILES: COc1cc(Nc2nc(NCc3cc4ccccc4[nH]3)c(F)cc2C(N)=O)cc(OC)c1] |
| Example 16-17 | 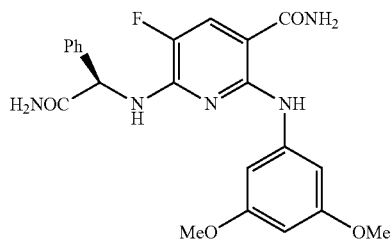 [SMILES: COc1cc(Nc2nc(N[C@@H](C(N)=O)c3ccccc3)c(F)cc2C(N)=O)cc(OC)c1] |

TABLE 8-continued
| Example 16-18 | 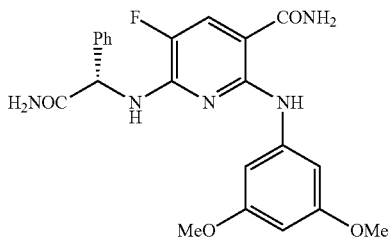 [SMILES: COc1cc(Nc2nc(N[C@H](C(N)=O)c3ccccc3)c(F)cc2C(N)=O)cc(OC)c1] |
| Example 16-19 (*) | 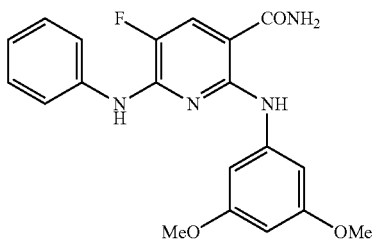 [SMILES: COc1cc(Nc2nc(Nc3ccccc3)c(F)cc2C(N)=O)cc(OC)c1] |
| Example 16-20 (*) | 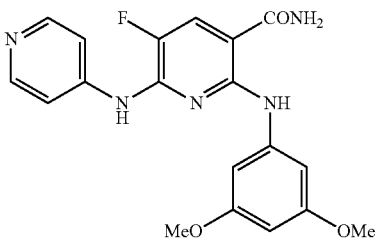 [SMILES: COc1cc(Nc2nc(Nc3ccncc3)c(F)cc2C(N)=O)cc(OC)c1] |
| Example 16-21 (*) | 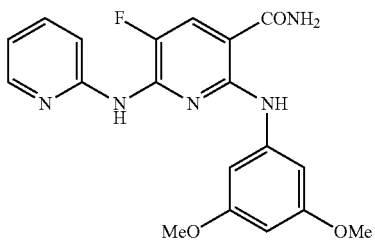 [SMILES: COc1cc(Nc2nc(Nc3ccccn3)c(F)cc2C(N)=O)cc(OC)c1] |
| Example 16-22 (*) | 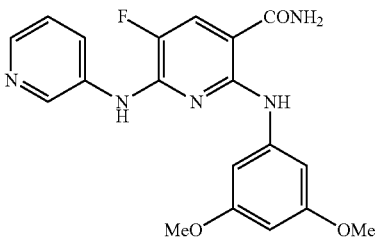 [SMILES: COc1cc(Nc2nc(Nc3cccnc3)c(F)cc2C(N)=O)cc(OC)c1] |
| Example 16-23 | 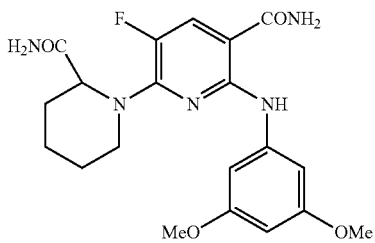 [SMILES: COc1cc(Nc2nc(N3CCCCC3C(N)=O)c(F)cc2C(N)=O)cc(OC)c1] |

TABLE 8-continued

| Example 16-24 | 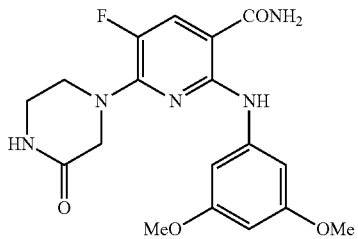 [SMILES: COc1cc(Nc2nc(N3CCNC(=O)C3)c(F)cc2C(N)=O)cc(OC)c1] | | |
|---|---|---|---|
| Number | Compound name | ¹H-NMR | MS (ESI, m/z) |
| Example 16-1 | 2-((3,5-dimethoxyphenyl)amino)-6-(ethylamino)-5-fluoronicotinamide | ¹H-NMR (DMSO-$d_6$, 400 MHz) δ: 11.70 (s, 1H), 7.81 (d, 1H, J = 12.8 Hz), 7.27 (t, 1H, J = 5.4 Hz), 6.87 (t, 2H, J = 2.2 Hz), 6.07 (t, 1H, J = 2.2 Hz), 3.71 (s, 6H), 3.45 (dt, 2H, J = 7.1 Hz, 12.8 Hz), 1.17 (t, 3H, J = 7.1 Hz). | 335 (M + H) |
| Example 16-2 | 2-((3,5-dimethoxyphenyl)amino)-5-fluoro-6-(isopropylamino)-nicotinamide | ¹H-NMR (DMSO-$d_6$, 400 MHz) δ: 11.67 (s, 1H), 7.81 (d, 1H, J = 12.7 Hz), 7.02 (d, 1H, J = 7.9 Hz), 6.83 (d, 2H, J = 2.2 Hz), 6.07 (t, 1H, J = 2.2 Hz), 4.35-4.25 (m, 1H), 3.71 (s, 6H), 1.20 (d, 6H, J = 6.5 Hz). | 349 (M + H) |
| Example 16-3 | 2-((3,5-dimethoxyphenyl)amino)-6-(ethyl(methyl)amino)-5-fluoro-nicotinamide | ¹H-NMR (DMSO-$d_6$, 400 MHz) δ: 11.53 (s, 1H), 7.88 (d, 1H, J = 15.5 Hz), 6.80 (d, 2H, J = 2.2 Hz), 6.08 (t, 1H, J = 2.3 Hz), 3.71 (s, 6H), 3.61-3.54 (m, 2H), 3.15-3.12 (m, 3H), 1.15 (t, 3H, J = 7.0 Hz). | 349 (M + H) |
| Example 16-4 | 6-((4-(1E)-3-amino-3-oxoprop-1-en-1-yl)benzyl)amino)-2-((3,5-dimethoxyphenyl)amino)-5-fluoronicotinamide | ¹H-NMR (DMSO-$d_6$, 400 MHz) δ: 11.66 (s, 1H), 7.93-7.85 (m, 2H), 7.54-7.27 (m, 6H), 7.10-7.02 (m, 1H), 6.78 (s, 2H), 6.60-6.50 (m, 1H), 6.06 (s, 1H), 4.75-4.64 (m, 2H), 3.62 (s, 6H). | 466 (M + H) |
| Example 16-5 | 6-((2-amino-2-oxoethyl)amino)-2-((3,5-dimethoxyphenyl))amino)-5-fluoronicotinamide | ¹H-NMR (CD$_3$OD, 400 MHz) δ: 7.61 (d, 1H, J = 12.0 Hz), 6.73 (d, 2H, J = 2.3 Hz), 6.01 (t, 1H, J = 2.3 Hz), 4.09 (s, 2H), 3.67 (s, 6H). | 362 (M − H) |
| Example 16-6 | 6-(cyclohexylamino)-2-((3,5-dimethoxyphenyl)amino)-5-fluoronicotinamide | ¹H-NMR (DMSO-$d_6$, 400 MHz) δ: 11.61 (s, 1H), 7.81 (d, 1H, J = 12.8 Hz), 7.74-7.56 (m, 1H), 7.20-7.05 (m, 1H), 7.00 (d, 1H, J = 7.7 Hz), 6.83 (d, 2H, J = 2.2 Hz), 6.11 (t, 1H, J = 2.1 Hz), 3.97-3.85 (m, 1H), 3.73 (s, 6H), 1.95-1.87 (m, 2H), 1.78-1.70 (m, 2H), 1.63-1.60 (m, 1H), 1.43-1.26 (m, 4H), 1.20-1.07 (m, 1H). | 387 (M − H) |
| Example 16-7 | 6-(benzylamino)-2-((3,5-dimethoxyphenyl)amino)-5-fluoro-nicotinamide | ¹H-NMR (DMSO-$d_6$, 400 MHz) δ: 11.68 (s, 1H), 7.88 (d, 1H, J = 12.7 Hz), 7.34 (d, 2H, J = 7.1 Hz), 7.28 (t, 2H, J = 7.4 Hz), 7.21 (t, 1H, J = 7.2 Hz), 6.80 (d, 2H, J = 2.2 Hz), 6.05 (t, 1H, J = 2.2 Hz), 4.68 (d, 2H, J = 6.3 Hz), 3.60 (s, 6H). | MS (DART, m/z) 397 (M + H) |
| Example 16-8 | 6-((cyclopropylmethyl)amino)-2-((3,5-dimethoxyphenyl)amino)-5-fluoronicotinamide | ¹H-NMR (CD$_3$OD, 400 MHz) δ: 7.52 (d, 1H, J = 12.2 Hz), 6.86 (d, 2H, J = 2.3 Hz), 6.00 (t, 1H, J = 2.3 Hz), 3.68 (s, 6H), 3.33 (d, 2H, J = 7.1 Hz), 1.16-1.06 (m, 1H), 0.43-0.39 (m, 2H), 0.20-0.16 (m, 2H). | 359 (M − H) |
| Example 16-9 | 6-((2-amino-2-oxo-1-phenylethyl)amino)-2-((3,5-dimethoxyphenyl)-amino)-5-fluoronicotinamide | ¹H-NMR (CD$_3$OD, 400 MHz) δ: 7.61 (d, 1H, J = 11.9 Hz), 7.48-7.32 (s, 3H), 7.26-7.16 (m, 2H), 6.69 (d, 2H, J = 2.2 Hz), 6.07 (t, 1H, J = 2.2 Hz), 5.70 (s, 1H), 3.68 (s, 6H). | 440 (M + H), 438 (M − H) |
| Example 16-10 | 2-((3,5-dimethoxyphenyl)amino)-6-(dimethylamino)-5-fluoronico-tinamide | ¹H-NMR (DMSO-$d_6$, 400 MHz) δ: 11.57 (s, 1H), 7.91 (d, 1H, J = 15.4 Hz), 7.81 (brs, 1H), 7.26 (brs, 1H), 6.83 (d, 2H, J = 2.2 Hz), 6.09 (t, 1H, J = 2.2 Hz), 3.72 (s, 6H), 3.17 (s, 3H), 3.16 (s, 3H). | 335 (M + H) |
| Example 16-11 | 2-((3,5-dimethoxyphenyl)amino)-5-fluoro-6-((2-(1H-imidazol-5-yl)-ethyl)amino)nicotinamide | ¹H-NMR (DMSO-$d_6$, 400 MHz) δ: 11.90 (brs, 1H), 11.72 (s, 1H), 7.84 (d, 1H, J = 12.7 Hz), 7.69 (brs, 1H), 7.57 (s, 1H), 7.39-7.31 (m, 1H), 7.15 (brs, 1H), 6.87 (d, 2H, J = 2.2 Hz), 6.83 (s, 1H), 6.06 (t, 1H, J = 2.2 Hz), 3.70-3.62 (m, 8H), 2.83 (t, 2H, J = 7.4 Hz). | 401 (M + H), 399 (M − H) |
| Example 16-12 | 2-((3,5-dimethoxyphenyl)amino)-5-fluoro-6-(prop-2-yn-1-ylamino)-nicotinamide | ¹H-NMR (DMSO-$d_6$, 400 MHz) δ: 11.73 (s, 1H), 7.90 (d, 1H, J = 12.4 Hz), 7.84-7.64 (m, 2H), 7.23 (brs, 1H), 6.88 (d, 1H, J = 2.2 Hz), 6.09 (t, 1H, J = 2.2 Hz), 4.20 (dd, 2H, J = 2.3, 5.9 Hz), 3.75 (s, 6H), 3.08 (t, 1H, J = 2.3 Hz). | MS (DART, m/z): 345 (M + H) |

TABLE 8-continued

| | | | |
|---|---|---|---|
| Example 16-13 | 6-(benzyl(methyl)amino)-2-((3,5-dimethoxyphenyl)amino)-5-fluoronicotinamide | $^1$H-NMR (DMSO-d$_6$, 400 MHz) δ: 11.53 (s, 1H), 7.92 (d, 1H, J = 15.4 Hz), 7.35-7.21 (m, 5H), 6.76 (d, 2H, J = 2.2 Hz), 6.06 (t, 1H, J = 2.2 Hz), 4.81 (s, 2H), 3.62 (s, 6H), 3.14-3.11 (m, 3H). | 411 (M + H) |
| Example 16-14 | 6-((2-aminobenzyl))amino)-2-((3,5-methoxyphenyl)amino)-5-fluoronicotinamide | $^1$H-NMR (DMSO-d$_6$, 400 MHz) δ: 11.71 (s, 1H), 7.87 (d, 2H, J = 12.7 Hz), 7.81-7.48 (m, 2H), 7.32-6.76 (m, 5H), 6.64-6.54 (m, 1H), 6.50-6.39 (m, 1H), 6.08-6.01 (m, 1H), 4.99 brs, 2H), 4.50 (d, 2H, J = 5.8 Hz), 3.60 (s, 6H). | MS (DART, m/z): 412 (M + H) |
| Example 16-15 | 6-((4-aminobenzyl))amino)-2-((3,5-dimethoxyphenyl))amino)-5-fluoronicotinamide | $^1$H-NMR (DMSO-d$_6$, 400 MHz) δ: 11.71 (s, 1H), 7.84 (d, 1H, J = 12.4 Hz), 7.80-7.56 (m, 2H), 7.30-6.97 (m, 3H), 6.86 (d, 2H, J = 2.0 Hz), 6.46 (d, 2H, J = 8.3 Hz), 6.12-6.01 (m, 1H), 4.92 (brs, 2H), 4.50 (d, 2H, J = 6.1 Hz), 3.63 (s, 6H). | MS (DART, /z): 412 (M + H) |
| Example 16-16 | 2-((3,5-dimethoxyphenyl))amino)-5-fluoro-6-(((1H-indol-2-yl)methyl)amino)nicotinamide | $^1$H-NMR (DMSO-d$_6$, 400 MHz) δ: 11.69 (s, 1H), 10.86 (s, 1H), 7.98-7.62 (m, 3H), 7.46-7.10 (m, 3H), 7.07-6.81 (m, 4H), 6.33-6.27 (m, 1H), 6.07-6.02 (m, 1H), 4.82 (d, 2H, J = 5.9 Hz), 3.59 (s, 6H). | MS (DART, m/z) 436 (M + H) |
| Example 16-17 | 6-(((1R)-2-amino-2-oxo-1-phenyl-ethyl)amino)-2-((3,5-dimethoxy-phenyl)amino)-5-fluoro-nicotinamide | $^1$H-NMR (DMSO-d$_6$, 400 MHz) δ: 11.60 (s, 1H), 7.92 (d, 1H, J = 12.4 Hz), 7.80-7.26 (m, 9H), 7.14 (d, 1H, J = 8.2 Hz), 6.69 (d, 2H, J = 2.0 Hz), 6.14-6.10 (m, 1H), 5.67 (d, 1H, J = 8.2 Hz), 3.73 (s, 6H). | 440 (M + H) |
| Example 16-18 | 6-(((1S)-2-amino-2-oxo-1-phenyl-ethyl)amino)-2-((3,5-dimethoxy-phenyl)amino)-5-fluoronicotinamide | | 440 (M + H), 438 (M − H) |
| Example 16-19 (*) | 6-anilino-2-((3,5-dimethoxy-phenyl)amino)-5-fluoronicotinamide | $^1$H-NMR (DMSO-d$_6$, 400 MHz) δ: 11.42 (s, 1H), 9.18-9.14 (m, 1H), 8.03 (d, 1H, J = 12.4 Hz), 7.94-7.78 (m, 1H), 7.69 (d, 2H, J = 7.8 Hz), 7.40-7.28 (m, 1H), 7.27-7.19 (m, 2H), 7.00 (t, 1H, J = 7.2 Hz), 6.68 (d, 2H, J = 2.1 Hz), 6.11 (t, 1H, J = 2.1 Hz), 3.57 (s, 6H). | 383 (M + H) |
| Example 16-20 (*) | 2-((3,5-dimethoxyphenyl)amino)-5-fluoro-6-(pyridin-4-ylamino)-nicotinamide | $^1$H-NMR (DMSO-d$_6$, 400 MHz) δ: 11.30 (s, 1H), 9.62 (s, 1H), 8.29-8.24 (m, 2H), 8.12 (d, 1H, J = 12.2 Hz), 8.06-7.94 (m, 1H), 7.76-7.72 (m, 2H), 7.54-7.45 (m, 1H), 6.68 (d, 2H, J = 2.2 Hz), 6.21 (t, 1H, J = 2.2 Hz), 3.65 (s, 6H). | 384 (M + H) |
| Example 16-21 (*) | 2-((3,5-dimethoxyphenyl)amino)-5-fluoro-6-(pyridin-2-ylamino)-nicotinamide | $^1$H-NMR (DMSO-d$_6$, 400 MHz) δ: 11.35 (s, 1H), 9.33 (s, 1H), 8.33-8.29 (m, 1H), 8.08 (d, 1H, J = 12.0 Hz), 8.01-7.92 (m, 1H), 7.92-7.87 (m, 1H), 7.62-7.56 (m, 1H), 7.49-7.41 (m, 1H), 7.05-7.00 (m, 1H), 6.74 (d, 2H, J = 2.2 Hz), 6.16 (t, 1H, J = 2.2 Hz), 3.64 (s, 6H). | 384 (M + H) |
| Example 16-22 (*) | 2-(3,5-dimethoxyphenylamino)-5-fluoro-6-(pyridin-3-ylamino)-nicotinamide | $^1$H-NMR (DMSO-d$_6$, 400 MHz) δ: 11.38 (s, 1H), 9.41-9.37 (s, 1H), 8.78 (d, 1H, J = 2.6 Hz), 8.21 (dd, 1H, J = 1.5 Hz, 4.7 Hz), 8.15 (ddd, 1H, J = 1.5 Hz, 2.6 Hz, 8.3 Hz), 8.07 (d, 1H, J = 12.3 Hz), 7.98-7.86 (m, 1H), 7.46-7.34 (m, 1H), 7.22 (dd, 1H, J = 4.7 Hz, 8.3 Hz), 6.62 (d, 2H, J = 2.3 Hz), 6.12 (t, 1H, J = 2.3 Hz), 3.57 (s, 6H). | 384 (M + H) |
| Example 16-23 | 6-(2-(aminocarbonyl)piperidin-1-yl)-2-((3,5-dimethoxyphenyl)-amino)-5-fluoronicotinamide | | 416 (M − H) |
| Example 16-24 | 2-((3,5-dimethoxyphenyl)amino)-5-fluoro-6-(3-oxopiperazin-1-yl)nicotinamide | $^1$H-NMR (CD$_3$OD, 400 MHz) δ: 7.71 (d, 1H, J = 14.4 Hz), 6.72 (d, 2H, J = 2.3 Hz), 6.04 (t, 1H, J = 2.3 Hz), 4.23 (s, 2H), 3.87-3.80 (m, 2H), 3.68 (s, 6H), 3.40-3.34 (m, 2H). | 412 (M + Na), 388 (M − H) |

Example 17

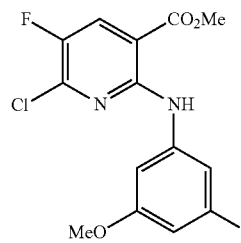

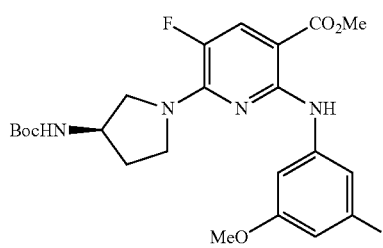

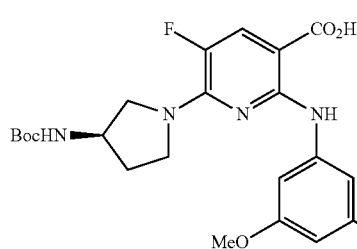

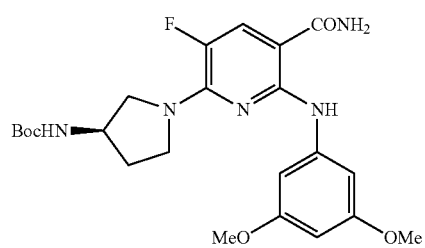

[Formula 497]

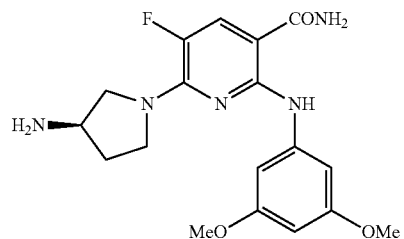

1st, 2nd, and 3rd Steps

The following compound was obtained as described in Example 15.

tert-Butyl((3R)-1-(5-carbamoyl-6-(3,5-dimethox-yphenylamino)-3-fluoropyridin-2-yl)pyrrolidin-3-yl) carbamate $^1$H-NMR (DMSO-d$_6$, 400 MHz) δ:11.66 (s, 1H), 7.89 (d, 1H, J=14.8 Hz), 7.76 (brs, 1H), 7.30-7.14 (m, 2H), 6.89-6.83 (m, 2H), 6.10-6.05 (m, 1H), 4.14-4.03 (m, 1H), 3.91-3.73 (m, 3H), 3.72 (s, 6H), 3.55-3.49 (m, 1H), 2.15-2.01 (m, 1H), 1.94-1.82 (m, 1H), 1.39 (s, 9H)

MS (ESI, m/z): 476 (M−H), 474 (M−H)

The following compound was obtained as described in the 2nd step of Example 1.

6-((3R)-3-aminopyrrolidin-1-yl)-2-(3,5-dimethox-yphenylamino)-5-fluoronicotinamide ($^1$H-NMR and ESI-MS data are shown in table 9.)

Example 18

The compounds listed in table 9 were obtained as described in Example 17.

TABLE 9

| Number | Structure |
|---|---|
| Example 18-1 HCl salt | 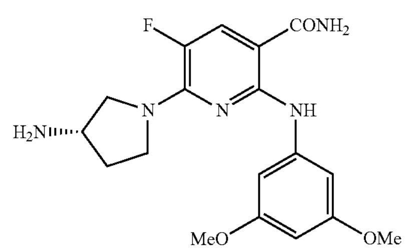 [SMILES: COc1cc(Nc2nc(N3CC[C@H](N)C3)c(F)cc2C(N)=O)cc(OC)c1] |

TABLE 9-continued

| Example 18-2 (Example 17) HCl salt | 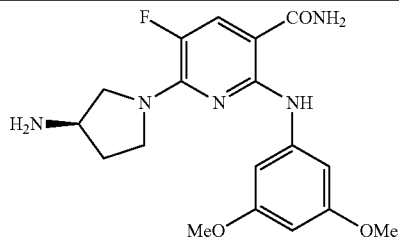 |

| Number | Compound name | ¹H-NMR | MS(ESI, m/z) |
|---|---|---|---|
| Example 18-1 HCl salt | 6-((3S)-3-aminopyrrolidin-1-yl)-2-((3,5-dimethoxyphenyl)amino)-5-fluoronicotinamide | ¹H-NMR (DMSO-d₆, 400 MHz) δ: 11.65 (s, 1H), 8.20-8.12 (m, 3H), 7.95 (d, 1H, J = 14.6 Hz), 7.82 (brs, 1H), 7.28 (brs, 1H), 6.84 (d, 2H), J = 2.2 Hz), 6.10 (t, 1H, J = 2.2 Hz), 3.98-3.76 (m, 5H), 3.73 (s, 6H), 2.35-2.22 (m, 1H), 2.12-2.02 (m, 1H). | 376 (M + H) |
| Example 18-2 HCl salt | 6-((3R)-3-aminopyrrolidin-1-yl)-2-((3,5-dimethoxyphenyl)amino)-5-fluoronicotinamide | ¹H-NMR (DMSO-d₆, 400 MHz) δ: 11.64 (s, 1H), 8.20-8.12 (m, 3H), 7.95 (d, 1H, J = 14.6 Hz), 7.82 (brs, 1H), 7.27 (brs, 1H), 6.84 (d, 2H, J = 2.2 Hz), 6.10 (t, 1H, J = 2.2 Hz), 3.97-3.75 (m, 5H), 3.73 (s, 6H), 2.35-2.22 (m, 1H), 2.12-2.03 (m, 1H). | 376 (M + H) |

Example 19

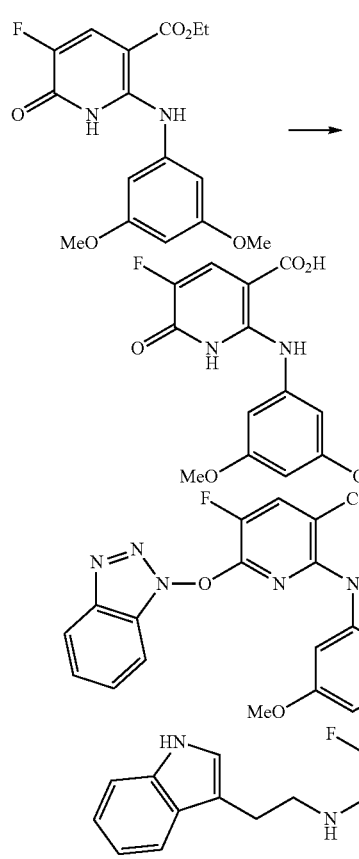

[Formula 498]

1st Step

The following compound was obtained as described in the 1st step of Reference Example 3.

2-(3,5-dimethoxyphenylamino)-5-fluoro-6-oxo-1,6-dihydropyridin-3-carboxylic acid ¹H-NMR (DMSO-d₆, 400 MHz) δ:10.37 (s, 1H), 7.81 (d, 1H, J=11.0 Hz), 6.80-6.70 (br, 2H), 6.26-6.20 (br, 1H), 3.75 (s, 6H)

MS (ESI, m/z): 309 (M+H), 331 (M+Na), 307 (M−H)

2nd Step

A mixture of 2-(3,5-dimethoxyphenylamino)-5-fluoro-6-oxo-1,6-dihydropyridin-3-carboxylic acid (200 mg), WSC.HCl (312 mg), HOBt.H₂O (249 mg), and DMF (2 ml) was stirred at room temperature for 45 minutes. 25% ammonia water (1 ml) was added, followed by stirring at the same temperature for 2 hours. Ethyl acetate was added to the reaction mixture. The resultant was washed with saturated saline and dried over anhydrous magnesium sulfate, the solvent was distilled away under reduced pressure. The obtained residue was purified by silica gel chromatography (hexane:ethyl acetate=7:3 to 1:1), and a yellow solid of 6-(1H-1,2,3-benzotriazol-1-yloxy)-2-(3,5-dimethoxyphenylamino)-5-fluoronicotinamide (109 mg) was thus obtained.

¹H-NMR (DMSO-d₆, 400 MHz) δ:11.30 (s, 1H), 8.52 (d, 1H, J=11.0 Hz), 8.30 (brs, 1H), 8.18 (d, 1H, J=8.6 Hz), 7.90-7.76 (m, 2H), 7.66-7.58 (m, 1H), 7.56-7.48 (m, 1H), 5.96-5.91 (m, 1H), 5.88 (d, 2H, J=2.2 Hz), 3.51 (s, 6H)

MS (ESI, m/z): 425 (M+H), 423 (M−H)

3rd Step

Potassium carbonate (27 mg) and tryptamine (32 mg) were added to an N-methylpyrrolidone (1 ml) solution containing 6-(1H-1,2,3-benzotriazol-1-yloxy)-2-(3,5-dimethoxyphenylamino)-5-fluoronicotinamide (41 mg), followed by stirring at 90° C. for 7 hours. The reaction mixture was cooled to room temperature, and potassium carbonate (14 mg) and tryptamine (16 mg) were added, followed by stirring at 90° C. for 7 hours. The reaction mixture was cooled to room temperature, and then water, sodium chloride, and ethyl acetate were added. The organic layer was collected and dried over anhydrous magnesium sulfate, and the solvent was distilled away under reduced pressure. The obtained residue was purified by silica gel chromatography (chloroform:methanol=10:0 to 20:1), diisopropylether was added, solid matter was collected by filtration, and a light brown solid of 2-(3,5-dimethoxyphenylamino)-5-fluoro-6-(2-(1H-indole-3-yl) ethylamino)nicotinamide (19 mg) was thus obtained.

($^1$H-NMR and ESI-MS data are shown in table 10.)

Example 20

The compounds listed in table 10 below were obtained as described in Example 19.

TABLE 10

| Number | Structure |
|---|---|
| Example 20-1 | (structure: 5-fluoro-6-(cyclopropyl(methyl)amino)-2-((3,5-dimethoxyphenyl)amino)nicotinamide) |
| Example 20-2 (Example 19) | (structure: 2-((3,5-dimethoxyphenyl)amino)-5-fluoro-6-((2-(1H-indol-3-yl)ethyl)amino)nicotinamide) |

| Number | Compound name | $^1$H-NMR | MS (ESI, m/z) |
|---|---|---|---|
| Example 20-1 | 6-(cyclopropyl(methyl)amino)-2-((3,5-dimethoxyphenyl)amino)-5-fluoronicotinamide | $^1$H-NMR (DMSO-$d_6$, 400 MHz) δ: 11.5 (s, 1H), 7.92 (d, 1H, J = 14.4 Hz), 7.84 (brs, 1H), 7.29 (brs, 1H), 6.88 (d, 2H, J = 2.2 Hz), 6.09 (t, 1H, J = 2.2 Hz), 3.71 (s, 6H), 3.13 (d, 3H, J = 1.0 Hz), 3.02-2.96 (m, 1H), 0.84-0.76 (m, 2H), 0.70-0.62 (m, 2H). | 359 (M − H) |
| Example 20-2 | 2-((3,5-dimethoxyphenyl)amino)-5-fluoro-6-((2-(1H-indol-3-yl)ethyl)amino)nicotinamide | $^1$H-NMR (DMSO-$d_6$, 400 MHz) δ: 11.71 (s, 1H), 10.85 (s, 1H), 7.92-7.46 (m, 3H), 7.43-7.30 (m, 2H), 7.28-6.91 (m, 4H), 6.87 (d, 2H, J = 2.2 Hz), 6.05 (t, 1H, J = 2.2 Hz), 3.80-3.55 (m, 8H), 3.03 (t, 2H, J = 7.7 Hz). | MS (DART, m/z) 450 (M + H) |

Example 21

[Formula 499]

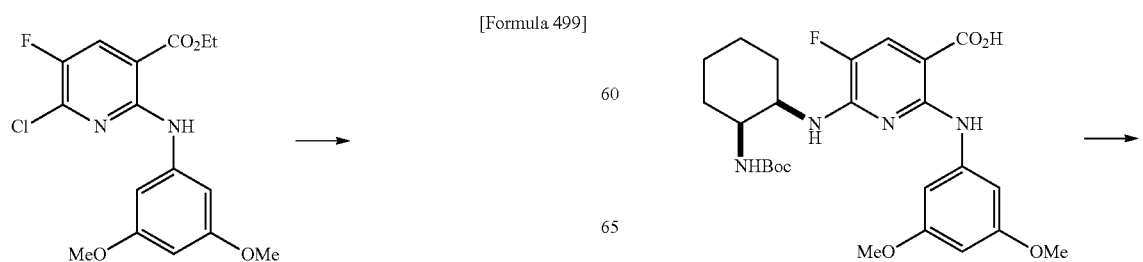

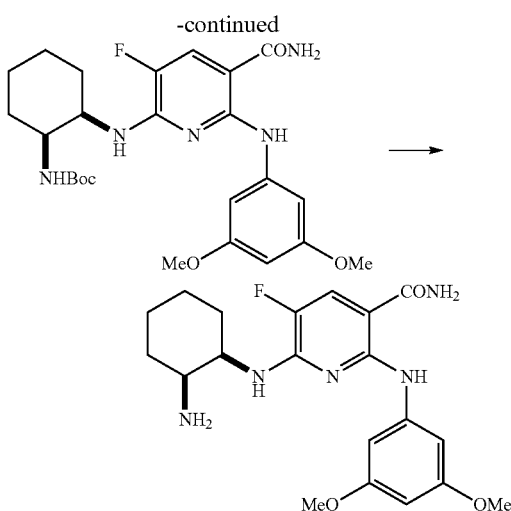

1st Step
The following compound was obtained as described in the 1st step of Example 15.

Ethyl 6-(cis-2-(tert-butoxycarbonylamino)cyclohexylamino)-2-(3,5-dimethoxyphenylamino)-5-fluoronicotinate MS (ESI, m/z): 533 (M+H), 531 (M−H)

2nd, 3rd, and 4th Steps
The following compound was obtained as described in the 2nd and 3rd steps of Example 15 and the 1st step of Example.

6-(cis-2-aminocyclohexylamino)-2-(3,5-dimethoxyphenylamino)-5-fluoronicotinamide ($^1$H-NMR and ESI-MS data are shown in table 11.)

Example 22

The compounds listed in table 11 were obtained as described in Example 21.

TABLE 11

| Number | Structure |
|---|---|
| Example 22-1 HCl salt | 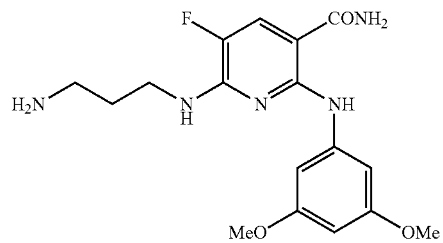 [SMILES: COc1cc(Nc2nc(NCCCN)c(F)cc2C(N)=O)cc(OC)c1] |
| Example 22-2 HCl salt | 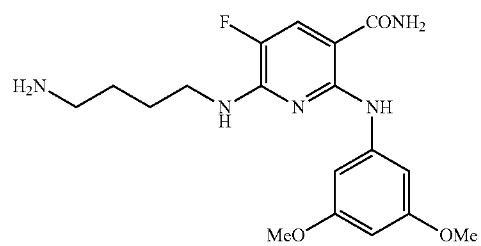 [SMILES: COc1cc(Nc2nc(NCCCCN)c(F)cc2C(N)=O)cc(OC)c1] |
| Example 22-3 (Example 21) HCl salt | 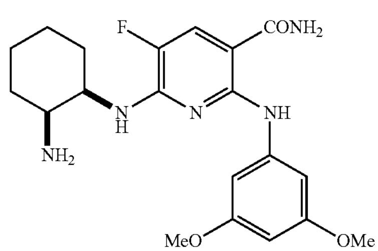 |
| Example 22-4 HCl salt | 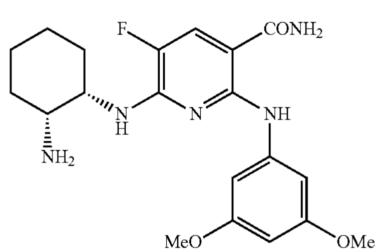 [SMILES: COc1cc(Nc2nc(N[C@H]3CCCC[C@H]3N)c(F)cc2C(N)=O)cc(OC)c1] |

TABLE 11-continued

Example 22-5
HCl salt
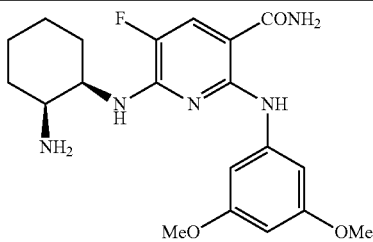

Example 22-6
HCl salt
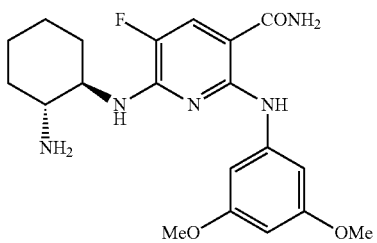 [SMILES: COc1cc(Nc2nc(N[C@@H]3CCCC[C@H]3N)c(F)cc2C(N)=O)cc(OC)c1]

Example 22-7
HCl salt
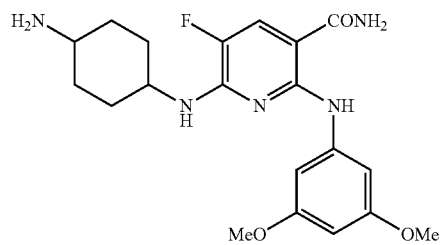 [SMILES: COc1cc(Nc2nc(NC3CCC(N)CC3)c(F)cc2C(N)=O)cc(OC)c1]

Example 22-8
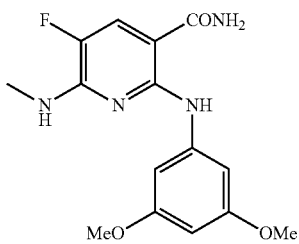 [SMILES: CNc1nc(Nc2cc(OC)cc(OC)c2)c(C(N)=O)cc1F]

| Number | Compound name | $^1$H-NMR | MS (ESI, m/z) |
| --- | --- | --- | --- |
| Example 22-1 HCl salt | 6-((3-aminopropyl)amino)-2-(3,5-dimethoxyphenylamino)-5-fluoronicotinamide | $^1$H-NMR (DMSO-$d_6$, 400 MHz) δ: 11.70 (s, 1H), 7.92-7.60 (m, 3H), 7.85 (d, 1H, J = 12.8 Hz), 7.45-7.37 (m, 1H), 6.85 (s, 2H), 6.10 (s, 1H), 3.72 (s, 6H), 3.51-3.44 (m, 2H), 2.89-2.80 (m, 2H), 1.93-1.82 (m, 2H). | 364 (M + H) |
| Example 22-2 HCl salt | 6-((4-aminobutyl)amino)-2-(3,5-dimethoxyphenylamino)-5-fluoronicotinamide | $^1$H-NMR (DMSO-$d_6$, 400 MHz) δ: 11.71 (s, 1H), 7.84 (d, 1H, J = 12.8 Hz), 7.80-7.64 (m, 3H), 7.37-7.31 (m, 1H), 6.87 (d, 2H, J = 2.3 Hz), 6.10 (t, 1H, J = 2.2 Hz), 3.73 (s, 6H), 3.56-3.42 (m, 2H), 2.84-2.73 (m, 2H), 1.70-1.52 (m, 4H). | 376 (M − H) |
| Example 22-3 HCl salt | 6-(cis-2-aminocyclohexylamino)-2-(3,5-dimethoxyphenylamino)-5-fluoronicotinamide | $^1$H-NMR (DMSO-$d_6$, 400 MHz) δ: 11.58 (s, 1H), 7.90 (d, 1H, J = 12.4 Hz), 7.87-7.76 (m, 3H), 7.32-7.16 (m, 1H), 6.89-6.83 (m, 1H), 6.75 (d, 2H, J = 2.1 Hz), 6.13 (t, 1H, J = 2.1 Hz), 4.29-4.20 (m, 1H), 3.72 (s, 6H), 3.68-3.60 (m, 1H), 1.93-1.30 (m, 8H). | 404 (M + H) |
| Example 22-4 HCl salt | 6-(((1S,2R)-2-aminocyclohexyl)amino)-2-(3,5-dimethoxyphenylamino)-5-fluoronicotinamide | $^1$H-NMR (DMSO-$d_6$) 400 MHz) δ: 11.59 (s, 1H), 7.91 (d, 1H, J = 12.6 Hz), 7.84-7.70 (m, 3H), 7.32-7.19 (m, 1H), 6.88-6.83 (m, 1H), 6.76 (d, 2H, J = 2.2 Hz), 6.14 (t, 1H, J = 2.2 Hz), 4.30-4.20 (m, 1H), 3.73 (s, 6H), 3.68-3.60 (m, 1H), 1.92-1.33 (m, 8H). | 404 (M + H) |
| Example 22-5 HCl salt | 6-((1R,2S)-2-aminocyclohexyl-amino)-2-(3,5-dimethoxyphenyl-amino)-5-fluoronicotinamide | $^1$H-NMR (DMSO-$d_6$, 400 MHz) δ: 11.59 (s, 1H), 7.91 (d, 1H, J = 12.6 Hz), 7.82-7.68 (m, 3H), 7.31-7.19 (m, 1H), 6.88-6.82 (m, 1H), 6.76 (d, 2H, J = 2.2 Hz), 6.14 (t, 1H, J = 2.2 Hz), 4.30-4.21 (m, 1H), 3.73 (s, 6H), 3.68-3.62 (m, 1H), 1.92-1.34 (m, 8H). | 402 (M − H) |

TABLE 11-continued

| Example 22-6 HCl salt | 6-(((1R,2R)-2-aminocyclohexyl)amino)-2-(3,5-dimethoxyphenylamino)-5-fluoronicotinamide | ¹H-NMR (DMSO-d₆, 400 MHz) δ: 11.61 (s, 1H), 7.95-7.85 (m, 3H), 7.89 (d, 1H, J = 12.4 Hz), 7.21-7.14 (m, 1H), 6.79 (d, 2H, J = 2.2 Hz), 6.14 (t, 1H, J = 2.1 Hz), 4.07-3.96 (m, 1H), 3.74 (s, 6H), 3.30-3.18 (m, 1H), 2.15-2.03 (m, 2H), 1.81-1.65 (m, 2H), 1.51-1.19 (m, 4H). | 404 (M + H) |
| --- | --- | --- | --- |
| Example 22-7 HCl salt | 6-((4-aminocyclohexyl)amino)-2-(3,5-dimethoxyphenylamino)-5-fluoronicotinamide | ¹H-NMR (DMSO-d₆, 400 MHz) δ: 11.65 (s, 1H), 7.87 (d, 1H, J = 12.7 Hz), 7.87-7.81 (m, 3H), 6.81 (d, 2H, J = 2.3 Hz), 6.76-6.72 (m, 1H), 6.11 (t, 1H, J = 2.3 Hz), 4.07-4.00 (m, 1H), 3.72 (s, 6H), 3.26-3.16 (m, 1H), 2.00-1.89 (m, 2H), 1.80-1.68 (m, 6H). | 404 (M + H) |
| Example 22-8 | 2-((3,5-dimethoxyphenyl)amino)-5-fluoro-6-(methylamino)nicotinamide | ¹H-NMR (DMSO-d₆, 400 MHz) δ: 11.72 (s, 1H), 7.82 (d, 1H, J = 12.7 Hz), 7.31-7.25 (m, 1H), 6.93 (d, 2H, J = 2.2 Hz), 6.08 (t, 1H, J = 2.2 Hz), 3.72 (s, 6H), 2.95 (d, 3H, J = 4.5 Hz). | 321 (M + H) |

Example 23

[Formula 500]

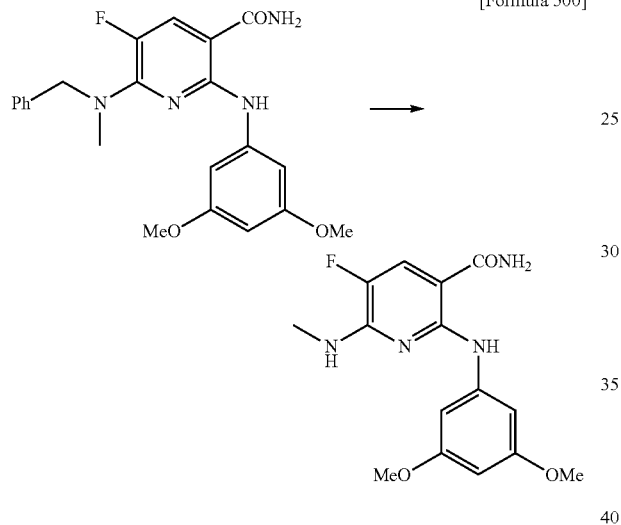

The following compound was obtained as described in Reference Example 9.

2-(3,5-dimethoxyphenylamino)-5-fluoro-6-(methylamino)nicotinamide

¹H-NMR (DMSO-d₆, 400 MHz) δ:11.72 (s, 1H), 7.82 (d, 1H, J=12.7 Hz), 7.31-7.25 (m, 1H), 6.93 (t, 2H, J=2.2 Hz), 6.08 (t, 1H, J=2.2 Hz), 3.72 (s, 6H), 2.95 (d, 3H, J=4.5 Hz)

MS (ESI, m/z): 321 (M+H)

Example 24

[Formula 501]

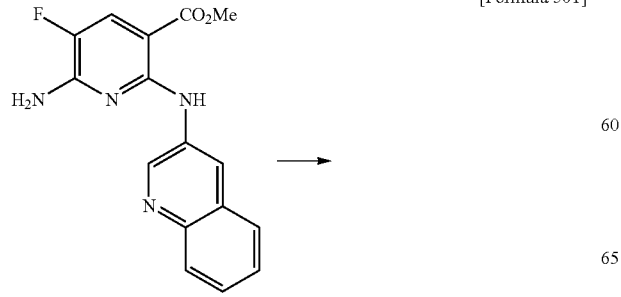

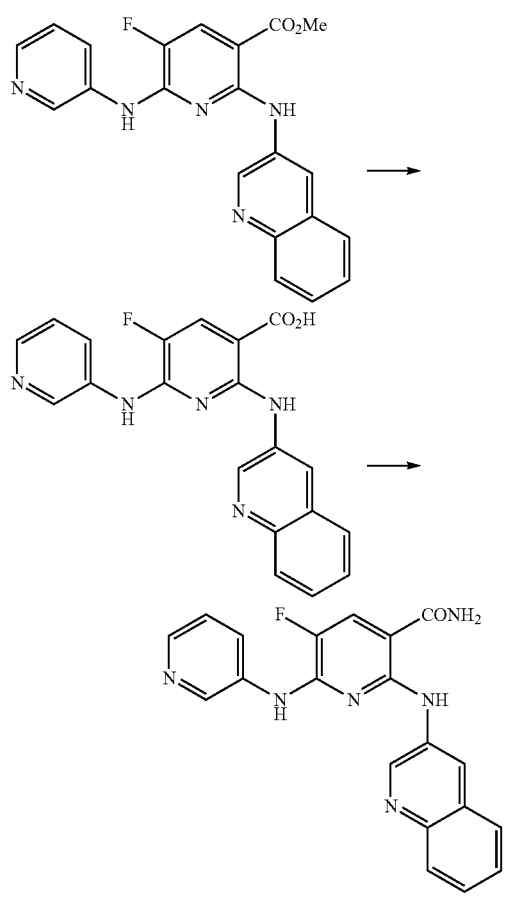

The following compound was obtained as described in the 1st step of Example 1

Methyl 5-fluoro-6-(pyridin-3-ylamino)-2-(quinolin-3-ylamino)nicotinate

The following compound was obtained as described in the 1st and 2nd steps of Reference Example 27 or the 3rd and 4th steps of Example 7.

5-fluoro-6-(pyridin-3-ylamino)-2-(quinolin-3-ylamino)nicotinamide ($^{1}$H-NMR and ESI-MS data are shown in table 12.)

Example 25

The compounds listed in table 12 were obtained as described in Example 24.

TABLE 12

| Number | Structure |
|---|---|
| Example 25-1 | 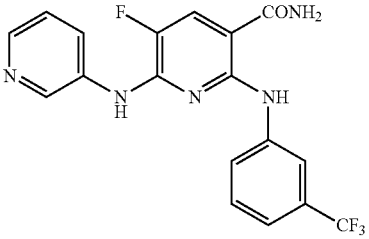 [SMILES: NC(=O)c1cc(F)c(Nc2cccnc2)nc1Nc1cccc(C(F)(F)F)c1] |
| Example 25-2 (Example 24) | 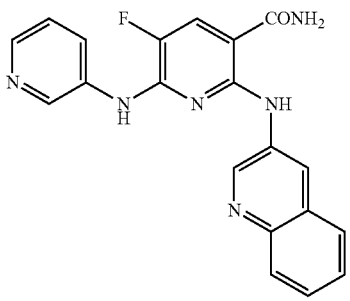 [SMILES: NC(=O)c1cc(F)c(Nc2cccnc2)nc1Nc1cnc2ccccc2c1] |

| Number | Compound name | $^{1}$H-NMR | MS (ESI, m/z) |
|---|---|---|---|
| Example 25-1 | 5-fluoro-6-(pyridin-3-ylamino)-2-((3-(trifluoromethyl)phenyl)-amino)nicotinamide | $^{1}$H-NMR (DMSO-d$_{6}$, 400 MHz) δ: 11.71 (s, 1H), 9.43 (s, 1H), 8.71 (d, 1H, J = 2.6 Hz), 8.24-8.20 (m, 1H), 8.10 (d, 1H, J = 12.3 Hz), 8.04-7.90 (m, 2H), 7.79 (s, 1H), 7.65 (d, 1H, J = 7.9 Hz), 7.54-7.40 (m, 1H), 7.40 (t, 1H, J = 8.0 Hz), 7.27-7.18 (m, 2H). | 392 (M + H) |
| Example 25-2 | 5-fluoro-6-(pyridin-3-ylamino)-2-(quinolin-3-ylamino)-nicotinamide | $^{1}$H-NMR (DMSO-d$_{6}$, 400 MHz) δ: 12.01 (s, 1H), 9.54-9.50 (m, 1H), 8.84 (d, 1H, J = 2.7 Hz), 8.71 (d, 1H, J = 2.7 Hz), 8.57 (d, 1H, J = 2.3 Hz), 8.38-8.34 (m, 1H), 8.17 (d, 1H, J = 12.1 Hz), 8.05-7.98 (m, 2H), 7.93-7.88 (m, 1H), 7.58-7.47 (m, 4H), 7.28 (dd, 1H, J = 4.6 Hz, 8.2 Hz). | 375 (M + H) |

Example 26

[Formula 502]

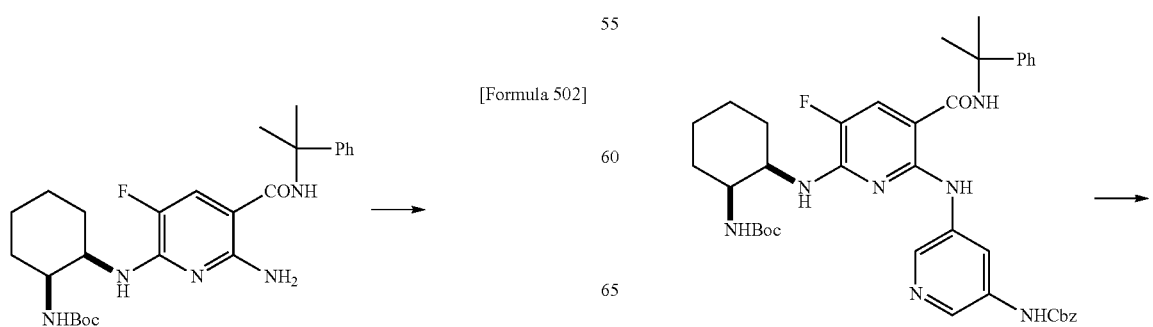

1st Step

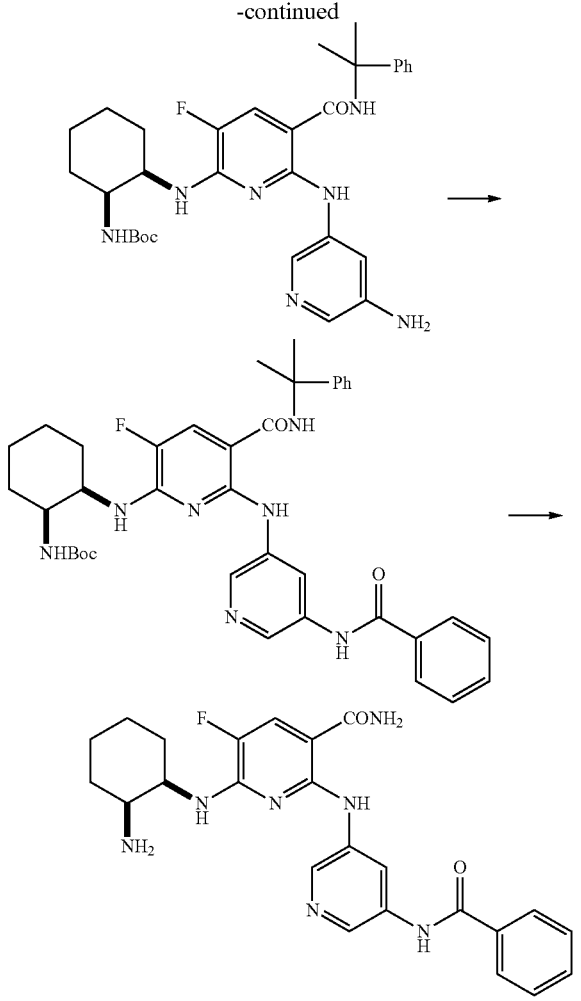

The following compound was obtained as described in the 1st step of Example 3.

Benzyl(5-(6-(cis-2-(tert-butoxycarbonylamino)cyclo-hexylamino)-5-fluoro-3-(2-phenylpropan-2-ylami-nocarbonyl)pyridin-2-ylamino)pyridin-3-yl)carbamate $^1$H-NMR (DMSO-d$_6$, 400 MHz) δ:11.18 (s, 1H), 9.88 (s, 1H), 8.39 (d, 1H, J=2.1 Hz), 8.20-8.08 (m, 4H), 7.44-7.25 (m, 9H), 7.19-7.14 (m, 1H), 6.69-6.61 (m, 2H), 5.16 (s, 2H), 4.16-4.08 (m, 1H), 3.92-3.84 (m, 1H), 1.80-1.10 (m, 23H)
MS (ESI, m/z): 712 (M+H), 710 (M−H)

2nd Step

The following compound was obtained as described in the 2nd step of Reference Example 53.

tert-Butyl cis-2-(6-(5-aminopyridin-3-ylamino)-3-fluoro-5-(2-phenylpropan-2-ylaminocarbonyl)pyridin-2-ylamino)cyclohexylcarbamate $^1$H-NMR (DMSO-d$_6$, 400 MHz) δ:10.99 (s, 1H), 8.16-8.04 (m, 3H), 7.51 (d, 1H, J=2.3 Hz), 7.39-7.34 (m, 2H), 7.32-7.25 (m, 2H), 7.19-7.13 (m, 1H), 7.04 (s, 1H), 6.72-6.65 (m, 1H), 6.59-6.53 (m, 1H), 4.16-4.06 (m, 1H), 3.96-3.87 (m, 1H), 1.84-1.11 (m, 23H)
MS (ESI, m/z): 578 (M+H), 576 (M−H)

3rd and 4th Steps

The following compound was obtained as described in the 2nd step of Reference Example 3 and the 2nd step of Example 1.

6-(cis-2-aminocyclohexylamino)-2-(5-benzoylami-nopyridin-3-ylamino)-5-fluoronicotinamide ($^1$H-NMR data and MS data are shown in table 13.)

Example 27

The compounds listed in table 13 were obtained as described in Example 26.

TABLE 13

| Number | Structure |
|---|---|
| Example 27-1 HCl salt | 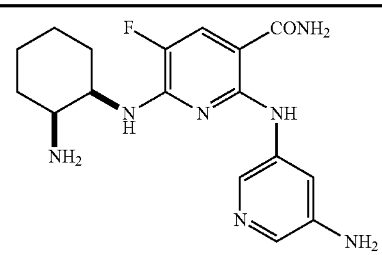 |
| Example 27-2 HCl salt | 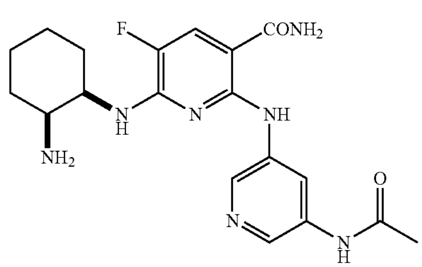 |

TABLE 13-continued
| | | |
|---|---|---|
| Example 27-3 (Example 26) HCl salt | 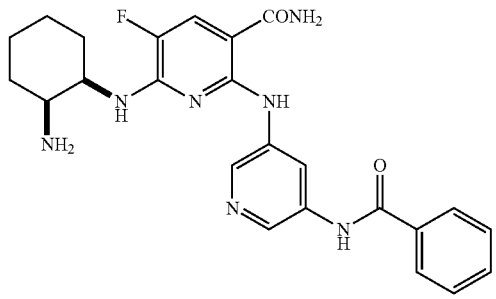 | |
| Example 27-4 HCl salt | 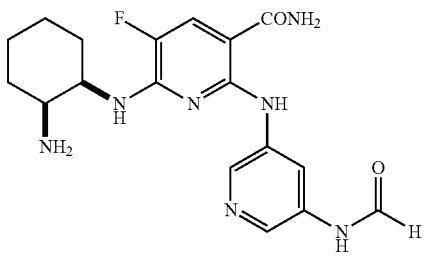 | |
| Example 27-5 HCl salt | 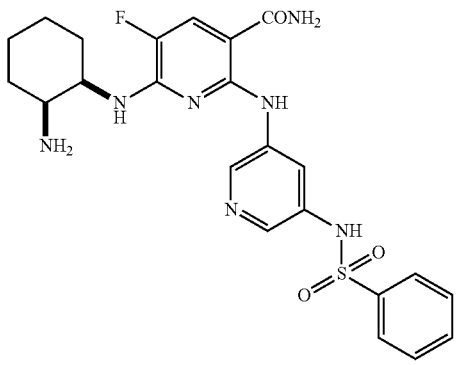 | |
| Example 27-6 HCl salt | 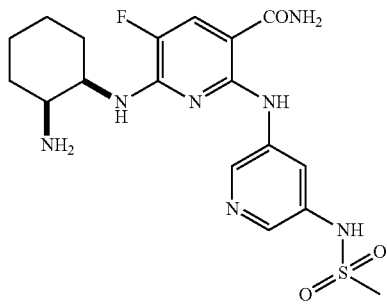 | |
| Number | Structure | Compound name |
|---|---|---|
| Example 27-7 | 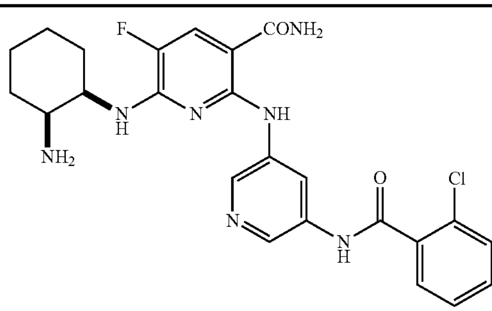 | 6-(cis-2-aminocyclohexylamino)-2-((5-(2-chlorobenzamide)pyridin-3-yl)amino)-5-fluoronicotinamide |

TABLE 13-continued

| | | |
|---|---|---|
| Example 27-8 | 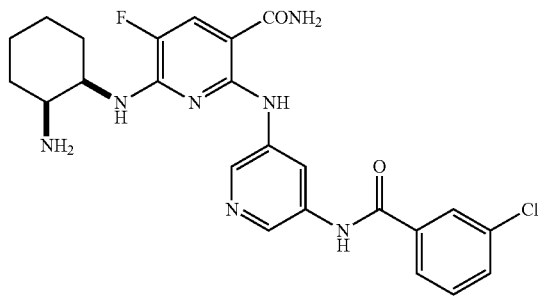 | 6-(cis-2-aminocyclohexylamino)-2-((5-(3-chlorobenzamide)pyridin-3-yl)amino)-5-fluoronicotinamide |
| Example 27-9 | 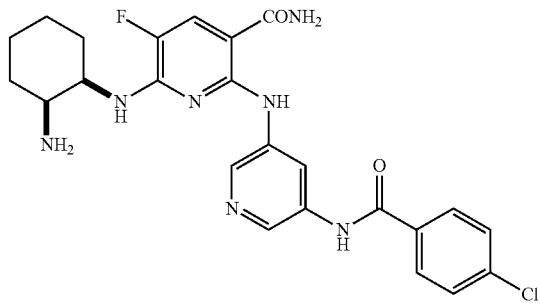 | 6-(cis-2-aminocyclohexylamino)-2-((5-(4-chlorobenzamide)pyridin-3-yl)amino)-5-fluoronicotinamide |
| Example 27-10 | 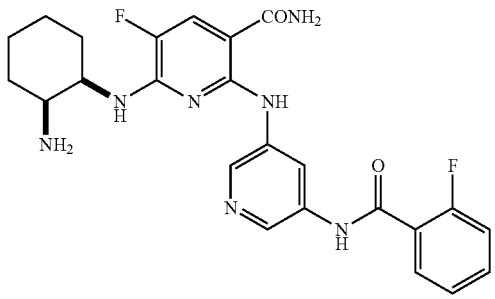 | 6-(cis-2-aminocyclohexylamino)-5-fluoro-2-((5-(2-fluorobenzamide)pyridin-3-yl)amino)-nicotinamide |
| Example 27-11 | 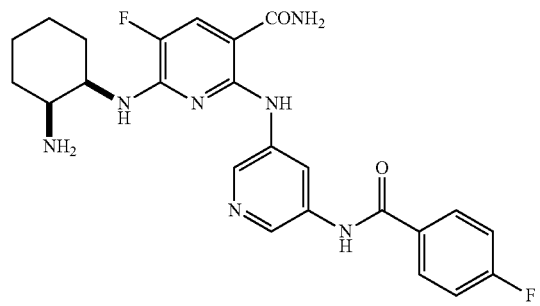 | 6-(cis-2-aminocyclohexylamino)-5-fluoro-2-((5-(4-fluorobenzamide)pyridin-3-yl)amino)-nicotinamide |
| Example 27-12 | 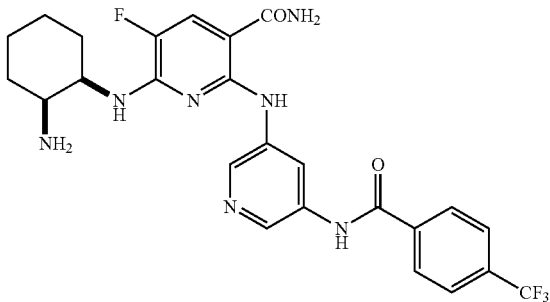 | 6-(cis-2-aminocyclohexylamino)-5-fluoro-2-((5-(4-(trifluoromethyl)benzamide)pyridin-3-yl)-amino)nicotinamide |

TABLE 13-continued

| | | |
|---|---|---|
| Example 27-13 | 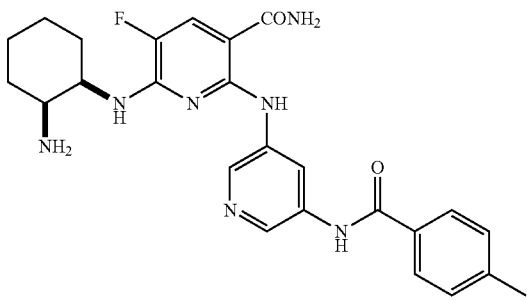 | 6-(cis-2-aminocyclohexylamino)-5-fluoro-2-((5-(4-methylbenzamide)pyridin-3-yl)amino)-nicotinamide |
| Example 27-14 | 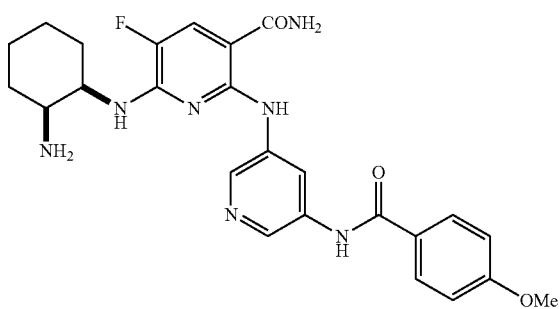 | 6-(cis-2-aminocyclohexylamino)-5-fluoro-2-((5-(4-methoxybenzamide)pyridin-3-yl)amino)-nicotinamide |
| Example 27-15 | 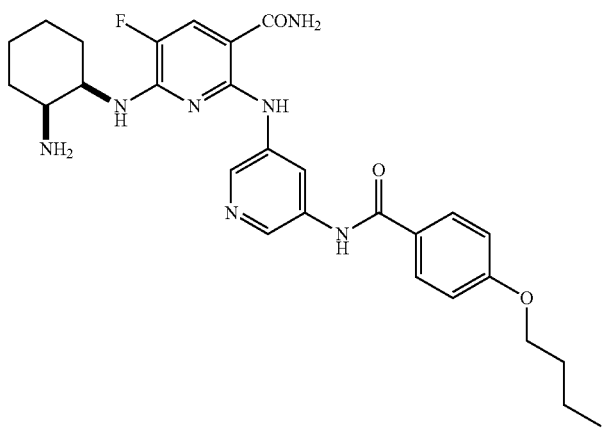 | 6-(cis-2-aminocyclohexylamino)-2-((5-(4-butoxybenzamide)pyridin-3-yl)amino)-5-fluoronicotinamide |
| Example 27-16 | 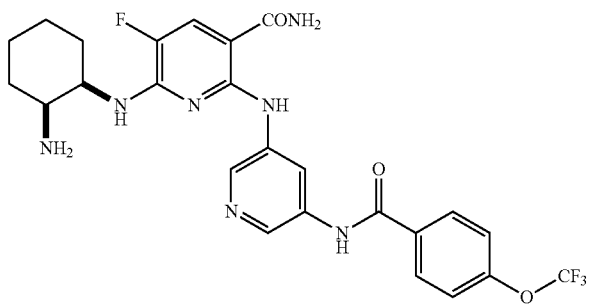 | 6-(cis-2-aminocyclohexylamino)-5-fluoro-2-((5-(4-trifluoromethoxybenzamide)pyridin-3-yl)amino)nicotinamide |

TABLE 13-continued

| | | |
|---|---|---|
| Example 27-17 | 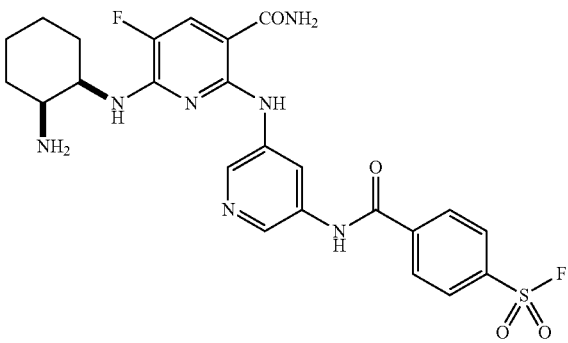 | 4-((5-(6-(cis-2-aminocyclohexylamino)-3-carbamoyl-5-fluoropyridin-2-yl)aminopyridin-3-yl)carbamoyl)benzene-1-sulfonyl fluoride |
| Example 27-18 | 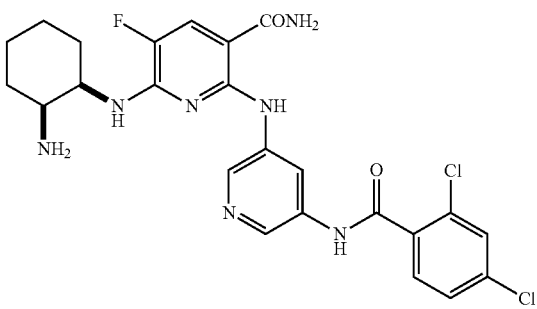 | 6-(cis-2-aminocyclohexylamino)-2-((5-(2,4-dichlorobenzamide)pyridin-3-yl)amino)-5-fluoronicotinamide |
| Example 27-19 | 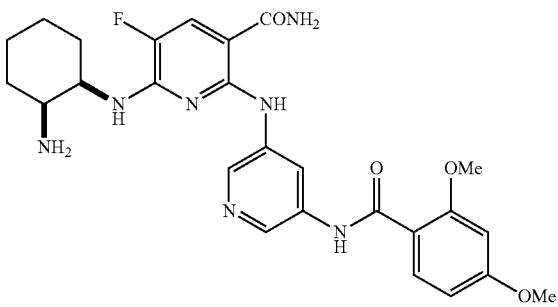 | 6-(cis-2-aminocyclohexylamino)-2-((5-(2,4-dimethoxybenzamide)pyridin-3-yl)amino)-5-fluoronicotinamide |
| Example 27-20 | 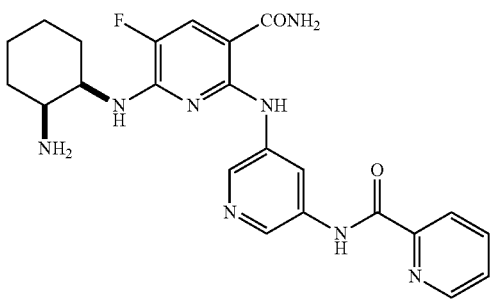 | N-(5-(6-(cis-2-aminocyclohexylamino)-3-carbamoyl-5-fluoropyridin-2-yl)aminopyridin-3-yl)picolinamide |
| Example 27-21 | 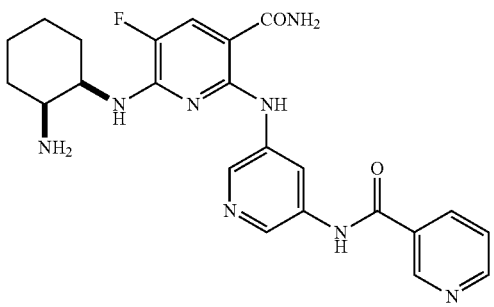 | 6-(cis-2-aminocyclohexylamino)-5-fluoro-2-((5-(nicotinamide)pyridin-3-yl)amino)-nicotinamide |

TABLE 13-continued

| Example 27-22 | 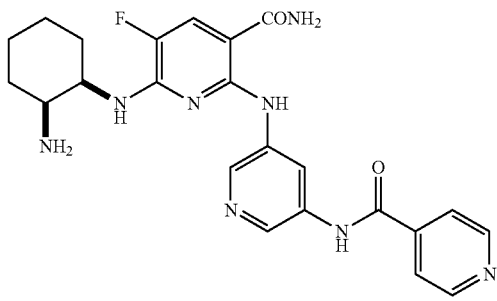 | 6-(cis-2-aminocyclohexylamino)-5-fluoro-2-((5-(isonicotinamide)pyridin-3-yl)amino)-nicotinamide |
| Example 27-23 | 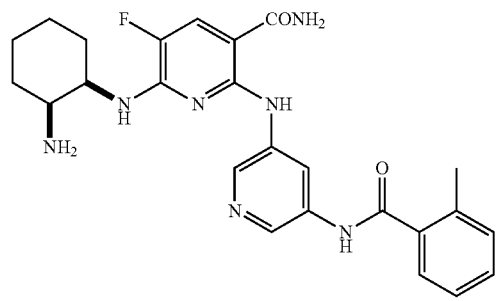 | 6-(cis-2-aminocyclohexylamino)-5-fluoro-2-((5-(2-methylbenzamide)pyridin-3-yl)amino)-nicotinamide |
| Example 27-24 | 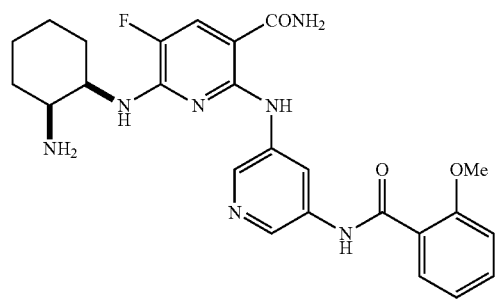 | 6-(cis-2-aminocyclohexylamino)-5-fluoro-2-((5-(2-methoxybenzamide)pyridin-3-yl)amino)-nicotinamide |
| Example 27-25 | 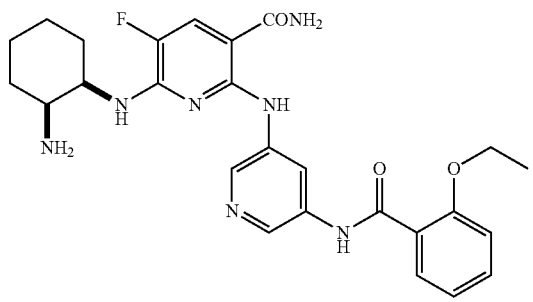 | 6-(cis-2-aminocyclohexylamino)-2-((5-(2-ethoxybenzamide)pyridin-3-yl)amino)-5-fluoronicotinamide |
| Example 27-26 | 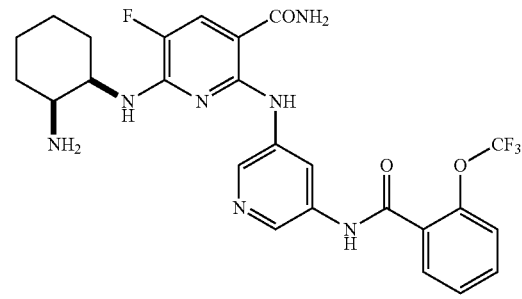 | 6-(cis-2-aminocyclohexylamino)-5-fluoro-2-((5-(2-(trifluoromethoxy)benzamide)pyridin-3-yl)amino)nicotinamide |

TABLE 13-continued

Example 27-27 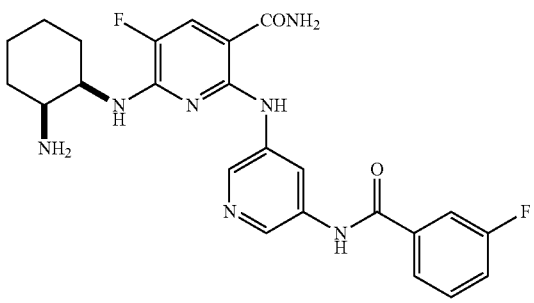 6-(cis-2-aminocyclohexylamino)-5-fluoro-2-((5-(3-fluorobenzamide)pyridin-3-yl)amino)-nicotinamide Example 27-28 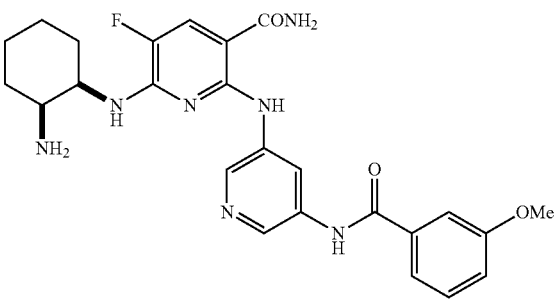 6-(cis-2-aminocyclohexylamino)-5-fluoro-2-((5-(3-methoxybenzamide)pyridin-3-yl)amino)-nicotinamide Example 27-29 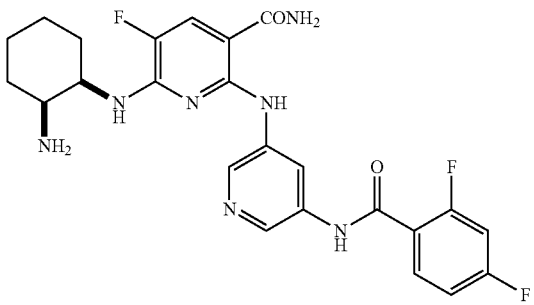 6-(cis-2-aminocyclohexylamino)-2-((5-(2,4-difluorobenzamide)pyridin-3-yl)amino)-5-fluoronicotinamide Example 27-30 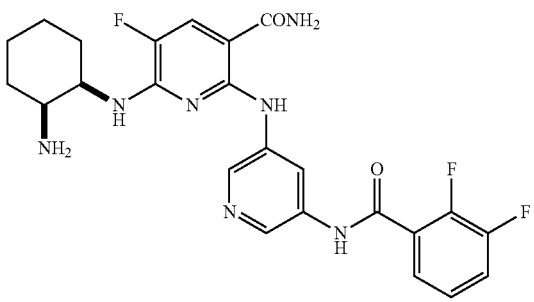 6-(cis-2-aminocyclohexylamino)-2-((5-(2,3-difluorobenzamide)pyridin-3-yl)amino)-5-fluoronicotinamide Example 27-31 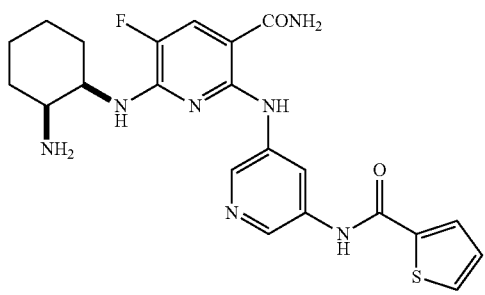 6-(cis-2-aminocyclohexylamino)-5-fluoro-2-((5-(thiophene-2-carboxamide)pyridin-3-yl)-amino)nicotinamide TABLE 13-continued

| Example 27-32 | 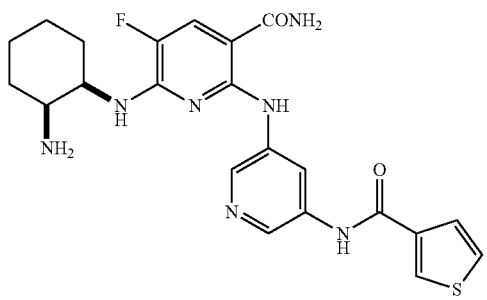 | 6-(cis-2-aminocyclohexylamino)-5-fluoro-2-((5-(thiophene-3-carboxamide)pyridin-3-yl)-amino)nicotinamide |
| --- | --- | --- |
| Example 27-33 | 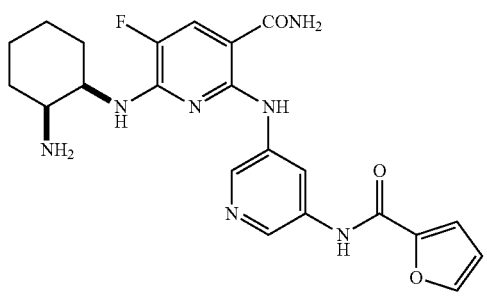 | 6-(cis-2-aminocyclohexylamino)-5-fluoro-2-((5-(furan-2-carboxamide)pyridin-3-yl)-amino)nicotinamide |
| Example 27-34 | 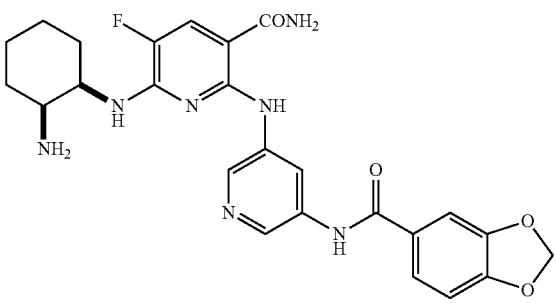 | 6-(cis-2-aminocyclohexylamino)-2-((5-(1,3-benzodioxole-5-carboxamide)pyridin-3-yl)-amino)-5-fluoronicotinamide |
| Example 27-35 | 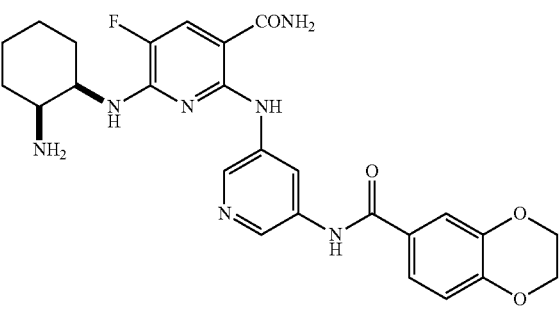 | 6-(cis-2-aminocyclohexylamino)-2-((5-(2,3-dihydro-1,4-benzodioxin-6-carboxamide)pyridin-3-yl)amino)-5-fluoronicotinamide |
| Example 27-36 | 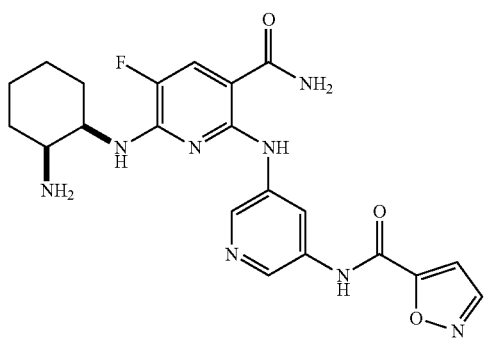 | N-(5-(6-(cis-2-aminocyclohexylamino)-3-carbamoyl-5-fluoropyridin-2-yl)aminopyridin-3-yl)isoxazole-5-carboxamide |

TABLE 13-continued

Example 27-37
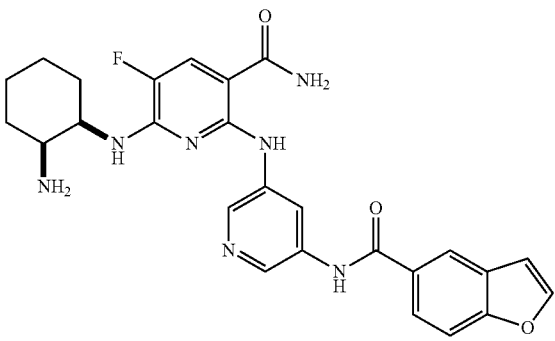
6-(cis-2-aminocyclohexylamino)-2-((5-(benzofuran-5-carboxamide)pyridin-3-yl)-amino)-5-fluoronicotinamide Example 27-38
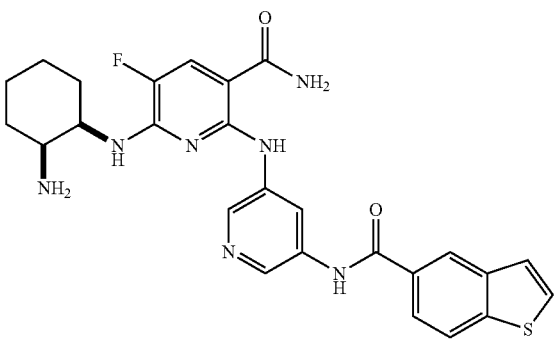
6-(cis-2-aminocyclohexylamino)-2-((5-(benzo[b]thiophene-5-carboxamide)pyridin-3-yl)amino)-5-fluoronicotinamide Example 27-39
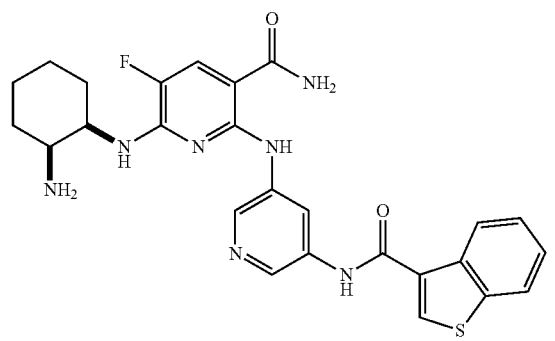
6-(cis-2-aminocyclohexylamino)-2-((5-(benzo[b]thiophene-3-carboxamide)pyridin-3-yl)amino)-5-fluoronicotinamide Example 27-40
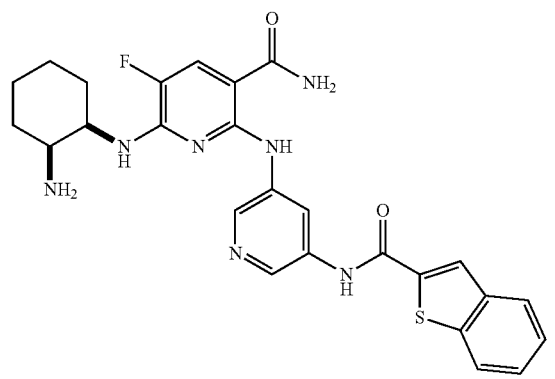
6-(cis-2-aminocyclohexylamino)-2-((5-(benzo[b]thiophene-2-carboxamide)pyridin-3-yl)amino)-5-fluoronicotinamide TABLE 13-continued

| Example 27-41 | | 6-(cis-2-aminocyclohexylamino)-2-((5-(benzofuran-2-carboxamide)pyridin-3-yl)-amino)-5-fluoronicotinamide |
| Example 27-42 | | N-(5-(6-(cis-2-aminocyclohexylamino)-3-carbamoyl-5-fluoropyridin-2-yl)aminopyridin-3-yl)-1-methyl-1H-benzo[d][1,2,3]triazol-5-carboxamide |

| Number | Compound name | $^1$H-NMR | MS (ESI, m/z) |
| --- | --- | --- | --- |
| Example 27-1 HCl salt | 6-(cis-2-aminocyclohexylamino)-2-((5-aminopyridin-3-yl)amino)-5-fluoronicotinamide | $^1$H-NMR (DMSO-d$_6$, 400 MHz) δ: 12.01 (s, 1H), 8.49 (s, 1H), 8.03-7.91 (m, 5H), 7.65 (d, 1H, J = 2.1 Hz), 7.57-7.53 (m, 1H), 7.52-7.46 (m, 1H), 7.08-7.03 (m, 1H), 6.46-6.33 (m, 1H), 4.34-4.25 (m, 1H), 3.63-3.53 (m, 1H), 1.93-1.36 (m, 8H). | 360 (M + H) |
| Example 27-2 HCl salt | 2-((5-acetylaminopyridin-3-yl)-amino)-6-(cis-2-aminocyclohexyl-amino)-5-fluoronicotinamide | $^1$H-NMR (DMSO-d$_6$, 400 MHz) δ: 11.98 (s, 1H), 10.73 (s, 1H), 8.73 (s, 1H), 8.58 (s, 1H), 8.48 (s, 1H), 7.99 (d, 1H, J = 12.2 Hz), 7.97-7.83 (m, 4H), 7.46 (brs, 1H), 7.06-7.00 (m, 1H), 4.40-4.30 (m, 1H), 3.63-3.53 (m, 1H), 2.13 (s, 3H), 1.90-1.34 (m, 8H). | 402 (M + H), 400 (M − H) |
| Example 27-3 HCl salt | 6-(cis-2-aminocyclohexylamino)-2-((5-benzoylaminopyridin-3-yl)-amino)-5-fluoronicotinamide | $^1$H-NMR (DMSO-d$_6$, 400 MHz) δ: 12.09 (s, 1H), 10.86 (s, 1H), 8.84 (s, 1H), 8.78 (s, 1H), 8.71 (s, 1H), 8.07-7.85 (m, 7H), 7.69-7.63 (m, 1H), 7.62-7.55 (m, 2H), 7.48 (brs, 1H), 7.07 (d, 1H, J = 5.4 Hz), 4.42-4.33 (m, 1H), 3.62-3.54 (m, 1H), 1.87-1.14 (m, 8H). | 464 (M + H), 462 (M − H) |
| Example 27-4 HCl salt | 6-(cis-2-aminocyclohexylamino)-5-fluoro-2-((5-formylamino-pyridin-3-yl)amino)nicotinamide | $^1$H-NMR (DMSO-d$_6$, 400 MHz) δ: 11.99 (s, 1H), 10.95 (s, 1H), 8.79 (s, 1H), 8.54-8.48 (m, 2H), 8.43 (d, 1H, J = 1.6 Hz), 8.06-7.91 (m, 5H), 7.52-7.40 (m, 1H), 7.04-6.98 (m, 1H), 4.41-4.32 (m, 1H), 3.62-3.53 (m, 1H), 1.92-1.36 (m, 8H). | 388 (M + H), 386 (M − H) |
| Example 27-5 HCl salt | 6-(cis-2-aminocyclohexylamino)-5-fluoro-2-((5-(phenylsulfonyl-amino)pyridin-3-yl)amino)-nicotinamide | $^1$H-NMR (DMSO-d$_6$, 400 MHz) δ: 11.84 (s, 1H), 10.76-10.67 (br, 1H), 8.60-8.55 (m, 1H), 8.03-7.75 (m, 9H), 7.68-7.62 (m, 1H), 7.62-7.54 (m, 2H), 7.50-7.32 (br, 1H), 7.02 (d, 1H, J = 6.1 Hz), 4.37-4.27 (m, 1H), 3.67-3.60 (m, 1H), 1.94-1.38 (m, 8H). $^1$H-NMR (DMSO-d$_6$ + D$_2$O, 400 MHz) δ: 8.49 (d, 1H, J = 2.2 Hz), 8.13-8.09 (m, 1H), 7.93 (d, 1H, J = 12.2 Hz), 7.78-7.74 (m, 3H), 7.70-7.63 (m, 1H), 7.62-7.55 (m, 1H), 4.42-4.28 (m, 1H), 3.67-3.60 (m, 1H), 1.90-1.43 (m, 8H). | 500 (M + H) |

TABLE 13-continued

| Example 27-6 HCl salt | 6-(cis-2-aminocyclohexylamino)-5-fluoro-2-((5-(methylsulfonyl-amino)pyridin-3-yl)amino)-nicotinamide | $^1$H-NMR (DMSO-$d_6$, 400 MHz) δ: 11.91 (s, 1H), 10.30-10.20 (br, 1H), 8.77-8.72 (m, 1H), 8.08 (d, 1H, J = 2.2 Hz), 8.04-8.01 (m, 1H), 7.98 (d, 1H, J = 12.4 Hz), 7.95-7.82 (m, 4H), 7.50-7.34 (br, 1H), 7.02 (d, 1H, J = 6.4 Hz), 4.37-4.27 (m, 1H), 3.65-3.58 (m, 1H), 3.11 (s, 3H), 1.92-1.38 (m, 8H). $^1$H-NMR (DMSO-$d_6$ + $D_2O$, 400 MHz) δ: 8.65 (d, 1H, J = 2.3 Hz), 8.11 (dd, 1H, J = 2.2, 2.3 Hz), 8.06 (d, 1H, J = 2.2 Hz), 7.95 (d, 1H, J = 12.2 Hz), 4.35-4.28 (m, 1H), 3.65-3.58 (m, 1H), 3.08 (s, 3H), 1.90-142 (m, 8H). | 438 (M + H) |

| Number | Salt | Solvent | NMR | 1HNMR | Mass (M + H) | Mass (M − H) | rt (min) |
|---|---|---|---|---|---|---|---|
| Example 27-7 | HCl | DMSO-d6 | 300 MHz | δ: 11.88 (s, 1H), 10.91 (s, 1H), 8.70-8.66 (m, 1H), 8.65-8.61 (m, 1H), 8.46-8.43 (m, 1H), 7.98 (d, 1H, J = 12.2 Hz), 7.88-7.70 (m, 4H), 7.65-7.30 (m, 5H), 7.01-6.93 (m, 1H), 4.45-4.34 (m, 1H), 3.66-3.56 (m, 1H), 1.93-1.30 (m, 8H). | 499 | 497 | 0.88 |
| Example 27-8 | HCl | DMSO-d6 | 300 MHz | δ: 11.90 (s, 1H), 10.69 (s, 1H), 8.72-8.68 (m, 1H), 8.71 (s, 1H), 8.54 (s, 1H), 8.08-8.03 (m, 1H), 8.02-7.85 (m, 3H), 7.80-7.68 (m, 4H), 7.65-7.58 (m, 1H), 7.50-7.30 (m, 1H), 7.05-6.97 (m, 1H), 4.42-4.29 (m, 1H), 3.66-3.56 (m, 1H), 1.85-1.12 (m, 8H). | 499 | 497 | 0.94 |
| Example 27-9 | HCl | DMSO-d6 | 300 MHz | δ: 11.92 (s, 1H), 10.70 (s, 1H), 8.73 (s, 1H), 8.64-8.59 (m, 1H), 8.57-8.52 (m, 1H), 8.04 (d, 2H, J = 8.6 Hz), 8.00-7.83 (m, 1H), 7.98 (d, 1H, J = 12.6 Hz), 7.83-7.79 (m, 3H), 7.66 (d, 2H, J = 8.6 Hz), 7.48-7.39 (m, 1H), 7.05-6.98 (m, 1H), 4.40-4.29 (m, 1H), 3.65-3.55 (m, 1H), 1.87-1.12 (m, 8H). | 499 | 497 | 0.95 |
| Example 27-10 | HCl | DMSO-d6 | 300 MHz | δ: 11.90 (s, 1H), 10.81 (s, 1H), 8.76-8.72 (m, 1H), 8.60 (s, 1H), 8.45 (s, 1H), 7.98 (d, 1H, J = 12.2 Hz), 7.95-7.58 (m, 6H), 7.45-7.33 (m, 3H), 7.00 (d, 1H, J = 6.3 Hz), 4.42-4.30 (m, 1H), 3.65-3.55 (m, 1H), 1.88-1.22 (m, 8H). | 483 | 481 | 0.83 |
| Example 27-11 | HCl | DMSO-d6 | 300 MHz | δ: 12.01 (s, 1H), 10.78 (s, 1H), 8.79-8.76 (m, 1H), 8.71 (s, 1H), 8.62 (s, 1H), 8.16-8.07 (m, 2H), 8.00 (d, 1H, J = 12.2 Hz), 7.98-7.76 (m, 4H), 7.48-7.38 (m, 3H), 7.04 (d, 1H, J = 6.3 Hz), 4.42-4.32 (m, 1H), 3.65-3.55 (m, 1H), 1.88-1.13 (m, 8H). | 483 | 481 | 0.87 |
| Example 27-12 | HCl | DMSO-d6 | 300 MHz | δ: 11.93 (s, 1H), 10.88 (s, 1H), 8.75-8.71 (m, 1H), 8.65 (s, 1H), 8.58-8.55 (m, 1H), 8.21 (d, 2H, J = 8.3 Hz), 8.02-7.60 (m, 4H), 7.98 (d, 1H, J = 12.6 Hz), 7.97 (d, 2H, J = 8.3 Hz), 7.53-7.33 (m, 1H), 7.01 (d, 1H, J = 5.6 Hz), 4.42-4.29 (m, 1H), 3.66-3.55 (m, 1H), 1.92-1.13 (m, 8H). | 533 | 531 | 1.03 |
| Example 27-13 | HCl | DMSO-d6 | 300 MHz | δ: 12.04 (s, 1H), 10.70 (s, 1H), 8.81 (s, 1H), 8.72 (s, 1H), 8.67 (s, 1H), 8.00 (d, 1H, J = 12.6 Hz), 8.00-7.90 (m, 1H), 7.95 (d, 2H, J = 7.9 Hz), 7.89-7.80 (m, 3H), 7.52-7.42 (m, 1H), 7.39 (d, 2H, J = 7.9 Hz), 7.05 (d, 1H, J = 6.3 Hz), 4.43-4.31 (m, 1H), 3.65-3.55 (m, 1H), 2.41 (s, 3H), 1.90-1.15 (m, 8H). | 479 | 477 | 0.92 |
| Example 27-14 | HCl | DMSO-d6 | 300 MHz | δ: 12.06 (s, 1H), 10.65 (s, 1H), 8.84-8.79 (m, 1H), 8.73 (s, 1H), 8.68 (s, 1H), 8.04 (d, 2H, J = 8.9 Hz), 8.00 (d, 1H, J = 12.2 Hz), 8.00-7.90 (m, 1H), 7.90-7.80 (m, 3H), 7.55-7.39 (m, 1H), 7.11 (d, 2H, J = 8.9 Hz), 7.06 (d, 1H, J = 6.6 Hz), 4.43-4.31 (m, 1H), 3.86 (s, 3H), 3.63-3.55 (m, 1H), 1.90-1.13 (m, 8H). | 495 | 493 | 0.84 |
| Example 27-15 | HCl | DMSO-d6 | 300 MHz | δ: 12.06 (s, 1H), 10.63 (s, 1H), 8.83-8.79 (m, 1H), 8.74 (s, 1H), 8.68 (s, 1H), 8.02 (d, 2H, J = 8.9 Hz), 8.00 (d, 1H, J = 12.6 Hz), 8.00-7.75 (m, 4H), 7.54-7.38 (m, 1H), 7.10 (d, 2H, J = 8.9 Hz), 7.09-7.03 (m, 1H), 4.43-4.30 (m, 1H), | 537 | 535 | 1.11 |

TABLE 13-continued

| | | | | | | | |
|---|---|---|---|---|---|---|---|
| | | | | 4.08 (t, 2H, J = 6.6 Hz), 3.64-3.55 (m, 1H), 1.90-1.15 (m, 12H), 0.95 (t, 3H, J = 7.4 Hz). | | | |
| Example 27-16 | HCl | DMSO-d6 | 300 MHz | δ: 11.97 (s, 1H), 10.81 (s, 1H), 8.77-8.72 (m, 1H), 8.69 (s, 1H), 8.58 (s, 1H), 8.15 (d, 2H, J = 8.8 Hz), 7.99 (d, 1H, J = 12.2 Hz), 7.97-7.70 (m, 4H), 7.59 (d, 2H, J = 8.8 Hz), 7.55-7.35 (m, 1H), 7.03 (d, 1H, J = 6.6 Hz), 4.42-4.30 (m, 1H), 3.65-3.55 (m, 1H), 1.90-1.13 (m, 8H). | 548 | 546 | 1.06 |
| Example 27-17 | HCl | DMSO-d6 | 300 MHz | δ: 11.95 (s, 1H), 11.06 (s, 1H), 8.73-8.63 (m, 2H), 8.58 (s, 1H), 8.41-8.31 (m, 4H), 8.00-7.72 (m, 4H), 7.99 (d, 1H, J = 12.2 Hz), 7.51-7.35 (m, 1H), 7.02 (d, 1H, J = 5.0 Hz), 4.42-4.31 (m, 1H), 3.65-3.55 (m, 1H), 1.88-1.15 (m, 8H). | 546 | 544 | 0.98 |
| Example 27-18 | HCl | DMSO-d6 | 300 MHz | δ: 11.94 (s, 1H), 11.04 (s, 1H), 8.69 (s, 1H), 8.68-8.64 (m, 1H), 8.50-8.45 (m, 1H), 8.02-7.72 (m, 4H), 7.99 (d, 1H, J = 12.6 Hz), 7.82 (d, 1H, J = 1.7 Hz), 7.69-7.59 (m, 2H), 7.53-7.33 (m, 1H), 7.00 (d, 1H, J = 6.3 Hz), 4.46-4.34 (m, 1H), 3.65-3.55 (m, 1H), 1.92-1.30 (m, 8H). | 532 | 530 | 0.99 |
| Example 27-19 | HCl | DMSO-d6 | 300 MHz | δ: 11.82 (s, 1H), 10.17 (s, 1H), 8.77 (s, 1H), 8.55 (s, 1H), 8.42 (s, 1H), 7.97 (d, 1H, J = 12.6 Hz), 7.97-7.80 (m, 1H), 7.77-7.68 (m, 3H), 7.76 (d, 1H, J = 8.6 Hz), 7.46-7.30 (m, 1H), 7.01-6.93 (m, 1H), 6.75-6.66 (m, 2H), 4.41-4.30 (m, 1H), 3.96 (s, 3H), 3.86 (s, 3H), 3.67-3.53 (m, 1H), 1.90-1.18 (m, 8H). | 524 | 522 | 0.92 |
| Example 27-20 | HCl | DMSO-d6 | 300 MHz | δ: 11.94 (s, 1H), 11.09 (s, 1H), 8.90 (s 1H), 8.80-8.75 (m, 1H), 8.75-8.71 (m, 1H), 8.63 (s, 1H), 8.23-8.08 (m, 2H), 7.99 (d, 1H, J = 12.2 Hz), 7.98-7.83 (m 1H), 7.83-7.70 (m, 4H), 7.53-7.35 (m, 1H), 7.06-6.99 (m( 1H), 4.46-4.32 (m, 1H), 3.65-3.56 (m, 1H), 1.90-1.10 (m, 8H). | 465 | 463 | 0.79 |
| Example 27-21 | HCl | DMSO-d6 | 300 MHz | δ: 12.11 (s, 1H), 11.15 (s, 1H), 9.21 (d, 1H, J = 2.3 Hz), 8.85-8.79 (m, 2H), 8.84 (dd, 1H, J = 1.7, 5.0 Hz), 8.71 (s, 1H), 8.47-8.41 (m, 1H), 8.01 (d, 1H, J = 12.2 Hz), 8.00-7.80 (m, 4H), 7.70-7.63 (m, 1H), 7.55-7.42 (m, 1H), 7.07 (d, 1H, J = 5.9 Hz), 4.44-4.33 (m, 1H), 3.65-3.55 (m, 1H), 1.90-1.15 (m, 8H). | 465 | 463 | 0.68 |
| Example 27-22 | HCl | DMSO-d6 | 300 MHz | δ: 12.04 (s, 1H), 11.10 (s, 1H), 8.90-8.84 (m, 2H), 8.80-8.74 (m, 2H), 8.65 (s, 1H), 8.04-7.78 (m, 7H), 7.54-7.39 (m, 1H), 7.09-7.01 (m, 1H), 4.42-4.30 (m, 1H), 3.65-3.55 (m, 1H), 1.90-1.16 (m, 8H). | 465 | 463 | 0.67 |
| Example 27-23 | HCl | DMSO-d6 | 300 MHz | δ: 11.92 (s, 1H), 10.72 (s, 1H), 8.71-8.65 (m, 2H), 8.51 (s, 1H), 7.98 (d, 1H, J = 12.2 Hz), 7.96-7.85 (m, 1H), 7.85-7.74 (m, 3H), 7.53-7.39 (m, 3H), 7.37-7.30 (m, 2H), 7.04-6.98 (m, 1H), 4.42-4.31 (m, 1H), 3.64-3.55 (m, 1H), 2.41 (s, 3H), 1.90-1.27 (m, 8H). | 478 | 476 | 0.87 |
| Example 27-24 | HCl | DMSO-d6 | 300 MHz | δ: 11.87 (s, 1H), 10.45 (s, 1H), 8.77 (s, 1H), 8.60 (s, 1H), 8.44 (s, 1H), 7.98 (d, 1H, J = 12.6 Hz), 7.95-7.82 (m, 1H), 7.82-7.73 (m, 3H), 7.67-7.62 (m, 1H), 7.60-7.51 (m, 1H), 7.48-7.35 (m, 1H), 7.22 (d, 1H, J = 8.6 Hz), 7.09 (dd, 1H, J = 6.9, 7.9 Hz), 6.98 (d, 1H, J = 6.6 Hz), 4.44-4.31 (m, 1H), 3.91 (s, 3H), 3.65-3.55 (m, 1H), 1.88-1.27 (m, 8H). | 494 | 492 | 0.89 |
| Example 27-25 | HCl | DMSO-d6 | 300 MHz | δ: 11.90 (s, 1H), 10.47 (s, 1H), 8.80 (s, 1H), 8.63 (s, 1H), 8.39 (s, 1H), 7.98 (d, 1H, J = 12.6 Hz), 7.98-7.84 (m, 1H), 7.83-7.73 (m, 3H), 7.69-7.64 (m, 1H), 7.58-7.50 (m, 1H), 7.50-7.35 (m, 1H), 7.20 (d, 1H, J = 8.3 Hz), 7.09 (dd, 1H, J = 7.6 Hz, 8.3 Hz), 7.00 (d, 1H, J = 6.3 Hz), 4.44-4.32 (m, 1H), 4.19 (q, 2H, J = 6.9 Hz), 3.65-3.55 (m, 1H), 1.89-1.22 (m, 8H), 1.39 (t, 3H, J = 6.9 Hz). | 508 | 506 | 0.99 |

TABLE 13-continued

| | | | | | | | |
|---|---|---|---|---|---|---|---|
| Example 27-26 | HCl | DMSO-d6 | 300 MHz | δ: 11.87 (s, 1H), 10.87 (s, 1H), 8.67-8.58 (m, 2H), 8.42 (s, 1H), 7.97 (d, 1H, J = 12.6 Hz), 7.97-7.83 (m, 1H), 7.81-7.62 (m, 5H), 7.50-7.33 (m, 1H), 7.01-6.93 (m, 1H), 4.45-4.33 (m, 1H), 3.65-3.55 (m, 1H), 1.92-1.25 (m, 8H). | 548 | 546 | 0.96 |
| Example 27-27 | HCl | DMSO-d6 | 300 MHz | δ: 11.93 (s, 1H), 10.71 (s, 1H), 8.74 (s, 1H), 8.62 (s, 1H), 8.56 (s, 1H), 7.98 (d, 1H, J = 12.2 Hz), 7.97-7.69 (m, 6H), 7.69-7.58 (m, 1H), 7.56-7.35 (m, 2H), 7.05-6.95 (m, 1H), 4.41-4.29 (m, 1H), 3.65-3.55 (m, 1H), 1.88-1.13 (m, 8H). | 482 | 480 | 0.87 |
| Example 27-28 | HCl | DMSO-d6 | 300 MHz | δ: 11.97 (s, 1H), 10.65 (s, 1H), 8.80-8.76 (m, 1H), 8.65 (s, 1H), 8.60 (s, 1H), 7.99 (d, 1H, J = 12.6 Hz), 7.97-7.83 (m, 1H), 7.83-7.73 (m, 3H), 7.63-7.35 (m, 4H), 7.25-7.18 (m, 1H), 7.05-6.98 (m, 1H), 4.43-4.31 (m, 1H), 3.65-3.55 (m, 1H), 3.58 (s, 3H), 1.90-1.13 (m, 8H). | 494 | 492 | 0.86 |
| Example 27-29 | HCl | DMSO-d6 | 300 MHz | δ: 11.92 (s, 1H), 10.83 (s, 1H), 8.78-8.67 (m, 1H), 8.66-8.61 (m, 1H), 8.48-8.43 (m, 1H), 7.98 (d, 1H, J = 12.6 Hz), 7.97-7.70 (m, 5H), 7.55-7.35 (m, 2H), 7.33-7.23 (m, 1H), 7.05-6.97 (m, 1H), 4.42-4.30 (m, 1H), 3.65-3.55 (m, 1H), 1.88-1.24 (m, 8H). | 500 | 498 | 0.88 |
| Example 27-30 | HCl | DMSO-d6 | 300 MHz | δ: 11.92 (s, 1H), 10.97 (s, 1H), 8.72-8.68 (m, 1H), 8.66-8.61 (m, 1H), 8.49-8.44 (m, 1H), 7.98 (d, 1H, J = 12.6 Hz), 7.97-7.75 (m, 4H), 7.75-7.62 (m, 1H), 7.57-7.49 (m, 1H), 7.46-7.38 (m, 2H), 7.00 (d, 1H, J = 5.9 Hz), 4.43-4.30 (m, 1H), 3.65-3.55 (m, 1H), 1.99-1.25 (m, 8H). | 500 | 498 | 0.88 |
| Example 27-31 | HCl | DMSO-d6 | 300 MHz | δ: 11.99 (s, 1H), 10.74 (s, 1H), 8.79 (s, 1H), 8.61 (s, 1H), 8.58 (s, 1H), 8.15 (d, 1H, J = 3.3 Hz), 7.99 (d, 1H, J = 12.6 Hz), 7.98-7.86 (m, 2H), 7.86-7.75 (m, 3H), 7.50-7.37 (m, 1H), 7.27 (dd, 1H, J = 4.0, 5.0 Hz), 7.05-6.98 (m, 1H), 4.45-4.33 (m, 1H), 3.65-3.55 (m, 1H), 1.88-1.17 (m, 8H). | 470 | 468 | 0.81 |
| Example 27-32 | HCl | DMSO-d6 | 300 MHz | δ: 11.93 (s, 1H), 10.49 (s, 1H), 8.76 (s, 1H), 8.63-8.53 (m, 2H), 8.50-8.45 (m, 1H), 7.98 (d, 1H, J = 12.6 Hz), 7.96-7.85 (m, 1H), 7.82-7.73 (m, 3H), 7.73-7.64 (m, 2H), 7.45-7.35 (m, 1H), 7.06-6.96 (m, 1H), 4.44-4.32 (m, 1H), 3.65-3.55 (m, 1H), 1.85-1.13 (m, 8H). | 470 | 468 | 0.79 |
| Example 27-33 | HCl | DMSO-d6 | 300 MHz | δ: 11.93 (s, 1H), 10.64 (s, 1H), 8.77-8.72 (m, 1H), 8.61 (s, 1H), 8.59-8.54 (m, 1H), 8.02-7.98 (m, 1H), 7.98 (d, 1H, J = 12.6 Hz), 7.96-7.85 (m, 1H), 7.83-7.73 (m, 3H), 7.50-7.38 (m, 2H), 7.05-6.97 (m, 1H), 6.78-6.73 (m, 1H), 4.42-4.37 (m, 1H), 3.65-3.55 (m, 1H), 1.90-1.16 (m, 8H). | 454 | 452 | 0.74 |
| Example 27-34 | HCl | DMSO-d6 | 300 MHz | δ: 11.95 (s, 1H), 10.49 (s, 1H), 8.75 (s, 1H), 8.64 (s, 1H), 8.58 (s, 1H), 7.99 (d, 1H, J = 12.2 Hz), 7.95-7.83 (m, 1H), 7.83-7.73 (m, 3H), 7.64 (dd, 1H, J = 2.0, 8.3 Hz), 7.56 (d, 1H, 2.0 Hz), 7.52-7.37 (m, 1H), 7.11 (d, 1H, J = 8.3 Hz), 7.06-6.98 (m, 1H), 6.16 (s, 2H), 4.42-4.30 (m, 1H), 3.65-3.55 (m, 1H), 1.88-1.15 (m, 8H). | 508 | 506 | 0.83 |
| Example 27-35 | HCl | | | no data | 522 | 520 | 0.87 |
| Example 27-36 | HCl | | | no data | 455 | 453 | 0.73 |
| Example 27-37 | HCl | DMSO-d6 | 300 MHz | δ: 11.99 (s, 1H), 10.75 (s, 1H), 8.81 (s, 1H), 8.70-8.61 (m, 2H), 8.38 (d, 1H, J = 1.7 Hz), 8.16 (d, 1H, J = 2.3 Hz), 8.03-7.86 (m, 3H), 7.99 (d, 1H, J = 12.2 Hz), 7.86-7.74 (m, 3H), 7.55-7.30 (m, 1H), 7.16-7.13 (m, 1H), 7.03 (d, 1H, J = 6.6 Hz), 4.43-4.31 (m, 1H), 3.65-3.55 (m, 1H), 1.87-1.08 (m, 8H). | 504 | 502 | 0.9 |
| Example 27-38 | HCl | DMSO-d6 | 300 MHz | δ: 11.95 (s, 1H), 10.75 (s, 1H), 8.80 (s, 1H), 8.67-8.55 (m, 3H), 8.21 (d, 1H, J = 8.6 Hz), 8.04-7.83 (m, 4H), 7.83-7.70 (m, 3H), 7.63 (d, 1H, J = 5.3 Hz), 7.50- | 520 | 518 | 0.94 |

TABLE 13-continued

| | | | | | | | |
|---|---|---|---|---|---|---|---|
| | | | | 7.38 (m, 1H), 7.05-6.99 (m, 1H), 4.44-4.30 (m, 1H), 3.68-3.56 (m, 1H), 1.90-1.10 (m, 8H). | | | |
| Example 27-39 | HCl | DMSO-d6 | 300 MHz | δ: 11.99 (s, 1H), 10.84 (s, 1H), 8.80-8.73 (m, 2H), 8.70 (s, 1H), 8.62 (s, 1H), 8.49-8.44 (m, 1H), 8.15-8.04 (m, 1H), 8.00 (d, 1H, J = 12.6 Hz), 7.97-7.85 (m, 1H), 7.85-7.73 (m, 3H), 7.55-7.40 (m, 3H), 7.06-6.98 (m, 1H), 4.44-4.30 (m, 1H), 3.65-3.55 (m, 1H), 1.87-1.08 (m, 8H). | 520 | 518 | 0.98 |
| Example 27-40 | HCl | DMSO-d6 | 300 MHz | δ: 11.98 (s, 1H), 10.99 (s, 1H), 8.83-8.78 (m, 1H), 8.64-8.57 (m, 2H), 8.49 (s, 1H), 8.13-8.02 (m, 2H), 7.99 (d, 1H, J = 12.6 Hz), 7.97-7.85 (m, 1H), 7.85-7.75 (m, 3H), 7.58-7.37 (m, 3H), 7.05-6.98 (m, 1H), 4.47-4.35 (m, 1H), 3.66-3.57 (m, 1H), 1.90-1.15 (m, 8H). | 520 | 518 | 0.98 1 |
| Example 27-41 | HCl | DMSO-d6 | 300 MHz | δ: 11.98 (s, 1H), 11.04 (s, 1H), 8.83-8.78 (m, 1H), 8.70-8.63 (m, 2H), 8.00 (d, 1H, J = 12.6 Hz), 7.97-7.71 (m, 7H), 7.60-7.52 (m, 1H), 7.50-7.35 (m, 2H), 7.08-7.00 (m, 1H), 4.44-4.33 (m, 1H), 3.66-3.57 (m, 1H), 1.87-1.13 (m, 8H). | 504 | 502 | 0.93 |
| Example 27-42 | HCl | | | | 519 | 517 | 0.75 |

Example 28

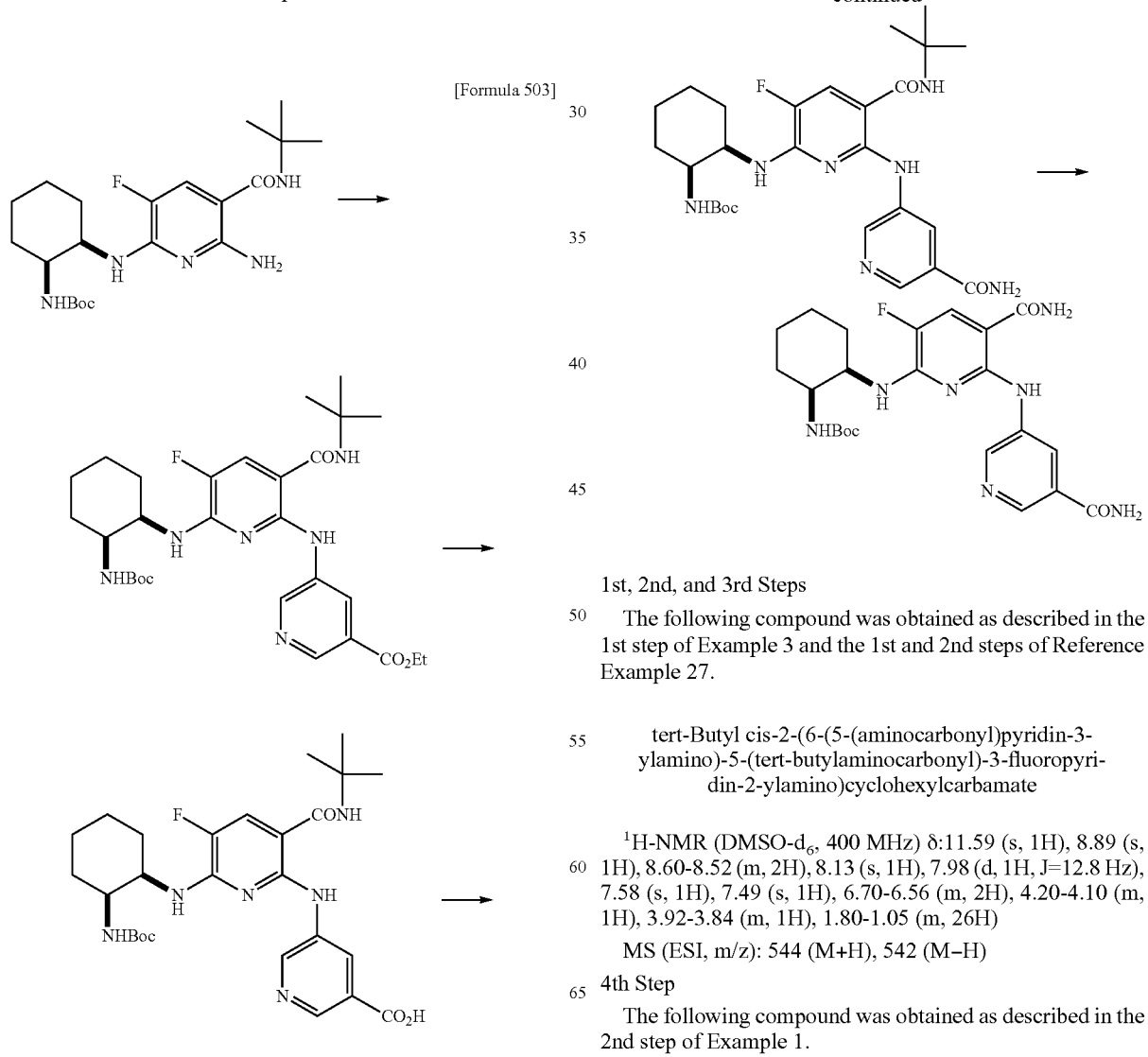

[Formula 503]

1st, 2nd, and 3rd Steps

The following compound was obtained as described in the 1st step of Example 3 and the 1st and 2nd steps of Reference Example 27.

tert-Butyl cis-2-(6-(5-(aminocarbonyl)pyridin-3-ylamino)-5-(tert-butylaminocarbonyl)-3-fluoropyridin-2-ylamino)cyclohexylcarbamate $^1$H-NMR (DMSO-d$_6$, 400 MHz) δ:11.59 (s, 1H), 8.89 (s, 1H), 8.60-8.52 (m, 2H), 8.13 (s, 1H), 7.98 (d, 1H, J=12.8 Hz), 7.58 (s, 1H), 7.49 (s, 1H), 6.70-6.56 (m, 2H), 4.20-4.10 (m, 1H), 3.92-3.84 (m, 1H), 1.80-1.05 (m, 26H)

MS (ESI, m/z): 544 (M+H), 542 (M−H)

4th Step

The following compound was obtained as described in the 2nd step of Example 1.

2-(5-aminocarbonylpyridin-3-ylamino)-6-(cis-2-aminocyclohexylamino)-5-fluoronicotinamide
($^1$H-NMR data and MS data are shown in table 14.)
Example 29
The compounds listed in table 14 were obtained as described in Example 28.
TABLE 14
| Number | Structure |
| --- | --- |
| Example 29-1<br>HCl salt | 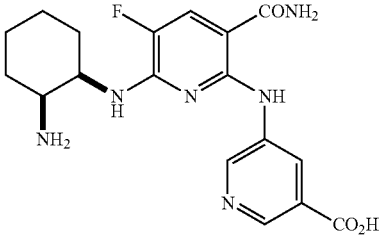 |
| Example 29-2<br>HCl salt | 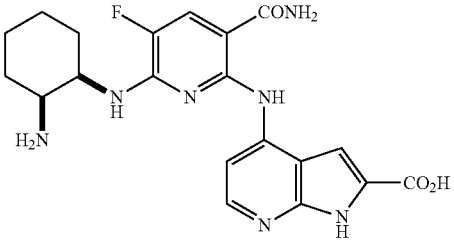 |
| Example 29-3<br>(Example 28)<br>HCl salt | 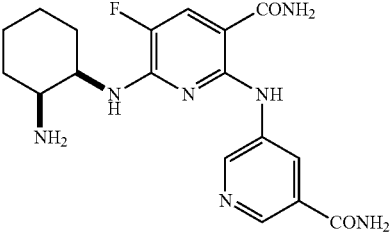 |
| Example 29-4 | 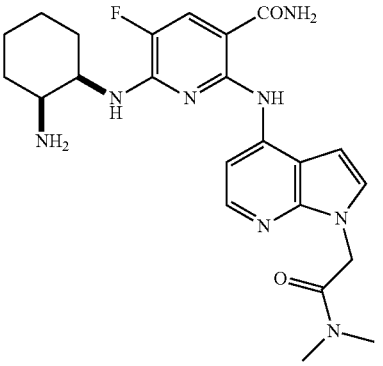 |

TABLE 14-continued
Example 29-5
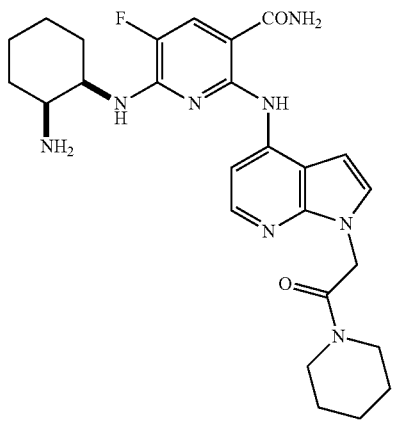
Example 29-6
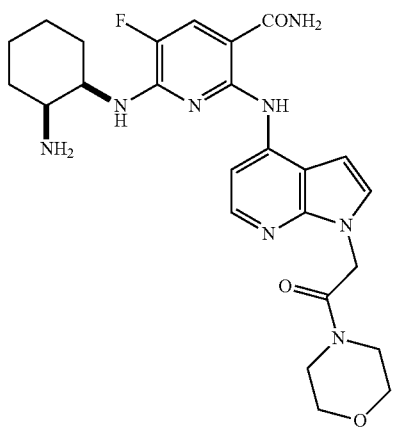
Example 29-7
HCl salt
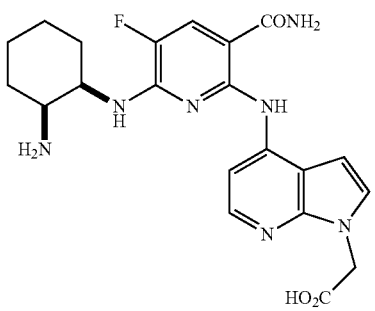
Example 29-8
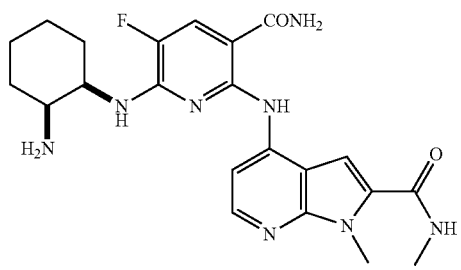

TABLE 14-continued
Example 29-9 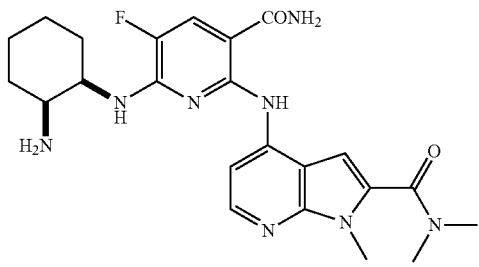
Example 29-10 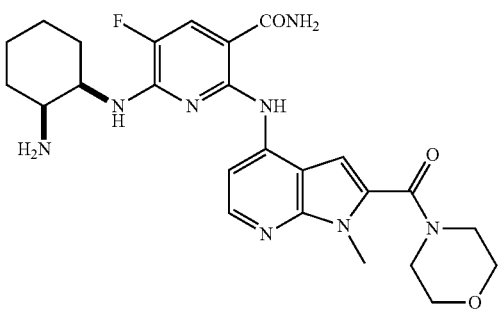
Example 29-11 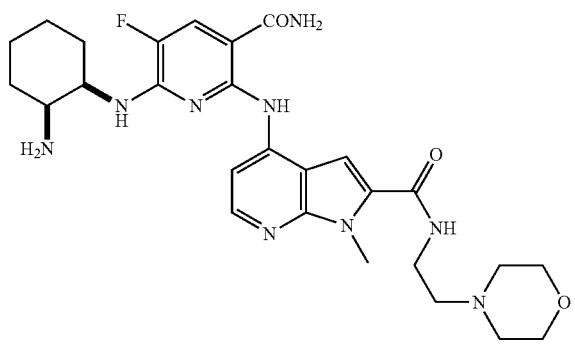
Example 29-12 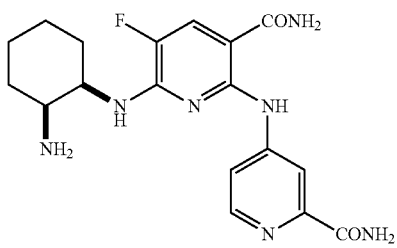
Example 29-13 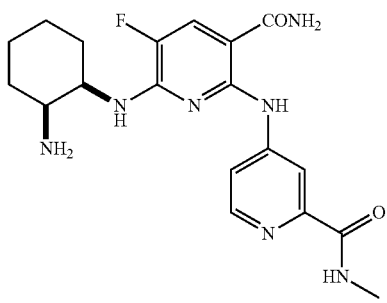

TABLE 14-continued
Example 29-14
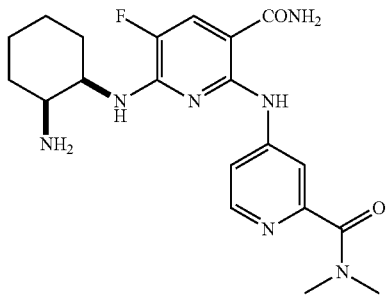
Example 29-15
HCl salt
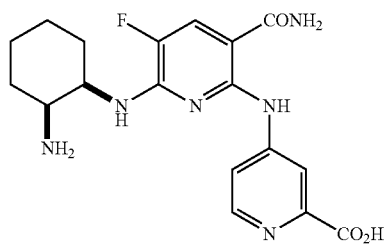
| Number | Structure | Compound name |
|---|---|---|
| Example 29-16 | 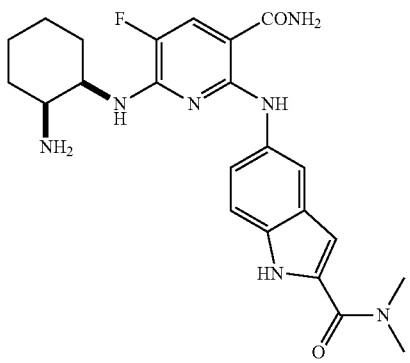 | 5-((6-(cis-2-aminocyclohexylamino)-3-carbamoyl-5-fluoropyridin-2-yl)amino)-N,N-dimethyl-1H-indole-2-carboxamide |
| Example 29-17 | 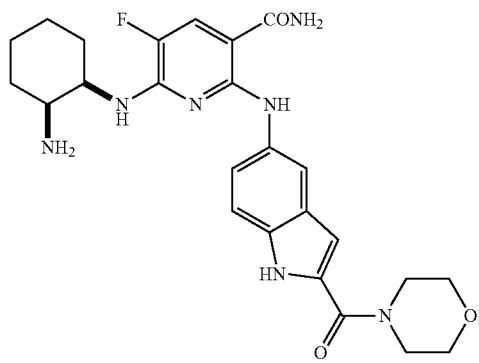 | 6-(cis-2-aminocyclohexylamino)-5-fluoro-2-((2-(morpholine-4-carbonyl)-1H-indol-5-yl)amino)nicotinamide |

TABLE 14-continued

| Example 29-18 | | 5-((6-(cis-2-aminocyclohexylamino)-3-carbamoyl-5-fluoropyridin-2-yl)amino)-N-benzyl-1H-indole-2-carboxamide |
| Example 29-19 | | 5-((6-(cis-2-aminocyclohexylamino)-3-carbamoyl-5-fluoropyridin-2-yl)amino)-N-(2-morpholinoethyl)-1H-indole-2-carboxamide |

| Number | Compound name | $^1$H-NMR | MS (ESI, m/z) |
| --- | --- | --- | --- |
| Example 29-1 HCl salt | 5-((3-aminocarbonyl-6-(cis-2-amino-cyclohexylamino)-5-fluoropyridin-2-yl)amino)nicotinic acid | $^1$H-NMR (DMSO-$d_6$ + $D_2O$, 400 MHz) δ: 8.89-8.84 (m, 2H), 8.68 (d, 1H, J = 1.7 Hz), 8.00 (d, 1H, J = 12.3 Hz), 4.40-4.30 (m, 1H), 3.58-3.50 (m, 1H), 1.95-1.35 (m, 8H). | 389 (M + H) |
| Example 29-2 HCl salt | 4-(3-aminocarbonyl-6-(cis-2-amino-cyclohexylamino)-5-fluoropyridin-2-ylamino)-1H-pyrrolo[2,3-b]pyridin-2-carboxylic acid | | 428 (M + H) |
| Example 29-3 HCl salt | 2-((5-aminocarbonylpyridin-3-yl)amino)-6-(cis-2-aminocyclohexyl-amino)-5-fluoronicotinamide | $^1$H-NMR (DMSO-$d_6$, 400 MHz) δ: 12.02 (s, 1H), 9.00-8.96 (m, 1H), 8.78 (s, 1H), 8.71-8.68 (m, 1H), 8.30 (s, 1H), 8.03-7.87 (m, 5H), 7.79 (s, 1H), 7.50-7.39 (m, 1H), 7.10-7.03 (m, 1H), 4.39-4.30 (m, 1H), 3.59-3.51 (m, 1H), 1.92-1.36 (m, 8H). | 388 (M + H) |
| Example 29-4 | 6-(cis-2-aminocyclohexylamino)-2-(1-(2-(dimethylamino)-2-oxoethyl)-1H-pyrrolo[2,3-b]pyridin-4-ylamino)-5-fluoronicotinamide | | 469 (M + H) |
| Example 29-5 | 6-(cis-2-aminocyclohexylamino)-5-fluoro-2-((1-(2-oxo-2-(piperidin-1-yl)ethyl)-1H-pyrrolo[2,3-b]pyridin-4-yl)amino)nicotinamide | | 509 (M + H) |
| Example 29-6 | 6-(cis-2-aminocyclohexylamino)-5-fluoro-2-((1-(2-(morpholin-4-yl)-2-oxoethyl)-1H-pyrrolo[2,3-b]pyridin-4-yl)amino)nicotinamide | | 511 (M + H) |
| Example 29-7 HCl salt | (4-((3-aminocarbonyl-6-(cis-2-amino-cyclohexylamino)-5-fluoropyridin-2-yl)amino)-1H-pyrrolo[2,3-b]pyridin-1-yl)acetic acid | | 442 (M + H) |
| Example 29-8 | 4-(3-aminocarbonyl-(6-(cis-2-amino-cyclohexylamino)-5-fluoropyridin-2-yl)amino)-N,1-dimethyl-1H-pyrrolo[2,3-b]pyridin-2-carboxamide | | 455 (M + H) |

TABLE 14-continued

| | | | | | | | |
|---|---|---|---|---|---|---|---|
| Example 29-9 | 4-((3-aminocarbonyl-6-(cis-2-amino-cyclohexylamino)-5-fluoropyridin-2-yl)amino)-N,N,1-trimethyl-1H-pyrrolo[2,3-b]pyridin-2-carboxamide | | | | | 469 (M + H) | |
| Example 29-10 | 6-(cis-2-aminocyclohexylamino)-5-fluoro-2-((1-methyl-2-((morpholin-4-yl)carbonyl)-1H-pyrrolo[2,3-b]pyridin-4-yl)amino)nicotinamide | | | | | 511 (M + H) | |
| Example 29-11 | 4-((3-aminocarbonyl-6-(cis-2-amino-cyclohexylamino)-5-fluoropyridin-2-yl)amino)-1-methyl-N-(2-(morpholin-4-yl)ethyl)-1H-pyrrolo[2,3-b]pyridin-2-carboxamide | | | | | 554 (M + H) | |
| Example 29-12 | 4-((3-aminocarbonyl-6-(cis-2-amino-cyclohexylamino)-5-fluoropyridin-2-yl)amino)pyridin-2-carboxamide | | | | | 388 (M + H) | |
| Example 29-13 | 4-((3-aminocarbonyl-6-(cis-2-amino-cyclohexylamino)-5-fluoropyridin-2-yl)amino)-N-methylpyridin-2-carboxamide | | | | | 402 (M + H) | |
| Example 29-14 | 4-((3-aminocarbonyl-6-(cis-2-amino-cyclohexylamino)-5-fluoropyridin-2-yl)amino)-N,N-dimethylpyridin-2-carboxamide | | | | | 416 (M + H) | |
| Example 29-15 HCl salt | 4-((3-aminocarbonyl-6-(cis-2-amino-cyclohexylamino)-5-fluoropyridin-2-yl)amino)pyridin-2-carboxylic acid | | | | | 389 (M + H) | |
| Number | Salt | Solvent | NMR | 1HNMR | Mass (M + H) | Mass (M − H) | rt (min) |
| Example 29-16 | free | | | | 454 | 452 | 0.81 |
| Example 29-17 | free | | | | 496 | 494 | 0.83 |
| Example 29-18 | free | | | | 516 | 514 | 1.03 |
| Example 29-19 | free | | | | 539 | 537 | 0.64 |

Example 30

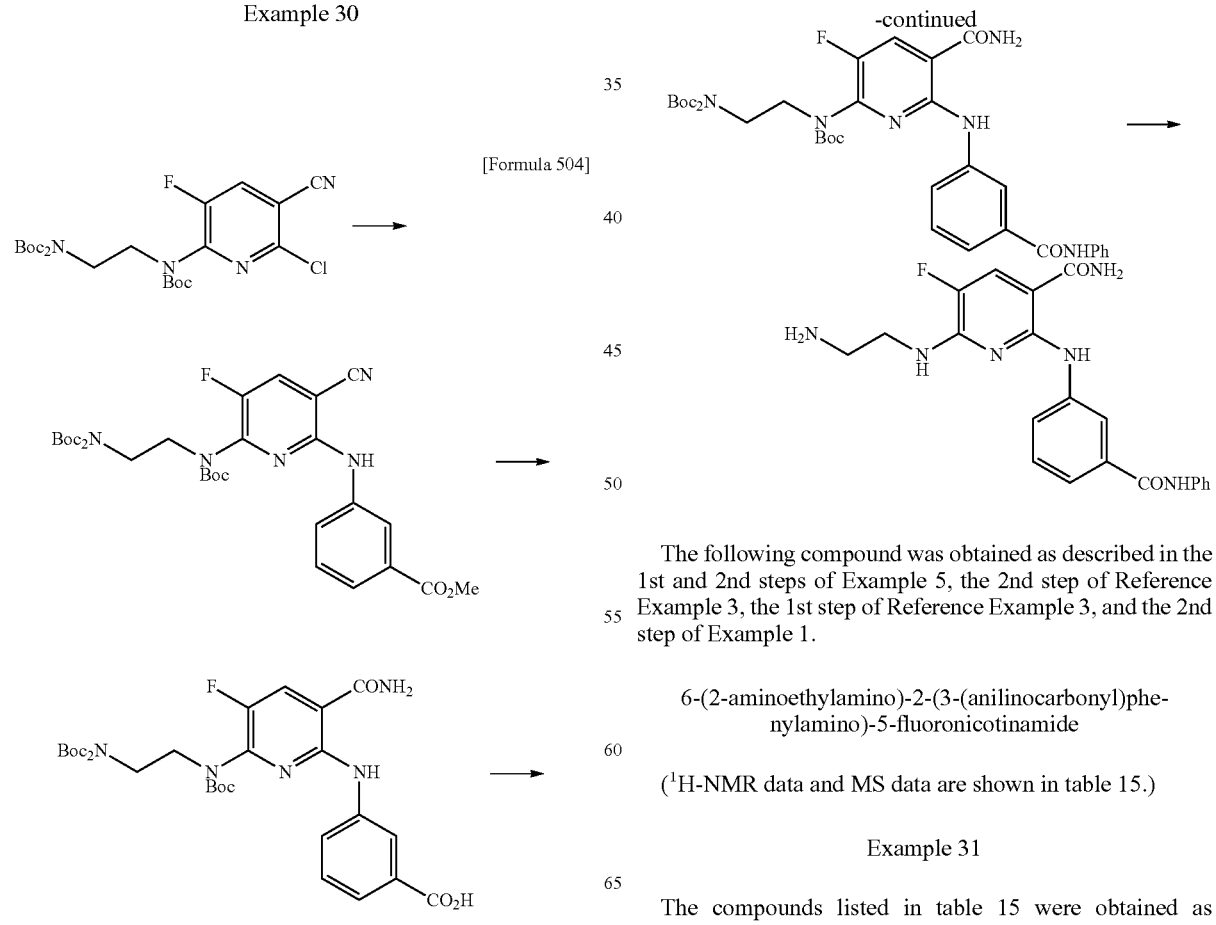

[Formula 504]

The following compound was obtained as described in the 1st and 2nd steps of Example 5, the 2nd step of Reference Example 3, the 1st step of Reference Example 3, and the 2nd step of Example 1.

6-(2-aminoethylamino)-2-(3-(anilinocarbonyl)phenylamino)-5-fluoronicotinamide ($^1$H-NMR data and MS data are shown in table 15.)

Example 31

The compounds listed in table 15 were obtained as described in Example 30.

TABLE 15

| Number | Structure |
|---|---|
| Example 31-1 HCl salt | (structure) |
| Example 31-2 HCl salt | (structure) |
| Example 31-3 HCl salt | (structure) |
| Example 31-4 (Example 30) HCl salt | (structure) |
| Example 31-5 HCl salt | (structure) |

TABLE 15-continued

| Example 31-6 HCl salt | 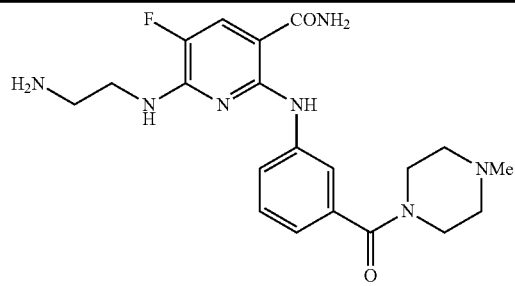 | | |
|---|---|---|---|

| Number | Compound name | ¹H-⁻NMR | MS (ESI, m/z) |
|---|---|---|---|
| Example 31-1 HCl salt | 6-((2-aminoethyl)amino)-2-((3-(dimethylaminocarbonyl)phenyl)-amino)-5-fluoronicotinamide | ¹H-⁻NMR (CD₃OD, 300 MHz) δ: 8.30-8.29 (m, 1H), 7.74 (d, 1H, J = 12.0 Hz), 7.28-7.33 (m, 1H), 7.25-7.19 (m, 1H), 7.05-7.00 (m, 1H), 3.77 (t, 2H, J = 6.6 Hz), 3.17 (t, 2H, J = 6.6 Hz), 3.12 (s, 3H), 3.07 (s, 3H). | 332 (M + H) |
| Example 31-2 HCl salt | 6-((2-aminoethyl)amino)-5-fluoro-2-((3-(piperidin-1-ylcarbonyl)-phenyl)amino)nicotinamide | ¹H-⁻NMR (CD₃OD, 300 MHz) δ: 8.24 (t, 1H, J = 1.5 Hz), 7.74 (d, 1H, J = 12.0 Hz), 7.39-7.33 (m, 1H), 7.26-7.22 (m, 1H), 7.01-6.97 (m, 1H), 3.79-3.69 (m, 4H), 3.50-3.43 (m, 2H), 3.16 (t, 2H, J = 6.6 Hz), 1.78-1.52 (m, 6H). | 401 (M + H) |
| Example 31-3 HCl salt | 6-((2-aminoethyl)amino)-2-((3-(cyclohexylaminocarbonyl)phe-nyl)amino)-5-fluoronicotinamide | ¹H-⁻NMR (CD₃OD, 300 MHz) δ: 8.89-8.88 (m, 1H), 7.74 (d, 1H, J = 12.0 Hz), 7.38-7.31 (m, 2H), 7.23-7.18 (m, 1H), 3.96-3.85 (m, 3H), 3.24 (t, 2H, J = 6.6 Hz), 1.99-1.65 (m, 5H), 1.48-1.20 (m, 5H). | 415 (M + H) |
| Example 31-4 HCl salt | 6-((2-aminoethyl)amino)-2-((3-(anilinocarbonyl)phenyl)amino)-5-fluoronicotinamide | ¹H-⁻NMR (CD₃OD, 300 MHz) δ: 9.01(s, 1H), 7.74 (d, 1H, J = 12.0 Hz), 7.69-7.67 (m, 2H), 7.56-7.53 (m, 1H), 7.45-7.33 (m, 3H), 7.29-7.14 (m, 1H), 7.20-7.13 (m, 1H), 3.90 (t, 2H, J = 6.6 Hz), 3.26 (t, 2H, J = 6.6 Hz). | 409 (M + H) |
| Example 31-5 HCl salt | 6-((2-aminoethyl)amino)-5-fluoro-2-((3-(morpholin-4-ylcarbonyl)-phenyl)amino)nicotinamide | ¹H-⁻NMR (CD₃OD, 300 MHz) δ: 8.31-8.19 (m, 1H), 7.74 (d, 1H, J = 12.0 Hz), 7.39-7.34 (m, 1H), 7.27-7.24 (m, 1H), 7.03-6.99 (m, 1H), 3.80-3.50 (m, 10H), 3.17 (t, 2H, J = 6.6 Hz). | |
| Example 31-6 HCl salt | 6-((2-aminoethyl)amino)-5-fluoro-2-((3-(4-methylpiperazin-1-ylcarbonyl)phenyl)amino)-nicotinamide | ¹H-⁻NMR (CD₃OD, 300 MHz) δ: 8.25-8.20 (m, 1H), 7.74 (d, 1H, J = 12.0 Hz), 7.42-7.40 (m, 2H), 7.09-6.96 (m, 1H), 3.79 (t, 2H, J = 6.6 Hz), 3.70-3.19 (m, 10H), 2.96 (s, 3H). | |

Example 32

[Formula 505]

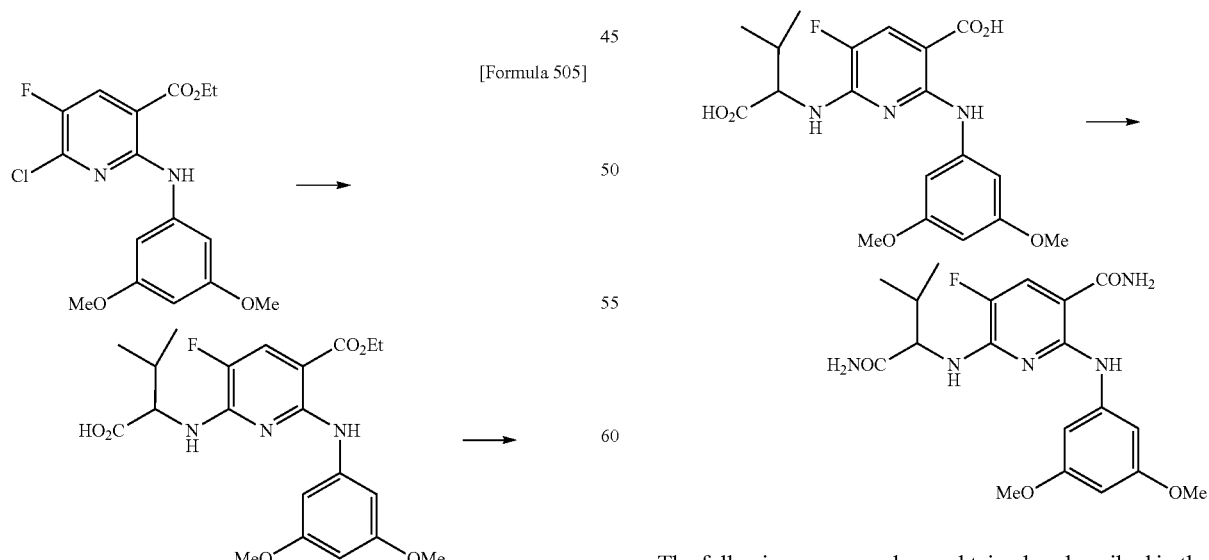

The following compound was obtained as described in the 1st step of Reference Example 2, the 2nd step of Reference Example 27, or the 4th step of Example 7.

6-(1-aminocarbonyl-2-methylpropylamino)-2-(3,5-dimethoxyphenylamino)-5-fluoro nicotinamide ($^1$H-NMR and ESI-MS data are shown in table 16.)

Example 33

The compounds listed in table 16 were obtained as described in Example 32.

TABLE 16

| Number | Structure | Number | Structure |
|---|---|---|---|
| Example 33-1 | 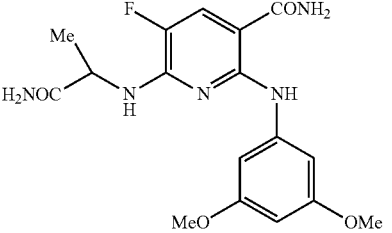 [SMILES: COc1cc(Nc2nc(NC(C)C(N)=O)c(F)cc2C(N)=O)cc(OC)c1] | Example 33-2 | 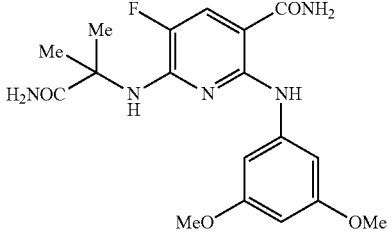 [SMILES: COc1cc(Nc2nc(NC(C)(C)C(N)=O)c(F)cc2C(N)=O)cc(OC)c1] |
| Example 33-3 | 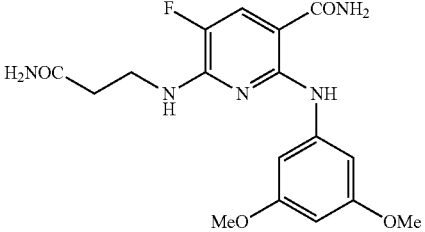 [SMILES: COc1cc(Nc2nc(NCCC(N)=O)c(F)cc2C(N)=O)cc(OC)c1] | Example 33-4 (Example 32) | 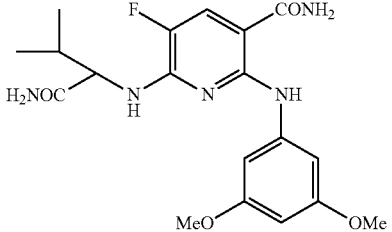 [SMILES: COc1cc(Nc2nc(NC(C(N)=O)C(C)C)c(F)cc2C(N)=O)cc(OC)c1] |
| Example 33-5 | 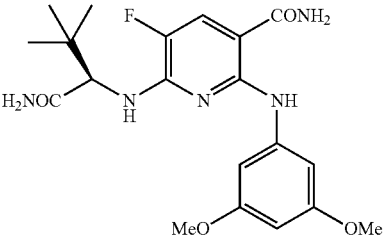 [SMILES: COc1cc(Nc2nc(N[C@@H](C(N)=O)C(C)(C)C)c(F)cc2C(N)=O)cc(OC)c1] | Example 33-6 | 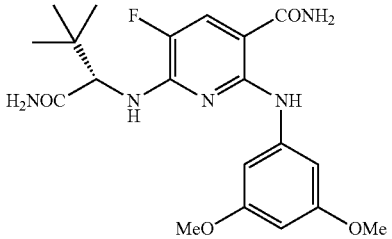 [SMILES: COc1cc(Nc2nc(N[C@H](C(N)=O)C(C)(C)C)c(F)cc2C(N)=O)cc(OC)c1] |
| Example 33-7 | 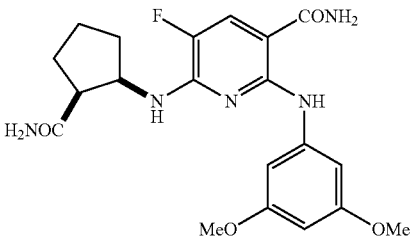 | Example 33-8 | 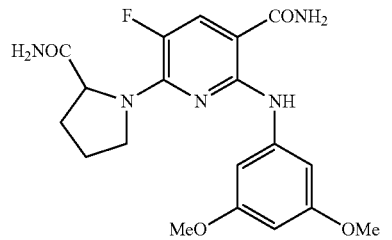 [SMILES: COc1cc(Nc2nc(N3CCCC3C(N)=O)c(F)cc2C(N)=O)cc(OC)c1] |

| Number | Compound name | $^1$H-NMR | MS (ESI, m/z) |
|---|---|---|---|
| Example 33-1 | 6-((2-amino-1-methyl-2-oxoethyl)amino)-2-(3,5-dimethoxyphenylamino)-5-fluoronicotinamide | $^1$H-NMR (CD$_3$OD, 400 MHz) δ: 7.69 (d, 1H, J = 12.0 Hz), 6.81 (d, 2H, J = 2.4 Hz), 6.13-6.10 (m, 1H), 4.50-5.00 (1H, overlapping with CH$_3$OH peak), 3.77 (s, 6H), 1.50 (d, 3H, J = 7.1 Hz). | 376 (M − H) |
| Example 33-2 | 6-((1-amino-2-methyl-1-oxopropan-2-yl)amino)-2-(3,5-dimethoxyphenylamino)-5-fluoronicotinamide | $^1$H-NMR (CD$_3$OD, 400 MHz) δ: 7.56 (d, 1H, J = 12.2 Hz), 6.58 (d, 2H, J = 2.2 Hz), 6.06 (t, 1H, J = 2.2 Hz), 3.68 (s, 6H), 1.57 (s, 6H). | 414 (M + Na), 390 (M − H) |
| Example 33-3 | 6-((3-amino-3-oxopropyl)amino)-2-(3,5-dimethoxyphenylamino)-5-fluoronicotinamide | $^1$H-NMR (CD$_3$OD, 400 MHz) δ: 7.54 (d, 1H, J = 12.4 Hz), 6.83 (d, 2H, J = 2.2 Hz), 6.01 (t, 1H, J = 2.2 Hz), 3.82-3.67 (m, 8H), 2.51 (t, 2H, J = 6.8 Hz). | 376 (M − H) |
| Example 33-4 | 6-((1-amino-3-methyl-1-oxobutan-2-yl)amino)-2-(3,5-dimethoxyphenylamino)-5-fluoronicotinamide | $^1$H-NMR (CD$_3$OD, 400 MHz) δ: 7.61 (d, 1H, J = 12.2 Hz), 6.73 (d, 2H, J = 2.2 Hz), 6.06 (t, 1H, J = 2.2 Hz), 4.53 (d, 1H, J = 6.4 Hz), 3.69 (s, 6H), 1.20-1.18 (m, 1H), 0.95-0.92 (m, 6H). | 428 (M + Na), 404 (M − H) |
| Example 33-5 | 6-((1R)-1-aminocarbonyl-2,2-dimethylpropylamino)-2-(3,5-dimethoxyphenylamino)-5-fluoronicotinamide | | 420 (M + H), 418 (M − H) |
| Example 33-6 | 6-(((2S)-1-amino-3,3-dimethyl-1-oxobutan-2-yl)amino)-2-(3,5-dimethoxyphenylamino)-5-fluoronicotinamide | $^1$H-NMR (CD$_3$OD, 400 MHz) δ: 7.62 (d, 1H, J = 12.2 Hz), 6.78 (d, 2H, J = 2.0 Hz), 6.08 (t, 1H, J = 2.0 Hz), 4.58-4.60 (m, 1H), 3.70 (s, 6H), 1.00 (s, 9H). | 442 (M + Na), 418 (M − H) |

TABLE 16-continued

| Example 33-7 | 6-((cis-2-aminocarbonylcyclopentyl)-amino)-2-(3,5-dimethoxyphenylamino)-5-fluoronicotinamide | | 416 (M − H) |
|---|---|---|---|
| Example 33-8 | 6-(2-aminocarbonylpyrrolidin-1-yl)-2-(3,5-dimethoxyphenylamino)-5-fluoronicotinamide | $^1$H-$^-$NMR (DMSO-d$_6$, 400 MHz) δ: 11.61 (s, 1H), 7.90-7.60 (m, 1H), 7.32-7.12 (m, 1H), 6.97 (brs, 1H), 6.85 (d, 2H, J = 2.2 Hz), 6.08 (t, 1H, J = 2.2 Hz), 4.60-4.52 (m, 1H), 3.90-3.82 (m, 2H), 3.73 (s, 6H), 2.30-2.16 (m, 1H), 2.04-1.96 (m, 1H), 1.94-1.76 (m, 2H). | 402 (M − H) |

Example 34

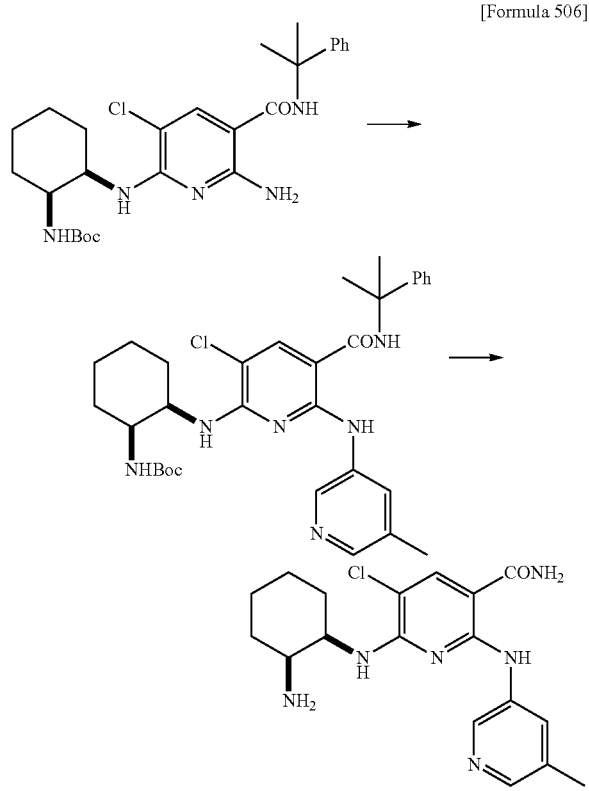

[Formula 506]

1st Step

Xantphos (5 mg) and Pd$_2$(dba)$_3$ (4 mg) were added to a mixture of tert-butyl cis-2-(6-amino-3-chloro-5-(2-phenylpropan-2-ylaminocarbonyl)pyridin-2-ylamino)cyclohexylcarbamate (20 mg), cesium carbonate (20 mg), 3-bromo-5-methylpyridine (9 mg), and 1,4-dioxane (2 ml) in a nitrogen atmosphere, followed by reflux for 3 hours in a nitrogen atmosphere. The reaction mixture was cooled to room temperature, and water and ethyl acetate were added. The organic layer was collected, washed with saturated saline, and dried over anhydrous sodium sulfate, and the solvent was distilled away under reduced pressure. The obtained residue was purified by silica gel chromatography (silica gel: Kanto Chemical Co., Inc., silica gel 60 (spherical shape), hexane•ethyl acetate=2:1 to 3:1), and a white solid of tert-butyl cis-2-(3-chloro-5-(2-phenylpropan-2-ylaminocarbonyl)-6-(5-methylpyridin-3-ylamino)pyridin-2-ylamino)cyclohexylcarbamate (13 mg) was thus obtained.

MS (ESI, m/z): 593 (M+H), 595 (M+H)

2nd Step

A mixture of tert-butyl cis-2-(3-chloro-5-(2-phenylpropan-2-ylaminocarbonyl)-6-(5-methylpyridin-3-ylamino)pyridin-2-ylamino)cyclohexylcarbamate (12 mg) and TFA (0.5 ml) was stirred at room temperature for 1 hour. The solvent was distilled away under reduced pressure (at 40° C. or less), ethyl acetate and 4N hydrogen chloride/1,4-dioxane (25 μl) were added, and the resultant was left at rest overnight at room temperature. Solid matter was collected by filtration, and a white solid of 6-(cis-2-aminocyclohexylamino)-5-chloro-2-(5-methylpyridin-3-ylamino)nicotinamide•hydrochloride (8 mg) was thus obtained.

($^1$H-NMR and ESI-MS data are shown in table 17.)

Example 35

The compounds shown in table 17 were obtained as described in Example 34.

TABLE 17

| Number | Structure | Number | Structure |
|---|---|---|---|
| Example 35-1 HCl salt | 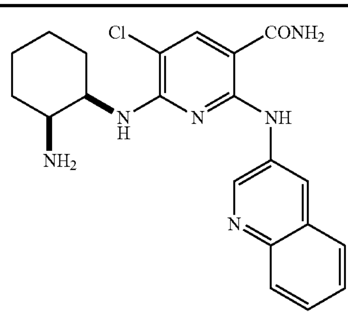 | Example 35-2 HCl salt | 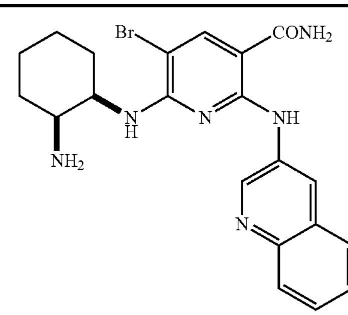 |

TABLE 17-continued

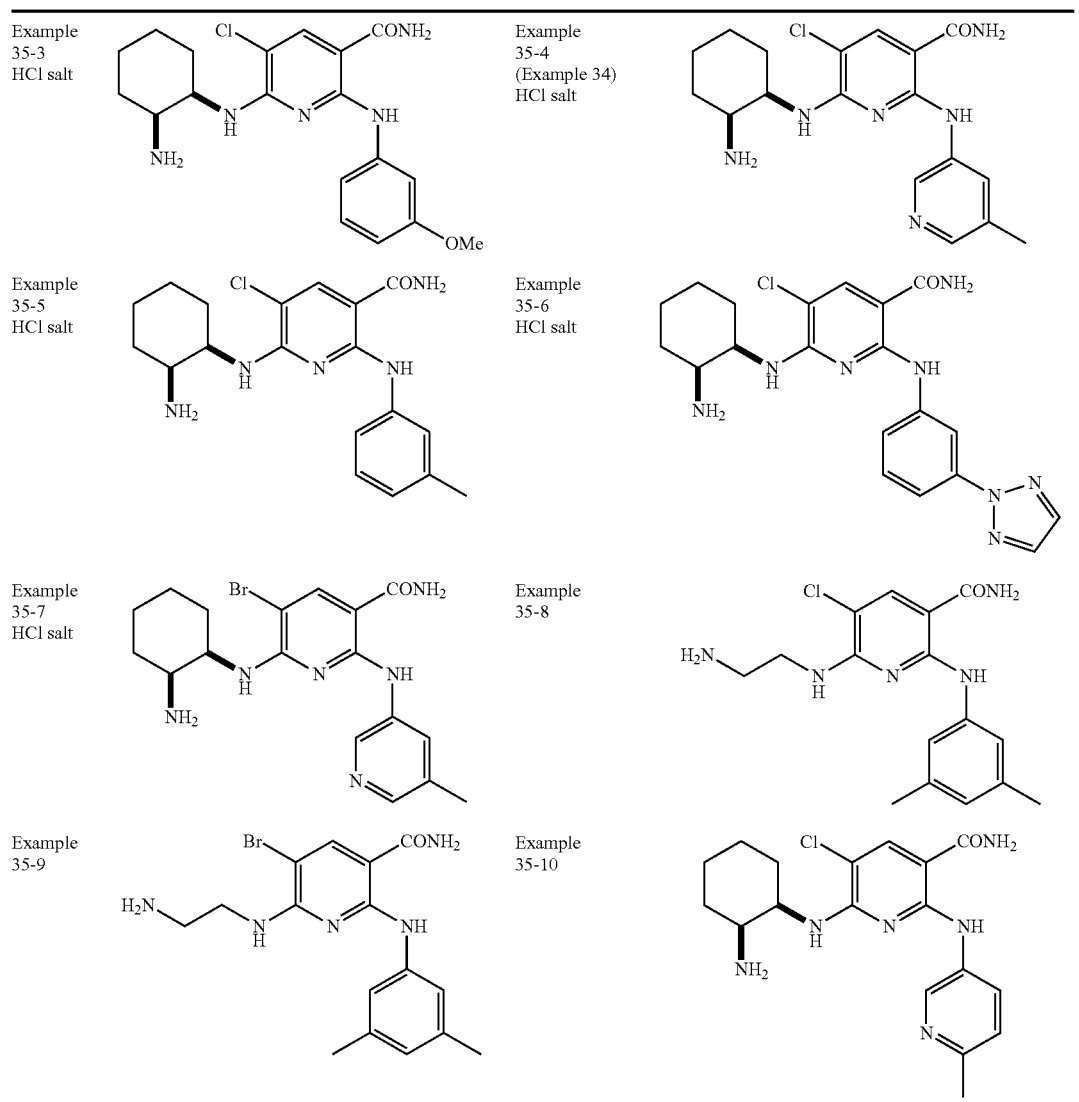

Compound name
6-(cis-2-aminocyclohexylamino)-5-chloro-2-
((6-methylpyridin-3-yl)amino)nicotinamide

| Number | Compound name | ¹H-NMR | MS (ESI, m/z) |
|---|---|---|---|
| Example 35-1 HCl salt | 6-(cis-2-aminocyclohexylamino)-5-chloro-2-(quinolin-3-ylamino)-nicotinamide | ¹H-NMR (DMSO-$d_6$, 400 MHz) δ: 12.07 (s, 1H), 9.25-9.20 (m, 1H), 8.90-8.85 (m, 1H), 8.24 (s, 1H), 8.12-7.98 (m, 6H), 7.77-7.66 (m, 2H), 7.56-7.38 (br, 1H), 6.37 (d, 1H, J = 7.1 Hz)), 4.48-4.36 (m, 1H), 3.65-3.55 (m, 1H), 2.00-1.38 (m, 8H). | 411 (M + H), 413 (M + H) |
| Example 35-2 HCl salt | 6-(cis-2-aminocyclohexylamino)-5-bromo-2-(quinolin-3-ylamino)-nicotinamide | ¹H-NMR (DMSO-$d_6$, 400 MHz) δ: 12.04 (s, 1H), 9.24-9.18 (m, 1H), 8.88-8.82 (m, 1H), 8.36 (s, 1H), 8.14-7.96 (m, 6H), 7.77-7.65 (m, 2H), 7.58-7.35 (br, 1H), 6.09 (d, 1H, J = 7.6 Hz)), 4.48-4.39 (m, 1H), 3.65-3.57 (1H, overlapping with H₂O peak), 2.00-1.37 (m, 8H). ¹H-NMR (DMSO-$d_6$ + D₂O, 400 MHz) δ: 9.18-9.14 (m, 1H), 8.78-8.84 (m, 1H), 8.33 (s, 1H), 8.10-7.95 (m, 2H), 7.80-7.68 (m, 2H), 4.46-4.37 (m, 1H), 3.65-3.57 (m, 1H), 1.86-1.40 (m, 8H). | 455 (M + H), 457 (M + H) |
| Example 35-3 HCl salt | 6-(cis-2-aminocyclohexylamino)-5-chloro-2-((3-methoxyphenyl)-amino)nicotinamide | ¹H-NMR (DMSO-$d_6$, 400 MHz) δ: 12.11 (s, 1H), 9.17-9.06 (br, 1H), 8.40-8.21 (m, 3H), 8.15-7.96 (m, 4H), 7.60-7.45 (m, 1H), 6.43 (d, 1H, J = 7.1 Hz), 4.40-4.28 (m, 1H), | 375 (M + H), 377 (M + H) |

TABLE 17-continued

| | | | Mass (M + H) |
|---|---|---|---|
| Example 35-4 HCl salt | 6-(cis-2-aminocyclohexylamino)-5-chloro-2-((5-methylpyridin-3-yl)amino)nicotinamide | ¹H-NMR (DMSO-d₆, 400 MHz) δ: 11.63 (s, 1H), 8.12 (s, 1H), 8.00-7.83 (m, 4H), 7.40-7.17 (m, 3H), 7.10-7.04 (m, 1H), 6.63-6.56 (m, 1H), 6.30 (d, 1H, J = 7.1 Hz), 4.32-4.22 (m, 1H), 3.76 (s, 3H), 3.70-3.60 (m, 1H), 1.95-1.36 (m, 8H). | 390 (M + H), 392 (M + H) |
| Example 35-5 HCl salt | 6-(cis-2-aminocyclohexylamino)-5-chloro-2-(3-methylphenylamino)nicotinamide | ¹H-NMR (DMSO-d₆, 400 MHz) δ: 11.56 (s, 1H), 8.11 (s, 1H), 8.00-7.75 (m, 4H), 7.43-7.15 (m, 4H), 6.81 (d, 1H, J = 7.1 Hz), 6.24 (d, 1H, J = 7.0 Hz), 4.32-4.22 (m, 1H), 3.70-3.60 (m, 1H), 2.30 (s, 3H), 1.94-1.36 (m, 8H). | 374 (M + H), 376 (M + H) |
| Example 35-6 HCl salt | 6-(cis-2-aminocyclohexylamino)-5-chloro-2-((3-(2H-1,2,3-triazol-2-yl)phenyl)amino)nicotinamide | ¹H-NMR (DMSO-d₆, 400 MHz) δ: 11.93 (s, 1H), 8.64-8.60 (m, 1H), 8.18 (s, 1H), 8.15 (s, 2H), 8.05-7.77 (m, 4H), 7.66-7.61 (m, 1H), 7.51-7.30 (m, 3H), 6.28 (d, 1H, J = 6.8 Hz), 4.48-4.38 (m, 1H), 3.66-3.57 (m, 1H), 1.93-1.30 (m, 8H). | 427 (M + H), 429 (M + H) |
| Example 35-7 HCl salt | 6-(cis-2-aminocyclohexylamino)-5-bromo-2-((5-methylpyridin-3-yl)amino)nicotinamide | ¹H-NMR (DMSO-d₆, 400 MHz) δ: 12.06 (s, 1H), 9.12-9.05 (m, 1H), 8.48-8.30 (m, 2H), 8.30-8.22 (m, 1H), 8.15-7.96 (m, 4H), 7.60-7.44 (br, 1H), 6.13 (d, 1H, J = 7.8 Hz), 4.40-4.29 (m, 1H), 3.60-3.50 (m, 1H), 2.43 (s, 1H), 1.93-1.39 (m, 8H). | 419 (M + H), 421 (M + H) |
| Example 35-8 | 6-((2-aminoethyl)amino)-5-chloro-2-((3,5-dimethylphenyl)amino)nicotinamide | ¹H-NMR (CD₃OD, 400 MHz) δ: 7.96-7.86 (br, 1H), 7.36-7.24 (br, 2H), 6.56-6.68 (br, 1H), 3.68-3.56 (m, 2H), 3.00-2.80 (m, 2H), 2.36-2.24 (brs, 6H). | 334 (M + H), 336 (M + H) |
| Example 35-9 | 6-((2-aminoethyl)amino)-5-bromo-2-((3,5-dimethylphenyl)amino)nicotinamide | ¹H-NMR (CD₃OD, 400 MHz) δ: 8.15-7.98 (m, 1H), 7.35-7.20 (br, 2H), 6.74-6.59 (br, 1H), 3.74-3.50 (m, 2H), 3.00-2.82 (m, 2H), 2.36-2.24 (brs, 6H). | |

| Number | Salt | Solvent | NMR | 1HNMR | Mass (M + H) | Mass (M − H) | rt(min) |
|---|---|---|---|---|---|---|---|
| Example 35-10 | HCl | DMSO-d6 | 300 MHz | δ: 12.05 (s, 1H), 9.14 (s, 1H), 8.38 (d, 1H, J = 8.4 Hz), 8.23 (s, 1H), 8.14-7.90 (m, 4H), 7.74 (d, 1H, J = 8.4 Hz), 7.51 (br, 1H), 6.40 (d, 1H, J = 7.8 Hz), 4.40-4.28 (m, 1H), 3.64-3.48 (m, 1H), 2.65 (s, 3H), 1.95-1.35 (m, 8H). | 373 375 | 371 373 | 0.61 |

Example 36

[Formula 507]

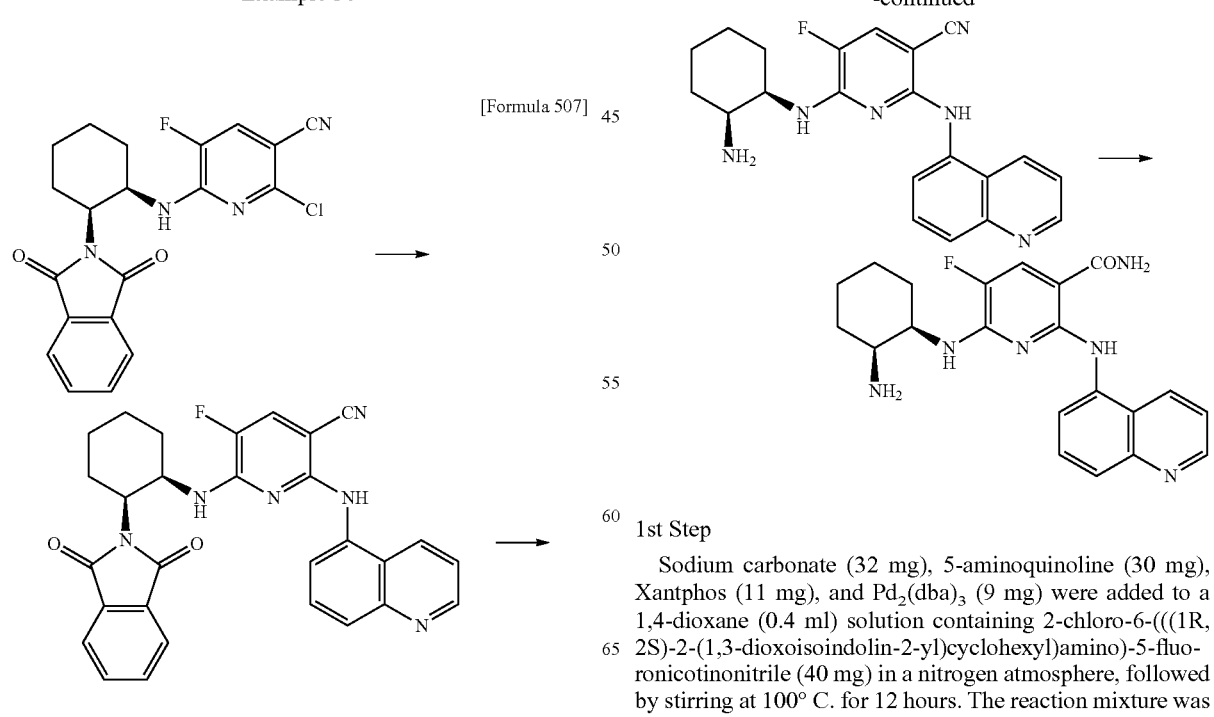

1st Step

Sodium carbonate (32 mg), 5-aminoquinoline (30 mg), Xantphos (11 mg), and Pd₂(dba)₃ (9 mg) were added to a 1,4-dioxane (0.4 ml) solution containing 2-chloro-6-((((1R, 2S)-2-(1,3-dioxoisoindolin-2-yl)cyclohexyl)amino)-5-fluoronicotinonitrile (40 mg) in a nitrogen atmosphere, followed by stirring at 100° C. for 12 hours. The reaction mixture was

1069 adjusted to room temperature, and ethyl acetate was added, followed by filtration. The solvent was distilled away under reduced pressure, and the obtained residue was purified by silica gel chromatography (n-hexane ethyl acetate=9:1 to 1:1), and 6-(((1R,2S)-2-(1,3-dioxoisoindolin-2-yl)cyclohexyl)amino)-5-fluoro-2-(quinolin-5-ylamino)nicotinonitrile (30 mg) was thus obtained.

MS (ESI m/z): 508 (M+H)
RT (min): 1.37

2nd Step

Hydrazine•monohydrate (50 μl) was added to an ethanol/tetrahydrofuran (1 ml/0.2 ml) solution containing 6-(((1R,2S)-2-(1,3-dioxoisoindolin-2-yl)cyclohexyl)amino)-5-fluoro-2-(quinolin-5-ylamino)nicotinonitrile (30 mg), followed by stirring at room temperature for 2.5 hours. Water was added to the reaction solution, followed by extraction with ethyl acetate. The resultant was washed with saturated saline and dried over anhydrous sodium sulfate, the solvent was distilled away under reduced pressure, and 6-(((1R,2S)-2-aminocyclohexyl)amino)-5-fluoro-2-(quinolin-5-ylamino)nicotinonitrile (20 mg) was thus obtained.

MS (ESI m/z): 377 (M+H)
RT (min): 0.73

3rd Step

A 5M sodium hydroxide aqueous solution (0.1 ml) and a 30% hydrogen peroxide solution (0.1 ml) were added to a solution of dimethyl sulfoxide (1 ml) and ethanol (0.5 ml) containing 6-(((1R,2S)-2-aminocyclohexyl)amino)-5-fluoro-2-(quinolin-5-ylamino)nicotinonitrile (20 mg), followed by stirring at room temperature for 1 hour. Water was added to the reaction solution, followed by extraction with ethyl acetate. The organic layer was washed with water and saturated saline and dried over anhydrous sodium sulfate, and the solvent was distilled away under reduced pressure. 4M hydrogen chloride/1,4-dioxane (0.5 ml) was added to the obtained residue, the resulting precipitate was collected by filtration, and a red solid of 6-(((1R,2S)-2-aminocyclohexyl)amino)-5-fluoro-2-(quinolin-5-ylamino)nicotinamide (12 mg) was thus obtained.

MS (ESI m/z): 395 (M+H)
RT (min): 0.70

Example 37

The compounds shown in table 18 were obtained as described in Example 36.

TABLE 18

| Number | Structure | Compound name |
|---|---|---|
| Example 37-1 (Example 36) | 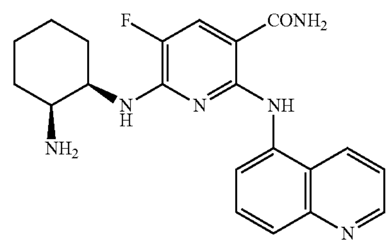 [SMILES: NC(=O)c1cc(F)c(N[C@@H]2CCCC[C@@H]2N)nc1Nc1cccc2ncccc12] | 6-((1R,2S)-2-aminocyclohexylamino)-5-fluoro-2-((quinolin-5-yl)amino)nicotinamide |
| Example 37-2 | 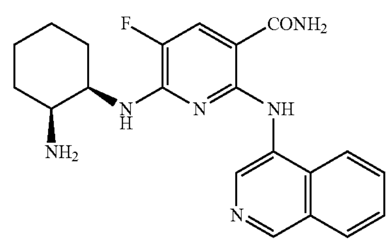 [SMILES: NC(=O)c1cc(F)c(N[C@@H]2CCCC[C@@H]2N)nc1Nc1cncc2ccccc12] | 6-((1R,2S)-2-aminocyclohexylamino)-5-fluoro-2-((isoquinolin-4-yl)amino)nicotinamide |
| Example 37-3 | 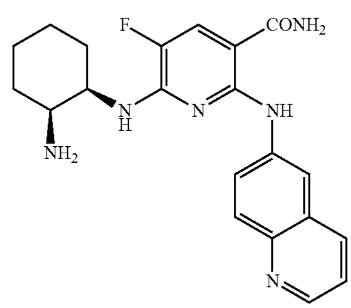 [SMILES: NC(=O)c1cc(F)c(N[C@@H]2CCCC[C@@H]2N)nc1Nc1ccc2ncccc2c1] | 6-((1R,2S)-2-aminocyclohexylamino)-5-fluoro-2-((quinolin-6-yl)amino)nicotinamide |

TABLE 18-continued
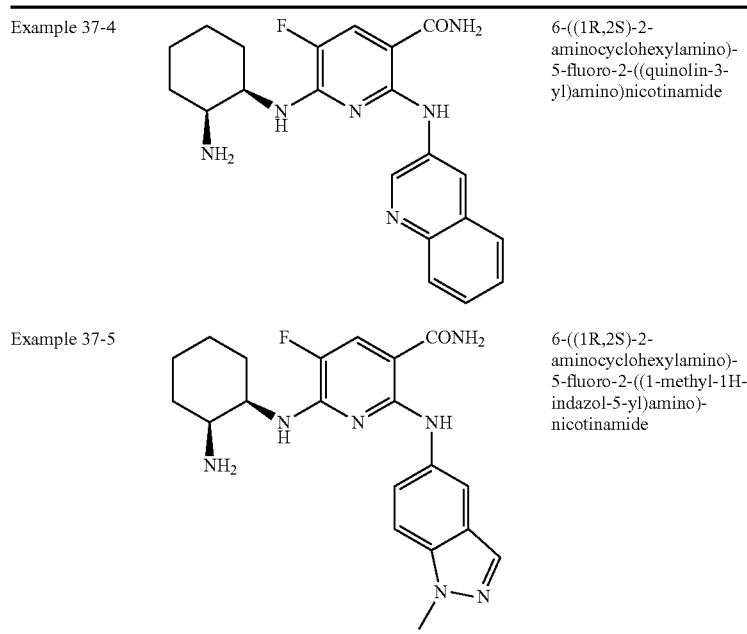
| Example 37-4 | | 6-((1R,2S)-2-aminocyclohexylamino)-5-fluoro-2-((quinolin-3-yl)amino)nicotinamide |
| Example 37-5 | | 6-((1R,2S)-2-aminocyclohexylamino)-5-fluoro-2-((1-methyl-1H-indazol-5-yl)amino)-nicotinamide |
| Number | Salt | Solvent | NMR | 1HNMR | Mass (M + H) | Mass (M − H) | rt(min) |
|---|---|---|---|---|---|---|---|
| Example 37-1 (Example 36) | HCl | | | | 395 | 393 | 0.65 |
| Example 37-2 | HCl | | | | 395 | 393 | 0.67 |
| Example 37-3 | HCl | | | | 395 | 393 | 0.64 |
| Example 37-4 | HCl | | | | 395 | 393 | 0.81 |
| Example 37-5 | HCl | | | | 398 | 396 | 0.84 |
Example 38
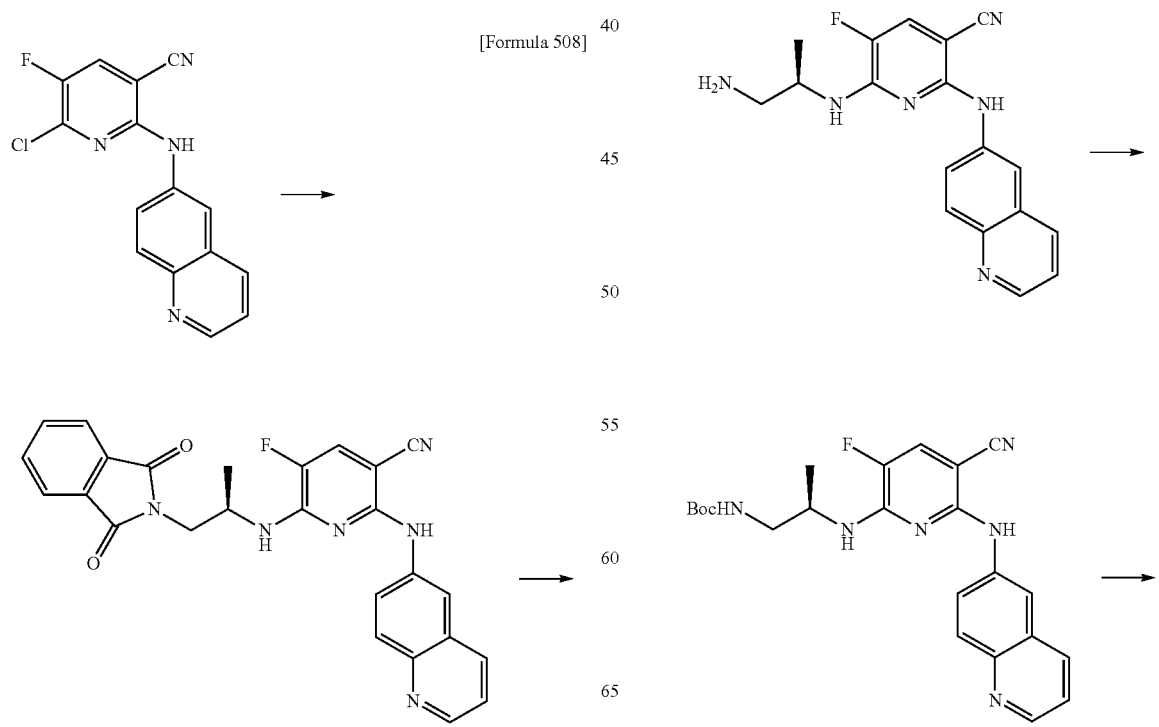

1073

-continued

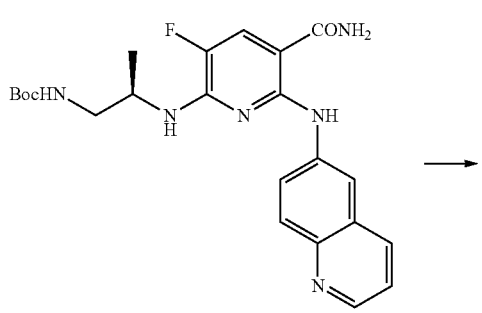

1st Step

Potassium carbonate (115 mg) and 6-chloro-5-fluoro-2-(quinolin-6-ylamino)nicotinonitrile (50 mg) were added to a tube containing a 1,4-dioxane (2 ml) solution containing (R)-2-(2-aminopropyl)isoindoline-1,3-dione (52 mg) and the tube was sealed, followed by stirring with heating at 140° C. for 13 hours. The reaction solution was adjusted to room temperature, and a saturated aqueous sodium hydrogen carbonate solution was added, followed by extraction with ethyl acetate. The organic layer was dried over anhydrous sodium sulfate. Subsequently, the solvent was distilled away under reduced pressure, the obtained residue was purified by silica gel chromatography (n-hexane:ethyl acetate=3:2), and a yellow solid of (R)-6-((1-(1,3-dioxoisoindolin-2-yl)propan-2-yl)amino)-5-fluoro-2-(quinolin-6-ylamino)nicotinonitrile (57 mg) was thus obtained.

MS (ESI m/z): 467 (M+H)
RT (min): 1.03

2nd Step

The following compound was obtained as described in the 3rd step of Reference Example 379.

(R)-6-((1-aminopropan-2-yl)amino)-5-fluoro-2-(quinolin-6-ylamino)nicotinonitrile MS (ESI m/z): 337 (M+H)
RT (min): 0.60

3rd Step

The following compound was obtained as described in the 2nd step of Reference Example 2.

(R)-tert-butyl(2-((5-cyano-3-fluoro-6-(quinolin-6-ylamino)pyridin-2-yl)amino)propyl)carbamate MS (ESI m/z): 437 (M+H)
RT (min): 1.14

4th and 5th Steps

The following compound was obtained as described in the 2nd and 3rd steps of Example 5.

(R)-tert-butyl(2-((5-carbamoyl-3-fluoro-6-(quinolin-6-ylamino)pyridin-2-yl)amino)propyl)carbamate MS (ESI m/z): 455 (M+H)
RT (min): 1.02

(R)-6-(1-aminopropan-2-yl)amino)-5-fluoro-2-(quinolin-6-ylamino)nicotinamide

MS (ESI m/z): 355 (M+H)
RT (min): 0.56

Example 39

The compounds listed in table 19 were obtained as described in Example 38.

TABLE 19

| Number | Structure | Compound name |
|---|---|---|
| Example 39-1 | ![structure] | 6-(((2R,3S)-3-aminobutan-2-yl)amino)-5-fluoro-2-((quinolin-6-yl)amino)nicotinamide<br>6-(((2S,3R)-3-aminobutan-2-yl)amino)-5-fluoro-2-((quinolin-6-yl)amino)nicotinamide |

TABLE 19-continued

Example 39-2 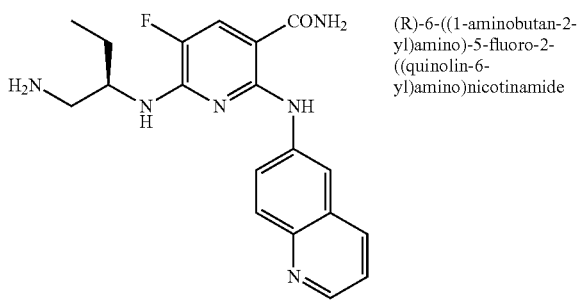 (R)-6-((1-aminobutan-2-yl)amino)-5-fluoro-2-((quinolin-6-yl)amino)nicotinamide Example 39-3 (Example 38) 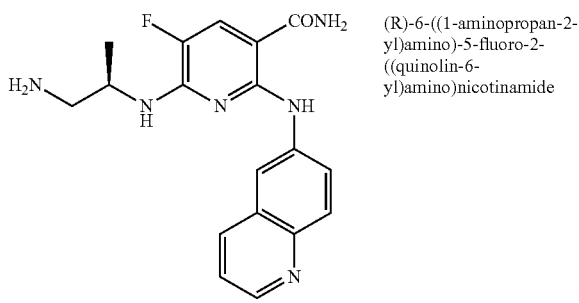 (R)-6-((1-aminopropan-2-yl)amino)-5-fluoro-2-((quinolin-6-yl)amino)nicotinamide Example 39-4 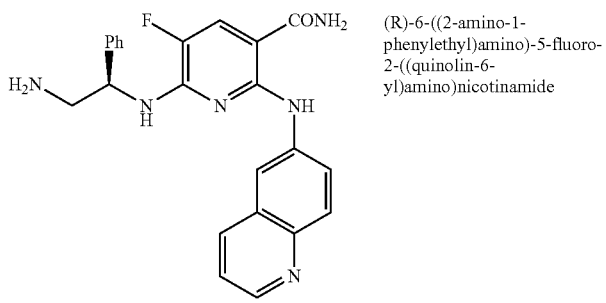 (R)-6-((2-amino-1-phenylethyl)amino)-5-fluoro-2-((quinolin-6-yl)amino)nicotinamide Example 39-5 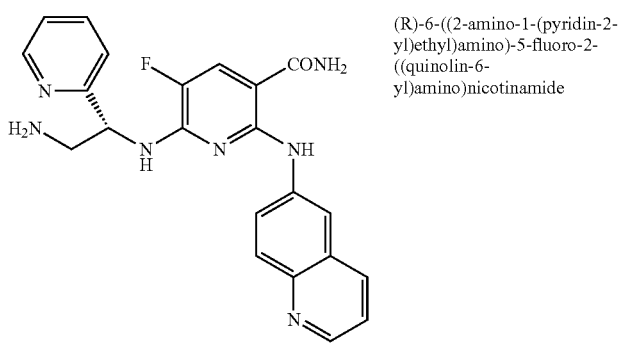 (R)-6-((2-amino-1-(pyridin-2-yl)ethyl)amino)-5-fluoro-2-((quinolin-6-yl)amino)nicotinamide

| Number | Salt | Solvent | NMR | 1HNMR | Mass (M + H) | Mass (M − H) | rt(min) |
|---|---|---|---|---|---|---|---|
| Example 39-1 | HCl | | | | 369 | 367 | 0.57 |
| Example 39-2 | HCl | | | | 369 | 367 | 0.62 |
| Example 39-3 (Example 38) | HCl | | | | 355 | 353 | 0.56 |
| Example 39-4 | HCl | | | | 417 | 415 | 0.71 |
| Example 39-5 | HCl | | | | 418 | 416 | 0.62 |

1077
Example 40

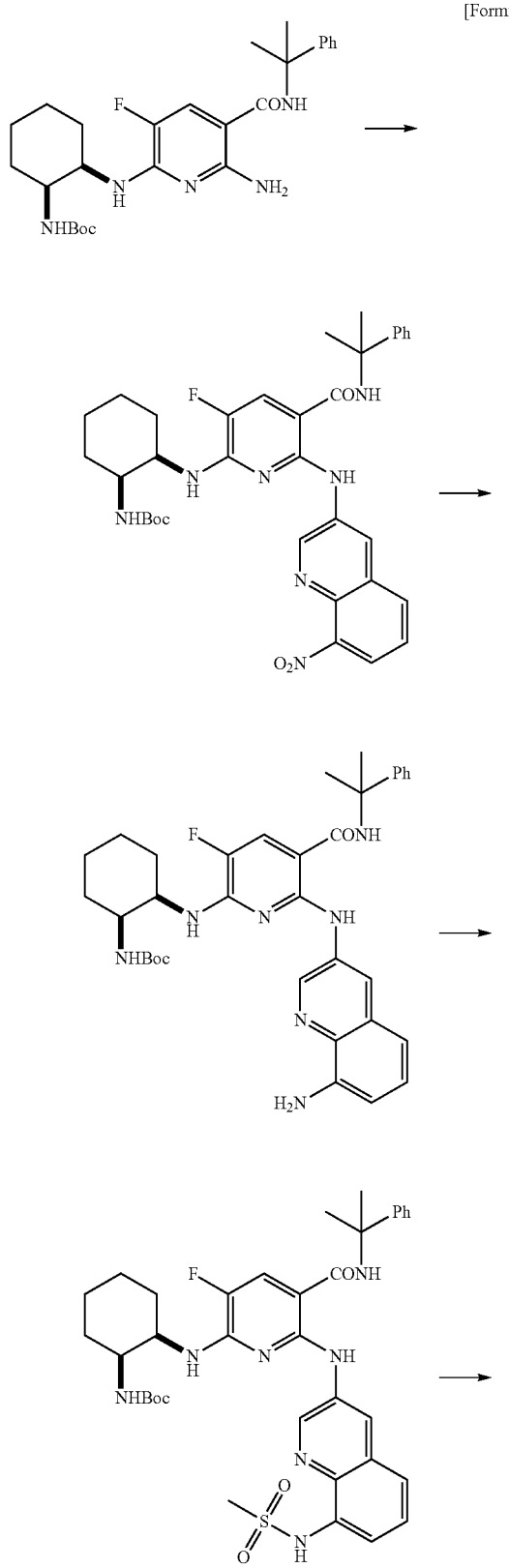

[Formula 509]

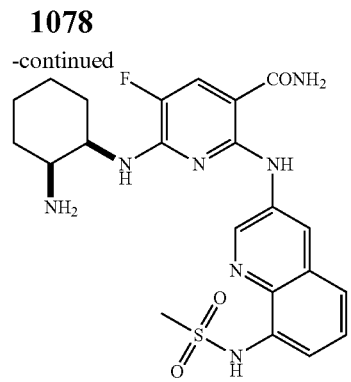

1st Step

Cesium carbonate (238 mg), 3-bromo-8-nitroquinoline (92 mg), 2-dicyclohexylphosphino-2',4',6'-triisopropylbiphenyl (23 mg), and Pd$_2$(dba)$_3$ (22 mg) were added to a 1,4-dioxane solution (2 ml) containing tert-butyl((cis)-2-((6-amino-3-fluoro-5-((2-phenylpropan-2-yl)carbamoyl)pyridin-2-yl)amino)cyclohexyl)carbamate (118 mg) in a nitrogen atmosphere, followed by stirring at 100° C. for 45 minutes. The reaction solution was adjusted to room temperature, ethyl acetate was added, and insoluble matter was filtered. Then, the solvent was distilled away under reduced pressure, the obtained residue was purified by silica gel chromatography (n-hexane ethyl acetate=9:1 to 3:7), and tert-butyl((cis)-2-((3-fluoro-6-((8-nitroquinolin-3-yl)amino)-5-((2-phenylpropan-2-yl)carbamoyl)pyridin-2-yl)amino)cyclohexyl)carbamate (98 mg) was thus obtained.

MS (ESI m/z): 658 (M+H)
RT (min): 2.08

2nd Step

The following compound was obtained as described in the 2nd step of Reference Example 186.

tert-Butyl((cis)-2-((6-((8-aminoquinolin-3-yl)amino)-3-fluoro-5-((2-phenylpropan-2-yl)carbamoyl)pyridin-2-yl)amino)cyclohexyl)carbamate MS (ESI m/z): 629 (M+H), 627 (M–H)
RT (min): 1.98

3rd Step

Triethylamine (4 µl) and methanesulfonyl chloride (1.4 µl) were added to a dichloromethane (1 ml) solution containing tert-butyl((cis)-2-(6-((8-aminoquinolin-3-yl)amino)-3-fluoro-5-((2-phenylpropan-2-yl)carbamoyl)pyridin-2-yl)amino)cyclohexyl)carbamate (10 mg) obtained in the 2nd step, followed by stirring at room temperature for 1 hour. Triethylamine (12 µl) and methanesulfonyl chloride (5 µl) were added again to the reaction mixture, followed by stirring at room temperature for 1 hour. Saturated sodium bicarbonate water was added, followed by extraction with ethyl acetate. The organic layer was washed with saturated saline and dried over anhydrous sodium sulfate, the solvent was distilled away under reduced pressure, and tert-butyl((cis)-2-(3-fluoro-6-((8-(methylsulfonamide)quinolin-3-yl)amino)-5-((2-phenylpropan-2-yl)carbamoyl)pyridin-2-yl)amino)cyclohexyl)carbamate (12 mg) was thus obtained.

MS (ESI m/z): 707 (M+H)
RT (min): 2.06

4th Step

The following compound was obtained as described in the 2nd step of Example 1.

6-(((cis)-2-aminocyclohexyl)amino)-5-fluoro-2-((8-(methylsulfonamide)quinolin-3-yl)amino)nicotinamide MS (ESI m/z): 488 (M+H), 486 (M–H)
RT (min): 0.97

Example 41

The compounds listed in table 20 were obtained as described in Example 40.

TABLE 20

| Number | Structure | Compound name |
| --- | --- | --- |
| Example 41-1 | 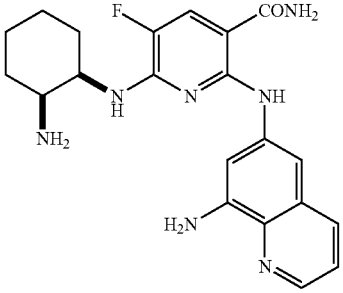 | 6-(cis-2-aminocyclohexylamino)-2-((8-aminoquinolin-6-yl)amino)-5-fluoronicotinamide |
| Example 41-2 (Example 40) | 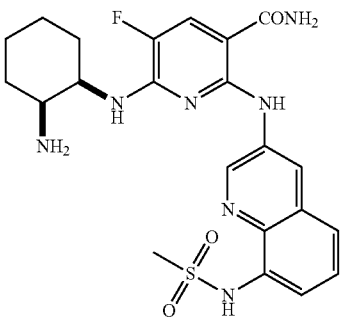 | 6-(cis-2-aminocyclohexylamino)-5-fluoro-2-((8-(methylsulphonamide)quinolin-3-yl)amino)nicotinamide |
| Example 41-3 | 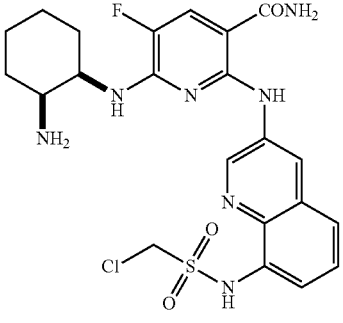 | 6-(cis-2-aminocyclohexylamino)-2-((8-(2-chloromethylsulphonamide)quinolin-3-yl)amino)-5-fluoronicotinamide |
| Example 41-4 | 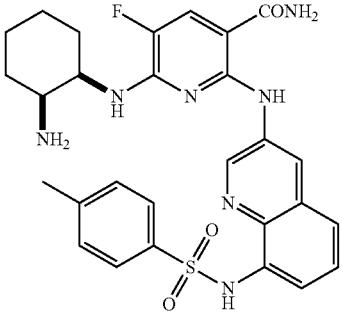 | 6-(cis-2-aminocyclohexylamino)-5-fluoro-2-((8-(4-methylphenylsulphonamide)quinolin-3-yl)amino)nicotinamide |

TABLE 20-continued

| Example 41-5 | 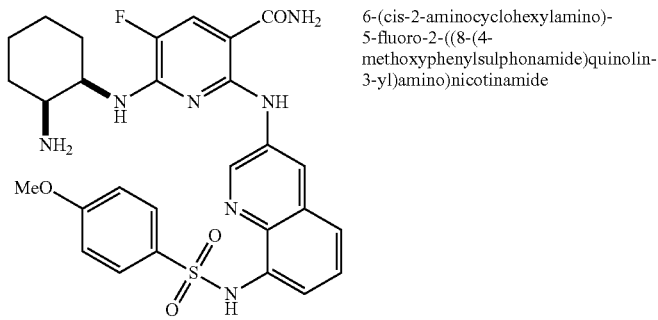 | 6-(cis-2-aminocyclohexylamino)-5-fluoro-2-((8-(4-methoxyphenylsulphonamide)quinolin-3-yl)amino)nicotinamide |
| Example 41-6 | 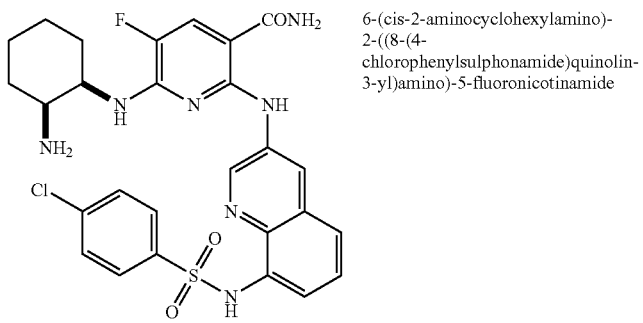 | 6-(cis-2-aminocyclohexylamino)-2-((8-(4-chlorophenylsulphonamide)quinolin-3-yl)amino)-5-fluoronicotinamide |
| Example 41-7 | 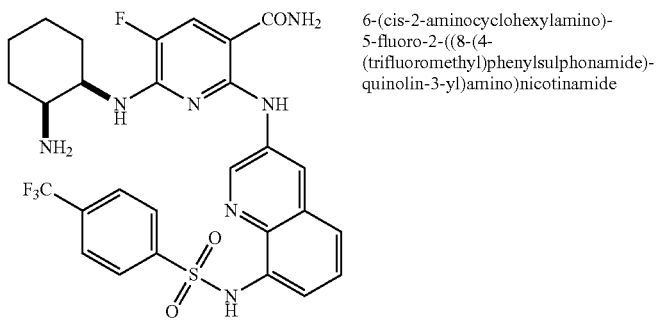 | 6-(cis-2-aminocyclohexylamino)-5-fluoro-2-((8-(4-(trifluoromethyl)phenylsulphonamide)-quinolin-3-yl)amino)nicotinamide |
| Example 41-8 | 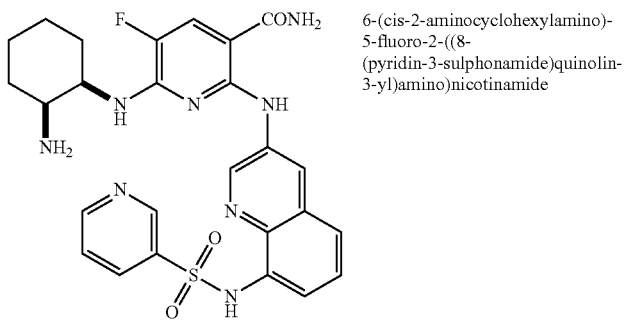 | 6-(cis-2-aminocyclohexylamino)-5-fluoro-2-((8-(pyridin-3-sulphonamide)quinolin-3-yl)amino)nicotinamide |

TABLE 20-continued

| Example 41-9 | 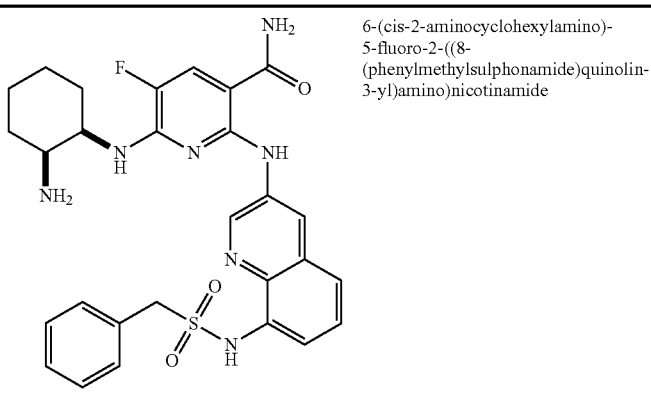 | 6-(cis-2-aminocyclohexylamino)-5-fluoro-2-((8-(phenylmethylsulphonamide)quinolin-3-yl)amino)nicotinamide |
| --- | --- | --- |
| Example 41-10 | 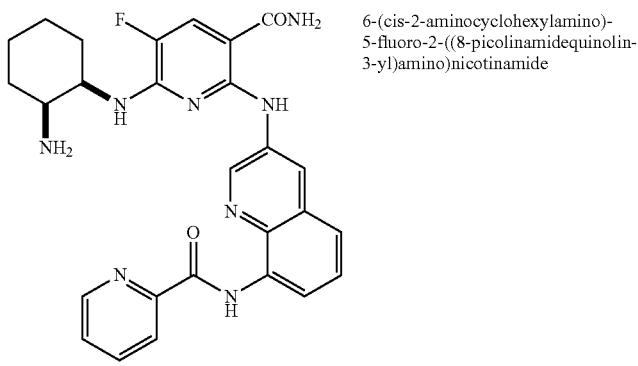 | 6-(cis-2-aminocyclohexylamino)-5-fluoro-2-((8-picolinamidequinolin-3-yl)amino)nicotinamide |
| Example 41-11 | 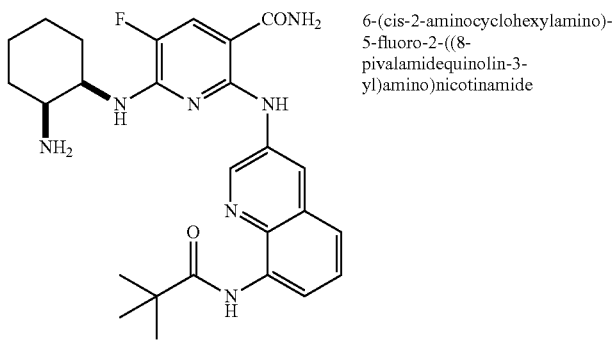 | 6-(cis-2-aminocyclohexylamino)-5-fluoro-2-((8-pivalamidequinolin-3-yl)amino)nicotinamide |
| Example 41-12 | 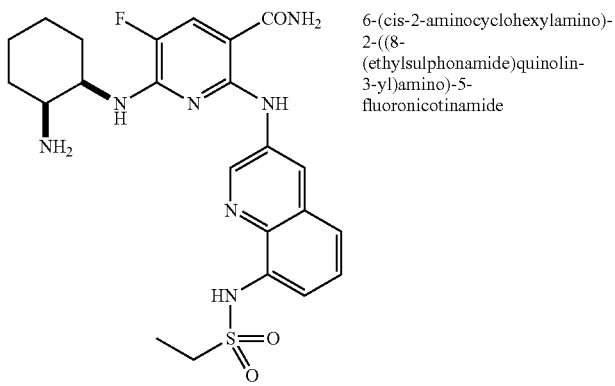 | 6-(cis-2-aminocyclohexylamino)-2-((8-(ethylsulphonamide)quinolin-3-yl)amino)-5-fluoronicotinamide |

| Number | Salt | Solvent | NMR | 1HNMR | Mass (M + H) | Mass (M − H) | rt(min) |
| --- | --- | --- | --- | --- | --- | --- | --- |
| Example 41-1 | HCl | | | | 410 | 408 | 0.77 |
| Example 41-2 (Example 40) | HCl | | | | 488 | 486 | 0.95 |
| Example 41-3 | HCl | | | | 522 | 520 | 1.05 |
| Example 41-4 | HCl | | | | 564 | 562 | 1.21 |

TABLE 20-continued

| | | | | |
|---|---|---|---|---|
| Example 41-5 | HCl | 580 | 578 | 1.16 |
| Example 41-6 | HCl | 584 | 582 | 1.25 |
| Example 41-7 | HCl | 618 | 616 | 1.29 |
| Example 41-8 | HCl | 551 | 549 | 1.02 |
| Example 41-9 | HCl | 564 | 562 | 1.17 |
| Example 41-10 | HCl | 515 | 513 | 1.15 |
| Example 41-11 | HCl | 494 | 492 | 1.18 |
| Example 41-12 | HCl | 502 | 500 | 1.01 |

Example 42

[Formula 510]

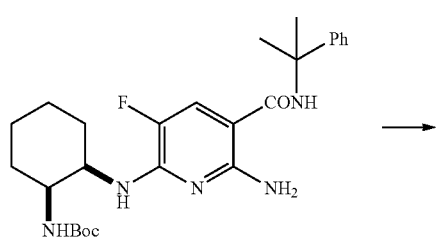

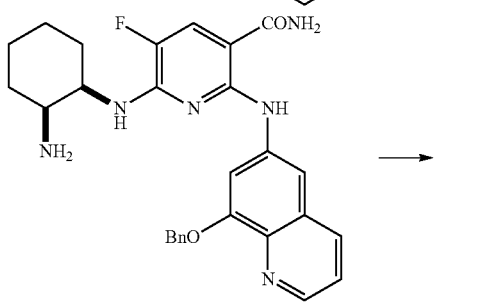

1st Step

The following compound was obtained as described in the 1st step of Example 40.

tert-Butyl((cis)-2-((6-((8-(benzyloxy)quinolin-6-yl)amino)-3-fluoro-5-((2-phenylpro pan-2-yl)carbamoyl)pyridin-2-yl)amino)cyclohexyl)carbamate MS (ESI m/z): 720 (M+H), 718 (M−H)
RT (min): 1.75

2nd Step

The following compound was obtained as described in the 2nd step of Example 1.

6-(((cis)-2-aminocyclohexyl)amino)-2-((8-(benzyloxy)quinolin-6-yl)amino)-5-fluoronicotinamide MS (ESI m/z): 502 (M+H)
RT (min): 0.87

3rd Step

A methanol (5 ml) solution containing 6-(((cis)-2-aminocyclohexyl)amino)-2-((8-(benzyloxy)quinolin-6-yl)amino)-5-fluoronicotinamide (20 mg) was prepared and was subjected to a hydrogenation reaction (room temperature; 1 bar; flow rate: 1 ml/min; 20% Pd(OH)$_2$/C) using H-cube™. Then, the solvent was distilled away under reduced pressure. The residue was dissolved in ethyl acetate, 4M hydrogen chloride/1,4-dioxane (50 μl) was added, the resulting precipitate was collected by filtration, and a yellow solid of 6-(((cis)-2-aminocyclohexyl)amino)-5-fluoro-2-((8-hydroxyquinolin-6-yl)amino)nicotinamide (12 mg) was thus obtained.

6-(((cis)-2-aminocyclohexyl)amino)-5-fluoro-2-((8-hydroxyquinolin-6-yl)amino)nicotinamide MS (ESI m/z): 411 (M+H)
RT (min): 0.66

Example 43

[Formula 511]

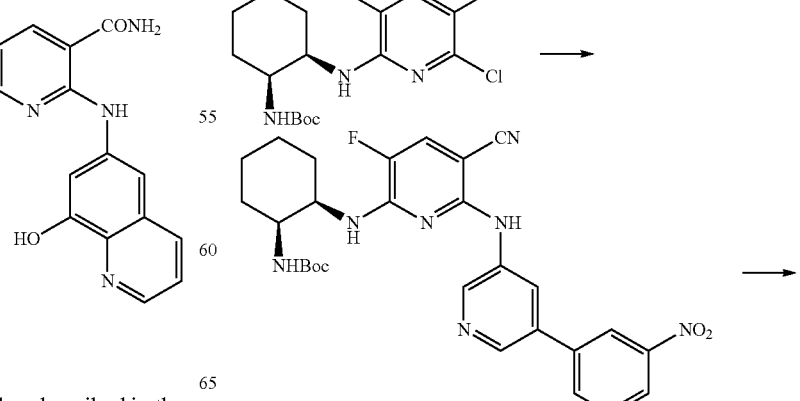

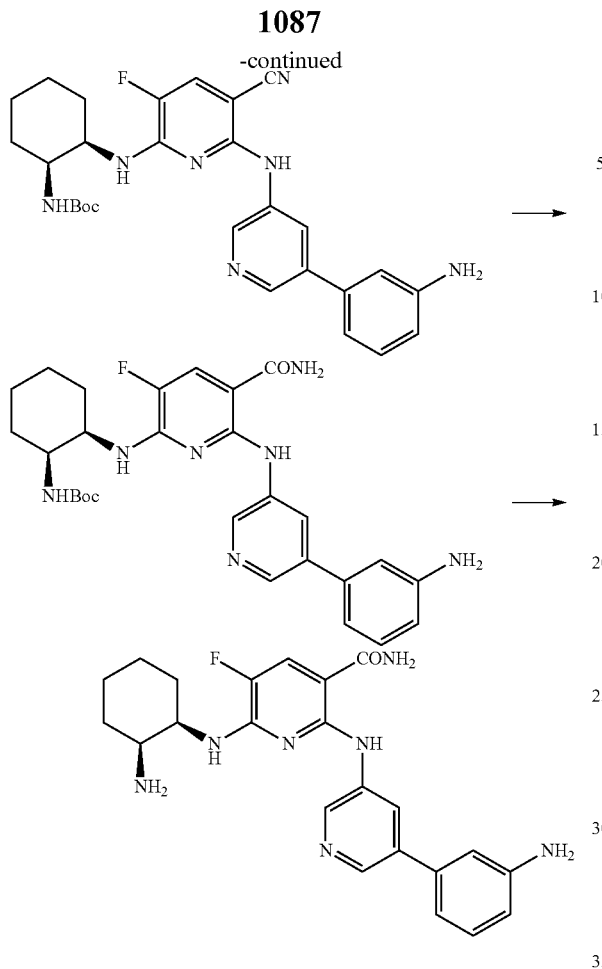

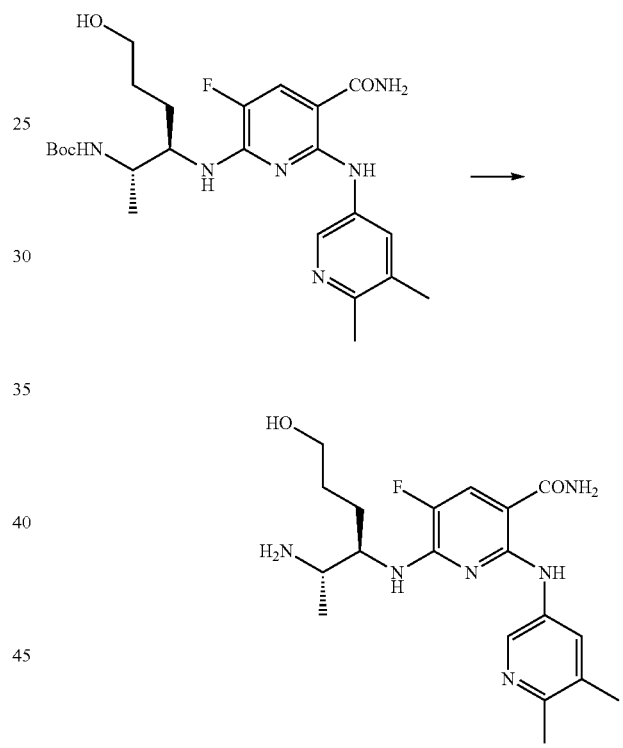

1st Step

The following compound was obtained as described in the 1st step of Example 5.

tert-Butyl((1S,2R)-2-((5-cyano-3-fluoro-6-((5-(3-nitrophenyl)pyridin-3-yl)amino)pyridin-2-yl)amino)cyclohexyl)carbamate MS (ESI m/z): 548 (M+H)
RT (min): 1.69

2nd Step

Ammonium formate (0.2 g) and 10% Pd/C (0.2 g) were added to a methanol (10 ml) solution containing tert-butyl ((1S,2R)-2-((5-cyano-3-fluoro-6-((5-(3-nitrophenyl)pyridin-3-yl)amino)pyridin-2-yl)amino)cyclohexyl)carbamate (87 mg), followed by reflux with heating for 30 minutes. The reaction mixture was cooled to room temperature and filtered with Celite, the solvent was distilled away under reduced pressure, and a yellow solid of tert-butyl((1S,2R)-2-((6-((5-(3-aminophenyl)pyridin-3-yl)amino)-5-cyano-3-fluoropyridin-2-yl)amino)cyclohexyl)carbamate (90 mg) was thus obtained.

MS (ESI m/z): 518 (M+H)
RT (min): 1.32

3rd Step

The following compound was obtained as described in the 2nd step of Example 5.

tert-Butyl((1S,2R)-2-((6-((5-(3-aminophenyl)pyridin-3-yl)amino)-5-carbamoyl-3-fluoropyridin-2-yl)amino)cyclohexyl)carbamate MS (ESI m/z): 536 (M+H)
RT (min): 1.18

4th Step

The following compound was obtained as described in the 2nd step of Example 1.

6-(((1R,2S)-2-aminocyclohexyl)amino)-2-((5-(3-aminophenyl)pyridin-3-yl)amino)-5-fluoronicotinamide MS (ESI m/z): 436 (M+H)
RT (min): 0.70

Example 44

[Formula 512]

The following compound was obtained as described in the 3rd step of Example 5.

6-(((2S,3R)-2-amino-6-hydroxyhexan-3-yl)amino)-2-((5,6-dimethylpyridin-3-yl)amino)-5-fluoronicotinamide $^1$H-NMR (DMSO-$d_6$, 300 MHz) δ:12.20 (d, 1H, J=6.6 Hz), 9.38 (s, 1H), 8.25-7.86 (m, 6H), 7.55-7.43 (m, 1H), 7.40-7.25 (m, 1H), 4.45-4.25 (m, 2H), 3.49-3.34 (m, 1H), 2.82-2.67 (m, 2H), 2.63 (s, 3H), 2.39 (s, 3H), 1.80-1.32 (m, 4H), 1.25 (d, 3H, J=5.9 Hz).

MS (ESI m/z): 391 (M+H)
RT (min): 0.51

Example 45

[Formula 513]

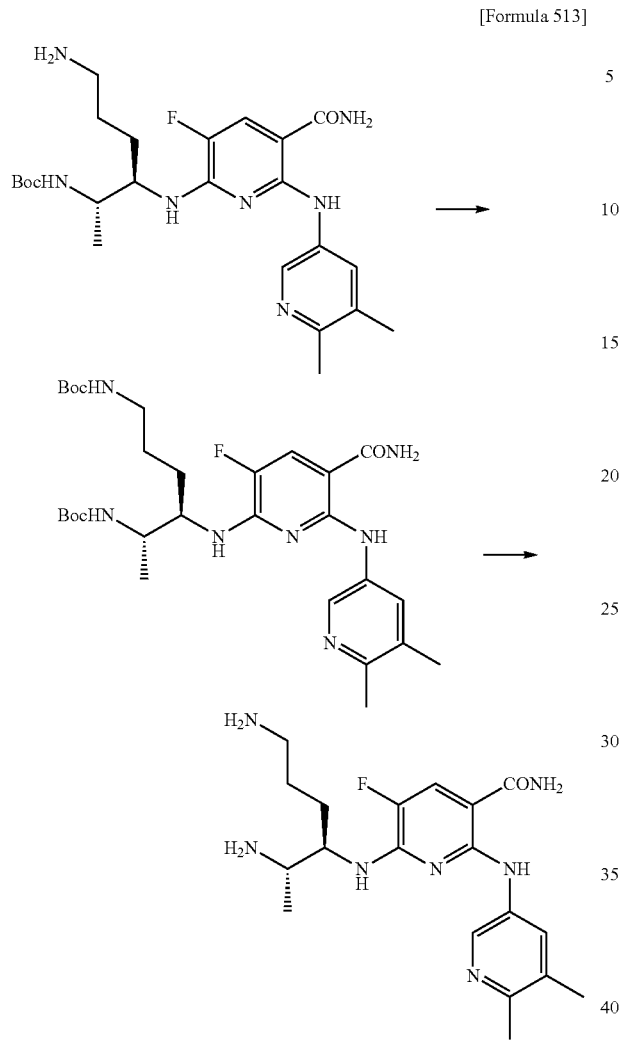

1st Step

N,N-diisopropylethylamine (3.4 ul) and di-tert-butyl dicarbonate (4.4 mg) were added to a tetrahydrofuran solution (1 ml) containing tert-butyl((2S,3R)-6-amino-3-((5-carbamoyl-6-((5,6-dimethylpyridin-3-yl)amino)-3-fluoropyridin-2-yl)amino)hexan-2-yl)carbamate (7 mg), followed by stirring at room temperature for 15 minutes. The solvent was distilled away under reduced pressure, the residue was purified by silica gel chromatography (ethyl acetate) and used in the subsequent reaction.

2nd Step

The following compound was obtained as described in the 3rd step of Example 5.

6-(((2S,3R)-2-amino-6-aminohexan-3-yl)amino)-2-((5,6-dimethylpyridin-3-yl)amino)-5-fluoronicotinamide $^1$H-NMR (DMSO-$d_6$) δ: 12.20 (s, 1H), 9.40 (s, 1H), 8.26-7.34 (m, 11H), 4.40 (s, 2H), 3.49-3.34 (m, 1H), 2.62 (s, 3H), 2.39 (s, 3H), 1.86-1.50 (m, 4H), 1.26 (d, 3H, J=6.6 Hz)

MS (ESI m/z): 390 (M+H)

RT (min): 0.35

Example 46

[Formula 514]

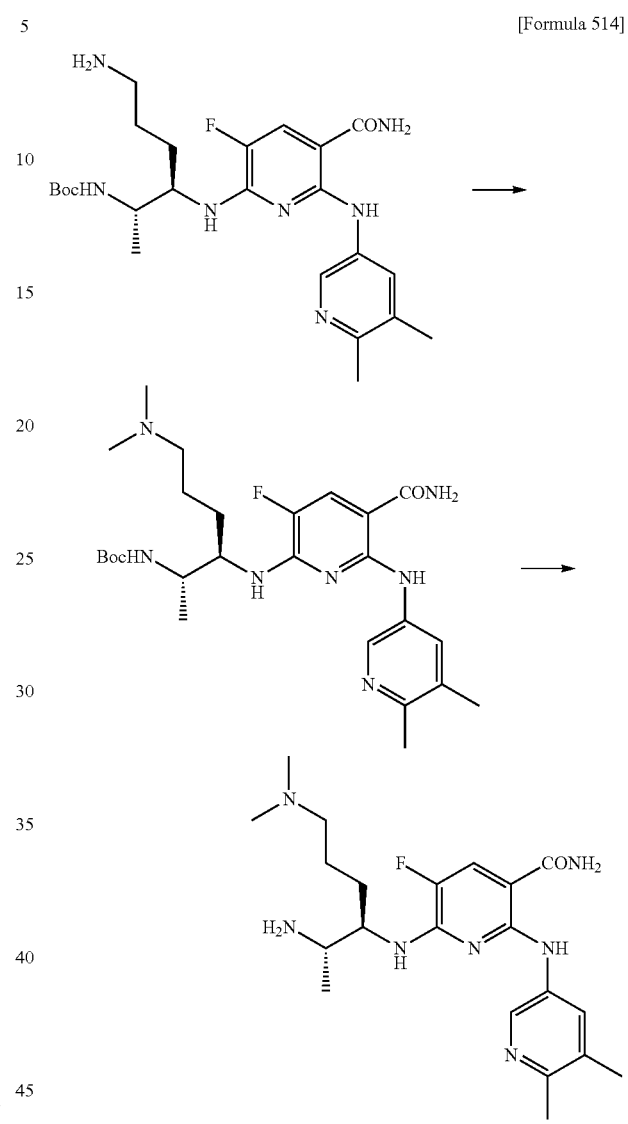

1st Step

Sodium triacetoxyborohydride (10.6 mg) was added to a mixture of tert-butyl((2S,3R)-6-amino-3-((5-carbamoyl-6-((5,6-dimethylpyridin-3-yl)amino)-3-fluoropyridin-2-yl)amino)hexan-2-yl)carbamate (7 mg), chloroform (1 ml), and a 35% formaldehyde aqueous solution (6.0 ul), followed by stirring at room temperature for 15 minutes. The solvent was distilled away under reduced pressure, the residue was purified by silica gel chromatography (ethyl acetate:methanol=9:1) and used in the subsequent reaction.

2nd Step

The following compound was obtained as described in the 3rd step of Example 5.

6-(((2S,3R)-2-amino-6-(dimethylamino)hexan-3-yl)amino)-2-((5,6-dimethylpyridin-3-yl)amino)-5-fluoronicotinamide $^1$H-NMR (DMSO-$d_6$) δ:12.17 (s, 1H), 9.95-9.70 (m, 1H), 9.45-9.25 (m, 1H), 8.30-7.84 (m, 5H), 7.55-7.25 (m, 2H), 4.45-4.35 (m, 1H), 3.49-3.34 (m, 1H), 3.07-2.95 (m, 2H), 2.73-2.62 (m, 9H), 2.39 (s, 3H), 1.82-1.58 (m, 4H), 1.26 (d, 3H, J=6.6 Hz)

MS (ESI m/z): 417 (M+H)

RT (min): 0.43

Example 47

[Formula 515]

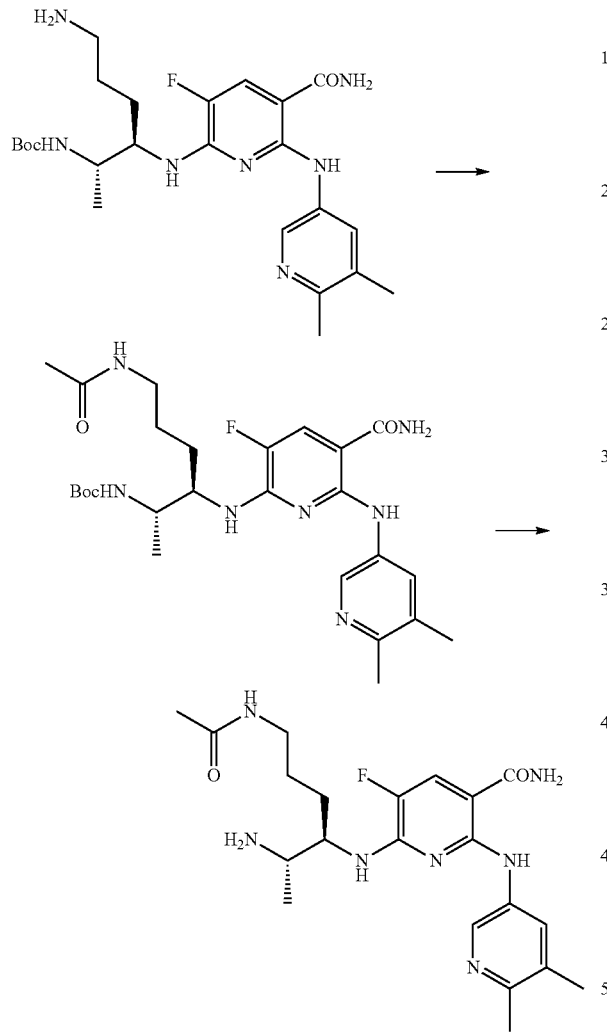

1st Step

Acetyl chloride (1.2 μl) was added to a mixture of tert-butyl ((2S,3R)-6-amino-3-((5-carbamoyl-6-((5,6-dimethylpyridin-3-yl)amino)-3-fluoropyridin-2-yl)amino)hexan-2-yl)carbamate (7 mg), dichloromethane (1 ml), and N,N-diisopropylethylamine (3.4 ul), followed by stirring at room temperature for 15 minutes. The solvent was distilled away under reduced pressure, the residue was purified by silica gel chromatography (ethyl acetate:methanol=9:1) and used in the subsequent reaction.

2nd Step

The following compound was obtained as described in the 3rd step of Example 5.

6-(((2S,3R)-6-acetamide-2-aminohexan-3-yl)amino)-2-((5,6-dimethylpyridin-3-yl)amino)-5-fluoronicotinamide $^1$H-NMR (DMSO-$d_6$) δ:12.19 (s, 1H), 9.38 (s, 1H), 8.20-7.78 (m, 7H), 7.55-7.25 (m, 2H), 4.45-4.30 (m, 1H), 3.49-3.34 (m, 1H), 3.05-2.90 (m, 2H), 2.65 (s, 3H), 2.39 (s, 3H), 1.80-1.30 (m, 7H), 1.24 (d, 3H, J=6.6 Hz)

MS (ESI m/z): 432 (M+H)

RT (min): 0.53

Test Example 1

Syk Enzyme Assay

Table 21 shows the results of a test performed according to the test method described in "syk enzyme assay" in Test Example 1. In addition, the following are standards for evaluating $IC_{50}$ of Syk-inhibitory activity used in Table 21.

A: Up to 10 nM
B: 10 to 50 nM
C: 50 to 100 nM
D: 100 to 1000 nM

The set of numbers (XYZ-xyz) given in each Example number column indicates the corresponding Example number (Example XYZ-xyz) in Table 21.

TABLE 21

| | |
|---|---|
| 002-001 | A |
| 002-002 | C |
| 002-003 | A |
| 002-004 | A |
| 002-005 | B |
| 002-006 | A |
| 002-007 | B |
| 002-009 | B |
| 002-010 | C |
| 002-011 | D |
| 002-012 | D |
| 002-013 | A |
| 002-014 | A |
| 002-015 | A |
| 002-016 | A |
| 002-017 | B |
| 002-018 | A |
| 002-019 | B |
| 002-020 | B |
| 002-021 | B |
| 002-022 | B |
| 002-023 | A |
| 002-024 | A |
| 002-025 | A |
| 002-026 | A |
| 002-027 | A |
| 002-028 | A |
| 002-029 | B |
| 002-030 | A |
| 002-031 | A |
| 002-032 | A |
| 002-033 | A |
| 002-034 | A |
| 002-035 | B |
| 002-036 | C |
| 002-037 | A |
| 002-038 | A |
| 002-039 | B |
| 002-040 | B |
| 002-041 | A |
| 002-042 | B |
| 002-043 | B |
| 002-044 | B |
| 002-045 | B |
| 002-046 | A |
| 002-047 | B |

TABLE 21-continued

| | |
|---|---|
| 002-048 | A |
| 002-049 | B |
| 002-050 | B |
| 002-051 | A |
| 002-052 | A |
| 002-053 | A |
| 002-054 | B |
| 002-055 | A |
| 002-056 | B |
| 002-057 | A |
| 002-058 | A |
| 002-059 | B |
| 002-060 | A |
| 002-061 | A |
| 002-062 | A |
| 002-063 | A |
| 002-064 | D |
| 002-065 | A |
| 002-066 | A |
| 002-067 | B |
| 002-068 | A |
| 002-069 | A |
| 002-070 | A |
| 002-071 | B |
| 002-072 | B |
| 002-073 | B |
| 002-074 | C |
| 002-075 | B |
| 002-076 | C |
| 002-077 | C |
| 002-078 | B |
| 002-079 | C |
| 002-080 | D |
| 002-081 | B |
| 002-082 | A |
| 002-083 | A |
| 002-084 | A |
| 002-085 | B |
| 002-086 | B |
| 002-087 | B |
| 002-088 | A |
| 002-089 | B |
| 002-090 | A |
| 002-091 | A |
| 002-092 | A |
| 002-093 | A |
| 002-094 | B |
| 002-095 | A |
| 002-096 | B |
| 002-097 | A |
| 002-098 | A |
| 002-099 | A |
| 002-100 | A |
| 002-101 | A |
| 002-102 | B |
| 002-103 | A |
| 002-104 | A |
| 002-105 | B |
| 002-106 | C |
| 002-107 | A |
| 002-108 | B |
| 002-109 | B |
| 002-110 | A |
| 002-111 | B |
| 002-112 | A |
| 002-113 | A |
| 002-114 | A |
| 002-115 | B |
| 002-116 | C |
| 002-117 | A |
| 002-118 | B |
| 002-119 | A |
| 002-120 | A |
| 002-121 | D |
| 002-122 | A |
| 002-123 | A |
| 002-124 | A |
| 002-125 | A |
| 002-126 | A |
| 002-127 | B |

TABLE 21-continued

| | |
|---|---|
| 002-128 | D |
| 002-129 | D |
| 002-130 | D |
| 002-131 | A |
| 002-132 | B |
| 002-133 | A |
| 002-134 | A |
| 002-135 | B |
| 002-136 | C |
| 002-137 | A |
| 002-138 | C |
| 002-139 | A |
| 002-140 | A |
| 002-141 | A |
| 002-142 | A |
| 002-143 | A |
| 002-144 | A |
| 002-145 | A |
| 002-146 | A |
| 002-147 | A |
| 002-148 | B |
| 002-149 | B |
| 002-150 | B |
| 002-151 | B |
| 002-152 | B |
| 002-153 | B |
| 002-154 | B |
| 002-155 | B |
| 002-156 | C |
| 002-157 | D |
| 002-158 | D |
| 002-159 | D |
| 002-160 | B |
| 002-161 | C |
| 002-162 | D |
| 002-163 | B |
| 002-164 | C |
| 002-165 | B |
| 002-166 | D |
| 002-167 | B |
| 002-168 | B |
| 002-169 | B |
| 002-170 | B |
| 002-171 | C |
| 002-172 | B |
| 002-173 | B |
| 002-174 | C |
| 002-175 | A |
| 002-176 | A |
| 002-177 | A |
| 002-178 | A |
| 002-179 | C |
| 002-180 | C |
| 002-181 | C |
| 002-182 | D |
| 002-183 | A |
| 002-184 | A |
| 002-185 | A |
| 002-186 | A |
| 002-187 | A |
| 002-188 | A |
| 002-189 | A |
| 002-190 | A |
| 002-191 | A |
| 002-192 | A |
| 002-193 | A |
| 002-194 | A |
| 002-195 | A |
| 002-196 | A |
| 002-197 | A |
| 002-198 | A |
| 002-199 | A |
| 002-200 | A |
| 002-201 | A |
| 002-202 | D |
| 002-203 | B |
| 002-204 | A |
| 002-205 | A |
| 002-206 | A |
| 002-207 | A |

TABLE 21-continued

| | |
|---|---|
| 002-208 | A |
| 002-209 | A |
| 002-210 | A |
| 004-001 | D |
| 004-002 | B |
| 004-003 | B |
| 004-004 | B |
| 004-005 | A |
| 004-006 | A |
| 004-007 | A |
| 004-008 | A |
| 004-009 | A |
| 004-010 | B |
| 004-011 | B |
| 004-012 | A |
| 004-013 | A |
| 004-014 | A |
| 004-015 | D |
| 004-016 | A |
| 004-017 | B |
| 004-018 | B |
| 004-019 | B |
| 004-020 | A |
| 004-021 | D |
| 004-022 | B |
| 004-024 | C |
| 004-025 | A |
| 004-026 | A |
| 004-027 | B |
| 004-028 | A |
| 004-029 | A |
| 004-030 | A |
| 004-031 | A |
| 004-032 | A |
| 004-033 | A |
| 004-034 | C |
| 004-035 | A |
| 004-036 | A |
| 004-037 | A |
| 004-038 | A |
| 004-039 | A |
| 004-040 | A |
| 004-041 | C |
| 004-042 | A |
| 004-043 | D |
| 004-044 | A |
| 004-045 | B |
| 004-046 | A |
| 004-047 | B |
| 004-048 | B |
| 004-049 | A |
| 004-050 | B |
| 004-051 | A |
| 004-052 | B |
| 004-053 | A |
| 004-054 | A |
| 004-055 | A |
| 004-056 | A |
| 004-057 | A |
| 004-058 | A |
| 004-059 | A |
| 004-060 | A |
| 004-061 | A |
| 004-062 | A |
| 004-063 | A |
| 004-064 | D |
| 004-065 | A |
| 004-066 | A |
| 004-067 | A |
| 004-068 | A |
| 004-069 | A |
| 004-070 | A |
| 004-071 | A |
| 004-072 | A |
| 004-073 | A |
| 004-074 | A |
| 004-075 | A |
| 004-076 | A |
| 004-077 | A |
| 004-078 | A |
| 004-079 | A |
| 004-080 | A |
| 004-081 | A |
| 004-082 | A |
| 004-083 | A |
| 004-084 | A |
| 004-085 | A |
| 004-086 | A |
| 004-087 | A |
| 004-088 | A |
| 004-089 | A |
| 004-090 | B |
| 004-091 | A |
| 004-092 | A |
| 004-093 | A |
| 004-094 | A |
| 004-095 | A |
| 004-096 | B |
| 004-097 | A |
| 004-098 | B |
| 004-099 | A |
| 004-100 | A |
| 004-101 | B |
| 004-102 | C |
| 004-103 | B |
| 004-104 | B |
| 004-105 | B |
| 004-106 | A |
| 004-107 | B |
| 004-108 | D |
| 004-109 | A |
| 004-110 | A |
| 004-111 | A |
| 004-112 | A |
| 004-113 | A |
| 004-114 | A |
| 004-115 | A |
| 004-116 | A |
| 004-117 | A |
| 004-118 | A |
| 004-119 | A |
| 004-120 | A |
| 004-121 | A |
| 004-122 | A |
| 004-123 | A |
| 004-124 | A |
| 004-125 | A |
| 004-126 | B |
| 004-127 | A |
| 004-128 | A |
| 004-129 | A |
| 004-130 | D |
| 004-131 | B |
| 004-132 | B |
| 004-133 | B |
| 004-134 | B |
| 004-135 | B |
| 004-136 | A |
| 004-137 | A |
| 004-138 | A |
| 004-139 | A |
| 004-140 | B |
| 004-141 | A |
| 004-142 | B |
| 004-143 | A |
| 004-144 | A |
| 004-145 | A |
| 004-146 | A |
| 004-147 | A |
| 004-148 | B |
| 004-149 | A |
| 004-150 | D |
| 004-151 | D |
| 004-152 | D |
| 004-153 | D |
| 004-154 | D |
| 004-155 | A |
| 004-156 | A |
| 004-157 | B |
| 004-158 | B |

TABLE 21-continued

| | |
|---|---|
| 004-159 | A |
| 004-160 | B |
| 004-161 | B |
| 004-162 | A |
| 004-163 | A |
| 004-164 | A |
| 004-165 | A |
| 004-166 | A |
| 004-167 | A |
| 004-168 | A |
| 004-169 | A |
| 004-170 | A |
| 004-171 | A |
| 004-172 | A |
| 004-173 | A |
| 004-174 | A |
| 004-175 | A |
| 004-176 | A |
| 004-177 | B |
| 004-178 | B |
| 004-179 | A |
| 004-180 | B |
| 004-181 | A |
| 004-182 | A |
| 004-183 | C |
| 004-184 | B |
| 004-185 | A |
| 004-186 | A |
| 004-187 | A |
| 004-188 | B |
| 004-189 | C |
| 004-190 | A |
| 004-191 | B |
| 004-192 | C |
| 004-193 | C |
| 004-194 | B |
| 004-195 | A |
| 004-196 | A |
| 004-197 | A |
| 004-198 | A |
| 004-199 | A |
| 004-200 | A |
| 004-201 | A |
| 004-202 | A |
| 004-203 | A |
| 004-204 | A |
| 004-205 | A |
| 004-206 | A |
| 004-207 | A |
| 004-208 | A |
| 004-209 | A |
| 004-210 | A |
| 004-211 | D |
| 004-212 | B |
| 004-213 | B |
| 004-214 | B |
| 004-215 | A |
| 004-216 | B |
| 004-217 | A |
| 004-218 | A |
| 004-219 | A |
| 004-220 | A |
| 004-221 | A |
| 004-222 | A |
| 004-223 | A |
| 004-224 | A |
| 004-225 | B |
| 004-226 | A |
| 004-227 | A |
| 004-228 | B |
| 004-229 | A |
| 004-230 | B |
| 004-231 | B |
| 004-232 | A |
| 004-233 | D |
| 004-234 | B |
| 004-235 | A |
| 006-002 | D |
| 006-003 | D |
| 006-005 | D |

TABLE 21-continued

| | |
|---|---|
| 006-006 | D |
| 006-007 | C |
| 006-008 | D |
| 006-009 | D |
| 006-010 | C |
| 006-011 | D |
| 006-018 | C |
| 006-020 | D |
| 006-021 | B |
| 006-022 | D |
| 006-023 | B |
| 006-024 | D |
| 006-025 | D |
| 006-026 | A |
| 006-027 | D |
| 006-028 | D |
| 006-029 | D |
| 006-030 | C |
| 006-031 | D |
| 006-032 | C |
| 006-033 | B |
| 006-034 | A |
| 006-035 | A |
| 006-036 | D |
| 006-037 | C |
| 006-038 | A |
| 006-039 | A |
| 006-040 | A |
| 006-041 | A |
| 006-042 | D |
| 006-044 | B |
| 006-045 | B |
| 006-046 | B |
| 006-047 | A |
| 006-048 | D |
| 006-049 | A |
| 006-050 | B |
| 006-051 | B |
| 006-052 | A |
| 006-053 | A |
| 006-054 | A |
| 006-055 | A |
| 006-056 | A |
| 006-057 | B |
| 006-058 | B |
| 006-059 | A |
| 006-060 | A |
| 006-061 | A |
| 006-062 | A |
| 006-063 | A |
| 006-064 | B |
| 006-065 | A |
| 006-067 | C |
| 006-068 | A |
| 006-070 | A |
| 006-071 | A |
| 006-072 | B |
| 006-073 | A |
| 006-074 | D |
| 006-075 | A |
| 006-076 | A |
| 006-077 | B |
| 006-078 | A |
| 006-079 | A |
| 006-080 | A |
| 006-081 | A |
| 006-082 | A |
| 006-083 | A |
| 006-084 | A |
| 006-085 | A |
| 006-086 | A |
| 006-087 | A |
| 006-088 | B |
| 006-089 | B |
| 006-090 | D |
| 006-091 | B |
| 006-092 | A |
| 006-093 | A |
| 006-094 | B |
| 006-095 | D |

TABLE 21-continued

| | |
|---|---|
| 006-096 | B |
| 006-097 | A |
| 006-098 | A |
| 006-099 | B |
| 006-100 | A |
| 006-101 | B |
| 006-102 | B |
| 006-103 | A |
| 006-104 | A |
| 006-107 | A |
| 006-108 | B |
| 006-109 | A |
| 006-110 | A |
| 006-111 | A |
| 006-112 | A |
| 006-113 | A |
| 006-114 | A |
| 006-115 | D |
| 006-116 | A |
| 006-118 | D |
| 006-119 | B |
| 006-120 | B |
| 006-121 | A |
| 006-122 | A |
| 006-123 | A |
| 006-124 | A |
| 006-125 | A |
| 006-126 | A |
| 006-127 | B |
| 006-128 | B |
| 006-129 | A |
| 006-130 | B |
| 006-131 | A |
| 006-132 | A |
| 006-133 | B |
| 006-134 | B |
| 006-135 | A |
| 006-136 | A |
| 006-137 | B |
| 006-138 | B |
| 006-139 | B |
| 006-140 | C |
| 006-141 | D |
| 006-142 | A |
| 006-143 | A |
| 006-144 | A |
| 006-145 | A |
| 006-146 | A |
| 006-147 | A |
| 006-148 | A |
| 006-149 | B |
| 006-150 | B |
| 006-151 | B |
| 006-152 | B |
| 006-153 | A |
| 006-154 | A |
| 006-155 | A |
| 006-156 | A |
| 006-157 | A |
| 006-158 | B |
| 006-159 | A |
| 006-160 | A |
| 006-161 | A |
| 006-162 | C |
| 006-163 | A |
| 006-164 | B |
| 006-165 | B |
| 006-166 | A |
| 006-167 | A |
| 006-168 | A |
| 006-169 | A |
| 006-170 | A |
| 006-171 | A |
| 006-172 | A |
| 006-173 | A |
| 006-174 | A |
| 006-175 | B |
| 006-176 | A |
| 006-177 | A |
| 006-178 | A |
| 006-179 | C |
| 006-180 | A |
| 006-181 | D |
| 006-182 | A |
| 006-183 | A |
| 006-184 | A |
| 006-185 | B |
| 006-186 | A |
| 006-187 | A |
| 006-188 | A |
| 006-189 | B |
| 006-190 | A |
| 006-191 | B |
| 006-192 | B |
| 006-193 | A |
| 006-194 | B |
| 006-195 | A |
| 006-196 | B |
| 006-197 | B |
| 006-198 | A |
| 006-199 | A |
| 006-200 | A |
| 006-201 | A |
| 006-202 | C |
| 006-203 | D |
| 006-204 | A |
| 006-205 | A |
| 006-206 | A |
| 006-207 | A |
| 006-208 | A |
| 006-209 | A |
| 006-210 | A |
| 006-211 | A |
| 006-212 | A |
| 006-213 | A |
| 006-214 | A |
| 006-215 | A |
| 006-216 | B |
| 006-217 | A |
| 006-218 | A |
| 006-219 | A |
| 006-220 | A |
| 006-221 | A |
| 006-222 | A |
| 006-223 | A |
| 006-224 | B |
| 006-225 | B |
| 006-226 | A |
| 006-227 | A |
| 006-228 | A |
| 006-229 | A |
| 006-230 | B |
| 006-231 | A |
| 006-232 | A |
| 006-233 | B |
| 006-234 | A |
| 006-235 | B |
| 006-236 | A |
| 006-237 | A |
| 006-238 | A |
| 006-239 | A |
| 006-240 | A |
| 006-241 | A |
| 006-242 | A |
| 006-243 | B |
| 006-244 | A |
| 006-245 | A |
| 006-246 | B |
| 006-247 | A |
| 006-248 | A |
| 006-249 | A |
| 006-250 | A |
| 006-251 | A |
| 006-252 | A |
| 006-253 | B |
| 006-254 | B |
| 006-255 | A |
| 006-256 | A |
| 006-257 | A |
| 006-258 | C |

TABLE 21-continued

| | |
|---|---|
| 006-259 | A |
| 006-260 | A |
| 006-261 | A |
| 006-262 | A |
| 006-263 | A |
| 006-264 | A |
| 006-265 | B |
| 006-266 | A |
| 006-267 | A |
| 006-268 | A |
| 006-269 | B |
| 006-270 | A |
| 006-271 | A |
| 006-272 | B |
| 006-273 | D |
| 006-274 | A |
| 006-275 | A |
| 006-276 | A |
| 006-277 | A |
| 006-278 | A |
| 006-279 | A |
| 006-280 | A |
| 006-281 | A |
| 006-282 | A |
| 006-283 | B |
| 006-284 | A |
| 006-285 | A |
| 006-286 | A |
| 006-287 | A |
| 006-288 | A |
| 006-289 | A |
| 006-290 | A |
| 006-291 | B |
| 006-292 | A |
| 006-293 | A |
| 006-294 | B |
| 006-295 | B |
| 006-296 | A |
| 006-297 | A |
| 006-298 | A |
| 006-299 | A |
| 006-300 | A |
| 006-301 | B |
| 006-302 | B |
| 006-303 | A |
| 006-304 | A |
| 006-305 | B |
| 006-306 | A |
| 006-307 | A |
| 006-308 | A |
| 006-309 | A |
| 006-310 | A |
| 006-311 | A |
| 006-312 | A |
| 006-313 | A |
| 006-314 | A |
| 006-315 | A |
| 006-316 | B |
| 006-317 | A |
| 006-318 | B |
| 006-319 | B |
| 006-320 | C |
| 006-321 | A |
| 006-322 | A |
| 006-323 | A |
| 006-324 | A |
| 006-325 | A |
| 006-326 | A |
| 006-327 | A |
| 006-328 | A |
| 006-329 | A |
| 006-330 | A |
| 006-331 | A |
| 006-332 | A |
| 006-333 | A |
| 006-334 | A |
| 006-335 | A |
| 006-336 | A |
| 006-337 | B |
| 006-338 | B |

TABLE 21-continued

| | |
|---|---|
| 006-339 | B |
| 006-340 | A |
| 006-341 | B |
| 006-342 | A |
| 006-343 | A |
| 006-344 | A |
| 006-345 | A |
| 006-346 | A |
| 006-347 | B |
| 006-348 | B |
| 006-349 | A |
| 006-350 | A |
| 006-351 | A |
| 006-352 | A |
| 006-353 | A |
| 006-354 | A |
| 006-355 | A |
| 006-356 | A |
| 006-357 | B |
| 006-358 | A |
| 006-359 | A |
| 006-360 | A |
| 006-361 | A |
| 006-362 | A |
| 006-363 | A |
| 006-364 | A |
| 006-365 | A |
| 006-366 | C |
| 006-367 | B |
| 006-368 | A |
| 006-369 | A |
| 006-370 | A |
| 006-371 | A |
| 006-372 | B |
| 006-373 | A |
| 006-374 | B |
| 006-375 | A |
| 006-376 | A |
| 006-377 | A |
| 006-378 | A |
| 006-379 | A |
| 006-380 | B |
| 006-381 | B |
| 006-382 | B |
| 006-383 | A |
| 006-384 | A |
| 006-385 | A |
| 006-386 | A |
| 006-387 | A |
| 006-388 | A |
| 006-389 | A |
| 006-390 | A |
| 006-391 | B |
| 006-392 | A |
| 006-393 | B |
| 006-394 | A |
| 006-395 | B |
| 006-396 | A |
| 006-397 | A |
| 006-398 | A |
| 006-399 | A |
| 006-400 | A |
| 006-401 | B |
| 006-402 | A |
| 006-403 | B |
| 006-404 | A |
| 006-405 | A |
| 006-406 | A |
| 006-407 | A |
| 006-408 | A |
| 006-409 | A |
| 006-410 | A |
| 006-411 | A |
| 006-412 | A |
| 006-413 | A |
| 006-414 | A |
| 006-415 | A |
| 006-416 | A |
| 006-417 | A |
| 006-418 | A |

TABLE 21-continued

| | |
|---|---|
| 006-419 | A |
| 006-420 | A |
| 006-421 | C |
| 006-422 | A |
| 006-423 | B |
| 006-424 | B |
| 006-425 | B |
| 006-426 | D |
| 006-428 | C |
| 006-429 | A |
| 006-430 | A |
| 006-431 | B |
| 006-432 | B |
| 006-433 | A |
| 006-434 | C |
| 006-435 | A |
| 006-436 | B |
| 006-437 | B |
| 006-438 | B |
| 006-439 | B |
| 006-440 | B |
| 006-441 | B |
| 006-442 | A |
| 006-443 | A |
| 006-444 | C |
| 006-445 | A |
| 006-446 | B |
| 006-447 | B |
| 006-448 | C |
| 006-449 | C |
| 006-450 | D |
| 006-451 | A |
| 006-452 | A |
| 006-453 | A |
| 006-454 | A |
| 006-455 | A |
| 006-456 | A |
| 006-457 | A |
| 006-458 | A |
| 006-459 | A |
| 006-460 | A |
| 006-461 | A |
| 006-462 | A |
| 006-463 | A |
| 006-464 | A |
| 006-465 | A |
| 006-466 | B |
| 006-467 | B |
| 006-468 | A |
| 006-469 | A |
| 006-470 | B |
| 006-471 | A |
| 006-472 | A |
| 006-473 | A |
| 006-474 | A |
| 006-475 | A |
| 006-476 | A |
| 006-477 | A |
| 006-478 | A |
| 006-479 | A |
| 006-480 | A |
| 006-481 | D |
| 006-482 | A |
| 006-483 | A |
| 006-484 | B |
| 006-485 | A |
| 006-486 | A |
| 006-487 | A |
| 006-488 | A |
| 006-489 | A |
| 006-490 | C |
| 006-491 | B |
| 006-492 | B |
| 006-493 | B |
| 006-494 | B |
| 006-495 | A |
| 006-496 | A |
| 006-497 | A |
| 006-498 | A |
| 006-499 | B |
| 006-500 | B |
| 006-501 | B |
| 006-502 | A |
| 006-503 | A |
| 006-504 | C |
| 006-505 | A |
| 006-506 | A |
| 006-507 | A |
| 006-508 | A |
| 006-509 | A |
| 006-510 | A |
| 006-511 | A |
| 006-512 | A |
| 006-513 | A |
| 006-514 | C |
| 006-515 | A |
| 006-516 | A |
| 006-517 | A |
| 006-518 | C |
| 006-519 | A |
| 006-520 | A |
| 006-521 | A |
| 006-522 | A |
| 006-523 | A |
| 006-524 | A |
| 006-525 | A |
| 006-526 | A |
| 006-527 | C |
| 006-528 | B |
| 006-529 | D |
| 006-530 | A |
| 006-531 | A |
| 006-532 | D |
| 006-533 | B |
| 006-534 | D |
| 006-535 | C |
| 006-536 | D |
| 006-537 | B |
| 006-538 | A |
| 006-539 | A |
| 006-540 | A |
| 006-541 | A |
| 006-542 | A |
| 006-543 | A |
| 006-544 | A |
| 006-545 | A |
| 006-546 | A |
| 006-547 | A |
| 006-548 | A |
| 006-549 | A |
| 006-550 | A |
| 006-551 | A |
| 006-552 | B |
| 006-553 | A |
| 006-554 | B |
| 006-555 | A |
| 006-556 | A |
| 006-557 | A |
| 006-558 | A |
| 006-559 | A |
| 006-560 | B |
| 006-561 | A |
| 006-562 | A |
| 006-563 | A |
| 006-564 | D |
| 006-565 | D |
| 006-566 | D |
| 006-567 | B |
| 006-568 | C |
| 006-569 | B |
| 006-570 | B |
| 006-571 | C |
| 006-572 | B |
| 006-573 | B |
| 006-574 | B |
| 006-575 | B |
| 006-576 | A |
| 006-577 | A |
| 006-578 | A |
| 006-579 | A |

TABLE 21-continued

| | |
|---|---|
| 006-580 | A |
| 006-581 | A |
| 006-582 | A |
| 006-583 | A |
| 006-584 | A |
| 006-585 | A |
| 006-586 | A |
| 006-587 | A |
| 006-588 | A |
| 006-589 | A |
| 006-590 | A |
| 006-591 | A |
| 006-592 | A |
| 006-593 | A |
| 006-594 | A |
| 006-595 | A |
| 006-596 | A |
| 006-597 | A |
| 006-598 | A |
| 008-001 | B |
| 008-002 | B |
| 008-003 | D |
| 008-004 | A |
| 008-005 | A |
| 008-006 | A |
| 008-007 | A |
| 008-008 | A |
| 008-009 | A |
| 008-010 | A |
| 008-011 | B |
| 010-001 | A |
| 010-002 | B |
| 012-003 | D |
| 012-004 | B |
| 012-005 | B |
| 012-006 | B |
| 012-007 | D |
| 012-008 | B |
| 012-009 | A |
| 012-012 | B |
| 012-013 | B |
| 012-014 | D |
| 012-015 | C |
| 012-016 | D |
| 012-017 | D |
| 012-018 | D |
| 012-019 | C |
| 012-020 | D |
| 012-021 | A |
| 012-022 | D |
| 012-023 | D |
| 012-024 | D |
| 012-025 | B |
| 012-026 | D |
| 012-027 | C |
| 012-028 | D |
| 012-029 | D |
| 012-030 | D |
| 012-031 | B |
| 012-032 | C |
| 012-033 | B |
| 012-034 | D |
| 012-035 | D |
| 012-036 | B |
| 012-037 | C |
| 012-038 | B |
| 014-001 | A |
| 014-002 | A |
| 014-003 | C |
| 014-004 | B |
| 014-005 | A |
| 014-007 | C |
| 014-008 | D |
| 014-009 | A |
| 014-010 | B |
| 014-011 | B |
| 014-012 | C |
| 014-013 | B |
| 014-014 | A |
| 014-015 | C |

TABLE 21-continued

| | |
|---|---|
| 014-016 | A |
| 014-017 | A |
| 014-018 | B |
| 014-019 | A |
| 014-020 | D |
| 014-021 | D |
| 016-001 | D |
| 016-005 | D |
| 016-008 | D |
| 016-009 | B |
| 016-011 | D |
| 016-012 | D |
| 016-014 | D |
| 016-015 | D |
| 016-016 | D |
| 016-017 | B |
| 016-018 | D |
| 016-020 | D |
| 016-024 | D |
| 018-001 | D |
| 019-019 | D |
| 020-002 | D |
| 022-002 | D |
| 022-003 | A |
| 022-004 | D |
| 022-005 | A |
| 022-006 | C |
| 022-007 | D |
| 022-008 | D |
| 027-001 | A |
| 027-002 | B |
| 027-003 | A |
| 027-004 | A |
| 027-005 | D |
| 027-006 | D |
| 027-007 | B |
| 027-008 | B |
| 027-009 | B |
| 027-010 | B |
| 027-011 | B |
| 027-012 | C |
| 027-013 | B |
| 027-014 | B |
| 027-015 | D |
| 027-016 | D |
| 027-017 | B |
| 027-018 | C |
| 027-019 | B |
| 027-020 | B |
| 027-021 | B |
| 027-022 | B |
| 027-023 | C |
| 027-024 | B |
| 027-025 | B |
| 027-026 | C |
| 027-027 | B |
| 027-028 | B |
| 027-029 | B |
| 027-030 | B |
| 027-031 | A |
| 027-032 | A |
| 027-033 | A |
| 027-034 | B |
| 027-035 | B |
| 027-036 | A |
| 027-037 | B |
| 027-038 | B |
| 027-039 | B |
| 027-040 | B |
| 027-041 | A |
| 027-042 | A |
| 029-001 | C |
| 029-003 | B |
| 029-004 | A |
| 029-005 | A |
| 029-006 | A |
| 029-007 | B |
| 029-008 | B |
| 029-009 | D |
| 029-010 | D |

TABLE 21-continued

| | |
|---|---|
| 029-011 | D |
| 029-012 | A |
| 029-013 | B |
| 029-014 | C |
| 029-015 | C |
| 029-016 | A |
| 029-017 | A |
| 029-018 | A |
| 029-019 | A |
| 031-001 | D |
| 031-002 | D |
| 031-003 | D |
| 031-004 | B |
| 031-005 | D |
| 031-006 | D |
| 033-002 | D |
| 033-003 | D |
| 033-004 | C |
| 033-005 | D |
| 033-006 | D |
| 033-007 | D |
| 035-001 | A |
| 035-002 | A |
| 035-003 | A |
| 035-004 | A |
| 035-005 | A |
| 035-006 | A |
| 035-007 | A |
| 035-008 | A |
| 035-009 | A |
| 035-009 | B |
| 037-001 | A |
| 037-002 | A |
| 037-003 | A |
| 037-004 | A |
| 037-005 | A |
| 039-001 | A |
| 039-002 | A |
| 039-003 | A |
| 039-004 | A |
| 039-005 | C |
| 041-001 | A |
| 041-002 | A |
| 041-003 | B |
| 041-004 | C |
| 041-005 | C |
| 041-006 | C |
| 041-007 | D |
| 041-008 | B |
| 041-009 | B |
| 041-010 | A |
| 041-011 | A |
| 041-012 | A |
| 042-000 | A |
| 043-000 | A |
| 044-000 | B |
| 045-000 | D |
| 046-000 | D |
| 047-000 | C |

The concentrations of test compounds were adjusted to 100 nM. The test compounds were examined using Profiler Pro kits (Caliper) in terms of activity against each of 170 types of kinases excluding Syk. As a result, highly selective compounds (Example 6-296, Example 6-368, and Example 6-395) having kinase inhibitory rates of 75% or more with respect to only 0 to 2 types of kinases were obtained. A compound (Example 6-157) having a kinase inhibitory rate of 75% or more with respect to 12 types of kinases was also obtained. Further, an inhibitor (Example 6-373) having a kinase inhibitory rate of 75% or more with respect to 24 types of kinases was obtained.

Test Example 2

TNFα Generation Assay

Table 22 shows the test results obtained by the test method described in "TNFα generation assay" in Test Example 2. In addition, the following are used in Table 22 to denote criteria for evaluating $IC_{50}$ in TNFα generation assay.

A: Up to 65 nM
B: 65 to 130 nM
C: 130 to 200 nM

TABLE 22

| | |
|---|---|
| 002-001 | A |
| 002-003 | B |
| 002-004 | C |
| 002-005 | C |
| 002-007 | B |
| 002-013 | B |
| 002-014 | B |
| 002-015 | C |
| 002-017 | C |
| 002-020 | B |
| 002-024 | C |
| 002-025 | B |
| 002-030 | C |
| 002-032 | C |
| 002-037 | C |
| 002-038 | B |
| 002-041 | B |
| 002-042 | C |
| 002-048 | C |
| 002-053 | B |
| 002-054 | B |
| 002-055 | C |
| 002-056 | C |
| 002-057 | B |
| 002-058 | B |
| 002-059 | C |
| 002-060 | B |
| 002-066 | C |
| 002-073 | C |
| 002-097 | C |
| 002-100 | C |
| 002-110 | C |
| 002-113 | C |
| 002-114 | A |
| 002-115 | C |
| 002-117 | B |
| 002-118 | C |
| 002-123 | C |
| 002-125 | B |
| 002-126 | B |
| 002-131 | B |
| 002-134 | B |
| 002-137 | C |
| 002-139 | B |
| 002-140 | C |
| 002-141 | B |
| 002-142 | C |
| 002-144 | C |
| 002-155 | B |
| 002-160 | C |
| 002-163 | C |
| 002-165 | B |
| 002-169 | C |
| 002-170 | B |
| 002-172 | C |
| 002-173 | C |
| 002-175 | A |
| 002-185 | A |
| 002-186 | B |
| 002-187 | A |
| 002-188 | B |
| 002-189 | B |
| 002-190 | C |
| 002-191 | B |
| 002-193 | C |

TABLE 22-continued

| | |
|---|---|
| 002-196 | B |
| 002-197 | C |
| 002-198 | B |
| 002-199 | C |
| 002-200 | A |
| 002-201 | B |
| 002-204 | B |
| 002-205 | B |
| 002-206 | A |
| 002-207 | B |
| 002-208 | B |
| 002-209 | B |
| 002-210 | B |
| 004-002 | A |
| 004-003 | A |
| 004-004 | B |
| 004-005 | B |
| 004-006 | B |
| 004-007 | B |
| 004-008 | A |
| 004-011 | C |
| 004-012 | A |
| 004-013 | A |
| 004-014 | C |
| 004-016 | B |
| 004-017 | B |
| 004-018 | B |
| 004-019 | C |
| 004-020 | C |
| 004-022 | B |
| 004-023 | B |
| 004-024 | C |
| 004-025 | A |
| 004-026 | A |
| 004-027 | C |
| 004-028 | B |
| 004-029 | C |
| 004-030 | C |
| 004-031 | C |
| 004-032 | C |
| 004-033 | C |
| 004-035 | C |
| 004-036 | B |
| 004-037 | B |
| 004-039 | C |
| 004-040 | C |
| 004-042 | B |
| 004-043 | B |
| 004-044 | C |
| 004-046 | C |
| 004-049 | C |
| 004-050 | C |
| 004-051 | C |
| 004-053 | B |
| 004-054 | B |
| 004-055 | B |
| 004-056 | C |
| 004-058 | B |
| 004-059 | A |
| 004-060 | A |
| 004-061 | A |
| 004-062 | A |
| 004-064 | A |
| 004-065 | B |
| 004-068 | B |
| 004-069 | B |
| 004-071 | C |
| 004-072 | C |
| 004-073 | B |
| 004-074 | B |
| 004-075 | C |
| 004-076 | C |
| 004-077 | B |
| 004-078 | B |
| 004-079 | A |
| 004-082 | C |
| 004-089 | B |
| 004-091 | B |
| 004-092 | B |
| 004-093 | C |
| 004-094 | C |
| 004-095 | C |
| 004-096 | B |
| 004-097 | B |
| 004-103 | B |
| 004-104 | C |
| 004-105 | C |
| 004-106 | C |
| 004-109 | C |
| 004-113 | C |
| 004-114 | B |
| 004-117 | C |
| 004-118 | B |
| 004-123 | C |
| 004-125 | B |
| 004-127 | C |
| 004-128 | B |
| 004-129 | B |
| 004-132 | B |
| 004-134 | C |
| 004-141 | B |
| 004-143 | B |
| 004-149 | C |
| 004-159 | B |
| 004-160 | C |
| 004-161 | C |
| 004-162 | C |
| 004-163 | A |
| 004-164 | C |
| 004-168 | C |
| 004-172 | B |
| 004-181 | C |
| 004-188 | B |
| 004-190 | C |
| 004-191 | B |
| 004-195 | B |
| 004-196 | C |
| 004-197 | B |
| 004-198 | B |
| 004-199 | C |
| 004-201 | C |
| 004-213 | B |
| 004-214 | C |
| 004-215 | B |
| 004-217 | B |
| 004-218 | B |
| 004-219 | B |
| 004-220 | B |
| 004-222 | C |
| 004-226 | C |
| 004-227 | C |
| 004-228 | B |
| 004-229 | B |
| 004-235 | B |
| 006-026 | A |
| 006-035 | A |
| 006-040 | A |
| 006-043 | C |
| 006-044 | A |
| 006-046 | C |
| 006-049 | A |
| 006-050 | B |
| 006-051 | B |
| 006-052 | B |
| 006-053 | A |
| 006-054 | B |
| 006-055 | A |
| 006-056 | A |
| 006-057 | B |
| 006-058 | B |
| 006-060 | A |
| 006-061 | A |
| 006-062 | A |
| 006-063 | A |
| 006-064 | C |
| 006-065 | B |
| 006-068 | C |
| 006-070 | B |
| 006-072 | A |
| 006-075 | A |

TABLE 22-continued

| | |
|---|---|
| 006-076 | A |
| 006-078 | C |
| 006-080 | C |
| 006-082 | B |
| 006-083 | B |
| 006-087 | B |
| 006-092 | A |
| 006-093 | A |
| 006-094 | B |
| 006-096 | A |
| 006-097 | A |
| 006-098 | A |
| 006-099 | A |
| 006-100 | B |
| 006-101 | B |
| 006-102 | B |
| 006-103 | A |
| 006-104 | B |
| 006-107 | A |
| 006-108 | B |
| 006-109 | B |
| 006-110 | B |
| 006-111 | B |
| 006-112 | B |
| 006-113 | A |
| 006-114 | B |
| 006-116 | C |
| 006-117 | A |
| 006-119 | C |
| 006-121 | C |
| 006-122 | B |
| 006-123 | C |
| 006-124 | C |
| 006-125 | B |
| 006-126 | A |
| 006-128 | C |
| 006-129 | A |
| 006-130 | B |
| 006-132 | C |
| 006-133 | C |
| 006-142 | A |
| 006-143 | C |
| 006-144 | B |
| 006-145 | B |
| 006-146 | A |
| 006-147 | C |
| 006-148 | C |
| 006-153 | A |
| 006-154 | B |
| 006-155 | B |
| 006-156 | C |
| 006-157 | B |
| 006-159 | C |
| 006-160 | B |
| 006-161 | A |
| 006-163 | B |
| 006-165 | B |
| 006-166 | A |
| 006-167 | A |
| 006-168 | A |
| 006-169 | A |
| 006-170 | B |
| 006-172 | B |
| 006-173 | B |
| 006-174 | A |
| 006-176 | B |
| 006-177 | C |
| 006-178 | A |
| 006-180 | C |
| 006-182 | C |
| 006-184 | B |
| 006-185 | B |
| 006-186 | A |
| 006-187 | C |
| 006-188 | B |
| 006-190 | A |
| 006-192 | B |
| 006-193 | A |
| 006-194 | B |
| 006-195 | A |

TABLE 22-continued

| | |
|---|---|
| 006-196 | B |
| 006-198 | B |
| 006-199 | B |
| 006-200 | B |
| 006-201 | C |
| 006-204 | B |
| 006-206 | C |
| 006-207 | A |
| 006-208 | B |
| 006-209 | B |
| 006-210 | A |
| 006-211 | A |
| 006-212 | C |
| 006-213 | C |
| 006-214 | B |
| 006-215 | B |
| 006-216 | B |
| 006-217 | A |
| 006-218 | B |
| 006-219 | B |
| 006-220 | A |
| 006-221 | B |
| 006-222 | B |
| 006-223 | A |
| 006-224 | A |
| 006-226 | B |
| 006-227 | C |
| 006-228 | C |
| 006-229 | B |
| 006-232 | C |
| 006-233 | C |
| 006-234 | B |
| 006-236 | A |
| 006-237 | A |
| 006-238 | A |
| 006-239 | A |
| 006-240 | A |
| 006-241 | B |
| 006-242 | B |
| 006-244 | B |
| 006-245 | B |
| 006-247 | C |
| 006-248 | B |
| 006-249 | A |
| 006-250 | C |
| 006-251 | A |
| 006-252 | B |
| 006-253 | C |
| 006-255 | B |
| 006-256 | B |
| 006-257 | A |
| 006-258 | C |
| 006-259 | A |
| 006-260 | A |
| 006-261 | A |
| 006-262 | A |
| 006-263 | A |
| 006-264 | A |
| 006-265 | C |
| 006-266 | A |
| 006-267 | A |
| 006-268 | A |
| 006-269 | B |
| 006-270 | A |
| 006-271 | A |
| 006-272 | B |
| 006-274 | B |
| 006-275 | A |
| 006-276 | A |
| 006-277 | B |
| 006-278 | A |
| 006-279 | B |
| 006-281 | A |
| 006-282 | A |
| 006-284 | C |
| 006-285 | B |
| 006-286 | A |
| 006-287 | B |
| 006-288 | C |
| 006-289 | A |

TABLE 22-continued

| | |
|---|---|
| 006-290 | A |
| 006-291 | C |
| 006-293 | B |
| 006-294 | B |
| 006-295 | C |
| 006-296 | B |
| 006-297 | B |
| 006-298 | A |
| 006-299 | A |
| 006-300 | A |
| 006-301 | B |
| 006-302 | C |
| 006-303 | C |
| 006-304 | C |
| 006-306 | B |
| 006-307 | B |
| 006-308 | B |
| 006-309 | B |
| 006-310 | B |
| 006-311 | B |
| 006-312 | B |
| 006-313 | B |
| 006-314 | A |
| 006-315 | A |
| 006-316 | C |
| 006-317 | C |
| 006-318 | C |
| 006-321 | C |
| 006-322 | A |
| 006-323 | B |
| 006-324 | C |
| 006-329 | A |
| 006-330 | A |
| 006-331 | B |
| 006-332 | A |
| 006-333 | B |
| 006-334 | B |
| 006-335 | C |
| 006-336 | C |
| 006-338 | B |
| 006-342 | A |
| 006-343 | B |
| 006-344 | A |
| 006-345 | B |
| 006-346 | C |
| 006-348 | B |
| 006-350 | B |
| 006-351 | B |
| 006-352 | A |
| 006-353 | A |
| 006-354 | B |
| 006-355 | B |
| 006-356 | A |
| 006-357 | B |
| 006-358 | A |
| 006-359 | A |
| 006-360 | B |
| 006-361 | B |
| 006-362 | C |
| 006-363 | B |
| 006-364 | B |
| 006-365 | B |
| 006-368 | A |
| 006-369 | A |
| 006-370 | A |
| 006-371 | B |
| 006-372 | B |
| 006-373 | A |
| 006-374 | C |
| 006-375 | B |
| 006-376 | A |
| 006-377 | A |
| 006-378 | B |
| 006-379 | C |
| 006-380 | B |
| 006-381 | B |
| 006-383 | A |
| 006-384 | A |
| 006-385 | B |
| 006-386 | A |

TABLE 22-continued

| | |
|---|---|
| 006-387 | B |
| 006-388 | B |
| 006-389 | B |
| 006-390 | B |
| 006-392 | B |
| 006-394 | B |
| 006-395 | B |
| 006-396 | B |
| 006-397 | A |
| 006-398 | B |
| 006-400 | A |
| 006-401 | C |
| 006-402 | C |
| 006-403 | C |
| 006-404 | C |
| 006-405 | C |
| 006-406 | B |
| 006-407 | C |
| 006-408 | C |
| 006-409 | C |
| 006-410 | B |
| 006-411 | C |
| 006-412 | C |
| 006-414 | B |
| 006-415 | B |
| 006-416 | B |
| 006-417 | B |
| 006-418 | B |
| 006-420 | B |
| 006-429 | B |
| 006-430 | B |
| 006-431 | B |
| 006-432 | B |
| 006-433 | B |
| 006-434 | A |
| 006-435 | B |
| 006-442 | A |
| 006-443 | B |
| 006-444 | B |
| 006-445 | B |
| 006-446 | C |
| 006-447 | C |
| 006-449 | C |
| 006-451 | A |
| 006-452 | A |
| 006-453 | A |
| 006-454 | B |
| 006-455 | B |
| 006-456 | C |
| 006-457 | C |
| 006-458 | C |
| 006-459 | B |
| 006-460 | B |
| 006-461 | B |
| 006-464 | B |
| 006-465 | C |
| 006-466 | B |
| 006-468 | A |
| 006-469 | A |
| 006-470 | B |
| 006-471 | A |
| 006-472 | B |
| 006-473 | A |
| 006-474 | B |
| 006-475 | C |
| 006-477 | C |
| 006-478 | B |
| 006-480 | C |
| 006-483 | A |
| 006-484 | B |
| 006-485 | B |
| 006-486 | C |
| 006-487 | C |
| 006-488 | B |
| 006-489 | C |
| 006-493 | C |
| 006-494 | C |
| 006-495 | C |
| 006-496 | B |
| 006-497 | B |

TABLE 22-continued

| | |
|---|---|
| 006-498 | B |
| 006-499 | C |
| 006-500 | B |
| 006-501 | C |
| 006-502 | B |
| 006-503 | B |
| 006-505 | C |
| 006-506 | C |
| 006-507 | C |
| 006-508 | B |
| 006-509 | B |
| 006-510 | B |
| 006-511 | A |
| 006-512 | B |
| 006-513 | B |
| 006-515 | C |
| 006-516 | A |
| 006-517 | B |
| 006-519 | B |
| 006-520 | A |
| 006-521 | B |
| 006-522 | A |
| 006-523 | A |
| 006-524 | A |
| 006-525 | B |
| 006-526 | A |
| 006-531 | B |
| 006-537 | B |
| 006-539 | C |
| 006-541 | C |
| 006-543 | B |
| 006-544 | B |
| 006-545 | B |
| 006-546 | C |
| 006-547 | B |
| 006-548 | B |
| 006-550 | C |
| 006-551 | C |
| 006-552 | B |
| 006-553 | C |
| 006-554 | C |
| 006-555 | B |
| 006-556 | B |
| 006-557 | C |
| 006-558 | B |
| 006-559 | B |
| 006-563 | C |
| 006-564 | B |
| 006-565 | B |
| 006-572 | C |
| 006-575 | C |
| 006-576 | A |
| 006-577 | A |
| 006-578 | B |
| 006-579 | B |
| 006-580 | C |
| 006-581 | A |
| 006-583 | A |
| 006-584 | B |
| 006-585 | A |
| 006-586 | B |
| 006-587 | B |
| 006-588 | A |
| 006-589 | B |
| 006-590 | C |
| 006-591 | C |
| 006-592 | C |
| 006-593 | B |
| 006-596 | B |
| 006-597 | B |
| 006-598 | C |
| 008-001 | B |
| 008-006 | A |
| 008-011 | B |
| 010-001 | A |
| 010-002 | C |
| 012-005 | C |
| 012-008 | B |
| 012-009 | B |
| 012-013 | C |
| 012-031 | B |
| 012-036 | B |
| 014-001 | A |
| 014-002 | A |
| 014-005 | A |
| 014-009 | A |
| 014-010 | B |
| 014-013 | C |
| 014-014 | C |
| 014-016 | B |
| 014-017 | C |
| 014-019 | B |
| 027-020 | C |
| 027-030 | C |
| 027-033 | C |
| 029-016 | C |
| 035-001 | B |
| 035-002 | B |
| 035-003 | B |
| 035-004 | B |
| 035-005 | C |
| 035-006 | C |
| 035-007 | B |
| 035-009 | C |
| 037-001 | A |
| 037-002 | A |
| 037-003 | A |
| 037-004 | A |
| 037-005 | B |
| 039-001 | A |
| 039-002 | A |
| 039-003 | A |
| 039-004 | B |
| 041-001 | C |
| 041-012 | C |
| 043-000 | B |
| 044-000 | B |

Test Example 3

Intracellular Phosphorylation Signaling Assay

THP-1 cells induced to differentiate by IFNγ were collected as described in Test Example 2 and incubated with test compounds for 30 minutes. Thereafter, the cells mixed with the compounds were seeded on a human IgG coating plate, followed by incubation at 37° C. for 45 minutes. Then, a cell lysate was prepared using AlphaScreen SureFire Lysis buffer (PerkinElmer). Subsequently, ImmunoPure Lane Marker Reducing Sample Buffer (Thermo) was added, followed by treatment at 95° C. for 5 minutes. Thus, Western blot samples were prepared, followed by SDS electrophoresis for protein separation, and the samples were transferred to an Immobilon FL PVDF membrane (Millipore). The membrane to which the proteins had been transferred was incubated in Odyssey Blocking buffer (LI-COR) at room temperature for 1 hour for blocking treatment. Subsequently, the proteins were reacted overnight with primary antibodies [SLP76 Antibody, AKT Antibody, Phospho-AKT (Ser473) Antibody, MEK Antibody, Phospho-MEK (Tyr128) Antibody, Phospho-p38 (Thr180/Tyr182) Antibody, Phospho-JNK (Thr183/Tyr185) Antibody (Cell Signaling Technology), Phospho-SLP76 (Tyr128) Antibody, p38 Antibody, and JNK Antibody (BD Biosciences)] at 4° C.

On the following day, the proteins were reacted with fluorescent-labeled secondary antibodies [IRDye 680 donkey anti-rabbit IgG, IRDye 680 donkey anti-mouse IgG, IRDye 800CW donkey anti-rabbit IgG, and IRDye 800CW donkey anti-mouse IgG (LI-COR)] at room temperature for 1 hour and detection was conducted using an Odyssey Infrared Imaging System. As a result, it was revealed that the addition of the compounds causes inhibition of phosphorylation of SLP76, Akt, Mek, p38MAPK, and JNK2, which are molecules located downstream of Syk, as shown in FIG. 1.

Test Example 4

Osteoclast Differentiation Assay

Figure 2:
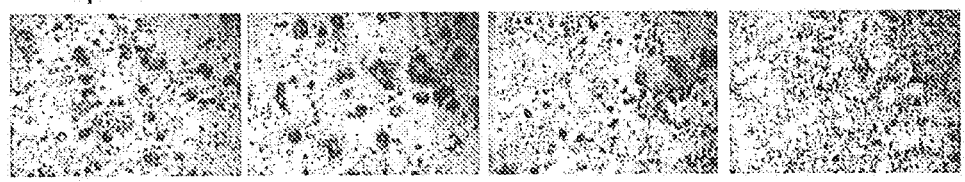
FIG. 2 shows the results of an osteoclast differentiation assay.
Figure 2:
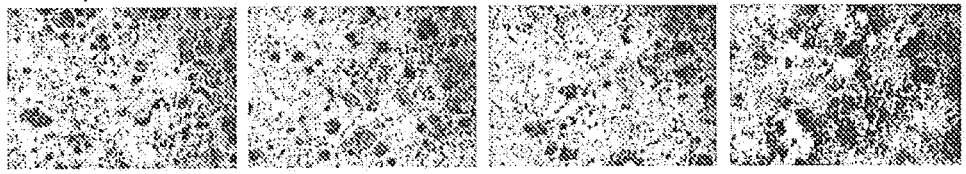
Figure 2:
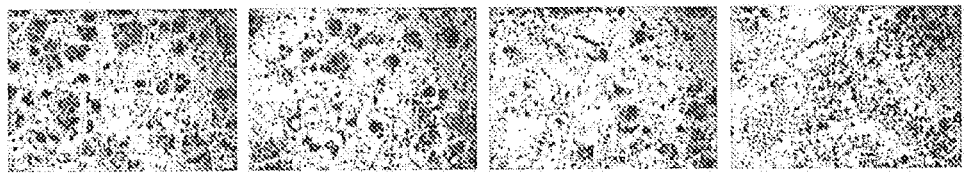

RAW264 cells which are mouse macrophage-like cell line were seeded on a 96 well plate (3,000 cells/well), to each cell of which RANKL (R&D) (final concentration: 150 ng/ml) and a test compound had been added, and were cultured for 4 days, followed by staining of tartrate-resistant acid phosphatase (TRAP), which is an osteoclast marker. FIG. 2 shows an example where a compound that was able to inhibit osteoclast differentiation was used.

Test Example 5

Antibody-Dependent Phagocytosis Assay

THP-1 cells ($2 \times 10^5$ cells/ml) which are human monocyte-like cell line were cultured in the presence of 10 ng/ml IFNγ for 2 days, so that the cells were induced to differentiate into macrophage-like cells. THP-1 cells that had been induced to differentiate were collected. The cells ($5 \times 10^4$ cells/well) were reacted with test compounds having given concentrations at room temperature for 30 minutes. Thereafter, *Escherichia coli* (Life Technologies) labeled with a pH-sensitive dye (pH-rodo) was subjected to opsonization using an anti-*Escherichia coli* antibody (Molecular Probes). Then, the resultant was added to THP-1 cells mixed with test compounds that had been induced to differentiate, followed by incubation at 37° C. for 3 hours. At the time of addition of opsonized *Escherichia coli*, cell-permeable fluorescent dye (Calcein AM) were simultaneously added thereto, and phagocytosis of opsonized *Escherichia coli* in viable cells was quantitatively determined using an IN Cell Analyzer.

The test results obtained by the above test method are listed in Table 23 below. In addition, the following are used in Table 23 to denote standards for evaluating $IC_{50}$ upon phagocytosis inhibition.
A: Up to 1 μM
B: 1 to 3 μM
C: 3 to 6 μM

TABLE 23

| | |
|---|---|
| 002-001 | B |
| 002-134 | B |
| 004-008 | A |
| 004-013 | B |
| 004-017 | C |
| 004-031 | B |
| 004-042 | B |
| 004-060 | B |
| 004-079 | B |
| 004-120 | A |
| 004-228 | B |
| 006-021 | B |
| 006-038 | B |
| 006-049 | C |
| 006-050 | C |
| 006-052 | B |
| 006-054 | B |
| 006-060 | B |
| 006-087 | B |
| 006-098 | A |
| 006-157 | A |
| 006-165 | B |
| 006-173 | B |

TABLE 23-continued

| | |
|---|---|
| 006-177 | B |
| 006-211 | B |
| 006-219 | B |
| 006-249 | B |
| 006-257 | B |
| 006-263 | B |
| 006-270 | B |
| 006-278 | B |
| 006-301 | B |
| 006-311 | B |
| 006-322 | A |
| 006-342 | B |
| 006-368 | A |
| 006-375 | B |
| 006-376 | B |
| 006-377 | B |
| 006-383 | B |
| 006-384 | A |
| 006-395 | B |
| 006-433 | B |
| 006-468 | A |
| 008-005 | B |
| 008-006 | A |
| 008-007 | C |
| 008-009 | C |
| 012-008 | B |
| 014-001 | B |
| 022-003 | B |
| 022-005 | A |
| 029-012 | C |

Test Example 6

Ames Test

Four *Salmonella typhimurium* strains (TA100, TA1535, TA98, and TA1537) and one *Escherichia coli* strain (WP2uvrA) were used for the Ames test.

A solution containing a test compound (0.1 ml) was added to a test tube. 0.1 M Na-phosphate buffer (0.5 ml) was added to the tube for no metabolic activation (S9(−)) or an S-9 mix (Kikkoman) (0.5 ml) was added to the tube for metabolic activation (S9(+)). Further, a precultured bacterial cell suspension (0.1 ml) was added to the tube, followed by shaking at 37° C. for 20 minutes. Thereafter, 2-ml top agar (a solution prepared by mixing 5 mM L-histidine and a 5 mM D-biotin preparation solution at a volume ratio of 99:1 in a Bacto™ Agar aqueous solution for *salmonella*, or a solution prepared by mixing a 5 mM L-tryptophan aqueous solution and a 5 mM D-biotin preparation solution at a volume ratio of 99:1 in a Bacto™ Agar aqueous solution for *Escherichia coli*) was added, followed by sufficient stirring. The content of the tube was poured onto a minimal glucose agar plate medium and cultured at 37° C. for 48 hours.

The number of colony was counted by using an auto colony counter. In addition, the measurement value was defined as the average of colony counts for two plates.

Test results were obtained for different doses. When the average number of revertant colonies per plate for a test compound was at least two times or less than two times that for a negative control (DMSO solvent alone), such test compound was determined to yield a positive or negative test result, respectively. In addition, a test substance was comprehensively assessed to yield a positive test result when an increase in the average number of revertant colonies correlated with dose dependence or reproducibility.

Compounds listed in Table 24 were tested by the above test method. As a result, each compound was found to yield a negative test result.

TABLE 24

002-082
002-085
002-086
002-088
002-090
002-093
002-097
002-100
002-125
002-127
002-131
002-134
002-137
002-155
002-204
002-206
002-208
002-209
004-143
004-149
004-153
004-157
004-158
004-172
004-188
004-195
004-196
004-198
004-199
004-219
006-125
006-129
006-134
006-141
006-142
006-146
006-149
006-150
006-153
006-154
006-156
006-157
006-161
006-165
006-169
006-170
006-177
006-180
006-190
006-191
006-192
006-193
006-194
006-195
006-196
006-199
006-207
006-208
006-210
006-214
006-219
006-220
006-221
006-234
006-237
006-238
006-248
006-249
006-270
006-278
006-312
006-356
006-368
006-373
006-375
006-377
006-383
006-388
006-392
006-395

TABLE 24-continued 006-400
006-416
006-418
006-429
006-431
006-434
006-435
006-464
006-466
006-468
006-471
006-484

Test Example 7

Micronucleus Test Using Culture Cells

CHL cells (from Chinese hamster lung) were seeded on a 96 well plate (5000 cells/well) and cultured at 37° C. at 5% $CO_2$ for 24 hours. Thereafter, CHL cells were divided into a no metabolic activation (S9(−)) group and a metabolic activation (S9(+)) group. Phosphate buffered saline (hereinafter abbreviated as PBS(−)) or thawed frozen S-9 mix for a chromosomal abnormality test (Kikkoman) was added to each group. Test substances were also added, followed by culture at 37° C. and 5% $CO_2$ for 6 hours. Then, the plate was washed with PBS(−) and a culture solution (100 μl) was again added thereto, followed by culture at 37° C. and 5% $CO_2$ for 18 hours. Cells were fixed with ethanol, followed by removal of PBS(−). 100 μL of PBS(−) containing 2 μg/mL Hoechst 33342 (Invitrogen) and 2 μg/mL CellMask (Invitrogen) was added each cell, and the cells were stained at room temperature for 30 minutes. Cells were washed once with PBS(−), PBS(−) (100 μL) was added thereto, and image analysis was performed using an IN Cell Analyzer (GE) for detection of cells having micronuclei. At least 1000 cells were analyzed per well for calculation of the frequency of micronuclei. In addition, a cell toxicity test using CellTiter-GloBuffer (Promega) was conducted at the same time as the micronucleus test in order to assess the mutagenicity of each test substance according to the criteria described below. Dunnett's statistical analysis was conducted for a statistical significance test.

Compounds listed in Table 25 were tested by the above test method. As a result, each compound was found to yield a negative test result. The following are assessment standards.

Positive: Statistically significant increase and dose relationship
Negative: No significant increase
False positive: Significant increase and no dose relationship or Significant increase and strong cell toxicity (survival rate: 50% or less)

TABLE 25

002-134
002-155
002-186
002-203
002-056
004-143
004-198
004-216
004-219
004-228
006-144
006-154
006-177

TABLE 25-continued 006-195
006-200
006-201
006-211
006-219
006-220
006-237
006-257
006-267
006-268
006-270
006-278
006-281
006-285
006-286
006-290
006-296
006-311
006-313
006-322
006-330
006-332
006-342
006-350
006-356
006-368
006-373
006-376
006-383
006-384
006-386
006-392
006-416
006-429
006-431
006-432
006-433
006-434
006-435
006-446
006-451
006-452
006-459
006-461
006-471
006-483
006-484
006-495
006-506
006-507
006-508
006-522
006-523
006-524
006-526

Test Example 8

Mouse Type-II-Collagen-Antibody-Induced Arthritis

The compound synthesized in Example 8-1 was tested to examine effects upon mouse-type-II-collagen-antibody-induced arthritis. An anti-type II collagen antibody mixture (Chondrex) was intraperitoneally injected into 7-week-old female BALB/c mice (Charles River Laboratories Japan, Inc.) (1.5 mg per mouse) (Day 0). An LPS solution 0111:B4 (Chondrex) (50 μg) was intraperitoneally injected thereinto three days later (Day 3), thereby inducing arthritis. Swelling scores were determined for four limbs of each mouse once daily from Day 3 to Day 14. Specifically, evaluation was carried out using a twelve-point scale for the sum of the scores for the four limbs for each mouse: 0 point: no change; 1 point: mild erythema/swelling on the carpal region or the ankle/calcaneal region; 2 points: obvious swelling on the carpal region or the ankle/calcaneal region; 3 points: severe swelling over forelimbs or hindlimbs. The compound synthesized in Example 8-1 was intraperitoneally administered at 30 mg/kg/day twice daily on consecutive days (from Day 0 to Day 13).

The bone destruction score was determined based on soft X-ray images of four limbs taken on Day 14. Specifically, the osteoporosis score (0: no change; 0.5: an osteoporosis image of a joint and the vicinity of the joint) and the bone erosion score (0: no change; 1: a partial bone destruction image of a joint and the vicinity of the joint; 2: a complete bone destruction image of a joint and the vicinity of the joint) were determined for the following evaluation sites:

forelimb: the 2nd to 5th interphalangeal joints, the 1st to 5th metacarpophalangeal joints, and the carpal region;
hindlimb: the 2nd to 5th interphalangeal joints, the 1st to 5th metatarsophalangeal joints, the ankle region, and the calcaneal bone.

The bone destruction score was obtained as the sum of the both scores to calculate the total score for four limbs (the maximum bone destruction score: 105 points per mouse). The compound synthesized in Example 8-1 was found to have almost completely inhibited the increase in the swelling score and the increase in the bone destruction score.

Test Example 9

Mouse Type-II Collagen-Induced Arthritis
(Prophylactic Administration Test and Therapeutic Administration Test)

The compounds synthesized in Example 8-1, Example 4-17, and Example 6-49 were tested to examine effects upon mouse type II collagen arthritis. To 2 mg/mL bovine type II collagen solution (Koken Co., Ltd.) dissolved in 0.1 mol/L acetic acid, an equal amount of Freund's complete adjuvant (Wako Pure Chemical Industries, Ltd.) was added to prepare an emulsion. A portion of the emulsion was intradermally injected into the tail bases of 7- or 8-week-old male DBA/1J mice (Charles River Laboratories Japan, Inc.) at a dose of 0.2 mL per mouse (antigen amount: 0.2 mg/mouse) on Day 0 and Day 21 twice, so as to induce arthritis. Each compound was administered once daily from Day 21 to Day 34 in the prophylactic administration test (1 to 30 mg/kg/day), and administered once daily from Day 27 to Day 35 in the therapeutic administration test (25 mg/kg/day). Arthritis scores for four limbs for each mouse were determined starting from Day 21. Specifically, the total score of four limbs of a mouse was designated as the individual arthritis score (12 points at a maximum per mouse) based on the following: score 0: no change; score 1: swelling of 1 or 2 digit joints or mild swelling of the carpal region/the ankle region alone; score 2: swelling of joints of at least 3 digits or obvious swelling of the carpal region/the ankle region; and score 3: obvious swelling over forelimbs or hindlimbs.

The compounds synthesized in Example 8-1, Example 4-17, and Example 6-49 strongly inhibited the advancement of arthritis after the onset, and the compound synthesized in Example 6-49 strongly inhibited advancement of arthritis in the therapeutic administration test as well.

Test Example 10

Rat Type-II-Collagen-Induced Arthritis

The compounds were tested to examine effects upon rat type II collagen arthritis. To 3 mg/mL bovine type II collagen solution (Collagen Gijutsu Kenshu-Kai) dissolved in 0.05 mol/L acetic acid, an equal amount of Freund's incomplete adjuvant (Wako Pure Chemical Industries, Ltd.) was added to prepare an emulsion. A portion of the emulsion (0.5 ml) was intradermally injected into the tail bases of 7- or 8-week-old female Lewis rats (Charles River Laboratories Japan, Inc.) (Day 0). Each rat was subjected to the same treatment on Day 7 after the initial inoculation so as to induce arthritis. Each test compound was orally administered from Day 7 to Day 20 once daily. At a given time during the period from Day 7 to Day 21, the rat hindlimb volume was determined using a plethysmometer (UGO BASILE), and the result was designated as an arthritis index. The following compound group inhibited hindlimb swelling by 85% or greater compared with the control group in the case of oral administration at 10 mg/kg/day: the compounds of Example 4-17, Example 6-49, Example 6-117, Example 6-157, Example 6-249, Example 6-322, Example 6-375, and Example 6-395.

Test Example 11

Mouse Thrombocytopenia Model

Test compounds were tested to examine effects upon mouse thrombocytopenia. Each test compound was administered to 5- to 7-week-old female CD1 mice (Charles River Laboratories Japan, Inc.). One hour thereafter, an anti-mouse CD41 (Integrin can) antibody (SCB) (1 μg (200 μl)) was intravenously administered to each mouse so as to induce thrombocytopenia. Four hours after administration of the anti-CD41 antibody, blood sampling from the saphenous vein was performed. The number of platelet was counted by using an automated hematology analyzer.

The following compounds were tested by the above test method, and as a result, improvement of the number of platelet (50% or more improvement) was observed:
Example 4-228, Example 6-165, Example 6-168, Example 6-177, Example 6-211, Example 6-249, Example 6-257, Example 6-263, Example 6-268, Example 6-296, Example 6-301, Example 6-311, Example 6-322, Example 6-342, Example 6-368, Example 6-375, Example 6-377, Example 6-383, Example 6-384, Example 6-395, Example 6-433, Example 6-435, and Example 6-468.

[Industrial Applicability]

The nicotinamide derivative or a salt thereof of the present invention has excellent Syk inhibitory activity and thus is useful as a pharmaceutical composition for treatment of Syk-related diseases.

The claimed embodiments of the present inventions are described below.
(1) A nicotinamide derivative represented by the following formula (I) or a salt thereof:

[Formula 516]

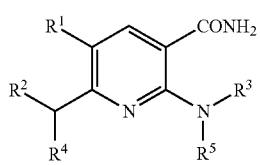

(I)

wherein
$R^1$ represents a halogen atom;
$R^2$ represents a $C_{1-12}$ alkyl group optionally having at least one substituent, a $C_{2-12}$ alkenyl group optionally having at least one substituent, a $C_{2-12}$ alkynyl group optionally having at least one substituent, a $C_{3-8}$ cycloalkyl group optionally having at least one substituent, an aryl group optionally having at least one substituent, an ar-$C_{1-6}$ alkyl group optionally having at least one substituent or a heterocyclic group optionally having at least one substituent;
$R^3$ represents an aryl group optionally having at least one substituent or a heterocyclic group optionally having at least one substituent; and
$R^4$ and $R^5$ each independently represent a hydrogen atom, a $C_{1-12}$ alkyl group optionally having at least one substituent, a $C_{2-12}$ alkenyl group optionally having at least one substituent, or a $C_{2-12}$ alkynyl group optionally having at least one substituent.

(2) The nicotinamide derivative or a salt thereof according to (1), wherein the substituent optionally possessed by the $C_{1-12}$ alkyl group, $C_{2-12}$ alkenyl group, $C_{2-12}$ alkynyl group, $C_{3-8}$ cycloalkyl group, aryl group, ar-$C_{1-6}$ alkyl group or heterocyclic group, represented by $R^2$, is selected from the following substituent group $\alpha_{1-1}$, wherein the substituent group $\alpha_{1-1}$ consists of a halogen atom; a cyano group; a nitro group; an oxo group; an optionally protected carboxyl group; an optionally protected hydroxyl group; an optionally protected amino group; a $C_{1-6}$ alkyl group optionally having at least one substituent; a $C_{2-6}$ alkenyl group optionally having at least one substituent; a $C_{2-6}$ alkynyl group optionally having at least one substituent; a $C_{3-8}$ cycloalkyl group optionally having at least one substituent; an aryl group optionally having at least one substituent; a $C_{1-6}$ alkoxy group optionally having at least one substituent; an aryloxy group optionally having at least one substituent; an acyl group optionally having at least one substituent; a $C_{1-6}$ alkylsulfonyl group optionally having at least one substituent; an arylsulfonyl group optionally having at least one substituent; a heterocyclic group optionally having at least one substituent; and a group represented by the formula -$Q^1$-$Q^2$-$NR^6R^7$ (wherein $R^6$ and $R^7$ each independently represent a hydrogen atom, an amino-protecting group, a $C_{1-6}$ alkyl group optionally having at least one substituent, a $C_{2-6}$ alkenyl group optionally having at least one substituent, a $C_{2-6}$ alkynyl group optionally having at least one substituent, a $C_{3-8}$ cycloalkyl group optionally having at least one substituent, a $C_{1-6}$ alkoxy group optionally having at least one substituent, an aryl group optionally having at least one substituent, or a heterocyclic group optionally having at least one substituent, or $R^6$ and $R^7$ may form a cyclic amino group optionally having at least one substituent, together with the nitrogen atom to which they bind; $Q^1$ represents —NH—, a $C_{1-6}$ alkylene group optionally having at least one substituent, a $C_{2-6}$ alkynylene group optionally having at least one substituent, a $C_{2-6}$ alkynylene group optionally having at least one substituent, or a bond; $Q^2$ represents a group represented by —C(=$X^7$)— (wherein $X^7$ represents an oxygen atom, a sulfur atom, or a group represented by =$NR^{29}$ (wherein $R^{29}$ represents a hydrogen atom, a $C_{1-12}$ alkyl group optionally having at least one substituent, a $C_{2-12}$ alkenyl group optionally having at least one substituent, a $C_{2-12}$ alkynyl group optionally having at least one substituent, a $C_{3-8}$ cycloalkyl group optionally having at least one substituent or a $C_{1-6}$ alkoxy group optionally having at least one substituent)), a $C_{1-6}$ alkylene group, or a bond).

(3) The nicotinamide derivative or a salt thereof according to (1) or (2), wherein the substituent optionally possessed by the $C_{1-12}$ alkyl group, $C_{2-12}$ alkenyl group, $C_{2-12}$ alkynyl group, $C_{3-8}$ cycloalkyl group, aryl group, ar-$C_{1-6}$ alkyl group or heterocyclic group, represented by $R^2$, is selected from the following substituent group $\alpha_{1-2}$, wherein the substituent group $\alpha_{1-2}$ consists of a halogen atom; a cyano group; a nitro group; an oxo group; an optionally protected carboxyl group; an optionally protected hydroxyl group; an optionally protected amino group; a $C_{1-6}$ alkyl group optionally having at least one substituent selected from the following substituent group $\beta_{1-1}$; a $C_{2-6}$ alkenyl group optionally having at least one substituent selected from the following substituent group $\beta_{1-1}$; a $C_{2-6}$ alkynyl group optionally having at least one substituent selected from the following substituent group $\beta_{1-1}$; a $C_{3-8}$ cycloalkyl group optionally having at least one substituent selected from the following substituent group $\beta_{1-1}$; an aryl group optionally having at least one substituent selected from the following substituent group $\beta_{1-1}$; a $C_{1-6}$ alkoxy group optionally having at least one substituent selected from the following substituent group $\beta_{1-1}$; an aryloxy group optionally having at least one substituent selected from the following substituent group $\beta_{1-1}$; an acyl group optionally having at least one substituent selected from the following substituent group $\beta_{1-1}$; a $C_{1-6}$ alkylsulfonyl group optionally having at least one substituent selected from the following substituent group $\beta_{1-1}$; an arylsulfonyl group optionally having at least one substituent selected from the following substituent group $\beta_{1-1}$; a heterocyclic group optionally having at least one substituent selected from the following substituent group $\beta_{1-1}$; and a group represented by the formula -$Q^1$-$Q^2$-$NR^6R^7$ (wherein $Q^1$, $Q^2$, $R^6$ and $R^7$ each have the same definitions as those described in claim 2), wherein the substituent group $\beta_{1-1}$ consists of a halogen atom, a cyano group, a nitro group, an oxo group, an optionally protected carboxyl group, an optionally protected hydroxyl group, an optionally protected amino group, a $C_{1-6}$ alkyl group optionally having at least one halogen atom, a $C_{3-8}$ cycloalkyl group optionally having at least one halogen atom, a $C_{1-6}$ alkoxy group optionally having at least one halogen atom, an aryl group optionally having at least one halogen atom, and a heterocyclic group optionally having at least one halogen atom.

(4) The nicotinamide derivative or a salt thereof according to any one of (1) to (3), wherein the substituent optionally possessed by the $C_{1-12}$ alkyl group, $C_{2-12}$ alkenyl group, $C_{2-12}$ alkynyl group, $C_{3-8}$ cycloalkyl group, aryl group, ar-$C_{1-6}$ alkyl group or heterocyclic group, represented by $R^2$, is selected from the following substituent group $\alpha_{1-3}$, wherein the substituent group $\alpha_{1-3}$ consists of a cyano group; an oxo group; an optionally protected hydroxyl group; an optionally protected amino group; an aryl group optionally having at least one substituent selected from the following substituent group $\beta_{1-2}$; a $C_{1-6}$ alkoxy group optionally having at least one substituent selected from the following substituent group $\beta_{1-2}$; a heterocyclic group optionally having at least one substituent selected from the following substituent group $\beta_{1-2}$; and a group represented by the formula -$Q^1$-$Q^2$-$NR^6R^7$ (wherein $Q^1$, $Q^2$, $R^6$ and $R^7$ each have the same definitions as those described in claim 2); wherein the substituent group $\beta_{1-2}$ consists of a halogen atom and an optionally protected amino group.

(5) The nicotinamide derivative or a salt thereof according to any one of (1) to (4), wherein $R^2$ represents a $C_{1-12}$ alkyl group having, as a substituent, an optionally protected amino group or a heterocyclic group optionally having at least one substituent, or a $C_{3-8}$ cycloalkyl group having, as a substituent, an optionally protected amino group or a heterocyclic group optionally having at least one substituent.

(6) The nicotinamide derivative or a salt thereof according to (1), wherein $R^2$ is a substituent represented by any one of the following formulae (II) to (V) and (VII):

[Formula 517]

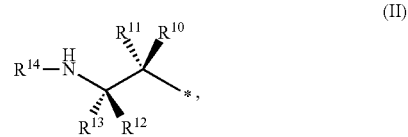

(II)

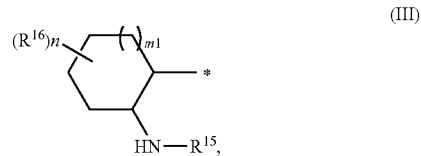

(III)

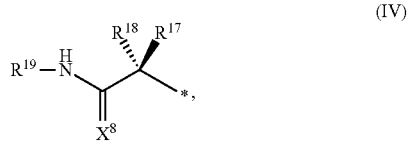

(IV)

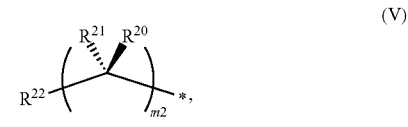

(V)

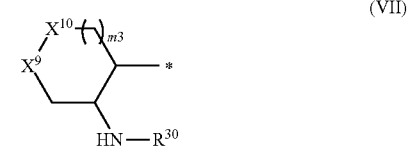

(VII)

wherein $R^{10}$, $R^{11}$, $R^{12}$, $R^{13}$, $R^{16}$, $R^{17}$, $R^{18}$, $R^{20}$ and $R^{21}$ each independently represent a hydrogen atom, or a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent, $R^{14}$, $R^{15}$, $R^{19}$ and $R^{30}$ each independently represent a hydrogen atom, or a $C_{1-12}$ alkyl or acyl group, each optionally having at least one substituent, $X^8$ represents an oxygen atom, a sulfur atom or =$NR^{23}$ (wherein $R^{23}$ represents a hydrogen atom, or a $C_{1-12}$ alkyl, $C_{2-12}$ alkenyl, $C_{2-12}$ alkynyl, $C_{3-8}$ cycloalkyl or $C_{1-6}$ alkoxy group, each optionally having at least one substituent), $R^{22}$ represents a heterocyclic group optionally having at least one substituent, $X^9$ and $X^{10}$ each independently represent an oxygen atom, —$NR^{31}$— (wherein $R^{31}$ represents a hydrogen atom, or a $C_{1-12}$ alkyl, $C_{2-12}$ alkenyl, $C_{2-12}$ alkynyl, $C_{3-8}$ cycloalkyl, $C_{1-6}$ alkoxy, acyl, $C_{1-6}$ alkoxycarbonyl, aryloxycarbonyl or heterocyclic oxycarbonyl group, each optionally having at least one substituent), or a methylene group (wherein either one of $X^9$ and $X^{10}$ represents a methylene group, and when m3 is 0, $X^{10}$ represents a methylene group), m1 and m3 each independently represent an integer from 0 to 2, m2 represents an integer of 1 or 2, wherein $R^{20}$ and $R^{21}$ may be different from each other when m2 is 2, n represents an integer from 0 to 4, $R^{16}$s may be different from one another when n is 2 to 4, and wherein $R^{10}$ and $R^{11}$, $R^{12}$ and $R^{13}$, $R^{17}$ and $R^{18}$, and $R^{20}$ and $R^{21}$ may each together form a $C_{3-8}$ cycloalkyl or heterocyclic group, each optionally having at least one substituent.

(7) The nicotinamide derivative or a salt thereof according to (6), wherein $R^2$ is a substituent represented by the following formula (II-1):

[Formula 518]

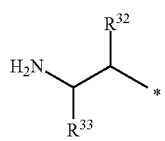

(II-1)

wherein $R^{32}$ and $R^{33}$ each independently represent a hydrogen atom, or a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent selected from the following substituent group $\gamma_{1-2}$, wherein the substituent group $\gamma_{1-2}$ consists of a halogen atom, and $C_{1-6}$ alkyl, $C_{3-8}$ cycloalkyl, aryl and heterocyclic groups, each optionally having at least one substituent.

(8) The nicotinamide derivative or a salt thereof according to (7), wherein $R^{32}$ represents an alkyl group; an alkyl group substituted with a cycloalkyl group; a cycloalkyl group; or a cycloalkyl group substituted with an alkyl group, each containing 3 to 5 carbon atoms in total, or an alkoxyalkyl group containing 2 to 4 carbon atoms in total.

(9) The nicotinamide derivative or a salt thereof according to (7), wherein $R^{32}$ represents a methyl or ethyl group substituted with a heterocyclic group.

(10) The nicotinamide derivative or a salt thereof according to any one of (7) to (9), wherein $R^{33}$ represents a hydrogen atom, or a $C_{1-6}$ alkyl or $C_{3-8}$ cycloalkyl group.

(11) The nicotinamide derivative or a salt thereof according to (6), wherein $R^2$ is a substituent represented by the following (III-4):

[Formula 519]

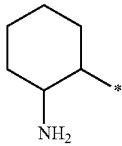

(III-4)

(12) The nicotinamide derivative or a salt thereof according to any one of (1) to (11), wherein $R^4$ and $R^5$ each represent a hydrogen atom.

(13) The nicotinamide derivative or a salt thereof according to any one of (1) to (6), which is represented by the following formula (I-1):

[Formula 520]

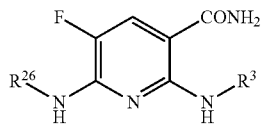

(I-1)

wherein $R^{26}$ is a substituent represented by any one of the above formulae (II) to (V) and (VII), and $R^3$ has the same definitions as those described in claim 1.

(14) The nicotinamide derivative or a salt thereof according to any one of (1) to (13), wherein the aryl group or the heterocyclic group of the aryl group or the heterocyclic group each optionally having at least one substituent, represented by $R^3$, is a phenyl, pyridyl, pyridazinyl, quinoxalinyl or indazolyl group.

(15) The nicotinamide derivative or a salt thereof according to (14), wherein the aryl group or the heterocyclic group of the aryl group or the heterocyclic group each optionally having at least one substituent, represented by $R^3$, is a pyridyl, quinoxalinyl or indazolyl group.

(16) The nicotinamide derivative or a salt thereof according to any one of (1) to (15), wherein the substituent optionally possessed by the aryl or heterocyclic group represented by $R^3$ is selected from the following substituent group $\alpha_{2-1}$, wherein the substituent group $\alpha_{2-1}$ consists of a halogen atom; a cyano group; a nitro group; an oxo group; an optionally protected carboxyl group; an optionally protected hydroxyl group; an optionally protected amino group; a $C_{1-6}$ alkyl group optionally having at least one substituent; a $C_{2-6}$ alkenyl group optionally having at least one substituent; a $C_{2-6}$ alkynyl group optionally having at least one substituent; a $C_{3-8}$ cycloalkyl group optionally having at least one substituent; an aryl group optionally having at least one substituent; a $C_{1-6}$ alkoxy group optionally having at least one substituent; an aryloxy group optionally having at least one substituent; an acyl group optionally having at least one substituent; a $C_{1-6}$ alkylsulfonyl group optionally having at least one substituent; an arylsulfonyl group optionally having at least one substituent; a heterocyclic group optionally having at least one substituent; and a group represented by the formula -$Q^3$-$Q^4$-$NR^{24}R^{25}$ (wherein $R^{24}$ and $R^{25}$ each independently represent a hydrogen atom, an amino-protecting group, a $C_{1-6}$ alkyl group optionally having at least one substituent, a $C_{2-6}$ alkenyl group optionally having at least one substituent, a $C_{2-6}$ alkynyl group optionally having at least one substituent, a $C_{3-8}$ cycloalkyl group optionally having at least one substituent, a $C_{1-6}$ alkoxy group optionally having at least one substituent, an ar-$C_{1-6}$ alkyl group optionally having at least one substituent, an aryl group optionally having at least one substituent, a heterocyclic group optionally having at least one substituent, or $R^{24}$ and $R^{25}$ may form a cyclic amino group optionally having at least one substituent, together with the nitrogen atom to which they bind; $Q^3$ represents —NH—, a $C_{1-6}$ alkylene group optionally having at least one substituent, a $C_{2-6}$ alkenylene group optionally having at least one substituent, a $C_{2-6}$ alkynylene group optionally having at least one substituent, or a bond; and $Q^4$ represents —C(=O)—, a $C_{1-6}$ alkylene group, or a bond).

(17) The nicotinamide derivative or a salt thereof according to (16), wherein the substituent optionally possessed by the aryl or heterocyclic group represented by $R^3$ is selected from the following substituent group $\alpha_{2-2}$, wherein the substituent group $\alpha_{2-2}$ consists of a halogen atom; a cyano group; a nitro group; an oxo group; an optionally protected carboxyl group; an optionally protected hydroxyl group; an optionally protected amino group; a $C_{1-6}$ alkyl group optionally having at least one substituent selected from the following substituent group $\beta_{2-1}$; a $C_{2-6}$ alkenyl group optionally having at least one substituent selected from the following substituent group $\beta_{2-1}$; a $C_{2-6}$ alkynyl group optionally having at least one substituent selected from the following substituent group $\beta_{2-1}$; a $C_{3-8}$ cycloalkyl group optionally having at least one substituent selected from the following substituent group $\beta_{2-1}$; an aryl group optionally having at least one substituent selected from the following substituent group $\beta_{2-1}$; a $C_{1-6}$ alkoxy group optionally having at least one substituent selected from the following substituent group $\beta_{2-1}$; an aryloxy group optionally having at least one substituent selected from the following substituent group $\beta_{2-1}$; an acyl group optionally having at least one substituent selected from the following substituent group $\beta_{2-1}$; a $C_{1-6}$ alkylsulfonyl group optionally having at least one substituent selected from the following substituent group $\beta_{2-1}$; an arylsulfonyl group optionally having at least one substituent selected from the following substituent group $\beta_{2-1}$; a heterocyclic group optionally having at least one substituent selected from the following substituent group $\beta_{2-1}$; and a group represented by the formula $-Q^3-Q^4-NR^{24}R^{25}$ (wherein $Q^3$, $Q^4$, $R^{24}$ and $R^{25}$ each have the same definitions as those described in claim 9); wherein the substituent group $\beta_{2-1}$ consists of a halogen atom, a cyano group, a nitro group, an oxo group, an optionally protected carboxyl group, an optionally protected hydroxyl group, an optionally protected amino group, a $C_{1-6}$ alkyl group optionally having at least one halogen atom, a $C_{3-8}$ cycloalkyl group optionally having at least one halogen atom, a $C_{1-6}$ alkoxy group optionally having at least one halogen atom, an ar-$C_{1-6}$ alkyl group optionally having at least one halogen atom, an aryl group optionally having at least one halogen atom, and a heterocyclic group optionally having at least one halogen atom.

(18) The nicotinamide derivative or a salt thereof according to (17), wherein the substituent optionally possessed by the aryl or heterocyclic group represented by $R^3$ is selected from the following substituent group $\alpha_{2-3}$, wherein the substituent group $\alpha_{2-3}$ consists of a halogen atom; a cyano group; a nitro group; an oxo group; an optionally protected carboxyl group; an optionally protected amino group; a $C_{1-6}$ alkyl group optionally having at least one substituent selected from the following substituent group $\beta_{2-2}$; a $C_{3-8}$ cycloalkyl group optionally having at least one substituent selected from the following substituent group $\beta_{2-2}$; an aryl group optionally having at least one substituent selected from the following substituent group $\beta_{2-2}$; a $C_{1-6}$ alkoxy group optionally having at least one substituent selected from the following substituent group $\beta_{2-2}$; an aryloxy group optionally having at least one substituent selected from the following substituent group $\beta_{2-2}$; an acyl group optionally having at least one substituent selected from the following substituent group $\beta_{2-2}$; a $C_{1-6}$ alkylsulfonyl group optionally having at least one substituent selected from the following substituent group $\beta_{2-2}$; a heterocyclic group optionally having at least one substituent selected from the following substituent group $\beta_{2-2}$; and a group represented by the formula $-Q^3-Q^4-NR^{24}R^{25}$ (wherein $Q^3$, $Q^4$, $R^{24}$ and $R^{25}$ each have the same definitions as those described in claim 9); wherein the substituent group $\beta_{2-2}$ consists of a halogen atom, an optionally protected hydroxyl group, a $C_{1-6}$ alkyl group optionally having at least one halogen atom, a $C_{3-8}$ cycloalkyl group optionally having at least one halogen atom, a $C_{1-6}$ alkoxy group optionally having at least one halogen atom, an aryl group optionally having at least one halogen atom, and a heterocyclic group optionally having at least one halogen atom.

(19) The nicotinamide derivative or a salt thereof according to any one of (1) to (18), wherein $R^3$ represents a pyridyl group optionally having a substituent selected from the following substituent group $\alpha_{2-4}$, wherein the substituent group $\alpha_{2-4}$ consists of a halogen atom; a cyano group; a nitro group; an oxo group; an optionally protected carboxyl group; an optionally protected hydroxyl group; an optionally protected amino group; a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent selected from the following substituent group $\beta_{2-3}$; and the formula $-Q^3-Q^4-NR^{24}R^{25}$ (wherein $Q^3$, $Q^4$, $R^{24}$ and $R^{25}$ have the same definitions as those described above); wherein the substituent group $\beta_{2-3}$ consists of a halogen atom; a cyano group; a nitro group; an oxo group; an optionally protected carboxyl group; an optionally protected hydroxyl group; an optionally protected amino group; and a $C_{1-6}$ alkyl, $C_{3-8}$ cycloalkyl, $-Q^5m4-R^{36}$ (wherein $Q^5$ represents a $C_{1-6}$ alkyleneoxy group (wherein the $R^{36}$ side is an alkylene group), $R^{36}$ represents a hydrogen atom, or a $C_{1-6}$ alkyl, $C_{3-8}$ cycloalkyl, aryl or heterocyclic group, m4 represents an integer from 1 to 3, and $Q^5$s may be different from one another when m4 is 2 or 3), aryl, or heterocyclic group, each optionally having at least one halogen atom.

(20) The nicotinamide derivative or a salt thereof according to (19), wherein $R^3$ represents a pyridyl group represented by the following formula (VIII-1) or (VIII-2):

[Formula 521]

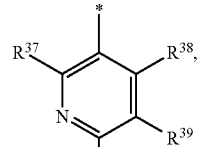

(VIII-1)

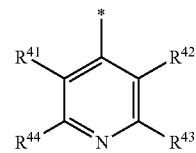

(VIII-2)

wherein $R^{37}$, $R^{38}$, $R^{39}$, $R^{40}$, $R^{41}$, $R^{42}$, $R^{43}$ and $R^{44}$ each independently represent a hydrogen atom, or a substituent selected from the following substituent group $\alpha_{2-6}$; wherein the substituent group $\alpha_{2-6}$ consists of a halogen atom; and a $C_{1-6}$ alkyl, $C_{3-8}$ cycloalkyl, aryl, $C_{1-6}$ alkoxy or heterocyclic group, each optionally having at least one substituent selected from the following substituent group $\beta_{2-5}$; wherein the substituent group $\beta_{2-5}$ consists of a halogen atom; and a $C_{1-6}$ alkyl, $C_{3-8}$ cycloalkyl, $-Q^5m4-R^{36}$ (wherein $Q^5$, $R^{36}$, and m4 have the same definitions as those described above), aryl or heterocyclic group, each optionally having at least one halogen atom.

(21) The nicotinamide derivative or a salt thereof according to (20), wherein $R^3$ represents a pyridyl group represented by the following formula (VIII-3) or (VIII-4):

[Formula 522]

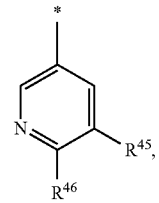

(VIII-3)

(VIII-4)

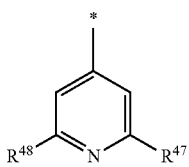

wherein $R^{45}$, $R^{46}$, $R^{47}$ and $R^{48}$ each independently represent a hydrogen atom, or a substituent selected from the above-described substituent group $\alpha_{2-6}$.

(22) The nicotinamide derivative or a salt thereof according to (21), wherein $R^{45}$ represents a 5-membered ring heterocyclic group optionally having at least one substituent selected from among a halogen atom, $C_{1-6}$ alkyl, $C_{3-8}$ cycloalkyl, and -$Q^5$m4-$R^{36}$ (wherein $Q^5$, $R^{36}$, and m4 have the same definitions as described above), and $R^{48}$ represents a halogen atom, a $C_{1-6}$ alkyl group or a $C_{1-6}$ alkoxy group.

(23) The nicotinamide derivative or a salt thereof according to (21), wherein $R^{45}$ represents a halogen atom; or a $C_{1-6}$ alkyl or $C_{1-6}$ alkoxy group optionally having at least one halogen atom, and $R^{46}$ represents a 5-membered ring or 6-membered ring heterocyclic group, each optionally having at least one substituent selected from among a halogen atom, $C_{1-6}$ alkyl, $C_{3-8}$ cycloalkyl, and -$Q^5$m4-$R^{36}$ (wherein $Q^5$, $R^{36}$, and m4 have the same definitions as those described above).

(24) The nicotinamide derivative or a salt thereof according to (21), wherein $R^{47}$ and $R^{48}$ each independently represent a hydrogen atom; a halogen atom; or a $C_{1-6}$ alkyl, aryl, $C_{1-6}$ alkoxy or heterocyclic group, each optionally having at least one substituent independently selected from among a halogen atom, $C_{1-6}$ alkyl, $C_{3-8}$ cycloalkyl and -$Q^5$m4-$R^{36}$ (wherein $Q^5$, $R^{36}$, and m4 have the same definitions as those described above).

(25) The nicotinamide derivative or a salt thereof according to (19), wherein $R^3$ represents an indazolyl group represented by any one of the following formulae (IX-1) to (IX-6):

[Formula 523]

(IX-1)

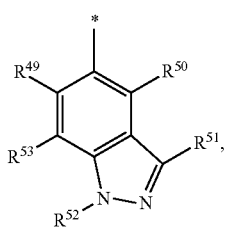

(IX-2)

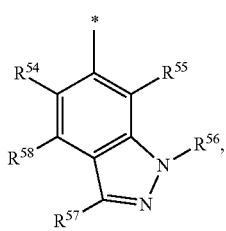

(IX-3)

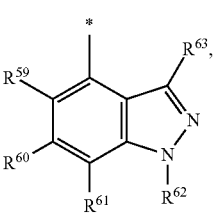

(IX-4)

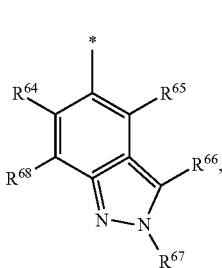

(IX-5)

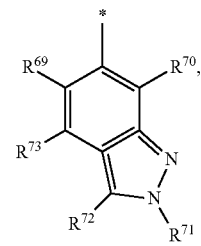

(IX-6)

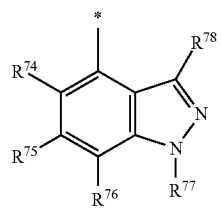

wherein $R^{49}$, $R^{50}$, $R^{51}$, $R^{52}$, $R^{53}$, $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{75}$, $R^{76}$, $R^{77}$ and $R^{78}$ each independently represent a hydrogen atom, or a substituent selected from the above-described substituent group $\alpha_{2-6}$.

(26) The nicotinamide derivative or a salt thereof according to (25), wherein $R^3$ represents an indazolyl group represented by the following formula (IX-7) or (IX-8):

[Formula 524]

(IX-7)

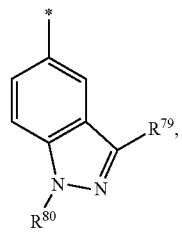

1133

-continued (IX-8)

wherein $R^{79}$, $R^{80}$, $R^{81}$ and $R^{82}$ each independently represent a hydrogen atom, or a substituent selected from the above-described substituent group $\alpha_{2\text{-}6}$.

(27) The nicotinamide derivative or a salt thereof according to (1), wherein the formula (I) is represented by the following formula (I-2):

[Formula 525]

(I-2)

wherein $R^{83}$, $R^{84}$, $R^{85}$ and $R^{86}$ each independently represent a hydrogen atom, or a $C_{1\text{-}6}$ alkyl, $C_{2\text{-}6}$ alkenyl, $C_{2\text{-}6}$ alkynyl, $C_{3\text{-}8}$ cycloalkyl, aryl, $C_{1\text{-}6}$ alkoxy, aryloxy, acyl, $C_{1\text{-}6}$ alkylsulfonyl, arylsulfonyl or heterocyclic group, each optionally having at least one substituent, $R^{87}$ has the same definitions as those of $R^3$ described in claim 1, wherein $R^{83}$ and $R^{84}$, and $R^{85}$ and $R^{86}$ may each together form a $C_{3\text{-}8}$ cycloalkyl or heterocyclic group, each optionally having at least one substituent.

(28) The nicotinamide derivative or a salt thereof according to (1), wherein the formula (I) is represented by the following formula (I-6):

[Formula 526]

(I-6)

wherein $R^{94}$ has the same definitions as those of $R^3$ described in claim 1.

(29) A pharmaceutical composition comprising the nicotinamide derivative or a salt thereof according to any one of (1) to (28).

(30) The pharmaceutical composition according to (29), which is for use in the treatment of a Syk-related disease.

(31) The pharmaceutical composition according to (29), which is for use in the treatment of a disease selected from the group consisting of rheumatism and idiopathic thrombocytopenic purpura.

1134

The invention claimed is:

1. A nicotinamide derivative represented by the following formula (I) or a salt thereof:

[Formula 1]

(I)

wherein $R^1$ represents a halogen atom;

$R^2$ represents a $C_{1\text{-}12}$ alkyl group optionally having at least one substituent, a $C_{2\text{-}12}$ alkenyl group optionally having at least one substituent, a $C_{2\text{-}12}$ alkynyl group optionally having at least one substituent, a $C_{3\text{-}8}$ cycloalkyl group optionally having at least one substituent, an aryl group optionally having at least one substituent, an ar-$C_{1\text{-}6}$ alkyl group optionally having at least one substituent or a heterocyclic group optionally having at least one substituent;

$R^3$ represents an aryl group optionally having at least one substituent or a heterocyclic group optionally having at least one substituent; and $R^4$ and $R^5$ each independently represent a hydrogen atom, a $C_{1\text{-}12}$ alkyl group, a $C_{2\text{-}12}$ alkenyl group, or a $C_{2\text{-}12}$ alkynyl group;

wherein the substituent optionally possessed by the $C_{1\text{-}12}$ alkyl group, $C_{2\text{-}12}$ alkenyl group, $C_{2\text{-}12}$ alkynyl group, $C_{3\text{-}8}$ cycloalkyl group, aryl group, ar-$C_{1\text{-}6}$ alkyl group or heterocyclic group, represented by $R^2$, is selected from the following substituent group $\alpha_{1\text{-}2}$, wherein the substituent group $\alpha_{1\text{-}2}$ consists of a halogen atom; a cyano group; a nitro group; an oxo group; an optionally protected carboxyl group; an optionally protected hydroxyl group; an optionally protected amino group; a $C_{1\text{-}6}$ alkyl group optionally having at least one substituent selected from the following substituent group $\beta_{1\text{-}1}$; a $C_{2\text{-}6}$ alkenyl group optionally having at least one substituent selected from the following substituent group $\beta_{1\text{-}1}$; a $C_{2\text{-}6}$ alkynyl group optionally having at least one substituent selected from the following substituent group $\beta_{1\text{-}1}$; a $C_{3\text{-}8}$ cycloalkyl group optionally having at least one substituent selected from the following substituent group $\beta_{1\text{-}1}$; an aryl group optionally having at least one substituent selected from the following substituent group $\beta_{1\text{-}1}$; a $C_{1\text{-}6}$ alkoxy group optionally having at least one substituent selected from the following substituent group $\beta_{1\text{-}1}$; an aryloxy group optionally having at least one substituent selected from the following substituent group $\beta_{1\text{-}1}$; an acyl group optionally having at least one substituent selected from the following substituent group $\beta_{1\text{-}1}$; a $C_{1\text{-}6}$ alkylsulfonyl group optionally having at least one substituent selected from the following substituent group $\beta_{1\text{-}1}$; an arylsulfonyl group optionally having at least one substituent selected from the following substituent group $\beta_{1\text{-}1}$; a heterocyclic group optionally having at least one substituent selected from the following substituent group $\beta_{1\text{-}1}$; and a group represented by the formula $-Q^1-Q^2-NR^6R^7$ (wherein $R^6$ and $R^7$ each independently represent a hydrogen atom, an amino-protecting group, a $C_{1\text{-}6}$ alkyl group optionally having at least one substituent, a $C_{2-6}$ alkenyl group optionally having at least one substituent, a $C_{2-6}$ alkynyl group optionally having at least one substituent, a $C_{3-8}$ cycloalkyl group optionally having at least one substituent, a $C_{1-6}$ alkoxy group optionally having at least one substituent, an aryl group optionally having at least one substituent, or a heterocyclic group optionally having at least one substituent, or $R^6$ and $R^7$ may form a cyclic amino group optionally having at least one substituent, together with the nitrogen atom to which they bind; $Q^1$ represents —NH—, a $C_{1-6}$ alkylene group optionally having at least one substituent, a $C_{2-6}$ alkenylene group optionally having at least one substituent, a $C_{2-6}$ alkynylene group optionally having at least one substituent, or a bond; $Q^2$ represents a group represented by —C(=X$^7$)— (wherein X$^7$ represents an oxygen atom, a sulfur atom, or a group represented by =NR$^{29}$ (wherein R$^{29}$ represents a hydrogen atom, a $C_{1-12}$ alkyl group optionally having at least one substituent, a $C_{2-12}$ alkenyl group optionally having at least one substituent, a $C_{2-12}$ alkynyl group optionally having at least one substituent, a $C_{3-8}$ cycloalkyl group optionally having at least one substituent or a $C_{1-6}$ alkoxy group optionally having at least one substituent)), a $C_{1-6}$ alkylene group, or a bond), wherein the substituent group $\beta_{1-1}$ consists of a halogen atom, a cyano group, a nitro group, an oxo group, an optionally protected carboxyl group, an optionally protected hydroxyl group, an optionally protected amino group, a $C_{1-6}$ alkyl group optionally having at least one halogen atom, a $C_{3-8}$ cycloalkyl group optionally having at least one halogen atom, a $C_{1-6}$ alkoxy group optionally having at least one halogen atom, an aryl group optionally having at least one halogen atom, and a heterocyclic group optionally having at least one halogen atom;

wherein the substituent optionally possessed by the aryl or heterocyclic group represented by $R^3$ is selected from the following substituent group $\alpha_{2-2}$, wherein the substituent group $\alpha_{2-2}$ consists of a halogen atom; a cyano group; a nitro group; an oxo group; an optionally protected carboxyl group; an optionally protected hydroxyl group; an optionally protected amino group; a $C_{1-6}$ alkyl group optionally having at least one substituent selected from the following substituent group $\beta_{2-1}$; a $C_{2-6}$ alkenyl group optionally having at least one substituent selected from the following substituent group $\beta_{2-1}$; a $C_{2-6}$ alkynyl group optionally having at least one substituent selected from the following substituent group $\beta_{2-1}$; a $C_{3-8}$ cycloalkyl group optionally having at least one substituent selected from the following substituent group $\beta_{2-1}$; an aryl group optionally having at least one substituent selected from the following substituent group $\beta_{2-1}$; a $C_{1-6}$ alkoxy group optionally having at least one substituent selected from the following substituent group $\beta_{2-1}$; an aryloxy group optionally having at least one substituent selected from the following substituent group $\beta_{2-1}$; an acyl group optionally having at least one substituent selected from the following substituent group $\beta_{2-1}$; a $C_{1-6}$ alkylsulfonyl group optionally having at least one substituent selected from the following substituent group $\beta_{2-1}$; an arylsulfonyl group optionally having at least one substituent selected from the following substituent group $\beta_{2-1}$; a heterocyclic group optionally having at least one substituent selected from the following substituent group $\beta_{2-1}$; and a group represented by the formula -$Q^3$-$Q^4$-NR$^{24}$R$^{25}$ (wherein R$^{24}$ and R$^{25}$ each independently represent a hydrogen atom, an amino-protecting group, a $C_{1-6}$ alkyl group optionally having at least one substituent, a $C_{2-6}$ alkenyl group optionally having at least one substituent, a $C_{2-6}$ alkynyl group optionally having at least one substituent, a $C_{3-8}$ cycloalkyl group optionally having at least one substituent, a $C_{1-6}$ alkoxy group optionally having at least one substituent, an ar-$C_{1-6}$ alkyl group optionally having at least one substituent, an aryl group optionally having at least one substituent, a heterocyclic group optionally having at least one substituent, or $R^{24}$ and $R^{25}$ may form a cyclic amino group optionally having at least one substituent, together with the nitrogen atom to which they bind; $Q^3$ represents —NH—, a $C_{1-6}$ alkylene group optionally having at least one substituent, a $C_{2-6}$ alkenylene group optionally having at least one substituent, a $C_{2-6}$ alkynylene group optionally having at least one substituent, or a bond; and $Q^4$ represents —C(=O)—, a $C_{1-6}$ alkylene group, or a bond);

wherein the substituent group $\beta_{2-1}$ consists of a halogen atom, a cyano group, a nitro group, an oxo group, an optionally protected carboxyl group, an optionally protected hydroxyl group, an optionally protected amino group, a $C_{1-6}$ alkyl group optionally having at least one halogen atom, a $C_{3-8}$ cycloalkyl group optionally having at least one halogen atom, a $C_{1-6}$ alkoxy group optionally having at least one halogen atom, an ar-$C_{1-6}$ alkyl group optionally having at least one halogen atom, an aryl group optionally having at least one halogen atom, and a heterocyclic group optionally having at least one halogen atom;

wherein the heterocyclic group is selected from the group consisting of azetidinyl, pyrrolidinyl, pyrrolinyl, pyrrolyl, piperidyl, tetrahydropyridyl, pyridyl, homopiperidinyl, octahydroazocinyl, imidazolidinyl, imidazolinyl, imidazolyl, pyrazolidinyl, pyrazolinyl, pyrazolyl, piperazinyl, pyrazinyl, pyridazinyl, pyrimidinyl, homopiperazinyl, triazolyl, tetrazolyl, tetrahydrofuranyl, furanyl, tetrahydropyranyl, pyranyl, thienyl, oxazolyl, isoxazolyl, oxadiazolyl, morpholinyl, thiazolyl, isothiazolyl, thiadiazolyl, thiomorpholinyl, 1-oxide-thiomorpholinyl, 1,1-dioxide-thiomorpholinyl, indolinyl, indolyl, isoindolinyl, isoindolyl, benzimidazolyl, indazolyl, benzotriazolyl, quinolyl, tetrahydroquinolinyl, quinolyl, tetrahydroisoquinolinyl, isoquinolinyl, quinolizinyl, cinnolinyl, phthalazinyl, quinazolinyl, dihydroquinoxalinyl, quinoxalinyl, naphthyridinyl, pyrrolopyridyl, imidazopyridyl, indolidinyl, dihydrocyclopentapyridyl, triazolopyridyl, pyrazolopyridyl, pyridopyrazyl, purinyl, pteridinyl, quinuclidinyl, 2,3-dihydrobenzofuranyl, benzofuranyl, isobenzofuranyl, chromanyl, chromenyl, isochromanyl, 1,3-benzodioxolyl, 1,3-benzodioxanyl, 1,4-benzodioxanyl, 2,3-dihydrobenzothienyl, benzothienyl, benzoxazolyl, benzoisoxazolyl, benzoxadiazolyl, benzomorpholinyl, dihydropyranopyridyl, dihydrodioxinopyridyl, 1,3-dioxolopyridyl, dihydropyridooxazinyl, benzothiazolyl, benzoisothiazolyl, benzothiadiazolyl and thiazolopyridyl; and wherein the acyl group is a formyl group, a succinyl group, a glutaryl group, a maleoyl group, a phthaloyl group, a $C_{2-12}$ alkanoyl group, an aroyl group, or an (α-substituted) amino acetyl group.

2. The nicotinamide derivative or a salt thereof according to claim 1, wherein the substituent optionally possessed by the $C_{1-12}$ alkyl group, $C_{2-12}$ alkenyl group, $C_{2-12}$ alkynyl group, $C_{3-8}$ cycloalkyl group, aryl group, ar-$C_{1-6}$ alkyl group or heterocyclic group, represented by $R^2$, is selected from the following substituent group $\alpha_{1-3}$, wherein the substituent group $\alpha_{1-3}$ consists of a cyano group; an oxo group; an optionally protected hydroxyl group; an optionally protected amino group; an aryl group optionally having at least one substituent selected from the following substituent group $\beta_{1-2}$; a $C_{1-6}$ alkoxy group optionally having at least one substituent selected from the following substituent group $\beta_{1-2}$; a heterocyclic group optionally having at least one substituent selected from the following substituent group $\beta_{1-2}$; and a group represented by the formula -$Q^1$-$Q^2$-$NR^6R^7$ (wherein $Q^1$, $Q^2$, $R^6$ and $R^7$ each have the same definitions as those described in claim 2);

wherein the substituent group $\beta_{1-2}$ consists of a halogen atom and an optionally protected amino group.

3. The nicotinamide derivative or a salt thereof according to claim 1, wherein $R^2$ represents a $C_{1-12}$ alkyl group having, as a substituent, an optionally protected amino group or a heterocyclic group optionally having at least one substituent, or a $C_{3-8}$ cycloalkyl group having, as a substituent, an optionally protected amino group or a heterocyclic group optionally having at least one substituent.

4. The nicotinamide derivative or a salt thereof according to claim 1, wherein $R^2$ is a substituent represented by any one of the following formulae (II) to (V) and (VII):

[Formula 2]

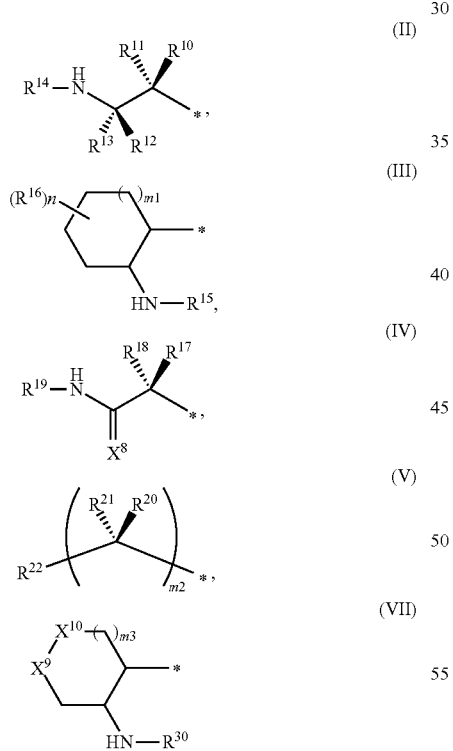

wherein $R^{10}$, $R^{11}$, $R^{12}$, $R^{13}$, $R^{16}$, $R^{17}$, $R^{18}$, $R^{20}$ and $R^{21}$ each independently represent a hydrogen atom, or a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent, $R^{14}$, $R^{15}$, $R^{19}$ and $R^{30}$ each independently represent a hydrogen atom, or a $C_{1-6}$ alkyl or acyl group, $X^8$ represents an oxygen atom, a sulfur atom or =$NR^{23}$ (wherein $R^{23}$ represents a hydrogen atom, or a $C_{1-12}$ alkyl, $C_{2-12}$ alkenyl, $C_{2-12}$ alkynyl, $C_{3-8}$ cycloalkyl or $C_{1-6}$ alkoxy group), $R^{22}$ represents a heterocyclic group, $X^9$ and $X^{10}$ each independently represent an oxygen atom, —$NR^{31}$— (wherein $R^{31}$ represents a hydrogen atom, or a $C_{1-12}$ alkyl, $C_{2-12}$ alkenyl, $C_{2-12}$ alkynyl, $C_{3-8}$ cycloalkyl, $C_{1-6}$ alkoxy, acyl, $C_{1-6}$ alkoxycarbonyl, aryloxycarbonyl or heterocyclic oxycarbonyl group), or a methylene group (wherein either one of $X^9$ and $X^{10}$ represents a methylene group, and when m3 is 0, $X^{10}$ represents a methylene group), m1 and m3 each independently represent an integer from 0 to 2, m2 represents an integer of 1 or 2, wherein $R^{20}$ and $R^{21}$ may be different from each other when m2 is 2, n represents an integer from 0 to 4, $R^{16}$s may be different from one another when n is 2 to 4, and wherein $R^{10}$ and $R^{11}$, $R^{12}$ and $R^{13}$, $R^{17}$ and $R^{18}$, and $R^{20}$ and $R^{21}$ may each together form a $C_{3-8}$ cycloalkyl or heterocyclic group, each optionally having at least one substituent;

wherein the substituent is selected from the following substituent group $\gamma_{1-1}$, wherein the substituent group $\gamma_{1-1}$ consists of a halogen atom; a cyano group; a nitro group; an oxo group; an optionally protected carboxyl group; an optionally protected hydroxyl group; an optionally protected amino group; a $C_{1-6}$ alkyl, $C_{3-8}$ cycloalkyl or heterocyclic group; and the formula -$Q^5$-$Q^6$-$NR^{27}R^{28}$ (wherein $R^{27}$ and $R^{28}$ each independently represent a hydrogen atom; an amino-protecting group; or a $C_{1-6}$ alkyl, $C_{2-6}$ alkenyl, $C_{2-6}$ alkynyl, $C_{3-8}$ cycloalkyl, $C_{1-6}$ alkoxy, aryl or heterocyclic group; $Q^5$ represents —NH—; a $C_{1-6}$ alkylene, $C_{2-6}$ alkenylene or $C_{2-6}$ alkynylene group; or a bond; and $Q^6$ represents —C(=O)—, a $C_{1-6}$ alkylene group or a bond).

5. The nicotinamide derivative or a salt thereof according to claim 4, wherein $R^2$ is a substituent represented by the following formula (II-1):

[Formula 3]

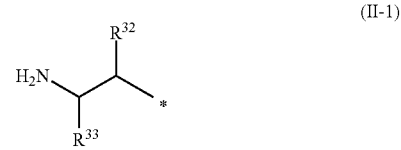

wherein $R^{32}$ and $R^{33}$ each independently represent a hydrogen atom, or a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent selected from the following substituent group $\gamma_{1-2}$, wherein the substituent group $\gamma_{1-2}$ consists of a halogen atom, and $C_{1-6}$ alkyl, $C_{3-8}$ cycloalkyl, aryl and heterocyclic groups.

6. The nicotinamide derivative or a salt thereof according to claim 5, wherein $R^{32}$ represents an alkyl group; an alkyl group substituted with a cycloalkyl group; a cycloalkyl group; or a cycloalkyl group substituted with an alkyl group, each containing 3 to 5 carbon atoms in total, or an alkoxyalkyl group containing 2 to 4 carbon atoms in total.

7. The nicotinamide derivative or a salt thereof according to claim 5, wherein $R^{32}$ represents a methyl or ethyl group substituted with a heterocyclic group.

8. The nicotinamide derivative or a salt thereof according to claim 5, wherein $R^{33}$ represents a hydrogen atom, or a $C_{1-6}$ alkyl or $C_{3-8}$ cycloalkyl group.

9. The nicotinamide derivative or a salt thereof according to claim 4, wherein $R^2$ is a substituent represented by the following (III-4):

[Formula 4]

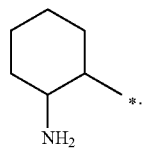

(III-4)

10. The nicotinamide derivative or a salt thereof according to claim 1, wherein $R^4$ and $R^5$ each represent a hydrogen atom.

11. The nicotinamide derivative or a salt thereof according to claim 1, which is represented by the following formula (I-1):

[Formula 5]

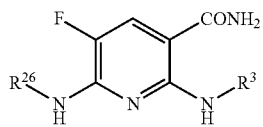

(I-1)

wherein $R^{26}$ is a substituent represented by any one of the above formulae (II) to (V) and (VII), and $R^3$ has the same definitions as those described in claim 1.

12. The nicotinamide derivative or a salt thereof according to claim 1, wherein the aryl group or the heterocyclic group of the aryl group or the heterocyclic group each optionally having at least one substituent, represented by $R^3$, is a phenyl, pyridyl, pyridazinyl, quinoxalinyl or indazolyl group.

13. The nicotinamide derivative or a salt thereof according to claim 12, wherein the aryl group or the heterocyclic group of the aryl group or the heterocyclic group each optionally having at least one substituent, represented by $R^3$, is a pyridyl, quinoxalinyl or indazolyl group.

14. The nicotinamide derivative or a salt thereof according to claim 1, wherein the substituent optionally possessed by the aryl or heterocyclic group represented by $R^3$ is selected from the following substituent group $\alpha_{2-3}$, wherein the substituent group $\alpha_{2-3}$ consists of a halogen atom; a cyano group; a nitro group; an oxo group; an optionally protected carboxyl group; an optionally protected amino group; a $C_{1-6}$ alkyl group optionally having at least one substituent selected from the following substituent group $\beta_{2-2}$; a $C_{3-8}$ cycloalkyl group optionally having at least one substituent selected from the following substituent group $\beta_{2-2}$; an aryl group optionally having at least one substituent selected from the following substituent group $\beta_{2-2}$; a $C_{1-6}$ alkoxy group optionally having at least one substituent selected from the following substituent group $\beta_{2-2}$; an aryloxy group optionally having at least one substituent selected from the following substituent group $\beta_{2-2}$; an acyl group optionally having at least one substituent selected from the following substituent group $\beta_{2-2}$; a $C_{1-6}$ alkylsulfonyl group optionally having at least one substituent selected from the following substituent group $\beta_{2-2}$; a heterocyclic group optionally having at least one substituent selected from the following substituent group $\beta_{2-2}$; and a group represented by the formula $-Q^3-Q^4-NR^{24}R^{25}$ (wherein $Q^3$, $Q^4$, $R^{24}$ and $R^{25}$ each have the same definitions as those described in claim 9); wherein the substituent group $\beta_{2-2}$ consists of a halogen atom, an optionally protected hydroxyl group, a $C_{1-6}$ alkyl group optionally having at least one halogen atom, a $C_{3-8}$ cycloalkyl group optionally having at least one halogen atom, a $C_{1-6}$ alkoxy group optionally having at least one halogen atom, an aryl group optionally having at least one halogen atom, and a heterocyclic group optionally having at least one halogen atom.

15. The nicotinamide derivative or a salt thereof according to claim 1, wherein $R^3$ represents a pyridyl group optionally having a substituent selected from the following substituent group $\alpha_{2-4}$, wherein the substituent group $\alpha_{2-4}$ consists of a halogen atom; a cyano group; a nitro group; an oxo group; an optionally protected carboxyl group; an optionally protected hydroxyl group; an optionally protected amino group; a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent selected from the following substituent group $\beta_{2-3}$; and the formula $-Q^3-Q^4-NR^{24}R^{25}$ (wherein $Q^3$, $Q^4$, $R^{24}$ and $R^{25}$ have the same definitions as those described above); wherein the substituent group $\beta_{2-3}$ consists of a halogen atom; a cyano group; a nitro group; an oxo group; an optionally protected carboxyl group; an optionally protected hydroxyl group; an optionally protected amino group; and a $C_{1-6}$ alkyl, $C_{3-8}$ cycloalkyl, $-Q^5m4-R^{36}$ (wherein $Q^5$ represents a $C_{1-6}$ alkyleneoxy group (wherein the $R^{36}$ side is an alkylene group), $R^{36}$ represents a hydrogen atom, or a $C_{1-6}$ alkyl, $C_{3-8}$ cycloalkyl, aryl or heterocyclic group, m4 represents an integer from 1 to 3, and $Q^5$s may be different from one another when m4 is 2 or 3), aryl, or heterocyclic group, each optionally having at least one halogen atom.

16. The nicotinamide derivative or a salt thereof according to claim 15, wherein $R^3$ represents a pyridyl group represented by the following formula (VIII-1) or (VIII-2):

[Formula 6]

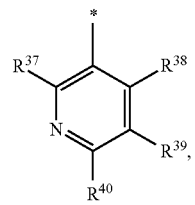

(VIII-1)

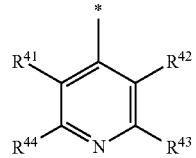

(VIII-2)

wherein $R^{37}$, $R^{38}$, $R^{39}$, $R^{40}$, $R^{41}$, $R^{42}$, $R^{43}$ and $R^{44}$ each independently represent a hydrogen atom, or a substituent selected from the following substituent group $\alpha_{2-6}$; wherein the substituent group α$_{2-6}$ consists of a halogen atom; and a C$_{1-6}$ alkyl, C$_{3-8}$ cycloalkyl, aryl, C$_{1-6}$ alkoxy or heterocyclic group, each optionally having at least one substituent selected from the following substituent group β$_{2-5}$; wherein the substituent group β$_{2-5}$ consists of a halogen atom; and a C$_{1-6}$ alkyl, C$_{3-8}$ cycloalkyl, -Q$^5$m4-R$^{36}$ (wherein Q$^5$, R$^{36}$, and m4 have the same definitions as those described above), aryl or heterocyclic group, each optionally having at least one halogen atom.

17. The nicotinamide derivative or a salt thereof according to claim 16, wherein R$^3$ represents a pyridyl group represented by the following formula (VIII-3) or (VIII-4):

[Formula 7]

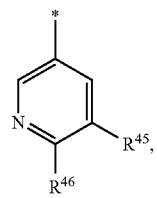

(VIII-3)

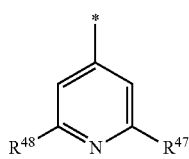

(VIII-4)

wherein R$^{45}$, R$^{46}$, R$^{47}$ and R$^{48}$ each independently represent a hydrogen atom, or a substituent selected from the above-described substituent group α$_{2-6}$.

18. The nicotinamide derivative or a salt thereof according to claim 17, wherein R$^{45}$ represents a 5-membered ring heterocyclic group optionally having at least one substituent selected from among a halogen atom, C$_{1-6}$ alkyl, C$_{3-8}$ cycloalkyl, and -Q$^5$m4-R$^{36}$ (wherein Q$^5$, R$^{36}$, and m4 have the same definitions as described above), and R$^{48}$ represents a halogen atom, a C$_{1-6}$ alkyl group or a C$_{1-6}$ alkoxy group.

19. The nicotinamide derivative or a salt thereof according to claim 17, wherein R$^{45}$ represents a halogen atom; or a C$_{1-6}$ alkyl or C$_{1-6}$ alkoxy group optionally having at least one halogen atom, and R$^{46}$ represents a 5-membered ring or 6-membered ring heterocyclic group, each optionally having at least one substituent selected from among a halogen atom, C$_{1-6}$ alkyl, C$_{3-8}$ cycloalkyl, and -Q$^5$m4-R$^{36}$ (wherein Q$^5$, R$^{36}$, and m4 have the same definitions as those described above).

20. The nicotinamide derivative or a salt thereof according to claim 17, wherein R$^{47}$ and R$^{48}$ each independently represent a hydrogen atom; a halogen atom; or a C$_{1-6}$ alkyl, aryl, C$_{1-6}$ alkoxy or heterocyclic group, each optionally having at least one substituent independently selected from among a halogen atom, C$_{1-6}$ alkyl, C$_{3-8}$ cycloalkyl and -Q$^5$m4-R$^{36}$ (wherein Q$^5$, R$^{36}$, and m4 have the same definitions as those described above).

21. The nicotinamide derivative or a salt thereof according to claim 15, wherein R$^3$ represents an indazolyl group represented by any one of the following formulae (IX-1) to (IX-6):

[Formula 8]

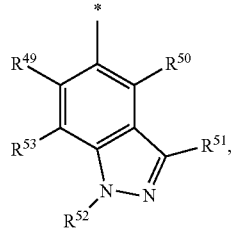

(IX-1)

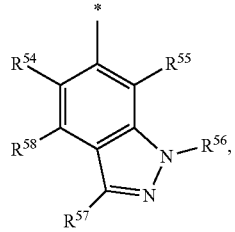

(IX-2)

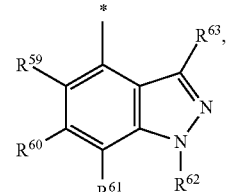

(IX-3)

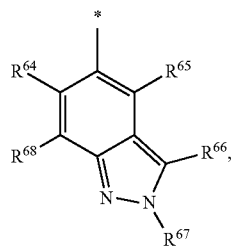

(IX-4)

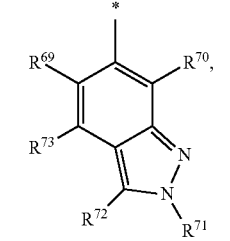

(IX-5)

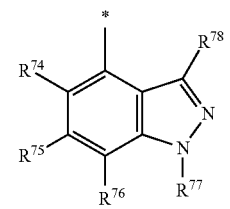

(IX-6)

wherein R$^{49}$, R$^{50}$, R$^{51}$, R$^{52}$, R$^{53}$, R$^{54}$, R$^{55}$, R$^{56}$, R$^{57}$, R$^{58}$, R$^{59}$, R$^{60}$, R$^{61}$, R$^{62}$, R$^{63}$, R$^{64}$, R$^{65}$, R$^{66}$, R$^{67}$, R$^{68}$, R$^{69}$, R$^{70}$, R$^{71}$, R$^{72}$, R$^{73}$, R$^{74}$, R$^{75}$, R$^{76}$, R$^{77}$ and R$^{78}$ each independently represent a hydrogen atom, or a substituent selected from the above-described substituent group α$_{2-6}$.

22. The nicotinamide derivative or a salt thereof according to claim 21, wherein $R^3$ represents an indazolyl group represented by the following formula (IX-7) or (IX-8):

[Formula 9]

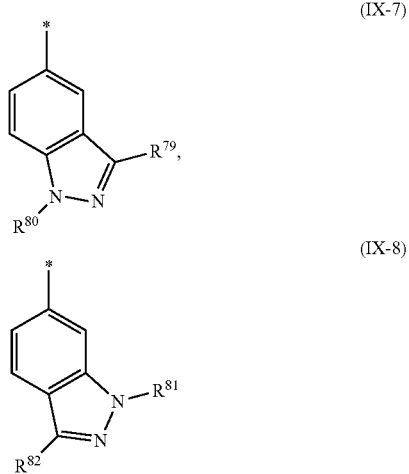

wherein $R^{79}$, $R^{80}$, $R^{81}$ and $R^{82}$ each independently represent a hydrogen atom, or a substituent selected from the above-described substituent group $\alpha_{2-6}$.

23. The nicotinamide derivative or a salt thereof according to claim 1, wherein the formula (I) is represented by the following formula (I-2):

[Formula 10]

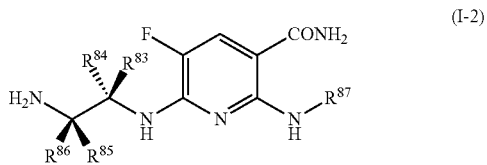

wherein $R^{83}$, $R^{84}$, $R^{85}$ and $R^{86}$ each independently represent a hydrogen atom, or a $C_{1-6}$ alkyl, $C_{2-6}$ alkenyl, $C_{2-6}$ alkynyl, $C_{3-8}$ cycloalkyl, aryl, $C_{1-6}$ alkoxy, aryloxy, acyl, $C_{1-6}$ alkylsulfonyl, arylsulfonyl or heterocyclic group, each optionally having at least one substituent, $R^{87}$ has the same definitions as those of $R^3$ described in claim 1, wherein $R^{83}$ and $R^{84}$, and $R^{85}$ and $R^{86}$ may each together form a $C_{3-8}$ cycloalkyl or heterocyclic group, each optionally having at least one substituent.

24. The nicotinamide derivative or a salt thereof according to claim 1, wherein the formula (I) is represented by the following formula (I-6):

[Formula 11]

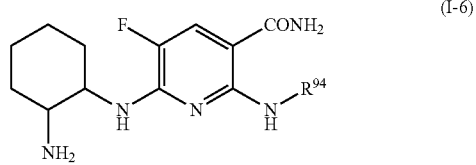

wherein $R^{94}$ has the same definitions as those of $R^3$ described in claim 1.

25. A pharmaceutical composition comprising the nicotinamide derivative or a salt thereof according to claim 1.

26. A method for the treatment of a Syk-related disease, comprising administering the pharmaceutical composition of claim 25 to a patient in need thereof, wherein the disease is selected from the group consisting of rheumatism and idiopathic thrombocytopenic purpura.

27. A compound which is selected from the group consisting of:
  6-(cis-2-aminocyclohexylamino)-5-fluoro-2-(5-phenylpyridin-3-ylamino)nicotinamide;
  6-(cis-2-aminocyclohexylamino)-5-fluoro-2-(3-methylphenylamino)nicotinamide;
  6-(cis-2-aminocyclohexylamino)-5-fluoro-2-(4-(morpholin-4-yl)phenylamino)nicotinamide;
  6-(cis-2-aminocyclohexylamino)-5-fluoro-2-(3,4,5-trimethoxyphenylamino)nicotinamide;
  6-(cis-2-aminocyclohexylamino)-5-fluoro-2-(2-methoxypyridin-4-ylamino)nicotinamide;
  6-(cis-2-aminocyclohexylamino)-2-(2,6-dimethoxypyridin-4-ylamino)-5-fluoronicotinamide;
  6-(cis-2-aminocyclohexylamino)-5-fluoro-2-(2-(morpholin-4-yl)pyridin-4-ylamino)nicotinamide;
  6-(cis-2-aminocyclohexylamino)-5-fluoro-2-(6-(morpholin-4-yl)pyridin-3-ylamino)nicotinamide;
  6-(cis-2-aminocyclohexylamino)-5-fluoro-2-(pyrimidin-5-ylamino)nicotinamide;
  6-(cis-2-aminocyclohexylamino)-5-fluoro-2-(1,5-naphthyridin-3-ylamino)nicotinamide;
  6-(cis-2-aminocyclohexylamino)-5-fluoro-2-(1,6-naphthyridin-3-ylamino)nicotinamide;
  6-(cis-2-aminocyclohexylamino)-5-fluoro-2-(1,6-naphthyridin-8-ylamino)nicotinamide;
  6-(cis-2-aminocyclohexylamino)-5-fluoro-2-(8-nitroquinolin-3-ylamino)nicotinamide;
  6-(cis-2-aminocyclohexylamino)-5-fluoro-2-(1-methyl-1H-pyrrolo[2,3-c]pyridin-4-ylamino)nicotinamide;
  6-(cis-2-aminocyclohexylamino)-5-fluoro-2-(1-(2-(pyrrolidin-1-yl)ethyl)-1H-pyrrolo[2,3-c]pyridin-4-ylamino)nicotinamide;
  2-(8-acetylaminoquinolin-3-ylamino)-6-(cis-2-aminocyclohexylamino)-5-fluoronicotinamide;
  6-(cis-2-aminocyclohexylamino)-5-fluoro-2-(5-(anilinocarbonyl)pyridin-3-ylamino)nicotinamide;
  6-(cis-2-aminocyclohexylamino)-5-fluoro-2-(1-methyl-1H-pyrrolo[2,3-b]pyridin-5-ylamino)nicotinamide;
  6-(cis-2-aminocyclohexylamino)-5-fluoro-2-(1-methyl-1H-pyrrolo[2,3-b]pyridin-4-ylamino)nicotinamide;
  methyl 5-(3-aminocarbonyl-6-(cis-2-aminocyclohexylamino)-5-fluoropyridin-2-ylamino)nicotinate;
  6-(cis-2-aminocyclohexylamino)-5-fluoro-2-(6-methylpyridin-3-ylamino)nicotinamide;
  6-(cis-2-aminocyclohexylamino)-5-fluoro-2-(2-methylpyridin-4-ylamino)nicotinamide;
  6-(cis-2-aminocyclohexylamino)-5-fluoro-2-(1-(2-(pyrrolidin-1-yl)ethyl)-1H-pyrrolo[2,3-b]pyridin-5-ylamino)nicotinamide;
  6-(cis-2-aminocyclohexylamino)-5-fluoro-2-(1-(2-(pyrrolidin-1-yl)ethyl)-1H-pyrrolo[2,3-b]pyridin-4-ylamino)nicotinamide;
  6-(cis-2-aminocyclohexylamino)-5-fluoro-2-(1-(2-(morpholin-4-yl)ethyl)-1H-pyrrolo[2,3-b]pyridin-4-ylamino)nicotinamide;
  6-(cis-2-aminocyclohexylamino)-5-fluoro-2-([1,3]thiazolo[4,5-b]pyridin-6-ylamino)nicotinamide;

6-(cis-2-aminocyclohexylamino)-2-(1-(2-(diethylamino)ethyl)-1H-pyrrolo[2,3-b]pyridin-4-ylamino)-5-fluoronicotinamide;
6-(cis-2-aminocyclohexylamino)-5-fluoro-2-(1-(2-methoxyethyl)-1H-pyrrolo[2,3-b]pyridin-4-ylamino)nicotinamide;
6-(cis-2-aminocyclohexylamino)-5-fluoro-2-(1-isobutyl-1H-pyrrolo[2,3-b]pyridin-4-ylamino)nicotinamide;
6-(cis-2-aminocyclohexylamino)-2-(1-cyclopropyl-1H-pyrrolo[2,3-b]pyridin-4-ylamino)-5-fluoronicotinamide;
6-(cis-2-aminocyclohexylamino)-2-(1-(cyclopropylmethyl)-1H-pyrrolo[2,3-b]pyridin-4-ylamino)-5-fluoronicotinamide;
6-(cis-2-aminocyclohexylamino)-5-fluoro-2-(5-(2H-1,2,3-triazol-2-yl)pyridin-3-ylamino)-nicotinamide;
6-(cis-2-aminocyclohexylamino)-5-fluoro-2-(5-(1H-pyrrol-2-yl)pyridin-3-ylamino)nicotinamide;
6-(cis-2-aminocyclohexylamino)-5-fluoro-2-(5-(2-thienyl)pyridin-3-ylamino)nicotinamide;
6-(cis-2-aminocyclohexylamino)-2-(5-cyclopropylpyridin-3-ylamino)-5-fluoronicotinamide;
6-(cis-2-aminocyclohexylamino)-5-fluoro-2-(5-(2-furyl)pyridin-3-ylamino)nicotinamide;
6-(cis-2-aminocyclohexylamino)-2-(8-aminoquinolin-3-ylamino)-5-fluoronicotinamide;
6-(cis-2-aminocyclohexylamino)-5-fluoro-2-(1H-pyrrolo[2,3-b]pyridin-4-ylamino)nicotinamide;
6-(cis-2-aminocyclohexylamino)-5-fluoro-2-(1H-pyrrolo[2,3-b]pyridin-5-ylamino)nicotinamide;
6-(cis-2-aminocyclohexylamino)-5-fluoro-2-(1H-pyrrolo[2,3-c]pyridin-4-ylamino)nicotinamide;
2-(8-(aminocarbonyl)aminoquinolin-3-ylamino)-6-(cis-2-aminocyclohexylamino)-5-fluoronicotinamide;
6-(2-aminoethylamino)-5-fluoro-2-(pyridin-4-ylamino)nicotinamide;
6-(2-aminoethylamino)-5-fluoro-2-(quinolin-6-ylamino)nicotinamide;
6-(cis-2-aminocyclohexylamino)-2-(2,1,3-benzothiadiazol-5-ylamino)-5-fluoronicotinamide;
6-(cis-2-aminocyclohexylamino)-2-(1,3-benzothiazol-6-ylamino)-5-fluoronicotinamide;
6-(cis-2-aminocyclohexylamino)-5-fluoro-2-(1-methyl-1H-indazol-6-ylamino)nicotinamide;
6-(cis-2-aminocyclohexylamino)-5-fluoro-2-(2-methyl-1,3-benzoxazol-6-ylamino)nicotinamide;
6-(2-aminoethylamino)-2-(1,3-benzothiazol-6-ylamino)-5-fluoronicotinamide;
6-(cis-2-aminocyclohexylamino)-5-fluoro-2-(2-methyl-1,3-benzoxazol-5-ylamino)nicotinamide;
6-(cis-2-aminocyclohexylamino)-5-fluoro-2-(5-methylpyridin-3-ylamino)nicotinamide;
6-(cis-2-aminocyclohexylamino)-2-(1,3-dimethyl-1H-pyrazolo[3,4-b]pyridin-5-ylamino)-5-fluoronicotinamide;
6-(cis-2-aminocyclohexylamino)-2-(2,3-dihydro-1,4-benzodioxin-6-ylamino)-5-fluoronicotinamide;
6-(cis-2-aminocyclohexylamino)-5-fluoro-2-(3-(2H-1,2,3-triazol-2-yl)phenylamino)nicotinamide;
6-(cis-2-aminocyclohexylamino)-5-fluoro-2-(6-methoxyquinolin-3-ylamino)nicotinamide;
6-(cis-2-aminocyclohexylamino)-5-fluoro-2-(quinolin-5-ylamino)nicotinamide;
6-(cis-2-aminocyclohexylamino)-5-fluoro-2-(quinoxalin-6-ylamino)nicotinamide;
6-(cis-2-aminocyclohexylamino)-2-(1,3-benzothiazol-5-ylamino)-5-fluoronicotinamide;
6-(2-aminoethylamino)-5-fluoro-2-(isoquinolin-4-ylamino)nicotinamide;
6-(2-aminoethylamino)-5-fluoro-2-(quinolin-5-ylamino)nicotinamide;
6-(cis-2-aminocyclohexylamino)-5-fluoro-2-(1-methyl-1H-indazol-5-ylamino)nicotinamide;
6-(cis-2-aminocyclohexylamino)-5-fluoro-2-(1-methyl-1H-benzoimidazol-6-ylamino)nicotinamide;
6-(cis-2-aminocyclohexylamino)-5-fluoro-2-(quinazolin-6-ylamino)nicotinamide;
6-(cis-2-aminocyclohexylamino)-5-fluoro-2-(quinazolin-7-ylamino)nicotinamide;
cis-6-(2-aminocyclohexylamino)-5-fluoro-2-(1-methyl-1H-benzoimidazol-5-ylamino)nicotinamide;
6-(cis-2-aminocyclohexylamino)-5-fluoro-2-(2-methylquinolin-6-ylamino)nicotinamide;
6-(cis-2-aminocyclohexylamino)-5-fluoro-2-(quinolin-7-ylamino)nicotinamide;
6-(cis-2-aminocyclohexylamino)-5-fluoro-2-(1-methyl-1H-indazol-4-ylamino)nicotinamide;
6-(cis-2-aminocyclohexylamino)-5-fluoro-2-(2-methylquinoxalin-6-ylamino)nicotinamide;
6-(cis-2-aminocyclohexylamino)-5-fluoro-2-(1-(2-(pyrrolidin-1-yl)ethyl)-1H-indazol-5-ylamino)nicotinamide;
6-(cis-2-aminocyclohexylamino)-5-fluoro-2-(2-(2-(pyrrolidin-1-yl)ethyl)-2H-indazol-5-ylamino)nicotinamide;
6-(cis-2-aminocyclohexylamino)-5-fluoro-2-(1H-indazol-5-ylamino)nicotinamide;
6-(2-aminoethylamino)-2-(3,5-dimethoxyphenylamino)-5-fluoronicotinamide;
6-(cis-2-aminocyclohexylamino)-5-fluoro-2-(quinolin-3-ylamino)nicotinamide;
6-(cis-2-aminocyclohexylamino)-5-fluoro-2-(quinolin-6-ylamino)nicotinamide;
6-(cis-2-aminocyclohexylamino)-2-(3-chlorophenylamino)-5-fluoronicotinamide;
6-(2-aminoethylamino)-5-fluoro-2-(quinolin-3-ylamino)nicotinamide;
6-(cis-2-aminocyclohexylamino)-5-fluoro-2-(isoquinolin-4-ylamino)nicotinamide;
6-(cis-2-aminocyclohexylamino)-5-fluoro-2-(1,8-naphthyridin-3-ylamino)nicotinamide;
5-fluoro-6-(2-(1H-imidazol-5-yl)ethylamino)-2-(quinolin-3-ylamino)nicotinamide;
6-((1R)-2-amino-2-oxo-1-phenylethylamino)-5-fluoro-2-(quinolin-6-ylamino)nicotinamide;
6-((2R)-1-amino-4-methyl-1-oxopentan-2-ylamino)-5-fluoro-2-(quinolin-6-ylamino)nicotinamide;
6-((2R)-1-amino-1-oxobutan-2-ylamino)-5-fluoro-2-(quinolin-6-ylamino)nicotinamide;
6-((2S)-2-aminobutylamino)-5-fluoro-2-(quinolin-6-ylamino)nicotinamide;
6-((2S)-2-amino-3-methylbutylamino)-5-fluoro-2-(quinolin-6-ylamino)nicotinamide;
6-((2S)-2-amino-2-phenylethylamino)-5-fluoro-2-(quinolin-6-ylamino)nicotinamide;
6-((2R)-2-amino-3-methoxypropylamino)-5-fluoro-2-(quinolin-6-ylamino)nicotinamide;
6-((2S)-2-aminopropylamino)-5-fluoro-2-(quinolin-6-ylamino)nicotinamide;
6-((2S)-2-amino-4-methylpentylamino)-5-fluoro-2-(quinolin-6-ylamino)nicotinamide;
6-(3-aminopropylamino)-2-(3,5-dimethoxyphenylamino)-5-fluoronicotinamide;

6-(cis-2-aminocyclohexylamino)-2-(3,5-dimethoxyphenylamino)-5-fluoronicotinamide;
6-((1R,2S)-2-aminocyclohexylamino)-2-(3,5-dimethoxyphenylamino)-5-fluoronicotinamide;
6-(cis-2-aminocyclohexylamino)-5-chloro-2-(quinolin-3-ylamino)nicotinamide;
6-(cis-2-aminocyclohexylamino)-5-bromo-2-(quinolin-3-ylamino)nicotinamide;
6-(cis-2-aminocyclohexylamino)-5-chloro-2-(3-methoxyphenylamino)nicotinamide;
6-(cis-2-aminocyclohexylamino)-5-chloro-2-(5-methylpyridin-3-ylamino)nicotinamide; and
6-(cis-2-aminocyclohexylamino)-5-bromo-2-(5-methylpyridin-3-ylamino)nicotinamide.

28. A compound which is selected from the group consisting of:
6-(cis-2-aminocyclohexylamino)-5-fluoro-2-(6-methylpyridin-3-ylamino)nicotinamide;
6-((cis-2-aminocyclohexyl)amino)-2-((5-cyano-6-morpholinopyridin-3-yl)amino)-5-fluoronicotinamide;
6-(cis-2-aminocyclohexylamino)-5-fluoro-2-(5-methylpyridin-3-ylamino)nicotinamide;
(R)-6-((1-amino-4-methylpentan-2-yl)amino)-5-fluoro-2-((quinolin-6-yl)amino)nicotinamide;
(R)-6-((1-amino-4-methylpentan-2-yl)amino)-5-fluoro-2-((2-(2-methoxyethoxy)pyridin-4-yl)amino)nicotinamide ;
6-((1R,2S)-2-aminocyclohexylamino)-5-fluoro-2-((6-morpholinopyridin-3-yl)amino)nicotinamide;
2-((5-(1H-pyrazol-1-yl)pyridin-3-yl)amino)-6-((1R,2S)-2-aminocyclohexylamino)-5-fluoronicotinamide;
(R)-6-((1-amino-4-methylpentan-2-yl)amino)-2-((5,6-dimethylpyridin-3-yl)amino)-5-fluoronicotinamide;
6-(((2S,3R)-2-aminopentane3-yl)amino)-2-((1-ethyl-1H-indazol-5-yl)amino)-5-fluoronicotinamide;
6-(((2S,3R)-2-aminohexane3-yl)amino)-5-fluoro-2-((2-methoxypyridin-4-yl)amino)nicotinamide;
6-(((2S,3R)-2-aminopentane3-yl)amino)-5-fluoro-2-((5-(2-fluorophenyl)pyridin-3-yl)amino)nicotinamide;
6-(((2S,3R)-2-aminopentane3-yl)amino)-5-fluoro-2-((1-methoxyisoquinolin-6-yl)amino)nicotinamide;
6-(((2S,3R)-2-aminopentane3-yl)amino)-5-fluoro-2-((1-methyl-1H-indazol-4-yl)amino)nicotinamide;
6-(((2S,3R)-2-aminohexane3-yl)amino)-2-((5,6-dimethylpyridin-3-yl)amino)-5-fluoronicotinamide;
6-(((2S,3R)-2-aminohexane3-yl)amino)-5-fluoro-2-((5-fluoropyridin-3-yl)amino)nicotinamide;
6-(((2S,3R)-2-aminohexane3-yl)amino)-5-fluoro-2-((2-propoxypyridin-4-yl)amino)nicotinamide;
(R)-6-((1-amino-4-methylpentan-2-yl)amino)-2-((1-ethyl-1H-indazol-5-yl)amino)-5-fluoronicotinamide;
6-(((2R,3S)-3-amino-1-cyclopropylbutan-2-yl)amino)-2-((1-ethyl-1H-indazol-5-yl)amino)-5-fluoronicotinamide;
6-(((1R,2S)-2-amino-1-cyclopropylpropyl)amino)-5-fluoro-2-(quinolin-6-ylamino)nicotinamide;
6-(((1R,2S)-2-aminocyclohexyl)amino)-5-fluoro-2(6-methyl-5-(2H-1,2,3-triazol-2-yl)pyridin-3-yl)amino)nicotinamide;
6-(((1R,2S)-2-aminocyclohexyl)amino)-5-fluoro-2-((6-methoxy-5-(2H-1,2,3-triazol-2-yl)pyridin-3-yl)amino)nicotinamide;
6-(((2S,3R)-2-amino-5-methylhexane3-yl)amino)-5-fluoro-2-((1-methyl-1H-indazol-5-yl)amino)nicotinamide;
6-(((2S,3R)-2-amino-5-methylhexane3-yl)amino)-2-((1-ethyl-1H-indazol-5-yl)amino)-5-fluoronicotinamide;
6-(((1R,2S)-2-aminocyclohexyl)amino)-5-fluoro-2-((5-fluoro-6-morpholinopyridin-3-yl)amino)nicotinamide;
6-(((1R,2S)-2-aminocyclohexyl)amino)-2((2-ethoxy-3-fluoropyridin-4-yl)amino)-5-fluoronicotinamide;
6-(((2R,3S)-3-amino-1-cyclopropylbutan-2-yl)amino)-2-((5,6-dimethylpyridin-3-yl)amino)-5-fluoronicotinamide;
6-(((2S,3S)-3-amino-1-methoxybutan-2-yl)amino)-5-fluoro-2-(quinolin-6-ylamino)nicotinamide; and
6-(2-aminoethylamino)-2-(3,5-dimethoxyphenylamino)-5-fluoronicotinamide.

29. A compound which is selected from the group consisting of:
6-(cis-2-aminocyclohexylamino)-5-fluoro-2-((6-methyl-5-phenylpyridin-3-yl)amino)nicotinamide;
6-(cis-2-aminocyclohexylamino)-2-((5,6-dimethylpyridin-3-yl)amino)-5-fluoronicotinamide;
2-(1H-indazol-4-yl)amino)-6-(cis-2-aminocyclohexylamino)-5-fluoronicotinamide;
6-(cis-2-aminocyclohexylamino)-5-fluoro-2-((1-(2-(pyrrolidin-1-yl)ethyl)-1H-indazol-4-yl)amino)nicotinamide;
6-(cis-2-aminocyclohexylamino)-5-fluoro-2-((1-(2-morpholinoethyl)-1H-indazol-4-yl)amino)nicotinamide;
6-(cis-2-aminocyclohexylamino)-2-((1-(cyclopropylmethyl)-1H-indazol-4-yl)amino)-5-fluoronicotinamide;
6-(cis-2-aminocyclohexylamino)-5-fluoro-2-((1-(2-methoxyethyl)-1H-indazol-4-yl)amino)nicotinamide;
6-(cis-2-aminocyclohexylamino)-2-((1(2-(2-ethoxyethoxy)ethyl)-1H-indazol-4-yl)amino)-5-fluoronicotinamide;
6-(cis-2-aminocyclohexylamino)-2-((2-(cyclopropylmethyl)-2H-indazol-4-yl)amino)-5-fluoronicotinamide;
6-(cis-2-aminocyclohexylamino)-2((2-benzyl-2H-indazol-4-yl)amino)-5-fluoronicotinamide;
6-(cis-2-aminocyclohexylamino)-5-fluoro-2(2-(2-methoxyethyl)-2H-indazol-4-yl)amino)nicotinamide;
6-(cis-2-aminocyclohexylamino)-2((2-benzyl-2H-indazol-5-yl)amino)-5-fluoronicotinamide;
6-(cis-2-aminocyclohexylamino)-2-((5-ethylpyridin-3-yl)amino)-5-fluoronicotinamide;
6-(cis-2-aminocyclohexylamino)-5-fluoro-2(2-methyl-2H-indazol-5-yl)amino)nicotinamide;
6-(cis-2-aminocyclohexylamino)-2-((1-(cyclopropylmethyl)-1H-indazol-6-yl)amino)-5-fluoronicotinamide;
6-(cis-2-aminocyclohexylamino)-5-fluoro-2-((1-(2-methoxyethyl)-1H-indazol-6-yl)amino)nicotinamide;
2-(2-(1H-pyrrol-2-yl)pyridin-4-yl)amino)-6-(cis-2-aminocyclohexylamino)-5-fluoronicotinamide;
6-(cis-2-aminocyclohexylamino)-5-fluoro-2-((2-phenylpyridin-4-yl)amino)nicotinamide;
6-(cis-2-aminocyclohexylamino)-5-fluoro-2-((2-(furan-2-yl)pyridin-4-yl)amino)nicotinamide;
6-(cis-2-aminocyclohexylamino)-5-fluoro-2-((2-isopropoxypyridin-4-yl)amino)nicotinamide;
6-(cis-2-aminocyclohexylamino)-5-fluoro-2-((2-(furan-3-yl)pyridin-4-yl)amino)nicotinamide;
6-(cis-2-aminocyclohexylamino)-5-fluoro-2-((2-(methylamino)pyridin-4-yl)amino)nicotinamide;
6-(cis-2-aminocyclohexylamino)-2-(2-ethoxypyridin-4-yl)amino)-5-fluoronicotinamide;
6-(cis-2-aminocyclohexylamino)-2-(2,6-diethoxypyridin-4-yl)amino)-5-fluoronicotinamide;
6-(cis-2-aminocyclohexylamino)-5-fluoro-2-((5-(5-methylfuran-2-yl)pyridin-3-yl)amino)nicotinamide;
6-(cis-2-aminocyclohexylamino)-5-fluoro-2-((2-((5-methylfuran-2-yl)pyridin-4-yl)amino)nicotinamide;

6-(cis-2-aminocyclohexylamino)-5-fluoro-2-((2-methoxy-6-phenylpyridin-4-yl)amino)nicotinamide;
6-(cis-2-aminocyclohexylamino)-5-fluoro-2-((2-(2-methoxyethoxy)pyridin-4-yl)amino)nicotinamide;
6-(cis-2-aminocyclohexylamino)-5-fluoro-2-((2-morpholino-6-phenylpyridin-4-yl)amino)nicotinamide;
2-((5-(1H-pyrazol-4-yl)pyridin-3-yl)amino)-6-(cis-2-aminocyclohexylamino)-5-fluoronicotinamide;
2-(2-(1H-pyrazol-4-yl)pyridin-4-yl)amino)-6-(cis-2-aminocyclohexylamino)-5-fluoronicotinamide;
6-(cis-2-aminocyclohexylamino)-5-fluoro-2-((2-propoxypyridin-4-yl)amino)nicotinamide;
6-(cis-2-aminocyclohexylamino)-5-fluoro-2-((2-butoxypyridin-4-yl)amino)-5-fluoronicotinamide;
6-(cis-2-aminocyclohexylamino)-5-fluoro-2-((2-isobutoxypyridin-4-yl)amino)nicotinamide;
6-(cis-2-aminocyclohexylamino)-5-fluoro-2-((2-methoxyquinolin-7-yl)amino)nicotinamide;
6-(cis-2-aminocyclohexylamino)-5-fluoro-2-((2-(2-methoxyethoxy)quinolin-7-yl)amino)nicotinamide;
6-(cis-2-aminocyclohexylamino)-5-fluoro-2-((2-((1-methoxypropan-2-yl)oxy)quinolin-7-yl)amino)nicotinamide;
6-(cis-2-aminocyclohexylamino)-5-fluoro-2-((2-(3-methoxybutoxy)quinolin-7-yl)amino)nicotinamide;
6-(cis-2-aminocyclohexylamino)-2-((2-(2-(2-ethoxyethoxy)ethoxy)quinolin-7-yl)amino)-5-fluoronicotinamide;
6-(cis-2-aminocyclohexylamino)-2-((5-(1-cyclohexen-1-yl)pyridin-3-yl)amino)-5-fluoronicotinamide;
6-(cis-2-aminocyclohexylamino)-5-fluoro-2-((2-(2-methoxyethoxy)quinolin-6-yl)amino)nicotinamide;
6-(cis-2-aminocyclohexylamino)-5-fluoro-2-((2-((1-methoxypropan-2-yl)oxy)quinolin-6-yl)amino)nicotinamide;
6-(cis-2-aminocyclohexylamino)-5-fluoro-2-((2-(3-methoxybutoxy)quinolin-6-yl)amino)nicotinamide;
6-(cis-2-aminocyclohexylamino)-2-((2-(2-(2-ethoxyethoxy)ethoxy)quinolin-6-yl)amino)-5-fluoronicotinamide;
6-(cis-2-aminocyclohexylamino)-2-((2-methoxyquinolin-6-yl)amino)nicotinamide;
6-(cis-2-aminocyclohexylamino)-2-((2-ethoxyquinolin-6-yl)amino)-5-fluoronicotinamide;
6-(cis-2-aminocyclohexylamino)-5-fluoro-2-((2-propoxyquinolin-6-yl)amino)nicotinamide;
6-(cis-2-aminocyclohexylamino)-2-((2-(2-ethoxyethoxy)quinolin-6-yl)amino)-5-fluoronicotinamide;
6-(cis-2-aminocyclohexylamino)-5-fluoro-2-((2-(2-(2-methoxyethoxy)ethoxy)quinolin-6-yl)amino)nicotinamide;
6-(cis-2-aminocyclohexylamino)-5-fluoro-2-((2-((tetrahydrofuran-2-yl)methoxy)quinolin-6-yl)amino)nicotinamide;
6-(cis-2-aminocyclohexylamino)-5-fluoro-2-((2-(2-(2-oxopyrrolidin-1-yl)ethoxy)quinolin-6-yl)amino)nicotinamide;
2-((2-(1H-1,2,4-triazol-1-yl)pyridin-4-yl)amino)-6-(cis-2-aminocyclohexylamino)-5-fluoronicotinamide;
6-(cis-2-aminocyclohexylamino)-5-fluoro-2-((5-(furan-3-yl)-6-methylpyridin-3-yl)amino)nicotinamide;
6-(cis-2-aminocyclohexylamino)-2-((2,3-dimethoxyquinoxalin-6-yl)amino)-5-fluoronicotinamide;
6-(cis-2-aminocyclohexylamino)-2-((2,3-diethoxyquinoxalin-6-yl)amino)-5-fluoronicotinamide;
6-(cis-2-aminocyclohexylamino)-5-fluoro-2-((4-methyl-3,4-dihydro-2H-[1,4]oxazino[2,3-b]quinoxalin-7-yl)amino)nicotinamide;
6-(cis-2-aminocyclohexylamino)-2-((2,3-dimethylquinoxalin-6-yl)amino)-5-fluoronicotinamide;
6-(cis-2-aminocyclohexylamino)-2-((2,3-diethylquinoxalin-6-yl)amino)-5-fluoronicotinamide;
6-(cis-2-aminocyclohexylamino)-2-((1-ethyl-1H-indazol-5-yl)amino)-5-fluoronicotinamide;
6-(cis-2-aminocyclohexylamino)-5-fluoro-2-((1-propyl-1H-indazol-5-yl)amino)nicotinamide;
6-(cis-2-aminocyclohexylamino)-5-fluoro-2-((2-(2-fluorophenyl)pyridin-4-yl)amino)nicotinamide;
6-(cis-2-aminocyclohexylamino)-2-((2-(2,4-difluorophenyl)pyridin-4-yl)amino)-5-fluoronicotinamide;
6-(cis-2-aminocyclohexylamino)-5-fluoro-2-((6-methyl-5-(2H-1,2,3-triazol-2-yl)pyridin-3-yl)amino)nicotinamide;
2-((5-(1H-1,2,4-triazol-1-yl)pyridin-3-yl)amino)-6-(cis-2-aminocyclohexylamino)-5-fluoronicotinamide;
6-(cis-2-aminocyclohexylamino)-5-fluoro-2-((2-(2-fluoro-3-methoxyphenyl)pyridin-4-yl)amino)nicotinamide;
6-(cis-2-aminocyclohexylamino)-5-fluoro-2-((2-(2-fluoro-4-methoxyphenyl)pyridin-4-yl)amino)nicotinamide;
6-(cis-2-aminocyclohexylamino)-5-fluoro-2-((2-(2-fluoro-5-methoxyphenyl)pyridin-4-yl)amino)nicotinamide;
6-(cis-2-aminocyclohexylamino)-2-((6-cyclopropylpyridin-3-yl)amino)-5-fluoronicotinamide;
2-((3-(1H-pyrazol-1-yl)quinolin-7-yl)amino)-6-(cis-2-aminocyclohexylamino)-5-fluoronicotinamide;
6-(cis-2-aminocyclohexylamino)-2-((2-(2,3-difluorophenyl)pyridin-4-yl)amino)-5-fluoronicotinamide;
6-(cis-2-aminocyclohexylamino)-2-((2-(2,5-difluorophenyl)pyridin-4-yl)amino)-5-fluoronicotinamide;
6-(cis-2-aminocyclohexylamino)-2-((2-(3-chloro-2-fluorophenyl)pyridin-4-yl)amino)-5-fluoronicotinamide;
6-(cis-2-aminocyclohexylamino)-2-((2-((5-chloro-2-fluorophenyl)pyridin-4-yl)amino)-5-fluoronicotinamide;
6-(cis-2-aminocyclohexylamino)-2-((5-(benzo[d][1,3]dioxol-5-yl)pyridin-3-yl)amino)-5-fluoronicotinamide;
6-(cis-2-aminocyclohexylamino)-2-((2-(benzo[d][1,3]dioxol-5-yl)pyridin-4-yl)amino)-5-fluoronicotinamide;
6-(cis-2-aminocyclohexylamino)-5-fluoro-2-((5-(3-oxo-3,4-dihydro-2H-benzo[b][1,4]oxazin-6-yl)pyridin-3-yl)amino)nicotinamide;
6-(cis-2-aminocyclohexylamino)-5-fluoro-2-((2-(3-oxo-3,4-dihydro-2H-benzo[b][1,4]oxazin-6-yl)pyridin-4-yl)amino)nicotinamide;
6-(cis-2-aminocyclohexylamino)-5-fluoro-2-((2-(3-methoxyphenyl)pyridin-4-yl)amino)nicotinamide;
6-(cis-2-aminocyclohexylamino)-5-fluoro-2-((2-(4-methoxyphenyl)pyridin-4-yl)amino)nicotinamide;
6-((cis-2-aminocyclohexyl)amino)-2-((1-ethyl-1H-indazol-6-yl)amino)-5-fluoronicotinamide;
6-((cis-2-aminocyclohexyl)amino)-2-((1-ethyl-1H-indazol-4-yl)amino)-5-fluoronicotinamide;
6-((cis-2-aminocyclohexyl)amino)-2-((1-(2,2-difluoroethyl)-1H-indazol-5-yl)amino)-5-fluoronicotinamide;
6-((cis-2-aminocyclohexyl)amino)-2-((1-(2,2-difluoroethyl)-1H-indazol-6-yl)amino)-5-fluoronicotinamide;
6-((cis-2-aminocyclohexyl)amino)-5-fluoro-2-((5-(quinolin-7-yl)pyridin-3-yl)amino)nicotinamide;
6-((cis-2-aminocyclohexyl)amino)-5-fluoro-2-((5-(isoquinolin-6-yl)pyridin-3-yl)amino)nicotinamide;

6-((cis-2-aminocyclohexyl)amino)-5-fluoro-2-((5-(isoquinolin-7-yl)pyridin-3-yl)amino)nicotinamide;
6-((cis-2-aminocyclohexyl)amino)-5-fluoro-2-((2-(quinolin-7-yl)pyridin-4-yl)amino)nicotinamide;
6-((cis-2-aminocyclohexyl)amino)-5-fluoro-2-((2-(isoquinolin-6-yl)pyridin-4-yl) amino)nicotinamide;
6-((cis-2-aminocyclohexyl)amino)-5-fluoro-2-((2-(isoquinolin-7-yl)pyridin-4-yl)amino)nicotinamide;
6-(((cis)-2-aminocyclohexyl)amino)-2-((benzofuro[2,3-b]pyridin-3-yl)amino)-5-fluoronicotinamide;
6-((cis-2-aminocyclohexyl)amino)-5-fluoro-2-((3-fluoro-1-methyl-1H-indazol-5-yl)amino)nicotinamide;
6-((cis-2-aminocyclohexyl)amino)-2-((1-ethyl-3-fluoro-1H-indazol-5-yl)amino)-5-fluoronicotinamide;
6-((cis-2-aminocyclohexyl)amino)-5-fluoro-2-((3-fluoro-1-methyl-1H-indazol-6-yl)amino)nicotinamide;
6-((cis-2-aminocyclohexyl)amino)-2-((1-ethyl-3-fluoro-1H-indazol-6-yl)amino)-5-fluoronicotinamide;
6-((cis-2-aminocyclohexyl)amino)-5-fluoro-2-((1-(2-fluoroethyl)-1H-indazol-5-yl)amino)nicotinamide;
6-((cis-2-aminocyclohexyl)amino)-5-fluoro-2-((1-(2-fluoroethyl)-1H-indazol-6-yl)amino)nicotinamide;
6-((cis-2-aminocyclohexyl)amino)-5-fluoro-2-((3-fluoro-1-(2-fluoroethyl)-1H-indazol-5-yl)amino)nicotinamide;
6-((cis-2-aminocyclohexyl)amino)-5-fluoro-2-((3-fluoro-1-(2-fluoroethyl)-1H-indazol-6-yl)amino)nicotinamide;
6-((cis-2-aminocyclohexyl)amino)-2-((1,3-dimethyl-1H-indazol-5-yl)amino)-5-fluoronicotinamide;
6-((cis-2-aminocyclohexyl)amino)-2-((1-ethyl-3-methyl-1H-indazol-5-yl)amino)-5-fluoronicotinamide;
6-((cis-2-aminocyclohexyl)amino)-5-fluoro-2-((1-(2-methoxyethyl)-3-methyl-1H-indazol -5-yl)amino)nicotinamide;
6-((cis-2-aminocyclohexyl)amino)-5-fluoro-2-((1-(2-fluoroethyl)-3-methyl-1H-indazol-5-yl)amino)nicotinamide; and
6-((cis-2-aminocyclohexyl)amino)-2-((1-(2,2-difluoroethyl)-3-methyl-1H-indazol-5-yl)amino)-5-fluoronicotinamide.

* * * * *

UNITED STATES PATENT AND TRADEMARK OFFICE
CERTIFICATE OF CORRECTION

PATENT NO. : 8,895,585 B2  
APPLICATION NO. : 13/730000  
DATED : November 25, 2014  
INVENTOR(S) : Hideyasu Fujiwara et al.

Page 1 of 1

It is certified that error appears in the above-identified patent and that said Letters Patent is hereby corrected as shown below:

In the claims:

Column 1148, Line 11, in Claim 28, delete "5-fluoronicotinamide.", and insert

--5-fluoronicotinamide;

6-(((1R,2S)-2-aminocyclohexyl)amino)-5-fluoro-2-((5-methylpyridin-3-yl)amino)nicotinamide; and 6-(((1R,2S)-2-aminocyclohexyl)amino-5-fluoro-2-((6-methylpyridin-3-yl)amino)nicotinamide.--

Signed and Sealed this
Second Day of August, 2016

Michelle K. Lee
*Director of the United States Patent and Trademark Office*